US011440923B2

(12) United States Patent
Thede et al.

(10) Patent No.: US 11,440,923 B2
(45) Date of Patent: Sep. 13, 2022

(54) SUBSTITUTED MACROCYCLIC INDOLE DERIVATIVES

(71) Applicants: Bayer Aktiengesellschaft, Leverkusen (DE); Bayer Pharma Aktiengesellschaft, Berlin (DE); The Broad Institute, Inc., Cambridge, MA (US)

(72) Inventors: Kai Thede, Leverkusen (DE); Anne Mengel, Leverkusen (DE); Clara Christ, Leverkusen (DE); Joachim Kuhnke, Leverkusen (DE); Sarah Anna Liesa Johannes, Leverkusen (DE); Philipp Buchgraber, Leverkusen (DE); Ulrich Klar, Leverkusen (DE); Ulrike Rauh, Leverkusen (DE); Stefan Kaulfuss, Leverkusen (DE); Amaury Ernesto Fernandez-Montalvan, Leverkusen (DE); Nicolas Werbeck, Leverkusen (DE); Ursula Mönning, Leverkusen (DE); Katrin Nowak-Reppel, Leverkusen (DE); Sven Wittrock, Leverkusen (DE); David McKinney, Cambridge, MA (US); Michael H. Serrano-Wu, Cambridge, MA (US); Chris Lemke, Cambridge, MA (US); Mark Fitzgerald, Cambridge, MA (US); Christopher Nasveschuk, Cambridge, MA (US); Kiel Lazarski, Cambridge, MA (US); Steven J. Ferrara, Cambridge, MA (US); Laura Furst, Cambridge, MA (US); Guo Wei, Cambridge, MA (US); Patrick R. McCarren, Cambridge, MA (US); Rebecca Ann Harvey, Lancashire (GB)

( * ) Notice: Subject to any disclaimer, the term of this patent is extended or adjusted under 35 U.S.C. 154(b) by 0 days.

(21) Appl. No.: 16/764,668

(22) PCT Filed: Nov. 15, 2018

(86) PCT No.: PCT/EP2018/081406

§ 371 (c)(1),
(2) Date: May 15, 2020

(87) PCT Pub. No.: WO2019/096922

PCT Pub. Date: May 23, 2019

(65) Prior Publication Data

US 2021/0269456 A1 Sep. 2, 2021

Related U.S. Application Data

(60) Provisional application No. 62/587,935, filed on Nov. 17, 2017.

(51) Int. Cl.
*C07D 498/14* (2006.01)
*A61P 35/02* (2006.01)
(Continued)

(52) U.S. Cl.
CPC ........ *C07D 498/14* (2013.01); *A61K 31/4162* (2013.01); *A61K 31/437* (2013.01);
(Continued)

(58) Field of Classification Search
CPC .. C07D 498/14; C07D 471/22; C07D 487/14; C07D 487/22; C07D 498/22;
(Continued)

(56) References Cited

U.S. PATENT DOCUMENTS

| | | | |
|---|---|---|---|
| 10,981,932 | B2 | 4/2021 | Johannes et al. |
| 2015/0336925 | A1 | 11/2015 | Lee et al. |

(Continued)

FOREIGN PATENT DOCUMENTS

| | | | |
|---|---|---|---|
| WO | WO-2008/130970 | A1 | 10/2008 |
| WO | WO-2008/131000 | A2 | 10/2008 |

(Continued)

OTHER PUBLICATIONS

Burke; J. Med. Chem. 2015, 58, 9, 3794-3805. doi: 10.1021/jm501984f (Year: 2015).*

(Continued)

*Primary Examiner* — Daniel R Carcanague
(74) *Attorney, Agent, or Firm* — Foley Hoag LLP; David P. Halstead

(57) ABSTRACT

The present invention relates to substituted macrocyclic indole derivatives of general formula (I):

(I)

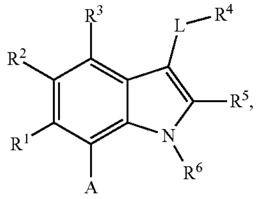

in which $R^1$, $R^2$, $R^3$, $R^4$, $R^5$, $R^6$, A and L are as defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients.

15 Claims, 6 Drawing Sheets

Specification includes a Sequence Listing.

(51) Int. Cl.

| | |
|---|---|
| ***A61P 35/00*** | (2006.01) |
| ***A61K 31/4162*** | (2006.01) |
| ***A61K 31/437*** | (2006.01) |
| ***A61K 31/496*** | (2006.01) |
| ***A61K 31/5377*** | (2006.01) |
| ***A61K 45/06*** | (2006.01) |
| ***C07D 471/22*** | (2006.01) |
| ***C07D 487/14*** | (2006.01) |
| ***C07D 487/22*** | (2006.01) |
| ***C07D 498/22*** | (2006.01) |

(52) U.S. Cl.

CPC ........ *A61K 31/496* (2013.01); *A61K 31/5377* (2013.01); *A61K 45/06* (2013.01); *A61P 35/00* (2018.01); *A61P 35/02* (2018.01); *C07D 471/22* (2013.01); *C07D 487/14* (2013.01); *C07D 487/22* (2013.01); *C07D 498/22* (2013.01)

(58) Field of Classification Search

CPC ...... A61P 35/02; A61P 35/00; A61K 31/4162; A61K 31/437; A61K 31/496; A61K 31/5377; A61K 45/06

See application file for complete search history.

(56) References Cited

U.S. PATENT DOCUMENTS

| | | | |
|---|---|---|---|
| 2016/0106731 | A1 | 4/2016 | Lee et al. |
| 2017/0305926 | A1 | 10/2017 | Hird et al. |
| 2020/0087322 | A1 | 3/2020 | Johannes et al. |
| 2021/0079018 | A1 | 3/2021 | Ferrara et al. |
| 2021/0253598 | A1 | 8/2021 | Thede et al. |
| 2021/0269456 | A1 | 9/2021 | Thede et al. |
| 2021/0277022 | A1 | 9/2021 | Thede et al. |
| 2021/0292341 | A1 | 9/2021 | Furst et al. |

FOREIGN PATENT DOCUMENTS

| | | | |
|---|---|---|---|
| WO | WO-2014/047427 | A2 | 3/2014 |
| WO | WO-2015/031608 | A1 | 3/2015 |
| WO | WO-2015/148854 | A1 | 10/2015 |
| WO | WO-2017/152076 | A1 | 9/2017 |
| WO | WO-2017/182625 | A1 | 10/2017 |
| WO | WO-2017/198341 | A1 | 11/2017 |
| WO | WO-2018/098534 | A1 | 6/2018 |
| WO | WO-2019/096905 | A1 | 5/2019 |
| WO | WO-2019/096907 | A1 | 5/2019 |
| WO | WO-2019/096909 | A1 | 5/2019 |
| WO | WO-2019/096911 | A1 | 5/2019 |
| WO | WO-2019/096914 | A1 | 5/2019 |
| WO | WO-2019/096922 | A1 | 5/2019 |
| WO | WO-2020/151738 | A1 | 7/2020 |
| WO | WO-2020/236556 | A1 | 11/2020 |

OTHER PUBLICATIONS

Quinn; Expert Opinion on Investigational Drugs, 2011, 20, 1397-1411. doi: 10.1517/13543784.2011.609167 (Year: 2011).*

Zhao; Biochemistry 2018, 57, 32, 4952-4958. doi: 10.1021/acs.biochem.8b00626 (Year: 2018).*

Adams et al., "The Bcl-2 apoptotic switch in cancer development and therapy," Oncogene, 26:1324-1337 (2007).

Beroukhim et al., "The Landscape of Somatic Copy-Number Alteration Across Human Cancers," Nature, 463(7283):899-905 (2010).

Glaser et al., "Anti-apoptotic Mcl-1 is essential for the development and sustained growth of acute myeloid leukemia," Genes Dev, 26:120-125 (2012).

Hanahan et al., "Hallmarks of Cancer: The Next Generation," Cell 144(5):646-674 (2011).

International Preliminary Report on Patentability for International Application No. PCT/EP2017/000629 dated Nov. 20, 2018.

International Preliminary Report on Patentability for International Application No. PCT/EP2018/081370 dated May 19, 2020.

International Preliminary Report on Patentability for International Application No. PCT/EP2018/081374 dated May 19, 2020.

International Preliminary Report on Patentability for International Application No. PCT/EP2018/081378 dated May 19, 2020.

International Preliminary Report on Patentability for International Application No. PCT/EP2018/081381 dated May 19, 2020.

International Preliminary Report on Patentability for International Application No. PCT/EP2018/081388 dated May 19, 2020.

International Preliminary Report on Patentability for International Application No. PCT/EP2018/081406 dated May 19, 2020.

International Search Report and Written Opinion for International Application No. PCT/EP2017/000629 dated Sep. 6, 2017.

International Search Report and Written Opinion for International Application No. PCT/EP2018/081370 dated Feb. 13, 2019.

International Search Report and Written Opinion for International Application No. PCT/EP2018/081374 dated Feb. 13, 2019.

International Search Report and Written Opinion for International Application No. PCT/EP2018/081378 dated Jan. 9, 2019.

International Search Report and Written Opinion for International Application No. PCT/EP2018/081381 dated Jan. 15, 2019.

International Search Report and Written Opinion for International Application No. PCT/EP2018/081388 dated Feb. 14, 2019.

International Search Report and Written Opinion for International Application No. PCT/EP2018/081406 dated Feb. 11, 2019.

International Search Report and Written Opinion for International Application No. PCT/US2020/033067 dated Jul. 19, 2020.

Korsmeyer, "BCL-2 Gene Family and the Regulation of Programmed Cell Death," Cancer Res Suppl, 59(7):1693s-1700s (1999).

Pelz et al., "Discovery of 2-Indole-acylsulfonamide Myeloid Cell Leukemia 1 (Mcl-1) Inhibitors Using Fragment-Based Methods," Journal of Medicinal Chemistry, 59(5): 2054-2066 (2016).

Wertz et al., "Sensitivity to antitubulin chemotherapeutics is regulated by MCL1 and FBW7," Nature, 471:110-114 (2011).

Zhou et al., "MCL1 transgenic mice exhibit a high incidence of B-cell lymphoma manifested as a spectrum of histologic subtypes," Blood, 97(12):3902-3909 (2001).

Zhang et al., "Research progress of GSK-3 inhibitors," Progress in Chemistry, 19(4): 614-623 (2007).

* cited by examiner

SUBSTITUTED MACROCYCLIC INDOLE DERIVATIVES

RELATED APPLICATIONS

This application is the U.S. national phase of International Patent Application No. PCT/EP2018/081406, filed Nov. 15, 2018, which claims the benefit of U.S. Provisional Application No. 62/587,935 filed on Nov. 17, 2017. The International Patent Application No. PCT/EP2018/081406 is hereby incorporated by reference in its entirety.

BACKGROUND

The present invention covers macrocyclic indole derivatives of general formula (I) which inhibit the antiapoptotic activity of MCL-1 by inhibiting its interaction with proapoptotic proteins.

Apoptosis, also called programmed cell death, is a natural process which allows a damaged or unwanted cell to die in a controlled manner. Deregulation of this process leads to unrestrained cell proliferation and is thus a hallmark of cancer (Hanahan and Weinberg, 2011).

Apoptosis is highly controlled by proteins of the B-cell lymphoma 2 (BCL-2) family. These proteins are characterized by their conserved regions known as BCL-2 homology (BH) domains (BH1-BH4) (Korsmeyer, 1999) through which they interact with each other. The BCL-2 family can be divided into pro-apoptotic members including BAX, BAK, BAD, BID, BIM, BMF, NOXA and PUMA, which induce cell death and anti-apoptotic members such as BCL-2, BCL-XL, BCLw, Bfl1-A1 and myeloid cell leukemia-1 (MCL-1) which block apoptosis (Adams and Cory, 2007). The relative expression level of these two opponent groups of the BCL-2 family will decide if a cell will go into apoptosis or not.

MCL-1 has been identified as an important therapeutic target in cancer. MCL-1 is highly expressed in a variety of human cancers and amplification of the MCL-1 locus is one of the most frequent somatic genetic events in human cancer, further pointing to its centrality in the pathogenesis of malignancy (Beroukhim et al., 2010). Its expression has been linked to deregulated anti-apoptotic pathways in cancer, thus leading to increased cancer cell survival, tumor development (Zhou et al., 2001) and resistance to anticancer therapies (Wertz et al., 2011). MCL-1 protein has been shown to mediate survival in models of acute myeloid leukemia (Glaser et al., 2012), lymphomas (Kelly et al., 2014) and multiple myeloma (Zhang et al., 2002). Many chemotherapeutics as well as radiation aim at inducing apoptosis in cancer cells. However, in malignant cells, apoptotic signaling is often deregulated, leading to uncontrolled growth and therapeutic resistance. One key resistance mechanism to apoptosis is to upregulate or genetically amplify MCL-1.

MCI-1 is a major inhibitor of apoptosis in cancer. MCL-1 is the largest member of the anti-apoptotic BCI-2 proteins. Its expression is tightly controlled with a half-life of only 1-4 h. With its BH-3 domain, MCL-1 tightly binds to BH-3 only containing pro-apoptotic proteins such as BAK or BAX and hinders them from inducing pores in the mitochondrial membrane, thereby blocking the intrinsic apoptotic pathway.

Thus, the specific inhibition of the interaction of MCL-1 with BH-3 only containing pro-apoptotic proteins like BAK or BAX represents a very attractive therapeutic principle to induce apoptosis in cancer cells and to address resistance against chemotherapeutics, radiation and new targeted agents. However, from WO 2015/148854, US 2016/0106731, WO 2008/130970, some indole derivatives are known as MCL-1 inhibitors. As no inhibitors have shown efficacy in the clinic yet, there is still a need for further MCL-1 inhibitors to be provided.

SUMMARY

It has now been found that the compounds of the present invention effectively inhibit the activity of the anti-apoptotic BCL-2 family member Myeloid cell leukemia-1 (MCL-1) protein for which data are given in the biological experimental section and may therefore be used for the treatment or prophylaxis of hyperproliferative disorders, such as cancer disorders.

In accordance with a first aspect, the present invention provides compounds of general formula (I):

(I)

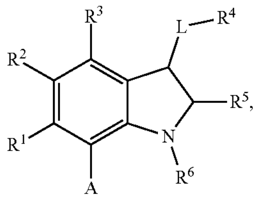

wherein

A is (A1)

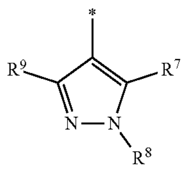

or (A2)

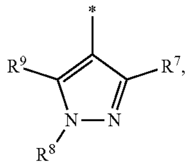

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

or

A is (A3)

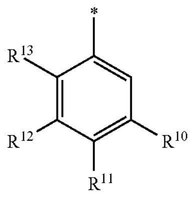

wherein optionally one or two of the groups selected from $CR^{11}$, $CR^{12}$ and $CR^{13}$ are replaced by a nitrogen atom, wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —$S(O)_2$—($C_1$-$C_3$-alkyl) group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8-membered saturated or partially unsaturated heterocyclic ring having 1-2 heteroatoms independently selected from an oxygen atom, a sulfur atom, a —S(O)— group, a —$S(O)_2$— group and a —$NR^{14}$— group;

E is a bond, an oxygen atom, a sulfur atom, a —S(O)— group, a —$S(O)_2$— group or a —$NR^{14}$— group and constitutes the connecting element to $R^4$;

m is 2, 3, or 4;

$R^5$ is selected from a COOH group, a

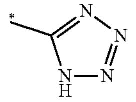 [SMILES: *c1nnn[nH]1]

group, a —C(O)—$NHS(O)_2$($C_1$-$C_6$-alkyl) group, a —C(O)—$NHS(O)_2$($C_3$-$C_6$-cycloalkyl) group, a —C(O)—$NHS(O)_2$(aryl) group, a —C(O)—$NHS(O)_2(CH_2)_s$NHCO($C_1$-$C_6$-alkyl) group, a —C(O)—$NHS(O)_2(CH_2)_s$NHCO($C_3$-$C_6$-cycloalkyl) group and a —C(O)—$NHS(O)_2$$(CH_2)_s$NHCO(aryl) group;

s is 0, 1 or 2;

—$R^6$-$R^7$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

—$R^6$-$R^{10}$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, where one or more —$CH_2$— groups are substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the phenyl moiety bearing the $R^{10}$ substituent;

n is 2, 3, 4, 5, 6, 7, 8, or 9, if B is selected from —O—, —S—, —S(O)—, —$S(O)_2$— and —$N(R^{15})$—, and n is 1, 2, 3, 4, 5, 6, 7 or 8, if B is selected from a —$C(O)NR^{15}$— group and a —$NR^{15}C(O)$— group, and n is 0, 1, 2, 3, 4, 5, 6 or 7, if B is selected from a —$N(R^{15})$—C(=O)—$N(R^{15})$— group, a —O—C(=O)—$N(R^{15})$— group and a —$N(R^{15})$—C(=O)—O— group;

t is 1;

where the integers selected for variables n and t, together with the methylene group $CR^{22}R^{23}$ and the other non-variable atoms of the pyrazole and the indole moiety result in forming a 9-membered to 16-membered ring independently from the selection of variable A1, A2 or A3;

B is independently selected from a —$C(O)NR^{15}$— group, a —$NR^{15}C(O)$— group, a —$N(R^{15})$— group, a —$N(R^{15})$—C(=O)—$N(R^{15})$— group, a —O—C(=O)—$N(R^{15})$— group, a —$N(R^{15})$—C(=O)—O— group, —O—, —S—, —S(O)— and —$S(O)_2$—;

$R^8$ is selected from a hydrogen atom, a $C_1$-$C_6$-alkyl group which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group;

a $C_1$-$C_3$-haloalkyl group, a $C_3$-$C_6$-cycloalkyl group, and a $C_1$-$C_6$-alkyl group in which one or two not directly adjacent carbon atoms are independently replaced by a heteroatom selected from —O— and —NH—;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)- group, a $C_2$-$C_6$-haloalkenyl group, a $C_1$-$C_6$-alkyl-O— group, a $C_1$-$C_4$-haloalkoxy group, a $C_1$-$C_6$-alkyl-O—($C_1$-$C_3$-alkylene)- group, a ($C_3$-$C_7$)-cycloalkyl group, a ($C_3$-$C_7$)-cycloalkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a $R^{18}$-(phenylene)-($C_1$-$C_3$-alkylene)-O—($C_1$-$C_3$-alkylene)- group, a $R^{18}$-(phenylene)-O—($C_1$-$C_3$-alkylene)- group, a $R^{18}$-(phenylene)-(heteroarylene)-O—($C_1$-$C_3$-alkylene)-group, a ($R^{18}$)-(heterocycloalkylene)-($C_1$-$C_3$-alkylene)- group, a ($R^{18}$)-(heterocycloalkylene)-(phenylene)-O—($C_1$-$C_3$-alkylene)- group, a (heterocycloalkenyl)-(phenylene)-O—($C_1$-$C_3$-alkylene)- group, a ($R^{18}$)-(heteroarylene)-($C_1$-$C_3$-alkylene)-O—($C_1$-$C_3$-alkylene)- group, a ($R^{18}$)-(heteroarylene)-(phenylene)-O—($C_1$-$C_3$-alkylene)- group, a ($R^{19}$)—$S(O)_2$-(phenylene)-O—($C_1$-$C_3$-alkylene)-group, a ($R^{19}$)—$S(O)_2$—NH-(phenylene)-O—($C_1$-$C_3$-alkylene)-group, a ($R^{19}$)—$S(O)_2$—NH-(phenylene)-O—($C_1$-$C_3$-alkylene)-group, a ($R^{19}$)—$S(O)_2$—N($C_1$-$C_6$-alkyl)-(phenylene)-O—($C_1$-$C_3$-alkylene)- group, a ($R^{19}$)—$S(O)_2$-(heterocycloalkylene)-(phenylene)-O—($C_1$-$C_3$-alkylene)- group, a ($R^{18}$)-(heterocycloalkylene)-(heteroarylene)-O—($C_1$-$C_3$-alkylene)- group, a ($R^{19}$)-(heteroarylene)-O—($C_1$-$C_3$-alkylene)- group, a ($R^{18}$)-(heteroarylene)-O—($C_1$-$C_3$-alkylene)- group, a ($R^{19}$)—$S(O)_2$-(heteroarylene)-O—($C_1$-$C_3$-alkylene)-group, a ($R^{19}$)—$S(O)_2$-(heterocycloalkylene)-(heteroarylene)-O—($C_1$-$C_3$-alkylene)- group, a $NR^{20}R^{21}$—($C_1$-$C_3$-alkylene)- group, a ($C_1$-$C_3$-alkyl)-NH—($C_1$-$C_3$-alkylene)- group, a ($C_1$-$C_3$-haloalkyl)-($C_1$-$C_3$-alkylene)-NH—($C_1$-$C_3$-alkylene)- group, a ($C_1$-$C_3$-haloalkyl)-NH—($C_1$-$C_3$-alkylene)- group, a ($C_1$-$C_3$-alkyl)-NH—C(O)—($C_1$-$C_3$-alkylene)- group, a ($C_1$-$C_3$-alkyl)-$NR^{15}$—C(O)—($C_1$-$C_3$-alkylene)- group, a ($C_1$-$C_3$-alkyl)-C(O)—NH—($C_1$-$C_3$-alkylene)- group, a ($C_1$-$C_3$-alkyl)-C(O)—$NR^{15}$—($C_1$-$C_3$-alkylene)- group, a

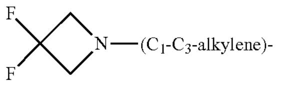

group and a

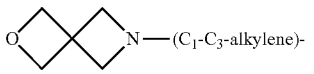

group, where the phenyl ring is unsubstituted or substituted with a halogen atom, a hydroxy group or a $C_1$-$C_3$-alkoxy group and the heterocycloalkyl group is unsubstituted or substituted with an oxo (=O) group or is unsubstituted or substituted with one or more substituents independently selected from a halogen atom, a hydroxy group, a $C_1$-$C_3$-alkyl group and a $C_1$-$C_3$-alkoxy group, or $R^8$ and $R^9$ together form a 5-membered or 6-membered ring optionally comprising one or two heteroatoms independently selected from —O— and —$NR^{14}$—;

$R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group;

$R^{14}$ is a hydrogen atom or a $C_1$-$C_3$-alkyl group;

$R^{15}$ is independently selected from a hydrogen atom, a $C_1$-$C_6$-alkyl group which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—$S(O)_2$-arylene-O— group, a ($R^{19}$)$S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group;

a $C_1$-$C_3$-alkylene-C(O)— group, a heterocycloalkyl-($C_1$-$C_3$-alkylene)-C(O)— group, a heterocycloalkyl-($C_1$-$C_3$-alkylene)-$S(O)_2$— group, a heterocyclyl-NH—C(O)— group, a heterocycloalkyl-($C_1$-$C_3$-alkylene)-NH—C(O)— group, an aryl-($C_1$-$C_3$-alkylene)-NH—C(O)— group which is unsubstituted or substituted with 1, 2, or 3 substituents independently selected from a halogen atom, a $C_1$-$C_3$-alkyl group and a $C_1$-$C_3$-alkoxy group;

a heterocycloalkyl-heteroarylene-$S(O)_2$— group, a phenyl group, a group

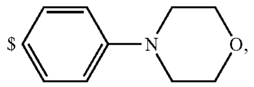

a group

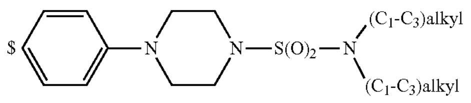

and a group

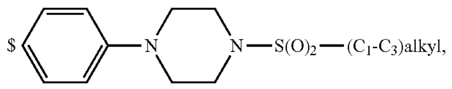

where $ is the point of attachment to the nitrogen atom, to which $R^{15}$ is attached;

or $R^{15}$ and $R^{22}$ together, including the atoms to which they are attached, may form a 5-membered or 6-membered ring, both optionally comprising one or two additional heteroatoms independently selected from —O— and —$NR^{14}$—;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(═O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a NR$^{20}$R$^{21}$ group;

$R^{20}$ and $R^{21}$ are each independently selected from a hydrogen atom and a $C_1$-$C_6$-alkyl group;

$R^{22}$ is independently selected from a halogen atom, a $C_1$-$C_6$-alkyl group which is unsubstituted or substituted with one or more substituents selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a (R$^{18}$)-(heterocycloalkylene)-(arylene)-O— group, a (heterocycloalkyl)-(arylene)-O— group, an aryl-O— group, an aryl-($C_1$-$C_3$-alkylene)-O— group, a (R$^{19}$)—S(O)$_2$-arylene-O— group, a (R$^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group;

a $C_1$-$C_3$-alkyl-C(O)— group, a $C_3$-$C_6$-cycloalkyl group, an aryl group, a heterocycloalkyl group, and a heteroaryl group;

whereby any heterocycloalkyl group of $R^{22}$ may optionally be itself further substituted with a $C_1$-$C_3$-alkyl group or one or two halogen atoms;

$R^{23}$ is independently selected from a hydrogen atom, a halogen atom, a hydroxy group, a $C_1$-$C_6$-alkyl group and a $C_1$-$C_6$-haloalkyl group, or $R^{22}$ and $R^{23}$ together with the carbon atom to which they are attached form a 3-membered to 6-membered carbocyclic ring or a 3-membered to 6-membered heterocyclic ring comprising one or two heteroatoms selected from nitrogen, oxygen and sulfur;

or a tautomer, an N-oxide, or a salt thereof, or a salt of a tautomer, or a salt of an N-oxide, or a mixture of same.

DETAILED DESCRIPTION

Definitions

Figure 1:
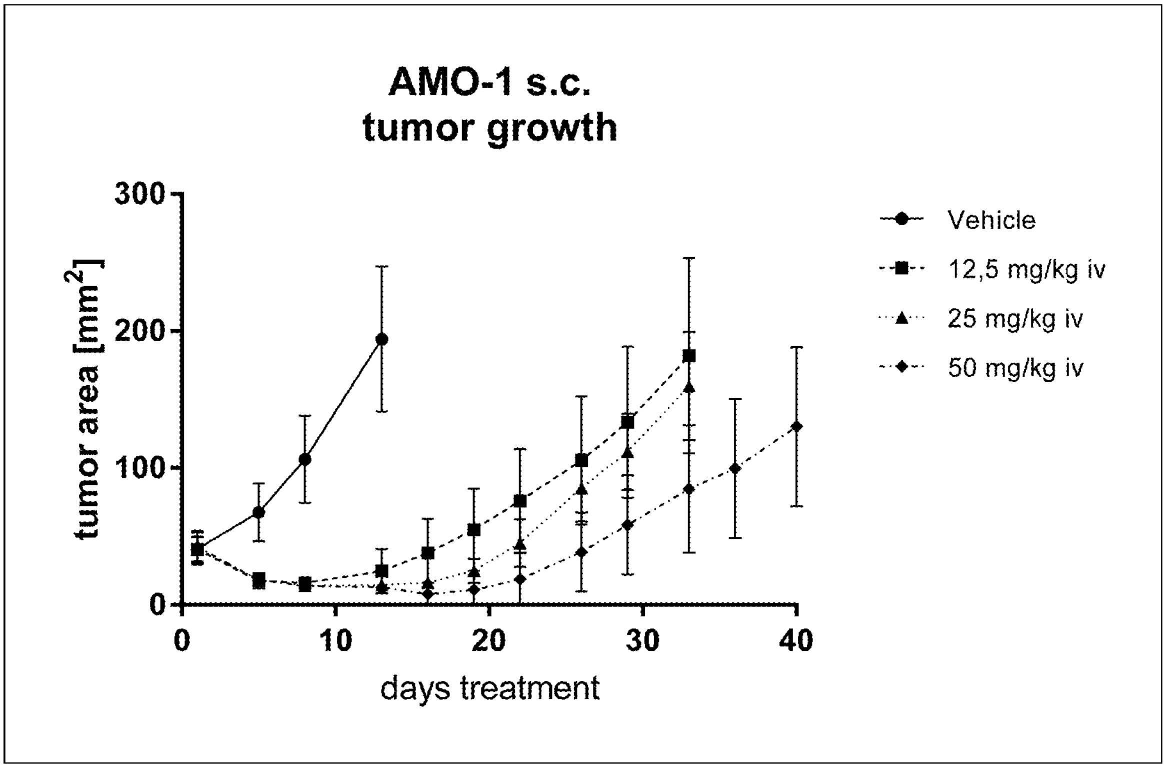
FIG. 1 shows a comparison of tumor growth of AMO-1 multiple myeloma cells growing subcutaneously in immunocompromised mice with untreated animals (Vehicle) and groups treated with different concentration of the compound example 47 (n=10 animals/group).

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, particularly with one, two or three substituents.

The terms "oxo", "an oxo group" or "an oxo substituent" mean a doubly attached oxygen atom ═O. Oxo may be attached to atoms of suitable valency, for example to a saturated carbon atom or to a sulfur atom. For example, but without limitation, one oxo group can be attached to a carbon atom, resulting in the formation of a carbonyl group C(═O), or two oxo groups can be attached to one sulfur atom, resulting in the formation of a sulfonyl group —S(═O)$_2$.

The term "ring substituent" means a substituent attached to an aromatic or nonaromatic ring which replaces an available hydrogen atom on the ring.

Should a composite substituent be composed of more than one part, e.g., ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of.

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings:

The term "halogen atom" means a fluorine, chlorine, bromine or iodine atom, particularly a fluorine, chlorine or bromine atom.

The term "$C_1$-$C_8$-alkyl-" means a linear or branched, saturated hydrocarbon group having 1, 2, 3, 4, 5, 6, 7 or 8 carbon atoms, e.g., a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-, n-heptyl-, 5-methylhexyl-, 4-methylhexyl-, 2-methylhexyl-, 1-methylhexyl-, 2-ethylpentyl-, 1-ethylpentyl-, 3,3-dimethylpentyl-, 2,2-dimethylpentyl-, 1,1-dimethylpentyl-, 2,3-dimethylpentyl-, 1,3-dimethylpentyl-, 1,2-dimethylpentyl-, n-octyl-, 6-methylheptyl-, 4-methylheptyl-, 2-methylheptyl-, 1-methylheptyl-, 2-ethylhexyl-, 1-ethylhexyl-, 3,3-dimethylhexyl-, 2,2-dimethylhexyl-, 1,1-dimethylhexyl-, 2,3-dimethylhexyl-, 1,3-dimethylhexyl-, 1,2-dimethylhexyl- group, or an isomer thereof. Preferably, said group has 1, 2, 3, 4, 5 or 6 carbon atoms ("$C_1$-$C_6$-alkyl-"), e.g., a methyl-, ethyl-, n-propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl- or 1,2-dimethylbutyl group, or an isomer thereof. More preferably, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or tert-butyl- group, 1, 2 or 3 carbon atoms ("$C_1$-$C_3$-alkyl-"), e.g., a methyl-, ethyl-, n-propyl- or iso-propyl group, or 1 or 2 carbon atoms ("$C_1$-$C_2$-alkyl-"), e.g., a methyl group, an ethyl group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_2$-$C_6$-alkylene" means a linear or branched, saturated, divalent hydrocarbon chain (or "tether") having 2, 3, 4, 5 or 6 carbon atoms, e.g., $—CH_2—CH_2—$ ("ethylene" or "$C_2$-alkylene"), $—CH_2—CH_2—CH_2—$, $—C(H)(CH_3)—CH_2—$ or $—C(CH_3)_2—$ ("propylene" or "$C_3$-alkylene"), or, for example $—CH_2—C(H)(CH_3)—CH_2—$, $—CH_2—C(CH_3)_2—$, $—CH_2—CH_2—CH_2—CH_2—$ ("butylene" or "$C_4$-alkylene"), "$C_5$-alkylene", e.g., $—CH_2—CH_2—CH_2—CH_2—CH_2—$ ("n-pentylene"), or "$—C_6$-alkylene-", e.g., $—CH_2—CH_2—CH_2—CH_2—CH_2—CH_2—$ ("n-hexylene") or a $—C(CH_3)_2—C(CH_3)_2$ group.

The term "hydroxy-($C_1$-$C_6$-alkyl)-" means a linear or branched, saturated, hydrocarbon group in which one or more hydrogen atoms of a "$C_1$-$C_6$-alkyl-" as defined supra are each replaced by a hydroxy group, e.g., a hydroxymethyl-, 1-hydroxyethyl-, 2-hydroxyethyl-, 1,2-dihydroxyethyl-, 3-hydroxypropyl-, 2-hydroxypropyl-, 2,3-dihydroxypropyl-, 1,3-dihydroxypropan-2-yl-, 3-hydroxy-2-methyl-propyl-, 2-hydroxy-2-methyl-propyl-, or a 1-hydroxy-2-methyl-propyl- group. Particularly the hydroxyalkyl group means a linear or branched, saturated, monovalent hydrocarbon group has 1, 2 or 3 carbon atoms in which 1 hydrogen atom is replaced with a hydroxy group e.g. a hydroxymethyl-, 1-hydroxyethyl-, 2-hydroxyethyl-, 3-hydroxypropyl-, 2-hydroxypropyl-, 1-hydroxypropyl-, 2-hydroxy-2-methyl-ethyl group.

The term "$C_1$-$C_6$-haloalkyl" means a linear or branched, saturated, monovalent hydrocarbon group in which the term "$C_1$-$C_6$-alkyl" is as defined supra and in which one or more of the hydrogen atoms are replaced, identically or differently, with a halogen atom. Preferably, said halogen atom is a fluorine atom. Said $C_1$-$C_6$-haloalkyl, particularly a $C_1$-$C_3$-haloalkyl group is, for example, fluoromethyl-, difluoromethyl-, trifluoromethyl-, 2-fluoroethyl-, 2,2-difluoroethyl-, 2,2,2-trifluoroethyl-, pentafluoroethyl-, 3,3,3-trifluoropropyl- or a 1,3-difluoropropan-2-yl group.

The term "$C_1$-$C_6$-alkoxy" means a linear or branched, saturated, monovalent group of formula ($C_1$-$C_6$-alkyl)-O—, in which the term "$C_1$-$C_6$-alkyl" group is as defined supra, e.g. methoxy-, ethoxy-, n-propoxy-, isopropoxy-, n-butoxy-, sec-butoxy-, isobutoxy-, tert-butoxy-, pentyloxy-, isopentyloxy- or a n-hexyloxy group, or an isomer thereof.

The term "$C_1$-$C_6$-alkylthio" or "$C_1$-$C_6$-thioalkyl" means a linear or branched, saturated, monovalent group of formula ($C_1$-$C_6$-alkyl)-S—, in which the term "$C_1$-$C_6$-alkyl" is as defined supra, e.g. methylthio-, ethylthio-, n-propylthio-, isopropylthio-, n-butylthio-, sec-butylthio-, isobutylthio-, tert-butylthio-, pentylthio-, isopentylthio- or a n-hexylthio group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Preferably, said halogen atom in "$C_1$-$C_6$-haloalkoxy-" is fluorine, resulting in a group referred to herein as "$C_1$-$C_6$-fluoroalkoxy-". Representative $C_1$-$C_6$-fluoroalkoxy groups include, for example, $—OCF_3$, $—OCHF_2$, $—OCH_2F$, $—OCF_2CF_3$ and $—OCH_2CF_3$.

The term "$C_1$-$C_6$-haloalkylthio" or "$C_1$-$C_6$-halothioalkyl" or "$C_1$-$C_6$-haloalkyl-S—" means a linear or branched, saturated, monovalent $C_1$-$C_6$-alkylthio group, as defined supra, in which one or more of the hydrogen atoms is replaced, identically or differently, with a halogen atom. Preferably, said halogen atom in "$C_1$-$C_6$-haloalkylthio-" is fluorine.

The term "$C_2$-$C_6$-alkenyl-" means a linear or branched, monovalent hydrocarbon group, which contains one or more double bonds and which has 2, 3, 4, 5 or 6 carbon atoms, preferably 2, 3 or 4 carbon atoms ("$C_2$-$C_4$-alkenyl-") or 2 or 3 carbon atoms ("$C_2$-$C_3$-alkenyl-"), it being understood that in the case in which said alkenyl- group contains more than one double bond, then said double bonds may be isolated from, or conjugated with, each other. Representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and a 1-(1,1-dimethylethyl-)ethenyl group. Particularly, said group is a ethenyl- or prop-2-enyl group.

The same definitions can be applied should the alkenyl group be placed within a chain as a bivalent "$C_1$-$C_6$-alkenylene" moiety. All names as mentioned above then will bear a "ene" added to their end, thus e.g., a "pentenyl" becomes a bivalent "pentenylene" group.

The term "$C_2$-$C_6$-haloalkenyl-" means a linear or branched hydrocarbon group in which one or more of the hydrogen atoms of a "$C_2$-$C_6$-alkenyl-" as defined supra are each replaced, identically or differently, by a halogen atom. Preferably, said halogen atom is fluorine, resulting in a group referred herein as "$C_2$-$C_6$-fluoroalkenyl-". Representative $C_2$-$C_6$-fluoroalkenyl- groups include, for example, $-CH{=}CF_2$, $-CF{=}CH_2$, $-CF{=}CF_2$, $-C(CH_3){=}CF_2$, $-CH{=}C(F)-CH_3$, $-CH_2-CF{=}CF_2$ and $-CF_2-CH{=}CH_2$.

The term "$C_2$-$C_6$-alkynyl-" means a linear or branched, monovalent hydrocarbon group which contains one or more triple bonds and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl- groups include, for example, an ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and 3,3-dimethylbut-1-ynyl- group. Particularly, said alkynyl- group is ethynyl-, prop-1-ynyl- or prop-2-ynyl group.

The term "$C_3$-$C_{10}$-cycloalkyl-" means a saturated monocyclic or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl- group may be, for example, a monocyclic hydrocarbon ring, e.g., cyclopropyl-, cyclobutyl-, cyclopentyl-, cyclohexyl- or cycloheptyl-, or a bicyclic hydrocarbon ring, such as decalinyl-. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl- group, or said hydrocarbon ring is monocyclic and contains 3, 4, 5 or 6 carbon atoms ("$C_3$-$C_6$-cycloalkyl-"), e.g., a cyclopropyl-, cyclobutyl-, cyclopentyl- or cyclohexyl group. A cycloalkyl group may be optionally substituted as defined at the respective part wherein such term is used.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., cyclobutenyl-, cyclopentenyl-, cyclohexenyl-, cycloheptenyl- or a cyclooctenyl group, or a bicyclic hydrocarbon ring, e.g., a bicyclo[2.2.1]hept-2-enyl- or a bicyclo[2.2.2]oct-2-enyl group.

The term "4- to 10-membered heterocycloalkyl-" means a saturated mono- or bicyclic hydrocarbon ring which contains 3, 4, 5, 6, 7, 8 or 9 carbon atoms and which contains 1, 2, 3 or 4 heteroatoms which may be identical or different, said heteroatoms preferably selected from oxygen, nitrogen or sulfur and wherein carbon atoms and heteroatoms add up to 4, 5, 6, 7, 8, 9 or 10 ring atoms in total, it being possible for said heterocycloalkyl- group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, said "4- to 10-membered heterocycloalkyl-" group is monocyclic and contains 3, 4, 5 or 6 carbon atoms and one or two of the above-mentioned heteroatoms, adding up to 4, 5, 6 or 7 ring atoms in total (a "4- to 7-membered monocyclic heterocycloalkyl-"), or contains 3, 4 or 5 carbon atoms and one or two of the above-mentioned heteroatoms, adding up to 4, 5 or 6 ring atoms in total (a "4- to 6-membered monocyclic heterocycloalkyl-"), or contains 3, 4 or 5 carbon atoms and one or two of the above-mentioned heteroatoms, adding up to 5 or 6 ring atoms in total (a "5- to 6-membered monocyclic heterocycloalkyl-"); it being possible for said heterocycloalkyl- group to be attached to the rest of the molecule via any one of the carbon atoms or the nitrogen atoms, if present.

Exemplarily, without being limited thereto, said "4- to 7-membered monocyclic heterocycloalkyl-", can be a 4-membered ring, a "4-membered heterocycloalkyl-" group, such as azetidinyl- or an oxetanyl group; or a 5-membered ring, a "5-membered heterocycloalkyl-" group, such as a tetrahydrofuranyl-, dioxolinyl-, pyrrolidinyl-, imidazolidinyl-, pyrazolidinyl- or a pyrrolinyl group; or a 6-membered ring, a "6-membered heterocycloalkyl-" group, such as a tetrahydropyranyl-, piperidinyl-, morpholinyl-, 3-oxomorpholin-4-yl, dithianyl-, thiomorpholinyl- or a piperazinyl group; or a 7-membered ring, a "7-membered heterocycloalkyl-" group, such as an azepanyl-, diazepanyl- or an oxazepanyl group, for example. The heterocycloalkyl groups may be one or more times substituted with $C_1$-$C_3$-alkyl, $C_1$-$C_3$-alkoxy, hydroxy, halogen or a carbonyl group.

The term "5- to 7-membered heterocycloalkenyl" means a monocyclic, unsaturated, nonaromatic heterocycle with 5, 6, or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, a 4H-pyranyl-, 3,6-dihydro-2H-pyran-4-yl-, 2H-pyranyl-, dihydropyridinyl-, tetrahydropyridinyl-, 2-oxopyridin-1(2H)-yl-, 2,5-dihydro-1H-pyrrolyl-, [1,3]dioxolyl-, 4H-[1,3,4]thiadiazinyl-, 2,5-dihydrofuranyl-, 2,3-dihydrofuranyl-, 2,5-dihydrothiophenyl-, 2,3-dihydrothiophenyl-, 4,5-dihydrooxazolyl- or a 4H-[1,4]thiazinyl group. Those heterocycloalkenyl groups may be substituted with a hydroxy group or a methoxy group.

The term "fused heterocycloalkyl" or "heterobicycloalkyl-" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl or "heterobicycloalkyl-" group is, for example, a azabicyclo[3.3.0]octyl-, azabicyclo[4.3.0]nonyl-, diazabicyclo[4.3.0]nonyl-, oxazabicyclo[4.3.0]nonyl-, thiazabicyclo[4.3.0]nonyl- or a azabicyclo[4.4.0]decyl group.

The term "aryl" means a phenyl-, naphthyl-, 5,6-dihydronaphthyl-, 7,8-dihydronaphthyl-, 5,6,7,8-tetrahydronaphthyl-, an indanyl-, or an indenyl group, which is unsubstituted or substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, particularly halogen, $C_1$-$C_3$-alkyl, $C_1$-$C_3$-haloalkyl, $C_1$-$C_3$-alkoxy, and $C_1$-$C_3$-haloalkoxy.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms and which contains 1, 2, 3 or 4 heteroatoms which may be identical or different, said heteroatoms being selected from oxygen, nitrogen and sulfur. Said heteroaryl-group can be a 5-membered heteroaryl group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or a tetrazolyl group; or a 6-membered heteroaryl group, such as, for example, a pyridyl-, pyridazinyl-, pyrimidyl-, pyrazinyl- or a triazinyl group; or a benzo-fused 5-membered heteroaryl- group, such as, for example, a benzofuranyl-, benzothienyl-, benzoxazolyl-, benzisoxazolyl-, benzimidazolyl-, benzothiazolyl-, benzotriazolyl-, indazolyl-, indolyl- or a isoindolyl group; or a benzo-fused 6-membered heteroaryl group, such as, for example, a quinolinyl-, quinazolinyl-, isoquinolinyl-, cinnolinyl-, phthalazinyl- or quinoxalinyl-; or another bicyclic group, such as, for example, indolizinyl-, purinyl- or a pteridinyl group; or a tricyclic heteroaryl- group, such as, for example, a carbazolyl-, acridinyl- or a phenazinyl group Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur ("5- to 6-membered monocyclic heteroaryl-"), such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or a triazinyl group.

In general and unless otherwise mentioned, said heteroaryl- groups include all the possible isomeric forms thereof, e.g., the positional isomers thereof. Thus, for some illustrative non-restricting examples, the term pyridyl- includes pyridin-2-yl-, pyridin-3-yl- and pyridin-4-yl-; the term thienyl- includes thien-2-yl- and thien-3-yl-. Furthermore, said heteroaryl- groups can be attached to the rest of the molecule via any one of the carbon atoms, or, if applicable, a nitrogen atom, e.g., pyrrol-1-yl-, pyrazol-1-yl- or imidazol-1-yl-.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl- includes pyridin-2-yl-, pyridin-3-yl- and pyridin-4-yl-; or the term thienyl- includes thien-2-yl- and thien-3-yl-.

Particularly, the heteroaryl group is a pyridyl group or pyrimidyl group or an imidazolyl group, including a hydroxy substitution of the pyridyl group leading e.g. to a 2-hydroxy-pyridyl group which is the tautomeric form to a 2-oxo-2(1H)-pyridyl group.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$, preferably $C_1$-$C_2$, $C_1$-$C_3$, $C_1$-$C_4$, $C_1$-$C_5$, $C_1$-$C_6$, more preferably $C_1$-$C_4$; in the case of "$C_1$-$C_6$-haloalkyl-" or "$C_1$-$C_6$-haloalkoxy-" even more preferably $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_4$, $C_2$-$C_5$, preferably $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl- group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

As used herein, the term "leaving group" refers to an atom or a group of atoms that is displaced in a chemical reaction as stable species taking with it the bonding electrons, e.g., typically forming an anion. Preferably, a leaving group is selected from the group comprising: halo, in particular a chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl)sulfonyl]oxy-, [(4-isopropylphenyl)sulfonyl]oxy-, [(2,4,6-triisopropylphenyl)sulfonyl]oxy-, [(2,4,6-trimethylphenyl)sulfonyl]oxy-, [(4-tert-butylphenyl)sulfonyl]oxy-, (phenylsulfonyl)oxy- and a [(4-methoxyphenyl)sulfonyl]oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T. W. Greene and P. G. M. Wuts in *Protective Groups in Organic Synthesis,* 4th edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc. and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

It is possible for the compounds of general formula (I) to exist as isotopic variants. The invention therefore includes one or more isotopic variant(s) of the compounds of general formula (I), particularly deuterium-containing compounds of general formula (I).

The invention also includes all suitable isotopic variations of a compound of the invention.

The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

An isotopic variation of a compound of the invention is defined as one in which at least one atom is replaced by an atom having the same atomic number but an atomic mass different from the atomic mass usually or predominantly found in nature.

Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Accordingly, recitation of "hydrogen" or "H" should be understood to encompass $^{1}H$ (protium), $^{2}H$ (deuterium) and $^{3}H$ (tritium) unless otherwise specified. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful, e.g., in drug and/or substrate tissue distribution studies. These isotopes are particularly preferred for the ease of their incorporation and detectability. Positron-emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g., cytochrome $P_{450}$.

For example, in some embodiments, the present invention concerns a deuterium-containing compound of general formula (I), e.g.:

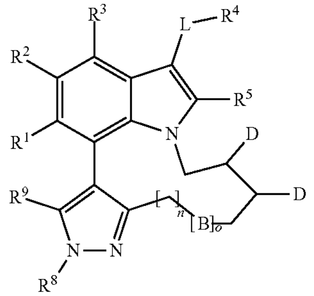

or

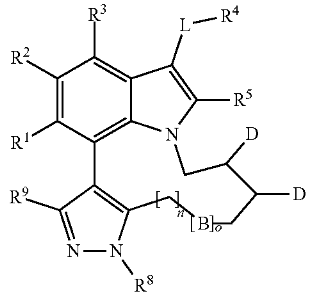

or

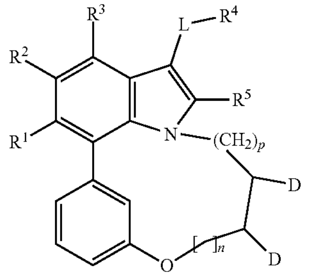

Such deuterium-containing compounds can be prepared by methods well-known to the person skilled in the art. Particularly, such deuterium-containing compounds can be prepared from the corresponding olefins, which are available by methods known to the person skilled in the art, such as ring closing metathesis reactions, as discussed e.g., in the general description of the synthesis of compounds of general formula (I), infra, in the context of Schemes 2c and 2j, respectively.

Where the plural form of the word compounds, salts, polymorphs, hydrates, solvates and the like, is used herein, this is taken to mean also a single compound, salt, polymorph, isomer, hydrate, solvate or the like. The terms "a" or "an," as used in herein means one or more.

By "stable compound' or "stable structure" is meant a compound that is sufficiently robust to survive isolation to a useful degree of purity from a reaction mixture and formulation into an efficacious therapeutic agent.

Compounds of the present invention, as well as the corresponding macrocyclic intermediates of formula (II), are typically chiral merely as a result of restricted rotation around at least one single bond, which is due to limited conformational flexibility of their macrocyclic core as a whole or even of open chain precursors. Hence, compounds of the present invention as well as the corresponding macrocyclic intermediates such as e.g. of formula (II), can exist as atropisomers. In the specific situation of the embodiments claimed and disclosed herein having a group $CR^{22}R^{23}$ present in the compounds of formula (I) as well as in various intermediates the atropisomerism may occur at different stages of synthesis as soon as both $R^{22}$ and $R^{23}$ do have different meanings and are present in its claimed form or as suitable precursors e.g. already upon Suzuki coupling of starting materials of formulae (VII) and (VI) to give intermediates of formula (V). Atropisomers represent a subclass of conformers which arise from restricted rotation around a single bond. The conformers (called atropisomers) can be isolated as separated species (IUPAC Gold book, http://goldbook.iupac.org/A00511.html; *Pure and Appl. Chem.*, 2009, 68, 2193-2222). This induced chirality belongs to the axial type of chirality. The compounds of the present invention as well as the corresponding macrocyclic intermediates of formula (II), furthermore optionally contain one or more asymmetric centers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers. Hence, compounds of the present invention, as well as the corresponding macrocyclic intermediates of formula (II), featuring the abovementioned atropisomerism and an additional asymmetric centre can also exist as diasteromeric mixtures as described supra.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one isomer (enantiomer) displays the desired biological activity and the second isomer (enantiomer) is inactive, the preferred isomer is the one which produces the more desirable biological activity. Should one isomer (enantiomer/diastereomer) display better activity than the other isomer (enantiomer/diastreromer) the preferred isomer is the one which produces the better biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel O D and Chiracel O J, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

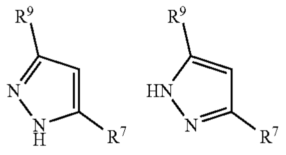

1H tautomer 2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

An embodiment of the invention are the compounds of formula (I) and a tautomer, an N-oxide, or a salt thereof, or a salt of a tautomer, or a salt of an N-oxide, or a mixture of same.

Another embodiment of the invention are the compounds of formula (I) and a tautomer, or a salt thereof, or a salt of a tautomer, or a mixture of same.

Another embodiment of the invention are the compounds of formula (I) and a salt thereof, more specifically an amine salt, or an organic acid salt, more particularly a diethylamine salt, an acetic acid salt or a citric acid salt.

The present invention also includes useful forms of the compounds of the present invention, such as metabolites, hydrates, solvates, prodrugs and salts, in particular pharmaceutically acceptable salts and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemihydrate, (semihydrate), monohydrate, sesquihydrate, dihydrate, trihydrate, tetrahydrate, pentahydrate etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19. It includes any physiologically acceptable salt as referred to below.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, and nitric acid or with an organic acid, such as formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)-benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonate acid, itaconic acid, sulfamic acid, trifluoromethanesulfonic acid, dodecylsulfuric acid, ethansulfonic acid, benzenesulfonic acid, para-toluenesulfonic acid, methansulfonic acid, 2-naphthalenesulfonic acid, naphthalenedisulfonic acid, camphorsulfonic acid acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid and thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl) aminomethane, aminopropanediol, Sovak base and 1-amino-2,3,4-butanetriol.

Additionally, the compounds according to the invention may form salts with a quaternary ammonium ion obtainable, e.g., by quaternisation of a basic nitrogen-containing group with agents such as lower alkylhalides, such as alkylchlorides, e.g. methylchloride, ethylchloride, propylchloride and butylchloride; such as alkylbromides, e.g. methylbromide, ethylbromide, propylbromide and butylbromide; and such as alkyliodides; e.g. methyliodide, ethyliodide, propyliodide and butyliodide; dialkylsulfates such as dimethylsulfate, diethylsulfate, dibutylsulfate and diamylsulfates, long chain halides such as e.g. decylchloride, laurylchloride, myristylchloride and stearylchloride, decylbromide, laurylbromide, myristylbromide and stearylbromide, decyliodide, lauryliodide, myristyliodide and stearyliodide, aralkylhalides such as benzylchloride, benzylbromide, benzyliodide and phenethylbromides and others. Examples of suitable quaternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Unless specified otherwise, suffixes to chemical names or structural formulae relating to salts, such as "hydrochloride", "trifluoroacetate", "sodium salt", or "× HCl", "× $CF_3COOH$", "× $Na^+$", for example, mean a salt form, the stoichiometry of which salt form not being specified.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as a single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. For example, a prodrug may be in the form of an in vivo hydrolysable ester of the specified compound. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

DESCRIPTION

In accordance with a first aspect, the present invention provides compounds of formula (I)

(I)

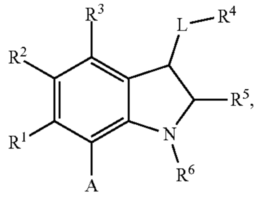

wherein

A is (A1)

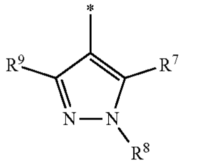

or (A2)

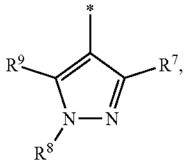

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

or

A is (A3)

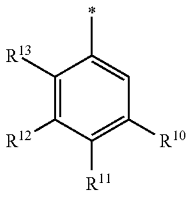

wherein optionally one or two of the groups selected from $CR^{11}$, $CR^{12}$ and $CR^{13}$ are replaced by a nitrogen atom, wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —$S(O)_2$—($C_1$-$C_3$-alkyl) group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —$S(O)_2$— group and a —$NR^{14}$— group;

E is a bond, an oxygen atom, a sulfur atom, a —S(O)— group, a —$S(O)_2$— group or a —$NR^{14}$— group and constitutes the connecting element to $R^4$;

m is 2, 3, or 4;

$R^5$ is selected from a COOH group, a

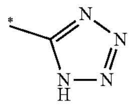 [SMILES: *c1nnn[nH]1]

group, a —C(O)—$NHS(O)_2$($C_1$-$C_6$-alkyl) group, a —C(O)—$NHS(O)_2$($C_3$-$C_6$-cycloalkyl) group, a —C(O)—$NHS(O)_2$(aryl) group, a —C(O)—$NHS(O)_2(CH_2)_s$NHCO($C_1$-$C_6$-alkyl) group, a —C(O)—$NHS(O)_2(CH_2)_s$NHCO($C_3$-$C_6$-cycloalkyl) group and a —C(O)—$NHS(O)_2(CH_2)_s$NHCO(aryl) group;

s is 0, 1 or 2;

—$R^6$-$R^7$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

—$R^6$-$R^{10}$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, where one or more —$CH_2$— groups are substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein # is the point of attachment with the indole nitrogen atom and ## is the point of attachment with the carbon atom of the phenyl moiety bearing the $R^{10}$ substituent;

n is 2, 3, 4, 5, 6, 7, 8, or 9, if B is selected from —O—, —S—, —S(O)—, —$S(O)_2$— and —N($R^{15}$)—, and n is 1, 2, 3, 4, 5, 6, 7 or 8, if B is selected from a —C(O)$NR^{15}$— group and a —$NR^{15}$C(O)— group, and n is 0, 1, 2, 3, 4, 5, 6 or 7, if B is selected from a —N($R^{15}$)—C(=O)—N($R^{15}$)— group, a —O—C(=O)—N($R^{15}$)— group and a —N($R^{15}$)—C(=O)—O— group;

t is 1;

where the integers selected for variables n and t, together with the methylene group $CR^{22}R^{23}$ and the other non-variable atoms of the pyrazole and the indole moiety result in forming a 9- to 16-membered ring independently from the selection of variable A1, A2 or A3;

B is independently selected from a —C(O)$NR^{15}$— group, a —$NR^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)— and —$S(O)_2$—;

$R^8$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group;

a $C_1$-$C_3$-haloalkyl group, a $C_3$-$C_6$-cycloalkyl group, and a $C_1$-$C_6$-alkyl group in which one or two not directly adjacent carbon atoms are independently replaced by a heteroatom selected from —O— and —NH—;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group, a $C_2$-$C_6$-haloalkenyl group, a $C_1$-$C_6$-alkyl-O— group, a $C_1$-$C_4$-haloalkoxy group, a $C_1$-$C_6$-alkyl-O—($C_1$-$C_3$-alkylene)- group, a ($C_3$-$C_7$)-cycloalkyl group, a ($C_3$-$C_7$)-cycloalkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a $R^{18}$-(phenylene)-($C_1$-$C_3$-alkylene)-O—($C_1$-$C_3$-alkylene)- group, a $R^{18}$-(phenylene)-O—($C_1$-$C_3$-alkylene)- group, a $R^{18}$-(phenylene)-(heteroarylene)-O—($C_1$-$C_3$-alkylene)-group, a ($R^{18}$)-(heterocycloalkylene)-($C_1$-$C_3$-alkylene)- group, a ($R^{18}$)-(heterocycloalkylene)-(phenylene)-O—($C_1$-$C_3$-alkylene)- group, a (heterocycloalkenyl)-(phenylene)-O—($C_1$-$C_3$-alkylene)- group, a ($R^{18}$)-(heteroarylene)-($C_1$-$C_3$-alkylene)-O—($C_1$-$C_3$-alkylene)- group, a ($R^{18}$)-(heteroarylene)-(phenylene)-O—($C_1$-$C_3$-alkylene)- group, a ($R^{19}$)—$S(O)_2$-(phenylene)-O—($C_1$-$C_3$-alkylene)-group, a ($R^{19}$)—$S(O)_2$—NH-(phenylene)-O—($C_1$-$C_3$-alkylene)-group, a ($R^{18}$)—$S(O)_2$—NH-(phenylene)-O—($C_1$-$C_3$-alkylene)-group, a ($R^{19}$)—$S(O)_2$—N($C_1$-$C_6$-alkyl)-(phenylene)-O—($C_1$-$C_3$-alkylene)- group, a ($R^{19}$)—$S(O)_2$-(heterocycloalkylene)-(phenylene)-O—($C_1$-$C_3$-alkylene)- group, a ($R^{18}$)-(heterocycloalkylene)-(heteroarylene)-O—($C_1$-$C_3$-alkylene)- group, a ($R^{19}$)-(heteroarylene)-O—($C_1$-$C_3$-alkylene)- group, a ($R^{18}$)-(heteroarylene)-O—($C_1$-$C_3$-alkylene)- group, a ($R^{19}$)—$S(O)_2$-(heteroarylene)-O—($C_1$-$C_3$-alkylene)-group, a ($R^{19}$)—$S(O)_2$-(heterocycloalkylene)-(heteroarylene)-O—($C_1$-$C_3$-alkylene)- group, a $NR^{20}R^{21}$—($C_1$-$C_3$-alkylene)- group, a ($C_1$-$C_3$-alkyl)-NH—($C_1$-$C_3$-alkylene)- group, a ($C_1$-$C_3$-haloalkyl)-($C_1$-$C_3$-alkylene)-NH—($C_1$-$C_3$-alkylene)- group, a ($C_1$-$C_3$-haloalkyl)-NH—($C_1$-$C_3$-alkylene)- group, a ($C_1$-$C_3$-alkyl)-NH—C(O)—($C_1$-$C_3$-alkylene)- group, a ($C_1$-$C_3$-alkyl)-$NR^{15}$—C(O)—($C_1$-$C_3$-alkylene)- group, a ($C_1$-$C_3$-alkyl)-C(O)—NH—($C_1$-$C_3$-alkylene)- group, a ($C_1$-$C_3$-alkyl)-C(O)—$NR^{15}$—($C_1$-$C_3$-alkylene)- group, a

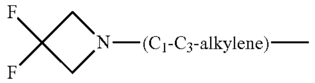

group and a

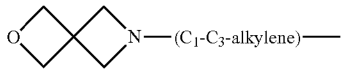

group, where the phenyl ring is unsubstituted or substituted with a halogen atom, a hydroxy group or a $C_1$-$C_3$-alkoxy group and the heterocycloalkyl group is unsubstituted or substituted with an oxo (=O) group or is unsubstituted or substituted with one or more substituents independently selected from a halogen atom, a hydroxy group, a $C_1$-$C_3$-alkyl group and a $C_1$-$C_3$-alkoxy group, or $R^8$ and $R^9$ together form a 5-membered or 6-membered ring optionally comprising one or two heteroatoms independently selected from —O— and —$NR^{14}$—;

$R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group;

$R^{14}$ is a hydrogen atom or a $C_1$-$C_3$-alkyl group;

$R^{15}$ is independently selected from a hydrogen atom, a $C_1$-$C_6$-alkyl group which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group;

a $C_1$-$C_3$-alkylene-C(O)— group, a heterocycloalkyl-($C_1$-$C_3$-alkylene)-C(O)— group, a heterocycloalkyl-($C_1$-$C_3$-alkylene)-S(O)$_2$— group, a heterocyclyl-NH—C(O)— group, a heterocycloalkyl-($C_1$-$C_3$-alkylene)-NH—C(O)— group, an aryl-($C_1$-$C_3$-alkylene)-NH—C(O)— group, which is unsubstituted or substituted with 1, 2, or 3 substituents independently selected from a halogen atom, a $C_1$-$C_3$-alkyl group and a $C_1$-$C_3$-alkoxy group;

a heterocycloalkyl-heteroarylene-S(O)$_2$— group, a phenyl group, a group

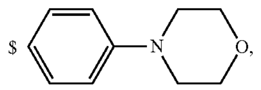

a group

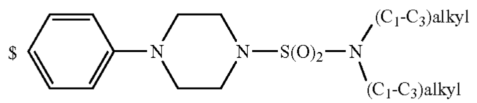

and a group

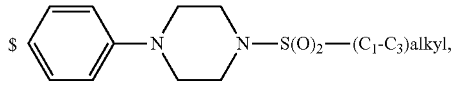

where $ is the point of attachment to the nitrogen atom, to which $R^{15}$ is attached;

or $R^{15}$ and $R^{22}$ together, including the atoms to which they are attached, may form a 5-membered or 6-membered ring, both optionally comprising one or two additional heteroatoms independently selected from —O— and —$NR^{14}$—;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a N$R^{20}R^{21}$ group; and $R^{20}$ and $R^{21}$ are each independently selected from a hydrogen atom and a $C_1$-$C_6$-alkyl group;

$R^{22}$ is independently selected from, a halogen atom, a $C_1$-$C_6$-alkyl group which is unsubstituted or substituted with one or more substituents selected from a halogen atom, a hydroxy group, a N$R^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group;

a $C_1$-$C_3$-alkyl-C(O)— group, a $C_3$-$C_6$-cycloalkyl group, an aryl group, a heterocycloalkyl group, and a heteroaryl group;

whereby any heterocycloalkyl group of $R^{22}$ may optionally be itself further substituted with a $C_1$-$C_3$-alkyl group or one or two halogen atoms;

$R^{23}$ is independently selected from a hydrogen atom, a halogen atom, a hydroxy group, a $C_1$-$C_6$-alkyl group and a $C_1$-$C_6$-haloalkyl group, or $R^{22}$ and $R^{23}$ together with the carbon atom to which they are attached form a 3-membered to 6-membered carbocyclic ring or a 3-membered to 6-membered heterocyclic ring comprising one or two heteroatoms selected from nitrogen, oxygen and sulfur;

or a tautomer, an N-oxide, or a salt thereof, or a salt of a tautomer, or a salt of an N-oxide, or a mixture of same.

FURTHER EMBODIMENTS OF THE FIRST ASPECT OF THE PRESENT INVENTION

In accordance with a further aspect, the present invention provides compounds of general formula (I): wherein A is (A1)

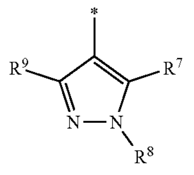

or (A2)

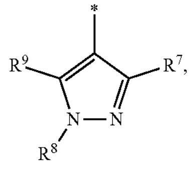

wherein $R^6$ and $R^7$, together with two carbon atoms of the pyrazole ring, two carbon atoms of the indole moiety and the nitrogen atom to which $R^6$ is attached, form a 9-membered to 13-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group $—(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group;

E is a bond, an oxygen atom, a sulfur atom, or a $—NR^{14}—$ group and constitutes the connecting element to $R^4$;

m is 2, 3, or 4;

$R^5$ is selected from a COOH group and a

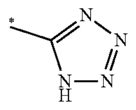

group;

$—R^6$-$R^7—$ is $^{\#}—(CH_2)_n—(B)_t—CR^{22}R^{23}—^{\#\#}$ or $^{\#}—(C_2$-$C_6$-alkenylene)-$(B)_t—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group;

n is 2, 3, 4, 5 or 6 if B is selected from —O—, —S—, —S(O)—, $—S(O)_2—$ and $—N(R^{15})—$, and n is 1, 2, 3, 4, or 5, if B is selected from $—C(O)NR^{15}—$ group and a $—NR^{15}C(O)—$ group, and n is 0, 1, 2, 3 or 4; if B is selected from a $—N(R^{15})—C(=O)—N(R^{15})—$ group, a $—O—C(=O)—N(R^{15})—$ group and a $—N(R^{15})—C(=O)—O—$ group;

t is 1 where the integers selected for variables n and t, together with the methylene group $CR^{22}R^{23}$ and the other non-variable atoms of the pyrazole and the indole moiety result in forming a 9-membered or 13-membered ring independently from the selection of variable A1 or A2;

B is independently selected from a $—C(O)NR^{15}—$ group, a $—NR^{15}C(O)—$ group, a $—N(R^{15})—$ group, a $—N(R^{15})—C(=O)—N(R^{15})—$ group, a $—O—C(=O)—N(R^{15})—$ group, a $—N(R^{15})—C(=O)—O—$ group, —O—, —S—, —S(O)— and $—S(O)_2—$;

$R^9$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group, a $C_2$-$C_6$-haloalkenyl group, a $C_1$-$C_6$-alkyl-O— group, a $C_1$-$C_4$-haloalkoxy group, a $C_1$-$C_6$-alkyl-O—($C_1$-$C_3$-alkylene)- group, a ($C_1$-$C_3$-alkyl)-NH—($C_1$-$C_3$-alkylene)- group, a ($C_3$-$C_7$)-cycloalkyl group and a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom, a $C_1$-$C_6$-alkyl group which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a $(R^{18})$-(heterocycloalkylene)-(arylene)-O— group, an aryl-O— group, an aryl-($C_1$-$C_3$-alkylene)-O— group, a $(R^{19})—S(O)_2$-arylene-O— group, a $(R^{19})S(O)_2$-heterocycloalkylene-arylene-O— group and an aryl-heteroarylene-O— group;

a phenyl group, a group

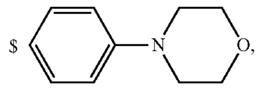

a group

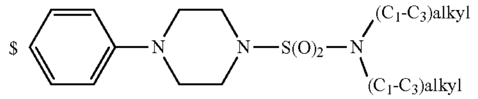

and a group

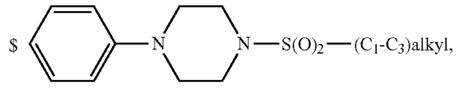

where $ is the point of attachment to the nitrogen atom, to which $R^{15}$ is attached, or $R^{15}$ and $R^{22}$ together, including the atoms to which they are attached, may form a 5-membered or 6-membered ring, both optionally comprising one or two additional heteroatoms independently selected from —O— and $—NR^{14}—$;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS$(O)_2$— group and a $C_1$-$C_3$-alkyl-O—C(═O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group; and $R^{20}$ and $R^{21}$ are each independently selected from a hydrogen atom and a $C_1$-$C_6$-alkyl group;

$R^{22}$ is independently selected from a halogen atom a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group and a phenyl group, a $C_3$-$C_6$-cycloalkyl group, a phenyl group, a heterocycloalkyl group and a heteroaryl group;

whereby any heterocycloalkyl group of $R^{22}$ may optionally be itself further substituted with a $C_1$-$C_3$-alkyl group or one or two halogen atoms;

$R^{23}$ is independently selected from a hydrogen atom, a halogen atom, a hydroxy group and a $C_1$-$C_4$-alkyl group; or $R^{22}$ and $R^{23}$ together with the carbon atom to which they are attached form a 3-membered to 6-membered carbocyclic ring or a 3-membered to 6-membered heterocyclic ring comprising one or two heteroatoms selected from nitrogen, oxygen and sulfur;

or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

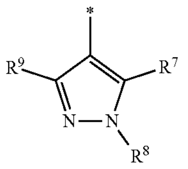

or (A2)

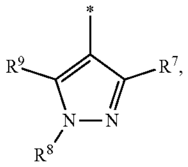

wherein $R^6$ and $R^7$, together with two carbon atoms of the pyrazole ring, two carbon atoms of the indole moiety and the nitrogen atom to which $R^6$ is attached, form a 10-membered to 12-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two or three substituents and each substituent is independently selected from a halogen atom and a $C_1$-$C_3$-alkyl group;

L is a group —$(CH_2)_m$-E-;

E is a bond or an oxygen atom and constitutes the connecting element to $R^4$;

m is 2, 3, or 4;

$R^5$ is a COOH group;

—$R^6$-$R^7$— is $^{\#}$—$(CH_2)_n$—$(B)_t$—$CR^{22}R^{23}$—$^{\#\#}$ or $^{\#}$—($C_3$-$C_5$-alkenylene)-$(B)_t$—$CR^{22}R^{23}$—$^{\#\#}$, wherein # is the point of attachment with the indole nitrogen atom and ## is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 3, 4 or 5;

t is 1;

where the integers selected for variables n and t together with the methylene group $CR^{22}R^{23}$ and the other non-variable atoms of the pyrazole and the indole moiety result in forming a 10-membered to 12-membered ring independently from the selection of variable A1 or A2;

B is independently selected from a —N($R^{15}$)— group and —O—;

$R^8$ is selected from a hydrogen atom, and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group, a $C_1$-$C_3$-hydroxyalkyl group, a $C_1$-$C_3$-haloalkyl group, a $C_1$-$C_3$-alkyl-O— group, a $C_1$-$C_3$-haloalkoxy group, a $C_1$-$C_3$-alkyl-O—($C_1$-$C_3$-alkylene)- group, a ($C_3$-$C_6$)-cycloalkyl group, a $R^{19}$-(phenylene)-O—($C_1$-$C_3$-alkylene)- group, a $NR^{20}R^{21}$—($C_1$-$C_3$-alkylene)- group and a ($C_1$-$C_3$-alkyl)-NH—($C_1$-$C_3$-alkylene)- group;

$R^{15}$ is independently selected from a hydrogen atom and a $C_1$-$C_6$-alkyl group which is unsubstituted or substituted with a substituent selected from a heterocycloalkyl group and an aryl group; or $R^{15}$ and $R^{22}$ together, including the atoms to which they are attached, may form a 5-membered or 6-membered ring, both optionally comprising one or two heteroatoms independently selected from —O— and —$NR^{14}$—;

$R^{16}$ and $R^{17}$ are each independently selected from a hydrogen atom, a $C_1$-$C_6$-alkyl group, a $C_1$-$C_6$-haloalkyl group and a $C_1$-$C_6$-alkoxy group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)$OR^{21}$—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_3$-alkyl group;

$R^{22}$ is independently selected from a halogen atom a $C_1$-$C_5$-alkyl group which is unsubstituted or substituted with a group selected from a hydroxy group, $NR^{16}R^{17}$ group, a $C_1$-$C_3$-haloalkyl group, a $C_1$-$C_4$-alkoxy group, a $C_3$-$C_6$-cycloalkyl group, a heterocycloalkyl group and a phenyl group;

a $C_3$-$C_6$-cycloalkyl group, a phenyl group, a heteroaryl group, a heterocycloalkyl group;

whereby any heterocycloalkyl group of $R^{22}$ may optionally be itself further substituted with a $C_1$-$C_3$-alkyl group or one or two halogen atoms;

$R^{23}$ is independently selected from a hydrogen atom, a halogen atom, a hydroxy group and a $C_1$-$C_4$-alkyl group, or $R^{22}$ and $R^{23}$ together form a 3-membered to 6-membered carbocyclic ring;

or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

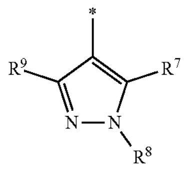

or (A2)

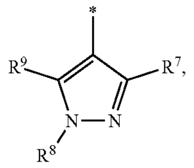

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group $-(CH_2)_m$-E-;

E is an oxygen atom and constitutes the connecting element to $R^4$;

m is 3;

$R^5$ is a COOH group;

$-R^6$-$R^7-$ is $^{\#}-(CH_2)_n-(B)_t-CR^{22}R^{23}-^{\#\#}$ or $^{\#}-(C_3$-$C_4$-alkenylene)-$(B)_t-CR^{22}R^{23}-^{\#\#}$, wherein $^{\#}$ is the point of attachment with the indole nitrogen atom and $^{\#\#}$ is the point of attachment with the pyrazole carbon atom bearing the $R^7$ substituent;

n is 4;

t is 1;

where the integers selected for variables n and t together with the methylene group $CR^{22}R^{23}$ and the other non-variable atoms of the pyrazole and the indole moiety result in forming a 11-membered ring independently from the selection of variable A1 or A2;

B is independently selected from a $-N(R^{15})-$ group and —O—;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group;

$R^{15}$ is independently selected from a hydrogen atom and a $C_1$-$C_6$-alkyl group which is unsubstituted or substituted with a heterocycloalkyl group;

or $R^{15}$ and $R^{22}$ together, including the atoms to which they are attached, may form a 5-membered or 6-membered ring, both optionally comprising one or two heteroatoms independently selected from —O— and $-NR^{14}-$;

$R^{16}$ and $R^{17}$ are each independently selected from a hydrogen atom, a $C_1$-$C_3$-alkyl group, a $C_1$-$C_6$-haloalkyl group and a $C_1$-$C_3$-alkoxy group;

$R^{22}$ is independently selected from a halogen atom, a $C_3$-$C_6$-cycloalkyl group, a phenyl group and a $C_1$-$C_5$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is independently selected from a hydrogen atom, a halogen atom, a hydroxy group and a $C_1$-$C_3$-alkyl group or $R^{22}$ and $R^{23}$ together form a 3-6-membered carbocyclic ring;

or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

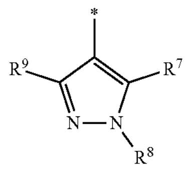

or

-continued (A2)

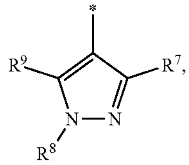

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group $-(CH_2)_m$-E-;

E is an oxygen atom and constitutes the connecting element to $R^4$;

m is 3;

$R^5$ is a COOH group;

$-R^6$-$R^7-$ is $^{\#}-(CH_2)_n-(B)_t-CR^{22}R^{23}-^{\#\#}$ or $^{\#}-(C_2$-$C_4$-alkenylene)-$(B)_t-CR^{22}R^{23}-^{\#\#}$, wherein $^{\#}$ is the point of attachment with the indole nitrogen atom and $^{\#\#}$ is the point of attachment with the pyrazole carbon atom bearing the $R^7$ substituent;

n is 4;

t is 1 where the integers selected for variables n and t together with the methylene group $CR^{22}R^{23}$ and the other non-variable atoms of the pyrazole and the indole moiety result in forming a 11-membered ring independently from the selection of variable A1 or A2;

B is independently selected from a $-N(R^{15})-$ group and $-O-$;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group;

$R^{15}$ is independently selected from a hydrogen atom and a $C_1$-$C_6$-alkyl group which is unsubstituted or substituted with a heterocycloalkyl group; or $R^{15}$ and $R^{22}$ together, including the atoms to which they are attached, may form a 5-membered or 6-membered ring optionally comprising one or two heteroatoms independently selected from $-O-$ and $-NR^{14}-$;

$R^{16}$ and $R^{17}$ are each independently selected from a hydrogen atom, a $C_1$-$C_3$-alkyl group, a $C_1$-$C_6$-haloalkyl group and a $C_1$-$C_3$-alkoxy group;

$R^{22}$ is independently selected from a halogen atom, a $C_3$-$C_6$-cycloalkyl group, a phenyl group, a $C_1$-$C_5$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is independently selected from a hydrogen atom, a halogen atom, a hydroxy group and a $C_1$-$C_3$-alkyl group, or $R^{22}$ and $R^{23}$ together form a 3-membered to 6-membered carbocyclic ring;

or a tautomer, or a salt thereof, or a salt of a tautomer, or a mixture of same.

In accordance with a further aspect, the present invention provides compounds of general formula (I): wherein wherein A is (A2)

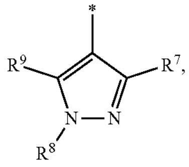

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and Ware each a hydrogen atom;

$R^4$ is a naphthyl group which is unsubstituted or substituted with a fluorine atom;

L is a group $-(CH_2)_3-O-$;

$R^5$ is a COOH group;

$-R^6$-$R^7-$ is $^{\#}-(CH_2)_4-O-CR^{22}R^{23}-^{\#\#}$, or $^{\#}-(CH_2)_4-NR^{15}-CR^{22}R^{23}-^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group and a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

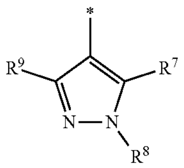

or (A2)

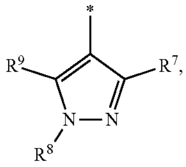

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is an aryl group, which is unsubstituted or substituted with a halogen atom;

L is a group $—(CH_2)_m$-E-;

E is an oxygen atom and constitutes the connecting element to $R^4$;

m is 3;

$R^5$ is a COOH group;

$—R^6$-$R^7—$ is $^{\#}—(CH_2)_n—(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

n is 4;

t is 1;

where the integers selected for variables n and t together with the methylene group $CR^{22}R^{23}$ and the other non-variable atoms of the pyrazole and the indole moiety result in forming a 11-membered ring independently from the selection of variable A1 or A2;

B is independently selected from a $—N(R^{15})—$ group and —O—;

$R^8$ is selected from a hydrogen atom and a $C_1$-$C_3$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_3$-alkyl group;

$R^{15}$ is independently selected from a hydrogen atom and a $C_1$-$C_6$-alkyl group which is unsubstituted or substituted with a heterocycloalkyl group; or $R^{15}$ and $R^{22}$ together, including the atoms to which they are attached, may form a 5-membered or 6-membered ring optionally comprising one or two heteroatoms independently selected from —O— and $—NR^{14}—$;

$R^{16}$ and $R^{17}$ are each independently selected from a hydrogen atom, a $C_1$-$C_3$-alkyl group, a $C_1$-$C_6$-haloalkyl group and a $C_1$-$C_3$-alkoxy group;

$R^{22}$ is independently selected from a halogen atom, a $C_3$-$C_6$-cycloalkyl group, a phenyl group, a $C_1$-$C_5$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A2)

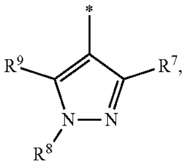

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group which is unsubstituted or substituted with a fluorine atom;

L is a group $—(CH_2)_3—O—$;

$R^5$ is a COOH group;

$—R^6$-$R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

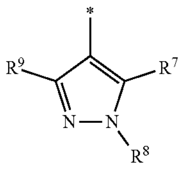

or (A2)

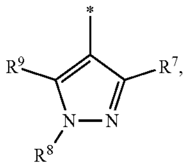

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and $R^3$ are each a hydrogen atom;

$R^4$ is a naphthyl group which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$, or $^{\#}—(CH_2)_4—NR^{15}—CR^{22}R^{23}\neq^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A2)

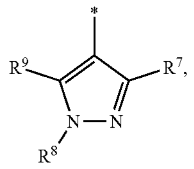

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and $R^3$ each a hydrogen atom;

$R^4$ is a naphthyl group which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A2)

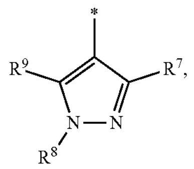

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and Ware each a hydrogen atom;

$R^4$ is a naphthyl group which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and $R^8$ is a methyl group;

$R^9$ is a methyl group or an ethyl group;

$R^{15}$ is a methyl group;

$R^{22}$ is independently selected from a methyl group, an ethyl group, a hydroxyethyl group, a trifluoromethyl group, a cyclopropyl group, a methoxyethyl group, a 2-hydroxy-2-methyl-propyl group, a 3-hydroxy-3-methylbutyl group, a (methoxymethyl-amino)ethyl group, a (dimethylamino)ethyl group, a (morpholin-4-yl)ethyl group, a 3-(morpholin-4-yl)propyl group, a 2-(oxan-4-yl)ethyl group, a 2-(4-methylpiperazin-1-yl)ethyl group, a 2-(3,3-difluoroazetidin-1-yl)ethyl group, a 2-(3,3-difluoropyrrolidin-1-yl)ethyl group, a phenyl group, or $R^{15}$ and $R^{22}$ together with the atoms to which they are attached form a group

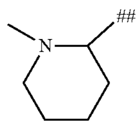

or a group

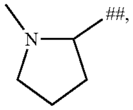

whereby $^{\#\#}$ is the point of attachment with the pyrazole carbon atom bearing the $R^7$ substituent and the nitrogen atom, which is the $—N(R^{15})—$ group, is attached to the $^{\#}—(CH_2)_4—$ moiety of the $R^6\text{-}R^7$ chain, $R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

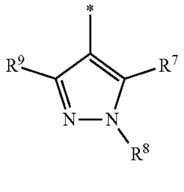

or

-continued (A2)

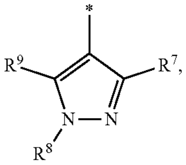

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and Ware each a hydrogen atom;

$R^4$ is a naphthyl group which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups may be unsubstituted or substituted with one or more halogen atoms, $R^8$ is a $C_1\text{-}C_3$-alkyl group;

$R^9$ is a $C_1\text{-}C_3$-alkyl group;

$R^{15}$ is a $C_1\text{-}C_3$-alkyl group, or $R^{15}$ and $R^{22}$ together, including the atoms to which they are attached, may form a 5-membered or a 6-membered ring;

$R^{16}$ and $R^{17}$ are each independently selected from a hydrogen atom, a $C_1\text{-}C_3$-alkyl group and a $C_1\text{-}C_3$-alkoxy group;

$R^{22}$ is independently selected from a $C_3\text{-}C_6$-cycloalkyl group, a phenyl group, a $C_1\text{-}C_5$-alkyl group which is unsubstituted or substituted with a substituent selected from a hydroxy group, a $NR^{16}R^{17}$ group, a $C_1\text{-}C_3$-haloalkyl group, a $C_1\text{-}C_3$-alkoxy group, a $C_3\text{-}C_6$-cycloalkyl group, a heterocycloalkyl group and a phenyl group;

whereby any heterocycloalkyl group of $R^{22}$ may optionally itself be further substituted with a $C_1\text{-}C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

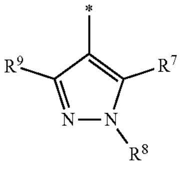

or

-continued (A2)

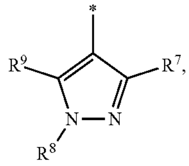

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups may be unsubstituted or substituted with one or more fluorine atoms, $R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

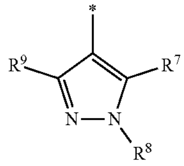

or

-continued (A2)

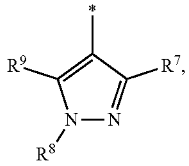

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and Ware each a hydrogen atom;

$R^4$ is a naphthyl group which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups may be unsubstituted or substituted with one or more fluorine atoms, $R^8$ is a $C_1$-$C_2$-alkyl group;

$R^9$ is a $C_1$-$C_2$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

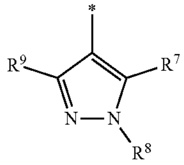

or

-continued (A2)

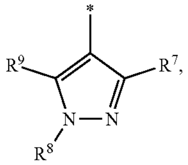

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group which is substituted with a fluorine atom;

L is a group $—(CH_2)_3—O—$;

$R^5$ is a COOH group;

$—R^6-R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A2)

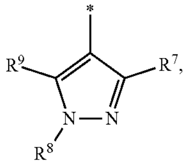

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group or 6-fluoro-naphthyl group;

L is a group $—(CH_2)_3—O—$;

$R^5$ is a COOH group;

$—R^6-R^7—$ is $^{\#}—(CH_2)_4—O—CR^{22}R^{23}—^{\#\#}$, or $^{\#}—(CH_2)_4—NR^{15}—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group, a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I): wherein wherein A is (A2)

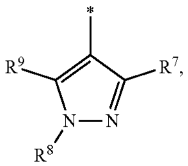

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and $R^3$ are each a hydrogen atom;

$R^4$ is a naphthyl group which is unsubstituted or substituted with a fluorine atom;

L is a group $—(CH_2)_3—O—$;

$R^5$ is a COOH group;

$—R^6$-$R^7—$ is selected from $^{\#}—(CH_2)_4—O—CH(CH_3)—^{\#\#}$, $^{\#}—(CH_2)_4—O—CH(CH_2CH_3)—^{\#\#}$, $^{\#}—(CH_2)_4—O—CH(CF_3)—^{\#\#}$; $^{\#}—(CH_2)_4—O—CH[(CH_2)_2—OH]—^{\#\#}$, $^{\#}—(CH_2)_4O—CH[CH_2—C(CH_3)_2OH]—^{\#\#}$, $^{\#}—(CH_2)_4—O—CH[(CH_2)_2—CH(CH_3)_2OH]^{\#\#}$, $(CH_2)_4—O—CH[(CH_2)_2—OCH_3]^{\#\#}$, $^{\#}—(CH_2)_4—O—CH[(CH_2)_2—N(CH_3)_2]^{\#\#}$, $^{\#}—(CH_2)_4—O—CH[(CH_2)_2—N(CH_3)OCH_3]—^{\#\#}$, $^{\#}—(CH_2)_4—O—CH$(cyclopropyl)-$^{\#\#}$, $^{\#}—(CH_2)_4—O—CH[(CH_2)_2$-morpholino]-$^{\#\#}$, $^{\#}—(CH_2)_4—O—CH[(CH_2)_3$-morpholino]-$^{\#\#}$, $^{\#}—(CH_2)_4—O—CH[(CH_2)_2$-oxan-4-yl]- $^{\#\#}$, $^{\#}—(CH_2)_4—O—CH[(CH_2)_2$-4-methyl-piperazin-1-yl]-$^{\#\#}$, $^{\#}—(CH_2)_4—O—CH[(CH_2)_2$-(3,3-difluoropyrrolidin-1-yl)]-$^{\#\#}$, $^{\#}—(CH_2)_4—O—CH[(CH_2)_2$-(3,3-difluoro-azetidin-1-yl)]-$^{\#\#}$, $^{\#}—(CH_2)_4—O—CH$-phenyl-$^{\#\#}$, $^{\#}—(CH_2)_4—O—CH$-benzyl-$^{\#\#}$, $^{\#}—(CH_2)_2—CF_2—CH_2—O—CH[(CH_2)_2$-morpholino)]-$^{\#\#}$, $^{\#}—(CH_2)_4—N(CH_3)—CH[(CH_2)_2$-morpholino]-$^{\#\#}$, $^{\#}—(CH_2)_4—N(CH_3)—CH[(CH_2)_2$-oxetan-4-yl]-$^{\#\#}$,

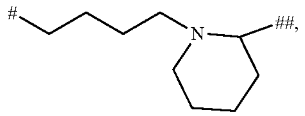

and

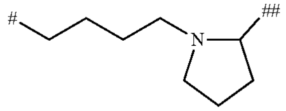

wherein # is the point of attachment with the indole nitrogen atom and ## is the point of attachment with the pyrazole carbon atom bearing the $R^7$ substituent;

or a tautomer, or a salt thereof, or a salt of a tautomer, or a mixture of same.

In accordance with a further aspect, the present invention provides compounds of general formula (I): wherein wherein A is (A2)

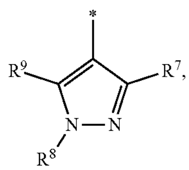

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and $R^3$ are each a hydrogen atom;

$R^4$ is a naphthyl group which is unsubstituted or substituted with a fluorine atom;

L is a group $—(CH_2)_3—O—$;

$R^5$ is a COOH group;

$—R^6$-$R^7—$ is selected from $^{\#}—(CH_2)_4—O—CH(CH_3)—^{\#\#}$, $^{\#}—(CH_2)_4—O—CH(CH_2CH_3)—^{\#\#}$, $^{\#}—(CH_2)_4—O—CH(CF_3)—^{\#\#}$; $^{\#}—(CH_2)_4—O—CH[(CH_2)_2—OH]—^{\#\#}$, $^{\#}—(CH_2)_4O—CH[CH_2—C(CH_3)_2OH]—^{\#\#}$, $^{\#}—(CH_2)_4—O—CH[(CH_2)_2—C(CH_3)_2OH]—^{\#\#}$, $^{\#}—(CH_2)_4—O—CH[(CH_2)_2—OCH_3]—^{\#\#}$, $^{\#}—(CH_2)_4—O—CH[(CH_2)_2—N(CH_3)_2]—^{\#\#}$, $^{\#}—(CH_2)_4—O—CH[(CH_2)_2—N(CH_3)OCH_3]—^{\#\#}$, $^{\#}—(CH_2)_4—O—CH$(cyclopropyl)-$^{\#\#}$, $^{\#}—(CH_2)_4O—CH[(CH_2)_2$-morpholino]-$^{\#\#}$, $^{\#}—(CH_2)_4—O—CH[(CH_2)_3$-morpholino]-$^{\#\#}$, $^{\#}—(CH_2)_4—O—CH[(CH_2)_2$-oxan-4-yl]- $^{\#\#}$, $^{\#}—(CH_2)_4—O—CH[(CH_2)_2$-4-methyl-piperazin-1-yl]-$^{\#\#}$, $^{\#}—(CH_2)_4—O—CH[(CH_2)_2$-(3,3-difluoropyrrolidin-1-yl)]-$^{\#\#}$, $^{\#}—(CH_2)_4—O—CH[(CH_2)_2$-(3,3-difluoro-azetidin-1-yl)]-$^{\#\#}$, $^{\#}—(CH_2)_4—O—CH$-phenyl-$^{\#\#}$, $^{\#}—(CH_2)_4—O—CH$-benzyl-$^{\#\#}$, $^{\#}—(CH_2)_2—CF_2—CH_2—O—CH[(CH_2)_2$-morpholino)]-$^{\#\#}$, $^{\#}—(CH_2)_4—N(CH_3)—CH[(CH_2)_2$-morpholino]-$^{\#\#}$, $^{\#}—(CH_2)_4—N(CH_3)—CH[(CH_2)_2$-oxetan-4-yl]-$^{\#\#}$, $^{\#}—(CH_2)_4$-[1-piperadin-2-yl]- $^{\#\#}$, and $^{\#}—(CH_2)_4$-[1-pyrrolidin-2-yl]-$^{\#\#}$, wherein # is the point of attachment with the indole nitrogen atom and ## is the point of attachment with the pyrazole carbon atom bearing the $R^7$ substituent;

or a tautomer, or a salt thereof, or a salt of a tautomer, or a mixture of same.

In accordance with a further aspect, the present invention provides compounds of general formula (I): wherein (I)

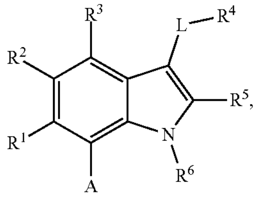

wherein

A is (A1)

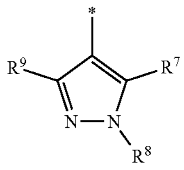

or (A2)

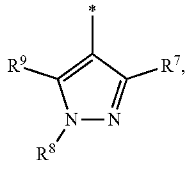

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;

or

A is (A3)

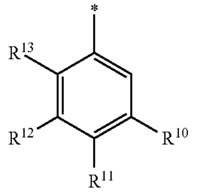

wherein optionally one or two of the groups selected from $CR^{11}$, $CR^{12}$ and $CR^{13}$ are replaced by a nitrogen atom, wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —$S(O)_2$—($C_1$-$C_3$-alkyl) group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8-membered saturated or partially unsaturated heterocyclic ring having 1-2 heteroatoms independently selected from an oxygen atom, a sulfur atom, a —S(O)— group, a —$S(O)_2$— group and a —$NR^{14}$— group;

E is a bond, an oxygen atom, a sulfur atom, a —S(O)— group, a —$S(O)_2$— group or a —$NR^{14}$— group and constitutes the connecting element to $R^4$, m is 2, 3, or 4;

$R^5$ is selected from a COOH group, a

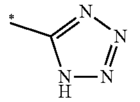 [SMILES: *c1nnn[nH]1]

group, a —C(O)—$NHS(O)_2$($C_1$-$C_6$-alkyl) group, a —C(O)—$NHS(O)_2$($C_3$-$C_6$-cycloalkyl) group, a —C(O)—$NHS(O)_2$(aryl) group, a —C(O)—$NHS(O)_2(CH_2)_s$NHCO($C_1$-$C_6$-alkyl) group, a —C(O)—$NHS(O)_2(CH_2)_s$NHCO($C_3$-$C_6$-cycloalkyl) group and a —C(O)—$NHS(O)_2$$(CH_2)_s$NHCO(aryl) group;

—$R^6$-$R^7$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

—$R^6$-$R^{10}$— is $^{\#}$—$(CH_2)_n$—$(B)_t$—$CR^{22}R^{23}$—$^{\#\#}$or $^{\#}$—($C_2$-$C_9$-alkenylene)-$(B)_t$—$CR^{22}R^{23}$—$^{\#\#}$, where one or more —$CH_2$— groups are substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the phenyl moiety bearing the $R^{19}$ substituent;

n is 2, 3, 4, 5, 6, 7, 8, or 9;

t is 1;

s is 0, 1 or 2;

where the integers selected for variables n, and t result in forming a 9- to 16-membered ring independently from the selection of variable A1, A2 or A3;

B is independently selected from a —$C(O)NR^{15}$— group, a —$NR^{15}C(O)$— group, a —$N(R^{15})$— group, a —$N(R^{15})$—C(=O)—$N(R^{15})$— group, a —O—C(=O)—$N(R^{15})$— group, a —$N(R^{15})$—C(=O)—O— group, —O—, —S—, —S(O)— and —$S(O)_2$—;

$R^9$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group and a $C_1$-$C_3$-haloalkyl group, a $C_3$-$C_6$-cycloalkyl group, and a $C_1$-$C_6$-alkyl group in which one or two not directly adjacent carbon atoms are independently replaced by a heteroatom selected from —O— and —NH—, $R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group, a $C_2$-$C_6$-haloalkenyl group, a $C_1$-$C_6$-alkyl-O— group, a $C_1$-$C_4$-haloalkoxy group, a $C_1$-$C_6$-alkyl-O—($C_1$-$C_3$-alkylene)- group, a ($C_3$-$C_7$)-cycloalkyl group, a ($C_3$-$C_7$)-cycloalkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a $R^{18}$-(phenylene)-($C_1$-$C_3$-alkylene)-O—($C_1$-$C_3$-alkylene)- group, a $R^{18}$-(phenylene)-O—($C_1$-$C_3$-alkylene)- group, a $R^{18}$-(phenylene)-(heteroarylene)-O—($C_1$-$C_3$-alkylene)-group, a ($R^{18}$)-(heterocycloalkylene)-($C_1$-$C_3$-alkylene)- group, a ($R^{18}$)-(heterocycloalkylene)-(phenylene)-O—($C_1$-$C_3$-alkylene)- group, a (heterocycloalkenyl)-(phenylene)-O—($C_1$-$C_3$-alkylene)- group, a ($R^{18}$)-(heteroarylene)-($C_1$-$C_3$-alkylene)-O—($C_1$-$C_3$-alkylene)- group, a ($R^{18}$)-(heteroarylene)-(phenylene)-O—($C_1$-$C_3$-alkylene)- group, a ($R^{19}$)—$S(O)_2$-(phenylene)-O—($C_1$-$C_3$-alkylene)-group, a ($R^{19}$)—$S(O)_2$—NH-(phenylene)-O—($C_1$-$C_3$-alkylene)-group, a ($R^{19}$)—$S(O)_2$—NH-(phenylene)-O—($C_1$-$C_3$-alkylene)-group, a ($R^{19}$)—$S(O)_2$—N($C_1$-$C_6$-alkyl)-(phenylene)-O—($C_1$-$C_3$-alkylene)- group, a ($R^{19}$)—$S(O)_2$-(heterocycloalkylene)-(phenylene)-O—($C_1$-$C_3$-alkylene)- group, a ($R^{18}$)-(heterocycloalkylene)-(heteroarylene)-O—($C_1$-$C_3$-alkylene)- group, a ($R^{19}$)-(heteroarylene)-O—($C_1$-$C_3$-alkylene)- group, a ($R^{18}$)-(heteroarylene)-O—($C_1$-$C_3$-alkylene)- group, a ($R^{19}$)—$S(O)_2$-(heteroarylene)-O—($C_1$-$C_3$-alkylene)-group, a ($R^{19}$)—$S(O)_2$-(heterocycloalkylene)-(heteroarylene)-O—($C_1$-$C_3$-alkylene)- group, a $NR^{20}R^{21}$—($C_1$-$C_3$-alkylene)- group, a ($C_1$-$C_3$-alkyl)-NH—($C_1$-$C_3$-alkylene)- group, a ($C_1$-$C_3$-haloalkyl)-($C_1$-$C_3$-alkylene)-NH—($C_1$-$C_3$-alkylene)- group, a ($C_1$-$C_3$-haloalkyl)-NH—($C_1$-$C_3$-alkylene)- group, a ($C_1$-$C_3$-alkyl)-NH—C(O)—($C_1$-$C_3$-alkylene)- group, a ($C_1$-$C_3$-alkyl)-$NR^{15}$—C(O)—($C_1$-$C_3$-alkylene)- group, a ($C_1$-$C_3$-alkyl)-C(O)—NH—($C_1$-$C_3$-alkylene)- group, a ($C_1$-$C_3$-alkyl)-C(O)—$NR^{15}$—($C_1$-$C_3$-alkylene)- group, a

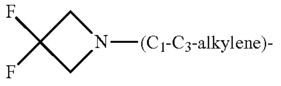

group and a

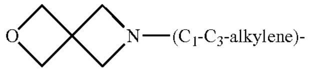

group, where the phenyl ring is unsubstituted or substituted with a halogen atom, a hydroxy group, or a $C_1$-$C_3$-alkoxy group and the heterocycloalkyl group is unsubstituted or substituted with an oxo (═O) group or is unsubstituted or substituted with one or more substituents independently selected from a halogen atom, a hydroxy group, a $C_1$-$C_3$-alkyl group and a $C_1$-$C_3$-alkoxy group, or $R^8$ and $R^9$ together form a 5-membered or 6-membered ring optionally comprising one or two heteroatoms independently selected from —O— and —$NR^{14}$—;

$R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group;

$R^{14}$ is a hydrogen atom or a $C_1$-$C_3$-alkyl group;

$R^{15}$ is independently selected from a hydrogen atom, a $C_1$-$C_6$-alkyl group which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—$S(O)_2$-arylene-O— group, a ($R^{19}$)$S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group;

a $C_1$-$C_3$-alkylene-C(O)— group, a heterocycloalkyl-($C_1$-$C_3$-alkylene)-C(O)— group, a heterocycloalkyl-($C_1$-$C_3$-alkylene)-$S(O)_2$— group, a heterocyclyl-NH—C(O)— group, a heterocycloalkyl-($C_1$-$C_3$-alkylene)-NH—C(O)— group, an aryl-($C_1$-$C_3$-alkylene)-NH—C(O)— group, which is unsubstituted or substituted with 1, 2, or 3 substituents independently selected from a halogen atom, a $C_1$-$C_3$-alkyl group and a $C_1$-$C_3$-alkoxy group, a heterocycloalkyl-heteroarylene-$S(O)_2$— group, a phenyl group, a group

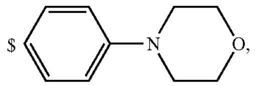

a group

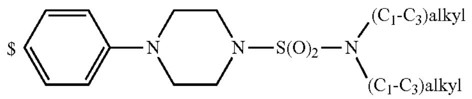

and a group

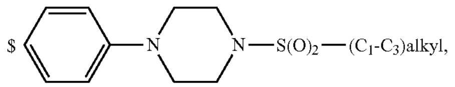

where $ is the point of attachment to the nitrogen atom, to which $R^{15}$ is attached;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS$(O)_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a N$R^{20}R^{21}$ group;

$R^{20}$ and $R^{21}$ are each independently selected from a hydrogen atom and a $C_1$-$C_6$-alkyl group;

$R^{22}$ is independently selected from a halogen atom, a $C_1$-$C_6$-alkyl group which is unsubstituted or substituted with one or more substituents selected from a halogen atom, a hydroxy group, a N$R^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S$(O)_2$-arylene-O— group, a ($R^{19}$)S$(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S$(O)_2$— group and a heterocycloalkylene-heteroarylene-S$(O)_2$— group; and a $C_1$-$C_3$-alkyl-C(O)— group;

$R^{23}$ is independently selected from a hydrogen atom, a halogen atom, a hydroxy group, a $C_1$-$C_6$-alkyl group and a $C_1$-$C_6$-haloalkyl group, or $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur;

or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

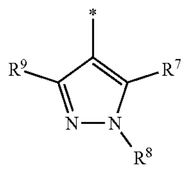

or (A2)

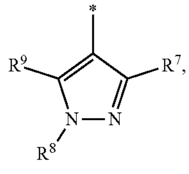

wherein $R^6$ and $R^7$, together with two carbon atoms of the pyrazole ring, two carbon atoms of the indole moiety and the nitrogen atom to which $R^6$ is attached, form a 9- to 13-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group;

E is a bond, an oxygen atom, a sulfur atom, or a —N$R^{14}$— group and constitutes the connecting element to $R^4$;

m is 2, 3, or 4;

$R^5$ is selected from a COOH group and a

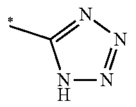 [SMILES: *c1nnn[nH]1]

group;

—$R^6$-$R^7$— is $^{\#}$—$(CH_2)_n$—$(B)_t$—C$R^{22}R^{23}$—$^{\#\#}$or $^{\#}$—($C_2$-$C_9$-alkenylene)-$(B)_t$—C$R^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a N$R^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group;

n is 2, 3, 4, 5 or 6;

t is 1 where the integers selected for variables n and t, result in forming a 9- or 13-membered ring independently from the selection of variable A1 or A2;

B is independently selected from a —C(O)N$R^{15}$— group, a —N$R^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)— and —S$(O)_2$—;

$R^8$ is selected from a hydrogen atom, and a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a N$R^{20}R^{21}$ group;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)-group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group and
a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom,
a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—S(O)$_2$— arylene-O— group, a ($R^{19}$)S(O)$_2$-heterocycloalkylene-arylene-O— group and an aryl-heteroarylene-O— group;
a phenyl group,
a group

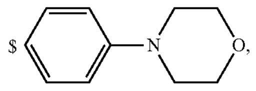

a group

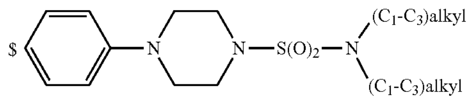

and
a group

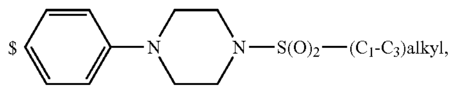

where $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(═O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a NR$^{20}$R$^{21}$ group; and $R^{20}$ and $R^{21}$ are each independently selected from a hydrogen atom and a $C_1$-$C_6$-alkyl group;

$R^{22}$ is independently selected from
a halogen atom
a $C_1$-$C_6$-alkyl group which is unsubstituted or substituted with one or more substituents selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group and a phenyl group,
a $C_3$-$C_6$-cycloalkyl group,
a heterocycloalkyl group,
a phenyl group and
a heteroaryl group;

$R^{23}$ is independently selected from a hydrogen atom, a halogen atom, a hydroxy group and a $C_1$-$C_4$-alkyl group; or $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur;

or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

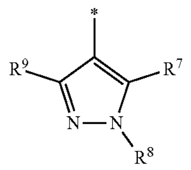

or (A2)

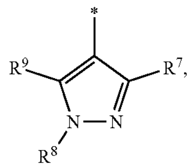

wherein $R^6$ and $R^7$, together with two carbon atoms of the pyrazole ring, two carbon atoms of the indole moiety and the nitrogen atom to which $R^6$ is attached, form a 10- to 12-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two or three substituents and each substituent is independently selected from a halogen atom and a $C_1$-$C_3$-alkyl group;

L is a group —(CH$_2$)$_m$-E-;

E is a bond or an oxygen atom and constitutes the connecting element to $R^4$, m is 2, 3, or 4;

$R^5$ is a COOH group;

$—R^6-R^7—$ is $^{\#}—(CH_2)_n—(B)_t—CR^{22}R^{23}—^{\#\#}$ or $^{\#}—(C_2-C_9\text{-alkenylene})-(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 3, 4 or 5;

t is 1;

where the integers selected for variables n and t result in forming a 10- or 12-membered ring independently from the selection of variable A1 or A2;

B is independently selected from a $—N(R^{15})—$ group and $—O—$;

$R^8$ is selected from a hydrogen atom, a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group, a $C_1$-$C_3$-hydroxyalkyl group, a $C_1$-$C_3$-haloalkyl group, a $C_1$-$C_3$-alkyl-O— group, a $C_1$-$C_3$-haloalkoxy group, a $C_1$-$C_3$-alkyl-O—($C_1$-$C_3$-alkylene)- group, a ($C_3$-$C_6$)-cycloalkyl group, a $R^{19}$-(phenylene)-O—($C_1$-$C_3$-alkylene)- group, a $NR^{20}R^{21}$—($C_1$-$C_3$-alkylene)- group and a ($C_1$-$C_3$-alkyl)-NH—($C_1$-$C_3$-alkylene)- group;

$R^{15}$ is independently selected from a hydrogen atom and a $C_1$-$C_6$-alkyl group which is unsubstituted or substituted with a substituent selected from a heterocycloalkyl group and an aryl group;

$R^{16}$ and $R^{17}$ are each independently selected from a hydrogen atom, a $C_1$-$C_6$-alkyl group, a $C_1$-$C_6$-haloalkyl group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $C(O)OR^{21}$—($C_1$-$C_3$-alkylene)- group, a $—C(O)OR^{21}$ group, a $—C(O)NR^{20}R^{21}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_3$-alkyl group; and $R^{22}$ is independently selected from a halogen atom, a $C_1$-$C_4$-alkyl group which is unsubstituted or substituted with a group selected from a hydroxy group, $NR^{16}R^{17}$ group, a $C_1$-$C_4$-alkoxy group, a $C_3$-$C_6$-cycloalkyl group, a heterocycloalkyl group and a phenyl group;

a phenyl group, a heteroaryl group, a $C_3$-$C_6$-cycloalkyl group, and a heterocycloalkyl group, $R^{23}$ is independently selected from a hydrogen atom, a halogen atom, a hydroxy group and a $C_1$-$C_4$-alkyl group or $R^{22}$ and $R^{23}$ together form a 3-6-membered carbocyclic ring; or a tautomer, an N-oxide, or a salt thereof, or a salt of a tautomer, or a salt of an N-oxide, or a mixture of same.

In accordance with a further aspect, the present invention provides compounds of general formula (I): wherein A is (A1)

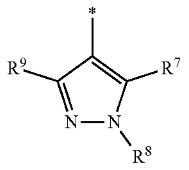

or (A2)

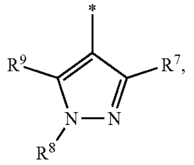

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group $—(CH_2)_m$-E-;

E is an oxygen atom and constitutes the connecting element to $R^4$, m is 3;

$R^5$ is a COOH group;

$—R^6-R^7—$ is $^{\#}—(CH_2)_n—(B)_t—CR^{22}R^{23}—^{\#\#}$ or $^{\#}—(C_2-C_9\text{-alkenylene})-(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

n is 4 or 5;

t is 1 where the integers selected for variables n and t result in forming a 11-membered ring independently from the selection of variable A1 or A2;

B is independently selected from a $—N(R^{15})—$ group and $—O—$;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group;

$R^{15}$ is independently selected from a hydrogen atom and a $C_1$-$C_6$-alkyl group which is unsubstituted or substituted with a heterocycloalkyl group;

$R^{22}$ is independently selected from a halogen atom, a phenyl group, a $C_3$-$C_6$-cycloalkyl group, a $C_1$-$C_3$-alkyl group which is unsubstituted or substituted with one or more substituents selected from a hydroxy group, a $NR^{17}R^{18}$ group, a $C_1$-$C_3$-haloalkyl group, a $C_1$-$C_3$-alkoxy group, a $C_3$-$C_6$-cycloalkyl group, a heterocycloalkyl group and a phenyl group;

$R^{23}$ is independently selected from a hydrogen atom, a halogen atom, a hydroxy group and a $C_1$-$C_3$-alkyl group, or $R^{22}$ and $R^{23}$ together form a 3-6-membered carbocyclic ring;

or a tautomer, or a salt thereof, or a salt of a tautomer, or a mixture of same.

In accordance with a further aspect, the present invention provides compounds of general formula (I): wherein A is (A1)

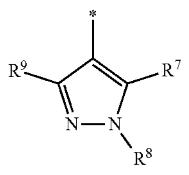

or (A2)

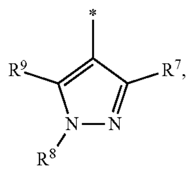

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is unsubstituted or substituted with a fluorine atom;

L is a group $-(CH_2)_3-O-$;

$R^5$ is a COOH group;

$-R^6$-$R^7-$ is $^{\#}-(CH_2)_4-O-CR^{22}R^{23}-^{\#\#}$, wherein # is the point of attachment with the indole nitrogen atom and ## is the point of attachment with the pyrazole carbon atom bearing the $R^7$ substituent; and wherein one or more $-CH_2-$ groups may be unsubstituted or substituted with one or more substituents independently a halogen atom;

$R^8$ is a $C_1$-$C_3$-alkyl group, which is unsubstituted or substituted with a heterocycloalkyl group;

$R^9$ is a $C_1$-$C_3$-alkyl group;

$R^{22}$ is a $C_1$-$C_3$-alkyl group, which is unsubstituted or substituted with a heterocycloalkyl group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

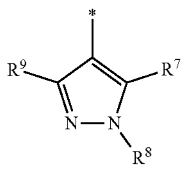

or (A2)

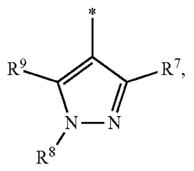

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is unsubstituted or substituted with a fluorine atom;

L is a group $-(CH_2)_3-O-$;

$R^5$ is a COOH group;

$-R^6$-$R^7-$ is $^{\#}-(CH_2)_4-O-CR^{22}R^{23}-^{\#\#}$, wherein # is the point of attachment with the indole nitrogen atom and ## is the point of attachment with the pyrazole carbon atom bearing the $R^7$ substituent; and wherein one or more $-CH_2-$ groups may be unsubstituted or substituted with one or more fluorine atoms;

$R^8$ is a $C_1$-$C_3$-alkyl group, which is unsubstituted or substituted with a morpholino group or a piperazine group;

$R^9$ is a $C_1$-$C_3$-alkyl group;

$R^{22}$ is independently selected from a methyl group and a $-(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

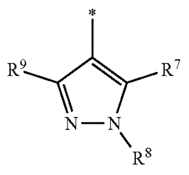

or (A2)

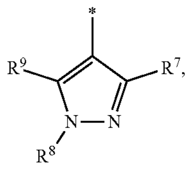

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is unsubstituted or substituted with a fluorine atom;

L is a group $—(CH_2)_3—O—$;

$R^5$ is a COOH group;

$—R^6-R^7—$ is $^{\#}—(CH_2)_4—O—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is a $C_1$-$C_2$-alkyl group, which is unsubstituted or substituted with a morpholino group or a piperazine group;

$R^9$ is a $C_1$-$C_2$-alkyl group;

$R^{22}$ is independently selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

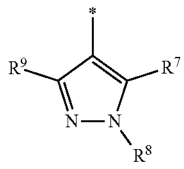

or (A2)

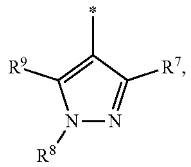

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, substituted with a fluorine atom;

L is a group $—(CH_2)_3—O—$;

$R^5$ is a COOH group;

$—R^6-R^7—$ is $^{\#}—(CH_2)_4—O—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is a $C_1$-$C_2$-alkyl group, which is unsubstituted or substituted with a morpholino group or a piperazine group;

$R^9$ is a $C_1$-$C_2$-alkyl group;

$R^{22}$ is independently selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

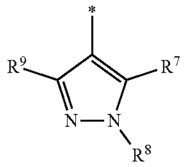

or (A2)

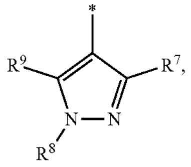

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a 6-fluoro-naphthyl group;

L is a group $—(CH_2)_3—O—$;

$R^5$ is a COOH group;

$—R^6-R^7—$ is $^{\#}—(CH_2)_4—O—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is a $C_1$-$C_2$-alkyl group, which is unsubstituted or substituted with a morpholino group or a piperazine group;

$R^9$ is a $C_1$-$C_2$-alkyl group;

$R^{22}$ is independently selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

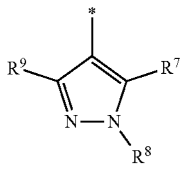

or

-continued (A2)

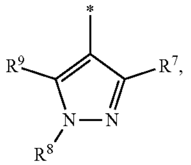

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is unsubstituted or substituted with a fluorine atom;

L is a group $—(CH_2)_3—NR^{15}—$;

$R^5$ is a COOH group;

$—R^6\text{-}R^7—$ is $^{\#}—(CH_2)_4—N(R^{15})—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more substituents independently selected from a halogen atom;

$R^8$ is a $C_1$-$C_3$-alkyl group which is unsubstituted or substituted with a heterocycloalkyl group;

$R^9$ is a $C_1$-$C_3$-alkyl group;

$R^{15}$ is independently selected from a hydrogen atom and a $C_1$-$C_3$-alkyl group, which is unsubstituted or substituted with a heterocycloalkyl group or a $C_1$-$C_3$-haloalkyl group;

$R^{22}$ is a $C_1$-$C_3$-alkyl group, which is unsubstituted or substituted with a heterocycloalkyl group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

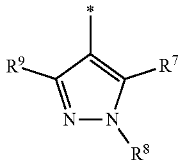

or (A2)

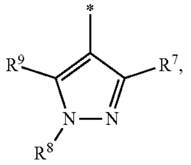

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is unsubstituted or substituted with a fluorine atom; L is a group $—(CH_2)_3—O—$;

$R^5$ is a COOH group;

$—R^6\text{-}R^7—$ is $^{\#}—(CH_2)_4—N(R^{15})—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is a $C_1$-$C_3$-alkyl group, which is unsubstituted or substituted with a morpholino group or a piperazine group;

$R^9$ is a $C_1$-$C_3$-alkyl group;

$R^{15}$ is selected from a hydrogen atom, a methyl group, a $CH_2CF_3$ and a $CH_2CHF_2$ group;

$R^{22}$ is selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

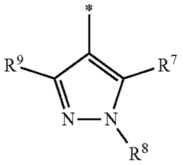

or (A2)

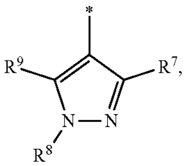

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is unsubstituted or substituted with a fluorine atom;

L is a group $—(CH_2)_3—O—$;

$R^5$ is a COOH group;

$—R^6\text{-}R^7—$ is $^{\#}—(CH_2)_4—N(R^{15})—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is a $C_1$-$C_2$-alkyl group, which is unsubstituted or substituted with a morpholino group or a piperazine group;

$R^9$ is a $C_1$-$C_2$-alkyl group;

$R^{15}$ is independently selected from a hydrogen atom, a methyl group, a $CH_2CF_3$ and a $CH_2CHF_2$ group;

$R^{22}$ is independently selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

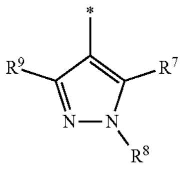

or (A2)

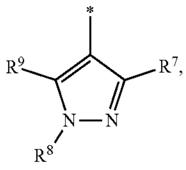

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a naphthyl group, which is substituted with a fluorine atom;

L is a group $—(CH_2)_3—O—$;

$R^5$ is a COOH group;

$—R^6\text{-}R^7—$ is $^{\#}—(CH_2)_4—N(R^{15})—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is $C_1$-$C_2$-alkyl group, which is unsubstituted or substituted with a morpholino group or a piperazine group;

$R^9$ is a $C_1$-$C_2$-alkyl group;

$R^{15}$ is independently selected from a hydrogen atom, a methyl group, a $CH_2CF_3$ and a $CH_2CHF_2$ group;

$R^{22}$ is independently selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

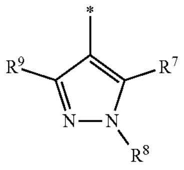

or

-continued (A2)

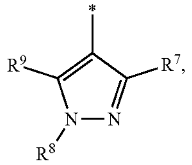

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is a 6-fluoro-naphthyl group;

L is a group $—(CH_2)_3—O—$;

$R^5$ is a COOH group;

$—R^6\text{-}R^7—$ is $^{\#}—(CH_2)_4—N(R^{15})—CR^{22}R^{23}—^{\#\#}$, wherein # is the point of attachment with the indole nitrogen atom and ## is the point of attachment with the pyrazole carbon atom bearing the $R^7$ substituent; and wherein one or more $—CH_2—$ groups may be unsubstituted or substituted with one or more fluorine atoms;

$R^8$ is $C_1$-$C_2$-alkyl group, which is unsubstituted or substituted with a morpholino group or a piperazine group;

$R^9$ is a $C_1$-$C_2$-alkyl group;

$R^{15}$ is independently selected from a hydrogen atom, a methyl group, a $CH_2CF_3$ and a $CH_2CHF_2$ group;

$R^{22}$ is independently selected from a methyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A2)

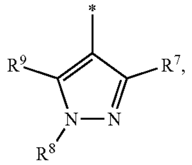

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is naphthyl which is unsubstituted or substituted with a fluorine atom;

L is a group $—(CH_2)_3—O—$;

$R^5$ is a COOH group;

$—R^6\text{-}R^7—$ is $^{\#}—(CH_2)_4—O—CR^{22}R^{23}—^{\#\#}$;

$R^8$ is a $C_1$-$C_3$-alkyl group;

$R^9$ is a $C_1$-$C_3$-alkyl group;

$R^{22}$ is independently selected from a $C_1$-$C_3$-haloalkyl group and a $C_1$-$C_3$-alkyl group which is unsubstituted or substituted with a hydroxy group, a $C_3$-$C_5$-cycloalkyl group, or a heterocyclyl group;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A2)

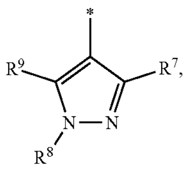

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent $R^1$ is selected from a hydrogen atom, fluorine atom and a chlorine atom;

$R^2$ and $R^3$ are each a hydrogen atom;

$R^4$ is selected from naphthyl and 6-fluoro-naphth-1-yl;

L is a group $—(CH_2)_3—O—$;

$R^5$ is a COOH group;

$—R^6$-$R^7—$ is $^{\#}—(CH_2)_4—O—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{22}$ is independently selected from a $C_1$-$C_3$-haloalkyl group and a $C_1$-$C_3$-alkyl group which is unsubstituted or substituted with a hydroxy group, a $C_3$-$C_5$-cycloalkyl group or a heterocyclyl group;

$R^{23}$ is a hydrogen atom;

or a tautomer, or a salt thereof, or a salt of a tautomer, or a mixture of same.

In accordance with a further aspect, the present invention provides compounds of general formula (I): wherein A is (A1)

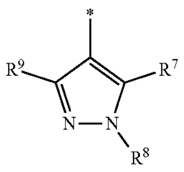

or (A2)

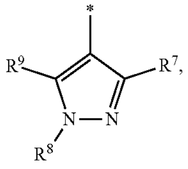

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is selected from naphthyl and 6-fluoro-naphth-1-yl;

L is a group $—(CH_2)_3—O—$;

$R^5$ is a COOH group;

$—R^6$-$R^7—$ is $^{\#}—(CH_2)_4—O—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a methyl group;

$R^9$ is selected from a methyl group and an ethyl group;

$R^{22}$ is independently selected from a methyl group, an ethyl group, a hydroxyethyl group, a $—(CH_2)_2$-morpholino group, a trifluoromethyl group and a cyclopropyl group;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A2)

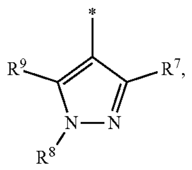

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom, a fluorine atom and a chlorine atom;

$R^3$ is a hydrogen atom;

$R^4$ is selected from naphthyl and 6-fluoro-naphth-1-yl;

L is a group $—(CH_2)_3—O—$;

$R^5$ is a COOH group;

$—R^6$-$R^7—$ is $^{\#}—(CH_2)_4—O—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a methyl group;

$R^9$ is selected from a methyl group and an ethyl group;

$R^{22}$ is independently selected from methyl group, an ethyl group, a hydroxyethyl group, a trifluoromethyl group, a cyclopropyl group and a $—(CH_2)_2$-morpholino group;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A1)

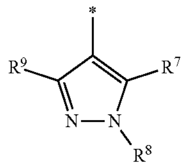

or (A2)

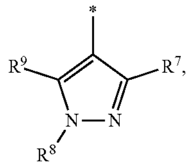

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is selected from naphthyl and 6-fluoro-naphth-1-yl;

L is a group $-(CH_2)_3-O-$;

$R^5$ is a COOH group;

$-R^6-R^7-$ is $^{\#}-(CH_2)_4-O-CH(CH_3)-^{\#\#}$, $^{\#}-(CH_2)_4-O-CH[(CH_2)_2$-morpholino]-$^{\#\#}$, $^{\#}-(CH_2)_4-O-CH[(CH_2)_2-$N-methylpiperazino]-$^{\#\#}$, $^{\#}-(CH_2)_4-O-CH[(CH_2)_2$-pyrrolidino]-$^{\#\#}$, $^{\#}-(CH_2)_4-O-CH$(cyclopropyl)-$^{\#\#}$, $^{\#}-(CH_2)_4-O-CH[(CH_2)_2$-cyclopropyl]-$^{\#\#}$, $^{\#}-(CH_2)_4-O-CH[(CH_2)_2-O-CH_3]-^{\#\#}$, $^{\#}-(CH_2)_4-O-CH[(CH_2)_2-OH]-^{\#\#}$, $^{\#}-(CH_2)_4-O-CH(CH_2CH_3)-^{\#\#}$, or $^{\#}-(CH_2)_4-O-CH(CF_3)-^{\#\#}$; wherein $^{\#}$ is the point of attachment with the indole nitrogen atom and $^{\#\#}$ is the point of attachment with the pyrazole carbon atom bearing the $R^7$ substituent;

$R^8$ is a methyl group;

$R^9$ is selected from a methyl group and an ethyl group;

or a tautomer, or a salt thereof, or a salt of a tautomer, or a mixture of same.

In accordance with a further aspect, the present invention provides compounds of general formula (I):

wherein

A is (A1)

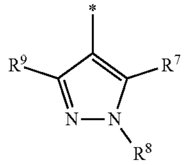

or

-continued (A2)

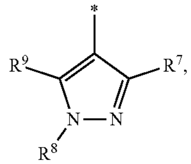

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is selected from naphthyl and 6-fluoro-naphthalin-1-yl;

L is a group $-(CH_2)_3-O-$;

$R^5$ is a COOH group;

$-R^6-R^7-$ is selected from $^{\#}-(CH_2)_4-O-CH(CH_3)-^{\#\#}$, $^{\#}-(CH_2)_4-O-CH[(CH_2)_2$-morpholino]-$^{\#\#}$, $^{\#}-(CH_2)_4-O-CH$(cyclopropyl)-$^{\#\#}$, $^{\#}-(CH_2)_4-O-CH[(CH_2)_2-OH]-^{\#\#}$, $^{\#}-(CH_2)_4-O-CH(CH_2CH_3)-^{\#\#}$ and $^{\#}-(CH_2)_4-O-CH(CF_3)-^{\#\#}$; wherein $^{\#}$ is the point of attachment with the indole nitrogen atom and $^{\#\#}$ is the point of attachment with the pyrazole carbon atom bearing the $R^7$ substituent;

$R^8$ is a methyl group;

$R^9$ is selected from a methyl group and an ethyl group;

or a tautomer, or a salt thereof, or a salt of a tautomer or a mixture of same.

In accordance with a further aspect, the present invention provides compounds of general formula (I):

wherein

A is (A2)

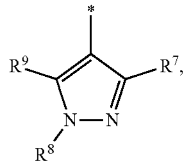

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group which is unsubstituted or substituted with a fluorine atom;

L is a group $-(CH_2)_3-O-$;

$R^5$ is a COOH group;

$-R^6-R^7-$ is $^{\#}-(CH_2)_4-O-CR^{22}R^{23}-^{\#\#}$ or $^{\#}-(CH_2)_4-NR^{15}-CR^{22}R^{23}-^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from
- a $C_3$-$C_4$-cycloalkyl group,
- a phenyl group,
- a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a heterocycloalkyl group and a phenyl group;
- whereby any heterocycloalkyl group of $R^{22}$ may optionally itself be further substituted with a $C_1$-$C_3$-alkyl group or one or two halogen atoms;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A1)

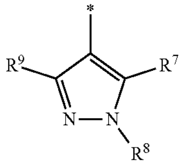

or (A2)

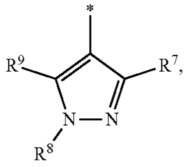

, wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is selected from naphthyl and 6-fluoro-naphth-1-yl;

L is a group $—(CH_2)_3—O—$;

$R^5$ is a COOH group;

$—R^6$-$R^7—$ is selected from $^{\#}—(CH_2)_4—O—CH(CH_3)—^{\#\#}$, $^{\#}—(CH_2)_4—O—CH[(CH_2)_2$-(oxan-4-yl)]-$^{\#\#}$, $^{\#}—(CH_2)_4—O—CH[(CH_2)_2$-morpholino]-$^{\#\#}$, $^{\#}—(CH_2)_4—O—CH[(CH_2)_2$-(4-methylpiperazin-1-yl)]-$^{\#\#}$, $^{\#}—(CH_2)_4—O—CH[(CH_2)_2$-(3,3-difluoropyrrolidin-1-yl)]-$^{\#\#}$, $^{\#}—(CH_2)_4—O—CH[(CH_2)_2$-(3-fluoroazetidin-1-yl)]-$^{\#\#}$, $^{\#}—(CH_2)_4—O—CH[(CH_2)_2$-(3,3-difluoroazetidin-1-yl)]-$^{\#\#}$, $^{\#}—(CH_2)_4—O—CH$(cyclopropyl)-$^{\#\#}$, $^{\#}—(CH_2)_4—O—CH$(phenyl)-$^{\#\#}$, $^{\#}—(CH_2)_4—O—CH(CH_2$-phenyl)-$^{\#\#}$, $^{\#}—(CH_2)_4—O—CH[(CH_2)_3$-morpholino]-$^{\#\#}$, $^{\#}—(CH_2)_4—O—CH[(CH_2)_2—OH]—^{\#\#}$, $^{\#}—(CH_2)_4—O—CH_2C(CH_3)_2(OH)—^{\#\#}$, $^{\#}—(CH_2)_4—O—(CH_2)_2C(CH_3)_2(OH)—^{\#\#}$, $^{\#}—(CH_2)_4—O—CH[(CH_2)_2—OCH_3]—^{\#\#}$, $^{\#}—(CH_2)_4—O—CH[(CH_2)_2N(CH_3)(OCH_3)]—^{\#\#}$, $^{\#}—(CH_2)_4—O—CH[(CH_2)_2N(CH_3)_2]—^{\#\#}$, $^{\#}—(CH_2)_4—O—CH(CH_2CH_3)—^{\#\#}$, from $^{\#}—(CH_2)_4—O—CH(CF_3)—^{\#\#}$, $^{\#}—(CH_2)_2—CF_2—CH_2—CH[(CH_2)_2$-morpholine], $^{\#}—(CH_2)_4—N(CH_3)—CH[(CH_2)_2$-morpholino]-$^{\#\#}$, $^{\#}—(CH_2)_4—N(CH_3)—CH[(CH_2)_2$-(oxan-4-yl)]-$^{\#\#}$,

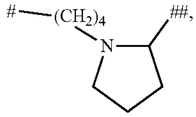

, wherein $^{\#}$ is the point of attachment with the indole nitrogen atom and $^{\#\#}$ is the point of attachment with the pyrazole carbon atom bearing the $R^7$ substituent;

$R^8$ is a methyl group;

$R^9$ is selected from a methyl group and an ethyl group;

or a tautomer, or a salt thereof, or a salt of a tautomer or a mixture of same.

In accordance with a further aspect, the present invention provides compounds of general formula (I):

wherein

A is (A1)

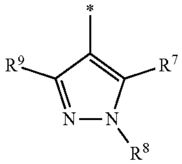

or (A2)

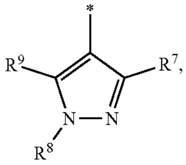

, wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and $R^3$ are each a hydrogen atom;

$R^4$ is selected from naphth-1-yl and 6-fluoro-naphth-1-yl;

L is a group $—(CH_2)_3—O—$;

$R^5$ is a COOH group;

$—R^6$-$R^7—$ is $^{\#}—(CH_2)_4—O—CR^{22}R^{23}—^{\#\#}$; wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{22}$ is independently selected from a $C_1$-$C_3$-alkyl group and a —$(CH_2)_2$-heterocycloalkyl group;

$R^{23}$ is a hydrogen atom;

or a tautomer, or a salt thereof, or a salt of a tautomer, or a mixture of same.

In accordance with a further aspect, the present invention provides compounds of general formula (I):

wherein

A is (A1)

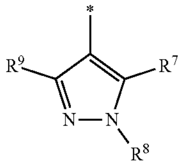

or (A2)

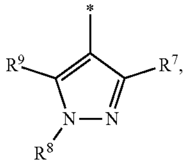

, wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a fluorine atom and a chlorine atom;

$R^2$ and $R^3$ are each a hydrogen atom;

$R^4$ is selected from naphth-1-yl and 6-fluoro-naphth-1-yl;

L is a group —$(CH_2)_3$—O—;

$R^5$ is a COOH group;

—$R^6$-$R^7$— is $^{\#}$—$(CH_2)_4$—O—CH[$(CH_2)_2$-morpholino]-$^{\#\#}$; wherein $^{\#}$ is the point of attachment with the indole nitrogen atom and $^{\#\#}$ is the point of attachment with the pyrazole carbon atom bearing the $R^7$ substituent;

$R^5$ is a methyl group;

$R^9$ is selected from a methyl group and an ethyl group;

or a tautomer, or a salt thereof, or a salt of a tautomer, or a mixture of same.

In some embodiments, the present invention includes compounds of general formula (I) selected from (rac)-2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 1), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 2), (rac)-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3-dimethyl-15-[2-(morpholin-4-yl)ethyl]-7-[3-(naphthalen-1-yloxy) propyl]-2,10,11,12,13,15-hexahydropyrazolo[4',3':9,10][1,6]oxazacycloundecino[8,7,6-hi]indole-8-carboxylic acid (stereoisomer 1), 2,3-dimethyl-15-[2-(morpholin-4-yl)ethyl]-7-[3-(naphthalen-1-yloxy) propyl]-2,10,11,12,13,15-hexahydropyrazolo[4',3':9,10][1,6]oxazacycloundecino[8,7,6-hi]indole-8-carboxylic acid (stereoisomer 2), (rac)-4-fluoro-2,3-dimethyl-15-[2-(morpholin-4-yl)ethyl]-7-[3-(naphthalen-1-yloxy) propyl]-2,10,11,12,13,15-hexahydropyrazolo[4',3':9,10][1,6]oxazacycloundecino[8,7,6-hi]indole-8-carboxylic acid, 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2)

(rac)-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-fluoro-7-{3-[(6-fluoronaphthalen-1-yl)oxy]propyl}-2,3-dimethyl-15-[2-(morpholin-4-yl)ethyl]-2,10,11,12,13,15- hexahydropyrazolo[4',3':9,10][1,6]oxazacycloundecino[8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), (−)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 2), (rac)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-Chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid, (rac)-4-Chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (+)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), (−)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 1), (−)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 2), (rac)-4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid, (15R)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt, (rac)-3-Ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-(15-rac)-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—2-hydroxypropane-1,2,3-tricarboxylic acid salt, 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid N-ethylethanamine salt (enantiomer 2), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (rac)-4-chloro-3-ethyl-7-{3-[(6-fluoronaphthalen-1-yl)oxy]propyl}-2-methyl-15-phenyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, (−)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 1 of stereoisomers), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 1), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 2), 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 2 of stereoisomers 2), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 3), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid (stereoisomer 4), (rac)-4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10]

[1,6]oxazacycloundecino[8,7,6-hi]indole-8-carboxylic acid—N-ethylethanamine salt (enantiomer 1), (−)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-{2-[methoxy(methyl)amino]ethyl}-2-methyl-2,10,11,12,13,15-hexahydropyrazolo[4',3':9,10][1,6]oxazacycloundecino[8,7,6-hi]indole-8-carboxylic acid, (rac)-4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 1), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 2), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 3), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 4), 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 3), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 4), (rac)-15-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-2,14-dimethyl-15-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid—N-ethylethanamine salt—Stereoisomer 3, (rac)-4-chloro-3-ethyl-2,14-dimethyl-15-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid—N-ethylethanamine salt—Stereoisomer 4, 4-chloro-3-ethyl-7-{3-[(6-fluoro-1-naphthyl)oxy]propyl}-2,14-dimethyl-15-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylic acid (mixture of 4 Isomers), (rac)-18-chloro-1-ethyl-2-methyl-15-[3-(1-napht (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acidhyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 1), (rac)-18-chloro-1-ethyl-2-methyl-15-[3-(1-naphthyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 2), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (+)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1), (−)-17-chloro-1-ethyl-14-{3-[(6-fluoronaphthalen-1-yl)oxy]propyl}-2-methyl-3b,4,5,6,8,9,10,11-octahydro-2H- pyrazolo[3',4':8,9]pyrrolo[1',2':6,7][1,6]diazacycloundecino[10,11,1-hi]indole-13-carboxylic acid (enantiomer 2), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1) and (rac)-4-chloro-3-ethyl-15-[2-(rac)-(3-fluoroazetidin-1-yl)ethyl]-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid or a tautomer, or a salt thereof, or a salt of a tautomer, or a mixture of same.

In some embodiments, the present invention includes compounds of general formula (I) selected from the below list of selected compounds (+)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), (−)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 1), (−)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 2), (rac)-4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid, (15R)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt, (rac)-3-Ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-(15-rac)-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—2-hydroxypropane-1,2,3-tricarboxylic acid salt, 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid N-ethylethanamine salt (enantiomer 2), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (rac)-4-chloro-3-ethyl-7-{3-[(6-fluoronaphthalen-1-yl)oxy]propyl}-2-methyl-15-phenyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, (−)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 1 of stereoisomers), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 1), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 2), 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 2 of stereoisomers 2), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 3), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid (stereoisomer 4), (rac)-4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-{2-[methoxy(methyl)amino]ethyl}-2-methyl-2,10,11,12,13,15-hexahydropyrazolo[4',3':9,10][1,6]oxazacycloundecino[8,7,6-hi]indole-8-carboxylic acid, (rac)-4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 1), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 2), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 3), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 4), 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 3), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 4), (rac)-15-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-2,14-dimethyl-15-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid—N-ethylethanamine salt—Stereoisomer 3, (rac)-4-chloro-3-ethyl-2,14-dimethyl-15-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid—N-ethylethanamine salt—Stereoisomer 4, 4-chloro-3-ethyl-7-{3-[(6-fluoro-1-naphthyl)oxy]propyl}-2,14-dimethyl-15-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylic acid (mixture of 4 Isomers), (rac)-18-chloro-1-ethyl-2-methyl-15-[3-(1-napht (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acidhyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 1), (rac)-18-chloro-1-ethyl-2-methyl-15-[3-(1-naphthyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 2), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (+)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1), (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (enantiomer 2), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1) and (rac)-4-chloro-3-ethyl-15-[2-(rac)-(3-fluoroazetidin-1-yl)ethyl]-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid or a tautomer, or a salt thereof, or a salt of a tautomer, or a mixture of same.

In some embodiments, the present invention includes compounds of general formula (I) selected from the below list of selected compounds (rac)-2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 1), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 2), (rac)-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (stereoisomer 1), 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (stereoisomer 2), (rac)-4-fluoro-2,3-dimethyl-15-[2-(morpholin-4-yl)ethyl]-7-[3-(naphthalen-1-yloxy) propyl]-2,10,11,12,13,15-hexahydropyrazolo[4',3':9,10][1,6]oxazacycloundecino[8,7,6-hi]indole-8-carboxylic acid, 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), (−)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 2), (rac)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-15-(2- hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-Chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid, (rac)-4-Chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (+)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), (−)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 1), (−)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 2), (rac)-4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 2), (−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid, (15R)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt, (rac)-3-Ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1) and (−)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2)

or a tautomer, or a salt thereof, or a salt of a tautomer, or a mixture of same.

In some embodiments, the present invention includes compounds of general formula (I) selected from the below list of selected compounds (rac)-4-fluoro-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-fluoro-7-{3-[(6-fluoronaphthalen-1-yl)oxy]propyl}-2,3-dimethyl-15-[2-(morpholin-4-yl)ethyl]-2,10,11,12,13,15- hexahydropyrazolo[4',3':9,10][1,6]oxazacycloundecino [8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino [8,7,6-hi]indole-8-carboxylic acid (enantiomer 2), (rac)-4-chloro-3-ethyl-7-{3-[(6-fluoronaphthalen-1-yl)oxy] propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy] propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), (−)-4-chloro-3-ethyl-7-{3-[(6-fluoronaphthalen-1-yl)oxy] propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 2), (rac)-4-chloro-3-ethyl-7-{3-[(6-fluoronaphthalen-1-yl)oxy] propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy] propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy] propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-3-ethyl-7-{3-[(6-fluoronaphthalen-1-yl)oxy] propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid, (15R)-4-chloro-3-ethyl-7-{3-[(6-fluoronaphthalen-1-yl) oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt, (rac)-3-Ethyl-4-fluoro-7-{3-[(6-fluoronaphthalen-1-yl)oxy] propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-3-ethyl-4-fluoro-7-{3-[(6-fluoronaphthalen-1-yl)oxy] propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-3-ethyl-4-fluoro-7-{3-[(6-fluoronaphthalen-1-yl)oxy] propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy] propyl}-(15-rac)-(2-hydroxy-2-methylpropyl)-2-methyl-2,10,11,12,13,15-hexahydropyrazolo[4',3':9,10][1,6] oxazacycloundecino[8,7,6-hi]indole-8-carboxylic acid, (+)-4-chloro-3-ethyl-7-{3-[(6-fluoronaphthalen-1-yl)oxy] propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy] propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoropyrrolidin-1-yl) ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—2-hydroxypropane-1,2,3-tricarboxylic acid salt, 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid N-ethylethanamine salt (enantiomer 2), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (rac)-4-chloro-3-ethyl-7-{3-[(6-fluoronaphthalen-1-yl)oxy] propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino [8,7,6-hi]indole-8-carboxylic acid (enantiomer 1), (−)-4-chloro-3-ethyl-7-{3-[(6-fluoronaphthalen-1-yl)oxy] propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy] propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 1)

(−)-4-chloro-3-ethyl-7-{3-[(6-fluoronaphthalen-1-yl)oxy] propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy] propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy] propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, (−)-4-chloro-3-ethyl-7-{3-[(6-fluoronaphthalen-1-yl)oxy] propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-(15-rac)-[2-(4-methylpiperazin-1-yl) ethyl]-2,10,11,12,13,15-hexahydropyrazolo[4',3':9,10][1,6]oxazacycloundecino[8,7,6-hi]indole-8-carboxylic acid—N-ethylethanamine salt (mixture 1 of stereoisomers), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 1), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 2), 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 2 of stereoisomers 2), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 3), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid (stereoisomer 4), (rac)-4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-{2-[methoxy(methyl)amino]ethyl}-2-methyl-2,10,11,12,13,15-hexahydropyrazolo[4',3':9,10][1,6]oxazacycloundecino[8,7,6-hi]indole-8-carboxylic acid, 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-,hexahydropyrazolo[4',3':9,10][1,6]oxazacycloundecino[8,7,6-hi]indole-8-carboxylic acid (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 3), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 4), (rac)-15-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoro-1-naphthyl)oxy]propyl}-2,14-dimethyl-15-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylic acid (mixture of 4 Isomers), (rac)-18-chloro-1-ethyl-2-methyl-15-[3-(1-napht (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acidhyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 1) and (rac)-18-chloro-1-ethyl-2-methyl-15-[3-(1-naphthyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 2)

or a tautomer, or a salt thereof, or a salt of a tautomer, or a mixture of same.

In some embodiments, the present invention includes compounds of general formula (I) selected from the below list of selected compounds (rac)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (+)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), (−)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoronaphthalen-1-yl)oxy]propyl}-2-methyl-15-phenyl-2,10,11,12,13,15-hexahydropyrazolo[4',3':9,10][1,6]oxazacycloundecino[8,7,6-hi]indole-8-carboxylic acid, (rac)-4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 1), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 2), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 3), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 4), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid and (+)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid or a tautomer, or a salt thereof, or a salt of a tautomer, or a mixture of same.

In some embodiments, the present invention includes compounds of general formula (I) selected from the below list of selected compounds (rac)-4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 2), (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1), (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (enantiomer 2) and (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1)

or a tautomer, or a salt thereof, or a salt of a tautomer, or a mixture of same.

In some embodiments, the present invention includes compounds of general formula (I) selected from the below list of selected compounds (rac)-2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 1), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 2), (rac)-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (stereoisomer 1), 2,3-dimethyl-15-[2-(morpholin-4-yl)ethyl]-7-[3-(naphthalen-1-yloxy) propyl]-2,10,11,12,13,15-hexahydropyrazolo[4',3':9,10][1,6]oxazacycloundecino[8,7,6-hi]indole-8-carboxylic acid (stereoisomer 2), (rac)-4-fluoro-2,3-dimethyl-15-[2-(morpholin-4-yl)ethyl]-7-[3-(naphthalen-1-yloxy) propyl]-2,10,11,12,13,15-hexahydropyrazolo[4',3':9,10][1,6]oxazacycloundecino[8,7,6-hi]indole-8-carboxylic acid, 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), (−)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 2), (rac)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-Chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid and (rac)-4-Chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid or a tautomer, or a salt thereof, or a salt of a tautomer, or a mixture of same.

In some embodiments, the present invention includes compounds of general formula (I) selected from:

4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1) and (+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1)

or a tautomer, or a salt thereof, or a salt of a tautomer, or a mixture of same.

In some embodiments, the present invention includes compounds of general formula (I) selected from:

4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15- hexahydropyrazolo[4',3':9,10][1,6]oxazacycloundecino[8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1)

(+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1) and (+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid or a tautomer, or a salt thereof, or a salt of a tautomer, or a mixture of same.

In some embodiments, the present invention includes compounds of general formula (I) selected from:

4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), (+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1) and (+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid or a tautomer, or a salt thereof, or a salt of a tautomer, or a mixture of same.

In some embodiments, the present invention includes compounds of general formula (I) selected from:

4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer1) and 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1)

or a tautomer, or a salt thereof, or a salt of a tautomer, or a mixture of same.

In some embodiments, the present invention includes intermediate compounds 1-208 as well as their use for the preparation of compounds of general formula (I).

In some embodiments, the present invention includes intermediate compounds 1-74 as well as their use for the preparation of compounds of general formula (I).

In some embodiments, the present invention includes intermediate compounds 74-208 as well as their use for the preparation of compounds of general formula (I).

In some embodiments, the present invention includes all compounds of general formula (I) as disclosed in the example section, starting from example 1 and ending up with example 28, or a tautomer, an N-oxide, or a salt thereof, or a salt of a tautomer, or a salt of an N-oxide, or a mixture of same.

In some embodiments, the present invention includes all compounds of general formula (I) as disclosed in the example section, starting from example 1 and ending up with example 108, or a tautomer, an N-oxide, or a salt thereof, or a salt of a tautomer, or a salt of an N-oxide, or a mixture of same.

In some embodiments, the present invention includes all compounds of general formula (I) as disclosed in the example section, starting from example 29 and ending up with example 108, or a tautomer, an N-oxide, or a salt thereof, or a salt of a tautomer, or a salt of an N-oxide, or a mixture of same.

In some embodiments, the present invention includes compounds of formula (I), supra, in which $R^1$, $R^2$ and $R^3$ are each selected from a hydrogen atom, a halogen atom and a $C_1$-$C_3$-alkyl group, or a tautomer, an N-oxide, or a salt thereof, or a salt of a tautomer, or a salt of an N-oxide, or a mixture of same.

In some embodiments, the present invention includes compounds of formula (I), supra, in which $R^1$ and $R^2$ are each independently selected from a hydrogen atom, a halogen atom, a cyano group, a $C_1$-$C_3$-alkyl group and a $C_1$-$C_3$-alkoxy group or a tautomer, an N-oxide, or a salt thereof, or a salt of a tautomer, or a salt of an N-oxide, or a mixture of same.

In some embodiments, the present invention includes compounds of formula (I), supra, in which $R^1$ and $R^2$ are each independently selected from a hydrogen atom and a halogen atom or a tautomer, an N-oxide, or a salt thereof, or a salt of a tautomer, or a salt of an N-oxide, or a mixture of same.

In some embodiments, the present invention includes compounds of formula (I), supra, in which $R^1$ and $R^2$ are each independently selected from a hydrogen atom, a fluorine atom and a chlorine atom or a tautomer, an N-oxide, or a salt thereof or a salt of a tautomer or a salt of an N-oxide or a mixture of same.

In some embodiments, the present invention includes compounds of formula (I), supra, in which $R^1$ is selected from a hydrogen atom, fluorine atom and a chlorine atom; and $R^2$ and $R^3$ are each a hydrogen atom; or a tautomer, an N-oxide, or a salt thereof or a salt of a tautomer or a salt of an N-oxide or a mixture of same.

In some embodiments, the present invention includes compounds of formula (I), supra, in which $R^1$ is a halogen atom or a tautomer, an N-oxide, or a salt thereof, or a salt of a tautomer, or a salt of an N-oxide, or a mixture of same.

In some embodiments, the present invention includes compounds of formula (I), supra, in which $R^1$ is a chlorine atom or a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^1$ is a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —$S(O)_2$—($C_1$-$C_3$-alkyl) group, a $C_1$-$C_3$-haloalkoxy group, a $C_1$-$C_3$-haloalkylthio group and a $C_3$-$C_5$-cycloalkyl group or a tautomer, an N-oxide, or a salt thereof, or a salt of a tautomer, or a salt of an N-oxide, or a mixture of same.

In some embodiments, the present invention includes compounds of formula (I), supra, in which $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group or a tautomer, an N-oxide, or a salt thereof, or a salt of a tautomer, or a salt of an N-oxide, or a mixture of same.

In some embodiments, the present invention includes compounds of formula (I), supra, in which $R^3$ is a hydrogen atom or a tautomer, an N-oxide, or a salt thereof or a salt of a tautomer or a salt of an N-oxide or a mixture of same.

In some embodiments, the present invention includes compounds of formula (I), supra, in which $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group; or a tautomer, an N-oxide, or a salt thereof or a salt of a tautomer or a salt of an N-oxide or a mixture of same.

In some embodiments, the present invention includes compounds of formula (I), supra, in which $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group; or a tautomer, an N-oxide, or a salt thereof or a salt of a tautomer or a salt of an N-oxide or a mixture of same.

In other embodiments, the present invention includes compounds of formula (I), supra, in which $R^4$ is selected from an aryl group and a heteroaryl group, each of which is unsubstituted or substituted with one, two or three substituents and each substituent is independently selected from a halogen atom and a $C_1$-$C_3$-alkyl group; or a tautomer, an N-oxide, or a salt thereof or a salt of a tautomer or a salt of an N-oxide or a mixture of same.

In other embodiments, the present invention includes compounds of formula (I), supra, in which $R^4$ is selected from an aryl group and a heteroaryl group, each of which is unsubstituted or substituted with one or two substituents and each substituent is independently selected from a halogen atom and a $C_1$-$C_3$-alkyl group or a tautomer, an N-oxide, or a salt thereof or a salt of a tautomer or a salt of an N-oxide or a mixture of same.

In other embodiments, the present invention provides compounds of formula (I), supra, in which $R^4$ is selected from naphthyl group which is unsubstituted or substituted with a fluorine atom or a chlorine atom or a tautomer, an N-oxide, or a salt thereof, or a salt of a tautomer, or a salt of an N-oxide, or a mixture of same.

In other embodiments, the present invention provides compounds of formula (I), supra, in which $R^4$ is selected from naphthyl group which is unsubstituted or substituted with a fluorine atom or a tautomer, an N-oxide, or a salt thereof, or a salt of a tautomer, or a salt of an N-oxide, or a mixture of same.

In other embodiments, the present invention provides compounds of formula (I), supra, in which $R^4$ is selected from naphth-1-yl group and 6-fluoro-naphth-1-yl group or a tautomer, an N-oxide, or a salt thereof, or a salt of a tautomer, or a salt of an N-oxide, or a mixture of same.

In other embodiments, the present invention provides compounds of formula (I), supra, in which $R^4$ is a naphth-1-yl group or a tautomer, an N-oxide, or a salt thereof, or a salt of a tautomer, or a salt of an N-oxide, or a mixture of same.

In other embodiments, the present invention provides compounds of formula (I), supra, in which $R^4$ is a 6-fluoro-naphth-1-yl group or a tautomer, an N-oxide, or a salt thereof, or a salt of a tautomer, or a salt of an N-oxide, or a mixture of same.

In other embodiments, the present invention includes compounds of formula (I), supra, in which L is a group —$(CH_2)_m$-E- which is optionally substituted with one or two substituents and each substituent is independently selected from a halogen atom, a cyano group, a hydroxy group, a $C_1$-$C_3$-alkyl group and a $C_1$-$C_3$-alkoxy group, or two substituents are taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —$S(O)_2$— group and a —$NR^{14}$— group or a tautomer, an N-oxide, or a salt thereof, or a salt of a tautomer, or a salt of an N-oxide, or a mixture of same.

In other embodiments, the present invention includes compounds of formula (I), supra, in which L is a group —$(CH_2)_m$-E- which is optionally substituted with one or two substituents and each substituent is independently selected from a halogen atom, a hydroxy group, a $C_1$-$C_3$-alkyl group and a $C_1$-$C_3$-alkoxy group, or two substituents are taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —$S(O)_2$— group and a —$NR^{14}$— group, or a tautomer, an N-oxide, or a salt thereof, or a salt of a tautomer, or a salt of an N-oxide, or a mixture of same.

In other embodiments, the present invention includes compounds of formula (I), supra, in which L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group or a tautomer, an N-oxide, or a salt thereof, or a salt of a tautomer, or a salt of an N-oxide, or a mixture of same.

In other embodiments, the present invention includes compounds of formula (I), supra, in which L is a group —$(CH_2)_m$-E- or a tautomer, an N-oxide, or a salt thereof, or a salt of a tautomer, or a salt of an N-oxide, or a mixture of same.

In other embodiments, the present invention includes compounds of formula (I), supra, in which L is a group —$(CH_2)_m$-E- and m is 2, 3, or 4 or a tautomer, an N-oxide, or a salt thereof, or a salt of a tautomer, or a salt of an N-oxide, or a mixture of same.

In other embodiments, the present invention includes compounds of formula (I), supra, in which L is a group $—(CH_2)_m$-E- and m is 3 or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group $—(CH_2)_m$-E-, or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group $—(CH_2)_m$-E-, E is oxygen or $NR^{15}$ and m is 3 or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group $—(CH_2)_m$-E-, E is oxygen and m is 3. or a tautomer, an N-oxide, or a salt thereof, or a salt of a tautomer, or a salt of an N-oxide, or a mixture of same.

In other embodiments, the present invention includes compounds of formula (I), supra, in which L is a group $—(CH_2)_3—O—$ or a tautomer, an N-oxide, or a salt thereof, or a salt of a tautomer, or a salt of an N-oxide, or a mixture of same.

In further embodiments the present invention includes compounds of formula (I), supra, in which E is an oxygen atom, or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group $—(CH_2)_m$-E- and E is an oxygen atom or a tautomer, an N-oxide, or a salt thereof, or a salt of a tautomer, or a salt of an N-oxide, or a mixture of same.

In yet further embodiments, the present invention includes compounds of formula (I), supra, in which $R^5$ is a COOH group, a

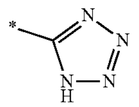

group, a $—C(O)—NHS(O)_2(C_1\text{-}C_6\text{-alkyl})$ group, a $—C(O)—NHS(O)_2(C_3\text{-}C_6\text{-cycloalkyl})$ group, a $—C(O)—NHS(O)_2(\text{aryl})$ group, a $—C(O)—NHS(O)_2(CH_2)_2NHCO(C_1\text{-}C_6\text{-alkyl})$ group, a $—C(O)—NHS(O)_2(CH_2)_2NHCO(C_3\text{-}C_6\text{-cycloalkyl})$ group or a $—C(O)—NHS(O)_2(CH_2)_2NHCO(\text{aryl})$ group, or a tautomer, an N-oxide, or a salt thereof, or a salt of a tautomer, or a salt of an N-oxide, or a mixture of same.

In further embodiments, the present invention includes compounds of formula (I), supra, in $R^5$ is a COOH group, or a

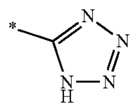 [SMILES: *c1nnn[nH]1]

group, or a tautomer, an N-oxide, or a salt thereof, or a salt of a tautomer, or a salt of an N-oxide, or a mixture of same.

In further embodiments, the present invention includes compounds of formula (I), supra, in $R^5$ is a COOH group, or a tautomer, an N-oxide, or a salt thereof, or a salt of a tautomer, or a salt of an N-oxide, or a mixture of same.

In other embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_2\text{-}C_9\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups are unsubstituted or substituted with one or more substituents independently selected from a halogen atom, a hydroxy group, a $NR^{16}R^{17}$ group, a $C_1\text{-}C_3$-alkyl group, a $C_1\text{-}C_3$-haloalkyl group, a $C_1\text{-}C_3$-alkoxy group, a $C_1\text{-}C_3$-haloalkoxy group, a $C_3\text{-}C_6$-cycloalkyl group and a (heterocycloalkyl)-($C_1\text{-}C_3$-alkylene)- group, or a tautomer, an N-oxide, or a salt thereof, or a salt of a tautomer, or a salt of an N-oxide, or a mixture of same.

In further embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_2\text{-}C_6\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups are unsubstituted or substituted with one or more substituents independently selected from a halogen atom, a hydroxy group, a $NR^{16}R^{17}$ group, a $C_1\text{-}C_3$-alkyl group, a $C_1\text{-}C_3$-haloalkyl group, a $C_1\text{-}C_3$-alkoxy group, a $C_1\text{-}C_3$-haloalkoxy group, or a tautomer, an N-oxide, or a salt thereof, or a salt of a tautomer, or a salt of an N-oxide, or a mixture of same.

In further embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_3\text{-}C_6\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups are unsubstituted or substituted with one or more substituents independently selected from a halogen atom, a hydroxy group, a $NR^{16}R^{17}$ group, a $C_1\text{-}C_3$-alkyl group, a $C_1\text{-}C_3$-haloalkyl group, a $C_1\text{-}C_3$-alkoxy group, a $C_1\text{-}C_3$-haloalkoxy group, or a tautomer, an N-oxide, or a salt thereof, or a salt of a tautomer, or a salt of an N-oxide, or a mixture of same.

In other embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_3\text{-}C_5\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups may be unsubstituted or substituted with one or more substituents independently selected from a halogen atom or a tautomer, or a salt thereof, or a salt of a tautomer, or a mixture of same.

In other embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_3\text{-}C_4\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent; and wherein one or more $—CH_2—$ groups are unsubstituted or substituted with one or more substituents independently selected from a halogen atom or a tautomer, or a salt thereof, or a salt of a tautomer, or a mixture of same.

In other embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_3\text{-}C_4\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent or a tautomer, or a salt thereof, or a salt of a tautomer, or a mixture of same.

In other embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_3\text{-}C_4\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent and wherein one or more $—CH_2—$ groups may be unsubstituted or a tautomer, or a salt thereof or a salt of a tautomer or a salt of an N-oxide or a mixture of same.

In other embodiments, the present invention includes compounds of formula (I), supra, in which $—R^6\text{-}R^7—$ is $^{\#}—(CH_2)_n—(B)_t—CR^{22}R^{23}—^{\#\#}$ or $^{\#}—(C_3\text{-}C_4\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent and wherein one or more $—CH_2—$ groups are substituted with one or more substituents independently selected from a halogen atom or a tautomer, or a salt thereof or a salt of a tautomer or a salt of an N-oxide or a mixture of same.

In other embodiments, the present invention includes compounds of formula (I), supra, in which $—R^6\text{-}R^7—$ is $^{\#}—(CH_2)_4—O—CR^{22}R^{23}—^{\#\#}$ or $^{\#}—(CH_2)_4—NR^{15}—CR^{22}R^{23}—^{\#\#}$, or a tautomer, an N-oxide, or a salt thereof, a salt of an N-oxide, or a salt of a tautomer or a mixture of same.

In other embodiments, the present invention includes compounds of formula (I), supra, in which $—R^6\text{-}R^7—$ is $^{\#}—(CH_2)_4—O—CR^{22}R^{23}—^{\#\#}$ or a tautomer, an N-oxide, or a salt thereof or a salt of a tautomer, a salt of an N-oxide, or a mixture of same.

In other embodiments, the present invention includes compounds of formula (I), supra, in which $—R^6\text{-}R^7—$ is $^{\#}—(C_2\text{-}C_9\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent or a tautomer, or a salt thereof, or a salt of a tautomer, or a mixture of same.

In other embodiments, the present invention includes compounds of formula (I), supra, in which $—R^6\text{-}R^7—$ is $^{\#}—(C_2\text{-}C_9\text{-alkenylene})\text{-}(B)_t—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent and wherein one or more $—CH_2—$ groups may be unsubstituted or substituted with one or more substituents independently selected from a halogen atom or a tautomer, an N-oxide, or a salt thereof, or a salt of a tautomer, or a salt of an N-oxide, or a mixture of same.

In other embodiments, the present invention includes compounds of formula (I), supra, in which $—R^6\text{-}R^7—$ is $^{\#}—(CH_2)_4—N(R^{15})—CR^{22}R^{23}—^{\#\#}$ or a tautomer, an N-oxide or a salt thereof, or a salt of a tautomer, a salt of an N-oxide or a mixture of same.

In other embodiments, the present invention includes compounds of formula (I), supra, in which $—R^6\text{-}R^7—$ is $^{\#}—(CH_2)_4—N(R^{15})—CR^{22}R^{23}—^{\#\#}$ or a tautomer, or a salt thereof, or a salt of a tautomer, or a mixture of same.

In other embodiments, the present invention includes compounds of formula (I), supra, in which $—R^6\text{-}R^7—$ is $^{\#}—(CH_2)_4—N(R^{15})—CR^{22}R^{23}—^{\#\#}$, wherein $^{\#}$ is the point of attachment with the indole nitrogen atom and $^{\#\#}$ is the point of attachment with the pyrazole carbon atom bearing the $R^7$ substituent and wherein one or more $—CH_2—$ groups may be unsubstituted or substituted with one or more substituents independently selected from a halogen atom or a tautomer, or a salt thereof, or a salt of a tautomer, or a mixture of same.

In other embodiments, the present invention includes compounds of formula (I), supra, in which $—R^6\text{-}R^7—$ is selected from $^{\#}—(CH_2)_4—O—CH(CH_3)—^{\#\#}$, $^{\#}—(CH_2)_4—O—CH[(CH_2)_2\text{-morpholino}]\text{-}^{\#\#}$, $^{\#}—(CH_2)_4—O—CH[(CH_2)_2—N\text{-methylpiperazino}]\text{-}^{\#\#}$, $^{\#}—(CH_2)_4—O—CH[(CH_2)_2\text{-pyrrolidino}]\text{-}^{\#\#}$, $^{\#}—(CH_2)_4—O—CH[(CH_2)_2\text{-cyclopropyl}]\text{-}^{\#\#}$, $^{\#}—(CH_2)_4—O—CH(\text{cyclopropyl})\text{-}^{\#\#}$, $^{\#}—(CH_2)_4—O—CH[(CH_2)_2—O—CH_3]—^{\#\#}$, $^{\#}—(CH_2)_4—O—CH[(CH_2)_2—OH]—^{\#\#}$, $^{\#}—(CH_2)_4—O—CH(CH_2CH_3)—^{\#\#}$, and $^{\#}—(CH_2)_4—O—CH(CF_3)—^{\#\#}$, or a tautomer, or a salt thereof, or a salt of a tautomer, or a mixture of same.

In other embodiments, the present invention includes compounds of formula (I), supra, in which $—R^6\text{-}R^7—$ is selected from $^{\#}—(CH_2)_4—O—CH(CH_3)—^{\#\#}$, $^{\#}—(CH_2)_4—O—CH[(CH_2)_2\text{-morpholino}]\text{-}^{\#\#}$, $^{\#}—(CH_2)_4—O—CH(\text{cyclopropyl})\text{-}^{\#\#}$, $^{\#}—(CH_2)_4—O—CH[(CH_2)_2—OH]—^{\#\#}$, $^{\#}—(CH_2)_4—O—CH(CH_2CH_3)—^{\#\#}$, and $^{\#}—(CH_2)_4—O—CH(CF_3)—^{\#\#}$, or a tautomer, or a salt thereof, or a salt of a tautomer, or a mixture of same.

In other embodiments, the present invention includes compounds of formula (I), supra, in which $—R^6\text{-}R^7—$ is selected from $^{\#}—(CH_2)_4—O—CH(CH_3)—^{\#\#}$, $^{\#}—(CH_2)_4—O—CH[(CH_2)_2\text{-(oxan-4-yl)}]\text{-}^{\#\#}$, $^{\#}—(CH_2)_4—O—CH[(CH_2)_2\text{-morpholino}]\text{-}^{\#\#}$, $^{\#}—(CH_2)_4—O—CH[(CH_2)_2\text{-(4-methylpiperazin-1-yl)}]\text{-}^{\#\#}$, $^{\#}—(CH_2)_4—O—CH[(CH_2)_2\text{-(3,3-difluoropyrrolidin-1-yl)}]\text{-}^{\#\#}$, $^{\#}—(CH_2)_4—O—CH[(CH_2)_2\text{-(3-fluoroazetidin-1-yl)}]\text{-}^{\#\#}$, $^{\#}—(CH_2)_4—O—CH[(CH_2)_2\text{-(3,3-difluoroazetidin-1-yl)}]\text{-}^{\#\#}$, $^{\#}—(CH_2)_4—O—CH(\text{cyclopropyl})\text{-}^{\#\#}$, $^{\#}—(CH_2)_4—O—CH(\text{phenyl})\text{-}^{\#\#}$, $^{\#}—(CH_2)_4—O—CH(CH_2\text{-phenyl})\text{-}^{\#\#}$, $^{\#}—(CH_2)_4—O—CH[(CH_2)_3\text{-morpholino}]\text{-}^{\#\#}$, $^{\#}—(CH_2)_4—O—CH[(CH_2)_2—OH]—^{\#\#}$, $^{\#}—(CH_2)_4—O—CH_2C(CH_3)_2(OH)—^{\#\#}$, $^{\#}—(CH_2)_4—O—(CH_2)_2C(CH_3)_2(OH)—^{\#\#}$, $^{\#}—(CH_2)_4—O—CH[(CH_2)_2—OCH_3]—^{\#\#}$, $^{\#}—(CH_2)_4—O—CH[(CH_2)_2N(CH_3)(OCH_3)]—^{\#\#}$, $^{\#}—(CH_2)_4—O—CH[(CH_2)_2N(CH_3)_2]—^{\#\#}$, $^{\#}—(CH_2)_4—O—CH(CH_2CH_3)—^{\#\#}$, $^{\#}—(CH_2)_4—O—CH(CF_3)—^{\#\#}$, $^{\#}—(CH_2)_2—CF_2—CH_2—CH[(CH_2)_2\text{-morpholino}]$, $^{\#}—(CH_2)_4—N(CH_3)—CH[(CH_2)_2\text{-morpholino}]\text{-}^{\#\#}$, $^{\#}—(CH_2)_4—N(CH_3)—CH[(CH_2)_2\text{-(oxan-4-yl)}]\text{-}^{\#\#}$,

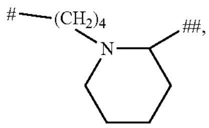

, and

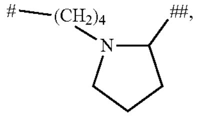

, or a tautomer, or a salt thereof, or a salt of a tautomer, or a mixture of same.

In other embodiments, the present invention includes compounds of formula (I), supra, in which $—R^6-R^{10}$ is $^{\#}—(CH_2)_n—(B)_t—CR^{22}R^{23}—^{\#\#}$ or $^{\#}—(C_2-C_9\text{-alkenylene})-(B)_t—CR^{22}R^{23}—^{\#\#}$, where one or more $—CH_2—$ groups are substituted with one or more substituents independently selected from a halogen atom, a hydroxy group, a $NR^{16}R^{17}$ group, a $C_1-C_3$-alkyl group, a $C_1-C_3$-haloalkyl group, a $C_1-C_3$-alkoxy group and a $C_1-C_3$-haloalkoxy group, wherein $^{\#}$ is the point of attachment with the indole nitrogen atom and $^{\#\#}$ is the point of attachment with the carbon atom of the phenyl moiety bearing the $R^{10}$ substituent;

or a tautomer, an N-oxide, or a salt thereof, or a salt of a tautomer, or a salt of an N-oxide, or a mixture of same.

In further embodiments, the present invention includes compounds of formula (I), supra, in which n is 2, 3, 4, 5, 6, 7, 8, or 9, if B is selected from —O—, —S—, —S(O)— and $—S(O)_2—$, $NR^{15}$ and n is 1, 2, 3, 4, 5, 6, 7, 8 if B is selected from $—C(O)NR^{15}—$ group, and a $—NR^{15}C(O)—$ group and n is 0, 1, 2, 3, 4, 5, 6 or 7 if B is selected from a $—N(R^{15})—C(=O)—N(R^{15})—$ group, a $—O—C(=O)—N(R^{15})—$ group and a $—N(R^{15})—C(=O)—O—$ group; or a tautomer, an N-oxide, or a salt thereof, or a salt of a tautomer, or a salt of an N-oxide, or a mixture of same.

In further embodiments, the present invention includes compounds of formula (I), supra, in which n is 2, 3, 4, 5 or 6 if B is selected from —O—, —S—, —S(O)—, $—S(O)_2—$ and $—N(R^{15})—$ and n is 1, 2, 3, 4, or 5, if B is selected from $—C(O)NR^{15}—$ group, and a $—NR^{15}C(O)—$ group and n is 0, 1, 2, 3, or 4 if B is selected from a $—N(R^{15})—C(=O)—N(R^{15})—$ group, a $—O—C(=O)—N(R^{15})—$ group and a $—N(R^{15})—C(=O)—O—$ group; and t is 1 or a tautomer, an N-oxide, or a salt thereof, or a salt of a tautomer, or a salt of an N-oxide, or a mixture of same.

In further embodiments, the present invention includes compounds of formula (I), supra, in which n is 2, 3, 4, 5, 6, 7, 8, or 9; and t is 1 or a tautomer, an N-oxide, or a salt thereof, or a salt of a tautomer, or a salt of an N-oxide, or a mixture of same.

In further embodiments, the present invention includes compounds of formula (I), supra, in which n is 2, 3, 4, 5 or 6; and t is 1 or a tautomer, an N-oxide, or a salt thereof, or a salt of a tautomer, or a salt of an N-oxide, or a mixture of same.

In further embodiments, the present invention includes compounds of formula (I), supra, in which n is 3, 4 or 5; and t is 1 or a tautomer, an N-oxide, or a salt thereof, or a salt of a tautomer, or a salt of an N-oxide, or a mixture of same.

In further embodiments, the present invention includes compounds of formula (I), supra, in which n is 4 or 5; and t is 1 or a tautomer, an N-oxide, or a salt thereof, or a salt of a tautomer, or a salt of an N-oxide, or a mixture of same.

In further embodiments, the present invention includes compounds of formula (I), supra, in which n is 4 and t is 1 or a tautomer, an N-oxide, or a salt thereof, or a salt of a tautomer, or a salt of an N-oxide, or a mixture of same.

In further embodiments, the present invention includes compounds of formula (I), supra, in which B is independently selected from a $—C(O)NR^{15}—$ group, a $—NR^{15}C(O)—$ group, a $—N(R^{15})—$ group, a $—N(R^{15})—C(=O)—N(R^{15})—$ group, a $—O—C(=O)—N(R^{15})—$ group, a $—N(R^{15})—C(=O)—O—$ group, —O—, —S—, —S(O)— and $—S(O)_2—$, or a tautomer, an N-oxide, or a salt thereof, or a salt of a tautomer, or a salt of an N-oxide, or a mixture of same.

In further embodiments, the present invention includes compounds of formula (I), supra, in which is independently selected from a $—N(R^{15})—$ group and —O—, or a tautomer, or a salt thereof, or a salt of a tautomer, or a mixture of same.

In further embodiments, the present invention includes compounds of formula (I), supra, in which B is an oxygen atom or a tautomer, or a salt thereof, or a salt of a tautomer, or a mixture of same.

In further embodiments, the present invention includes compounds of formula (I), supra, in which B is a $—NR^{15}—$ group atom or a tautomer, an N-oxide, or a salt thereof, or a salt of a tautomer, or a salt of an N-oxide, or a mixture of same.

In other embodiments, the present invention includes compounds of formula (I), supra, in which A is A1, or a tautomer, an N-oxide, or a salt thereof, or a salt of a tautomer, or a salt of an N-oxide, or a mixture of same.

In further embodiments, the present invention includes compounds of formula (I), supra, in which A is A2, or a tautomer, an N-oxide, or a salt thereof, or a salt of a tautomer, or a salt of an N-oxide, or a mixture of same.

In yet other embodiments, the present invention includes compounds of formula (I), supra, in which A is A3, or a tautomer, an N-oxide, or a salt thereof, or a salt of a tautomer, or a salt of an N-oxide, or a mixture of same.

In yet other embodiments, the present invention includes compounds of formula (I), supra, in which A is A3 and the macrocyclic ring is a 9-membered ring, a 10-membered ring, a 11-membered ring, a 12-membered ring, a 13-membered ring, a 14-membered ring, a 15-membered ring or a 16-membered ring, particularly a 9-membered ring, a 10-membered ring, a 11-membered ring or a 12-membered ring, more particularly a 12-membered ring or a tautomer, an N-oxide, or a salt thereof, or a salt of a tautomer, or a salt of an N-oxide, or a mixture of same.

In further embodiments, the present invention includes compounds of formula (I), supra, in which A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which A is A1 or A2 and the macrocyclic ring is a 9-membered ring, a 10-membered ring, a 11-membered ring, a 12-membered ring, a 13-membered ring, a 14-membered ring, a 15-membered ring or a 16-membered ring, particularly a 9-membered to 12-membered ring, or a 12-membered to a 13-membered ring, more particularly a 10-membered to 11-membered ring, or a tautomer, an N-oxide, or a salt thereof, or a salt of a tautomer, or a salt of an N-oxide, or a mixture of same.

In other embodiments, the present invention includes compounds of formula (I), supra, in which A is A1 or A2, which together with the indole moiety and the $R^6-R^7$ form a 9-membered macrocyclic ring, a 10-membered macrocyclic ring or a 11-membered macrocyclic ring or a tautomer, an N-oxide, or a salt thereof, or a salt of a tautomer, or a salt of an N-oxide, or a mixture of same.

In other embodiments, the present invention includes compounds of formula (I), supra, in which A is A1 or A2, which together with the indole moiety and the $R^6-R^7$ form a 9-membered macrocyclic ring, a 10-membered macrocyclic ring, a 11-membered macrocyclic ring or a 12-membered macrocyclic ring or a tautomer, an N-oxide, or a salt thereof, or a salt of a tautomer, or a salt of an N-oxide, or a mixture of same.

In other embodiments, the present invention includes compounds of formula (I), supra, in which A is A1, which together with the indole moiety and the $R^6$-$R^7$ form a 9-membered macrocyclic ring, a 10-membered macrocyclic ring or a 11-membered macrocyclic ring or a tautomer, or a salt thereof, or a salt of a tautomer, or a mixture of same.

In yet other embodiments, the present invention includes compounds of formula (I), supra, in which A is A1, which together with the indole moiety and the $R^6$-$R^7$ form a 9-membered macrocyclic ring, a 10-membered macrocyclic ring, a 11-membered macrocyclic ring or a 12-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A2, which together with the indole moiety and the $R^6$-$R^7$ form a 9-membered macrocyclic ring, a 10-membered macrocyclic ring or a 11-membered macrocyclic ring or a tautomer, or a salt thereof, or a salt of a tautomer, or a mixture of same.

In yet other embodiments, the present invention includes compounds of formula (I), supra, in which A is A2, which together with the indole moiety and the $R^6$-$R^7$ form a 9-membered macrocyclic ring, a 10-membered macrocyclic ring, a 11-membered macrocyclic ring or a 12-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the $R^6$-$R^7$ form a 10-membered macrocyclic ring or a 11-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the $R^6$-$R^7$ form a 11-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2 and $R^8$ and $R^9$ are independently selected from $C_1$-$C_3$-alkyl, particularly methyl or ethyl or a tautomer, an N-oxide, or a salt thereof, or a salt of a tautomer, or a salt of an N-oxide, or a mixture of same.

In yet other embodiments, the present invention includes compounds of formula (I), supra, in which A is A1 and $R^8$ and $R^9$ are independently selected from $C_1$-$C_3$-alkyl, particularly methyl or ethyl or a tautomer, an N-oxide, or a salt thereof, or a salt of a tautomer, or a salt of an N-oxide, or a mixture of same.

In still other embodiments, the present invention includes compounds of formula (I), supra, in which A is A2 and $R^8$ and $R^9$ are independently selected from $C_1$-$C_3$-alkyl, particularly from methyl or ethyl or a tautomer, an N-oxide, or a salt thereof, or a salt of a tautomer, or a salt of an N-oxide, or a mixture of same.

In further embodiments, the present invention includes compounds of formula (I), supra, in which $R^8$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group;

a $C_1$-$C_3$-haloalkyl group, a $C_3$-$C_6$-cycloalkyl group and a $C_1$-$C_6$-alkyl group in which one or two not directly adjacent carbon atoms are independently replaced by a hetero atom selected from —O— and —NH—, or a tautomer, an N-oxide, or a salt thereof or a salt of a tautomer or a salt of an N-oxide or a mixture of same.

In further embodiments, the present invention includes compounds of formula (I), supra, in which $R^8$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group, or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from a hydrogen atom, a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group; or a tautomer, an N-oxide, or a salt thereof or a salt of a tautomer or a salt of an N-oxide or a mixture of same.

In further embodiments, the present invention includes compounds of formula (I), supra, in which $R^8$ is a $C_1$-$C_6$-alkyl group or a tautomer, an N-oxide, or a salt thereof, or a salt of a tautomer, or a salt of an N-oxide, or a mixture of same.

In further embodiments, the present invention includes compounds of formula (I), supra, in which $R^8$ is selected from a hydrogen atom, and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group or a tautomer, or a salt thereof, or a salt of a tautomer, or a mixture of same.

In further embodiments, the present invention includes compounds of formula (I), supra, in which $R^8$ is a $C_1$-$C_3$-alkyl group;

or a tautomer, or a salt thereof, or a salt of a tautomer, or a mixture of same.

In further embodiments, the present invention includes compounds of formula (I), supra, in which $R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group, a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-($C_1$-$C_3$-alkylene)-O—($C_1$-$C_3$-alkylene)-group,
a $R^{19}$-phenylene-O—($C_1$-$C_3$-alkylene)- group,
a $R^{19}$-phenyl-heteroaryl-O—($C_1$-$C_3$-alkylene) group,
a ($R^{19}$)-(heterocycloalkyl)-($C_1$-$C_3$-alkylene)- group,
a ($R^{19}$)-(heterocycloalkylene)-(phenylene)-O—($C_1$-$C_3$-alkylene)- group,
a (heterocycloalkenylene)-(phenylene)-O—($C_1$-$C_3$-alkylene)- group,
a ($R^{19}$)-(heteroaryl-($C_1$-$C_3$-alkylene)-O—($C_1$-$C_3$-alkylene)-group,
a ($R^{19}$)-(heteroaryl)-(phenylene)-O—($C_1$-$C_3$-alkylene)-group,
a ($R^{20}$)—$S(O)_2$-(phenylene)-O—($C_1$-$C_3$-alkylene)- group,
a ($R^{20}$)—$S(O)_2$—NH-(phenylene)-O—($C_1$-$C_3$-alkylene)-group,
a ($R^{20}$)—$S(O)_2$—NH-(phenylene)-O—($C_1$-$C_3$-alkylene)-group,
a ($R^{20}$)—$S(O)_2$—N($C_1$-$C_6$-alkyl)-(phenylene)-O—($C_1$-$C_3$-alkylene)- group,
a ($R^{20}$)—$S(O)_2$-(heterocycloalkylene)-(phenylene)-O—($C_1$-$C_3$-alkylene)- group,
a ($R^{19}$)-(heterocycloalkylene)-(heteroarylene)-O—($C_1$-$C_3$-alkylene)- group,
a ($R^{20}$)-(heteroarylene)-O—($C_1$-$C_3$-alkylene)- group,
a ($R^{19}$)-(heteroarylene)-O—($C_1$-$C_3$-alkylene)- group,
a ($R^{20}$)—$S(O)_2$-(heteroarylene)-O—($C_1$-$C_3$-alkylene)-group,
a ($R^{20}$)—$S(O)_2$-(heterocycloalkylene)-(heteroarylene)-O—($C_1$-$C_3$-alkylene)- group,
a $NR^{21}R^{22}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

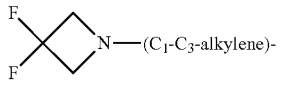

group and a

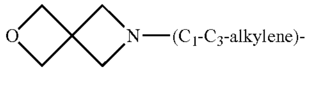

group, where the phenyl ring is optionally substituted with a halogen atom, a hydroxy group, or a $C_1$-$C_3$-alkoxy group and the heterocycloalkyl group is optionally substituted with an oxo (═O) group or is optionally substituted with one or more substituents independently selected from a halogen atom and a $C_1$-$C_3$-alkyl group, or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)-group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group and
a ($C_3$-$C_7$)-cycloalkyl-O—($C_1$-$C_3$-alkylene)- group;

and where $R^{19}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $C(O)OR^{21}$—($C_1$-$C_3$-alkylene)- group, a —$C(O)OR^{21}$ group, a —$C(O)NR^{20}R^{21}$ group, a ($C_1$-$C_3$-alkyl)-O—($C_1$-$C_3$-alkylene)-C(O)—group, a ($C_1$-$C_6$-alkyl)-C(O)— group and a $C_3$-$C_6$-cycloalkyl-C(O)— group;

where $R^{19}$ is selected from a $C_1$-$C_3$-alkyl group, a $C_3$-$C_6$-cycloalkyl group and a $NR^{20}R^{21}$ group where $R^{29}$ and $R^{21}$ are independently selected from a hydrogen atom or a $C_1$-$C_6$-alkyl group;

or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)-group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group and
a ($C_3$-$C_7$)-cycloalkyl-O—($C_1$-$C_3$-alkylene)- group;

or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{19}$-(phenylene)-O—($C_1$-$C_3$-alkylene)- group,
a $NR^{20}R^{21}$—($C_1$-$C_3$-alkylene)- group and
a ($C_1$-$C_3$-alkyl)-NH—($C_1$-$C_3$-alkylene)- group;

or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_4$- alkyl group or a tautomer, or a salt thereof, or a salt of a tautomer, or a mixture of same.

In further embodiments, the present invention includes compounds of formula (I), supra, in which $R^9$ is a $C_1$-$C_3$-alkyl group or a tautomer, or a salt thereof, or a salt of a tautomer, or a mixture of same.

In further embodiments, the present invention includes compounds of formula (I), supra, in which $R^8$ and $R^9$ together form a 5-membered ring or a 6-membered ring optionally comprising one or two heteroatoms independently selected from —O— and —$NR^{14}$—; or a tautomer, an N-oxide, or a salt thereof, or a salt of a tautomer, or a salt of an N-oxide, or a mixture of same.

In further embodiments, the present invention includes compounds of formula (I), supra, in which $R^{11}$ and $R^{13}$ are each independently selected from a hydrogen atom, a halogen atom, a $C_1$-$C_3$-alkyl group and a $C_1$-$C_3$-alkoxy group; and $R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group; or a tautomer, an N-oxide, or a salt thereof, or a salt of a tautomer, or a salt of an N-oxide, or a mixture of same.

In further embodiments, the present invention includes compounds of formula (I), supra, in which $R^{14}$ is a hydrogen atom or a $C_1$-$C_3$-alkyl group; or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom, a $C_1$-$C_6$-alkyl group which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—$S(O)_2$-arylene-O— group, a ($R^{19}$)$S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group;

a $C_1$-$C_3$-alkylene-C(O)— group, a heterocycloalkyl-($C_1$-$C_3$-alkylene)-C(O)— group, a heterocycloalkyl-($C_1$-$C_3$-alkylene)-$S(O)_2$— group, a heterocyclyl-NH—C(O)— group, a heterocycloalkyl-($C_1$-$C_3$-alkylene)-NH—C(O)— group, an aryl-($C_1$-$C_3$-alkylene)-NH—C(O)— group, which unsubstituted or substituted with 1, 2, or 3 substituents independently selected form a halogen atom, a $C_1$-$C_3$-alkyl group or a $C_1$-$C_3$-alkoxy group, a heterocycloalkyl-heteroarylene-$S(O)_2$— group, a phenyl group, a group

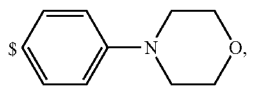

a group

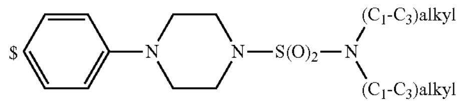

and a group

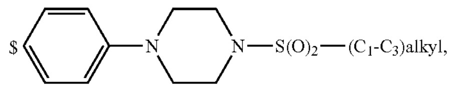

where $ is the point of attachment to the nitrogen atom, to which $R^{15}$ is attached or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom, a $C_1$-$C_6$-alkyl group which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—$S(O)_2$— arylene-O— group, a ($R^{19}$)$S(O)_2$-heterocycloalkylene-arylene-O— group and an aryl-heteroarylene-O— group;

a phenyl group, a group

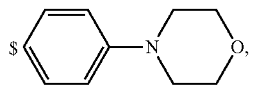

a group

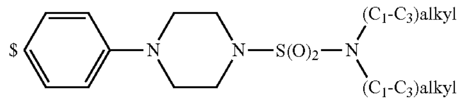

and a group

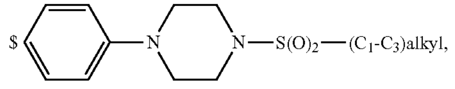

where $ is the point of attachment to the nitrogen atom, to which $R^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom and a $C_1$-$C_6$-alkyl group which is unsubstituted or substituted with a substituent selected from a heterocycloalkyl group and an aryl group.

or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom and a $C_1$-$C_6$-alkyl group which is unsubstituted or substituted with a heterocycloalkyl group or a tautomer, or a salt thereof, or a salt of a tautomer, or a mixture of same.

In further embodiments, the present invention includes compounds of formula (I), supra, in which $R^{15}$ is a $C_1$-$C_3$-alkyl group or a tautomer, or a salt thereof, or a salt of a tautomer, or a mixture of same.

In further embodiments, the present invention includes compounds of formula (I), supra, in which $R^{15}$ and $R^{22}$ together, including the atoms to which they are attached, may form a 5-membered or 6-membered ring optionally comprising one or two heteroatoms independently selected from —O— and —$NR^{14}$— or a tautomer, or a salt thereof, or a salt of a tautomer, or a mixture of same.

In further embodiments, the present invention includes compounds of formula (I), supra, in which $R^{15}$ and $R^{22}$ together, including the atoms to which they are attached, may form a 5-membered or 6-membered ring or a tautomer, or a salt thereof, or a salt of a tautomer, or a mixture of same. In another embodiment $R^{15}$ and $R^{22}$ together with the atoms to which they are attached form a group

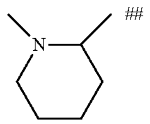

or a group

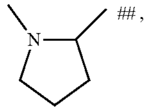

whereby ## is the point of attachment with the pyrazole carbon atom bearing the $R^7$ substituent and the nitrogen atom, which is the —$N(R^{15})$— group, is attached to the #—$(CH_2)_4$— moiety of the $R^6$-$R^7$ chain, or a tautomer, or a salt thereof, or a salt of a tautomer, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS$(O)_2$— group and a $C_1$-$C_3$-alkyl-O—C(=O)— group; or a tautomer, or a salt thereof, or a salt of a tautomer, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS$(O)_2$— group and a $C_1$-$C_3$-alkyl-O—C(=O)— group; or a tautomer, or a salt thereof, or a salt of a tautomer, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group and a $C_1$-$C_6$-alkoxy group; or a tautomer, or a salt thereof, or a salt of a tautomer, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, and a $C_1$-$C_6$-haloalkyl group; or a tautomer, or a salt thereof, or a salt of a tautomer, or a mixture of same.

In yet further embodiments, the present invention includes compounds of formula (I), supra, in which $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)-group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group; or a tautomer, or a salt thereof, or a salt of a tautomer, or a mixture of same.

In yet further embodiments, the present invention includes compounds of formula (I), supra, in which $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)$OR^{21}$—($C_1$-$C_3$-alkylene)-group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group or a tautomer, or a salt thereof, or a salt of a tautomer, or a mixture of same.

In yet further embodiments, the present invention includes compounds of formula (I), supra, in which $R^{19}$ is selected from a $C_1$-$C_3$-alkyl group, a $C_3$-$C_6$-cycloalkyl group and a $NR^{20}R^{21}$ group or a tautomer, or a salt thereof, or a salt of a tautomer, or a mixture of same.

In yet further embodiments, the present invention includes compounds of formula (I), supra, in which $R^{20}$ and $R^{21}$ are each independently selected from a hydrogen atom and a $C_1$-$C_6$-alkyl group; or a tautomer, an N-oxide, or a salt thereof, or a salt of a tautomer, or a salt of an N-oxide, or a mixture of same.

In yet further embodiments, the present invention includes compounds of formula (I), supra, in which $R^{20}$ and $R^{21}$ are each independently selected from a hydrogen atom and a $C_1$-$C_3$-alkyl group; or a tautomer, an N-oxide, or a salt thereof, or a salt of a tautomer, or a salt of an N-oxide, or a mixture of same.

In yet further embodiments, the present invention includes compounds of formula (I), supra, in which $R^{22}$ s independently selected from a halogen atom a $C_1$-$C_6$-alkyl group which is unsubstituted or substituted with one or more substituents selected from a halogen atom, a hydroxy group, $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-

O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group;

a $C_1$-$C_3$-alkylene-C(O)— group, a $C_3$-$C_6$-cycloalkyl group, and an aryl group;

whereby any heterocycloalkyl group of $R^{22}$ may optionally be itself further substituted with a $C_1$-$C_3$-alkyl group or one or two halogen atoms;

or a tautomer, an N-oxide, or a salt thereof, or a salt of a tautomer, or a salt of an N-oxide, or a mixture of same.

In yet further embodiments, the present invention includes compounds of formula (I), supra, in which $R^{22}$ s independently selected from a halogen atom a $C_1$-$C_6$-alkyl group which is unsubstituted or substituted with one or more substituents selected from a halogen atom, a hydroxy group, $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group; and a $C_1$-$C_3$-alkylene-C(O)— group, or a tautomer, an N-oxide, or a salt thereof, or a salt of a tautomer, or a salt of an N-oxide, or a mixture of same.

In yet further embodiments, the present invention includes compounds of formula (I), supra, in which $R^{22}$ is independently selected from a halogen atom, a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group and a phenyl group, a $C_3$-$C_6$-cycloalkyl group, a phenyl group and a heterocycloalkyl group, and a heteroaryl group;

whereby any heterocycloalkyl group of $R^{22}$ may optionally be itself further substituted with a $C_1$-$C_3$-alkyl group or one or two halogen atoms;

or a tautomer, an N-oxide, or a salt thereof, or a salt of a tautomer, or a salt of an N-oxide, or a mixture of same.

In further embodiments, the present invention includes compounds of formula (I), supra, wherein $R^{22}$ is independently selected from a halogen atom a $C_1$-$C_6$-alkyl group which is unsubstituted or substituted with one or more substituents selected from a halogen atom, a hydroxy group, $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group, a $C_3$-$C_6$-cycloalkyl group, a heterocycloalkyl group, a phenyl group, and a heteroaryl group or a tautomer, an N-oxide, or a salt thereof, or a salt of a tautomer, or a salt of an N-oxide, or a mixture of same.

In further embodiments, the present invention includes compounds of formula (I), supra, wherein $R^{22}$ is independently selected from a halogen atom, a $C_1$-$C_4$-alkyl group which is unsubstituted or substituted with a group selected from a hydroxy group, $NR^{16}R^{17}$ group, a $C_1$-$C_3$-haloalkyl group, a $C_1$-$C_4$-alkoxy group, a $C_3$-$C_6$-cycloalkyl group, a heterocycloalkyl group and a phenyl group;

a $C_3$-$C_6$-cycloalkyl group, a phenyl group, a heteroaryl group, and a heterocycloalkyl group;

whereby any heterocycloalkyl group of $R^{22}$ may optionally be itself further substituted with a $C_1$-$C_3$-alkyl group or one or two halogen atoms; or a tautomer, an N-oxide, or a salt thereof, or a salt of a tautomer, or a salt of an N-oxide, or a mixture of same.

In further embodiments, the present invention includes compounds of formula (I), supra, wherein $R^{22}$ is independently selected from a halogen atom, a $C_1$-$C_4$-alkyl group which is unsubstituted or substituted with a group selected from a hydroxy group, $NR^{16}R^{17}$ group, a $C_1$-$C_4$-alkoxy group, a $C_3$-$C_6$-cycloalkyl group, a heterocycloalkyl group and a phenyl group;

a phenyl group, a heteroaryl group a $C_3$-$C_6$-cycloalkyl group, and a heterocycloalkyl group, or a tautomer, an N-oxide, or a salt thereof, or a salt of a tautomer, or a salt of an N-oxide, or a mixture of same.

In further embodiments, the present invention includes compounds of formula (I), supra, in which $R^{22}$ is independently selected from a halogen atom, a $C_3$-$C_6$-cycloalkyl group, a phenyl group, and a $C_1$-$C_5$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms; or a tautomer, an N-oxide, or a salt thereof, or a salt of a tautomer, or a salt of an N-oxide, or a mixture of same.

In further embodiments, the present invention includes compounds of formula (I), supra, in which $R^{22}$ is independently selected from

- a halogen atom,
- a phenyl group,
- a $C_3$-$C_6$-cycloalkyl group, and
- a $C_1$-$C_3$-alkyl group which is unsubstituted or substituted with one or more substituents selected from a hydroxy group, $NR^{17}R^{18}$ group, a $C_1$-$C_3$-haloalkyl group, a $C_1$-$C_3$-alkoxy group, a $C_3$-$C_6$-cycloalkyl group, a heterocycloalkyl group and a phenyl group;

or a tautomer, or a salt thereof, or a salt of a tautomer, or a mixture of same.

In yet further embodiments, the present invention includes compounds of formula (I), supra, wherein $R^{22}$ is independently selected from

- a $C_3$-$C_6$-cycloalkyl group,
- a phenyl group, and
- a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms; or a tautomer, or a salt thereof, or a salt of a tautomer, or a mixture of same.

In yet further embodiments, the present invention includes compounds of formula (I), supra, wherein $R^{22}$ is independently selected from a $C_1$-$C_3$-haloalkyl-group, and a $C_1$-$C_3$-alkyl group which is unsubstituted or substituted with a hydroxy group, a $C_3$-$C_5$-cycloalkyl group, or a heterocyclyl group; or a tautomer, or a salt thereof, or a salt of a tautomer, or a mixture of same.)

In other embodiments, the present invention includes compounds of formula (I), supra, wherein $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a $—(CH_2)_2$-morpholino group, a $—(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, and a phenylmethyl group or a tautomer, or a salt thereof, or a salt of a tautomer, or a mixture of same.

In other embodiments, the present invention includes compounds of formula (I), supra, wherein $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a $—(CH_2)_2$-morpholino group, a $—(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, and a phenylmethyl group or $R^{22}$ and $R^{15}$ together with the atoms to which they are attached form a 5- or 6-membered ring or a tautomer, or a salt thereof, or a salt of a tautomer, or a mixture of same.

In other embodiments, the present invention includes compounds of formula (I), supra, wherein $R^{22}$ is independently selected from a $—(CH_2)_2$-morpholino group, a $—(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, or a tautomer, or a salt thereof, or a salt of a tautomer, or a mixture of same.

In other embodiments, the present invention includes compounds of formula (I), supra, wherein $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a cyclopropyl group, a phenyl group, and a phenylmethyl group or $R^{22}$ and $R^{15}$ together with the atoms to which they are attached form a 5- or 6-membered ring or a tautomer, or a salt thereof, or a salt of a tautomer, or a mixture of same.

In other embodiments, the present invention includes compounds of formula (I), supra, wherein $R^{22}$ is independently selected from a $—(CH_2)_2$-morpholino group, a $—(CH_2)_3$-morpholino group, a (3,3-difluoropyrrolidin-1-yl) ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, a phenylmethyl group or a tautomer, or a salt thereof, or a salt of a tautomer, or a mixture of same.

In other embodiments, the present invention includes compounds of formula (I), supra, wherein $R^{22}$ and $R^{15}$ together with the atoms to which they are attached form a 5- or 6-membered ring or a tautomer, or a salt thereof, or a salt of a tautomer, or a mixture of same.

In other embodiments, the present invention includes compounds of formula (I), supra, wherein $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a $—(CH_2)_2$-morpholino group, a $—(CH_2)_3$-morpholino group, a (3,3-difluoropyrrolidin-1-yl)ethyl group, a (3,3-difluoroazetidin-1-yl) ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, a phenylmethyl group and $R^{22}$ and $R^{15}$ together with the atoms to which they are attached form a 5- or 6-membered ring or a tautomer, or a salt thereof, or a salt of a tautomer, or a mixture of same and $R^{23}$ is hydrogen or a tautomer, or a salt thereof, or a salt of a tautomer, or a mixture of same.

In other embodiments, the present invention includes compounds of formula (I), supra, wherein $R^{22}$ is a $—(CH_2)_2$-morpholino group or a tautomer, or a salt thereof, or a salt of a tautomer, or a mixture of same.

In other embodiments, the present invention includes compounds of formula (I), supra, wherein $R^{22}$ is a $—(CH_2)_2$-morpholin-4-yl group or a tautomer, or a salt thereof, or a salt of a tautomer, or a mixture of same.

In other embodiments, the present invention includes compounds of formula (I), supra, wherein $R^{22}$ is independently selected from a methyl group, an ethyl group, a hydroxyethyl group, a $—(CH_2)_2$-morpholino group, trifluoromethyl group and a cyclopropyl group; or a tautomer, or a salt thereof, or a salt of a tautomer, or a mixture of same.

In yet further embodiments, the present invention includes compounds of formula (I), supra, wherein $R^{23}$ is independently selected from a hydrogen atom, a halogen atom, a hydroxy group, a $C_1$-$C_6$-alkyl group and a $C_1$-$C_6$-haloalkyl group, or a tautomer, an N-oxide, or a salt thereof, or a salt of a tautomer, or a salt of an N-oxide, or a mixture of same.

In yet further embodiments, the present invention includes compounds of formula (I), supra, wherein $R^{23}$ is independently selected from a hydrogen atom, a halogen atom, a hydroxy group and a $C_1$-$C_4$-alkyl group or a tautomer, an N-oxide, or a salt thereof, or a salt of a tautomer, or a salt of an N-oxide, or a mixture of same.

In yet further embodiments, the present invention includes compounds of formula (I), supra, wherein $R^{23}$ is independently selected from a hydrogen atom, a halogen atom, a hydroxy group and a $C_1$-$C_4$-alkyl group or a salt thereof or a salt of a tautomer or a salt of an N-oxide or a mixture of same.

In yet further embodiments, the present invention includes compounds of formula (I), supra, wherein $R^{23}$ is a hydrogen atom, a salt thereof or a salt of a tautomer or a salt of an N-oxide or a mixture of same.

In yet further embodiments, the present invention includes compounds of formula (I), supra, wherein $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur or a tautomer, an N-oxide, or a salt thereof, or a salt of a tautomer, or a salt of an N-oxide, or a mixture of same.

In further embodiments, the present invention includes compounds of formula (I), wherein $R^{23}$ is independently selected from a hydrogen atom, a halogen atom, a hydroxy group and a $C_1$-$C_3$-alkyl group or a tautomer, or a salt thereof, or a salt of a tautomer, or a mixture of same.

In further embodiments, the present invention includes compounds of formula (I), wherein $R^{23}$ is independently selected from a hydrogen atom and a $C_1$-$C_3$-alkyl group or a tautomer, or a salt thereof, or a salt of a tautomer, or a mixture of same.

In further embodiments, the present invention includes compounds of formula (I), wherein $R^{22}$ and $R^{23}$ together form a 3-6-membered carbocyclic ring; or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ and $R^{23}$ together with the carbon atom to which they are attached form a 3-6-membered heterocyclic ring comprising one or two heteroatoms selected from nitrogen, oxygen or sulfur or a tautomer, an N-oxide, or a salt thereof, or a salt of a tautomer, or a salt of an N-oxide, or a mixture of same.

In further embodiments, the present invention includes compounds of formula (I), or a tautomer, an N-oxide, or a salt thereof or a salt of a tautomer or a salt of an N-oxide or a mixture of same In further embodiments, the present invention includes compounds of formula (I), or a tautomer, or a salt thereof, or a salt of a tautomer, or a mixture of same In yet further embodiments, the present invention includes compounds of formula (I), or a salt thereof or a mixture of same In further embodiments, the present invention includes compounds of formula (I), which are salts.

In further embodiments, the present invention includes compounds of formula (I), which are amine salts or salts with organic acids.

In further embodiments, the present invention includes compounds of formula (I), which are amine salts, particularly formed with pharmaceutically acceptable amines.

In further embodiments, the present invention includes compounds of formula (I), which are amine salts, particularly diethylamine salts.

In further embodiments, the present invention includes compounds of formula (I), which are amine salts or salts with organic acids, more particularly with trifluoroacetic acid or citric acid.

In further embodiments, the present invention includes compounds of formula (I), which are a tautomer, or a salt thereof or a salt of a tautomer or a mixture of same In further embodiments, the present invention includes compounds of formula (I), which are a an N-oxide, or a salt thereof or a salt of an N-oxide or a mixture of same In further embodiments of the first aspect, the present invention provides combinations of two or more of the above mentioned embodiments under the heading "further embodiments of the first aspect of the present invention".

Furthermore it is understood that the invention includes any subcombination of the disclosed single embodiments herein for certain residues or combined with a subcombination of residues of formula (I) as outlined in the claims.

The present invention includes any sub-combination within any embodiments or aspects of the present invention of compounds of general formula (I), supra.

The present invention includes any sub-combination within any embodiments or aspects of the present invention of compounds or intermediate compounds of general formula (I or II). The present invention includes the compounds of general formula (I) which are disclosed in the Example Section of this text, infra.

General Synthesis of Compounds of General Formula (I) of the Present Invention

A. General Synthesis Route

Scheme 1

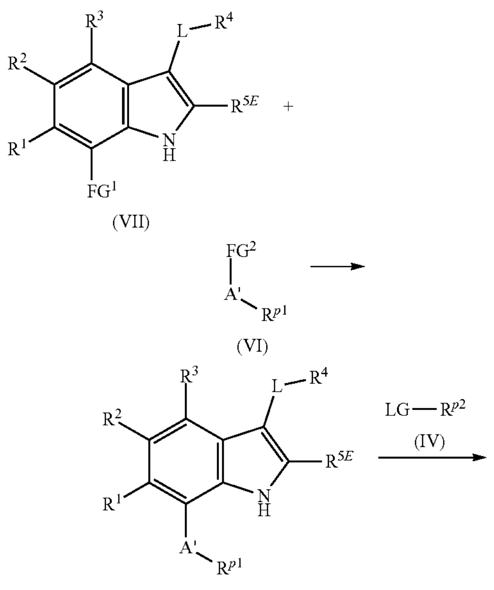

(VII)

(VI)

(IV)

(V)

-continued

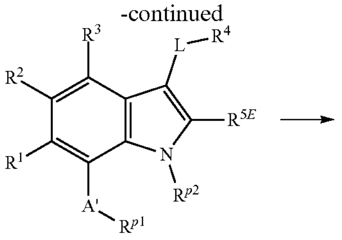

(III)

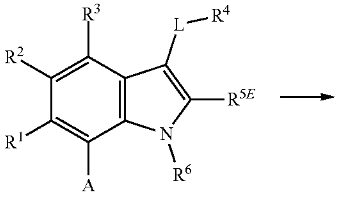

(II)

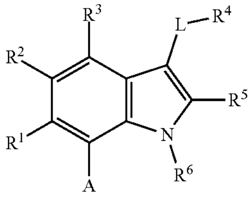

(I)

Compounds of general formula (I) can be synthesized according to the general synthesis route depicted in Scheme 1, encompassing a Suzuki coupling of starting materials of formulae (VII) and (VI) to give intermediates of formula (V), elaboration of the macrocylic core by attachment of a group $R^{P2}$ to the indole nitrogen present in compounds of formula (V), by reaction with compounds of formula (IV), in which LG represents a leaving group as defined herein, and in which $R^{P2}$ represents a group suitable to act as a precursor for the group $R^6$ as defined for the compounds of general formula (I), followed by (or together in one step with) macrocyclisation of the resulting intermediates of formula (III), e.g. by intramolecular nucleophilic substitution, to give macrocyclic intermediates of formula (II). Dependent inter alia on the nature of $R^{P1}$ and $R^{P2}$, which together give rise to a group $^{\#}—(CH_2)_n—(B)_t—CR^{22}R^{23}—^{\#\#}$ or $^{\#}—(C_2\text{-}C_9\text{-alkenylene})\text{-}(B)_t—CR^{22}R^{23}—^{\#\#}$ as defined for the compounds of general formula (I) after elaboration into the compounds of the present invention, the conversion of compounds of formula (V) into said macrocyclic intermediates of formula (II) may proceed with or without the intermediacy of intermediates of formula (III). Preferably, and e.g. as shown in Schemes 2a to 2c, formation of macrocyclic intermediates of formula (II) from compounds of formula (V) is accomplished in one synthetic step. Finally, conversion of $R^{5E}$ into $R^5$, e.g. by ester saponification, optionally followed by conversion of the resulting carboxylic acid into an acylsulfonamide according to methods known to the person skilled in the art (see for example: *Bioorg. Med. Chem. Lett.* 2006, 16, 3639-3641; *Bioorg. Med. Chem. Lett.* 2012, 22, 713-717; *Org. Lett.* 2012, 14(2), 556-559), yields the compounds of formula (I).

Said general synthesis route commences with a well-known Suzuki coupling of compounds of formula (VII), in which $R^1$, $R^2$, $R^3$, $R^4$ and L are as defined for the compounds of general formula (I), and in which $R^{5E}$ represents a group suitable to act as a precursor of a —C(═O)OH or a tetrazol-5-yl group, preferably a group $—C(═O)O—C_{1\text{-}4}$-alkyl, with compounds of formula (VI), in which A', together with the group $R^{P1}$ attached to it, represents a group suitable to act as precursor of a group A as defined for the compounds of general formula (I), to give compounds of formula (V). The group $R^4$, constituting the terminus of the side chain attached to C-3 of the indole core in formula (VII), can alternatively be established on later stage (see e.g. Scheme 2c and its discussion for details). Examples of groups A' are exemplified further below in this chapter.

In formulae (VI) and (VII), $FG^1$ in combination with $FG^2$ represents a pair of functional groups together enabling a Suzuki coupling; either $FG^1$ represents chloro, bromo, iodo or a trifluoromethanesulfonyl- group, preferably bromo or iodo and $FG^2$ represents a group $—B(OR^B)_2$, or vice versa. Said group $—B(OR^B)_2$ may be a boronic acid moiety ($R^B$═—H) or an alkyl ester of the boronic acid, e.g. its isopropyl ester ($R^B$═$C_1$-$C_2$-alkyl, e.g. $—CH(CH_3)_2$), or an ester derived from a diol such as e.g. pinacol in which the boronic acid intermediate forms a cyclic boronic ester, preferably a 4,4,5,5-tetramethyl-1,3,2-dioxaborolane ($R^B$—$R^B$═$C_2$-$C_6$-alkylene, preferably $—C(CH_3)_2—C(CH_3)_2—$). Many boronic acids and their esters are commercially available and their synthesis is well-known to the person skilled in the art; see e.g. D. G. Hall, Boronic Acids, 2005 WILEY-VCH Verlag GmbH & Co. KGaA, Weinheim, ISBN 3-527-30991-8 and references cited therein and Journal of Medicinal Chemistry, 2015, 58, 2180-2194. Alternatively to boronic acid derivatives, also tetrafluoroborates, in which $—BF_4^-$ replaces the $—B(OR^B)_2$ moiety, can be employed.

Said Suzuki coupling reaction can be catalysed by palladium catalysts, exemplified by but not limited to by Pd(0) catalysts such as e.g. tetrakis(triphenylphosphine)palladium (0) $[Pd(PPh_3)_4]$, tris(dibenzylideneacetone)di-palladium(0) $[Pd_2(dba)_3]$ in combination with a ligand, e.g. a phosphine such as e.g. triphenylphosphine, or by Pd(II) catalysts such as e.g. dichlorobis(triphenylphosphine)-palladium(II) $[Pd(PPh_3)_2Cl_2]$, dichloropalladium-tricyclohexylphosphine (1:2), palladium(II) acetate in combination with a ligand, e.g. a phosphine such as e.g. triphenylphosphine, chloro(2-dicyclohexylphosphino-2',4',6'-triisopropyl-1,1'-biphenyl) [2-(2'-amino-1,1'-biphenyl)]palladium(II) (herein also referred to as XPhos Pd G2), (2-Dicyclohexylphosphino-2',4',6'-triisopropyl-1,1'-biphenyl)[2-(2'-amino-1,1'-biphenyl)] palladium(II) methanesulfonate (herein also referred as XPhos Pd G3), (2'-aminobiphenyl-2-yl)(methanesulfonato-kappaO)palladium-[2',6'-bis(propan-2-yloxy)biphenyl-2-yl] (dicyclohexyl)phosphane (1:1) (herein also referred to as RuPhos Pd G3), or by [1,1'-bis(diphenylphosphino)ferrocene]-palladium dichloride, in free form $[Pd(dppf)Cl_2]$ or as complex with dichloromethane $[Pd(dppf)Cl_2 \times CH_2Cl_2]$.

The reaction is preferably carried out in solvents such as e.g. 1,2-dimethoxyethane, 1,4-dioxane, DMF, THF, toluene, or n-propanol, or mixtures thereof, optionally also in mixture with water, and in the presence of a base such as e.g. aqueous potassium carbonate, aqueous sodium carbonate or, preferably, aqueous potassium triphosphate.

The reaction is performed at temperatures ranging from room temperature (i.e. 20° C.) to the boiling point of the solvent. Additionally, the reaction can be performed at temperatures above the boiling point using pressure tubes and a microwave oven. (For a review on Suzuki couplings see: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Synthetic approaches to starting materials of formulae (VI) and (VII) are discussed in paragraph D. of this chapter, infra.

Compounds of formula (II) can be obtained from compounds of formula (V) using various methods described in more detail below, e.g. by reacting said compounds of formula (V) with compounds of formula (IV) in which LG represents a leaving group, preferably bromo or iodo, and in which $R^{P2}$ represents a group suitable to act as a precursor for the group $R^6$ as defined for the compounds of general formula (I). The following paragraphs outline, inter alia, more specific examples of said conversion of compounds of formulae (Va), (Vb), (Vf) and (Vg) into compounds of (IIa), (IIa), (IIc), (IIg), (IIh) and (IIi), which constitute subcompartments of formulae (V) and (II), respectively, as discussed in the context of Scheme 1.

Said macrocyclic intermediates of formula (II) can finally be converted into the compounds of general formula (I) as described in further detail in context of Scheme 3, infra.

The reader is referred to the fact that the presence of the group —$C(R^{22})(R^{23})$—, as defined herein, results in the presence of a stereogenic centre whenever the groups $R^{22}$ and $R^{23}$ are different from each other. Moreover, the compounds of the present invention can form separable atropisomers, as a result of hindered rotation at the bond linking the group A, as defined herein, to the indole core. Said atropisomerism can establish, dependent on the steric bulk in the vicinity of said bond linking the group A to the indole core, which may vary e.g. dependent from $R^1$ representing either a hydrogen atom or a sterically more demanding substituent, such as e.g. a chlorine atom, either upon the formation of the macrocyclic intermediates of formula (II), or already upon said Suzuki coupling of starting materials of formulae (VII) and (VI) to give intermediates of formula (V). As readily understood by the person skilled in the art, groups $R^{22}$ and $R^{23}$ being different from each other can, in combination with said atropisomerism, result in the formation of diastereomers, which may, inter alia, differ in reactivity. Specific examples of said differing reactivity are given in the Experimental section, infra.

B. More Specific Synthesis Routes for Establishing the Macrocyclic Core, Schemes 2a-2g:

Examples for $R^{P1}$ and $R^{P2}$ Groups, as Referred to in the General Synthesis Route of Scheme 1 above, can be derived from the examples disclosed in the Experimental Section.

-continued

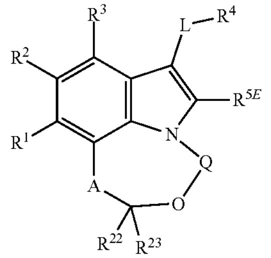

(IIa)

According to Scheme 2a, compounds of formula (IIa), in which $R^7$ (which is a feature of group A as defined for the compounds of general formula (I)) and $R^6$ together form a $^{\#}$-Q-O—$CR^{22}R^{23}$—$^{\#\#}$ group, in which Q represents a —($C_2$-$C_9$-alkenylene)- group, $R^{22}$ and $R^{23}$ are as defined for the compounds of the general formula (I), $^{\#}$ represents the point of attachment to the indole nitrogen atom and $^{\#\#}$ represents the point of attachment to the pyrazole carbon atom bearing the $R^7$ substituent, can be obtained from compounds of formula (Va), in which $R^1$, $R^2$, $R^3$, $R^4$, $R^{22}$, $R^{23}$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P2}$ represents a hydrogen atom and $R^{P1}$ (see General Synthesis Route, Scheme 1) represents a —$C(R^{22})(R^{23})$—OH group, by reacting with compounds of formula (IVa), in which Q represents a —($C_2$-$C_9$-alkenylene)- group, and $LG^1$ and $LG^2$ represent, independently from each other, a leaving group, preferably chloro, bromo or iodo, giving rise to the corresponding macrocyclic intermediates of formula (IIa). If compounds of formula (IVa) are being employed as (Z)-alkenes, macrocyclic compounds of formula (IIa) can be obtained as single (Z) double bond isomers.

Said reaction can be advantageously accomplished by reacting a compound of formula (Va) with a compound of formula (IVa) in the presence of a base such as e.g. an alkali carbonate or an alkali phosphate, preferably cesium carbonate, preferably in the presence of an alkali iodide, preferably sodium iodide (to convert LG' and/or $LG^2$ into iodo in situ), in a solvent such as e.g. dimethylformamide (DMF), 1,2-dimethoxyethane, bis-(2-methoxymethyl) ether or acetonitrile, preferably acetonitrile, at a temperature between 0° C. and 100° C., preferably ranging from 40° C. to 80° C., more preferably between 50° C. and 80° C.

Scheme 2a

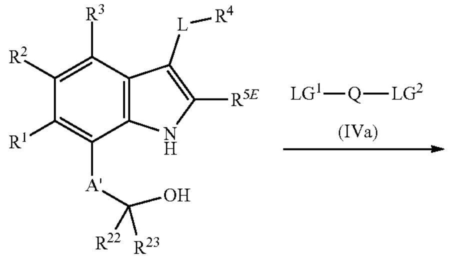

(Va)

Scheme 2b

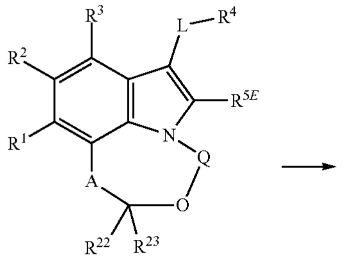

(IIa)

-continued

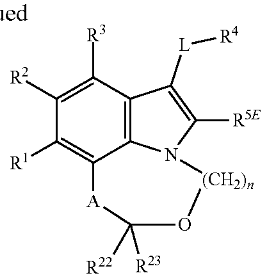

(IIb)

According to Scheme 2b, compounds of formula (IIb), in which $R^7$ (which is a feature of group A as defined for the compounds of general formula (I)) and $R^6$ together form a $^{\#}—(CH_2)_n—O—CR^{22}R^{23}—^{\#\#}$ group, in which n, $R^{22}$ and $R^{23}$ are as defined for the compounds of the general formula (I), $^{\#}$ represents the point of attachment to the indole nitrogen atom and $^{\#\#}$ represents the point of attachment to the pyrazole carbon atom bearing the $R^7$ substituent, can be obtained from compounds of formula (IIa), in which $R^1$, $R^2$, $R^3$, $R^4$, $R^{22}$, $R^{23}$ and L are as defined for the compounds of general formula (I), in which Q represents a $—(C_2\text{-}C_5\text{-}$alkenylene)- group, in which $R^{5E}$ represents a group suitable to act as a precursor of a —C(═O)OH or a tetrazol-5-yl group, preferably a group $—C(═O)O—C_{1\text{-}4}$-alkyl, by hydrogenation of the olefinic double bond.

Said hydrogenation of the olefinic double bond can be advantageously accomplished by catalytic hydrogenation which is well known to the person skilled in the art, e.g. by reacting a solution of a compound of formula (IIa) in a solvent such as e.g. methanol, ethanol, tetrahydrofuran or ethyl acetate, with an atmosphere of hydrogen under ambient or elevated pressure, in the presence of a hydrogenation catalyst such as e.g. palladium on carbon, or e.g. by reacting a solution of a compound of formula (IIa) in a solvent such as e.g. a mixture of ethanol with tetrahydrofuran or with dichloromethane, with an atmosphere of hydrogen under ambient or elevated pressure, in the presence of a hydrogenation catalyst such as e.g. tris(triphenylphosphine)rhodium (I)chloride, at a temperature ranging from 0° C. to 50° C., preferably at room temperature, that is, at a temperature ranging from 20° C. to 25° C.

Scheme 2c

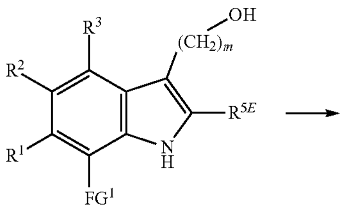

(VIIa)

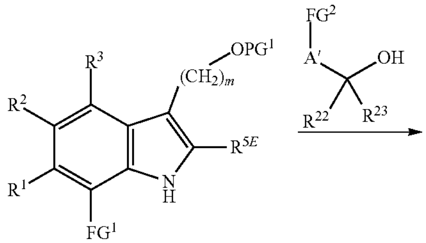

(VIIb)

-continued

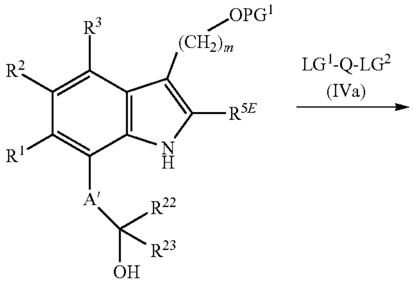

(Vb)

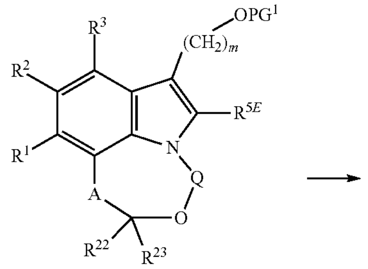

(VIII)

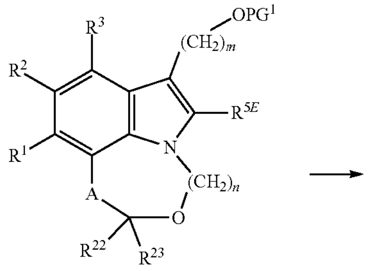

(IX)

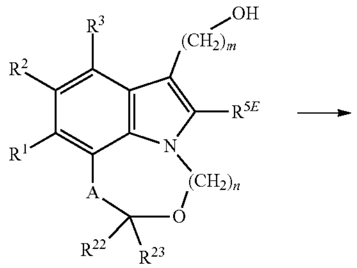

(X)

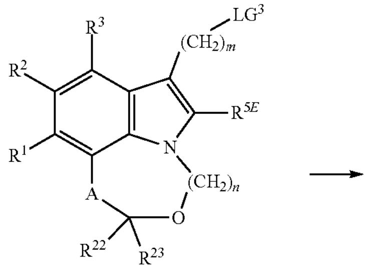

(XI)

-continued

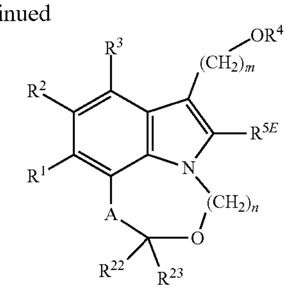

(IIc)

Scheme 2c outlines a modified general synthesis route for certain macrocyclic intermediates of general formula (IIc), constituting a sub-compartment of formula (II), supra, in which E represents an oxygen atom, which employs indole starting materials of formula (VIIa). The approach differs from the ones described in the preceding Schemes 2a-2b in that the group $R^4$ is only introduced on late stage, after elaboration of the macrocyclic core, rendering this approach particularly useful for preparing multiple compounds of the present invention with many different $R^4$ groups.

As shown in Scheme 2c, indole starting materials of formula (VIIa), in which $R^1$, $R^2$, $R^3$ and m are as defined for the compounds of general formula (I), in which $R^{5E}$ represents a group suitable to act as a precursor of a —C(═O)OH or a tetrazol-5-yl group, preferably a group —C(═O)O—$C_{1-4}$-alkyl, and in which $FG^1$ represents chloro, bromo, iodo, a trifluoromethanesulfonyl-group, or a group —$B(OR^B)_2$, preferably bromo or iodo, more preferably a group —$B(OR^B)_2$, can be protected at their free hydroxy group attached to —$(CH_2)_m$— with $PG^1$, a protective group for hydroxy groups as defined herein, such as e.g. tert-butyldimethylsilyl-, by reaction with a suitable reagent such as e.g. tert-butylchlorodimethylsilane, in the presence of a base such as e.g. imidazole, and, optionally, N,N-dimethylpyridin-4-amine, using a halogenated aliphatic hydrocarbon, such as e.g. dichloromethane, as a solvent, to give indole derivatives of formula (VIIb). It is well possible to elaborate said —$B(OR^B)_2$ group, if not present already in the compounds of formula (VIIa), from bromo upon introduction of the protective group $PG^1$. Specific examples are given in the Experimental Section, infra. In formulae (VIa), (VIIa) and (VIIb), $FG^1$ in combination with $FG^2$ represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$, or vice versa. Said group —$B(OR^B)_2$ may be a boronic acid moiety ($R^B$═—H) or an alkyl ester of the boronic acid, e.g. its isopropyl ester ($R^B$═$C_1$-$C_4$-alkyl, e.g. —$CH(CH_3)_2$), or an ester derived from a diol such as e.g. pinacol in which the boronic acid intermediate forms a cyclic boronic ester, preferably a 4,4,5,5-tetramethyl-1,3,2-dioxaborolane ($R^B$—$R^B$═$C_2$-$C_6$-alkylene, preferably —$C(CH_3)_2$—$C(CH_3)_2$—).

Said indole derivatives of formula (VIIb) can, in analogy to the methods discussed in the context of Scheme 1, be reacted in a well-known Suzuki coupling with compounds of formula (VIa), in which $R^{22}$ and $R^{23}$ are as defined for the compound of general formula (I), in which $FG^2$ is as discussed above and in which A', together with the group —$C(R^{22})(R^{23})$—OH attached to it, represents a group suitable to act as precursor of a group A as defined for the compounds of general formula (I), to give compounds of formula (Vb). Said indole starting materials of formula (VIIa) are well known to the person skilled in the art and can be prepared as described infra.

In a subsequent step, the macrocyclic core can be elaborated using approaches such as e.g. those outlined and discussed in the context of Schemes 2a and 2b, by reacting said compounds of formula (Vb) with compounds of formula (IVa), in which Q represents a —($C_2$-$C_9$-alkenylene)-group, and $LG^1$ and $LG^2$ represent, independently from each other, a leaving group, preferably chloro, bromo or iodo, to furnish macrocyclic intermediate compounds of formula (VIII). If compounds of formula (IVa) are being employed as (Z)-alkenes, macrocyclic compounds of formulas (VIII) can be obtained as single (Z) double bond isomers. In a subsequent step, the olefinic double bond present in the group Q can by hydrogenated by methods such as e.g. those outlined and discussed in the context of Scheme 2b, to give macrocyclic intermediates of formula (IX).

Said macrocyclic intermediate compounds of formula (IX) can be subsequently subjected to a cleavage of the protective group $PG^1$, according to methods known to the person skilled in the art (see e.g. T. W. Greene and P. G. M. Wuts in Protective Groups in Organic Synthesis, 4th edition, Wiley 2006), e.g. by reacting with tetrabutylammonium fluoride in tetrahydrofuran in case $PG^1$ represents a tert-butyldimethylsilyl- group, to give compounds of the formula (X). The hydroxy group present in said compounds of the formula (X) can then be converted into $LG^3$, representing a leaving group as defined herein, by methods known to the person skilled in the art, such as e.g. the reaction with tetrabromomethane in the presence of triphenylphosphine, in a suitable solvent such as e.g. a halogenated aliphatic hydrocarbon, e.g. dichloromethane, giving rise to compounds of the formula (XI). The group $R^4$ can finally be introduced by reaction of said compounds of the formula (XI) with a compound of the formula $R^4$—OH, in which $R^4$ is as defined for the compounds of formula (I), in the presence of a base, such as e.g. sodium hydride or cesium carbonate, in a solvent such as e.g. tetrahydrofuran or N,N-dimethylformamide (DMF), to give compounds of formula (IIc). A specific example is given in the Experimental section, infra.

Scheme 2d

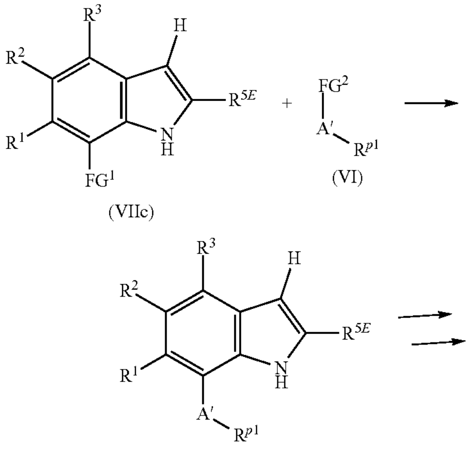

(VIIc) (VI) (Vc)

-continued

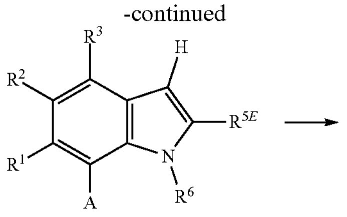

(IId)

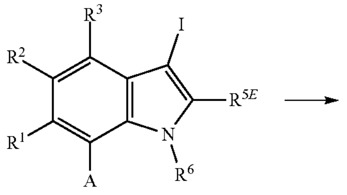

(IIe)

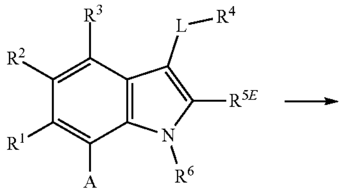

(II)

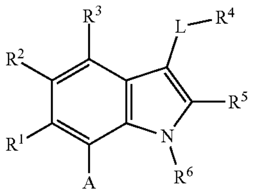

(I)

Scheme 2d outlines a modified general synthesis route for compounds of general formula (I) which employs indole starting materials of formula (VIIc) which differ from aforementioned indole starting materials of formula (VII) in that the C-3 carbon atom of the indole moiety is not substituted by -L-$R^4$ but completely void of substitution.

In a general sense, and in analogy to the discussion regarding Scheme 1, indole starting materials of formula (VIIc), in which $R^1$, $R^2$ and $R^3$ are as defined for the compounds of general formula (I), in which $R^{5E}$ represents a group suitable to act as a precursor of a —C(═O)OH or a tetrazol-5-yl group, preferably a group —C(═O)O—$C_{1-4}$-alkyl, and in which $FG^1$ represents chloro, bromo, iodo, a trifluoromethanesulfonyl- group or a group —$B(OR^B)_2$, preferably bromo or iodo, more preferably a group —$B(OR^B)_2$, can be reacted in a well-known Suzuki coupling with compounds of formula (VI), in which A', together with the group $R^{P1}$ attached to it, represents a group suitable to act as precursor of a group A as defined for the compounds of general formula (I), to give compounds of formula (Vc). Said indole starting materials of formula (VIIc) are well known to the person skilled in the art and are commercially available in certain cases. In a subsequent step (or series of steps), the macrocyclic core can be elaborated using approaches such as e.g. those outlined and discussed in the context of the preceding Schemes 2a to 2c, or analogous methods, to furnish macrocyclic intermediate compounds of formula (IId). Said intermediate compounds of formula (IId) can be subsequently subjected to a halogenation reaction, e.g. with a N-halosuccinimide, such as e.g. N-iodosuccinimide, in a solvent such as e.g. tetrahydrofurane, at a temperature between 0° C. and 80° C., to give intermediate compounds of formula (IIe), in which the hitherto unsubstituted C-3 carbon of the indole is halogenated, preferably iodinated, allowing to subject said compounds of formula (IIe) to various transition metal catalysed, preferably palladium catalysed coupling reactions suitable for the introduction of a group -L-$R^4$, in which $R^4$ and L are as described for the compounds of general formula (I), or a suitable precursor group. Such reagents may be alkynes (to be employed in the well-known Sonogashira coupling), or vinylboronic acid derivatives (to be employed in the well-known Suzuki coupling). Conversion of the thus introduced alkenyl or alkynyl substituents attached to C-3 of the indole can be converted into L-$R^4$ groups by well-known methods such as e.g. catalytic hydrogenolysis or hydroboration, followed by a Mitsunobu coupling (see for example: K. C. K. Swamy et al, Chem. Rev. 2009, 109, 2551), to give compounds of formula (II), which can be converted into compounds of general formula (I) as described in the context of Scheme 3, infra.

Scheme 2e

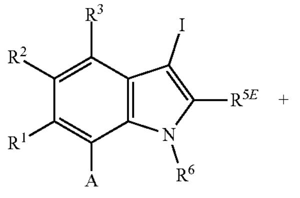

(IIe)

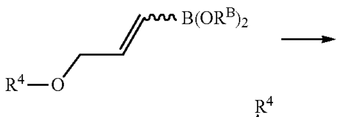

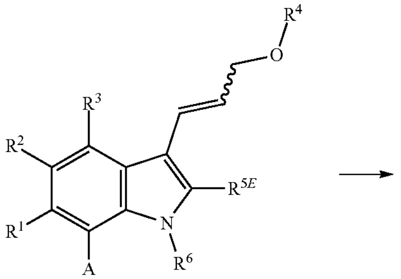

(IIf)

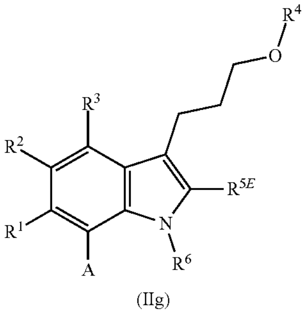

(IIg)

Said vinylboronic acid derivative may be void of further substitution, rendering further elaboration of the -L-$R^4$ group e.g. via hydroboration and Mitsunobu etherification mandatory, or may already feature a group -E-$R^4$, in which E and $R^4$ are as defined for the compounds of general formula (I), e.g. an allylic ether to a group $R^4$, (or a suitable precursor group thereof, e.g. —$OPG^1$ as defined and discussed in context of Scheme 2c) and, as shown exemplarily in Scheme 2e, limiting further elaboration to a hydrogenation of the olefinic double bond present in the resulting intermediates of formula (IIf) to give advanced intermediates of formula (IIg).

Scheme 2f

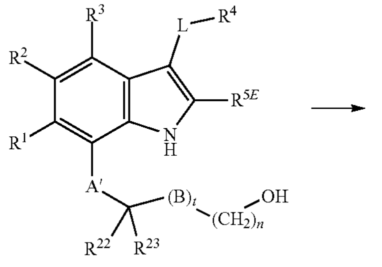

(Vf)

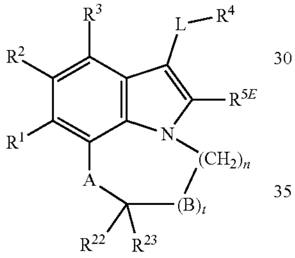

(IIh)

According to Scheme 2f, compounds of formula (IIh), in which $R^7$ (which is a feature of group A as defined for the compounds of general formula (I)) and $R^6$ together form a $^{\#}$—$(CH_2)_n$—$(B)_t$—$CR^{22}R^{23}$—$^{\#\#}$ group, in which B, t, n, $R^{22}$ and $R^{23}$ are as defined for the compounds of the general formula (I), and in which B is preferably —O—, $^{\#}$ represents the point of attachment to the indole nitrogen atom and $^{\#\#}$ represents the point of attachment to the pyrazole carbon atom bearing the $R^7$ substituent, can be obtained from compounds of formula (Vf), in which $R^1$, $R^2$, $R^3$, $R^4$, $R^{22}$, $R^{23}$, B, t, n, and L are as defined for the compounds of general formula (I), in which $R^{5E}$ represents a group suitable to act as a precursor of a —C(═O)OH or a tetrazol-5-yl group, preferably a group —C(═O)O—$C_{1-4}$-alkyl, in which $R^{p2}$ represents a hydrogen atom and $R^{p1}$ (see General Synthesis Route, Scheme 1) represents a —$C(R^{22})(R^{23})$—$(B)_t$—$(CH_2)_n$—OH group, by reacting in a so-called Mitsunobu reaction (see e.g. O. Mitsunobu, *Synthesis* 1981, 1, 1-28) with an azodicarboxylate of the formula $C_1$-$C_4$-alkyl-$O_2C$—N═N—$CO_2$—$C_1$-$C_4$-alkyl, preferably diisopropyl azodicarboxylate or di-tert-butyl azodicarboxylate, and a phosphine $(R^P)_3P$, in which the three groups $R^P$ are independently selected from each other from $C_1$-$C_4$-alkyl, phenyl, and furan-2-yl, whereby phenyl is optionally substituted one or two times with $C_1$-$C_3$-alkyl, $C_1$-$C_3$-alkoxy, or halogen, triphenylphosphine being used preferably; giving rise to the corresponding macrocyclic intermediates of formula (IIh).

Optionally, instead of said azodicarboxylates and phosphines, cyanomethylene phosphoranes of the formula NC—C═$PR^P_3$ can be used, wherein the three groups $R^P$ are as defined above, preferably wherein the three groups $R^P$ are selected from $C_1$-$C_4$-alkyl, more preferably wherein the three groups $R^P$ are n-butyl. Cyanomethylene phosphoranes are easily accessible to a skilled person via literature procedures (see e.g. T. Tsunoda, *Tetrahedron Lett.* 1994, 35, 5081) and/or commercially available.

Said reaction can be advantageously accomplished in a solvent selected from an acyclic or cyclic ether, such tetrahydrofuran, tetrahydropyran, 1,2-dimethoxyethane, bis-(2-methoxymethyl) ether, diethyl ether, or in a dipolar aprotic solvent, such as e.g. N,N-dimethylformamide, N,N-dimethylacetamide or acetonitrile, or an aliphatic halogenated hydrocarbon of the formula $C_1$-$C_3$-haloalkyl-H, such as e.g. dichloromethane, chloroform, or 1,2-dichloroethane, at a temperature ranging from 0° C. to 60° C. Preferably, the reaction is carried out in tetrahydrofuran at room temperature, that is, at a temperature ranging from 20° C. to 25° C.

For the preparation of pyrazole precursors of formula (VIo), suitable for the synthesis of Intermediates of the formula (Vf) via Suzuki coupling as discussed in context of Scheme 1, see Scheme 4f, infra. Phosphines $(R^P)_3P$ and azodicarboxylates of the formula $C_1$-$C_4$-alkyl-$O_2C$—N═N—$CO_2$—$C_1$-$C_4$-alkyl are widely commercially available.

Scheme 2g

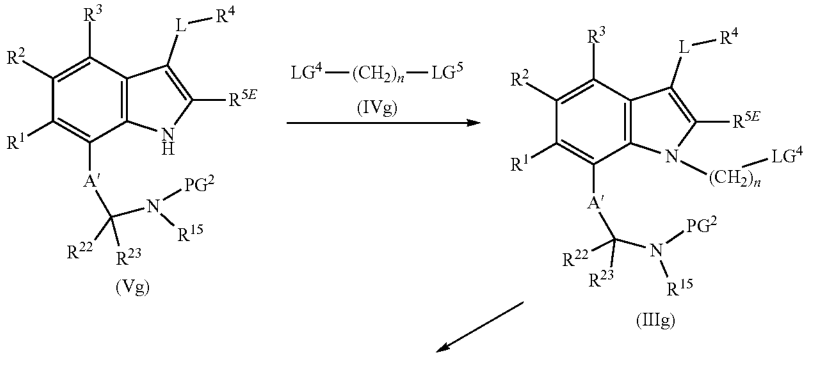

(Vg) (IIIg)

-continued

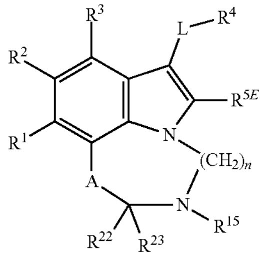

(IIi)

According to Scheme 2g, compounds of formula (IIi), in which $R^7$ (which is a feature of group A as defined for the compounds of general formula (I)) and $R^6$ together form a $^{\#}$—$(CH_2)_n$—$N(R^{15})$—$CR^{22}R^{23}$—$^{\#\#}$ group, in which n, $R^{15}$, $R^{22}$ and $R^{23}$ are as defined for the compounds of the general formula (I), $^{\#}$ represents the point of attachment to the indole nitrogen atom and $^{\#\#}$ represents the point of attachment to the pyrazole carbon atom bearing the $R^7$ substituent, can be obtained from compounds of formula (Vg), in which $R^1$, $R^2$, $R^3$, $R^4$, $R^{15}$, $R^{22}$, $R^{23}$, n, and L are as defined for the compounds of general formula (I), in which $R^{5E}$ represents a group suitable to act as a precursor of a —C(═O)OH or a tetrazol-5-yl group, preferably a group —C(═O)O—$C_{1-4}$-alkyl, in which $PG^2$ represents a protective group for amino groups as defined herein, preferably tert.-butoxycarbonyl, in which $R^{P2}$ represents a hydrogen atom and $R^{P1}$ (see General Synthesis Route, Scheme 1) represents a —$C(R^{22})(R^{23})$—$N(R^{15})$—H group, by (i) reacting with compounds of formula (IVg), in which $LG^4$ and $LG^5$ represent, independently from each other, a leaving group, preferably bromo or iodo, giving rise to intermediate compounds of formula (IIIg). Said compounds of formula (IIIg) can (ii) be subjected to cleavage of said protective group $PG^2$, followed (iii) by intramolecular nucleophilic substitution to afford the corresponding macrocyclic intermediates of formula (IIi).

This reaction sequence can be modified e.g. by replacing compounds of formula (IVg) by compounds of formula (IVa), as defined and discussed in context of Scheme 2a, resulting in macrocyclic intermediates featuring an olefinic double bond, which can be subsequently converted into the corresponding macrocyclic intermediates of formula (IIi) by catalytic hydrogenation as discussed in context of Scheme 2b. Noteworthily, such variant is advantageous for the preparation of macrocyclic intermediates of formula (IIi) in which $R^{15}$ and $R^{22}$, together with the atoms to which they are attached, form a 5- or 6-membered ring.

The abovementioned sequence of transformations can be advantageously accomplished by (i) reacting a compound of formula (Vg) with a compound of formula (IVg), or with said compound of formula (IVa), in the presence of a base such as e.g. an alkali carbonate, an alkali phosphate, or an alkali $C_1$-$C_4$-alkoxide (optionally in combination with an aliphatic amine of the formula $(C_1$-$C_4$-alkyl$)_3N)$, preferably potassium tert-butoxide (for reaction with a compound of formula (IVg)), or cesium carbonate, optionally in combination with diisopropylethylamine (for reaction with a compound of formula (IVa)), in a solvent such as e.g. dimethylformamide (DMF), dimethylacetamide or acetonitrile, preferably acetonitrile, at a temperature ranging from 0° C. to 100° C., preferably from 10° C. to 60° C., more preferably from 20° C. to 45° C.

Subsequently, the protective group $PG^2$ can (ii) be cleaved off using methods well known to the person skilled in the art ($PG^2$ preferably being tert.-butoxycarbonyl and being cleaved by reacting the respective intermediate compound of formula (IIIg) with an acid, preferably trifluoroacetic acid, in an aliphatic halogenated hydrocarbon of the formula $C_1$-$C_3$-haloalkyl-H as a solvent, such as e.g. dichloromethane, chloroform, or 1,2-dichloroethane, at a temperature ranging from 0° C. and 40° C., preferably at room temperature, that is, at a temperature ranging from 20° C. to 25° C.), followed by evaporation of all volatiles in vacuo. The subsequent intramolecular nucleophilic substitution (iii) can be favourably accomplished by reacting the crude product from step (ii) in the presence of an aliphatic amine of the formula $(C_1$-$C_4$-alkyl$)_3N$, preferably diisopropylethylamine, in a solvent such as e.g. dimethylformamide (DMF), dimethylacetamide or acetonitrile, preferably acetonitrile, at a temperature ranging from 0° C. to 100° C., preferably from 10° C. to 60° C., more preferably from 20° C. to 45° C.

In case compounds of formula (Vg) had been reacted with a compound of formula (IVa) in step (i), hydrogenation of the olefinic double bond being present in the resulting macrocyclic intermediates can be advantageously accomplished by reacting said intermediates in a solvent such as e.g. methanol, ethanol, tetrahydrofuran or ethyl acetate, with an atmosphere of hydrogen under ambient or elevated pressure, in the presence of a hydrogenation catalyst such as e.g. palladium on carbon, preferably at room temperature, that is, at a temperature ranging from 20° C. to 25° C.

For the preparation of pyrazole precursors of formulae (VIk), (VIm), and (VIp), suitable for the synthesis of Intermediates of the formula (Vg) via Suzuki coupling as discussed in context of Scheme 1, see Schemes 4e, 4f, and 4g.

It is readily recognised by the person skilled in the art that the elaboration of the macrocycle as present in intermediates of formula (II) can follow further different routes, thus allowing to introduce further groups —B—, as defined for the compounds of general formula (I), such groups e.g. being different from —O—, e.g. by employing starting materials of formula (VI) with functional groups different from —OH (as in formula (VIa)), such as e.g. amino, carboxy, or —SH functional groups, or to elaborate said —OH functional group into said amino, carboxy, or —SH functional groups, using methods known to the person skilled in the art.

C. Conversion into Compounds of Formula (I), Scheme 3:

Scheme 3

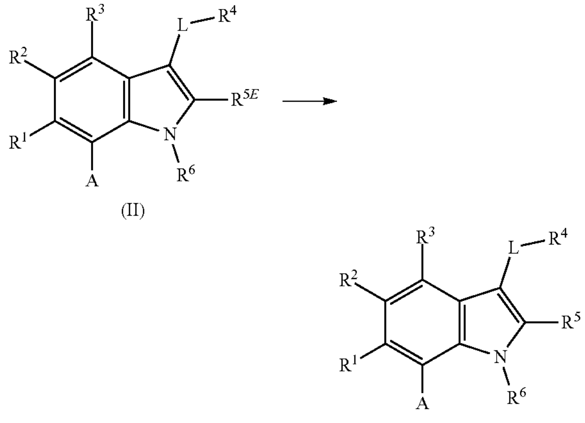

(II)

(I)

According to Scheme 3, compounds of formula (II) (such as e.g. the compounds of the formulae (IIa), (IIb), (IIc), (IIg), (IIh) and (IIi), in which $R^1$, $R^2$, $R^3$, $R^4$, $R^6$, A and L are as defined for the compounds of general formula (I), and in which $R^{5E}$ represents a group suitable to act as a precursor of a —C(=O)OH or a tetrazol-5-yl group, preferably a carboxylic ester group, such as e.g. e.g. a —C(=O)O—$C_{1-4}$-alkyl group or a benzyl ester, can be readily converted into compounds of formula (I) by transforming group $R^{5E}$ into group $R^5$ as defined for the compounds of general formula (I), preferably by reacting with an alkali hydroxide, such as e.g. potassium hydroxide, sodium hydroxide, lithium hydroxide, preferably lithium hydroxide and/or sodium hydroxide, in a mixture of water with THF and/or an aliphatic alcohol of the formula $C_1$-$C_3$-alkyl-OH, preferably methanol or ethanol, at a temperature between 0° C. and 100° C., preferably at a temperature ranging from 20° C. to 80° C., more preferably between 20° C. and 60° C. and subsequent usual workup as known by the person skilled in the art and as for example disclosed in the experimental section.

Said compounds of general formula (I) may be obtained as free acids or converted into pharmaceutically acceptable salts thereof, such as e.g. alkali salts, e.g. sodium or potassium salts, earth alkali salts, e.g. magnesium or calcium salts, and ammonium salts, e.g. ammonium ($NH_4^+$), diethylammonium (herein also referred to as N-ethylethanamine salts) or triethylammonium salts, by methods known to the person skilled in the art. Compounds of the invention featuring a basic nitrogen atom can also be isolated as inner carbon/late salts or as salts with a counteranion of said basic nitrogen, such as e.g. chloride, bromide, methylsulfonate, and the like. Further, compounds of formula (I) in which $R^5$ represents a free carboxylic acid group can be optionally converted into an acylsulfonamide according to methods known to the person skilled in the art (see for example: *Bioorg. Med. Chem. Lett.* 2006, 16, 3639-3641; *Bioorg. Med. Chem. Lett.* 2012, 22, 713-717; *Org. Lett.* 2012, 14(2), 556-559).

As discussed at the end of paragraph A. of this chapter, the compounds of the present invention may feature one or more elements of chirality, resulting in their formation as mixtures of stereoisomers, which may be mixtures of enantiomers as well as mixtures of diastereomers. by the synthetic methods described herein. Further, mixtures of stereoisomers of said compounds of general formula (I) may be separated by methods known to the person skilled in the art, such as e.g. preparative HPLC on a chiral stationary phase, as described supra, and as exemplified in the Experimental Section, infra.

D. Synthesis Routes to Starting Materials of Formulae (VI) and (VII); Schemes 4a-4h:

As outlined in Schemes 4a, 4b, 4c, 4d, 4e, 4f, 4g and 4h below, several approaches, which are intended to illustrate but not to limit the synthetic routes available to the person skilled in the art for this purpose, can be followed in order to prepare starting materials of the formula (VI), as defined in the context of Scheme 1, supra, i.e. in which A', together with the group $R^{P1}$ attached to it, represents a group suitable to act as precursor of a group A as defined for the compounds of general formula (I), and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$ as defined supra, or vice versa. Preferably in particular, $FG^2$ represents bromo. Conversion of compounds, in which $FG^2$ represents bromo, into compounds in which $FG^2$ represents a group —$B(OR^B)_2$, is possible on various steps of the outlined synthesis routes using methods well known to the person skilled in the art.

Scheme 4a

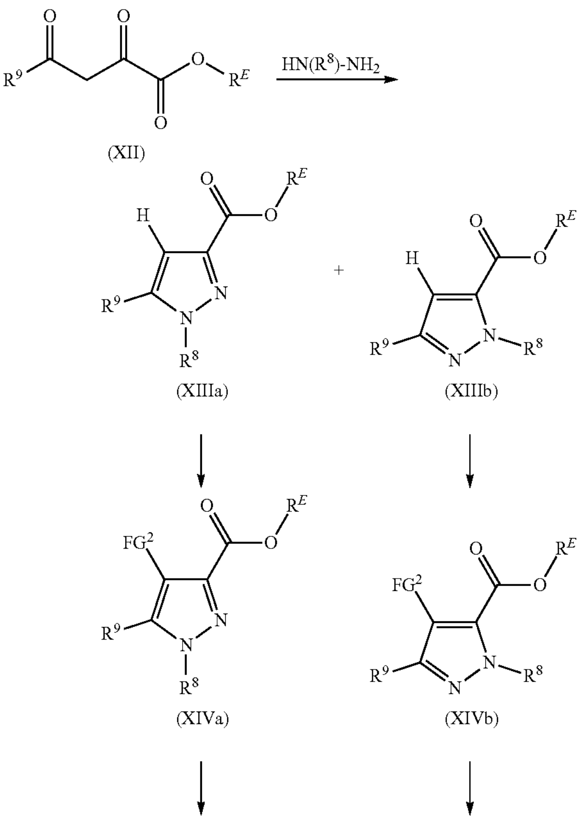

(XII)

(XIIIa) + (XIIIb)

(XIVa) (XIVb)

-continued

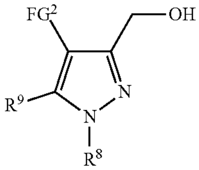

(VIb)

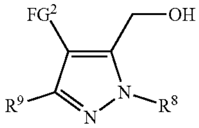

(VIc)

Scheme 4a illustrates the synthesis route enabling the preparation of compounds of formula (VI), in which A' is derived from pyrazole, namely compounds of formulae (VIb) and (VIc), both of them constituting precursors for intermediates of formula (V).

Said compounds of formulae (VIb) and (VIc) can be prepared from well-known α,γ-diketoesters of formula (XII), in which $R^9$ is as defined for the compounds of general formula (I), and in which $R^E$ represents a $C_1$-$C_6$-alkyl group, by reaction with hydrazines of the formula $HN(R^8)$—$NH_2$, in which $R^8$ is as defined for the compounds of general formula (I), to give regioisomeric mixtures of pyrazole derivatives of formulae (XIIIa) and (XIIIb) (see e.g. R. Roman et al., Org. Proc. Res. Development 2014, 18(9), 1027-1036; WO 20171157991A1, p. 106-107), which can be separated on this step or on one of the steps described below. Said hydrazines of the formula $HN(R^8)$—$NH_2$ are well known to the person skilled in the art, and are widely commercially available. If unsubstituted hydrazine ($R^8$═H) is used, $R^8$ groups different from a hydrogen atom can be introduced into compounds of formulae (XIIIa) and (XIIIb) e.g. by suitable alkylating agents such as e.g. a $C_1$-$C_6$-alkyl halide or a di($C_1$-$C_6$-alkyl)sulfate in the presence of a base, such as e.g. sodium carbonate, in a solvent such as e.g. dichloromethane or N,N-dimethylformamide.

Said pyrazole derivatives of formulae (XIIIa) and (XIIIb) can subsequently be reacted with reagents suitable to introduce $FG^2$, such as e.g. N-halo succinimides or solutions of elemental halogens, to give pyrazole derivatives of formulae (XIVa) and (XIVb); preferably, N-bromo succinimide in a halogenated hydrocarbon, such as e.g. 1,2-dichloroethane, as a solvent, or bromine in a solvent such as e.g. glacial acetic acid or a halogenated hydrocarbon, such as e.g. dichloromethane, can be used. Said pyrazole derivatives of formulae (XIVa) and (XIVb) can subsequently be reduced by a suitable reducing agent not interfering with the groups $FG^2$, such as e.g. lithium borohydride, in a solvent such as e.g. tetrahydrofurane, to give pyrazolyl methanols of formulae (VIb) and (VIc).

Scheme 4b

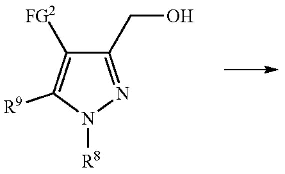

(VIb)

-continued

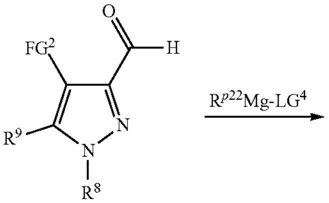

(VId)

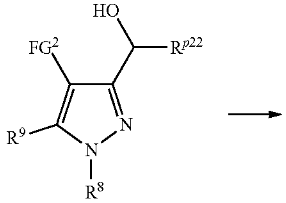

(VIe)

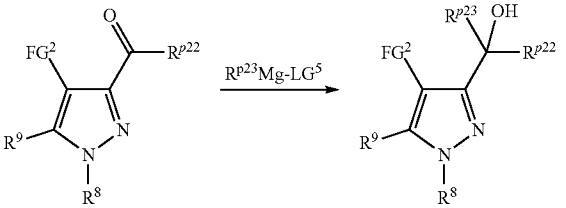

(VIf) (VIg)

Said —$CH_2OH$ group present in said pyrazolyl methanols of formulae (VIb) and (VIc) can be converted into various $R^{p1}$ groups which give rise to the group $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, as defined for the compounds of general formula (I), after elaboration into the compounds of the present invention. As shown in Scheme 4b, pyrazolyl methanols of formula (VIb) can be oxidised by well-known methods, e.g. by reacting with oxalyl chloride and dimethylsulfoxide in the presence of a base such as e.g. triethylamine (the so-called Swern oxidation), to give the corresponding aldehydes of formula (VId), which can be reacted with reagents of the formula $R^{p22}$-Mg-$LG^4$, in which $LG^4$ represents a leaving group selected from chloro, bromo and iodo, and in which $R^{p22}$ represents a group $R^{22}$ as defined for the compound of general formula (I), or a precursor group thereof, in a solvent such as e.g. tetrahydrofuran or diethyl ether, to give secondary pyrazolyl carbinols of formula (Vie). The conversion of aldehydes of formula (VId) into secondary pyrazolyl carbinols of formula (Vie) can also be accomplished with other methods; for an instructive example, see e.g. Intermediate 97 in the Experimental Section, infra and Zhang, Shu-Yu; Tu, Yong-Qiang; Fan, Chun-An; Jiang, Yi-Jun; Shi, Lei; Cao, Ke; Advanced Synthesis and Catalysis; vol. 350; nb. 14-15; (2008); p. 2189-2193.

Examples for said groups $R^{p22}$ and their conversion into groups $R^{22}$ are given below; specific examples are provided in the Experimental section, infra. Said secondary pyrazolyl carbinols of formula (Vie), in turn, can be oxidised again, using well-known methodology, such as e.g. a reaction with hypervalent iodine species, e.g. 1,1-bis(acetyloxy)-3-oxo-3H-1λ$^5$,2-benziodaoxol-1-yl acetate, in a solvent such as e.g. dichloromethane, to give the corresponding ketones of formula (VIf). To introduce a group $R^{23}$ being different from a hydrogen atom, and in analogy to the conversion of aldehydes of formula (VId) into secondary carbinols of formula (Vie), said ketones of formula (VIf) can be reacted with reagents of the formula $R^{p23}$-Mg-$LG^5$, in which $LG^5$ represents a leaving group selected from chloro, bromo and iodo, and in which $R^{p23}$ represents a group $R^{23}$ as defined for the compound of general formula (I), or a precursor group thereof, in a solvent such as e.g. tetrahydrofuran or diethyl ether, to give tertiary pyrazolyl carbinols of formula (VIg). Said oxidation reagents, and reagents of the formulae $R^{p22}$-Mg-$LG^4$ and $R^{p23}$-Mg-$LG^5$, so-called Grignard reagents, are well known to the person skilled in the art and are widely commercially available.

Scheme 4c

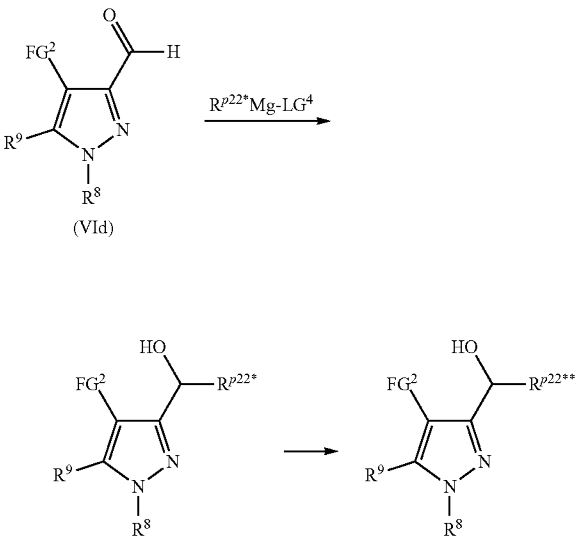

(VId)
(VIe*)
(VIe**)

Said conversion of groups $R^{p22}$ and their conversion into groups $R^{22}$ are shown in a general fashion in Scheme 4c. A specific group $R^{p22}$, herein referred to as $R^{p22*}$, which can e.g. be a $C_1$-$C_7$-alkenyl group, such as e.g. an allyl group, can be introduced in analogy to the methods discussed in context of Scheme 4b, and can be converted into a specific group $R^{22}$, herein referred to as $R^{22}$, by well-known methods such as e.g. ozonolysis of the olefinic double bond present in said $C_1$-$C_7$-alkenyl group, i.e. by treatment of a compound of formula (VIe*), in which $R^{p22*}$ represents a $C_1$-$C_7$-alkenyl group, in an inert solvent such as e.g. dichloromethane, with ozone at low temperature, e.g. −78° C., followed by treatment with triphenylphosphine, to give an intermediate group H(O)C—, or H(O)C—$C_1$-$C_5$-alkyl, which in turn can be reacted with a secondary amine, e.g. an amine such as e.g. diethylamine or dimethylamine, or cyclic secondary amine, such as e.g. pyrrolidine, piperidine, morpholine, or N-methyl piperazine, in a so-called reductive amination reaction, i.e. in the presence of a reagent such as e.g. sodium triacetoxyborohydride or sodium cyanoborohydride, in a solvent such as e.g. tetrahydrofuran or acetonitrile, to give pyrazole compounds of the formula (VIe), in which $R^{22}$ represents a specific group $R^{22}$ amenable to this kind of approach, such as e.g. a $C_1$-$C_6$-alkyl group substituted with a group —$NR^{16}R^{17}$, or with a heterocycloalkyl group. Ozone, as well as the secondary amines mentioned in this paragraph, are well-known, and readily available, to the person skilled in the art.

Scheme 4d

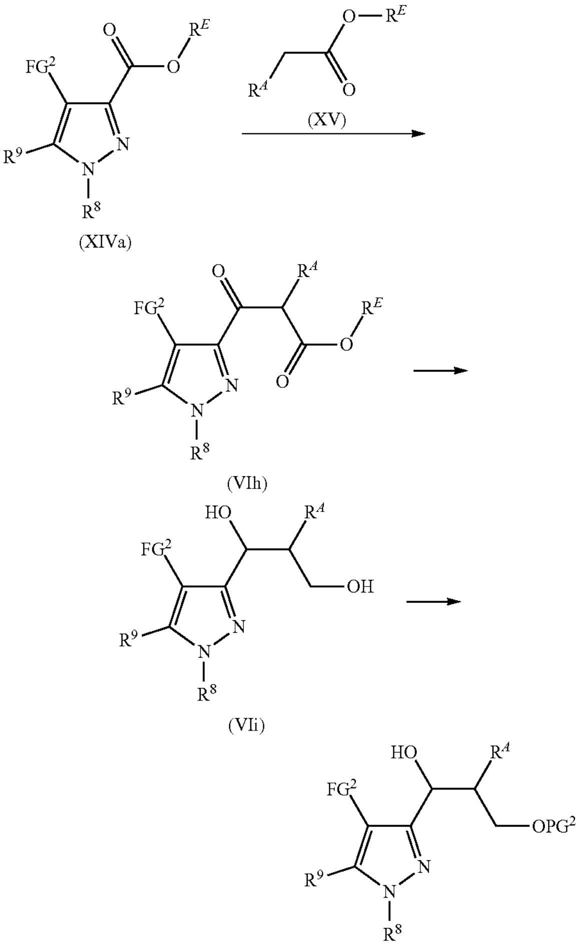

(XIVa)
(VIh)
(VIi)
(VIj)

Scheme 4d shows an example of an alternative strategy to elaborate groups $R^{22}$, or precursor groups $R^{p22}$ thereof, in which pyrazole carboxylates of formula (XIVa), in which $R^8$ and $R^9$ are as defined for the compounds of general formula (I), $FG^2$ is as defined and discussed supra, preferably bromo, and $R^E$ represents a $C_1$-$C_6$-alkyl group, can be reacted with an alkyl ester of an aliphatic carboxylic ester of formula (XV), in which RA represents a hydrogen atom or a $C_1$-$C_3$-alkyl group, and in which $R^E$ represents a $C_1$-$C_6$-alkyl group, in the presence of a strong base such as e.g. lithium trimethyl-N-(trimethylsilyl)silanaminide, in a solvent such as e.g. tetrahydrofuran, to give pyrazole derivatives of formula (VIh), which can be subsequently reduced by methods known to the person skilled in the art, e.g. by reacting with sodium borohydride in a solvent such as e.g. methanol, to give diols of formula (VIi), featuring a $C_3$-$C_6$-alkyl group substituted with two hydroxy groups, as an example of a $R^{22}$ group as defined for the compounds of formula (I). Said $C_3$-$C_6$-alkyl group substituted with two hydroxy groups can be prepared for further manipulation, or for elaboration into the compounds of the present invention e.g. by selective attachment of a protective group $PG^2$, such as e.g. tert-butyldimethylsilyl, to the primary hydroxy group therein, by reacting said diols of formula (VIi) with tert-butyl(chloro)dimethylsilane, in the presence of a base such as e.g. imidazole, in a solvent such as e.g. N,N-dimethylformamide, to give compounds of formula (VIj), featuring yet another example of a group $R^{p22}$ acting as a precursor group as defined for the compounds of general formula (I).

Scheme 4e

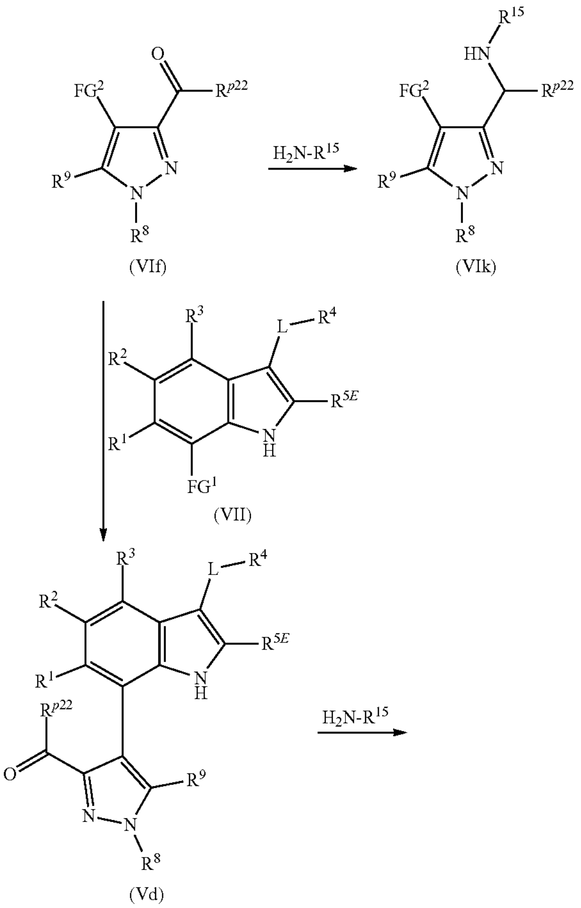

(VIf) (VIk) (VII) (Vd)

-continued

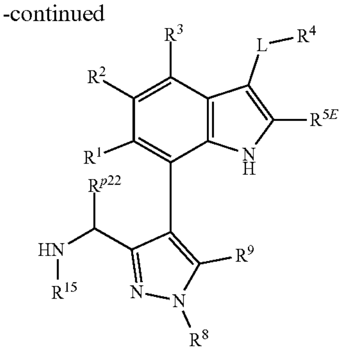

(Ve)

Furthermore, it is readily recognised by the person skilled in the art, that, as shown in Scheme 4e, said ketones of formula (VIf) as shown and discussed in context of Scheme 4b, or the corresponding compounds of formula (Vd), obtainable from these according to the methods described e.g. in context of Scheme 1 by Suzuki coupling with indole derivatives of formula (VII) as defined supra, can readily be subjected to a well-known reductive amination, i.e. a reaction with an amine of the formula $H_2N—R^{15}$, in which $R^{15}$ is as defined for the compounds of formula (I) but preferably different from a hydrogen atom, in the presence of a reagent such as e.g. sodium triacetoxyborohydride or sodium cyanoborohydride, or a combination of sodium borohydride and a Lewis acid such as e.g. titanium tetraisopropoxide (Ti $(OiPr)_4$), in a solvent such as e.g. a halogenated aliphatic hydrocarbon such as e.g. dichloromethane, 1,2-dichloroethane, or chloroform, or acetonitrile or tetrahydrofuran, to give amine compounds of formulae (VIk) or (Ve), respectively, featuring a group $—N(R^{15})H$ suitable for establishing various groups B as defined for the compounds of general formula (I) which are different from —O—.

Scheme 4f

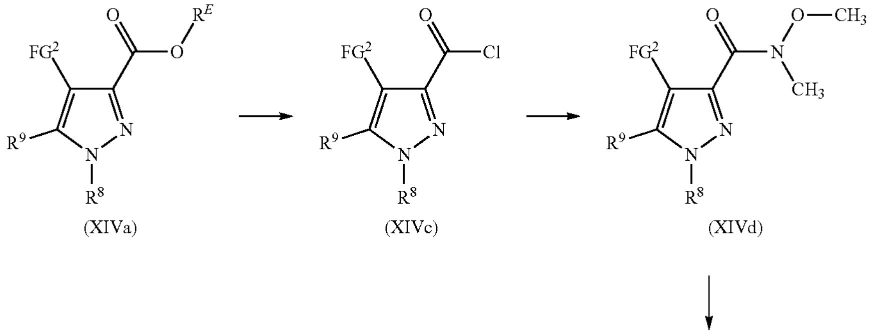

(XIVa) (XIVc) (XIVd)

-continued

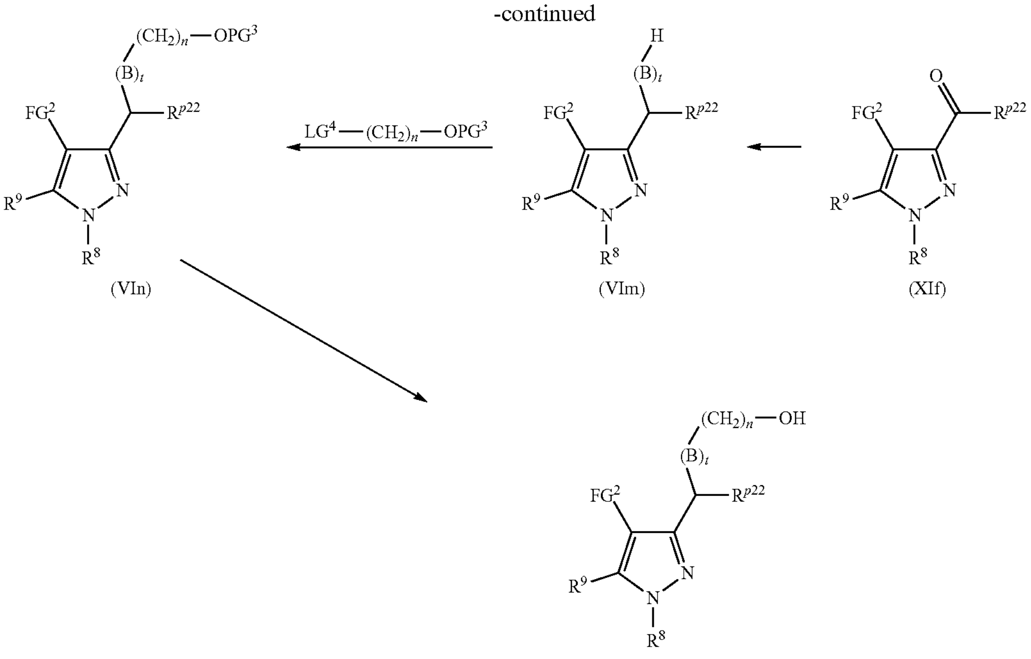

(VIn) (VIm) (XIf) (VIo)

Scheme 4f shows yet another example of an alternative strategy to elaborate groups $R^{22}$, or precursor groups $R^{p22}$ thereof, in which pyrazole carboxylates of formula (XIVa), in which $R^8$ and $R^9$ are as defined for the compounds of general formula (I), $FG^2$ is as defined and discussed supra, preferably bromo or iodo ($FG^2$ can alternatively be introduced also on later stage in the synthesis, e.g. after introduction of $R^{p22}$, or after reduction of the carbonyl group present in compounds of formula (VIf)), and $R^E$ represents a $C_1$-$C_6$-alkyl group, can be reacted with aqueous alkali hydroxide in a solvent such as e.g. an aliphatic alcohol of the formula $C_1$-$C_3$-alkyl-OH, such as e.g. ethanol, to give the corresponding carboxylic acids (not shown), followed by reaction with a halogenating agent, such as e.g. oxalyl chloride, to give acyl chlorides of the formula (XIVc), which in turn can be readily converted into N-methoxy-N-methyl-carboxamides, also known to the person skilled in the art as Weinreb amides, of the formula (XIVd), by reacting with N-methoxymethanamine hydrogen chloride in the presence of an aliphatic amine of the formula $(C_1$-$C_3$-alkyl$)_3N$, such as e.g. triethylamine, in a solvent such as e.g. tetrahydrofuran or dichloromethane. Alternatively, said N-methoxy-N-methyl-carboxamides of formula (XIVd) can be obtained from abovementioned carboxylic acids by reaction with N-methoxymethanamine hydrogen chloride in the presence of an aliphatic amine of the formula $(C_1$-$C_3$-alkyl$)_3N$, such as e.g. diisopropyl ethylamine, in the presence of a well-known amide coupling reagent such as e.g. HOBt. The resulting N-methoxy-N-methyl-carboxamides of formula (XIVd) can be reacted with reagents of the formula $R^{p22}$-Mg-$LG^4$, in which $LG^4$ represents a leaving group selected from chloro, bromo and iodo, and in which $R^{p22}$ represents a group $R^{22}$ as defined for the compound of general formula (I), or a precursor group thereof, in a solvent such as e.g. tetrahydrofuran or diethyl ether, to give pyrazolyl ketones of formula (VIf). On this step, but also later in the synthesis, a precursor group $R^{p22}$ can be converted into a group $R^{22}$, as defined for the compound of general formula (I), by methods discussed e.g. in context of Scheme 4c, supra; or, particularly, if $R^{p22}$ is a vinyl group, it can be reacted e.g. with a secondary amine of the formula $HNR^{16}R^{17}$ or a secondary cyclic aliphatic amine, such as e.g. pyrrolidine, morpholine, piperidine or a N-monosubstituted piperazine, to give compounds of formula (VIf) in which $R^{22}$ is an ethyl group substituted with a group —$NR^{16}R^{17}$ or with a heterocycloalkyl group.

The carbonyl group present in compounds of formula (VIf) can then be employed for the introduction of a variety of —$(B)_t$—H groups, using methods well known to the person skilled in the art, such as e.g. (i) reduction with well-known reagents such as e.g. sodium borohydride or lithium borohydride, to give an —OH group, which in turn can be converted into a leaving group suitable for displacement with a thioacetate or sulphide ion allowing the introduction of a —SH group, or (ii) by reaction with an amine of the formula $H_2NR^{15}$ in a so-called reductive amination, as discussed in more detail in context of Scheme 4e, for the introduction of a —$N(R^{15})$H group, to furnish compounds of formula (Vim). For an instructive example of a stereoselective reduction according to (i), see Intermediate 124 in the Experimental Section, infra. It is readily recognised by the person skilled in the art that said compounds of formula (Vim) can be advantageously used for various synthetic routes laid out herein, e.g. in Schemes 2a, 2d and 2d. Further, the resulting compounds of formula (Vim) can subsequently reacted with a protected alcohol synthon of the formula $LG^{\#}$—$(CH_2)_n$—$OPG^3$, in which $LG^4$ represents a leaving group selected from chloro, bromo and iodo, n is as defined for the compound of general butyldimethylsilyl, in the presence of a base such as e.g. sodium hydride, in a solvent such as e.g. tetrahydrofuran, 1,2-dimethoxyethane or 1,4-dioxan, or in a dipolar aprotic solvent, such as e.g. N,N-dimethylformamide or N,N-dimethylacetamide, or mixtures thereof, to give compounds of formula (VIn) which are readily converted into pyrazole-derived intermediates of formula (VIo), suitable for further conversion according to Scheme 2f, by cleavage of $PG^3$, according to methods well known to the person skilled in the art, e.g. treatment with an acid such as e.g. para-toluenesulfonic acid in an aliphatic alcohol of the formula $C_1$-$C_3$-alkyl-OH, such as e.g. ethanol, as a solvent. Said pyrazole-derived intermediates of formula (VIo) can also be approached by different synthetic routes; for an instructive example, see e.g. Intermediates 148-154 in the Experimental Section, infra, MOCHIDA PHARMACEUTICAL CO., LTD.; Okano, Akihiro; Ohkouchi, Munetaka; Makabe, Muneyoshi; US2013/203739; (2013); (A1).

Scheme 4g

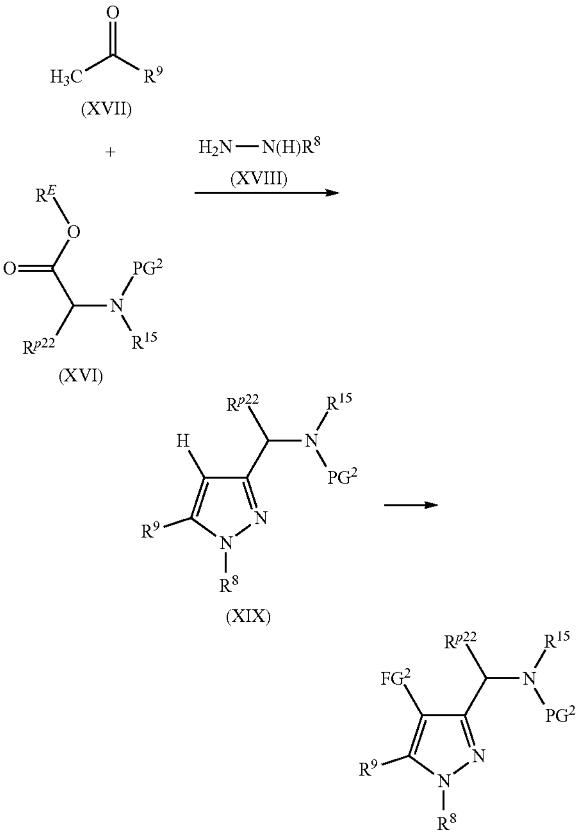

(XVII)

(XVI)

(XIX)

(VIp)

Scheme 4g shows a further route to yet another subcompartment of formula (VI), namely to pyrazole derivatives of formula (VIp), in which B is a group —$NR^{15}$—. Said pyrazole derivatives of formula (VIp) can be prepared by reacting amino acid esters of formula (XVI), in which $R^{15}$ is as defined for the compounds of formula (I), in which $R^{p22}$ represents a group $R^{22}$ as defined for the compound of general formula (I), or a precursor group thereof, in which RE represents a $C_1$-$C_6$-alkyl group, and in which $PG^2$ represents a protective group for amino groups as defined herein, preferably tert.-butoxycarbonyl, with a methyl ketone of formula (XVII), in which $R^9$ is as defined for the compounds of formula (I), in the presence of a strong base, such as e.g. an alkali bis(trimethylsilyl)amide or an alkali $C_1$-$C_4$-alkoxide, such as e.g. sodium hydride (see WO 2005/082864, Example 10A) or potassium tert-butoxide. The crude reaction product resulting thereof can subsequently be reacted with a hydrazine of formula (XVIII), in which $R^8$ is as defined for the compounds of formula (I), to give the corresponding pyrazole derivatives of formula (XIX), into which $FG^2$, which is as defined and discussed supra, preferably iodo or bromo, can be introduced using methods well known to the person skilled in the art, such as e.g. by reacting with 1-iodo- or 1-bromopyrrolidine-2,5-dione (also known as N-iodo or N-bromosuccinimide) in an aliphatic halogenated hydrocarbon of the formula $C_1$-$C_3$-haloalkyl-H as a solvent, such as e.g. dichloromethane, chloroform, or 1,2-dichloroethane, to give said pyrazole derivatives of formula (VIp). This approach can be advantageously used for the preparation of pyrazole derivatives of formula (VIp) in which $R^{15}$ and $R^{p22}$, together with the atoms to which they are attached, form a 5- or 6-membered ring.

Starting materials of the formulae (XVI), (XVII) and (XVIII) for the synthesis according to Scheme 4g are well known to the person skilled in the art and widely commercially available.

Scheme 4h

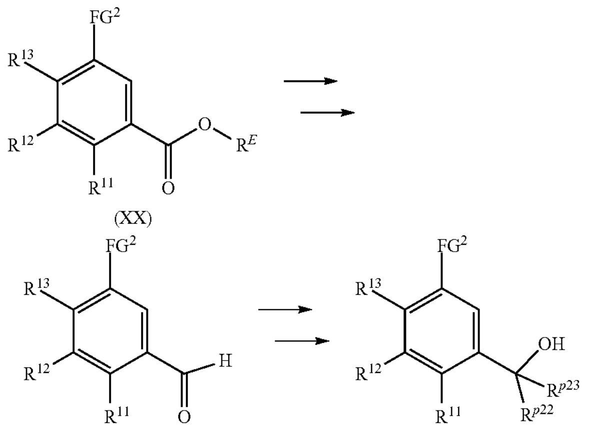

(XX)

(XXI)

(VIq)

Scheme 4h illustrates synthesis routes enabling the preparation of compounds of formula (VI), in which A' is derived from phenyl, pyridinyl, pyrimidinyl or pyridazinyl, namely compounds of formula (VIq), constituting yet another subcompartment of formula (VI).

Starting from compounds of formula (XX), in which $R^{11}$, $R^{12}$, and $R^{13}$ are as defined for the compounds of general formula (I), and wherein one or two of the groups selected from $CR^{11}$, $CR^{12}$ or $CR^{13}$ may be replaced by a nitrogen atom, $R^E$ represents a group —$C_1$-$C_6$-alkyl, and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$ as defined supra, or vice versa, can be readily converted to aldehydes of formula (XXI), using methods well known to the person skilled in the art, e.g. those discussed in context of Schemes 4a and 4b. Further, compounds of formula (XX) and also of formula (XXI) are commercially available in considerable variety. Said aldehydes of formula (XXI) can be converted in to compounds of formula (VIq) by known methods, e.g. in analogy to Scheme 4b and its discussion, supra.

Indole based starting materials of formula (VII), in which $R^1$, $R^2$, $R^3$, $R^4$ and L are as defined for the compounds of general formula (I), in which $R^{5E}$ represents a group suitable to act as a precursor of a —C(═O)OH or a tetrazol-5-yl group, preferably a group —C(═O)O—$C_{1-4}$-alkyl, and in which $FG^1$ represents chloro, bromo, iodo, a trifluoromethanesulfonyl- group, or a group —$B(OR^B)_2$, preferably bromo or iodo, more preferably group —$B(OR^B)_2$, can be prepared using methods well known to the person skilled in the art, see e.g. Journal of Medicinal Chemistry, 2015, 58, 2180-2194. Said group —$B(ORB)_2$ may be a boronic acid moiety ($R^B$═—H) or an alkyl ester of the boronic acid, e.g. its isopropyl ester ($R^B$═$C_1$-$C_4$-alkyl, e.g. —$CH(CH_3)_2$), or an ester derived from a diol such as e.g. pinacol in which the boronic acid intermediate forms a cyclic boronic ester, preferably a 4,4,5,5-tetramethyl-1,3,2-dioxaborolane ($R^B$—$R^B$═$C_2$-$C_6$-alkylene, preferably —$C(CH_3)_2$—$C(CH_3)_2$—). Alternatively to boronic acid derivatives, also tetrafluoroborates, in which —$BF_4^-$ replaces the —$B(OR^B)_2$ moiety, can also be employed.

In the synthesis routes shown herein, modification of any of the substituents, such as $R^1$, $R^2$, $R^3$, $R^4$, $R^5$, $R^{5E}$, $R^6$, $R^7$, $R^8$, $R^9$, $R^{10}$, $R^{11}$, $R^{12}$, $R^{13}$, $R^{p1}$ and $R^{p2}$ can be achieved before and/or after the exemplified transformation. However, also other routes may be used to synthesise the target compounds, in accordance with common general knowledge of a person skilled in the art of organic synthesis. Also, suitable and optionally protected precursor groups of said substituents can be carried through the synthesis routes described in context of the Schemes above, to be elaborated into the actual substituents as defined for the general formula (I), as exemplified e.g. for $R^4$ in Intermediates 44 to 50 in the Experimental Section below.

In particular, conversion of groups $R^{p22}$ and/or $R^{p23}$, in case they represent precursor groups of the groups $R^{22}$ and $R^{23}$ as defined for the compounds of general formula (I), into said groups $R^{22}$ and/or $R^{23}$, by methods well known to the person skilled in the art, e.g. those exemplarily discussed in context of Schemes 4c and 4d, supra, can be performed also on later stage, or even after completion of the elaboration of the macrocycle, in the synthesis of the compounds of the invention. Hence, in the synthesis routes shown e.g. in Schemes 2a, 2b, 2c, 2f and 2g starting materials and intermediates featuring groups $R^{p22}$ and/or $R^{p23}$ can be used instead of the starting materials and intermediates shown in said Schemes, featuring the groups $R^{22}$ and $R^{23}$ as defined for the compounds of general formula (I).

Said modifications can be such as the introduction of protective groups, cleavage of protective groups, reduction or oxidation of functional groups, formation or cleavage of esters or carboxamides, halogenation, metallation, substitution or other reactions known to a person skilled in the art. These transformations include those which introduce a functionality which allows for further interconversion of substituents. Appropriate protective groups and their introduction and cleavage are well-known to a person skilled in the art (see for example T. W. Greene and P. G. M. Wuts in Protective Groups in Organic Synthesis, 4th edition, Wiley 2006). Further, it is possible that two or more successive steps may be performed without work-up being performed between said steps, e.g. a "one-pot" reaction, as it is well-known to a person skilled in the art.

In accordance with a further aspect, the present invention provides a method of preparing a compound of general formula (I) according to any one of claims 1 to 5, said method comprising the step of reacting an intermediate compound of general formula (II):

(II)

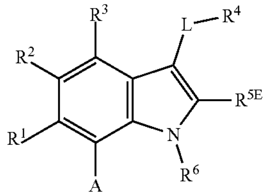

wherein $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester group, with an alkali hydroxide in a mixture of water and THF and/or an aliphatic alcohol of formula $C_1$-$C_3$-alkyl-OH, at a temperature from 0° C. to 100° C., to transform the group $R^{5E}$ into a group $R^5$ as defined for the compounds of general formula (I), and subsequently optionally to convert the free acid group $R^5$ into a pharmaceutically acceptable salt thereof to obtain a compound of general formula (I)

(I)

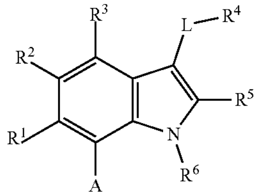

wherein $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and optionally separating enantiomers by means of preparative HPLC on a chiral stationary phase.

In accordance with a further aspect, the present invention covers a method of preparing compounds of general formula (I) according to any one of claims 1 to 5, said method comprising the step of reacting an intermediate compound of general formula (II)

(II)

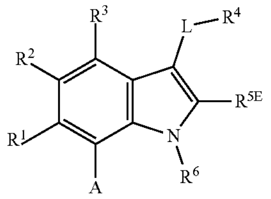

wherein $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester with an alkali hydroxide such as potassium hydroxide, sodium hydroxide, lithium hydroxide, preferably lithium hydroxide, in a mixture of water and THF and/or an aliphatic alcohol of the formula $C_1$-$C_3$-alkyl-OH, preferably methanol or ethanol, at a temperature from 0° C. to 100° C., preferably from 20° C. to 60° C., to transform the group $R^{5E}$ into a group $R^5$ as defined for the compounds of general formula (I), and subsequently optionally to convert the free acid group $R^5$ into a pharmaceutically acceptable salts thereof to obtain a compound of general formula (I)

(I)

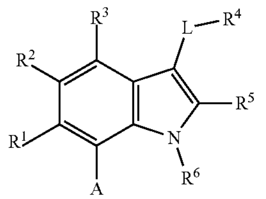

wherein $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and subsequently optionally separating enantiomers by means of preparative HPLC on a chiral stationary phase.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (II)

(II)

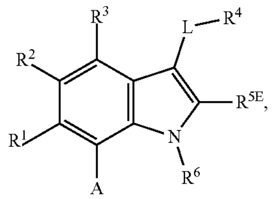

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl group.

In accordance with another aspect, the present invention provides the use of said intermediate compounds for the preparation of a compound of general formula (I) as defined supra.

In accordance with another aspect, the present invention provides a method of using the intermediate compound of general formula (II) for the preparation of a compound of general formula (I).

The present invention provides the intermediate compounds which are disclosed in the Example Section of this text, infra.

The present invention provides any sub-combination within any embodiment or aspect of the present invention of intermediate compounds of general formula (II), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

The X-ray crystallographic analysis described in the MCL-1 structural analysis section infra, provides an atomic resolution view of the relative arrangement of the atoms of MBP-MCL1 in complex with example 47. In this way, the experimental X-ray structure determination of MBP-MCL1 in complex with example 47 provided further information:

First, it proved a clear and direct interaction between example 47 and the target, MCL1.

Second, it provided experimental confirmation of the molecular structure of example 47.

Third, it provided the unequivocal determination the exact stereochemistry of the most active stereoisomer, thereby informing stereospecific syntheses.

Thus a further aspect of the invention is the crystalline structure of the MBP-MCL1 complex with a MCL1-inhibitor, particularly with example 47.

Methods and Administration

Compounds of general formula (I) of the present invention demonstrate a valuable pharmacological spectrum of action and pharmacokinetic profile, both of which could not have been predicted. Compounds of the present invention have surprisingly been found to effectively inhibit MCL-1 activity, and it is possible therefore that said compounds can be used for the treatment or prophylaxis of diseases, preferably hyperproliferative disorders in humans and animals.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

Compounds of the present invention can be utilized to inhibit, block, reduce, and/or decrease cell proliferation and/or cell division, and/or induce apoptosis. Disclosed methods include administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypothalmic glioma, cerebellar and cerebral astrocytoma, medulloblastoma, ependymoma, as well as neuroectodermal and pineal tumours.

Tumours of the male reproductive organs include, but are not limited to, prostate and testicular cancer.

Tumours of the female reproductive organs include, but are not limited to, endometrial, cervical, ovarian, vaginal and vulvar cancer, as well as sarcoma of the uterus.

Tumours of the digestive tract include, but are not limited to, anal, colon, colorectal, oesophageal, gallbladder, gastric, pancreatic, rectal, small-intestine and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma) and mixed hepatocellular cholangiocarcinoma.

Skin cancers include, but are not limited to, basal cell carcinoma, squamous cell carcinoma, Kaposi's sarcoma, malignant melanoma, Merkel cell skin cancer and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, osteosarcoma, malignant fibrous histiocytoma, lymphosarcoma and rhabdomyosarcoma.

Leukemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia and also myelodysplastic syndrome (MDS), which can develop into an acute myeloid leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opththalmol. Vis. Sci., 1996, 37, 855], neovascular glaucoma, psoriasis, retrolental fibroplasias, angiofibroma, inflammation, rheumatoid arthritis (RA), restenosis, in-stent restenosis and vascular graft restenosis. In addition, the increased blood supply associated with cancerous and neoplastic tissue encourages growth, leading to rapid tumour enlargement and metastasis. Moreover, the growth of new blood and lymph vessels in a tumour provides an escape route for rapidly dividing cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing and/or decreasing endothelial cell proliferation, or other pathways involved in angiogenesis, as well as causing cell death or apoptosis of such cell types.

These disorders have been well characterized in humans, but also exist with a similar etiology in other mammals and can be treated by administering pharmaceutical compositions of the present invention.

By "subject" is meant a mammal, including, but not limited to, a human or non-human mammal, such as a bovine, equine, canine, ovine, or feline.

The term "treating" or "treatment" as stated throughout this document is used conventionally, for example the management or care of a subject for the purpose of combating, alleviating, reducing, relieving and/or improving the condition of a disease or disorder, such as a carcinoma.

The compounds of the present invention can be used in particular in therapy and prevention, i.e., prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In some embodiments of the present invention, the compounds of general formula (I) of the present invention may be used to sensitize a cell to radiation, i.e., treatment of a cell with a compound of the present invention prior to radiation treatment of the cell renders the cell more susceptible to DNA damage and cell death than the cell would be in the absence of any treatment with a compound of the present invention. In some embodiments, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In some embodiments, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e., after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g., cis platin), ionizing radiation (X-rays, ultraviolet radiation), carcinogenic agents and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In some embodiments, a compound of general formula (I) of the present invention is administered to a cell prior to the radiation or other induction of DNA damage in the cell. In some embodiments, a compound of general formula (I) of the present invention is administered to a cell concomitantly with the radiation or other induction of DNA damage in the cell. In some embodiments, a compound of general formula (I) of the present invention is administered to a cell immediately after radiation or other induction of DNA damage in the cell has begun.

In some embodiments, the cell is in vitro. In some embodiments, the cell is in vivo.

Thus in some embodiments, the present invention includes a method of inhibiting proliferation of a cell and/or the induction of apoptosis in a cell, comprising contacting the cell with a compound of formula (I) according to any one of claims 1-6.

Another aspect of the invention is a method for controlling cancer (e.g., through treatment and/or prophylaxis) in a subject (e.g., human, other mammal, such as rat, etc.) by administering an effective amount of at least one compound of general formula (I), or a pharmaceutically acceptable salt, polymorph, metabolite, hydrate, solvate or ester thereof to the subject.

In some embodiments, the subject may be administered a medicament, comprising at least one compound of general formula (I) and one or more pharmaceutically acceptable carriers, excipients and/or diluents.

Furthermore in some embodiments, the present invention includes a method of using a compound of general formula (I) for the treatment of diseases.

Particularly in some embodiments, the present invention includes a method of treating a hyperproliferative disease, more particularly cancer, comprising administering an effective amount of at least one compound of general formula (I) according to any one of claims 1-6.

In some embodiments, the method of treatment and/or prophylaxis of a hyperproliferative disorder in a subject may comprise administering to the subject an effective amount of a compound of general formula (I). The hyperproliferative disorder may be, for example, cancer (e.g., lung cancer, acute myeloid leukemia, lymphoma, glioblastoma, prostate cancer, etc.).

In some embodiments, the method of treatment and/or prophylaxis of a hyperproliferative disorder in a subject may comprise administering to the subject an effective amount of a compound of general formula (I). The hyperproliferative disorder may be, for example, cancer (e.g., acute myeloid leukemia, lung cancer, lymphoma, glioblastoma, prostate cancer, etc.).

A method of inhibiting dihydroorotate dehydrogenase activity in a cancer cell is also provided, wherein the method comprises contacting a cancer cell with a compound of general formula (I). The cancer cell may be in vitro or in vivo.

Furthermore in some embodiments, the present invention includes a method of treating cancer, particularly lymphoma, non-Hodgkin-lymphoma type, diffuse large B-cell lymphoma subtype, acute leukemia, acute myeloid leukemia type, multiple myeloma, ovarian cancer, comprising administering an effective amount of at least one compound of formula (I) according to any one of claims 1-6.

Furthermore in some embodiments, the present invention includes a method of treating cancer, particularly breast cancer, lymphoma (including non-Hodgkin-lymphoma type, diffuse large B-cell lymphoma subtype, mantle cell lymphoma), leukemia (including acute monocytic leukemia), liver cancer, multiple myeloma, melanoma, non-small cell lung cancer, small cell lung cancer, ovarian cancer, ovarian carcinoma, stomach cancer, squamous cell carcinoma, comprising administering an effective amount of at least one compound of formula (I) according to any one of claims 1-6.

Furthermore in some embodiments, the present invention includes a method of treating cancer, particularly breast cancer, diffuse large B-cell lymphoma subtype, mantle cell lymphoma, acute monocytic leukemia, liver cancer, multiple myeloma, melanoma, non-small cell lung cancer, small cell lung cancer, ovarian cancer, ovarian carcinoma, prostate cancer, stomach cancer, squamous cell carcinoma, comprising administering an effective amount of at least one compound of formula (I) according to any one of claims 1-6.

Furthermore in some embodiments, the present invention includes a method of treating cancer, particularly bladder cancer, bone cancer, brain cancer, breast cancer, colon cancer (colorectal cancer), endometrial (uterine) cancer, gastric cancer, head and neck cancer, kidney cancer, leukemia, liver cancer, lung cancer, lymphoma, lung cancer, myeloma, neuroblastoma, ovarian cancer, pancreatic cancer, rhabdoid tumor, sarcoma and skin cancer comprising administering an effective amount of at least one compound of formula (I) according to any one of claims 1-6.

Furthermore in some embodiments, the present invention includes a method of treating cancer, particularly bladder cancer, bone cancer (including osteosarcoma), brain cancer (including medulloblastoma, glioma and glioblastoma), breast cancer (including ductal), colon cancer (colorectal cancer), endometrial (uterine) cancer, gastric cancer (including stomach cancer, adenocarcinoma, small cell gastric cancer), head and neck cancer (including squamous cell carcinoma), kidney cancer (including renal medullary carcinoma), leukemia (including acute myelogenous leukemia (AML), acute lymphoblastic leukemia (ALL, T-cell ALL and B-cell ALL), chronic myelogenous leukemia (including blast crisis), plasma cell leukemia (PCL)), liver cancer (including hepatocellular carcinoma), lung cancer (including non-small cell lung cancer and adenocarcinoma, small cell lung cancer) lymphoma (including B-cell lymphoma, diffuse large B-cell lymphoma (DLBCL), mantle cell lymphoma, Hodgkin's lymphoma; non-Hodgkins lymphoma (NHL, including B-cell NHL, T-cell NHL, cutaneous NHL, mantle cell lymphoma, Sezary syndrome, anaplastic large cell NHL (ALCL)), mesothelioma, multiple myeloma, neuroblastoma, ovarian cancer (including ovarian carcinoma, adenocarcinoma high grade serous and serous papillary, serous, cystadenocarcinoma), pancreatic cancer, rhabdoid tumor, sarcoma (including rhabdomyosarcoma), skin cancer (including melanoma) comprising administering an effective amount of at least one compound of formula (I) according to any one of claims 1-6.

Furthermore in some embodiments, the present invention includes a method of treating cancer, particularly bladder cancer; bone cancer, including osteosarcoma; brain cancer, including medulloblastoma, glioma and glioblastoma; breast cancer, including ductal; colorectal cancer; endometrial. uterine cancer; gastric cancer, including stomach cancer, adenocarcinoma, small cell gastric cancer; head and neck cancer, including squamous cell carcinoma; kidney cancer, including renal medullary carcinoma; leukemia, including acute myelogenous leukemia (AML), acute lymphoblastic leukemia (ALL, T-cell ALL and B-cell ALL), chronic myelogenous leukemia (including blast crisis), plasma cell leukemia (PCL); liver cancer, including hepatocellular carcinoma; lung cancer, including non-small cell lung cancer and adenocarcinoma, small cell lung cancer; lymphoma, including B-cell lymphoma, diffuse large B-cell lymphoma (DLBCL), mantle cell lymphoma, Hodgkin's lymphoma; non-Hodgkins lymphoma (NHL, including B-cell NHL, T-cell NHL, cutaneous NHL, mantle cell lymphoma, Sezary syndrome, anaplastic large cell NHL (ALCL); mesothelioma; multiple myeloma; neuroblastoma; ovarian cancer, including ovarian carcinoma, adenocarcinoma high grade serous and serous papillary, serous, cystadenocarcinoma; pancreatic cancer; rhabdoid tumor; sarcoma, including rhabdomyosarcoma; skin cancer, including melanoma comprising administering an effective amount of at least one compound of formula (I) according to any one of claims 1-6.

Furthermore in some embodiments, the present invention includes a method of treating cancer, particularly bladder cancer, bone cancer, brain cancer, breast cancer, colon cancer (colorectal cancer), endometrial (uterine) cancer, gastric cancer, head and neck cancer, kidney cancer, leukemia, acute monocytic leukemia, liver cancer, lung cancer, non-small cell lung cancer, small cell lung cancer, lymphoma, B-cell lymphoma, diffuse large B-cell lymphoma subtype, mantle cell lymphoma, multiple myeloma, melanoma, neuroblastoma, ovarian cancer, ovarian carcinoma, pancreatic cancer, prostate cancer, rhabdoid tumor, sarcoma, skin cancer, stomach cancer, squamous cell carcinoma comprising administering an effective amount of at least one compound of formula (I) according to any one of claims 1-6.

Furthermore in some embodiments, the present invention includes a method of treating cancer, particularly bladder cancer, bone cancer, brain cancer, breast cancer, colon cancer (colorectal cancer), endometrial (uterine) cancer, gastric cancer, head and neck cancer, kidney cancer, liver cancer, lung cancer, non-small cell lung cancer, small cell lung cancer, multiple myeloma, melanoma, neuroblastoma, ovarian cancer, ovarian carcinoma, pancreatic cancer, prostate cancer, rhabdoid tumor, sarcoma, skin cancer, stomach cancer, squamous cell carcinoma comprising administering an effective amount of at least one compound of formula (I) according to any one of claims 1-6.

Furthermore in some embodiments, the present invention includes a method of treating cancer, particularly lymphoma, non-Hodgkin-lymphoma type, diffuse large B-cell lymphoma subtype, acute leukemiacute myeloid leukemia type, multiple myeloma, ovarian cancer, comprising administering an effective amount of at least one compound of formula (I) according to any one of claims 1-6.

Furthermore in some embodiments, the present invention includes a method of treating cancer, more particularly breast cancer; liver cancer; lung cancer; lymphoma leukemia; melanoma; multiple myeloma; and ovarian cancer, even more particularly leukemia and melanoma, especially acute monocytic leukemia and melanoma comprising administering an effective amount of at least one compound of formula (I) according to any one of claims 1-6.

Furthermore in some embodiments, the present invention includes a method of treating cancer, more particularly breast cancer; liver cancer; lung cancer; lymphoma particularly including B-cell lymphoma and mantle cell lymphoma, leukemia, particularly including acute monocytic leukemia; melanoma; multiple myeloma; and ovarian cancer, even more particularly leukemia and melanoma, especially acute monocytic leukemia and melanoma comprising administering an effective amount of at least one compound of formula (I) according to any one of claims 1-6.

Furthermore in some embodiments, the present invention includes a method of treating cancer, particularly multiple myeloma, ovarian carcinoma, acute monocytic leukemia, melanoma and lung cancer comprising administering an effective amount of at least one compound of formula (I) according to any one of claims 1-6.

Furthermore in some embodiments, the present invention includes a method of treating cancer, more particularly breast cancer; liver cancer; lung cancer; lymphoma leukemia; melanoma; multiple myeloma; and ovarian cancer, even more particularly leukemia, especially acute monocytic leukemia or melanoma comprising administering an effective amount of at least one compound of formula (I) according to any one of claims 1-6.

In some embodiments the present invention provides for compounds of general formula (I) for use in a method of treating cancer, particularly where the cancer disease is breast cancer; liver cancer, lung cancer; lymphoma leukemia; melanoma; multiple myeloma; and ovarian cancer, more particularly leukemia, especially acute monocytic leukemia or melanoma.

In some embodiments the present invention provides for compounds of general formula (I) for use in a method of treating cancer, particularly where the cancer disease is breast cancer; liver cancer; lung cancer; lymphoma particularly including B-cell lymphoma and mantle cell lymphoma, leukemia, particularly including acute monocytic leukemia; melanoma; multiple myeloma; and ovarian cancer, even more particularly leukemia and melanoma, especially acute monocytic leukemia and melanoma.

In some embodiments the present invention provides for compounds of general formula (I) for use in a method of treating cancer, particularly where the cancer disease is breast cancer, diffuse large B-cell lymphoma subtype, mantle cell lymphoma, acute monocytic leukemia, liver cancer, multiple myeloma, melanoma, non-small cell lung cancer, small cell lung cancer, ovarian cancer, ovarian carcinoma, prostate cancer, stomach cancer, squamous cell carcinoma.

In some embodiments the present invention provides for compounds of general formula (I) for use in a method of treating cancer, particularly where the cancer disease is bladder cancer, bone cancer, brain cancer, breast cancer, colon cancer (colorectal cancer), endometrial (uterine) cancer, gastric cancer, head and neck cancer, kidney cancer, leukemia, liver cancer, lung cancer, lymphoma, lung cancer, myeloma, neuroblastoma, ovarian cancer, pancreatic cancer, rhabdoid tumor, sarcoma and skin cancer.

In some embodiments the present invention provides for compounds of general formula (I) for use in a method of treating cancer, particularly where the cancer disease is bladder cancer, bone cancer, brain cancer, breast cancer, colon cancer (colorectal cancer), endometrial (uterine) cancer, gastric cancer, head and neck cancer, kidney cancer, leukemia, acute monocytic leukemia, liver cancer, lung cancer, non-small cell lung cancer, small cell lung cancer, lymphoma, B-cell lymphoma, mantle cell lymphoma, multiple myeloma, melanoma, neuroblastoma, ovarian cancer, ovarian carcinoma, pancreatic cancer, prostate cancer, rhabdoid tumor, sarcoma, skin cancer, stomach cancer, squamous cell carcinoma.

In some embodiments the present invention provides for compounds of general formula (I) for use in a method of treating cancer, particularly where the cancer disease is bladder cancer, bone cancer (including osteosarcoma), brain cancer (including medulloblastoma, glioma and glioblastoma), breast cancer (including ductal), colon cancer (colorectal cancer), endometrial (uterine) cancer, gastric cancer (including stomach cancer, adenocarcinoma, small cell gastric cancer), head and neck cancer (including squamous cell carcinoma), kidney cancer (including renal medullary carcinoma), leukemia (including acute myelogenous leukemia (AML), acute lymphoblastic leukemia (ALL, T-cell ALL and B-cell ALL), chronic myelogenous leukemia (including blast crisis), plasma cell leukemia (PCL)), liver cancer (including hepatocellular carcinoma), lung cancer (including non-small cell lung cancer and adenocarcinoma, small cell lung cancer) lymphoma (including B-cell lymphoma, diffuse large B-cell lymphoma (DLBCL), mantle cell lymphoma, Hodgkin's lymphoma; non-Hodgkins lymphoma (NHL, including B-cell NHL, T-cell NHL, cutaneous NHL, mantle cell lymphoma, Sezary syndrome, anaplastic large cell NHL (ALCL)), mesothelioma, multiple myeloma, neuroblastoma, ovarian cancer (including ovarian carcinoma, adenocarcinoma high grade serous and serous papillary, serous, cystadenocarcinoma), pancreatic cancer, prostate cancer; rhabdoid tumor, sarcoma (including rhabdomyosarcoma), skin cancer (including melanoma).

In some embodiments the present invention provides for compounds of general formula (I) for use in a method of treating cancer, particularly where the cancer disease is bladder cancer; bone cancer, including osteosarcoma; brain cancer, including medulloblastoma, glioma and glioblastoma; breast cancer, including ductal; colorectal cancer; endometrial. uterine cancer; gastric cancer, including stomach cancer, adenocarcinoma, small cell gastric cancer; head and neck cancer, including squamous cell carcinoma; kidney cancer, including renal medullary carcinoma; leukemia, including acute myelogenous leukemia (AML), acute lymphoblastic leukemia (ALL, T-cell ALL and B-cell ALL), chronic myelogenous leukemia (including blast crisis), plasma cell leukemia (PCL); liver cancer, including hepatocellular carcinoma; lung cancer, including non-small cell lung cancer and adenocarcinoma, small cell lung cancer; lymphoma, including B-cell lymphoma, diffuse large B-cell lymphoma (DLBCL), mantle cell lymphoma, Hodgkin's lymphoma; non-Hodgkins lymphoma (NHL, including B-cell NHL, T-cell NHL, cutaneous NHL, mantle cell lymphoma, Sezary syndrome, anaplastic large cell NHL (ALCL); mesothelioma; multiple myeloma; neuroblastoma; ovarian cancer, including ovarian carcinoma, adenocarcinoma high grade serous and serous papillary, serous, cystadenocarcinoma; pancreatic cancer; prostate cancer, rhabdoid tumor; sarcoma, including rhabdomyosarcoma; skin cancer, including melanoma.

In some embodiments the present invention provides for compounds of general formula (I) for use in a method of treating cancer, particularly where the cancer disease is bladder cancer, bone cancer (including osteosarcoma), brain cancer (including medulloblastoma, glioma and glioblastoma), breast cancer (including ductal), colon cancer (colorectal cancer), endometrial (uterine) cancer, gastric cancer (including stomach cancer, adenocarcinoma, small cell gastric cancer), head and neck cancer (including squamous cell carcinoma), kidney cancer (including renal medullary carcinoma), liver cancer (including hepatocellular carcinoma), lung cancer (including non-small cell lung cancer and adenocarcinoma, small cell lung cancer), mesothelioma, multiple myeloma, neuroblastoma, ovarian cancer (including ovarian carcinoma, adenocarcinoma high grade serous and serous papillary, serous, cystadenocarcinoma), pancreatic cancer, prostate cancer, rhabdoid tumor, sarcoma (including rhabdomyosarcoma), skin cancer (including melanoma).

Furthermore in some embodiments, the present invention includes a method of treating cancer, particularly lymphoma including, but not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome, and leukemia including, but not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia and also myelodysplastic syndrome (MDS), which can develop into an acute myeloid leukemia.

Furthermore in some embodiments, the present invention provides compounds of general formula (I) for use in a method of treating cancer, particularly where the cancer disease is particularly lymphoma including, but not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome, and leukemia including, but not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia and also myelodysplastic syndrome (MDS), which can develop into an acute myeloid leukemia.

Furthermore in some embodiments, the present invention includes a method of treating cancer, particularly breast cancer; lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; pancreas cancer comprising administering an effective amount of at least one compound of formula (I) according to any one of claims 1-6**. *GC-DLBCL means Germinal B-cell Diffuse Large B-Cell Lymphoma and **ABC-DLBCL means Activated B-cell Diffuse Large B-Cell Lymphoma.

Furthermore in some embodiments, the present invention includes a method of treating cancer, particularly breast cancer, lung cancer, diffuse large B-cell lymphoma subtype including GC-DLBCL* and ABC-DLBCL subtypes, mantle cell lymphomacute monocytic leukemia, melanoma, ovarian cancer, pancreas cancer comprising administering an effective amount of at least one compound of formula (I) according to any one of claims 1-6**. Furthermore in accordance with another aspect, the present invention provides a compound of formula (I) for use of treating diseases.

In some embodiments, the present invention includes a compound of general formula (I) for use in a method of inhibiting proliferation of a cell and/or the induction of apoptosis in a cell, comprising contacting the cell with a compound of formula (I) according to any one of claims 1-6.

Furthermore in some embodiments, the present invention includes a method of treating leukemia, especially acute monocytic leukemia or melanoma in a subject, the method comprising administering to the subject an effective amount of a compound of formula (I).

Particularly in some embodiments, the present invention includes compounds of general formula (I) for use in a method of treating a hyperproliferative disease, more particularly wherein the hyperproliferative disease is cancer, and yet even more particularly wherein the cancer disease is breast cancer; liver cancer, lung cancer; lymphoma leukemia; melanoma; multiple myeloma; and ovarian cancer.

Particularly in some embodiments, the present invention includes compounds of general formula (I) for use in a method of treating a hyperproliferative disease, more particularly wherein the hyperproliferative disease is cancer, and yet even more particularly wherein the cancer disease is lymphoma including, but not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome, and leukemia including, but not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia and also myelodysplastic syndrome (MDS), which can develop into an acute myeloid leukemia.

Particularly in some embodiments, the present invention includes compounds of general formula (I) for use in a method of treating a hyperproliferative disease, more particularly wherein the hyperproliferative disease is cancer, and yet even more particularly wherein the cancer disease is bladder cancer, bone cancer, brain cancer, colon cancer (colorectal cancer), endometrial (uterine) cancer, gastric cancer, head and neck cancer, kidney cancer, leukemia, acute monocytic leukemia, liver cancer, lung cancer, non-small cell lng cancer, small cell lung cancer, lymphoma, B-cell lymphoma, mantle cell lymphoma, multiple myeloma, melanoma, neuroblastoma, ovarian cancer, ovarian carcinoma, pancreatic cancer, prostate cancer, rhabdoid tumor, sarcoma, skin cancer, stomach cancer, squamous cell carcinoma.

In some embodiments, the present invention includes compounds of general formula (I) for use in a method of treating leukemia, especially acute monocytic leukemia or melanoma Particularly in some embodiments, the present invention includes compounds of general formula (I) for use in a method of treating a hyperproliferative disease, more particularly wherein the hyperproliferative disease is cancer, and yet even more particularly wherein the cancer disease breast cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; ovarian cancer; pancreas cancer.

In some embodiments, the present invention includes use of the compounds of general formula (I) for the manufacture of a medicament for the treatment of a hyperproliferative disease, particularly cancer and more particularly breast cancer; lung cancer; lymphoma leukemia; melanoma; multiple myeloma; and ovarian cancer.

In some embodiments, the present invention includes use of the compounds of general formula (I) for the manufacture of a medicament for the treatment of a hyperproliferative disease, particularly cancer and more particularly bladder cancer, bone cancer, brain cancer, breast cancer, colon cancer (colorectal cancer), endometrial (uterine) cancer, gastric cancer, head and neck cancer, kidney cancer, leukemia, acute monocytic leukemia, liver cancer, lung cancer, non-small cell lung cancer, small cell lung cancer, lymphoma, B-cell lymphoma, mantle cell lymphoma, multiple myeloma, melanoma, neuroblastoma, ovarian cancer, ovarian carcinoma, pancreatic cancer, prostate cancer, rhabdoid tumor, sarcoma, skin cancer, stomach cancer, squamous cell carcinoma.

In some embodiments, the present invention includes use of the compounds of general formula (I) for the manufacture of a medicament for the treatment of a hyperproliferative disease, particularly cancer and more particularly bladder cancer, bone cancer (including osteosarcoma), brain cancer (including medulloblastoma, glioma and glioblastoma), breast cancer (including ductal), colon cancer (colorectal cancer), endometrial (uterine) cancer, gastric cancer (including stomach cancer, adenocarcinoma, small cell gastric cancer), head and neck cancer (including squamous cell carcinoma), kidney cancer (including renal medullary carcinoma), leukemia (including acute myelogenous leukemia (AML), acute lymphoblastic leukemia (ALL, T-cell ALL and B-cell ALL), chronic myelogenous leukemia (including blast crisis), plasma cell leukemia (PCL)), liver cancer (including hepatocellular carcinoma), lung cancer (including non-small cell lung cancer and adenocarcinoma, small cell lung cancer) lymphoma (including B-cell lymphoma, diffuse large B-cell lymphoma (DLBCL), mantle cell lymphoma, Hodgkin's lymphoma; non-Hodgkins lymphoma (NHL, including B-cell NHL, T-cell NHL, cutaneous NHL, mantle cell lymphoma, Sezary syndrome, anaplastic large cell NHL (ALCL)), mesothelioma, multiple myeloma, neuroblastoma, ovarian cancer (including ovarian carcinoma, adenocarcinoma high grade serous and serous papillary, serous, cystadenocarcinoma), pancreatic cancer, prostate cancer, rhabdoid tumor, sarcoma (including rhabdomyosarcoma), skin cancer (including melanoma).

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, or otic route or as an implant or stent.

For these administration routes, it is possible for the compounds according to the invention to be administered in suitable administration forms.

For oral administration, it is possible to formulate the compounds according to the invention into dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatin capsules), sugar-coated tablets, granules, pellets, powders, emulsions, suspensions, aerosols or solutions. It is possible to incorporate the compounds according to the invention in crystalline and/or amorphous and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation (inter alia powder inhalers, nebulizers), nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixture agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example, cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example, polyethylene glycols, cacao butter, hard fat),
- solvents (for example, water, ethanol, isopropanol, glycerol, propylene glycol, medium chain-length triglycerides, fatty oils, liquid polyethylene glycols, paraffins),
- surfactants, emulsifiers, dispersants or wetters (for example, sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example, phosphates, carbonates, citric acid, acetic acid, hydrochloric acid, sodium hydroxide solution, ammonium carbonate, trometamol, triethanolamine),
- isotonicity agents (for example, glucose, sodium chloride),
- adsorbents (for example, highly-disperse silicas),
- viscosity-increasing agents, gel formers, thickeners and/or binders (for example, polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatin),
- disintegrants (for example, modified starch, carboxymethylcellulose-sodium, sodium starch glycolate (such as, for example, Explotab®)), cross- linked polyvinylpyrrolidone, croscarmellose-sodium (such as, for example, AcDiSol®)),
- flow regulators, lubricants, glidants and mould release agents (for example, magnesium stearate, stearic acid, talc, highly-disperse silicas (such as, for example, Aerosil®)),
- coating materials (for example, sugar, shellac) and film formers for films or diffusion membranes which dissolve rapidly or in a modified manner (for example, polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example, gelatin, hydroxypropylmethylcellulose),

- synthetic polymers (for example, polylactides, polyglycolides, polyacrylates, polymethacrylates (such as, for example, Eudragit®)), polyvinylpyrrolidones (such as, for example, Kollidon®), polyvinyl alcohols, polyvinyl acetates, polyethylene oxides, polyethylene glycols and their copolymers and blockcopolymers),
- plasticizers (for example, polyethylene glycols, propylene glycol, glycerol, triacetine, triacetyl citrate, dibutyl phthalate),
- penetration enhancers,
- stabilisers (for example, antioxidants such as, for example, ascorbic acid, ascorbyl palmitate, sodium ascorbate, butylhydroxyanisole, butylhydroxytoluene, propyl gallate),
- preservatives (for example, parabens, sorbic acid, thiomersal, benzalkonium chloride, chlorhexidine acetate, sodium benzoate),
- colourants (for example, inorganic pigments such as, for example, iron oxides, titanium dioxide), and
- flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In some embodiments, the present invention includes pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention includes a pharmaceutical combination, which comprises:

- one or more first active ingredients, in particular compounds of general formula (I) as defined supra, and
- one or more further active ingredients, in particular for the treatment and/or prophylaxis of hyperproliferative disorder, particularly cancer.

The term “combination” in the present invention is used as known to persons skilled in the art, it being possible for said combination to be a fixed combination, a non-fixed combination or a kit-of-parts.

A “fixed combination” in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a “fixed combination” is a pharmaceutical composition wherein a first active ingredient and a further active ingredient are present in admixture for simultaneous administration, such as in a formulation. Another example of a “fixed combination” is a pharmaceutical combination wherein a first active ingredient and a further active ingredient are present in one unit without being in admixture.

A non-fixed combination or “kit-of-parts” in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent, or in combination with one or more other pharmaceutically active ingredients where the combination causes no unacceptable adverse effects. The present invention also includes such pharmaceutical combinations. For example, the compounds of the present invention can be combined with known anti-cancer agents.

Examples of Anti-Cancer Agents Include:

131I-chTNT, abarelix, abiraterone, aclarubicin, adotrastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 40 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 3000 mg of active ingredient, and can be administered one or more times per day or less than once a day. The average daily dosage for administration by injection, including intravenous, intramuscular, subcutaneous and parenteral injections, and use of infusion techniques will preferably be from about 0.01 to about 200 mg/kg of total body weight. The average daily rectal dosage regimen will preferably be from about 0.01 to about 200 mg/kg of total body weight. The average daily vaginal dosage regimen will preferably be from about 0.01 to about 200 mg/kg of total body weight. The average daily topical dosage regimen will preferably be from about 0.1 to about 200 mg administered between one to four times daily. The transdermal concentration will preferably be that required to maintain a daily dose of from about 0.01 to about 200 mg/kg. The average daily inhalation dosage regimen will preferably be from about 0.01 to about 100 mg/kg of total body weight.

In one embodiment the average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from abut 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Experimental Section—NMR Spectra

To the extent NMR peak forms and multiplicities are specified, they are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Experimental Section—Abbreviations

The following table lists the abbreviations used in this paragraph and in the Intermediates and Examples section as far as they are not explained within the text body. Other abbreviations have their meanings customary per se to the skilled person. A comprehensive list of the abbreviations utilized by organic chemists of ordinary skill in the art appears presented in the first issue of each volume of the Journal of Organic Chemistry; this list is typically presented in a table titled "Standard List of Abbreviations". In case of doubt, the abbreviations and/or their meaning according to the following table shall prevail.

TABLE 1

Abbreviations

| Abbreviation | Meaning |
|---|---|
| br. | broad signal (NMR) |
| BPR | Back Pressure Regulator |
| d | doublet (NMR) |
| DAD | Diode array detector |
| dd | doublet of doublet (NMR) |
| dt | doublet of triplet (NMR) |
| DMF | N,N-Dimethylformamide |
| DMSO | dimethylsulfoxide |
| EDC | N-[3-(dimethylamino)propyl]-N'-ethylcarbodiimide hydrochloride |
| EDTA | ethylenediaminetetraacetic acid |
| ee | enantiomeric excess |
| ESI | electrospray (ES) ionisation |
| h, hr (hours) | hour(s) |
| HCl | hydrogen chloride, hydrochloric acid |
| HMBC | heteronuclear multiple bond correlation |
| HOBt | Benzotriazol-1-ol |
| HPLC | high performance liquid chromatography |
| HRP | horseradish peroxidase |
| HSQC | Heteronuclear Single Quantum Coherence |
| LC-MS | liquid chromatography-mass spectrometry |
| m | multiplet (NMR) |
| Min | minute(s) |
| MS | mass spectrometry |
| MTP | microtiter plate |
| MWD | Multiple wavelength detector |
| Na—K-tartrate | Sodium potassium tartrate |
| NHS | N-hydroxysuccinimide |
| NMR | nuclear magnetic resonance spectroscopy: chemical shifts (δ) are given in ppm. The chemical shifts were corrected by setting the DMSO signal to 2.50 ppm using dmso-d6 unless otherwise stated. |
| $NAD^+$ | nicotinamide adenine dinucleotide |
| PBS | phosphate buffered saline |
| $Pd(dppf)Cl_2x$ $CH_2Cl_2$ | [1,1'-Bis-(diphenylphosphino)-ferrocen]-dichloropalladium(II), complex with dichloromethanen |
| q | quartet (NMR) |
| quin | quintet (NMR) |
| $R_f$ | Retardation factor in thin layer chormatography |
| rt, RT | room temperature |
| $R_t$, Rt | retention time |
| RuPhos Pd G3 | (2'-aminobiphenyl-2-yl)(methanesulfonato-kappaO)palladium - [2',6'-bis(propan-2-yloxy)biphenyl-2-yl](dicyclohexyl)phosphane (1:1) (Cas No: 1445085-77-7) |
| s | singulet (NMR) |
| SFC | Supercritical Fluid Chromatography |
| SPA | Scintillation proximity assay |
| t | triplet (NMR) |
| td | triplet of doublet (NMR) |
| TFA | trifluoroacetic acid |
| THF | tetrahydrofuran |
| TLC | thin layer chromatography |
| UPLC | ultra performance liquid chromatography |
| UV | ultraviolet |
| wt-% | percent of weight |

TABLE 1-continued

| Abbreviations | |
|---|---|
| Abbreviation | Meaning |
| $[^3H]$— | tritium |
| δ | chemical shift |
| XPhos Pd G2 | Chloro(2-dicyclohexylphosphino-2',4',6'-triisopropyl-1,1'-biphenyl)[2-(2'-amino-1,1'-biphenyl)]palladium(II) (Cas No: 1310584-14-5) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate (Cas No: 1445085-55-1) |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. Reactions were set up and started, e.g. by the addition of reagents, at temperatures as specified in the protocols; if no temperature is specified, the respective working step was performed at ambient temperature, i.e. between 18 and 25° C.

"Silicone filter" or "water resistant filter" refers to filter papers which are made hydrophobic (impermeable to water) by impregnation with a silicone. With the aid of these filters, water can be separated from water-immiscible organic solvents by means of a filtration (i.e. filter paper type MN 617 WA, Macherey-Nagel).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization.

In some cases, impurities may be removed by trituration using a suitable solvent or solvent mixture. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/ethanol. In flash column chromatography, unmodified ("regular") silica gel may be used as well as aminophase functionalized silica gel. As used herein, "Biotage SNAP cartridge silica" refers to the use of regular silica gel; "Biotage SNAP cartridge $NH_2$ silica" refers to the use of aminophase functionalized silica gel. If reference is made to flash column chromatography or to flash chromatography in the experimental section without specification of a stationary phase, regular silica gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid, diethylamine or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−).

Analytical UPLC Methods:

Method 1:

Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Method 2:

Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 3:

Instrument: Waters Acquity UPLCMS SingleQuad; Colum: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm Method 4:

Instrument: Waters Affiance HT; Column: Waters Cortecs 30 mm×3 mm×2.7 μm; eluent A: Water (MilliQ))+0.01 vol % formic acid, eluent acetonitrile+0.01 vol % formic acid; gradient: 0-1.7 min 3-95% B, 1.7-2.2 min 95% B; 2.3-2.5 min 3% B; flow: 1.75 mL/min; temperature: 45° C.; DAD scan: 200-500 nm.

Method 5:

Instrument: Waters Affiance HT; Column: Waters Cortecs 30 mm×3 mm×2.7 μm; eluent A: Water (MilliQ)+0.01 vol % formic acid, eluent B: acetonitrile+0.01 vol % formic acid; gradient: 0-6.8 min 5-95% B, 6.8-7.3 min 95% B; 7.3-7.5 min 5% B; flow: 1.75 mL/min; temperature: 45° C.; DAD scan: 200-500 nm.

Method 6:

Instrument: Waters Acquity; Column: Waters Acquity BEH C18 50 mm×2.1 mm×1.7 μm; eluent A: Water (MilliQ)+0.01 vol % formic acid, eluent B: acetonitrile+0.01 vol % formic acid; gradient: 0-0.3 min 3-4% B, 0.3-1.5 min 4-95% B, 1.5-1.9 min 95% B; 1.9-2.0 min 5% B; flow: 0.65 mL/min; temperature: 50° C.; DAD scan: 200-500 nm.

Method 7:

Instrument: Waters Acquity; Column: Waters Acquity BEH C18 50 mm×2.1 mm×1.7 μm; eluent A: Water (MilliQ)+0.01 vol formic acid, eluent B: acetonitrile+0.01 vol % formic acid; gradient: 0-0.5 min 2% B, 0.5-1.5 min 2-95% B, 1.5-1.9 min 95% B; 1.9-2.0 min 95-2% B, 2.0-2.5 min, 2% B; flow: 0.65 mL/min; temperature: 45° C.; DAD scan: 200-500 nm.

Method 8:

Instrument: Waters Acquity; Column: Waters Acquity BEH C18 50 mm×2.1 mm×1.7 μm; eluent A: Water (MilliQ)+0.01 vol formic acid, eluent B: acetonitrile+0.01 vol % formic acid; gradient: 0-0.5 min 2-5% B, 0.5-4.0 min 5-95% B, 4.0-4.5 min 95% B, 4.5-5.0 min 95-2% B; flow: 0.65 mL/min; temperature: 45° C.; DAD scan: 200-500 nm.

Method 9:

MS instrument type: Shimadzu LCMS-2020; HPLC instrument type: Shimadzu UV SPD-M20A; column: Kinetex EVO C18 2.1*30 mm*5 um; mobile phase A: 0.025% NH3.H2O in water (v/v), mobile phase B: acetonitrile; gradient: 0.00 min 5% B—0.80 min 95% B—1.2 min 95% B—1.21 min 5% B—1.5 min 5% B; flow rate: 1.5 mL/min; Column Temp: 40° C.; UV detection: 220 nm & 254 nm.

Method 10:

MS instrument type: Shimadzu LCMS-2020; HPLC instrument type: Shimadzu UV SPD-M20A; column: Chromolith Flash RP-18e 25*2 mm; mobile phase A: 0.0375% TFA in water, mobile phase B: 0.01875% TFA in acetonitrile; gradient: 0.00 min 5% B—0.80 min 95% B—1.20 min 95% B—1.21 min 5.0% B—1.55 min 5% B; flow rate: 1.5 mL/min; oven temperature: 50° C.; UV detection: 220 nm & 254 nm.

Method 11:

MS instrument type: Shimadzu LCMS-2020; HPLC instrument type: Shimadzu UV SPD-M20A; column: Kinetex EVO C18 2.1*30 mm*5 um; mobile phase A: 0.025% NH3.H2O in water (v/v), mobile phase B: acetonitrile; gradient: 0 min 5% B→3.00 min 95% B→3.50 min 95% B→3.51 min 5% B→4.00 min 5% B; flow rate: 0.8 mL/min; Column Temp: 40° C.; UV detection: 220 nm & 254 nm.

Method 12: SFC

AD-3_MeOH (DEA)_5_40_3 mL-35T: Column: Chiralpak AD-3 50×4.6 mm I.D., 3 um; Mobile phase: methanol (0.05% DEA) in $CO_2$ from 5% to 40%; Flow rate: 3 mL/min Wavelength: 220 nm.

Method 13: SFC

IC-3_5 CM_MEOH (DEA)_5_40_3 ML_T35: Column: Chiralpak IC-3 50×4.6 mm I.D., 3 um; Mobile phase: methanol (0.05% DEA) in $CO_2$ from 5% to 40%; Flow rate: 3 mL/min; Wavelength: 220 nm.

Preparative HPLC Methods:

Method P1:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 μm, 125×30 mm; solvent A: water+0.1 vol-% formic acid, solvent B: acetonitrile gradient: 0.00-0.50 min 40% B (150 mL/min), 0.50-6.00 min 40-80% B (150 mL/min), 6.00-6.10 min 80-100% B (150 mL/min), 6.10-8.00 min 100% B (150 mL/min), UV-Detection.

Method P2:

Instrument: pump: Labomatic HD-5000 or HD-3000, head HDK 280, low pressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; Eluent basic: solvent A: water+0.2 vol-% aqueous ammonia (32%), solvent B: acetonitrile gradient: 0.00-0.50 min 15% B (150 mL/min), 0.50-6.00 min 15-55% B (150 mL/min), 6.00-6.10 min 55-100% B (150 mL/min), 6.10-8.00 min 100% B (150 mL/min), UV-Detection Method P3:

Instrument: pump: Labomatic HD-5000 or HD-3000, head HDK 280, low pressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; Eluent acidic: solvent A: water+0.1 vol-% formic acid, solvent B: acetonitrile;

0.00-0.50 min 65% B (150 ml/min), 0.50-6.00 min 65-100% B (150 ml/min), 6.00-8.00 min 100% B (150 ml/min)

Specific Optial Rotation Methods:

Method O1:

Instrument: JASCO P2000 Polarimeter; wavelength 589 nm; temperature: 20° C.; integration time 10 s; path length 100 mm.

INTERMEDIATES

Intermediate 1 ethyl 3-[3-(naphthalen-1-yloxy)propyl]-7-(4,4,5,5-tetramethyl-1,3,2-dioxaborolan-2-yl)-1H-indole-2-carboxylate

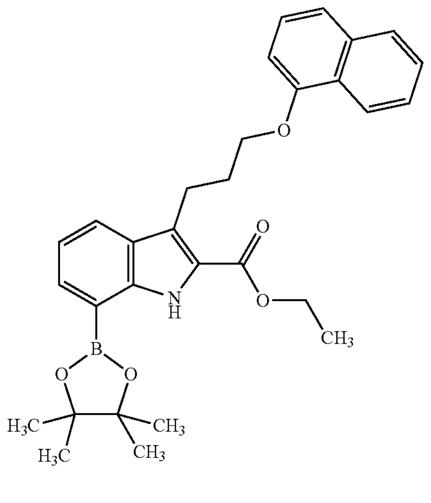 [SMILES: CCOC(=O)c1[nH]c2c(B3OC(C)(C)C(C)(C)O3)cccc2c1CCCOc1cccc2ccccc12]

Ethyl-3-[3-(naphthalen-1-yloxy)propyl]-7-(4,4,5,5-tetramethyl-1,3,2-dioxaborolan-2-yl)-1H-indole-2-carboxylate was prepared as described in the literature (Journal of Medicinal Chemistry, 2015, 58, 2180-2194).

Intermediate 2 ethyl-7-bromo-3-(3-ethoxy-3-oxopropyl)-6-fluoro-1H-indole-2-carboxylate

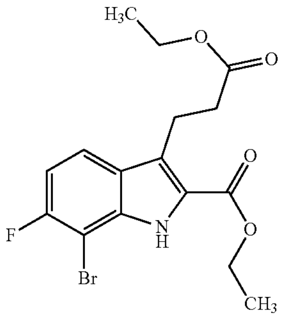 [SMILES: CCOC(=O)CCc1c(C(=O)OCC)[nH]c2c(Br)c(F)ccc12]

To a stirred solution of 2-bromo-3-fluoroaniline (CAS 111721-75-6, 9.50 g, 50.0 mmol, 1.00 eq.) in an aqueous hydrochloric acid solution (12.5 mL conc. HCl in 80.0 mL of water, 150 mmol, 3.00 eq.) was added dropwise a 2.5 M solution of sodium nitrite (20.0 mL, 50.0 mmol, 1.00 eq.) in water at a temperature of 0° C. After complete addition, a 4.5 M solution of sodium acetate in water (62.4 mL, 281 mmol, 5.62 eq.) was added via dropping funnel, followed by dropwise addition of ethyl-2-oxocyclopentanecarboxylate (CAS 611-10-9, 7.40 mL, 50.0 mmol, 1.00 eq.). The resulting yellow suspension was maintained at 0° C. for 15 minutes and then warmed to room temperature and stirred for 2 hours. The reaction mixture was extracted thrice with dichloromethane (100 mL each) and the combined organic extracts were dried over magnesium sulfate, filtered and concentrated under reduced pressure to give the crude hydrazone as a red oil (18.1 g). The residue was dissolved in ethanol (50.0 mL, 1.00 M), after which sulfuric acid (6.63 mL, 125 mmol, 2.50 eq.) was added dropwise. The dark orange solution was heated at 95° C. for 6 days and then cooled to room temperature. The dark brown solution was poured onto ice/water (200 mL) and extracted thrice with dichloromethane (200 mL each). The combined organic extracts were washed with saturated aqueous bicarbonate solution (200 mL), dried over magnesium sulfate, filtered and concentrated under reduced pressure to give a brown solid. The residue was purified by flash column chromatography (0-30% ethyl acetate/hexane gradient) and then recrystallized from hot ethyl acetate/hexane (9:1) to give the title compound as a light yellow solid (8.35 g, 42%).

Rf=0.22 (15% ethyl acetate/hexane, UV).

Intermediate 3 ethyl-7-bromo-6-fluoro-3-(3-hydroxpropyl)-1H-indole-2-carboxylate

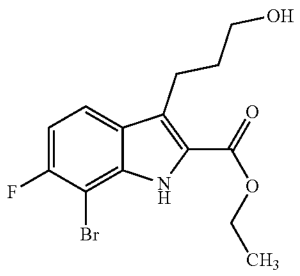 [SMILES: CCOC(=O)c1[nH]c2c(Br)c(F)ccc2c1CCCO]

To a stirred solution of ethyl-7-bromo-3-(3-ethoxy-3-oxopropyl)-6-fluoro-1H-indole-2-carboxylate (see Intermediate 2, 16.6 g, 42.9 mmol, 1.00 eq.) in anhydrous tetrahydrofuran (429 mL) at 0° C. was added borane dimethyl sulfide complex (CAS 13292-87-0, 16.1 mL, 171 mmol, 4.00 eq.). The resulting mixture was stirred at 0° C. for 30 minutes and was then warmed to room temperature and stirred for 2 days. Methanol was added to the mixture to decompose any remaining borane, and the mixture was concentrated three times from methanol to give a light yellow solid. The residue was purified by flash column chromatography (50-100% ethyl acetate/hexane gradient) to give the title compound as a white fluffy solid (11.7 g).

Rf=0.33 (50% ethyl acetate/hexane, UV).

Intermediate 4

Ethyl-7-bromo-6-fluoro-3-(3-(naphthalen-1-yloxy)propyl)-1H-indole-2-carboxylate

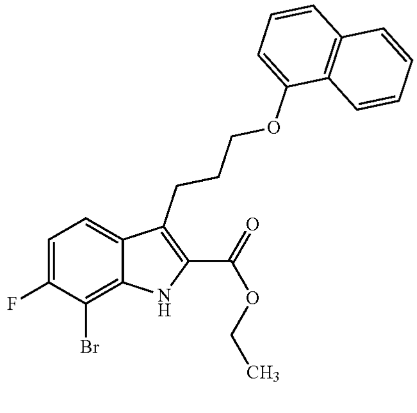 [SMILES: CCOC(=O)c1[nH]c2c(Br)c(F)ccc2c1CCCOc1cccc2ccccc12]

To a stirred suspension of ethyl-7-bromo-6-fluoro-3-(3-hydroxpropyl)-1H-indole-2-carboxylate (see Intermediate 3, 11.7 g, 33.9 mmol, 1.00 eq.), 1-naphthol (CAS 90-15-3, 5.85 g, 40.6 mmol, 1.20 eq.) and triphenylphosphine (10.6 g, 40.6 mmol, 1.30 eq.) in anhydrous tetrahydrofuran (113 mL) was carefully added di-tert-butyl azodicarboxylate (9.34 g, 40.6 mmol, 1.30 eq.) in small portions at a temperature of 0° C. After complete addition, the yellow solution was warmed to room temperature, stirred for 17 hours and was then concentrated under reduced pressure. The residue was redissolved in dichloromethane (200 mL) and then washed with water (200 mL), saturated aqueous bicarbonate solution (200 mL) and brine (200 mL). The organic layer was dried over magnesium sulfate, filtered and concentrated under reduced pressure to give an orange oil (40.3 g). The residue was purified by flash column chromatography (10-20% ethyl acetate/hexane gradient) and was then recrystallised from hot ethanol to give the title compound as an off-white solid (12.3 g).

Rf=0.30 (15% ethyl acetate/hexane, UV).

Intermediate 5 ethyl-6-fluoro-3-[3-(naphthalen-1-yloxy)propyl]-7-(4,4,5,5-tetramethyl-1,3,2-dioxaborolan-2-yl)-1H-indole-2-carboxylate

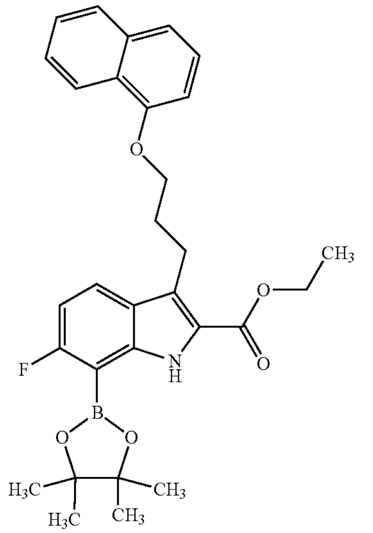 [SMILES: CCOC(=O)c1[nH]c2c(B3OC(C)(C)C(C)(C)O3)c(F)ccc2c1CCCOc1cccc2ccccc12]

Under an argon atmosphere, to ethyl-7-bromo-6-fluoro-3-[3-(naphthalen-1-yloxy)propyl]-1H-indole-2-carboxylate (see Intermediate 4, 3.00 g, 6.38 mmol) in 60 mL 1,4-dioxane were added 4,4,4',4',5,5,5',5'-octamethyl-2,2'-bi-1,3,2-dioxaborolane (CAS 78183-34-3, 4.68 g, 19.1 mmol), potassium acetate (2.88 g, 29.3 mmol) and 1,1' Bis(diphenylphosphino)ferrocene-palladium(II)dichloride dichloromethane complex (1.04 g, 1.28 mmol). The reaction mixture was stirred at 90° C. for 23 hours, was filtered through a Celite plug, was diluted with water and extracted with ethyl acetate. The combined organic layers were filtered and dried with a water resistant filter and concentrated under reduced pressure. The residue was purified by flash column chromatography using silica gel (ethyl acetate/hexane gradient). The product was triturated with 2-methoxy-2-methylpropane, the solid material was isolated by filtration, washed with 2-methoxy-2-methylpropane and dried to give the title compound (2.68 g).

LC-MS (Method 1): $R_t$=1.82 min; MS (ESIpos): m/z=518 $[M+H]^+$ $^1$H-NMR (400 MHz, CHLOROFORM-d) δ [ppm]: 1.172 (0.49), 1.191 (3.93), 1.304 (1.34), 1.322 (3.13), 1.340 (1.65), 1.353 (16.00), 1.514 (3.72), 2.237 (0.51), 3.299 (0.48), 3.318 (0.81), 3.336 (0.46), 4.062 (0.51), 4.077 (1.05), 4.092 (0.49), 4.279 (0.42), 4.297 (1.32), 4.315 (1.35), 4.333 (0.42), 6.632 (0.45), 6.649 (0.50), 6.671 (0.49), 6.693 (0.53), 6.695 (0.52), 6.717 (0.45), 7.253 (0.65), 7.272 (0.55), 7.324 (0.60), 7.400 (0.43), 7.406 (0.63), 7.415 (0.97), 7.425 (0.74), 7.430 (0.51).

Intermediate 6 ethyl-7-bromo-6-chloro-3-(3-hydroxpropyl)-1H-indole-2-carboxylate

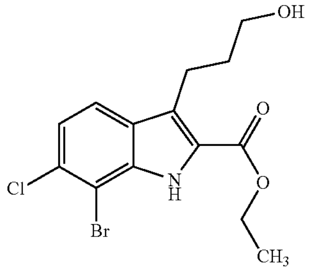 [SMILES: CCOC(=O)c1[nH]c2c(Br)c(Cl)ccc2c1CCCO]

The title compound was prepared as described in J. Med. Chem. 2015, 58, 3794-3805.

Intermediate 7 ethyl-7-bromo-6-chloro-3-[3-(naphthalen-1-yloxy)propyl]-1H-indole-2-carboxylate

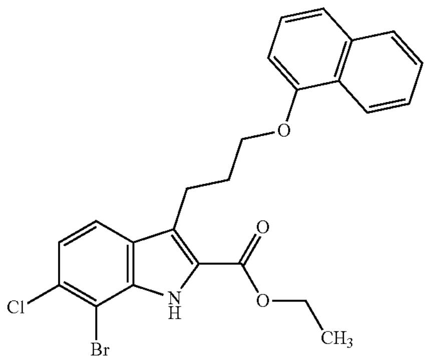 [SMILES: CCOC(=O)c1[nH]c2c(Br)c(Cl)ccc2c1CCCOc1cccc2ccccc12]

To a mixture of ethyl-7-bromo-6-chloro-3-(3-hydroxypropyl)-1H-indole-2-carboxylate (see Intermediate 6, 6.62 g, 18.4 mmol), 1-naphthol (CAS 90-15-3, 3.21 g, 22.0 mmol) and triphenylphosphine (5.84 g, 22.0 mmol) in tetrahydrofuran (150 mL) was added diisopropyl azodicarboxylate (4.4 mL, 22 mmol) at 10° C., and the mixture was stirred for 24 hours at room temperature. For work-up, the mixture was diluted with ethyl acetate and was washed with aqueous sodium bicarbonate solution and brine. The organic phase was dried over sodium sulfate, filtered, and the filtrate was concentrated under reduced pressure. The crude product was purified by flash chromatography (hexane/dichloromethane gradient 20-100% dichloromethane) to give, after trituration with methanol, the title compound (3.5 g).

LC-MS (Method 2): Rt=1.78 min; MS (ESIpos): m/z=486 $[M+H]^+$ $^1$H-NMR (400 MHz, DMSO-d6) δ[ppm]: 1.283 (7.11), 1.300 (16.00), 1.318 (7.27), 2.160 (0.50), 2.177 (1.51), 2.193 (2.15), 2.212 (1.56), 2.227 (0.52), 2.518 (1.77), 2.522 (1.06), 3.286 (1.94), 3.306 (3.21), 3.323 (2.04), 4.143 (2.14), 4.159 (4.48), 4.173 (2.10), 4.277 (2.03), 4.294 (6.62), 4.312 (6.50), 4.330 (1.94), 6.860 (2.56), 6.878 (2.70), 7.170 (5.69), 7.192 (5.72), 7.350 (1.86), 7.370 (3.55), 7.389 (2.83), 7.431 (3.62), 7.452 (2.86), 7.468 (1.92), 7.471 (2.25), 7.475 (1.13), 7.489 (2.07), 7.492 (1.95), 7.498 (1.88), 7.502 (1.99), 7.518 (2.21), 7.521 (2.09), 7.535 (1.11), 7.539 (0.94), 7.727 (5.10), 7.748 (4.43), 7.842 (2.42), 7.860 (2.22), 7.863 (2.00), 8.070 (2.21), 8.090 (2.04), 11.520 (3.24).

Intermediate 8 ethyl-6-chloro-3-[3-(naphthalen-1-yloxy)propyl]-7-(4,4,5,5-tetramethyl-1,3,2-dioxaborolan-2-yl)-1H-indole-2-carboxylate

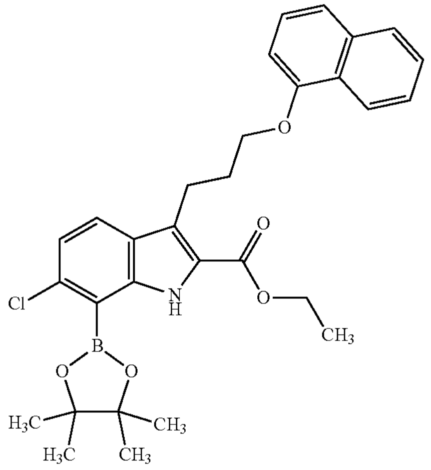 [SMILES: CCOC(=O)c1[nH]c2c(B3OC(C)(C)C(C)(C)O3)c(Cl)ccc2c1CCCOc1cccc2ccccc12]

To a degassed mixture of ethyl-7-bromo-6-chloro-3-[3-(naphthalen-1-yloxy)propyl]-1H-indole-2-carboxylate (see Intermediate 7, 5.50 g, 11.3 mmol) and 4,4,4',4',5,5,5',5'-octamethyl-2,2'-bi-1,3,2-dioxaborolane (CAS 78183-34-3, 8.61 g, 33.9 mmol) in 1,4-dioxane (97 mL) was added potassium acetate (4.44 g, 45.2 mmol). To this mixture was added 1,1'-Bis(diphenylphosphino)ferrocenpalladium(II) chloride (827 mg, 1.13 mmol) and it was purged with argon for 10 minutes. The mixture was stirred for 24 hours at 80° C. For work-up, the mixture was concentrated and the residue was purified by flash chromatography (Biotage SNAP cartridge silica, hexane/ethyl acetate gradient, 7%-25% ethyl acetate) to give the title compound (1.5 g).

LC-MS (Method 1): Rt=1.90 min; MS (ESIneg): m/z=532 $[M-H]^-$

Intermediate 9

Ethyl-7-bromo-6-fluoro-3-{3-[(6-fluoronaphthalen-1-yl)oxy]propyl}-1H-indole-2-carboxylate

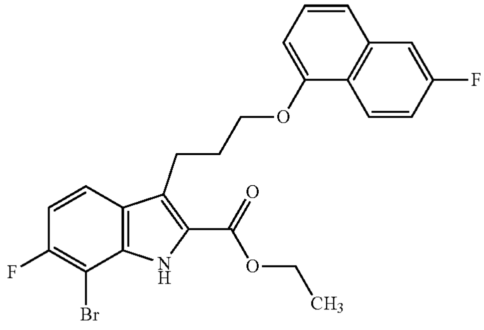 [SMILES: CCOC(=O)c1[nH]c2c(Br)c(F)ccc2c1CCCOc1cccc2cc(F)ccc12]

Triphenylphosphine (4.19 g, 16.0 mmol) was dissolved in 50 mL of tetrahydrofuran. 6-Fluoronaphthalen-1-ol (CAS 804498-72-4, 2.59 g, 16.0 mmol) was added and the mixture was cooled to 0° C. Under cooling, diisopropyl azodicarboxylate (3.1 mL, 16 mmol) was added dropwise into the reaction mixture. The mixture was stirred for 10 minutes, and ethyl-7-bromo-6-fluoro-3-(3-hydroxypropyl)-1H-indole-2-carboxylate (see Intermediate 3, 5.00 g, 14.5 mmol), dissolved in 50 mL of tetrahydrofuran, was added dropwise under cooling. After complete addition, the mixture was allowed to warm to room temperature and was stirred for 24 hours. The mixture was diluted with water and extracted with ethyl acetate. The combined organic layers were washed with brine, dried using a water resistant filter and concentrated under reduced pressure. The crude material was purified by flash chromatography using silica gel (gradient hexane/ethyl acetate). The product was triturated with methanol at 40° C. After cooling to room temperature, the solid material was isolated by filtration, was washed with methanol and was dried to give the title compound (4.80 g).

LC-MS (Method 1): $R_t$=1.72 min; MS (ESIneg): m/z=486 $[M-H]^-$ $^1$H-NMR (400 MHz, DMSO-d6) δ[ppm]: 1.130 (0.54), 1.153 (1.08), 1.169 (7.27), 1.185 (6.94), 1.272 (7.19), 1.289 (16.00), 1.307 (7.23), 1.986 (1.37), 2.160 (0.50), 2.176 (1.45), 2.192 (2.08), 2.210 (1.45), 2.225 (0.50), 2.331 (0.50), 2.518 (2.41), 2.523 (1.66), 3.285 (2.04), 3.304 (3.53), 3.322 (3.16), 4.148 (2.04), 4.163 (4.28), 4.178 (2.04), 4.263 (2.12), 4.281 (6.77), 4.298 (6.61), 4.316 (1.95), 4.750 (0.50), 4.765 (0.62), 4.781 (0.50), 6.835 (1.87), 6.842 (1.95), 6.849 (1.50), 6.856 (1.83), 6.992 (2.45), 7.014 (3.41), 7.037 (2.45), 7.317 (0.50), 7.322 (0.87), 7.325 (1.29), 7.331 (1.41), 7.346 (1.87), 7.354 (1.99), 7.369 (1.29), 7.376 (1.33), 7.391 (0.58), 7.412 (3.45), 7.418 (3.66), 7.426 (8.35), 7.439 (0.54), 7.624 (2.12), 7.631 (2.16), 7.650 (2.12), 7.657 (2.08), 7.722 (2.20), 7.735 (2.24), 7.743 (2.29), 7.756 (2.20), 8.071 (1.83), 8.086 (1.95), 8.094 (1.87), 8.109 (1.75), 8.883 (1.29), 11.624 (1.12).

Intermediate 10

Ethyl-6-fluoro-3-{3-[(6-fluoronaphthalen-1-yl)oxy]propyl}-7-(4,4,5,5-tetramethyl-1,3,2-dioxaborolan-2-yl)-1H-indole-2-carboxylate

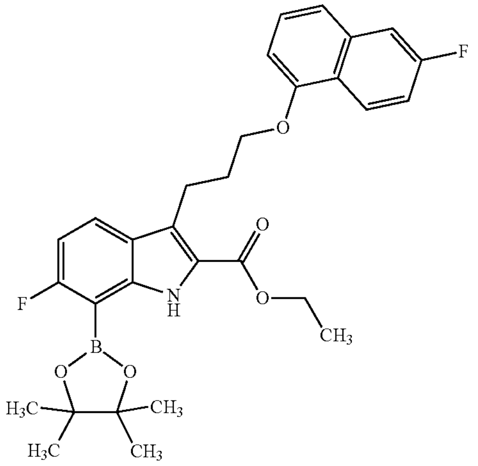 [SMILES: CCOC(=O)c1[nH]c2c(B3OC(C)(C)C(C)(C)O3)c(F)ccc2c1CCCOc1cccc2cc(F)ccc12]

Ethyl-7-bromo-6-fluoro-3-{3-[(6-fluoronaphthalen-1-yl)oxy]propyl}-1H-indole-2-carboxylate (see Intermediate 9, 4.28 g) was dissolved in 30 mL of N,N-dimethylformamide, and 4,4,4',4',5,5,5',5'-octamethyl-2,2'-bi-1,3,2-dioxaborolane (CAS 78183-34-3, 3.34 g, 13.1 mmol), potassium acetate (2.58 g, 26.3 mmol) and [1,1'-Bis(diphenylphosphino)ferrocene]dichloro-palladium(II) (716 mg, 876 μmol) were added. The mixture was purged with argon for 10 minutes and stirred at 90° C. for 22 hours. The reaction mixture was diluted with water and extracted with ethyl acetate. The combined organic layers were washed with brine, dried using a water resistant filter and was concentrated under reduced pressure. The crude material was purified by flash chromatography using silica gel (gradient hexane/ethyl acetate) to give the title compound (2.82 g).

LC-MS (Method 1): $R_t$=1.80 min; MS (ESIpos): m/z=536 $[M+H]^+$ $^1$H-NMR (400 MHz, DMSO-d6) δ[ppm]: 1.155 (0.65), 1.163 (16.00), 1.171 (0.97), 1.253 (1.09), 1.271 (2.41), 1.289 (1.13), 1.368 (9.01), 1.987 (1.21), 2.455 (0.53), 2.518 (0.45), 3.320 (0.68), 4.164 (0.77), 4.251 (1.09), 4.268 (1.08), 6.843 (0.46), 6.865 (0.42), 7.408 (0.62), 7.414 (0.65), 7.422 (1.44).

Intermediate 11

Ethyl 4-bromo-1,5-dimethyl-1H-pyrazole-3-carboxylate

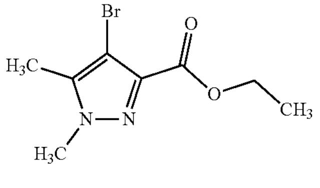

N-Bromosuccinimide (16.3 g, 90.5 mmol, CAS 128-08-5) was added to a solution of ethyl 1,5-dimethyl-1H-pyrazole-3-carboxylate (7.25 g, 43.1 mmol, CAS 5744-51-4) in 1,2-dichloroethane (150 mL), and the mixture was stirred for 15 hours at 80° C. For work-up, the mixture was diluted with dichloromethane, washed with water and the organic phase was filtered through a water resistant filter and concentrated. The residue was purified by flash chromatography (Biotage SNAP cartridge silica 340 g, hexane/dichloromethane gradient, 0-100% dichloromethane) to give the title compound (6.49 g).

LC-MS (Method 1): Rt=0.97 min; MS (ESIpos): m/z=247 $[M+H]^+$ $^1$H-NMR (400 MHz, DMSO-d6) δ[ppm]: 1.261 (4.14), 1.278 (8.78), 1.296 (4.21), 2.268 (14.94), 2.518 (0.74), 2.523 (0.49), 3.857 (16.00), 4.229 (1.31), 4.247 (4.03), 4.264 (3.94), 4.282 (1.24).

Intermediate 12

(4-bromo-1,5-dimethyl-1H-pyrazol-3-yl)methanol

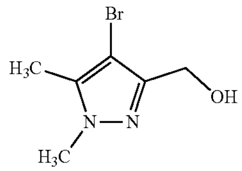

Lithium borohydride (711 mg, 32.6 mmol) was added to a solution of ethyl 4-bromo-1,5-dimethyl-1H-pyrazole-3-carboxylate (6.45 g, 26.1 mmol, see Intermediate 11) in tetrahydrofuran (150 mL) and the mixture was stirred for 1 hour at room temperature, followed by stirring for 7 hours at 60° C. The reaction was stopped by the addition of saturated aqueous ammonium chloride solution, and the mixture was extracted with ethyl acetate. The organic phase was filtered through a water resistant filter and concentrated. The residue was purified by flash chromatography (hexane/ethyl acetate gradient, 50%-100% ethyl acetate) to give the title compound (4.07 g).

LC-MS (Method 1): Rt=0.68 min; MS (ESIpos): m/z=205 $[M+H]^+$ $^1$H-NMR (400 MHz, DMSO-d6) δ[ppm]: 2.205 (16.00), 2.518 (0.43), 3.330 (10.35), 4.285 (3.97), 4.299 (4.13), 4.933 (1.00), 4.946 (2.22), 4.960 (0.93).

Intermediate 13

4-bromo-1,5-dimethyl-1H-pyrazole-3-carbaldehyde

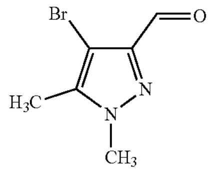

DMSO (15 mL, 220 mmol) was added to a solution of oxalyl chloride (9.2 mL, 110 mmol) in dichloromethane (100 mL) at −78° C. After 15 minutes, a solution of (4-bromo-1,5-dimethyl-1H-pyrazol-3-yl)methanol (see Intermediate 12, 14.9 g, 72.4 mmol) in dichloromethane (100 mL) was added dropwise, followed by triethylamine (61 mL, 430 mmol), and the mixture was allowed to warm to room temperature overnight. For work-up, water was added, and the mixture was extracted with a mixture of dichloromethane and 2-propanol (4:1). The combined organic phases were filtered through a water resistant filter and concentrated to give the title compound (18.8 g) which was used in the next step without further purification.

LC-MS (Method 1): Rt=0.81 min; MS (ESIpos): m/z=203 $[M+H]^+$ $^1$H-NMR (400 MHz, DMSO-$d_6$): δ [ppm]=9.80 (s, 1H), 3.92 (s, 3H), 2.28 (s, 3H).

Intermediate 14

(rac)-1-(4-bromo-1,5-dimethyl-1H-pyrazol-3-yl) ethanol

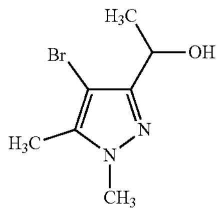

A solution of methylmagnesium bromide (3.0 mL, 3.0 M in diethyl ether, 8.9 mmol) was added dropwise to a solution of 4-bromo-1,5-dimethyl-1H-pyrazole-3-carbaldehyde (900 mg, 4.43 mmol, see Intermediate 13) in tetrahydrofuran (50 mL) at 4° C., and the mixture was allowed to warm to room temperature over 3 hours. An additional portion of methylmagnesium bromide solution (0.8 mL, 3.0 M in diethyl ether, 2.4 mmol) was added, and the mixture was stirred for 16 hours at room temperature. For work-up, aqueous hydrochloric acid (2 M) was added and the mixture was extracted with a mixture of dichloromethane and 2-propanol (4:1). The combined organic phases were filtered through a water resistant filter and concentrated. The residue was purified by flash chromatography (28 g Biotage SNAP cartridge $NH_2$ silica gel, hexane/ethyl acetate gradient 0%-60% ethyl acetate) to give the title compound (910 mg).

LC-MS (Method 1): $R_t$=0.76 min; MS (ESIpos): m/z=219 $[M+H]^+$ $^1$H-NMR (400 MHz, DMSO-$d_6$): δ [ppm]=4.91 (d, 1H), 4.70-4.61 (m, 1H), 3.71 (s, 3H), 2.19 (s, 3H), 1.36 (d, 3H).

Intermediate 15

(rac)-1-(4-bromo-1,5-dimethyl-1H-pyrazol-3-yl)but-3-en-1-ol

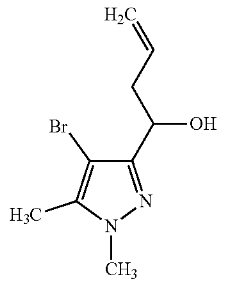

4-Bromo-1,5-dimethyl-1H-pyrazole-3-carbaldehyde (see Intermediate 13, 7.00 g, 34.5 mmol) was dissolved in 300 mL of tetrahydrofuran and cooled to 4° C. At this temperature, a solution of allylmagnesium chloride solution (CAS 2622-05-1, 21 mL, 2.0 M in tetrahydrofuran, 41 mmol) was added. After complete addition, the mixture was allowed to warm to rt within 16 hours. allylmagnesium chloride solution (7 mL, 2.0 M, 13.7 mmol) was added and stirring was continued at rt for 2 hours. The mixture was acidified until the pH value had reached 5, using aqueous 2-molar hydrochloric acid, and the resulting layers were separated. The aqueous layer was extracted with dichloromethane/2-propanol (8/2) three times. The combined organic layers were dried using a water resistant filter, and the clear filtrate was concentrated under reduced pressure. The crude material was purified by flash chromatography using a silica gel column, gradient hexane/ethyl acetate 0-100% to obtain the title compound (3.57 g).

$^1$H-NMR (400 MHz, DMSO-d6) δ[ppm]: 2.199 (16.00), 2.522 (0.48), 2.527 (0.79), 2.530 (1.24), 2.533 (0.74), 3.330 (7.77), 4.479 (0.56), 4.491 (0.63), 4.496 (1.25), 4.509 (1.31), 4.514 (0.59), 4.527 (0.56), 4.937 (0.82), 4.939 (0.78), 4.942 (0.94), 4.945 (0.45), 4.959 (0.41), 4.962 (0.89), 4.965 (0.80), 4.967 (1.04), 4.970 (0.47), 5.001 (0.93), 5.005 (0.60), 5.007 (0.84), 5.040 (0.44), 5.044 (1.05), 5.048 (0.67), 5.050 (0.94), 5.078 (3.18), 5.091 (3.04), 5.694 (0.73), 5.719 (1.00), 5.737 (0.96), 5.762 (0.61).

Intermediate 16

(rac)-3-(4-bromo-1,5-dimethyl-1H-pyrazol-3-yl)-3-hydroxypropanal

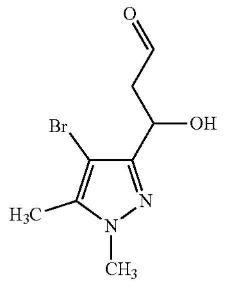

A solution of (rac)-1-(4-bromo-1,5-dimethyl-1H-pyrazol-3-yl)but-3-en-1-ol (see Intermediate 15, 1.00 g, 4.08 mmol) in a mixture of dichloromethane (50 mL) and methanol (50 mL) was cooled to −78° C. Ozone was passed through the reaction mixture until it turned blue. The mixture was stirred for additional 10 minutes during which nitrogen gas was passed through in order to remove ozone. Triphenylphosphine (1.28 g, 4.90 mmol) was added, and stirring was continued at −78° C. for 1 hour. The mixture was diluted with saturated aqueous sodium bicarbonate solution and the resulting layers were separated. The aqueous layer was extracted with dichloromethane/2-propanol (8/2) three times. The combined organic layers were dried using a water resistant filter, and the clear filtrate was concentrated under reduced pressure to give the title compound (2.52 g) which was used in the next step without further purification.

Intermediate 17

(rac)-1-(4-bromo-1,5-dimethyl-1H-pyrazol-3-yl)-3-(morpholin-4-yl)propan-1-ol

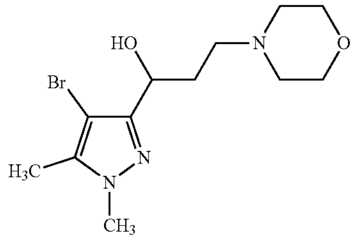 [SMILES: Cc1c(Br)c(C(O)CCN2CCOCC2)nn1C]

To a solution of (rac)-3-(4-bromo-1,5-dimethyl-1H-pyrazol-3-yl)-3-hydroxypropanal (see Intermediate 16, 2.40 g) in tetrahydrofuran (100 mL), morpholine (CAS 110-91-8, 1.7 mL, 19 mmol) was added, and the mixture was stirred for 1 hour at rt. Sodium triacetoxyborohydride (6.18 g, 29.1 mmol) was added, and the mixture was stirred at 50° C. for 2 hours followed by stirring at rt for 70 hours. Water was added carefully to the reaction mixture, and the resulting layers were separated. The aqueous layer was washed with dichloromethane/2-propanol (8/2) thrice. As the title compound was present only in the aqueous layer, as judged by UPLC/MS, the aqueous layer was concentrated under reduced pressure. The residue was diluted with tetrahydrofuran and stirred 30 minutes at 50° C. Undissolved solid was filtered off washed with tetrahydrofuran, and the filtrate was concentrated under vacuo to give the title compound (4.74 g) which was used in the next step without further purification.

LC-MS (Method 1): $R_t$=0.54 min; MS (ESIpos): m/z=318 $[M+H]^+$ $^1$H-NMR (400 MHz, DMSO-d6) δ[ppm]: 1.035 (1.00), 1.052 (2.38), 1.070 (1.08), 1.352 (0.70), 1.902 (16.00), 1.983 (14.10), 2.195 (1.72), 2.322 (0.47), 2.518 (0.76), 2.522 (0.50), 2.691 (1.88), 2.703 (1.76), 2.714 (1.93), 3.388 (1.09), 3.393 (1.53), 3.399 (1.98), 3.404 (2.46), 3.413 (2.04), 3.417 (1.85), 3.428 (0.99), 3.445 (1.05), 3.507 (2.68), 3.519 (3.44), 3.531 (2.78), 3.547 (2.08), 3.559 (1.96), 3.571 (1.21), 3.716 (1.78).

Intermediate 18 ethyl 5-ethyl-1-methyl-1H-pyrazole-3-carboxylate

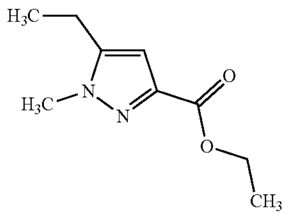

Ethyl 2,4-dioxohexanoate (CAS 13246-52-1, 5.00 g, 29.0 mmol) was dissolved in 20 mL of acetic acid. Under ice cooling, methylhydrazine (1.5 mL, 29.0 mmol) was added and the mixture was stirred at rt for 23 hours. An additional portion of methylhydrazine (0.5 mL, 10.0 mmol) was added, and stirring was continued at rt for 24 hours. The reaction mixture was poured into ice water and was extracted with ethyl acetate. The combined organic layers were washed with brine, dried using a water resistant filter and concentrated under reduced pressure. The crude material was purified by flash chromatography using silica gel (gradient hexane/ethyl acetate) to obtain of the title compound (2.13 g, 40% yield).

LC-MS (Method 1): $R_t$=0.92 min; MS (ESIpos): m/z=183 $[M+H]^+$ $^1$H-NMR (400 MHz, DMSO-d6) δ[ppm]: 1.170 (6.09), 1.188 (12.55), 1.208 (6.57), 1.245 (7.14), 1.263 (16.00), 1.280 (7.23), 2.601 (1.10), 2.602 (1.08), 2.619 (3.24), 2.621 (3.35), 2.638 (3.29), 2.640 (3.34), 2.657 (1.02), 2.659 (1.03), 3.331 (8.78), 4.200 (1.95), 4.218 (6.25), 4.236 (6.29), 4.254 (1.95), 5.759 (0.98), 6.518 (4.92).

Intermediate 19 ethyl 4-bromo-5-ethyl-1-methyl-1H-pyrazole-3-carboxylate

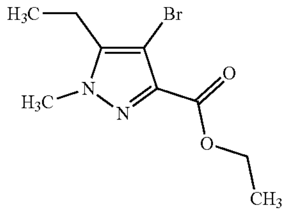

Ethyl 5-ethyl-1-methyl-1H-pyrazole-3-carboxylate (see Intermediate 18, 2.10 g, 11.5 mmol) was dissolved in 15 mL of acetic acid. A solution of bromine in acetic acid (23 mL, 1.0 M, 23 mmol) was added dropwise, and the reaction mixture was stirred for 18 hours at rt. The mixture was poured into ice water and aqueous sodium thiosulfate solution (10%) was added. The mixture was extracted with ethyl acetate, and the combined organic layers were washed with brine, dried using a water resistant filter and concentrated under reduced pressure to obtain 2.97 g of the title compound. The crude title compound was used without further purification in the next step.

LC-MS (Method 1): $R_t$=1.08 min; MS (ESIpos): m/z=261 $[M+H]^+$ $^1$H-NMR (400 MHz, DMSO-d6) δ[ppm]: 1.077 (2.69), 1.096 (6.29), 1.115 (2.81), 1.260 (3.48), 1.278 (7.87), 1.295 (3.68), 1.907 (1.63), 2.518 (0.62), 2.523 (0.41), 2.673 (0.89), 2.692 (2.71), 2.711 (2.65), 2.730 (0.75), 3.894 (16.00), 4.231 (1.11), 4.249 (3.60), 4.266 (3.59), 4.284 (1.10).

Intermediate 20

(4-bromo-5-ethyl-1-methyl-1H-pyrazol-3-yl)methanol

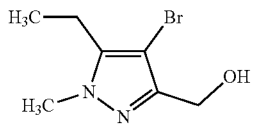

Ethyl 4-bromo-5-ethyl-1-methyl-1H-pyrazole-3-carboxylate (see Intermediate 19, 2.97 g) was dissolved in 45 mL of THF, and lithium borohydride (310 mg, 14.2 mmol) was added portionwise. This mixture was stirred for 20 hours at rt, followed by stirring for 22 hours at 60° C. An additional portion of lithium borohydride (50 mg, 2.3 mmol) was added, and stirring was continued for 24 hours at rt, followed by stirring 3 hours at 60° C. The reaction mixture was diluted with saturated aqueous ammonium chloride solution and extracted with ethyl acetate. The combined organic layers were washed with brine, dried using a water resistant filter, and concentrated under reduced pressure to obtain the title compound (2.18 g). The crude title compound was used without further purification in the next step.

LC-MS (Method 1): $R_t$=0.79 min; MS (ESIpos): m/z=219 $[M+H]^+$ $^1$H-NMR (400 MHz, DMSO-d6) δ[ppm]: 1.068 (3.21), 1.087 (7.19), 1.105 (3.37), 2.518 (0.44), 2.609 (1.02), 2.628 (3.36), 2.647 (3.29), 2.666 (1.04), 3.761 (16.00), 4.287 (4.77), 4.301 (4.91), 4.941 (1.34), 4.955 (2.69), 4.969 (1.21).

Intermediate 21

4-bromo-5-ethyl-1-methyl-1H-pyrazole-3-carbaldehyde

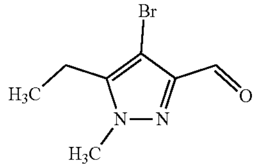

Oxalyl chloride (25 mL, 2.0 M in dichloromethane, 50 mmol) was dissolved in 60 mL of dichloromethane and was cooled to −72° C. Dry dimethyl sulfoxide (7.0 mL, 99.3 mmol) was added dropwise into the mixture (gas formation). After 15 minutes of stirring, a solution of (4-bromo-5-ethyl-1-methyl-1H-pyrazol-3-yl)methanol (see Intermediate 20, 7.25 g, 33.1 mmol) in 60 mL of dichloromethane and triethylamine (27.7 mL, 199 mmol) were added dropwise into the reaction mixture. The mixture was allowed to warm up to rt within 1.5 hours. Water was added and the mixture was extracted with dichloromethane. The combined organic layers were washed with brine, dried using a water resistant filter and concentrated under reduced pressure to obtain the title compound (7.70 g).

LC-MS (Method 1): $R_t$=0.94 min; MS (ESIpos): m/z=217 $[M+H]^+$ $^1$H-NMR (400 MHz, DMSO-d6) δ[ppm]: 1.096 (2.98), 1.115 (6.57), 1.134 (2.96), 2.518 (0.46), 2.540 (0.58), 2.691 (0.95), 2.710 (3.03), 2.729 (2.97), 2.748 (0.88), 3.958 (16.00), 9.801 (5.10).

Intermediate 22

(rac)-1-(4-bromo-5-ethyl-1-methyl-1H-pyrazol-3-yl)but-3-en-1-ol

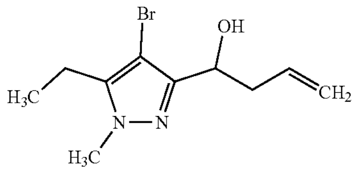

4-Bromo-5-ethyl-1-methyl-1H-pyrazole-3-carbaldehyde (see Intermediate 21, 7.70 g) was dissolved in 700 mL of tetrahydrofuran and cooled to 4° C. A solution of allylmagnesium chloride solution (CAS 2622-05-1, 19.6 mL, 2.0 M in tetrahydrofuran, 39.2 mmol) was added, and the mixture was stirred at rt for 24 hours. The mixture was cooled to 6° C. and an additional portion of allylmagnesium chloride solution (10 mL, 2.0 M, 19.5 mmol) was added and stirring was continued at rt for 22 hours. A further portion of allylmagnesium chloride solution (5 mL, 2.0 M, 10 mmol) was added, and stirring was continued at rt for 4 hours. Water was added and the mixture was acidified to a pH value of 5 using an aqueous solution of hydrogen chloride (1 M). The mixture was extracted with ethyl acetate and the combined organic layers were washed with brine, were dried using a water resistant filter and were concentrated under reduced pressure. The crude material was purified by flash chromatography using silica gel (gradient hexane/ethyl acetate) to obtain the title compound (5.50 g).

LC-MS (Method 1): $R_t$=1.01 min; MS (ESIpos): m/z=259 $[M+H]^+$ $^1$H-NMR (400 MHz, DMSO-d6) δ[ppm]: 1.062 (2.86), 1.081 (6.83), 1.100 (3.01), 1.172 (0.57), 1.987 (1.10), 2.523 (0.65), 2.526 (0.95), 2.529 (0.94), 2.604 (0.88), 2.623 (2.92), 2.642 (2.75), 2.661 (0.80), 3.757 (16.00), 4.490 (0.47), 4.496 (0.78), 4.508 (0.82), 4.513 (0.44), 4.941 (0.75), 4.944

(0.75), 4.947 (0.86), 4.950 (0.43), 4.967 (0.84), 4.969 (0.77), 4.972 (0.99), 4.975 (0.46), 5.005 (0.86), 5.007 (0.56), 5.011 (0.79), 5.045 (0.43), 5.048 (0.98), 5.050 (0.64), 5.054 (0.88), 5.092 (1.57), 5.105 (1.52), 5.703 (0.67), 5.729 (0.89), 5.746 (0.89), 5.772 (0.55).

Intermediate 23

(rac)-3-(4-bromo-5-ethyl-1-methyl-1H-pyrazol-3-yl)-3-hydroxypropanal

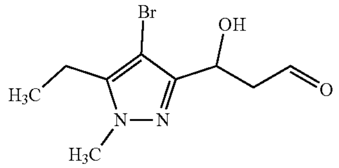

A solution of (rac)-1-(4-bromo-5-ethyl-1-methyl-1H-pyrazol-3-yl)but-3-en-1-ol (see Intermediate 22, 3.80 g, 14.7 mmol) in a mixture of dichloromethane (40 mL) and methanol (40 mL) was cooled to −78° C. Ozone was passed through the reaction mixture until it turned blue. The mixture was stirred for additional 10 minutes during which nitrogen gas was passed through in order to remove ozone. Triphenylphosphine (4.62 g, 17.6 mmol) was added and stirring was continued at −78° C. for 1.5 hours, followed by stirring for an additional 19 hours at rt. The reaction mixture was concentrated under reduced pressure to obtain the crude title compound (9.13 g) which was used without further purification.

LC-MS (Method 2): $R_t$=0.78 min; MS (ESIpos): m/z=261 $[M+H]^+$ $^1$H-NMR (400 MHz, DMSO-d6) δ[ppm]: 1.066 (3.87), 1.073 (2.25), 1.081 (4.10), 1.085 (8.44), 1.092 (2.78), 1.097 (2.44), 1.104 (3.91), 1.111 (1.05), 1.154 (1.96), 1.171 (3.91), 1.189 (1.86), 1.905 (1.61), 1.987 (6.78), 2.322 (0.80), 2.326 (1.07), 2.332 (0.78), 2.518 (3.82), 2.522 (2.68), 2.621 (1.57), 2.631 (2.23), 2.635 (2.50), 2.640 (2.12), 2.650 (2.03), 2.654 (2.14), 2.659 (1.68), 2.664 (1.36), 2.668 (1.68), 2.673 (1.37), 2.788 (0.41), 2.801 (0.50), 2.819 (0.46), 2.826 (0.46), 2.839 (0.52), 2.846 (0.45), 3.159 (1.59), 3.172 (1.59), 3.188 (2.27), 3.199 (0.68), 3.211 (2.12), 3.216 (14.13), 3.227 (0.62), 3.248 (1.41), 3.565 (2.87), 3.582 (1.11), 3.720 (1.23), 3.739 (1.55), 3.748 (2.28), 3.751 (5.44), 3.753 (4.64), 3.758 (9.44), 3.780 (8.10), 3.782 (8.99), 3.791 (0.78), 3.796 (1.00), 3.999 (0.48), 4.017 (1.46), 4.034 (1.43), 4.052 (0.45), 4.518 (1.77), 4.538 (1.75), 4.637 (1.20), 4.643 (0.57), 4.666 (0.62), 4.674 (0.73), 4.691 (0.55), 4.788 (0.64), 4.805 (0.80), 4.930 (0.45), 4.947 (0.82), 4.958 (0.52), 4.964 (0.87), 5.061 (0.46), 5.067 (0.50), 5.081 (0.54), 5.246 (0.59), 5.261 (0.55), 5.315 (0.43), 5.405

(0.80), 5.420 (0.71), 6.162 (0.59), 6.859 (0.43), 7.214 (2.37), 7.221 (2.41), 7.226 (1.59), 7.229 (3.44), 7.233 (3.21), 7.238 (4.42), 7.249 (2.62), 7.252 (1.28), 7.255 (1.37), 7.257 (2.76), 7.383 (0.82), 7.387 (1.36), 7.392 (8.15), 7.395 (8.42), 7.399 (6.94), 7.401 (6.44), 7.407 (4.26), 7.409 (5.74), 7.412 (3.46), 7.417 (1.20), 7.421 (0.89), 7.525 (2.94), 7.528 (4.41), 7.533 (3.28), 7.535 (4.23), 7.540 (2.94), 7.544 (7.49), 7.546 (10.81), 7.549 (9.92), 7.551 (7.06), 7.554 (9.15), 7.558 (7.28), 7.564 (12.54), 7.572 (10.47), 7.591 (8.60), 7.596 (15.55), 7.601 (3.57), 7.606 (5.64), 7.608 (7.94), 7.612 (13.04), 7.614 (11.17), 7.621 (14.18), 7.625 (16.00), 7.629 (8.06), 7.631 (7.55), 7.638 (5.03), 7.642 (8.81), 7.645 (8.94), 7.648 (3.42), 7.652 (1.03), 9.566 (0.91), 9.711 (0.61), 9.715 (0.66), 9.718 (0.77), 9.722 (0.57).

Intermediate 24

(rac)-1-(4-bromo-5-ethyl-1-methyl-1H-pyrazol-3-yl)-3-(morpholin-4-yl)propan-1-ol

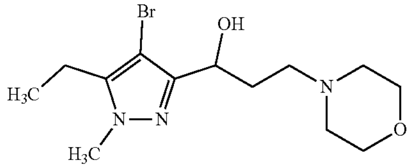 [SMILES: CCc1c(Br)c(C(O)CCN2CCOCC2)nn1C]

To a solution of crude (rac)-3-(4-bromo-5-ethyl-1-methyl-1H-pyrazol-3-yl)-3-hydroxpropanal (see Intermediate 23, 9.10 g) in tetrahydrofuran (50 mL), morpholine (CAS 110-91-8, 3.0 mL, 35 mmol) was added, and the mixture was stirred for 2 hours at rt. Sodium triacetoxyborohydride (11.1 g, 52.3 mmol) was added, and the mixture was stirred at rt for 2 hours. Water was added and the mixture was extracted with ethyl acetate. The combined organic layers were dried using a water resistant filter and concentrated under reduced pressure. The residue was discarded. The aqueous phase was extracted with dichloromethane. The combined organic layers were washed with brine, dried using a water resistant filter and concentrated under reduced pressure. The crude material was purified by preparative HPLC (Method P2) to obtain the title compound (1.71 g).

LC-MS (Method 2): $R_t$=0.87 min; MS (ESIpos): m/z=332 $[M+H]^+$ $^1$H-NMR (400 MHz, DMSO-d6) δ[ppm]: 1.060 (2.74), 1.079 (6.69), 1.098 (2.86), 1.816 (0.45), 1.833 (0.53), 1.836 (0.47), 1.850 (0.49), 1.873 (0.43), 1.878 (0.50), 1.893 (0.63), 1.912 (0.45), 2.074 (0.66), 2.284 (0.42), 2.296 (1.14), 2.314 (3.00), 2.326 (2.68), 2.331 (2.62), 2.346 (0.85), 2.518 (0.83), 2.523 (0.58), 2.601 (0.81), 2.620 (2.67), 2.639 (2.54), 2.658 (0.75), 3.534 (2.35), 3.546 (3.58), 3.557 (2.36), 3.751 (16.00), 4.567 (0.55), 5.126 (0.61).

Intermediate 25

(rac)-ethyl 7-{3-[1-hydroxyethyl]-1,5-dimethyl-1H-pyrazol-4-yl}-3-[3-(naphthalen-1-yloxy)propyl]-1H-indole-2-carboxylate (Mixture of Stereoisomers)

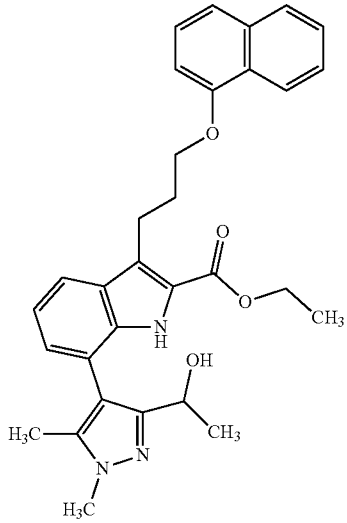 [SMILES: CCOC(=O)c1[nH]c2c(-c3c(C(C)O)nn(C)c3C)cccc2c1CCCOc1cccc2ccccc12]

XPhos Pd G2 (105 mg, 133 μmol) was added to a degassed mixture of ethyl 3-[3-(naphthalen-1-yloxy)propyl]-7-(4,4,5,5-tetramethyl-1,3,2-dioxaborolan-2-yl)-1H-indole-2-carboxylate (see Intermediate 1, 1.98 g, 3.96 mmol), (rac)-1-(4-bromo-1,5-dimethyl-1H-pyrazol-3-yl)ethanol (910 mg, 4.15 mmol, see Intermediate 14), aqueous potassium triphosphate solution (16 mL, 0.50 M, 7.9 mmol) and tetrahydrofuran (48 mL), and the mixture was stirred for 3 hours at 50° C.

For work-up, ethyl acetate was added, the mixture was filtered through a pad of celite, eluted with ethyl acetate and the organic phase was washed with brine, filtered through a water resistant filter and concentrated. The residue was purified by flash chromatography (55 g Biotage SNAP cartridge $NH_2$ silica, hexane/ethyl acetate gradient, 0%-15% ethyl acetate) to give the title compound (1.60 g).

LC-MS (Method 1): $R_t$=1.59 min; MS (ESIneg): m/z=510 $[M-H]^-$ $^1$H-NMR (400 MHz, DMSO-$d_6$): δ [ppm]=11.30 (br s, 1H), 8.27-8.22 (m, 1H), 7.90-7.85 (m, 1H), 7.69-7.64 (m, 1H), 7.56-7.37 (m, 4H), 7.11-7.05 (m, 2H), 6.91 (d, 1H), 5.64 (d, 1H), 4.69-4.41 (m, 1H), 4.28-4.18 (m, 4H), 3.79 (s, 3H), 3.39-3.34 (m, 2H), 2.27-2.18 (m, 2H), 2.12 (s, 3H), 1.45-1.19 (m, 6H).

Intermediate 26

(rac)-ethyl-(11Z)-2,3,15-trimethyl-7-[3-(naphthalen-1-yloxy)propyl]-2,10,13,15-tetrahydropyrazolo-[4',3':9,10][1,6]oxazacycloundecino[8,7,6-hi]indole-8-carboxylate (Mixture of Stereoisomers)

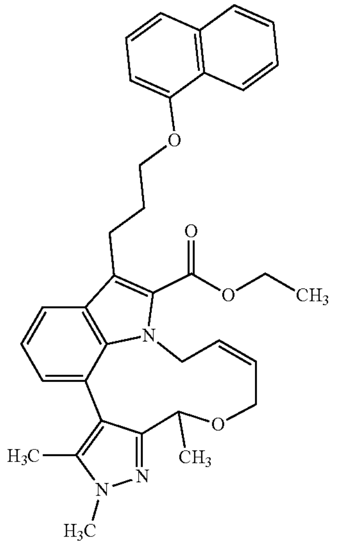 [SMILES: CCOC(=O)c1c(CCCOc2cccc3ccccc23)c2cccc3c2n1C/C=C\COC(C)c1nn(C)c(C)c1-3]

A mixture of (rac)-ethyl 7-{3-[1-hydroxyethyl]-1,5-dimethyl-1H-pyrazol-4-yl}-3-[3-(naphthalen-1-yloxy)propyl]-1H-indole-2-carboxylate (mixture of stereoisomers; 700 mg, 1.37 mmol, see Intermediate 25), (2Z)-1,4-dichlorobut-2-ene (CAS 1476-11-5, 173 μL, 1.6 mmol), sodium iodide (410 mg, 2.74 mmol) and cesium carbonate (2.23 g, 6.84 mmol) in acetonitrile (20 mL) was stirred for 4 hours at room temperature, followed by stirring for 16 hours at 60° C. For work-up, water was added and the mixture was extracted with a mixture of dichloromethane and 2-propanol (4:1). The combined organic phases were filtered through a water resistant filter and concentrated. The residue was purified by flash chromatography (50 g Biotage SNAP cartridge silica, hexane/ethyl acetate gradient, 0%-100% ethyl acetate) to give the title compound (340 mg).

LC-MS (Method 1): Rt=1.71 min; MS (ESIpos): m/z=564 $[M+H]^+$ $^1$H-NMR (400 MHz, DMSO-d6) δ[ppm]: 1.066 (0.76), 1.154 (4.29), 1.172 (8.58), 1.190 (4.32), 1.210 (0.63), 1.215 (0.56), 1.232 (0.53), 1.245 (0.48), 1.266 (4.04), 1.284 (8.35), 1.301 (4.01), 1.320 (4.26), 1.335 (4.19), 1.355 (0.73), 1.372 (0.71), 1.799 (0.81), 1.826 (11.96), 1.871 (0.71), 1.988 (16.00), 2.193 (1.62), 2.244 (1.11), 2.518 (5.85), 2.523 (4.09), 3.283 (0.56), 3.299 (0.71), 3.352 (0.93), 3.371 (0.56), 3.629 (0.48), 3.648 (0.73), 3.659 (1.34), 3.674 (0.71), 3.714 (1.59), 3.725 (0.76), 3.755 (1.31), 3.779 (0.50), 3.787 (0.63), 3.839 (11.99), 4.000 (1.19), 4.018 (3.58), 4.035 (3.63), 4.053 (1.19), 4.224 (0.98), 4.233 (1.82), 4.250 (3.26), 4.263 (1.41), 4.269 (1.87), 4.289 (1.51), 4.306 (1.26), 4.316 (0.71), 4.325 (0.43), 4.334 (0.76), 4.356 (1.36), 4.372 (1.31), 4.764 (0.48), 4.776 (0.63), 4.802 (0.76), 4.907 (0.83), 4.940 (0.58), 4.964 (0.48), 4.991 (0.83), 5.018 (0.48), 5.185 (0.53), 5.197 (0.48), 5.759 (3.23), 6.864 (1.46), 6.879 (1.62), 6.920 (1.59), 6.938 (1.67), 7.093 (1.44), 7.112 (1.82), 7.131 (1.26), 7.379 (1.03), 7.400 (2.17), 7.419 (1.67), 7.454 (2.32), 7.476 (1.34), 7.495 (1.11), 7.498 (1.09), 7.513 (1.89), 7.517 (2.15), 7.535 (1.54), 7.549 (0.63), 7.772 (1.51), 7.790 (1.36), 7.863 (1.41), 7.880 (1.46), 7.885 (1.21), 8.189 (1.14), 8.208 (1.11).

Intermediate 27

(rac)-ethyl-2,3,15-trimethyl-7-[3-(naphthalen-1-yloxy)propyl]-2,10,11,12,13,15-hexahydropyrazolo-[4',3':9,10][1,6]oxazacycloundecino[8,7,6-hi]indole-8-carboxylate (Mixture of Stereoisomers)

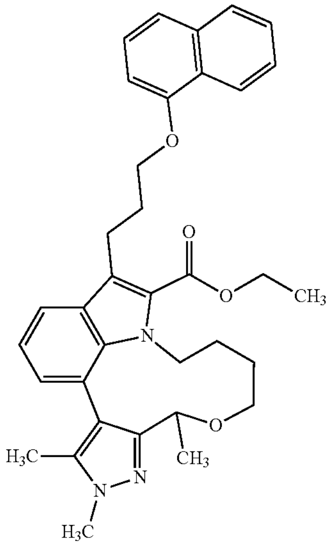 [SMILES: CCOC(=O)c1c(CCCOc2cccc3ccccc23)c2cccc3c2n1CCCCOC(C)c1nn(C)c(C)c1-3]

An autoclave was charged with (rac)-ethyl-(11Z)-2,3,15-trimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (mixture of stereoisomers, 340 mg, 603 μmol, see Intermediate 26), ethanol (11 mL), tetrahydrofuran (2.2 mL) and palladium 10% on charcoal (64.2 mg, 10% purity, 60.3 μmol), and the mixture was stirred under hydrogen atmosphere at a pressure of 26 bar and at room temperature for 20 hours. For work-up, the mixture was filtered through a pad of celite, eluted with ethyl acetate and the combined filtrates were concentrated under reduced pressure to give the title compound (300 mg), which was directly used in the next step.

LC-MS (Method 1): $R_t$=1.73 min; MS (ESIpos): m/z=566 $[M+H]^+$ $^1$H-NMR (400 MHz, DMSO-d6) δ[ppm]: 0.629 (1.05), 0.648 (0.51), 0.988 (0.41), 1.035 (7.59), 1.053 (16.00), 1.066 (0.81), 1.070 (7.07), 1.163 (1.21), 1.179 (1.28), 1.197 (0.45), 1.207 (0.45), 1.218 (0.51), 1.223 (0.52), 1.259 (2.27), 1.266 (1.17), 1.277 (4.76), 1.284 (2.23), 1.290 (1.08), 1.295 (2.28), 1.301 (1.37), 1.352 (3.39), 1.414 (2.31), 1.431 (2.32), 1.858 (6.47), 1.864 (1.32), 1.873 (0.47), 2.006 (2.18), 2.181 (0.63), 2.190 (1.08), 2.216 (0.65), 2.327 (0.56), 2.332 (0.41), 2.518 (2.47), 2.523 (1.64), 2.665 (0.45), 2.669 (0.67), 2.673 (0.51), 3.259 (0.47), 3.276 (0.75), 3.288 (0.72), 3.304 (0.48), 3.405 (1.16), 3.418 (1.21), 3.422 (3.08), 3.435 (3.16), 3.440 (3.38), 3.452 (3.43), 3.457 (1.09), 3.470 (1.07), 3.624 (1.29), 3.769 (2.38), 3.814 (7.06), 4.199 (0.96), 4.216 (1.27), 4.226 (1.49), 4.244 (1.31), 4.261 (0.93), 4.280 (1.23), 4.297 (0.91), 4.307 (0.48), 4.324 (0.55), 4.345 (2.55), 4.357 (4.64), 4.370 (2.30), 4.533 (0.73), 4.549 (0.79), 4.661 (0.53), 4.674 (0.51), 6.877 (0.73), 6.880 (0.87), 6.894 (1.64), 6.898 (1.12), 6.913 (1.07), 7.052 (0.84), 7.060 (0.47), 7.069 (0.85), 7.072 (1.01), 7.090 (0.75), 7.369 (0.59), 7.389 (1.07), 7.399 (0.49), 7.408 (0.89), 7.450 (1.15), 7.471 (0.68), 7.506 (0.69), 7.510 (0.68), 7.514 (1.03), 7.522 (1.69), 7.530 (1.15), 7.533 (0.87), 7.539 (1.08), 7.746 (0.79), 7.749 (0.81), 7.766 (0.73), 7.769 (0.72), 7.863 (0.76), 7.868 (0.51), 7.878 (0.75), 7.884 (0.65), 8.212 (0.55), 8.218 (0.52), 8.236 (0.71).

Intermediate 28

(rac)-ethyl-7-{3-[1-hydroxy-3-(morpholin-4-yl)propyl]-1,5-dimethyl-1H-pyrazol-4-yl}-3-[3-(naphthalen-1-yloxy)propyl]-1H-indole-2-carboxylate (Mixture of Stereoisomers)

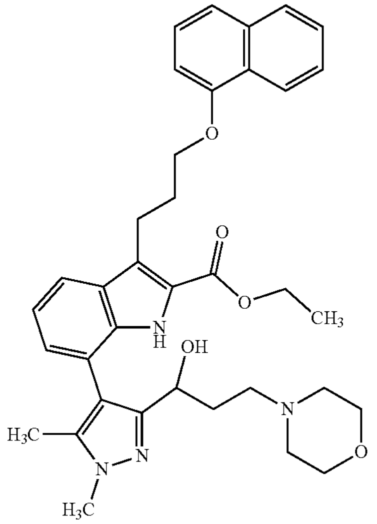 [SMILES: CCOC(=O)c1[nH]c2c(-c3c(C(O)CCN4CCOCC4)nn(C)c3C)cccc2c1CCCOc1cccc2ccccc12]

A solution of ethyl-3-[3-(naphthalen-1-yloxy)propyl]-7-(4,4,5,5-tetramethyl-1,3,2-dioxaborolan-2-yl)-1H-indole-2-carboxylate (see Intermediate 1, 3.59 g, 7.18 mmol) and (rac)-1-(4-bromo-1,5-dimethyl-1H-pyrazol-3-yl)-3-(morpholin-4-yl)propan-1-ol (see Intermediate 17, 4.00 g, 12.6 mmol) in tetrahydrofuran (150 mL) was purged with argon for 5 minutes. XPhos Pd G2 (317 mg, 403 μmol) and aqueous potassium triphosphate solution (48 mL, 0.50 M, 24 mmol) were added and again, argon was purged through the mixture for 5 minutes, which was subsequently heated for 2 hours at 50° C. The reaction mixture was diluted with water and then extracted with ethyl acetate. The combined organic layers were dried using a water resistant filter and concentrated under reduced pressure. The crude material was purified by flash chromatography using a silica column, gradient dichloromethane/ethanol 0-20%, to obtain the title compound (1.58 g).

LC-MS (Method 1): $R_t$=1.43 min; MS (ESIpos): m/z=611 $[M+H]^+$ $^1$H-NMR (400 MHz, DMSO-d6) δ[ppm]: 0.798 (0.47), 0.814 (0.50), 0.821 (0.55), 0.904 (0.63), 1.053 (0.55), 1.071 (0.55), 1.260 (6.96), 1.278 (16.00), 1.295 (7.14), 2.038 (0.75), 2.104 (7.94), 2.189 (1.32), 2.207 (2.42), 2.225 (2.47), 2.518 (3.92), 2.523 (2.57), 3.349 (3.39), 3.368 (2.80), 3.788 (12.05), 4.194 (1.70), 4.209 (3.50), 4.224 (1.80), 4.231 (2.15), 4.249 (5.62), 4.266 (5.17), 4.283 (1.52), 5.759 (5.97), 6.897 (2.14), 6.914 (2.32), 7.056 (0.70), 7.074 (3.45), 7.081 (3.67), 7.089 (7.57), 7.098 (0.87), 7.369 (1.95), 7.390 (3.49), 7.409 (2.92), 7.450 (3.45), 7.471 (1.97), 7.488 (0.57), 7.492 (0.85), 7.505 (2.22), 7.509 (2.00), 7.514 (2.49), 7.521 (4.96), 7.529 (2.52), 7.533 (2.17), 7.538 (2.49), 7.551 (0.90), 7.555 (0.57), 7.659 (1.79), 7.667 (1.52), 7.674 (1.60), 7.682 (1.58), 7.860 (1.99), 7.868 (1.08), 7.878 (1.87), 7.884 (1.74), 8.233 (1.57), 8.238 (1.47), 8.249 (0.83), 8.257 (1.52), 11.210 (2.42).

Intermediate 29

(rac)-ethyl (11Z)-2,3-dimethyl-15-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate (Mixture of Stereoisomers)

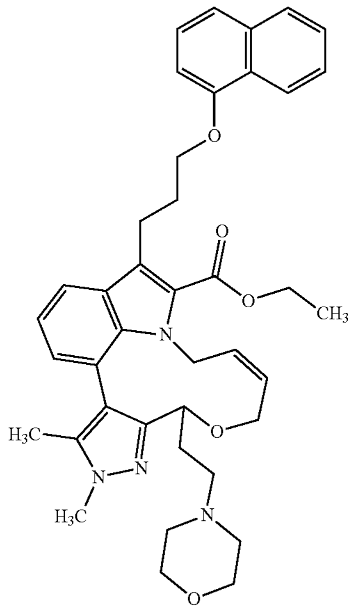 [SMILES: CCOC(=O)c1c(CCCOc2cccc3ccccc23)c2cccc3c2n1C/C=C\COC(CCN1CCOCC1)c1nn(C)c(C)c1-3]

To a mixture of (rac)-ethyl 7-{3-[1-hydroxy-3-(morpholin-4-yl)propyl]-1,5-dimethyl-1H-pyrazol-4-yl}-3-[3-(naphthalen-1-yloxy)propyl]-1H-indole-2-carboxylate (mixture of stereoisomers, see Intermediate 28, 1.58 g, 2.59 mmol) in acetonitrile (39 mL) were added cesium carbonate (4.21 g, 12.9 mmol), (2Z)-1,4-dichlorobut-2-ene (CAS 1476-11-5, 330 μL, 3.1 mmol) and sodium iodide (776 mg, 5.17 mmol). The reaction mixture was stirred for 4 hours at rt. Another portion of (2Z)-1,4-dichlorobut-2-ene (55 μL, 0.5 mmol) was added, and the mixture was stirred for 4 hours at 60° C. The mixture was diluted with water and extracted with dichloromethane/2-propanol (8/2) three times. The combined organic layers were dried using a water resistant filter and were concentrated under reduced pressure to obtain the title compound (1.37 g) which was used in the next step without further purification.

Intermediate 30

(rac)-ethyl 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (Mixture of Stereoisomers)

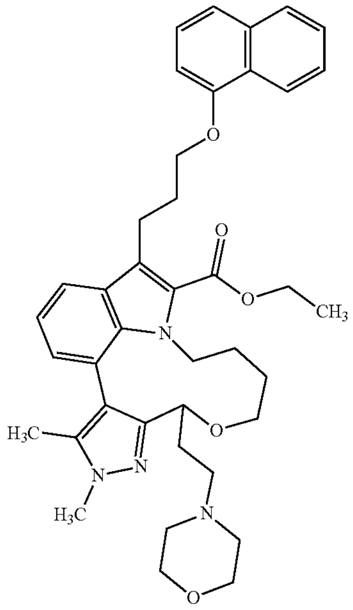 [SMILES: CCOC(=O)c1c(CCCOc2cccc3ccccc23)c2cccc3c2n1CCCCOC(CCN1CCOCC1)c1nn(C)c(C)c1-3]

In an autoclave, (rac)-ethyl (11Z)-2,3-dimethyl-15-[2-(morpholin-4-yl)ethyl]-7-[3-(naphthalen-1-yloxy)propyl]-2,10,13,15-tetrahydropyrazolo-[4',3':9,10][1,6]oxazacycloundecino[8,7,6-hi]indole-8-carboxylate (mixture of stereoisomers, see Intermediate 29, 320 mg, 483 μmol) was dissolved in a mixture of 12 mL of tetrahydrofuran/ethanol (1:5). Palladium (on carbon, 51.4 mg, 10% purity, 48.3 μmol) was added, and the mixture was mixed with hydrogen under a pressure of 24.1 bar at rt for 26 hours. The catalyst was filtered off the reaction mixture under vacuo, and the clear filtrate was concentrated under reduced pressure to give the title compound (280 mg).

LC-MS (Method 1): $R_t$=1.52 min; MS (ESIpos): m/z=665 $[M+H]^+$ $^1$H-NMR (400 MHz, DMSO-d6) δ[ppm]: 0.589 (0.43), 0.609 (1.08), 0.627 (1.32), 0.646 (0.61), 0.730 (0.47), 0.749 (0.78), 0.759 (0.92), 0.778 (0.56), 0.850 (0.49), 1.001 (1.59), 1.035 (1.86), 1.053 (3.00), 1.070 (1.68), 1.146 (0.83), 1.201 (2.49), 1.218 (3.00), 1.230 (2.33), 1.261 (5.87), 1.279 (11.63), 1.296 (5.89), 1.327 (0.85), 1.353 (2.38), 1.736 (1.23), 1.874 (15.55), 1.900 (1.12), 2.024 (2.29), 2.038 (2.44), 2.218 (2.98), 2.234 (2.71), 2.285 (2.42), 2.327 (2.29), 2.436 (0.43), 2.548 (0.54), 2.669 (1.39), 2.687 (0.74), 2.888 (0.43), 2.907 (0.87), 2.935 (0.96), 2.953 (0.45), 3.248 (1.37), 3.264 (2.15), 3.280 (2.40), 3.369 (1.48), 3.385 (1.46), 3.405 (1.34), 3.423 (1.17), 3.435 (1.05), 3.440 (1.03), 3.453 (1.01), 3.505 (3.11), 3.726 (1.10), 3.733 (1.01), 3.746 (1.25), 3.772 (2.22), 3.791 (0.81), 3.822 (16.00), 3.992 (0.87), 4.018 (0.69), 4.037 (0.85), 4.054 (0.78), 4.182 (0.96), 4.201 (2.42), 4.210 (2.64), 4.219 (4.39), 4.227 (4.15), 4.245 (2.78), 4.264 (1.66), 4.281 (2.17), 4.299 (1.93), 4.308 (1.25), 4.317 (0.83), 4.326 (1.21), 4.344 (0.94), 4.356 (1.10), 4.373 (1.14), 4.386

(0.72), 4.408 (0.90), 4.439 (1.03), 4.457 (2.02), 4.474 (0.92), 6.884 (2.40), 6.898 (3.90), 6.914 (3.07), 6.930 (0.81), 7.043 (0.54), 7.055 (1.86), 7.074 (2.62), 7.093 (1.61), 7.125 (0.40), 7.370 (1.55), 7.390 (3.27), 7.400 (1.03), 7.409 (2.42), 7.418 (0.69), 7.452 (3.97), 7.472 (2.29), 7.498 (0.85), 7.516 (3.94), 7.526 (4.57), 7.535 (4.19), 7.540 (2.87), 7.552 (0.90), 7.721 (0.61), 7.754 (2.31), 7.773 (2.11), 7.863 (2.51), 7.873 (1.39), 7.880 (1.93), 7.886 (2.04), 8.222 (1.68), 8.229 (1.57), 8.245 (1.90).

Intermediate 31

(rac)-ethyl 6-fluoro-7-{3-[1-hydroxy-3-(morpholin-4-yl)propyl]-1,5-dimethyl-1H-pyrazol-4-yl}-3-[3-(naphthalen-1-yloxy)propyl]-1H-indole-2-carboxylate (Mixture of Stereoisomers)

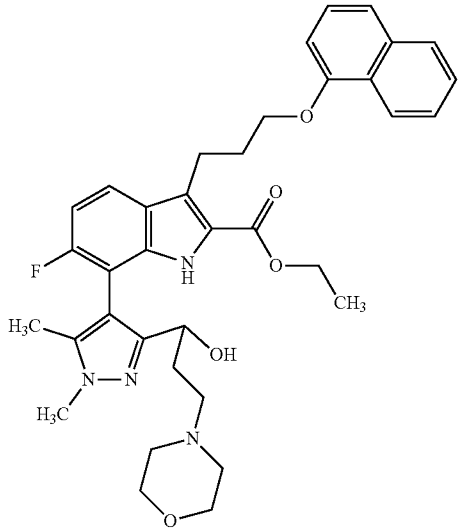 [SMILES: CCOC(=O)c1[nH]c2c(-c3c(C(O)CCN4CCOCC4)nn(C)c3C)c(F)ccc2c1CCCOc1cccc2ccccc12]

A solution of ethyl 6-fluoro-3-[3-(naphthalen-1-yloxy)propyl]-7-(4,4,5,5-tetramethyl-1,3,2-dioxaborolan-2-yl)-1H-indole-2-carboxylate (see Intermediate 5, 1.10 g, 2.13 mmol), (rac)-1-(4-bromo-1,5-dimethyl-1H-pyrazol-3-yl)-3-(morpholin-4-yl)propan-1-ol (see Intermediate 17, 541 mg, 1.70 mmol) and XPhos Pd G3 (504 mg, 595 μmol) in 1,4-dioxane (10 mL) was purged with argon for 10 minutes. Potassium triphosphate (1.08 g, 5.10 mmol), dissolved in 4 mL of water, was added and the mixture was stirred for 20 minutes at 100° C. in a microwave reactor. The reaction mixture was diluted with water and extracted with ethyl acetate. The combined organic layers were washed with brine, dried using a water resistant filter and concentrated. The crude material was purified by flash chromatography using silica gel (gradient dichloromethane/ethanol) to obtain the title compound (1.02 g), which was formed as a mixture of two racemic diastereomers as a result of atropisomerism at the newly formed bi-heteroaryl bond.

LC-MS (Method 2): $R_t$=1.58 min; MS (ESIpos): m/z=629 $[M+H]^+$ $^1$H-NMR (400 MHz, DMSO-d6) δ[ppm]: 1.036 (1.59), 1.053 (3.34), 1.066 (16.00), 1.071 (2.46), 1.232 (0.54), 1.237 (0.47), 1.249 (3.22), 1.266 (6.15), 1.284 (2.92), 1.925 (0.49), 1.944 (0.65), 1.955 (0.69), 1.963 (0.66), 1.980 (0.58), 2.007 (2.87), 2.010 (2.94), 2.042 (2.75), 2.045 (2.82), 2.173 (0.78), 2.186 (0.78), 2.208 (1.15), 2.225 (1.55), 2.242 (0.90), 2.518 (1.28), 2.523 (0.87), 3.410 (0.86), 3.423 (2.03), 3.436 (1.31), 3.441 (0.84), 3.453 (0.74), 3.784 (5.09), 3.809 (5.11), 3.939 (2.61), 4.185 (0.49), 4.200 (1.28), 4.213 (1.31), 4.222 (1.15), 4.240 (2.63), 4.258 (2.44), 4.275 (0.77), 4.344 (0.52), 4.357 (0.99), 4.369 (0.49), 6.891 (0.58), 6.904 (0.65), 6.908 (0.70), 6.921 (0.65), 6.967 (0.48), 6.979 (0.50), 6.989 (0.61), 6.993 (0.62), 7.001 (0.59), 7.005 (0.57), 7.015 (0.51), 7.027 (0.47), 7.369 (0.51), 7.373 (0.53), 7.390 (1.15), 7.409 (0.81), 7.412 (0.83), 7.450 (1.68), 7.471 (0.94), 7.497 (0.59), 7.502 (0.95), 7.506 (0.62), 7.511 (0.75), 7.513 (0.82), 7.516 (1.17), 7.520 (1.44), 7.527 (0.76), 7.530 (0.78), 7.534 (0.83), 7.537 (0.71), 7.701 (0.62), 7.713 (0.66), 7.722 (0.65), 7.735 (0.61), 7.859 (0.96), 7.877 (1.02), 7.882 (0.81), 8.205 (0.45), 8.210 (0.45), 8.224 (0.70), 8.229 (0.82), 8.248 (0.41), 11.138 (0.87), 11.156 (0.89).

Intermediate 32

(rac)-ethyl (11Z)-4-fluoro-2,3-dimethyl-15-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate

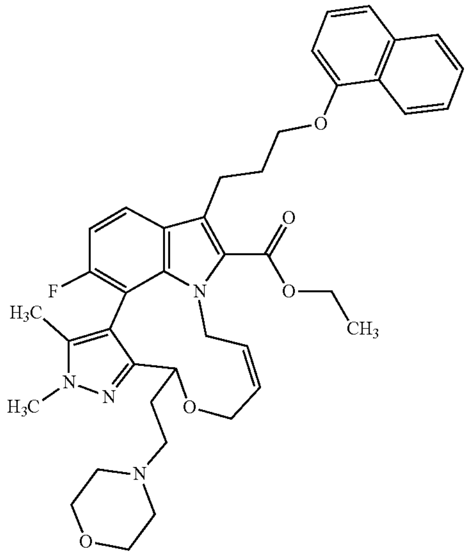 [SMILES: CCOC(=O)c1c(CCCOc2cccc3ccccc23)c2ccc(F)c3c2n1C/C=C\COC(CCN1CCOCC1)c1nn(C)c(C)c1-3]

To a mixture of (rac)-ethyl-6-fluoro-7-{3-[1-hydroxy-3-(morpholin-4-yl)propyl]-1,5-dimethyl-1H-pyrazol-4-yl}-3-[3-(naphthalen-1-yloxy)propyl]-1H-indole-2-carboxylate (mixture of stereoisomers, see Intermediate 31, 1.00 g) in acetonitrile (10 mL), cesium carbonate (2.20 g, 6.76 mmol) was added. After 10 minutes of stirring at rt, (2Z)-1,4-dichlorobut-2-ene (CAS 1476-11-5, 210 μL, 2.0 mmol) and sodium iodide (405 mg, 2.70 mmol) were added, and the reaction mixture was stirred for 23 hours at 65° C. Additional portions of (2Z)-1,4-dichlorobut-2-ene (210 μL, 2.0 mmol) and sodium iodide (405 mg, 2.70 mmol) were added, and the mixture was stirred for 48 hours at 65° C., followed by dilution with water and extraction with ethyl acetate. The combined organic layers were washed with brine, dried using a water resistant filter and concentrated. The crude material was purified by flash chromatography using silica gel (gradient dichloromethane/ethanol) to obtain the title compound (382 mg), which was formed as a racemic mixture of two enantiomers as only one of the two diastereomers formed in the preceding step underwent the macrocyclisation reaction.

LC-MS (Method 2): $R_t$=1.64 min; MS (ESIpos): m/z=681 $[M+H]^+$ $^1$H-NMR (400 MHz, DMSO-d6) δ[ppm]: 0.797 (0.46), 0.813 (0.48), 0.820 (0.49), 0.903 (0.60), 1.035 (6.67), 1.053 (16.00), 1.066 (1.25), 1.071 (7.19), 1.197 (0.44), 1.249 (0.61), 1.259 (1.34), 1.266 (1.22), 1.277 (2.61), 1.284 (0.66), 1.294 (1.19), 1.850 (0.41), 1.859 (3.31), 1.889 (0.50), 2.009 (0.54), 2.047 (0.55), 2.209 (0.71), 2.228 (0.78), 2.518 (0.96), 2.523 (0.71), 3.305 (0.62), 3.405 (1.07), 3.418 (1.20), 3.423 (2.58), 3.436 (2.64), 3.441 (2.45), 3.452 (2.38), 3.457 (1.04), 3.470 (0.93), 3.663 (0.64), 3.730 (0.41), 3.786 (0.79), 3.812 (0.86), 3.862 (3.17), 4.201 (0.42), 4.219 (0.64), 4.228 (0.78), 4.237 (0.81), 4.241 (1.18), 4.245 (1.06), 4.258 (0.83), 4.264 (0.72), 4.282 (0.59), 4.300 (0.50), 4.326 (0.45), 4.347 (1.40), 4.359 (2.28), 4.372 (1.13), 6.912 (0.53), 6.931 (0.50), 7.046 (0.43), 7.378 (0.41), 7.398 (0.74), 7.417 (0.62), 7.454 (1.01), 7.475 (0.59), 7.498 (0.59), 7.502 (0.63), 7.512 (0.71), 7.517 (1.02), 7.521 (0.82), 7.532 (0.66), 7.535 (0.71), 7.861 (0.74), 7.880 (0.63), 7.884 (0.53), 8.207 (0.44).

Intermediate 33

(rac)-ethyl-4-fluoro-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

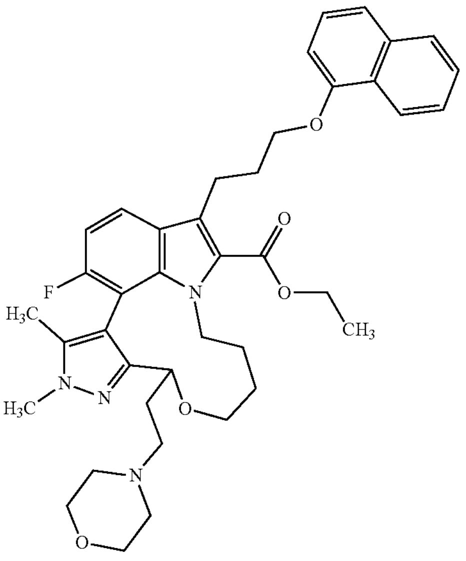 [SMILES: CCOC(=O)c1c(CCCOc2cccc3ccccc23)c2ccc(F)c3c2n1CCCCOC(CCN1CCOCC1)c1nn(C)c(C)c1-3]

To a solution of (rac)-ethyl-(11Z)-4-fluoro-2,3-dimethyl-15-[2-(morpholin-4-yl)ethyl]-7-[3-(naphthalen-1-yloxy)-propyl]-2,10,13,15-tetrahydropyrazolo[4',3':9,10][1,6]oxazacycloundecino[8,7,6-hi]indole-8-carboxylate (see Intermediate 32, 381 mg) in ethanol (10 mL) and dichloromethane (0.5 mL) was added tris(triphenylphosphine) rhodium(I) chloride (1.04 g, 1.12 mmol), and the mixture was stirred under an atmosphere of hydrogen at rt for 6 hours. The catalyst was filtered off, and the filtrate was concentrated under reduced pressure. The crude material was purified by flash chromatography using silica gel (gradient dichloromethane/ethanol) to give the title compound (176 mg).

LC-MS (Method 2): $R_t$=1.71 min; MS (ESIpos): m/z=683 $[M+H]^+$ $^1$H-NMR (400 MHz, DMSO-d6) δ[ppm]: 0.797 (0.90), 0.802 (0.43), 0.814 (0.99), 0.821 (0.99), 0.839 (0.52), 0.885 (0.62), 0.904 (1.10), 0.922 (0.56), 1.012 (0.92), 1.229 (1.40), 1.253 (5.85), 1.270 (11.29), 1.288 (5.40), 1.772 (0.80), 1.886 (15.29), 1.907 (2.37), 1.985 (0.73), 2.002 (1.83), 2.020 (2.04), 2.037 (0.92), 2.189 (1.46), 2.208 (2.02), 2.222 (2.19), 2.238 (2.34), 2.268 (3.74), 2.331 (1.01), 2.518 (4.92), 2.523 (3.20), 2.948 (0.65), 2.958 (0.56), 2.976 (0.69), 3.230 (0.69), 3.247 (0.90), 3.264 (1.38), 3.283 (1.38), 3.295 (1.35), 3.475 (2.95), 3.486 (4.41), 3.497 (2.95), 3.789 (0.84), 3.835 (16.00), 3.990 (0.54), 4.007 (0.77), 4.023 (0.67), 4.041 (0.43), 4.174 (0.58), 4.191 (1.63), 4.201 (1.91), 4.219 (3.29), 4.227 (1.76), 4.236 (2.34), 4.254 (1.31), 4.272 (1.85), 4.290 (1.74), 4.299 (1.10), 4.308 (0.67), 4.317 (1.31), 4.334 (1.05), 4.346 (0.58), 4.368 (0.77), 4.385 (1.12), 4.403 (1.98), 4.420 (0.88), 5.758 (0.56), 6.891 (1.98), 6.909 (2.19), 6.990 (1.48), 7.012 (2.52), 7.035 (1.53), 7.369 (1.72), 7.389 (3.12), 7.408 (2.56), 7.450 (3.40), 7.471 (2.09), 7.488 (0.80), 7.491 (0.99), 7.504 (2.00), 7.509 (2.06), 7.513 (2.41), 7.521 (4.06), 7.529 (2.58), 7.532 (2.34), 7.536 (2.30), 7.549 (1.35), 7.554 (0.97), 7.564 (0.71), 7.573 (0.67), 7.595 (0.80), 7.612 (0.67), 7.624 (0.80), 7.641 (0.52), 7.793 (1.40), 7.807 (1.51), 7.815 (1.57), 7.829 (1.48), 7.860 (1.91), 7.868 (1.12), 7.877 (1.72), 7.883 (1.68), 8.196 (1.46), 8.202 (1.38), 8.212 (0.88), 8.220 (1.46).

Intermediate 34

(rac)-ethyl 7-{5-ethyl-3-[1-hydroxy-3-(morpholin-4-yl)propyl]-1-methyl-1H-pyrazol-4-yl}-6-fluoro-3-[3-(naphthalen-1-yloxy)propyl]-1H-indole-2-carboxylate (Mixture of Stereoisomers)

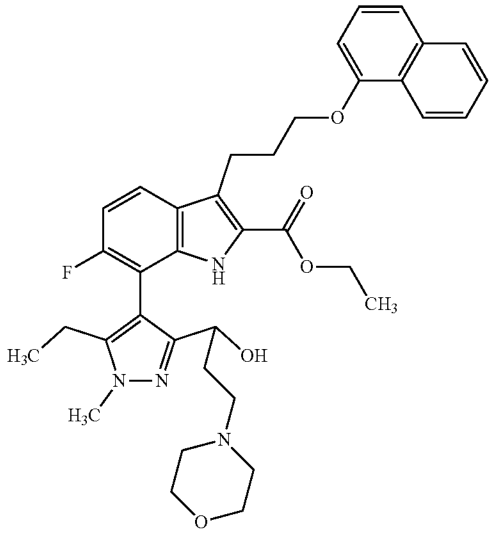 [SMILES: CCOC(=O)c1[nH]c2c(-c3c(C(O)CCN4CCOCC4)nn(C)c3CC)c(F)ccc2c1CCCOc1cccc2ccccc12]

A solution of ethyl 6-fluoro-3-[3-(naphthalen-1-yloxy)propyl]-7-(4,4,5,5-tetramethyl-1,3,2-dioxaborolan-2-yl)-1H-indole-2-carboxylate (see Intermediate 5, 1.10 g, 2.13 mmol), (rac)-1-(4-bromo-5-ethyl-1-methyl-1H-pyrazol-3-yl)-3-(morpholin-4-yl)propan-1-ol (see Intermediate 5, 565 mg, 1.70 mmol) and XPhos Pd G3 (504 mg, 595 μmol) in 1,4-dioxane (10 mL) was purged with argon for 10 minutes. Potassium triphosphate (1.08 g, 5.10 mmol), dissolved in 4 mL of water, was added and the mixture was stirred for 20 minutes at 100° C. in a microwave reactor. The reaction mixture was diluted with water and was extracted with ethyl acetate. The combined organic layers were washed with brine, dried using a water resistant filter and concentrated. The crude material was purified by flash chromatography using silica gel (gradient dichloromethane/ethanol) to obtain the title compound (948 mg, 82% yield), which was formed as a mixture of two racemic diastereomers as a result of atropisomerism at the newly formed bi-heteroaryl bond.

LC-MS (Method 2): $R_t$=1.62 min; MS (ESIpos): m/z=643 $[M+H]^+$ $^1$H-NMR (400 MHz, DMSO-d6) δ[ppm]: 0.890 (0.59), 0.909 (1.73), 0.930 (1.84), 0.949 (0.73), 1.066 (16.00), 1.245 (1.84), 1.263 (3.91), 1.280 (1.87), 1.985 (0.42), 1.997 (0.41), 2.145 (0.41), 2.160 (0.48), 2.190 (0.74), 2.204 (1.03), 2.222 (0.96), 2.240 (0.49), 2.420 (0.45), 2.439 (0.51), 2.457 (0.47), 2.518 (1.40), 2.523 (0.96), 2.539 (0.70), 3.401 (0.91), 3.819 (3.07), 3.843 (3.69), 3.939 (2.20), 4.206 (0.81), 4.217 (0.93), 4.222 (1.03), 4.232 (0.50), 4.240 (1.74), 4.258 (1.73), 4.275 (0.60), 5.758 (0.56), 6.905 (0.46), 6.912 (0.43), 6.922 (0.48), 7.373 (0.41), 7.392 (0.93), 7.412 (0.66), 7.452 (1.15), 7.473 (0.63), 7.504 (0.42), 7.508 (0.62), 7.513 (0.67), 7.521 (0.99), 7.523 (0.91), 7.528 (0.56), 7.532 (0.73), 7.537 (0.58), 7.701 (0.47), 7.713 (0.51), 7.723 (0.51), 7.736 (0.47), 7.861 (0.65), 7.878 (0.58), 7.884 (0.55), 8.236 (0.41), 8.243 (0.49), 10.933 (0.51), 10.957 (0.53).

Intermediate 35

(rac)-ethyl-(11Z)-3-ethyl-4-fluoro-2-methyl-15-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate

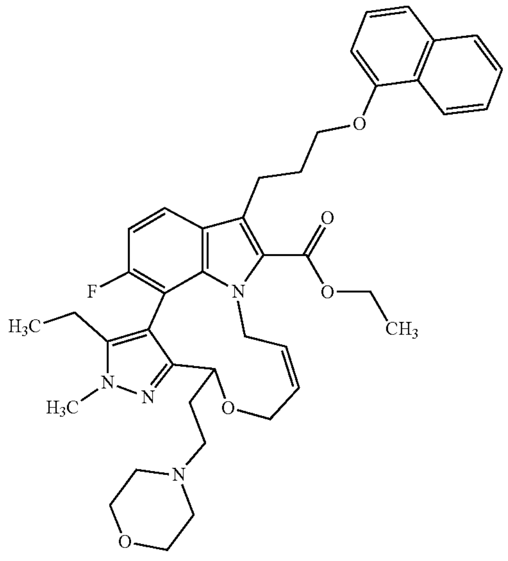 [SMILES: CCOC(=O)c1c(CCCOc2cccc3ccccc23)c2ccc(F)c3c2n1C/C=C\COC(CCN1CCOCC1)c1nn(C)c(CC)c1-3]

To a mixture of (rac)-ethyl 7-{5-ethyl-3-[1-hydroxy-3-(morpholin-4-yl)propyl]-1-methyl-1H-pyrazol-4-yl}-6-fluoro-3-[3-(naphthalen-1-yloxy)propyl]-1H-indole-2-carboxylate (mixture of stereoisomers; see Intermediate 34, 945 mg, 1.47 mmol) in acetonitrile (15 mL), cesium carbonate (2.40 g, 7.35 mmol) was added. After 10 minutes of stirring, (2Z)-1,4-dichlorobut-2-ene (CAS 1476-11-5, 230 μL, 2.2 mmol) and sodium iodide (441 mg, 2.94 mmol) were added, and the reaction mixture was stirred for 20 hours at 65° C. The reaction mixture was diluted with water and extracted with ethyl acetate. The combined organic layers were washed with brine, dried using a water resistant filter and concentrated. The crude material was purified by flash chromatography using silica gel (gradient dichloromethane/ethanol) to obtain the title compound (542 mg, 50% yield), which was formed as a racemic mixture of two enantiomers as only one of the two diastereomers formed in the preceding step underwent the macrocyclisation reaction.

LC-MS (Method 2): $R_t$=1.68 min; MS (ESIpos): m/z=695 $[M+H]^+$ $^1$H-NMR (400 MHz, DMSO-d6) δ[ppm]: 0.797 (1.00), 0.813 (4.07), 0.821 (1.86), 0.832 (8.59), 0.839 (2.10), 0.851 (4.96), 0.863 (1.64), 0.870 (1.29), 0.880 (1.10), 0.885 (1.40), 0.899 (1.08), 0.904 (1.80), 0.922 (1.02), 0.930 (0.62), 0.944 (0.54), 1.066 (0.78), 1.146 (0.81), 1.164 (1.91), 1.171 (0.97), 1.180 (1.70), 1.189 (1.59), 1.198 (0.78), 1.206 (0.84), 1.235 (0.86), 1.258 (6.38), 1.276 (12.93), 1.294 (6.03), 1.781 (0.46), 1.907 (0.48), 2.083 (0.67), 2.209 (3.42), 2.227 (4.47), 2.240 (4.63), 2.259 (3.77), 2.277 (2.02), 2.296 (1.13), 2.322 (1.67), 2.327 (2.07), 2.331 (1.70), 2.373 (0.51), 2.388 (0.48), 2.411 (0.43), 2.518 (6.33), 2.523 (4.07), 2.539 (0.67), 2.664 (1.24), 2.669 (1.64), 2.673 (1.21), 3.292 (1.54), 3.309 (2.91), 3.402 (2.15), 3.531 (0.67), 3.661 (0.70), 3.681 (1.08), 3.694 (0.94), 3.716 (2.07), 3.722 (2.07), 3.738 (1.16), 3.768 (3.18), 3.794 (0.97), 3.800 (0.92), 3.806 (0.92), 3.816 (0.70), 3.830 (0.65), 3.846 (1.56), 3.892 (16.00), 4.111 (0.57), 4.130 (0.65), 4.149 (0.57), 4.168 (0.57), 4.186 (0.70), 4.199 (0.84), 4.217 (2.18), 4.226 (3.23), 4.235 (3.34), 4.243 (4.93), 4.255 (2.42), 4.262 (3.15), 4.281 (2.40), 4.291 (0.70), 4.299 (2.24), 4.308 (2.15), 4.320 (1.78), 4.326 (1.97), 4.341 (1.19), 4.717 (0.48), 4.756 (0.70), 4.781 (0.75), 4.923 (1.21), 4.960 (0.94), 5.028 (0.81), 5.055 (1.35), 5.081 (0.73), 5.182 (0.51), 5.194 (0.48), 5.211 (0.81), 5.222 (0.78), 5.759 (1.97), 6.908 (2.18), 6.919 (1.27), 6.925 (2.45), 6.938 (0.86), 7.023 (1.40), 7.046 (2.24), 7.068 (1.37), 7.376 (1.70), 7.382 (0.73), 7.396 (3.39), 7.403 (1.32), 7.415 (2.75), 7.422 (0.97), 7.454 (4.07), 7.475 (2.34), 7.485 (1.02), 7.498 (2.10), 7.502 (1.94), 7.512 (2.67), 7.517 (4.07), 7.523 (3.26), 7.531 (2.75), 7.535 (2.69), 7.549 (1.00), 7.789 (0.51), 7.802 (0.54), 7.823 (1.45), 7.837 (1.45), 7.845 (1.54), 7.862 (2.94), 7.880 (2.69), 7.885 (2.15), 8.187 (1.54), 8.192 (1.62), 8.212 (1.80), 8.239 (0.62).

Intermediate 36

(rac)-ethyl-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

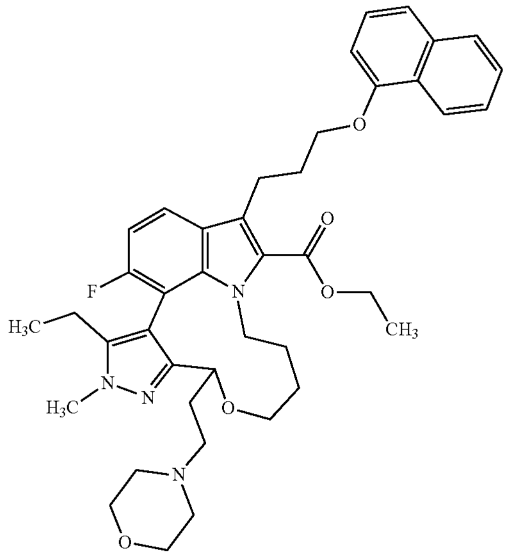 [SMILES: CCOC(=O)c1c(CCCOc2cccc3ccccc23)c2ccc(F)c3c2n1CCCCOC(CCN1CCOCC1)c1nn(C)c(CC)c1-3]

To a solution of (rac)-ethyl-(11Z)-3-ethyl-4-fluoro-2-methyl-15-[2-(morpholin-4-yl)ethyl]-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 35, 540 mg, 777 μmol) in ethanol (20 mL) and dichloromethane (0.5 mL) was added tris(triphenylphosphine)rhodium(I) chloride (1.44 g, 1.55 mmol), and the mixture was stirred under an atmosphere of hydrogen at rt for 6 hours. The catalyst was filtered off, and the filtrate was concentrated under reduced pressure. The crude material was purified by flash chromatography using silica gel (gradient dichloromethane/ethanol) to give the title compound (393 mg).

LC-MS (Method 2): $R_t$=1.72 min; MS (ESIpos): m/z=697 $[M+H]^+$ $^1$H-NMR (400 MHz, DMSO-d6) δ[ppm]: 0.797 (0.65), 0.804 (0.73), 0.814 (0.76), 0.826 (3.35), 0.845 (7.44), 0.864 (3.38), 0.885 (0.42), 0.904 (0.70), 1.020 (0.85), 1.160 (0.47), 1.188 (0.71), 1.253 (5.64), 1.270 (11.29), 1.288 (5.38), 1.907 (3.07), 1.995 (0.56), 2.010 (1.46), 2.028 (1.60), 2.045 (0.76), 2.221 (1.83), 2.240 (2.29), 2.259 (3.67), 2.277 (4.62), 2.292 (3.26), 2.311 (1.21), 2.322 (1.02), 2.327 (1.27), 2.518 (3.50), 2.523 (2.36), 2.664 (0.68), 2.669 (0.93), 2.673 (0.67), 2.975 (0.56), 3.002 (0.62), 3.217 (0.42), 3.233 (0.67), 3.250 (0.87), 3.267 (1.10), 3.290 (1.33), 3.306 (1.58), 3.492 (3.88), 3.820 (1.26), 3.864 (16.00), 3.999 (0.54), 4.017 (0.70), 4.035 (0.70), 4.175 (0.56), 4.193 (1.81), 4.202 (1.72), 4.211 (3.05), 4.220 (2.88), 4.228 (1.57), 4.238 (2.17), 4.255 (0.87), 4.276 (2.03), 4.293 (2.36), 4.303 (1.47), 4.311 (1.01), 4.320 (1.30), 4.338 (0.57), 4.383 (0.90), 4.401 (1.89), 4.418 (0.84), 5.758 (3.60), 6.886 (2.02), 6.903 (2.14), 6.991 (1.46), 7.013 (2.50), 7.036 (1.44), 7.367 (1.80), 7.387 (3.07), 7.406 (2.47), 7.450 (3.26), 7.471 (2.02), 7.489 (0.68), 7.493 (0.93), 7.505 (1.95), 7.511 (2.09), 7.513 (2.56), 7.522 (3.89), 7.530 (2.60), 7.537 (2.16), 7.549 (0.96), 7.554 (0.67), 7.625 (0.42), 7.793 (1.38), 7.807 (1.44), 7.815 (1.46), 7.828 (1.35), 7.860 (1.86), 7.869 (1.01), 7.877 (1.49), 7.883 (1.55), 8.205 (1.43), 8.211 (1.27), 8.221 (0.81), 8.229 (1.38).

Intermediate 37

(rac)-ethyl 6-chloro-7-{3-[1-hydroxy-3-(morpholin-4-yl)propyl]-1,5-dimethyl-1H-pyrazol-4-yl}-3-{3-[(naphthalen-1-yl)oxy]propyl}-1H-indole-2-carboxylate (Mixture of Stereoisomers)

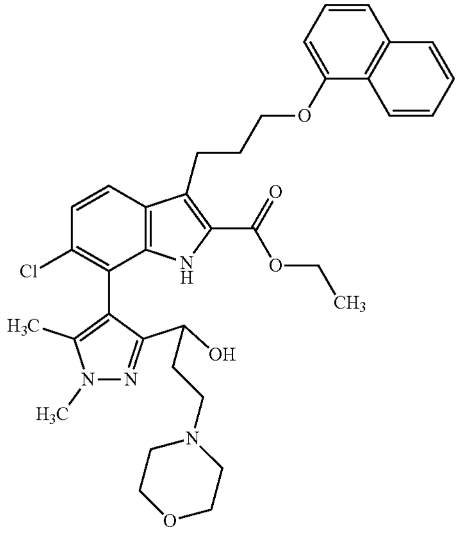 [SMILES: CCOC(=O)c1[nH]c2c(-c3c(C(O)CCN4CCOCC4)nn(C)c3C)c(Cl)ccc2c1CCCOc1cccc2ccccc12]

The reaction was performed in three identical preparations using a third of all materials.

A solution of ethyl-6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 8, 10.5 g, 19.6 mmol), (rac)-1-(4-bromo-1,5-dimethyl-1H-pyrazol-3-yl)-3-(morpholin-4-yl)propan-1-ol (see Intermediate 17, 5.00 g, 15.7 mmol) and XPhos Pd G3 (6.65 g, 7.86 mmol) in 1,4-dioxane (30 mL) was purged with argon for 10 minutes. Potassium triphosphate (10.0 g, 47.1 mmol), dissolved in 7.5 mL of water, was added and the reaction mixture was stirred for 20 minutes at 100° C. in a microwave reactor. The reaction mixtures resulting from said three preparations were combined, diluted with water and extracted with ethyl acetate. The combined organic layers were washed with brine, dried using a water resistant filter and concentrated. The crude material was purified by flash chromatography using silica gel (gradient dichloromethane/ethanol) to obtain the title compound (2.07 g), which was formed as a mixture of two racemic diastereomers as a result of atropisomerism at the newly formed bi-heteroaryl bond.

LC-MS (Method 2): $R_t$=1.61 min; MS (ESIpos): m/z=645 $[M+H]^+$ $^1$H-NMR (400 MHz, DMSO-d6) δ[ppm]: 1.035 (3.10), 1.052 (6.20), 1.065 (4.98), 1.070 (3.22), 1.243 (5.76), 1.261 (12.31), 1.279 (5.84), 1.297 (0.39), 1.828 (0.67), 1.845 (1.88), 1.862 (2.00), 1.880 (0.82), 1.954 (5.29), 1.983 (14.82), 2.111 (1.14), 2.143 (1.73), 2.161 (1.33), 2.191 (3.18), 2.195 (3.61), 2.213 (2.71), 2.230 (2.35), 2.248 (1.49), 2.261 (0.98), 2.270 (5.61), 2.272 (5.49), 2.303 (0.51), 2.322 (1.06), 2.326 (1.25), 2.331 (1.14), 2.337 (1.22), 2.349 (1.41), 2.518 (4.82), 2.522 (2.78), 2.610 (0.94), 2.628 (2.00), 2.646

(1.25), 2.664 (0.71), 2.668 (0.86), 2.673 (0.63), 3.006 (1.18), 3.025 (2.04), 3.043 (0.98), 3.391 (3.37), 3.404 (2.51), 3.417 (0.94), 3.422 (1.84), 3.435 (1.65), 3.440 (1.41), 3.452 (1.37), 3.457 (0.59), 3.469 (0.55), 3.509 (1.57), 3.521 (2.04), 3.533 (1.80), 3.545 (0.55), 3.626 (0.67), 3.716 (1.25), 3.738 (0.67), 3.750 (0.75), 3.783 (5.29), 3.805 (12.51), 3.808 (16.00), 3.942 (0.90), 4.203 (2.08), 4.215 (3.45), 4.229 (3.29), 4.247 (4.90), 4.265 (4.55), 4.283 (1.41), 4.348 (0.90), 4.361 (1.76), 4.374 (0.90), 5.174 (1.06), 5.186 (1.10), 6.481 (1.53), 6.483 (1.49), 6.897 (0.63), 6.908 (1.76), 6.914 (0.86), 6.925 (1.96), 7.158 (3.06), 7.172 (1.41), 7.179 (3.22), 7.193 (1.37), 7.375 (1.49), 7.395 (2.67), 7.414 (2.24), 7.453 (3.37), 7.473 (1.88), 7.487 (0.59), 7.491 (0.86), 7.504 (2.04), 7.509 (1.92), 7.514 (2.24), 7.521 (4.47), 7.528 (2.39), 7.533 (2.08), 7.538 (2.24), 7.550 (0.86), 7.555 (0.59), 7.697 (3.57), 7.718 (3.25), 7.861 (1.96), 7.868 (1.18), 7.878 (1.88), 7.884 (1.73), 8.214 (1.29), 8.220 (1.29), 8.231 (1.10), 8.239 (1.37), 8.248 (0.55), 10.791 (1.73), 10.816 (0.71).

Intermediate 38

(rac)-ethyl-(11Z)-4-chloro-2,3-dimethyl-15-[2-(morpholin-4-yl)ethyl]-7-{3-[(naphthalen-1-yl)oxy]propyl}-2,10,13,15-tetrahydropyrazolo[4',3':9,10][1,6]oxazacycloundecino[8,7,6-hi]indole-8-carboxylate

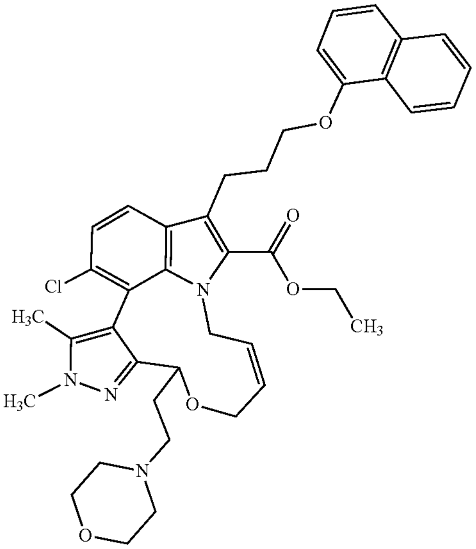 [SMILES: CCOC(=O)c1c(CCCOc2cccc3ccccc23)c2ccc(Cl)c3c2n1C/C=C\COC(CCN1CCOCC1)c1nn(C)c(C)c1-3]

To a mixture of (rac)-ethyl-6-chloro-7-{3-[1-hydroxy-3-(morpholin-4-yl)propyl]-1,5-dimethyl-1H-pyrazol-4-yl}-3-{3-[(naphthalen-1-yl)oxy]propyl}-1H-indole-2-carboxylate (see Intermediate 37, 2.07 g, 3.21 mmol) in acetonitrile (20 mL), cesium carbonate (5.23 g, 16.0 mmol) was added. After 10 minutes of stirring, (2Z)-1,4-dichlorobut-2-ene (CAS 1476-11-5, 510 μL, 4.8 mmol) and sodium iodide (962 mg, 6.42 mmol) were added, and the reaction mixture was stirred for 23 hours at 70° C., followed by dilution with water and extraction with ethyl acetate. The combined organic layers were washed with brine, dried using a water resistant filter and concentrated. The crude material was purified by flash chromatography using silica gel (gradient dichloromethane/ethanol) to obtain the title compound (927 mg), which was formed as a racemic mixture of two enantiomers as only one of the two diastereomers formed in the preceding step underwent the macrocyclisation reaction.

LC-MS (Method 2): $R_t$=1.68 min; MS (ESIpos): m/z=697 $[M+H]^+$ $^1$H-NMR (400 MHz, DMSO-d6) δ[ppm]: 0.798 (0.67), 0.814 (0.75), 0.821 (0.75), 0.886 (0.42), 0.904 (0.84), 0.922 (0.42), 1.168 (0.77), 1.182 (0.86), 1.188 (0.94), 1.200 (0.44), 1.206 (0.48), 1.259 (5.41), 1.277 (11.53), 1.294 (5.33), 1.761 (0.42), 1.797 (16.00), 1.825 (1.19), 1.866 (0.75), 1.955 (0.52), 2.197 (2.65), 2.210 (2.53), 2.229 (2.65), 2.249 (2.07), 2.271 (4.07), 2.323 (1.59), 2.327 (1.96), 2.332 (1.67), 2.518 (4.72), 2.523 (3.28), 2.665 (0.90), 2.669 (1.25), 2.673 (0.92), 3.029 (0.58), 3.263 (0.73), 3.280 (1.07), 3.297 (1.36), 3.366 (2.19), 3.384 (2.01), 3.513 (0.92), 3.524 (1.21), 3.535 (0.96), 3.656 (1.88), 3.668 (0.75), 3.687 (0.98), 3.700 (0.90), 3.717 (1.04), 3.730 (0.79), 3.754 (0.63), 3.793 (1.15), 3.806 (6.08), 3.822 (1.48), 3.859 (15.29), 4.205 (0.75), 4.223 (2.65), 4.240 (4.14), 4.250 (2.92), 4.268 (2.67), 4.286 (2.51), 4.294 (1.30), 4.304 (2.57), 4.313 (1.59), 4.323 (1.23), 4.331 (1.04), 4.712 (0.44), 4.738 (0.56), 4.751 (0.65), 4.779 (0.75), 4.906 (1.09), 4.946 (0.75), 5.022 (0.48), 5.048 (0.92), 5.079 (0.61), 5.180 (0.42), 5.191 (0.48), 5.207 (0.65), 5.219 (0.65), 5.759 (0.92), 6.484 (0.88), 6.913 (2.03), 6.930 (2.09), 7.254 (3.95), 7.275 (3.89), 7.378 (1.50), 7.398 (2.84), 7.417 (2.38), 7.455 (3.32), 7.476 (1.90), 7.485 (0.92), 7.498 (1.75), 7.502 (1.67), 7.513 (2.30), 7.518 (3.03), 7.522 (2.55), 7.532 (2.07), 7.536 (2.28), 7.549 (0.94), 7.553 (0.71), 7.774 (0.40), 7.806 (3.47), 7.827 (3.13), 7.863 (2.01), 7.869 (1.34), 7.881 (2.05), 7.886 (1.73), 8.181 (1.40), 8.185 (1.50), 8.205 (1.61).

Intermediate 39

(rac)-ethyl-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

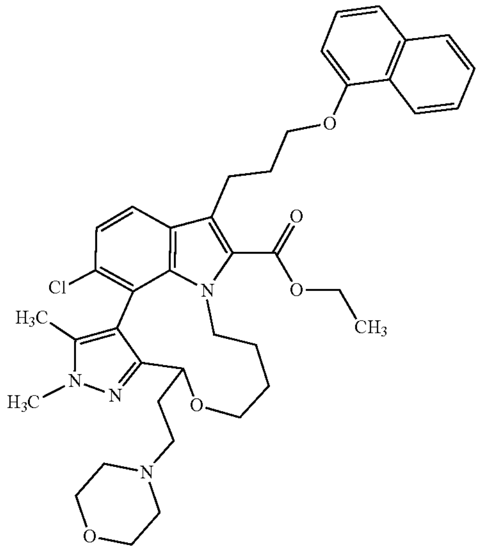 [SMILES: CCOC(=O)c1c(CCCOc2cccc3ccccc23)c2ccc(Cl)c3c2n1CCCCOC(CCN1CCOCC1)c1nn(C)c(C)c1-3]

To a solution of (rac)-ethyl-(11Z)-4-chloro-2,3-dimethyl-15-[2-(morpholin-4-yl)ethyl]-7-{3-[(naphthalen-1-yl)-oxy]propyl}-2,10,13,15-tetrahydropyrazolo[4',3':9,10][1,6]oxazacycloundecino[8,7,6-hi]indole-8-carboxylate (see Intermediate 38, 925 mg) in ethanol (15 mL) and dichloromethane (7 mL), tris(triphenylphosphine)rhodium(I) chloride (2.46 g, 2.65 mmol) was added, and the mixture was stirred under an atmosphere of hydrogen at rt for 11 hours.

The catalyst was filtered off, and the filtrate was concentrated under reduced pressure. The crude material was purified by flash chromatography using silica gel (gradient dichloromethane/ethanol) to give the title compound (772 mg).

LC-MS (Method 2): $R_t$=1.70 min; MS (ESIpos): m/z=699 $[M+H]^+$ $^1$H-NMR (400 MHz, DMSO-d6) δ[ppm]: 0.797 (0.48), 0.814 (0.51), 0.821 (0.51), 0.904 (0.62), 1.017 (0.82), 1.053 (0.48), 1.066 (0.45), 1.070 (0.43), 1.111 (0.43), 1.123 (0.51), 1.142 (0.48), 1.236 (0.65), 1.253 (5.53), 1.271 (11.69), 1.289 (5.45), 1.808 (15.18), 1.907 (3.40), 2.013 (0.48), 2.032 (0.91), 2.043 (1.11), 2.057 (1.08), 2.075 (0.62), 2.190 (0.96), 2.208 (1.30), 2.223 (1.05), 2.242 (0.79), 2.290 (3.49), 2.323 (1.53), 2.327 (1.79), 2.332 (1.45), 2.472 (0.62), 2.518 (3.86), 2.523 (2.61), 2.665 (0.77), 2.669 (1.08), 2.673 (0.77), 3.031 (0.51), 3.046 (0.54), 3.221 (0.51), 3.238 (0.71), 3.256 (0.99), 3.277 (1.11), 3.295 (1.16), 3.308 (1.59), 3.367 (0.60), 3.499 (3.49), 3.833 (16.00), 3.934 (0.60), 3.951 (0.65), 3.969 (0.71), 4.180 (0.68), 4.190 (0.94), 4.198 (2.10), 4.206 (2.04), 4.216 (2.18), 4.225 (2.44), 4.243 (1.90), 4.252 (0.57), 4.263 (1.30), 4.281 (2.24), 4.290 (0.60), 4.299 (2.18), 4.307 (1.16), 4.316 (0.71), 4.325 (1.02), 4.397 (0.91), 4.413 (1.50), 4.431 (0.85), 5.758 (3.89), 6.891 (1.84), 6.908 (1.99), 7.226 (4.31), 7.248 (4.34), 7.369 (1.59), 7.390 (2.75), 7.409 (2.27), 7.450 (2.89), 7.471 (1.70), 7.487 (0.60), 7.491 (0.82), 7.504 (1.82), 7.508 (1.67), 7.513 (2.01), 7.521 (3.77), 7.528 (2.07), 7.533 (1.82), 7.537 (1.96), 7.549 (1.02), 7.554 (0.71), 7.565 (0.43), 7.596 (0.48), 7.612 (0.40), 7.621 (0.45), 7.625 (0.45), 7.779 (3.66), 7.801 (3.23), 7.860 (1.65), 7.868 (0.91), 7.878 (1.56), 7.884 (1.36), 8.190 (1.39), 8.196 (1.28), 8.207 (0.71), 8.214 (1.30).

Intermediate 40

(rac)-ethyl-6-fluoro-3-{3-[(6-fluoronaphthalen-1-yl)oxy]propyl}-7-{3-[1-hydroxy-3-(morpholin-4-yl)propyl]-1,5-dimethyl-1H-pyrazol-4-yl}-1H-indole-2-carboxylate (Mixture of Stereoisomers)

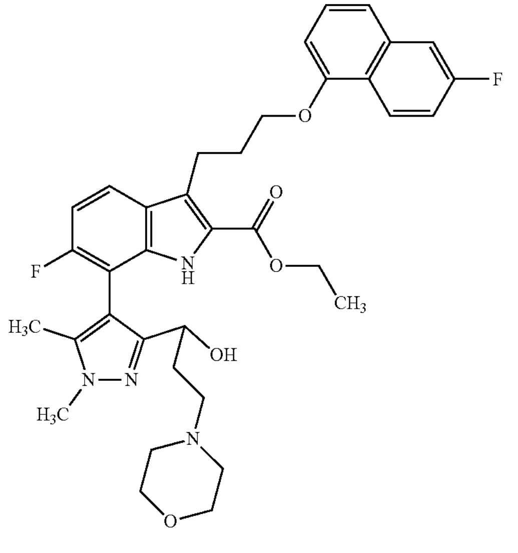 [SMILES: CCOC(=O)c1[nH]c2c(-c3c(C(O)CCN4CCOCC4)nn(C)c3C)c(F)ccc2c1CCCOc1cccc2cc(F)ccc12]

The reaction was performed in two identical preparations using half of all materials.

A solution of (rac)-1-(4-bromo-1,5-dimethyl-1H-pyrazol-3-yl)-3-(morpholin-4-yl)propan-1-ol (see Intermediate 17, 1.33 g, 4.18 mmol), ethyl-6-fluoro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 10, 2.80 g, 5.23 mmol) and XPhos Pd G3 (1.24 g, 1.46 mmol) in 1,4-dioxane (20 mL) was purged with argon for 10 minutes. Potassium triphosphate (2.66 g, 12.6 mmol), dissolved in 3 mL of water, was added and the mixture was stirred for 20 minutes at 100° C. in a microwave reactor. The combined reaction mixtures were diluted with water and extracted with ethyl acetate. The combined organic layers were washed with brine, dried using a water resistant filter and concentrated. The crude material was purified by flash chromatography using silica gel (gradient dichloromethane/ethanol) to obtain the title compound (2.43 g), which was formed as a mixture of two racemic diastereomers as a result of atropisomerism at the newly formed bi-heteroaryl bond.

LC-MS (Method 2): $R_t$=1.57 min; MS (ESIpos): m/z=647 $[M+H]^+$ $^1$H-NMR (400 MHz, DMSO-d6) δ[ppm]: 1.066 (16.00), 1.156 (0.47), 1.238 (0.88), 1.240 (0.91), 1.255 (1.91), 1.258 (1.97), 1.273 (0.89), 1.275 (0.90), 2.005 (1.24), 2.007 (1.27), 2.040 (1.23), 2.043 (1.24), 2.224 (0.61), 2.518 (0.74), 2.523 (0.53), 3.418 (0.62), 3.784 (2.30), 3.809 (2.34), 3.939 (2.88), 4.199 (0.54), 4.213 (0.77), 4.229 (0.88), 4.231 (0.91), 4.249 (0.83), 7.435 (0.59), 7.440 (0.74), 7.448 (1.57).

Intermediate 41

(rac)-ethyl-(11Z)-4-fluoro-7-{3-[(6-fluoronaphthalen-1-yl)oxy]propyl}-2,3-dimethyl-15-[2-(morpholin-4-yl)ethyl]-2,10,13,15-tetrahydropyrazolo[4',3':9,10][1,6]oxazacycloundecino[8,7,6-hi]indole-8-carboxylate

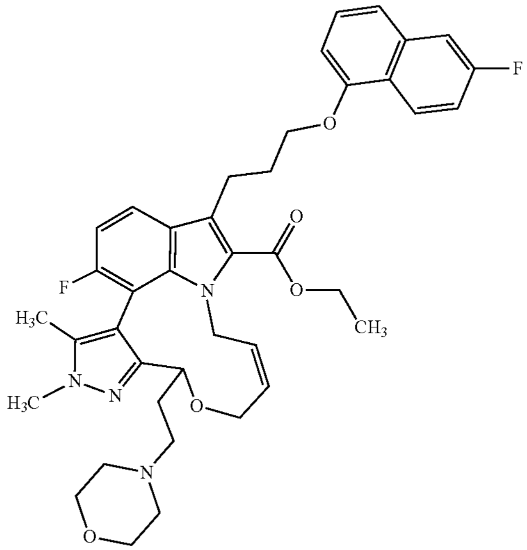 [SMILES: CCOC(=O)c1c(CCCOc2cccc3cc(F)ccc23)c2ccc(F)c3c2n1C/C=C\COC(CCN1CCOCC1)c1nn(C)c(C)c1-3]

To a mixture of (rac)-ethyl-6-fluoro-3-{3-[(6-fluoronaphthalen-1-yl)oxy]propyl}-7-{3-[1-hydroxy-3-(morpholin-4-yl)propyl]-1,5-dimethyl-1H-pyrazol-4-yl}-1H-indole-2-carboxylate (mixture of stereoisomers; see Intermediate 40, 2.43 g) in acetonitrile (30 mL), cesium carbonate (6.12 g, 18.8 mmol) was added. After 10 minutes of stirring, (2Z)-1,4-dichlorobut-2-ene (CAS 1476-11-5, 590 μL, 5.64 mmol) and sodium iodide (1.13 g, 7.51 mmol) were added, and the reaction mixture was stirred for 48 hours at 70° C., followed by dilution with water and extraction with ethyl acetate. The combined organic layers were washed with brine, dried using a water resistant filter and concentrated. The crude material was purified by flash chromatography using silica gel (gradient dichloromethane/ethanol) to obtain the title compound (1.20 g), which was formed as a racemic mixture of two enantiomers as only one of the two diastereomers formed in the preceding step underwent the macrocyclisation reaction.

LC-MS (Method 2): $R_t$=1.64 min; MS (ESIpos): m/z=699 $[M+H]^+$ $^1$H-NMR (400 MHz, DMSO-d6) δ[ppm]: 0.797 (0.74), 0.814 (0.77), 0.821 (0.77), 0.886 (0.46), 0.904 (0.98), 0.922 (0.49), 1.053 (0.88), 1.066 (16.00), 1.148 (2.00), 1.166 (4.53), 1.176 (2.53), 1.183 (2.84), 1.186 (3.82), 1.193 (4.95), 1.204 (1.86), 1.211 (2.46), 1.238 (2.00), 1.254 (6.00), 1.272 (10.67), 1.289 (4.70), 1.645 (0.70), 1.812 (2.77), 1.838 (1.61), 1.849 (7.02), 1.857 (13.47), 1.884 (4.04), 1.907 (0.81), 2.007 (2.46), 2.041 (2.46), 2.226 (4.21), 2.323 (1.86), 2.327 (2.46), 2.332 (1.82), 2.457 (0.49), 2.461 (0.63), 2.518 (6.88), 2.523 (5.09), 2.665 (1.47), 2.669 (2.11), 2.673 (1.44), 3.280 (2.00), 3.299 (2.53), 3.363 (2.46), 3.404 (3.44), 3.661 (8.74), 3.686 (0.95), 3.697 (0.84), 3.729 (5.16), 3.741 (1.47), 3.767 (1.30), 3.784 (3.54), 3.800 (1.54), 3.811 (3.82), 3.860 (13.33), 3.938 (2.53), 4.091 (0.67), 4.109 (0.84), 4.117 (0.98), 4.124 (0.81), 4.134 (1.47), 4.151 (1.23), 4.168 (0.81), 4.173 (0.91), 4.186 (1.51), 4.190 (1.16), 4.204 (1.89), 4.216 (3.40), 4.231 (5.65), 4.243 (5.54), 4.260 (3.40), 4.278 (2.42), 4.296 (2.18), 4.305 (1.65), 4.313 (1.58), 4.323 (2.21), 4.330 (1.37), 4.341 (1.12), 4.736 (0.46), 4.775 (0.67), 4.801 (0.67), 4.916 (1.30), 4.953 (0.67), 5.030 (0.74), 5.050 (1.09), 5.071 (1.23), 5.109 (0.60), 5.180 (0.42), 5.196 (0.42), 5.216 (0.98), 5.683 (0.39), 5.710 (0.49), 5.718 (0.42), 5.749 (0.56), 5.758 (10.53), 5.768 (0.46), 5.956 (0.53), 5.983 (0.63), 5.999 (0.46), 6.025 (0.49), 6.596 (0.53), 6.630 (0.49), 6.689 (0.88), 6.722 (0.84), 6.877 (1.12), 6.889 (2.35), 6.899 (2.39), 6.904 (2.18), 6.911 (1.75), 6.917 (1.26), 6.994 (0.46), 7.005 (0.46), 7.026 (1.26), 7.048 (2.39), 7.055 (0.95), 7.060 (0.63), 7.071 (1.96), 7.077 (1.16), 7.093 (0.63), 7.100 (0.67), 7.106 (0.42), 7.364 (1.02), 7.371 (1.44), 7.386 (2.00), 7.392 (2.49), 7.403 (1.33), 7.409 (1.44), 7.416 (1.89), 7.419 (1.72), 7.425 (1.19), 7.444 (7.44), 7.453 (8.98), 7.650 (3.02), 7.656 (2.53), 7.676 (2.91), 7.681 (2.35), 7.699 (0.46), 7.712 (0.49), 7.720 (0.49), 7.734 (0.46), 7.781 (0.81), 7.794 (1.05), 7.802 (0.95), 7.818 (1.51), 7.832 (1.23), 7.841 (1.16), 7.854 (1.09), 8.134 (0.56), 8.204 (1.19), 8.219 (1.51), 8.226 (1.89), 8.241 (1.93), 8.248 (1.72), 8.263 (1.33), 8.272 (0.70), 8.288 (0.42), 11.151 (0.39).

Intermediate 42

(rac)-ethyl-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

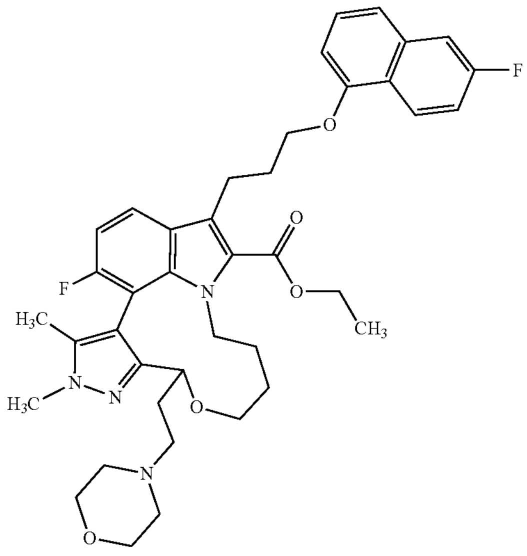 [SMILES: CCOC(=O)c1c(CCCOc2cccc3cc(F)ccc23)c2ccc(F)c3c2n1CCCCOC(CCN1CCOCC1)c1nn(C)c(C)c1-3]

To a solution of (rac)-ethyl-(11Z)-4-fluoro-7-{3-[(6-fluoronaphthalen-1-yl)oxy]propyl}-2,3-dimethyl-15-[2-(morpholin-4-yl)ethyl]-2,10,13,15-tetrahydropyrazolo[4',3':9,10][1,6]oxazacycloundecino[8,7,6-hi]indole-8-carboxylate (see Intermediate 41, 1.20 g) in a mixture of ethanol (20 mL) and dichloromethane (20 mL), tris(triphenylphosphine)rhodium (I) chloride (3.19 g, 3.43 mmol) was added, and the mixture was stirred under an atmosphere of hydrogen at rt for 12 hours. The catalyst was filtered off, and the filtrate was concentrated under reduced pressure. The crude material was purified by flash chromatography using silica gel (gradient dichloromethane/ethanol) to give the title compound (472 mg).

LC-MS (Method 2): $R_t$=1.66 min; MS (ESIpos): m/z=701 $[M+H]^+$ $^1$H-NMR (400 MHz, DMSO-d6) δ[ppm]: 0.797 (1.56), 0.802 (0.76), 0.814 (1.60), 0.821 (1.56), 0.840 (0.85), 0.885 (0.85), 0.904 (1.79), 0.922 (0.94), 1.009 (0.99), 1.052 (0.57), 1.065 (0.57), 1.142 (0.52), 1.155 (0.76), 1.248 (6.23), 1.266 (12.18), 1.284 (5.76), 1.769 (0.76), 1.800 (0.47), 1.884 (15.48), 1.906 (3.40), 1.985 (0.90), 2.003 (1.98), 2.021 (2.12), 2.039 (1.09), 2.170 (0.99), 2.190 (1.70), 2.204 (2.17), 2.222 (2.45), 2.239 (2.60), 2.270 (3.96), 2.318 (1.13), 2.322 (2.17), 2.327 (2.88), 2.331 (2.17), 2.336 (1.04), 2.412 (0.52), 2.518 (10.71), 2.523 (7.27), 2.669 (2.83), 2.673 (2.03), 2.678 (0.94), 2.946 (0.71), 2.974 (0.76), 3.207 (0.57), 3.225 (0.90), 3.240 (1.13), 3.259 (1.51), 3.279 (1.65), 3.474 (3.07), 3.486 (4.48), 3.497 (3.02), 3.789 (0.80), 3.835 (16.00), 3.967 (0.47), 3.983 (0.61), 4.002 (0.80), 4.019 (0.76), 4.037 (0.52), 4.170 (0.90), 4.188 (1.98), 4.198 (2.22), 4.206 (2.69), 4.215 (4.29), 4.232 (3.16), 4.251 (1.56), 4.269 (2.08), 4.279 (0.71), 4.287 (1.94), 4.296 (1.27), 4.304 (0.80), 4.313 (1.51), 4.329 (1.04), 4.341 (0.66), 4.364 (0.80), 4.387 (0.99), 4.405 (2.03), 4.422 (0.90), 5.758 (1.98), 6.868 (1.56), 6.875 (1.60), 6.882 (1.46), 6.889 (1.70), 6.989 (1.60), 7.012 (2.55), 7.035

(1.65), 7.372 (1.70), 7.379 (1.84), 7.395 (2.31), 7.402 (2.55), 7.412 (1.65), 7.417 (2.03), 7.424 (2.31), 7.433 (4.01), 7.440 (4.53), 7.447 (7.88), 7.529 (0.99), 7.536 (0.94), 7.545 (1.37), 7.547 (1.65), 7.550 (1.60), 7.555 (1.51), 7.565 (1.84), 7.573 (1.70), 7.591 (1.42), 7.595 (2.22), 7.612 (1.89), 7.621 (2.22), 7.624 (2.17), 7.641 (1.79), 7.647 (2.64), 7.653 (2.55), 7.673 (2.31), 7.679 (2.31), 7.788 (1.51), 7.801 (1.60), 7.809 (1.65), 7.823 (1.56), 8.212 (1.56), 8.227 (1.60), 8.235 (1.65), 8.250 (1.51).

Intermediate 43 ethyl-7-bromo-3-(3-{[tert-butyl(dimethyl)silyl]oxy}propyl)-6-chloro-1H-indole-2-carboxylate

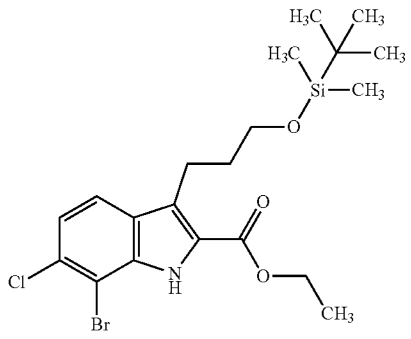 [SMILES: CCOC(=O)c1[nH]c2c(Br)c(Cl)ccc2c1CCCO[Si](C)(C)C(C)(C)C]

Ethyl-7-bromo-6-chloro-3-(3-hydroxypropyl)-1H-indole-2-carboxylate (see Intermediate 6, 20.0 g, 55.5 mmol) was dissolved in 400 mL of tetrahydrofuran and 1H-imidazole (5.66 g, 83.2 mmol), N,N-dimethylpyridin-4-amine (339 mg, 2.77 mmol) and tert-butyl(chloro)dimethylsilane (CAS 18162-48-6, 10.0 g, 66.5 mmol) were added. This mixture was stirred at room temperature for 3 hours, was diluted with water and extracted with dichloromethane. The combined organic layers were dried using sodium sulfate, filtered and concentrated under reduced pressure. The crude material was purified by flash chromatography using silica gel (gradient hexane/ethyl acetate) to give the title compound (23.7 g, 87% yield).

LC-MS (Method 1): $R_t$=1.94 min; MS (ESIpos): m/z=476 $[M+H]^+$ $^1$H-NMR (400 MHz, DMSO-d6) δ[ppm]: −0.008 (0.46), 0.007 (0.55), 0.842 (0.87), 0.849 (16.00), 0.856 (1.01), 1.326 (1.22), 1.344 (2.74), 1.361 (1.25), 3.027 (0.47), 3.574 (0.45), 3.590 (1.01), 3.605 (0.44), 4.327 (1.21), 4.345 (1.19), 7.256 (0.94), 7.277 (1.00), 7.680 (0.97), 7.701 (0.83).

Intermediate 44 ethyl-3-(3-{[tert-butyl(dimethyl)silyl]oxy}propyl)-6-chloro-7-(4,4,5,5-tetramethyl-1,3,2-dioxaborolan-2-yl)-1H-indole-2-carboxylate

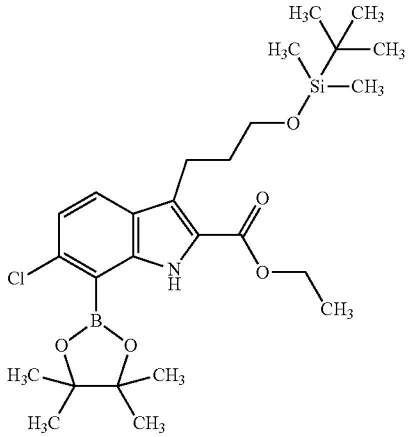 [SMILES: CCOC(=O)c1[nH]c2c(B3OC(C)(C)C(C)(C)O3)c(Cl)ccc2c1CCCO[Si](C)(C)C(C)(C)C]

To a degassed mixture of ethyl-7-bromo-3-(3-{[tert-butyl(dimethyl)silyl]oxy}propyl)-6-chloro-1H-indole-2-carboxylate (see Intermediate 43, 13.7 g, 28.8 mmol) and 4,4,4',4',5,5,5',5'-octamethyl-2,2'-bi-1,3,2-dioxaborolane (CAS 78183-34-3, 8.79 g, 34.6 mmol) in anhydrous 1,4-dioxane (30 mL), potassium acetate (5.66 g, 57.7 mmol) and 1,1'-bis(diphenylphosphino)-ferrocenpalladium(II)chloride (1.18 g, 1.44 mmol) were added. The mixture was stirred for 3 days at 90° C., was filtered and purified by flash chromatography using silica gel (gradient hexane/ethyl acetate) to give the title compound (7.90 g, 50% yield).

$^1$H-NMR (400 MHz, DMSO-d6) δ[ppm]: −0.007 (0.60), 0.007 (0.48), 0.844 (1.28), 0.850 (16.00), 0.857 (0.99), 1.281 (0.56), 1.325 (1.24), 1.342 (2.82), 1.360 (1.64), 1.373 (12.47), 3.044 (0.49), 3.568 (0.46), 3.584 (1.00), 3.600 (0.44), 4.318 (1.18), 4.336 (1.16), 7.120 (0.94), 7.141 (0.98), 7.791 (0.66), 7.812 (0.60), 9.956 (0.51).

Intermediate 45

(rac)-ethyl-3-(3-{[tert-butyl(dimethyl)silyl]oxy}propyl)-6-chloro-7-{3-[1-hydroxy-3-(morpholin-4-yl)propyl]-1,5-dimethyl-1H-pyrazol-4-yl}-1H-indole-2-carboxylate (Mixture of Stereoisomers)

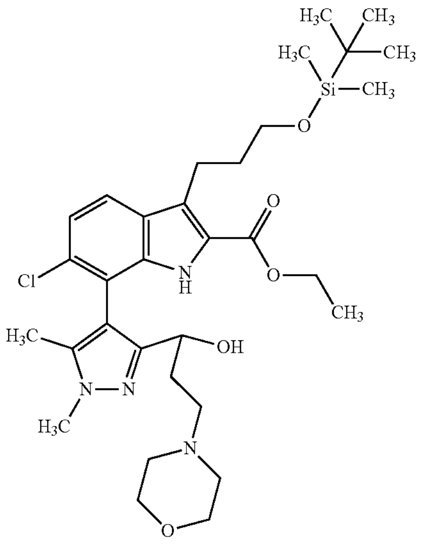 [SMILES: CCOC(=O)c1[nH]c2c(-c3c(C(O)CCN4CCOCC4)nn(C)c3C)c(Cl)ccc2c1CCCO[Si](C)(C)C(C)(C)C]

The reaction was performed in three separate preparations, twice using 2.00 g and once using 1.10 g of ethyl-3-(3-{[tert-butyl(dimethyl)silyl]oxy}propyl)-6-chloro-7-(4,4,5,5-tetramethyl-1,3,2-dioxaborolan-2-yl)-1H-indole-2-carboxylate (see Intermediate 44) and all other materials according to the relative ratios described below.

A solution of (rac)-1-(4-bromo-1,5-dimethyl-1H-pyrazol-3-yl)-3-(morpholin-4-yl)propan-1-ol (see Intermediate 17, 2.49 g, 7.82 mmol), ethyl-3-(3-{[tert-butyl(dimethyl)silyl]oxy}propyl)-6-chloro-7-(4,4,5,5-tetramethyl-1,3,2-dioxaborolan-2-yl)-1H-indole-2-carboxylate (see Intermediate 44, 5.10 g, 9.77 mmol) and Xphos Pd G3 (3.31 g, 3.91 mmol) in 1,4-dioxane (25 mL) was purged with argon for 10 minutes. Potassium triphosphate (4.98 g, 23.4 mmol), dissolved in 10 mL of water, was added and the reaction mixture was stirred for 20 minutes at 100° C. in a microwave reactor. The combined reaction mixtures were diluted with water and extracted with ethyl acetate. The combined organic layers were washed with brine, dried using a water resistant filter and concentrated. The crude material was purified by flash chromatography using silica gel (gradient dichloromethane/ethanol) to obtain the title compound (1.08 g, 21% yield), which was formed as a mixture of two racemic diastereomers as a result of atropisomerism at the newly formed bi-heteroaryl bond.

LC-MS (Method 2): $R_t$=1.75 min; MS (ESIpos): m/z=633 $[M+H]^+$ $^1$H-NMR (400 MHz, DMSO-d6) δ[ppm]: 0.000 (3.99), 0.009 (11.82), 0.017 (0.64), 0.841 (0.47), 0.851 (5.79), 0.856 (16.00), 0.873 (0.44), 0.878 (0.42), 1.045 (3.79), 1.262 (0.50), 1.266 (1.20), 1.280 (1.06), 1.284 (2.66), 1.298 (0.56), 1.301 (1.28), 1.767 (0.44), 1.818 (0.50), 1.835 (0.51), 1.935 (1.18), 1.964 (3.60), 2.123 (0.42), 2.171 (0.61), 2.250 (2.94), 2.306 (0.45), 2.311 (0.42), 2.319 (0.58), 2.331 (0.77), 2.341 (0.61), 2.497 (1.46), 2.502 (0.93), 2.590 (0.53), 2.608 (1.11), 2.626 (0.64), 2.986 (0.66), 3.005 (1.17), 3.022 (0.80), 3.044 (0.48), 3.372 (0.85), 3.489 (0.86), 3.501 (1.12), 3.513 (0.87), 3.606 (0.59), 3.624 (0.93), 3.640 (0.41), 3.761 (1.16), 3.785 (8.14), 3.918 (0.55), 4.255 (1.01), 4.272 (0.99), 5.738 (2.35), 6.460 (0.84), 6.462 (0.83), 7.192 (0.70), 7.214 (0.74), 7.632 (0.66), 7.654 (0.57), 10.700 (0.45).

Intermediate 46

(rac)-ethyl (11Z)-7-(3-{[tert-butyl(dimethyl)silyl]oxy}propyl)-4-chloro-2,3-dimethyl-15-[2-(morpholin-4-yl)ethyl]-2,10,13,15-tetrahydropyrazolo[4',3':9,10][1,6]oxazacycloundecino[8,7,6-hi]indole-8-carboxylate

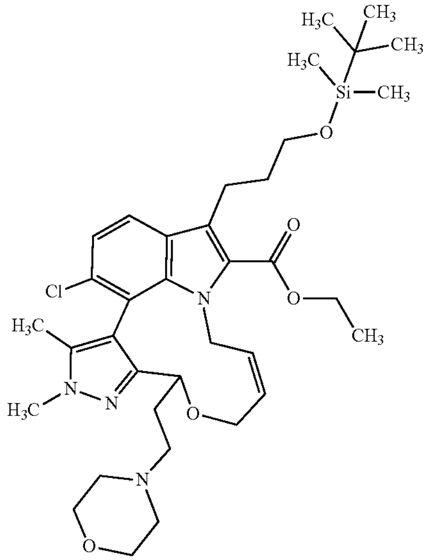 [SMILES: CCOC(=O)c1c(CCCO[Si](C)(C)C(C)(C)C)c2ccc(Cl)c3c2n1C/C=C\COC(CCN1CCOCC1)c1nn(C)c(C)c1-3]

To a mixture of (rac)-ethyl-3-(3-{[tert-butyl(dimethyl)silyl]oxy}propyl)-6-chloro-7-{3-[1-hydroxy-3-(morpholin-4-yl)propyl]-1,5-dimethyl-1H-pyrazol-4-yl}-1H-indole-2-carboxylate (mixture of stereoisomers; see Intermediate 45, 920 mg, 1.45 mmol) in acetonitrile (10 mL), cesium carbonate (2.37 g, 7.26 mmol) was added. After 10 minutes of stirring, (2Z)-1,4-dichlorobut-2-ene (CAS 1476-11-5, 310 μL, 2.91 mmol) and sodium iodide (435 mg, 2.91 mmol) were added, and the reaction mixture was stirred for 24 hours at 70° C. in a sealed tube. The reaction mixture was diluted with water and extracted with ethyl acetate. The combined organic layers were dried using a water resistant filter and were concentrated under reduced pressure. The crude material was purified by flash chromatography using silica gel (gradient dichloromethane/ethanol) to obtain the title compound (416 mg), which was formed as a racemic mixture of two enantiomers as only one of the two diastereomers formed in the preceding step underwent the macrocyclisation reaction.

LC-MS (Method 2): $R_t$=1.83 min; MS (ESIpos): m/z=685 $[M+H]^+$ $^1$H-NMR (400 MHz, DMSO-d6) δ[ppm]: −0.007 (0.69), 0.000 (11.03), 0.016 (1.39), 0.019 (1.54), 0.847 (16.00), 0.854 (2.77), 0.859 (2.87), 0.861 (2.62), 1.294 (1.30), 1.311 (2.70), 1.329 (1.27), 1.759 (0.53), 1.785 (3.98), 2.226 (0.57), 2.244 (0.47), 2.251 (1.33), 2.299 (0.42), 2.304 (0.53), 2.308 (0.42), 2.495 (1.29), 2.500 (0.92), 2.646 (0.42), 3.608 (0.61), 3.624 (1.11), 3.640 (1.03), 3.716 (0.42), 3.728 (0.47), 3.731

(0.47), 3.777 (0.41), 3.785 (1.96), 3.842 (3.00), 4.277 (0.61), 4.295 (0.75), 4.314 (0.57), 4.332 (0.44), 7.284 (0.53), 7.306 (0.54), 7.726 (0.68), 7.747 (0.60).

Intermediate 47

(rac)-ethyl-7-(3-{[tert-butyl(dimethyl)silyl]oxy}propyl)-4-chloro-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

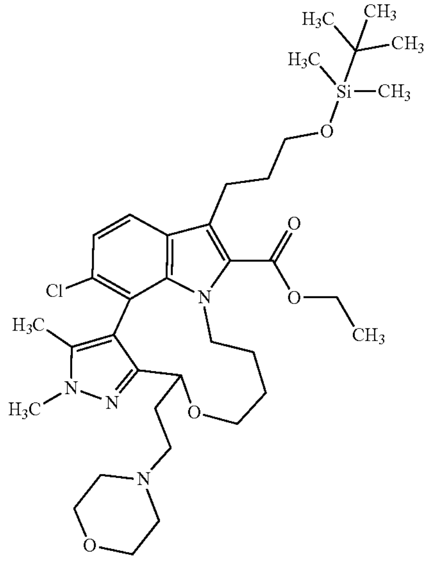 [SMILES: CCOC(=O)c1c(CCCO[Si](C)(C)C(C)(C)C)c2ccc(Cl)c3c2n1CCCCOC(CCN1CCOCC1)c1nn(C)c(C)c1-3]

To a solution of (rac)-ethyl-(11Z)-7-(3-{[tert-butyl(dimethyl)silyl]oxy}propyl)-4-chloro-2,3-dimethyl-15-[2-(morpholin-4-yl)ethyl]-2,10,13,15-tetrahydropyrazolo[4',3':9,10][1,6]oxazacycloundecino[8,7,6-hi]indole-8-carboxylate (see Intermediate 46, 420 mg) in ethanol (10 mL), tris(triphenylphosphine)rhodium(I) chloride (1.14 g, 1.23 mmol) was added, and the mixture was stirred under an atmosphere of hydrogen at rt for 6 hours. The catalyst was filtered off, and the filtrate was concentrated under reduced pressure. The crude material was purified by flash chromatography using silica gel (gradient dichloromethane/ethanol) to give the title compound (309 mg).

LC-MS (Method 2): $R_t$=1.87 min; MS (ESIpos): m/z=687 $[M+H]^+$ $^1$H-NMR (400 MHz, DMSO-d6) δ[ppm]: 0.848 (1.26), 0.855 (16.00), 1.297 (1.17), 1.315 (2.45), 1.332 (1.17), 1.768 (0.42), 1.805 (3.54), 2.275 (0.82), 2.311 (0.44), 2.315 (0.53), 2.320 (0.45), 2.506 (1.43), 2.511 (0.97), 2.657 (0.41), 3.484 (0.82), 3.608 (0.62), 3.822 (3.53), 4.263 (0.48), 4.280 (0.52), 4.320 (0.41), 5.747 (0.43), 7.275 (0.97), 7.297 (0.95), 7.714 (0.80), 7.735 (0.72).

Intermediate 48

(rac)-ethyl-4-chloro-7-(3-hydroxpropyl)-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

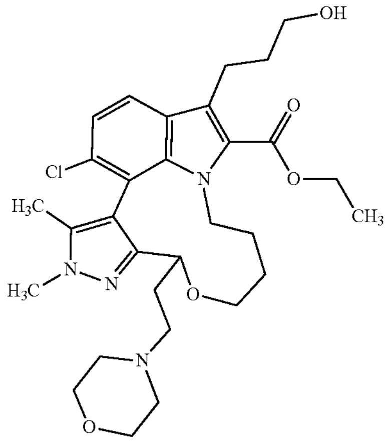 [SMILES: CCOC(=O)c1c(CCCO)c2ccc(Cl)c3c2n1CCCCOC(CCN1CCOCC1)c1nn(C)c(C)c1-3]

To a solution of (rac)-ethyl-7-(3-{[tert-butyl(dimethyl)silyl]oxy}propyl)-4-chloro-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 47, 305 mg) in tetrahydrofuran (7 mL) was added tetrabutylammonium fluoride solution (530 µL, 1.0 M in tetrahydrofuran, 530 µmol) dropwise at a temperature of 0° C. After complete addition, the mixture was allowed to warm to room temperature and stirring was continued for 4.5 hours. The mixture was concentrated under reduced pressure, the residue was diluted with a solution of hydrogen chloride (1 M) and water (pH 1-2) and was extracted with ethyl acetate. The combined organic layers were washed with brine, dried using a water resistant filter and concentrated under reduced pressure to give a first batch of crude material. Using an aqueous, saturated sodium bicarbonate solution the aqueous layer was adjusted to pH 3-4 and was extracted with ethyl acetate. The combined organic layers were dried using a water resistant filter and concentrated under reduced pressure to give a second batch of crude material. The combined batches of crude material were purified by flash chromatography using silica gel (gradient dichloromethane/ethanol) to give the title compound (204 mg).

LC-MS (Method 2): $R_t$=1.14 min; MS (ESIpos): m/z=573 $[M+H]^+$ $^1$H-NMR (400 MHz, DMSO-d6) δ[ppm]: 0.814 (0.44), 0.821 (0.44), 0.904 (0.56), 0.915 (5.99), 0.922 (0.94), 0.933 (16.00), 0.951 (7.43), 1.035 (0.47), 1.052 (0.70), 1.069 (0.68), 1.088 (0.44), 1.105 (0.44), 1.233 (0.65), 1.260 (0.65), 1.278 (1.82), 1.296 (3.20), 1.311 (4.32), 1.329 (6.46), 1.347 (2.88), 1.524 (0.65), 1.544 (1.50), 1.563 (1.91), 1.584 (1.32), 1.602 (0.56), 1.715 (0.59), 1.732 (0.85), 1.750 (0.68), 1.829 (5.43), 1.907 (0.91), 2.323 (0.85), 2.327 (1.09), 2.332 (0.88), 2.336 (0.53), 2.518 (4.14), 2.523 (2.67), 2.539 (1.09), 2.665 (0.65), 2.669 (0.88), 2.673 (0.65), 2.969 (0.41), 2.987 (0.59), 3.007 (0.47), 3.043 (0.53), 3.062 (0.65), 3.081 (0.41), 3.138 (2.35), 3.160 (2.03), 3.180 (2.23), 3.407 (0.59), 3.412 (0.59), 3.422 (1.03), 3.429 (0.94), 3.436 (1.00), 3.441 (1.03), 3.452 (0.65), 3.843 (5.52), 4.242 (0.59), 4.261 (0.68), 4.270 (1.03), 4.278 (0.41), 4.287 (1.06), 4.305 (0.47), 4.320 (0.41), 4.338 (0.91), 4.356 (0.85), 4.365 (0.56), 4.383 (0.53), 4.410 (0.47), 4.428 (0.82), 4.444 (0.44), 4.490 (0.62), 4.502 (1.35), 4.515 (0.62), 5.758 (2.67), 7.296 (1.67), 7.317 (1.79), 7.749 (1.35), 7.771 (1.23).

Intermediate 49

(rac)-ethyl-7-(3-bromopropyl)-4-chloro-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

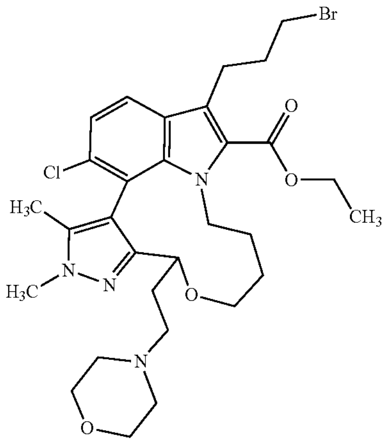 [SMILES: CCOC(=O)c1c(CCCBr)c2ccc(Cl)c3c2n1CCCCOC(CCN1CCOCC1)c1nn(C)c(C)c1-3]

To a solution of (rac)-ethyl-4-chloro-7-(3-hydroxypropyl)-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 48, 200 mg, 349 μmol) in dichloromethane (5 mL) was added triphenylphosphine (101 mg, 384 μmol) at a temperature of 0° C. After 10 minutes of stirring, tetrabromomethane (CAS 558-13-4, 127 mg, 384 μmol) was added and stirring was continued for 30 minutes. The reaction mixture was allowed to warm to rt and was purified by flash chromatography using silica gel (gradient dichloromethane/ethanol) to give the title compound (152 mg).

LC-MS (Method 1): $R_t$=1.14 min; MS (ESIpos): m/z=637 $[M+H]^+$ $^1$H-NMR (400 MHz, DMSO-d6) δ[ppm]: 0.913 (6.18), 0.932 (16.00), 0.950 (7.53), 1.034 (3.76), 1.051 (8.34), 1.069 (4.30), 1.085 (0.54), 1.259 (0.81), 1.277 (1.88), 1.295 (3.23), 1.314 (3.23), 1.319 (2.29), 1.323 (3.23), 1.332 (2.15), 1.337 (3.09), 1.341 (5.78), 1.355 (1.34), 1.359 (2.69), 1.522 (0.67), 1.543 (1.48), 1.562 (1.88), 1.581 (1.34), 1.600 (0.54), 1.836 (6.32), 2.035 (0.40), 2.102 (0.81), 2.120 (1.08), 2.138 (0.81), 2.156 (0.40), 2.318 (0.67), 2.322 (1.08), 2.327 (1.48), 2.331 (1.08), 2.336 (0.67), 2.518 (5.24), 2.523 (3.50), 2.660 (0.40), 2.665 (0.94), 2.669 (1.34), 2.673 (0.94), 3.017 (0.40), 3.053 (0.40), 3.073 (0.40), 3.088 (0.54), 3.107 (0.81), 3.136 (2.55), 3.163 (2.42), 3.178 (2.55), 3.197 (0.54), 3.404 (1.61), 3.416 (1.34), 3.421 (1.75), 3.433 (1.61), 3.438 (1.48), 3.451 (1.48), 3.455 (0.81), 3.468 (0.67), 3.527 (0.54), 3.544 (0.81), 3.551 (0.81), 3.568 (1.34), 3.590 (1.34), 3.606 (0.81), 3.615 (0.67), 3.669 (0.54), 3.691 (0.54), 3.847 (7.39), 3.906 (0.40), 3.922 (0.40), 3.941 (0.40), 4.269 (0.54), 4.287 (0.67), 4.291 (0.54), 4.296 (1.08), 4.308 (0.67), 4.314 (1.08), 4.332 (0.67), 4.351 (1.21), 4.359 (0.81), 4.370 (1.34), 4.379 (0.67), 4.384 (0.67), 4.396 (0.54), 4.411 (0.67), 4.429 (0.81), 4.445 (0.54), 7.324 (1.75), 7.345 (1.88), 7.547 (0.54), 7.550 (0.54), 7.555 (0.54), 7.565 (0.67), 7.573 (0.54), 7.590 (0.54), 7.594 (0.81), 7.610 (0.67), 7.614 (0.67), 7.620 (0.81), 7.627 (0.54), 7.640 (0.54), 7.788 (0.54), 7.798 (1.34), 7.810 (0.67), 7.819 (1.21).

Intermediate 50

(rac)-ethyl-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

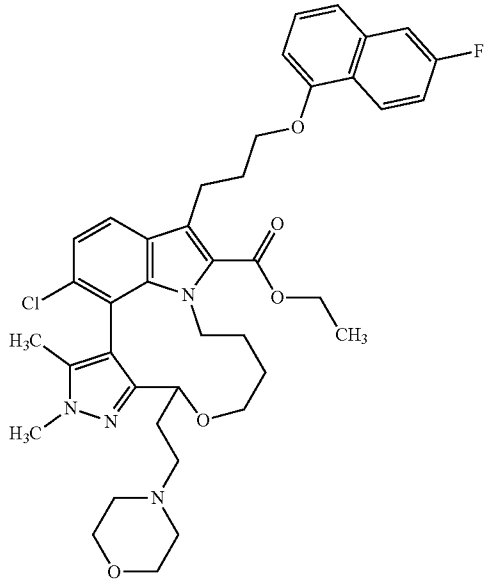 [SMILES: CCOC(=O)c1c(CCCOc2cccc3cc(F)ccc23)c2ccc(Cl)c3c2n1CCCCOC(CCN1CCOCC1)c1nn(C)c(C)c1-3]

To a solution of (rac)-ethyl-7-(3-bromopropyl)-4-chloro-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 49, 152 mg) in tetrahydrofuran (3 mL), cesium carbonate (467 mg, 1.43 mmol) and 6-fluoronaphthalen-1-ol (CAS 804498-72-4, 77.5 mg, 478 μmol) were added. The mixture was stirred at 55° C. overnight and was purified by flash chromatography using silica gel (gradient dichloromethane/ethanol) to give the title compound (96.7 mg).

LC-MS (Method 1): $R_t$=1.30 min; MS (ESIpos): m/z=717 $[M+H]^+$ $^1$H-NMR (400 MHz, DMSO-d6) δ[ppm]: 1.014 (0.95), 1.068 (0.46), 1.113 (0.54), 1.250 (5.33), 1.267 (10.74), 1.278 (1.13), 1.285 (5.15), 1.319 (0.41), 1.337 (0.85), 1.354 (0.44), 1.805 (14.92), 1.820 (1.41), 1.906 (0.51), 2.043 (1.36), 2.059 (1.36), 2.074 (0.72), 2.187 (1.00), 2.203 (1.44), 2.220 (1.10), 2.242 (0.77), 2.290 (4.56), 2.322 (1.95), 2.326 (2.23), 2.331 (1.92), 2.518 (6.41), 2.522 (3.90), 2.562 (2.15), 2.664 (1.10), 2.669 (1.51), 2.673 (1.10), 3.029 (0.62), 3.044 (0.67), 3.217 (0.54), 3.234 (0.72), 3.251 (1.03), 3.270 (1.03), 3.307 (2.49), 3.499 (4.26), 3.833 (16.00), 3.857 (0.62), 3.929 (0.67), 3.945 (0.72), 3.963 (0.77), 4.195 (1.87), 4.205 (2.18), 4.213 (2.69), 4.222 (2.59), 4.239 (2.05), 4.260 (1.44), 4.278 (2.31), 4.296 (2.21), 4.305 (1.26), 4.313 (0.67), 4.323 (0.97), 4.403 (0.95), 4.419 (1.62), 4.437 (0.95), 5.759 (6.74), 6.867 (1.31), 6.875 (1.36), 6.882 (1.21), 6.889 (1.38), 7.226 (3.74), 7.247 (3.87), 7.370 (0.82), 7.376 (0.97), 7.392 (1.36), 7.399

(1.49), 7.414 (1.08), 7.421 (1.08), 7.433 (2.59), 7.440 (2.85), 7.447 (5.90), 7.460 (0.41), 7.647 (1.59), 7.653 (1.62), 7.673 (1.56), 7.679 (1.56), 7.773 (3.44), 7.794 (3.13), 8.200 (1.36), 8.215 (1.44), 8.224 (1.38), 8.238 (1.33).

Intermediate 51 ethyl 7-bromo-6-chloro-3-{3-[(6-fluoronaphthalen-1-yl)oxy]propyl}-1H-indole-2-carboxylate

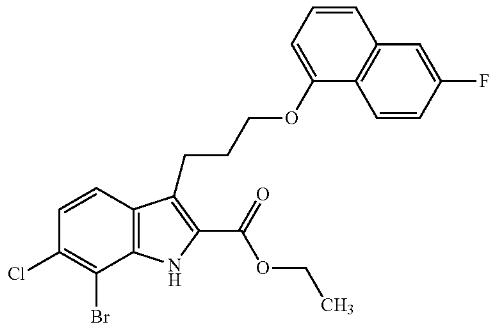 [SMILES: CCOC(=O)c1[nH]c2c(Br)c(Cl)ccc2c1CCCOc1cccc2cc(F)ccc12]

To a solution of triphenylphosphine (1.60 g, 6.10 mmol) in THF (20 mL), 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes, and ethyl 7-bromo-6-chloro-3-(3-hydroxypropyl)-1H-indole-2-carboxylate (see Intermediate 6, 2.00 g, 5.55 mmol), dissolved in THF (20 mL), was added dropwise. The mixture was allowed to warm to rt and was stirred overnight. The reaction mixture was concentrated under reduced pressure and the residue was triturated with methanol. The remaining solids were isolated by filtration.

In a second preparation, to a solution of triphenylphosphine (1.60 g, 6.10 mmol) in THF (20 mL), 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes and ethyl 7-bromo-6-chloro-3-(3-hydroxypropyl)-1H-indole-2-carboxylate (see Intermediate 6, 2.00 g, 5.55 mmol), dissolved in THF (20 mL), was added dropwise. The mixture was allowed to warm to rt and was stirred for 3 days. The reaction mixture was concentrated under reduced pressure and the residue was triturated with methanol. The remaining solids were isolated by filtration.

In a third preparation, to a solution of triphenylphosphine (1.60 g, 6.10 mmol) in THF (20 mL), 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes, and ethyl 7-bromo-6-chloro-3-(3-hydroxypropyl)-1H-indole-2-carboxylate (see Intermediate 6, 2.00 g, 5.55 mmol), dissolved in THF (20 mL), was added dropwise. The mixture was allowed to warm to rt and was stirred overnight. The reaction mixture was concentrated under reduced pressure and the residue was triturated with methanol. The remaining solids were isolated by filtration.

Combined with the products of the other preparations, the crude material was purified by flash chromatography using silica gel (hexane/ethyl acetate gradient). The obtained material was triturated with a mixture of tert.-butyl methyl ether and petroleum ether, and the remaining solids were isolated by filtration and dried to give the title compound (2.4 g). The filtrate was concentrated and triturated with methanol. The remaining solids were isolated by filtration and dried to give a second batch of the title compound (1.88 g).

LC-MS (Method 1): $R_t$=1.80 min; MS (ESIneg): m/z=502 $[M-H]^-$ $^1$H-NMR (400 MHz, DMSO-d6) δ[ppm]: 1.191 (0.89), 1.208 (1.68), 1.226 (0.79), 1.275 (7.17), 1.286 (1.82), 1.293 (16.00), 1.303 (2.45), 1.310 (7.38), 1.321 (1.00), 2.177 (1.63), 2.194 (2.33), 2.211 (1.65), 2.227 (0.56), 2.518 (5.40), 2.523 (3.59), 3.280 (2.10), 3.299 (3.61), 3.317 (2.70), 4.147 (2.35), 4.162 (4.59), 4.176 (2.33), 4.190 (0.84), 4.269 (2.24), 4.286 (7.10), 4.304 (6.99), 4.322 (2.10), 5.759 (0.86), 6.834 (1.79), 6.842 (1.91), 6.848 (1.61), 6.856 (1.91), 7.168 (5.12), 7.189 (5.66), 7.240 (0.68), 7.249 (0.72), 7.261 (0.61), 7.271 (0.61), 7.316 (1.23), 7.322 (1.37), 7.333 (1.19), 7.339 (2.17), 7.345 (2.33), 7.360 (1.21), 7.367 (1.37), 7.391 (0.51), 7.412 (3.59), 7.418 (3.89), 7.426 (8.20), 7.438 (0.54), 7.579 (0.51), 7.600 (0.49), 7.624 (2.17), 7.630 (2.17), 7.650 (2.14), 7.656 (2.07), 7.721 (4.87), 7.743 (4.59), 7.757 (0.58), 7.778 (0.47), 8.046 (1.89), 8.061 (1.98), 8.069 (1.91), 8.084 (1.82), 11.517 (3.28).

On larger scale the title compound could be obtained in a similar manner with slightly modified reaction conditions in two batches: To a stirred solution of ethyl 7-bromo-6-chloro-3-(3-hydroxypropyl)-1H-indole-2-carboxylate (see Intermediate 6, 2000 g) and N,N-diethylethanamine (1.77 kg) in dichloromethane (20.0 L) was added methanesulfonyl chloride (1.30 kg) dropwise over 3 hours at 0-5° C. under an atmosphere of nitrogen. After addition, the reaction mixture was stirred at 25° C. for 16 hours. The mixture was washed with water (8 L) and concentrated to give a brown solid (3.99 kg, crude). This material (697 g) was added to a stirred solution of 6-fluoronaphthalen-1-ol (CAS 804498-72-4, 214 g) and potassium carbonate (428 g) in acetonitrile (5400 mL) under an atmosphere of nitrogen, and the reaction mixture was stirred at 85° C. for 16 hours. The mixture was filtered, and the solution was concentrated. The residue was purified by silica gel chromatography (petrol ether/dichloromethane=3/1) to obtain a crude material, which was then slurried in petrol ether/dichloromethane (800/200 mL) at 20 C for 16 hours, and was filtered to obtain the title compound (262 g).

Intermediate 52 ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate

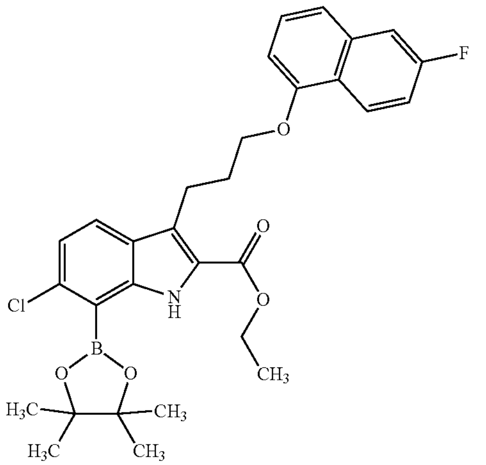 [SMILES: CCOC(=O)c1[nH]c2c(B3OC(C)(C)C(C)(C)O3)c(Cl)ccc2c1CCCOc1cccc2cc(F)ccc12]

To a solution of ethyl-7-bromo-6-chloro-3-{3-[(6-fluoronaphthalen-1-yl)oxy]propyl}-1H-indole-2-carboxylate (see Intermediate 51, 200 mg, 396 μmol) in DMF (3 mL), 4,4,4',4',5,5,5',5'-octamethyl-2,2'-bi-1,3,2-dioxaborolane (CAS 78183-34-3151 mg, 594 μmol), potassium acetate (117 mg, 1.19 mmol) and [1,1'-Bis(diphenylphosphino)ferrocene]dichloro-palladium(II) (32.4 mg, 39.6 μmol) were added. The mixture was purged with argon for 10 minutes. The tube was sealed and stirred at 95° C. for 12 hours. After cooling to rt the mixture was filtered and purified by preparative HPLC (Method P3) to give the title compound (34 mg, 12% yield).

LC-MS (Method 1): $R_t$=1.90 min; MS (ESIpos): m/z=552 $[M+H]^+$ $^1$H-NMR (400 MHz, DMSO-d6) δ[ppm]: 1.257 (2.02), 1.275 (4.69), 1.292 (2.08), 1.324 (2.13), 1.373 (2.56), 1.383 (16.00), 2.202 (0.58), 2.219 (0.41), 2.518 (1.69), 2.522 (1.13), 3.301 (0.50), 3.320 (1.26), 4.144 (0.54), 4.159 (1.11), 4.173 (0.52), 4.235 (0.54), 4.252 (1.83), 4.270 (1.80), 4.288 (0.51), 5.758 (0.73), 6.824 (0.49), 6.832 (0.50), 6.838 (0.42), 6.846 (0.53), 7.045 (1.22), 7.067 (1.18), 7.319 (0.49), 7.326 (0.53), 7.408 (0.98), 7.414 (1.04), 7.422 (2.36), 7.622 (0.57), 7.629 (0.58), 7.648 (0.58), 7.655 (0.57), 7.839 (0.81), 7.861 (0.72), 8.010 (0.44), 8.024 (0.47), 8.033 (0.47), 8.047 (0.45), 9.978 (0.64).

On larger scale the title compound could be obtained in a similar manner with slightly modified reaction conditions: To a stirred solution of 4,4,4',4',5,5,5',5'-octamethyl-2,2'-bi-1,3,2-dioxaborolane (CAS 78183-34-3151 mg, 91.7 g), sodium carbonate (76.6 g) and [1,1'-Bis(diphenylphosphino)ferrocene]dichloro-palladium(II) (4.40 g) in 1,4-dioxane (700 mL) was added ethyl-7-bromo-6-chloro-3-{3-[(6-fluoronaphthalen-1-yl)oxy]propyl}-1H-indole-2-carboxylate (see Intermediate 51, 70 g) under an atmosphere of nitrogen, and the reaction mixture was stirred at 100° C. for 40 hours. The residue was slurried in a mixture of ethanol and dichloromethane (300 and 50 mL) at 20° C. for 16 hours, then recrystallized in dichloromethane (80 mL) from 50° C. to 0° C. for 3 hours, and filtered to obtain the title compound (84.8 g). The filtrate was purified by silica gel column chromatography (petrol ether/ethyl acetate/dichloromethane=20/0/0-20/1/1) to obtain the title compound (21.2 g).

Intermediate 53

(rac)-ethyl-6-chloro-7-{5-ethyl-3-[1-hydroxy-3-(morpholin-4-yl)propyl]-1-methyl-1H-pyrazol-4-yl}-3-{3-[(6-fluoronaphthalen-1-yl)oxy]propyl}-1H-indole-2-carboxylate (Mixture of Stereoisomers)

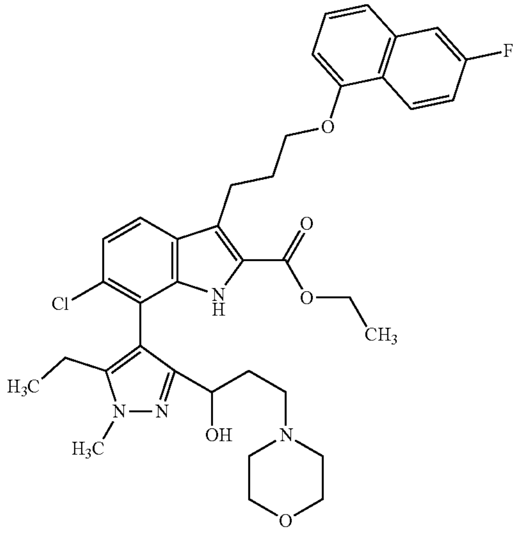 [SMILES: CCOC(=O)c1[nH]c2c(-c3c(C(O)CCN4CCOCC4)nn(C)c3CC)c(Cl)ccc2c1CCCOc1cccc2cc(F)ccc12]

To a solution of ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52; 2.41 g, 4.36 mmol) and (rac)-1-(4-bromo-5-ethyl-1-methyl-1H-pyrazol-3-yl)-3-(morpholin-4-yl)propan-1-ol (see Intermediate 24, 1.45 g, 4.36 mmol) in a mixture of 1,4-dioxane (30 mL) and water (10 mL) was added potassium triphosphate (1.85 g, 8.73 mmol), and the mixture was purged with argon for 10 minutes. RuPhos Pd G3 (183 mg, 218 μmol) was added, and the mixture was stirred for 30 minutes at 110° C. in a microwave reactor. The reaction mixture was purified by flash chromatography using silica gel (gradient dichloromethane/ethanol) to obtain the title compound (875 mg), which was formed as a mixture of two racemic diastereomers as a result of atropisomerism at the newly formed bi-heteroaryl bond.

LC-MS (Method 2): $R_t$=1.65 min; MS (ESIneg): m/z=675 $[M-H]^-$ $^1$H-NMR (400 MHz, DMSO-d6) δ[ppm]: 0.832 (0.18), 0.852 (0.87), 0.871 (1.34), 0.889 (0.55), 1.035 (0.19), 1.053 (0.39), 1.066 (16.00), 1.156 (2.35), 1.190 (0.27), 1.230 (0.90), 1.247 (1.95), 1.265 (0.92), 1.988 (0.18), 2.144 (0.47), 2.157 (0.43), 2.173 (0.31), 2.192 (0.34), 2.213 (0.29), 2.233 (0.26), 2.251 (0.21), 2.323 (0.17), 2.327 (0.23), 2.332 (0.17), 2.347 (0.24), 2.365 (0.36), 2.373 (0.26), 2.384 (0.25), 2.393 (0.24), 2.523 (0.42), 2.669 (0.17), 3.297 (0.25), 3.318 (0.49), 3.382 (0.48), 3.394 (0.50), 3.404 (0.27), 3.815 (0.88), 3.817 (0.96), 3.839 (2.47), 3.938 (2.62), 4.207 (0.36), 4.219 (0.59), 4.240 (0.75), 4.258 (0.65), 4.275 (0.20), 4.862 (0.20), 4.874 (0.19), 6.885 (0.22), 6.893 (0.23), 6.899 (0.20), 6.907 (0.21), 7.157 (0.55), 7.169 (0.21), 7.178 (0.56), 7.190 (0.21), 7.386 (0.17), 7.401 (0.26), 7.407 (0.28), 7.424 (0.17), 7.430 (0.20), 7.438 (0.48), 7.444 (0.56), 7.452 (1.12), 7.650 (0.30), 7.656

(0.31), 7.676 (0.31), 7.682 (0.31), 7.696 (0.44), 7.717 (0.40), 8.247 (0.20), 8.262 (0.28), 8.270 (0.22), 8.285 (0.26), 10.711 (0.49).

Intermediate 54

(rac)-ethyl-(11Z)-4-chloro-3-ethyl-7-{3-[(6-fluoronaphthalen-1-yl)oxy]propyl}-2-methyl-15-[2-(morpholin-4-yl)ethyl]-2,10,13,15-tetrahydropyrazolo[4',3':9,10][1,6]oxazacycloundecino[8,7,6-hi]indole-8-carboxylate

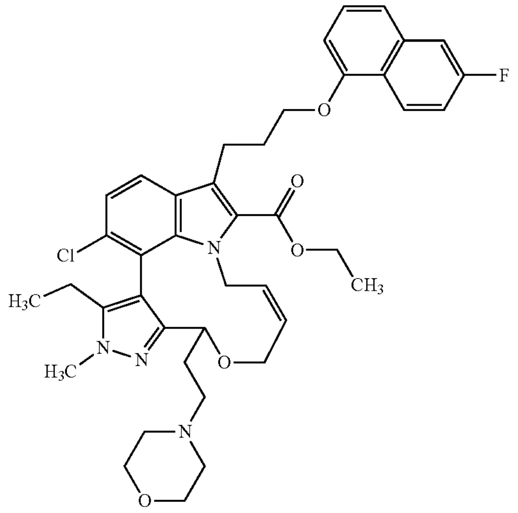 [SMILES: CCOC(=O)c1c(CCCOc2cccc3cc(F)ccc23)c2ccc(Cl)c3c2n1C/C=C\COC(CCN1CCOCC1)c1nn(C)c(CC)c1-3]

To a mixture of (rac)-ethyl-6-chloro-7-{5-ethyl-3-[1-hydroxy-3-(morpholin-4-yl)propyl]-1-methyl-1H-pyrazol-4-yl}-3-{3-[(6-fluoronaphthalen-1-yl)oxy]propyl}-1H-indole-2-carboxylate (mixture of stereoisomers, see Intermediate 53; 875 mg) in acetonitrile (80 mL), cesium carbonate (2.10 g, 6.46 mmol), sodium iodide (387 mg, 2.58 mmol) and (2Z)-1,4-dichlorobut-2-ene (CAS 1476-11-5, 200 μL, 1.94 mmol) were added. The reaction mixture was stirred for 2 days at 65° C. The mixture was filtered and concentrated, and the residue was dissolved in ethyl acetate and washed with water. The organic layer was dried over sodium sulfate, filtered and concentrated under reduced pressure to obtain the title compound (850 mg), which was formed as a racemic mixture of two enantiomers as only one of the two diastereomers formed in the preceding step underwent the macrocyclisation reaction. The crude material was used without further purification in the next step.

LC-MS (Method 2): $R_t$=1.71 min; MS (ESIpos): m/z=729 $[M+H]^+$ $^1$H-NMR (400 MHz, DMSO-d6) δ[ppm]: 0.778 (0.67), 0.797 (1.45), 0.816 (0.71), 0.846 (3.14), 0.861 (0.17), 1.065 (16.00), 1.135 (0.19), 1.155 (1.43), 1.171 (0.41), 1.189 (0.41), 1.208 (0.22), 1.219 (0.19), 1.239 (0.22), 1.251 (1.11), 1.269 (2.19), 1.287 (1.09), 1.899 (0.24), 1.906 (0.24), 1.919 (0.24), 1.986 (0.29), 2.123 (0.24), 2.141 (0.31), 2.159 (0.52), 2.171 (0.57), 2.178 (0.60), 2.190 (0.71), 2.208 (0.69), 2.237 (0.73), 2.272 (0.40), 2.322 (0.50), 2.327 (0.59), 2.331 (0.45), 2.349 (0.26), 2.363 (0.26), 2.382 (0.19), 2.518 (2.04), 2.523 (1.24), 2.632 (0.17), 2.669 (0.50), 2.673 (0.36), 3.276 (0.36), 3.395 (0.59), 3.407 (0.52), 3.420 (0.43), 3.511 (0.28), 3.523 (0.31), 3.534 (0.26), 3.555 (0.16), 3.565 (0.17), 3.637 (0.17), 3.650 (0.19), 3.669 (0.24), 3.681 (0.24), 3.714 (0.40), 3.780 (0.31), 3.791 (0.22), 3.814 (0.83), 3.845 (0.26), 3.850 (0.26), 3.877 (0.76), 3.888 (3.16), 3.903 (0.43), 3.916 (0.31), 3.943 (0.52), 4.198 (0.24), 4.216 (0.67), 4.226 (0.62), 4.234 (1.05), 4.243 (0.78), 4.260 (0.59), 4.281 (0.55), 4.298 (0.55), 4.308 (0.40), 4.325 (0.19), 4.396 (0.19), 4.695 (0.16), 4.722 (0.17), 4.888 (0.24), 4.927 (0.17), 4.948 (0.17), 4.975 (0.24), 5.757 (0.52), 6.879 (0.31), 6.886 (0.36), 6.894 (0.33), 6.901 (0.38), 7.257 (0.71), 7.279 (0.74), 7.335 (0.17), 7.359 (0.26), 7.365 (0.28), 7.381 (0.35), 7.388 (0.38), 7.403 (0.29), 7.410 (0.31), 7.436 (0.66), 7.443 (1.00), 7.451 (1.49), 7.650 (0.38), 7.657 (0.43), 7.667 (0.17), 7.676 (0.38), 7.683 (0.40), 7.804 (0.64), 7.826 (0.57), 8.203 (0.26), 8.217 (0.29), 8.225 (0.29), 8.241 (0.28).

Intermediate 55

(rac)-ethyl-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

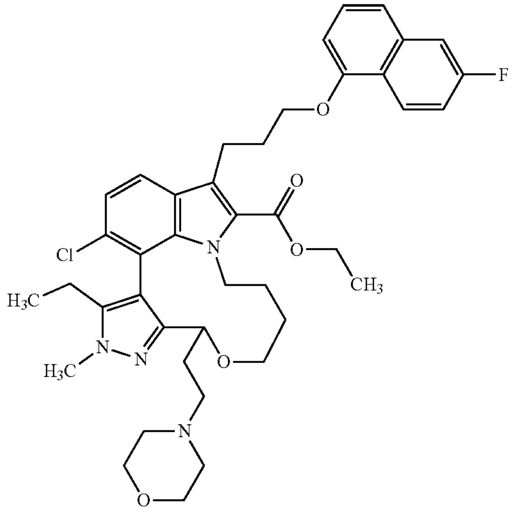 [SMILES: CCOC(=O)c1c(CCCOc2cccc3cc(F)ccc23)c2ccc(Cl)c3c2n1CCCCOC(CCN1CCOCC1)c1nn(C)c(CC)c1-3]

To a solution of (rac)-ethyl-(11Z)-4-chloro-3-ethyl-7-{3-[(6-fluoronaphthalen-1-yl)oxy]propyl}-2-methyl-15-[2-(morpholin-4-yl)ethyl]-2,10,13,15-tetrahydropyrazolo[4',3':9,10][1,6]oxazacycloundecino[8,7,6-hi]indole-8-carboxylate (see Intermediate 54, 850 mg) in a mixture of ethanol (30 mL) and THF (10 mL) was added tris(triphenylphosphine)rhodium(I) chloride (541 mg, 583 μmol). The mixture was stirred under an atmosphere of hydrogen at room temperature for 5 h. The catalyst was filtered off, and the filtrate was purified by flash chromatography using silica gel (gradient dichloromethane/ethanol) to give the title compound (412 mg).

LC-MS (Method 2): $R_t$=1.74 min; MS (ESIpos): m/z=731 $[M+H]^+$ $^1$H-NMR (400 MHz, DMSO-d6) δ[ppm]: 0.788 (1.29), 0.797 (0.53), 0.807 (2.83), 0.826 (1.33), 1.035 (2.00), 1.052 (3.43), 1.065 (16.00), 1.070 (3.24), 1.248 (2.10), 1.266 (3.96), 1.284 (1.93), 1.907 (0.94), 2.052 (0.54), 2.069 (0.64), 2.178 (0.90), 2.185 (0.99), 2.197 (1.08), 2.204 (1.19), 2.298 (1.26), 2.322 (1.13), 2.326 (1.26), 2.331 (1.02), 2.522 (2.19), 2.664 (0.51), 2.668 (0.68), 2.673 (0.51), 3.255 (0.53), 3.274 (0.62), 3.292 (0.80), 3.422 (0.73), 3.435 (0.79), 3.439 (0.79), 3.452 (0.78), 3.507 (1.56), 3.861 (5.65), 3.939 (2.77), 4.195 (0.92), 4.204 (1.01), 4.213 (1.24), 4.222 (1.19), 4.240 (0.93), 4.262 (0.49), 4.279 (0.77), 4.297 (0.62), 4.306 (0.41), 4.345 (0.50), 4.358 (0.89), 4.370 (0.46), 4.426 (0.65), 6.860 (0.53), 6.866 (0.57), 6.875 (0.53), 6.881 (0.60), 7.225 (1.35), 7.246 (1.35), 7.370 (0.41), 7.377 (0.46), 7.393 (0.66), 7.400 (0.72), 7.409 (0.42), 7.415 (0.50), 7.422 (0.58), 7.430 (1.11), 7.440 (1.35), 7.445 (2.42), 7.646 (0.70), 7.653 (0.72), 7.672 (0.68), 7.679 (0.68), 7.771 (1.23), 7.792 (1.11), 8.205 (0.51), 8.220 (0.55), 8.229 (0.55), 8.243 (0.54).

Intermediate 56

(rac)-1-(4-bromo-1,5-dimethyl-1H-pyrazol-3-yl)propan-1-ol

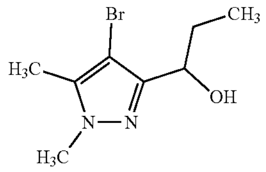

4-Bromo-1,5-dimethyl-1H-pyrazole-3-carbaldehyde (see Intermediate 13, 3.00 g) was dissolved in 15 mL of THF and cooled to 4° C. A solution of bromido(ethyl)magnesium in THF (CAS 925-90-6, 30 mL, 1.0 M, 30 mmol) was added dropwise into the reaction mixture. After complete addition the mixture was stirred under cooling for 20 minutes and for additional 20 hours at it Saturated aqueous ammonium chloride solution was added to the reaction mixture, which was extracted with ethyl acetate. The combined organic layers were washed with brine, dried using a water resistant filter and concentrated under reduced pressure. The crude material was purified by flash chromatography using silica gel (gradient hexane/ethyl acetate) to give 423 mg of the title compound.

LC-MS (Method 2): $R_t$=0.86 min; MS (ESIpos): m/z=233 $[M+H]^+$ $^1$H-NMR (400 MHz, DMSO-d6) δ[ppm]: 0.786 (2.83), 0.804 (6.64), 0.822 (3.03), 1.699 (0.48), 1.717 (1.84), 1.735 (2.49), 1.753 (1.60), 2.198 (14.63), 2.518 (0.59), 2.522 (0.40), 3.719 (16.00), 4.342 (0.44), 4.355 (0.53), 4.359 (0.97), 4.373 (0.99), 4.377 (0.50), 4.390 (0.45), 4.915 (2.50), 4.928 (2.43).

Intermediate 57

(rac)-ethyl-6-chloro-7-{3-[1-hydroxypropyl]-1,5-dimethyl-1H-pyrazol-4-yl}-3-{3-[(naphthalen-1-yl)oxy]propyl}-1H-indole-2-carboxylate (Mixture of Stereoisomers)

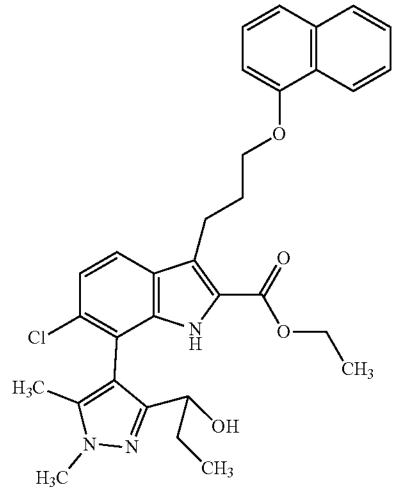 [SMILES: CCOC(=O)c1[nH]c2c(-c3c(C(O)CC)nn(C)c3C)c(Cl)ccc2c1CCCOc1cccc2ccccc12]

A solution of ethyl-6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 8, 437 mg), (rac)-1-(4-bromo-1,5-dimethyl-1H-pyrazol-3-yl)propan-1-ol (see Intermediate 56, 210 mg) and potassium triphosphate (348 mg, 1.64 mmol) in 5 mL of 1,4-dioxane and 2 mL of water was purged with argon for 5 minutes. RuPhos Pd G3 (37.7 mg, 45.0 μmol) was added and again it was purged with argon for 5 minutes. The reaction mixture was stirred for 20 minutes at 110° C. in a microwave reactor. The mixture was diluted with water and extracted with ethyl acetate. The combined organic layers were dried using a water resistant filter and concentrated. The crude material was purified by flash chromatography using silica gel (gradient dichloromethane/ethanol) to obtain the title compound (341 mg), which was formed as a mixture of two racemic diastereomers as a result of atropisomerism at the newly formed bi-heteroaryl bond.

LC-MS (Method 2): $R_t$=1.67 min; MS (ESIpos): m/z=560 $[M+H]^+$ $^1$H-NMR (400 MHz, DMSO-d6) δ[ppm]: 0.598 (0.51), 0.617 (1.22), 0.635 (0.56), 0.713 (1.62), 0.731 (3.78), 0.750 (1.71), 0.786 (1.43), 0.791 (0.40), 0.805 (3.33), 0.810 (0.80), 0.823 (1.59), 0.828 (0.40), 0.901 (0.41), 1.053 (0.48), 1.066 (16.00), 1.088 (0.48), 1.156 (0.64), 1.242 (2.97), 1.259 (6.31), 1.277 (2.98), 1.718 (1.22), 1.736 (1.63), 1.754 (1.06), 1.801 (0.53), 1.818 (0.45), 1.941 (2.85), 1.988 (8.16), 2.065 (0.54), 2.192 (1.53), 2.197 (8.19), 2.215 (0.95), 2.231 (0.69), 2.332 (0.43), 2.518 (2.62), 2.522 (1.67), 2.673 (0.43), 3.307 (0.99), 3.627 (1.35), 3.719 (7.90), 3.786 (2.87), 3.815 (8.14), 3.938 (2.65), 3.969 (0.75), 3.982 (0.76), 4.200 (0.96), 4.216 (2.03), 4.226 (1.36), 4.237 (1.23), 4.244 (2.53), 4.254 (0.98), 4.262 (2.43), 4.280 (0.77), 4.360 (0.57), 4.373 (0.59), 4.915 (1.55), 4.927 (1.46), 5.050 (1.89), 5.063 (1.79), 5.477 (0.57), 5.485 (0.58), 6.914 (0.97), 6.931 (1.06), 7.163 (2.13), 7.170 (0.79), 7.185 (2.16), 7.192 (0.80), 7.377 (0.77), 7.398 (1.45), 7.417 (1.17), 7.454 (1.87), 7.475 (1.03), 7.504 (0.97), 7.508 (0.93), 7.514 (1.11), 7.521 (2.18), 7.528 (1.11), 7.533 (1.06), 7.538 (1.13), 7.551 (0.44), 7.687 (0.53), 7.696 (1.48), 7.710 (0.52), 7.718 (1.35), 7.861 (1.06), 7.868 (0.61), 7.879 (1.06), 7.884 (0.93), 8.212 (0.71), 8.217 (0.71), 8.229 (0.58), 8.234 (0.87), 10.730 (0.48), 10.802 (1.44).

Intermediate 58

(rac)-ethyl (11Z)-4-chloro-15-ethyl-2,3-dimethyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate

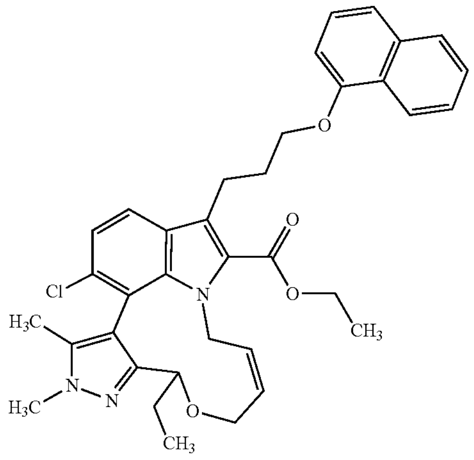 [SMILES: CCOC(=O)c1c(CCCOc2cccc3ccccc23)c2ccc(Cl)c3c2n1C/C=C\COC(CC)c1nn(C)c(C)c1-3]

To a mixture of (rac)-ethyl-6-chloro-7-{3-[1-hydroxypropyl]-1,5-dimethyl-1H-pyrazol-4-yl}-3-{3-[(naphthalen-1-yl)oxy]propyl}-1H-indole-2-carboxylate (mixture of stereoisomers, see Intermediate 57, 660 mg) in acetonitrile (8 mL), cesium carbonate (1.82 g, 5.60 mmol) was added. After 10 minutes of stirring, (2Z)-1,4-dichlorobut-2-ene (CAS 1476-11-5, 240 μL, 2.2 mmol) and sodium iodide (336 mg, 2.24 mmol) were added, and the reaction mixture was stirred for 21 hours at 70° C. in a sealed tube. The reaction mixture was diluted with water and extracted with ethyl acetate. The combined organic layers were dried using a water resistant filter and were concentrated under reduced pressure. The crude material was purified by flash chromatography using silica gel (gradient dichloromethane/ethanol) to obtain the title compound (516 mg), which was formed as a racemic mixture of two enantiomers as only one of the two diastereomers formed in the preceding step underwent the macrocyclisation reaction.

LC-MS (Method 2): $R_t$=1.80 min; MS (ESIpos): m/z=612 $[M+H]^+$ $^1$H-NMR (400 MHz, DMSO-d6) δ[ppm]: 0.786 (1.34), 0.804 (2.95), 0.822 (1.46), 0.859 (2.80), 0.877 (6.54), 0.895 (2.95), 0.901 (0.88), 0.929 (1.40), 0.944 (2.01), 0.952 (1.03), 0.957 (0.97), 0.971 (0.97), 1.019 (0.82), 1.038 (1.70), 1.056 (0.97), 1.070 (0.52), 1.087 (1.43), 1.102 (1.28), 1.231 (0.88), 1.245 (1.03), 1.249 (1.37), 1.258 (5.41), 1.266 (1.16), 1.276 (10.89), 1.293 (5.05), 1.717 (1.00), 1.735 (1.43), 1.744 (1.03), 1.754 (1.43), 1.762 (1.43), 1.782 (16.00), 1.800 (0.97), 1.817 (0.46), 1.947 (0.79), 1.958 (0.79), 1.978 (0.43), 1.995 (1.03), 2.017 (0.49), 2.052 (1.13), 2.065 (0.55), 2.197 (7.36), 2.213 (1.73), 2.230 (1.86), 2.268 (2.07), 2.332 (1.00), 2.518 (6.69), 2.522 (4.35), 2.673 (1.00), 2.868 (0.97), 2.886 (1.10), 2.905 (0.70), 2.924 (0.40), 3.186 (0.64), 3.200 (0.52), 3.276 (0.91), 3.294 (1.28), 3.359 (0.91), 3.658 (0.55), 3.670 (0.67), 3.690 (0.91), 3.703 (0.82), 3.719 (6.66), 3.789 (1.06), 3.800 (3.35), 3.817 (1.34), 3.859 (15.27), 3.917 (0.61), 3.929 (0.88), 3.934 (0.91), 3.940 (0.64), 3.946 (0.76), 3.951 (2.10), 4.071 (1.06), 4.082 (1.16), 4.092 (1.31), 4.102 (1.06), 4.203 (1.00), 4.221 (1.86), 4.230 (2.56), 4.239 (2.49), 4.247 (3.80), 4.260 (1.79), 4.266 (2.56), 4.285 (2.10), 4.295 (0.67), 4.303 (1.76), 4.312 (1.13), 4.320 (0.64), 4.330 (0.97), 4.360 (0.55), 4.373 (0.58), 4.691 (0.52), 4.717 (0.61), 4.732 (0.76), 4.758 (0.85), 4.900 (1.00), 4.915 (1.64), 4.927 (1.49), 4.938 (0.70), 4.997 (0.55), 5.023 (0.94), 5.050 (0.55), 5.185 (0.49), 5.197 (0.67), 5.214 (0.70), 5.226 (1.10), 6.471 (0.46), 6.920 (1.92), 6.937 (1.95), 7.204 (0.67), 7.209 (0.55), 7.225 (0.55), 7.230 (0.43), 7.260 (3.92), 7.282 (3.83), 7.379 (1.49), 7.400 (2.74), 7.418 (2.25), 7.454 (3.04), 7.475 (2.10), 7.491 (1.61), 7.495 (1.55), 7.509 (2.77), 7.514 (3.35), 7.522 (1.52), 7.528 (2.46), 7.532 (2.56), 7.545 (1.16), 7.549 (0.88), 7.804 (3.50), 7.826 (3.10), 7.860 (2.01), 7.879 (2.19), 7.883 (1.83), 8.164 (1.25), 8.168 (1.37), 8.186 (1.31), 8.237 (0.43).

Intermediate 59

(rac)-ethyl-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

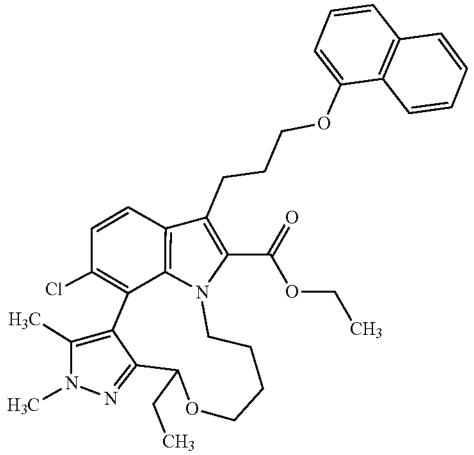 [SMILES: CCOC(=O)c1c(CCCOc2cccc3ccccc23)c2ccc(Cl)c3c2n1CCCCOC(CC)c1nn(C)c(C)c1-3]

To a solution of (rac)-ethyl-(11Z)-4-chloro-15-ethyl-2,3-dimethyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate (see Intermediate 58, 514 mg) in a mixture of ethanol (6 mL) and THF (3 mL), tris(triphenylphosphine)rhodium(I) chloride (935 mg, 1.01 mmol) was added, and the mixture was stirred under an atmosphere of hydrogen at rt for 6 hours. The catalyst was filtered off, and the filtrate was concentrated under reduced pressure. The crude material was purified by flash chromatography using silica gel (gradient dichloromethane/ethanol) to give the title compound (349 mg).

LC-MS (Method 2): $R_t$=1.82 min; MS (ESIpos): m/z=614 $[M+H]^+$ $^1$H-NMR (400 MHz, DMSO-d6) δ[ppm]: 0.736 (0.42), 0.785 (0.42), 0.845 (2.92), 0.863 (6.71), 0.882 (3.03), 0.931 (0.53), 0.950 (1.25), 0.959 (0.99), 0.968 (1.52), 0.974 (1.10), 0.986 (0.95), 1.019 (0.42), 1.038 (0.57), 1.154 (1.40), 1.171 (2.27), 1.190 (1.14), 1.244 (1.02), 1.253 (5.69), 1.271 (11.53), 1.289 (5.35), 1.805 (15.62), 1.863 (0.42), 1.879

(0.95), 1.896 (1.59), 1.907 (0.83), 1.914 (1.44), 1.931 (0.95), 1.947 (0.42), 1.987 (3.91), 2.000 (0.80), 2.018 (0.42), 2.047 (0.80), 2.208 (1.36), 2.223 (1.02), 2.270 (0.45), 2.332 (0.95), 2.336 (0.42), 2.518 (5.73), 2.522 (3.64), 2.673 (0.95), 2.678 (0.42), 3.027 (0.42), 3.038 (0.53), 3.054 (0.57), 3.221 (0.49), 3.256 (1.55), 3.274 (1.10), 3.284 (0.87), 3.299 (1.14), 3.372 (0.42), 3.800 (0.76), 3.831 (16.00), 3.923 (0.42), 3.942 (0.49), 3.951 (1.10), 3.955 (1.06), 3.964 (0.61), 3.981 (0.68), 3.999 (0.99), 4.017 (1.21), 4.034 (0.91), 4.115 (1.02), 4.133 (2.05), 4.151 (1.06), 4.180 (0.83), 4.188 (0.99), 4.198 (2.20), 4.204 (1.97), 4.215 (2.46), 4.225 (2.58), 4.242 (2.24), 4.260 (1.40), 4.281 (2.20), 4.299 (1.93), 4.308 (1.29), 4.317 (0.57), 4.326 (1.02), 6.890 (1.82), 6.907 (2.01), 7.201 (0.53), 7.225 (4.32), 7.246 (4.40), 7.369 (1.67), 7.389 (3.00), 7.408 (2.54), 7.430 (0.49), 7.449 (3.18), 7.469 (1.93), 7.482 (0.95), 7.485 (1.06), 7.499 (2.05), 7.502 (1.90), 7.510 (2.16), 7.516 (3.75), 7.523 (2.27), 7.530 (2.12), 7.534 (2.27), 7.547 (1.55), 7.551 (1.06), 7.565 (0.76), 7.572 (0.68), 7.591 (0.57), 7.595 (0.83), 7.612 (0.76), 7.621 (0.83), 7.625 (0.80), 7.641 (0.53), 7.645 (0.53), 7.778 (3.72), 7.799 (3.37), 7.858 (1.78), 7.865 (1.10), 7.876 (1.86), 7.881 (1.52), 8.176 (1.36), 8.181 (1.33), 8.201 (1.33).

Intermediate 60 ethyl-3-(4-bromo-1,5-dimethyl-1H-pyrazol-3-yl)-3-oxopropanoate

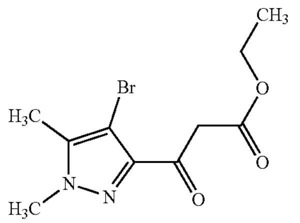 [SMILES: CCOC(=O)CC(=O)c1nn(C)c(C)c1Br]

Ethyl-4-bromo-1,5-dimethyl-1H-pyrazole-3-carboxylate (see Intermediate 11, 10.0 g) was dissolved in THF (300 mL), ethyl acetate (20 mL, 200 mmol) was added and the mixture was cooled to −30° C. A solution of lithium trimethyl-N-(trimethylsilyl)silanaminide in THF (100 mL, 1.0 M, 100 mmol) was added dropwise into the reaction mixture. After complete addition the mixture was allowed to warm to 0° C. in 1 hour. A saturated aqueous ammonium chloride solution was added and the resulting mixture was extracted with ethyl acetate. The combined organic layers were dried using sodium sulfate, filtered and concentrated under reduced pressure. The crude material was purified by flash chromatography using silica gel (gradient hexane/ethyl acetate) to give 7.00 g of the title compound.

LC-MS (Method 1): $R_t$=1.03 min; MS (ESIneg): m/z=289 $[M+H]^+$ $^1$H-NMR (400 MHz, DMSO-d6) δ[ppm]: 1.145 (4.45), 1.163 (9.35), 1.181 (4.47), 2.263 (14.47), 2.509 (0.62), 2.514 (0.41), 3.874 (16.00), 3.945 (10.64), 4.056 (1.31), 4.073 (4.03), 4.091 (4.02), 4.109 (1.30).

Intermediate 61

(rac)-1-(4-bromo-1,5-dimethyl-1H-pyrazol-3-yl)propane-1,3-diol

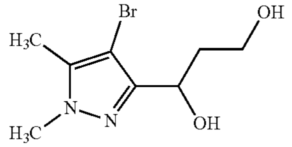

Ethyl-3-(4-bromo-1,5-dimethyl-1H-pyrazol-3-yl)-3-oxopropanoate (see Intermediate 60, 7.00 g) was dissolved in methanol (250 mL), and sodium borohydride (7.33 g, 194 mmol) was added portionwise. The mixture was stirred under reflux overnight, cooled to room temperature and then concentrated under reduced pressure. Ethyl acetate was added and the mixture was washed with water. The aqueous phase was extracted with THF. The combined organic layers were dried using sodium sulfate, filtered and concentrated under reduced pressure. The crude material was purified by flash chromatography using silica gel (gradient dichloromethane/ethanol) to give 4.45 g of the title compound.

LC-MS (Method 1): $R_t$=0.64 min; MS (ESIpos): m/z=251 $[M+H]^+$ $^1$H-NMR (400 MHz, DMSO-d6) δ[ppm]: 1.052 (0.63), 1.791 (0.44), 1.807 (0.65), 1.824 (0.83), 1.838 (0.75), 1.907 (0.71), 1.912 (0.43), 1.922 (0.51), 1.928 (0.79), 1.942 (0.63), 1.961 (0.42), 2.197 (16.00), 3.337 (15.39), 3.412 (0.69), 3.426 (0.95), 3.439 (1.20), 3.454 (1.20), 3.468 (0.83), 3.484 (0.50), 4.359 (1.59), 4.372 (2.89), 4.384 (1.28), 4.599 (0.56), 4.612 (1.17), 4.621 (0.73), 4.626 (0.74), 4.634 (1.18), 4.647 (0.58), 4.892 (3.02), 4.906 (2.72).

Intermediate 62

(rac)-1-(4-bromo-1,5-dimethyl-1H-pyrazol-3-yl)-3-{[tert-butyl(dimethyl)silyl]oxy}propan-1-ol

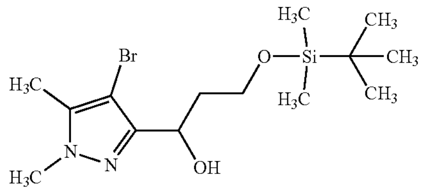 [SMILES: Cc1c(Br)c(C(O)CCO[Si](C)(C)C(C)(C)C)nn1C]

A solution of (rac)-1-(4-bromo-1,5-dimethyl-1H-pyrazol-3-yl)propane-1,3-diol (see Intermediate 61, 4.45 g) in DMF (100 mL) was cooled to 0° C., and tert-butyl(chloro)dimethylsilane (CAS 18162-48-6, 2.96 g, 19.7 mmol) and 1H-imidazole (1.82 g, 26.8 mmol) were added. The ice bath was removed and the mixture was stirred at room temperature overnight. Water was added and the reaction mixture was extracted with dichloromethane. The organic layer was washed with brine, dried over sodium sulfate, filtered and concentrated under reduced pressure. The residue was triturated with pentane, the solvent was dencanted and the remaining material was concentrated under reduced pressure to give 5.70 g of the title compound.

LC-MS (Method 2): $R_t$=1.42 min; MS (ESIpos): m/z=363 $[M+H]^+$ $^1$H-NMR (400 MHz, DMSO-d6) δ[ppm]: 0.000 (4.63), 0.011 (4.56), 0.844 (0.74), 0.852 (16.00), 0.859 (0.80), 1.170 (0.44), 1.985 (0.86), 2.194 (4.58), 3.715 (5.41), 4.906 (0.65), 4.919 (0.60).

Intermediate 63

(rac)-ethyl 7-{3-[3-{[tert-butyl(dimethyl)silyl]oxy}-1-hydroxpropyl]-1,5-dimethyl-1H-pyrazol-4-yl}-6-chloro-3-{3-[(naphthalen-1-yl)oxy]propyl}-1H-indole-2-carboxylate (Mixture of Stereoisomers)

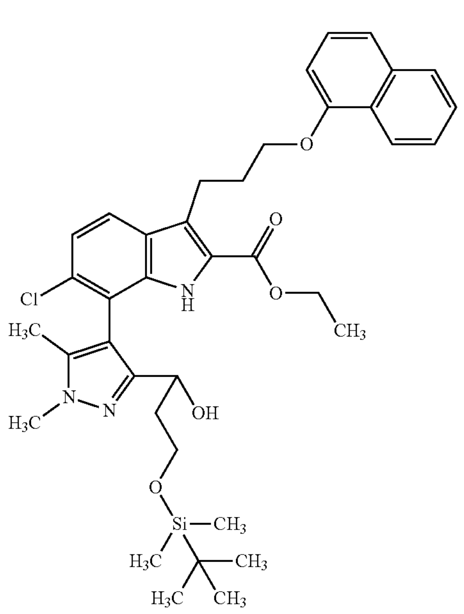 [SMILES: CCOC(=O)c1[nH]c2c(-c3c(C(O)CCO[Si](C)(C)C(C)(C)C)nn(C)c3C)c(Cl)ccc2c1CCCOc1cccc2ccccc12]

A solution of ethyl-6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 8, 1.00 g, 1.87 mmol), (rac)-1-(4-bromo-1,5-dimethyl-1H-pyrazol-3-yl)-3-{[tert-butyl(dimethyl)silyl]oxy}propan-1-ol (see Intermediate 62, 749 mg, 2.06 mmol), potassium triphosphate (795 mg, 3.75 mmol) and RuPhos Pd G3 (78.3 mg, 93.7 μmol) in a mixture of 15 mL of 1,4-dioxane and 5.0 mL of water was stirred for 1 hour at 110° C. in a microwave reactor. The reaction mixture was purified by flash chromatography using silica gel (gradient dichloromethane/ethyl acetate) to obtain the title compound (650 mg), which was formed as a mixture of two racemic diastereomers as a result of atropisomerism at the newly formed bi-heteroaryl bond.

LC-MS (Method 1): $R_t$=1.87 min; MS (ESIpos): m/z=690 $[M+H]^+$ $^1$H-NMR (400 MHz, DMSO-d6) δ[ppm]: −0.201 (1.61), −0.196 (1.64), −0.179 (5.26), 0.000 (5.09), 0.011 (4.99), 0.620 (10.99), 0.691 (4.71), 0.852 (16.00), 0.859 (0.97), 1.152 (0.62), 1.170 (1.25), 1.188 (0.61), 1.245 (1.01), 1.262 (2.15), 1.280 (1.02), 1.921 (0.45), 1.939 (1.36), 1.986 (2.40), 2.005 (2.71), 2.194 (5.29), 2.516 (1.41), 2.521 (0.89), 3.312 (0.85), 3.427 (0.43), 3.593 (0.49), 3.715 (5.53), 3.780 (1.20), 3.812 (2.81), 4.016 (0.53), 4.033 (0.53), 4.205 (0.63), 4.215 (0.41), 4.222 (0.48), 4.224 (0.48), 4.242 (0.92), 4.260 (0.92), 6.916 (0.41), 7.138 (0.70), 7.160 (0.76), 7.391 (0.63), 7.410 (0.47), 7.450 (0.71), 7.470 (0.40), 7.510 (0.42), 7.517 (0.77), 7.530 (0.40), 7.534 (0.42), 7.680 (0.58), 7.701 (0.53), 7.858 (0.42), 7.876 (0.41), 10.815 (0.52).

Intermediate 64

(rac)-ethyl-(11Z)-15-(2-{[tert-butyl(dimethyl)silyl]oxy}ethyl)-4-chloro-2,3-dimethyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate

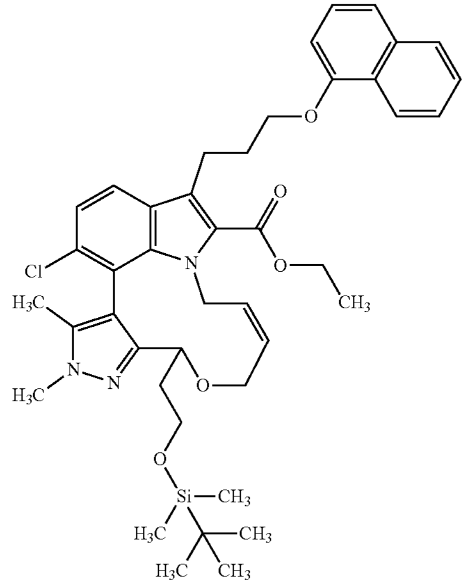 [SMILES: CCOC(=O)c1c(CCCOc2cccc3ccccc23)c2ccc(Cl)c3c2n1C/C=C\COC(CCO[Si](C)(C)C(C)(C)C)c1nn(C)c(C)c1-3]

To a mixture of (rac)-ethyl-7-{3-[3-{[tert-butyl(dimethyl)silyl]oxy}-1-hydroxpropyl]-1,5-dimethyl-1H-pyrazol-4-yl}-6-chloro-3-{3-[(naphthalen-1-yl)oxy]propyl}-1H-indole-2-carboxylate (mixture of stereoisomers, see Intermediate 63, 650 mg) in acetonitrile (20 mL), cesium carbonate (1.53 g, 4.71 mmol), (2Z)-1,4-dichlorobut-2-ene (CAS 1476-11-5, 150 μL, 1.4 mmol) and sodium iodide (282 mg, 1.88 mmol) were added, and the reaction mixture was stirred for 72 hours at 70° C. The reaction mixture was filtered and concentrated under reduced pressure. The crude material was purified by flash chromatography using silica gel (gradient dichloromethane/ethanol) to obtain the title compound (397 mg), which was formed as a racemic mixture of two enantiomers as only one of the two diastereomers formed in the preceding step underwent the macrocyclisation reaction.

LC-MS (Method 1): $R_t$=1.95 min; MS (ESIpos): m/z=742 $[M+H]^+$ $^1$H-NMR (400 MHz, DMSO-d6) δ[ppm]: −0.181 (2.91), −0.171 (2.97), −0.011 (4.65), 0.000 (4.70), 0.518 (8.72), 0.696 (0.47), 0.834 (0.87), 0.841 (16.00), 0.847 (0.89), 1.142 (1.05), 1.160 (2.26), 1.177 (1.15), 1.255 (0.70), 1.272 (1.51), 1.290 (0.71), 1.791 (2.29), 1.975 (3.92), 2.183 (4.89), 2.505 (1.45), 2.510 (0.90), 3.567 (0.40), 3.582 (0.54), 3.704 (5.10), 3.844 (2.31), 4.004 (0.81), 4.022 (0.78), 4.895 (0.72), 4.909 (0.57), 7.201 (0.59), 7.223 (0.59), 7.443 (0.42), 7.505 (0.48), 7.760 (0.50), 7.781 (0.46).

Intermediate 65

(rac)-ethyl-15-(2-{[tert-butyl(dimethyl)silyl]oxy}ethyl)-4-chloro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

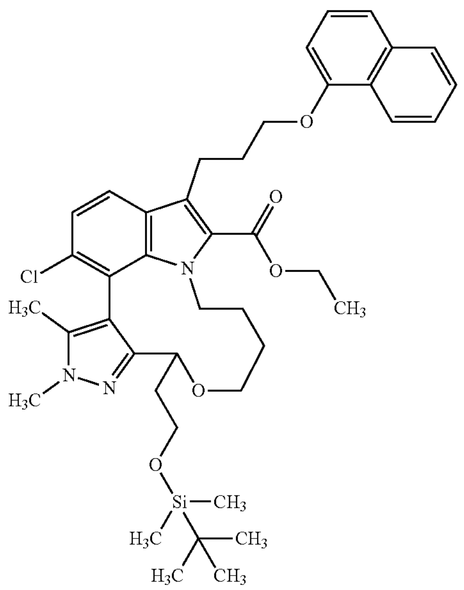 [SMILES: CCOC(=O)c1c(CCCOc2cccc3ccccc23)c2ccc(Cl)c3c2n1CCCCOC(CCO[Si](C)(C)C(C)(C)C)c1nn(C)c(C)c1-3]

To a solution of (rac)-ethyl-(11Z)-15-(2-{[tert-butyl(dimethyl)silyl]oxy}ethyl)-4-chloro-2,3-dimethyl-7-{3-[(naphthalen-1-yl)oxy]propyl}-2,10,13,15-tetrahydropyrazolo[4',3':9,10]-[1,6]oxazacycloundecino[8,7,6-hi]indole-8-carboxylate (see Intermediate 64, 390 mg, 525 μmol) in a mixture of ethanol (30 mL) and THF (10 mL), tris(triphenylphosphine)rhodium(I) chloride (244 mg, 263 μmol) was added, and the mixture was stirred at rt under an atmosphere of hydrogen for 7 hours and under an atmosphere of argon overnight. The mixture was stirred at rt for two additional days under an atmosphere of hydrogen during daytime for 7 hours and under an atmosphere of argon overnight. The catalyst was filtered off, and the filtrate was concentrated under reduced pressure. The crude material was purified by flash chromatography using silica gel (gradient hexane/ethyl acetate) to give the title compound (287 mg).

$^1$H-NMR (400 MHz, DMSO-d6) δ[ppm]: −0.082 (4.87), −0.058 (4.87), 0.000 (2.64), 0.011 (2.58), 0.710 (0.89), 0.717 (16.00), 0.724 (0.86), 0.844 (0.51), 0.852 (8.87), 0.859 (0.50), 1.153 (2.46), 1.170 (4.90), 1.188 (2.39), 1.255 (1.19), 1.273 (2.62), 1.291 (1.19), 1.823 (3.62), 1.985 (7.84), 2.194 (2.86), 2.516 (2.30), 2.521 (1.50), 3.715 (2.98), 3.833 (3.74), 3.998 (0.72), 4.016 (1.87), 4.033 (1.81), 4.051 (0.59), 4.195 (0.40), 4.201 (0.44), 4.206 (0.41), 4.229 (0.47), 4.246 (0.44), 4.281 (0.45), 4.298 (0.47), 4.906 (0.49), 4.919 (0.44), 6.882 (0.43), 6.900 (0.46), 7.188 (0.92), 7.210 (0.99), 7.384 (0.64), 7.403 (0.52), 7.448 (0.65), 7.503 (0.40), 7.512 (0.48), 7.519 (0.86), 7.527 (0.47), 7.531 (0.41), 7.536 (0.44), 7.762 (0.84), 7.783 (0.76).

Intermediate 66

(rac)-ethyl-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

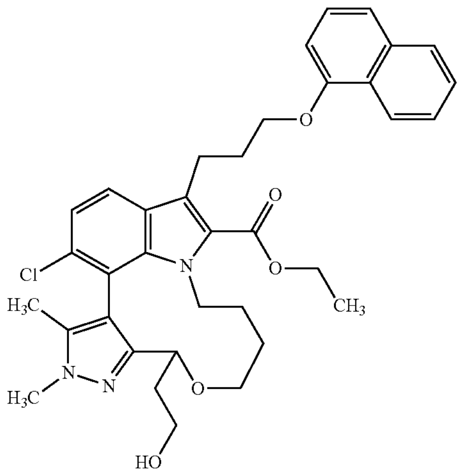 [SMILES: CCOC(=O)c1c(CCCOc2cccc3ccccc23)c2ccc(Cl)c3c2n1CCCCOC(CCO)c1nn(C)c(C)c1-3]

(rac)-Ethyl-15-(2-{[tert-butyl(dimethyl)silyl]oxy}ethyl)-4-chloro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 65, 285 mg, 383 μmol) was dissolved in THF (20 mL) and a solution of tetrabutylammonium fluoride in THF (420 μL, 1.0 M, 420 μmol) was added. After stirring at room temperature overnight again a solution of tetrabutylammonium fluoride in THF (200 μL, 1.0 M) was added and stirring was continued for 2 days. The reaction mixture was purified by flash chromatography using silica gel (gradient dichloromethane/ethanol) to give the title compound (176 mg).

LC-MS (Method 2): $R_t$=1.59 min; MS (ESIpos): m/z=630 $[M+H]^+$ $^1$H-NMR (400 MHz, DMSO-d6) δ[ppm]: −0.025 (0.72), 0.000 (0.70), 0.775 (2.28), 1.018 (0.51), 1.048 (0.60), 1.065 (0.77), 1.091 (1.33), 1.109 (2.11), 1.127 (1.25), 1.145 (0.42), 1.167 (0.44), 1.186 (0.47), 1.204 (0.40), 1.288 (1.07), 1.309 (5.46), 1.327 (11.12), 1.344 (5.21), 1.859 (15.46), 1.881 (0.63), 2.044 (0.40), 2.059 (0.67), 2.079 (0.89), 2.093 (0.74), 2.111 (0.40), 2.122 (0.47), 2.130 (0.68), 2.151 (0.79), 2.165 (0.60), 2.242 (0.88), 2.258 (1.26), 2.275 (0.93), 2.574 (3.82), 2.579 (2.82), 3.059 (0.42), 3.070 (0.56), 3.085 (0.58), 3.093 (0.47), 3.277 (0.47), 3.293 (0.67), 3.310 (1.02), 3.330 (1.04), 3.341 (0.82), 3.357 (1.04), 3.403 (0.88), 3.479 (0.74), 3.482 (0.89), 3.491 (1.05), 3.496 (2.26), 3.509 (1.84), 3.513 (1.89), 3.527 (0.93), 3.887 (16.00), 3.996 (0.61), 4.014 (0.70), 4.032 (0.74), 4.236 (0.70), 4.245 (0.96), 4.254 (1.96), 4.260 (1.95), 4.264 (1.98), 4.272 (1.91), 4.281 (2.47), 4.290 (0.72), 4.299 (1.93), 4.318 (1.35), 4.337 (2.23), 4.346 (0.56), 4.354 (2.21), 4.363 (1.16), 4.372 (0.67), 4.381 (1.00), 4.399 (0.49), 4.410 (1.49), 4.423 (3.42), 4.436 (1.33), 4.505 (1.00), 4.518 (1.11), 4.526 (1.21), 4.540 (0.93), 5.814 (0.58), 6.949 (1.82), 6.968 (2.00), 7.275 (4.12), 7.297 (4.16), 7.428 (1.40), 7.448 (2.60), 7.467 (2.16), 7.508 (2.81), 7.529 (1.54), 7.546 (0.44), 7.550 (0.67), 7.563 (1.72), 7.567 (1.65), 7.571 (1.98), 7.579 (3.68), 7.587 (2.11), 7.591 (1.77), 7.595 (1.88), 7.600 (0.42), 7.608 (0.88), 7.612 (0.60), 7.621 (0.44), 7.652 (0.58), 7.669

(0.46), 7.678 (0.54), 7.681 (0.56), 7.828 (3.44), 7.848 (3.16), 7.916 (1.63), 7.924 (0.82), 7.934 (1.37), 7.940 (1.32), 8.253 (1.39), 8.259 (1.26), 8.270 (0.68), 8.277 (1.23).

Intermediate 67

(rac)-1-(4-Bromo-5-ethyl-1-methyl-1H-pyrazol-3-yl)-2,2,2-trifluoroethan-1-ol

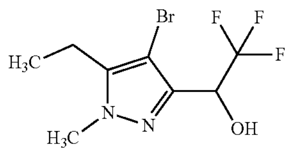

4-Bromo-5-ethyl-1-methyl-1H-pyrazole-3-carbaldehyde (see Intermediate 21, 3.00 g, 13.8 mmol) was dissolved in 50 mL THF and trimethyl(trifluoromethyl)silane (CAS 81290-20-2, 12 mL, 2.0 M, 25 mmol) and tetra-n-butylammonium fluoride (690 μl, 1.0 M, 690 μmol) were added at 0° C. The reaction mixture was stirred at rt over night. A further portion of tetra-n-butylammonium fluoride (1.1 mL, 1.0 M, 1.1 mmol) was added and the mixture was stirred for 30 minutes at rt. Aqueous ammonium chloride solution was added and the mixture was extracted with ethyl acetate. The organic layer was dried with sodium sulfate, filtered and concentrated under reduced pressure. The crude product was purified by column chromatography to provide the title compound in 83% purity: 3.32 g.

LC-MS (Method 1): $R_t$=0.03 min; MS (ESIpos): m/z=288 $[M+H]^+$ $^1$H-NMR (400 MHz, DMSO-d6) δ[ppm]: 0.068 (1.24), 1.069 (2.98), 1.076 (0.72), 1.081 (0.64), 1.088 (7.02), 1.107 (3.00), 2.098 (0.56), 2.508 (1.16), 2.513 (0.76), 2.632 (0.91), 2.651 (2.94), 2.659 (0.49), 2.670 (2.73), 2.689 (0.77), 3.750 (0.99), 3.773 (0.56), 3.809 (16.00), 4.968 (0.70), 4.984 (0.83), 4.987 (0.74), 5.003 (0.69), 6.730 (2.40), 6.747 (2.47).

Intermediate 68

(rac)-Ethyl 6-chloro-7-{5-ethyl-1-methyl-3-[(2,2,2-trifluoro-1-hydroxyethyl]-1H-pyrazol-4-yl}-3-{3-[(naphthalen-1-yl)oxy]propyl}-1H-indole-2-carboxylate

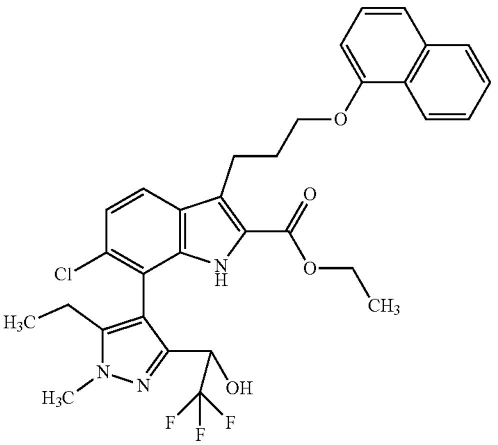 [SMILES: CCOC(=O)c1[nH]c2c(-c3c(C(O)C(F)(F)F)nn(C)c3CC)c(Cl)ccc2c1CCCOc1cccc2ccccc12]

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 8, 2.00 g, 3.75 mmol) and (rac)-1-(4-bromo-5-ethyl-1-methyl-1H-pyrazol-3-yl)-2,2,2-trifluoroethan-1-ol (see Intermediate 67, 1.18 g) were coupled as described for the preparation of Intermediate 34 to provide the title compound in 70% purity: 2.3 g, which was formed as a mixture of two racemic diastereomers as a result of atropisomerism at the newly formed bi-heteroaryl bond.

LC-MS (Method 1): $R_t$=1.68 min; MS (ESIpos): m/z=614 $[M+H]^+$ $^1$H-NMR (400 MHz, DMSO-d6) δ[ppm]: 0.776 (0.62), 0.782 (0.61), 0.801 (1.22), 0.805 (0.46), 0.820 (0.55), 0.824 (0.52), 0.957 (3.25), 0.975 (6.25), 0.988 (16.00), 0.992 (4.24), 1.000 (1.59), 1.019 (3.53), 1.038 (1.56), 1.077 (1.38), 1.095 (0.81), 1.114 (0.41), 1.162 (0.59), 1.167 (0.87), 1.180 (1.16), 1.185 (1.72), 1.197 (0.59), 1.203 (0.80), 1.987 (0.59), 2.440 (0.68), 2.445 (0.48), 2.564 (0.45), 2.582 (1.44), 2.601 (1.35), 3.243 (0.53), 3.327 (0.51), 3.340 (0.56), 3.345 (1.55), 3.357 (1.59), 3.362 (1.54), 3.375 (1.58), 3.379 (0.50), 3.392 (0.48), 3.487 (7.42), 3.621 (1.54), 3.741 (7.63), 3.752 (0.51), 3.787 (1.15), 3.808 (2.27), 3.861 (2.87), 4.141 (0.43), 4.148 (0.57), 4.166 (0.45), 4.173 (0.41), 4.184 (0.72), 4.201 (0.66), 4.267 (1.08), 4.279 (2.09), 4.292 (1.07), 4.917 (0.43), 5.680 (1.59), 6.150 (0.56), 6.165 (0.54), 6.662 (1.43), 6.679 (1.38), 7.102 (0.62), 7.123 (0.60), 7.321 (0.45), 7.379 (0.60), 7.439 (0.63), 7.448 (0.78), 7.458 (0.66), 7.463 (0.43), 10.673 (0.41).

Intermediate 69

(rac)-Ethyl (11Z)-4-chloro-3-ethyl-2-methyl-7-{3-[(naphthalen-1-yl)oxy]propyl}-15-(trifluoromethyl)-2,10,13,15-tetrahydropyrazolo[4',3':9,10][1,6]oxazacycloundecino[8,7,6-hi]indole-8-carboxylate

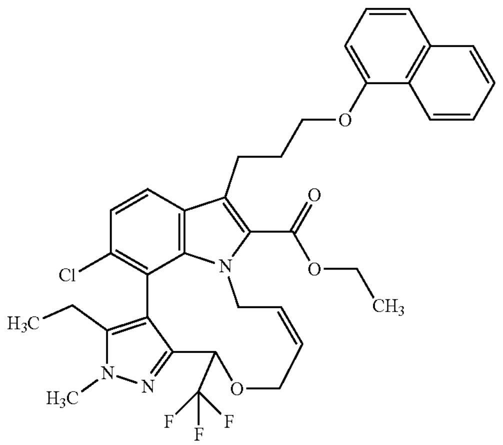 [SMILES: CCOC(=O)c1c(CCCOc2cccc3ccccc23)c2ccc(Cl)c3c2n1C/C=C\COC(C(F)(F)F)c1nn(C)c(CC)c1-3]

(rac)-Ethyl 6-chloro-7-{5-ethyl-1-methyl-3-[2,2,2-trifluoro-1-hydroxyethyl]-1H-pyrazol-4-yl}-3-{3-[(naphthalen-1-yl)oxy]propyl}-1H-indole-2-carboxylate (see Intermediate 68, 2.30 g, 3.75 mmol) was reacted in analogy to the preparation of Intermediate 35 to provide the title compound in 65% purity: 1.64 g, which was formed as a racemic mixture of two enantiomers as only one of the two diastereomers formed in the preceding step underwent the macrocyclisation reaction.

LC-MS (Method 1): $R_t$=1.81 min; MS (ESIpos): m/z=666 $[M+H]^+$ $^1$H-NMR (400 MHz, DMSO-d6) δ[ppm]: 0.794 (0.78), 0.813 (1.82), 0.832 (0.83), 0.872 (0.42), 0.928 (0.53), 0.944 (0.57), 1.065 (16.00), 1.078 (1.90), 1.087 (1.07), 1.097 (3.87), 1.108 (0.80), 1.115 (1.82), 1.154 (0.68), 1.169 (0.45), 1.173 (1.13), 1.192 (0.60), 1.229 (0.47), 1.237 (0.45), 1.255 (0.53), 1.262 (1.33), 1.270 (0.63), 1.279 (2.52), 1.288 (0.40), 1.297 (1.18), 2.183 (0.55), 2.201 (0.57), 2.220 (0.57), 2.240 (0.60), 2.258 (0.50), 2.322 (0.40), 2.326 (0.50), 2.518 (2.22), 2.522 (1.40), 2.641 (0.55), 2.660 (1.65), 2.668 (0.77), 2.673 (0.70), 2.679 (1.55), 2.698 (0.48), 3.296 (0.45), 3.314 (0.98), 3.698 (1.73), 3.759 (0.55), 3.771 (0.48), 3.818 (6.38), 3.822 (2.35), 3.824 (2.32), 3.833 (1.30), 3.839 (0.80), 3.856 (0.52), 3.860 (0.48), 3.888 (0.87), 3.903 (0.42), 3.912 (0.92), 3.941 (2.62), 3.960 (3.67), 4.215 (0.40), 4.231 (0.72), 4.246 (0.95), 4.254 (0.77), 4.261 (0.50), 4.272 (0.58), 4.286 (0.67), 4.304 (0.47), 4.994 (0.50), 4.997 (0.52), 5.013 (0.40), 5.758 (0.45), 6.743 (1.05), 6.759 (1.13), 6.905 (0.50), 6.924 (0.53), 7.293 (0.85), 7.314 (0.92), 7.392 (0.72), 7.411 (0.60), 7.445 (0.82), 7.455 (0.78), 7.466 (0.53), 7.472 (0.55), 7.476 (0.57), 7.488 (0.43), 7.491 (0.47), 7.509 (0.63), 7.511 (0.63), 7.525 (0.52), 7.528 (0.50), 7.853 (0.52), 7.870 (1.17), 7.891 (0.75).

Intermediate 70

(rac)-Ethyl-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylate

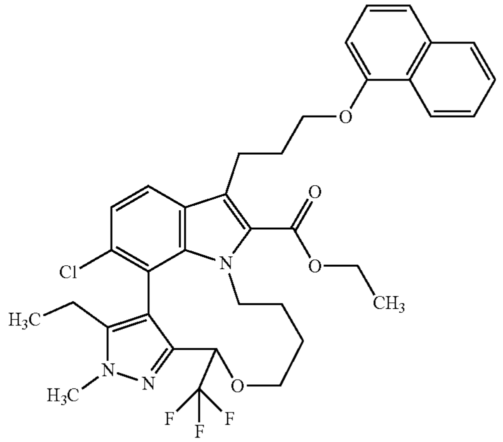 [SMILES: CCOC(=O)c1c(CCCOc2cccc3ccccc23)c2ccc(Cl)c3c2n1CCCCOC(C(F)(F)F)c1nn(C)c(CC)c1-3]

(rac)-Ethyl (11Z)-4-chloro-3-ethyl-2-methyl-7-{3-[(naphthalen-1-yl)oxy]propyl}-15-(trifluoromethyl)-2,10,13,15-tetrahydropyrazolo[4',3':9,10][1,6]oxazacycloundecino[8,7,6-hi]indole-8-carboxylate (see Intermediate 69, 1.64 g, 2.46 mmol) was reacted in analogy to the preparation of Intermediate 55 to provide the title compound in 51% purity: 1.72 g.

LC-MS (Method 1): $R_t$=1.82 min; MS (ESIpos): m/z=668 $[M+H]^+$ $^1$H-NMR (400 MHz, DMSO-d6) δ[ppm]: 0.760 (0.57), 0.779 (0.49), 0.793 (2.16), 0.812 (4.89), 0.821 (1.48), 0.830 (2.50), 0.867 (0.64), 0.883 (1.36), 0.888 (0.91), 0.901 (2.20), 0.920 (1.36), 0.929 (1.52), 0.944 (1.63), 0.958 (0.64), 0.977 (0.49), 0.991 (0.61), 1.009 (0.61), 1.035 (2.84), 1.053 (4.82), 1.066 (1.93), 1.070 (3.37), 1.078 (4.32), 1.088 (2.46), 1.097 (8.95), 1.116 (4.28), 1.154 (1.18), 1.159 (0.80), 1.173 (1.90), 1.176 (1.18), 1.192 (1.25), 1.228 (2.43), 1.242 (1.44), 1.246 (1.33), 1.254 (3.83), 1.259 (2.16), 1.264 (1.59), 1.272 (7.13), 1.289 (3.79), 1.549 (0.80), 1.906 (1.67), 2.065 (2.05), 2.181 (0.80), 2.199 (1.36), 2.217 (2.05), 2.236 (1.67), 2.322 (0.99), 2.327 (1.29), 2.332 (0.99), 2.418 (0.53), 2.437 (0.57), 2.455 (0.49), 2.518 (5.54), 2.523 (3.49), 2.590 (0.57), 2.609 (0.61), 2.627 (0.45), 2.641 (1.33), 2.660 (3.98), 2.669 (2.05), 2.673 (1.59), 2.679 (3.64), 2.698 (1.06), 3.223 (0.45), 3.240 (0.57), 3.256 (0.76), 3.273 (0.95), 3.294 (1.14), 3.365 (0.80), 3.374 (0.76), 3.381 (0.42), 3.390 (0.72), 3.405 (0.76), 3.418 (0.87), 3.422 (1.36), 3.435 (1.33), 3.440 (1.40), 3.452 (1.36), 3.457 (0.72), 3.470 (0.76), 3.502 (0.64), 3.698 (2.27), 3.715 (0.72), 3.719 (0.53), 3.760 (0.61), 3.793 (0.80), 3.819 (16.00), 3.826 (6.75), 3.833 (2.54), 3.850 (1.71), 3.856 (1.06), 3.869 (0.80), 3.889 (1.93), 3.910 (9.97), 4.140 (0.49), 4.157 (0.49), 4.202 (1.97), 4.211 (2.09), 4.219 (1.97), 4.229 (1.93), 4.246 (1.44), 4.264 (0.61), 4.270 (0.53), 4.289 (1.36), 4.302 (0.91), 4.306 (1.25), 4.315 (0.87), 4.324 (0.61), 4.333 (0.87), 4.346 (0.91), 4.359 (1.40), 4.371 (0.76), 4.665 (0.72), 4.683 (0.68), 4.959 (0.68), 4.978 (1.02), 4.995 (0.99), 5.014 (0.68), 5.758 (4.40), 6.655 (0.42), 6.742 (2.35), 6.758 (2.39), 6.874 (1.21), 6.891 (1.40), 6.906 (0.49), 7.170 (0.49), 7.192 (0.57), 7.218 (0.42), 7.228 (0.49), 7.238 (0.42), 7.278 (2.46), 7.300 (2.43), 7.362 (1.21), 7.382 (2.16), 7.401 (1.93), 7.441 (2.12), 7.454 (1.29), 7.462 (1.90), 7.480 (1.67), 7.483 (1.55), 7.499 (2.27), 7.504 (2.31), 7.516 (1.67), 7.525 (3.26), 7.528 (3.26), 7.533 (2.88), 7.536 (3.37), 7.540 (2.73), 7.544 (4.63), 7.546 (5.99), 7.549 (5.76), 7.554 (5.16), 7.558 (4.40), 7.565 (6.52), 7.572 (5.73), 7.591 (4.70), 7.596 (8.15), 7.601 (2.12), 7.606 (3.26), 7.608 (4.44), 7.612 (6.90), 7.622 (7.73), 7.625 (8.68), 7.629 (4.70), 7.638 (2.84), 7.642 (4.74), 7.645 (4.63), 7.648 (1.93), 7.726 (0.42), 7.747 (0.42), 7.855 (3.07), 7.871 (1.44), 7.876 (2.77), 8.133 (0.87), 8.137 (0.91), 8.156 (0.83).

Intermediate 71

(rac)-(4-Bromo-1,5-dimethyl-1H-pyrazol-3-yl)(cyclopropyl)methanol

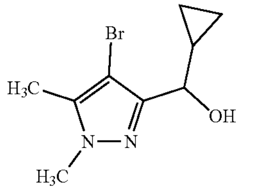

4-Bromo-1,5-dimethyl-1H-pyrazole-3-carbaldehyde (see Intermediate 13, 2.80 g, 13.8 mmol) and bromido(cyclopropyl)magnesium (55 mL, 0.50 M, 28 mmol) were reacted in analogy to the preparation of Intermediate 56 to provide the title compound in 96% purity: 2.30 g.

LC-MS (Method 2): $R_t$=0.85 min; MS (ESIpos): m/z=245 $[M+H]^+$ $^1$H-NMR (400 MHz, DMSO-d6) δ[ppm]: 0.022 (0.85), 0.036 (0.81), 0.044 (0.48), 0.229 (0.49), 0.231 (0.53), 0.244 (1.72), 0.251 (0.69), 0.259 (1.41), 0.263 (1.14), 0.269 (0.54), 0.272 (0.65), 0.282 (0.49), 0.368 (0.46), 0.373 (0.58), 0.382 (0.53), 0.388 (0.42), 0.393 (0.72), 0.400 (0.46), 0.403 (0.50), 1.219 (0.44), 1.232 (0.77), 1.239 (0.45), 1.244 (0.47), 1.252 (0.73), 1.265 (0.40), 2.114 (15.06), 2.431 (0.75), 2.436 (0.46), 3.636 (16.00), 3.688 (1.06), 3.700 (1.10), 3.709 (1.06), 3.721 (1.05), 4.908 (2.75), 4.920 (2.76).

Intermediate 72

(rac)-Ethyl 6-chloro-7-{3-[cyclopropyl(hydroxy)methyl]-1,5-dimethyl-1H-pyrazol-4-yl}-3-{3-[(naphthalen-1-yl)oxy]propyl}-1H-indole-2-carboxylate

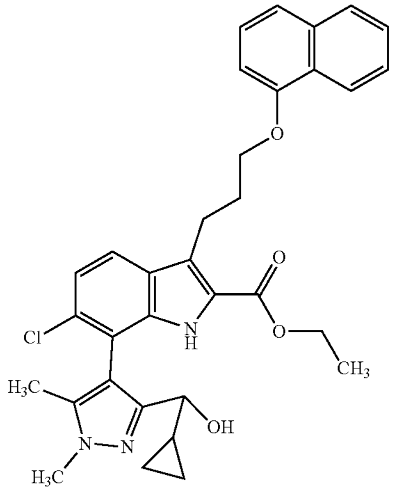 [SMILES: CCOC(=O)c1[nH]c2c(-c3c(C(O)C4CC4)nn(C)c3C)c(Cl)ccc2c1CCCOc1cccc2ccccc12]

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 8, 1.88 g, 3.52 mmol) and (rac)-(4-bromo-1,5-dimethyl-1H-pyrazol-3-yl)(cyclopropyl)methanol (see Intermediate 71, 950 mg, 3.88 mmol) were coupled as described for the preparation of Intermediate 34 to provide the title compound in 90% purity: 1.7 g, which was formed as a mixture of two racemic diastereomers as a result of atropisomerism at the newly formed bi-heteroaryl bond.

LC-MS (Method 2): $R_t$=1.63 min; MS (ESIpos): m/z=572 $[M+H]^+$ $^1$H-NMR (400 MHz, DMSO-d6) δ[ppm]: −0.139 (0.42), 0.284 (0.58), 0.300 (0.62), 0.312 (0.43), 0.887 (1.56), 0.899 (0.66), 0.907 (0.64), 1.019 (16.00), 1.108 (0.48), 1.195 (1.93), 1.198 (1.05), 1.205 (0.57), 1.213 (4.22), 1.216 (2.08), 1.231 (1.98), 1.234 (1.01), 1.900 (2.36), 1.932 (5.61), 2.154 (5.59), 2.236 (2.07), 2.471 (1.50), 2.476 (1.03), 3.247 (0.57), 3.265 (1.08), 3.334 (0.53), 3.346 (0.52), 3.355 (0.48), 3.367 (0.49), 3.518 (1.48), 3.676 (5.29), 3.730 (0.48), 3.737 (2.29), 3.750 (0.47), 3.763 (0.52), 3.779 (5.76), 3.786 (3.94), 3.892 (2.86), 4.145 (0.71), 4.160 (1.50), 4.177 (1.12), 4.195 (1.81), 4.199 (1.03), 4.213 (1.77), 4.217 (1.00), 4.231 (0.55), 4.947 (0.95), 4.959 (0.91), 5.047 (1.27), 5.059 (1.21), 5.256 (0.47), 5.265 (0.47), 5.711 (0.66), 6.419 (0.52), 6.421 (0.54), 6.860 (0.66), 6.877 (0.70), 7.103 (1.61), 7.125 (1.64), 7.327 (0.53), 7.347 (0.98), 7.363 (0.41), 7.366 (0.81), 7.405 (1.37), 7.425 (0.76), 7.455 (0.62), 7.459 (0.78), 7.466 (0.82), 7.472 (1.35), 7.475 (0.86), 7.479 (0.80), 7.486 (0.80), 7.489 (0.76), 7.635 (1.10), 7.656 (1.00), 7.814 (0.80), 7.821 (0.44), 7.831 (0.80), 7.836 (0.66), 8.163 (0.50), 8.168 (0.48), 8.185 (0.59), 8.187 (0.63), 10.678 (0.98).

Intermediate 73

(rac)-Ethyl (11Z)-4-chloro-15-cyclopropyl-2,3-dimethyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate

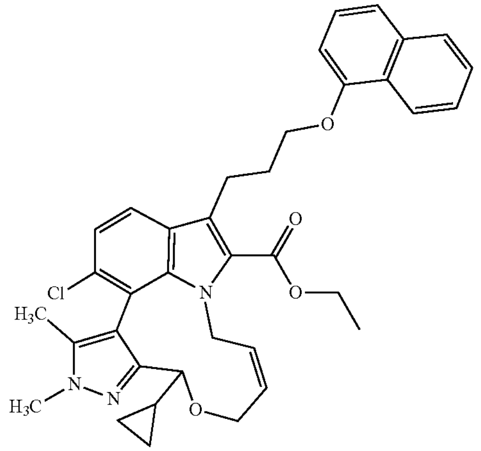 [SMILES: CCOC(=O)c1c(CCCOc2cccc3ccccc23)c2ccc(Cl)c3c2n1C/C=C\COC(C1CC1)c1nn(C)c(C)c1-3]

(rac)-Ethyl 6-chloro-7-{3-[cyclopropyl(hydroxy)methyl]-1,5-dimethyl-1H-pyrazol-4-yl}-3-{3-[(naphthalen-1-yl)oxy]propyl}-1H-indole-2-carboxylate (see Intermediate 72, 1.70 g, 90% purity, 2.67 mmol) was reacted as described for the preparation of Intermediate 35 to provide the title compound in 80% purity: 685 mg, which was formed as a racemic mixture of two enantiomers as only one of the two diastereomers formed in the preceding step underwent the macrocyclisation reaction.

LC-MS (Method 2): $R_t$=1.77 min; MS (ESIpos): m/z=624 $[M+H]^+$ $^1$H-NMR (400 MHz, DMSO-d6) δ[ppm]: 0.000 (0.48), 0.021 (0.80), 0.027 (0.80), 0.048 (0.41), 0.061 (0.86), 0.075 (0.83), 0.083 (0.89), 0.093 (0.86), 0.121 (0.51), 0.269 (0.51), 0.283 (1.59), 0.298 (1.43), 0.308 (1.08), 0.321 (1.43), 0.325 (1.62), 0.341 (1.40), 0.345 (1.50), 0.362 (0.54), 0.407 (0.41), 0.411 (0.54), 0.421 (0.48), 0.432 (0.60), 0.441 (0.41), 0.763 (0.41), 1.106 (4.04), 1.124 (8.30), 1.141 (4.26), 1.154 (0.67), 1.166 (1.11), 1.181 (1.27), 1.186 (1.27), 1.199 (2.29), 1.204 (5.44), 1.222 (11.01), 1.239 (5.18), 1.250 (0.45), 1.258 (0.45), 1.271 (0.73), 1.278 (0.41), 1.283 (0.45), 1.291 (0.67), 1.303 (0.45), 1.760 (15.94), 1.902 (0.80), 1.924 (1.84), 1.939 (13.87), 2.152 (15.11), 2.167 (1.78), 2.185 (1.18), 2.469 (4.68), 2.474 (3.15), 3.201 (0.60), 3.217 (0.95), 3.234 (1.37), 3.253 (1.30), 3.444 (2.54), 3.465 (2.42), 3.619 (0.60), 3.632 (0.73), 3.650 (1.18), 3.664 (1.08), 3.675 (15.05), 3.728 (1.97), 3.740 (1.30), 3.749 (1.40), 3.761 (2.07), 3.787 (0.73), 3.827 (16.00), 3.904 (1.91), 3.914 (0.86), 3.951 (1.08), 3.969 (3.15), 3.987 (3.18), 4.004 (1.11), 4.150 (0.67), 4.168 (1.88), 4.177 (2.32), 4.186 (2.74), 4.194 (4.33), 4.212 (2.74), 4.229 (2.23), 4.246 (1.81), 4.255 (0.89), 4.264 (0.57), 4.273 (0.89), 4.522 (0.45), 4.752 (0.48), 4.776 (0.57), 4.791 (0.99), 4.816 (1.11), 4.854 (1.21), 4.893 (0.54), 4.945 (2.93), 4.957 (2.77), 5.065 (0.48), 5.071 (0.48), 5.091 (0.92), 5.098 (0.92), 5.117 (0.70), 5.122 (0.73), 5.149 (0.54), 5.162 (0.57), 5.176 (0.73), 5.189 (0.67), 6.870 (1.88), 6.887 (2.07), 7.125 (0.48), 7.146 (0.51), 7.215 (4.20), 7.237 (4.17), 7.330 (1.50), 7.337 (0.45), 7.350 (2.86), 7.358 (0.70), 7.369 (2.42), 7.377 (0.54), 7.406 (3.05), 7.426 (2.07), 7.442 (1.69), 7.445 (1.69), 7.461 (3.37), 7.466 (3.56), 7.481 (1.94), 7.484 (2.04), 7.498 (0.89), 7.501 (0.73), 7.687 (0.45), 7.709 (0.41), 7.752 (3.72), 7.774 (3.37), 7.814 (1.91), 7.831 (2.00), 7.835 (1.65), 8.118 (1.43), 8.122 (1.50), 8.141 (1.43).

Intermediate 74

(rac)-Ethyl-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

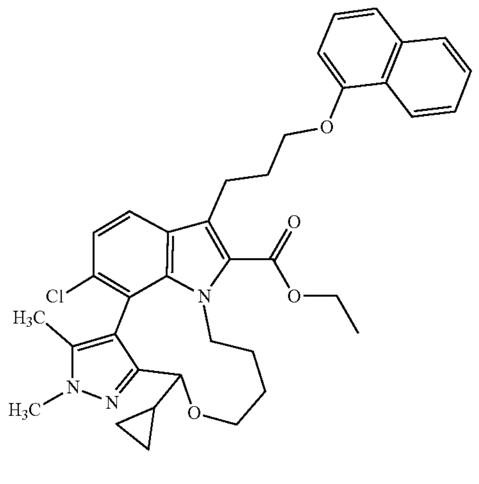 [SMILES: CCOC(=O)c1c(CCCOc2cccc3ccccc23)c2ccc(Cl)c3c2n1CCCCOC(C1CC1)c1nn(C)c(C)c1-3]

(rac)-Ethyl (11Z)-4-chloro-15-cyclopropyl-2,3-dimethyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate (see Intermediate 73, 685 mg, 80% purity, 878 μmol) was reacted as described for the preparation of Intermediate 55 to provide the title compound in 90% purity: 456 mg.

LC-MS (Method 2): $R_t$=1.76 min; MS (ESIpos): m/z=626 $[M+H]^+$ $^1$H-NMR (400 MHz, DMSO-d6) δ[ppm]: 0.490 (0.69), 0.511 (0.64), 1.066 (16.00), 1.154 (1.05), 1.172 (2.15), 1.189 (1.07), 1.251 (1.95), 1.269 (4.12), 1.287 (1.99), 1.800 (5.65), 1.987 (3.68), 2.201 (0.53), 2.518 (1.25), 2.522 (0.78), 3.481 (0.89), 3.504 (0.85), 3.849 (5.83), 3.939 (2.92), 4.016 (0.82), 4.034 (0.79), 4.196 (0.97), 4.205 (0.82), 4.213 (0.73), 4.223 (0.91), 4.231 (0.48), 4.241 (0.80), 4.280 (0.72), 4.298 (0.62), 6.887 (0.68), 6.905 (0.73), 7.202 (1.47), 7.223 (1.55), 7.367 (0.53), 7.387 (1.01), 7.406 (0.82), 7.448 (1.05), 7.469 (0.64), 7.499 (0.66), 7.503 (0.61), 7.510 (0.69), 7.517 (1.34), 7.523 (0.72), 7.530 (0.65), 7.534 (0.72), 7.755 (1.35), 7.777 (1.21), 7.858 (0.59), 7.876 (0.60), 7.881 (0.52), 8.183 (0.50), 8.189 (0.50), 8.208 (0.50).

Intermediate 75

(rac)-ethyl 4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

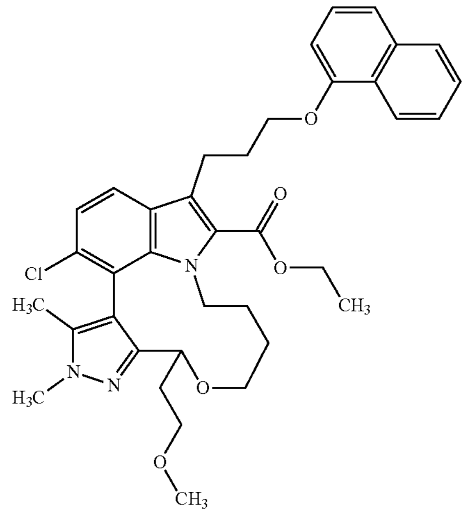 [SMILES: CCOC(=O)c1c(CCCOc2cccc3ccccc23)c2ccc(Cl)c3c2n1CCCCOC(CCOC)c1nn(C)c(C)c1-3]

(Rac)-ethyl 4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 66, 55.0 mg) was dissolved in 5 mL of tetrahydrofuran, sodium hydride (7.6 mg, 55% purity, 175 μmol) was added and the mixture was stirred at room temperature for 5 minutes. Iodomethane (22.0 μL, 350 μmol) was added and the mixture was stirred over night at room temperature and for 4 hours at 40° C. Cesium carbonate (142 mg, 436 μmol), iodomethane (22.0 μL, 350 μmol) and 3 mL of acetonitrile were added and the mixture was stirred at 60° C. over night. Cesium carbonate (142 mg, 436 μmol) and iodomethane (100 μL, 159 mmol) were added and the mixture was stirred over night at 60° C. Cesium carbonate (100 mg, 307 μmol) and iodomethane (100 μL, 159 mmol) were added and the mixture was stirred for 16 h at 60° C. The reaction mixture was concentrated under reduced pressure, water was added and the mixture was extracted with ethyl acetate. The combined organic layers were concentrated under reduced pressure and the crude product was purified by HPLC (Method P3) to provide 22.0 mg of the title compound.

LC-MS (Method 1): $R_t$=1.74 min; MS (ESIpos): m/z=644 $[M+H]^+$ $^1$H-NMR (400 MHz, DMSO-d6) δ[ppm]: 1.143 (0.46), 1.232 (0.71), 1.253 (3.26), 1.270 (6.57), 1.288 (3.11), 1.352 (16.00), 1.757 (1.02), 1.807 (9.12), 2.074 (0.56), 2.100 (0.41), 2.117 (1.12), 2.133 (1.07), 2.150 (0.51), 2.181 (2.50), 2.206 (0.82), 2.327 (2.24), 2.331 (1.68), 2.336 (0.76), 2.518 (9.58), 2.522 (5.81), 2.669 (2.29), 2.673 (1.68), 2.678 (0.76), 3.165 (13.71), 3.240 (0.41), 3.259 (0.76), 3.276 (0.76), 3.364 (0.76), 3.381 (0.97), 3.398 (0.51), 3.404 (0.51), 3.582 (0.46), 3.599 (0.82), 3.649 (0.51), 3.763 (0.46), 3.835 (9.22), 3.964 (0.41), 3.982 (0.41), 4.197 (1.12), 4.208 (1.27), 4.215 (1.63), 4.224 (1.53), 4.241 (1.12), 4.262 (0.56), 4.272 (0.46), 4.281 (1.17), 4.290 (0.51), 4.298 (1.12), 4.307 (0.87), 4.316 (0.41), 4.325 (0.66), 4.389 (0.56), 4.407 (1.12), 4.425 (0.56), 6.654 (0.46), 6.867 (1.27), 6.896 (1.07), 6.913 (1.17), 7.229 (2.29), 7.251 (2.39), 7.372 (0.82), 7.392 (1.53), 7.412 (1.27), 7.452 (1.68), 7.472 (0.92), 7.505 (0.92), 7.509 (0.92), 7.514 (1.12), 7.522 (2.09), 7.530 (1.17), 7.533 (1.07), 7.538 (1.12), 7.550 (0.41), 7.782 (2.04), 7.804 (1.83), 7.861 (0.97), 7.869 (0.51), 7.878 (0.87), 7.884 (0.87), 8.191 (0.82), 8.198 (0.76), 8.216 (0.76).

Intermediate 76

(rac)-(4-bromo-5-ethyl-1-methyl-1H-pyrazol-3-yl)(cyclopropyl)methanol

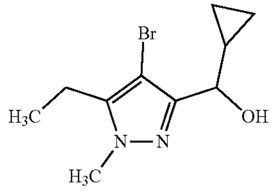

4-Bromo-5-ethyl-1-methyl-1H-pyrazole-3-carbaldehyde (see Intermediate 21, 2.00 g) was dissolved in 15 mL of tetrahydrofuran. Bromo(cyclopropyl)magnesium solution (37 mL, 0.50 M in THF, 18 mmol) was added at 4° C. and the mixture was stirred for 20 minutes at 4° C. and for 18 h at room temperature. A saturated aqueous ammonium chloride solution was added and the mixture was extracted with ethyl acetate. The combined organic layers were washed with brine, filtered using a water resistant filter and concentrated under reduced pressure. The crude material was purified by flash chromatography using silica gel (gradient hexane/ethylacetate) to give 1.59 g of the title compound.

LC-MS (Method 2): $R_t$=0.95 min; MS (ESIpos): m/z=259 $[M+H]^+$ $^1$H-NMR (400 MHz, DMSO-d6) δ[ppm]: 0.021 (0.62), 0.035 (0.70), 0.225 (0.41), 0.227 (0.49), 0.238 (1.38), 0.246 (0.69), 0.250 (1.11), 0.260 (1.10), 0.263 (0.62), 0.273 (0.50), 0.360 (0.51), 0.382 (0.62), 0.391 (0.45), 0.971 (2.80), 0.990 (6.69), 1.009 (2.96), 1.219 (0.68), 1.227 (0.43), 1.232 (0.43), 1.239 (0.65), 2.419 (0.41), 2.508 (0.85), 2.527 (2.86), 2.546 (2.72), 2.565 (0.84), 3.660 (16.00), 3.682 (0.91), 3.693 (0.94), 3.702 (0.90), 3.714 (0.90), 4.904 (2.28), 4.916 (2.21).

Intermediate 77 ethyl 6-chloro-7-{3-[(rac)-cyclopropyl(hydroxy)methyl]-5-ethyl-1-methyl-1H-pyrazol-4-yl}-3-{3-[(6-fluoronaphthalen-1-yl)oxy]propyl}-1H-indole-2-carboxylate

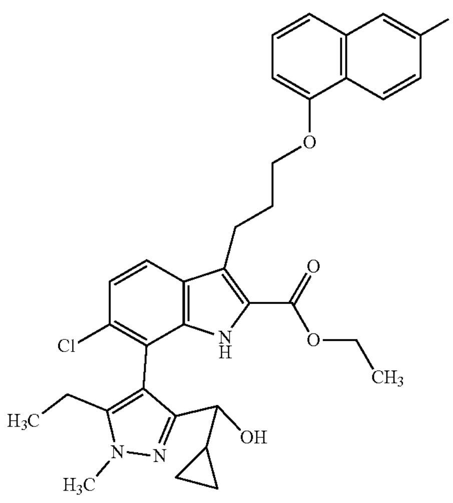

The reaction was performed in two identical preparations using half of all materials. Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 2.90 g, 5.26 mmol), (rac)-(4-bromo-5-ethyl-1-methyl-1H-pyrazol-3-yl)(cyclopropyl)methanol (see Intermediate 76, 1.50 g, 5.79 mmol) and tripotassium phosphate (2.23 g, 10.5 mmol) were provided in a mixture of 15 mL of 1,4-dioxane and 5 mL of water and purged with argon for 5 minutes. RuPhos Pd G3 (242 mg, 289 μmol) was added and the mixture was purged with argon for 5 minutes and stirred for 20 minutes at 110° C. in a microwave reactor. The reaction mixtures of said two preparations were combined, diluted with water and extracted with ethyl acetate. The combined organic layers were washed with brine, dried using a water resistant filter and concentrated under reduced pressure. The crude material was purified by flash chromatography using silica gel (gradient hexane/ethyl acetate) to provide 1.25 g (37% yield) of the title compound which was formed as a mixture of two racemic diastereomers as a result of atropisomerism at the newly formed bi-heteroaryl bond.

LC-MS (Method 2): $R_t$=1.67 min; MS (ESIpos): m/z=604 $[M+H]^+$ $^1$H-NMR (400 MHz, DMSO-d6) δ[ppm]: −0.099 (0.43), −0.087 (0.57), −0.075 (0.94), −0.063 (1.02), −0.053 (0.70), 0.084 (0.67), 0.104 (0.72), 0.110 (0.59), 0.123 (0.78), 0.133 (1.09), 0.146 (0.92), 0.156 (0.61), 0.244 (0.72), 0.255 (0.80), 0.266 (0.81), 0.279 (0.59), 0.288 (0.80), 0.297 (0.61), 0.311 (0.81), 0.318 (0.78), 0.331 (0.74), 0.339 (0.43), 0.833 (1.17), 0.847 (3.77), 0.852 (3.26), 0.866 (8.21), 0.885 (3.61), 0.919 (0.61), 0.934 (0.63), 1.060 (0.46), 1.078 (1.31), 1.093 (0.74), 1.097 (0.50), 1.144 (2.42), 1.162 (4.98), 1.180 (2.50), 1.218 (5.12), 1.221 (2.35), 1.235 (11.43), 1.239 (4.62), 1.253 (5.48), 1.257 (2.35), 1.266 (0.52), 1.275 (0.65), 1.287 (0.98), 1.295 (0.72), 1.307 (0.96), 1.319 (0.54), 1.978 (8.71), 2.177 (1.09), 2.197 (1.61), 2.212 (1.29), 2.301 (0.52), 2.317 (1.92), 2.338 (2.00), 2.357 (2.39), 2.376 (1.59), 2.395 (0.70), 2.508 (5.09), 2.513 (3.27), 2.654 (0.91), 2.659 (1.11), 2.664 (0.81), 3.271 (1.39), 3.290 (2.42), 3.356 (1.55), 3.366 (1.55), 3.376 (1.46), 3.387 (1.42), 3.718 (0.46), 3.726 (0.46), 3.738 (0.46), 3.750 (1.87), 3.811 (5.18), 3.849 (16.00), 3.989 (0.65), 4.007 (1.91), 4.024 (1.85), 4.043 (0.63), 4.184 (1.81), 4.199 (3.74), 4.209 (2.63), 4.227 (5.01), 4.244 (4.68), 4.262 (1.44), 4.769 (3.79), 4.779 (3.68), 4.933 (1.09), 4.942 (1.07), 6.862 (0.48), 6.873 (1.39), 6.880 (1.52), 6.887 (1.22), 6.894 (1.33), 7.132 (1.33), 7.140 (3.79), 7.154 (1.42), 7.161 (3.85), 7.366 (0.87), 7.373 (1.13), 7.377 (0.48), 7.389 (1.42), 7.394 (1.78), 7.406 (0.63), 7.411 (1.05), 7.417 (1.29), 7.427 (2.81), 7.434 (3.57), 7.441 (6.46), 7.454 (0.57), 7.641 (1.96), 7.647 (2.02), 7.667 (3.05), 7.672 (4.35), 7.693 (2.63), 8.232 (1.31), 8.247 (1.39), 8.256 (1.68), 8.270 (1.61), 8.280 (0.46), 10.522 (0.91), 10.639 (2.92).

Intermediate 78

(rac)-ethyl (11Z)-4-chloro-(15-rac)-cyclopropyl-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate

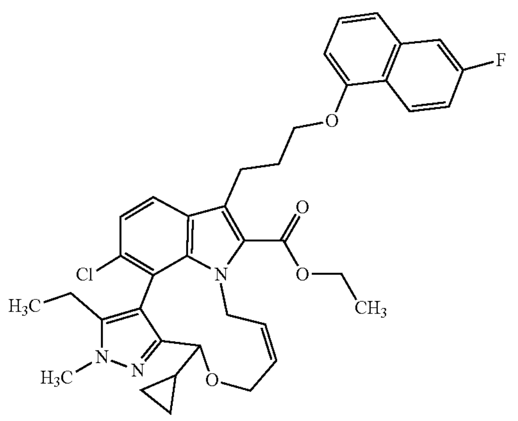 [SMILES: CCOC(=O)c1c(CCCOc2cccc3cc(F)ccc23)c2ccc(Cl)c3c2n1C/C=C\COC(C1CC1)c1nn(C)c(CC)c1-3]

Ethyl 6-chloro-7-{3-[(rac)-cyclopropyl(hydroxy)methyl]-5-ethyl-1-methyl-1H-pyrazol-4-yl}-3-{3-[(6-fluoronaphthalen-1-yl)oxy]propyl}-1H-indole-2-carboxylate (see Intermediate 77, 1.25 g, 1.97 mmol) was dissolved in 10 mL of acetonitrile, cesium carbonate (3.20 g, 9.83 mmol) was added and the mixture was stirred for 10 minutes at room temperature. (2Z)-1,4-dichlorobut-2-ene (410 μL, 3.93 mmol) and sodium iodide (589 mg, 3.93 mmol) were added and the suspension was stirred for 22 h at 70° C. in a sealed tube. The reaction mixture was diluted with water and extracted with ethyl acetate. The combined organic layers were washed with brine, dried using a water resistant filter and concentrated under reduced pressure. The crude material was purified by flash chromatography using silica gel (gradient hexane/ethyl acetate) to give 805 mg (59% yield) of the title compound which was formed as a racemic mixture of two enantiomers as only one of the two diastereomers formed in the preceding step underwent the macrocyclization reaction.

LC-MS (Method 2): $R_t$=1.80 min; MS (ESIpos): m/z=656 $[M+H]^+$ $^1$H-NMR (400 MHz, DMSO-d6) δ[ppm]: 0.124 (0.50), 0.138 (1.07), 0.150 (0.98), 0.177 (0.96), 0.189 (0.91), 0.393 (2.17), 0.414 (2.03), 0.793 (3.27), 0.812 (7.50), 0.831 (3.36), 0.914 (0.41), 1.089 (0.64), 1.154 (2.70), 1.172 (5.51), 1.189 (2.74), 1.233 (0.85), 1.239 (0.89), 1.248 (5.37), 1.265 (11.25), 1.283 (5.42), 1.987 (9.44), 2.125 (0.46), 2.144 (0.82), 2.163 (1.42), 2.182 (1.46), 2.190 (1.60), 2.209 (2.17), 2.227 (1.81), 2.239 (1.12), 2.331 (0.96), 2.336 (0.46), 2.518 (5.46), 2.523 (3.43), 2.673 (0.98), 3.262 (0.78), 3.280 (1.37), 3.295 (1.37), 3.313 (1.14), 3.501 (2.49), 3.521 (2.42), 3.642 (0.55), 3.654 (0.69), 3.673 (1.01), 3.686 (0.91), 3.751 (0.98), 3.759 (1.53), 3.780 (1.37), 3.813 (0.82), 3.908 (16.00), 3.986 (0.48), 3.999 (0.85), 4.016 (2.03), 4.035 (2.01), 4.053 (0.73), 4.194 (0.46), 4.212 (1.21), 4.222 (2.01), 4.229 (1.85), 4.238 (4.27), 4.257 (2.70), 4.276 (2.08), 4.286 (0.41), 4.294 (1.74), 4.303 (0.89), 4.311 (0.53), 4.321 (0.85), 4.726 (0.50), 4.752 (0.62), 4.766 (0.82), 4.792 (0.96), 4.890 (1.10), 4.928 (0.69), 5.028 (0.53), 5.034 (0.50), 5.056 (0.98), 5.061 (1.01), 5.081 (0.62), 5.168 (0.41), 5.181 (0.43), 5.196 (0.69), 5.209 (0.66), 6.887 (1.26), 6.896 (1.30), 6.901 (1.14), 6.909 (1.39), 7.267 (3.89), 7.288 (3.77), 7.351 (0.87), 7.358 (0.98), 7.374 (1.33), 7.381 (1.51), 7.396 (0.98), 7.402 (1.17), 7.417 (0.53), 7.438 (2.72), 7.443 (3.04), 7.452 (6.10), 7.464 (0.48), 7.649 (1.58), 7.655 (1.69), 7.675 (1.58), 7.681 (1.62), 7.799 (3.45), 7.821 (3.04), 8.192 (1.30), 8.206 (1.42), 8.215 (1.39), 8.230 (1.35).

Intermediate 79

(rac)-ethyl 4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

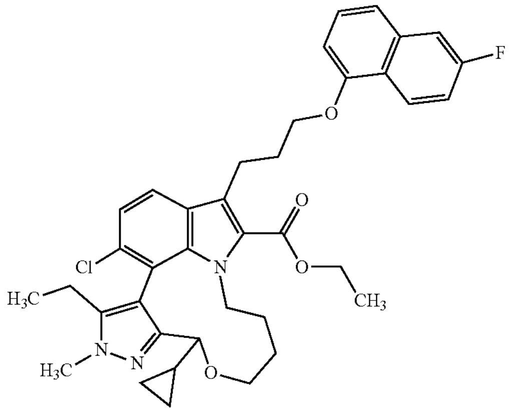 [SMILES: CCOC(=O)c1c(CCCOc2cccc3cc(F)ccc23)c2ccc(Cl)c3c2n1CCCCOC(C1CC1)c1nn(C)c(CC)c1-3]

(Rac)-ethyl (11Z)-4-chloro-(15-rac)-cyclopropyl-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate (see Intermediate 78, 800 mg, 1.22 mmol) was dissolved in a mixture of 8 mL of ethanol and 4 mL of tetrahydrofuran, tris(triphenylphosphine)rhodium(I)-chloride (566 mg, 610 μmol) was added and the mixture was stirred for 6 h under hydrogen atmosphere at room temperature. The reaction mixture was filtered and concentrated under reduced pressure. The crude material was purified by flash chromatography using silica gel (gradient hexane/ethyl acetate) to provide 615 mg (69% yield) of the title compound.

LC-MS (Method 2): $R_t$=1.81 min; MS (ESIpos): m/z=658 $[M+H]^+$ $^1$H-NMR (400 MHz, DMSO-d6) δ[ppm]: 0.124 (0.46), 0.136 (0.62), 0.147 (0.60), 0.154 (0.50), 0.316 (0.48), 0.323 (0.60), 0.335 (0.71), 0.349 (0.50), 0.505 (1.79), 0.516 (0.89), 0.525 (1.75), 0.791 (2.99), 0.810 (7.40), 0.829 (3.08), 1.036

(1.29), 1.249 (4.83), 1.266 (10.43), 1.284 (5.09), 1.592 (0.53), 1.603 (0.55), 1.615 (0.53), 1.905 (0.84), 2.152 (0.76), 2.171 (2.39), 2.190 (2.77), 2.209 (1.58), 2.518 (3.49), 2.523 (2.60), 3.136 (0.41), 3.159 (1.55), 3.172 (1.48), 3.228 (0.58), 3.245 (0.89), 3.256 (0.65), 3.265 (0.64), 3.276 (0.95), 3.293 (0.62), 3.309 (0.60), 3.410 (0.62), 3.422 (0.50), 3.436 (0.52), 3.476 (2.18), 3.501 (2.10), 3.877 (16.00), 3.938 (0.48), 3.957 (0.45), 4.169 (0.43), 4.178 (1.02), 4.195 (2.41), 4.205 (2.34), 4.213 (1.84), 4.223 (2.29), 4.231 (0.86), 4.240 (2.08), 4.258 (0.67), 4.263 (0.58), 4.280 (1.69), 4.298 (1.57), 4.307 (0.89), 4.316 (0.45), 4.324 (0.89), 6.854 (1.17), 6.860 (1.22), 6.869 (1.05), 6.876 (1.26), 7.189 (4.03), 7.211 (3.77), 7.360 (0.84), 7.366 (0.96), 7.382 (1.24), 7.389 (1.38), 7.404 (1.24), 7.411 (1.03), 7.426 (2.17), 7.435 (2.48), 7.441 (5.37), 7.456 (0.48), 7.642 (1.45), 7.648 (1.50), 7.668 (1.43), 7.674 (1.45), 7.741 (3.37), 7.762 (2.99), 8.172 (1.20), 8.187 (1.27), 8.195 (1.24), 8.210 (1.17).

Intermediate 80 ethyl 3-(4-bromo-5-ethyl-1-methyl-1H-pyrazol-3-yl)-3-oxopropanoate

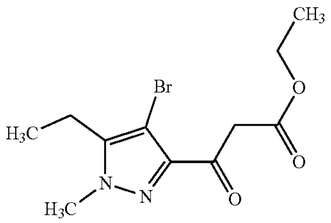 [SMILES: CCOC(=O)CC(=O)c1nn(C)c(CC)c1Br]

Ethyl 4-bromo-5-ethyl-1-methyl-1H-pyrazole-3-carboxylate (see Intermediate 19, 10.0 g) was dissolved in a mixture of 300 mL of tetrahydrofuran and 19 mL of ethyl acetate and lithium bis(trimethylsilyl)amide (96 mL, 1.0 M in 2-methoxy-2-methyl-propane, 96 mmol) was added at −30° C. dropwise. The mixture was allowed to warm up to 0° C. within 1 h, a saturated aqueous ammonium chloride solution was added and the mixture was extracted with ethyl acetate. The combined organic layers were dried over sodium sulfate, filtered, concentrated under reduced pressure. The crude product was purified by flash chromatography using silica gel (gradient hexane/ethyl acetate) to provide 10.9 g of the title compound.

LC-MS (Method 1): $R_t$=1.13 min; MS (ESIpos): m/z=303 $[M+H]^+$ $^1$H-NMR (400 MHz, DMSO-d6) δ[ppm]: 1.075 (2.73), 1.087 (0.40), 1.094 (6.63), 1.113 (2.79), 1.145 (4.68), 1.157 (0.44), 1.163 (10.04), 1.175 (0.62), 1.181 (4.74), 1.978 (1.06), 2.160 (0.62), 2.671 (0.74), 2.690 (2.52), 2.709 (2.48), 2.728 (0.69), 3.913 (16.00), 3.949 (9.28), 4.058 (1.19), 4.076 (3.72), 4.094 (3.74), 4.111 (1.22).

Intermediate 81

(rac)-1-(4-bromo-5-ethyl-1-methyl-1H-pyrazol-3-yl) propane-1,3-diol

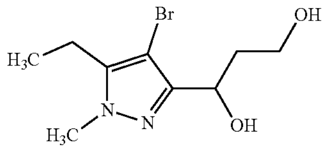

Ethyl 3-(4-bromo-5-ethyl-1-methyl-1H-pyrazol-3-yl)-3-oxopropanoate (see Intermediate 80, 10.9 g) was dissolved in 300 mL of methanol, sodium borohydride (10.9 g, 287 mmol) was added portionwise at room temperature. The mixture was stirred over night at reflux and was afterwards concentrated under reduced pressure. Ethyl acetate was added and the mixture was washed with water. The organic layer was dried over sodium sulfate, filtered and concentrated under reduced pressure to give 8.40 g of the title compound which was used without further purification.

LC-MS (Method 1): $R_t$=0.74 min; MS (ESIpos): m/z=263 $[M+H]^+$

Intermediate 82

(rac)-1-(4-bromo-5-ethyl-1-methyl-1H-pyrazol-3-yl)-3-{[tert-butyl(dimethyl)silyl]oxy}propan-1-ol

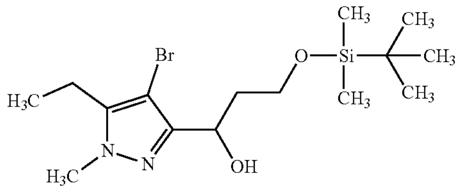 [SMILES: CCc1c(Br)c(C(O)CCO[Si](C)(C)C(C)(C)C)nn1C]

(Rac)-1-(4-bromo-5-ethyl-1-methyl-1H-pyrazol-3-yl) propane-1,3-diol (see Intermediate 81, 8.40 g) was dissolved in 100 mL of N,N-dimethylformamide, tert-butyl(chloro) dimethylsilane (5.29 g, 35.1 mmol) and imidazole (3.26 g, 47.9 mmol) were added at 0° C. and the mixture was allowed to warmed up to room temperature and was stirred for 72 h at room temperature. Water was added and the mixture was extracted with dichloromethane. The combined organic layers were washed with brine, dried over sodium sulfate, filtered and concentrated under reduced pressure. The crude material was purified by flash chromatography using silica gel (gradient hexane/ethyl acetate) to provide 10.2 g of the title compound which was used without further purification.

LC-MS (Method 2): $R_t$=1.50 min; MS (ESIpos): m/z=377 $[M+H]^+$ $^1$H-NMR (400 MHz, DMSO-d6) δ[ppm]: −0.177 (1.29), −0.051 (0.33), −0.015 (1.70), −0.011 (5.05), 0.000 (5.55), 0.005 (1.66), 0.021 (0.21), 0.801 (3.96), 0.832 (0.73), 0.836 (1.07), 0.843 (16.00), 0.849 (1.37), 0.858 (4.41), 1.037 (0.26), 1.052 (1.07), 1.056 (0.89), 1.071 (2.45), 1.075 (0.86), 1.090 (1.05), 1.835 (0.19), 1.850 (0.22), 1.868 (0.19), 1.918 (0.23), 1.939 (0.26), 1.952 (0.20), 2.511 (0.57), 2.516 (0.39), 2.596 (0.37), 2.615 (1.23), 2.634 (1.19), 2.653 (0.39), 2.662 (0.17), 2.721 (0.83), 2.882 (1.01), 3.564 (0.27), 3.575 (0.28), 3.590 (0.36), 3.605 (0.16), 3.648 (0.18), 3.662 (0.27), 3.666 (0.27), 3.673 (0.20), 3.680 (0.22), 3.688 (0.19), 3.691 (0.18), 3.744 (6.23), 3.748 (2.01), 3.778 (0.18), 3.888 (0.17), 4.607 (0.19), 4.621 (0.35), 4.628 (0.24), 4.635 (0.20), 4.642 (0.35), 4.914 (0.95), 4.928 (0.82).

Intermediate 83 ethyl 7-{3-[3-{[tert-butyl(dimethyl)silyl]oxy}-(1-rac)-hydroxpropyl]-5-ethyl-1-methyl-1H-pyrazol-4-yl}-6-chloro-3-{3-[(6-fluoronaphthalen-1-yl)oxy] propyl}-1H-indole-2-carboxylate

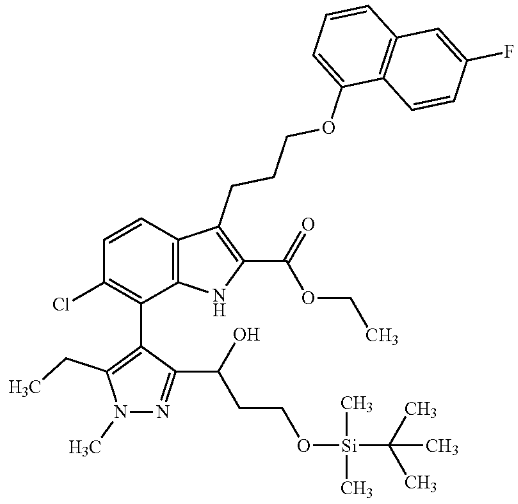 [SMILES: CCOC(=O)c1[nH]c2c(-c3c(C(O)CCO[Si](C)(C)C(C)(C)C)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.00 g, 1.81 mmol), (rac)-1-(4-bromo-5-ethyl-1-methyl-1H-pyrazol-3-yl)-3-{[tert-butyl(dimethyl)silyl]oxy}propan-1-ol (see Intermediate 82, 845 mg) and potassium triphosphate (769 mg, 3.62 mmol) were provided in a mixture of 40 mL of 1,4-dioxane and 8 mL of water. RuPhos Pd G3 (75.8 mg, 9.1 μmol) was added and the mixture was stirred for 30 minutes at 110° C. The aqueous phase was removed and the organic layer was concentrated under reduced pressure. The crude material was purified by flash chromatography using silica gel (gradient dichloromethane/ethanol) to give 1.14 g of the title compound which was formed as a mixture of two racemic diastereomers as a result of atropisomerism at the newly formed bi-heteroaryl bond.

$^1$H-NMR (400 MHz, DMSO-d6) δ[ppm]: −0.208 (0.38), −0.203 (0.80), −0.189 (0.79), −0.177 (2.22), −0.168 (4.57), −0.016 (2.50), −0.011 (5.39), 0.000 (6.08), 0.004 (3.40), 0.595 (0.38), 0.643 (7.64), 0.650 (1.25), 0.679 (0.60), 0.686 (2.30), 0.738 (0.45), 0.742 (0.22), 0.786 (0.19), 0.800 (6.25), 0.812 (0.47), 0.836 (1.41), 0.843 (16.00), 0.849 (4.83), 0.857 (7.38), 0.866 (1.47), 0.877 (0.28), 0.885 (0.53), 0.895 (0.19), 1.029 (0.55), 1.037 (0.47), 1.046 (1.31), 1.052 (1.30), 1.056 (1.51), 1.059 (2.94), 1.063 (1.18), 1.071 (2.49), 1.089 (1.12), 1.133 (0.26), 1.139 (0.22), 1.149 (2.43), 1.170 (0.27), 1.228 (0.95), 1.246 (1.67), 1.264 (0.81), 1.774 (0.18), 1.790 (0.19), 1.817 (0.22), 1.835 (0.43), 1.850 (0.46), 1.868 (0.27), 1.919 (0.24), 1.939 (0.29), 1.953 (0.23), 1.973 (0.16), 2.058 (0.21), 2.204 (0.30), 2.315 (0.27), 2.320 (0.33), 2.325 (0.25), 2.380 (0.29), 2.399 (0.29), 2.516 (0.85), 2.541 (0.17), 2.560 (0.16), 2.596 (0.41), 2.615 (1.29), 2.634 (1.25), 2.653 (0.45), 2.662 (0.29), 2.667 (0.22), 3.269 (0.19), 3.287 (0.36), 3.303 (0.39), 3.415 (0.33), 3.428 (0.30), 3.433 (0.34), 3.446 (0.30), 3.451 (0.17), 3.525 (0.23), 3.531 (0.21), 3.550 (0.23), 3.559 (0.46), 3.562 (0.42), 3.571 (0.44), 3.575 (0.43), 3.590 (0.49), 3.605 (0.24), 3.629 (0.88), 3.648 (0.22), 3.666 (0.36), 3.674 (0.29), 3.681 (0.30), 3.688 (0.27), 3.744 (5.61), 3.747 (3.56), 3.778 (0.17), 3.800 (0.27), 3.809 (0.67), 3.837 (2.02), 3.933 (0.44), 4.206 (0.60), 4.218 (0.57), 4.230 (0.46), 4.235 (0.85), 4.253 (0.73), 4.271 (0.22), 4.339 (0.19), 4.351 (0.35), 4.364 (0.19), 4.608 (0.18), 4.622 (0.34), 4.629 (0.23), 4.635 (0.22), 4.642 (0.35), 4.656 (0.17), 4.736 (0.46), 4.749 (0.44), 4.916 (0.92), 4.929 (0.89), 5.752 (2.11), 5.926 (0.19), 6.872 (0.24), 6.880 (0.25), 6.887 (0.24), 6.894 (0.26), 7.130 (0.47), 7.146 (0.19), 7.151 (0.50), 7.367 (0.17), 7.374 (0.19), 7.390 (0.31), 7.396 (0.30), 7.412 (0.26), 7.418 (0.26), 7.429 (0.54), 7.436 (0.63), 7.443 (1.06), 7.641 (0.32), 7.648 (0.33), 7.668 (0.40), 7.673 (0.74), 7.694 (0.45), 7.936 (0.20), 8.247 (0.22), 8.262 (0.24), 8.270 (0.24), 8.285 (0.21), 10.681 (0.44).

Intermediate 84

(rac)-ethyl (11Z,15-rac)-(2-{[tert-butyl(dimethyl) silyl]oxy}ethyl)-4-chloro-3-ethyl-7-{3-[(6-fluoronaphthalen-1-yl)oxy]propyl}-2-methyl-2,10,13,15-tetrahydropyrazolo[4',3':9,10][1,6] oxazacycloundecino[8,7,6-hi]indole-8-carboxylate

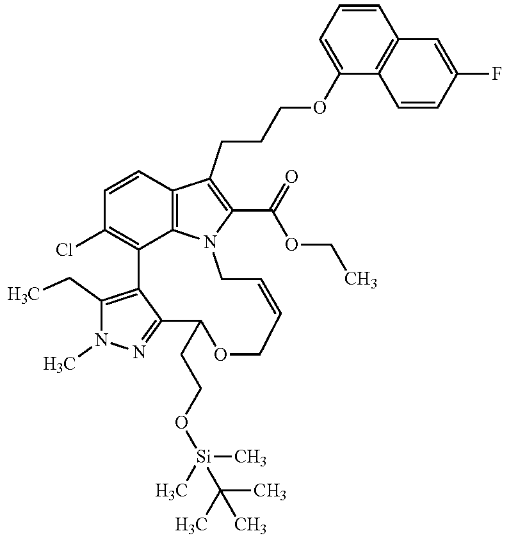 [SMILES: CCOC(=O)c1c(CCCOc2cccc3cc(F)ccc23)c2ccc(Cl)c3c2n1C/C=C\COC(CCO[Si](C)(C)C(C)(C)C)c1nn(C)c(CC)c1-3]

Ethyl 7-{3-[3-{[tert-butyl(dimethyl)silyl]oxy}-(1-rac)-hydroxypropyl]-5-ethyl-1-methyl-1H-pyrazol-4-yl}-6-chloro-3-{3-[(6-fluoronaphthalen-1-yl)oxy]propyl}-1H-indole-2-carboxylate (see Intermediate 83, 1.10 g) was dissolved in 100 mL of acetonitrile, treated with cesium carbonate (2.48 g, 7.61 mmol), sodium iodide (457 mg, 3.05 mmol) and (2Z)-1,4-dichlorobut-2-ene (0.24 mL, 2.28 mmol) were added and the mixture was stirred for 72 h at 70° C. The mixture was filtered and concentrated under reduced pressure. The crude product was purified by flash chromatography using silica gel (gradient hexane/ethyl acetate) to provide 300 mg of the title compound which was formed as a racemic mixture of two enantiomers as only one of the two diastereomers formed in the preceding step underwent the macrocyclization reaction.

LC-MS (Method 2): $R_t$=1.98 min; MS (ESIpos): m/z=774 $[M+H]^+$ $^1$H-NMR (400 MHz, DMSO-d6) δ[ppm]: −0.170 (5.19), −0.165 (0.68), −0.158 (0.27), −0.150 (5.24), −0.020 (0.52), −0.011 (3.18), 0.000 (3.21), 0.007 (0.36), 0.011 (0.26), 0.521 (0.87), 0.527 (16.00), 0.781 (0.83), 0.797 (1.70), 0.800 (2.09), 0.818 (0.90), 0.836 (0.63), 0.843 (11.30), 0.849 (1.21), 1.052 (0.72), 1.060 (8.75), 1.071 (1.62), 1.077 (0.24), 1.090 (0.69), 1.148 (1.94), 1.165 (3.72), 1.183 (1.75), 1.254 (1.29), 1.272 (2.84), 1.290 (1.30), 1.906 (0.34), 1.918 (0.41), 1.932 (0.32), 1.939 (0.28), 1.952 (0.16), 1.981 (6.47), 2.142 (0.18), 2.160 (0.40), 2.178 (0.52), 2.197 (0.44), 2.215 (0.36), 2.234 (0.35), 2.251 (0.21), 2.512 (0.94), 2.517 (0.63), 2.596 (0.19), 2.615 (0.66), 2.634 (0.64), 2.653 (0.25), 3.260 (0.30), 3.279 (0.57), 3.298 (0.35), 3.565 (0.16), 3.576 (0.16), 3.590 (0.61), 3.605 (0.55), 3.622 (0.27), 3.629 (0.29), 3.648 (0.22), 3.656 (0.19), 3.662 (0.21), 3.666 (0.18), 3.674 (0.30), 3.681 (0.23), 3.688 (0.29), 3.744 (3.93), 3.778 (0.52), 3.801 (0.23), 3.831 (0.32), 3.861 (0.21), 3.881 (4.45), 3.888 (0.77), 3.933 (1.32), 3.993 (0.51), 4.011 (1.57), 4.028 (1.54), 4.046 (0.50), 4.203 (0.29), 4.220 (0.66), 4.226 (0.47), 4.238 (0.43), 4.248 (0.54), 4.265 (0.55), 4.281 (0.56), 4.299 (0.45), 4.308 (0.22), 4.326 (0.21), 4.403 (0.26), 4.413 (0.26), 4.424 (0.25), 4.434 (0.24), 4.621 (0.19), 4.642 (0.22), 4.739 (0.18), 4.765 (0.22), 4.892 (0.26), 4.914 (0.57), 4.928 (0.67), 4.939 (0.24), 4.966 (0.26), 6.868 (0.33), 6.874 (0.34), 6.883 (0.30), 6.889 (0.35), 7.208 (1.02), 7.229 (1.08), 7.359 (0.24), 7.366 (0.27), 7.382 (0.36), 7.389 (0.39), 7.404 (0.26), 7.410 (0.32), 7.429 (0.62), 7.437 (0.71), 7.444 (1.52), 7.643 (0.40), 7.650 (0.41), 7.669 (0.40), 7.676 (0.39), 7.762 (0.89), 7.783 (0.77), 8.230 (0.35), 8.244 (0.36), 8.253 (0.34), 8.268 (0.33).

Intermediate 85

(rac)-ethyl (15-rac)-(2-{[tert-butyl(dimethyl)silyl]oxy}ethyl)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

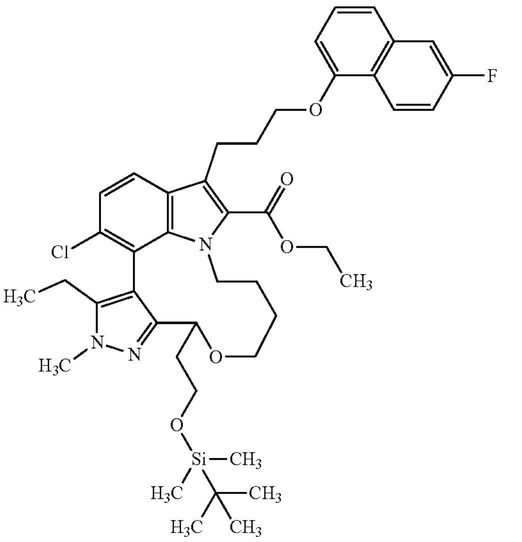 [SMILES: CCOC(=O)c1c(CCCOc2cccc3cc(F)ccc23)c2ccc(Cl)c3c2n1CCCCOC(CCO[Si](C)(C)C(C)(C)C)c1nn(C)c(CC)c1-3]

(Rac)-ethyl (11Z,15-rac)-(2-{[tert-butyl(dimethyl)silyl]oxy}ethyl)-4-chloro-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate (see Intermediate 84, 1.50 g) was dissolved in a mixture of 30 mL of tetrahydrofuran and 10 mL of ethanol, tris(triphenylphosphine)rhodium(I) chloride (899 mg, 968 μmol) was added and the mixture was stirred at room temperature under hydrogen atmosphere for 5 h. The reaction mixture was filtered a and concentrated under reduced pressure. The crude product was purified by flash chromatography using silica gel (gradient hexane/ethyl acetate) to give 1.03 g of the title compound.

$^1$H-NMR (400 MHz, DMSO-d6) δ[ppm]: −0.093 (0.20), −0.085 (4.91), −0.078 (0.22), −0.065 (0.21), −0.058 (5.02), −0.050 (0.20), −0.011 (1.93), 0.000 (1.95), 0.707 (0.86), 0.714 (16.00), 0.721 (0.85), 0.792 (0.77), 0.811 (1.86), 0.830 (0.85), 0.835 (0.44), 0.843 (6.90), 0.850 (0.40), 1.006 (0.20), 1.023 (0.17), 1.052 (0.42), 1.071 (0.97), 1.090 (0.42), 1.148 (1.15), 1.165 (2.11), 1.183 (1.02), 1.245 (1.24), 1.262 (2.66), 1.280 (1.21), 1.981 (3.84), 2.081 (0.18), 2.177 (0.30), 2.195 (0.58), 2.199 (0.51), 2.214 (0.49), 2.219 (0.48), 2.237 (0.20), 2.321 (0.19), 2.512 (0.67), 2.517 (0.45), 2.615 (0.37), 2.634 (0.35), 2.663 (0.19), 3.243 (0.19), 3.263 (0.20), 3.284 (0.27), 3.290 (0.17), 3.301 (0.33), 3.313 (0.42), 3.613 (0.26), 3.629 (0.40), 3.638 (0.29), 3.649 (0.24), 3.744 (2.20), 3.856 (4.03), 3.993 (0.35), 4.011 (0.90), 4.028 (0.88), 4.046 (0.28), 4.169 (0.17), 4.175 (0.19), 4.185 (0.40), 4.193 (0.40), 4.199 (0.42), 4.211 (0.37), 4.220 (0.45), 4.238 (0.45), 4.256 (0.28), 4.263 (0.19), 4.274 (0.50), 4.284 (0.19), 4.292 (0.44), 4.301 (0.33), 4.310 (0.17), 4.319 (0.26), 4.489 (0.22), 4.502 (0.24), 4.512 (0.26), 4.524 (0.21), 4.914 (0.37), 4.928 (0.33), 6.844 (0.31), 6.849 (0.32), 6.861 (0.30), 6.866 (0.33), 7.186 (1.01), 7.207 (1.01), 7.366 (0.21), 7.373 (0.24), 7.388 (0.32), 7.396 (0.42), 7.411 (0.25), 7.418 (0.71), 7.436 (1.04), 7.640 (0.37), 7.647 (0.38), 7.666 (0.37), 7.673 (0.37), 7.750 (0.83), 7.771 (0.72), 8.227 (0.31), 8.242 (0.32), 8.250 (0.31), 8.265 (0.30).

Intermediate 86

(rac)-ethyl 4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylate

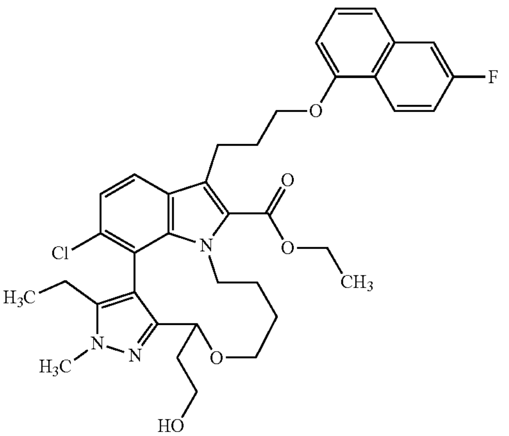 [SMILES: CCOC(=O)c1c(CCCOc2cccc3cc(F)ccc23)c2ccc(Cl)c3c2n1CCCCOC(CCO)c1nn(C)c(CC)c1-3]

(Rac)-ethyl (15-rac)-(2-{[tert-butyl(dimethyl)silyl]oxy}ethyl)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8- carboxylate (see Intermediate 85, 1.03 g) was dissolved in 70 mL of tetrahydrofuran, a solution of N,N,N-tributylbutan-1-aminium fluoride (1.5 mL, 1.0 M in THF, 1.50 mmol) was added and the mixture was stirred over night at room temperature. The reaction mixture was diluted with water and extracted with ethyl acetate. The combined organic layers were dried over sodium sulfate, filtered and concentrated under reduced pressure. The crude product was purified by flash chromatography using silica gel (gradient dichloromethane/ethanol) to provide 640 mg of the title compound.

LC-MS (Method 2): $R_t$=1.65 min; MS (ESIpos): m/z=662 $[M+H]^+$ $^1$H-NMR (400 MHz, DMSO-d6) δ[ppm]: 0.000 (3.94), 0.835 (3.20), 0.854 (7.52), 0.873 (3.35), 0.883 (6.04), 0.947 (0.42), 1.080 (3.24), 1.090 (1.22), 1.097 (5.83), 1.114 (3.09), 1.133 (0.86), 1.291 (5.28), 1.309 (10.97), 1.326 (5.20), 2.032 (0.42), 2.046 (0.63), 2.066 (0.84), 2.080 (0.67), 2.110 (0.55), 2.135 (0.67), 2.157 (0.78), 2.169 (0.63), 2.183 (0.42), 2.192 (0.55), 2.202 (0.86), 2.220 (2.02), 2.224 (2.13), 2.243 (2.63), 2.376 (0.86), 2.563 (5.16), 2.567 (3.12), 2.718 (0.88), 3.070 (0.57), 3.082 (0.63), 3.262 (0.42), 3.279 (0.67), 3.297 (0.95), 3.318 (1.33), 3.338 (1.66), 3.356 (1.56), 3.449 (0.44), 3.462 (0.51), 3.467 (1.33), 3.479 (2.04), 3.484 (1.75), 3.497 (2.88), 3.512 (1.87), 3.526 (0.95), 3.904 (16.00), 3.978 (0.59), 3.995 (0.63), 4.012 (0.69), 4.220 (0.69), 4.239 (2.08), 4.244 (1.92), 4.251 (2.04), 4.256 (2.36), 4.265 (2.67), 4.274 (1.39), 4.283 (2.13), 4.301 (0.88), 4.305 (1.09), 4.323 (1.89), 4.332 (0.42), 4.340 (1.60), 4.350 (0.93), 4.358 (0.51), 4.367 (0.93), 4.390 (0.82), 4.403 (1.73), 4.407 (1.54), 4.415 (1.20), 4.420 (3.45), 4.432 (1.39), 4.502 (1.01), 4.515 (1.12), 4.524 (1.20), 4.538 (0.95), 5.315 (0.57), 6.909 (1.28), 6.915 (1.33), 6.924 (1.18), 6.930 (1.37), 7.266 (3.94), 7.287 (3.92), 7.424 (0.84), 7.431 (0.99), 7.446 (1.37), 7.453 (1.54), 7.469 (1.03), 7.477 (2.57), 7.487 (2.80), 7.493 (5.73), 7.508 (0.46), 7.694 (1.56), 7.701 (1.60), 7.720 (1.58), 7.727 (1.52), 7.809 (3.35), 7.831 (3.07), 8.279 (1.35), 8.293 (1.39), 8.302 (1.35), 8.317 (1.31).

Intermediate 87

(rac)-ethyl 4-chloro-3-ethyl-7-{3-[(6-fluoronaphthalen-1-yl)oxy]propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylate

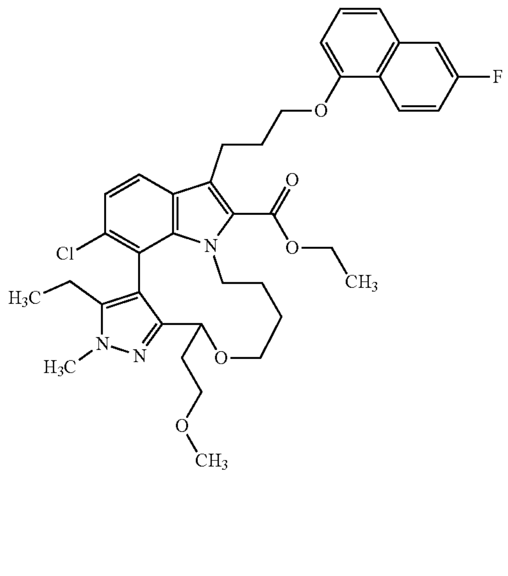 [SMILES: CCOC(=O)c1c(CCCOc2cccc3cc(F)ccc23)c2ccc(Cl)c3c2n1CCCCOC(CCOC)c1nn(C)c(CC)c1-3]

(Rac)-ethyl 4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylate (see Intermediate 86, 369 mg) was dissolved in 20 mL of tetrahydrofuran, sodium hydride (48.6 mg, 55% purity, 1.11 mmol) was added and the mixture was stirred for 30 minutes at room temperature. Iodomethane (170 μL, 2.8 mmol) was added and the mixture was stirred for 72 h at rt. The reaction mixture was diluted with water and extracted with ethyl acetate. The combined organic layers were dried over sodium sulfate, filtered and concentrated under reduced pressure. The crude product was purified by flash chromatography using silica gel (gradient dichloromethane/ethanol) to provide 390 mg of the title compound.

LC-MS (Method 2): $R_t$=1.78 min; MS (ESIpos): m/z=676 $[M+H]^+$

Intermediate 88

4-bromo-5-ethyl-1-methyl-1H-pyrazole-3-carboxylic Acid

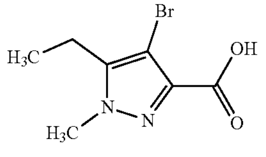

Ethyl 4-bromo-5-ethyl-1-methyl-1H-pyrazole-3-carboxylate (see Intermediate 19, 50.0 g, 191 mmol) was dissolved in 600 mL of methanol and a solution of potassium hydroxide (25.3 g, 85 purity, 383 mmol) in 120 mL of water was added at 0° C. dropwise. The mixture was stirred for 30 minutes at 0° C. and over night at rt. The mixture was concentrated to a third of the volume and water and an aqueous solution of hydrogen chloride (1N) was added at 0° C. until a pH value of 3 was reached. The precipitate was isolated by filtration, washed with water and dried to give 43.3 g (97% yield) of the title compound.

LC-MS (Method 1): $R_t$=0.79 min; MS (ESIpos): m/z=233 $[M+H]^+$ $^1$H-NMR (400 MHz, DMSO-d6) δ[ppm]: 1.077 (2.66), 1.096 (6.48), 1.115 (2.75), 2.518 (0.89), 2.523 (0.57), 2.663 (0.83), 2.682 (2.61), 2.701 (2.54), 2.720 (0.71), 3.877 (16.00).

Intermediate 89

4-bromo-5-ethyl-1-methyl-1H-pyrazole-3-carbonyl Chloride

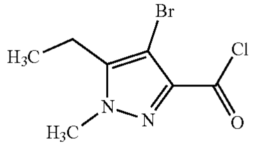

4-Bromo-5-ethyl-1-methyl-1H-pyrazole-3-carboxylic acid (see Intermediate 88, 23.2 g, 99.5 mmol) was dissolved in 200 mL of tetrahydrofuran, 200 μL of N,N-dimethyl formamide and oxalyl chloride (21.7 mL, 249 mmol) were added at 0° C. and the mixture was stirred for 2 h at 0° C. The reaction mixture was concentrated under reduced pressure to give 25.0 g of the title compound which was used without further purification.

Intermediate 90

4-bromo-5-ethyl-N-methoxy-N,1-dimethyl-1H-pyrazole-3-carboxamide

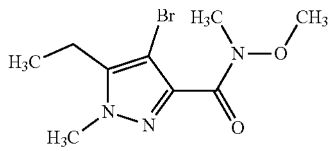

N-Methoxymethanamine hydrogen chloride (1/1) (9.10 g, 93.3 mmol) and triethylamine (26 mL, 187 mmol) were dissolved in 100 mL tetrahydrofuran and a solution of 4-bromo-5-ethyl-1-methyl-1H-pyrazole-3-carbonyl chloride (see Intermediate 89, 15.7 g) in 80 mL of tetrahydrofuran was added at 0° C. dropwise and the mixture was stirred for 1 h at 0° C. and for 72 h at room temperature. The mixture was filtered and concentrated under reduced pressure. The crude material was purified by flash chromatography using silica gel (aminophase, gradient hexane/ethyl acetate) to provide 10.1 g of the title compound.

LC-MS (Method 2): $R_t$=0.88 min; MS (ESIpos): m/z=276 $[M+H]^+$ $^1$H-NMR (400 MHz, DMSO-d6) δ[ppm]: 1.092 (3.05), 1.111 (7.13), 1.130 (3.12), 2.657 (0.90), 2.675 (2.92), 2.694 (2.85), 2.713 (0.83), 3.238 (10.88), 3.337 (13.44), 3.846 (16.00).

Intermediate 91

1-(4-bromo-5-ethyl-1-methyl-1H-pyrazol-3-yl)prop-2-en-1-one

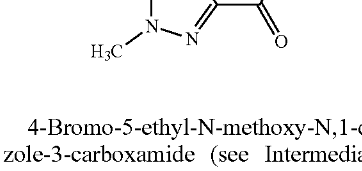

4-Bromo-5-ethyl-N-methoxy-N,1-dimethyl-1H-pyrazole-3-carboxamide (see Intermediate 90, 18.4 g, 66.5 mmol) was dissolved in 240 mL of tetrahydrofuran, a solution of bromo(vinyl)magnesium (133 mL, 1.0 M in THF, 133 mmol) was added at 0° C. dropwise and the mixture was stirred for 15 minutes at 0° C. The reaction mixture was used directly in the next step.

Intermediate 92

1-(4-bromo-5-ethyl-1-methyl-1H-pyrazol-3-yl)-3-(morpholin-4-yl)propan-1-one

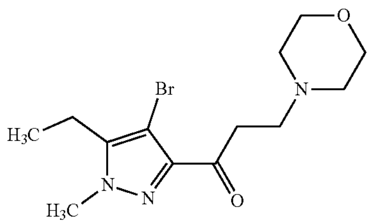

Morpholine (23.2 mL, 266 mmol) was dissolved in 20 mL of tetrahydrofuran, a solution of 1-(4-bromo-5-ethyl-1-methyl-1H-pyrazol-3-yl)prop-2-en-1-one (see Intermediate 91) in tetrahydrofuran was added dropwise at 0° C. and the mixture was stirred for 30 minutes at 0 C. The reaction mixture was filtered, concentrated, diluted with water and extracted with dichloromethane. The combined organic layers were dried over sodium sulfate and concentrated. The crude material was purified by flash chromatography silica gel (aminophase, gradient dichloromethane/ethyl acetate) to give 16.5 g of the title compound.

LC-MS (Method 2): $R_t$=0.97 min; MS (ESIpos): m/z=330 $[M+H]^+$ $^1$H-NMR (400 MHz, DMSO-d6) δ[ppm]: 1.078 (2.81), 1.097 (6.63), 1.116 (2.81), 1.983 (9.02), 2.327 (0.43), 2.344 (1.63), 2.355 (2.26), 2.366 (1.72), 2.518 (1.13), 2.522 (0.72), 2.608 (1.59), 2.626 (3.35), 2.644 (1.85), 2.671 (1.00), 2.690 (2.68), 2.709 (2.57), 2.728 (0.89), 3.042 (1.79), 3.060 (3.29), 3.077 (1.55), 3.388 (0.78), 3.393 (1.08), 3.404 (1.70), 3.412 (1.36), 3.417 (1.23), 3.506 (1.39), 3.514 (3.10), 3.518 (2.56), 3.525 (3.68), 3.537 (2.64), 3.547 (1.32), 3.559 (1.23), 3.571 (0.83), 3.917 (16.00).

Intermediate 93

(rac)-1-(4-bromo-5-ethyl-1-methyl-1H-pyrazol-3-yl)-3-(morpholin-4-yl)propan-1-ol

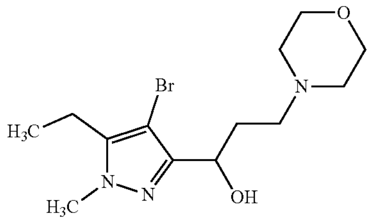 [SMILES: CCc1c(Br)c(C(O)CCN2CCOCC2)nn1C]

1-(4-Bromo-5-ethyl-1-methyl-1H-pyrazol-3-yl)-3-(morpholin-4-yl)propan-1-one (see Intermediate 92, 7.40 g, 22.4 mmol) was dissolved in 60 mL of methanol, sodium borohydride (3.39 g, 89.6 mmol) was added and the mixture was stirred for 22 h at room temperature. Water was added and the mixture was extracted with ethyl acetate. The combined organic layers were washed with brine, filtered using a water resistant filter and concentrated under reduced pressure to provide 5.68 g (74% yield) of the title compound.

LC-MS (Method 2): $R_t$=0.88 min; MS (ESIpos): m/z=332 [M+H]$^+$ $^1$H-NMR (400 MHz, DMSO-d6) δ[ppm]: 1.060 (2.63), 1.079 (6.44), 1.098 (2.75), 1.154 (0.73), 1.172 (1.55), 1.190 (0.77), 1.816 (0.42), 1.833 (0.50), 1.836 (0.44), 1.850 (0.47), 1.873 (0.42), 1.878 (0.47), 1.893 (0.59), 1.912 (0.42), 1.987 (2.56), 2.296 (1.09), 2.314 (2.81), 2.326 (2.49), 2.331 (2.41), 2.346 (0.79), 2.518 (0.63), 2.523 (0.42), 2.601 (0.78), 2.620 (2.58), 2.639 (2.46), 2.658 (0.72), 3.534 (2.22), 3.546 (3.34), 3.557 (2.20), 3.751 (16.00), 4.017 (0.58), 4.035 (0.57), 4.557 (0.47), 4.566 (0.47), 4.578 (0.48), 5.113 (0.77), 5.125 (0.84).

Intermediate 94 ethyl 7-{5-ethyl-3-[(rac)-1-hydroxy-3-(morpholin-4-yl)propyl]-1-methyl-1H-pyrazol-4-yl}-6-fluoro-3-{3-[(6-fluoronaphthalen-1-yl)oxy]propyl}-1H-indole-2-carboxylate

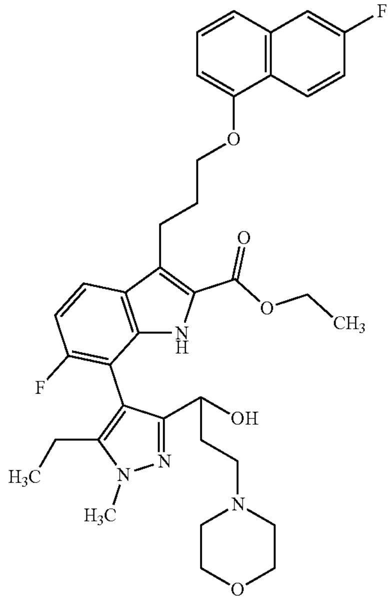 [SMILES: CCOC(=O)c1[nH]c2c(-c3c(C(O)CCN4CCOCC4)nn(C)c3CC)c(F)ccc2c1CCCOc1cccc2cc(F)ccc12]

In a first preparation ethyl 6-fluoro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 10, 293 mg), (rac)-1-(4-bromo-5-ethyl-1-methyl-1H-pyrazol-3-yl)-3-(morpholin-4-yl)propan-1-ol (see Intermediate 93, 200 mg, 0.60 mmol) and potassium triphosphate (232 mg, 1.09 mmol) were provided in a mixture of 3 mL of 1,4-dioxane and 1 mL of water and purged with argon for 5 minutes. RuPhos Pd G3 (25.2 mg, 30.1 μmol) was added and the mixture was purged with argon for 5 minutes and stirred for 20 minutes at 110° C. in a microwave reactor. In two additional, identical preparations using half of all materials ethyl 6-fluoro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 10, 2.93 g), (rac)-1-(4-bromo-5-ethyl-1-methyl-1H-pyrazol-3-yl)-3-(morpholin-4-yl)propan-1-ol (see Intermediate 93, 2.00 g, 6.02 mmol) and potassium triphosphate (2.32 g, 10.9 mmol) were provided in a mixture of 18 mL of 1,4-dioxane and 6 mL of water and purged with argon for 5 minutes. RuPhos Pd G3 (252 mg, 301 μmol) was added and the mixture was purged with argon for 5 minutes and stirred for 20 minutes at 110° C. in a microwave reactor. The reaction mixtures of the said three preparations were combined, diluted with water and extracted with ethyl acetate. The combined organic layers were washed with brine, dried using a water resistant filter and concentrated under reduced pressure. The crude material was purified by flash chromatography using silica gel (gradient dichloromethane/ethanol) to provide 2.32 g of the title compound which was formed as a mixture of two racemic diastereomers as a result of atropisomerism at the newly formed bi-heteroaryl bond.

LC-MS (Method 2): $R_t$=1.61 min; MS (ESIpos): m/z=661 [M+H]$^+$ $^1$H-NMR (400 MHz, DMSO-d6) δ[ppm]: 0.889 (0.89), 0.908 (2.55), 0.928 (2.60), 0.948 (0.99), 1.052 (0.35), 1.065 (16.00), 1.190 (0.30), 1.234 (3.06), 1.251 (6.90), 1.269 (3.14), 1.465 (0.16), 1.482 (0.31), 1.498 (0.41), 1.515 (0.32), 1.822 (0.17), 1.839 (0.35), 1.854 (0.49), 1.871 (0.37), 1.888 (0.18), 1.983 (0.61), 1.993 (0.58), 2.085 (0.20), 2.099 (0.28), 2.116 (0.54), 2.133 (0.51), 2.142 (0.57), 2.157 (0.69), 2.187 (1.06), 2.202 (1.40), 2.221 (1.30), 2.238 (0.62), 2.253 (0.28), 2.318 (0.22), 2.337 (0.30), 2.357 (0.33), 2.375 (0.40), 2.397 (0.41), 2.417 (0.65), 2.436 (0.70), 2.454 (0.66), 2.474 (0.96), 2.518 (1.99), 2.523 (1.24), 2.659 (0.19), 3.294 (0.55), 3.397 (1.19), 3.819 (4.83), 3.842 (5.21), 3.941 (2.74), 4.189 (0.49), 4.205 (1.19), 4.212 (1.63), 4.229 (3.07), 4.247 (2.72), 4.265 (1.02), 4.549 (0.19), 4.568 (0.29), 4.583 (0.18), 5.329 (0.23), 5.563 (0.23), 5.758 (1.43), 6.870 (0.40), 6.879 (0.60), 6.887 (0.64), 6.893 (0.70), 6.902 (0.46), 6.963 (0.46), 6.975 (0.45), 6.985 (0.61), 6.989 (0.58), 6.997 (0.57), 7.001 (0.54), 7.011 (0.48), 7.023 (0.43), 7.370 (0.31), 7.377 (0.41), 7.381 (0.34), 7.393 (0.50), 7.398 (0.71), 7.403 (0.52), 7.415 (0.54), 7.419 (0.42), 7.422 (0.45), 7.426 (0.40), 7.435 (1.47), 7.442 (1.68), 7.450 (3.55), 7.463 (0.24), 7.648 (0.86), 7.655 (0.85), 7.674 (0.87), 7.681 (0.84), 7.698 (0.71), 7.711 (0.75), 7.720 (0.75), 7.733 (0.68), 8.241 (0.43), 8.256 (0.48), 8.264 (0.56), 8.279 (0.54), 8.284 (0.44), 8.299 (0.38), 10.936 (0.86), 10.959 (0.90).

Intermediate 95

(rac)-ethyl (11Z)-3-ethyl-4-fluoro-7-{3-[(6-fluoronaphthalen-1-yl)oxy]propyl}-2-methyl-(15-rac)-[2-(morpholin-4-yl)ethyl]-2,10,13,15-tetrahydropyrazolo[4',3':9,10][1,6]oxazacycloundecino[8,7,6-hi]indole-8-carboxylate

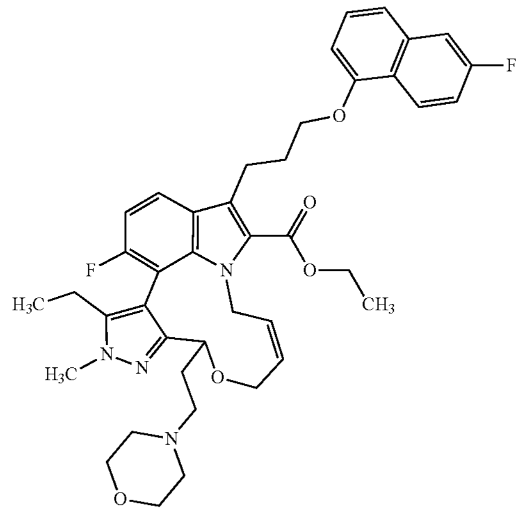 [SMILES: CCOC(=O)c1c(CCCOc2cccc3cc(F)ccc23)c2ccc(F)c3c2n1C/C=C\COC(CCN1CCOCC1)c1nn(C)c(CC)c1-3]

Ethyl 7-{5-ethyl-3-[(rac)-1-hydroxy-3-(morpholin-4-yl)propyl]-1-methyl-1H-pyrazol-4-yl}-6-fluoro-3-{3-[(6-fluoronaphthalen-1-yl)oxy]propyl}-1H-indole-2-carboxylate (see Intermediate 94, 2.32 g, 3.51 mmol) was dissolved in 25 mL of acetonitrile, cesium carbonate (5.72 g, 17.6 mmol) was added and the mixture was stirred for 10 minutes at rt. Sodium iodide (1.05 g, 7.02 mmol) and (2Z)-1,4-dichlorobut-2-ene (550 μL, 5.3 mmol) were added and the mixture was stirred for 24 h at 70° C. The reaction mixture was diluted with water and extracted with ethyl acetate. The combined organic layers were washed with brine, filtered using a water resistant filter and concentrated under reduced pressure. The crude product was purified by flash chromatography using silica gel (gradient hexane/ethyl acetate) to provide 1.22 g of the title compound which was formed as a racemic mixture of two enantiomers as only one of the two diastereomers formed in the preceding step underwent the macrocyclization reaction.

LC-MS (Method 2): $R_t$=1.67 min; MS (ESIpos): m/z=713 $[M+H]^+$

H-NMR (400 MHz, DMSO-d6) δ[ppm]: 0.810 (1.28), 0.821 (0.63), 0.829 (2.72), 0.842 (0.81), 0.848 (1.71), 0.861 (1.13), 0.868 (0.44), 0.880 (0.76), 0.898 (0.66), 0.904 (0.54), 0.908 (0.44), 0.917 (0.42), 0.929 (0.44), 1.035 (3.67), 1.053 (7.38), 1.066 (16.00), 1.070 (4.07), 1.138 (0.52), 1.156 (1.30), 1.159 (1.03), 1.171 (1.22), 1.177 (1.79), 1.189 (0.59), 1.195 (0.84), 1.235 (0.52), 1.253 (2.43), 1.271 (4.19), 1.289 (1.82), 2.205 (1.30), 2.223 (1.76), 2.237 (1.71), 2.255 (1.30), 2.274 (0.73), 2.318 (0.59), 2.323 (0.95), 2.327 (1.25), 2.332 (1.06), 2.518 (3.46), 2.523 (2.59), 2.665 (0.74), 2.669 (1.03), 2.673 (0.73), 3.256 (0.47), 3.285 (0.63), 3.405 (1.33), 3.418 (1.25), 3.422 (2.01), 3.435 (1.91), 3.440 (1.84), 3.452 (1.74), 3.457 (0.73), 3.470 (0.64), 3.717 (2.45), 3.723 (1.57), 3.767 (1.64), 3.778 (0.41), 3.817 (0.54), 3.821 (0.61), 3.846 (1.12), 3.893 (4.82), 3.938 (2.50), 4.175 (0.41), 4.193 (0.47), 4.202 (0.47), 4.214 (1.01), 4.231 (1.77), 4.240 (2.03), 4.258 (1.22), 4.278 (0.81), 4.296 (0.74), 4.305 (0.78), 4.317 (0.66), 4.323 (0.76), 4.336 (0.42), 4.344 (0.98), 4.357 (1.69), 4.369 (0.84), 4.915 (0.44), 6.884 (0.66), 6.892 (0.84), 6.896 (0.74), 6.905 (0.90), 6.914 (0.44), 7.050 (0.68), 7.073 (0.47), 7.078 (0.57), 7.386 (0.68), 7.393 (0.63), 7.400 (0.54), 7.407 (0.64), 7.414 (0.52), 7.423 (0.42), 7.439 (1.49), 7.444 (2.28), 7.452 (3.36), 7.456 (1.88), 7.651 (1.10), 7.657 (1.03), 7.677 (1.12), 7.683 (0.98), 7.822 (0.44), 7.836 (0.44), 7.844 (0.42), 8.206 (0.44), 8.221 (0.49), 8.229 (0.54), 8.234 (0.44), 8.244 (0.57), 8.249 (0.47).

Intermediate 96

(rac)-ethyl 3-ethyl-4-fluoro-7-{3-[(6-fluoronaphthalen-1-yl)oxy]propyl}-2-methyl-(15-rac)-[2-(morpholin-4-yl)ethyl]-2,10,11,12,13,15-hexahydropyrazolo[4',3':9,10][1,6]oxazacycloundecino[8,7,6-hi]indole-8-carboxylate

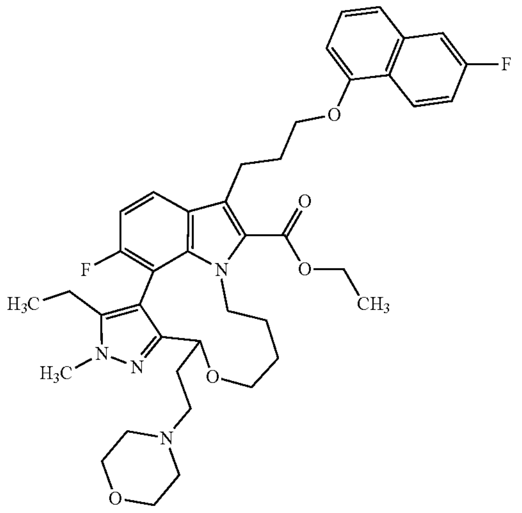 [SMILES: CCOC(=O)c1c(CCCOc2cccc3cc(F)ccc23)c2ccc(F)c3c2n1CCCCOC(CCN1CCOCC1)c1nn(C)c(CC)c1-3]

(Rac)-ethyl (11Z)-3-ethyl-4-fluoro-7-{3-[(6-fluoronaphthalen-1-yl)oxy]propyl}-2-methyl-15-[2-(morpholin-4-yl)ethyl]-2,10,13,15-tetrahydropyrazolo[4',3':9,10][1,6]oxazacycloundecino[8,7,6-hi]indole-8-carboxylate (see Intermediate 95, 1.20 g) was dissolved in a mixture of 8 mL of ethanol and 3 mL of tetrahydrofuran, tris(triphenylphosphine)rhodium(I)-chloride (586 mg, 631 μmol) was added and the mixture was stirred for 6 h under hydrogen atmosphere at rt. The reaction mixture was filtered and concentrated under reduced pressure. The crude material was purified by flash chromatography using silica gel (gradient dichloromethane/ethanol) to provide 795 mg of the title compound.

LC-MS (Method 2): $R_t$=1.70 min; MS (ESIpos): m/z=715 $[M+H]^+$ $^1$H-NMR (400 MHz, DMSO-d6) δ[ppm]: 0.622 (0.65), 0.730 (0.55), 0.742 (0.70), 0.748 (0.94), 0.761 (1.24), 0.767 (0.60), 0.779 (0.84), 0.797 (1.04), 0.802 (1.24), 0.814 (1.19), 0.823 (3.63), 0.843 (7.50), 0.861 (3.58), 0.872 (1.14), 0.885 (0.84), 0.904 (1.39), 0.922 (0.84), 1.018 (1.04), 1.035 (1.09), 1.052 (1.04), 1.065 (1.04), 1.070 (0.80), 1.159 (1.14), 1.167 (1.24), 1.177 (1.74), 1.184 (2.04), 1.191 (1.59), 1.202 (1.44), 1.209 (1.14), 1.234 (1.54), 1.248 (5.96), 1.265 (11.58), 1.283 (5.52), 1.753 (0.45), 1.907 (3.23), 1.993 (0.75), 2.010 (1.64), 2.028 (1.79), 2.046 (0.99), 2.065 (0.55), 2.119 (0.80), 2.217 (2.63), 2.235 (2.88), 2.254 (3.93), 2.270 (5.32), 2.288 (4.07), 2.306 (1.34), 2.318 (1.29), 2.322 (2.09), 2.327 (2.78), 2.331 (1.99), 2.397 (0.40), 2.518 (9.69), 2.523 (6.16), 2.660 (0.89), 2.665 (1.79), 2.669 (2.48), 2.673 (1.79), 2.974 (0.60), 3.000 (0.65), 3.211 (0.70), 3.228 (0.99), 3.245 (1.24), 3.262 (1.59), 3.490 (4.42), 3.770 (1.59), 3.775 (2.34), 3.819 (2.34), 3.842 (0.84), 3.863 (16.00), 3.978 (0.45), 3.995 (0.70), 4.011 (0.80), 4.028 (0.80), 4.047 (0.50), 4.110 (0.45), 4.119 (0.50), 4.139 (0.60), 4.147 (0.75), 4.170 (0.94), 4.189 (2.04), 4.198 (2.48), 4.207 (3.18), 4.215 (4.72), 4.233 (3.23), 4.254 (1.19), 4.272 (2.39), 4.290 (2.53), 4.299 (1.74), 4.308 (1.34), 4.317

(1.64), 4.334 (0.84), 4.384 (0.99), 4.402 (1.94), 4.419 (0.89), 5.758 (0.99), 6.861 (1.49), 6.868 (1.64), 6.876 (1.49), 6.883 (1.84), 6.894 (0.65), 6.989 (1.59), 7.011 (2.73), 7.034 (1.69), 7.373 (1.29), 7.379 (1.64), 7.395 (1.94), 7.402 (2.29), 7.408 (1.39), 7.417 (1.59), 7.424 (1.99), 7.430 (3.68), 7.439 (4.37), 7.445 (8.20), 7.453 (2.29), 7.547 (0.60), 7.555 (0.50), 7.565 (0.65), 7.573 (0.60), 7.595 (0.75), 7.612 (0.70), 7.621 (0.75), 7.624 (0.80), 7.647 (2.53), 7.653 (2.53), 7.673 (2.43), 7.679 (2.39), 7.762 (0.40), 7.774 (0.45), 7.787 (1.49), 7.800 (1.54), 7.808 (1.54), 7.822 (1.44), 8.216 (1.49), 8.230 (1.54), 8.239 (1.69), 8.254 (1.64).

Intermediate 97

(rac)-1-(4-bromo-5-ethyl-1-methyl-1H-pyrazol-3-yl)-3-methylbutane-1,3-diol

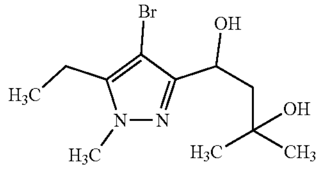 [SMILES: CCc1c(Br)c(C(O)CC(C)(C)O)nn1C]

2-Methylpropan-2-ol (2.2 mL, 23.0 mmol) was provided in 6 mL of toluene, tris(triphenylphosphine)rhodium(I)chloride (171 mg, 184 μmol) was added and the mixture was stirred for 20 minutes at 30° C. A solution of 4-bromo-5-ethyl-1-methyl-1H-pyrazole-3-carbaldehyde (see Intermediate 21, 2.00 g) in 4 mL of toluene and cesium carbonate (60.0 mg, 184 μmol) were added and the mixture was stirred for 20 min at 30° C. Boron trifluoride diethyl etherate (1.8 mL, 13.8 mmol) was added and the mixture was stirred for 23 h at 50° C. The reaction mixture was diluted with ethyl acetate, a saturated aqueous solution of sodium bicarbonate was added, the phases were separated and the aqueous phase was extracted with ethyl acetate. The combined organic layers were filtered using a water resistant filter and concentrated under reduced pressure. The crude product was purified by preparative HPLC (Method P2) to give 615 mg of the title compound.

LC-MS (Method 2): $R_t$=0.91 min; MS (ESIpos): m/z=291 $[M+H]^+$ $^1$H-NMR (400 MHz, DMSO-d6) δ[ppm]: 1.058 (2.60), 1.077 (6.37), 1.096 (2.86), 1.110 (8.18), 1.139 (7.87), 1.699 (0.71), 1.708 (0.72), 1.734 (0.90), 1.743 (0.89), 1.970 (0.87), 1.993 (0.88), 2.005 (0.70), 2.028 (0.68), 2.518 (0.67), 2.523 (0.49), 2.601 (0.75), 2.620 (2.58), 2.639 (2.48), 2.658 (0.71), 3.749 (16.00), 4.520 (3.38), 4.787 (0.67), 4.797 (0.47), 4.800 (0.47), 4.810 (0.67), 5.060 (1.50), 5.071 (1.37), 5.759 (0.63).

Intermediate 98 ethyl 6-chloro-7-{3-[(1-rac)-1,3-dihydroxy-3-methylbutyl]-5-ethyl-1-methyl-1H-pyrazol-4-yl}-3-{3-[(6-fluoronaphthalen-1-yl)oxy]propyl}-1H-indole-2-carboxylate

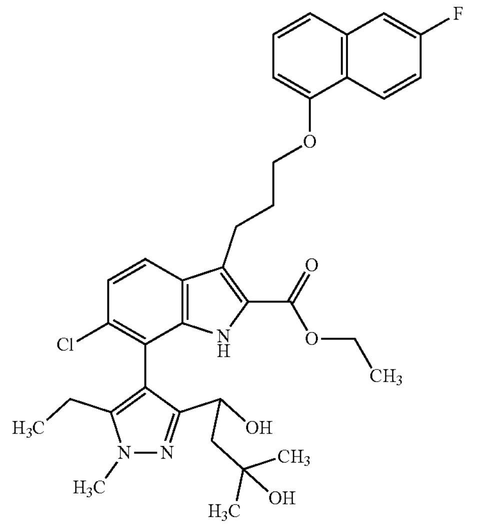 [SMILES: CCOC(=O)c1[nH]c2c(-c3c(C(O)CC(C)(C)O)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.63 g, 2.95 mmol), (rac)-1-(4-bromo-5-ethyl-1-methyl-1H-pyrazol-3-yl)-3-methylbutane-1,3-diol (see Intermediate 97, 945 mg, 3.25 mmol) and potassium triphosphate (1.25 g, 5.90 mmol) were provided in a mixture of 8 mL of 1,4-dioxane and 3 mL of water and purged with argon for 5 minutes. RuPhos Pd G3 (136 mg, 162 μmol) was added and the mixture was purged with argon and stirred for 20 minutes at 110° C. in a microwave reactor. The reaction mixture was diluted with water and extracted with ethyl acetate. The combined organic layers were washed with brine, dried using a water resistant filter and concentrated under reduced pressure. The crude material was purified by flash chromatography using silica gel (gradient dichloromethane/ethanol) to provide 1.34 g of the title compound which was formed as a mixture of two racemic diastereomers as a result of atropisomerism at the newly formed bi-heteroaryl bond.

LC-MS (Method 2): $R_t$=1.65 min; MS (ESIpos): m/z=636 $[M+H]^+$ $^1$H-NMR (400 MHz, DMSO-d6) δ[ppm]: 0.788 (2.16), 0.807 (4.80), 0.826 (2.22), 0.883 (0.22), 0.901 (0.35), 0.919 (0.25), 0.928 (0.46), 0.943 (0.49), 1.008 (1.03), 1.025 (1.03), 1.035 (0.62), 1.052 (0.86), 1.070 (1.16), 1.082 (7.77), 1.097 (7.79), 1.239 (0.90), 1.246 (3.73), 1.256 (1.44), 1.264 (7.56), 1.274 (0.92), 1.282 (3.59), 2.040 (0.44), 2.060 (0.47), 2.064 (0.60), 2.076 (0.90), 2.096 (0.83), 2.120 (0.90), 2.131 (1.04), 2.145 (0.55), 2.156 (0.86), 2.163 (1.21), 2.175 (1.18), 2.182 (1.39), 2.194 (1.48), 2.518 (3.02), 2.522 (1.90), 2.952 (0.39), 2.964 (0.43), 2.989 (0.21), 3.218 (0.30), 3.234 (0.47), 3.253 (0.65), 3.272 (0.65), 3.291 (0.73), 3.762 (0.20), 3.818 (0.96), 3.857 (10.50), 3.878 (0.38), 3.898 (0.48), 3.917 (0.42), 4.114 (0.46), 4.168 (5.29), 4.194 (1.42), 4.212 (2.26), 4.220 (2.00), 4.229 (1.26), 4.238 (1.53), 4.256 (0.60), 4.261 (0.56), 4.279 (1.20), 4.288 (0.29), 4.296 (1.11), 4.306 (0.65), 4.314 (0.34), 4.323 (0.62), 4.341 (0.18), 4.701 (0.66), 4.712 (0.87), 4.721

(0.72), 4.731 (0.66), 5.759 (0.92), 6.868 (0.92), 6.874 (0.88), 6.884 (0.86), 6.890 (0.92), 7.228 (2.69), 7.250 (2.65), 7.381 (0.68), 7.388 (0.83), 7.404 (1.11), 7.411 (1.48), 7.426 (0.87), 7.433 (2.35), 7.443 (2.09), 7.448 (4.18), 7.463 (0.47), 7.525 (2.43), 7.528 (4.05), 7.532 (3.10), 7.535 (3.92), 7.539 (2.71), 7.543 (6.82), 7.546 (9.83), 7.549 (9.53), 7.554 (8.48), 7.557 (7.14), 7.564 (11.49), 7.572 (9.51), 7.592 (7.84), 7.595 (14.39), 7.601 (3.54), 7.605 (5.35), 7.608 (7.22), 7.612 (11.88), 7.621 (13.07), 7.625 (16.00), 7.629 (8.23), 7.638 (4.93), 7.641 (8.34), 7.645 (7.97), 7.648 (4.02), 7.657 (1.44), 7.676 (1.20), 7.682 (1.17), 7.749 (0.36), 7.764 (2.37), 7.785 (2.15), 8.241 (0.87), 8.256 (0.94), 8.264 (0.96), 8.278 (0.92).

Intermediate 99

(rac)-ethyl (11Z)-4-chloro-3-ethyl-7-{3-[(6-fluoronaphthalen-1-yl)oxy]propyl}-(15-rac)-(2-hydroxy-2-methylpropyl)-2-methyl-2,10,13,15-tetrahydropyrazolo[4',3':9,10][1,6]oxazacycloundecino[8,7,6-hi]indole-8-carboxylate

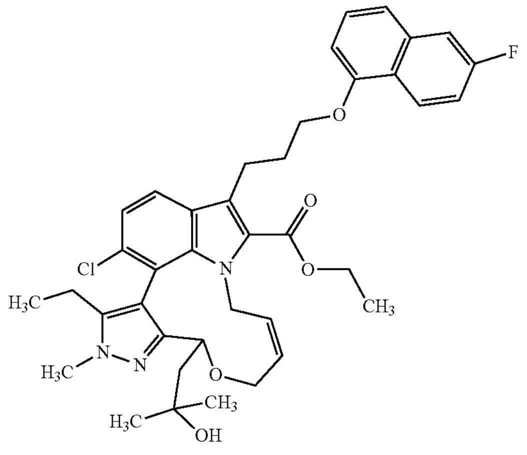 [SMILES: CCOC(=O)c1c(CCCOc2cccc3cc(F)ccc23)c2ccc(Cl)c3c2n1C/C=C\COC(CC(C)(C)O)c1nn(C)c(CC)c1-3]

Ethyl 6-chloro-7-{3-[(1-rac)-1,3-dihydroxy-3-methylbutyl]-5-ethyl-1-methyl-1H-pyrazol-4-yl}-3-{3-[(6-fluoronaphthalen-1-yl)oxy]propyl}-1H-indole-2-carboxylate (see Intermediate 98, 1.04 g) was dissolved in 8 mL of acetonitrile, cesium carbonate (2.26 g, 6.95 mmol) was added and the mixture was stirred for 10 minutes at rt. Sodium iodide (417 mg, 2.78 mmol) and (2Z)-1,4-dichlorobut-2-ene (292 μL, 2.78 mmol) were added and the mixture was stirred for 72 h at 70° C. in a sealed tube. The reaction mixture was diluted with water and extracted with ethyl acetate. The combined organic layers were washed with brine, filtered using a water resistant filter and concentrated under reduced pressure. The crude product was purified by flash chromatography using silica gel (gradient dichloromethane/ethanol) to provide 705 mg of the title compound.

LC-MS (Method 2): $R_t$=1.72 min; MS (ESIpos): m/z=688 $[M+H]^+$

Intermediate 100

(rac)-ethyl 4-chloro-3-ethyl-7-{3-[(6-fluoronaphthalen-1-yl)oxy]propyl}-(15-rac)-(2-hydroxy-2-methylpropyl)-2-methyl-2,10,11,12,13,15-hexahydropyrazolo[4',3':9,10][1,6]oxazacycloundecino[8,7,6-hi]indole-8-carboxylate

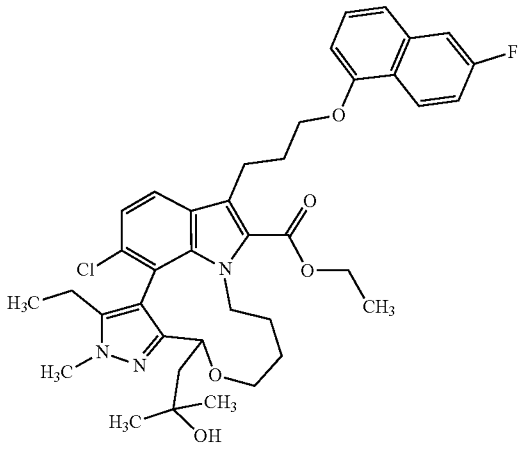 [SMILES: CCOC(=O)c1c(CCCOc2cccc3cc(F)ccc23)c2ccc(Cl)c3c2n1CCCCOC(CC(C)(C)O)c1nn(C)c(CC)c1-3]

(Rac)-ethyl (11Z)-4-chloro-3-ethyl-7-{3-[(6-fluoronaphthalen-1-yl)oxy]propyl}-(15-rac)-(2-hydroxy-2-methylpropyl)-2-methyl-2,10,13,15-tetrahydropyrazolo[4',3':9,10][1,6]oxazacycloundecino[8,7,6-hi]indole-8-carboxylate (see Intermediate 99, 165 mg) was dissolved in a mixture of 5 mL of ethanol and 1 mL of tetrahydrofuran, tris(triphenylphosphine)rhodium(I)-chloride (89.0 mg, 96 μmol) was added and the mixture was stirred for 6 h under hydrogen atmosphere at room temperature. The reaction mixture was concentrated under reduced pressure.

(Rac)-ethyl (11Z)-4-chloro-3-ethyl-7-{3-[(6-fluoronaphthalen-1-yl)oxy]propyl}-(15-rac)-(2-hydroxy-2-methylpropyl)-2-methyl-2,10,13,15-tetrahydropyrazolo[4',3':9,10][1,6]oxazacycloundecino[8,7,6-hi]indole-8-carboxylate (see Intermediate 99, 705 mg) was dissolved in a mixture of 6 mL of ethanol and 2 mL of tetrahydrofuran, tris(triphenylphosphine)rhodium(I)-chloride (428 mg, 461 μmol) was added and the mixture was stirred for 6 h under hydrogen atmosphere at room temperature. The reaction mixture was concentrated under reduced pressure.

The combined crude materials were purified by flash chromatography twice using silica gel (1. gradient hexane/ethyl acetate; 2. gradient dichloromethane/ethyl acetate) to provide 795 mg of the title compound.

LC-MS (Method 2): $R_t$=1.75 min; MS (ESIpos): m/z=690 $[M+H]^+$ $^1$H-NMR (400 MHz, DMSO-d6) δ[ppm]: 0.788 (2.16), 0.807 (4.80), 0.826 (2.22), 0.928 (0.46), 0.943 (0.49), 1.008 (1.03), 1.025 (1.03), 1.035 (0.62), 1.052 (0.86), 1.070 (1.16), 1.082 (7.77), 1.097 (7.79), 1.239 (0.90), 1.246 (3.73), 1.256 (1.44), 1.264 (7.56), 1.274 (0.92), 1.282 (3.59), 2.040 (0.44), 2.060 (0.47), 2.064 (0.60), 2.076 (0.90), 2.096 (0.83), 2.120 (0.90), 2.131 (1.04), 2.145 (0.55), 2.156 (0.86), 2.163 (1.21), 2.175 (1.18), 2.182 (1.39), 2.194 (1.48), 2.518 (3.02), 2.522 (1.90), 2.964 (0.43), 3.234 (0.47), 3.253 (0.65), 3.272 (0.65), 3.291 (0.73), 3.818 (0.96), 3.857 (10.50), 3.898 (0.48), 3.917 (0.42), 4.114 (0.46), 4.168 (5.29), 4.194 (1.42), 4.212 (2.26), 4.220 (2.00), 4.229 (1.26), 4.238 (1.53), 4.256 (0.60), 4.261 (0.56), 4.279 (1.20), 4.296 (1.11), 4.306 (0.65), 4.323 (0.62), 4.701 (0.66), 4.712 (0.87), 4.721 (0.72), 4.731 (0.66), 5.759 (0.92), 6.868 (0.92), 6.874 (0.88), 6.884 (0.86), 6.890 (0.92), 7.228 (2.69), 7.250 (2.65), 7.381 (0.68), 7.388 (0.83), 7.404 (1.11), 7.411 (1.48), 7.426 (0.87), 7.433 (2.35), 7.443 (2.09), 7.448 (4.18), 7.463 (0.47), 7.525 (2.43), 7.528 (4.05), 7.532 (3.10), 7.535 (3.92), 7.539 (2.71), 7.543 (6.82), 7.546 (9.83), 7.549 (9.53), 7.554 (8.48), 7.557 (7.14), 7.564 (11.49), 7.572 (9.51), 7.592 (7.84), 7.595 (14.39), 7.601 (3.54), 7.605 (5.35), 7.608 (7.22), 7.612 (11.88), 7.621 (13.07), 7.625 (16.00), 7.629 (8.23), 7.638 (4.93), 7.641 (8.34), 7.645 (7.97), 7.648 (4.02), 7.657 (1.44), 7.676 (1.20), 7.682 (1.17), 7.764 (2.37), 7.785 (2.15), 8.241 (0.87), 8.256 (0.94), 8.264 (0.96), 8.278 (0.92).

Intermediate 101

1-(4-bromo-5-ethyl-1-methyl-1H-pyrazol-3-yl)-3-(3,3-difluoropyrrolidin-1-yl)propan-1-one

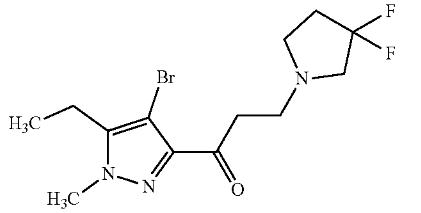 [SMILES: CCc1c(Br)c(C(=O)CCN2CCC(F)(F)C2)nn1C]

4-Bromo-5-ethyl-N-methoxy-N,1-dimethyl-1H-pyrazole-3-carboxamide (see Intermediate 90, 4.00 g, 14.5 mmol) and N,N-diisopropylethylamine (2.5 mL, 14.5 mmol) were dissolved in 15 mL of THF and a solution of bromo(vinyl)magnesium (29.0 mL, 1.0 M in 29.0 mmol) was added at 2° C. The mixture was stirred at 2° C. for 30 minutes and then added dropwise to a mixture of 3,3-difluoropyrrolidine-hydrogen chloride (1/1) (8.27 g, 57.6 mmol) in 50 mL of THF at 2° C. The mixture was stirred for 1 h at 0° C. and afterwards diluted with water and ethyl acetate. The phases were separated and the aqueous phase was extracted with ethyl acetate. The combined organic layers were washed with brine, filtered using a water resistant filter and concentrated under reduced pressure. The crude material was purified by flash chromatography using silica gel (gradient hexane/ethyl acetate) to provide 4.32 g of the title compound.

LC-MS (Method 2): $R_t$=1.17 min; MS (ESIpos): m/z=350 $[M+H]^+$ $^1$H-NMR (400 MHz, DMSO-d6) δ[ppm]: 1.080 (1.96), 1.099 (4.74), 1.117 (1.96), 1.173 (0.43), 1.988 (0.73), 2.157 (0.53), 2.178 (0.52), 2.196 (1.01), 2.213 (0.60), 2.234 (0.50), 2.483 (1.31), 2.518 (0.64), 2.523 (0.44), 2.665 (1.10), 2.674 (0.82), 2.682 (1.82), 2.692 (2.05), 2.699 (0.97), 2.711 (1.92), 2.730 (0.57), 2.742 (0.71), 2.760 (1.60), 2.777 (0.88), 2.844 (1.13), 2.877 (2.31), 2.911 (1.14), 3.043 (1.24), 3.060 (2.23), 3.078 (0.98), 3.325 (1.81), 3.330 (16.00), 3.924 (12.53).

Intermediate 102

(rac)-1-(4-bromo-5-ethyl-1-methyl-1H-pyrazol-3-yl)-3-(3,3-difluoropyrrolidin-1-yl)propan-1-ol

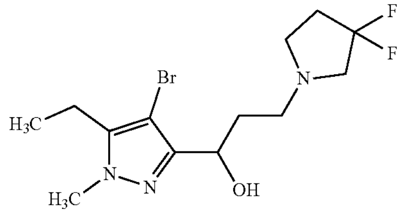 [SMILES: CCc1c(Br)c(C(O)CCN2CCC(F)(F)C2)nn1C]

1-(4-Bromo-5-ethyl-1-methyl-1H-pyrazol-3-yl)-3-(3,3-difluoropyrrolidin-1-yl)propan-1-one (see Intermediate 101, 4.32 g) was dissolved in 25 mL of methanol, sodium borohydride (1.59 g, 41.9 mmol) was added and the mixture was stirred for 18 h at room temperature. Water was added, methanol was removed and the remaining aqueous phase was extracted with ethyl acetate. The combined organic layers were washed with brine, filtered using a water resistant filter and concentrated under reduced pressure to give 4.34 g of the title compound which was used without further purification.

LC-MS (Method 2): $R_t$=1.05 min; MS (ESIpos): m/z=352 $[M+H]^+$ $^1$H-NMR (400 MHz, DMSO-d6) δ[ppm]: 1.062 (2.69), 1.081 (6.57), 1.099 (2.75), 1.154 (0.56), 1.172 (1.14), 1.190 (0.55), 1.812 (0.46), 1.831 (0.56), 1.845 (0.49), 1.876 (0.51), 1.897 (0.58), 1.914 (0.41), 1.987 (1.78), 2.169 (0.66), 2.189 (0.68), 2.208 (1.28), 2.225 (0.78), 2.246 (0.62), 2.433 (1.06), 2.451 (1.96), 2.465 (1.42), 2.469 (1.15), 2.518 (1.09), 2.522 (0.71), 2.603 (0.87), 2.622 (2.87), 2.628 (1.63), 2.641 (3.18), 2.645 (2.85), 2.662 (1.49), 2.794 (1.22), 2.827 (2.50), 2.862 (1.17), 3.381 (1.55), 3.754 (16.00), 4.017 (0.43), 4.035 (0.42), 4.543 (0.77), 4.551 (0.54), 4.557 (0.50), 4.564 (0.80), 5.049 (2.27), 5.062 (2.06).

Intermediate 103 ethyl 6-chloro-7-{3-[3-(3,3-difluoropyrrolidin-1-yl)-(1-rac)-hydroxpropyl]-5-ethyl-1-methyl-1H-pyrazol-4-yl}-3-{3-[(6-fluoronaphthalen-1-yl)oxy]propyl}-1H-indole-2-carboxylate

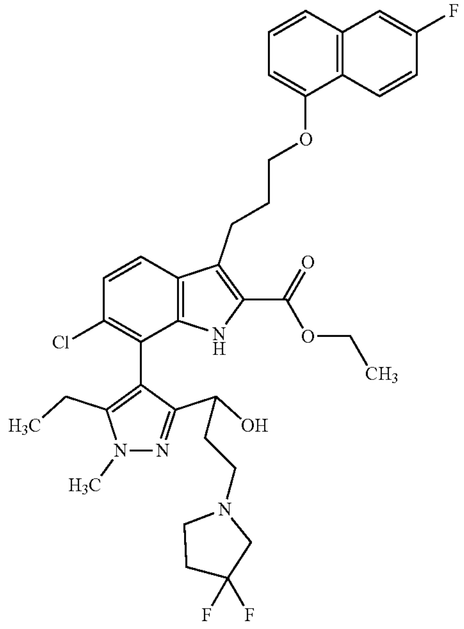 [SMILES: CCOC(=O)c1[nH]c2c(-c3c(C(O)CCN4CCC(F)(F)C4)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.50 g, 2.72 mmol), (rac)-1-(4-bromo-5-ethyl-1-methyl-1H-pyrazol-3-yl)-3-(3,3-difluoropyrrolidin-1-yl)propan-1-ol (see Intermediate 102, 1.17 g) and potassium triphosphate (1.15 g, 5.44 mmol) were provided in a mixture of 8 mL of 1,4-dioxane and 3 mL of water and purged with argon for 5 minutes. RuPhos Pd G3 (125 mg, 149 μmol) was added and the mixture was purged with argon for 5 minutes and stirred for 20 minutes at 110° C. in a microwave reactor. The reaction mixture was diluted with water and extracted with ethyl acetate. The combined organic layers were washed with brine, dried using a water resistant filter and concentrated under reduced pressure. The crude material was purified by flash chromatography using silica gel (gradient hexane/ethyl acetate) and preparative HPLC (Method P3) to provide 428 mg of the title compound which was formed as a mixture of two racemic diastereomers as a result of atropisomerism at the newly formed bi-heteroaryl bond.

LC-MS (Method 2): $R_t$=1.70 min; MS (ESIpos): m/z=697 $[M+H]^+$ $^1$H-NMR (400 MHz, DMSO-d6) δ[ppm]: 0.834 (0.96), 0.850 (3.99), 0.869 (8.22), 0.888 (3.59), 0.928 (1.28), 0.944 (1.24), 1.087 (1.40), 1.102 (1.40), 1.227 (6.10), 1.245 (12.49), 1.263 (5.79), 1.471 (0.44), 1.489 (0.48), 1.751 (0.44), 1.765 (0.56), 1.785 (1.00), 1.799 (1.36), 1.813 (1.00), 1.831 (0.56), 2.036 (0.60), 2.050 (0.64), 2.058 (0.68), 2.073 (3.91), 2.089 (0.92), 2.105 (0.60), 2.128 (0.48), 2.208 (1.60), 2.227 (1.24), 2.256 (0.40), 2.298 (0.60), 2.317 (1.20), 2.327 (2.03), 2.331 (1.80), 2.335 (1.80), 2.342 (1.64), 2.347 (1.44), 2.354 (2.07), 2.368 (2.00), 2.372 (1.80), 2.387 (2.15), 2.405 (1.16), 2.413 (0.64), 2.424 (0.44), 2.437 (0.44), 2.462 (1.28), 2.518 (4.03), 2.523 (2.55), 2.539 (0.56), 2.624 (0.80), 2.630 (0.56), 2.636 (0.76), 2.658 (1.60), 2.665 (1.44), 2.669 (2.27), 2.692 (0.72), 2.697 (0.56), 2.703 (0.72), 3.288 (1.28), 3.304 (2.27), 3.308 (2.23), 3.818 (4.31), 3.840 (16.00), 4.140 (0.48), 4.154 (0.96), 4.159 (0.72), 4.166 (0.84), 4.172 (0.88), 4.186 (0.72), 4.202 (1.76), 4.217 (3.47), 4.220 (3.11), 4.232 (2.59), 4.238 (4.71), 4.251 (1.44), 4.256 (4.19), 4.274 (1.24), 4.790 (2.19), 4.802 (2.11), 5.052 (0.52), 5.062 (0.48), 6.634 (0.44), 6.655 (0.48), 6.874 (0.48), 6.881 (0.44), 6.888 (1.52), 6.896 (1.64), 6.903 (1.12), 6.910 (1.32), 7.162 (4.03), 7.167 (1.12), 7.183 (4.19), 7.188 (1.16), 7.378 (1.08), 7.384 (1.28), 7.400 (1.64), 7.407 (1.80), 7.417 (0.60), 7.422 (1.20), 7.429 (1.36), 7.438 (2.75), 7.445 (3.35), 7.453 (6.26), 7.466 (0.56), 7.650 (1.88), 7.657 (1.96), 7.676 (1.96), 7.683 (2.00), 7.695 (3.15), 7.717 (2.83), 8.249 (1.32), 8.263 (1.72), 8.271 (1.40), 8.277 (0.52), 8.286 (1.60), 10.709 (2.71).

Intermediate 104

(rac)-ethyl (11Z)-4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate

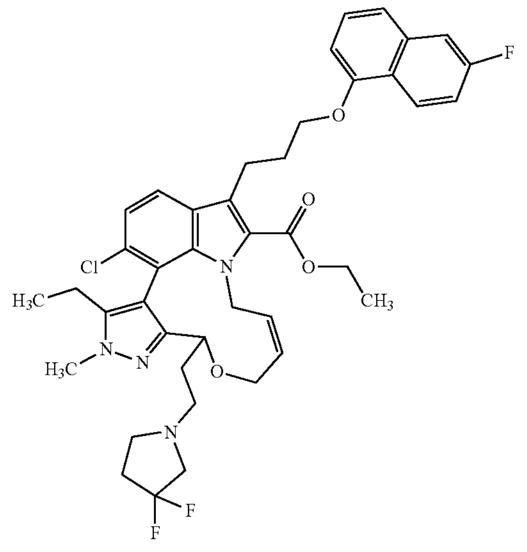 [SMILES: CCOC(=O)c1c(CCCOc2cccc3cc(F)ccc23)c2ccc(Cl)c3c2n1C/C=C\COC(CCN1CCC(F)(F)C1)c1nn(C)c(CC)c1-3]

Ethyl 6-chloro-7-{3-[(1-rac)-3-(3,3-difluoropyrrolidin-1-yl)-1-hydroxypropyl]-5-ethyl-1-methyl-1H-pyrazol-4-yl}-3-{3-[(6-fluoronaphthalen-1-yl)oxy]propyl}-1H-indole-2-carboxylate (see Intermediate BRKT643, 425 mg, 579 μmol) was dissolved in 5 mL of acetonitrile, cesium carbonate (943 mg, 2.90 mmol) was added and the mixture was stirred for 10 minutes at rt. (2Z)-1,4-dichlorobut-2-ene (122 μL, 1.16 mmol) and sodium iodide (174 mg, 1.16 mmol) were added and the mixture was stirred for 26 h at 70° C. in a sealed tube. The reaction mixture was diluted with water and extracted with ethyl acetate. The combined organic layers were washed with brine, dried using a water resistant filter and concentrated under reduced pressure. The crude material was purified by flash chromatography using silica gel (gradient dichloromethane/ethanol) to give 236 mg of the title compound.

LC-MS (Method 2): $R_t$=1.76 min; MS (ESIpos): m/z=749 $[M+H]^+$ $^1$H-NMR (400 MHz, DMSO-d6) δ[ppm]: 0.627 (0.61), 0.646 (0.69), 0.775 (3.37), 0.795 (7.35), 0.802 (2.07), 0.814 (4.36), 0.821 (3.90), 0.840 (4.67), 0.851 (1.68), 0.859 (2.60), 0.871 (1.99), 0.877 (1.53), 0.886 (1.99), 0.896 (1.91), 0.905 (2.76), 0.915 (2.53), 0.922 (2.14), 0.929 (9.11), 0.945 (8.73), 1.053 (1.53), 1.071 (2.30), 1.088 (9.42), 1.103 (9.03), 1.135 (3.52), 1.152 (6.20), 1.170 (3.22), 1.221 (3.44), 1.239 (6.05), 1.251 (7.12), 1.257 (4.06), 1.268 (11.71), 1.286 (5.67), 1.491 (0.77), 1.580 (1.30), 1.640 (1.22), 1.709 (0.84), 1.747 (1.07), 1.760 (1.00), 1.905 (1.07), 1.953 (0.84), 1.964 (1.00), 1.987 (0.92), 2.073 (1.84), 2.092 (2.14), 2.111 (2.37), 2.129 (2.45), 2.156 (3.37), 2.179 (3.75), 2.198 (3.29), 2.218 (2.99), 2.238 (2.76), 2.276 (1.45), 2.295 (1.30), 2.318 (2.53), 2.323 (4.13), 2.327 (5.51), 2.332 (4.13), 2.336 (2.22), 2.358 (0.92), 2.374 (1.00), 2.388 (1.15), 2.412 (1.38), 2.449 (2.37), 2.518 (15.39), 2.523 (11.79), 2.546 (1.22), 2.556 (2.22), 2.574 (3.44), 2.592 (1.84), 2.635 (1.00), 2.660 (2.14), 2.665 (4.13), 2.669 (5.44), 2.673 (3.75), 2.679 (2.14), 2.707 (1.00), 2.741 (1.53), 2.770 (1.45), 2.802 (0.77), 2.831 (0.38), 3.256 (1.91), 3.273 (1.91), 3.288 (2.30), 3.377 (0.69), 3.646 (1.00), 3.668 (1.15), 3.679 (1.15), 3.717 (7.50), 3.727 (1.68), 3.779 (2.07), 3.786 (1.91), 3.793 (4.59), 3.806 (4.36), 3.836 (3.29), 3.893 (16.00), 4.047 (0.92), 4.066 (1.07), 4.074 (1.30), 4.092 (1.30), 4.110 (0.92), 4.127 (0.92), 4.158 (1.68), 4.176 (1.99), 4.207 (4.36), 4.214 (4.67), 4.225 (6.12), 4.232 (5.74), 4.241 (6.74), 4.255 (3.67), 4.259 (4.06), 4.280 (2.60), 4.298 (2.14), 4.307 (1.38), 4.316 (1.00), 4.325 (1.15), 4.343 (0.61), 4.373 (0.69), 4.388 (1.38), 4.403 (1.76), 4.418 (1.38), 4.433 (0.61), 4.532 (0.61), 4.545 (0.92), 4.558 (0.61), 4.618 (0.77), 4.645 (0.84), 4.658 (0.92), 4.686 (0.84), 4.782 (1.00), 4.885 (1.30), 4.916 (1.22), 4.937 (1.30), 4.964 (0.92), 5.059 (0.69), 5.087 (0.84), 5.113 (0.69), 5.156 (1.00), 5.271 (0.54), 5.719 (0.46), 5.746 (0.69), 5.753 (0.61), 5.759 (0.77), 5.780 (0.77), 5.938 (0.54), 5.981 (0.46), 6.454 (0.92), 6.488 (0.84), 6.634 (2.76), 6.656 (2.99), 6.886 (1.99), 6.894 (2.60), 6.900 (2.68), 6.908 (2.37), 6.946 (0.46), 6.955 (0.46), 6.962 (0.46), 6.970 (0.46), 7.146 (0.61), 7.167 (0.69), 7.183 (1.00), 7.203 (1.68), 7.219 (1.30), 7.224 (1.15), 7.240 (1.45), 7.264 (1.00), 7.270 (2.60), 7.273 (4.13), 7.294 (4.44), 7.355 (1.22), 7.362 (1.53), 7.378 (2.37), 7.385 (3.29), 7.400 (2.91), 7.406 (3.37), 7.422 (2.30), 7.444 (7.89), 7.452 (9.72), 7.456 (6.97), 7.651 (3.14), 7.657 (3.52), 7.677 (3.06), 7.683 (3.22), 7.726 (0.61), 7.734 (0.84), 7.744 (1.22), 7.758 (2.07), 7.766 (1.07), 7.779 (1.84), 7.802 (0.84), 7.810 (3.67), 7.831 (3.14), 8.191 (1.30), 8.207 (1.45), 8.215 (1.53), 8.229 (1.61), 8.237 (1.30), 8.252 (1.38), 8.260 (1.38), 8.275 (1.45), 8.298 (0.61), 8.312 (0.46).

Intermediate 105

(rac)-ethyl 4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

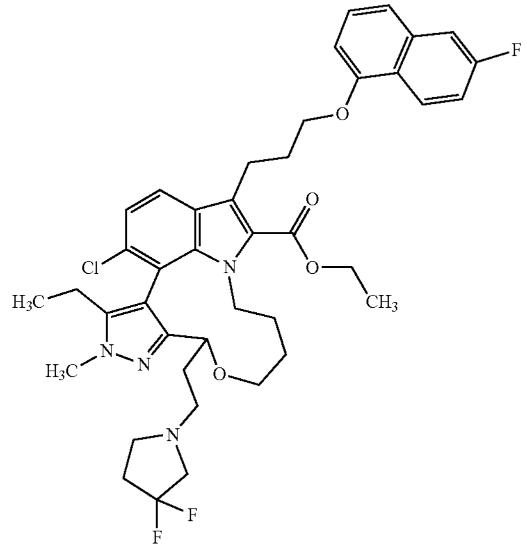 [SMILES: CCOC(=O)c1c(CCCOc2cccc3cc(F)ccc23)c2ccc(Cl)c3c2n1CCCCOC(CCN1CCC(F)(F)C1)c1nn(C)c(CC)c1-3]

(Rac)-ethyl (11Z)-4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate (see Intermediate 104, 300 mg) was dissolved in a mixture of 5 mL of ethanol and 1 mL of tetrahydrofuran, tris(triphenylphosphine)rhodium(I)-chloride (130 mg, 140 μmol) was added and the mixture was stirred for 6 h under hydrogen atmosphere at room temperature. The reaction mixture was concentrated under reduced pressure. The crude material was purified by flash chromatography using silica gel (gradient dichloromethane/ethanol) to provide 264 mg of the title compound.

LC-MS (Method 2): $R_t$=1.81 min; MS (ESIpos): m/z=751 $[M+H]^+$ $^1$H-NMR (400 MHz, DMSO-d6) δ[ppm]: 0.764 (0.58), 0.783 (1.39), 0.787 (1.75), 0.807 (3.73), 0.825 (1.83), 0.840 (0.73), 0.859 (1.02), 0.878 (0.66), 0.904 (0.44), 0.929 (3.29), 0.945 (3.29), 1.071 (1.17), 1.088 (3.80), 1.103 (3.58), 1.147 (0.80), 1.154 (1.90), 1.165 (1.32), 1.172 (3.51), 1.182 (0.80), 1.190 (1.97), 1.232 (1.46), 1.247 (3.29), 1.265 (5.77), 1.283 (2.78), 1.579 (0.51), 1.641 (0.51), 1.757 (0.80), 1.774 (0.51), 1.987 (5.84), 2.066 (0.80), 2.162 (1.10), 2.181 (2.05), 2.199 (2.05), 2.332 (2.34), 2.336 (1.17), 2.518 (14.47), 2.523 (9.13), 2.609 (0.51), 2.627 (0.88), 2.637 (0.88), 2.673 (2.26), 2.805 (0.58), 2.829 (0.51), 3.778 (1.53), 3.845 (0.73), 3.864 (7.67), 3.999 (0.51), 4.017 (1.32), 4.035 (1.24), 4.053 (0.51), 4.195 (1.53), 4.205 (1.68), 4.213 (1.90), 4.222 (1.83), 4.240 (1.39), 4.279 (1.02), 4.297 (0.88), 4.305 (0.51), 4.324 (0.51), 4.388 (0.58), 4.404 (0.80), 4.411 (0.80), 4.418 (0.58), 4.427 (0.51), 5.758 (13.95), 6.635 (1.02), 6.656 (1.10), 6.862 (0.66), 6.869 (0.80), 6.879 (0.80), 6.884 (0.95), 7.204 (0.66), 7.226 (2.05), 7.233 (0.66), 7.248 (2.05), 7.254 (0.58), 7.371 (0.88), 7.377 (0.88), 7.392 (1.10), 7.400 (1.24), 7.409 (0.95), 7.415 (0.95), 7.421 (1.10), 7.431 (1.83), 7.440 (2.41), 7.445

(3.87), 7.454 (1.32), 7.526 (3.07), 7.528 (4.46), 7.533 (3.51), 7.536 (4.60), 7.540 (3.29), 7.545 (8.18), 7.547 (11.47), 7.549 (10.52), 7.555 (9.86), 7.558 (8.04), 7.565 (12.93), 7.573 (11.40), 7.591 (9.35), 7.595 (15.93), 7.601 (3.80), 7.606 (6.36), 7.609 (8.55), 7.612 (13.37), 7.615 (11.84), 7.622 (16.00), 7.625 (15.56), 7.629 (9.13), 7.632 (8.11), 7.637 (5.70), 7.641 (10.23), 7.645 (9.94), 7.649 (4.68), 7.653 (2.26), 7.674 (1.10), 7.679 (1.10), 7.724 (0.51), 7.746 (0.51), 7.770 (1.75), 7.792 (1.61), 8.207 (0.66), 8.221 (0.73), 8.230 (0.73), 8.245 (0.73).

Intermediate 106

(rac)-(4-bromo-5-ethyl-1-methyl-1H-pyrazol-3-yl)(phenyl)methanol

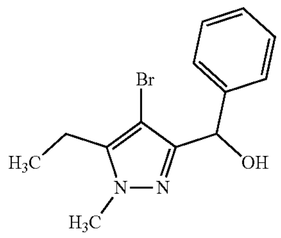 [SMILES: CCc1c(Br)c(C(O)c2ccccc2)nn1C]

4-Bromo-5-ethyl-1-methyl-1H-pyrazole-3-carbaldehyde (see Intermediate 21, 10.0 g, 46.1 mmol) was dissolved in tetrahydrofuran (50 mL) and the mixture cooled to −78° C., then phenylmagnesium bromide (38 mL, 3.0 M in diethyl ether, 120 mmol) was added dropwise over 1 h, the mixture was stirred for an additional 1 h at −78° C. and then warmed to room temperature over 16 hours. The reaction mixture was carefully treated with saturated aqueous ammonium chloride solution and extracted repeatedly with dichloromethane. Combined organic layers were washed with saturated aqueous ammonium chloride solution, dried over magnesium sulfate and concentrated under reduced pressure. The residue was purified by flash chromatography on silica gel (gradient hexane/ethyl acetate) to provide the title compound as a light yellow material (9 g).

$^1$H-NMR (300 MHz, CHLOROFORM-d) delta [ppm]: 1.131 (3.13), 1.156 (7.01), 1.181 (3.32), 1.245 (0.49), 1.269 (0.99), 1.293 (0.49), 2.053 (1.74), 2.598 (1.05), 2.648 (2.85), 2.674 (0.83), 3.331 (2.07), 3.351 (2.14), 3.787 (16.00), 4.118 (0.38), 4.142 (0.38), 5.838 (1.36), 5.858 (1.32), 7.239 (0.16), 7.244 (0.31), 7.249 (0.19), 7.258 (0.25), 7.286 (0.63), 7.291 (1.17), 7.296 (0.63), 7.308 (0.27), 7.317 (1.50), 7.321 (0.75), 7.335 (1.05), 7.341 (2.46), 7.358 (0.40), 7.364 (1.05), 7.369 (0.66), 7.451 (0.32), 7.458 (1.89), 7.461 (2.05), 7.465 (1.08), 7.478 (0.48), 7.484 (1.47), 7.490 (1.04).

Intermediate 107 ethyl 6-chloro-7-{5-ethyl-3-[(rac)-hydroxy(phenyl)methyl]-1-methyl-1H-pyrazol-4-yl}-3-{3-[(6-fluoronaphthalen-1-yl)oxy]propyl}-1H-indole-2-carboxylate

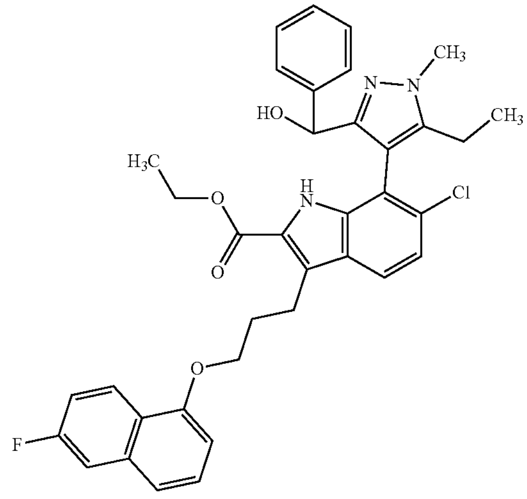 [SMILES: CCOC(=O)c1[nH]c2c(-c3c(C(O)c4ccccc4)nn(C)c3CC)c(Cl)ccc2c1CCCOc1cccc2cc(F)ccc12]

(rac)-(4-Bromo-5-ethyl-1-methyl-1H-pyrazol-3-yl)(phenyl)methanol (see Intermediate 106, 1.00 g, 3.39 mmol) was dissolved in toluene (20 mL), treated with RuPhos Pd G3 (258 mg, 308 μmol), ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.70 g, 3.08 mmol) and tripotassium phosphate (4.6 mL, 1.0 M in water, 4.6 mmol) and transferred to a preheated 100° C. block for 2 hours. The mixture was cooled to room temperature, treated with celite, concentrated under reduced pressure. The residue was purified by HPLC (Chromatorex C-18 10 μm; 125*30 mm (gradient acetonitrile/water (0.1% formic acid)) to give the title compound (100 mg), which was formed as a mixture of two racemic diastereomers as a result of atropisomerism at the newly formed bi-heteroaryl bond.

$^1$H-NMR (300 MHz, CHLOROFORM-d) delta [ppm]: 0.967 (3.25), 0.979 (1.32), 0.992 (7.86), 1.010 (5.87), 1.018 (3.73), 1.030 (5.35), 1.130 (0.92), 1.151 (1.74), 1.167 (6.17), 1.188 (5.77), 1.266 (0.73), 1.343 (1.05), 1.355 (4.81), 1.362 (2.54), 1.367 (1.88), 1.379 (9.89), 1.386 (4.14), 1.402 (4.80), 1.410 (2.02), 1.627 (0.80), 1.765 (0.68), 1.827 (0.40), 1.874 (0.34), 1.899 (0.34), 2.015 (1.69), 2.310 (1.20), 2.332 (1.66), 2.352 (1.38), 2.376 (1.15), 2.401 (1.49), 2.414 (0.51), 2.427 (1.37), 2.440 (1.23), 2.452 (0.48), 2.465 (1.32), 2.489 (0.69), 2.514 (0.39), 3.319 (0.97), 3.329 (0.94), 3.343 (1.67), 3.355 (1.63), 3.368 (0.91), 3.385 (1.10), 3.410 (0.60), 3.949 (16.00), 3.966 (1.58), 4.147 (0.69), 4.167 (1.55), 4.188 (2.38), 4.209 (3.31), 4.230 (1.41), 4.326 (1.74), 4.349 (4.40), 4.368 (2.45), 4.373 (4.03), 4.386 (1.07), 4.392 (1.92), 4.397 (1.33), 4.405 (1.11), 4.415 (0.56), 4.426 (0.75), 5.309 (2.91), 5.633 (4.80), 6.567 (1.87), 6.594 (2.03), 6.667 (0.39), 6.676 (0.33), 6.686 (0.40), 6.696 (0.40), 6.727 (1.26), 6.733 (1.11), 6.749 (1.38), 6.755 (1.22), 6.851 (0.85), 6.980 (1.58), 6.986 (2.26), 6.997 (8.36), 7.020 (1.78), 7.042 (0.77), 7.048 (0.82), 7.070 (3.38), 7.080 (0.61), 7.098 (3.83), 7.198 (0.92), 7.207 (0.40), 7.226 (1.38), 7.232 (1.11), 7.241 (1.24), 7.253 (1.19), 7.291 (0.94), 7.299 (0.97), 7.343 (2.10), 7.351 (1.19), 7.375

(4.94), 7.397 (2.37), 7.406 (1.71), 7.415 (1.58), 7.423 (1.34), 7.439 (1.52), 7.447 (1.49), 7.476 (0.61), 7.500 (0.32), 7.519 (2.26), 7.548 (1.98), 7.572 (0.75), 7.601 (0.64), 8.039 (5.71), 8.133 (1.28), 8.244 (0.38), 8.263 (0.37), 8.275 (0.38), 8.293 (0.34), 8.352 (1.22), 8.371 (1.25), 8.383 (1.20), 8.402 (1.16).

Intermediate 108 ethyl (11Z,15 rac)-4-chloro-3-ethyl-7-{3-[(6-fluoronaphthalen-1-yl)oxy]propyl}-2-methyl-15-phenyl-2,10,13,15-tetrahydropyrazolo[4',3':9,10][1,6]oxazacycloundecino[8,7,6-hi]indole-8-carboxylate

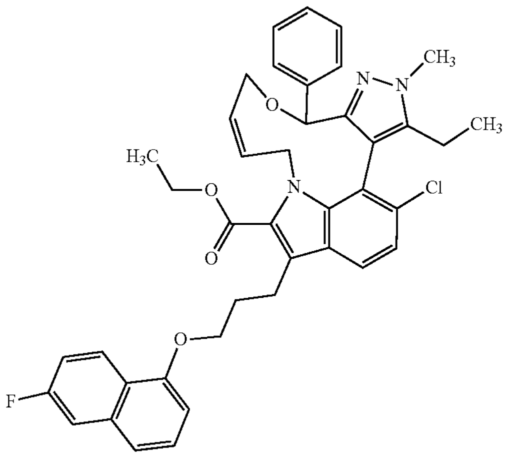 [SMILES: CCOC(=O)c1c(CCCOc2cccc3cc(F)ccc23)c2ccc(Cl)c3c2n1C/C=C\COC(c1ccccc1)c1nn(C)c(CC)c1-3]

Ethyl-6-chloro-7-{5-ethyl-3-[(rac)-hydroxy(phenyl)methyl]-1-methyl-1H-pyrazol-4-yl}-3-{3-[(6-fluoronaphthalen-1-yl)oxy]propyl}-1H-indole-2-carboxylate (see Intermediate 107, 610 mg, 858 μmol) was dissolved acetonitrile (10 mL), cesium carbonate (1.40 g, 4.29 mmol) was added and the mixture stirred for 10 minutes at room temperature. A solution of (2Z)-1,4-dichlorobut-2-ene (180 μL, 1.7 mmol) dissolved in acetonitrile (5 mL) was then added dropwise to the reaction mixture, followed by sodium iodide (257 mg, 1.72 mmol) and the mixture was then heated at 70° C. for 16 hours. After cooling to room temperature water was added and the reaction mixture was extracted repeatedly with ethyl acetate. The combined organic phases were washed with saturated aqueous sodium chloride solution and dried over magnesium sulfate, concentrated under reduced pressure and the residue purified by HPLC (Chromatorex C-18 10 μm; 125*30 mm) to provide the target compound (240 mg).

$^{1}$H-NMR (400 MHz, CHLOROFORM-d) delta [ppm]: 0.887 (4.18), 0.905 (8.19), 0.924 (3.96), 1.014 (1.75), 1.028 (1.73), 1.173 (2.26), 1.188 (1.90), 1.268 (1.05), 1.381 (5.22), 1.399 (9.34), 1.416 (4.61), 2.015 (0.94), 2.233 (1.45), 2.251 (3.56), 2.270 (3.54), 2.288 (1.55), 2.354 (2.24), 2.370 (3.02), 2.386 (2.10), 3.352 (1.83), 3.370 (2.29), 3.400 (1.93), 3.416 (1.15), 4.010 (16.00), 4.061 (1.67), 4.176 (1.79), 4.207 (2.55), 4.246 (5.70), 4.261 (2.68), 4.360 (2.47), 4.381 (3.07), 4.401 (2.32), 4.922 (0.87), 4.948 (1.10), 4.962 (1.32), 4.988 (1.45), 5.135 (2.02), 5.176 (1.44), 5.249 (1.26), 5.278 (1.95), 5.309 (5.07), 5.416 (5.97), 6.742 (2.28), 6.758 (2.35), 7.191 (2.82), 7.212 (3.99), 7.232 (3.05), 7.301 (5.31), 7.319 (2.60), 7.358 (2.13), 7.378 (6.91), 7.395 (2.91), 7.417 (3.00), 7.443 (2.41), 7.527 (5.26), 7.546 (4.35), 7.639 (3.02), 7.660 (2.76), 8.033 (2.50), 8.339 (1.41), 8.361 (1.79), 8.375 (1.52).

Intermediate 109 ethyl (rac)-4-chloro-3-ethyl-7-{3-[(6-fluoronaphthalen-1-yl)oxy]propyl}-2-methyl-15-rac)-phenyl-2,10,11,12,13,15-hexahydropyrazolo[4',3':9,10][1,6]oxazacycloundecino[8,7,6-hi]indole-8-carboxylate

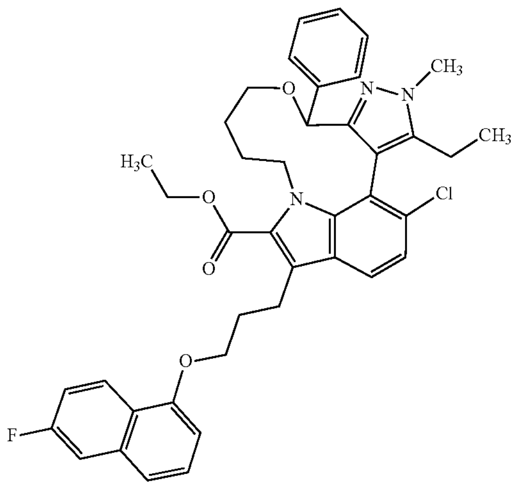 [SMILES: CCOC(=O)c1c(CCCOc2cccc3cc(F)ccc23)c2ccc(Cl)c3c2n1CCCCOC(c1ccccc1)c1nn(C)c(CC)c1-3]

Ethyl-(rac)-4-chloro-3-ethyl-7-{3-[(6-fluoronaphthalen-1-yl)oxy]propyl}-2-methyl-15-phenyl-2,10,13,15-tetrahydropyrazolo[4',3':9,10][1,6]oxazacycloundecino[8,7,6-hi]indole-8-carboxylate (see Intermediate 108, 240 mg, 312 μmol) was dissolved in ethanol (5 mL), treated with Tris(triphenylphosphine)rhodium(I)-chloride (144 mg, 156 μmol) and stirred under hydrogen atmosphere at room temperature for two days. The reaction mixture was filtered through celite, the filter cake washed with ethanol twice, and the combined filtrates concentrated under reduced pressure to provide the title compound (115 mg).

$^{1}$H-NMR (300 MHz, CHLOROFORM-d) delta [ppm]: 0.894 (3.13), 0.920 (7.31), 0.937 (1.48), 0.945 (3.52), 0.960 (2.42), 0.984 (1.83), 1.028 (0.72), 1.051 (0.38), 1.072 (0.77), 1.097 (1.69), 1.107 (0.78), 1.122 (0.83), 1.266 (2.09), 1.360 (4.42), 1.374 (1.63), 1.384 (9.32), 1.397 (2.47), 1.407 (4.36), 1.421 (1.03), 1.622 (1.13), 2.014 (0.56), 2.255 (0.88), 2.280 (2.23), 2.306 (2.39), 2.331 (1.61), 2.349 (1.32), 2.372 (0.85), 3.253 (0.34), 3.292 (0.51), 3.323 (0.96), 3.347 (1.23), 3.372 (0.95), 3.404 (1.50), 3.416 (1.02), 3.443 (0.82), 3.456 (1.00), 3.471 (0.68), 3.585 (0.38), 3.611 (0.75), 3.635 (0.47), 3.651 (0.45), 3.855 (16.00), 3.920 (2.95), 3.948 (0.61), 3.970 (0.94), 4.003 (0.34), 4.192 (1.23), 4.213 (2.35), 4.267 (0.36), 4.290 (0.73), 4.303 (0.58), 4.314 (0.76), 4.327 (1.74), 4.345 (1.30), 4.351 (1.81), 4.367 (2.13), 4.391 (1.79), 4.403 (0.74), 4.414 (0.52), 4.427 (0.69), 4.463 (1.15), 4.482 (1.78), 4.502 (1.09), 5.161 (0.96), 5.265 (3.06), 5.308 (7.63), 6.705 (1.03), 6.714 (0.93), 6.725 (1.38), 6.734 (1.42), 6.755 (0.47), 7.036 (0.34), 7.113 (2.14), 7.135 (0.81), 7.163 (0.79), 7.223 (0.78), 7.231 (1.27), 7.252 (4.62), 7.261 (3.59), 7.281 (5.56), 7.290 (1.99), 7.334 (2.01), 7.358 (7.62), 7.365 (3.20), 7.373 (2.12), 7.378 (2.97), 7.397 (1.78), 7.406 (1.81), 7.431 (1.51), 7.439 (1.42), 7.552 (2.72), 7.576 (2.17), 7.599 (0.80), 7.616 (0.49), 7.628 (0.65), 7.662 (3.26), 7.691 (2.78), 7.988 (0.69), 8.327 (1.12), 8.346 (1.31), 8.358 (1.16), 8.377 (1.29), 8.398 (0.38).

Intermediate 110

1-(4-bromo-5-ethyl-1-methyl-1H-pyrazol-3-yl)-4-(morpholin-4-yl)butan-1-one

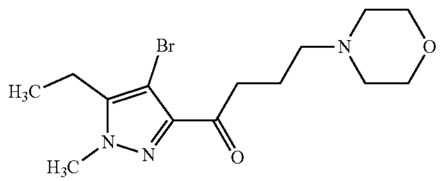 [SMILES: CCc1c(Br)c(C(=O)CCCN2CCOCC2)nn1C]

Magnesium (891 mg, 36.7 mmol) and a small amount of iodine were stirred at rt for 15 minutes. Tetrahydrofuran (10 mL) and 4-(3-chloropropyl)morpholine (3.00 g, 18.3 mmol) were added and the mixture was stirred for 1 h at 50° C. and for 1 h at 70° C. After filtration, the solution was added dropwise to a solution of 4-bromo-5-ethyl-N-methoxy-N,1-dimethyl-1H-pyrazole-3-carboxamide (see Intermediate 90, 1.78 g, 6.45 mmol) in 10 mL of tetrahydrofuran at 2° C. The mixture was stirred for 1 h at 0° C., a saturated aqueous solution of ammonium chloride was added and the mixture was extracted with ethyl acetate. The combined organic layers were filtered through a water resistant filter and the filtrate was concentrated under reduced pressure. The crude material was purified by flash chromatography using silica gel (gradient dichloromethane/ethanol) to provide 1.93 g of the title compound.

LC-MS (Method 2): $R_t$=1.02 min; MS (ESIpos): m/z=344 $[M+H]^+$ $^1$H-NMR (400 MHz, DMSO-d6) δ[ppm]: 1.074 (2.65), 1.093 (6.42), 1.112 (2.71), 1.727 (1.30), 1.744 (2.09), 1.762 (1.40), 2.248 (1.72), 2.266 (4.16), 2.283 (3.07), 2.518 (0.66), 2.523 (0.45), 2.670 (0.86), 2.689 (2.59), 2.708 (2.53), 2.727 (0.72), 2.883 (1.62), 2.900 (3.36), 2.919 (1.49), 3.465 (1.99), 3.476 (2.96), 3.488 (2.07), 3.908 (16.00).

Intermediate 111

(rac)-1-(4-bromo-5-ethyl-1-methyl-1H-pyrazol-3-yl)-4-(morpholin-4-yl)butan-1-ol

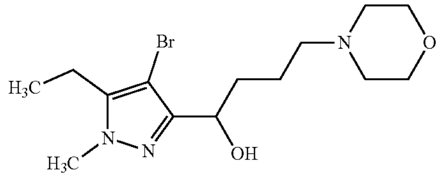 [SMILES: CCc1c(Br)c(C(O)CCCN2CCOCC2)nn1C]

1-(4-Bromo-5-ethyl-1-methyl-1H-pyrazol-3-yl)-4-(morpholin-4-yl)butan-1-one (see Intermediate 110, 1.99 g, 5.78 mmol) was dissolved in 10 mL of methanol, sodium borohydride (875 mg, 23.1 mmol) was added portionwise and the mixture was stirred for 24 h at room temperature. The reaction mixture was diluted with water, methanol was removed under reduced pressure and the aqueous phase was extracted with ethyl acetate. The combined organic layers were washed with brine, filtered through a water resistant filter and the filtrate was concentrated under reduced pressure to give 1.94 g (97% yield) of the title compound which was used without further purification.

LC-MS (Method 2): $R_t$=0.91 min; MS (ESIpos): m/z=346 $[M+H]^+$ $^1$H-NMR (400 MHz, DMSO-d6) δ[ppm]: 1.059 (2.60), 1.078 (6.46), 1.097 (2.73), 1.723 (0.68), 1.728 (0.51), 1.738 (0.73), 1.744 (0.69), 1.753 (0.50), 1.760 (0.58), 2.215 (1.15), 2.233 (2.00), 2.251 (1.05), 2.287 (1.75), 2.518 (0.64), 2.523 (0.42), 2.601 (0.75), 2.620 (2.51), 2.639 (2.39), 2.658 (0.68), 3.530 (2.16), 3.541 (3.27), 3.552 (2.22), 3.748 (16.00), 4.458 (0.51), 4.470 (0.52), 5.050 (0.90), 5.062 (0.91).

Intermediate 112 ethyl 6-chloro-7-{5-ethyl-3-[(1-rac)-hydroxy-4-(morpholin-4-yl)butyl]-1-methyl-1H-pyrazol-4-yl}-3-{3-[(6-fluoronaphthalen-1-yl)oxy]propyl}-1H-indole-2-carboxylate

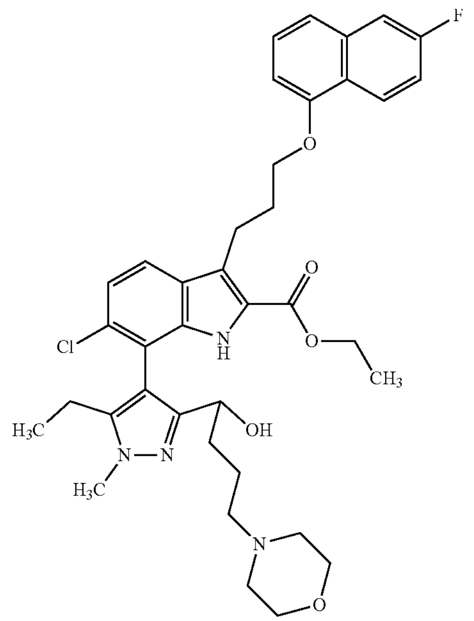 [SMILES: CCOC(=O)c1[nH]c2c(-c3c(C(O)CCCN4CCOCC4)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.35 g, 2.45 mmol), (rac)-1-(4-bromo-5-ethyl-1-methyl-1H-pyrazol-3-yl)-4-(morpholin-4-yl)butan-1-ol (see Intermediate 111, 932 mg, 2.69 mmol) and potassium triphosphate (1.04 g, 4.89 mmol) were provided in a mixture of 8 mL of 1,4- dioxane and 2 mL of water and purged with argon for 5 minutes. RuPhos Pd G3 (113 mg, 135 μmol) was added and the mixture was purged with argon for 5 minutes and stirred for 1 h at 110° C. in a microwave reactor. The reaction mixture was diluted with water and extracted with ethyl acetate. The combined organic layers were dried using a water resistant filter and concentrated under reduced pressure. The crude material was purified by flash chromatography using silica gel (gradient dichloromethane/ethanol) to provide 814 mg (45% yield) of the title compound which was formed as a mixture of two racemic diastereomers as a result of atropisomerism at the newly formed bi-heteroaryl bond.

LC-MS (Method 2): $R_t$=1.66 min; MS (ESIpos): m/z=691 $[M+H]^+$ $^1$H-NMR (400 MHz, DMSO-d6) δ[ppm]: 0.816 (0.89), 0.820 (0.62), 0.835 (2.01), 0.848 (3.53), 0.867 (7.83), 0.885 (3.53), 0.903 (0.43), 1.065 (0.39), 1.168 (1.32), 1.186 (3.10), 1.205 (1.74), 1.228 (5.73), 1.246 (12.09), 1.263 (5.62), 1.284 (0.54), 1.300 (0.77), 1.323 (0.85), 1.340 (0.77), 1.361 (0.70), 1.381 (0.58), 1.671 (0.54), 1.691 (0.66), 1.707 (0.81), 1.719 (0.93), 1.737 (1.16), 1.755 (0.85), 2.091 (2.21), 2.109 (3.53), 2.126 (1.59), 2.193 (3.84), 2.229 (1.43), 2.247 (1.20), 2.265 (1.24), 2.283 (1.05), 2.298 (0.81), 2.322 (1.05), 2.326 (1.12), 2.331 (0.89), 2.340 (0.77), 2.359 (1.16), 2.378 (1.74), 2.383 (1.51), 2.397 (1.47), 2.403 (1.51), 2.421 (0.62), 2.518 (4.07), 2.522 (2.44), 2.620 (0.81), 2.639 (0.81), 2.659 (0.58), 2.664 (0.74), 2.669 (0.97), 2.673 (0.74), 2.869 (0.62), 2.887 (1.20), 2.905 (0.58), 3.291 (1.24), 3.308 (2.32), 3.323 (3.22), 3.394 (0.89), 3.405 (1.39), 3.417 (1.01), 3.447 (2.71), 3.459 (4.07), 3.469 (2.75), 3.497 (1.01), 3.509 (1.28), 3.519 (0.89), 3.808 (6.12), 3.816 (4.18), 3.840 (16.00), 4.048 (0.77), 4.058 (0.77), 4.198 (1.59), 4.213 (3.33), 4.219 (2.60), 4.228 (1.82), 4.236 (4.92), 4.254 (4.61), 4.272 (1.36), 5.007 (1.05), 5.019 (1.05), 5.758 (3.91), 6.476 (1.24), 6.881 (1.43), 6.889 (1.51), 6.895 (1.39), 6.903 (1.32), 7.162 (4.80), 7.184 (4.92), 7.370 (0.89), 7.377 (1.16), 7.393 (1.32), 7.399 (1.70), 7.406 (0.54), 7.415 (1.36), 7.422 (1.28), 7.436 (2.98), 7.443 (3.33), 7.450 (7.21), 7.463 (0.46), 7.648 (1.67), 7.655 (1.70), 7.674 (1.70), 7.681 (1.74), 7.687 (0.93), 7.695 (2.79), 7.709 (0.77), 7.717 (2.52), 8.229 (1.32), 8.244 (1.36), 8.253 (1.36), 8.267 (1.32), 10.648 (0.74), 10.725 (2.83).

Intermediate 113

(rac)-ethyl (11Z)-4-chloro-3-ethyl-7-{3-[(6-fluoronaphthalen-1-yl)oxy]propyl}-2-methyl-(15-rac)-[3-(morpholin-4-yl)propyl]-2,10,13,15-tetrahydropyrazolo[4',3':9,10][1,6]oxazacycloundecino[8,7,6-hi]indole-8-carboxylate

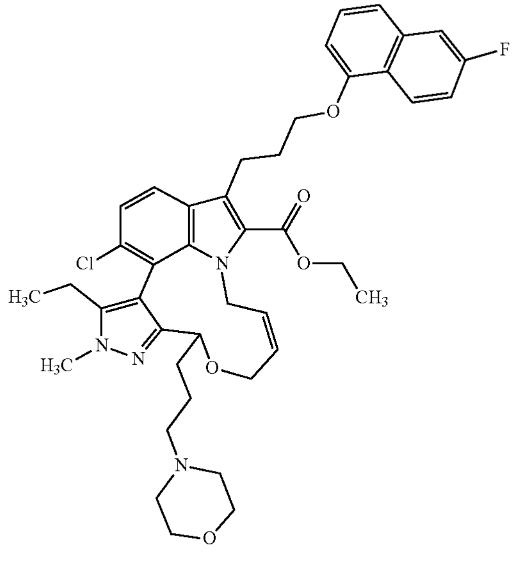 [SMILES: CCOC(=O)c1c(CCCOc2cccc3cc(F)ccc23)c2ccc(Cl)c3c2n1C/C=C\COC(CCCN1CCOCC1)c1nn(C)c(CC)c1-3]

Ethyl 6-chloro-7-{5-ethyl-3-[(1-rac)-hydroxy-4-(morpholin-4-yl)butyl]-1-methyl-1H-pyrazol-4-yl}-3-{3-[(6-fluoronaphthalen-1-yl)oxy]propyl}-1H-indole-2-carboxylate (see Intermediate 112, 810 mg, 1.17 mmol) was dissolved in 8 mL of acetonitrile, treated with cesium carbonate (1.91 g, 5.86 mmol) was added and the mixture was stirred for 15 minutes at room temperature. (2Z)-1,4-dichlorobut-2-ene (136 μL, 1.29 mmol) and sodium iodide (351 mg, 2.34 mmol) were added and the mixture was stirred for 21 h at 50° C. in a sealed tube. The reaction mixture was diluted with water and extracted with ethyl acetate. The combined organic layers were dried using a water resistant filter and concentrated under reduced pressure. The crude material was purified by flash chromatography using silica gel (gradient dichloromethane/ethanol) to give 549 mg of the title compound which was formed as a racemic mixture of two enantiomers as only one of the two diastereomers formed in the preceding step underwent the macrocyclization reaction.

LC-MS (Method 2): $R_t$=1.74 min; MS (ESIpos): m/z=743 $[M+H]^+$ $^1$H-NMR (400 MHz, DMSO-d6) δ[ppm]: 0.773 (3.36), 0.792 (8.00), 0.811 (3.69), 0.821 (0.76), 0.826 (0.90), 0.841 (0.47), 0.845 (0.47), 0.860 (0.57), 0.904 (0.57), 1.066 (0.85), 1.136 (0.57), 1.154 (1.09), 1.169 (1.80), 1.188 (3.55), 1.206 (1.75), 1.231 (0.52), 1.251 (5.07), 1.268 (10.93), 1.287 (5.11), 1.425 (0.43), 1.772 (0.71), 1.797 (0.85), 2.130 (1.37), 2.148 (2.51), 2.157 (2.65), 2.167 (2.79), 2.176 (2.98), 2.194 (2.46), 2.213 (2.37), 2.230 (2.37), 2.318 (0.99), 2.323 (1.66), 2.327 (2.08), 2.332 (1.56), 2.518 (6.53), 2.523 (4.54), 2.625 (0.95), 2.643 (0.95), 2.665 (1.42), 2.669 (1.85), 2.673 (1.28), 2.896 (0.47), 3.255 (0.62), 3.271 (1.04), 3.288 (1.70), 3.309 (2.27), 3.434 (1.66), 3.514 (0.99), 3.565 (2.22), 3.645 (0.62), 3.657 (0.71), 3.677 (0.95), 3.690 (0.80), 3.713 (1.75), 3.786 (0.95), 3.810 (6.96), 3.847 (0.80), 3.852 (0.80), 3.887 (16.00), 3.910 (0.43), 4.197 (0.66), 4.214 (2.79), 4.219 (2.79), 4.233 (4.78), 4.242 (3.55), 4.259 (2.18), 4.280 (1.89), 4.290 (0.43), 4.299 (1.70), 4.307 (0.90), 4.316 (0.52), 4.325 (0.85), 4.674 (0.52), 4.686 (0.57), 4.713 (0.62), 4.891 (1.04), 4.938 (0.90), 4.967 (0.99), 4.993 (0.52), 5.169 (0.43), 5.181 (0.43), 5.197 (0.66), 5.209 (0.62), 6.481 (1.14), 6.883 (1.37), 6.891 (1.51), 6.898 (1.42), 6.905 (1.56), 7.264 (3.74), 7.286 (3.79), 7.357 (0.95), 7.364 (1.04), 7.380 (1.56), 7.386 (1.66), 7.402 (1.18), 7.409 (1.28), 7.417 (0.57), 7.438 (2.93), 7.445 (3.50), 7.452 (6.53), 7.465 (0.47), 7.651 (1.89), 7.658 (1.94), 7.677 (1.89), 7.684 (1.85), 7.803 (2.98), 7.824 (2.60), 8.202 (1.33), 8.217 (1.37), 8.225 (1.33), 8.240 (1.37).

Intermediate 114

(rac)-ethyl 4-chloro-3-ethyl-7-{3-[(6-fluoronaphthalen-1-yl)oxy]propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylate

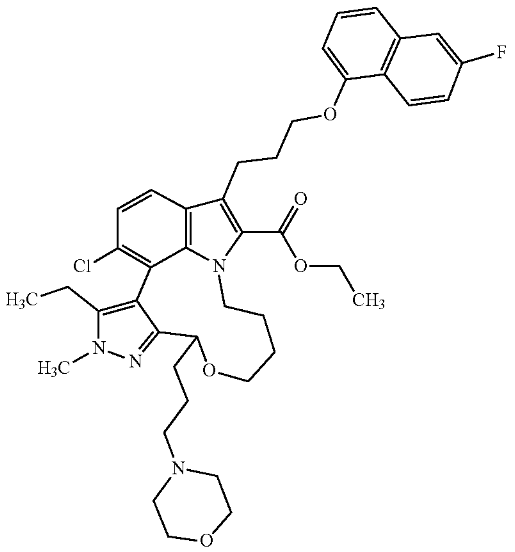 [SMILES: CCOC(=O)c1c(CCCOc2cccc3cc(F)ccc23)c2ccc(Cl)c3c2n1CCCCOC(CCCN1CCOCC1)c1nn(C)c(CC)c1-3]

(Rac)-ethyl-(11Z)-4-chloro-3-ethyl-7-{3-[(6-fluoronaphthalen-1-yl)oxy]propyl}-2-methyl-(15-rac)-[3-(morpholin-4-yl)propyl]-2,10,13,15-tetrahydropyrazolo[4',3':9,10][1,6]oxazacycloundecino[8,7,6-hi]indole-8-carboxylate (see Intermediate 113, 546 mg) was dissolved in a mixture of 10 mL of ethanol and 1 mL of THF, tris(triphenylphosphine)rhodium(I)-chloride (273 mg, 294 μmol) was added and the mixture was stirred for 6 h under hydrogen atmosphere at room temperature. Tris(triphenylphosphine)rhodium(I)-chloride (109 mg, 118 μmol) was added and the mixture was stirred for 4 h under hydrogen atmosphere at room temperature. THF (5 mL) and tris(triphenylphosphine)rhodium(I)-chloride (273 mg, 294 μmol) were added and the mixture was stirred for 4 h under hydrogen atmosphere at room temperature. Tris(triphenylphosphine)rhodium(I)-chloride (137 mg, 147 μmol) was added and the mixture was stirred for 5 h under hydrogen atmosphere at room temperature. The reaction mixture was concentrated under reduced pressure. The crude material was purified by flash chromatography using silica gel (gradient dichloromethane/ethanol) to provide 442 mg of the title compound.

LC-MS (Method 2): $R_t$=1.77 min; MS (ESIpos): m/z=745 $[M+H]^+$ $^1$H-NMR (400 MHz, DMSO-d6) δ[ppm]: 0.786 (3.28), 0.797 (1.70), 0.805 (7.74), 0.814 (1.52), 0.824 (3.52), 0.839 (0.53), 0.886 (0.53), 0.903 (1.05), 0.922 (0.64), 1.003 (0.82), 1.052 (0.59), 1.070 (0.59), 1.095 (0.53), 1.105 (0.53), 1.168 (0.59), 1.187 (1.23), 1.206 (0.70), 1.231 (0.94), 1.248 (5.63), 1.266 (11.49), 1.284 (5.45), 1.425 (0.59), 1.444 (0.76), 1.471 (0.76), 1.490 (0.59), 1.893 (0.70), 1.907 (4.34), 1.911 (1.58), 1.931 (1.58), 1.949 (0.59), 2.155 (0.76), 2.173 (1.76), 2.183 (1.82), 2.192 (2.11), 2.201 (2.34), 2.210 (1.82), 2.219 (1.76), 2.230 (1.41), 2.279 (2.64), 2.318 (1.05), 2.323 (1.52), 2.327 (1.82), 2.332 (1.29), 2.336 (0.70), 2.518 (5.57), 2.523 (3.75), 2.660 (0.59), 2.665 (1.05), 2.669 (1.41), 2.674 (1.00), 2.679 (0.47), 2.888 (0.41), 3.027 (0.53), 3.041 (0.53), 3.219 (0.47), 3.235 (0.76), 3.254 (1.23), 3.271 (1.47), 3.287 (1.70), 3.517 (4.10), 3.808 (2.34), 3.824 (0.59), 3.856 (16.00), 3.934 (0.59), 3.951 (0.64), 3.969 (0.70), 4.177 (0.70), 4.184 (0.88), 4.195 (2.23), 4.199 (1.82), 4.213 (2.52), 4.222 (2.75), 4.240 (2.34), 4.258 (1.05), 4.261 (1.23), 4.275 (1.29), 4.279 (2.17), 4.292 (2.11), 4.297 (2.05), 4.306 (1.35), 4.324 (1.05), 5.757 (0.76), 6.477 (0.47), 6.856 (1.29), 6.862 (1.35), 6.871 (1.17), 6.878 (1.41), 7.216 (4.28), 7.238 (4.28), 7.363 (1.00), 7.369 (1.11), 7.385 (1.47), 7.392 (1.58), 7.407 (1.47), 7.414 (1.23), 7.427 (2.46), 7.436 (2.81), 7.442 (6.04), 7.457 (0.59), 7.595 (0.47), 7.622 (0.47), 7.625 (0.41), 7.644 (1.70), 7.650 (1.76), 7.670 (1.58), 7.676 (1.64), 7.765 (3.63), 7.786 (3.22), 8.186 (1.29), 8.201 (1.41), 8.209 (1.35), 8.224 (1.29).

Intermediate 115

1-(4-bromo-5-ethyl-1-methyl-1H-pyrazol-3-yl)-3-(4-methylpiperazin-1-yl)propan-1-one

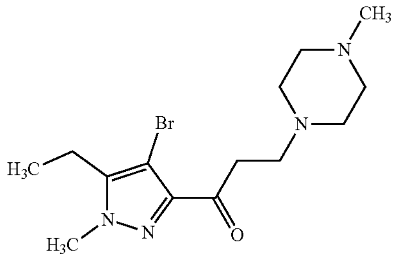 [SMILES: CCc1c(Br)c(C(=O)CCN2CCN(C)CC2)nn1C]

4-Bromo-5-ethyl-N-methoxy-N,1-dimethyl-1H-pyrazole-3-carboxamide (see Intermediate 90, 4.00 g, 14.5 mmol) was dissolved in 50 mL of THF and a solution of bromo(vinyl)magnesium (29.0 mL, 1.0 M in 29.0 mmol) was added at 0° C. The mixture was stirred at 0° C. for 15 minutes and then added dropwise to a mixture of 1-methylpiperazine (6.4 mL, 57.9 mmol) in 4 mL of tetrahydrofuran at 0° C. The mixture was stirred for 30 minutes at 0° C. Ethyl acetate was added and the mixture was stirred for 15 minutes. Water was added, the mixture was filtered through a pad of celite, the phases were separated, the organic phase was filtered through a water resistant filter and concentrated under reduced pressure. The crude material was purified by flash chromatography using silica gel (aminophase, gradient dichloromethane/ethanol) to provide 4.00 g of the title compound.

LC-MS (Method 2): $R_t$=0.93 min; MS (ESIpos): m/z=343 $[M+H]^+$ $^1$H-NMR (400 MHz, DMSO-d6) δ[ppm]: 1.078 (2.90), 1.097 (7.06), 1.116 (2.99), 1.352 (0.44), 2.116 (12.92), 2.266 (0.61), 2.279 (0.63), 2.323 (0.60), 2.327 (0.65), 2.332 (0.64), 2.337 (0.61), 2.358 (0.65), 2.482 (0.60), 2.518 (0.61), 2.523 (0.44), 2.599 (1.51), 2.616 (3.18), 2.635 (1.81), 2.670 (0.98), 2.689 (2.73), 2.708 (2.65), 2.727 (0.76), 3.019 (1.78), 3.038 (3.20), 3.055 (1.50), 3.916 (16.00), 3.924 (0.66).

Intermediate 116

(rac)-1-(4-bromo-5-ethyl-1-methyl-1H-pyrazol-3-yl)-3-(4-methylpiperazin-1-yl)propan-1-ol

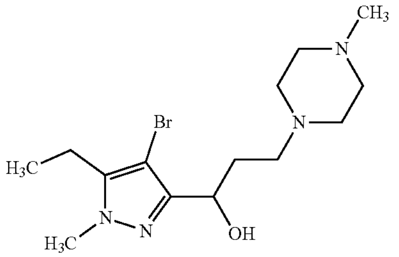 [SMILES: CCc1c(Br)c(C(O)CCN2CCN(C)CC2)nn1C]

1-(4-Bromo-5-ethyl-1-methyl-1H-pyrazol-3-yl)-3-(4-methylpiperazin-1-yl)propan-1-one (see Intermediate 115, 4.00 g, 11.7 mmol) was dissolved in 29 mL of methanol, sodium borohydride (1.10 g, 29.1 mmol) was added portionwise at 0° C. and the mixture was stirred for 30 minutes at 0° C. Water was added and the mixture was stirred for 30 minutes and afterwards concentrated under reduced pressure. The crude material was purified by flash chromatography using silica gel (gradient dichloromethane/ethanol) to provide 3.29 g of the title compound.

LC-MS (Method 2): $R_t$=0.85 min; MS (ESIpos): m/z=345 $[M+H]^+$ $^1$H-NMR (400 MHz, DMSO-d6) δ[ppm]: 1.060 (2.74), 1.079 (6.69), 1.098 (2.76), 1.786 (0.41), 1.802 (0.48), 1.819 (0.43), 1.870 (0.47), 1.886 (0.60), 1.905 (0.47), 2.128 (10.22), 2.270 (0.75), 2.289 (0.94), 2.301 (1.25), 2.318 (2.06), 2.326 (1.18), 2.335 (1.72), 2.353 (1.00), 2.364 (0.65), 2.368 (0.64), 2.383 (0.52), 2.391 (0.51), 2.407 (0.45), 2.465 (0.47), 2.518 (1.20), 2.523 (0.80), 2.600 (0.90), 2.619 (2.68), 2.638 (2.55), 2.656 (0.75), 3.749 (16.00), 4.547 (0.64), 4.559 (0.69), 4.567 (0.73), 4.580 (0.56).

Intermediate 117

1-[(3-rac)-3-(4-bromo-5-ethyl-1-methyl-1H-pyrazol-3-yl)-3-{4-[(2-rac)-tetrahydro-2H-pyran-2-yloxy]butoxy}propyl]-4-methylpiperazine

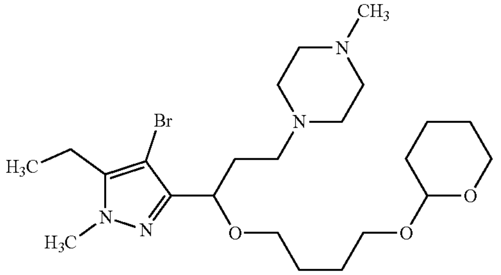 [SMILES: CCc1c(Br)c(C(CCN2CCN(C)CC2)OCCCCOC2CCCCO2)nn1C]

(Rac)-1-(4-bromo-5-ethyl-1-methyl-1H-pyrazol-3-yl)-3-(4-methylpiperazin-1-yl)propan-1-ol (see Intermediate 116, 3.07 g) was dissolved in 50 mL of tetrahydrofuran, sodium hydride (427 mg, 60% purity, 10.7 mmol) was added and the mixture was stirred at room temperature for 30 minutes. 2-(4-Bromobutoxy)tetrahydro-2H-pyran (2.0 mL, 10.7 mmol) was added and the mixture was stirred for 90 minutes at room temperature. DMF (2 mL) was added and the mixture was stirred for 30 minutes at 0° C. and over night at rt. Sodium hydride (285 mg, 60% purity, 7.13 mmol) was added and the mixture was stirred for 30 minutes at rt. 2-(4-Bromobutoxy)tetrahydro-2H-pyran (0.8 mL, 4.46 mmol) was added and the mixture was stirred for 2 h at room temperature. Water was added and the reaction mixture was concentrated under reduced pressure. The crude product was purified by flash chromatography using silica gel (gradient dichloromethane/ethanol) to provide 3.07 g of the title compound.

LC-MS (Method 2): $R_t$=1.22 min; MS (ESIpos): m/z=501 $[M+H]_+$ $^1$H-NMR (400 MHz, DMSO-d6) δ[ppm]: 1.053 (0.67), 1.068 (2.74), 1.087 (6.68), 1.105 (2.88), 1.233 (0.44), 1.430 (1.94), 1.440 (1.51), 1.449 (1.33), 1.458 (1.19), 1.475 (1.28), 1.496 (2.58), 1.505 (2.21), 1.525 (0.86), 1.542 (0.53), 1.551 (0.49), 1.579 (0.54), 1.598 (0.40), 1.672 (0.51), 1.684 (0.40), 1.693 (0.41), 1.791 (0.53), 1.810 (0.63), 1.825 (0.49), 1.951 (0.45), 1.967 (0.54), 1.986 (0.56), 2.085 (1.36), 2.128 (9.87), 2.180 (1.42), 2.221 (0.50), 2.253 (1.80), 2.272 (2.73), 2.289 (1.90), 2.318 (1.07), 2.323 (1.24), 2.327 (1.34), 2.332 (1.12), 2.336 (0.86), 2.367 (0.47), 2.466 (0.40), 2.518 (2.55), 2.523 (1.80), 2.609 (0.85), 2.628 (2.57), 2.647 (2.51), 2.665 (1.03), 2.669 (0.98), 2.673 (0.58), 2.728 (6.94), 2.888 (8.10), 3.211 (0.48), 3.225 (1.16), 3.240 (1.39), 3.257 (0.83), 3.266 (0.71), 3.273 (0.60), 3.282 (0.72), 3.289 (0.62), 3.379 (0.84), 3.393 (0.57), 3.400 (0.54), 3.406 (0.72), 3.417 (0.48), 3.540 (0.49), 3.557 (0.62), 3.563 (0.53), 3.581 (0.44), 3.668 (0.42), 3.689 (0.68), 3.696 (0.64), 3.717 (0.45), 3.749 (0.51), 3.764 (16.00), 4.326 (0.69), 4.340 (0.89), 4.345 (0.88), 4.360 (0.69), 4.495 (1.10), 4.500 (1.08), 4.511 (0.50), 7.951 (0.98).

Intermediate 118

4-[(1-rac)-(4-bromo-5-ethyl-1-methyl-1H-pyrazol-3-yl)-3-(4-methylpiperazin-1-yl)propoxy]butan-1-ol

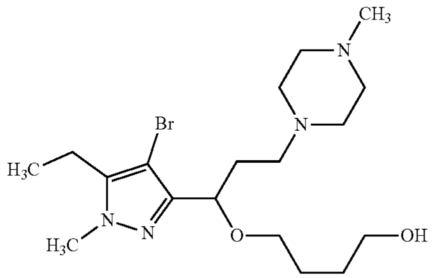 [SMILES: CCc1c(Br)c(C(CCN2CCN(C)CC2)OCCCCO)nn1C]

1-[(3-rac)-3-(4-bromo-5-ethyl-1-methyl-1H-pyrazol-3-yl)-3-{4-[(2-rac)-tetrahydro-2H-pyran-2-yloxy]butoxy}propyl]-4-methylpiperazine (see Intermediate 118, 3.07 g) was dissolved in 30 mL of ethanol, para-toluenesulfonic acid (1.05 g, 6.12 mmol) was added and the mixture was stirred at room temperature for 90 minutes. The reaction mixture was concentrated under reduced pressure and the residue was purified by flash chromatography using silica gel (aminophase, addition of triethylamine, gradient dichloromethane/ethanol) to give 1.51 g of the title compound.

LC-MS (Method 2): $R_t$=0.90 min; MS (ESIpos): m/z=417 $[M+H]^+$ $^1$H-NMR (400 MHz, DMSO-d6) δ[ppm]: 0.906 (1.16), 0.924 (2.53), 0.941 (1.21), 1.068 (2.54), 1.080 (0.75), 1.088 (6.28), 1.098 (0.53), 1.106 (2.70), 1.119 (0.48), 1.385 (0.49), 1.390 (0.54), 1.402 (0.94), 1.407 (0.94), 1.417 (1.52), 1.423 (1.27), 1.427 (1.27), 1.432 (1.57), 1.442 (1.02), 1.448 (0.93), 1.459 (0.60), 1.465 (0.55), 1.789 (0.51), 1.808 (0.58), 1.823 (0.45), 1.945 (0.45), 1.964 (0.53), 1.981 (0.44), 2.122 (10.93), 2.179 (1.70), 2.209 (0.40), 2.221 (0.54), 2.247 (1.81), 2.265 (2.80), 2.283 (2.03), 2.318 (0.98), 2.322 (1.12), 2.327 (1.23), 2.332 (1.05), 2.336 (0.78), 2.389 (0.53), 2.406 (1.20), 2.424 (1.14), 2.442 (0.41), 2.463 (0.50), 2.518 (2.60), 2.523 (1.77), 2.610 (0.74), 2.628 (2.43), 2.647 (2.36), 2.668 (0.99), 2.673 (0.58), 2.728 (1.38), 2.889 (1.60), 3.186 (0.52), 3.202 (1.52), 3.218 (1.49), 3.226 (0.44), 3.233 (0.56), 3.241 (0.44), 3.317 (0.87), 3.346 (2.06), 3.361 (0.92), 3.379 (0.73), 3.749 (1.02), 3.765 (16.00), 3.773 (0.86), 4.311 (1.43), 4.316 (0.86), 4.324 (3.23), 4.330 (1.02), 4.336 (1.95), 4.350 (0.71), 5.759 (3.96).

Intermediate 119 ethyl 6-chloro-7-{5-ethyl-3-[(1-rac)-(4-hydroxybutoxy)-3-(4-methylpiperazin-1-yl)propyl]-1-methyl-1H-pyrazol-4-yl}-3-{3-[(6-fluoronaphthalen-1-yl)oxy]propyl}-1H-indole-2-carboxylate

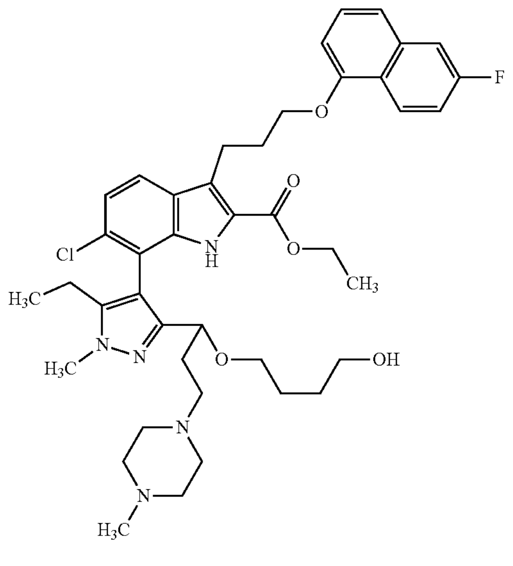 [SMILES: CCOC(=O)c1[nH]c2c(-c3c(C(CCN4CCN(C)CC4)OCCCCO)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 773 mg, 1.40 mmol), 4-[(1-rac)-(4-bromo-5-ethyl-1-methyl-1H-pyrazol-3-yl)-3-(4-methylpiperazin-1-yl)propoxy]butan-1-ol (see Intermediate 118, 585 mg, 1.40 mmol) and potassium triphosphate (595 mg, 2.80 mmol) were provided in a mixture of 14 mL of 1,4-dioxane and 4 mL of water and were purged with argon for 5 minutes. RuPhos Pd G3 (117 mg, 140 μmol) was added and the mixture was purged with argon for 5 minutes and stirred for 1 h at 110° C. in a microwave reactor. Another preparation was performed in the same way and the reaction mixtures were combined and concentrated under reduced pressure. The crude material was purified by flash chromatography using silica gel (aminophase, gradient dichloromethane/ethanol) to provide 852 mg of the title compound which was formed as a mixture of two racemic diastereomers as a result of atropisomerism at the newly formed bi-heteroaryl bond.

LC-MS (Method 2): $R_t$=1.59 min; MS (ESIpos): m/z=762 $[M+H]^+$ $^1$H-NMR (400 MHz, DMSO-d6) δ[ppm]: 0.873 (0.78), 0.884 (0.85), 0.892 (1.93), 0.902 (1.48), 0.907 (2.46), 0.920 (0.77), 0.926 (1.03), 1.036 (4.71), 1.053 (10.37), 1.066 (11.69), 1.071 (5.99), 1.087 (2.22), 1.106 (1.02), 1.138 (1.40), 1.145 (4.08), 1.164 (7.76), 1.183 (3.68), 1.197 (0.41), 1.225 (1.69), 1.230 (2.15), 1.243 (2.98), 1.248 (3.38), 1.261 (1.48), 1.266 (1.59), 1.387 (0.71), 1.399 (1.26), 1.403 (1.42), 1.411 (2.01), 1.418 (2.28), 1.425 (2.15), 1.433 (1.54), 1.449 (0.80), 1.668 (0.53), 1.677 (0.49), 1.690 (0.63), 1.710 (0.63), 1.724 (0.53), 1.791 (0.63), 1.810 (0.72), 1.826 (0.54), 1.846 (0.41), 1.966 (0.47), 2.007 (3.76), 2.042 (3.06), 2.066 (2.04), 2.092 (0.78), 2.123 (13.42), 2.221 (1.50), 2.231 (1.38), 2.257 (2.52), 2.266 (2.43), 2.275 (3.45), 2.294 (2.35), 2.323 (1.60), 2.327 (1.60), 2.332 (1.36), 2.336 (1.21), 2.354 (0.90), 2.373 (0.79), 2.390 (0.70), 2.407 (0.67), 2.419 (0.62), 2.429 (0.52), 2.438 (0.59), 2.449 (0.47), 2.518 (2.48), 2.523 (1.63), 2.539 (0.79), 2.558 (2.30), 2.577 (2.21), 2.595 (0.71), 2.628 (0.78), 2.647 (0.76), 2.665 (0.62), 2.669 (0.74), 2.673 (0.48), 3.150 (0.42), 3.165 (0.87), 3.173 (0.79), 3.180 (0.71), 3.188 (1.17), 3.203 (0.90), 3.218 (0.85), 3.233 (1.09), 3.246 (1.64), 3.261 (0.80), 3.269 (0.90), 3.288 (0.95), 3.310 (1.13), 3.352 (2.26), 3.367 (0.84), 3.405 (0.75), 3.418 (0.79), 3.423 (2.02), 3.436 (2.11), 3.440 (1.98), 3.452 (1.98), 3.457 (0.73), 3.470 (0.69), 3.651 (13.86), 3.765 (4.72), 3.812 (3.32), 3.821 (4.26), 3.939 (1.66), 3.983 (0.45), 3.998 (0.54), 4.165 (0.73), 4.179 (0.92), 4.185 (1.19), 4.199 (1.65), 4.215 (1.77), 4.228 (0.89), 4.238 (1.76), 4.255 (1.62), 4.266 (0.61), 4.273 (0.47), 4.319 (1.16), 4.326 (1.06), 4.333 (2.38), 4.345 (2.13), 4.357 (2.52), 4.370 (1.25), 5.758 (16.00), 5.929 (3.33), 6.871 (0.61), 6.879 (0.58), 6.885 (0.58), 7.139 (0.76), 7.151 (1.00), 7.161 (0.82), 7.173 (1.02), 7.383 (0.44), 7.399 (0.62), 7.405 (0.72), 7.421 (0.46), 7.427 (0.53), 7.435 (0.95), 7.442 (1.16), 7.450 (1.96), 7.649 (0.67), 7.656 (0.71), 7.675 (0.71), 7.682 (1.28), 7.708 (0.79), 8.254 (0.46), 8.269 (0.50), 8.278 (0.50), 8.291 (0.46), 10.777 (0.75), 10.904 (0.57).

Intermediate 120

(rac)-ethyl 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylate

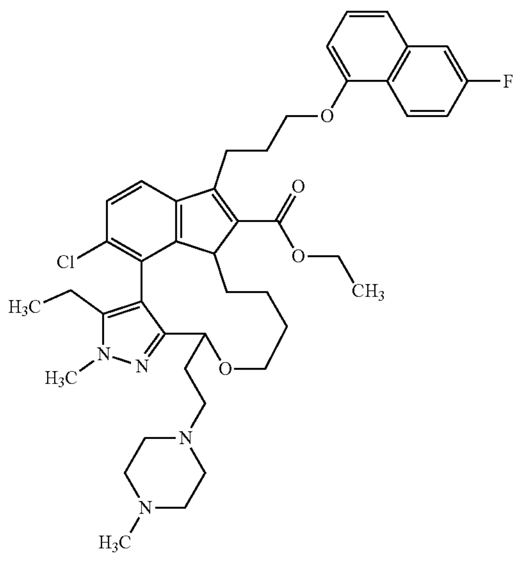 [SMILES: CCOC(=O)C1=C(CCCOc2cccc3cc(F)ccc23)c2ccc(Cl)c3c2C1CCCCOC(CCN1CCN(C)CC1)c1nn(C)c(CC)c1-3]

Ethyl 6-chloro-7-{5-ethyl-3-[(1-rac)-(4-hydroxybutoxy)-3-(4-methylpiperazin-1-yl)propyl]-1-methyl-1H-pyrazol-4-yl}-3-{3-[(6-fluoronaphthalen-1-yl)oxy]propyl}-1H-indole-2-carboxylate (see Intermediate 119, 845 mg, 1.11 mmol) was dissolved in 49 mL of tetrahydrofuran, triphenylphosphine (2.33 g, 8.87 mmol) and di-tert-butyl-azodicarboxylate (2.04 g, 8.87 mmol) were added and the mixture was stirred for 22 h at room temperature. The reaction mixture was diluted with a mixture of hexane and ethyl acetate, was concentrated under reduced pressure and diluted with hexane. After 2 h the precipitate was removed and the organic phase was concentrated under reduced pressure. The crude product was purified by flash chromatography using silica gel (aminophase, gradient dichloromethane/ethanol) to give 406 mg (49% yield) of the title compound as a mixture of two racemic diastereomers.

LC-MS (Method 2): $R_t$=1.74 min; MS (ESIpos): m/z=744 $[M+H]^+$ $^1$H-NMR (400 MHz, DMSO-d6) δ[ppm]: 0.777 (0.20), 0.786 (0.20), 0.796 (0.46), 0.805 (0.41), 0.814 (0.23), 0.824 (0.18), 1.066 (16.00), 1.232 (0.19), 1.240 (0.46), 1.247 (0.39), 1.258 (0.79), 1.265 (0.64), 1.276 (0.38), 1.283 (0.30), 1.428 (0.16), 2.102 (0.69), 2.112 (0.85), 2.183 (0.22), 2.200 (0.29), 2.217 (0.29), 2.235 (0.30), 2.258 (0.27), 2.274 (0.22), 2.318 (0.17), 2.322 (0.22), 2.326 (0.24), 2.331 (0.19), 2.518 (0.65), 2.522 (0.42), 3.822 (0.97), 3.858 (0.80), 3.939 (2.42), 4.202 (0.19), 4.211 (0.31), 4.221 (0.24), 4.228 (0.23), 4.277 (0.17), 7.216 (0.24), 7.228 (0.20), 7.237 (0.25), 7.249 (0.20), 7.431 (0.24), 7.447 (0.45), 7.741 (0.21), 7.763 (0.20), 7.768 (0.18).

Intermediate 121

5-ethyl-N-methoxy-N,1-dimethyl-1H-pyrazole-3-carboxamide

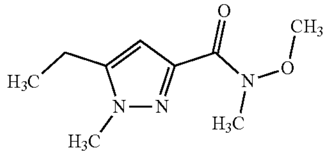

To a solution of 5-ethyl-1-methyl-pyrazole-3-carboxylic acid (CAS 165744-15-0, 200 g, 1.30 mol), N-methoxymethanamine hydrochloride (133 g, 1.36 mol) and HOBt (193 g, 1.43 mol) in anhydrous dichloromethane (2 L) at 0° C. was added diisopropyl ethylamine (201 g, 1.56 mol), followed by EDC (274 g, 1.43 mol) in portions. The mixture was gradually warmed to 15° C. and was then stirred for 16 hours under an atmosphere of nitrogen. Analysis by LC-MS indicated that the reaction was complete. The mixture was washed four times with water (2 L each). The combined aqueous phase was filtered, and the filtrate was extracted with dichloromethane (2 L). The combined organic phase was washed with brine (1.5 L), dried over sodium sulfate, filtered and concentrated in vacuum. The residue was purified by column chromatography on silica gel (petrol ether: ethyl acetate=3:1 to 1:1) to afford 5-ethyl-N-methoxy-N,1-dimethyl-1H-pyrazole-3-carboxamide (253 g) as a yellow oil.

$^1$H NMR (400 MHz, $CDCl_3$): δ=6.53 (s, 1H), 3.82 (s, 3H), 3.75 (s, 3H), 3.44 (s, 3H), 2.62 (q, 2H), 1.29 (t, 3H).

LC-MS (Method 9): $R_t$=0.731 min; m/z=198.2 $(M+H)^+$.

Intermediate 122

1-(5-ethyl-1-methyl-1H-pyrazol-3-yl)prop-2-en-1-one

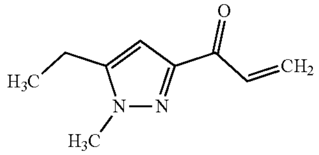

The reactions were performed in 6 batches in parallel: to a cooled solution of 5-ethyl-N-methoxy-N,1-dimethyl-1H-pyrazole-3-carboxamide (see Intermediate 121, 40 g) in THF (400 mL) at 0° C. was slowly added vinylmagnesium bromide (1 M solution in THF, 400 mL) under an atmosphere of nitrogen. After the addition was completed, the mixture was gradually warmed to 15° C. and stirred for 1 h. Analysis by LC-MS indicated that the reaction was completed. The reaction mixture (six batches) were slowly added into aqueous hydrochloric acid (1 M, 2.5 L), which was externally cooled by ice, and stirred for several minutes. Concentrated hydrochloric acid (12 M) was added until pH reached 1. The mixture was extracted twice with ethyl acetate (2 L each). The combined organic phase was washed with brine (2.5 L), dried over sodium sulfate, filtered and concentrated in vacuum. The residue was purified by column chromatography on silica gel (petrol ether:ethyl acetate=10:1 to 5:1) to afford 1-(5-ethyl-1-methyl-1H-pyrazol-3-yl)prop-2-en-1-one (60 g, 94.6% purity) as a yellow oil.

$^1$H NMR (400 MHz, CDCl3): δ=7.39 (dd, 1H), 6.67 (s, 1H), 6.53 (dd, 1H), 5.82 (dd, 1H), 3.86 (s, 3H), 2.63 (q, 2H), 1.31 (t, 3H).

LC-MS (Method 10): Rt=0.631 min; m/z=165.1 (M+H)+.

Intermediate 123

1-(5-ethyl-1-methyl-1H-pyrazol-3-yl)-3-morpholino-propan-1-one

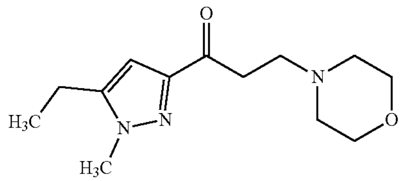 [SMILES: CCc1cc(C(=O)CCN2CCOCC2)nn1C]

A solution of 1-(5-ethyl-1-methyl-1H-pyrazol-3-yl)prop-2-en-1-one (see Intermediate 122, 59 g, 339.91 mmol, 94.6% purity) and morpholine (150 g, 1.72 mol) in ethanol (600 mL) was stirred at 25° C. for 2 hours. Analysis by TLC (Petrol ether:ethyl acetate=5:1) indicated that the reaction was completed. The mixture was diluted with water (400 mL) and the resulting mixture was extracted twice with 600 mL each of a mixture of dichloromethane and iso-propanol ($V_{dichloromethane}$:$V_{isopropanol}$=4:1). The combined organic phase was washed with brine (500 mL), dried over sodium sulfate, filtered and concentrated in vacuum. The residue was purified by column chromatography on silica gel (Petrol ether:ethyl acetate=1:1 to dichloromethane:methanol=10:1) to afford 1-(5-ethyl-1-methyl-1H-pyrazol-3-yl)-3-morpholino-propan-1-one (75 g, 88% yield) as a yellow oil.

$^1$H NMR (400 MHz, $CDCl_3$): δ=6.57 (s, 1H), 3.84 (s, 3H), 3.71 (t, 4H), 3.18 (t, 2H), 2.83 (t, 2H), 2.62 (q, 2H), 2.05 (s, 4H), 1.29 (t, 3H).

Intermediate 124

(R)-1-(5-ethyl-1-methyl-1H-pyrazol-3-yl)-3-morpholinopropan-1-ol

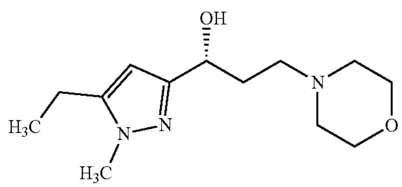

(S)-(−)-2-methyl-cbs-[1,3,2]oxazaborolidine (CAS 112022-81-8) (1 M solution in toluene, 100 mL, 100 mmol) was placed in a 1 L three-necked flask under an atmosphere of nitrogen and the resulting solution was cooled with a dry-ice/ethanol bath. Borane-THF (1 M in THF, 200 mL, 200 mmol) was added. The mixture was cooled to −70° C., and 1-(5-ethyl-1-methyl-1H-pyrazol-3-yl)-3-morpholino-propan-1-one (see Intermediate 123, 25 g, 99.47 mmol) in THF (250 mL) was added dropwise over 3 hours. After addition, the mixture was stirred at −70° C. for 6 hours. Analysis by LC-MS indicated formation of the product with the desired molecular mass, and the presence of some unreacted starting material. Methanol (200 mL) was slowly added at −70° C. The resulting mixture was gradually warmed to room temperature and stirred for several minutes. n-Butanol (100 mL) was added. The mixture was refluxed for 1 hour, and then concentrated in vacuum. The residue was combined with the residue of another batch (obtained from 1 g of 1-(5-ethyl-1-methyl-1H-pyrazol-3-yl)-3-morpholinopropan-1-one). The combined mixture was purified by reversed phase flash chromatography (0-25% of acetonitrile in water (containing 0.1% of aqueous ammonia)) to afford (R)-1-(5-ethyl-1-methyl-1H-pyrazol-3-yl)-3-morpholino-propan-1-ol (10 g) as a yellow oil. Meanwhile, 8.6 g of 1-(5-ethyl-1-methyl-1H-pyrazol-3-yl)-3-morpholino-propan-1-one was recovered as a yellow oil.

Analytical Chiral HPLC of the racemate (Method 12): $R_t$=0.954 min (peak 1); $R_t$=1.086 min (peak 2).

Analytical Chiral HPLC of Intermediate 124 (Method 12): $R_t$=1.094 min (peak 2).

Intermediate 125

(R)-1-(5-ethyl-4-iodo-1-methyl-1H-pyrazol-3-yl)-3-morpholinopropan-1-ol

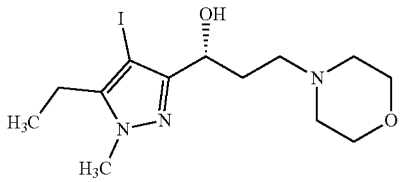 [SMILES: CCc1c(I)c([C@H](O)CCN2CCOCC2)nn1C]

(R)-1-(5-ethyl-1-methyl-pyrazol-3-yl)-3-morpholino-propan-1-ol (see Intermediate 124, 9.5 g, 37.50 mmol) was dissolved in TFA (70 mL) under cooling with an ice bath. Then 1-iodo-2,5-pyrrolidinedione (9.50 g, 42.23 mmol) was added in small portions at 0° C. The mixture was stirred at room temperature for 1 h. Analysis by TLC (dichloromethane:methanol=10:1) indicated that the reaction was completed. The reaction mixture was combined with another batch of reaction mixture (obtained from 0.5 g of (R)-1-(5-ethyl-1-methyl-1H-pyrazol-3-yl)-3-morpholinopropan-1-ol (see Intermediate 124)). Most of TFA was removed in high vacuum below 25° C. The residue was dissolved in ethyl acetate (350 mL) and the solution was neutralized with saturated aqueous potassium carbonate solution until pH reached 8-9. The aqueous layer was extracted twice with ethyl acetate (200 mL each). The combined organic layer was washed with saturated aqueous potassium carbonate solution (200 mL) and saturated brine (200 mL), dried over sodium sulfate, filtered and concentrated in vacuum. The residue was purified by reversed phase chromatography (0-40% of acetonitrile in water (containing 0.1% of aqueous ammonia)) to afford (R)-1-(5-ethyl-4-iodo-1-methyl-1H-pyrazol-3-yl)-3-morpholino-propan-1-ol (11.5 g) as a yellow gum.

HPLC-SFC_of the_Racemate (Method 13): Rt=1.831 min (peak 1); Rt=2.093 min (peak 2).

HPLC-SFC (Method 13): Rt=2.102 min (peak 2).

Intermediate 126

(R)-1-(5-ethyl-1-methyl-4-(4,4,5,5-tetramethyl-1,3,2-dioxaborolan-2-yl)-1H-pyrazol-3-yl)-3-morpholinopropan-1-ol

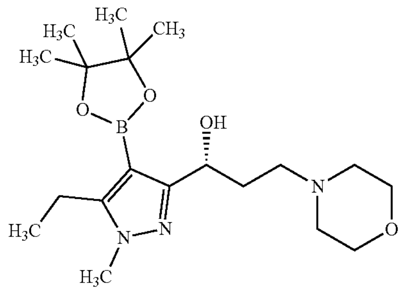 [SMILES: CCc1c(B2OC(C)(C)C(C)(C)O2)c([C@H](O)CCN2CCOCC2)nn1C]

To a solution of (R)-1-(5-ethyl-4-iodo-1-methyl-1H-pyrazol-3-yl)-3-morpholino-propan-1-ol (see Intermediate 125, 11 g, 29.01 mmol) and 2-isopropoxy-4,4,5,5-tetramethyl-1,3,2-dioxaborolane (16.19 g, 87.02 mmol) in THF (110 mL) was added chloro(propan-2-yl)magnesium (2 M solution in THF, 66 mL, 132 mmol) dropwise at 0-5° C. under an atmosphere of nitrogen. After addition, the mixture was gradually warmed to 25° C. and stirred for 20 hours. Analysis by LC-MS indicated that the reaction was completed. The reaction was stopped by the addition of saturated aqueous ammonium chloride solution (300 mL), and the resulting suspension was extracted twice with ethyl acetate (300 mL each). The combined organic layer was dried over magnesium sulfate, filtered and concentrated in vacuum. The residue was purified by column chromatography on silica gel (petrol ether:ethyl acetate=2:1 to 1:2, then dichloromethane:methanol=20:1) to afford (R)-1-[5-ethyl-1-methyl-4-(4,4,5,5-tetramethyl-1,3,2-dioxaborolan-2-yl)-1H-pyrazol-3-yl]-3-morpholino-propan-1-ol (7.8 g, 71% yield) as a yellow gum.

$^1$H NMR (400 MHz, CDCl3): δ=5.08-4.91 (m, 2H), 3.76-3.71 (m, 7H), 2.85-2.82 (m, 2H), 2.62-2.50 (m, 6H), 2.02-1.98 (m, 2H), 1.31 (s, 12H), 1.15 (t, 3H).

LC-MS (Method 11): $R_t$=2.123 min; m/z=380.3 $(M+H)^+$.

Intermediate 127 ethyl 6-chloro-7-{5-ethyl-3-[(1R)-hydroxy-3-(morpholin-4-yl)propyl]-1-methyl-1H-pyrazol-4-yl}-3-{3-[(6-fluoronaphthalen-1-yl)oxy]propyl}-1H-indole-2-carboxylate

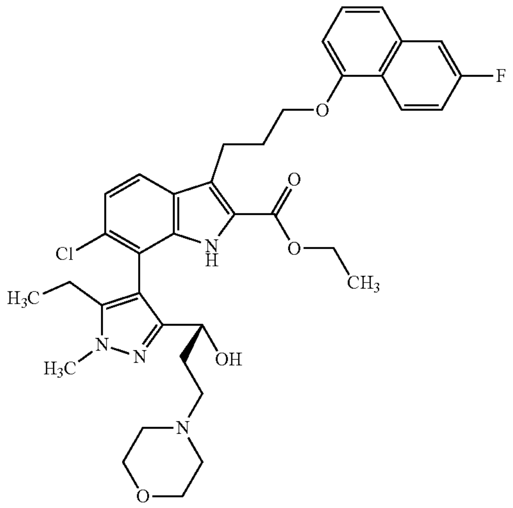 [SMILES: CCOC(=O)c1[nH]c2c(-c3c([C@H](O)CCN4CCOCC4)nn(C)c3CC)c(Cl)ccc2c1CCCOc1cccc2cc(F)ccc12]

The reaction was performed in four identical preparations using a quarter of all materials. Ethyl 7-bromo-6-chloro-3-{3-[(6-fluoronaphthalen-1-yl)oxy]propyl}-1H-indole-2-carboxylate (see Intermediate 51, 8.87 g, 17.6 mmol), (1R)-1-[5-ethyl-1-methyl-4-(4,4,5,5-tetramethyl-1,3,2-dioxaborolan-2-yl)-1H-pyrazol-3-yl]-3-(morpholin-4-yl)propan-1-ol (see Intermediate 126; 8.00 g, 21.1 mmol) and potassium triphosphate (7.46 g, 35.2 mmol) were provided in a mixture of 64 mL of 1,4-dioxane and 16 mL of water and purged with argon for 10 minutes. RuPhos Pd G3 (1.47 g, 1.76 mmol) was added, and the mixture was stirred for 3 h at 110° C. in a microwave reactor. The four reaction mixtures were combined, filtered through a water resistant filter and concentrated under reduced pressure. The crude material was purified by flash chromatography using silica gel (aminophase, gradient hexane/ethyl acetate) to provide 12.9 g of the title compound. 500 mg of this preparation were further purified by preparative HPLC (Method P3) to give 360 mg of the title compound which were combined with the remaining 12.4 g and were dried under reduced pressure to give 11.0 g of the title compound which was formed as a mixture of two diastereomers as a result of atropisomerism at the newly formed bi-heteroaryl bond.

LC-MS (Method 2): $R_t$=1.65 min; MS (ESIpos): m/z=677 $[M+H]^+$ $^1$H-NMR (400 MHz, DMSO-d6) δ[ppm]: 0.851 (0.75), 0.871 (1.35), 0.890 (0.56), 1.065 (16.00), 1.101 (0.16), 1.155 (0.99), 1.172 (0.55), 1.189 (0.30), 1.230 (0.86), 1.248 (1.82), 1.265 (0.86), 1.987 (0.96), 2.143 (0.45), 2.157 (0.42), 2.173 (0.30), 2.192 (0.33), 2.213 (0.28), 2.233 (0.26), 2.251 (0.22), 2.327 (0.21), 2.364 (0.29), 2.373 (0.24), 2.383 (0.24), 2.392 (0.23), 2.518 (0.53), 2.523 (0.35), 2.534 (0.18), 3.295 (0.23), 3.316 (0.43), 3.319 (0.43), 3.367 (0.31), 3.381 (0.50), 3.393 (0.50), 3.404 (0.25), 3.816 (0.55), 3.839 (2.57), 3.939 (2.90), 4.016 (0.19), 4.034 (0.18), 4.177 (0.17), 4.204 (0.32), 4.219 (0.57), 4.240 (0.75), 4.258 (0.65), 4.275 (0.20), 4.862 (0.31), 4.875 (0.30), 6.886 (0.22), 6.894 (0.23), 6.900 (0.19), 6.908 (0.22), 7.157 (0.62), 7.179 (0.63), 7.386 (0.18), 7.402 (0.25), 7.408 (0.27), 7.424 (0.18), 7.431 (0.22), 7.438 (0.48), 7.445 (0.54), 7.452 (1.05), 7.650 (0.29), 7.657 (0.30), 7.676 (0.30), 7.683 (0.30), 7.696 (0.45), 7.717 (0.40), 8.247 (0.21), 8.262 (0.26), 8.270 (0.22), 8.285 (0.24), 10.712 (0.50).

Intermediate 128 ethyl (11Z)-4-chloro-3-ethyl-7-{3-[(6-fluoronaphthalen-1-yl)oxy]propyl}-2-methyl-(15R)-[2-(morpholin-4-yl)ethyl]-2,10,13,15-tetrahydropyrazolo[4',3':9,10][1,6]oxazacycloundecino[8,7,6-hi]indole-8-carboxylate

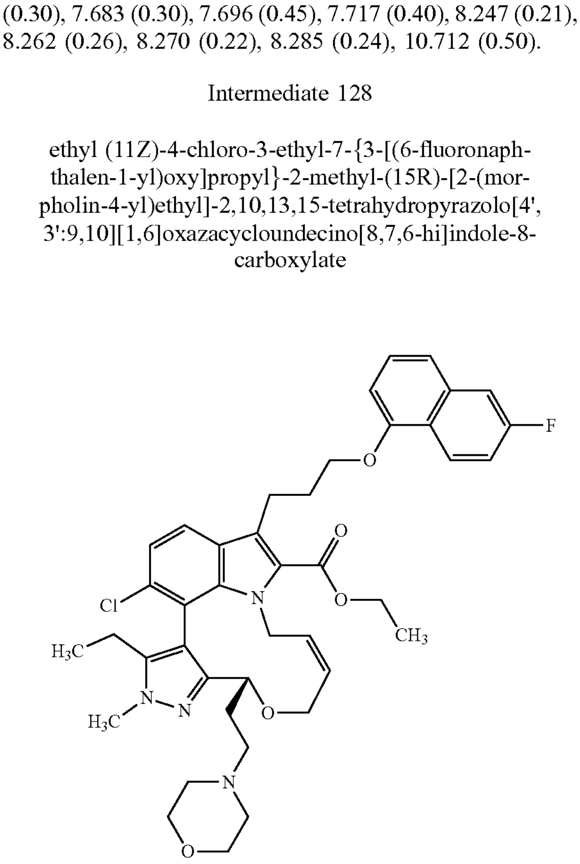

Ethyl 6-chloro-7-{5-ethyl-3-[(1R)-hydroxy-3-(morpholin-4-yl)propyl]-1-methyl-1H-pyrazol-4-yl}-3-{3-[(6-fluoronaphthalen-1-yl)oxy]propyl}-1H-indole-2-carboxylate (see Intermediate 127; 6.50 g) was dissolved in 250 mL of acetonitrile, cesium carbonate (14.1 g, 43.2 mmol), sodium iodide (2.59 g, 17.3 mmol) and (2Z)-1,4-dichlorobut-2-ene (1.00 mL, 9.50 mmol) were added and the mixture was stirred for 17 h at 50° C. Another portion of (2Z)-1,4-dichlorobut-2-ene (0.1 mL, 0.95 mmol) was added and the mixture was stirred for 4 h at 50° C. Yet another portion of (2Z)-1,4-dichlorobut-2-ene (0.05 mL, 0.48 mmol) was added and the mixture was stirred for 3 h at 50° C. The reaction mixture was poured into water and extracted with ethyl acetate. The combined organic layers were washed with brine, dried over sodium sulfate and concentrated under reduced pressure to give 6.33 g of the title compound which were used without further purification.

LC-MS (Method 2): $R_t$=1.72 min; MS (ESIpos): m/z=730 $[M+H]^+$ $^1$H-NMR (400 MHz, DMSO-d6) δ[ppm]: 0.779 (0.48), 0.798 (1.05), 0.817 (0.50), 0.929 (0.24), 0.944 (0.26), 1.066 (16.00), 1.088 (0.26), 1.103 (0.24), 1.154 (0.55), 1.172 (0.91), 1.190 (0.47), 1.252 (0.81), 1.270 (1.61), 1.288 (0.77), 1.900 (0.18), 1.920 (0.17), 1.987 (1.43), 2.142 (0.20), 2.160 (0.36), 2.172 (0.38), 2.179 (0.40), 2.191 (0.48), 2.209 (0.44), 2.231 (0.46), 2.273 (0.25), 2.303 (0.18), 2.323 (0.37), 2.327 (0.45), 2.332 (0.33), 2.518 (1.86), 2.523 (1.16), 2.665 (0.27), 2.669 (0.39), 2.673 (0.28), 3.276 (0.18), 3.291 (0.26), 3.370 (0.31), 3.382 (0.32), 3.397 (0.32), 3.408 (0.30), 3.420 (0.25), 3.682 (0.17), 3.715 (0.18), 3.782 (0.19), 3.815 (0.25), 3.877 (0.19), 3.889 (2.29), 3.903 (0.23), 3.938 (2.57), 4.017 (0.33), 4.035 (0.33), 4.217 (0.43), 4.226 (0.36), 4.235 (0.69), 4.244 (0.49), 4.262 (0.37), 4.282 (0.37), 4.289 (0.20), 4.300 (0.39), 4.309 (0.27), 4.889 (0.16), 6.880 (0.22), 6.887 (0.24), 6.894 (0.22), 6.902 (0.25), 7.258 (0.56), 7.280 (0.57), 7.366 (0.18), 7.382 (0.25), 7.389 (0.28), 7.404 (0.22), 7.411 (0.22), 7.437 (0.48), 7.444 (0.63), 7.451 (1.02), 7.651 (0.29), 7.658 (0.30), 7.677 (0.28), 7.684 (0.29), 7.804 (0.48), 7.826 (0.43), 8.204 (0.20), 8.219 (0.22), 8.227 (0.23), 8.242 (0.22).

Intermediate 129 ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylate

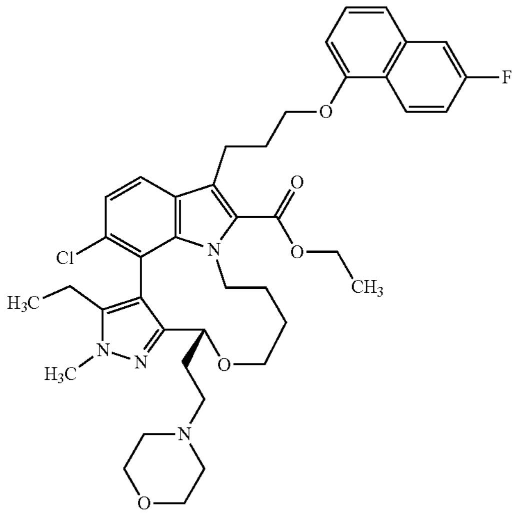 [SMILES: CCOC(=O)c1c(CCCOc2cccc3cc(F)ccc23)c2ccc(Cl)c3c2n1CCCCO[C@H](CCN1CCOCC1)c1nn(C)c(CC)c1-3]

Ethyl (11Z)-4-chloro-3-ethyl-7-{3-[(6-fluoronaphthalen-1-yl)oxy]propyl}-2-methyl-(15R)-[2-(morpholin-4-yl)ethyl]-2,10,13,15-tetrahydropyrazolo[4',3':9,10][1,6]oxazacycloundecino[8,7,6-hi]indole-8-carboxylate (see Intermediate 128; 6.33 g) was dissolved in a mixture of 250 mL of ethanol and 70 mL of tetrahydrofuran, tris(triphenylphosphine)rhodium(I)-chloride (3.63 g, 3.91 mmol) was added and the mixture was stirred for 4 h at rt under hydrogen atmosphere and for 72 h under argon. Another portion of tris(triphenylphosphine)rhodium(I)-chloride (1.00 g, 1.08 mmol) was added and the mixture was stirred for 7 h at rt under hydrogen atmosphere and subsequently under an atmosphere of argon overnight. The reaction mixture was concentrated under reduced pressure and the crude product was purified by flash chromatography using silica gel (gradient dichloromethane/ethanol) to provide 3.64 g of the title compound.

LC-MS (Method 2): $R_t$=1.75 min; MS (ESIpos): m/z=731 $[M+H]^+$ $^1$H-NMR (400 MHz, DMSO-d6) δ[ppm]: 0.788 (3.39), 0.797 (1.27), 0.807 (7.71), 0.825 (3.49), 0.904 (0.56), 1.035 (2.91), 1.052 (4.51), 1.065 (8.58), 1.070 (3.01), 1.087 (0.68), 1.248 (5.67), 1.266 (11.05), 1.284 (5.34), 1.907 (4.46), 2.054 (1.17), 2.071 (1.27), 2.161 (0.94), 2.179 (2.11), 2.185 (2.31), 2.197 (2.56), 2.204 (2.84), 2.215 (1.90), 2.221 (1.79), 2.240 (0.97), 2.248 (0.94), 2.300 (2.56), 2.318 (2.10), 2.322 (2.21), 2.327 (2.26), 2.331 (1.87), 2.518 (3.70), 2.523 (2.42), 2.665 (0.69), 2.669 (0.93), 2.673 (0.68), 3.021 (0.49), 3.034 (0.58), 3.044 (0.67), 3.221 (0.54), 3.238 (0.84), 3.255 (1.14), 3.274 (1.39), 3.292 (1.79), 3.417 (0.41), 3.422 (0.74), 3.435 (0.77), 3.440 (0.74), 3.452 (0.77), 3.457 (0.45), 3.469 (0.58), 3.508 (3.31), 3.861 (16.00), 3.919 (0.65), 3.940 (1.66), 3.954 (0.72), 4.177 (0.85), 4.187 (1.13), 4.195 (2.27), 4.203 (2.29), 4.213 (2.81), 4.222 (2.86), 4.240 (2.37), 4.258 (1.04), 4.262 (1.14), 4.279 (2.04), 4.290 (0.55), 4.298 (1.71), 4.306 (1.07), 4.315 (0.59), 4.324 (1.04), 4.345 (0.46), 4.358 (0.71), 4.410 (0.98), 4.427 (1.72), 4.445 (0.93), 6.859 (1.37), 6.865 (1.46), 6.875 (1.32), 6.881 (1.49), 7.225 (3.79), 7.246 (3.98), 7.370 (1.08), 7.377 (1.26), 7.393 (1.69), 7.399 (1.85), 7.408 (0.98), 7.415 (1.32), 7.421 (1.49), 7.429 (2.82), 7.439 (3.27), 7.445 (6.28), 7.459 (0.82), 7.646 (1.79), 7.653 (1.85), 7.672 (1.76), 7.679 (1.76), 7.771 (3.47), 7.792 (3.12), 8.205 (1.39), 8.220 (1.46), 8.229 (1.45), 8.243 (1.40).

Intermediate 130

1-(4-bromo-5-ethyl-1-methyl-1H-pyrazol-3-yl)-3-(2-methyl-1,3-dioxolan-2-yl)propan-1-one

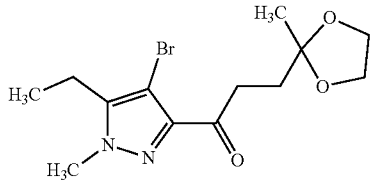 [SMILES: CCc1c(Br)c(C(=O)CCC2(C)OCCO2)nn1C]

Magnesium (685 mg, 28.2 mmol) was provided in 20 mL of tetrahydrofuran, 2-(2-bromoethyl)-2-methyl-1,3-dioxolane (5.00 g, 25.6 mmol) was added dropwise. After a sixth of the amount of 2-(2-bromoethyl)-2-methyl-1,3-dioxolane was added, the temperature was raised to 40° C. and a few crystals of iodine were added. The rest of the 2-(2-bromoethyl)-2-methyl-1,3-dioxolane was added dropwise keeping the temperature below 50° C. After complete addition the mixture was stirred for 20 minutes at 40° C. The solution was added dropwise to a solution of 4-bromo-5-ethyl-N-methoxy-N,1-dimethyl-1H-pyrazole-3-carboxamide (see Intermediate 90, 5.87 g, 21.3 mmol) in 29 mL of tetrahydrofuran and the mixture was stirred for 2 h at room temperature. The reaction mixture was diluted with an aqueous saturated solution of ammonium chloride and extracted with ethyl acetate. The combined organic layers were dried over sodium sulfate, filtered and concentrated under reduced pressure to give 3.70 g of the title compound.

LC-MS (Method 2): $R_t$=1.08 min; MS (ESIpos): m/z=331 $[M+H]^+$ $^1$H-NMR (400 MHz, DMSO-d6) δ[ppm]: 1.078 (2.67), 1.097 (6.34), 1.116 (2.72), 1.155 (0.78), 1.173 (2.02), 1.190 (2.90), 1.209 (1.11), 1.223 (0.93), 1.237 (12.67), 1.895 (1.70), 1.913 (2.40), 1.933 (1.87), 1.988 (3.01), 2.518 (0.90), 2.523 (0.61), 2.621 (0.57), 2.623 (0.58), 2.641 (0.55), 2.669 (0.95), 2.688 (2.50), 2.707 (2.45), 2.726 (0.69), 2.893 (0.55), 2.914 (2.38), 2.924 (0.41), 2.933 (2.39), 2.952 (1.66), 3.793 (0.43), 3.811 (1.57), 3.816 (5.75), 3.821 (1.98), 3.825 (2.56), 3.828 (4.80), 3.833 (1.82), 3.839 (4.67), 3.842 (3.18), 3.847 (2.09), 3.851 (1.54), 3.856 (1.48), 3.874 (0.45), 3.917 (16.00), 4.017 (0.67), 4.035 (0.65), 6.479 (0.87).

Intermediate 131

(rac)-1-(4-bromo-5-ethyl-1-methyl-1H-pyrazol-3-yl)-3-(2-methyl-1,3-dioxolan-2-yl)propan-1-ol

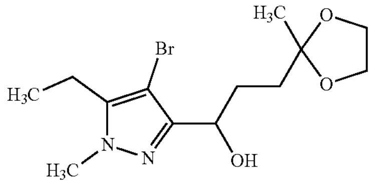 [SMILES: CCc1c(Br)c(C(O)CCC2(C)OCCO2)nn1C]

1-(4-bromo-5-ethyl-1-methyl-1H-pyrazol-3-yl)-3-(2-methyl-1,3-dioxolan-2-yl)propan-1-one (see Intermediate 130, 3.70 g) was dissolved in 100 mL of tetrahydrofuran, lithium borohydride (11.2 mL, 2.0 M in THF, 22.4 mmol) was added at rt and the mixture was stirred for 30 min at room temperature. The reaction mixture was poured into water and extracted with ethyl acetate. The combined organic layers were dried over sodium sulfate, filtered and concentrated under reduced pressure to give 3.38 g of the title compound which were used without further purification.

$^1$H-NMR (400 MHz, DMSO-d6) δ[ppm]: 1.061 (2.86), 1.080 (6.46), 1.087 (0.88), 1.099 (2.75), 1.109 (0.63), 1.142 (0.61), 1.153 (1.00), 1.158 (1.11), 1.161 (1.48), 1.172 (0.87), 1.179 (0.81), 1.189 (3.98), 1.195 (11.15), 1.210 (0.80), 1.222 (0.67), 1.230 (0.45), 1.353 (1.32), 1.427 (0.53), 1.436 (0.50), 1.439 (0.51), 1.456 (0.56), 1.465 (0.43), 1.645 (0.48), 1.660 (0.66), 1.673 (0.65), 1.693 (0.47), 1.702 (0.85), 1.709 (0.44), 1.729 (0.55), 1.741 (0.62), 1.756 (0.67), 1.762 (0.46), 1.771 (0.70), 1.779 (0.48), 1.787 (0.51), 1.790 (0.59), 1.799 (0.40), 1.807 (0.42), 1.819 (0.48), 2.518 (0.91), 2.523 (0.58), 2.602 (0.86), 2.621 (2.58), 2.640 (2.43), 2.652 (0.44), 2.659 (0.80), 2.669 (0.42), 3.635 (2.16), 3.732 (1.27), 3.734 (1.12), 3.752 (16.00), 3.768 (1.01), 3.771 (0.89), 3.782 (0.64), 3.789 (2.05), 3.793 (1.67), 3.797 (1.95), 3.802 (2.33), 3.806 (3.22), 3.809 (2.23), 3.813 (0.99), 3.821 (2.71), 3.825 (3.24), 3.828 (2.25), 3.833 (2.06), 3.837 (1.71), 3.842 (1.81), 3.851 (0.41), 3.859 (0.57), 4.427 (0.63), 4.432 (0.48), 4.441 (0.51), 4.445 (0.69), 4.958 (2.18), 4.971 (2.12), 5.917 (0.43).

Intermediate 132 ethyl 6-chloro-7-{5-ethyl-3-[(1-rac)-hydroxy-3-(2-methyl-1,3-dioxolan-2-yl)propyl]-1-methyl-1H-pyrazol-4-yl}-3-{3-[(6-fluoronaphthalen-1-yl)oxy]propyl}-1H-indole-2-carboxylate

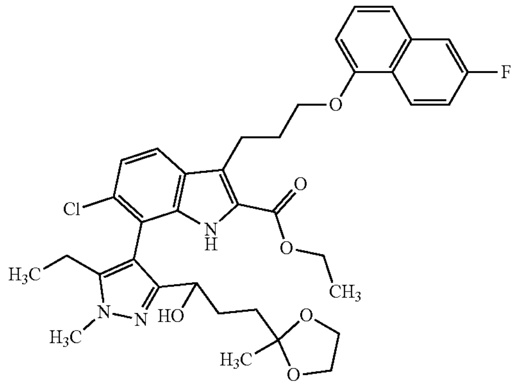 [SMILES: CCOC(=O)c1[nH]c2c(-c3c(C(O)CCC4(C)OCCO4)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 3.01 g, 5.46 mmol), (rac)-1-(4-bromo-5-ethyl-1-methyl-1H-pyrazol-3-yl)-3-(2-methyl-1,3-dioxolan-2-yl)propan-1-ol (see Intermediate 131, 2.00 g) and potassium triphosphate (2.32 g, 10.9 mmol) were provided in a mixture of 16 mL of 1,4-dioxane and 4 mL of water and were purged with argon for 10 minutes. RuPhos Pd G3 (456 mg, 546 μmol) was added and the mixture was stirred for 1 h at 110° C. in a microwave reactor. The aqueous phase was removed and the organic layer was concentrated under reduced pressure. The crude material was purified by flash chromatography using silica gel (aminophase, gradient hexane/ethyl acetate) to provide 2.20 g of the title compound which was formed as a mixture of two racemic diastereomers as a result of atropisomerism at the newly formed bi-heteroaryl bond in two batches (1. 1.60 g; 2. 605 mg). The two batches were combined.

Batch 1:

LC-MS (Method 2): $R_t$=1.67 min; MS (ESIpos): m/z=678 $[M+H]^+$ $^1$H-NMR (400 MHz, DMSO-d6) δ[ppm]: 0.821 (0.22), 0.840 (0.61), 0.847 (0.88), 0.866 (1.97), 0.885 (0.86), 0.933 (1.03), 1.061 (0.64), 1.066 (2.41), 1.080 (1.28), 1.099 (0.59), 1.118 (3.87), 1.142 (3.56), 1.154 (3.37), 1.161 (7.61), 1.172 (6.77), 1.179 (3.98), 1.190 (14.37), 1.195 (3.01), 1.228 (1.45), 1.246 (3.26), 1.263 (1.52), 1.337 (0.17), 1.378 (0.17), 1.384 (0.18), 1.406 (0.22), 1.419 (0.23), 1.435 (0.23), 1.446 (0.22), 1.456 (0.46), 1.474 (0.53), 1.481 (0.49), 1.501 (0.40), 1.507 (0.30), 1.537 (0.18), 1.552 (0.17), 1.565 (0.18), 1.600 (0.19), 1.619 (0.43), 1.631 (0.61), 1.645 (0.81), 1.653 (1.75), 1.658 (1.38), 1.664 (1.82), 1.674 (0.49), 1.681 (0.46), 1.693 (0.35), 1.702 (0.37), 1.715 (0.37), 1.730 (0.33), 1.745 (0.31), 1.757 (0.24), 1.772 (0.20), 1.791 (0.16), 1.987 (10.73), 2.193 (0.28), 2.210 (0.41), 2.228 (0.31), 2.331 (0.44), 2.336 (0.41), 2.356 (0.47), 2.365 (0.35), 2.375 (0.37), 2.384 (0.34), 2.402 (0.16), 2.518 (1.76), 2.523 (1.12), 2.529 (0.88), 2.548 (2.16), 2.567 (2.09), 2.586 (0.68), 2.602 (0.17), 2.621 (0.51), 2.640 (0.48), 2.673 (0.34), 3.288 (0.33), 3.312 (0.68), 3.583 (0.27), 3.635 (16.00), 3.668 (0.29), 3.681 (0.80), 3.687 (0.79), 3.692 (0.62), 3.702 (0.37), 3.712 (0.28), 3.738 (0.19), 3.742 (0.27), 3.752 (3.18), 3.763 (0.73), 3.770 (1.32), 3.786 (1.27), 3.789 (1.63), 3.794 (1.69), 3.801 (2.39), 3.806 (2.29), 3.818 (2.59), 3.822 (2.82), 3.825 (2.41), 3.830 (1.80), 3.835 (1.60), 3.839 (1.81), 3.844 (4.34), 3.855 (0.56), 3.858 (0.24), 3.938 (0.38), 3.999 (0.87), 4.017 (2.64), 4.035 (2.51), 4.053 (0.77), 4.201 (0.53), 4.217 (0.92), 4.238 (1.19), 4.256 (1.09), 4.274 (0.33), 4.339 (0.24), 4.353 (0.68), 4.365 (0.63), 4.370 (0.49), 4.382 (0.33), 4.731 (0.84), 4.743 (0.77), 4.849 (2.73), 4.862 (2.59), 4.958 (0.54), 4.970 (0.53), 5.068 (0.20), 5.076 (0.20), 5.917 (3.00), 6.889 (0.39), 6.896 (0.33), 6.902 (0.28), 6.910 (0.32), 7.155 (0.31), 7.160 (1.01), 7.176 (0.33), 7.182 (1.00), 7.379 (0.23), 7.386 (0.27), 7.402 (0.35), 7.408 (0.41), 7.424 (0.27), 7.431 (0.36), 7.434 (0.37), 7.440 (0.75), 7.445 (0.87), 7.453 (1.50), 7.651 (0.49), 7.657 (0.50), 7.677 (0.49), 7.684 (0.67), 7.693 (0.69), 7.705 (0.20), 7.714 (0.61), 8.249 (0.33), 8.263 (0.35), 8.272 (0.36), 8.287 (0.35), 10.613 (0.18), 10.695 (0.69).

Batch 2:

LC-MS (Method 2): $R_t$=1.67 min; MS (ESIpos): m/z=678 $[M+H]^+$ $^1$H-NMR (400 MHz, DMSO-d6) δ[ppm]: 0.821 (0.22), 0.840 (0.58), 0.846 (0.90), 0.866 (1.95), 0.884 (0.88), 0.933 (0.96), 1.066 (4.34), 1.118 (4.01), 1.136 (0.23), 1.141 (0.28), 1.154 (4.54), 1.160 (0.63), 1.172 (9.25), 1.179 (0.40), 1.189 (5.24), 1.228 (1.46), 1.246 (3.16), 1.263 (1.50), 1.295 (0.18), 1.378 (0.16), 1.384 (0.17), 1.405 (0.19), 1.412 (0.24), 1.420 (0.21), 1.430 (0.24), 1.448 (0.20), 1.553 (0.17), 1.565 (0.20), 1.716 (0.26), 1.731 (0.28), 1.746 (0.24), 1.758 (0.16), 1.987 (16.00), 2.193 (0.31), 2.210 (0.44), 2.227 (0.33), 2.318 (0.17), 2.322 (0.20), 2.327 (0.24), 2.336 (0.35), 2.356 (0.51), 2.365 (0.39), 2.375 (0.40), 2.384 (0.37), 2.402 (0.17), 2.518 (0.65), 2.522 (0.39), 2.669 (0.19), 3.288 (0.35), 3.306 (0.65), 3.582 (0.25), 3.635 (0.91), 3.668 (0.29), 3.682 (0.85), 3.687 (0.81), 3.692 (0.64), 3.702 (0.37), 3.712 (0.29), 3.738 (0.19), 3.742 (0.24), 3.750 (0.37), 3.762 (0.70), 3.770 (0.96), 3.788 (0.24), 3.794 (0.19), 3.801 (0.18), 3.806 (0.17), 3.818 (1.09), 3.830 (0.25), 3.844 (4.04), 3.939 (0.71), 3.999 (1.24), 4.017 (3.88), 4.035 (3.86), 4.053 (1.25), 4.200 (0.58), 4.216 (0.96), 4.238 (1.24), 4.256 (1.13), 4.274 (0.35), 4.731 (0.86), 4.743 (0.80), 5.068 (0.20), 5.077 (0.20), 5.917 (0.19), 6.887 (0.41), 6.895 (0.36), 6.901 (0.30), 6.908 (0.34), 7.155 (0.28), 7.160 (0.98), 7.176 (0.30), 7.181 (0.99), 7.379 (0.23), 7.385 (0.29), 7.401 (0.38), 7.408 (0.43), 7.418 (0.16), 7.423 (0.29), 7.430 (0.35), 7.439 (0.79), 7.445 (0.94), 7.452 (1.55), 7.650 (0.51), 7.657 (0.53), 7.676 (0.51), 7.683 (0.67), 7.691 (0.72), 7.705 (0.20), 7.713 (0.64), 8.249 (0.35), 8.263 (0.37), 8.271 (0.38), 8.287 (0.37), 10.614 (0.19), 10.695 (0.76).

Intermediate 133

(rac)-ethyl (11Z)-4-chloro-3-ethyl-7-{3-[(6-fluoronaphthalen-1-yl)oxy]propyl}-2-methyl-(15-rac)-[2-(2-methyl-1,3-dioxolan-2-yl)ethyl]-2,10,13,15-tetrahydropyrazolo[4',3':9,10][1,6]oxazacycloundecino[8,7,6-hi]indole-8-carboxylate

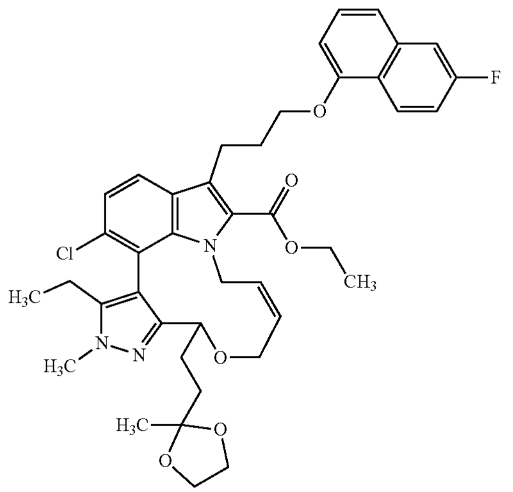 [SMILES: CCOC(=O)c1c(CCCOc2cccc3cc(F)ccc23)c2ccc(Cl)c3c2n1C/C=C\COC(CCC1(C)OCCO1)c1nn(C)c(CC)c1-3]

Ethyl 6-chloro-7-{5-ethyl-3-[(1-rac)-hydroxy-3-(2-methyl-1,3-dioxolan-2-yl)propyl]-1-methyl-1H-pyrazol-4-yl}-3-{3-[(6-fluoronaphthalen-1-yl)oxy]propyl}-1H-indole-2-carboxylate (see Intermediate 132, 2.20 g, 1.13 mmol) was dissolved in 40 mL of acetonitrile, cesium carbonate (5.28 g, 16.2 mmol), sodium iodide (972 mg, 6.49 mmol) and (2Z)-1,4-dichlorobut-2-ene (375 μL, 3.57 mmol) were added and the mixture was stirred for 17 h at 50° C. The reaction mixture was filtered, water was added and the mixture was extracted with ethyl acetate. The combined organic layers were washed with brine, dried over sodium sulfate, filtered and concentrated under reduced pressure. The crude material was purified by flash chromatography using silica gel (aminophase, gradient hexane/ethyl acetate) to give 685 mg of the title compound which was formed as a racemic mixture of two enantiomers as only one of the two diastereomers formed in the preceding step underwent the macrocyclization reaction.

LC-MS (Method 2): $R_t$=1.74 min; MS (ESIpos): m/z=730 $[M+H]^+$ $^1$H-NMR (400 MHz, DMSO-d6) δ[ppm]: 0.772 (1.36), 0.791 (3.26), 0.810 (1.42), 1.066 (1.47), 1.154 (10.50), 1.172 (8.61), 1.190 (4.59), 1.195 (0.29), 1.251 (2.12), 1.268 (4.58), 1.287 (2.16), 1.511 (0.40), 1.539 (0.27), 1.807 (0.62), 1.830 (0.96), 1.836 (1.03), 1.847 (0.41), 1.860 (0.22), 1.877 (0.19), 1.978 (0.16), 1.987 (16.00), 2.128 (0.27), 2.146 (0.65), 2.156 (0.55), 2.164 (0.56), 2.175 (0.57), 2.193 (0.32), 2.219 (0.37), 2.234 (0.52), 2.252 (0.39), 2.518 (1.32), 2.523 (0.85), 3.271 (0.31), 3.288 (0.55), 3.292 (0.53), 3.302 (0.61), 3.309 (0.53), 3.635 (0.51), 3.647 (0.26), 3.666 (0.40), 3.679 (0.56), 3.687 (0.42), 3.703 (0.80), 3.719 (0.46), 3.727 (0.40), 3.737 (0.56), 3.741 (0.75), 3.753 (0.56), 3.760 (0.91), 3.769 (0.98), 3.776 (0.49), 3.779 (0.82), 3.789 (1.34), 3.795 (1.07), 3.798 (1.53), 3.805 (0.44), 3.810 (0.42), 3.821 (0.24), 3.829 (0.34), 3.874 (0.21), 3.890 (7.29), 3.939 (0.22), 3.999 (1.13), 4.017 (3.38), 4.034 (3.27), 4.053 (1.05), 4.144 (0.37), 4.166 (0.51), 4.173 (0.31), 4.197 (0.17), 4.215 (0.56), 4.224 (0.70), 4.237 (1.29), 4.242 (1.19), 4.251 (0.67), 4.260 (0.95), 4.280 (0.86), 4.298 (0.73), 4.307 (0.37), 4.316 (0.21), 4.325 (0.36), 4.635 (0.20), 4.663 (0.26), 4.675 (0.31), 4.701 (0.31), 4.883 (0.40), 4.924 (0.77), 4.948 (0.45), 4.974 (0.24), 5.177 (0.25), 5.188 (0.25), 6.885 (0.53), 6.894 (0.58), 6.899 (0.49), 6.907 (0.58), 7.269 (1.78), 7.290 (1.84), 7.351 (0.37), 7.357 (0.42), 7.373 (0.53), 7.380 (0.61), 7.395 (0.39), 7.402 (0.42), 7.438 (1.19), 7.444 (1.28), 7.452 (2.61), 7.649 (0.68), 7.656 (0.71), 7.675 (0.68), 7.682 (0.70), 7.803 (1.57), 7.825 (1.37), 8.189 (0.58), 8.203 (0.61), 8.212 (0.60), 8.227 (0.56).

Intermediate 134

(rac)-ethyl 4-chloro-3-ethyl-7-{3-[(6-fluoronaphthalen-1-yl)oxy]propyl}-2-methyl-(15-rac)-[2-(2-methyl-1,3-dioxolan-2-yl)ethyl]-2,10,11,12,13,15-hexahydropyrazolo[4',3':9,10][1,6]oxazacycloundecino[8,7,6-hi]indole-8-carboxylate

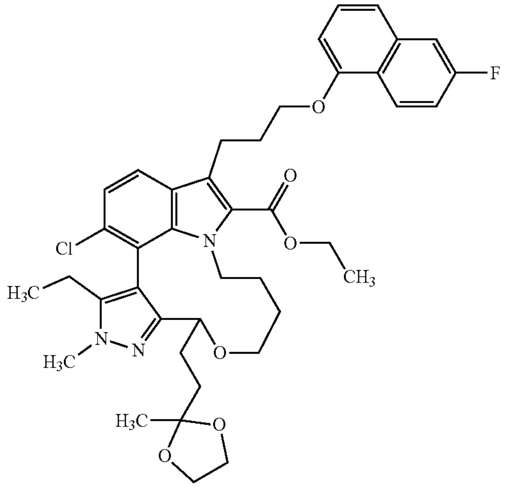 [SMILES: CCOC(=O)c1c(CCCOc2cccc3cc(F)ccc23)c2ccc(Cl)c3c2n1CCCCOC(CCC1(C)OCCO1)c1nn(C)c(CC)c1-3]

(Rac)-ethyl (11Z)-4-chloro-3-ethyl-7-{3-[(6-fluoronaphthalen-1-yl)oxy]propyl}-2-methyl-(15-rac)-[2-(2-methyl-1,3-dioxolan-2-yl)ethyl]-2,10,13,15-tetrahydropyrazolo[4',3':9,10][1,6]oxazacycloundecino[8,7,6-hi]indole-8-carboxylate (see Intermediate 133, 975 mg, 1.34 mmol) was dissolved in a mixture of 40 mL of ethanol and 10 mL of tetrahydrofuran, tris(triphenylphosphine)rhodium(I)-chloride (248 mg, 267 μmol) was added and the mixture was stirred for 8 h under hydrogen atmosphere at room temperature. The reaction mixture was concentrated under reduced pressure. The crude material was purified by flash chromatography using silica gel (aminophase, gradient hexane/ethyl acetate) to provide 593 mg (57% yield) of the title compound.

LC-MS (Method 2): $R_t$=1.78 min; MS (ESIpos): m/z=732 $[M+H]^+$ $^1$H-NMR (400 MHz, DMSO-d6) δ[ppm]: 0.786 (1.01), 0.805 (2.34), 0.824 (1.08), 0.994 (0.22), 1.012 (0.29), 1.030 (0.29), 1.066 (0.49), 1.088 (0.16), 1.154 (3.87), 1.172 (7.85), 1.190 (4.09), 1.220 (4.87), 1.248 (1.72), 1.266 (3.53), 1.284 (1.65), 1.572 (0.19), 1.586 (0.20), 1.599 (0.22), 1.613 (0.29), 1.636 (0.20), 1.649 (0.22), 1.930 (0.20), 1.944 (0.21), 1.956 (0.22), 1.978 (0.39), 1.987 (16.00), 2.155 (0.23), 2.173 (0.57), 2.179 (0.54), 2.192 (0.67), 2.197 (0.71), 2.215 (0.55), 2.331 (0.22), 2.518 (1.12), 2.523 (0.71), 2.673 (0.22), 3.018 (0.17), 3.030 (0.19), 3.236 (0.22), 3.255 (0.45), 3.273 (0.47), 3.288 (0.47), 3.304 (0.35), 3.780 (0.30), 3.796 (0.49), 3.801 (0.49), 3.807 (0.39), 3.812 (0.80), 3.821 (0.84), 3.825 (0.55), 3.831 (0.82), 3.835 (0.86), 3.839 (1.00), 3.842 (1.00), 3.847 (0.76), 3.862 (5.16), 3.925 (0.18), 3.941 (0.22), 3.960 (0.21), 3.999 (1.16), 4.017 (3.49), 4.035 (3.48), 4.053 (1.12), 4.177 (0.22), 4.187 (0.28), 4.195 (0.65), 4.202 (0.62), 4.213 (0.84), 4.222 (0.88), 4.240 (0.80), 4.245 (0.53), 4.262 (0.68), 4.279 (0.81), 4.297 (0.51), 4.306 (0.32), 4.315 (0.16), 4.324 (0.32), 6.860 (0.41), 6.866 (0.44), 6.874 (0.39), 6.881 (0.47), 7.216 (1.28), 7.238 (1.27), 7.366 (0.27), 7.372 (0.31), 7.388 (0.43), 7.395 (0.45), 7.410 (0.35), 7.417 (0.32), 7.429 (0.77), 7.438 (0.88), 7.444 (1.89), 7.644 (0.50), 7.650 (0.51), 7.670 (0.49), 7.676 (0.49), 7.764 (1.07), 7.785 (0.96), 8.191 (0.42), 8.206 (0.43), 8.214 (0.43), 8.229 (0.41).

Intermediate 135

(rac)-ethyl 4-chloro-3-ethyl-7-{3-[(6-fluoronaphthalen-1-yl)oxy]propyl}-2-methyl-(15-rac)-(3-oxobutyl)-2,10,11,12,13,15-hexahydropyrazolo[4',3':9,10][1,6]oxazacycloundecino[8,7,6-hi]indole-8-carboxylate

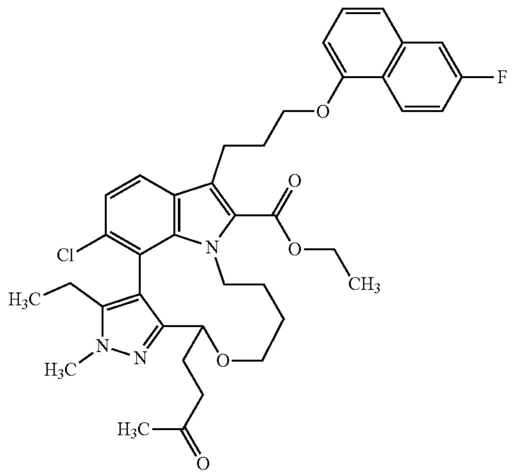 [SMILES: CCOC(=O)c1c(CCCOc2cccc3cc(F)ccc23)c2ccc(Cl)c3c2n1CCCCOC(CCC(C)=O)c1nn(C)c(CC)c1-3]

(Rac)-ethyl 4-chloro-3-ethyl-7-{3-[(6-fluoronaphthalen-1-yl)oxy]propyl}-2-methyl-(15-rac)-[2-(2-methyl-1,3-dioxolan-2-yl)ethyl]-2,10,11,12,13,15-hexahydropyrazolo[4',3':9,10][1,6]oxazacycloundecino[8,7,6-hi]indole-8-carboxylate (see Intermediate 134, 590 mg, 806 μmol) was dissolved in 10 mL of 1,4-dioxane, a solution of hydrogen chloride in 1,4-dioxane (2.0 mL, 4.0 M, 8.0 mmol) was added and the mixture was stirred for 72 h at room temperature. A solution of hydrogen chloride in 1,4-dioxane (1.0 mL, 4.0 M, 4.0 mmol) was added and the mixture was stirred for 5 h at room temperature. A solution of hydrogen chloride in 1,4-dioxane (1.0 mL, 4.0 M, 4.0 mmol) was added and the mixture was stirred over night at room temperature. The reaction mixture was poured into water and extracted with ethyl acetate. The organic layers were dried over sodium sulfate, filtered and concentrated under reduced pressure. The resulting material was stirred in a solution of hydrogen chloride in 1,4-dioxane (10 mL, 4.0 M, 40 mmol) for 72 h at room temperature. The reaction mixture was poured into water and extracted with ethyl acetate. The organic layers were dried over sodium sulfate, filtered and concentrated under reduced pressure to provide 537 mg of the title compound which was used without further purification.

LC-MS (Method 2): $R_t$=1.74 min; MS (ESIpos): m/z=688 $[M+H]^+$ $^1$H-NMR (400 MHz, DMSO-d6) δ[ppm]: 0.785 (2.47), 0.805 (5.87), 0.823 (2.67), 0.963 (0.49), 0.982 (0.53), 1.014 (0.44), 1.246 (4.20), 1.263 (9.06), 1.281 (4.20), 1.351 (2.89), 1.739 (0.61), 1.746 (0.53), 1.755 (1.73), 1.764 (0.51), 1.772 (0.53), 2.050 (16.00), 2.073 (0.89), 2.091 (1.21), 2.109 (0.96), 2.126 (0.44), 2.157 (0.59), 2.163 (0.52), 2.176 (1.44), 2.182 (1.57), 2.194 (1.69), 2.201 (1.86), 2.212 (1.21), 2.220 (1.12), 2.238 (0.43), 2.518 (2.38), 2.522 (1.26), 3.029 (0.44), 3.042 (0.45), 3.234 (0.51), 3.252 (1.00), 3.271 (1.05), 3.289 (1.12), 3.304 (0.69), 3.565 (12.76), 3.581 (0.66), 3.592 (0.48), 3.597 (1.36), 3.604 (0.45), 3.615 (0.54), 3.851 (0.44), 3.865 (13.51), 3.926 (0.47), 3.943 (0.51), 3.961 (0.55), 4.175 (0.54), 4.184 (0.69), 4.193 (1.63), 4.200 (1.43), 4.211 (1.90), 4.220 (2.10), 4.231 (1.74), 4.238 (1.87), 4.249 (2.06), 4.255 (0.88), 4.260 (0.94), 4.266 (1.24), 4.278 (1.69), 4.296 (1.36), 4.305 (0.82), 4.313 (0.41), 4.323 (0.83), 6.858 (1.00), 6.865 (1.16), 6.874 (0.93), 6.880 (1.11), 7.221 (3.13), 7.241 (3.43), 7.367 (0.69), 7.374 (0.78), 7.389 (1.01), 7.397 (1.15), 7.412 (0.78), 7.419 (0.89), 7.429 (1.89), 7.438 (2.14), 7.445 (4.69), 7.645 (1.23), 7.652 (1.29), 7.671 (1.22), 7.678 (1.25), 7.768 (2.84), 7.789 (2.66), 8.203 (1.03), 8.217 (1.09), 8.225 (1.07), 8.240 (1.01).

Intermediate 136

(rac)-ethyl 4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylate

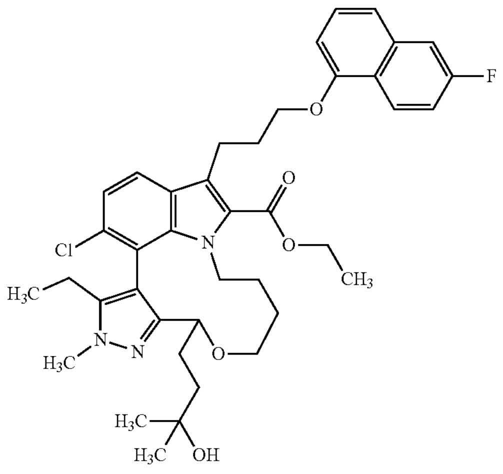 [SMILES: CCOC(=O)c1c(CCCOc2cccc3cc(F)ccc23)c2ccc(Cl)c3c2n1CCCCOC(CCC(C)(C)O)c1nn(C)c(CC)c1-3]

(Rac)-ethyl 4-chloro-3-ethyl-7-{3-[(6-fluoronaphthalen-1-yl)oxy]propyl}-2-methyl-(15-rac)-(3-oxobutyl)-2,10,11,12,13,15-hexahydropyrazolo[4',3':9,10][1,6]oxazacycloundecino[8,7,6-hi]indole-8-carboxylate (see Intermediate 135, 346 mg) was dissolved in 9.8 mL of tetrahydrofuran, a solution of chloro(methyl)magnesium (168 μL, 3.0 M in diethylether, 503 μmol) was added at 0° C. and the mixture was stirred over night at it A solution of chloro(methyl) magnesium (168 μL, 3.0 M in diethylether, 503 μmol) was added at 0° C. and the mixture was stirred over night at it A solution of chloro(methyl)magnesium (84 μL, 3.0 M in diethylether, 252 μmol) was added at 0° C. and the mixture was stirred for 6 h at rt. The reaction mixture was diluted with a saturated aqueous ammonium chloride solution and extracted with ethyl acetate. The combined organic layers were dried over sodium sulfate, filtered and concentrated under reduced pressure. The resulting material was stirred in a solution of chloro(methyl)magnesium (168 μL, 3.0 M in diethylether, 503 μmol) over night at rt. The reaction mixture was diluted with a saturated aqueous ammonium chloride solution and extracted with ethyl acetate. The combined organic layers were dried over sodium sulfate, filtered and concentrated under reduced pressure. The crude material was purified by flash chromatography using silica gel (gradient dichloromethane/ethanol). The resulting material was stirred in a solution of chloro(methyl)magnesium (168 μL, 3.0 M in diethylether, 503 μmol) for 3 h at rt. The reaction mixture was diluted with a saturated aqueous ammonium chloride solution and extracted with ethyl acetate. The combined organic layers were dried over sodium sulfate, filtered and concentrated under reduced pressure to give 345 mg of the title compound.

LC-MS (Method 2): $R_t$=1.72 min; MS (ESIpos): m/z=704 $[M+H]^+$ $^1$H-NMR (400 MHz, DMSO-d6) δ[ppm]: 0.788 (2.75), 0.807 (6.01), 0.825 (2.70), 1.070 (16.00), 1.136 (0.29), 1.154 (2.31), 1.172 (4.27), 1.189 (2.06), 1.241 (1.45), 1.249 (4.47), 1.258 (2.31), 1.267 (8.54), 1.284 (4.22), 1.314 (0.49), 1.328 (0.47), 1.352 (3.66), 1.405 (0.37), 1.417 (0.44), 1.436 (0.44), 1.446 (0.47), 1.468 (0.29), 1.480 (0.25), 1.602 (0.39), 1.757 (0.20), 1.880 (0.25), 1.914 (0.44), 1.928 (0.44), 1.945 (0.49), 1.958 (0.44), 1.987 (7.85), 2.050 (2.70), 2.071 (0.29), 2.090 (0.37), 2.108 (0.32), 2.156 (0.91), 2.175 (2.18), 2.195 (2.55), 2.213 (1.72), 2.331 (1.08), 2.336 (0.52), 2.518 (6.31), 2.523 (3.90), 2.673 (1.08), 2.678 (0.47), 3.020 (0.64), 3.202 (0.29), 3.219 (0.49), 3.236 (0.76), 3.253 (1.13), 3.271 (1.42), 3.288 (1.57), 3.307 (1.30), 3.357 (0.29), 3.861 (11.90), 3.927 (0.54), 3.944 (0.56), 3.962 (0.56), 3.999 (0.61), 4.017 (1.67), 4.035 (1.67), 4.053 (0.56), 4.096 (4.96), 4.179 (0.88), 4.196 (2.21), 4.205 (2.72), 4.213 (2.72), 4.223 (3.07), 4.241 (2.55), 4.258 (1.20), 4.279 (1.62), 4.289 (0.56), 4.297 (1.40), 4.306 (0.86), 4.315 (0.52), 4.324 (0.81), 4.342 (0.25), 5.758 (5.18), 6.861 (1.30), 6.868 (1.52), 6.876 (1.03), 6.882 (1.10), 7.172 (0.17), 7.194 (0.29), 7.214 (2.80), 7.221 (0.83), 7.236 (2.80), 7.243 (0.69), 7.369 (0.79), 7.376 (1.06), 7.391 (1.18), 7.398 (1.37), 7.414 (1.06), 7.420 (1.35), 7.431 (2.72), 7.439 (2.58), 7.445 (4.86), 7.459 (0.37), 7.644 (1.28), 7.651 (1.20), 7.660 (0.44), 7.670 (1.25), 7.677 (1.13), 7.760 (2.38), 7.769 (0.71), 7.781 (2.11), 7.790 (0.52), 8.192 (0.98), 8.207 (1.08), 8.216 (1.15), 8.230 (0.96).

Intermediate 137

1-(4-bromo-5-ethyl-1-methyl-1H-pyrazol-3-yl)-3-(3,3-difluoroazetidin-1-yl)propan-1-one

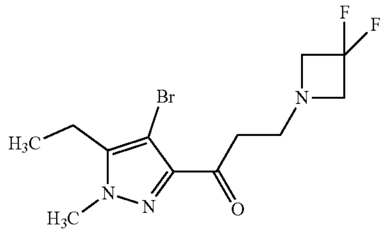 [SMILES: CCc1c(Br)c(C(=O)CCN2CC(F)(F)C2)nn1C]

4-Bromo-5-ethyl-N-methoxy-N,1-dimethyl-1H-pyrazole-3-carboxamide (see Intermediate 90, 3.00 g, 10.9 mmol) and N,N-diisopropylethylamine (1.9 mL, 10.9 mmol) were dissolved in 15 mL of THF and a solution of bromo(vinyl)magnesium (21.7 mL, 1.0 M in 21.7 mmol) was added at 2° C. The mixture was stirred at 2° C. for 30 minutes and then added dropwise to a mixture of 3,3-difluoroazetidine hydrogen chloride salt (5.63 g, 43.4 mmol) in 30 mL of tetrahydrofuran at 2° C. and the mixture was stirred for 1 h at 0° C. The reaction mixture was diluted with water and ethyl acetate, the phases were separated and the aqueous phase was extracted with ethyl acetate. The combined organic layers were washed with brine, filtered using a water resistant filter and concentrated under reduced pressure. The residue was purified by flash chromatography using silica gel (gradient hexane/ethyl acetate) to provide 3.23 g of the title compound.

LC-MS (Method 2): $R_t$=1.10 min; MS (ESIpos): m/z=336 $[M+H]^+$ $^1$H-NMR (400 MHz, DMSO-d6) δ[ppm]: 1.077 (2.92), 1.096 (6.89), 1.115 (3.02), 2.482 (5.40), 2.518 (0.73), 2.522 (0.46), 2.671 (1.05), 2.690 (3.22), 2.709 (3.16), 2.728 (0.92), 2.817 (0.55), 2.820 (0.56), 2.834 (1.35), 2.838 (1.60), 2.853 (1.08), 2.908 (0.56), 2.926 (1.92), 2.943 (2.59), 2.960 (0.77), 2.963 (0.72), 3.094 (0.53), 3.324 (7.37), 3.517 (3.76), 3.549 (8.00), 3.580 (3.75), 3.919 (16.00), 3.923 (6.96).

Intermediate 138

(rac)-1-(4-bromo-5-ethyl-1-methyl-1H-pyrazol-3-yl)-3-(3,3-difluoroazetidin-1-yl)propan-1-ol

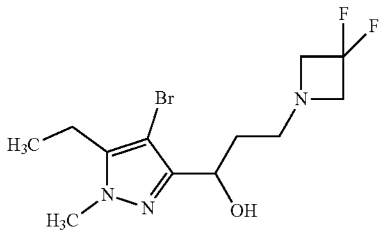 [SMILES: CCc1c(Br)c(C(O)CCN2CC(F)(F)C2)nn1C]

1-(4-Bromo-5-ethyl-1-methyl-1H-pyrazol-3-yl)-3-(3,3-difluoroazetidin-1-yl)propan-1-one (see Intermediate 137, 3.20 g) was dissolved in 15 mL of methanol. Sodium borohydride (1.08 g, 28.6 mmol) was added and the mixture was stirred for 24 h at room temperature. The reaction mixture was diluted with water, methanol was removed under reduced pressure and the aqueous phase was extracted with ethyl acetate. The combined organic layers were washed with brine, filtered through a water resistant filter and concentrated under reduced pressure. The residue was purified by flash chromatography using silica gel (gradient dichloromethane/ethanol) to give 3.02 g of the title compound.

LC-MS (Method 2): $R_t$=0.98 min; MS (ESIpos): m/z=338 $[M+H]^+$ $^1$H-NMR (400 MHz, DMSO-d6) δ[ppm]: 1.059 (2.80), 1.064 (1.46), 1.078 (6.69), 1.083 (3.09), 1.097 (2.97), 1.103 (1.41), 1.687 (0.48), 1.707 (0.67), 1.720 (0.56), 1.783 (0.51), 1.799 (0.49), 1.803 (0.52), 1.819 (0.46), 2.465 (4.62), 2.518 (1.17), 2.523 (1.35), 2.543 (1.66), 2.560 (0.82), 2.572 (0.49), 2.589 (0.94), 2.601 (0.96), 2.606 (0.82), 2.620 (2.86), 2.624 (1.52), 2.639 (2.75), 2.643 (1.40), 2.658 (0.82), 3.382 (6.51), 3.481 (3.31), 3.513 (6.71), 3.544 (3.24), 3.751 (16.00), 3.757 (6.66), 4.533 (0.71), 4.541 (0.51), 4.547 (0.50), 4.555 (0.73), 5.000 (0.58), 5.013 (0.54), 5.037 (1.59), 5.050 (1.51), 5.758 (1.77).

Intermediate 139 ethyl 6-chloro-7-{3-[(1-rac)-3-(3,3-difluoroazetidin-1-yl)-1-hydroxypropyl]-5-ethyl-1-methyl-1H-pyrazol-4-yl}-3-{3-[(6-fluoronaphthalen-1-yl)oxy]propyl}-1H-indole-2-carboxylate

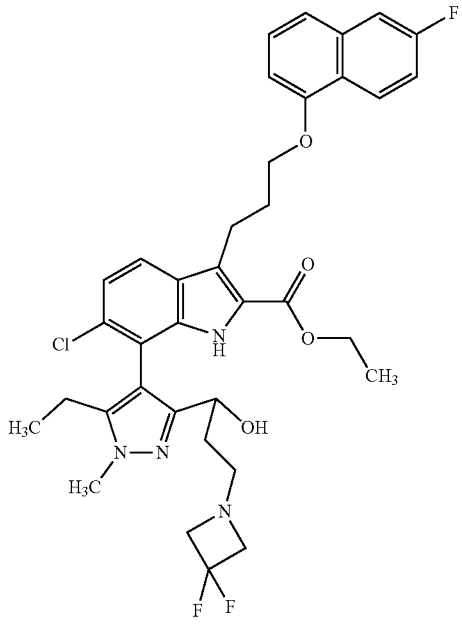 [SMILES: CCOC(=O)c1[nH]c2c(-c3c(C(O)CCN4CC(F)(F)C4)nn(C)c3CC)c(Cl)ccc2c1CCCOc1cccc2cc(F)ccc12]

Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 200 mg, 362 μmol), (rac)-1-(4-bromo-5-ethyl-1-methyl-1H-pyrazol-3-yl)-3-(3,3-difluoroazetidin-1-yl)propan-1-ol (see Intermediate 138, 135 mg, 399 μmol) and potassium triphosphate (154 mg, 725 μmol) were provided in a mixture of 4 mL of 1,4-dioxane and 0.5 mL of water and purged with argon for 5 minutes. RuPhos Pd G3 (16.7 mg, 20 μmol) was added and the mixture was purged with argon for 5 minutes and stirred for 1 h at 110° C. in a microwave reactor. Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.00 g, 1.81 mmol), (rac)-1-(4-bromo-5-ethyl-1-methyl-1H-pyrazol-3-yl)-3-(3,3-difluoroazetidin-1-yl)propan-1-ol (see Intermediate 138, 674 mg, 1.99 mmol) and potassium triphosphate (769 mg, 3.62 mmol) were provided in a mixture of 7 mL of 1,4-dioxane and 2 mL of water and purged with argon for 5 minutes. RuPhos Pd G3 (83.4 mg, 100 μmol) was added and the mixture was purged with argon for 5 minutes and stirred for 1 h at 110° C. in a microwave reactor. The combined reaction mixtures were diluted with water and extracted with ethyl acetate. The combined organic layers were dried using a water resistant filter and concentrated under reduced pressure. The crude material was purified by flash chromatography using silica gel (gradient dichloromethane/ethanol) to provide 901 mg of the title compound which was formed as a mixture of two racemic diastereomers as a result of atropisomerism at the newly formed bi-heteroaryl bond.

LC-MS (Method 2): $R_t$=1.67 min; MS (ESIpos): m/z=683 $[M+H]^+$ $^1$H-NMR (400 MHz, DMSO-d6) δ[ppm]: 0.845 (0.46), 0.850 (0.39), 0.864 (0.89), 0.868 (0.52), 0.883 (0.38), 1.059 (1.11), 1.065 (16.00), 1.078 (1.81), 1.083 (0.86), 1.096 (0.76), 1.101 (0.38), 1.227 (0.69), 1.244 (1.45), 1.263 (0.67), 1.707 (0.29), 1.720 (0.21), 1.726 (0.25), 2.195 (0.17), 2.211 (0.21), 2.322 (0.17), 2.327 (0.24), 2.331 (0.27), 2.347 (0.72), 2.369 (0.25), 2.387 (0.18), 2.464 (1.37), 2.518 (0.73), 2.522 (0.60), 2.542 (0.44), 2.560 (0.21), 2.589 (0.25), 2.600 (0.25), 2.605 (0.20), 2.619 (0.74), 2.623 (0.40), 2.638 (0.70), 2.642 (0.37), 2.656 (0.21), 2.664 (0.17), 2.668 (0.18), 3.171 (0.25), 3.294 (0.21), 3.306 (0.48), 3.312 (0.49), 3.368 (0.29), 3.374 (0.36), 3.381 (2.10), 3.480 (0.88), 3.511 (1.72), 3.543 (0.85), 3.750 (4.36), 3.756 (1.89), 3.816 (0.40), 3.818 (0.29), 3.838 (1.71), 3.846 (0.74), 3.941 (2.07), 4.205 (0.26), 4.220 (0.48), 4.234 (0.35), 4.239 (0.58), 4.257 (0.50), 4.533 (0.21), 4.554 (0.21), 4.999 (0.21), 5.012 (0.20), 5.037 (0.48), 5.050 (0.46), 5.757 (0.35), 6.890 (0.17), 6.898 (0.18), 7.170 (0.29), 7.192 (0.29), 7.402 (0.21), 7.408 (0.25), 7.431 (0.17), 7.440 (0.38), 7.446 (0.45), 7.453 (0.86), 7.651 (0.25), 7.657 (0.26), 7.677 (0.25), 7.683 (0.29), 7.701 (0.26), 7.723 (0.23), 8.251 (0.17), 8.266 (0.21), 8.275 (0.18), 8.289 (0.21), 10.715 (0.22).

Intermediate 140

(rac)-ethyl (11Z)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate

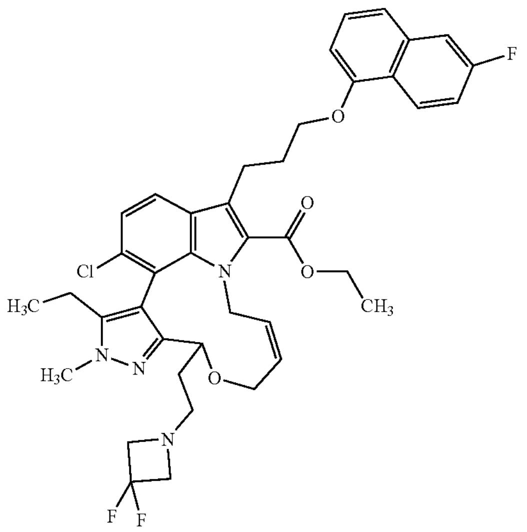 [SMILES: CCOC(=O)c1c(CCCOc2cccc3cc(F)ccc23)c2ccc(Cl)c3c2n1C/C=C\COC(CCN1CC(F)(F)C1)c1nn(C)c(CC)c1-3]

Ethyl 6-chloro-7-{3-[(1-rac)-3-(3,3-difluoroazetidin-1-yl)-1-hydroxypropyl]-5-ethyl-1-methyl-1H-pyrazol-4-yl}-3-{3-[(6-fluoronaphthalen-1-yl)oxy]propyl}-1H-indole-2-carboxylate (see Intermediate 139, 900 mg) was dissolved in 6 mL of acetonitrile, cesium carbonate (1.61 g, 4.94 mmol) was added and the mixture was stirred for 15 minutes at room temperature. (2Z)-1,4-dichlorobut-2-ene (114 μL, 1.08 mmol) and sodium iodide (296 mg, 1.98 mmol) were added and the mixture was stirred for 25 h at 50° C. in a sealed tube. The reaction mixture was diluted with water and extracted with ethyl acetate. The combined organic layers were dried using a water resistant filter and concentrated under reduced pressure. The residue was purified by flash chromatography using silica gel (gradient dichloromethane/ethanol) to give 610 mg of the title compound.

LC-MS (Method 2): $R_t$=1.77 min; MS (ESIpos): m/z=735 $[M+H]^+$ $^1$H-NMR (400 MHz, DMSO-d6) δ[ppm]: 0.771 (0.66), 0.782 (0.55), 0.790 (1.60), 0.801 (1.04), 0.809 (0.77), 0.820 (0.51), 0.884 (0.21), 0.901 (0.38), 0.920 (0.23), 1.035 (1.43), 1.042 (0.21), 1.052 (2.98), 1.059 (2.41), 1.066 (13.95), 1.070 (2.41), 1.078 (4.88), 1.083 (3.17), 1.097 (2.11), 1.102 (1.43), 1.154 (0.21), 1.172 (0.32), 1.190 (0.19), 1.235 (0.23), 1.249 (1.19), 1.252 (0.92), 1.266 (2.47), 1.270 (1.70), 1.284 (1.17), 1.287 (0.81), 1.672 (0.23), 1.687 (0.34), 1.707 (0.47), 1.720 (0.43), 1.739 (0.23), 1.764 (0.23), 1.782 (0.45), 1.803 (0.43), 1.819 (0.34), 1.833 (0.21), 1.853 (0.26), 1.866 (0.26), 1.885 (0.34), 1.900 (0.28), 1.927 (0.23), 1.943 (0.26), 1.962 (0.21), 1.978 (0.23), 1.987 (0.62), 1.995 (0.21), 2.065 (0.47), 2.074 (0.19), 2.130 (0.21), 2.149 (0.51), 2.168 (0.62), 2.188 (0.38), 2.236 (0.43), 2.336 (0.30), 2.386 (1.53), 2.464 (4.75), 2.518 (2.88), 2.522 (2.19), 2.543 (1.15), 2.560 (0.64), 2.574 (0.62), 2.589 (1.19), 2.600 (0.96), 2.605 (0.98), 2.619 (2.17), 2.623 (1.62), 2.638 (2.02), 2.642 (1.45), 2.658 (0.66), 3.183 (0.72), 3.257 (0.19), 3.273 (0.28), 3.289 (0.55), 3.381 (6.84), 3.404 (0.43), 3.417 (0.77), 3.422 (0.83), 3.434 (0.96), 3.439 (0.66), 3.452 (0.70), 3.457 (0.40), 3.464 (0.36), 3.469 (0.32), 3.480 (2.30), 3.512 (4.45), 3.543 (2.22), 3.641 (0.21), 3.662 (0.23), 3.674 (0.28), 3.718 (0.26), 3.724 (0.23), 3.751 (10.70), 3.757 (6.50), 3.771 (0.38), 3.801 (0.32), 3.815 (0.21), 3.832 (0.19), 3.889 (3.34), 3.896 (2.17), 3.939 (1.64), 4.213 (0.40), 4.226 (0.60), 4.234 (0.92), 4.240 (1.28), 4.258 (0.89), 4.279 (0.53), 4.297 (0.47), 4.305 (0.28), 4.314 (0.23), 4.324 (0.28), 4.345 (0.36), 4.357 (0.60), 4.370 (0.30), 4.520 (0.26), 4.533 (0.53), 4.541 (0.36), 4.546 (0.36), 4.554 (0.53), 4.567 (0.28), 4.591 (0.26), 4.603 (0.26), 4.612 (0.26), 4.627 (0.21), 4.642 (0.17), 4.670 (0.19), 4.882 (0.21), 4.901 (0.23), 4.924 (0.34), 4.998 (0.83), 5.010 (0.68), 5.035 (1.19), 5.048 (1.09), 5.182 (0.19), 5.758 (16.00), 6.881 (0.19), 6.889 (0.45), 6.896 (0.43), 6.903 (0.43), 6.910 (0.32), 7.252 (0.38), 7.273 (0.43), 7.285 (0.81), 7.306 (0.83), 7.361 (0.21), 7.367 (0.26), 7.388 (0.40), 7.405 (0.28), 7.412 (0.30), 7.416 (0.26), 7.438 (0.89), 7.445 (1.07), 7.452 (2.00), 7.651 (0.55), 7.658 (0.58), 7.677 (0.53), 7.684 (0.55), 7.799 (0.43), 7.814 (0.70), 7.821 (0.40), 7.836 (0.62), 8.198 (0.26), 8.212 (0.36), 8.221 (0.32), 8.236 (0.36), 8.248 (0.21).

Intermediate 141

(rac)-ethyl 4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

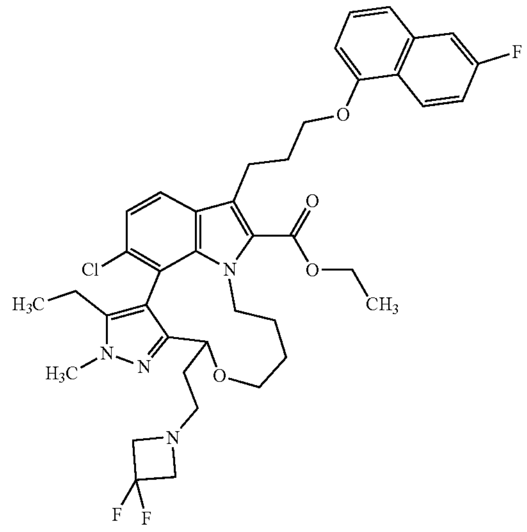 [SMILES: CCOC(=O)c1c(CCCOc2cccc3cc(F)ccc23)c2ccc(Cl)c3c2n1CCCCOC(CCN1CC(F)(F)C1)c1nn(C)c(CC)c1-3]

(Rac)-ethyl-(11Z)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate (see Intermediate 140, 610 mg) was dissolved in a mixture of 7.5 mL of ethanol and 1 mL of tetrahydrofuran, tris(triphenylphosphine)rhodium(I)-chloride (289 mg, 311 μmol) was added and the mixture was stirred for 7 h under hydrogen atmosphere at room temperature. The reaction mixture was concentrated under reduced pressure. The residue was purified by flash chromatography using silica gel (gradient dichloromethane/ethanol) to provide 332 mg of the title compound.

LC-MS (Method 2): $R_t$=1.79 min; MS (ESIpos): m/z=737 $[M+H]^+$ $^1$H-NMR (400 MHz, DMSO-d6) δ[ppm]: 0.785 (0.99), 0.791 (0.76), 0.804 (2.26), 0.810 (1.47), 0.823 (1.10), 0.829 (0.69), 1.042 (0.44), 1.066 (2.86), 1.083 (0.94), 1.102 (0.55), 1.247 (1.97), 1.265 (3.84), 1.282 (1.89), 1.896 (0.19), 1.914 (0.25), 1.928 (0.24), 1.957 (0.21), 1.971 (0.22), 1.991 (0.19), 2.123 (0.22), 2.136 (0.21), 2.161 (0.42), 2.180 (1.09), 2.199 (1.25), 2.446 (2.15), 2.464 (1.16), 2.518 (2.01), 2.522 (1.30), 2.574 (0.41), 2.589 (0.47), 2.605 (0.46), 2.624 (0.44), 2.643 (0.30), 3.032 (0.24), 3.221 (0.21), 3.237 (0.32), 3.255 (0.47), 3.274 (0.67), 3.292 (0.77), 3.346 (4.42), 3.381 (1.56), 3.455 (0.45), 3.471 (0.42), 3.487 (0.79), 3.503 (0.77), 3.519 (0.41), 3.534 (0.41), 3.757 (1.47), 3.770 (0.22), 3.859 (4.66), 3.868 (2.76), 3.889 (0.29), 3.896 (0.21), 3.910 (0.24), 3.927 (0.27), 3.940 (0.49), 3.962 (0.19), 4.177 (0.27), 4.194 (0.91), 4.204 (1.01), 4.212 (1.17), 4.222 (1.21), 4.239 (1.02), 4.257 (0.47), 4.277 (0.67), 4.296 (0.55), 4.304 (0.35), 4.313 (0.20), 4.322 (0.34), 4.386 (0.27), 4.401 (0.31), 4.406 (0.36), 4.421 (0.26), 5.758 (16.00), 6.863 (0.52), 6.869 (0.54), 6.878 (0.52), 6.884 (0.59), 7.223 (0.69), 7.236 (1.16), 7.245 (0.74), 7.257 (1.11), 7.372 (0.40), 7.379 (0.47), 7.394 (0.63), 7.401 (0.70), 7.410 (0.34), 7.417 (0.47), 7.423 (0.55), 7.431 (1.10), 7.440 (1.32), 7.446 (2.61), 7.460 (0.26), 7.526 (0.20), 7.528 (0.30), 7.533 (0.25), 7.536 (0.30), 7.545 (0.55), 7.547 (0.76), 7.549 (0.70), 7.555 (0.66), 7.557 (0.54), 7.564 (0.88), 7.573 (0.76), 7.591 (0.63), 7.595 (1.06), 7.601 (0.29), 7.608 (0.60), 7.612 (0.91), 7.621 (1.07), 7.624 (1.11), 7.629 (0.64), 7.638 (0.44), 7.641 (0.72), 7.645 (0.90), 7.647 (0.89), 7.653 (0.79), 7.673 (0.71), 7.679 (0.71), 7.770 (0.64), 7.774 (0.99), 7.792 (0.57), 7.796 (0.90), 8.212 (0.49), 8.227 (0.51), 8.235 (0.51), 8.250 (0.49).

Intermediate 142

1-(4-bromo-5-ethyl-1-methyl-1H-pyrazol-3-yl)-3-(dimethylamino)propan-1-one

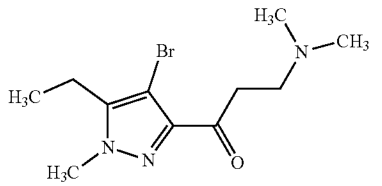 [SMILES: CCc1c(Br)c(C(=O)CCN(C)C)nn1C]

4-Bromo-5-ethyl-N-methoxy-N,1-dimethyl-1H-pyrazole-3-carboxamide (see Intermediate 90, 2.50 g, 9.05 mmol) and N,N-diisopropylethylamine (1.6 mL, 9.05 mmol) were dissolved in 15 mL of THF and a solution of bromo (vinyl)magnesium (18.1 mL, 1.0 M in 18.1 mmol) was added at 2° C. The mixture was stirred at 2° C. for 30 minutes and then added dropwise to a mixture of N-methylmethanamine (18.1 mL, 2.0 M in THF, 36.2 mmol) in 10 mL of tetrahydrofuran at 2° C. and the mixture was stirred for 1 h at 0° C. The reaction mixture was diluted with water and ethyl acetate and filtered through a pad of celite. The phases were separated and the aqueous phase was extracted with ethyl acetate. The combined organic phases were washed with brine, filtered through a water resistant filter and concentrated under reduced pressure. The residue was purified by flash chromatography using silica gel twice (1. aminophase, gradient dichloromethane/ethyl acetate; 2. gradient dichloromethane/ethanol) to give 1.42 g (52% yield) of the title compound.

LC-MS (Method 2): $R_t$=1.01 min; MS (ESIpos): m/z=288 $[M+H]^+$ $^1$H-NMR (400 MHz, DMSO-d6) δ[ppm]: 1.078 (1.68), 1.097 (4.07), 1.116 (1.70), 2.118 (16.00), 2.550 (0.93), 2.568 (2.08), 2.585 (1.10), 2.670 (0.52), 2.689 (1.61), 2.708 (1.57), 2.727 (0.45), 2.992 (1.20), 3.010 (2.24), 3.027 (1.02), 3.920 (9.40).

Intermediate 143

(rac)-1-(4-bromo-5-ethyl-1-methyl-1H-pyrazol-3-yl)-3-(dimethylamino)propan-1-ol

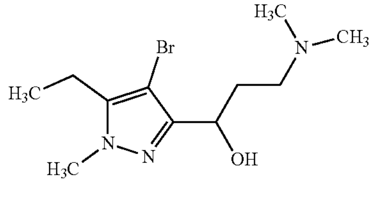 [SMILES: CCc1c(Br)c(C(O)CCN(C)C)nn1C]

1-(4-bromo-5-ethyl-1-methyl-1H-pyrazol-3-yl)-3-(dimethylamino)propan-1-one (see Intermediate 142, 1.40 g, 4.86 mmol) was dissolved in 10 mL of methanol, sodium borohydride (735 mg, 19.4 mmol) was added and the mixture was stirred for 24 h at rt. The reaction mixture was diluted with water and extracted with ethyl acetate. The combined organic layers were washed with brine, filtered through a water resistant filter and concentrated under reduced pressure to give 1.18 g (80% yield) of the title compound which was used without further purification.

LC-MS (Method 2): $R_t$=0.93 min; MS (ESIpos): m/z=290 $[M+H]^+$ $^1$H-NMR (400 MHz, DMSO-d6) δ[ppm]: 0.810 (0.23), 1.062 (1.81), 1.081 (4.37), 1.086 (0.55), 1.099 (1.84), 1.751 (0.17), 1.765 (0.28), 1.781 (0.31), 1.785 (0.25), 1.794 (0.21), 1.798 (0.26), 1.801 (0.21), 1.814 (0.17), 1.855 (0.23), 1.859 (0.25), 1.873 (0.32), 1.879 (0.21), 1.894 (0.29), 1.909 (0.16), 2.109 (16.00), 2.221 (0.16), 2.235 (0.41), 2.240 (0.17), 2.254 (0.69), 2.271 (0.72), 2.276 (0.46), 2.286 (0.18), 2.291 (0.35), 2.461 (0.30), 2.468 (0.33), 2.518 (0.38), 2.523 (0.24), 2.602 (0.53), 2.621 (1.70), 2.640 (1.62), 2.652 (0.17), 2.659 (0.50), 3.752 (10.22), 3.770 (0.59), 4.542 (0.33), 4.555 (0.37), 4.563 (0.39), 4.576 (0.32), 5.187 (0.40).

Intermediate 144

(3-rac)-(4-bromo-5-ethyl-1-methyl-1H-pyrazol-3-yl)-N,N-dimethyl-3-{4-[(2-rac)-tetrahydro-2H-pyran-2-yloxy]butoxy}propan-1-amine

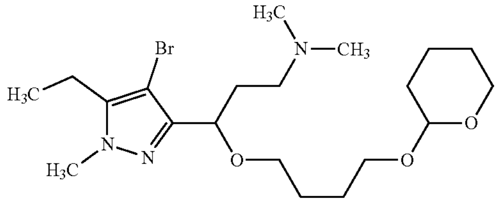 [SMILES: CCc1c(Br)c(C(CCN(C)C)OCCCCOC2CCCCO2)nn1C]

(Rac)-1-(4-bromo-5-ethyl-1-methyl-1H-pyrazol-3-yl)-3-(dimethylamino)propan-1-ol (see Intermediate 143, 980 mg, 3.38 mmol) was dissolved in 15 mL of N,N-dimethylformamide, sodium hydride (162 mg, 60% purity, 4.05 mmol) was added and the mixture was stirred for 2 h at rt. 2-(4-Bromobutoxy)tetrahydro-2H-pyran (740 μL, 4.1 mmol) was added and the mixture was stirred for 1 h at it Sodium hydride (162 mg, 60% purity, 4.05 mmol) was added and the mixture was stirred for 15 minutes at rt. 2-(4-Bromobutoxy)tetrahydro-2H-pyran (740 μL, 4.1 mmol) was added and the mixture was stirred for 21 h at rt. Sodium hydride (162 mg, 60 purity, 4.05 mmol) was added and the mixture was stirred for 15 minutes at rt. 2-(4-Bromobutoxy)tetrahydro-2H-pyran (740 μL, 4.1 mmol) was added and the mixture was stirred for 2 h at rt. The reaction mixture was diluted with water and extracted with ethyl acetate. The combined organic layers were filtered through a water resistant filter and concentrated under reduced pressure. The residue was purified by flash chromatography using silica gel (gradient dichloromethane/ethanol) to provide 973 mg (yield 63%) of the title compound.

LC-MS (Method 2): $R_t$=1.35 min; MS (ESIpos): m/z=446 $[M+H]^+$ $^1$H-NMR (400 MHz, DMSO-d6) δ[ppm]: 1.052 (0.22), 1.071 (2.64), 1.090 (6.71), 1.109 (2.68), 1.407 (0.74), 1.430 (1.75), 1.448 (1.41), 1.455 (1.18), 1.461 (1.21), 1.474 (1.14), 1.495 (2.58), 1.501 (2.79), 1.510 (2.76), 1.539 (0.47), 1.547 (0.48), 1.575 (0.56), 1.594 (0.38), 1.600 (0.44), 1.605 (0.39), 1.622 (0.22), 1.651 (0.27), 1.670 (0.49), 1.681 (0.37), 1.691 (0.47), 1.712 (0.26), 1.724 (0.16), 1.809 (0.22), 1.813 (0.22), 1.827 (0.38), 1.843 (0.38), 1.856 (0.25), 1.862 (0.34), 1.877 (0.20), 1.905 (0.38), 2.004 (0.16), 2.018 (0.26), 2.024 (0.34), 2.039 (0.48), 2.052 (0.27), 2.059 (0.39), 2.073 (0.31), 2.094 (0.23), 2.266 (8.45), 2.318 (0.26), 2.322 (0.39), 2.327 (0.54), 2.332 (0.59), 2.343 (3.12), 2.444 (0.69), 2.518 (1.72), 2.523 (1.15), 2.616 (0.75), 2.635 (2.45), 2.654 (2.39), 2.664 (0.41), 2.669 (0.57), 2.673 (0.92), 3.214 (0.34), 3.222 (0.63), 3.237 (1.51), 3.244 (1.41), 3.252 (1.22), 3.259 (1.06), 3.266 (0.98), 3.275 (0.93), 3.283 (1.13), 3.290 (1.23), 3.377 (1.23), 3.393 (0.94), 3.406 (1.00), 3.419 (0.69), 3.434 (0.37), 3.447 (0.26), 3.525 (0.21), 3.541 (0.50), 3.557 (0.59), 3.565 (0.50), 3.572 (0.38), 3.581 (0.42), 3.596 (0.28), 3.604 (0.29), 3.612 (0.18), 3.620 (0.17), 3.628 (0.22), 3.667 (0.39), 3.679 (0.32), 3.687 (0.60), 3.694 (0.62), 3.702 (0.36), 3.715 (0.50), 3.724 (0.37), 3.732 (0.17), 3.745 (0.20), 3.753 (0.22), 3.757 (0.22), 3.773 (16.00), 4.330 (0.72), 4.344 (0.84), 4.351 (0.86), 4.365 (0.69), 4.494 (0.97), 4.499 (1.00), 4.504 (0.77), 4.511 (0.45), 4.527 (0.24), 4.533 (0.41), 4.544 (0.26), 5.758 (3.26).

Intermediate 145

4-[(1-rac)-(4-bromo-5-ethyl-1-methyl-1H-pyrazol-3-yl)-3-(dimethylamino)propoxy]butan-1-ol

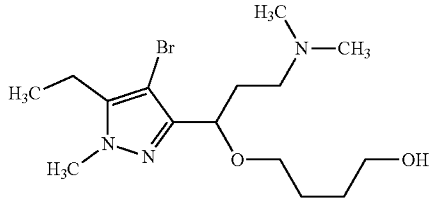 [SMILES: CCc1c(Br)c(C(CCN(C)C)OCCCCO)nn1C]

(3-rac)-(4-bromo-5-ethyl-1-methyl-1H-pyrazol-3-yl)-N,N-dimethyl-3-{4-[(2-rac)-tetrahydro-2H-pyran-2-yloxy]butoxy}propan-1-amine (see Intermediate 144, 970 mg, 2.17 mmol) was dissolved in 10 mL of ethanol, p-toluenesulfonic acid monohydrate (413 mg, 2.17 mmol) was added and the mixture was stirred for 3 h at rt. The reaction mixture was concentrated under reduced pressure and the residue was purified by flash chromatography using silica gel twice (1. gradient dichloromethane/ethanol; 2. aminophase, gradient dichloromethane/ethanol) to give 579 mg (70% yield) of the title compound.

LC-MS (Method 2): $R_t$=1.01 min; MS (ESIpos): m/z=362 $[M+H]^+$ $^1$H-NMR (400 MHz, DMSO-d6) δ[ppm]: 1.070 (1.58), 1.089 (3.87), 1.108 (1.63), 1.387 (0.49), 1.394 (0.50), 1.403 (1.16), 1.410 (0.81), 1.420 (1.14), 1.426 (0.83), 1.433 (0.97), 1.444 (0.58), 1.450 (0.54), 1.460 (0.31), 1.467 (0.29), 1.746 (0.20), 1.760 (0.32), 1.780 (0.42), 1.794 (0.30), 1.922 (0.18), 1.941 (0.27), 1.956 (0.33), 1.961 (0.24), 1.976 (0.34), 1.990 (0.20), 2.088 (16.00), 2.092 (5.74), 2.161 (0.22), 2.178 (0.16), 2.187 (0.82), 2.201 (0.63), 2.206 (1.28), 2.220 (0.44), 2.225 (0.43), 2.326 (0.19), 2.518 (0.79), 2.522 (0.48), 2.612 (0.45), 2.631 (1.49), 2.649 (1.45), 2.659 (0.17), 2.669 (0.59), 3.159 (1.17), 3.171 (1.20), 3.179 (0.29), 3.186 (0.36), 3.194 (0.21), 3.202 (0.97), 3.218 (0.93), 3.226 (0.21), 3.233 (0.34), 3.242 (0.25), 3.346 (1.10), 3.362 (0.48), 3.374 (0.28), 3.768 (9.52), 4.098 (0.22), 4.111 (0.22), 4.311 (0.58), 4.318 (0.44), 4.325 (0.80), 4.332 (1.27), 4.346 (0.73), 5.758 (0.18).

Intermediate 146 ethyl 6-chloro-7-{3-[3-(dimethylamino)-(1-rac)-(4-hydroxybutoxy)propyl]-5-ethyl-1-methyl-1H-pyrazol-4-yl}-3-{3-[(6-fluoronaphthalen-1-yl)oxy]propyl}-1H-indole-2-carboxylate

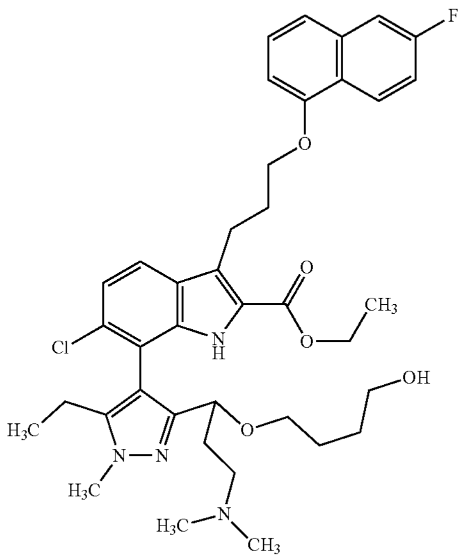 [SMILES: CCOC(=O)c1[nH]c2c(-c3c(C(CCN(C)C)OCCCCO)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 874 mg, 1.58 mmol), 4-[(1-rac)-(4-bromo-5-ethyl-1-methyl-1H-pyrazol-3-yl)-3-(dimethylamino)propoxy]butan-1-ol (see Intermediate 145, 631 mg, 1.74 mmol) and potassium triphosphate (672 mg, 3.17 mmol) were provided in a mixture of 5 mL of 1,4-dioxane and 1 mL of water and were purged with argon for 5 minutes. RuPhos Pd G3 (72.8 mg, 87.1 μmol) was added and the mixture was purged with argon for 5 minutes and stirred for 20 minutes at 110° C. in a microwave reactor. The reaction mixture was diluted with water and extracted with ethyl acetate. The combined organic layers were dried using a water resistant filter and concentrated under reduced pressure. The crude material was purified by flash chromatography using silica gel (gradient dichloromethane/ethanol) to provide 282 mg of the title compound which was formed as a mixture of two racemic diastereomers as a result of atropisomerism at the newly formed bi-heteroaryl bond.

LC-MS (Method 2): $R_t$=1.74 min; MS (ESIpos): m/z=707 $[M+H]^+$ $^1$H-NMR (400 MHz, DMSO-d6) δ[ppm]: 0.797 (0.64), 0.802 (0.30), 0.814 (0.67), 0.821 (0.69), 0.840 (0.36), 0.862 (0.77), 0.882 (2.13), 0.902 (2.77), 0.922 (1.26), 0.944 (0.18), 0.960 (0.20), 0.974 (0.21), 1.035 (0.21), 1.052 (0.43), 1.070 (1.84), 1.089 (4.07), 1.108 (2.15), 1.119 (1.25), 1.167 (0.49), 1.185 (0.34), 1.201 (0.41), 1.219 (2.94), 1.237 (5.56), 1.255 (2.69), 1.293 (0.21), 1.346 (0.18), 1.387 (0.38), 1.393 (0.43), 1.404 (0.66), 1.410 (0.67), 1.420 (0.97), 1.426 (0.82), 1.433 (0.97), 1.444 (0.64), 1.460 (0.38), 1.467 (0.34), 1.568 (0.21), 1.587 (0.36), 1.607 (0.39), 1.620 (0.41), 1.640 (0.30), 1.654 (0.30), 1.676 (0.28), 1.694 (0.25), 1.714 (0.20), 1.728 (0.20), 1.746 (0.28), 1.760 (0.39), 1.780 (0.49), 1.795 (0.38), 1.814 (0.28), 1.844 (8.47), 1.922 (0.25), 1.942 (6.24), 1.956 (0.56), 1.976 (0.59), 1.987 (0.38), 2.007 (0.25), 2.060 (0.43), 2.068 (0.43), 2.088 (16.00), 2.115 (0.33), 2.147 (0.21), 2.169 (0.48), 2.187 (1.35), 2.200 (1.39), 2.206 (1.69), 2.244 (0.20), 2.263 (0.21), 2.282 (0.25), 2.294 (0.18), 2.300 (0.21), 2.313 (0.28), 2.322 (0.74), 2.327 (1.00), 2.331 (1.02), 2.350 (0.30), 2.358 (0.18), 2.378 (0.31), 2.388 (0.33), 2.396 (0.41), 2.407 (0.34), 2.414 (0.36), 2.426 (0.23), 2.433 (0.20), 2.518 (4.18), 2.522 (2.66), 2.577 (0.21), 2.612 (0.49), 2.631 (1.54), 2.649 (1.48), 2.659 (0.44), 2.665 (0.84), 2.669 (1.35), 2.673 (0.80), 2.678 (0.38), 3.012 (0.21), 3.034 (0.26), 3.084 (0.20), 3.107 (0.16), 3.163 (0.36), 3.179 (0.43), 3.186 (0.46), 3.202 (1.02), 3.219 (1.15), 3.233 (0.89), 3.245 (0.69), 3.299 (0.94), 3.307 (1.07), 3.652 (0.49), 3.745 (0.18), 3.768 (9.35), 3.815 (3.95), 3.818 (4.96), 3.941 (0.26), 3.953 (0.25), 3.963 (0.21), 3.974 (0.21), 3.983 (0.31), 3.997 (0.31), 4.004 (0.38), 4.017 (0.30), 4.171 (0.72), 4.186 (1.41), 4.201 (0.92), 4.213 (0.62), 4.229 (1.18), 4.240 (0.69), 4.246 (1.30), 4.258 (0.94), 4.285 (0.18), 4.311 (0.61), 4.326 (0.80), 4.332 (1.12), 4.346 (0.71), 5.758 (13.77), 6.856 (0.48), 6.861 (0.49), 6.871 (0.51), 6.877 (0.51), 7.144 (0.97), 7.146 (1.31), 7.165 (1.02), 7.167 (1.35), 7.380 (0.48), 7.387 (0.56), 7.403 (0.74), 7.410 (0.95), 7.425 (0.62), 7.431 (1.53), 7.441 (1.35), 7.447 (2.66), 7.462 (0.30), 7.649 (0.77), 7.656 (0.79), 7.676 (0.89), 7.681 (1.89), 7.702 (1.17), 8.263 (0.43), 8.278 (0.48), 8.286 (0.44), 8.301 (0.39), 10.685 (0.69), 10.916 (0.49).

Intermediate 147

(rac)-ethyl 4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

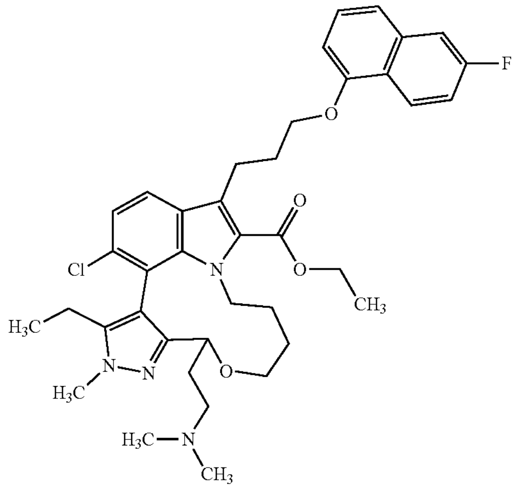

Ethyl 6-chloro-7-{3-[3-(dimethylamino)-(1-rac)-(4-hydroxybutoxy)propyl]-5-ethyl-1-methyl-1H-pyrazol-4-yl}-3-{3-[(6-fluoronaphthalen-1-yl)oxy]propyl}-1H-indole-2-carboxylate (see Intermediate 146, 280 mg) was dissolved in 8 mL of tetrahydrofuran, triphenylphosphine (831 mg, 3.17 mmol) and di-tert-butyl-azodicarboxylate (729 mg, 3.17 mmol) were added and the mixture was stirred for 22 h at rt. The mixture was filtered and concentrated under reduced pressure. The residue was purified by flash chromatography using silica gel (gradient hexane/ethyl acetate) to give 274 mg of the title compound as a mixture of racemic diastereomers.

LC-MS (Method 2): $R_t$=1.89 min; MS (ESIpos): m/z=689 $[M+H]^+$ $^1$H-NMR (400 MHz, DMSO-d6) δ[ppm]: 0.781 (1.05), 0.788 (0.86), 0.798 (3.28), 0.800 (2.98), 0.807 (1.90), 0.814 (3.06), 0.821 (3.37), 0.840 (1.38), 0.886 (2.04), 0.904 (4.36), 0.922 (2.46), 0.948 (0.47), 0.990 (0.47), 1.035 (7.17), 1.052 (16.00), 1.070 (9.02), 1.088 (6.21), 1.106 (3.06), 1.124 (0.69), 1.142 (0.77), 1.160 (0.77), 1.185 (0.63), 1.203 (0.72), 1.218 (2.10), 1.236 (4.44), 1.242 (3.01), 1.247 (2.37), 1.254 (2.87), 1.259 (4.72), 1.265 (3.28), 1.277 (2.76), 1.283 (2.26), 1.324 (6.59), 1.352 (10.54), 1.373 (11.17), 1.383 (13.05), 1.395 (12.91), 1.428 (5.63), 1.433 (5.77), 1.465 (1.05), 1.505 (0.61), 1.616 (0.52), 1.753 (0.50), 1.767 (0.69), 1.779 (1.02), 1.786 (0.83), 1.799 (0.72), 1.865 (2.21), 1.905 (1.10), 1.946 (0.61), 1.967 (1.24), 1.983 (0.77), 2.001 (0.55), 2.021 (0.55), 2.039 (0.66), 2.058 (7.14), 2.075 (0.86), 2.106 (15.31), 2.132 (0.74), 2.152 (0.69), 2.169 (1.21), 2.189 (1.88), 2.198 (2.15), 2.210 (2.62), 2.230 (2.48), 2.245 (1.02), 2.318 (0.72), 2.322 (1.35), 2.326 (1.88), 2.331 (1.46), 2.358 (0.47), 2.373 (0.55), 2.388 (0.58), 2.393 (0.66), 2.406 (0.58), 2.411 (0.74), 2.518 (7.28), 2.522 (4.86), 2.609 (0.83), 2.628 (2.57), 2.647 (2.48), 2.660 (0.83), 2.664 (1.71), 2.668 (2.10), 2.673 (1.32), 3.137 (0.63), 3.153 (0.66), 3.211 (1.24), 3.228 (1.21), 3.250 (0.97), 3.404 (0.97), 3.417 (1.02), 3.422 (2.26), 3.434 (2.51), 3.439 (2.37), 3.452 (2.37), 3.457 (1.05), 3.469 (0.86), 3.765 (12.69), 3.814 (1.96), 3.819 (4.72), 3.824 (6.07), 3.862 (3.06), 4.185 (1.41), 4.194 (1.16), 4.203 (1.52), 4.212 (1.85), 4.221 (1.41), 4.230 (1.71), 4.239 (1.02), 4.248 (1.30), 4.261 (0.91), 4.272 (0.63), 4.278 (0.99), 4.296 (0.77), 4.305 (0.61), 4.312 (0.99), 4.326 (1.10), 4.333 (1.08), 4.345 (1.66), 4.357 (2.26), 4.369 (1.27), 6.864 (0.99), 6.871 (1.08), 6.879 (0.97), 6.885 (0.77), 7.135 (0.88), 7.157 (0.88), 7.214 (1.27), 7.227 (0.83), 7.235 (1.30), 7.249 (0.80), 7.378 (0.58), 7.385 (0.47), 7.400 (1.08), 7.407 (0.88), 7.423 (0.77), 7.431 (2.10), 7.440 (2.23), 7.447 (4.14), 7.461 (0.41), 7.547 (0.61), 7.554 (0.52), 7.565 (0.69), 7.572 (0.63), 7.591 (0.50), 7.595 (0.86), 7.612 (0.74), 7.621 (0.88), 7.624 (0.88), 7.641 (0.66), 7.648 (1.43), 7.654 (1.38), 7.674 (2.10), 7.680 (1.41), 7.695 (0.80), 7.742 (1.16), 7.763 (1.02), 7.772 (0.69), 7.793 (0.58), 8.240 (0.47), 8.255 (0.52), 8.264 (0.72), 8.279 (0.74), 9.018 (0.47).

Intermediate 148

2,2-difluoropent-4-en-1-ol

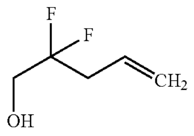

2,2-difluoropent-4-enoic acid (CAS, 55039-89-9, 20.0 g, 147 mmol) was added to a solution of lithium aluminium hydride (11.2 g, 294 mmol) in 400 mL diethyl ether at 0° C., stirred for 30 minutes and then warmed to room temperature and stirred for 2 hours. 11 mL water was added, followed by 2-molar aqueous sodium hydroxide (11 mL), followed by a further 30 mL of water and the slurry was stirred overnight, magnesium sulfate was added and the reaction mixture was passed through celite and the solvent was removed under reduced pressure (300 mbar) to give the desired compound which was carried forward to the next step without further purification (27.0 g).

$^{1}$H-NMR (400 MHz, $CDCl_3$) δ [ppm]=2.68-2.81 (m, 2H), 3.70-3.88 (m, 2H), 5.23-5.29 (m, 2H), 5.76-5.85 (m, 1H)—OH not visible.

$^{19}$F-NMR (376 MHz, $CDCl_3$) δ [ppm]=−107.89 (tt, 1F).

Intermediate 149 tert-butyl[(2,2-difluoropent-4-en-1-yl)oxy]diphenyl-silane

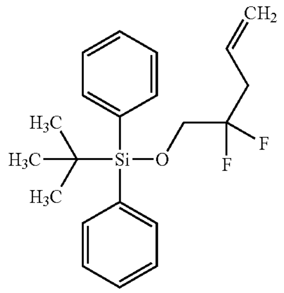 [SMILES: C=CCC(F)(F)CO[Si](c1ccccc1)(c1ccccc1)C(C)(C)C]

Tert-Butylchlorodiphenylsilane (24 mL, 92 mmol) was added to 2,2-difluoropent-4-en-1-ol (see Intermediate 148, 18.0 g), 4-dimethylaminopyridine (450 mg, 3.69 mmol) and N,N-diisopropylethylamine (77 mL, 440 mmol) in 1 L dichloromethane and stirred for 6 days at room temperature, with a further tert-butylchlorodiphenylsilane (24 mL, 92 mmol) added half way through, Aqueous sodium bicarbonate was added and the organic layer was washed with water, dried over magnesium sulfate, filtered and concentrated under reduced pressure. The crude product was purified by flash chromatography (0-20% ethylacetate/heptane). to give 99 g of desired compound which was carried forward to the next step.

Intermediate 150

4-{[tert-butyl(diphenyl)silyl]oxy}-3,3-difluorobutan-1-ol

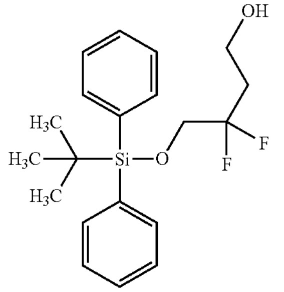 [SMILES: CC(C)(C)[Si](OCC(F)(F)CCO)(c1ccccc1)c1ccccc1]

Ozone was bubbled through a solution of tert-butyl[(2,2-difluoropent-4-en-1-yl)oxy]diphenylsilane (see Intermediate 149, 44.0 g, 50% purity) in 640 mL dichloromethane and 640 mL methanol for 2 hours at −78° C., The reaction mixture was then flushed with oxygen followed by argon and sodium borohydride (4.62 g, 122 mmol) was added to the reaction mixture. The reaction mixture was stirred for 1 hour at −78° C. then warmed to room temperature and stirred overnight. The solvent was removed under reduced pressure, The residue was dissolved in Ethyl acetate, washed with brine, dried over magnesium sulfate, filtered and the solvent was removed under reduced pressure. The residue was purified by flash chromatography (silica 1 kg, with 0-30% ethyl acetate in heptanes as eluent) to give the desired compound in 78% purity: 30 g, $^{1}$H-NMR (400 MHz, CHLOROFORM-D) δ [ppm]=1.06 (s, 9H), 1.73-2.01 (1H), 2.29 (tt, 2H), 3.79 (t, 2H), 3.89 (t, 2H), 7.38-7.47 (m, 6H), 7.64-7.68 (m, 4H).

$^{19}$F-NMR (376 MHz, CHLOROFORM-D) δ [ppm]=−104.96-105.11 (m, 2F)

Intermediate 151

(rac)-tert-butyl[2,2-difluoro-4-(tetrahydro-2H-pyran-2-yloxy)butoxy]diphenylsilane

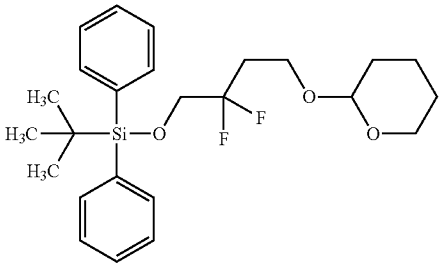 [SMILES: CC(C)(C)[Si](OCC(F)(F)CCOC1CCCCO1)(c1ccccc1)c1ccccc1]

4-{[tert-Butyl(diphenyl)silyl]oxy}-3,3-difluorobutan-1-ol (see Intermediate 150, 9.50 g, 26.1 mmol) was dissolved in 95 mL of dichloromethane under an argon atmosphere, 3,4-dihydro-2H-pyran (7.1 mL, 78.2 mmol) and pyridinium-p-toluenesulfonate (327 mg, 1.30 mmol) were added and the mixture was stirred for 36 h at rt. The reaction mixture was concentrated under reduced pressure and the residue was purified by flash chromatography using silica gel (gradient hexane/ethanol) to give 11.4 g (98% yield) of the title compound.

$^{1}$H-NMR (400 MHz, DMSO-d6) δ[ppm]: 0.995 (0.29), 1.016 (16.00), 1.331 (0.28), 1.342 (0.30), 1.350 (0.35), 1.361 (0.46), 1.372 (0.50), 1.394 (0.24), 1.400 (0.23), 1.416 (0.29), 1.424 (0.28), 1.433 (0.29), 1.441 (0.20), 1.453 (0.17), 1.462 (0.19), 1.485 (0.19), 1.493 (0.18), 1.509 (0.17), 1.516 (0.34), 1.524 (0.23), 1.541 (0.27), 1.547 (0.38), 1.570 (0.22), 1.579 (0.17), 1.987 (0.17), 2.221 (0.19), 2.230 (0.16), 2.245 (0.21), 2.260 (0.33), 2.272 (0.29), 2.285 (0.19), 2.301 (0.16), 2.311 (0.17), 2.318 (0.16), 2.322 (0.20), 2.327 (0.29), 2.331 (0.18), 2.518 (0.83), 2.523 (0.53), 2.669 (0.21), 3.375 (0.25), 3.390 (0.21), 3.403 (0.30), 3.414 (0.17), 3.454 (0.20), 3.469 (0.44), 3.480 (0.28), 3.485 (0.24), 3.495 (0.52), 3.511 (0.22), 3.613 (0.22), 3.620 (0.19), 3.634 (0.28), 3.641 (0.35), 3.648 (0.18), 3.661 (0.20), 3.744 (0.24), 3.761 (0.48), 3.770 (0.25), 3.776 (0.27), 3.786 (0.40), 3.802 (0.20), 3.838 (0.57), 3.872 (1.19), 3.906 (0.54), 4.512 (0.42), 4.519 (0.62), 4.529 (0.41), 7.426 (0.58), 7.431 (0.78), 7.434 (0.38), 7.447 (2.38), 7.465 (2.37), 7.470 (1.12), 7.475 (1.65), 7.479 (0.95), 7.485 (0.44), 7.492 (1.27), 7.502 (0.20), 7.507 (0.21), 7.511 (0.29), 7.610 (2.09), 7.613 (2.04), 7.629 (1.97), 7.633 (1.34).

Intermediate 152

(rac)-2,2-difluoro-4-(tetrahydro-2H-pyran-2-yloxy) butan-1-ol

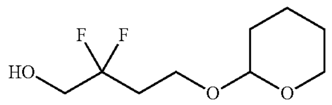 [SMILES: OCC(F)(F)CCOC1CCCCO1]

(Rac)-tert-butyl[2,2-difluoro-4-(tetrahydro-2H-pyran-2-yloxy)butoxy]diphenylsilane (see Intermediate 151, 11.4 g, 25.4 mmol) was dissolved in 75 mL of THF, a solution of tetra-n-butylammonium fluoride (51 mL, 1.0 M in THF, 51 mmol) was added and the mixture was stirred over night at rt. The reaction mixture was concentrated under reduced pressure and the residue was purified by flash chromatography twice using silica gel (gradient hexane/ethyl acetate) to give 3.90 g (72% yield) of the title compound.

$^1$H-NMR (400 MHz, DMSO-d6) δ[ppm]: 0.845 (2.79), 1.154 (0.73), 1.172 (1.45), 1.190 (0.68), 1.405 (2.69), 1.421 (5.43), 1.430 (6.70), 1.444 (10.62), 1.451 (16.00), 1.459 (12.78), 1.465 (12.27), 1.473 (7.40), 1.480 (5.51), 1.484 (4.68), 1.490 (5.54), 1.499 (4.22), 1.512 (1.88), 1.522 (1.29), 1.567 (2.72), 1.575 (3.82), 1.582 (2.96), 1.599 (4.39), 1.606 (4.63), 1.622 (3.34), 1.629 (3.34), 1.636 (1.64), 1.644 (1.42), 1.650 (1.27), 1.667 (2.36), 1.679 (4.59), 1.693 (2.88), 1.703 (3.30), 1.714 (2.05), 1.722 (1.48), 1.734 (0.92), 1.739 (0.72), 1.987 (2.69), 2.112 (3.02), 2.130 (6.43), 2.147 (3.73), 2.153 (6.53), 2.171 (13.05), 2.188 (6.77), 2.195 (3.45), 2.214 (6.07), 2.231 (3.02), 2.518 (4.01), 2.522 (2.64), 2.673 (0.68), 3.410 (2.29), 3.419 (4.30), 3.422 (4.49), 3.436 (4.16), 3.441 (2.95), 3.450 (5.89), 3.463 (3.22), 3.474 (5.67), 3.491 (11.48), 3.500 (7.05), 3.508 (5.94), 3.516 (12.93), 3.533 (7.18), 3.540 (5.51), 3.555 (5.60), 3.575 (10.46), 3.590 (10.70), 3.611 (5.24), 3.625 (5.27), 3.695 (3.52), 3.703 (3.84), 3.716 (4.66), 3.724 (7.15), 3.732 (3.77), 3.744 (10.48), 3.752 (3.69), 3.762 (13.91), 3.770 (6.37), 3.779 (7.08), 3.788 (11.57), 3.805 (5.32), 4.017 (0.56), 4.035 (0.56), 4.565 (6.93), 4.572 (12.96), 4.582 (7.72), 5.443 (4.86), 5.458 (12.39), 5.473 (4.73).

Intermediate 153

4-{3-[2,2-difluoro-4-(tetrahydro-2H-pyran-2-yloxy) butoxy]-3-(5-ethyl-4-iodo-1-methyl-1H-pyrazol-3-yl)propyl}morpholine

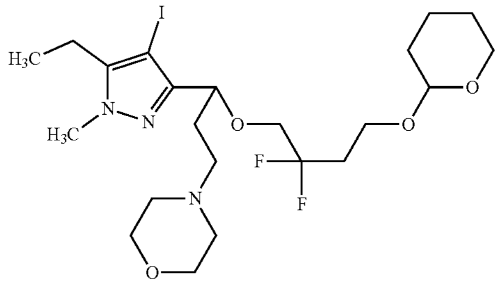 [SMILES: CCc1c(I)c(C(CCN2CCOCC2)OCC(F)(F)CCOC2CCCCO2)nn1C]

(1R)-1-(5-ethyl-4-iodo-1-methyl-1H-pyrazol-3-yl)-3-(morpholin-4-yl)propan-1-ol (see Intermediate 125, 1.50 g, 3.96 mmol) and (rac)-2,2-difluoro-4-(tetrahydro-2H-pyran-2-yloxy)butan-1-ol (see Intermediate 152, 998 mg, 4.75 mmol) were dissolved in 50 mL of toluene, 2-(tributylphosphoranylidene)acetonitrile (1.6 mL, 5.93 mmol) was added and the mixture was stirred for 6 h at 160° C. in a microwave reactor under an argon atmosphere. The reaction mixture was concentrated under reduced pressure and the residue was purified by flash chromatography using silica gel (gradient dichloromethane/ethanol) to give 1.03 g (45% yield) of the title compound as a mixture of stereoisomers.

LC-MS (Method 2): $R_t$=1.36 min; MS (ESIpos): m/z=572 $[M+H]^+$ $^1$H-NMR (400 MHz, DMSO-d6) δ[ppm]: 0.879 (0.25), 1.035 (0.91), 1.053 (3.68), 1.071 (7.00), 1.089 (2.55), 1.385 (0.39), 1.428 (1.52), 1.439 (1.04), 1.446 (0.97), 1.459 (0.73), 1.465 (0.72), 1.492 (0.36), 1.533 (0.17), 1.542 (0.33), 1.550 (0.30), 1.558 (0.29), 1.572 (0.49), 1.580 (0.34), 1.588 (0.35), 1.596 (0.45), 1.604 (0.36), 1.618 (0.41), 1.633 (0.46), 1.657 (0.33), 1.843 (0.31), 1.858 (0.49), 1.877 (0.61), 1.892 (0.46), 1.911 (0.21), 2.012 (0.37), 2.026 (0.47), 2.046 (0.45), 2.060 (0.26), 2.131 (0.26), 2.144 (0.36), 2.158 (0.38), 2.172 (0.50), 2.186 (0.67), 2.200 (0.55), 2.216 (0.36), 2.226 (0.35), 2.240 (0.39), 2.271 (0.97), 2.285 (1.64), 2.303 (2.81), 2.313 (2.17), 2.322 (1.61), 2.518 (1.42), 2.523 (0.96), 2.629 (0.67), 2.648 (2.26), 2.667 (2.34), 2.686 (0.62), 3.399 (0.56), 3.405 (0.63), 3.418 (1.00), 3.422 (1.13), 3.435 (1.31), 3.444 (1.78), 3.452 (0.78), 3.457 (0.58), 3.478 (2.00), 3.512 (1.03), 3.537 (2.44), 3.549 (4.05), 3.560 (2.48), 3.636 (0.23), 3.644 (0.23), 3.657 (0.43), 3.665 (0.57), 3.677 (0.57), 3.685 (0.59), 3.694 (0.96), 3.703 (0.45), 3.712 (1.02), 3.720 (0.68), 3.729 (0.33), 3.738 (0.68), 3.755 (0.22), 3.782 (0.19), 3.811 (16.00), 4.342 (0.29), 4.355 (0.55), 4.368 (0.26), 4.490 (0.60), 4.504 (0.78), 4.509 (0.81), 4.525 (1.25), 4.536 (0.85), 4.541 (0.80), 4.551 (0.44).

Intermediate 154

4-[1-(5-ethyl-4-iodo-1-methyl-1H-pyrazol-3-yl)-3-(morpholin-4-yl)propoxy]-3,3-difluorobutan-1-ol

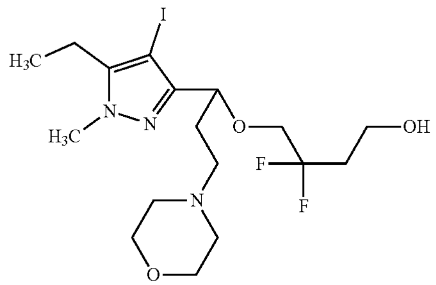 [SMILES: CCc1c(I)c(C(CCN2CCOCC2)OCC(F)(F)CCO)nn1C]

4-{3-[2,2-difluoro-4-(tetrahydro-2H-pyran-2-yloxy)butoxy]-3-(5-ethyl-4-iodo-1-methyl-1H-pyrazol-3-yl)propyl}morpholine (see Intermediate 153, 1.75 g, 3.07 mmol) was dissolved in 114 mL of ethanol, 4-toluenesulfonic acid (1.06 g, 6.14 mmol) was added and the mixture was stirred for 4 h at rt. Triethylamine (1.1 mL, 7.67 mmol) was added and the reaction mixture was concentrated under reduced pressure. The residue was purified by flash chromatography using silica gel (aminophase, gradient hexane/dichloromethane) to give 1.54 g (100% yield) of the title compound as a mixture of stereoisomers.

LC-MS (Method 2): $R_t$=1.05 min; MS (ESIpos): m/z=488 $[M+H]^+$ $^1$H-NMR (400 MHz, DMSO-d6) δ[ppm]: 0.879 (0.22), 0.905 (1.96), 0.923 (4.15), 0.941 (2.03), 1.054 (2.69), 1.073 (6.57), 1.092 (2.79), 1.119 (0.31), 1.137 (0.16), 1.172 (0.30), 1.232 (0.24), 1.841 (0.35), 1.857 (0.55), 1.876 (0.68), 1.891 (0.50), 1.909 (0.24), 1.987 (0.75), 2.005 (0.61), 2.019 (1.03), 2.025 (0.65), 2.033 (0.74), 2.039 (0.84), 2.052 (0.65), 2.061 (1.06), 2.075 (0.97), 2.092 (0.50), 2.102 (0.44), 2.119 (0.44), 2.135 (0.23), 2.236 (0.24), 2.249 (0.33), 2.266 (0.97), 2.285 (1.94), 2.303 (3.38), 2.314 (2.46), 2.322 (2.20), 2.352 (0.37), 2.387 (0.70), 2.405 (1.99), 2.423 (1.90), 2.441 (0.61), 2.518 (1.39), 2.522 (0.89), 2.555 (0.17), 2.632 (0.75), 2.650 (2.53), 2.669 (2.81), 2.688 (0.70), 3.412 (0.90), 3.416 (0.98), 3.446 (1.87), 3.449 (1.93), 3.480 (0.98), 3.497 (1.00), 3.514 (2.16), 3.528 (2.41), 3.539 (3.06), 3.551 (4.63), 3.562 (2.76), 3.785 (0.20), 3.814 (16.00), 4.481 (0.85), 4.496 (1.02), 4.501 (1.10), 4.516 (0.82), 4.630 (1.14), 4.644 (2.31), 4.656 (1.06), 5.758 (7.33).

Intermediate 155 ethyl 6-chloro-7-{3-[1-(2,2-difluoro-4-hydroxybutoxy)-3-(morpholin-4-yl)propyl]-5-ethyl-1-methyl-1H-pyrazol-4-yl}-3-{3-[(6-fluoro-1-naphthyl)oxy]propyl}-1H-indole-2-carboxylate

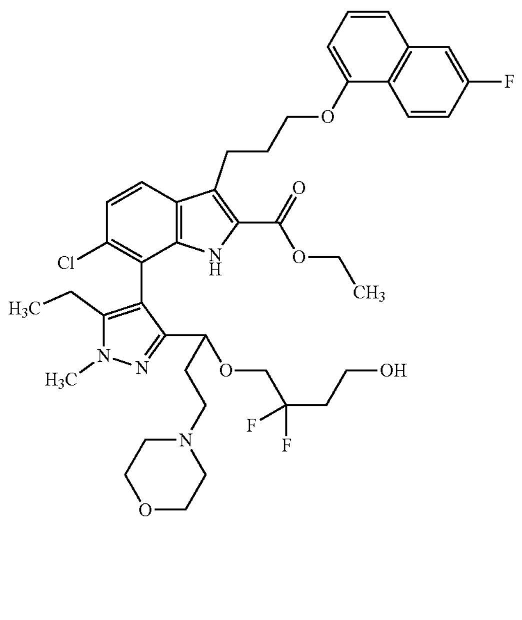 [SMILES: CCOC(=O)c1[nH]c2c(-c3c(C(CCN4CCOCC4)OCC(F)(F)CCO)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 77.3 mg, 140 µmol) and 4-[1-(5-ethyl-4-iodo-1-methyl-1H-pyrazol-3-yl)-3-(morpholin-4-yl)propoxy]-3,3-difluorobutan-1-ol (see Intermediate 154, 75.0 mg, 154 µmol) were provided in a mixture of 3.0 mL of 1,4-dioxane and 0.8 mL of water, potassium triphosphate (89.1 mg, 0.42 mmol) was added and the mixture was purged with argon for 5 minutes. RuPhos Pd G3 (11.7 mg, 14.0 µmol) was added and the mixture was purged with argon for 5 minutes and stirred for 1 h at 110° C. in a microwave reactor.

Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 371 mg, 672 µmol) and 4-[1-(5-ethyl-4-iodo-1-methyl-1H-pyrazol-3-yl)-3-(morpholin-4-yl)propoxy]-3,3-difluorobutan-1-ol (see Intermediate 154, 360 mg, 739 µmol) were provided in a mixture of 14.4 mL of 1,4-dioxane and 3.8 mL of water, potassium triphosphate (428 mg, 2.01 mmol) was added and the mixture was purged with argon for 5 minutes. RuPhos Pd G3 (56.2 mg, 67.2 µmol) was added and the mixture was purged with argon for 5 minutes and stirred for 1 h at 110° C. in a microwave reactor.

The two reaction mixtures were combined, filtered through a water resistant filter and concentrated under reduced pressure. The crude material was purified by flash chromatography using silica gel (gradient dichloromethane/ethanol) to provide 389 mg (61% yield) of the title compound which was formed as a mixture of two diastereomers as a result of atropisomerism at the newly formed biheteroaryl bond.

LC-MS (Method 2): $R_t$=1.66 min; MS (ESIpos): m/z=785 $[M+H]^+$ $^1$H-NMR (400 MHz, DMSO-d6) δ[ppm]: 0.884 (1.73), 0.897 (2.64), 0.903 (4.06), 0.916 (5.56), 0.922 (2.40), 0.935 (2.53), 1.066 (0.96), 1.222 (3.67), 1.225 (3.08), 1.240 (7.86), 1.243 (6.10), 1.258 (3.93), 1.260 (3.10), 1.711 (1.11), 1.727 (1.06), 1.871 (0.80), 1.887 (0.83), 1.907 (1.03), 1.912 (0.93), 1.930 (1.42), 1.955 (1.91), 2.024 (0.72), 2.083 (1.32), 2.183 (1.21), 2.201 (1.68), 2.219 (1.32), 2.259 (0.57), 2.280 (0.98), 2.299 (0.98), 2.318 (1.37), 2.323 (1.81), 2.327 (2.09), 2.331 (1.53), 2.337 (1.27), 2.359 (1.03), 2.379 (0.90), 2.401 (0.98), 2.420 (0.98), 2.439 (0.70), 2.460 (0.78), 2.518 (16.00), 2.523 (13.00), 2.665 (1.29), 2.669 (1.68), 2.673 (1.21), 3.141 (0.41), 3.230 (0.90), 3.263 (1.63), 3.278 (1.71), 3.300 (2.56), 3.383 (1.91), 3.406 (1.45), 3.424 (1.73), 3.437 (1.60), 3.455 (0.83), 3.512 (0.49), 3.539 (0.72), 3.568 (0.65), 3.838 (8.25), 3.843 (10.93), 4.134 (0.59), 4.151 (1.50), 4.167 (1.06), 4.198 (1.96), 4.206 (2.43), 4.219 (1.78), 4.227 (2.09), 4.236 (1.89), 4.245 (2.25), 4.254 (1.65), 4.264 (1.58), 4.272 (0.75), 4.281 (0.65), 4.511 (0.44), 4.524 (0.85), 4.543 (0.67), 4.557 (1.11), 4.569 (0.59), 5.759 (3.75), 6.862 (0.62), 6.869 (1.11), 6.877 (1.37), 6.884 (1.27), 6.891 (0.96), 7.141 (1.68), 7.162 (1.73), 7.170 (2.40), 7.192 (2.48), 7.379 (0.75), 7.386 (0.83), 7.402 (1.40), 7.408 (1.68), 7.424 (0.98), 7.432 (2.58), 7.442 (2.84), 7.448 (5.12), 7.462 (0.70), 7.650 (1.63), 7.657 (1.73), 7.676 (1.71), 7.683 (1.78), 7.695 (1.34), 7.705 (1.84), 7.717 (1.29), 7.726 (1.63), 8.260 (0.85), 8.266 (0.70), 8.274 (0.96), 8.282 (1.37), 8.290 (0.75), 8.297 (0.93), 8.304 (0.67), 11.053 (1.86), 11.158 (1.11).

Intermediate 156 ethyl 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylate

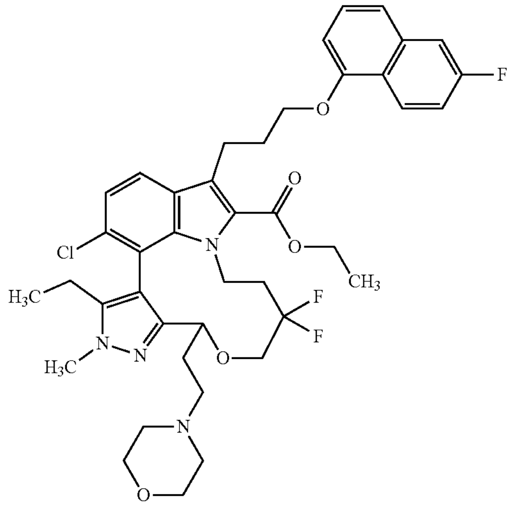 [SMILES: CCOC(=O)c1c(CCCOc2cccc3cc(F)ccc23)c2ccc(Cl)c3c2n1CCC(F)(F)COC(CCN1CCOCC1)c1nn(C)c(CC)c1-3]

Ethyl 6-chloro-7-{3-[1-(2,2-difluoro-4-hydroxybutoxy)-3-(morpholin-4-yl)propyl]-5-ethyl-1-methyl-1H-pyrazol-4-yl}-3-{3-[(6-fluoro-1-naphthyl)oxy]propyl}-1H-indole-2-carboxylate (see Intermediate 155, 287 mg, 365 μmol) was dissolved in 16.2 mL of tetrahydrofuran, triphenylphosphine (0.77 g, 2.92 mmol) and di-tert-butyl-azodicarboxylate (0.67 g, 2.92 mmol) were added and the mixture was stirred for 21 h at room temperature. Hexane was added and the precipitate was removed by filtration. The filtrate was concentrated under reduced pressure. The residue was purified by flash chromatography using silica gel (gradient dichloromethane/ethanol) to give 234 mg (83% yield) of the title compound as a mixture of two diastereomers.

LC-MS (Method 2): $R_t$=1.76 min; MS (ESIpos): m/z=767 $[M+H]^+$ $^1$H-NMR (400 MHz, DMSO-d6) δ[ppm]: 0.746 (3.04), 0.759 (3.19), 0.765 (7.35), 0.778 (5.84), 0.783 (3.83), 0.797 (2.53), 0.904 (0.41), 1.035 (0.89), 1.052 (1.99), 1.065 (0.54), 1.070 (0.92), 1.237 (0.97), 1.263 (7.25), 1.281 (14.95), 1.298 (7.35), 1.335 (1.07), 1.379 (5.64), 1.384 (3.19), 1.429 (1.76), 1.653 (0.43), 1.675 (0.54), 1.689 (0.59), 1.710 (0.51), 1.762 (0.48), 1.918 (0.59), 1.930 (0.82), 1.952 (0.87), 1.965 (0.77), 1.983 (0.61), 2.013 (0.66), 2.031 (0.94), 2.050 (1.51), 2.068 (1.84), 2.085 (2.07), 2.104 (1.84), 2.122 (1.48), 2.130 (1.07), 2.142 (1.48), 2.149 (2.02), 2.159 (1.22), 2.168 (1.94), 2.214 (2.42), 2.230 (2.14), 2.265 (4.93), 2.283 (3.96), 2.301 (3.09), 2.317 (2.88), 2.322 (3.04), 2.326 (3.14), 2.331 (2.17), 2.369 (0.48), 2.386 (0.79), 2.403 (0.56), 2.416 (0.61), 2.435 (0.56), 2.518 (6.63), 2.522 (4.26), 2.659 (0.59), 2.664 (1.15), 2.669 (1.53), 2.673 (1.15), 3.236 (0.43), 3.290 (2.27), 3.302 (3.19), 3.405 (0.46), 3.422 (0.79), 3.435 (0.84), 3.440 (0.71), 3.452 (0.71), 3.513 (4.85), 3.524 (7.40), 3.535 (4.87), 3.589 (0.43), 3.687 (0.71), 3.716 (0.94), 3.724 (1.17), 3.752 (1.00), 3.857 (16.00), 3.893 (10.95), 3.938 (0.84), 3.971 (0.51), 4.215 (2.91), 4.227 (4.36), 4.245 (2.42), 4.254 (1.96), 4.260 (1.48), 4.272 (1.79), 4.277 (1.35), 4.290 (0.79), 4.297 (0.74), 4.309 (1.30), 4.315 (1.76), 4.327 (1.33), 4.332 (1.68), 4.342 (1.33), 4.355 (1.25), 4.360 (1.25), 4.368 (0.56), 4.377 (0.97), 4.390 (0.64), 4.400 (0.87), 4.415 (0.84), 4.445 (1.15), 4.457 (1.25), 4.468 (1.10), 4.479 (0.94), 4.806 (0.46), 4.823 (0.79), 4.839 (0.43), 5.758 (3.73), 6.875 (1.86), 6.881 (1.86), 6.891 (1.81), 6.896 (1.86), 7.296 (4.70), 7.317 (4.85), 7.363 (0.66), 7.369 (1.38), 7.376 (1.10), 7.386 (1.12), 7.392 (2.30), 7.398 (1.63), 7.408 (1.28), 7.414 (1.61), 7.421 (1.25), 7.431 (3.42), 7.447 (7.25), 7.462 (0.69), 7.595 (0.46), 7.612 (0.43), 7.621 (0.48), 7.624 (0.54), 7.645 (1.61), 7.648 (2.07), 7.654 (1.84), 7.674 (1.99), 7.680 (1.74), 7.819 (2.76), 7.824 (3.67), 7.841 (2.53), 7.845 (3.27), 8.184 (0.89), 8.198 (0.97), 8.207 (0.94), 8.220 (1.89), 8.234 (1.38), 8.243 (1.33), 8.258 (1.30).

Intermediate 157

(rac)-tert-butyl N-[1-(4-bromo-5-ethyl-1-methyl-1H-pyrazol-3-yl)-3-(morpholin-4-yl)propyl]-N-methyl-carbamate

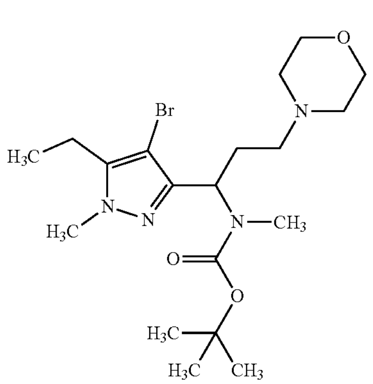 [SMILES: CCc1c(Br)c(C(CCN2CCOCC2)N(C)C(=O)OC(C)(C)C)nn1C]

A mixture of 1-(4-bromo-5-ethyl-1-methyl-1H-pyrazol-3-yl)-3-(morpholin-4-yl)propan-1-one (3.57 g, 10.8 mmol, see Intermediate 92), titanium tetraisopropoxide (5 ml, 16.8 mmol), and methyl amine (10 ml, 2M in tetrahydrofuran, 20 mmol) in tetrahydrofuran was stirred at room temperature for 18 hours. Volatiles removed under reduced pressure, the residue was dissolved in ethanol (25 ml), placed in an ice water bath, treated with sodium borohydride (1.2 g, 31.7 mmol), and allowed to warm to room temperature over 3 hours. Voltiles were removed and the residue suspended in dichloromethane (100 ml), treated with saturated sodium hydrogen carbonate (50 ml, aqueous), and di-tert-butyl dicarbonate (5 g, 22.9 mmol), and stirred at room temperature for 16 hours. The mixture was filtered through a pad of celite, after phase cut, the aqueous phase was extracted with dichloromethane, combined organics washed with saturated sodium chloride (aqueous), dried over sodium sulfate, insoluble materials removed by filtration, volatiles removed under reduced pressure and the residue purified by flash chromatography on silica gel eluting with a gradient of methanol with ammonia in dichloromethane (0-10%), to afford the title compound as a pale yellow gum (4.1 g).

LC-MS (Method 8): $R_t$=1.83 min; MS (ESIpos): m/z=445 $[M+H]^+$

Intermediate 158

(rac)-ethyl 7-[3-(1-{[(tert-butoxy)carbonyl](methyl)amino}-3-(morpholin-4-yl)propyl)-5-ethyl-1-methyl-1H-pyrazol-4-yl]-6-chloro-3-{3-[(6-fluoronaphthalen-1-yl)oxy]propyl}-1H-indole-2-carboxylate

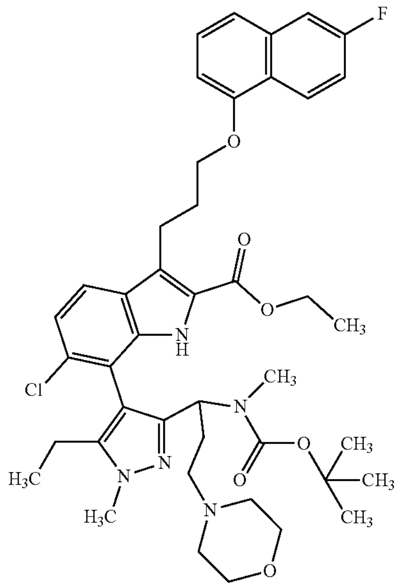 [SMILES: CCOC(=O)c1[nH]c2c(-c3c(C(CCN4CCOCC4)N(C)C(=O)OC(C)(C)C)nn(C)c3CC)c(Cl)ccc2c1CCCOc1cccc2cc(F)ccc12]

To a mixture of (rac)-tert-butyl N-[1-(4-bromo-5-ethyl-1-methyl-1H-pyrazol-3-yl)-3-(morpholin-4-yl)propyl]-N-methylcarbamate (3.1 g, 9.2 mmol, see Intermediate 157), ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (5 g, 9.06 mmol, see Intermediate 52), and RuPhos Pd G3 (424 mg, 0.507 mmol) under vacuum was treated with 1,4-dioxane (48 ml) and tripotassium phosphate (24 ml, 1M, aqueous), and after 5 minutes at room temperature this mixture was transferred to a preheated aluminum block at 110° C., after 5 minutes placed under nitrogen, after 2 hours, cooled to room temperature, treated with celite (10 g) and volatiles were removed under reduced pressure, the residue was purified by flash chromatography on silica gel eluting with a gradient of methanol in dichloromethane (0-30%) to obtain the title compound in moderate purity as a mixture of diastereomers as a brown gum (4.63 g), which was used without further manipulation. The mixture of two racemic diastereomers was formed as a result of atropisomerism at the newly formed bi-heteroaryl bond.

LC-MS (Method 8): $R_t$=2.82 and 2.89 min; MS (ESIneg): m/z=789 $[M-H]^-$

Intermediate 159

(rac)-ethyl 1-(4-bromobutyl)-7-[3-(1-{[(tert-butoxy)carbonyl]methyl)amino}-3-(morpholin-4-yl)propyl)-5-ethyl-1-methyl-1H-pyrazol-4-yl]-6-chloro-3-{3-[(6-fluoronaphthalen-1-yl)oxy]propyl}-1H-indole-2-carboxylate (Isomer 1)

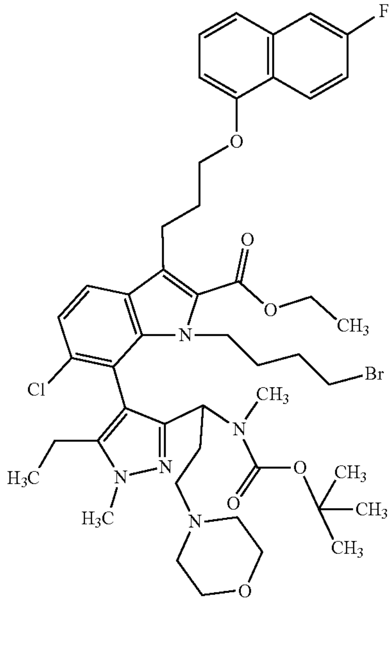 [SMILES: CCOC(=O)c1c(CCCOc2cccc3cc(F)ccc23)c2ccc(Cl)c(-c3c(C(CCN4CCOCC4)N(C)C(=O)OC(C)(C)C)nn(C)c3CC)c2n1CCCCBr]

AND

Intermediate 160

(rac)-ethyl 1-(4-bromobutyl)-7-[3-(1-{[(tert-butoxy)carbonyl]methyl)amino}-3-(morpholin-4-yl)propyl)-5-ethyl-1-methyl-1H-pyrazol-4-yl]-6-chloro-3-{3-[(6-fluoronaphthalen-1-yl)oxy]propyl}-1H-indole-2-carboxylate (Mixture of Isomers)

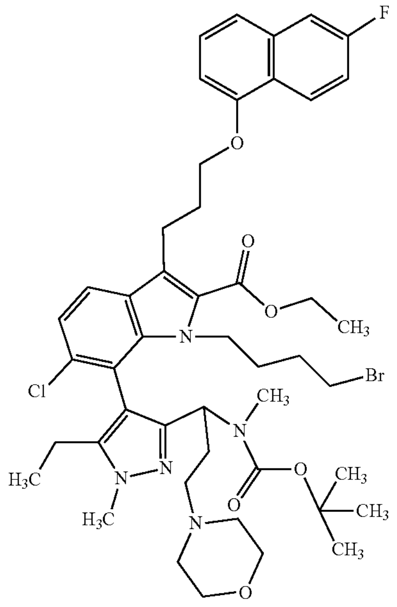 [SMILES: CCOC(=O)c1c(CCCOc2cccc3cc(F)ccc23)c2ccc(Cl)c(-c3c(C(CCN4CCOCC4)N(C)C(=O)OC(C)(C)C)nn(C)c3CC)c2n1CCCCBr]

A mixture of impure ethyl 7-[3-(1-{[(tert-butoxy)carbonyl](methyl)amino}-3-(morpholin-4-yl)propyl)-5-ethyl-1-methyl-1H-pyrazol-4-yl]-6-chloro-3-{3-[(6-fluoronaphthalen-1-yl)oxy]propyl}-1H-indole-2-carboxylate (5.8 g, see Intermediate 158), 1,4-dibromobutane (4 mL, 33.4 mmol) in acetonitrile (40 mL) was treated with potassium tert-butoxide (900 mg, 8.02 mmol) and stirred at room temperature for 16 hours, the mixture was treated with celite, volatiles were removed under reduced pressure, and the residue was purified by reverse phase chromatography on HP C18 eluting with a gradient of acetonitrile in water with 0.1% formic acid (10-100%) to afford the isomer 1 (Intermediate 159) as an off white solid (707 mg) and a mixture of isomers (Intermediate 159 and Intermediate 160) as an amber gum (1.5 g).

Isomer 1: LC-MS (Method 8): $R_t$=3.04 min; MS (ESIpos): m/z=927 $[M+H]^+$

Mixed isomers: LC-MS (Method 8): $R_t$=3.04 and 3.11 min; ratio: 6:4; MS (ESIpos): m/z=927 $[M+H]^+$ Intermediate 161 ethyl 19-chloro-3-ethyl-15-{3-[(6-fluoronaphthalen-1-yl)oxy]propyl}-4,8-dimethyl-7-[2-(morpholin-4-yl)ethyl]-4,5,8,13-tetraazatetracyclo[11.6.1.$0^{2,6}$.$0^{16,20}$]icosa-1(20),2,5,14,16,18-hexaene-14-carboxylate (Racemate 1)

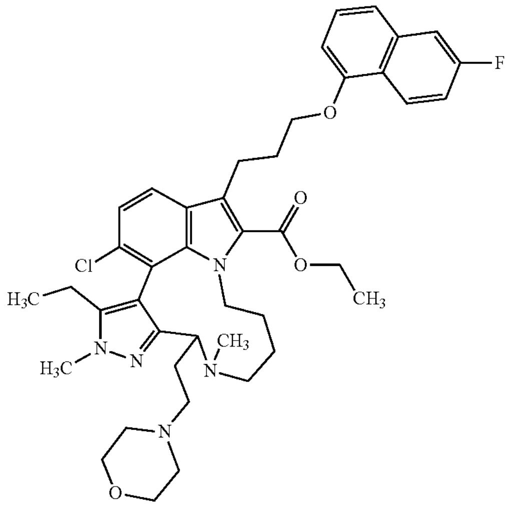 [SMILES: CCOC(=O)c1c(CCCOc2cccc3cc(F)ccc23)c2ccc(Cl)c3c2n1CCCCN(C)C(CCN1CCOCC1)c1nn(C)c(CC)c1-3]

To a solution of isomer 1 of (rac)-ethyl 1-(4-bromobutyl)-7-[3-(1-{[(tert-butoxy)carbonyl]methyl)amino}-3-(morpholin-4-yl)propyl)-5-ethyl-1-methyl-1H-pyrazol-4-yl]-6-chloro-3-{3-[(6-fluoronaphthalen-1-yl)oxy]propyl}-1H-indole-2-carboxylate (700 mg, 0.756 mmol, see Intermediate 159), in dichloromethane (45 mL) was added trifluoroacetic acid (5 mL, 64.8 mmol) and stirred at room temperature for 19 hours, volatiles were removed under reduced pressure and the residue dissolved in acetonitrile (40 mL), treated with diisopropylethylamine (10 mL, 57.4 mmol), and held at 45° C. for 20 hours. Volatiles were removed under reduced pressure and the brown residue was partitioned between ethyl acetate and a mixture of saturated sodium hydrogen carbonate (aqueous) and sodium hydroxide (1N, aqueous), the organic phase was then washed with saturated sodium chloride (aqueous) and dried over sodium sulfate. Insoluble materials were removed by filtration, volatiles removed under reduced pressure and the residue purified by flash chromatography on silica gel eluting with a gradient of methanol in dichloromethane (0-25%) to afford the title compound as a tan foam (400 mg).

LC-MS (Method 8): $R_t$=2.32 min; MS (ESIpos): m/z=745 $[M+H]^+$ $^1$H NMR (400 MHz, Chloroform-d) δ 8.35 (dd, J=9.3, 5.8 Hz, 1H), 7.57 (d, J=8.6 Hz, 1H), 7.44-7.38 (m, 1H), 7.38 (s, 2H), 7.24 (td, J=9.1, 8.6, 2.4 Hz, 1H), 7.15 (d, J=8.6 Hz, 1H), 6.70 (dd, J=6.7, 2.0 Hz, 1H), 4.33 (dddd, J=18.0, 10.9, 7.1, 3.7 Hz, 3H), 4.18 (t, J=6.2 Hz, 2H), 3.89 (s, 4H), 3.82 (s, 1H), 3.69 (t, J=4.7 Hz, 4H), 3.38 (dt, J=13.4, 7.5 Hz, 1H), 3.27 (dt, J=13.9, 7.1 Hz, 1H), 2.63 (ddd, J=11.9, 9.7, 5.4 Hz, 1H), 2.50 (dq, J=16.0, 5.3 Hz, 5H), 2.42-2.07 (m, 10H), 1.99

(dp, J=15.2, 4.8 Hz, 1H), 1.35 (t, J=7.1 Hz, 3H), 1.31-1.21 (m, 1H), 1.12 (p, J=7.5, 6.6 Hz, 3H), 0.90 (t, J=7.6 Hz, 3H).

$^{19}$F NMR (376 MHz, Chloroform-d) δ−114.85.

HSQC $^{13}$C NMR (101 MHz, $CDCl_3$) δ 124.75, 120.81, 110.46, 127.43, 119.39, 115.20, 121.67, 103.99, 60.65, 42.24, 67.58, 42.29, 36.52, 58.12, 66.94, 22.03, 21.84, 56.13, 53.79, 56.00, 53.73, 30.63, 17.84, 38.51, 23.09, 23.00, 14.52, 27.55, 19.36, 27.46, 12.39.

$^{1}$H NMR (400 MHz, $CDCl_3$) δ 8.38, 7.60, 7.43, 7.37, 7.36, 7.27, 7.18, 6.72, 4.35, 4.34, 4.21, 3.96, 3.91, 3.84, 3.72, 3.39, 3.30, 2.65, 2.55, 2.52, 2.51, 2.34, 2.26, 2.24, 2.24, 2.03, 1.38, 1.29, 1.17, 1.16, 0.92.

Intermediate 162 ethyl 19-chloro-3-ethyl-15-{3-[(6-fluoronaphthalen-1-yl)oxy]propyl}-4,8-dimethyl-7-[2-(morpholin-4-yl)ethyl]-4,5,8,13-tetraazatetracyclo[11.6.1.0$^{2,6}$.0$^{16,20}$]icosa-1(20),2,5,14,16,18-hexaene-14-carboxylate (Racemate 2)

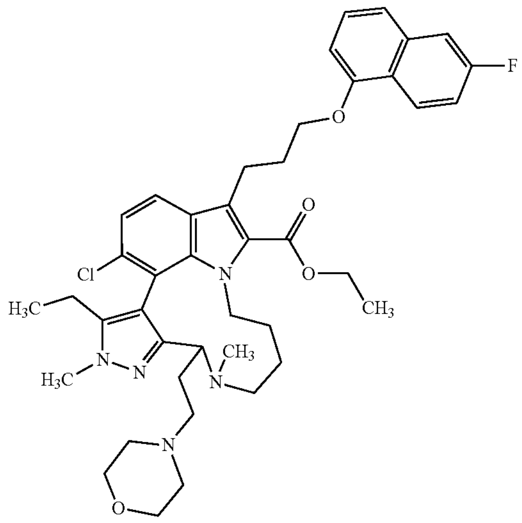 [SMILES: CCOC(=O)c1c(CCCOc2cccc3cc(F)ccc23)c2ccc(Cl)c3c2n1CCCCN(C)C(CCN1CCOCC1)c1nn(C)c(CC)c1-3]

To a solution of mixed isomers ethyl 1-(4-bromobutyl)-7-[3-(1-{[(tert-butoxy)carbonyl](methyl)amino}-3-(morpholin-4-yl)propyl)-5-ethyl-1-methyl-1H-pyrazol-4-yl]-6-chloro-3-{3-[(6-fluoronaphthalen-1-yl)oxy]propyl}-1H-indole-2-carboxylate (1490 mg, 1.61 mmol, see Intermediate 159 and Intermediate 160) in dichloromethane (60 mL) was added trifluoroacetic acid (7 mL, 90.3 mmol) and stirred at room temperature for 19 hours, volatiles were removed under reduced pressure and the residue was dissolved in acetonitrile (20 mL), volatiles were removed and the residue was dissolved in dry acetonitrile (60 ml), and treated with diisopropylethylamine (10 mL, 57.4 mmol) and stirred at 45° C. for 21 hours, volatiles were removed under reduced pressure and the residue partitioned between ethyl acetate and a mixture of saturated sodium hydrogen carbonate (aqueous) and sodium hydroxide (1N, aqueous), the organic phase was then washed with saturated sodium chloride (aqueous) and dried over sodium sulfate. Insoluble materials were removed by filtration, volatiles removed under reduced pressure and the residue purified by flash chromatography on silica gel eluting with a gradient of methanol in dichloromethane (0-25%) to afford the title compound as a tan gum (375 mg) and Intermediate 161 as a tan foam (605 mg).

LC-MS (Method 8): $R_t$=2.61 min; MS (ESIpos): m/z=745 $[M+H]^+$ $^{1}$H NMR (400 MHz, Chloroform-d) δ 8.34 (dd, J=9.2, 5.8 Hz, 1H), 7.55 (d, J=8.6 Hz, 1H), 7.39 (dd, J=10.0, 2.6 Hz, 1H), 7.36-7.29 (m, 2H), 7.22 (ddd, J=9.2, 8.3, 2.6 Hz, 1H), 7.12 (d, J=8.6 Hz, 1H), 6.68 (dd, J=6.6, 2.1 Hz, 1H), 4.40-4.23 (m, 2H), 4.17 (td, J=6.3, 2.0 Hz, 4H), 3.84 (s, 3H), 3.75-3.62 (m, 4H), 3.49-3.40 (m, 1H), 3.39-3.30 (m, 1H), 3.24 (ddd, J=13.4, 8.2, 6.8 Hz, 1H), 2.49-2.41 (m, 3H), 2.38 (t, J=7.5 Hz, 3H), 2.29 (ddt, J=13.9, 9.8, 4.7 Hz, 3H), 2.13 (ddp, J=22.4, 15.1, 7.6 Hz, 3H), 1.98 (s, 3H), 1.87-1.77 (m, 2H), 1.59-1.45 (m, 1H), 1.39-1.27 (m, 4H), 1.21 (ddt, J=15.3, 10.1, 5.2 Hz, 1H), 1.15-0.97 (m, 1H), 0.87 (t, J=7.6 Hz, 3H).

$^{19}$F NMR (376 MHz, Chloroform-d) δ−114.88.

$^{13}$C NMR (101 MHz, $CDCl_3$) δ 162.48, 160.04, 154.97, 151.12, 144.43, 139.39, 135.67, 135.58, 134.31, 127.41, 126.71, 126.60, 125.54, 124.92, 124.83, 122.75, 121.63, 120.75, 119.43, 118.69, 115.28, 115.03, 111.87, 110.74, 110.54, 103.97, 77.16, 67.67, 67.05, 64.62, 60.73, 57.57, 53.93, 51.55, 50.58, 41.69, 38.47, 36.40, 30.60, 28.83, 26.97, 21.84, 21.63, 17.70, 14.38, 12.49.

HSQC $^{13}$C NMR (101 MHz, $CDCl_3$) δ 124.75, 120.84, 110.60, 127.37, 119.33, 115.10, 121.62, 104.03, 60.66, 41.75, 67.61, 36.47, 66.95, 64.64, 21.78, 21.69, 53.89, 51.36, 57.46, 30.67, 17.67, 51.33, 38.55, 27.06, 26.90, 14.49, 26.97, 21.69, 21.51, 12.50

$^{1}$H NMR (400 MHz, $CDCl_3$) δ 8.36, 7.57, 7.42, 7.35, 7.34, 7.25, 7.14, 6.70, 4.33, 4.20, 4.19, 3.86, 3.71, 3.46, 3.35, 3.27, 2.46, 2.44, 2.40, 2.32, 2.15, 2.06, 2.00, 1.85, 1.54, 1.37, 1.34, 1.23, 1.11, 0.89.

Intermediate 163

(rac)-ethyl 7-(3-(1-((tert-butoxycarbonyl)(methyl)amino)-3-(rac)-morpholinopropyl)-5-ethyl-1-methyl-1H-pyrazol-4-yl)-6-chloro-3-(3-(naphthalen-1-yloxy)propyl)-1H-indole-2-carboxylate

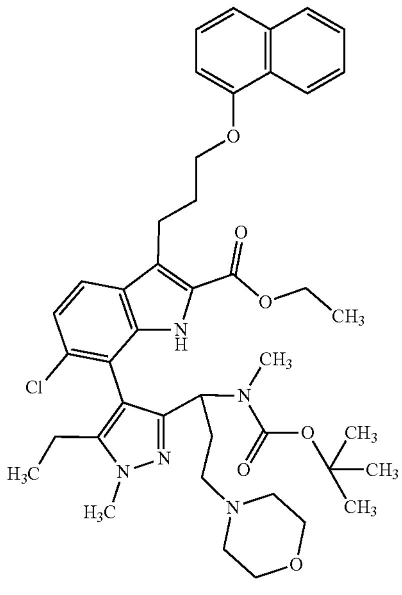

A mixture of tert-butyl N-[1-(4-bromo-5-ethyl-1-methyl-1H-pyrazol-3-yl)-3-(morpholin-4-yl)propyl]-N-methylcarbamate (4.1 g, 9.2 mmol, see Intermediate 157), ethyl 6-chloro-3-[3-(naphthalen-1-yloxy)propyl]-7-(4,4,5,5-tetramethyl-1,3,2-dioxaborolan-2-yl)-1H-indole-2-carboxylate (6 g, 11.2 mmol, Intermediate 8), RuPhos Pd G3 (384 mg, 0.46 mmol) under vacuum was treated with 1,4-dioxane (40 mL) and tripotassium phosphate (40 mL, 1M, aqueous), and stirred at room temperature under vacuum for 5 minutes, then transferred to a pre-heated aluminum block at 100° C., after 5 minutes placed under positive nitrogen pressure and heated for 2 hours. The mixture was cooled to room temperature, adsorbed onto celite, and the residue was purified by flash chromatography on silica gel eluting with gradient of ethyl acetate in hexanes (0-100%) followed by a gradient of ammonia (1 M in methanol) in dichloromethane (0-10%) to afford the title compound in moderate purity as a brown oil (3.52 g) material used without further manipulation as a mixture of isomers, The mixture of two racemic diastereomers was formed as a result of atropisomerism at the newly formed bi-heteroaryl bond.

Isomer 1: LC-MS (Method 8): $R_t$=2.79 min; MS (ESIneg): m/z=771 $[M-H]^-$

Isomer 2: LC-MS (Method 8): $R_t$=2.87 min; MS (ESIneg): m/z=771 $[M-H]^-$

Intermediate 164

(rac)-ethyl 1-(4-bromobutyl)-7-(3-(1-((tert-butoxycarbonyl)(methyl)amino)-3-(rac)-morpholinopropyl)-5-ethyl-1-methyl-1H-pyrazol-4-yl)-6-chloro-3-(3-(naphthalen-1-yloxy)propyl)-1H-indole-2-carboxylate

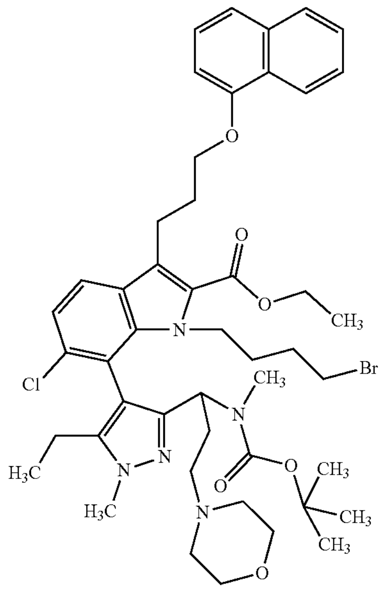

A mixture of impure ethyl 7-(3-(1-((tert-butoxycarbonyl)(methyl)amino)-3-morpholinopropyl)-5-ethyl-1-methyl-1H-pyrazol-4-yl)-6-chloro-3-(3-(naphthalen-1-yloxy)propyl)-1H-indole-2-carboxylate (3.52 g, 4.55 mmol, see Intermediate 163) and 1,4-dibromobutane (3 mL, 25 mmol) in acetonitrile (40 mL) was added potassium tert-butoxide (810 mg, 7.22 mmol) and the mixture heated to 45° C. for 2 hours, cooled to room temperature, and the reaction mixture was directly purified by flash chromatography on silica gel eluting with a gradient of ammonia (7M methanol) in dichloromethane to afford the title compound as a mixture of isomers as a brown gum (550 mg).

Isomer 1: LC-MS (Method 8): $R_t$=3.01 min; MS (ESIpos): m/z=912 $[M+H]^+$

Isomer 2: LC-MS (Method 8): $R_t$=3.08 min; MS (ESIpos): m/z=912 $[M+H]^+$

Intermediate 165 ethyl 13-chloro-12-ethyl-8,11-dimethyl-9-(2-morpholinoethyl)-1-(3-(naphthalen-1-yloxy)propyl)-5,6,7,8,9,11-hexahydro-4H-pyrazolo[3',4':8,9][1,6]diazacycloundecino[10,11,1-hi]indole-2-carboxylate (Racemate 1)

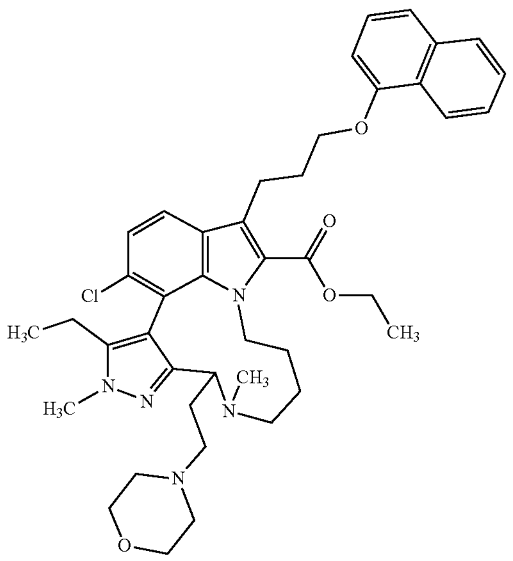 [SMILES: CCOC(=O)c1c(CCCOc2cccc3ccccc23)c2ccc(Cl)c3c2n1CCCCN(C)C(CCN1CCOCC1)c1nn(C)c(CC)c1-3]

and

Intermediate 166 ethyl 13-chloro-12-ethyl-8,11-dimethyl-9-(2-morpholinoethyl)-1-(3-(naphthalen-1-yloxy)propyl)-5,6,7,8,9,11-hexahydro-4H-pyrazolo[3',4':8,9][1,6]diazacycloundecino[10,11,1-hi]indole-2-carboxylate (Racemate 2)

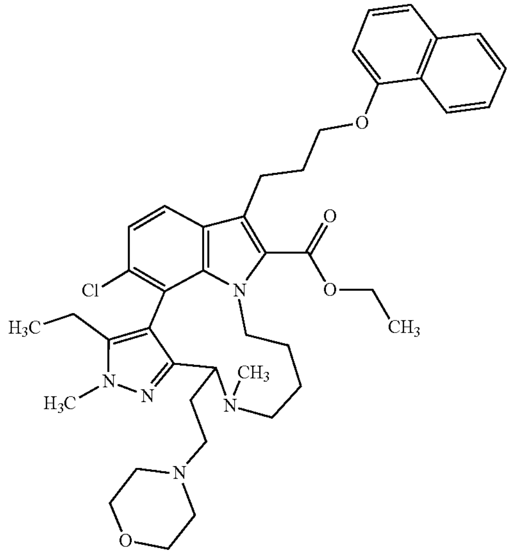 [SMILES: CCOC(=O)c1c(CCCOc2cccc3ccccc23)c2ccc(Cl)c3c2n1CCCCN(C)C(CCN1CCOCC1)c1nn(C)c(CC)c1-3]

To a solution of ethyl 1-(4-bromobutyl)-7-(3-(1-((tert-butoxycarbonyl)(methyl)amino)-3-morpholinopropyl)-5-ethyl-1-methyl-1H-pyrazol-4-yl)-6-chloro-3-(3-(naphthalen-1-yloxy)propyl)-1H-indole-2-carboxylate (550 mg, 0.606 mmol, mixture of isomers see Intermediate 164) in dichloromethane (10 mL) was added trifluoroacetic acid (4 mL) and the mixture stirred at room temperature for 21 hours. Volatiles were removed under reduced pressure and the residue dissolved in acetonitrile (30 mL), volatiles were removed and the residue dissolved in dry acetonitrile (100 mL), treated with diisopropylethylamine (4 mL, 22.9 mmol), and heated to 40° C. for 20 hours. The mixture was cooled to room temperature, volatiles were removed under reduced pressure and the residue partitioned between ethyl acetate and a mixture of saturated aqueous sodium hydrogen carbonate and aqueous sodium hydroxide (1M), the organic phase was washed with saturated aqueous sodium chloride, dried over sodium sulfate, and the residue purified by reverse phase chromatography on C18 eluting with a gradient of acetonitrile in water (containing 0.1% formic acid) (10-100%) to afford racemate 1 as a tan gum (208 mg) and racemate 2 as an off white foam (61 mg).

Intermediate 165 (Racemate 1)

LC-MS (Method 8): $R_t$=2.27 min; MS (ESIpos): m/z=727 $[M+H]^+$ $^1$H NMR (400 MHz, Chloroform-d) δ 8.42-8.29 (m, 1H), 7.77 (dd, J=6.1, 3.3 Hz, 1H), 7.62 (dd, J=8.6, 1.5 Hz, 1H), 7.50-7.43 (m, 2H), 7.39 (d, J=8.2 Hz, 1H), 7.36-7.29 (m, 1H), 7.10 (dd, J=8.6, 1.5 Hz, 1H), 6.76 (d, J=7.5 Hz, 1H), 4.54 (d, J=13.7 Hz, 1H), 4.30 (p, J=6.8 Hz, 2H), 4.18 (t, J=6.0 Hz, 2H), 4.07 (d, J=6.9 Hz, 1H), 3.99-3.83 (m, 4H), 3.66 (h, J=7.4 Hz, 4H), 3.32 (ddt, J=38.0, 13.9, 7.3 Hz, 2H), 2.89-2.59 (m, 10H), 2.29 (hept, J=8.7 Hz, 7H), 1.49-1.37 (m, 2H), 1.33 (td, J=7.1, 1.5 Hz, 3H), 1.26-1.02 (m, 2H), 0.96-0.85 (m, 3H).

$^{13}$C NMR (101 MHz, $CDCl_3$) δ 162.26, 154.61, 145.39, 143.57, 138.99, 134.51, 134.34, 127.51, 127.06, 126.43, 126.34, 126.20, 125.96, 125.70, 125.09, 121.93, 121.75, 121.54, 120.12, 115.00, 114.85, 104.71, 77.16, 67.41, 65.92, 60.86, 55.17, 54.24, 52.74, 51.56, 42.06, 40.88, 37.80, 30.59, 28.14, 25.57, 22.01, 17.86, 14.28, 12.14.

HSQC $^{13}$C NMR (101 MHz, $CDCl_3$) δ 121.96, 127.58, 121.81, 126.43, 125.18, 120.15, 126.03, 121.44, 104.75, 42.09, 60.83, 67.38, 55.19, 42.03, 37.06, 65.96, 21.98, 21.95, 51.58, 54.26, 37.86, 52.84, 51.64, 25.67, 30.82, 17.91, 25.67, 17.93, 28.20, 14.45, 28.02, 17.93, 12.17.

$^1$H NMR (400 MHz, $CDCl_3$) δ 8.37, 7.80, 7.64, 7.49, 7.49, 7.41, 7.35, 7.12, 6.78, 4.57, 4.32, 4.20, 4.09, 3.95, 3.91, 3.68, 3.38, 3.30, 2.81, 2.75, 2.70, 2.66, 2.35, 2.34, 2.32, 2.31, 2.25, 1.44, 1.41, 1.36, 1.22, 1.12, 0.92.

Intermediate 166 (Racemate 2)

LC-MS (Method 8): $R_t$=2.60 min; MS (ESIpos): m/z=727 $[M+H]^+$ $^1$H NMR (400 MHz, Chloroform-d) δ 8.41-8.33 (m, 1H), 7.88-7.77 (m, 1H), 7.62 (d, J=8.5 Hz, 1H), 7.55-7.45 (m, 2H), 7.42 (d, J=8.2 Hz, 1H), 7.35 (t, J=7.9 Hz, 1H), 7.12 (d, J=8.5 Hz, 1H), 6.76 (d, J=7.5 Hz, 1H), 4.34 (pd, J=11.1, 5.5 Hz, 2H), 4.27-4.07 (m, J=7.6, 7.1 Hz, 4H), 3.86 (d, J=8.1 Hz, 7H), 3.56 (dd, J=10.6, 4.1 Hz, 1H), 3.33 (ddt, J=40.7, 14.0, 7.4 Hz, 2H), 2.89 (d, J=6.7 Hz, 4H), 2.78 (dq, J=12.4, 6.9 Hz, 2H), 2.47-2.36 (m, 1H), 2.36-2.25 (m, 2H), 2.25-2.05 (m, 7H), 1.95 (dhept, J=10.9, 6.5 Hz, 1H), 1.51 (d, J=8.8 Hz, 1H), 1.35 (q, J=10.0, 8.5 Hz, 5H), 1.14 (s, 1H), 0.90 (t, J=7.6 Hz, 3H).

$^{13}$C NMR (101 MHz, $CDCl_3$) δ 162.49, 154.80, 148.93, 144.97, 139.07, 134.65, 133.86, 127.63, 127.08, 126.68, 126.48, 126.02, 125.86, 125.74, 125.22, 122.09, 121.45, 121.42, 120.23, 117.78, 112.44, 104.75, 77.16, 67.60, 65.06, 64.43, 60.89, 56.45, 52.32, 51.43, 41.81, 39.16, 36.64, 30.75, 27.14, 25.11, 21.97, 21.46, 17.78, 14.43, 12.46.

HSQC $^{13}$C NMR (101 MHz, $CDCl_3$) δ 121.94, 127.55, 121.36, 126.48, 125.19, 120.21, 126.02, 121.34, 104.76, 60.76, 41.72, 67.43, 41.79, 36.60, 64.95, 64.38, 21.87, 21.87, 52.20, 56.29, 56.29, 51.38, 30.78, 17.63, 51.27, 25.06, 39.01, 25.07, 27.06, 27.01, 14.29, 21.33, 21.35, 12.42.

$^1$H NMR (400 MHz, $CDCl_3$) δ 8.40, 7.83, 7.64, 7.52, 7.51, 7.44, 7.37, 7.14, 6.79, 4.36, 4.27, 4.22, 4.19, 3.90, 3.88, 3.59, 3.39, 3.31, 2.91, 2.89, 2.81, 2.44, 2.34, 2.23, 2.17, 2.14, 2.13, 1.97, 1.53, 1.39, 1.38, 1.31, 1.16, 0.93.

Intermediate 167

(rac)-tert-butyl 2-(5-ethyl-1-methyl-1H-pyrazol-3-yl)piperidine-1-carboxylate

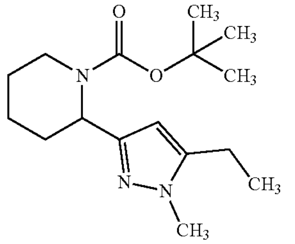 [SMILES: CCc1cc(C2CCCCN2C(=O)OC(C)(C)C)nn1C]

(rac)-1-tert-butyl 2-methyl piperidine-1,2-dicarboxylate (CAS 167423-93-0, 6.3 g, 25.8 mmol) and 2-butanone (13 g, 180 mmol) were dissolved in tetrahydrofuran (100 mL), treated with potassium tert-butoxide (3.1 g, 27.6 mmol), and heated to 50° C. for 18 hours. The mixture was cooled to room temperature and volatiles removed under reduced pressure, the residue was dissolved in a mixture of acetic acid (30 mL) and methanol (30 mL), treated with methyl hydrazine (1 mL, 19.1 mmol) and warmed to 35° C. for 3 hours. The mixture was cooled to room temperature, volatiles were removed under reduced pressure and the residue partitioned between ethyl acetate and sodium hydroxide solution (1N, aqueous), the organic phase was washed twice with saturated sodium hydrogen carbonate (aqueous), saturated sodium chloride (aqueous), combined aqueous phases were back extracted with ethyl acetate, combined organic phases were dried over sodium sulfate, insoluble materials were removed by filtration, volatiles removed under reduced pressure, and the residue purified by flash chromatography using silica gel (gradient hexanes/ethyl acetate) to give the title compound in moderate purity as an amber syrup (2.0 g), which was used without further manipulation.

LC-MS (Method 6): $R_t$=1.54 min; MS (ESIpos): m/z=294 $[M+H]^+$

Intermediate 168

(rac) tert-butyl 2-(5-ethyl-4-iodo-1-methyl-1H-pyrazol-3-yl)piperidine-1-carboxylate

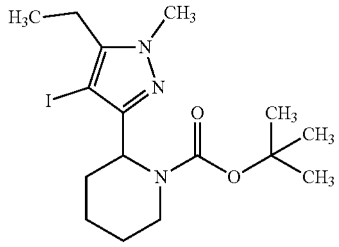 [SMILES: CCc1c(I)c(C2CCCCN2C(=O)OC(C)(C)C)nn1C]

(rac)-tert-butyl 2-(5-ethyl-1-methyl-1H-pyrazol-3-yl)piperidine-1-carboxylate (See Intermediate 167, 2.0 g) was dissolved in dichloromethane (20 mL), treated with 1-iodo-2,5-pyrrolidinedione (2 g, 8.8 mmol) and stirred at room temperature for 1 hour. Volatiles were removed under reduced pressure and the residue was portioned between ethyl acetate and sodium hydroxide solution (1N, aqueous), the organic phase was washed with saturated sodium chloride (aqueous), dried over sodium sulfate, filtered, concentrated under reduced pressure, and the residue purified by flash chromatography using silica gel (gradient hexanes/ethyl acetate) to provide the title compound as a pale-yellow gum (675 mg).

LC-MS (Method 5): $R_t$=4.63 min; MS (ESIpos): m/z=420 $[M+H]^+$ $^1$H NMR (400 MHz, Chloroform-d) δ 5.29 (s, 1H), 3.96 (d, J=13.5 Hz, 1H), 3.81 (s, 3H), 3.18 (td, J=12.9, 2.9 Hz, 1H), 2.67 (q, J=7.8 Hz, 2H), 2.08 (d, J=9.2 Hz, 1H), 1.75 (t, J=6.8 Hz, 2H), 1.68-1.46 (m, 3H), 1.45 (d, J=1.5 Hz, 9H), 1.14 (t, J=7.5 Hz, 3H).

HSQC $^{13}$C NMR (101 MHz, $CDCl_3$) δ 49.66, 40.93, 37.29, 40.95, 19.64, 28.44, 19.54, 28.39, 25.60, 19.56, 25.61, 28.63, 12.89.

$^1$H NMR (400 MHz, $CDCl_3$) δ 5.31, 4.00, 3.84, 3.21, 2.70, 2.11, 1.78, 1.77, 1.63, 1.60, 1.47, 1.47, 1.17.

Intermediate 169 ethyl 7-(3-(1-(tert-butoxycarbonyl)piperidin-2-yl)-5-ethyl-1-methyl-1H-pyrazol-4-yl)-6-chloro-3-(3-(naphthalen-1-yloxy)propyl)-1H-indole-2-carboxylate (Isomer 1)

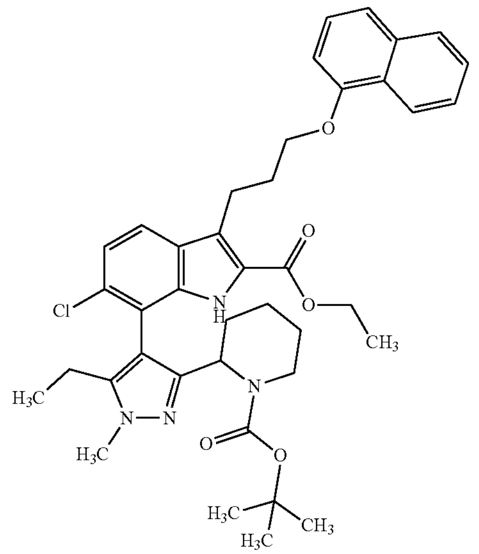 [SMILES: CCOC(=O)c1[nH]c2c(-c3c(C4CCCCN4C(=O)OC(C)(C)C)nn(C)c3CC)c(Cl)ccc2c1CCCOc1cccc2ccccc12]

AND

Intermediate 170 ethyl 7-(3-(1-(tert-butoxycarbonyl)piperidin-2-yl)-5-ethyl-1-methyl-1H-pyrazol-4-yl)-6-chloro-3-(3-(naphthalen-1-yloxy)propyl)-1H-indole-2-carboxylate (Isomer 2)

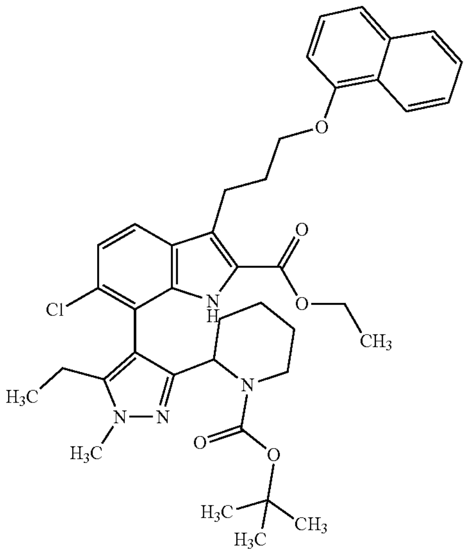 [SMILES: CCOC(=O)c1[nH]c2c(-c3c(C4CCCCN4C(=O)OC(C)(C)C)nn(C)c3CC)c(Cl)ccc2c1CCCOc1cccc2ccccc12]

To a mixture of tert-butyl 2-(5-ethyl-4-iodo-1-methyl-1H-pyrazol-3-yl)piperidine-1-carboxylate (see Intermediate 168, 2.3 g, 5.48 mmol), ethyl 6-chloro-3-[3-(naphthalen-1-yloxy)propyl]-7-(4,4,5,5-tetramethyl-1,3,2-dioxaborolan-2-yl)-1H-indole-2-carboxylate (see Intermediate 8, 4 g, 7.5 mmol), and RuPhos Pd G3 (229 mg, 0.274 mmol), under vacuum was added tripotassium phosphate (1M, 10 mL, aqueous) and 1,4-dioxane (10 mL), after two minutes at room temperature the mixture was placed in a preheated aluminum block at 100° C., after two minutes the mixture was placed under positive nitrogen pressure and continued at that temperature for 100 minutes. Mixture was cooled to room temperature, diluted with ethyl acetate, insoluble materials were remove by filtration, and the filtrate was further diluted with ethyl acetate and saturated sodium chloride solution (aqueous), layers were separated and the aqueous phase further extracted with ethyl acetate, combined organic phases were dried over sodium sulfate, insoluble materials were removed by filtration, concentrated under reduced pressure and the residue purified by flash chromatography using silica gel (gradient, hexanes/ethyl acetate) to afford the title compound Isomer 1 (1.03 g) as an amber gum followed by Isomer 2 (1.04 g) as a pale yellow oil.

Intermediate 169 (Isomer 1)

LC-MS (Method 8): $R_t$=4.36 min; MS (ESIpos): m/z=700 $[M+H]^+$ $^1$H NMR (400 MHz, Chloroform-d) δ 8.42-8.34 (m, 1H), 7.86-7.78 (m, 1H), 7.57 (d, J=8.6 Hz, 1H), 7.53-7.46 (m, 2H), 7.42 (d, J=8.2 Hz, 1H), 7.35 (t, J=7.8 Hz, 1H), 7.18-7.12 (m, 1H), 6.78 (d, J=7.5 Hz, 1H), 5.80 (s, 1H), 5.35 (s, 1H), 5.06 (s, 1H), 4.51-4.27 (m, 3H), 4.21 (t, J=6.1 Hz, 2H), 3.89 (s, 2H), 3.79 (d, J=20.0 Hz, 2H), 3.37 (t, J=7.4 Hz, 3H), 2.81 (s, 1H), 2.57 (q, J=7.4 Hz, 1H), 2.50-2.21 (m, 4H), 1.67-1.42 (m, 17H), 1.35 (td, J=7.1, 1.1 Hz, 4H), 1.30-1.11 (m, 7H), 1.05-0.88 (m, 3H).

Intermediate 170 (Isomer 2)

LC-MS (Method 8): $R_t$=4.17 min; MS (ESIneg): m/z=698 $[M-H]^-$ $^1$H NMR (400 MHz, Chloroform-d) δ 8.41-8.31 (m, 2H), 7.86-7.77 (m, 1H), 7.57 (d, J=11.7 Hz, 1H), 7.54-7.46 (m, 2H), 7.42 (d, J=8.2 Hz, 1H), 7.39-7.30 (m, 1H), 7.14 (d, J=8.6 Hz, 1H), 6.78 (d, J=7.5 Hz, 1H), 5.24 (s, 1H), 4.35 (q, J=7.4 Hz, 2H), 4.22 (t, J=6.1 Hz, 1H), 4.19-4.09 (m, 1H), 3.91 (d, J=1.1 Hz, 2H), 3.75 (t, J=16.4 Hz, 2H), 3.35 (hept, J=7.0 Hz, 2H), 2.99 (t, J=13.1 Hz, 1H), 2.51-2.27 (m, 4H), 1.91 (s, 5H), 1.72-1.44 (m, 9H), 1.26 (dd, J=11.5, 1.1 Hz, 25H), 1.14 (s, 6H), 1.04-0.92 (m, 3H).

Intermediate 171 ethyl (Z)-7-(3-(1-(tert-butoxycarbonyl)piperidin-2-yl)-5-ethyl-1-methyl-1H-pyrazol-4-yl)-6-chloro-1-(4-chlorobut-2-en-1-yl)-3-(3-(naphthalen-1-yloxy)propyl)-1H-indole-2-carboxylate (Isomer 1)

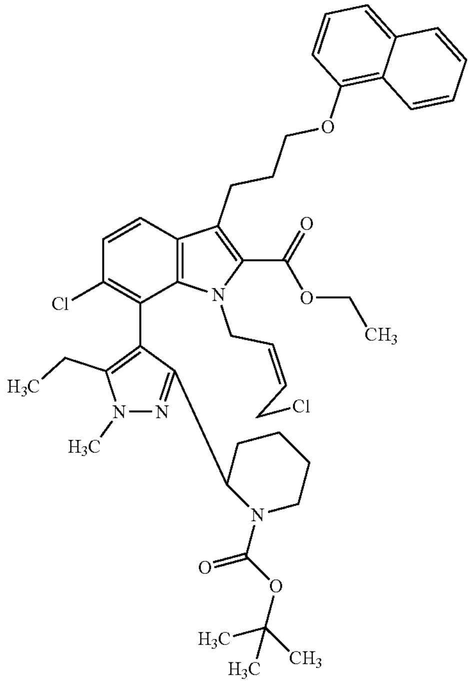 [SMILES: CCOC(=O)c1c(CCCOc2cccc3ccccc23)c2ccc(Cl)c(-c3c(C4CCCCN4C(=O)OC(C)(C)C)nn(C)c3CC)c2n1C/C=C\CCl]

Ethyl 7-(3-{1-[(tert-butoxy)carbonyl]piperidin-2-yl}-5-ethyl-1-methyl-1H-pyrazol-4-yl)-6-chloro-3-[3-(naphthalen-1-yloxy)propyl]-1H-indole-2-carboxylate (Isomer 1) (see Intermediate 169, 1.02 g, 1.45 mmol) was dissolved in acetonitrile (10 mL) and treated with cesium carbonate (1.0 g, 3.06 mmol), cis-1,4-dichlorobutene (0.8 mL, 7.6 mmol), and diisopropylethylamine (0.4 mL, 2.3 mmol), and heated to 40° C. for 72 hours. The mixture was treated with additional cis-1,4-dichlorobutene (0.8 mL, 7.6 mmol) and cesium carbonate (1.0 g, 3.06 mmol) and continued heating at that temperature for an additional 24 hours. The mixture was diluted with ethyl acetate, insoluble materials were removed by filtration, filtrate concentrated under reduced pressure and the residue purified by flash chromatography using silica gel (gradient ethyl acetate/hexanes) to afford the title compound as a colorless oil (828 mg).

LC-MS (Method 8): $R_t$=4.44 min; MS (ESIpos): m/z=788 $[M+H]^+$ $^1$H NMR (400 MHz, Chloroform-d) δ 8.41 (dt, J=7.0, 3.6 Hz, 1H), 7.84 (dt, J=7.0, 3.5 Hz, 1H), 7.65 (dd, J=8.7, 4.1 Hz, 1H), 7.53 (dt, J=6.6, 3.4 Hz, 2H), 7.46 (d, J=8.3 Hz, 1H), 7.39 (t, J=7.8 Hz, 1H), 7.27-7.16 (m, 1H), 6.82 (d, J=7.5 Hz, 1H), 5.57-5.06 (m, 4H), 5.05-4.71 (m, 2H), 4.35 (q, J=7.1 Hz, 2H), 4.25 (t, J=6.1 Hz, 2H), 4.15 (q, J=7.0 Hz, 1H), 4.04-3.76 (m, 6H), 3.54 (t, J=13.2 Hz, 1H), 3.37 (t, J=7.5 Hz, 2H), 3.22 (t, J=13.1 Hz, 0H), 2.34 (dtp, J=30.9, 15.0, 7.7 Hz, 5H), 2.07 (d, J=1.1 Hz, 1H), 1.91-1.72 (m, 2H), 1.72-1.44 (m, 4H), 1.44-1.30 (m, 9H), 1.28 (dd, J=7.0, 1.1 Hz, 2H), 1.04 (d, J=12.0 Hz, 7H).

Intermediate 172 ethyl (Z)-7-(3-(1-(tert-butoxycarbonyl)piperidin-2-yl)-5-ethyl-1-methyl-1H-pyrazol-4-yl)-6-chloro-1-(4-chlorobut-2-en-1-yl)-3-(3-(naphthalen-1-yloxy)propyl)-1H-indole-2-carboxylate (Isomer 2)

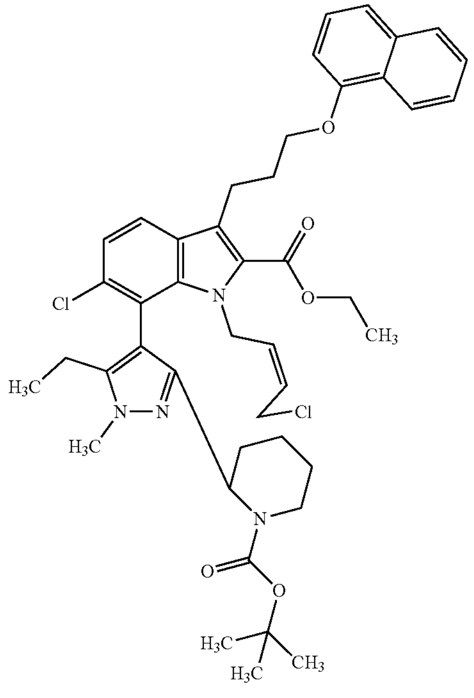 [SMILES: CCOC(=O)c1c(CCCOc2cccc3ccccc23)c2ccc(Cl)c(-c3c(C4CCCCN4C(=O)OC(C)(C)C)nn(C)c3CC)c2n1C/C=C\CCl]

Ethyl 7-(3-{1-[(tert-butoxy)carbonyl]piperidin-2-yl}-5-ethyl-1-methyl-1H-pyrazol-4-yl)-6-chloro-3-[3-(naphthalen-1-yloxy)propyl]-1H-indole-2-carboxylate (Isomer 2) (see Intermediate 170, 1.04 g, 1.48 mmol) was dissolved in acetonitrile (10 mL), treated with cesium carbonate (1.05 g, 3.25 mmol) cis-1,4-dichlorobutene (800 uL, 7.6 mmol) and diisopropylethylamine (0.4 mL, 2.3 mmol), and heated to 40° C. for 72 hours. The mixture was treated with additional cis-1,4-dichlorobutene (0.8 mL, 7.6 mmol) and cesium carbonate (1.0 g, 3.06 mmol) and continued heating at that temperature for an additional 24 hours. The mixture was diluted with ethyl acetate, insoluble materials were removed by filtration, filtrate concentrated under reduced pressure and the residue purified by flash chromatography using silica gel (gradient ethyl acetate/hexanes) to afford the title compound as an amber gum (585 mg).

LC-MS (Method 8): $R_t$=4.33 min; MS (ESIpos): m/z=788 $[M+H]^+$ $^1$H NMR (400 MHz, Chloroform-d) δ 8.44-8.30 (m, 1H), 7.87-7.77 (m, 1H), 7.59 (d, J=8.6 Hz, 1H), 7.50 (dtd, J=8.2, 4.4, 2.1 Hz, 2H), 7.43 (d, J=8.2 Hz, 1H), 7.36 (td, J=7.9, 1.4 Hz, 1H), 7.19 (d, J=8.5 Hz, 1H), 6.80 (d, J=7.5 Hz, 1H), 5.45 (q, J=8.6 Hz, 1H), 5.23 (d, J=34.3 Hz, 2H), 5.06 (dd, J=17.3, 5.3 Hz, 1H), 4.84 (dd, J=17.2, 5.0 Hz, 1H), 4.33 (q, J=7.1 Hz, 2H), 4.23 (t, J=6.0 Hz, 2H), 4.12 (qd, J=7.1, 1.5 Hz, 1H), 3.96-3.76 (m, 6H), 3.34 (t, J=7.5 Hz, 2H), 2.98 (t, J=13.1 Hz, 1H), 2.37 (dh, J=30.0, 7.3 Hz, 4H), 2.22-1.98 (m, 3H), 1.71-1.46 (m, 3H), 1.36 (qd, J=8.1, 7.1, 1.6 Hz, 4H), 1.31-0.93 (m, 14H).

Intermediate 173

(rac)-ethyl-(Z)-16-chloro-15-ethyl-14-methyl-1-(3-(naphthalen-1-yloxy)propyl)-4,7,9,10,11,12,12a,14-octahydropyrazolo[3',4':8,9]pyrido[1',2':6,7][1,6]diazacycloundecino[10,11,1-hi]indole-2-carboxylate (Isomer 1)

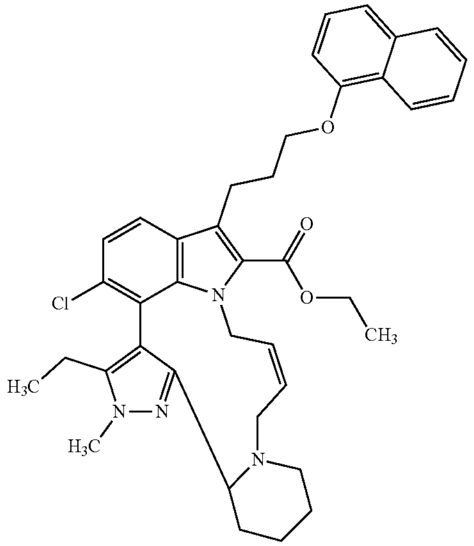 [SMILES: CCOC(=O)c1c(CCCOc2cccc3ccccc23)c2ccc(Cl)c3c2n1C/C=C\CN1CCCCC1c1nn(C)c(CC)c1-3]

Ethyl 7-(3-{1-[(tert-butoxy)carbonyl]piperidin-2-yl}-5-ethyl-1-methyl-1H-pyrazol-4-yl)-6-chloro-1-[(2Z)-4-chlorobut-2-en-1-yl]-3-[3-(naphthalen-1-yloxy)propyl]-1H-indole-2-carboxylate (Isomer 1) (see Intermediate 171, 828 mg) was dissolved in dichloromethane (10 mL), treated with trifluoroacetic acid (4 mL), and stirred at room temperature for 2 hours. Mixture was concentrated under reduced pressure and the residue dissolved in dichloromethane (20 mL), concentrated under reduced pressure, the residue dissolved in acetonitrile (20 ml), treated with diisopropyl ethylamine (4.5 mL), and stirred at room temperature for 72 hours. Mixture concentrated under reduced pressure and the residue partitioned between ethyl acetate and saturated sodium hydrogen carbonate, organic phase washed with saturated sodium chloride (aqueous), dried over sodium sulfate, insoluble materials removed by filtration, concentrated under reduced pressure and the residue purified by flash chromatography using silica gel (gradient ethyl acetate/hexanes) to give the title compound as a brown gum (630 mg).

LC-MS (Method 8): $R_t$=2.73 min; MS (ESIpos): m/z=651 $[M+H]^+$ $^1$H NMR (400 MHz, Chloroform-d) δ 8.41-8.31 (m, 1H), 7.85-7.76 (m, 1H), 7.63 (dd, J=8.5, 1.0 Hz, 1H), 7.54-7.46 (m, 2H), 7.42 (d, J=8.2 Hz, 1H), 7.39-7.30 (m, 1H), 7.21 (dd, J=8.5, 1.0 Hz, 1H), 6.78 (d, J=7.5 Hz, 1H), 5.42 (td, J=12.0, 3.7 Hz, 1H), 5.10-4.95 (m, 2H), 4.70 (dd, J=15.9, 10.8 Hz, 1H), 4.45-4.27 (m, 2H), 4.23 (t, J=6.1 Hz, 2H), 3.93 (d, J=1.1 Hz, 3H), 3.69-3.52 (m, 1H), 3.37 (qt, J=13.7, 7.5 Hz, 2H), 3.22 (d, J=10.2 Hz, 1H), 3.08-2.95 (m, 1H), 2.91 (dd, J=15.0, 4.3 Hz, 1H), 2.52 (t, J=11.1 Hz, 1H), 2.43-2.29 (m, 2H), 2.27-2.08 (m, 3H), 1.81 (dtd, J=29.1, 12.1, 11.1, 4.9 Hz, 3H), 1.68-1.54 (m, 1H), 1.37 (td, J=7.1, 1.1 Hz, 3H), 1.24-1.07 (m, 1H), 0.98-0.78 (m, 3H).

HSQC $^{13}$C NMR (101 MHz, $CDCl_3$) δ 121.98, 127.56, 121.17, 126.54, 125.17, 120.30, 126.08, 122.23, 104.82, 123.42, 130.33, 42.83, 42.82, 60.79, 67.53, 36.82, 49.23, 22.15, 56.04, 51.60, 49.25, 51.64, 30.72, 17.76, 33.86, 33.83, 24.69, 26.42, 26.43, 14.44, 24.82, 12.92

$^1$H NMR (400 MHz, $CDCl_3$) δ 8.38, 7.82, 7.65, 7.51, 7.51, 7.44, 7.37, 7.23, 6.80, 5.45, 5.05, 5.02, 4.73, 4.38, 4.25, 3.96, 3.62, 3.41, 3.24, 3.02, 2.92, 2.55, 2.38, 2.23, 2.16, 1.86, 1.80, 1.79, 1.63, 1.40, 1.19, 0.91.

Intermediate 174

(rac)-ethyl-(Z)-16-chloro-15-ethyl-14-methyl-1-(3-(naphthalen-1-yloxy)propyl)-4,7,9,10,11,12,12a,14-octahydropyrazolo[3',4':8,9]pyrido[1',2':6,7][1,6]diazacycloundecino[10,11,1-hi]indole-2-carboxylate (Isomer 2)

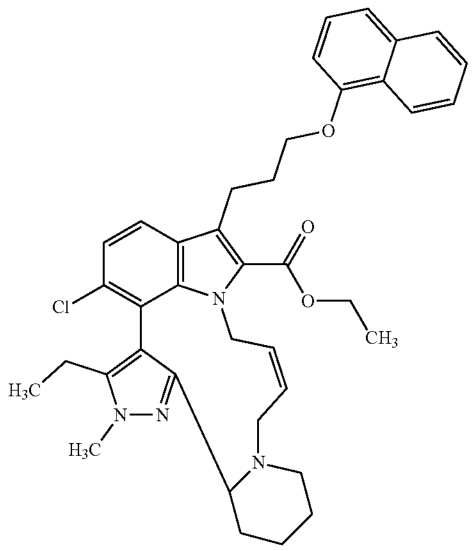 [SMILES: CCOC(=O)c1c(CCCOc2cccc3ccccc23)c2ccc(Cl)c3c2n1C/C=C\CN1CCCCC1c1nn(C)c(CC)c1-3]

Ethyl 7-(3-{1-[(tert-butoxy)carbonyl]piperidin-2-yl}-5-ethyl-1-methyl-1H-pyrazol-4-yl)-6-chloro-1-[(2Z)-4-chlorobut-2-en-1-yl]-3-[3-(naphthalen-1-yloxy)propyl]-1H-indole-2-carboxylate (Isomer 2) (see Intermediate 172, 585 mg, 0.743 mmol) was dissolved in dichloromethane (10 mL) and treated with trifluoroacetic acid (4 mL) and stirred at room temperature for 2 hours. Mixture was concentrated under reduced pressure and the residue dissolved in dichloromethane (20 mL), concentrated under reduced pressure, the residue dissolved in acetonitrile (20 mL), treated with diisopropyl ethylamine (4.5 mL), and stirred at room temperature for 72 hours. Mixture concentrated under reduced pressure and the residue partitioned between ethyl acetate and sodium hydroxide solution (1N, aqueous), organic phase washed with saturated sodium chloride (aqueous), dried over sodium sulfate, insoluble materials removed by filtration, concentrated under reduced pressure and the residue purified by flash chromatography using silica gel (gradient ethyl acetate/hexanes) to give the title compound as a white foam (420 mg).

LC-MS (Method 8): $R_t$=2.74 min; MS (ESIpos): m/z=651 $[M+H]^+$ $^1$H NMR (400 MHz, Chloroform-d) δ 8.40 (dt, J=6.4, 1.8 Hz, 1H), 7.80 (ddt, J=6.7, 5.0, 2.7 Hz, 1H), 7.60 (dd, J=8.5, 1.6 Hz, 1H), 7.50 (ddq, J=7.8, 4.1, 1.9, 1.4 Hz, 2H), 7.42 (d, J=8.2 Hz, 1H), 7.34 (td, J=7.9, 1.6 Hz, 1H), 7.12 (dd, J=8.6, 1.6 Hz, 1H), 6.75 (dd, J=7.6, 1.7 Hz, 1H), 5.84 (tdd, J=8.2, 6.7, 6.3, 3.4 Hz, 1H), 5.79 (s, 1H), 5.23 (ddd, J=13.1, 10.9, 1.6 Hz, 1H), 4.67 (dd, J=13.9, 4.4 Hz, 1H), 4.38 (qt, J=7.1, 1.7 Hz, 2H), 4.19 (dt, J=6.2, 3.1 Hz, 2H), 3.88 (d, J=1.7 Hz, 3H), 3.42 (dddd, J=23.0, 14.6, 9.6, 4.9 Hz, 2H), 3.34-3.21 (m, 2H), 2.80 (d, J=11.1 Hz, 1H), 2.42-2.22 (m, 4H), 2.20-2.08 (m, 1H), 1.92-1.78 (m, 2H), 1.67-1.51 (m, 2H), 1.39 (td, J=7.1, 1.6 Hz, 3H), 1.36-1.24 (m, 1H), 1.22-1.06 (m, 1H), 0.98 (td, J=7.6, 1.6 Hz, 3H), 0.94-0.77 (m, 1H).

HSQC $^{13}$C NMR (101 MHz, $CDCl_3$) δ 121.99, 127.53, 120.76, 125.21, 126.49, 120.17, 126.04, 121.38, 104.65, 132.41, 130.64, 41.56, 41.56, 60.77, 67.49, 36.54, 21.88, 50.63, 21.88, 63.21, 54.59, 30.78, 17.69, 50.54, 31.07, 54.61, 24.60, 31.02, 14.39, 26.03, 24.63, 12.67, 25.82

$^1$H NMR (400 MHz, $CDCl_3$) δ 8.42, 7.82, 7.62, 7.52, 7.52, 7.43, 7.35, 7.14, 6.77, 5.86, 5.77, 5.25, 4.68, 4.39, 4.21, 3.90, 3.45, 3.40, 3.30, 3.30, 2.82, 2.34, 2.33, 2.13, 1.89, 1.86, 1.60, 1.59, 1.41, 1.33, 1.18, 1.01, 0.89.

Intermediate 175

(rac)-ethyl16-chloro-15-ethyl-14-methyl-1-(3-(naphthalen-1-yloxy)propyl)-4,5,6,7,9,10,11,12,12a,14-decahydropyrazolo[3',4':8,9]pyrido[1',2':6,7][1,6]diazacycloundecino[10,11,1-hi]indole-2-carboxylate (Isomer 1)

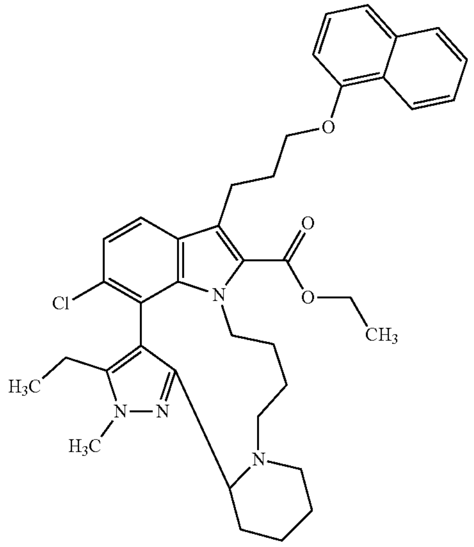 [SMILES: CCOC(=O)c1c(CCCOc2cccc3ccccc23)c2ccc(Cl)c3c2n1CCCCN1CCCCC1c1nn(C)c(CC)c1-3]

(rac)-Ethyl(Z)-16-chloro-15-ethyl-14-methyl-1-(3-(naphthalen-1-yloxy)propyl)-4,7,9,10,11,12,12a,14-octahydropyrazolo[3',4':8,9]pyrido[1',2':6,7][1,6]diazacycloundecino[10,11,1-hi]indole-2-carboxylate (Isomer 2) (see Intermediate 174, 420 mg) was dissolved in ethanol (50 mL), treated with palladium on carbon (10%, 700 mg), and stirred at room temperature under an atmosphere of hydrogen for 16 hours. The mixture was filtered through celite, concentrated under reduced pressure and the residue purified by flash chromatography using silica gel (gradient ethyl acetate/hexanes) to afford the title compound as an amber gum (170 mg).

LC-MS (Method 8): $R_t$=2.95 min; MS (ESIpos): m/z=654 $[M+H]^+$ $^1$H NMR (400 MHz, Chloroform-d) δ 8.45-8.34 (m, 1H), 7.81 (dq, J=5.4, 3.2 Hz, 1H), 7.61 (dd, J=8.5, 1.2 Hz, 1H), 7.53-7.46 (m, 2H), 7.42 (d, J=8.2 Hz, 1H), 7.34 (td, J=7.9, 1.2 Hz, 1H), 7.16 (dd, J=8.5, 1.2 Hz, 1H), 6.80-6.73 (m, 1H), 4.43-4.28 (m, 2H), 4.24-4.16 (m, 4H), 3.87 (d, J=1.3 Hz, 3H), 3.49-3.22 (m, 3H), 2.78 (d, J=11.3 Hz, 1H), 2.69 (td, J=13.0, 5.1 Hz, 1H), 2.34 (q, J=7.0 Hz, 2H), 2.14 (ddtd, J=22.4, 14.9, 7.6, 1.2 Hz, 2H), 1.98 (dt, J=13.1, 2.8 Hz, 1H), 1.90 (dd, J=13.4, 5.0 Hz, 1H), 1.78 (td, J=11.8, 2.6 Hz, 1H), 1.70-1.43 (m, 4H), 1.39 (qd, J=7.5, 7.0, 1.9 Hz, 5H), 1.24-1.00 (m, 3H), 0.89 (td, J=7.6, 1.2 Hz, 3H).

$^{13}$C NMR (101 MHz, $CDCl_3$) δ 162.52, 154.81, 151.06, 144.48, 138.99, 134.96, 134.63, 127.58, 127.09, 126.54, 126.43, 125.98, 125.86, 125.77, 125.17, 122.10, 121.76, 120.73, 120.16, 118.65, 112.57, 104.70, 77.16, 67.71, 63.17, 60.65, 52.60, 49.41, 41.57, 36.43, 30.71, 30.49, 26.63, 25.84, 24.86, 22.05, 21.36, 17.68, 14.45, 12.55.

HSQC $^{13}$C NMR (101 MHz, $CDCl_3$) δ 122.08, 127.51, 120.79, 126.53, 125.20, 120.15, 126.00, 121.70, 104.65, 60.59, 67.63, 41.56, 36.40, 22.04, 63.15, 21.87, 52.62, 49.38, 30.76, 17.57, 30.73, 49.37, 52.54, 30.49, 24.97, 26.62, 21.20, 26.15, 14.55, 24.85, 21.31, 25.91, 12.56.

$^1$H NMR (400 MHz, $CDCl_3$) δ 8.41, 7.83, 7.63, 7.52, 7.52, 7.44, 7.36, 7.18, 6.78, 4.38, 4.24, 4.23, 3.89, 3.43, 3.38, 3.33, 2.82, 2.71, 2.36, 2.19, 2.00, 1.94, 1.82, 1.69, 1.66, 1.57, 1.53, 1.44, 1.41, 1.24, 1.13, 1.11, 0.92.

Intermediate 176

(rac)-ethyl-16-chloro-15-ethyl-14-methyl-1-(3-(naphthalen-1-yloxy)propyl)-4,5,6,7,9,10,11,12,12a,14-decahydropyrazolo[3',4':8,9]pyrido[1',2':6,7][1,6]diazacycloundecino[10,11,1-hi]indole-2-carboxylate (Isomer 2)

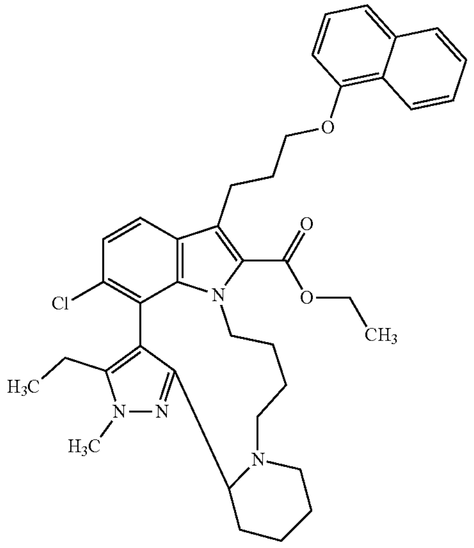 [SMILES: CCOC(=O)c1c(CCCOc2cccc3ccccc23)c2ccc(Cl)c3c2n1CCCCN1CCCCC1c1nn(C)c(CC)c1-3]

(rac)-Ethyl(Z)-16-chloro-15-ethyl-14-methyl-1-(3-(naphthalen-1-yloxy)propyl)-4,7,9,10,11,12,12a,14-octahydropyrazolo[3',4':8,9]pyrido[1',2':6,7][1,6]diazacycloundecino[10,11,1-hi]indole-2-carboxylate (Isomer 1) (see Intermediate 173, 630 mg) was dissolved in ethanol (50 mL), treated with palladium on carbon (10%, 700 mg), and stirred at room temperature under an atmosphere of hydrogen for 16 hours. The mixture was filtered through celite, concentrated under reduced pressure and the residue purified by flash chromatography using silica gel (gradient (ammonia (7M in methanol)/dichloromethane) to afford the title compound as an off-white gum (900 mg).

LC-MS (Method 8): $R_t$=2.80 min; MS (ESIneg): m/z=654 $[M+H]^+$ $^1$H NMR (400 MHz, Chloroform-d) δ 8.35 (dd, J=6.6, 3.4 Hz, 1H), 7.82-7.74 (m, 1H), 7.64 (dd, J=8.6, 1.2 Hz, 1H), 7.47 (dqd, J=6.9, 3.6, 1.2 Hz, 2H), 7.39 (d, J=8.3 Hz, 1H), 7.36-7.28 (m, 1H), 7.15 (dd, J=8.6, 1.2 Hz, 1H), 6.77 (d, J=7.5 Hz, 1H), 4.63 (d, J=14.2 Hz, 1H), 4.31 (ddddd, J=17.9, 10.9, 7.1, 3.8, 1.2 Hz, 2H), 4.20 (t, J=6.1 Hz, 2H), 3.99 (dd, J=16.8, 9.6 Hz, 1H), 3.92 (d, J=1.2 Hz, 3H), 3.33 (ddt, J=28.3, 14.3, 7.0 Hz, 3H), 2.73 (dd, J=13.1, 8.2 Hz, 1H), 2.46-2.36 (m, 1H), 2.30 (dtd, J=12.1, 6.8, 6.2, 3.3 Hz, 4H), 2.23-2.05 (m, 2H), 2.05-1.69 (m, 3H), 1.56-1.42 (m, 1H), 1.34 (td, J=7.1, 1.2 Hz, 4H), 1.20-0.95 (m, 2H), 0.90 (td, J=7.6, 1.2 Hz, 3H).

$^{13}$C NMR (101 MHz, $CDCl_3$) δ 162.29, 154.63, 143.42, 138.80, 135.13, 134.54, 127.54, 126.94, 126.66, 126.35, 126.01, 125.72, 125.10, 121.94, 121.78, 120.16, 104.82, 67.42, 60.96, 41.85, 37.25, 30.66, 29.67, 28.77, 23.28, 22.89, 22.09, 17.87, 14.30, 12.12.

HSQC $^{13}$C NMR (101 MHz, $CDCl_3$) δ 121.92, 127.59, 122.17, 126.36, 125.16, 120.24, 126.12, 121.78, 104.93, 41.85, 51.14, 60.94, 67.42, 67.21, 37.29, 41.92, 51.48, 21.95, 51.51, 53.70, 23.27, 29.89, 17.86, 30.76, 27.55, 23.43, 53.71, 23.40, 22.86, 16.83, 28.67, 14.49, 17.01, 28.72, 12.13

$^{1}$H NMR (400 MHz, $CDCl_3$) δ 8.39, 7.82, 7.68, 7.52, 7.51, 7.44, 7.39, 7.17, 6.82, 4.73, 4.52, 4.35, 4.24, 4.05, 3.97, 3.93, 3.88, 3.39, 3.19, 2.91, 2.80, 2.79, 2.35, 2.34, 2.28, 2.27, 2.26, 1.97, 1.83, 1.66, 1.57, 1.39, 1.19, 1.18, 0.95.d

Intermediate 177

(rac)-tert-butyl 2-(5-ethyl-1-methyl-1H-pyrazol-3-yl)pyrrolidine-1-carboxylate

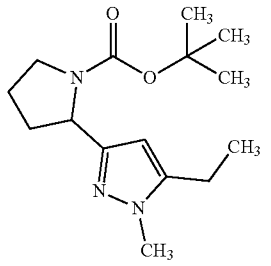 [SMILES: CCc1cc(C2CCCN2C(=O)OC(C)(C)C)nn1C]

(rac)-1-Tert-butyl 2-methyl pyrrolidine-1,2-dicarboxylate (10.2 g, 44.4 mmol, CAS 145681-01-2), 2-butanone (9.4 g, 130 mmol), was dissolved in tetrahydrofuran (100 ml), treated with a solution of sodium bis(trimethylsilyl)amide (45 mL, 1M in tetrahydrofuran), and heated to 70° C. for 18 hours. The mixture was cooled to room temperature and concentrated under reduced pressure, the residue was partitioned between ethyl acetate and hydrochloric acid (3N, aqueous), the layers were separated, organic phase was washed with brine, combined aqueous phase was back extracted with ethyl acetate, combined organic phases dried over sodium sulfate, insoluble materials removed by filtration, and concentrated under reduced pressure, the residue (13 g) was dissolved in acetic acid (100 mL), treated with methyl hydrazine (3 mL, 56.8 mmol), stirred at room temperature for 2 hours, and concentrated under reduced pressure. The residue was partitioned between a mixture of ethyl acetate and hexanes and sodium hydroxide solution (1N, aqueous), the organic phase was washed sequentially with sodium hydroxide solution (1N, aqueous, twice) and saturated sodium chloride (aqueous), combined aqueous washes were extracted with ethyl acetate, combined organic phases dried over sodium sulfate, insoluble materials removed by filtration, concentrated under reduced pressure, and the residue purified by flash chromatography using silica gel (gradient ethyl acetate/hexanes) to afford the title compound as a yellow oil (7.4 g) as a mixture of isomers, carried forward without further manipulation.

LC-MS (Method 6): $R_t$=1.39 min; MS (ESIpos): m/z=280 $[M-H]^-$

Intermediate 178

(rac)-tert-butyl 2-(5-ethyl-4-iodo-1-methyl-1H-pyrazol-3-yl)pyrrolidine-1-carboxylate

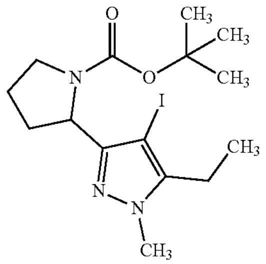 [SMILES: CCc1c(I)c(C2CCCN2C(=O)OC(C)(C)C)nn1C]

(rac)-Tert-butyl 2-(5-ethyl-1-methyl-1H-pyrazol-3-yl) pyrrolidine-1-carboxylate (see Intermediate 177, 7.4 g) was dissolved in dichloromethane (200 mL), treated with 1-iodopyrrolidine-2,5-dione (6.4 g, 28.4 mmol), and stirred at room temperature for 2 hours, additional 1-iodopyrrolidine-2,5-dione (3 g) was added and stirring at room temperature continued for 1 hour. The mixture was diluted with sodium hydroxide solution (1N, aqueous, 200 mL), treated with sodium thiosulfate (10 g), and the layers were separated, the aqueous phase was extracted with dichloromethane, combined organic phases were dried over sodium sulfate, insoluble materials were removed by filtration, concentrated under reduced pressure and the residue purified by flash chromatography using silica gel (gradient ethyl acetate/hexanes) to afford the title compound as an amber gum (3.85 g).

LC-MS (Method 5): $R_t$=3.61 min; MS (ESIpos): m/z=405 $[M+H]^{+s}$ $^{1}$H NMR (400 MHz, Chloroform-d) δ 5.00-4.52 (m, 1H), 3.73 (s, 3H), 3.66-3.32 (m, 2H), 2.58 (h, J=8.0 Hz, 2H), 2.27-1.61 (m, 4H), 1.14 (s, 9H), 1.06 (t, J=7.7 Hz, 3H).

$^{13}$C NMR (101 MHz, $CDCl_3$) δ 154.16, 152.96, 152.08, 145.47, 145.25, 78.89, 78.69, 77.16, 56.06, 55.89, 47.26, 46.90, 37.08, 36.97, 33.73, 33.09, 28.52, 28.24, 23.92, 23.65, 19.37, 19.25, 12.92.

HSQC $^{13}$C NMR (101 MHz, $CDCl_3$) δ 55.92, 55.93, 37.09, 47.09, 47.05, 47.09, 19.46, 33.57, 23.81, 33.44, 23.74, 28.43, 28.32, 12.92

$^{1}$H NMR (400 MHz, $CDCl_3$) δ 4.87, 4.70, 3.74, 3.61, 3.51, 3.41, 2.62, 2.16, 1.99, 1.82, 1.80, 1.40, 1.17, 1.09.

15N HMBC $^{15}$N NMR (41 MHz, $CDCl_3$) δ 302.40, 302.19, 194.47, 194.55, 99.81, 100.81

$^{1}$H NMR (400 MHz, $CDCl_3$) δ 4.71, 3.75, 3.75, 2.62, 2.16, 1.80.

Intermediate 179 ethyl 7-(3-(1-(tert-butoxycarbonyl)pyrrolidin-2-yl)-5-ethyl-1-methyl-1H-pyrazol-4-yl)-6-chloro-3-(3-((6-fluoronaphthalen-1-yl)oxy)propyl)-1H-indole-2-carboxylate (Isomer 1)

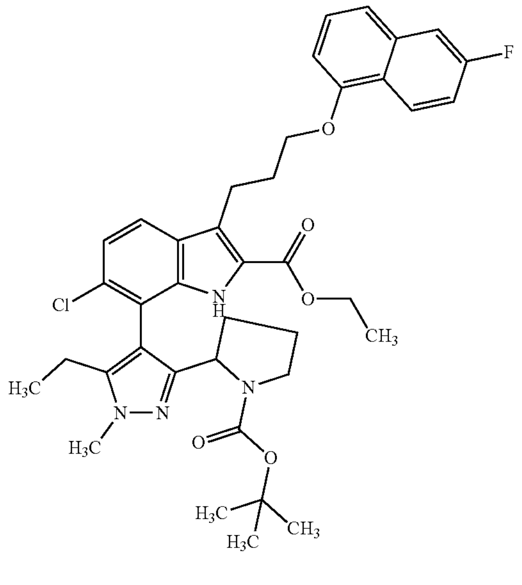 [SMILES: CCOC(=O)c1[nH]c2c(-c3c(C4CCCN4C(=O)OC(C)(C)C)nn(C)c3CC)c(Cl)ccc2c1CCCOc1cccc2cc(F)ccc12]

AND

Intermediate 180 ethyl 7-(3-(1-(tert-butoxycarbonyl)pyrrolidin-2-yl)-5-ethyl-1-methyl-1H-pyrazol-4-yl)-6-chloro-3-(3-((6-fluoronaphthalen-1-yl)oxy)propyl)-1H-indole-2-carboxylate (Isomer 2)

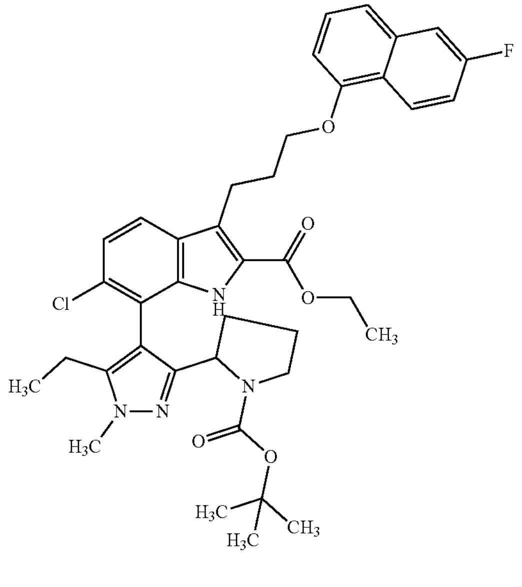 [SMILES: CCOC(=O)c1[nH]c2c(-c3c(C4CCCN4C(=O)OC(C)(C)C)nn(C)c3CC)c(Cl)ccc2c1CCCOc1cccc2cc(F)ccc12]

To a mixture of (rac)-tert-butyl 2-(5-ethyl-4-iodo-1-methyl-1H-pyrazol-3-yl)pyrrolidine-1-carboxylate (see Intermediate 178, 3.85 g, 9.5 mmol), Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 5.23 g, 7.5 mmol), and RuPhos Pd G3 (250 mg, 0.3 mmol), under vacuum was added tripotassium phosphate (1M, 10 mL, aqueous) and toluene (10 mL), after five minutes at room temperature the mixture was placed in a preheated aluminum block at 90° C., after five minutes the mixture was placed under positive nitrogen pressure and continued at that temperature for six hours. Mixture was cooled to room temperature, diluted with ethyl acetate and water, layers were separated and the organic phase washed sequentially with saturated sodium hydrogen carbonate solution (aqueous), and saturated sodium chloride (aqueous) combined aqueous phase further extracted with ethyl acetate, combined organic phases were dried over sodium sulfate, insoluble materials were removed by filtration, concentrated under reduced pressure and the residue purified by flash chromatography using silica gel (gradient, hexanes/ethyl acetate) to afford the title compound Isomer 1 (2.38 g) as a brown oil followed by Isomer 2 (690 mg) as a yellow oil.

Intermediate 179 (Isomer 1)

LC-MS (Method 5): $R_t$=6.64 min; MS (ESIneg): m/z=702 $[M-H]^-$ $^1$H NMR (400 MHz, Chloroform-d) δ 10.22 (s, 1H), 8.33 (dd, J=9.2, 5.8 Hz, 1H), 7.53 (d, J=8.6 Hz, 1H), 7.37 (dd, J=10.2, 2.6 Hz, 1H), 7.34-7.28 (m, 2H), 7.21 (td, J=8.9, 2.4 Hz, 1H), 7.11 (d, J=8.6 Hz, 1H), 6.68 (d, J=6.9 Hz, 1H), 5.00-4.82 (m, 1H), 4.73 (t, J=6.6 Hz, 2H), 4.48-4.21 (m, 3H), 4.18 (t, J=6.2 Hz, 2H), 4.09 (q, J=7.2 Hz, 4H), 3.79 (d, J=20.1 Hz, 15H), 3.69-3.18 (m, 13H), 2.64 (p, J=7.7 Hz, 8H), 2.52-2.24 (m, 7H), 2.24-2.10 (m, 4H), 2.01 (s, 10H), 1.96-1.71 (m, 11H), 1.67 (dt, J=12.2, 6.1 Hz, 1H), 1.43 (s, 21H), 1.37-1.04 (m, 59H), 0.96 (t, J=7.6 Hz, 4H).

HSQC $^{13}$C NMR (101 MHz, $CDCl_3$) δ 124.85, 120.64, 110.38, 127.39, 119.36, 115.18, 121.47, 103.96, 100.62, 55.99, 56.06, 60.43, 54.03, 60.66, 67.66, 60.38, 36.73, 46.99, 47.22, 21.45, 47.11, 19.50, 18.25, 30.54, 33.59, 23.82, 33.42, 23.78, 23.76, 28.42, 28.53, 12.66, 12.67

$^1$H NMR (400 MHz, $CDCl_3$) δ 8.35, 7.56, 7.40, 7.34, 7.33, 7.23, 7.13, 6.71, 5.82, 4.92, 4.75, 4.42, 4.34, 4.25, 4.20, 4.11, 3.84, 3.57, 3.46, 3.37, 3.31, 2.66, 2.39, 2.33, 2.20, 2.06, 1.90, 1.83, 1.69, 1.45, 1.21, 1.18, 0.98.

Intermediate 180 (Isomer 2)

LC-MS (Method 5): $R_t$=6.22 min; MS (ESIneg): m/z=702 $[M-H]^-$ $^1$H NMR (400 MHz, Chloroform-d) δ 8.46-8.18 (m, 2H), 7.48 (d, J=8.6 Hz, 1H), 7.33 (dd, J=10.0, 2.5 Hz, 1H), 7.26 (s, 2H), 7.23-7.12 (m, 1H), 7.04 (d, J=8.6 Hz, 1H), 6.67-6.55 (m, 1H), 4.85 (s, 1H), 4.26 (tt, J=11.5, 6.5 Hz, 2H), 4.15-3.94 (m, 2H), 3.79 (s, 3H), 3.30 (t, J=7.3 Hz, 2H), 2.97 (d, J=98.7 Hz, 1H), 2.28 (tt, J=15.1, 7.9 Hz, 5H), 1.96 (s, 2H), 1.57 (ddt, J=42.6, 12.9, 6.6 Hz, 2H), 1.38-0.78 (m, 15H).

HSQC $^{13}$C NMR (101 MHz, $CDCl_3$) δ 124.75, 120.87, 110.51, 127.32, 119.35, 115.16, 121.80, 103.97, 55.99, 60.78, 67.47, 36.54, 21.42, 46.79, 30.40, 17.95, 33.03, 33.04, 24.21, 24.14, 14.64, 28.46, 13.02

$^1$H NMR (400 MHz, $CDCl_3$) δ 8.38, 7.57, 7.43, 7.36, 7.36, 7.27, 7.13, 6.71, 4.94, 4.36, 4.20, 3.89, 3.40, 3.19, 2.37, 2.34, 2.09, 1.99, 1.74, 1.63, 1.37, 1.30, 0.98.

Intermediate 181 ethyl (Z)-7-(3-(1-(tert-butoxycarbonyl)pyrrolidin-2-yl)-5-ethyl-1-methyl-1H-pyrazol-4-yl)-6-chloro-1-(4-chlorobut-2-en-1-yl)-3-(3-((6-fluoronaphthalen-1-yl)oxy)propyl)-1H-indole-2-carboxylate (Isomer 1)

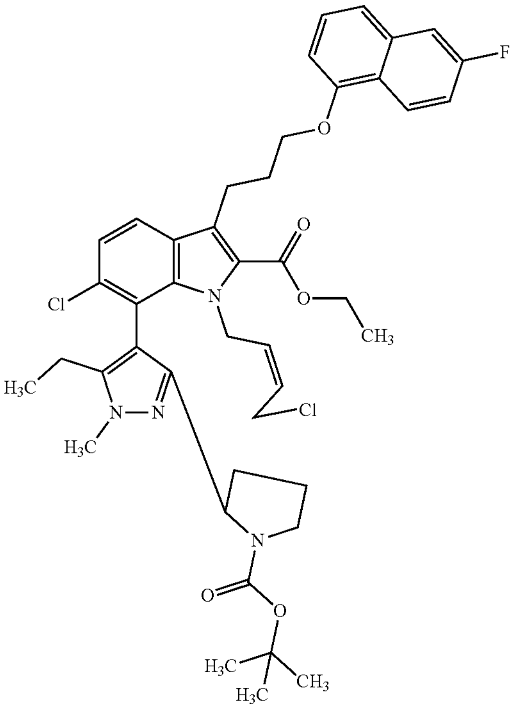 [SMILES: CCOC(=O)c1c(CCCOc2cccc3cc(F)ccc23)c2ccc(Cl)c(-c3c(C4CCCN4C(=O)OC(C)(C)C)nn(C)c3CC)c2n1C/C=C\CCl]

Ethyl-7-(3-(1-(tert-butoxycarbonyl)pyrrolidin-2-yl)-5-ethyl-1-methyl-1H-pyrazol-4-yl)-6-chloro-3-(3-((6-fluoronaphthalen-1-yl)oxy)propyl)-1H-indole-2-carboxylate (isomer 1) (see Intermediate 179, 2.38 g) was dissolved in acetonitrile (50 mL), treated with cesium carbonate (3.3 g, 10 mmol) and cis-1,4-dichlorobutene (0.7 mL, 6.64 mmol), the mixture was stirred at room temperature for 16 hours, then added additional cis-1,4-dichlorobutene (0.3 mL) and cesium carbonate (1 g) and stirred for an additional 24 hours. The mixture was diluted with ethyl acetate, insoluble materials were removed by filtration, concentrated under reduced pressure, and the residue purified by flash chromatography using silica gel (gradient ethyl acetate/hexanes) to afford the title compound as an amber gum (580 mg).

LC-MS (Method 5): $R_t$=6.97 min; MS (ESIpos): m/z=791 $[M+H]^+$ $^1$H NMR (300 MHz, Chloroform-d) δ 8.38 (dd, J=9.2, 5.8 Hz, 1H), 7.61 (d, J=8.6 Hz, 1H), 7.42 (dd, J=10.0, 2.6 Hz, 1H), 7.40-7.32 (m, 2H), 7.27 (ddd, J=9.2, 8.2, 2.6 Hz, 1H), 7.18 (d, J=8.5 Hz, 1H), 6.75 (dd, J=6.9, 1.8 Hz, 1H), 5.39 (d, J=4.1 Hz, 2H), 5.27 (dd, J=18.5, 3.3 Hz, 1H), 5.10 (d, J=18.1 Hz, 1H), 4.62 (dd, J=7.6, 2.9 Hz, 1H), 4.43-4.27 (m, 2H), 4.22 (t, J=6.2 Hz, 2H), 4.07-3.93 (m, 1H), 3.89-3.71 (m, 4H), 3.60 (ddd, J=11.1, 8.0, 3.2 Hz, 1H), 3.35 (t, J=8.0 Hz, 3H), 2.50-2.12 (m, 4H), 2.12-1.61 (m, 5H), 1.46 (s, 8H), 1.37 (t, J=7.1 Hz, 5H), 1.00 (t, J=7.6 Hz, 3H).

Intermediate 182

Ethyl-(Z)-7-(3-(1-(tert-butoxycarbonyl)pyrrolidin-2-yl)-5-ethyl-1-methyl-1H-pyrazol-4-yl)-6-chloro-1-(4-chlorobut-2-en-1-yl)-3-(3-((6-fluoronaphthalen-1-yl)oxy)propyl)-1H-indole-2-carboxylate (Isomer 2)

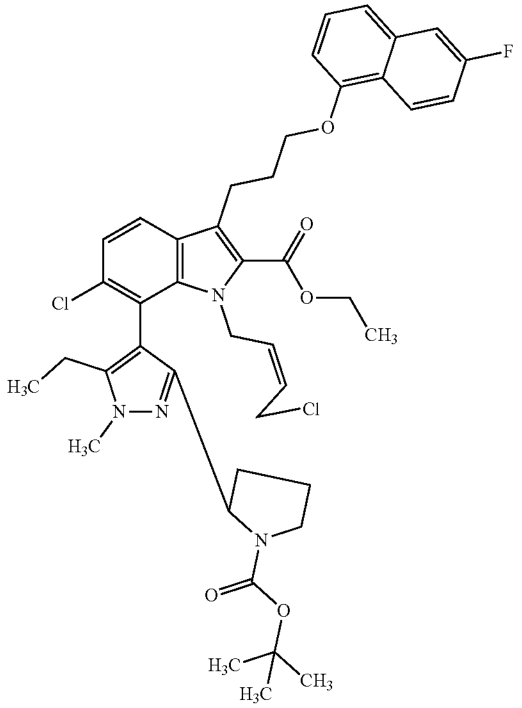 [SMILES: CCOC(=O)c1c(CCCOc2cccc3cc(F)ccc23)c2ccc(Cl)c(-c3c(C4CCCN4C(=O)OC(C)(C)C)nn(C)c3CC)c2n1C/C=C\CCl]

Ethyl-7-(3-(1-(tert-butoxycarbonyl)pyrrolidin-2-yl)-5-ethyl-1-methyl-1H-pyrazol-4-yl)-6-chloro-3-(3-((6-fluoronaphthalen-1-yl)oxy)propyl)-1H-indole-2-carboxylate (isomer 2) (see Intermediate 180, 690 mg, 0.9811 mmol) was dissolved in acetonitrile (50 mL), treated with cesium carbonate (960 mg, 2.94 mmol) and cis-1,4-dichlorobutene (0.3 mL, 2.84 mmol), the mixture was stirred at room temperature for 16 hours, then added additional cis-1,4-dichlorobutene (0.3 mL) and cesium carbonate (1 g) and stirred for an additional 24 hours. The mixture was diluted with ethyl acetate, insoluble materials were removed by filtration, concentrated under reduced pressure, and the residue purified by flash chromatography using silica gel (gradient ethyl acetate/hexanes) to afford the title compound as a brown gum (730 mg).

LC-MS (Method 5): $R_t$=6.72 min; MS (ESIpos): m/z=792 $[M+H]^+$ $^1$H NMR (300 MHz, Chloroform-d) δ 8.36 (dd, J=9.2, 5.8 Hz, 1H), 7.60 (d, J=8.6 Hz, 1H), 7.40 (dd, J=10.0, 2.6 Hz, 1H), 7.37-7.31 (m, 2H), 7.30-7.20 (m, 1H), 7.15 (d, J=8.6 Hz, 1H), 6.69 (dd, J=5.8, 2.8 Hz, 1H), 5.53-4.67 (m, 5H), 4.33 (q, J=7.1 Hz, 2H), 4.26-4.05 (m, 3H), 3.83 (s, 5H), 3.34 (t, J=7.4 Hz, 2H), 3.10 (s, 1H), 2.72 (s, OH), 2.49-2.18 (m, 5H), 2.03 (s, 3H), 1.66-1.46 (m, 1H), 1.44-1.15 (m, 16H), 1.05 (t, J=7.5 Hz, 3H).

Intermediate 183

Ethyl-(Z)-15-chloro-14-ethyl-1-(3-((6-fluoronaphthalen-1-yl)oxy)propyl)-13-methyl-4,7,10,11,11a,13-hexahydro-9H-pyrazolo[3',4':8,9]pyrrolo[1',2':6,7][1,6]diazacycloundecino[10,11,1-hi]indole-2-carboxylate (Isomer 1)

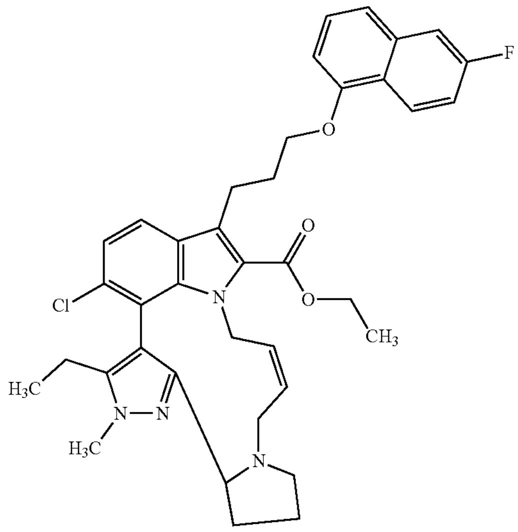 [SMILES: CCOC(=O)c1c(CCCOc2cccc3cc(F)ccc23)c2ccc(Cl)c3c2n1C/C=C\CN1CCCC1c1nn(C)c(CC)c1-3]

Ethyl-(Z)-7-(3-(1-(tert-butoxycarbonyl)pyrrolidin-2-yl)-5-ethyl-1-methyl-1H-pyrazol-4-yl)-6-chloro-1-(4-chlorobut-2-en-1-yl)-3-(3-((6-fluoronaphthalen-1-yl)oxy)propyl)-1H-indole-2-carboxylate (Isomer 1) (see Intermediate 181, 580 mg, 0.73 mmol) was dissolved in dichloromethane (10 mL), treated with trifluoroacetic acid (2 mL), and stirred at room temperature for 30 minutes. The mixture was concentrated under reduced pressure, the residue was dissolved in acetonitrile (10 mL), treated with diisopropyl ethylamine (2 mL), and stirred at room temperature for 30 minutes. The mixture was concentrated under reduced pressure and the residue purified by flash chromatography using silica gel (gradient (ammonia (7M in methanol))/dichloromethane) to afford the title compound in mixture with organic salts (695 mg), this material was dissolved in ethyl acetate and washed sequentially with sodium hydroxide solution (1N, aqueous, twice), saturated sodium hydrogen carbonate (aqueous), and saturated sodium chloride (aqueous), dried over sodium sulfate, insoluble materials removed by filtration and the filtrate concentrated under reduced pressure to provide the title compound as a pale yellow film (475 mg).

LC-MS (Method 5): $R_t$=4.70 min; MS (ESIpos): m/z=657 $[M+H]^+$

Intermediate 184

Ethyl-(Z)-15-chloro-14-ethyl-1-(3-((6-fluoronaphthalen-1-yl)oxy)propyl)-13-methyl-4,7,10,11,11a,13-hexahydro-9H-pyrazolo[3',4':8,9]pyrrolo[1',2':6,7][1,6]diazacycloundecino[10,11,1-hi]indole-2-carboxylate (Isomer 2)

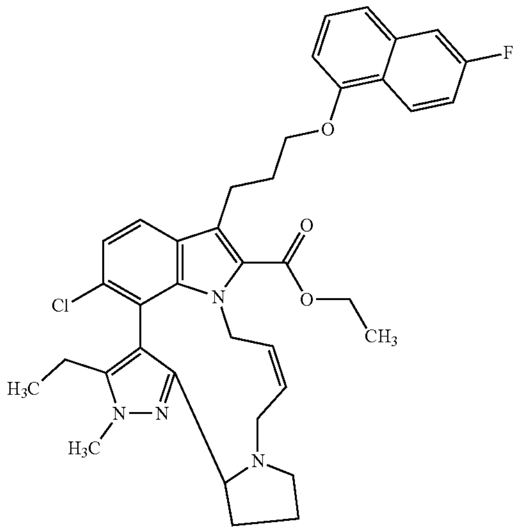 [SMILES: CCOC(=O)c1c(CCCOc2cccc3cc(F)ccc23)c2ccc(Cl)c3c2n1C/C=C\CN1CCCC1c1nn(C)c(CC)c1-3]

Ethyl-(Z)-7-(3-(1-(tert-butoxycarbonyl)pyrrolidin-2-yl)-5-ethyl-1-methyl-1H-pyrazol-4-yl)-6-chloro-1-(4-chlorobut-2-en-1-yl)-3-(3-((6-fluoronaphthalen-1-yl)oxy)propyl)-1H-indole-2-carboxylate (Isomer 2) (see Intermediate 182, 730 mg, 0.92 mmol) was dissolved in dichloromethane (10 mL), treated with trifluoroacetic acid (2 mL), and stirred at room temperature for 1 hour. The mixture was concentrated under reduced pressure, the residue was dissolved in acetonitrile (10 mL), treated with diisopropyl ethylamine (3 mL), and stirred at room temperature for 48 hours. The mixture was concentrated under reduced pressure and the residue purified by flash chromatography using silica gel (gradient (ammonia (7M in methanol))/dichloromethane) to afford the title compound in mixture with organic salts (920 mg), this material was dissolved in ethyl acetate and washed sequentially with sodium hydroxide solution (1N, aqueous, twice), saturated sodium hydrogen carbonate (aqueous), and saturated sodium chloride (aqueous), dried over sodium sulfate, insoluble materials removed by filtration and the filtrate concentrated under reduced pressure to provide the title compound as a pale yellow film (580 mg).

LC-MS (Method 5): $R_t$=4.71 min; MS (ESIpos): m/z=656 $[M+H]^+$

Intermediate 185

Ethyl-15-chloro-14-ethyl-1-(3-((6-fluoronaphthalen-1-yl)oxy)propyl)-13-methyl-4,5,6,7,10,11,11a,13-octahydro-9H-pyrazolo[3',4':8,9]pyrrolo[1',2':6,7][1,6]diazacycloundecino[10,11,1-hi]indole-2-carboxylate (Isomer 1)

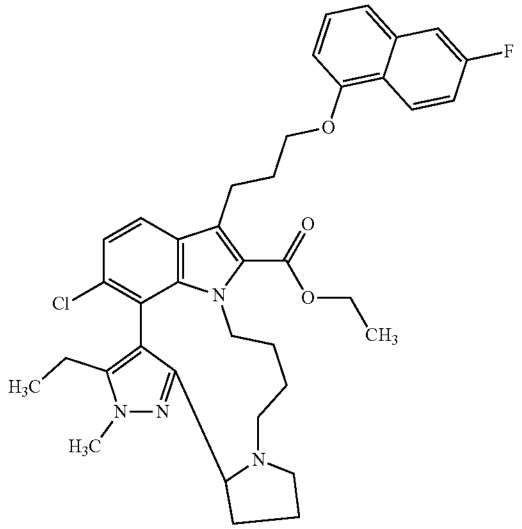 [SMILES: CCOC(=O)c1c(CCCOc2cccc3cc(F)ccc23)c2ccc(Cl)c3c2n1CCCCN1CCCC1c1nn(C)c(CC)c1-3]

Ethyl-(Z)-15-chloro-14-ethyl-1-(3-((6-fluoronaphthalen-1-yl)oxy)propyl)-13-methyl-4,7,10,11,11a,13-hexahydro-9H-pyrazolo[3',4':8,9]pyrrolo[1',2':6,7][1,6]diazacycloundecino[10,11,1-hi]indole-2-carboxylate (Isomer 1) (see Intermediate 183, 475 mg, 0.725 mmol) was dissolved in ethanol (100 mL), treated with palladium on carbon (10%, 771 mg), and stirred at room temperature under an atmosphere of hydrogen for 3 hours. The mixture was filtered through celite, treated with fresh palladium on carbon (10%, 300 mg), and stirred at room temperature under an atmosphere of hydrogen for 17 hours. The mixture was filtered through celite, concentrated under reduced pressure and the residue dissolved in ethanol and treated with fresh palladium on carbon (10%, 350 mg), and stirred at room temperature under an atmosphere of hydrogen for 3 hours, filtered through a pad of celite, concentrated under reduced pressure and the residue purified by flash chromatography using silica gel (gradient (ammonia (7M in methanol))/dichloromethane) to afford the title compound as an amber gum (290 mg).

LC-MS (Method 6): $R_t$=1.52 min; MS (ESIpos): m/z=657 $[M+H]^+$ $^1$H NMR (400 MHz, Chloroform-d) δ 8.37 (dd, J=9.3, 5.9 Hz, 1H), 7.62 (dd, J=8.5, 1.5 Hz, 1H), 7.45-7.39 (m, 1H), 7.37 (d, J=7.8 Hz, 2H), 7.30-7.22 (m, 1H), 7.20 (dd, J=8.5, 1.5 Hz, 1H), 6.72 (d, J=6.8 Hz, 1H), 4.70-4.57 (m, 1H), 4.46-4.27 (m, 2H), 4.26-4.11 (m, 3H), 3.94 (d, J=1.5 Hz, 3H), 3.79 (t, J=6.1 Hz, 1H), 3.42 (dt, J=14.5, 7.5 Hz, 1H), 3.31 (dt, J=14.1, 7.4 Hz, 1H), 3.02 (q, J=7.6, 7.1 Hz, 1H), 2.69 (dt, J=12.6, 8.6 Hz, 2H), 2.34 (p, J=7.8 Hz, 4H), 2.15 (dddd, J=25.8, 20.1, 17.2, 11.3 Hz, 4H), 1.79 (tq, J=11.8, 6.6, 6.1 Hz, 1H), 1.39 (td, J=7.1, 1.5 Hz, 4H), 1.31-1.07 (m, 2H), 1.04 (t, J=11.3 Hz, 1H), 0.98-0.87 (m, 3H).

$^{13}$C NMR (101 MHz, Chloroform-d) δ 162.42, 161.23 (d, J=245.9 Hz), 154.92, 150.44, 142.04, 139.36, 135.61 (d, J=9.2 Hz), 134.94, 127.40, 126.55, 126.14, 125.93, 124.83

(d, J=9.1 Hz), 122.71, 121.50, 120.88, 119.45 (d, J=4.9 Hz), 116.65, 115.12 (d, J=24.9 Hz), 114.66, 110.63 (d, J=20.3 Hz), 103.98 (d, J=2.2 Hz), 67.63, 60.74, 55.38, 52.36, 49.30, 43.07, 36.82, 31.29, 30.58, 30.09, 22.50, 22.06, 19.61, 17.95, 14.35, 12.38.

$^{19}$F NMR (376 MHz, Chloroform-d) δ −114.81.

HSQC $^{13}$C NMR (101 MHz, $CDCl_3$) δ 124.76, 120.84, 110.51, 127.40, 119.42, 115.16, 121.52, 104.00, 43.10, 60.69, 67.57, 43.13, 36.87, 55.41, 22.06, 22.00, 52.40, 49.31, 52.31, 30.74, 17.92, 31.47, 49.29, 31.40, 22.42, 22.42, 30.26, 14.53, 30.07, 19.70, 19.83, 12.44

$^1$H NMR (400 MHz, $CDCl_3$) δ 8.37, 7.62, 7.42, 7.37, 7.35, 7.26, 7.20, 6.73, 4.65, 4.37, 4.21, 4.18, 3.94, 3.79, 3.42, 3.33, 3.02, 2.70, 2.70, 2.35, 2.34, 2.24, 2.17, 2.14, 2.10, 1.81, 1.44, 1.39, 1.24, 1.21, 1.04, 0.95.

Intermediate 186

Ethyl-15-chloro-14-ethyl-1-(3-((6-fluoronaphthalen-1-yl)oxy)propyl)-13-methyl-4,5,6,7,10,11,11a,13-octahydro-9H-pyrazolo[3',4':8,9]pyrrolo[1',2':6,7][1,6]diazacycloundecino[10,11,1-hi]indole-2-carboxylate (Isomer 2)

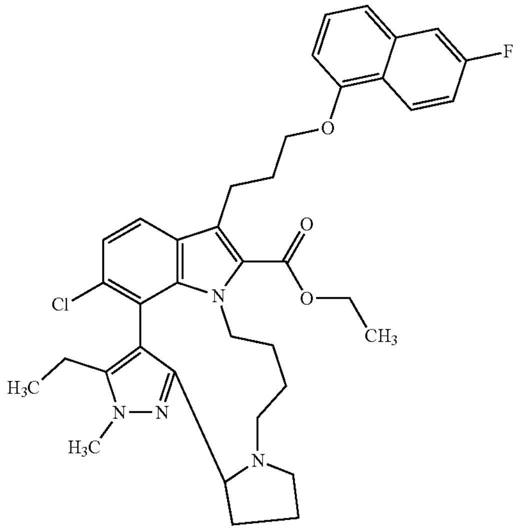 [SMILES: CCOC(=O)c1c(CCCOc2cccc3cc(F)ccc23)c2ccc(Cl)c3c2n1CCCCN1CCCC1c1nn(C)c(CC)c1-3]

Ethyl-(Z)-15-chloro-14-ethyl-1-(3-((6-fluoronaphthalen-1-yl)oxy)propyl)-13-methyl-4,7,10,11,11a,13-hexahydro-9H-pyrazolo[3',4':8,9]pyrrolo[1',2':6,7][1,6]diazacycloundecino[10,11,1-hi]indole-2-carboxylate (Isomer 2) (see Intermediate 184, 580 mg, 0.885 mmol) was dissolved in ethanol (100 mL), treated with palladium on carbon (10%, 942 mg), and stirred at room temperature under an atmosphere of hydrogen for 3 hours. The mixture was filtered through celite, concentrated under reduced pressure and the residue purified by flash chromatography using silica gel (gradient ethyl acetate/hexanes) to afford the title compound as a pale yellow oil (425 mg).

LC-MS (Method 5): $R_t$=4.58 min; MS (ESIpos): m/z=657 $[M+H]^+$ $^1$H NMR (400 MHz, Chloroform-d) δ 8.38 (dd, J=9.3, 5.9 Hz, 1H), 7.57 (d, J=8.4 Hz, 1H), 7.40 (dd, J=9.9, 2.5 Hz, 1H), 7.34 (t, J=3.3 Hz, 2H), 7.30-7.20 (m, 1H), 7.15 (d, J=8.5 Hz, 1H), 6.69 (dd, J=5.9, 2.7 Hz, 1H), 4.35 (tt, J=15.1, 7.8 Hz, 2H), 4.29-4.06 (m, 5H), 3.87 (s, 3H), 3.60 (t, J=8.2 Hz, 1H), 3.40 (dt, J=14.6, 7.6 Hz, 1H), 3.28 (dt, J=13.9, 7.4 Hz, 1H), 2.67 (tt, J=12.0, 5.8 Hz, 2H), 2.33 (p, J=7.3 Hz, 2H), 2.13 (s, 3H), 2.04 (s, 2H), 1.94 (q, J=8.7 Hz, 1H), 1.55 (h, J=11.4, 7.4 Hz, 2H), 1.37 (t, J=7.2 Hz, 3H), 1.26 (t, J=7.2 Hz, 3H), 0.90 (t, J=7.6 Hz, 3H).

$^{13}$C NMR (101 MHz, Chloroform-d) δ 162.45, 160.01, 154.94, 150.99, 144.23, 139.63, 135.60 (d, J=9.2 Hz), 134.20, 127.37, 127.10, 127.06, 125.77, 124.87 (d, J=9.1 Hz), 122.72, 121.60, 120.48, 119.38, 118.96, 115.10 (d, J=24.9 Hz), 112.23, 110.60 (d, J=20.4 Hz), 103.93, 67.64, 63.57, 60.60, 52.29, 49.04, 42.02, 36.32, 30.54, 29.47, 27.91, 23.38, 22.56, 21.83, 17.66, 14.38, 12.52.

HSQC $^{13}$C NMR (101 MHz, $CDCl_3$) δ 124.83, 120.56, 110.48, 127.37, 119.34, 115.16, 121.57, 103.95, 60.57, 42.00, 67.59, 42.10, 60.35, 36.35, 34.73, 63.57, 21.82, 21.84, 52.25, 49.11, 30.62, 49.12, 17.60, 29.34, 52.28, 23.26, 27.77, 14.52, 22.57, 22.61, 27.90, 12.54 $^{1}$H NMR (400 MHz, $CDCl_3$) δ 8.37, 7.56, 7.40, 7.34, 7.33, 7.24, 7.14, 6.68, 4.35, 4.22, 4.19, 4.16, 4.13, 3.86, 3.86, 3.60, 3.39, 3.29, 2.70, 2.67, 2.34, 2.19, 2.17, 2.09, 1.94, 1.57, 1.54, 1.38, 1.34, 1.29, 1.27, 0.91.

Intermediate 187

(rac)-1-(4-bromo-5-ethyl-1-methyl-1H-pyrazol-3-yl)-2-phenylethan-1-ol

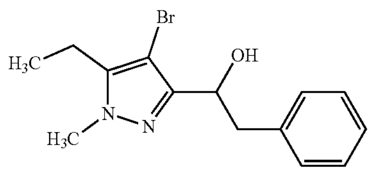 [SMILES: CCc1c(Br)c(C(O)Cc2ccccc2)nn1C]

To a solution of 4-bromo-5-ethyl-1-methyl-1H-pyrazole-3-carbaldehyde (see Intermediate 21, 5.0 g, 23.0 mmol) in anhydrous tetrahydrofuran (230 mL) at 0° C. was added a solution of benzylmagnesium chloride (28.7 mL, 57.4 mmol, 2 M in ether) dropwise. The resulting mixture was gradually warmed to room temperature and stirred for 4 h. Saturated aqueous ammonium chloride solution was added and the aqueous layer was extracted with ethyl acetate three times. The combined organic extracts were washed with brine, dried over sodium sulfate, filtered and concentrated. The residue was purified by flash column chromatography on silica gel (20-100% ethyl acetate/hexanes) to obtain the title compound (3.53 g) as a clear oil.

LC-MS (Method 4): $R_t$=1.31 min; MS (ESIpos): m/z=312 $[M+H]^+$ $^{1}$H NMR (300 MHz, Chloroform-d) δ 7.31-7.16 (m, 5H), 4.95 (ddd, 1H), 3.75 (s, 3H), 3.16-3.09 (m, 1H), 2.68-2.60 (m, 3H), 1.15 (t, 3H).

Intermediate 188

(rac)-ethyl 6-chloro-7-[5-ethyl-3-(1-hydroxy-2-phenylethyl)-1-methyl-1H-pyrazol-4-yl]-3-{3-[(6-fluoronaphthalen-1-yl)oxy]propyl}-1H-indole-2-carboxylate

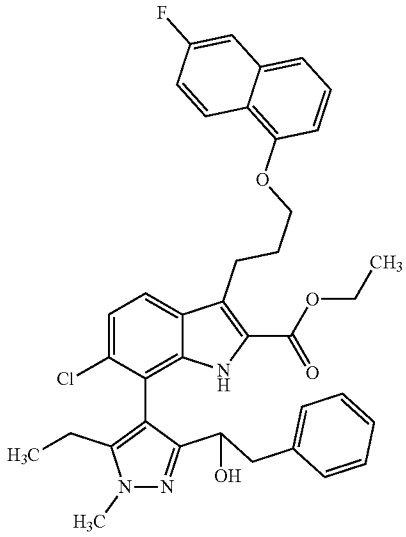 [SMILES: CCOC(=O)c1[nH]c2c(-c3c(C(O)Cc4ccccc4)nn(C)c3CC)c(Cl)ccc2c1CCCOc1cccc2cc(F)ccc12]

A round bottom flask equipped with a stir bar was charged with ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 8, 2.0 g, 3.62 mmol), (rac)-1-(4-bromo-5-ethyl-1-methyl-1H-pyrazol-3-yl)-2-phenylethan-1-ol (see Intermediate 187, 1.34 g, 4.34 mmol), tripotassium phosphate (1.53 g, 7.24 mmol), and RuPhos Pd G3 (166 mg, 199 μmol). The flask was purged with nitrogen and filled with degassed toluene (40 mL) and water (8 mL). The mixture was heated at 110° C. for 2 h, cooled to room temperature, and filtered over a pad of Celite. The mixture was diluted with water and extracted three times with ethyl acetate. The combined organic phases were washed with brine, dried over sodium sulfate, filtered, and concentrated. The crude residue was purified by flash chromatography on silica gel (0-80% acetone/dichloromethane) and fractions were re-purified by reverse-phase flash chromatography on C18-silica (10-100% acetonitrile/water with 0.1% formic acid) to obtain the title compound (0.931 g) as a 3.7:1 mixture of diastereomers, which was formed as a mixture of two racemic diastereomers as a result of atropisomerism at the newly formed bi-heteroaryl bond.

Diastereomer 1: LC-MS (Method 5): $R_t$=5.24 min; MS (ESIpos): m/z=654 $[M+H]^+$ Diastereomer 2: LC-MS (Method 5): $R_t$=5.78 min; MS (ESIpos): m/z=654 $[M+H]^+$ $^{1}$H NMR (400 MHz, Chloroform-d) δ 8.81 (s, 2H), 8.36 (dt, 2H), 7.59 (d, 2H), 7.45-7.31 (m, 5H), 7.25-7.11 (m, 7H), 7.09-6.99 (m, 3H), 6.93-6.86 (m, 1H), 6.71 (dd, 2H), 4.80 (t, 1H), 4.55 (t, 2H), 4.34 (m, 4H), 4.19 (t, 4H), 3.94 (d, 5H), 3.37 (t, 3H), 3.09 (d, 3H), 2.87 (d, 1H), 2.49 (m, 4H), 2.34 (h, 4H), 1.38-1.27 (m, 5H), 0.99 (m, 5H).

Intermediate 189

(rac)-ethyl (11Z)-15-benzyl-4-chloro-3-ethyl-7-{3-[(6-fluoro-1-naphthyl)oxy]propyl}-2-methyl-2,10,13,15-tetrahydropyrazolo[4',3':9,10][1,6]oxazacycloundecino[8,7,6-hi]indole-8-carboxylate

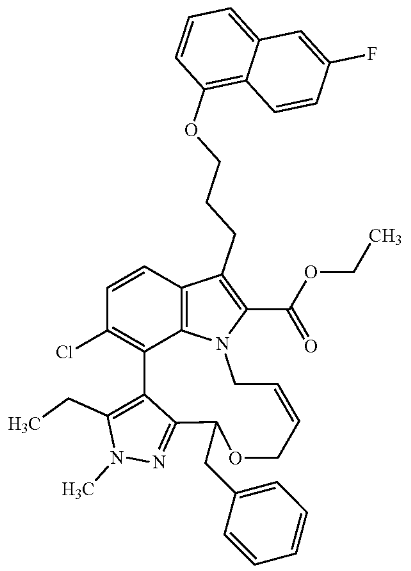 [SMILES: CCOC(=O)c1c(CCCOc2cccc3cc(F)ccc23)c2ccc(Cl)c3c2n1C/C=C\COC(Cc1ccccc1)c1nn(C)c(CC)c1-3]

To a solution of (rac)-ethyl 6-chloro-7-[5-ethyl-3-(1-hydroxy-2-phenylethyl)-1-methyl-1H-pyrazol-4-yl]-3-{3-[(6-fluoronaphthalen-1-yl)oxy]propyl}-1H-indole-2-carboxylate (see Intermediate 188, 0.5 g, 764 µmol) in nitrogen degassed anhydrous acetonitrile (8 mL) was added cesium carbonate (1.24 g, 3.81 mmol). After stirring for 10 minutes, (2Z)-1,4-dichlorobut-2-ene (87.5 µL, 840 µmol) was added to the mixture and the resulting suspension was heated at 40° C. for 2 days. The mixture was cooled to room temperature, filtered through a plug of Celite, and concentrated. The residue was purified by flash chromatography on silica gel (0-100% acetone/dichloromethane) to give the title compound (0.45 g) as an apparent mixture of isomers, which was carried forward without further purification.

$^1$H NMR (300 MHz, Chloroform-d) δ 8.36 (dd, 4H), 7.69-7.54 (m, 3H), 7.49-7.31 (m, 11H), 7.26 (s, 21H), 7.24-7.02 (m, 12H), 6.72 (dt, 3H), 6.40 (d, 1H), 6.16-5.84 (m, 2H), 5.70 (dt, 2H), 5.24-4.85 (m, 9H), 4.85-4.44 (m, 5H), 4.44-4.04 (m, 14H), 4.00 (s, 6H), 3.85 (s, 6H), 3.49-3.16 (m, 10H), 3.15-2.88 (m, 3H), 2.30 (dp, 12H), 2.11-2.02 (m, 3H), 1.36 (t, 5H), 1.24 (dt, 7H), 1.10-0.97 (m, 4H), 0.97-0.84 (m, 5H).

Intermediate 190

(rac)-ethyl-(15-rac)-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylate

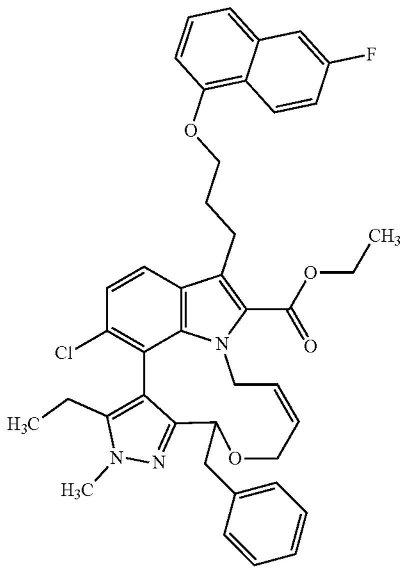 [SMILES: CCOC(=O)c1c(CCCOc2cccc3cc(F)ccc23)c2ccc(Cl)c3c2n1C/C=C\COC(Cc1ccccc1)c1nn(C)c(CC)c1-3]

To a solution of (rac)-ethyl (11Z)-15-benzyl-4-chloro-3-ethyl-7-{3-[(6-fluoro-1-naphthyl)oxy]propyl}-2-methyl-2,10,13,15-tetrahydropyrazolo[4',3':9,10][1,6]oxazacycloundecino[8,7,6-hi]indole-8-carboxylate (see Intermediate 189, 0.313 g, 443 µmol) in ethanol (4.5 mL) was added tris(triphenylphosphine)rhodium(I)-chloride (81.9 mg, 88.6 µmol). The resulting suspension was purged with nitrogen and then placed under a hydrogen atmosphere. After stirring for 24 h, the mixture was sparged with nitrogen and filtered over Celite, washing with ethanol, and concentrated. The residue was redissolved in ethanol (4.5 mL), purged with nitrogen, and treated with 10% palladium on carbon (94.1 mg, 88.6 µmol). The solution was saturated with hydrogen for 5 min and the mixture was kept under an atmosphere of hydrogen for 3 days while stirring. The mixture was filtered over Celite, concentrated, and purified by flash column chromatography on silica gel (0-100% ethyl acetate/hexanes) to obtain the title compound (0.214 g) as a 1.6:1 mixture of isomers.

Isomer 1: LC-MS (Method 5): $R_t$=6.22 min; MS (ESIpos): m/z=709 $[M+H]^+$

Isomer 2: LC-MS (Method 5): $R_t$=6.49 min; MS (ESIpos): m/z=709 $[M+H]^+$ $^1$H NMR (300 MHz, Chloroform-d) δ 8.35 (dt, 1H), 7.59 (dd, 1H), 7.50-7.29 (m, 2H), 7.26 (s, 12H), 6.75-6.62 (m, 1H), 4.58 (dd, 1H), 4.42-4.12 (m, 4H), 4.06-3.82 (m, 2H), 3.49-3.13 (m, 5H), 2.44-2.22 (m, 5H), 1.55 (s, 4H), 1.35 (m, 2H), 1.08-0.83 (m, 3H).

Intermediate 191 bromido[2-(oxan-4-yl)ethyl]magnesium

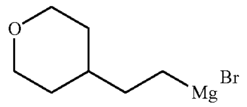

A mixture of magnesium turnings (252 mg, 10.4 mmol) and iodine under an argon atmosphere were stirred for 1 hour, after which tetrahydrofuran (5.0 mL) was added followed by dropwise addition of 4-(2-bromoethyl)oxane (770 μl, 5.2 mmol). The resulting mixture was heated at 65° C. for 2 hours, cooled to room temperature and then used directly in the next step.

Intermediate 192

1-(5-ethyl-1-methyl-1H-pyrazol-3-yl)-3-(oxan-4-yl) propan-1-one

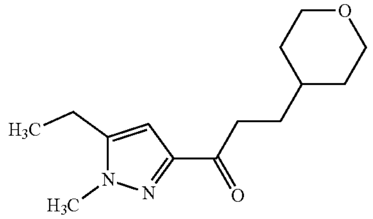

To a 0° C. stirred solution of 5-ethyl-N-methoxy-N,1-dimethyl-1H-pyrazole-3-carboxamide (see Intermediate 121, 511 mg, 2.59 mmol) in tetrahydrofuran (5.4 mL) was added a solution of bromido[2-(oxan-4-yl)ethyl]magnesium in tetrahydrofuran dropwise (see Intermediate 191 1.13 g, 5.18 mmol). The resulting mixture was warmed to room temperature and stirred overnight. Saturated aqueous ammonium chloride was added and and the aqueous layer was extracted with ethyl acetate. The combined organic extracts were washed with brine, dried (magnesium sulfate), filtered and concentrated under reduced pressure. The residue was purified by flash column chromatography (0-100% ethyl acetate/hexanes gradient) to give the title compound as a clear oil (450 mg).

LC-MS (Method 6): $R_t$=1.26 min; MS (ESIpos): m/z=252 $[M+H]^+$

1H-NMR (400 MHz, CHLOROFORM-d) delta [ppm]: 1.266 (0.61), 1.274 (3.95), 1.293 (8.47), 1.312 (4.43), 1.326 (1.15), 1.337 (1.08), 1.357 (0.58), 1.368 (0.57), 1.531 (0.41), 1.548 (0.46), 1.558 (0.53), 1.568 (0.43), 1.576 (0.42), 1.640 (1.47), 1.645 (1.38), 1.659 (1.47), 1.677 (3.44), 1.696 (2.30), 1.714 (0.98), 2.595 (1.00), 2.633 (2.85), 2.651 (0.93), 2.976 (2.38), 2.996 (3.29), 3.014 (2.25), 3.330 (1.05), 3.335 (1.12), 3.360 (2.08), 3.364 (2.10), 3.389 (1.20), 3.393 (1.18), 3.840 (16.00), 3.934 (1.23), 3.944 (1.22), 3.962 (1.14), 3.971 (1.09), 6.565 (3.51).

Intermediate 193

(rac)-1-(5-ethyl-1-methyl-1H-pyrazol-3-yl)-3-(oxan-4-yl)propan-1-ol

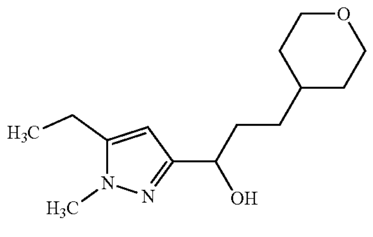 [SMILES: CCc1cc(C(O)CCC2CCOCC2)nn1C]

To a stirred solution of 1-(5-ethyl-1-methyl-1H-pyrazol-3-yl)-3-(oxan-4-yl)propan-1-one (see Intermediate 192, 400 mg, 1.60 mmol) in methanol (3.5 mL) was added sodium borohydride (242 mg, 6.39 mmol). The resulting mixture was stirred at room temperature overnight and then concentrated under reduced pressure. Water was added to the residue and extracted with ethyl acetate. The combined organic extracts were washed with brine, dried (magnesium sulfate), filtered and concentrated under reduced pressure. The residue was purified by flash column chromatography (0-100% ethyl acetate/hexanes gradient) to give the title compound (320 mg).

LC-MS (Method 6): $R_t$=1.10 min; MS (ESIpos): m/z=253 $[M+H]^+$

1H-NMR (400 MHz, CHLOROFORM-d) delta [ppm]: 1.231 (0.42), 1.254 (4.13), 1.272 (9.04), 1.291 (5.31), 1.303 (1.62), 1.312 (0.66), 1.322 (1.23), 1.328 (0.85), 1.338 (0.60), 1.344 (0.65), 1.359 (0.28), 1.414 (0.28), 1.432 (0.70), 1.449 (0.63), 1.454 (0.77), 1.464 (0.53), 1.471 (0.88), 1.479 (0.74), 1.488 (0.74), 1.499 (0.69), 1.514 (0.56), 1.524 (0.47), 1.531 (0.33), 1.541 (0.31), 1.551 (0.23), 1.602 (1.58), 1.637 (1.39), 1.699 (0.18), 1.761 (0.18), 1.781 (0.72), 1.786 (0.68), 1.804 (1.66), 1.813 (0.94), 1.821 (1.85), 1.826 (0.93), 1.839 (0.67), 1.842 (0.67), 2.052 (0.52), 2.231 (0.34), 2.566 (1.17), 2.585 (3.40), 2.604 (3.30), 3.337 (1.13), 3.366 (2.24), 3.392 (1.20), 3.744 (16.00), 3.927 (1.39), 3.937 (1.36), 3.954 (1.29), 3.964 (1.22), 4.661 (0.84), 4.677 (1.42), 4.693 (0.83), 5.964 (4.01).

Intermediate 194

(rac)-1-(5-ethyl-4-iodo-1-methyl-1H-pyrazol-3-yl)-3-(oxan-4-yl)propan-1-ol

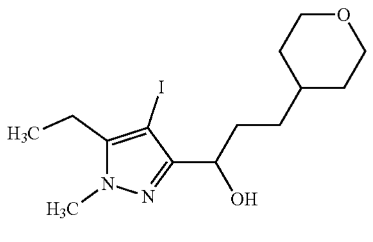 [SMILES: CCc1c(I)c(C(O)CCC2CCOCC2)nn1C]

To a stirred solution of (rac)-1-(5-ethyl-1-methyl-1H-pyrazol-3-yl)-3-(oxan-4-yl)propan-1-ol (see Intermediate 193, 3.10 g, 12.3 mmol) in acetonitrile (40.0 mL) was added trifluoroacetic acid (142 μl, 1.8 mmol) followed by N-iodosuccinimide (2.90 g, 12.9 mmol). The resulting mixture was stirred at room temperature for 30 min. 150 mL Water was added and the aqueous layer was extracted with ethyl acetate. The combined organic extracts were washed with brine, dried (magnesium sulfate), filtered and concentrated under reduced pressure. The residue was purified by flash column chromatography (70-100% ethyl acetate/hexanes gradient) to give the title compound as a colourless oil (3.60 g).

LC-MS (Method 6): $R_t$=1.27 min; MS (ESIpos): m/z=379 $[M+H]^+$ $^1$H-NMR (400 MHz, CHLOROFORM-d) δ [ppm]: 1.144 (3.46), 1.163 (7.45), 1.182 (3.68), 1.222 (0.22), 1.234 (0.33), 1.247 (1.00), 1.264 (2.08), 1.282 (1.52), 1.296 (1.20), 1.308 (0.86), 1.312 (0.94), 1.325 (0.89), 1.330 (0.77), 1.339 (0.75), 1.356 (0.64), 1.371 (0.30), 1.405 (0.26), 1.418 (0.37), 1.422 (0.41), 1.435 (0.52), 1.444 (0.41), 1.449 (0.55), 1.455 (0.37), 1.461 (0.54), 1.467 (0.40), 1.481 (0.55), 1.494 (0.58), 1.505 (0.50), 1.513 (0.43), 1.522 (0.52), 1.531 (0.43), 1.539 (0.29), 1.549 (0.29), 1.559 (0.18), 1.605 (0.78), 1.609 (0.88), 1.614 (0.97), 1.620 (0.90), 1.624 (0.81), 1.630 (0.80), 1.636 (0.76), 1.641 (0.76), 1.647 (0.80), 1.652 (0.72), 1.787 (0.18), 1.799 (0.21), 1.807 (0.20), 1.813 (0.23), 1.820 (0.55), 1.826 (0.27), 1.833 (0.56), 1.841 (0.51), 1.847 (0.61), 1.853 (0.50), 1.860 (0.44), 1.867 (0.54), 1.870 (0.50), 1.880 (0.54), 1.884 (0.79), 1.897 (0.73), 1.904 (0.35), 1.910 (0.63), 1.918 (0.40), 1.924 (0.44), 1.931 (0.35), 1.944 (0.29), 1.958 (0.16), 2.049 (2.48), 2.659 (1.18), 2.678 (3.51), 2.697 (3.39), 2.716 (1.05), 3.333 (0.98), 3.337 (1.04), 3.362 (2.00), 3.366 (1.99), 3.391 (1.12), 3.395 (1.02), 3.803 (0.25), 3.847 (16.00), 3.926 (1.24), 3.934 (1.24), 3.954 (1.14), 3.962 (1.10), 4.100 (0.20), 4.118 (0.58), 4.136 (0.57), 4.154 (0.19), 4.641 (1.03), 4.654 (1.18), 4.661 (1.09), 4.673 (1.00).

Intermediate 195 ethyl 6-chloro-7-{5-ethyl-3-[(1rac)-1-hydroxy-3-(oxan-4-yl)propyl]-1-methyl-1H-pyrazol-4-yl}-3-{3-[(6-fluoronaphthalen-1-yl)oxy]propyl}-1H-indole-2-carboxylate

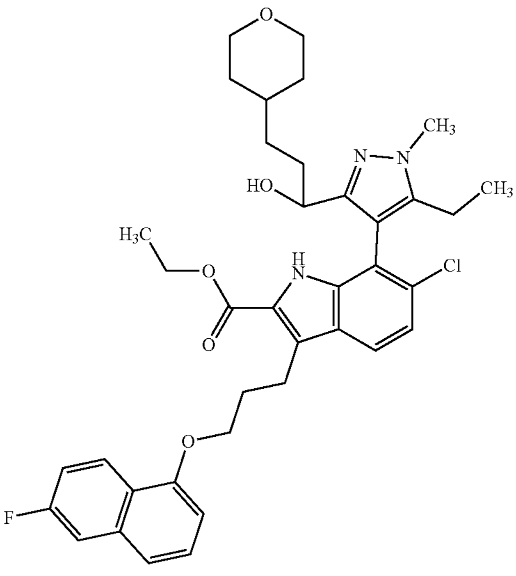 [SMILES: CCOC(=O)c1[nH]c2c(-c3c(C(O)CCC4CCOCC4)nn(C)c3CC)c(Cl)ccc2c1CCCOc1cccc2cc(F)ccc12]

To a solution of ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 4.38 g, 7.93 mmol) and (rac)-1-(5-ethyl-4-iodo-1-methyl-1H-pyrazol-3-yl)-3-(oxan-4-yl)propan-1-ol (see Intermediate 194, 3.60 g, 9.52 mmol) in 1,4-dioxane (32.0 mL) was added RuPhos Pd G3 (332 mg, 397 μmol) followed by 1.0 M aqueous tripotassium phosphate (16 mL, 16 mmol). The mixture was sparged with argon for 5 minutes and then transferred to a 80° C. preheated block and stirred at 80° C. for 17 hours. The mixture was concentrated under reduced pressure and then dry loaded onto celite. The residue was purified by reverse phase column chromatography (55-100% acetonitrile/water buffered with 0.1% formic acid) and then flash column chromatography (0-40% methanol/dichloromethane gradient) to give the title compound (2.00 g) which was formed as a mixture of two racemic diastereomers as a result of atropisomerism at the newly formed bi-heteroaryl bond.

LC-MS (Method 6): $R_t$=1.76 min; MS (ESIneg): m/z=674 $[M-H]^-$

Intermediate 196 ethyl 6-chloro-7-{5-ethyl-1-methyl-3-[(1rac)-1-(methylamino)-3-(oxan-4-yl)propyl]-1H-pyrazol-4-yl}-3-{3-[(6-fluoronaphthalen-1-yl)oxy]propyl}-1H-indole-2-carboxylate

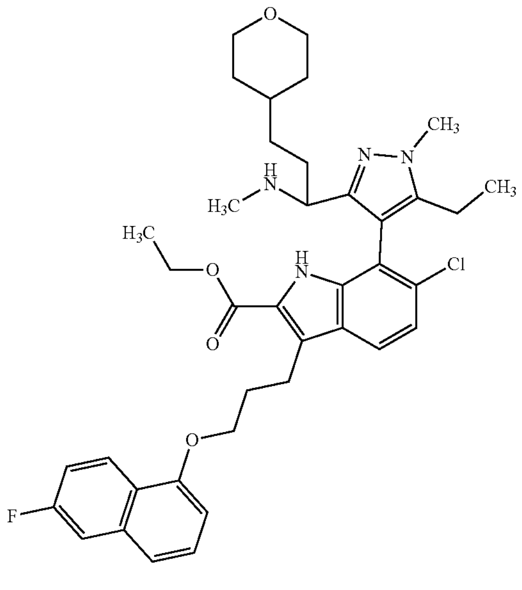 [SMILES: CCOC(=O)c1[nH]c2c(-c3c(C(CCC4CCOCC4)NC)nn(C)c3CC)c(Cl)ccc2c1CCCOc1cccc2cc(F)ccc12]

To a 0° C. stirred solution of ethyl 6-chloro-7-{5-ethyl-3-[(1rac)-1-hydroxy-3-(oxan-4-yl)propyl]-1-methyl-1H-pyrazol-4-yl}-3-{3-[(6-fluoronaphthalen-1-yl)oxy]propyl}-1H-indole-2-carboxylate (see Intermediate 195, 1.00 g, 1.48 mmol) in dichloromethane (12.0 mL) was added N,N-diisopropylethylamine (520 μl, 3.0 mmol) and methanesulfonyl chloride (150 μl, 1.9 mmol). The resulting mixture was warmed to room temperature, stirred overnight and then concentrated under reduced pressure. The residue was redissolved in acetonitrile (7.4 mL), after which a 2.0 M solution of methylamine in tetrahydrofuran (7.4 mL, 15 mmol) was added and the resulting mixture was heated at 60° C. over night. A 1:1 mixture of brine/saturated aqueous sodium carbonate solution was added and the aqueous layer was extracted with dichloromethane. The combined organic extracts were washed with brine, dried (magnesium sulfate, filtered and concentrated under reduced pressure. The residue was purified by flash column chromatography (0-20% methanol/dichloromethane gradient) to give the title compound (270 mg).

LC-MS (Method 6): $R_t$=1.39 min; MS (ESIpos): m/z=692 $[M+H]^+$

Intermediate 197

(rac)-ethyl 7-[3-[1-[tert-butoxycarbonyl(methyl)amino]-3-tetrahydropyran-4-yl-propyl]-5-ethyl-1-methyl-pyrazol-4-yl]-6-chloro-3-[3-[(6-fluoro-1-naphthyl)oxy]propyl]-1H-indole-2-carboxylate

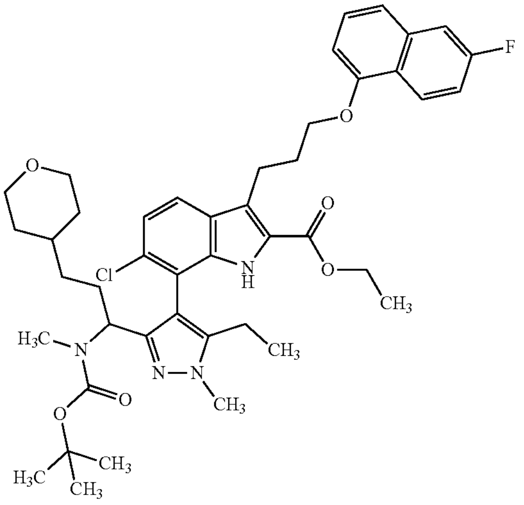 [SMILES: CCOC(=O)c1[nH]c2c(-c3c(C(CCC4CCOCC4)N(C)C(=O)OC(C)(C)C)nn(C)c3CC)c(Cl)ccc2c1CCCOc1cccc2cc(F)ccc12]

To a 0° C. stirred solution of ethyl 6-chloro-7-{5-ethyl-3-[(1rac)-1-hydroxy-3-(oxan-4-yl)propyl]-1-methyl-1H-pyrazol-4-yl}-3-{3-[(6-fluoronaphthalen-1-yl)oxy]propyl}-1H-indole-2-carboxylate (see Intermediate 196, 270 mg, 0.39 mmol, 1.00 eq.) and triethylamine (109 μL, 0.78 mmol, 2.00 eq.) in anhydrous dichloromethane (3.91 mL, 0.10 M) was added di-tert-butyl dicarbonate (94.0 mg, 0.43 mmol, 1.10 eq.) in one portion. The resulting light yellow solution was warmed to room temperature and stirred for 3 hours. The mixture was diluted with water (15 mL) and then extracted with dichlormethane (3×15 mL). The combined organic extracts were washed with water (15 mL), dried (magnesium sulfate), filtered and concentrated under reduced pressure. The residue was dry loaded onto Celite and then purified by flash column chromatography (0-60% acetone/dichloromethane gradient) to give a ~3:2 diastereomeric mixture of title compound as a white solid (261 mg).

LC-MS (Method 8): Major Rt=4.02 min; MS (ESIneg): m/z=787 $[M-H]^-$; Minor Rt=4.12 min; MS (ESIneg): m/z=787 $[M-H]^-$ 1H NMR (400 MHz, Chloroform-d) δ 8.41-8.28 (m, 2H), 7.63-7.48 (m, 1H), 7.45-7.31 (m, 3H), 7.31-7.06 (m, 6H), 6.81-6.68 (m, 1H), 5.18-4.70 (m, 1H), 4.54-4.24 (m, 2H), 4.27-4.14 (m, 2H), 4.03-3.84 (m, 3H), 3.52-3.17 (m, 2H), 2.73-2.21 (m, 5H), 2.11-1.78 (m, 1H), 1.64-1.28 (m, 13H), 1.30-0.83 (m, 16H).

Intermediate 198

(rac)-ethyl 7-[3-[1-[tert-butoxycarbonyl(methyl)amino]-3-tetrahydropyran-4-yl-propyl]-5-ethyl-1-methyl-pyrazol-4-yl]-6-chloro-1-[(E)-4-chlorobut-2-enyl]-3-[3-[(6-fluoro-1-naphthyl)oxy]propyl]indole-2-carboxylate

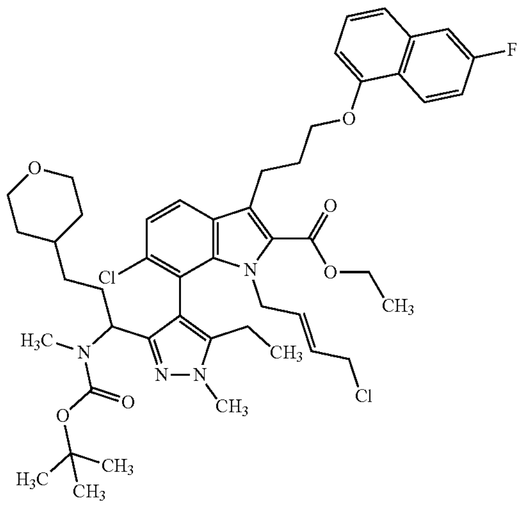 [SMILES: CCOC(=O)c1c(CCCOc2cccc3cc(F)ccc23)c2ccc(Cl)c(-c3c(C(CCC4CCOCC4)N(C)C(=O)OC(C)(C)C)nn(C)c3CC)c2n1C/C=C/CCl]

To a room temperature stirred suspension of (rac)-ethyl 7-[3-[1-[tert-butoxycarbonyl(methyl)amino]-3-tetrahydropyran-4-yl-propyl]-5-ethyl-1-methyl-pyrazol-4-yl]-6-chloro-3-[3-[(6-fluoro-1-naphthyl)oxy]propyl]-1H-indole-2-carboxylate (see Intermediate 197, 261 mg, 0.33 mmol, 1.00 eq.) and cesium carbonate (430 mg, 1.32 mmol, 4.00 eq.) in anhydrous acetonitrile (6.61 mL, 0.05 M) was added cis-1,4-dichloro-2-butene (69.5 μL, 0.66 mmol, 2.00 eq.) in one portion. The resulting yellow suspension was stirred at room temperature for 15 hours, filtered (washing with acetonitrile) and then concentrated under reduced pressure. The residue was dry loaded onto Celite and then purified by flash column chromatography (0-40% acetone/dichloromethane gradient) to give a ~3:2 diastereomeric mixture of title compound as a white solid (269 mg)

LC-MS (Method 8): Major Rt=4.22 min; MS (ESIpos): m/z=877 $[M+H]^+$; Minor Rt=4.29 min; MS (ESIneg): m/z=878 $[M+H]^+$ 1H NMR (400 MHz, Chloroform-d) δ 8.41-8.28 (m, 1H), 7.67-7.51 (m, 1H), 7.48-7.32 (m, 4H), 7.26 (s, 7H), 6.79-6.68 (m, 1H), 5.56-5.35 (m, 1H), 5.33-5.12 (m, 1H), 5.06-4.94 (m, 2H), 4.94-4.68 (m, 2H), 4.37-4.25 (m, 2H), 4.26-4.17 (m, 2H), 4.00-3.77 (m, 7H), 3.39-3.22 (m, 5H), 2.81-2.71 (m, 1H), 2.66-2.50 (m, 2H), 2.50-2.17 (m, 4H), 2.15-1.96 (m, 1H), 1.94-1.73 (m, 2H), 1.68-1.39 (m, 12H), 1.39-1.29 (m, 3H), 1.20 (d, J=39.0 Hz, 7H), 1.09-0.98 (m, 2H), 0.99-0.90 (m, 5H), 0.88-0.78 (m, 2H).

Intermediate 199

(rac)-ethyl (11Z)-4-chloro-3-ethyl-7-{3-[(6-fluoro-1-naphthyl)oxy]propyl}-2,14-dimethyl-(15-rac)-[2-(tetrahydro-2H-pyran-4-yl)ethyl]-10,13,14,15-tetrahydro-2H-pyrazolo[3',4':8,9][1,6]diazacycloundecino[10,11,1-hi]indole-8-carboxylate

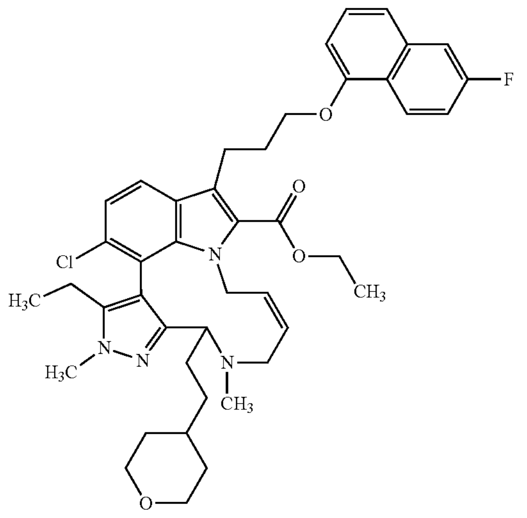 [SMILES: CCOC(=O)c1c(CCCOc2cccc3cc(F)ccc23)c2ccc(Cl)c3c2n1C/C=C\CN(C)C(CCC1CCOCC1)c1nn(C)c(CC)c1-3]

To a room temperature stirred solution of (rac)-ethyl 7-[3-[1-[tert-butoxycarbonyl(methyl)amino]-3-tetrahydropyran-4-yl-propyl]-5-ethyl-1-methyl-pyrazol-4-yl]-6-chloro-1-[(E)-4-chlorobut-2-enyl]-3-[3-[(6-fluoro-1-naphthyl)oxy]propyl]indole-2-carboxylate (see Intermediate 198, 266 mg, 0.30 mmol, 1.00 eq.) in anhydrous dichloromethane (6.05 mL, 0.05 M) was added trifluoroacetic acid dropwise (691 µL, 9.08 mmol, 30.0 eq.). The resulting mixture was stirred at room temperature for 4 hours and then concentrated under reduced pressure. The residue was resuspended in anhydrous acetonitrile (6.05 mL, 0.05 M), after which N,N-diisopropylethylamine (789 µL, 4.54 mmol, 15.0 eq.) was added. The resulting light yellow solution was stirred at room temperature for 2 days and then concentrated under reduced pressure. The residue was diluted with saturated aqueous sodium bicarbonate (20 mL) and extracted with dichloromethane (3×20 mL). The combined organic extracts were washed with water (20 mL), dried (magnesium sulfate), filtered and concentrated under reduced pressure. The residue was resuspended in dimethyl sulfoxide and purified by preparative reverse phase column chromatography (30×150, 5 uM Xbridge C18 column, 10-100% acetonitrile/water gradient buffered with 0.1% formic acid) to give a ~7:3 diastereomeric mixture of title compound as a white solid (184 mg).

LC-MS (Method 8): Major Rt=2.80 min; MS (ESIpos): m/z=741 $[M+H]^+$; Minor Rt=2.86 min; MS (ESIneg): m/z=741 $[M+H]^+$ 1H NMR (400 MHz, Chloroform-d) δ 8.42-8.26 (m, 2H), 7.69-7.55 (m, 1H), 7.46-7.32 (m, 3H), 7.29-7.21 (m, 4H), 7.21-7.09 (m, 1H), 6.78-6.66 (m, 1H), 5.82-5.70 (m, 1H), 5.66-5.44 (m, 1H), 5.16-5.05 (m, 1H), 5.03-4.92 (m, 1H), 4.91-4.79 (m, 1H), 4.62-4.49 (m, 1H), 4.44-4.26 (m, 2H), 4.25-3.01 (m, 20H), 2.92-2.77 (m, 1H), 2.70-2.46 (m, 2H), 2.41-1.97 (m, 5H), 1.77-1.03 (m, 12H), 1.00-0.81 (m, 3H).

Intermediate 200

(rac)-ethyl 4-chloro-3-ethyl-7-{3-[(6-fluoro-1-naphthyl)oxy]propyl}-2,14-dimethyl-(15-rac)-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylate

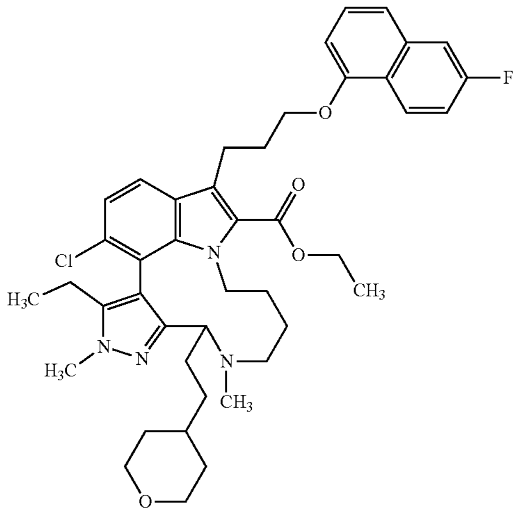 [SMILES: CCOC(=O)c1c(CCCOc2cccc3cc(F)ccc23)c2ccc(Cl)c3c2n1CCCCN(C)C(CCC1CCOCC1)c1nn(C)c(CC)c1-3]

To a stirred solution of (rac)- ethyl (11Z)-4-chloro-3-ethyl-7-{3-[(6-fluoro-1-naphthyl)oxy]propyl}-2,14-dimethyl-15-[2-(tetrahydro-2H-pyran-4-yl)ethyl]-10,13,14,15-tetrahydro-2H-pyrazolo[3',4':8,9][1,6]diazacycloundecino[10,11,1-hi]indole-8-carboxylate (see Intermediate 199, 181 mg, 0.24 mmol, 1.00 eq.) in absolute ethanol (4.88 mL, 0.05 M) was added, tris(triphenylphosphine)rhodium(I)-chloride (112 mg, 0.12 mmol, 0.50 eq.). The resulting dark suspension was evacuated and then placed under a hydrogen atmosphere, after which the mixture was stirred at room temperature for 21 hours. Following complete reduction, the mixture was sparged with nitrogen to remove any residual hydrogen, filtered through a Celite plug and concentrated under reduced pressure. The residue was dry loaded onto Celite and then purified by flash reverse phase column chromatography (50-100% acetonitrile/water gradient buffered with 0.1% formic acid) to give a ~7:3 diastereomeric mixture of title compound as a orange solid (123 mg).

LC-MS (Method 8): Rt=2.81 min; MS (ESIpos): m/z=743 $[M+H]^+$

1H NMR (400 MHz, Chloroform-d) δ 8.44-8.34 (m, 1H), 8.26 (s, 1H), 7.70-7.58 (m, 1H), 7.49-7.35 (m, 3H), 7.20-7.16 (m, 1H), 6.83-6.70 (m, 1H), 4.47-4.14 (m, 5H), 4.02-3.84 (m, 6H), 3.49-3.20 (m, 4H), 2.62-1.83 (m, 16H), 1.82-1.43 (m, 7H), 1.41-1.13 (m, 9H), 1.01-0.88 (m, 3H).

Intermediate 201

Ethyl (11Z,15rac)-4-chloro-3-ethyl-7-{3-[(6-fluoronaphthalen-1-yl)oxy]propyl}-2-methyl-(15-rac)-[2-(oxan-4-yl)ethyl]-2,10,13,15-tetrahydropyrazolo[4',3':9,10][1,6]oxazacycloundecino[8,7,6-hi]indole-8-carboxylate

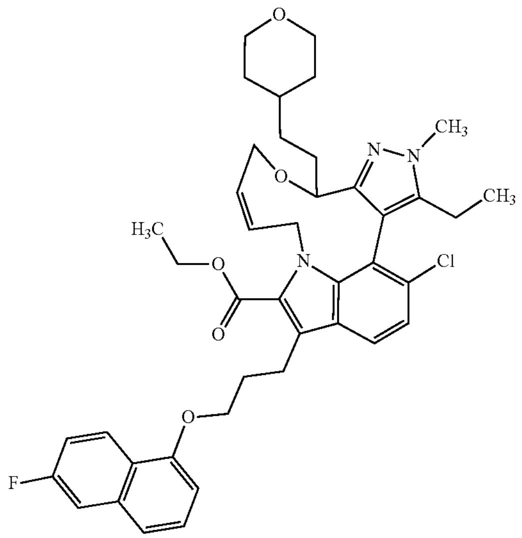 [SMILES: CCOC(=O)c1c(CCCOc2cccc3cc(F)ccc23)c2ccc(Cl)c3c2n1C/C=C\COC(CCC1CCOCC1)c1nn(C)c(CC)c1-3]

To a stirred solution of ethyl 6-chloro-7-{5-ethyl-3-[(1rac)-1-hydroxy-3-(oxan-4-yl)propyl]-1-methyl-1H-pyrazol-4-yl}-3-{3-[(6-fluoronaphthalen-1-yl)oxy]propyl}-1H-indole-2-carboxylate (see Intermediate 195, 750 mg, 1.11 mmol) in acetonitrile (9.60 mL) was added cesium carbonate (1.81 g, 5.55 mmol). After stirring for 10 minutes, (2Z)-1,4-dichlorobut-2-ene (230 μl, 2.2 mmol) and sodium iodide (332 mg, 2.22 mmol) were added and the resulting mixture was heated at 70° C. for 19 hours. Water was added and the aqueous layer was extracted with ethyl acetate. The combined organic extracts were washed with brine, dried (magnesium sulfate), filtered and concentrated under reduced pressure. The residue was purified by flash column chromatography (0-15% methanol/dichloromethane gradient) and then reverse phase column chromatography (50-100% acetonitrile/water gradient buffered with 0.1% formic acid) to give the title compound (240 mg).

LC-MS (Method 7): $R_t$=1.17 min; MS (ESIpos): m/z=730 $[M+H]^+$

1H-NMR (300 MHz, CHLOROFORM-d) delta [ppm]: 0.811 (0.94), 0.837 (2.20), 0.862 (0.89), 1.130 (0.32), 1.174 (0.49), 1.184 (0.48), 1.213 (0.39), 1.280 (1.56), 1.304 (2.99), 1.327 (1.44), 1.462 (0.44), 1.505 (0.40), 1.936 (3.45), 2.165 (0.78), 2.190 (0.72), 2.245 (0.36), 2.266 (0.47), 2.571 (1.82), 3.217 (0.40), 3.239 (0.46), 3.270 (0.69), 3.296 (0.48), 3.803 (0.73), 3.817 (0.61), 3.838 (0.40), 3.882 (0.40), 3.913 (4.82), 4.129 (0.56), 4.149 (1.04), 4.170 (0.43), 4.239 (0.38), 4.258 (0.70), 4.269 (0.45), 4.280 (1.04), 4.304 (0.60), 5.013 (0.48), 6.642 (0.38), 6.650 (0.32), 6.663 (0.41), 6.671 (0.38), 7.120 (0.95), 7.139 (0.32), 7.149 (1.25), 7.169 (0.55), 7.177 (0.70), 7.190 (16.00), 7.312 (0.62), 7.329 (0.49), 7.338 (0.50), 7.362 (0.47), 7.370 (0.40), 7.538 (0.97), 7.566 (0.84), 7.957 (2.53), 8.225 (0.39), 8.244 (0.40), 8.256 (0.38), 8.274 (0.35).

Intermediate 202

Ethyl (rac)-4-chloro-3-ethyl-7-{3-[(6-fluoronaphthalen-1-yl)oxy]propyl}-2-methyl-(15-rac)-[2-(oxan-4-yl)ethyl]-2,10,11,12,13,15-hexahydropyrazolo[4',3':9,10][1,6]oxazacycloundecino[8,7,6-hi]indole-8-carboxylate

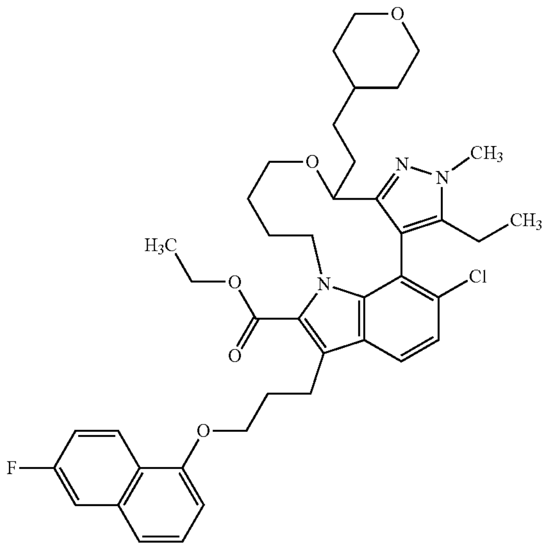 [SMILES: CCOC(=O)c1c(CCCOc2cccc3cc(F)ccc23)c2ccc(Cl)c3c2n1CCCCOC(CCC1CCOCC1)c1nn(C)c(CC)c1-3]

To a stirred solution of ethyl (11Z,15rac)-4-chloro-3-ethyl-7-{3-[(6-fluoronaphthalen-1-yl)oxy]propyl}-2-methyl-(15-rac)-[2-(oxan-4-yl)ethyl]-2,10,13,15-tetrahydropyrazolo[4',3':9,10][1,6]oxazacycloundecino[8,7,6-hi]indole-8-carboxylate (see Intermediate 201, 240 mg, 330 μmol) in ethanol (5.00 mL) was added tris(triphenylphosphine)rhodium(I)-chloride (153 mg, 165 μmol). The mixture was placed under a hydrogen atmosphere and stirred for 24 hours. The mixture was dry loaded onto Celite and then purified by flash column chromatography (0-50% methanol/dichloromethane gradient) followed by reverse phase column chromatography (0-100% acetonitrile/water gradient buffered with 0.1% formic acid) to give the title compound as a brown oil (160 mg).

LC-MS (Method 5): $R_t$=1.86 min; MS (ESIpos): m/z=733 $[M+H]^+$

1H-NMR (400 MHz, CHLOROFORM-d) delta [ppm]: 0.903 (3.73), 0.922 (7.43), 0.941 (3.63), 1.126 (1.77), 1.276 (2.49), 1.306 (2.60), 1.340 (2.94), 1.356 (6.35), 1.374 (9.70), 1.392 (5.84), 1.515 (1.07), 1.610 (1.59), 1.640 (2.66), 1.671 (1.26), 2.036 (1.35), 2.054 (2.61), 2.073 (2.39), 2.265 (2.82), 2.285 (3.06), 2.303 (2.39), 2.319 (2.36), 3.235 (1.16), 3.260 (1.24), 3.282 (1.05), 3.300 (1.28), 3.325 (2.67), 3.356 (4.44), 3.383 (2.93), 3.419 (1.50), 3.448 (1.01), 3.943 (16.00), 4.086 (0.97), 4.103 (1.15), 4.121 (1.27), 4.139 (0.71), 4.196 (3.75), 4.287 (0.83), 4.314 (1.66), 4.332 (1.85), 4.354 (3.21), 4.368 (4.50), 4.383 (2.94), 4.400 (1.69), 5.309 (4.92), 6.710 (1.97), 6.724 (2.13), 7.174 (2.54), 7.195 (2.78), 7.236 (1.14), 7.365 (6.18), 7.381 (2.52), 7.409 (2.15), 7.435 (1.99), 7.598 (2.72), 7.620 (2.47), 8.029 (0.77), 8.318 (1.31), 8.340 (1.62), 8.356 (1.34).

Intermediate 203

1-(4-bromo-5-ethyl-1-methyl-1H-pyrazol-3-yl)-3-(3-fluoroazetidin-1-yl)propan-1-one

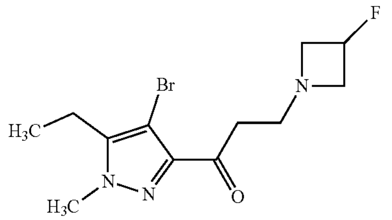 [SMILES: CCc1c(Br)c(C(=O)CCN2CC(F)C2)nn1C]

3-Fluoroazetidine-hydrogen chloride (1/1) (4.85 g, 43.4 mmol) as dissolved in 25 mL THF and cooled to 2° C. with an ice bath. 1-(4-Bromo-5-ethyl-1-methyl-1H-pyrazol-3-yl) prop-2-en-1-one (see Intermediate 91, 2.64 g, 10.9 mmol) was added dropwise and the reaction mixture was stirred for 1 h with ice bath cooling. Water and ethyl acetate were added, the aqueous layer was extracted with ethyl acetate thrice. The combined organic layers were washed with brine, filtered through a water resistant filter and concentrated under reduced pressure. The crude product was purified by chromatography (Isolera, 50 g ultra snap column, hexane/ethyl acetate, at 100 ethyl acetate 5-7% ethanol addition) to provide the 95% pure target compound: 2.38 g, 65 yield.

LC-MS (Method 2): $R_t$=1.02 min; MS (ESIpos): m/z=318 $[M+H]^+$ $^1$H-NMR (400 MHz, DMSO-d6) δ[ppm]: 1.076 (3.16), 1.095 (7.07), 1.114 (3.21), 1.988 (0.67), 2.669 (1.13), 2.687 (3.07), 2.706 (3.02), 2.725 (1.99), 2.741 (3.43), 2.758 (2.09), 2.880 (2.24), 2.897 (3.48), 2.915 (1.26), 2.987 (0.82), 2.992 (0.49), 2.999 (0.92), 3.005 (0.75), 3.011 (0.97), 3.017 (0.53), 3.022 (0.98), 3.047 (0.87), 3.052 (0.50), 3.058 (0.91), 3.065 (0.74), 3.071 (0.97), 3.077 (0.51), 3.083 (0.91), 3.474 (0.89), 3.479 (0.51), 3.488 (1.04), 3.493 (0.90), 3.498 (0.93), 3.507 (0.57), 3.513 (1.59), 3.518 (0.59), 3.527 (1.01), 3.532 (0.89), 3.537 (0.95), 3.546 (0.48), 3.551 (0.83), 3.918 (16.00), 5.004 (0.41), 5.016 (0.66), 5.148 (0.41), 5.161 (0.66), 5.174 (0.41).

Intermediate 204

(1-rac)-1-(4-bromo-5-ethyl-1-methyl-1H-pyrazol-3-yl)-3-(3-fluoroazetidin-1-yl)propan-1-ol

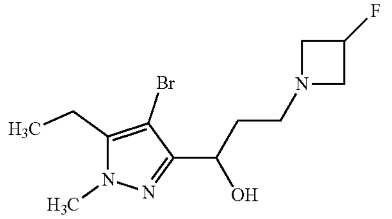

1-(4-Bromo-5-ethyl-1-methyl-1H-pyrazol-3-yl)-3-(3-fluoroazetidin-1-yl)propan-1-one (see Intermediate 203, 2.38 g, 7.48 mmol) was dissolved in 10 mL methanol. Sodium borohydride (1.13 g, 29.9 mmol) was added portionwise and the reaction mixture was stirred for 92 h at rt. Water was added and the reaction mixture was concentrated under reduced pressure. The aqueous layer was extracted with ethyl acetate thrice. The collected organic layers were washed with brine, filtered through a water resistant filter and concentrated under reduced pressure. The 95% pure crude product was used without further purification: 2.32 g, 92% yield.

LC-MS (Method 2): $R_t$=0.92 min; MS (ESIpos): m/z=320 $[M+H]^+$ $^1$H-NMR (400 MHz, DMSO-d6) δ[ppm]: 1.058 (2.67), 1.067 (1.20), 1.077 (6.63), 1.086 (2.55), 1.096 (2.78), 1.104 (1.08), 1.154 (1.22), 1.172 (2.63), 1.190 (1.37), 1.655 (0.47), 1.675 (0.67), 1.689 (0.58), 1.745 (0.53), 1.761 (0.48), 1.765 (0.55), 1.782 (0.44), 1.987 (4.99), 2.433 (1.27), 2.452 (2.27), 2.469 (1.17), 2.518 (0.89), 2.522 (0.56), 2.598 (0.77), 2.617 (2.68), 2.636 (2.71), 2.652 (1.05), 2.949 (0.59), 2.960 (0.68), 2.972 (0.70), 3.008 (0.64), 3.020 (0.71), 3.032 (0.66), 3.043 (0.46), 3.485 (0.55), 3.487 (0.51), 3.492 (0.41), 3.499 (0.52), 3.502 (0.58), 3.508 (0.53), 3.513 (0.45), 3.517 (0.51), 3.523 (0.59), 3.526 (0.53), 3.533 (0.41), 3.538 (0.51), 3.541 (0.53), 3.747 (16.00), 3.770 (5.45), 3.892 (0.43), 4.017 (1.10), 4.035 (1.11), 4.522 (0.46), 4.531 (0.47), 5.035 (0.43), 5.047 (1.01), 5.058 (0.84), 5.179 (0.51), 5.190 (0.66).

Intermediate 205

4-bromo-5-ethyl-3-[(1-rac)-3-(3-fluoroazetidin-1-yl)-1-(4-{[(2-rac)-oxan-2-yl]oxy}butoxy)propyl]-1-methyl-1H-pyrazole (Mixture of Stereoisomers)

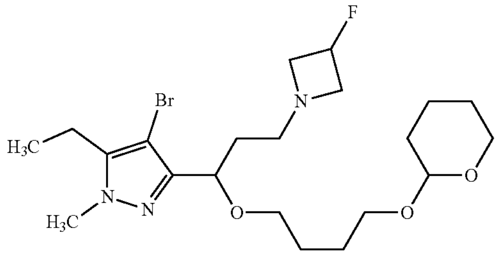 [SMILES: CCc1c(Br)c(C(CCN2CC(F)C2)OCCCCOC2CCCCO2)nn1C]

(1-rac)-1-(4-Bromo-5-ethyl-1-methyl-1H-pyrazol-3-yl)-3-(3-fluoroazetidin-1-yl)propan-1-ol (see Intermediate 204, 1.10 g, 3.44 mmol) was dissolved in 10 mL DMF. Sodium hydride (165 mg, 60% purity in mineral oil, 4.12 mmol) was added and stirred for 2 h at rt. (2-rac)-2-(4-Bromobutoxy) oxane (760 μL, 4.1 mmol) was added and the reaction mixture was stirred for 1 h at rt. Sodium hydride (165 mg, 60% purity in mineral oil, 4.12 mmol) was added and the reaction mixture was stirred for 15 min. Then (2-rac)-2-(4-bromobutoxy)oxane (380 μL, 2.1 mmol) was added and the reaction mixture was stirred for 1 h at rt. Sodium hydride (165 mg, 60% purity in mineral oil, 4.12 mmol) was added and the reaction mixture was stirred for 15 min. Then (2-rac)-2-(4-bromobutoxy)oxane (380 μL, 2.1 mmol) was added and the reaction mixture was stirred for 20 h at rt. Water was added carefully and the reaction mixture was extracted with ethyl acetate thrice. The collected organic layers were washed with brine, filtered through a water resistant filter and concentrated under reduced pressure. The crude product was purified by chromatography (Isolera, column ultra snap, dichloromethane/ethanol) to provide the analytically pure target compound: 1.03 g, 63% yield.

LC-MS (Method 2): $R_t$=1.34 min; MS (ESIpos): m/z=476 $[M+H]^+$ $^1$H-NMR (400 MHz, DMSO-d6) δ[ppm]: 1.066 (2.76), 1.085 (6.69), 1.104 (2.86), 1.407 (0.79), 1.429 (1.83), 1.448 (1.28), 1.463 (1.19), 1.475 (1.74), 1.484 (2.48), 1.489 (2.55), 1.498 (2.26), 1.519 (0.74), 1.549 (0.40), 1.579 (0.49), 1.629 (0.50), 1.644 (0.77), 1.663 (0.95), 1.678 (0.83), 1.696 (0.52), 1.857 (0.52), 1.877 (0.61), 1.891 (0.50), 2.395 (1.39), 2.413 (2.57), 2.430 (1.25), 2.518 (1.48), 2.523 (0.92), 2.608 (0.79), 2.627 (2.61), 2.645 (2.54), 2.664 (0.95), 2.938 (0.47), 2.943 (0.57), 2.950 (0.65), 2.954 (0.66), 2.962 (0.60), 2.966 (0.56), 2.973 (0.43), 2.999 (0.50), 3.003 (0.57), 3.010 (0.65), 3.014 (0.66), 3.022 (0.60), 3.026 (0.52), 3.221 (1.50), 3.226 (1.36), 3.235 (0.96), 3.255 (0.56), 3.263 (0.60), 3.270 (0.53), 3.279 (0.63), 3.287 (0.60), 3.377 (0.60), 3.393 (0.54), 3.406 (0.68), 3.418 (0.43), 3.480 (0.91), 3.487 (0.43), 3.494 (0.99), 3.499 (0.72), 3.518 (1.12), 3.525 (0.54), 3.533 (1.09), 3.537 (1.05), 3.552 (0.91), 3.560 (0.56), 3.576 (0.47), 3.667 (0.43), 3.687 (0.66), 3.694 (0.61), 3.715 (0.43), 3.764 (16.00), 4.305 (0.80), 4.320 (0.98), 4.325 (1.02), 4.340 (0.78), 4.494 (1.08), 4.498 (1.12), 4.509 (0.54), 5.041 (0.58), 5.186 (0.57), 5.758 (0.47).

Intermediate 206

4-[(1-rac)-1-(4-bromo-5-ethyl-1-methyl-1H-pyrazol-3-yl)-3-(3-fluoroazetidin-1-yl)propoxy]butan-1-ol

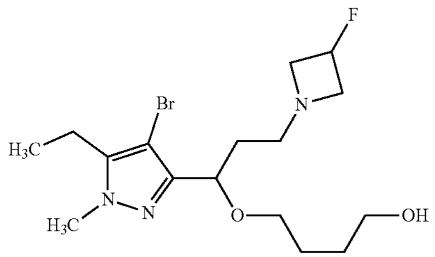 [SMILES: CCc1c(Br)c(C(CCN2CC(F)C2)OCCCCO)nn1C]

4-Bromo-5-ethyl-3-[(1-rac)-3-(3-fluoroazetidin-1-yl)-1-(4-{[(2-rac)-oxan-2-yl]oxy}butoxy)propyl]-1-methyl-1H-pyrazole (see Intermediate 205, 1.03 g, 2.16 mmol) was dissolved in 10 mL ethanol. p-Toluenesulfonic acid monohydrate (411 mg, 2.16 mmol) was added and the reaction mixture was stirred for 23 h at rt. The reaction mixture was concentrated under reduced pressure.

The crude product was purified by chromatography (Isolera, column: amino-phase, dichloromethane/ethanol) to provide the 80% pure target compound: 890 mg, 84% yield.

LC-MS (Method 2): $R_t$=1.00 min; MS (ESIpos): m/z=392 $[M+H]^+$ $^1$H-NMR (400 MHz, DMSO-d6) δ[ppm]: 1.067 (1.15), 1.086 (2.81), 1.105 (1.19), 1.395 (0.40), 1.411 (0.59), 1.417 (0.48), 1.427 (0.64), 1.438 (0.43), 1.444 (0.41), 2.393 (0.53), 2.411 (0.99), 2.429 (0.49), 2.518 (0.41), 2.627 (1.08), 2.646 (1.06), 3.198 (0.51), 3.206 (0.62), 3.494 (0.43), 3.518 (0.42), 3.765 (6.79), 4.314 (0.57), 4.319 (0.55), 4.328 (0.69), 4.334 (0.40), 5.757 (16.00).

Intermediate 207 ethyl 6-chloro-7-{5-ethyl-3-[(1-rac)-3-(3-fluoroazetidin-1-yl)-1-(4-hydroxybutoxy)propyl]-1-methyl-1H-pyrazol-4-yl}-3-{3-[(6-fluoronaphthalen-1-yl)oxy]propyl}-1H-indole-2-carboxylate

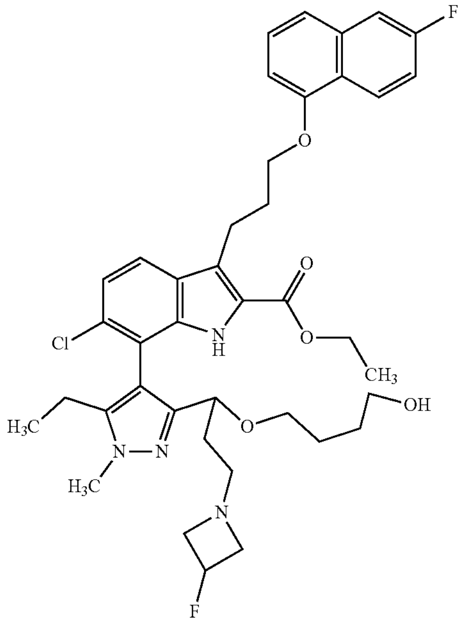 [SMILES: CCOC(=O)c1[nH]c2c(-c3c(C(CCN4CC(F)C4)OCCCCO)nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 52, 1.14 g, 2.06 mmol), 4-[(1-rac)-1-(4-bromo-5-ethyl-1-methyl-1H-pyrazol-3-yl)-3-(3-fluoroazetidin-1-yl)propoxy]butan-1-ol (see Intermediate 206, 890 mg, 2.27 mmol) and tripotassium phosphate (876 mg, 4.12 mmol) were dissolved in 4 mL dioxane and 1 mL water. The suspension was flushed with argon for 5 min. Then RuPhos Pd G3 (94.9 mg, 113 μmol) was added and the reaction mixture was flushed with argon for 5 min, and stirred for 1 h at 110° C. in a microwave oven. Water was added and the aqueous layer was extracted with ethyl acetate thrice. The collected organic layers were washed with brine, dried with a water resistant filter and concentrated under reduced pressure. The crude product was purified by chromatography (Isolera, column: ultra snap, dichloromethane/ethanol) to provide the 85% pure target compound: 606 mg, 34% yield, which was formed as a mixture of two racemic diastereomers as a result of atropisomerism at the newly formed bi-heteroaryl bond.

LC-MS (Method 2): $R_t$=1.65 min; MS (ESIpos): m/z=737 $[M+H]^+$ $^1$H-NMR (400 MHz, DMSO-d6) δ[ppm]: 0.876 (0.44), 0.901 (0.62), 1.067 (1.57), 1.086 (3.79), 1.105 (1.73), 1.159 (0.41), 1.163 (0.73), 1.221 (0.58), 1.239 (1.06), 1.256 (0.52), 1.395 (0.63), 1.401 (0.59), 1.411 (0.93), 1.427 (1.01), 1.438 (0.75), 1.444 (0.75), 1.454 (0.47), 1.460 (0.42), 1.660 (0.42), 2.327 (0.47), 2.393 (0.95), 2.401 (0.58), 2.411 (1.65), 2.428 (0.85), 2.518 (1.57), 2.523 (1.07), 2.608 (0.42), 2.627 (1.41), 2.646 (1.37), 2.665 (0.63), 2.669 (0.49), 2.943 (0.40), 2.950 (0.41), 2.954 (0.44), 3.003 (0.44), 3.010 (0.46), 3.015 (0.49), 3.183 (0.47), 3.190 (0.61), 3.198 (0.88), 3.206 (0.98), 3.221 (0.45), 3.228 (0.42), 3.302 (0.40), 3.358 (0.59), 3.480 (0.57), 3.494 (0.65), 3.499 (0.49), 3.513 (0.50), 3.518 (0.63), 3.533 (0.55), 3.650 (1.46), 3.765 (8.67), 3.812 (0.98), 3.817 (1.24), 4.299 (0.50), 4.314 (0.96), 4.319 (0.76), 4.328 (0.97), 4.334 (0.60), 4.341 (0.47), 5.758 (16.00), 7.449 (0.69).

Intermediate 208 ethyl (15-rac)-4-chloro-3-ethyl-15-[2-(3-rac-(fluoroazetidin-1-yl)ethyl]-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (Mixture of Stereoisomers)

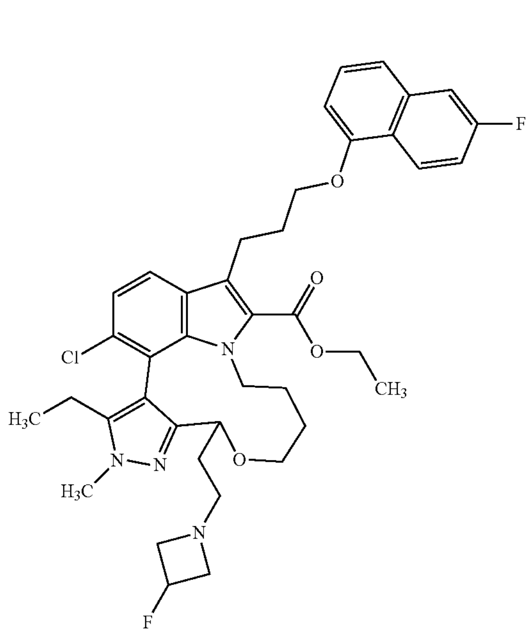 [SMILES: CCOC(=O)c1c(CCCOc2cccc3cc(F)ccc23)c2ccc(Cl)c3c2n1CCCCOC(CCN1CC(F)C1)c1nn(C)c(CC)c1-3]

(rac)-Ethyl 6-chloro-7-{5-ethyl-3-[(1-rac)-3-(3-fluoroazetidin-1-yl)-1-(4-hydroxybutoxy)propyl]-1-methyl-1H-pyrazol-4-yl}-3-{3-[(6-fluoronaphthalen-1-yl)oxy]propyl}-1H-indole-2-carboxylate (see Intermediate 207, 600 mg, 85% purity, 692 μmol) was dissolved in 10 mL THF. Triphenylphosphine (1.45 g, 5.53 mmol) and di-tert-butyl azodicarboxylate (1.27 g, 5.53 mmol) were added and the reaction mixture was stirred for 23 h at rt. Solids were filtered off, rinsed with THF twice and discarded. The filtrate was concentrated in vacuum. The crude product was purified by chromatography (Isolera, column: ultra snap, dichloromethane/ethanol) to provide the target compound in 60% purity: 635 mg, 77% yield.

LC-MS (Method 2): $R_t$=1.76 min; MS (ESIpos): m/z=719 $[M+H]^+$ $^1$H-NMR (400 MHz, DMSO-d6) δ[ppm]: 0.803 (0.42), 1.026 (0.47), 1.035 (7.92), 1.042 (0.55), 1.052 (16.00), 1.065 (1.38), 1.070 (7.47), 1.084 (2.65), 1.103 (1.16), 1.236 (0.48), 1.258 (0.59), 1.264 (0.65), 1.327 (0.87), 1.353 (3.85), 1.384 (4.12), 1.397 (4.79), 1.427 (1.58), 2.394 (0.68), 2.412 (1.13), 2.430 (0.56), 2.518 (1.36), 2.523 (0.85), 2.624 (1.14), 2.643 (1.11), 2.664 (0.45), 3.196 (0.54), 3.404 (0.64), 3.417 (0.78), 3.422 (1.98), 3.435 (2.05), 3.440 (1.95), 3.452 (1.95), 3.457 (0.86), 3.469 (0.82), 3.479 (0.41), 3.495 (0.45), 3.517 (0.41), 3.761 (5.86), 3.816 (0.48), 3.821 (0.67), 3.856 (0.72), 4.314 (0.47), 4.320 (0.48), 4.347 (1.01), 4.360 (1.92), 4.372 (0.96), 5.757 (0.98), 7.447 (0.60).

EXAMPLES

Example 1

(rac)-2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid (Mixture of Stereoisomers)

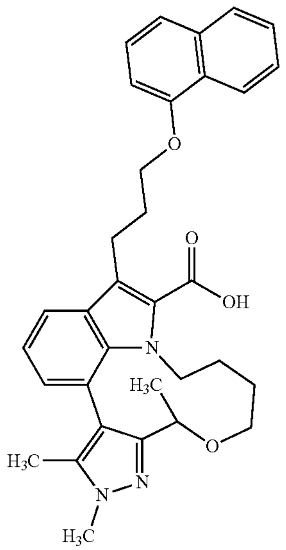 [SMILES: Cc1c2c(nn1C)C(C)OCCCCn1c(C(=O)O)c(CCCOc3cccc4ccccc34)c3cccc-2c31]

A mixture of (rac)-ethyl-2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (mixture of stereoisomers; 300 mg, 530 μmol, see Intermediate 27), ethanol (18 mL), tetrahydrofuran (25 mL) and aqueous lithium hydroxide (11 mL, 1.0 M, 11 mmol) was stirred for 16 h at 60° C. For work-up, citric acid was added to adjust the pH to 5-6, water was added and the mixture was extracted three times with a mixture of dichloromethane/2-propanol (4:1). The combined organic phases were filtered through a water resistant filter and concentrated. The residue was purified by preparative HPLC (Method P1) to give the title compound 77.4 mg (90% purity).

LC-MS (Method 1): Rt=1.53 min; MS (ESIpos): m/z=538 $[M+H]^+$ $^1$H-NMR (400 MHz, DMSO-$d_6$): δ [ppm]=13.14 (br s, 1H), 8.27-8.21 (m, 1H), 7.89-7.84 (m, 1H), 7.76-7.70 (m, 1H), 7.55-7.36 (m, 4H), 7.09-6.99 (m, 1H), 6.91-6.83 (m, 2H), 4.54 (q, 1H), 4.49-4.39 (m, 1H), 4.23-4.16 (m, 2H), 4.02 (dt, 1H), 3.81 (s, 3H), 3.41-3.34 (m, 1H), 3.32-3.23 (m, 2H), 2.97-2.86 (m, 1H), 2.21 (quin, 2H), 1.86 (s, 3H), 1.42 (d, 3H), 1.32-1.18 (m, 2H), 1.08-0.92 (m, 2H).

The racemic title compound (77 mg) was separated into stereoisomers by preparative chiral HPLC to give stereoisomer 1 (33 mg, Intermediate 2) and stereoisomer 2 (32 mg, Intermediate 3).

Preparative Chiral HPLC Method:

Instrument: Labomatic HD5000, Labocord-5000; Gilson GX-241, Labcol Vario 4000, column: Chiralpak AD 5μ 250×30 mm; eluent A: hexane+0.1 vol-% trifluoroacetic acid (99%); eluent B: ethanol; gradient: 20-50% B in 20 min; flow 40.0 mL/min; UV @ 254 nm Analytical Chiral HPLC Method:

Instrument: Agilent HPLC 1260; column: Chiralpak AD 3μ 100×4.6 mm; eluent A: hexane+0.1 vol-% trifluoroacetic acid (99%); eluent B: ethanol; isocratic: 90% A+10% B; flow 1.0 mL/min; temperature: 25° C.; DAD @ 254 nm Example 2

2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid Trifluoroacetic Acid Salt (Stereoisomer 1)

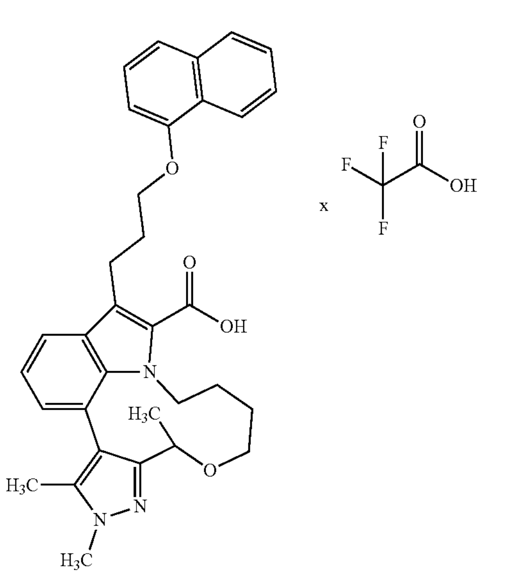 [SMILES: Cc1c2c(nn1C)C(C)OCCCCn1c(C(=O)O)c(CCCOc3cccc4ccccc34)c3cccc-2c31 ; O=C(O)C(F)(F)F]

For the preparation of the racemic title compound see Example 1. Separation of stereoisomers by preparative chiral HPLC (method see Example 1) gave the title compound (33 mg).

Analytical Chiral HPLC (method see Example 1): $R_t$=1.27 min.

Specific Optical Rotation (Method O1): +78.4° (c=10 mg/mL, methanol)

$^1$H-NMR (500 MHz, DMSO-d6) δ[ppm]: 0.000 (11.37), 0.977 (0.51), 0.992 (0.77), 1.002 (0.84), 1.015 (0.62), 1.162 (0.46), 1.234 (1.61), 1.260 (0.49), 1.422 (5.43), 1.435 (5.46), 1.865 (15.28), 2.206 (1.00), 2.220 (1.45), 2.234 (1.02), 2.366 (0.45), 2.520 (1.45), 2.523 (1.37), 2.527 (1.08), 2.545 (0.60), 2.640 (0.46), 2.927 (0.69), 2.935 (0.51), 2.942 (0.46), 2.949 (0.71), 3.270 (0.83), 3.282 (1.13), 3.291 (1.16), 3.298 (1.44), 3.314 (1.28), 3.383 (1.02), 3.398 (0.51), 3.819 (16.00), 4.017 (0.55), 4.030 (0.65), 4.044 (0.64), 4.188 (1.19), 4.201 (2.46), 4.213 (1.22), 4.424 (0.68), 4.435 (0.42), 4.452 (0.62), 4.530 (0.42), 4.543 (1.64), 4.557 (1.61), 4.569 (0.41), 6.853 (1.52), 6.855 (1.60), 6.867 (1.83), 6.869 (1.86), 6.875 (1.71), 6.891 (1.72), 7.031 (1.61), 7.046 (1.95), 7.061 (1.34), 7.366 (1.16), 7.383 (2.13), 7.398 (1.61), 7.442 (2.32), 7.459 (1.44), 7.494 (0.54), 7.504 (1.37), 7.507 (1.23), 7.515 (1.43), 7.519 (2.66), 7.523 (1.47), 7.530 (1.36), 7.533 (1.56), 7.544 (0.60), 7.547 (0.45), 7.723 (1.58), 7.725 (1.62), 7.739 (1.51), 7.741 (1.46), 7.854 (1.43), 7.859 (0.85), 7.868 (1.57), 7.872 (1.28), 8.231 (1.20), 8.235 (1.23), 8.250 (1.20), 8.311 (0.74).

Example 3

2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid Trifluoroacetic Acid Salt (Stereoisomer 2)

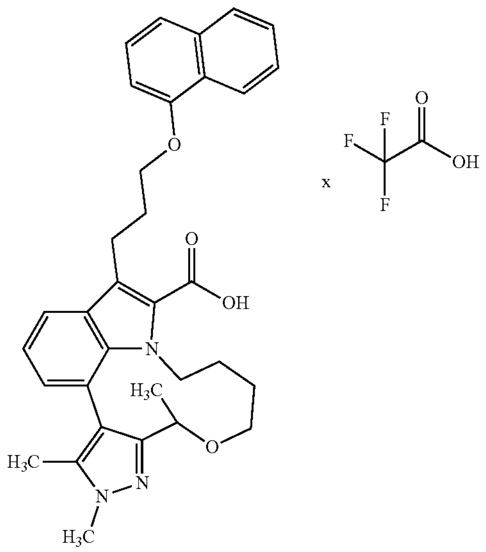 [SMILES: Cc1c2c(nn1C)C(C)OCCCCn1c(C(=O)O)c(CCCOc3cccc4ccccc34)c3cccc-2c31 ; O=C(O)C(F)(F)F]

For the preparation of the racemic title compound see Example 1. Separation of stereoisomers by preparative chiral HPLC (method see Example 1) gave the title compound (32 mg).

Analytical Chiral HPLC (method see Example 1): $R_t$=1.80 min.

Specific Optical Rotation (Method O1): −80.4° (c=10 mg/mL, methanol)

$^1$H-NMR (500 MHz, DMSO-d6) δ[ppm]: −0.007 (0.80), 0.006 (0.73), 0.971 (0.52), 0.994 (0.70), 1.158 (0.51), 1.234 (1.41), 1.419 (5.43), 1.433 (5.43), 1.862 (15.23), 2.187 (0.36), 2.201 (0.99), 2.216 (1.45), 2.230 (1.00), 2.243 (0.36), 2.360 (0.62), 2.364 (0.91), 2.368 (0.65), 2.517 (2.37), 2.521 (2.31), 2.525 (1.81), 2.543 (0.65), 2.634 (0.65), 2.638 (0.91), 2.642 (0.61), 2.907 (0.35), 2.922 (0.70), 2.930 (0.49), 2.937 (0.49), 2.945 (0.71), 2.959 (0.32), 3.267 (0.77), 3.279 (1.05), 3.289 (1.02), 3.294 (1.18), 3.310 (0.80), 3.354 (1.03), 3.369 (0.60), 3.380 (0.57), 3.818 (16.00), 4.012 (0.52), 4.026 (0.65), 4.039 (0.61), 4.055 (0.35), 4.188 (1.19), 4.200 (2.51), 4.213 (1.22), 4.409 (0.33), 4.420 (0.73), 4.431 (0.44), 4.437 (0.42), 4.447 (0.67), 4.527 (0.42), 4.540 (1.67), 4.554 (1.66), 4.566 (0.41), 6.853 (1.58), 6.856 (1.58), 6.867 (1.81), 6.870 (1.81), 6.880 (1.76), 6.895 (1.84), 7.031 (1.71), 7.047 (2.03), 7.062 (1.44), 7.369 (1.35), 7.385 (2.41), 7.400 (1.80), 7.446 (2.35), 7.463 (1.48), 7.492 (0.42), 7.495 (0.55), 7.506 (1.41), 7.509 (1.23), 7.517 (1.50), 7.521 (2.42), 7.525 (1.52), 7.533 (1.36), 7.536 (1.58), 7.546 (0.64), 7.550 (0.45), 7.725 (1.64), 7.728 (1.70), 7.741 (1.55), 7.744 (1.55), 7.858 (1.42), 7.863 (0.84), 7.872 (1.58), 7.876 (1.26), 8.229 (1.21), 8.232 (1.26), 8.248 (1.21), 8.318 (0.46).

Example 4

(rac)-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid (Mixture of Stereoisomers)

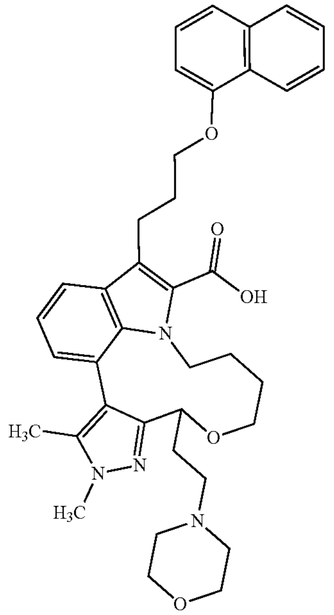 [SMILES: Cc1c2c(nn1C)C(CCN1CCOCC1)OCCCCn1c(C(=O)O)c(CCCOc3cccc4ccccc34)c3cccc-2c31]

A mixture of (rac)-ethyl 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (mixture of stereoisomers, see Intermediate 30, 280 mg, 421 μmol), ethanol (14 mL), tetrahydrofuran (20 mL) and aqueous lithium hydroxide (8.4 mL, 1.0 M, 8.4 mmol) was stirred for 16 h at 60° C. For work-up, citric acid was added to adjust the pH to 5-6, water was added and the mixture was extracted three times with a mixture of dichloromethane/2-propanol (4:1). The combined organic layers were filtered through a water resistant filter and concentrated. The residue was purified by preparative HPLC (Method P2, followed by the method described below) to give the title compound (20 mg, 97% purity).

Preparative HPLC Method:

Instrument: Waters Autopurification system; column: Phenomenex Kinetex C18 5μ 100×30 mm; Eluent A: water+0.2 Vol-% aq. ammonia (32%), Eluent B: acetonitrile; Gradient: 0.00-0.50 min 11% B (40→70 mL/min), 0.51-5.50 min 22-37% B (70 mL/min), DAD scan: 210-400 nm Analytical HPLC Method:

Instrument: Waters Acquity UPLCMS SingleQuad; column: Acquity UPLC BEH C18 1.7 μm, 50×2.1 mm; Eluent A: water+0.2 Vol-% aq. ammonia (32%), Eluent B: acetonitrile; Gradient: 0-1.6 min 1-99% B, 1.6-2.0 min 99% B; flow 0.8 mL/min; Temperature: 60° C.; DAD scan: 210-400 nm LC-MS (Method 1): $R_t$=1.23 min; MS (ESIpos): m/z=637 $[M+H]^+$ $^1$H-NMR (400 MHz, DMSO-d6) δ[ppm]: 0.983 (1.12), 1.145 (1.06), 1.729 (0.45), 1.884 (14.88), 1.905 (1.01), 1.973 (0.45), 1.990 (1.01), 2.007 (1.29), 2.021 (1.01), 2.038 (0.62), 2.095 (7.50), 2.181 (1.17), 2.198 (1.79), 2.217 (1.51), 2.231 (1.68), 2.250 (2.29), 2.276 (3.36), 2.337 (1.12), 2.458 (1.34), 2.463 (1.90), 2.467 (2.18), 2.472 (2.35), 2.518 (13.65), 2.523 (9.85), 2.536 (0.62), 2.540 (0.73), 2.884 (0.62), 2.895 (0.50), 2.913 (0.67), 3.212 (0.62), 3.237 (0.67), 3.252 (1.01), 3.269 (1.01), 3.479 (3.02), 3.490 (4.64), 3.501 (3.02), 3.727 (0.45), 3.819 (16.00), 3.901 (0.45), 4.170 (1.17), 4.187 (2.35), 4.202 (1.29), 4.413 (0.84), 4.430 (1.79), 4.447 (0.78), 4.552 (0.39), 6.743 (0.62), 6.866 (1.85), 6.884 (1.96), 6.947 (0.56), 6.965 (0.95), 6.984 (0.50), 7.352 (1.29), 7.372 (2.52), 7.391 (2.01), 7.434 (2.69), 7.455 (1.57), 7.489 (0.56), 7.501 (1.73), 7.507 (2.46), 7.516 (3.58), 7.526 (2.80), 7.532 (1.85), 7.544 (0.62), 7.623 (0.67), 7.639 (0.62), 7.849 (1.62), 7.860 (0.84), 7.867 (1.17), 7.873 (1.40), 8.231 (1.40), 8.238 (1.23), 8.244 (0.73), 8.255 (1.29), 8.737 (0.95), 9.580 (0.62).

The title compound (20 mg) was separated into stereoisomers by preparative chiral HPLC to give stereoisomer 1 (8 mg, see Example 5) and stereoisomer 2 (8 mg, see Example 6).

Preparative Chiral HPLC Method:

Instrument: Sepiatec: Prep SFC100; column: Chiralpak ID 5 μm 250×30 mm; Eluent A: $CO_2$, Eluent B: 2-propanol+0.4 Vol-% N-ethyl ethanamine (99%); isocratic: 29% B; flow 100.0 mL/min Temperature: 40° C.; BPR: 150 bar; MWD @ 254 nm Analytical Chiral HPLC Method:

Instrument: Agilent: 1260, Aurora SFC-Module; column: Chiralpak ID 5 μm 100×4.6 mm; Eluent A: $CO_2$, Eluent B: ethanol; isocratic: 29% B; flow 4.0 mL/min; Temperature: 37.5° C.; BPR: 100 bar; MWD @ 254 nm Example 5

2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid (Stereoisomer 1)

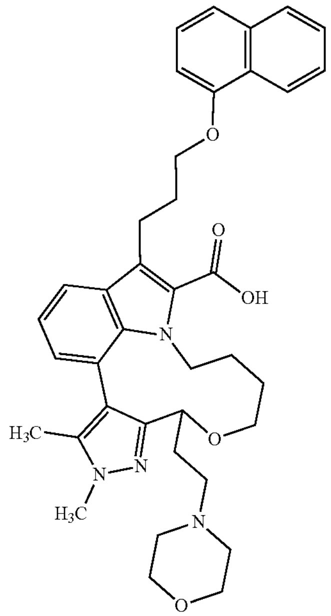 [SMILES: Cc1c2c(nn1C)C(CCN1CCOCC1)OCCCCn1c(C(=O)O)c(CCCOc3cccc4ccccc34)c3cccc-2c31]

For the preparation of the racemic title compound see Example 4. Separation of stereoisomers by preparative chiral HPLC (method see Example 4) gave the title compound (8 mg).

Analytical Chiral HPLC (method see Example 4): $R_t$=3.02 min.

LC-MS (Method 1): $R_t$=1.13 min; MS (ESIpos): m/z=637 $[M+H]^+$

Specific Optical Rotation (Method O1): +58.8° (c=10 mg/mL, DMSO)

$^1$H-NMR (400 MHz, DMSO-d6) δ[ppm]: 0.967 (2.07), 0.984 (1.40), 1.009 (0.74), 1.107 (2.53), 1.136 (1.09), 1.144 (1.05), 1.154 (2.18), 1.172 (1.30), 1.196 (0.63), 1.209 (1.09), 1.232 (1.33), 1.825 (0.63), 1.876 (15.33), 1.959 (0.42), 1.985 (0.53), 2.002 (1.12), 2.019 (1.44), 2.035 (1.23), 2.051 (0.63), 2.084 (0.46), 2.096 (0.53), 2.187 (1.19), 2.204 (1.75), 2.222 (1.44), 2.238 (2.07), 2.258 (2.88), 2.277 (3.58), 2.332 (1.65), 2.336 (0.77), 2.518 (7.65), 2.523 (5.16), 2.678 (0.63), 2.877 (0.53), 2.895 (1.30), 2.913 (1.09), 2.923 (0.77), 3.235 (0.95), 3.252 (1.51), 3.266 (1.82), 3.282 (1.65), 3.482 (3.23), 3.494 (4.91), 3.504 (3.30), 3.775 (0.70), 3.819 (16.00), 3.970 (0.56), 3.991 (0.49), 4.179 (1.40), 4.195 (2.77), 4.210 (1.37), 4.428 (0.91), 4.445 (2.00), 4.463 (1.09), 4.478 (0.67), 4.513 (0.56), 6.811 (1.16), 6.829 (1.30), 6.872 (1.93), 6.890 (2.00), 7.000 (1.16), 7.019 (1.68), 7.037 (0.98), 7.356 (1.33), 7.377 (2.56), 7.396 (2.04), 7.440 (2.81), 7.460 (1.61), 7.486 (0.42), 7.491 (0.63), 7.503 (1.82), 7.510 (2.46), 7.519 (3.65), 7.528 (2.60), 7.534 (1.89), 7.546 (0.63), 7.691 (1.33), 7.711 (1.23), 7.853 (1.65), 7.861 (0.91), 7.870 (1.26), 7.875 (1.37), 8.230 (1.40), 8.237 (1.26), 8.246 (0.70), 8.254 (1.33).

Example 6

2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid (Stereoisomer 2)

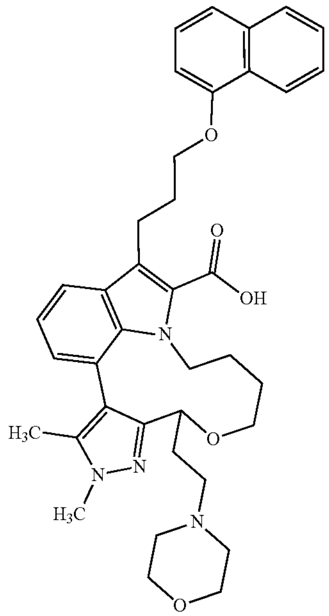 [SMILES: Cc1c2c(nn1C)C(CCN1CCOCC1)OCCCCn1c(C(=O)O)c(CCCOc3cccc4ccccc34)c3cccc-2c31]

For the preparation of the racemic title compound see Example 4. Separation of stereoisomers by preparative chiral HPLC (method see Example 4) gave the title compound (8 mg).

Analytical Chiral HPLC (method see Example 4): $R_t$=5.50 min.

LC-MS (Method 1): $R_t$=1.14 min; MS (ESIpos): m/z=637 $[M+H]^+$

Specific Optical Rotation (Method O1): −43.0° (c=10 mg/mL, DMSO)

$^1$H-NMR (400 MHz, DMSO-d6) δ[ppm]: 0.967 (2.26), 0.991 (1.23), 1.010 (0.70), 1.107 (3.33), 1.125 (0.70), 1.144 (2.04), 1.162 (0.86), 1.209 (0.70), 1.238 (1.18), 1.296 (0.48), 1.348 (0.54), 1.843 (0.64), 1.882 (14.71), 1.959 (0.64), 1.973 (0.48), 1.990 (1.02), 2.007 (1.45), 2.021 (1.07), 2.038 (0.64), 2.084 (0.97), 2.094 (7.03), 2.179 (1.18), 2.197 (1.83), 2.214 (1.45), 2.231 (1.72), 2.250 (2.36), 2.277 (3.38), 2.332 (2.31), 2.336 (1.07), 2.518 (13.53), 2.523 (8.43), 2.678 (1.02), 2.865 (0.43), 2.883 (0.75), 2.896 (0.59), 2.912 (0.75), 3.216 (0.70), 3.235 (0.75), 3.250 (1.02), 3.264 (1.07), 3.281 (1.40), 3.478 (3.17), 3.490 (4.83), 3.501 (3.22), 3.784 (0.70), 3.818 (16.00), 3.909 (0.48), 4.169 (1.29), 4.185 (2.47), 4.202 (1.29), 4.413 (0.81), 4.430 (1.83), 4.448 (0.81), 4.540 (0.48), 6.752 (0.70), 6.864 (1.83), 6.882 (1.93), 6.951 (0.64), 6.971 (1.13), 6.989 (0.59), 7.350 (1.29), 7.371 (2.52), 7.390 (1.99), 7.434 (2.74), 7.454 (1.61), 7.483 (0.43), 7.488 (0.64), 7.500 (1.72), 7.506 (2.58), 7.516 (3.54), 7.525 (2.79), 7.530 (1.93), 7.543 (0.70), 7.628 (0.81), 7.648 (0.75), 7.849 (1.66), 7.858 (0.91), 7.867 (1.29), 7.872 (1.40), 8.230 (1.40), 8.237 (1.23), 8.245 (0.81), 8.254 (1.50), 8.737 (0.81), 9.568 (0.54).

Example 7

(rac)-4-fluoro-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid

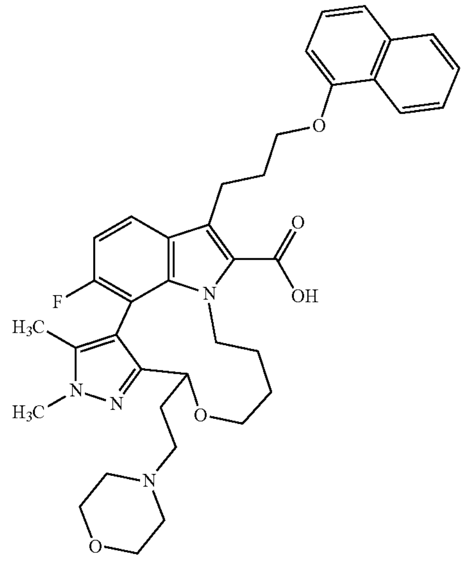 [SMILES: Cc1c2c(nn1C)C(CCN1CCOCC1)OCCCCn1c(C(=O)O)c(CCCOc3cccc4ccccc34)c3ccc(F)c-2c31]

To a solution of (rac)-ethyl-4-fluoro-2,3-dimethyl-15-[2-(morpholin-4-yl)ethyl]-7-[3-(naphthalen-1-yloxy)-propyl]-2,10,11,12,13,15-hexahydropyrazolo[4',3':9,10][1,6]oxaza-cycloundecino[8,7,6-hi]indole-8-carboxylate (see Intermediate 33, 170 mg) in of tetrahydrofuran (4 mL) were added aqueous lithium hydroxide solution (500 μL, 1.0 M, 500 μmol) and 500 μL of ethanol, and the mixture was stirred for 72 hours at 70° C. in a sealed tube. Additional aqueous lithium hydroxide solution (500 μL, 1.0 M, 500 μmol) was added and stirring at 70° C. was continued for 2 days. Additional aqueous lithium hydroxide solution (250 μL, 1.0 M, 250 μmol) was added and stirring at 70° C. was continued for 1 day, at rt for 5 days and at 70° C. for 1 day. The mixture was diluted with water and acidified using an aqueous, saturated solution of citric acid until the pH value had reached 3-4. The mixture was extracted with ethyl acetate. The combined organic layers were dried using a water resistant filter and were concentrated under reduced pressure. The crude material was purified by flash chromatography using silica gel (gradient dichloromethane/ethanol) to give the title compound (92.0 mg).

LC-MS (Method 2): $R_t$=0.86 min; MS (ESIpos): m/z=655 $[M+H]^+$ $^1$H-NMR (400 MHz, DMSO-d6) δ[ppm]: 0.814 (0.40), 0.821 (0.40), 0.904 (0.44), 1.035 (9.21), 1.052 (16.00), 1.070 (9.61), 1.206 (0.55), 1.232 (1.30), 1.255 (0.83), 1.776 (0.53), 1.896 (12.42), 2.168 (0.70), 2.185 (1.21), 2.201 (1.58), 2.218 (1.08), 2.331 (0.92), 2.518 (4.11), 2.523 (2.81), 2.639 (0.55), 2.678 (0.46), 2.699 (0.55), 2.907 (0.55), 2.922 (0.84), 2.932 (0.75), 2.951 (0.88), 2.969 (0.55), 3.233 (0.48), 3.251 (0.81), 3.266 (1.01), 3.285 (1.63), 3.405 (0.95), 3.423 (1.69), 3.433 (1.72), 3.440 (1.65), 3.450 (1.56), 3.468 (0.66), 3.697 (0.68), 3.798 (0.81), 3.851 (12.51), 3.904 (0.51), 3.922 (0.57), 3.939 (0.53), 4.178 (1.21), 4.193 (2.46), 4.208 (1.21), 4.350 (0.68), 4.362 (1.06), 4.428 (1.10), 4.443 (1.19), 4.462 (0.97), 6.879 (1.58), 6.896 (1.74), 6.973 (1.16), 6.996 (1.96), 7.019 (1.17), 7.366 (1.19), 7.387 (2.24), 7.406 (1.82), 7.447 (2.40), 7.468 (1.36), 7.487 (0.42), 7.491 (0.57), 7.504 (1.39), 7.508 (1.28), 7.516 (1.50), 7.522 (2.86), 7.528 (1.56), 7.535 (1.43), 7.540 (1.54), 7.552 (0.61), 7.557 (0.42), 7.776 (1.14), 7.790 (1.17), 7.798 (1.16), 7.812 (1.05), 7.857 (1.43), 7.863 (0.88), 7.875 (1.45), 7.880 (1.21), 8.134 (2.64), 8.208 (1.23), 8.213 (1.21), 8.232 (1.19).

The title compound (80 mg) was separated into enantiomers by preparative chiral HPLC to give enantiomer 1 (13 mg, see Example 8) and enantiomer 2 (7.8 mg, see Example 9).

Preparative Chiral HPLC Method:

Instrument: Labomatic HD5000, Labocord-5000; Gilson GX-241, Labcol Vario 4000, column: Chiralpak IG 5μ 250×30 mm; Eluent A: hexane+0.1 Vol-% N-ethyl ethanamine (99%); Eluent B: 2-propanol; isocratic 75% A+25% B; Flow 40.0 mL/min; UV 254 nm Analytical Chiral HPLC Method:

Instrument: Agilent HPLC 1260; column: Chiralpak IG 3μ 100×4.6 mm; Eluent A: hexane+0.1 Vol-% N-ethyl ethanamine (99%); Eluent B: 2-propanol; Gradient: 20-50% B in 7 min; Flow 1.4 mL/min; Temperature: 25° C.; DAD 254 nm Example 8

4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

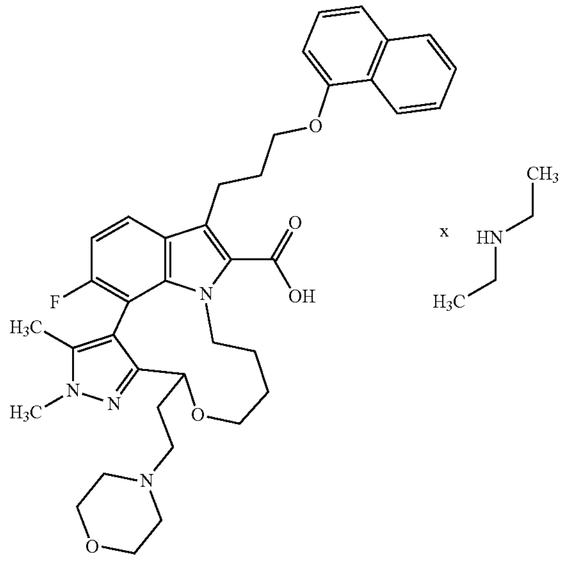

For the preparation of the racemic title compound see Example 7. Separation of enantiomers by preparative chiral HPLC (method see Example 7) gave the title compound (13 mg).

Analytical Chiral HPLC (method see Example 7): $R_t$=2.38 min.

LC-MS (Method 2): $R_t$=0.89 min; MS (ESIpos): m/z=655 $[M+H]^+$

Specific Optical Rotation (Method O1): +62.2° (c=10 mg/mL, DMSO)

$^1$H-NMR (400 MHz, DMSO-d6) δ[ppm]: 1.000 (0.58), 1.035 (0.50), 1.052 (0.78), 1.144 (7.11), 1.162 (16.00), 1.180 (7.37), 1.230 (0.58), 1.893 (5.45), 1.986 (0.61), 2.004 (0.67), 2.176 (0.49), 2.193 (0.72), 2.217 (0.70), 2.242 (0.91), 2.264 (1.42), 2.332 (0.48), 2.518 (2.40), 2.522 (1.63), 2.669 (0.66), 2.673 (0.48), 2.866 (2.11), 2.884 (6.70), 2.903 (6.44), 2.921 (2.07), 3.164 (0.58), 3.225 (0.53), 3.427 (0.45), 3.445 (0.40), 3.470 (1.24), 3.480 (1.72), 3.834 (5.82), 4.166 (0.54), 4.181 (1.07), 4.197 (0.53), 4.385 (0.73), 6.860 (0.72), 6.878 (0.79), 6.913 (0.62), 7.352 (0.53), 7.372 (0.99), 7.391 (0.78), 7.435 (1.08), 7.456 (0.63), 7.496 (0.64), 7.501 (0.61), 7.506 (0.73), 7.513 (1.37), 7.520 (0.71), 7.525 (0.66), 7.530 (0.67), 7.849 (0.66), 7.867 (0.63), 7.872 (0.54), 8.208 (0.57), 8.215 (0.53), 8.224 (0.41), 8.233 (0.53).

Example 9

4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

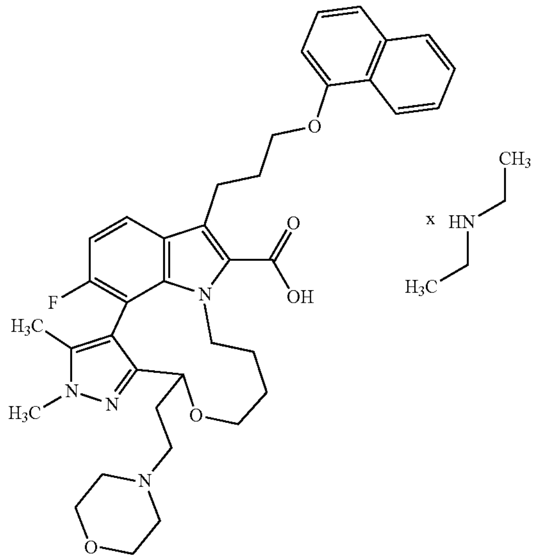

For the preparation of the racemic title compound see Example 7. Separation of enantiomers by preparative chiral HPLC (method see Example 7) gave the title compound (7.8 mg).

Analytical Chiral HPLC (method see Example 7): $R_t$=3.88 min.

LC-MS (Method 2): $R_t$=0.88 min; MS (ESIpos): m/z=655 $[M+H]^+$

Specific Optical Rotation (Method O1): −62.0° (c=10 mg/mL, DMSO)

$^1$H-NMR (400 MHz, DMSO-d6) δ[ppm]: 0.998 (1.52), 1.011 (1.29), 1.137 (4.43), 1.155 (9.80), 1.173 (4.86), 1.194 (0.68), 1.206 (0.73), 1.230 (1.62), 1.336 (0.56), 1.770 (0.61), 1.861 (0.58), 1.893 (14.99), 1.964 (0.68), 1.982 (1.72), 2.000 (1.90), 2.017 (0.89), 2.171 (1.39), 2.188 (2.05), 2.206 (1.75), 2.216 (2.00), 2.237 (2.63), 2.261 (4.15), 2.518 (6.66), 2.522 (4.48), 2.673 (1.09), 2.856 (1.27), 2.874 (3.72), 2.892 (3.67), 2.910 (1.39), 2.931 (0.78), 2.942 (0.61), 2.960 (0.84), 3.157 (0.41), 3.176 (0.71), 3.191 (0.81), 3.208 (1.06), 3.227 (0.76), 3.276 (2.33), 3.479 (4.84), 3.783 (0.78), 3.795 (0.66), 3.833 (16.00), 3.881 (0.66), 4.161 (1.47), 4.177 (2.91), 4.193 (1.44), 4.364 (0.94), 4.382 (2.00), 4.399 (0.89), 4.506 (0.63), 4.541 (0.58), 6.857 (2.08), 6.876 (2.91), 6.897 (1.59), 6.920 (0.89), 7.348 (1.37), 7.368 (2.66), 7.388 (2.03), 7.432 (2.99), 7.452 (1.72), 7.478 (0.46), 7.482 (0.68), 7.494 (1.67), 7.499 (1.77), 7.504 (2.03), 7.511 (3.57), 7.518 (2.03), 7.523 (1.92), 7.527 (1.85), 7.540 (0.73), 7.544 (0.46), 7.647 (0.73), 7.661 (0.89), 7.681 (0.68), 7.846 (1.80), 7.855 (0.96), 7.864 (1.62), 7.870 (1.49), 8.210 (1.54), 8.215 (1.42), 8.234 (1.47).

Example 10

(rac)-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic Acid

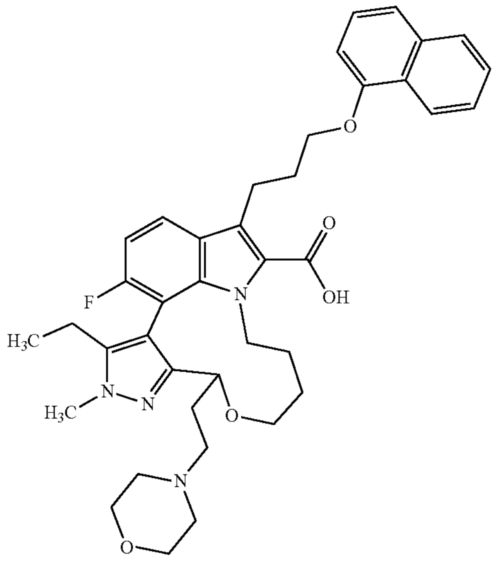 [SMILES: CCc1c2c(nn1C)C(CCN1CCOCC1)OCCCCn1c(C(=O)O)c(CCCOc3cccc4ccccc34)c3ccc(F)c-2c31]

To a solution of (rac)-ethyl-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 36, 390 mg) in tetrahydrofuran (4 mL) were added aqueous lithium hydroxide solution (1.1 mL, 1.0 M, 1.1 mmol) and 500 μL of ethanol, and the mixture was stirred for 72 hours at 70° C. in a sealed tube. Additional aqueous lithium hydroxide solution (1.1 mL, 1.0 M, 1.1 mmol) was added and stirring was continued at 70° C. for 2 days. A further portion of additional aqueous lithium hydroxide solution (550 μL, 1.0 M, 550 μmol) was added and stirring at 70° C. was continued for 1 day, at rt for 5 days and finally at 70° C. for 1 day. The mixture was diluted with water and acidified using an aqueous, saturated solution of citric acid until the pH value reached 3-4, and was extracted with ethyl acetate. The combined organic layers were dried using a water resistant filter and concentrated under reduced pressure. The crude material was purified by flash chromatography using silica gel (gradient dichloromethane/ethanol) to give the title compound (148 mg).

LC-MS (Method 2): $R_t$=0.87 min; MS (ESIpos): m/z=669 $[M+H]^+$ $^1$H-NMR (400 MHz, DMSO-d6) δ[ppm]: 0.814 (0.42), 0.821 (0.43), 0.835 (1.60), 0.854 (3.49), 0.873 (1.63), 0.904 (0.41), 1.035 (8.16), 1.052 (16.00), 1.070 (7.98), 1.231 (0.41), 2.171 (0.42), 2.190 (0.73), 2.208 (0.88), 2.225 (0.63), 2.272 (0.68), 2.284 (0.70), 2.291 (0.68), 2.303 (0.68), 2.322 (0.83), 2.327 (0.84), 2.331 (0.62), 2.518 (2.50), 2.523 (1.80), 2.665 (0.55), 2.669 (0.73), 2.673 (0.54), 2.960 (0.42), 2.986 (0.44), 3.274 (0.56), 3.405 (0.67), 3.423 (1.52), 3.434 (1.61), 3.440 (1.55), 3.451 (1.47), 3.457 (0.67), 3.469 (0.56), 3.830 (0.75), 3.882 (7.05), 4.177 (0.67), 4.193 (1.33), 4.208 (0.68), 4.348 (0.71), 4.361 (1.21), 4.373 (0.76), 4.383 (0.42), 4.427 (0.47), 4.441 (0.46), 6.874 (0.91), 6.891 (1.00), 6.977 (0.66), 6.999 (1.13), 7.022 (0.65), 7.365 (0.70), 7.385 (1.29), 7.404 (1.05), 7.448 (1.38), 7.469 (0.79), 7.505 (0.81), 7.510 (0.76), 7.517 (0.93), 7.524 (1.70), 7.530 (0.90), 7.537 (0.84), 7.541 (0.88), 7.779 (0.64), 7.792 (0.66), 7.800 (0.66), 7.814 (0.59), 7.858 (0.83), 7.864 (0.50), 7.876 (0.87), 7.881 (0.71), 8.214 (0.70), 8.219 (0.68), 8.239 (0.68).

The title compound (135 mg) was separated into enantiomers by preparative chiral HPLC to give enantiomer 1 (25 mg, see Example 11) and enantiomer 2 (23 mg, see Example 12).

Preparative Chiral HPLC Method:

Instrument: Labomatic HD5000, Labocord-5000; Gilson GX-241, Labcol Vario 4000, column: Chiralpak IG 5μ 250×30 mm; Eluent A: hexane+0.1 Vol-% N-ethyl ethanamine (99%); Eluent B: ethanol; isocratic 60% A+40% B; Flow 50.0 mL/min; UV 254 nm Analytical Chiral HPLC Method:

Instrument: Agilent HPLC 1260; column: Chiralpak IG 3μ 100×4.6 mm; Eluent A: hexane+0.1 Vol-% N-ethyl ethanamine (99%); Eluent B: ethanol; Gradient: 20-50% B in 7 min; Flow 1.4 mL/min; Temperature: 25° C.; DAD 254 nm

Example 11

3-ethyl-4-fluoro-2-methyl-15-[2-(morpholin-4-yl) ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

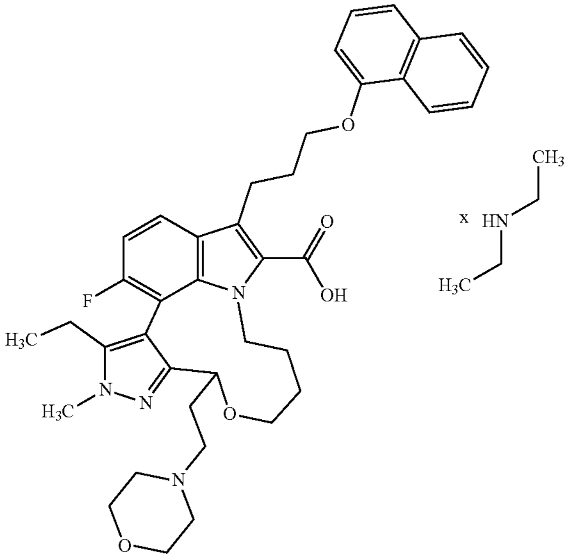

For the preparation of the racemic title compound see Example 10. Separation of enantiomers by preparative chiral HPLC (method see Example 10) gave the title compound (25 mg).

Analytical Chiral HPLC (method see Example 10): $R_t$=6.67 min.

LC-MS (Method 2): $R_t$=0.89 min; MS (ESIpos): m/z=669 $[M+H]^+$

Specific Optical Rotation (Method O1): +52.3° (c=10 mg/mL, DMSO)

$^1$H-NMR (400 MHz, DMSO-d6) δ[ppm]: 0.809 (0.53), 0.837 (3.38), 0.856 (7.46), 0.874 (3.43), 1.017 (1.29), 1.144 (7.16), 1.163 (15.12), 1.180 (7.40), 1.231 (1.23), 1.995 (1.59), 2.012 (1.76), 2.030 (0.82), 2.185 (1.32), 2.203 (1.94), 2.227 (2.17), 2.246 (3.05), 2.264 (5.46), 2.273 (4.99), 2.283 (5.37), 2.302 (2.11), 2.322 (1.88), 2.326 (1.91), 2.332 (1.38), 2.518 (7.43), 2.522 (4.87), 2.665 (1.23), 2.669 (1.67), 2.673 (1.23), 2.871 (2.17), 2.889 (6.05), 2.907 (5.90), 2.925 (2.03), 2.950 (0.44), 2.967 (0.79), 2.977 (0.65), 2.996 (0.85), 3.013 (0.41), 3.234 (1.09), 3.251 (1.67), 3.275 (2.38), 3.487 (4.84), 3.784 (0.50), 3.816 (1.14), 3.862 (16.00), 3.923 (0.53), 3.938 (0.70), 3.957 (0.56), 4.170 (1.47), 4.187 (2.94), 4.202 (1.50), 4.366 (0.94), 4.383 (2.00), 4.400 (0.91), 4.437 (0.62), 4.470 (0.56), 6.859 (2.06), 6.877 (2.17), 6.909 (1.09), 6.931 (1.79), 6.954 (1.00), 7.352 (1.32), 7.372 (2.67), 7.391 (2.00), 7.437 (3.17), 7.457 (1.76), 7.485 (0.65), 7.499 (1.64), 7.502 (1.70), 7.508 (2.03), 7.515 (3.58), 7.523 (2.00), 7.527 (1.91), 7.531 (1.85), 7.544 (0.73), 7.692 (0.85), 7.705 (0.97), 7.713 (0.97), 7.727 (0.73), 7.851 (1.82), 7.858 (0.97), 7.868 (1.59), 7.874 (1.53), 8.214 (1.50), 8.220 (1.44), 8.238 (1.53).

Example 12

3-ethyl-4-fluoro-2-methyl-15-[2-(morpholin-4-yl) ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

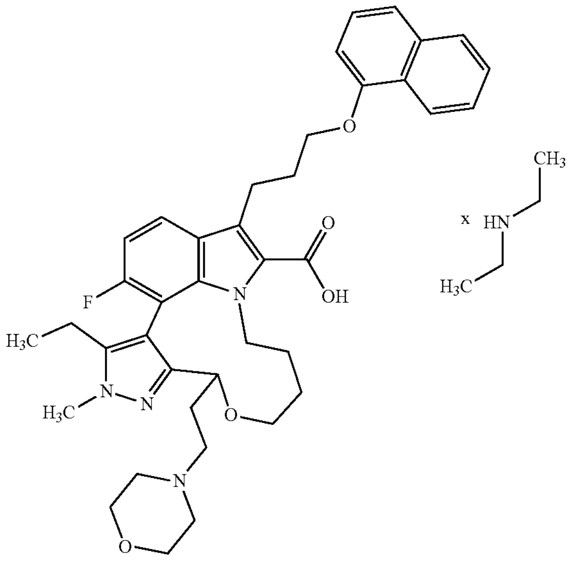

For the preparation of the racemic title compound see Example 10. Separation of enantiomers by preparative chiral HPLC (method see Example 10) gave the title compound (23 mg).

Analytical Chiral HPLC (method see Example 10): $R_t$=7.62 min.

LC-MS (Method 2): $R_t$=0.89 min; MS (ESIpos): m/z=669 $[M+H]^+$

Specific Optical Rotation (Method O1): −58.4° (c=10 mg/mL, DMSO)

$^1$H-NMR (400 MHz, DMSO-d6) δ[ppm]: 0.810 (0.52), 0.841 (3.43), 0.860 (7.23), 0.878 (3.47), 1.001 (1.73), 1.140 (2.43), 1.156 (4.58), 1.173 (2.74), 1.230 (1.87), 1.270 (0.40), 1.343 (0.64), 1.985 (1.54), 2.001 (1.68), 2.181 (1.54), 2.198 (2.20), 2.221 (2.51), 2.266 (6.07), 2.304 (1.87), 2.322 (1.82), 2.326 (1.77), 2.331 (1.23), 2.522 (4.54), 2.665 (1.06), 2.669 (1.39), 2.673 (1.04), 2.874 (1.94), 2.890 (1.91), 2.941 (0.50), 2.958 (0.92), 2.969 (0.73), 2.986 (0.97), 3.005 (0.50), 3.188 (0.95), 3.204 (1.23), 3.221 (1.68), 3.275 (3.57), 3.482 (5.53), 3.522 (0.87), 3.814 (1.06), 3.862 (16.00), 3.897 (0.80), 4.166 (1.47), 4.181 (2.77), 4.196 (1.51), 4.357 (1.04), 4.374 (2.03), 4.391 (0.97), 4.487 (0.69), 4.520 (0.61), 6.852 (2.15), 6.871 (3.17), 6.892 (1.82), 6.915 (1.02), 7.345 (1.30), 7.365 (2.67), 7.384 (1.91), 7.431 (3.12), 7.452 (1.89), 7.482 (0.66), 7.495 (1.70), 7.499 (1.87), 7.504 (2.15), 7.511 (3.47), 7.519 (2.15), 7.523 (2.10), 7.527 (1.89), 7.540 (0.69), 7.639 (0.90), 7.653 (1.06), 7.674 (0.78), 7.848 (1.94), 7.865 (1.65), 7.870 (1.58), 8.215 (1.54), 8.221 (1.49), 8.238 (1.54).

Example 13

(rac)-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid

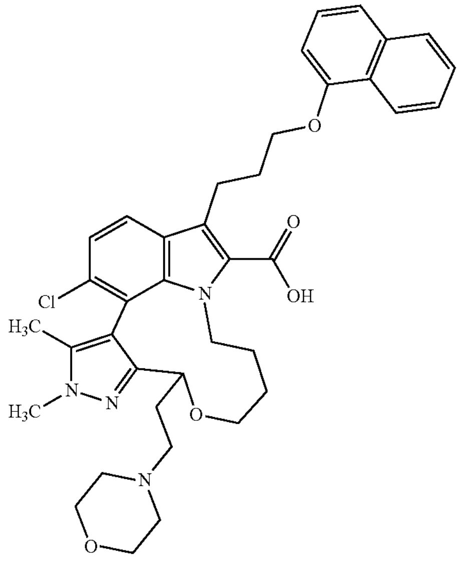

To a solution of (rac)-ethyl-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate see Intermediate 39, 770 mg, 1.10 mmol) in tetrahydrofuran (7 mL) in a reaction vessel were added aqueous lithium hydroxide solution (2.2 mL, 1.0 M, 2.2 mmol) and ethanol (700 μL), and the mixture was stirred for 23 hours at 70° C. in a sealed tube. Additional aqueous lithium hydroxide solution (1.1 mL, 1.0 M, 1.1 mmol) was added and stirring was continued at 70° C. for 3 days. The mixture was diluted with water, acidified using an aqueous, saturated solution of citric acid until the pH value reached 3-4, and extracted with ethyl acetate. The combined organic layers were dried using a water resistant filter and concentrated under reduced pressure. The crude material was purified by flash chromatography using silica gel (gradient dichloromethane/ethanol) to give the title compound (515 mg, 69% yield).

LC-MS (Method 2): $R_t$=0.90 min; MS (ESIpos): m/z=671 $[M+H]^+$ $^1$H-NMR (400 MHz, DMSO-d6) δ[ppm]: 0.797 (1.23), 0.802 (0.55), 0.813 (1.33), 0.820 (1.32), 0.839 (0.59), 0.885 (0.68), 0.903 (1.52), 0.922 (0.77), 1.035 (7.01), 1.052 (15.10), 1.070 (7.93), 1.123 (0.52), 1.141 (0.55), 1.160 (0.55), 1.254 (0.64), 1.273 (0.51), 1.827 (14.74), 2.169 (0.49), 2.184 (1.07), 2.201 (1.64), 2.218 (1.29), 2.229 (0.85), 2.322 (0.56), 2.327 (0.77), 2.331 (0.59), 2.387 (0.47), 2.393 (0.52), 2.406 (0.58), 2.411 (0.68), 2.437 (0.47), 2.518 (2.77), 2.523 (1.92), 2.625 (0.68), 2.663 (1.63), 2.669 (0.92), 2.673 (0.60), 2.728 (1.21), 2.767 (0.66), 3.017 (0.88), 3.038 (0.67), 3.129 (0.77), 3.225 (0.51), 3.243 (0.78), 3.259 (0.95), 3.278 (1.42), 3.409 (0.90), 3.427 (1.47), 3.445 (1.37), 3.808 (0.71), 3.856 (16.00), 3.891 (0.97), 4.172 (1.15), 4.188 (2.32), 4.203 (1.21), 4.379 (0.63), 4.396 (1.42), 4.409 (1.44), 4.419 (1.25), 4.431 (1.30), 6.877 (1.79), 6.894 (1.97), 7.210 (3.99), 7.231 (3.86), 7.366 (1.40), 7.386 (2.60), 7.405 (2.14), 7.448 (2.67), 7.469 (1.52), 7.486 (0.53), 7.490 (0.71), 7.504 (1.56), 7.507 (1.42), 7.518 (1.73), 7.523 (2.47), 7.527 (1.75), 7.538 (1.51), 7.542 (1.75), 7.555 (0.71), 7.559 (0.56), 7.770 (3.41), 7.792 (3.01), 7.857 (1.59), 7.863 (1.04), 7.876 (1.77), 7.880 (1.40), 8.199 (1.42), 8.204 (1.44), 8.222 (1.36).

The title compound (500 mg) was separated into enantiomers by preparative chiral HPLC to give enantiomer 1 (177 mg, see Example 14) and enantiomer 2 (178 mg, see Example 15).

Preparative Chiral HPLC Method:

Instrument: Sepiatec: Prep SFC100; column: Chiralpak IG 5 μm 250×30 mm; Eluent A: $CO_2$, Eluent B: 2-propanol+0.4 Vol-% N-ethyl ethanamine (99%); isocratic: 25% B; Flow 100.0 mL/min Temperature: 40° C.; BPR: 120 bar; MWD @ 220 nm Analytical Chiral HPLC Method:

Instrument: Agilent: 1260, Aurora SFC-Module; column: Chiralpak IG 5 μm 100×4.6 mm; Eluent A: $CO_2$, Eluent B: 2-propanol+0.2 Vol-% N-ethyl ethanamine (99%); isocratic: 30% B; Flow 4.0 mL/min; Temperature: 37.5° C.; BPR: 100 bar; MWD @ 220 nm Example 14

4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid (Enantiomer 1)

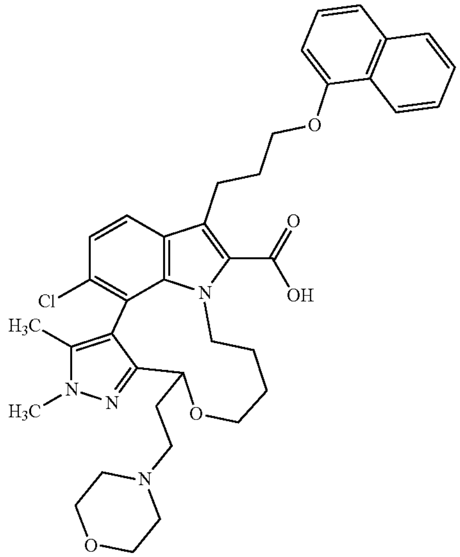 [SMILES: Cc1c2c(nn1C)C(CCN1CCOCC1)OCCCCn1c(C(=O)O)c(CCCOc3cccc4ccccc34)c3ccc(Cl)c-2c31]

For the preparation of the racemic title compound see Example 13. Separation of enantiomers by preparative chiral HPLC (method see Example 13) gave the title compound (177 mg).

Analytical Chiral HPLC (method see Example 13): $R_t$=1.51 min.

The compound was further purified by flash chromatography using silica gel (gradient dichloromethane/ethanol) to give the title compound (140 mg).

LC-MS (Method 2): $R_t$=0.90 min; MS (ESIpos): m/z=671 $[M+H]^+$

Specific Optical Rotation (Method O1): +58.6° (c=10 mg/mL, DMSO)

$^1$H-NMR (400 MHz, DMSO-d6) δ[ppm]: 0.814 (0.46), 0.821 (0.49), 0.904 (0.54), 1.018 (1.00), 1.035 (0.82), 1.053 (0.53), 1.066 (6.83), 1.187 (0.51), 1.205 (0.51), 1.231 (1.02), 1.807 (15.70), 2.042 (1.14), 2.057 (1.37), 2.075 (0.70), 2.181 (1.05), 2.199 (1.58), 2.216 (1.16), 2.231 (0.49), 2.308 (4.15), 2.322 (3.14), 2.326 (3.50), 2.345 (0.98), 2.356 (0.58), 2.518 (9.15), 2.522 (6.59), 2.664 (0.70), 2.669 (1.02), 2.673 (0.75), 3.029 (0.56), 3.046 (0.65), 3.211 (0.49), 3.229 (0.82), 3.245 (1.10), 3.263 (1.98), 3.504 (3.96), 3.831 (16.00), 3.882 (0.60), 3.899 (0.67), 3.916 (0.70), 3.934 (0.42), 4.171 (1.28), 4.187 (2.70), 4.202 (1.38), 4.352 (0.65), 4.366 (0.56), 4.385 (0.67), 4.395 (1.14), 4.411 (1.66), 4.429 (0.91), 5.758 (5.01), 6.871 (1.84), 6.888 (2.02), 7.186 (3.58), 7.207 (3.72), 7.359 (1.38), 7.380 (2.63), 7.399 (2.16), 7.442 (2.70), 7.463 (1.56), 7.482 (0.46), 7.487 (0.65), 7.499 (1.61), 7.504 (1.49), 7.509 (1.73), 7.517 (3.49), 7.523 (1.86), 7.529 (1.70), 7.533 (1.88), 7.546 (0.75), 7.551 (0.51), 7.734 (2.87), 7.755 (2.65), 7.853 (1.56), 7.860 (0.89), 7.870 (1.59), 7.875 (1.38), 8.202 (1.38), 8.207 (1.35), 8.219 (0.79), 8.226 (1.37).

Example 15

4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid (Enantiomer 2)

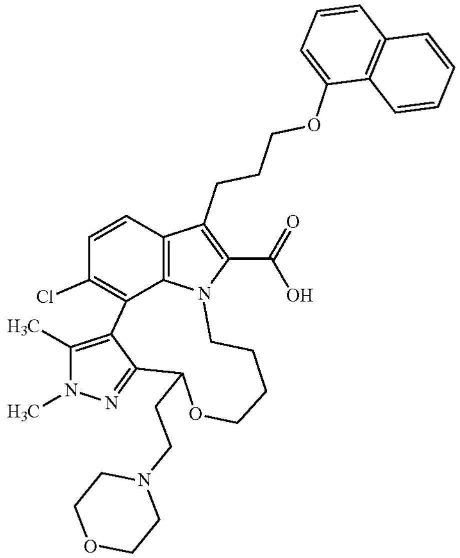

For the preparation of the racemic title compound see Example 13. Separation of enantiomers by preparative chiral HPLC (method see Example 13) gave the title compound (178 mg).

Analytical Chiral HPLC (method see Example 13): $R_t$=2.73 min.

The compound was further purified by flash chromatography using silica gel (gradient dichloromethane/ethanol) to give the title compound (120 mg).

LC-MS (Method 2): $R_t$=0.90 min; MS (ESIpos): m/z=671 $[M+H]^+$

Specific Optical Rotation (Method O1): −52.6° (c=10 mg/mL, DMSO)

$^1$H-NMR (400 MHz, DMSO-d6) δ[ppm]: 0.814 (0.42), 0.821 (0.46), 0.904 (0.48), 1.017 (0.96), 1.183 (0.50), 1.231 (1.45), 1.806 (15.29), 2.042 (1.13), 2.059 (1.32), 2.076 (0.65), 2.181 (1.05), 2.199 (1.55), 2.216 (1.09), 2.231 (0.44), 2.311 (3.94), 2.322 (3.18), 2.327 (3.60), 2.518 (4.73), 2.523 (3.31), 2.665 (0.86), 2.669 (1.21), 2.673 (0.86), 3.029 (0.59), 3.046 (0.63), 3.214 (0.65), 3.231 (1.05), 3.247 (1.42), 3.265 (2.53), 3.506 (4.02), 3.831 (16.00), 3.884 (0.61), 3.900 (0.65), 3.919 (0.69), 4.171 (1.30), 4.187 (2.68), 4.202 (1.32), 4.347 (0.65), 4.364 (0.54), 4.383 (0.61), 4.395 (1.17), 4.411 (1.63), 4.430 (0.86), 5.757 (5.07), 6.872 (1.82), 6.889 (1.97), 7.188 (3.66), 7.210 (3.73), 7.361 (1.36), 7.381 (2.62), 7.400 (2.12), 7.442 (2.70), 7.463 (1.53), 7.483 (0.42), 7.487 (0.61), 7.500 (1.59), 7.504 (1.40), 7.510 (1.76), 7.517 (3.54), 7.524 (1.76), 7.530 (1.59), 7.534 (1.76), 7.547 (0.69), 7.551 (0.44), 7.738 (2.93), 7.758 (2.62), 7.853 (1.57), 7.860 (0.90), 7.871 (1.53), 7.876 (1.36), 8.201 (1.38), 8.207 (1.34), 8.226 (1.32).

Example 16

(rac)-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid

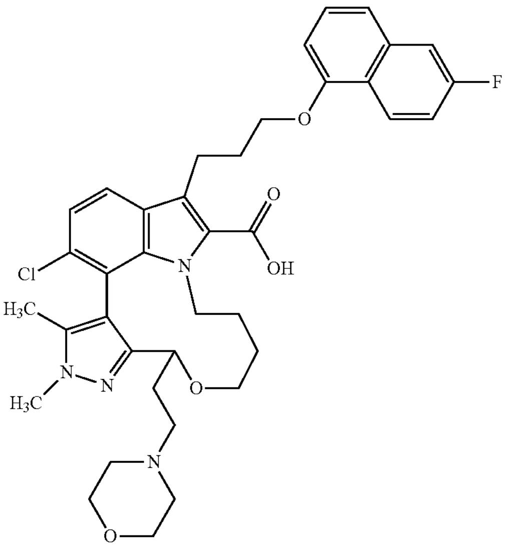 [SMILES: Cc1c2c(nn1C)C(CCN1CCOCC1)OCCCCn1c(C(=O)O)c(CCCOc3cccc4cc(F)ccc34)c3ccc(Cl)c-2c31]

To a solution of (rac)-ethyl-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]-indole-8-carboxylate (see Intermediate 50, 96.7 mg, 135 μmol) in a mixture of tetrahydrofuran (2 mL) and ethanol (1 mL) was added aqueous lithium hydroxide solution (270 μL, 1.0 M, 270 μmol), and the mixture was stirred at 65° C. overnight. Additional 200 μL of aqueous lithium hydroxide solution (1 M) was added, and stirring was continued at 65° C. for 18 hours. The mixture was concentrated under reduced pressure and the residue was diluted with water and acidified using an aqueous, saturated solution of citric acid. The mixture was extracted with tetrahydrofuran and the combined organic layers were concentrated under reduced pressure. The crude material was purified by flash chromatography using silica gel (gradient dichloromethane/ethanol) to give the title compound (68.2 mg, 73% yield).

LC-MS (Method 1): $R_t$=1.19 min; MS (ESIpos): m/z=689 $[M+H]^+$ $^1$H-NMR (400 MHz, DMSO-d6) δ[ppm]: 0.771 (1.00), 0.776 (0.42), 0.787 (1.02), 0.794 (1.02), 0.813 (0.52), 0.859 (0.52), 0.877 (1.13), 0.895 (0.58), 0.997 (0.52), 1.016 (0.56), 1.026 (0.56), 1.043 (0.58), 1.062 (0.61), 1.081 (0.56), 1.097 (0.73), 1.115 (0.61), 1.133 (0.54), 1.213 (0.63), 1.228 (0.69), 1.243 (0.52), 1.325 (0.65), 1.800 (14.89), 2.153 (1.15), 2.169 (1.73), 2.184 (1.44), 2.203 (0.92), 2.296 (0.79), 2.301 (1.09), 2.306 (0.81), 2.361 (0.42), 2.367 (0.48), 2.379 (0.52), 2.385 (0.58), 2.492 (4.26), 2.497 (2.88), 2.599 (0.81), 2.638 (2.11), 2.643 (1.32), 2.647 (0.90), 2.702 (1.38), 2.740 (0.77), 2.992 (0.94), 3.013 (0.75), 3.114 (0.71), 3.196 (0.56), 3.214 (0.82), 3.229 (1.00), 3.248 (1.53), 3.687 (0.54), 3.781 (0.40), 3.830 (16.00), 3.859 (1.06), 4.148 (1.29), 4.163 (2.59), 4.179 (1.32), 4.368 (0.75), 4.378 (1.32), 4.390 (1.34), 4.401 (1.57), 4.412 (1.11), 5.732 (8.17), 6.830 (1.34), 6.837 (1.36), 6.844 (1.21), 6.851 (1.40), 7.190 (3.80), 7.211 (3.99), 7.330 (0.90), 7.337 (1.02), 7.353 (1.38), 7.360 (1.50), 7.375 (0.92), 7.382 (1.11), 7.405 (2.59), 7.413 (2.90), 7.420 (6.12), 7.433 (0.42), 7.621 (1.63), 7.627 (1.65), 7.647 (1.61), 7.653 (1.61), 7.739 (3.41), 7.761 (3.03), 8.195 (1.44), 8.210 (1.48), 8.219 (1.42), 8.233 (1.34).

The title compound (63 mg) was separated into enantiomers by preparative chiral HPLC to give enantiomer 1 (21 mg, see Example 17) and enantiomer 2 (27 mg, see Example 18).

Preparative Chiral HPLC Method:

Instrument: Labomatic HD5000, Labocord-5000; Gilson GX-241, Labcol Vario 4000, column: Chiralpak IG 5μ 250×30 mm; Eluent A: hexane+0.1 Vol-% N-ethyl ethanamine (99%); Eluent B: ethanol; isocratic: 60% A+40% B; Flow 50.0 mL/min; UV 254 nm Analytical Chiral HPLC Method:

Instrument: Agilent HPLC 1260; column: Chiralpak IG 3μ 100×4.6 mm; Eluent A: hexane+0.1 Vol-% N-ethyl ethanamine (99%); Eluent B: ethanol; isocratic: 60% A+40% B; Flow 1.4 mL/min; Temperature: 25° C.; DAD 254 nm Example 17

4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid—N-ethylethanamine (Enantiomer 1)

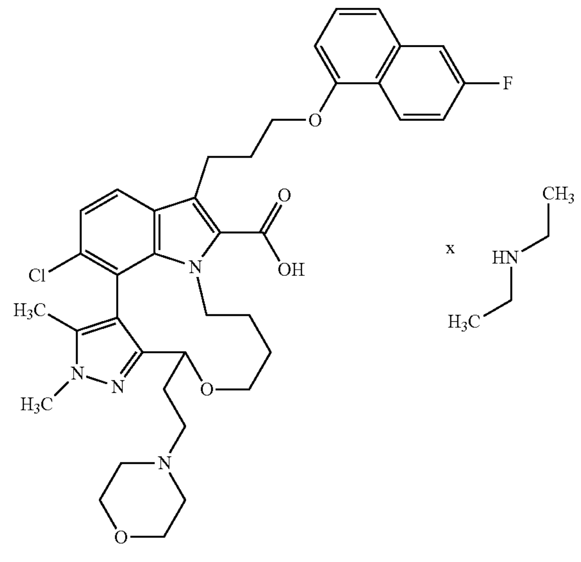

For the preparation of the racemic title compound see Example 16. Separation of enantiomers by preparative chiral HPLC (method see Example 16) gave the title compound (21 mg).

Analytical Chiral HPLC (method see Example 16): $R_t$=1.88 min.

LC-MS (Method 1): $R_t$=1.21 min; MS (ESIpos): m/z=689 $[M+H]^+$

Specific Optical Rotation (Method O1): +40.7° (c=10 mg/mL, DMSO)

$^1$H-NMR (400 MHz, DMSO-d6) δ[ppm]: 1.010 (1.17), 1.145 (7.17), 1.161 (14.75), 1.178 (7.21), 1.231 (1.53), 1.809 (13.50), 1.906 (0.52), 2.030 (1.45), 2.048 (1.61), 2.065 (0.81), 2.175 (1.09), 2.192 (1.57), 2.209 (1.13), 2.297 (4.11), 2.317 (2.78), 2.322 (2.74), 2.327 (3.14), 2.331 (2.50), 2.440 (1.17), 2.518 (8.99), 2.523 (5.72), 2.551 (1.01), 2.659 (0.81), 2.664 (1.65), 2.669 (2.34), 2.673 (1.69), 2.678 (0.77), 2.899 (5.96), 2.916 (5.80), 3.017 (0.69), 3.044 (0.73), 3.062 (0.40), 3.219 (0.77), 3.237 (1.13), 3.498 (3.91), 3.830 (16.00), 3.863 (0.60), 3.882 (0.56), 4.168 (1.17), 4.184 (2.26), 4.199 (1.17), 4.386 (1.17), 4.402 (1.93), 4.420 (1.13), 6.843 (1.13), 6.849 (1.13), 6.858 (1.09), 6.864 (1.17), 7.161 (1.81), 7.182 (1.89), 7.351 (0.77), 7.357 (0.85), 7.373 (1.25), 7.379 (1.37), 7.395 (0.93), 7.402 (1.01), 7.420 (2.22), 7.429 (2.74), 7.435 (5.32), 7.449 (0.40), 7.638 (1.57), 7.644 (1.61), 7.664 (1.61), 7.670 (1.61), 7.688 (1.29), 7.710 (1.17), 8.220 (1.25), 8.235 (1.33), 8.243 (1.25), 8.258 (1.21).

Example 18

4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 2)

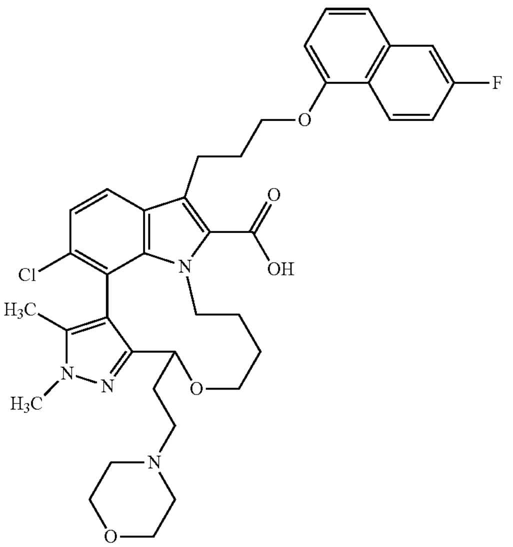 [SMILES: Cc1c2c(nn1C)C(CCN1CCOCC1)OCCCCn1c(C(=O)O)c(CCCOc3cccc4cc(F)ccc34)c3ccc(Cl)c-2c31]

For the preparation of the racemic title compound see Example 16. Separation of enantiomers by preparative chiral HPLC (method see Example 16) gave the title compound (27 mg).

Analytical Chiral HPLC (method see Example 16): $R_t$=4.17 min.

LC-MS (Method 1): $R_t$=1.21 min; MS (ESIpos): m/z=689 $[M+H]^+$

Specific Optical Rotation (Method O1): −50.8° (c=10 mg/mL, DMSO)

$^1$H-NMR (400 MHz, DMSO-d6) δ[ppm]: 0.994 (1.46), 1.158 (1.58), 1.230 (1.43), 1.812 (14.16), 1.906 (0.79), 2.019 (1.62), 2.036 (1.84), 2.053 (0.83), 2.168 (1.20), 2.185 (1.80), 2.202 (1.31), 2.290 (4.21), 2.303 (2.70), 2.322 (2.59), 2.326 (2.74), 2.331 (1.99), 2.518 (8.68), 2.522 (5.37), 2.664 (1.50), 2.669 (2.07), 2.673 (1.50), 2.911 (0.68), 2.994 (0.41), 3.011 (0.79), 3.039 (0.83), 3.058 (0.45), 3.171 (0.56), 3.186 (0.68), 3.204 (0.90), 3.223 (0.64), 3.267 (1.92), 3.492 (4.06), 3.829 (16.00), 4.162 (1.20), 4.177 (2.29), 4.192 (1.20), 4.371 (0.90), 4.388 (1.73), 4.405 (0.98), 4.427 (0.56), 4.462 (0.53), 6.837 (1.24), 6.844 (1.28), 6.853 (1.20), 6.859 (1.31), 7.127 (1.58), 7.148 (1.69), 7.348 (0.83), 7.355 (0.94), 7.371 (1.39), 7.377 (1.54), 7.393 (1.39), 7.400 (1.01), 7.415 (2.33), 7.424 (2.82), 7.430 (5.48), 7.445 (0.45), 7.634 (1.92), 7.640 (2.40), 7.660 (2.22), 7.666 (2.48), 8.225 (1.35), 8.239 (1.39), 8.248 (1.35), 8.263 (1.24).

Example 19

(rac)-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid

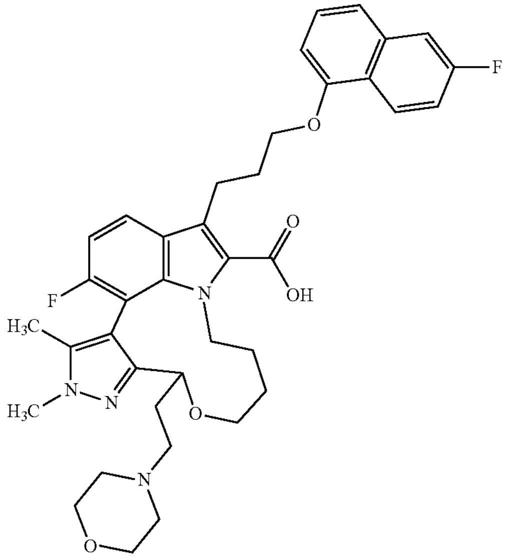 [SMILES: Cc1c2c(nn1C)C(CCN1CCOCC1)OCCCCn1c(C(=O)O)c(CCCOc3cccc4cc(F)ccc34)c3ccc(F)c-2c31]

To a solution of (rac)-ethyl-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]-indole-8-carboxylate (see Intermediate 42, 470 mg) in 5 mL of THF, aqueous lithium hydroxide solution (1.3 mL, 1.0 M, 1.3 mmol) and ethanol (500 μL) were added, and the mixture was stirred for 23 hours at 70° C. in a sealed tube. An additional portion of of aqueous lithium hydroxide solution (1.3 mL; 1.0 M) was added, and stirring was continued at 70° C. for 24 hours. A further additional portion of aqueous lithium hydroxide solution (1.3 mL; 1 M) was added, and stirring was continued at 70° C. for 48 hours. The mixture was diluted with water and acidified using an aqueous, saturated solution of citric acid until the pH value reached 3-4, and was extracted with ethyl acetate. The combined organic layers were dried using a water resistant filter and concentrated under reduced pressure. The crude material was purified by flash chromatography using silica gel (gradient dichloromethane/ethanol) to give the title compound (173 mg).

LC-MS (Method 2): $R_t$=0.89 min; MS (ESIpos): m/z=673 $[M+H]^+$ $^1$H-NMR (400 MHz, DMSO-d6) δ[ppm]: 0.797 (3.09), 0.802 (1.46), 0.814 (3.39), 0.821 (3.37), 0.839 (1.71), 0.885 (1.73), 0.903 (3.68), 0.922 (1.80), 1.052 (0.96), 1.070 (0.89), 1.089 (0.73), 1.107 (0.56), 1.123 (0.55), 1.141 (0.58), 1.160 (0.47), 1.230 (1.69), 1.235 (1.73), 1.254 (1.35), 1.270 (1.09), 1.287 (0.60), 1.774 (0.58), 1.870 (0.44), 1.893 (15.67), 2.169 (1.37), 2.179 (1.78), 2.196 (2.31), 2.209 (1.98), 2.229 (1.16), 2.332 (0.98), 2.358 (0.62), 2.372 (0.67), 2.387 (0.78), 2.393 (0.78), 2.397 (0.47), 2.406 (0.75), 2.411 (0.98), 2.518 (5.22), 2.522 (3.29), 2.539 (0.60), 2.599 (0.51), 2.637 (0.87), 2.698 (0.87), 2.736 (0.58), 2.904 (0.86), 2.922 (1.24), 2.931 (1.13), 2.949 (1.27), 2.968 (0.82), 3.230 (0.82), 3.248 (1.33), 3.262 (1.69), 3.282 (2.68), 3.710 (1.15), 3.746 (0.95), 3.751 (0.93), 3.798 (0.98), 3.851 (16.00), 3.882 (0.53), 3.899 (0.71), 3.917 (0.80), 3.934 (0.75), 4.179 (1.66), 4.194 (3.33), 4.209 (1.80), 4.429 (1.38), 4.446 (1.62), 4.462 (1.38), 5.758 (3.40), 6.856 (1.40), 6.864 (1.51), 6.871 (1.40), 6.878 (1.62), 6.977 (1.44), 7.000 (2.51), 7.022 (1.51), 7.359 (0.93), 7.365 (1.11), 7.381 (1.57), 7.388 (1.78), 7.403 (1.07), 7.410 (1.51), 7.431 (2.91), 7.437 (3.40), 7.445 (6.90), 7.457 (0.75), 7.645 (1.77), 7.651 (1.91), 7.671 (1.80), 7.677 (1.84), 7.770 (1.38), 7.784 (1.47), 7.792 (1.46), 7.806 (1.31), 8.232 (1.55), 8.247 (1.60), 8.255 (1.62), 8.270 (1.49).

The title compound (166 mg) was separated into enantiomers by preparative chiral HPLC to give enantiomer 1 (62 mg, see Example 20) and enantiomer 2 (60 mg, see Example 21).

Preparative Chiral HPLC Method:

Instrument: PrepCon Labomatic HPLC; Column: YMC Amylose SA 5μ 250×30; Eluent A: hexane+0.1% N-ethyl ethanamine; Eluent B: ethanol; Gradient: 20→50% B in 20 min; Flow: 40 mL/min; Temperature: 25° C.; UV: 254 nm Analytical Chiral HPLC Method:

Instrument: Agilent 1260 HPLC; Column: YMC Amylose SA 3μ 100×4.6; Eluent A: hexane+0.1% N-ethyl ethanamine; Eluent B: ethanol; Gradient: 20→50% B in 7 min; Flow: 1.4 mL/min; Temperature: 25° C.; UV: 254 nm

Example 20

4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid—N-ethylethanamine (Enantiomer 1)

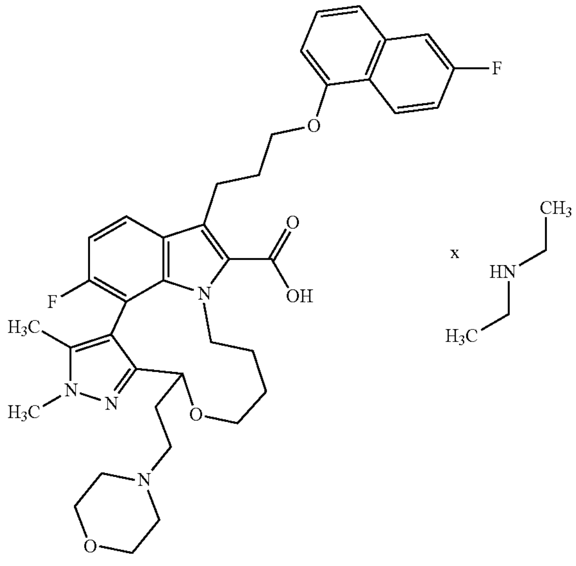

For the preparation of the racemic title compound see Example 19. Separation of enantiomers by preparative chiral HPLC (method see Example 19) gave the title compound (62 mg).

Analytical Chiral HPLC (method see Example 19): $R_t$=1.48 min.

LC-MS (Method 1): $R_t$=1.14 min; MS (ESIneg): m/z=671 $[M-H]^-$

Specific Optical Rotation (Method O1): +60.1° (c=10 mg/mL, DMSO)

$^1$H-NMR (400 MHz, DMSO-d6) δ[ppm]: 0.967 (0.62), 0.994 (0.83), 0.997 (0.79), 1.009 (0.77), 1.107 (0.89), 1.141 (7.19), 1.159 (16.00), 1.177 (7.36), 1.208 (0.65), 1.266 (0.42), 1.890 (8.05), 1.988 (0.86), 2.005 (0.98), 2.022 (0.50), 2.173 (0.65), 2.189 (1.03), 2.206 (0.83), 2.223 (1.00), 2.243 (1.33), 2.264 (2.07), 2.331 (0.69), 2.518 (3.84), 2.522 (2.40), 2.673 (0.65), 2.867 (2.08), 2.885 (6.36), 2.903 (6.45), 2.921 (2.04), 2.933 (0.42), 2.962 (0.44), 3.208 (0.42), 3.225 (0.60), 3.243 (0.47), 3.278 (1.22), 3.481 (2.40), 3.834 (9.02), 4.167 (0.74), 4.183 (1.51), 4.199 (0.77), 4.370 (0.47), 4.387 (1.03), 4.404 (0.48), 6.837 (0.71), 6.844 (0.74), 6.853 (0.65), 6.860 (0.77), 6.896 (0.44), 6.919 (0.80), 6.941 (0.44), 7.351 (0.50), 7.358 (0.56), 7.374 (0.79), 7.381 (0.83), 7.396 (0.71), 7.403 (0.63), 7.416 (1.30), 7.425 (1.53), 7.431 (3.19), 7.635 (0.88), 7.642 (0.91), 7.662 (1.07), 7.667 (1.16), 7.679 (0.47), 8.232 (0.79), 8.248 (0.80), 8.256 (0.77), 8.270 (0.74).

Example 21

4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 2)

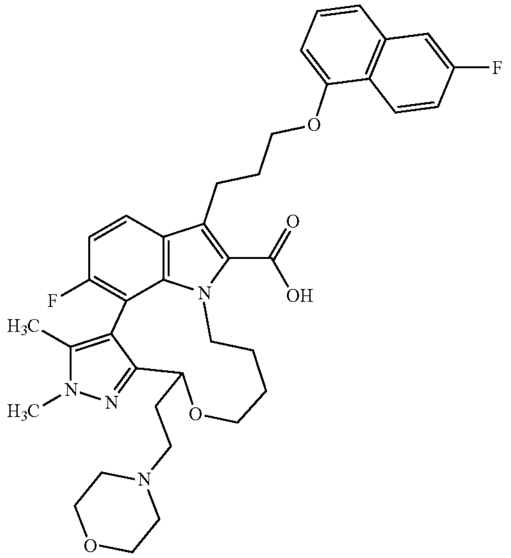 [SMILES: Cc1c2c(nn1C)C(CCN1CCOCC1)OCCCCn1c(C(=O)O)c(CCCOc3cccc4cc(F)ccc34)c3ccc(F)c-2c31]

For the preparation of the racemic title compound see Example 19. Separation of enantiomers by preparative chiral HPLC (method see Example 19) gave the title compound (60 mg).

Analytical Chiral HPLC (method see Example 19): $R_t$=3.37 min.

LC-MS (Method 1): $R_t$=1.14 min; MS (ESIneg): m/z=671 [M−H]$^-$

Specific Optical Rotation (Method O1): −69.6° (c=10 mg/mL, DMSO)

$^1$H-NMR (400 MHz, DMSO-d6) δ[ppm]: 0.810 (0.58), 0.859 (0.46), 0.967 (1.88), 0.994 (1.98), 1.009 (1.65), 1.107 (5.44), 1.137 (2.33), 1.144 (2.10), 1.155 (4.83), 1.173 (2.65), 1.203 (0.65), 1.208 (1.60), 1.229 (0.44), 1.319 (0.58), 1.332 (0.54), 1.767 (0.42), 1.891 (16.00), 1.964 (0.65), 1.982 (1.65), 2.000 (1.85), 2.017 (0.88), 2.152 (0.46), 2.168 (1.29), 2.185 (2.02), 2.202 (1.63), 2.217 (2.00), 2.236 (2.56), 2.261 (4.02), 2.332 (0.92), 2.336 (0.46), 2.518 (5.35), 2.522 (3.46), 2.673 (0.88), 2.855 (0.69), 2.873 (1.81), 2.891 (1.81), 2.909 (0.92), 2.928 (0.81), 2.940 (0.63), 2.957 (0.83), 3.173 (0.69), 3.188 (0.77), 3.205 (1.10), 3.225 (0.73), 3.275 (2.08), 3.287 (3.10), 3.304 (3.81), 3.320 (5.00), 3.336 (5.23), 3.479 (4.73), 3.783 (0.52), 3.873 (0.69), 4.163 (1.46), 4.179 (2.98), 4.195 (1.48), 4.364 (0.94), 4.382 (2.06), 4.399 (0.90), 4.513 (0.60), 4.546 (0.58), 6.833 (1.37), 6.839 (1.46), 6.848 (1.31), 6.855 (1.54), 6.874 (1.02), 6.896 (1.69), 6.919 (1.00), 7.349 (0.92), 7.355 (1.08), 7.371 (1.46), 7.378 (1.65), 7.393 (1.10), 7.400 (1.15), 7.411 (2.50), 7.421 (2.98), 7.426 (6.10), 7.441 (0.56), 7.632 (2.15), 7.638 (2.37), 7.658 (2.56), 7.664 (2.17), 8.234 (1.48), 8.250 (1.54), 8.258 (1.50), 8.272 (1.46).

Example 22

(rac)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid

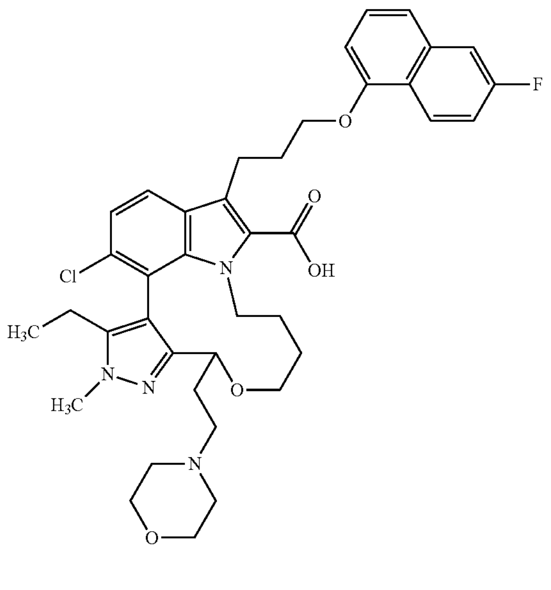 [SMILES: CCc1c2c(nn1C)C(CCN1CCOCC1)OCCCCn1c(C(=O)O)c(CCCOc3cccc4cc(F)ccc34)c3ccc(Cl)c-2c31]

To a solution of (rac)-ethyl-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino-[8,7,6-hi]indole-8-carboxylate (see Intermediate 55, 410 mg) in a mixture of tetrahydrofuran (10 mL) and ethanol (4 mL) was added aqueous lithium hydroxide solution (1.1 mL, 1.0 M, 1.1 mmol), and the mixture was stirred at 70° C. overnight. Additional aqueous lithium hydroxide solution (300 μL; 1.0 M) were added, and stirring was continued at 70° C. for 72 hours. The mixture was concentrated under reduced pressure, and the residue was diluted with water and acidified using an aqueous, saturated solution of citric acid. The mixture was extracted with a mixture of THF and ethyl acetate and the combined organic layers were concentrated under reduced pressure. The crude material was purified by flash chromatography using silica gel (gradient dichloromethane/ethanol) to give 235 mg of the title compound.

LC-MS (Method 2): $R_t$=0.93 min; MS (ESIpos): m/z=703 [M+H]$^+$ $^1$H-NMR (400 MHz, DMSO-d6) δ[ppm]: 0.793 (3.22), 0.797 (1.84), 0.803 (0.98), 0.812 (7.47), 0.821 (1.48), 0.831 (3.29), 0.840 (0.61), 0.886 (0.54), 0.904 (1.09), 0.922 (0.52), 1.029 (0.86), 1.052 (0.68), 1.124 (0.45), 1.142 (0.64), 1.268 (0.54), 2.109 (1.00), 2.144 (0.50), 2.162 (0.93), 2.180 (2.07), 2.191 (2.22), 2.200 (2.47), 2.210 (2.29), 2.228 (1.18), 2.247 (0.48), 2.318 (0.70), 2.322 (1.25), 2.327 (1.59), 2.332 (1.27), 2.336 (0.75), 2.359 (0.57), 2.373 (0.66), 2.388 (0.79), 2.394 (0.82), 2.406 (0.89), 2.412 (1.00), 2.518 (4.97), 2.523 (3.36), 2.660 (0.50), 2.664 (1.00), 2.669 (1.36), 2.673 (1.00), 2.678 (0.48), 3.034 (0.57), 3.049 (0.54), 3.261 (1.04), 3.278 (1.88), 3.295 (2.66), 3.554 (2.25), 3.824 (0.75), 3.864 (16.00), 3.887 (0.66), 3.903 (0.66), 3.922 (0.68), 4.173 (1.23), 4.188 (2.56), 4.203 (1.36), 4.314 (0.59), 4.331 (0.54), 4.349 (0.54), 4.404 (0.86), 4.421 (1.72), 4.438 (0.79), 5.758 (6.51), 6.844 (1.25), 6.850 (1.29), 6.859 (1.20), 6.865 (1.41), 7.204 (4.02), 7.225 (3.90), 7.353 (0.84), 7.359 (1.04), 7.375 (1.32), 7.382 (1.50), 7.397 (0.93), 7.404 (1.38), 7.425 (2.25), 7.433 (2.63), 7.440 (5.76), 7.454 (0.50), 7.641 (1.52), 7.648 (1.57), 7.667 (1.52), 7.674 (1.54), 7.747 (3.25), 7.768 (2.84), 8.219 (1.32), 8.234 (1.38), 8.243 (1.32), 8.257 (1.34).

The title compound (226 mg) was separated into enantiomers by preparative chiral HPLC to give enantiomer 1 (108 mg, see Example 23) and enantiomer 2 (98 mg, see Example 24).

Preparative Chiral HPLC Method:

Instrument: Labomatic HD5000, Labocord-5000; Gilson GX-241, Labcol Vario 4000, column: Chiralpak IG 5μ 250×30 mm; Eluent A: hexane+0.1 Vol-% N-ethyl ethanamine (99%); Eluent B: ethanol; isocratic: 70% A+30% B; Flow 50.0 mL/min; UV 254 nm Analytical Chiral HPLC Method:

Instrument: Agilent HPLC 1260; column: Chiralpak IG 3μ 100×4.6 mm; Eluent A: hexane+0.1 Vol-% N-ethyl ethanamine (99%); Eluent B: ethanol; isocratic 70% A+30% B; Flow 1.4 mL/min; Temperature: 25° C.; DAD 254 nm Example 23

(+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid—N-ethylethanamine (Enantiomer 1)

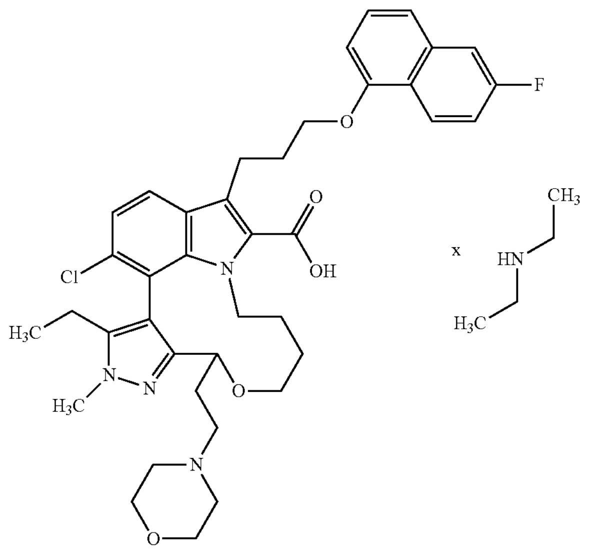

For the preparation of the racemic title compound see Example 22. Separation of enantiomers by preparative chiral HPLC (method see Example 22) gave the title compound (108 mg).

Analytical Chiral HPLC (method see Example 22): $R_t$=1.31 min.

LC-MS (Method 1): $R_t$=1.20 min; MS (ESIpos): m/z=703 $[M+H]^+$

Specific Optical Rotation (Method O1): +44.1° (c=10 mg/mL, DMSO)

$^1$H-NMR (400 MHz, DMSO-d6) δ[ppm]: 0.806 (1.75), 0.814 (0.65), 0.825 (3.99), 0.844 (1.87), 0.982 (0.75), 1.005 (0.44), 1.133 (7.48), 1.151 (16.00), 1.169 (7.96), 1.232 (0.44), 1.259 (0.63), 2.015 (0.85), 2.032 (0.94), 2.050 (0.43), 2.181 (0.84), 2.200 (1.63), 2.218 (1.40), 2.238 (0.66), 2.283 (1.49), 2.292 (1.47), 2.298 (1.49), 2.311 (1.21), 2.318 (0.97), 2.322 (1.12), 2.327 (1.34), 2.332 (1.05), 2.518 (3.11), 2.523 (2.19), 2.539 (6.12), 2.665 (0.62), 2.669 (0.87), 2.673 (0.62), 2.846 (2.05), 2.864 (6.59), 2.883 (6.36), 2.900 (1.93), 3.036 (0.41), 3.183 (0.56), 3.210 (0.44), 3.229 (0.69), 3.247 (0.62), 3.284 (1.35), 3.486 (1.90), 3.494 (1.91), 3.504 (1.15), 3.814 (0.49), 3.857 (8.43), 4.152 (0.44), 4.168 (0.88), 4.175 (0.90), 4.191 (0.47), 4.354 (0.47), 4.371 (0.99), 4.388 (0.44), 6.819 (0.66), 6.824 (0.69), 6.836 (0.66), 6.840 (0.72), 7.081 (1.15), 7.102 (1.19), 7.349 (0.44), 7.355 (0.52), 7.371 (0.71), 7.378 (0.81), 7.393 (0.52), 7.404 (1.13), 7.421 (2.25), 7.580 (0.84), 7.601 (0.75), 7.632 (0.81), 7.638 (0.85), 7.658 (0.81), 7.664 (0.82), 8.233 (0.71), 8.248 (0.74), 8.256 (0.71), 8.271 (0.66).

Example 24

(−)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (Enantiomer 2)

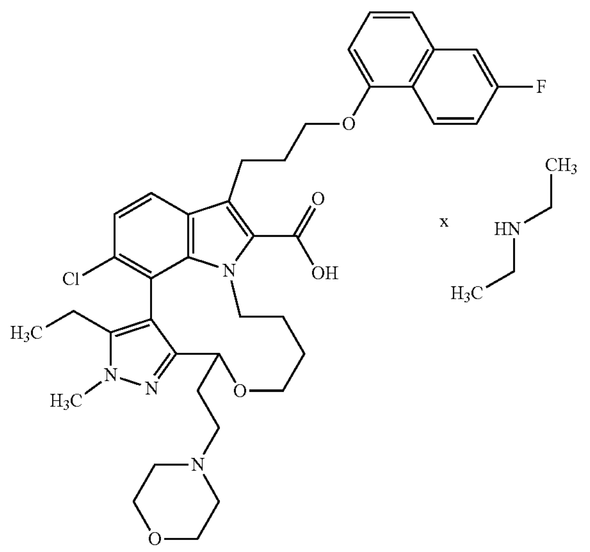

For the preparation of the racemic title compound see Example 22. Separation of enantiomers by preparative chiral HPLC (method see Example 22) gave the title compound (98 mg).

Analytical Chiral HPLC (method see Example 22): $R_t$=2.51 min.

LC-MS (Method 1): $R_t$=1.18 min; MS (ESIpos): m/z=703 $[M+H]^+$

Specific Optical Rotation (Method O1): −41.3° (c=10 mg/mL, DMSO)

$^1$H-NMR (400 MHz, DMSO-d6) δ[ppm]: 0.795 (0.74), 0.804 (3.50), 0.815 (1.27), 0.823 (7.82), 0.842 (3.65), 0.862 (0.50), 0.905 (0.50), 0.984 (1.49), 1.005 (1.13), 1.035 (0.53), 1.084 (0.99), 1.130 (7.36), 1.148 (16.00), 1.166 (7.89), 1.204 (0.88), 1.232 (1.10), 1.259 (1.95), 1.905 (0.42), 1.998 (0.64), 2.017 (1.66), 2.034 (1.88), 2.051 (0.81), 2.189 (2.16), 2.198 (3.15), 2.217 (2.69), 2.236 (1.45), 2.283 (2.97), 2.299 (3.01), 2.312 (2.41), 2.318 (2.19), 2.322 (2.55), 2.327 (2.97), 2.332 (2.48), 2.518 (9.13), 2.523 (5.95), 2.539 (3.15), 2.660 (0.67), 2.665 (1.45), 2.669 (2.09), 2.673 (1.49), 2.848 (1.91), 2.865 (5.73), 2.884 (5.70), 2.902 (1.73), 3.007 (0.71), 3.017 (0.57), 3.035 (0.78), 3.152 (0.53), 3.167 (0.71), 3.185 (0.96), 3.207 (0.88), 3.227 (1.17), 3.244 (0.99), 3.282 (2.02), 3.487 (3.65), 3.494 (3.65), 3.781 (0.81), 3.802 (0.67), 3.813 (0.60), 3.838 (0.60), 3.857 (15.96), 4.168 (1.73), 4.174 (1.73), 4.357 (0.88), 4.374 (1.84), 4.392 (0.85), 4.466 (0.50), 4.500 (0.46), 6.821 (1.31), 6.826 (1.35), 6.838 (1.27), 6.843 (1.35), 7.088 (1.70), 7.109 (1.70), 7.348 (0.88), 7.355 (1.03), 7.371 (1.42), 7.377 (1.56), 7.384 (0.78), 7.393 (1.03), 7.400 (1.38), 7.405 (2.19), 7.422 (4.57), 7.438 (0.57), 7.590 (1.17), 7.611 (1.10), 7.630 (1.66), 7.637 (1.59), 7.656 (1.59), 7.663 (1.52), 8.232 (1.38), 8.247 (1.42), 8.255 (1.35), 8.270 (1.38).

Example 25

(rac)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid

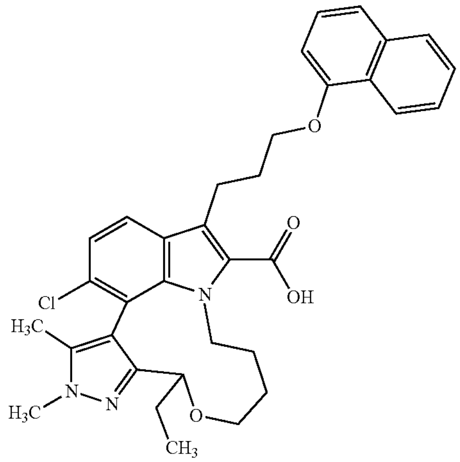 [SMILES: CCC1OCCCCn2c(C(=O)O)c(CCCOc3cccc4ccccc34)c3ccc(Cl)c(c32)-c2c1nn(C)c2C]

To a solution of (rac)-ethyl-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 59, 345 mg) in a mixture of tetrahydrofuran (4 mL) and ethanol (400 μL) was added aqueous lithium hydroxide solution (840 μL, 1.0 M, 840 μmol), and the mixture was stirred at 70° C. for 22 hours. Additional aqueous lithium hydroxide solution (420 μL, 1.0 M) was added and stirring was continued at 70° C. for 48 hours. The mixture was diluted with water and acidified using an aqueous, saturated solution of citric acid. The aqueous layer was extracted with ethyl acetate and the combined organic layers were dried using a water resistant filter and concentrated under reduced pressure. The crude material was purified by flash chromatography using silica gel (gradient dichloromethane/ethanol). The received material was again purified by preparative HPLC (Method P3) to give 162 mg of the title compound.

LC-MS (Method 1): $R_t$=1.64 min; MS (ESIpos): m/z=586 $[M+H]^+$ $^1$H-NMR (400 MHz, DMSO-d6) δ[ppm]: 0.847 (3.08), 0.865 (7.09), 0.884 (3.22), 0.968 (1.00), 0.979 (1.00), 1.199 (0.58), 1.229 (0.76), 1.253 (0.66), 1.802 (15.80), 1.862 (0.43), 1.878 (1.04), 1.895 (1.71), 1.912 (1.57), 1.930 (1.00), 1.946 (0.43), 2.073 (1.09), 2.185 (1.16), 2.202 (1.71), 2.219 (1.19), 2.237 (0.42), 2.518 (2.97), 2.522 (1.84), 3.027 (0.53), 3.039 (0.62), 3.054 (0.67), 3.220 (0.43), 3.240 (1.02), 3.253 (1.73), 3.271 (2.11), 3.294 (2.14), 3.828 (16.00), 3.922 (0.62), 3.939 (0.73), 3.955 (0.84), 4.118 (1.07), 4.135 (2.14), 4.153 (1.11), 4.172 (1.37), 4.187 (2.75), 4.202 (1.40), 4.332 (0.73), 4.347 (0.56), 4.367 (0.67), 6.872 (1.95), 6.889 (2.08), 7.194 (3.48), 7.215 (3.62), 7.361 (1.32), 7.381 (2.63), 7.400 (2.09), 7.441 (2.84), 7.462 (1.58), 7.478 (0.50), 7.482 (0.65), 7.495 (1.60), 7.499 (1.48), 7.507 (1.71), 7.514 (3.18), 7.519 (1.74), 7.527 (1.59), 7.531 (1.78), 7.544 (0.70), 7.549 (0.49), 7.745 (3.08), 7.766 (2.80), 7.851 (1.71), 7.858 (1.03), 7.870 (1.71), 7.874 (1.43), 8.187 (1.49), 8.191 (1.47), 8.211 (1.41).

Example 26

(rac)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid

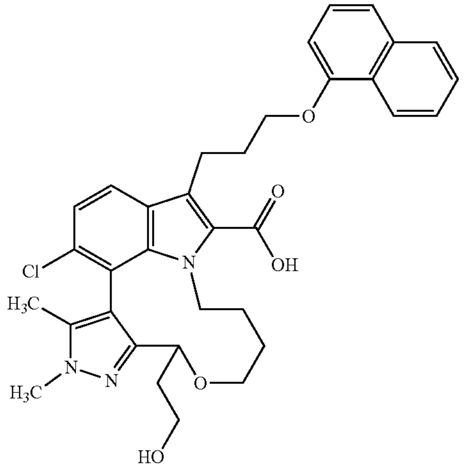 [SMILES: Cc1c2c(nn1C)C(CCO)OCCCCn1c(C(=O)O)c(CCCOc3cccc4ccccc34)c3ccc(Cl)c-2c31]

To a solution of (rac)-ethyl-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 66, 58.0 mg) in a mixture of tetrahydrofuran (2 mL) and ethanol (1 mL) was added aqueous lithium hydroxide solution (180 μL, 1.0 M, 180 μmol), and the mixture was stirred at 70° C. overnight. Additional aqueous lithium hydroxide solution (50 μL, 1.0 M) was added and stirring was continued at 70° C. for 72 hours. In another preparation, to another solution of (rac)-ethyl-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 66, 116 mg, 184 μmol) in a mixture of tetrahydrofuran (2 mL) and ethanol (1 mL) was added aqueous lithium hydroxide solution (370 μL, 1.0 M, 370 μmol), and the mixture was stirred at 70° C. overnight. Additional aqueous lithium hydroxide solution (100 μL, 1.0 M) was added and stirring was continued at 70° C. for 72 hours. The combined batches of both preparations were concentrated. The residue was diluted with water and neutralized using an aqueous, saturated solution of citric acid. The aqueous layer was extracted with a mixture of THF and ethyl acetate and the combined organic layers were dried over sodium sulfate, filtered and concentrated under reduced pressure. The crude material was purified by flash chromatography using silica gel (gradient dichloromethane/ethanol) to give 101 mg of the title compound.

LC-MS (Method 2): $R_t$=0.81 min; MS (ESIpos): m/z=602 $[M+H]^+$ $^1$H-NMR (400 MHz, DMSO-d6) δ[ppm]: 1.023 (0.77), 1.035 (2.48), 1.053 (4.04), 1.066 (0.58), 1.070 (2.10), 1.178 (0.48), 1.264 (0.54), 1.801 (15.47), 2.003 (0.63), 2.023 (0.88), 2.037 (0.72), 2.056 (0.41), 2.074 (0.66), 2.095 (0.80), 2.109 (0.60), 2.181 (1.05), 2.198 (1.56), 2.215 (1.09), 2.518 (3.08), 2.523 (2.03), 3.005 (0.47), 3.016 (0.55), 3.031 (0.58), 3.237 (0.53), 3.256 (0.88), 3.269 (1.71), 3.283 (1.20), 3.295 (1.45), 3.429 (0.99), 3.442 (1.97), 3.457 (1.80), 3.473 (0.86), 3.830 (16.00), 3.899 (0.60), 3.915 (0.66), 3.933 (0.72), 4.171 (1.33), 4.187 (2.76), 4.202 (1.33), 4.338 (0.76), 4.353 (1.55), 4.365 (2.07), 4.451 (1.01), 4.464 (1.12), 4.473 (1.23), 4.486 (0.96), 5.758 (4.28), 6.877 (1.84), 6.894 (2.03), 7.188 (3.62), 7.210 (3.75), 7.365 (1.36), 7.385 (2.61), 7.404 (2.10), 7.445 (2.74), 7.465 (1.52), 7.487 (0.41), 7.491 (0.60), 7.504 (1.59), 7.508 (1.47), 7.513 (1.72), 7.520 (3.43), 7.528 (1.85), 7.532 (1.65), 7.537 (1.75), 7.549 (0.69), 7.554 (0.42), 7.739 (3.04), 7.759 (2.74), 7.854 (1.58), 7.862 (0.85), 7.872 (1.46), 7.877 (1.36), 8.208 (1.40), 8.215 (1.30), 8.226 (0.72), 8.233 (1.31).

Example 27

(rac)-4-Chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic Acid

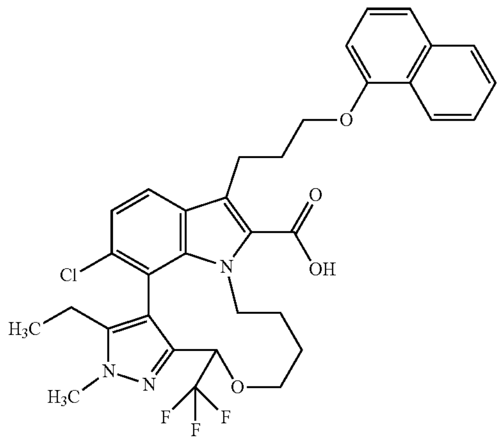 [SMILES: CCc1c2c(nn1C)C(C(F)(F)F)OCCCCn1c(C(=O)O)c(CCCOc3cccc4ccccc34)c3ccc(Cl)c-2c31]

(rac)-Ethyl-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylate (see Intermediate 70, 1.72 g, 51% purity) was reacted as described for the preparation of Example 26 to provide the title compound in 95% purity: 238 mg.

LC-MS (Method 1): $R_t$=1.65 min; MS (ESIpos): m/z=640 $[M+H]^+$ $^1$H-NMR (400 MHz, DMSO-d6) δ[ppm]: 0.795 (3.51), 0.814 (7.75), 0.833 (3.59), 0.882 (0.81), 0.901 (0.65), 1.053 (0.75), 1.330 (1.01), 1.987 (0.55), 2.074 (1.57), 2.174 (0.42), 2.192 (1.10), 2.210 (2.32), 2.225 (2.55), 2.243 (1.99), 2.262 (0.81), 2.332 (0.61), 2.518 (3.45), 2.523 (2.22), 3.278 (0.86), 3.295 (1.67), 3.370 (0.68), 3.387 (0.75), 3.399 (0.67), 3.414 (0.55), 3.425 (0.51), 3.485 (0.72), 3.514 (0.43), 3.819 (0.51), 3.826 (0.64), 3.833 (0.67), 3.853 (0.57), 3.908 (16.00), 4.173 (1.35), 4.189 (2.78), 4.204 (1.38), 4.368 (0.72), 4.380 (0.46), 4.391 (0.43), 4.403 (0.65), 4.627 (0.41), 4.646 (1.14), 4.664 (1.03), 6.857 (1.77), 6.874 (1.93), 7.251 (3.36), 7.273 (3.55), 7.354 (1.26), 7.374 (2.49), 7.393 (2.06), 7.433 (2.62), 7.454 (1.70), 7.460 (0.83), 7.473 (1.49), 7.476 (1.51), 7.493 (1.72), 7.497 (2.43), 7.501 (1.70), 7.516 (1.58), 7.520 (1.58), 7.533 (0.87), 7.537 (0.67), 7.825 (2.93), 7.846 (4.17), 7.863 (1.72), 7.867 (1.45), 8.133 (1.46), 8.136 (1.55), 8.155 (1.43).

Example 28

(rac)-4-Chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid

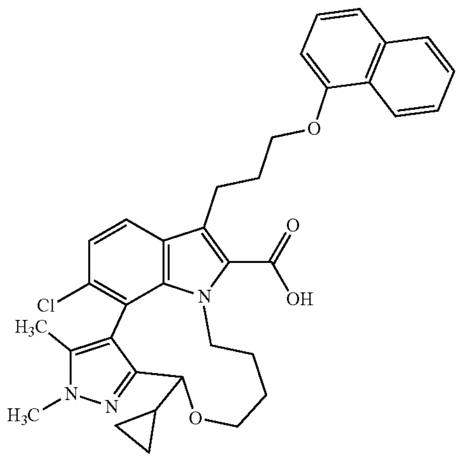 [SMILES: Cc1c2c(nn1C)C(C1CC1)OCCCCn1c(C(=O)O)c(CCCOc3cccc4ccccc34)c3ccc(Cl)c-2c31]

(rac)-Ethyl 4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 74, 450 mg, 90% purity, 647 μmol) was reacted as described for the preparation of Example 26 to provide the title compound in 99% purity: 254 mg.

LC-MS (Method 2): $R_t$=0.98 min; MS (ESIpos): m/z=598 $[M+H]^+$ $^1$H-NMR (400 MHz, DMSO-d6) δ[ppm]: 0.124 (0.55), 0.136 (0.72), 0.147 (0.57), 0.307 (0.55), 0.320 (0.67), 0.489 (1.79), 0.509 (1.64), 0.800 (0.44), 0.882 (1.07), 0.901 (2.44), 0.919 (1.27), 0.991 (0.81), 1.008 (1.11), 1.035 (2.31), 1.052 (4.81), 1.066 (15.82), 1.070 (3.51), 1.088 (0.50), 1.144 (0.50), 1.158 (0.86), 1.286 (0.47), 1.561 (0.60), 1.572 (0.59), 1.583 (0.59), 1.798 (15.37), 1.907 (0.68), 2.064 (3.22), 2.175 (0.96), 2.191 (1.45), 2.208 (1.04), 2.418 (0.63), 2.436 (0.62), 2.518 (2.93), 2.523 (1.90), 3.130 (0.46), 3.141 (0.57), 3.156 (0.59), 3.228 (0.55), 3.243 (0.75), 3.261 (1.24), 3.282 (1.27), 3.302 (2.16), 3.399 (1.30), 3.415 (1.06), 3.425 (0.96), 3.440 (0.80), 3.450 (0.49), 3.485 (2.42), 3.508 (2.28), 3.847 (16.00), 3.901 (0.60), 3.919 (0.63), 3.942 (0.89), 4.166 (1.01), 4.179 (2.03), 4.194 (1.04), 4.302 (0.60), 4.321 (0.55), 4.338 (0.55), 5.756 (5.97), 6.869 (1.72), 6.886 (1.90), 7.171 (3.76), 7.193 (3.98), 7.359 (1.37), 7.380 (2.47), 7.399 (2.02), 7.441 (2.59), 7.462 (1.48), 7.478 (0.46), 7.483 (0.62), 7.495 (1.53), 7.500 (1.37), 7.508 (1.66), 7.514 (3.24), 7.520 (1.66), 7.527 (1.51), 7.532 (1.69), 7.544 (0.70), 7.549 (0.46), 7.724 (3.24), 7.745 (2.91), 7.851 (1.51), 7.858 (0.89), 7.869 (1.59), 7.874 (1.30), 8.193 (1.33), 8.198 (1.32), 8.215 (1.24), 8.217 (1.28).

Example 29

(+)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

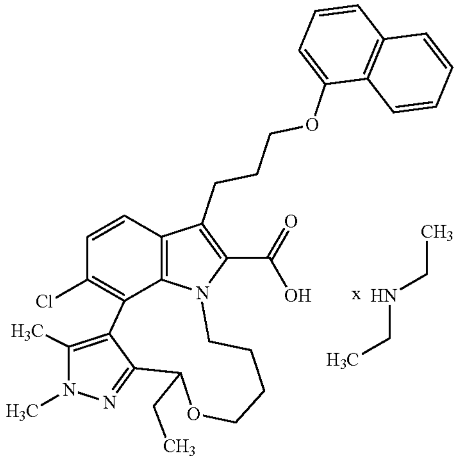

For the preparation of the racemic title compound see Example 25. Separation of enantiomers by preparative chiral HPLC gave the title compound (55 mg).

Preparative Chiral HPLC Method:

Instrument: Sepiatec: Prep SFC100; Column: Chiralpak IG 5 μm 250×30 mm; Eluent A: $CO_2$, Eluent B: 2-Propanol+0.4 Vol-% Diethylamine (99%); Isocratic: 24% B; Flow 100.0 mL/min Temperature: 40° C.; BPR: 150 bar; MWD @ 220 nm Analytical Chiral HPLC Method:

Instrument: Agilent: 1260, Aurora SFC-Module; Column: Chiralpak IG 5 μm 100×4.6 mm; Eluent A: $CO_2$, Eluent B: 2-Propanol+0.2 Vol-% Diethylamine (99%); Isocratic: 24% B; Flow 4.0 mL/min; Temperature: 37.5° C.; BPR: 100 bar; MWD@254 nm Analytical Chiral HPLC: $R_t$=1.66 min.

LC-MS (Method 2): $R_t$=0.94 min; MS (ESIpos): m/z=586 $[M+H]^+$

Specific Optical Rotation (Method O1): 55.6° (c=10 mg/mL, DMSO)

$^1$H-NMR (400 MHz, DMSO-d6) δ[ppm]: 0.830 (1.71), 0.849 (4.17), 0.856 (0.61), 0.867 (1.81), 0.949 (0.80), 0.964 (1.18), 1.105 (16.00), 1.137 (3.63), 1.142 (0.78), 1.155 (8.07), 1.173 (3.87), 1.194 (0.28), 1.205 (0.38), 1.221 (0.28), 1.312 (0.27), 1.330 (0.28), 1.344 (0.22), 1.813 (8.65), 1.840 (0.23), 1.855 (0.61), 1.862 (0.55), 1.874 (0.83), 1.879 (0.78), 1.892 (0.55), 1.898 (0.58), 1.915 (0.20), 2.151 (0.20), 2.167 (0.60), 2.185 (0.91), 2.202 (0.63), 2.219 (0.20), 2.332 (0.43), 2.336 (0.20), 2.518 (2.26), 2.522 (1.49), 2.678 (0.20), 2.857 (0.98), 2.876 (3.14), 2.894 (3.00), 2.912 (0.95), 2.997 (0.25), 3.015 (0.45), 3.026 (0.37), 3.033 (0.35), 3.043 (0.53), 3.062 (0.30), 3.120 (0.30), 3.138 (0.48), 3.154 (0.53), 3.171 (0.73), 3.190 (0.53), 3.251 (1.44), 3.269 (1.68), 3.283 (1.94), 3.783 (0.30), 3.822 (9.38), 3.850 (0.23), 4.081 (0.60), 4.098 (1.18), 4.117 (0.58), 4.148 (0.48), 4.155 (0.56), 4.164 (0.95), 4.171 (0.95), 4.180 (0.56), 4.187 (0.46), 4.466 (0.33), 4.479 (0.23), 4.499 (0.32), 6.854 (0.96), 6.872 (1.05), 7.083 (1.49), 7.104 (1.59), 7.343 (0.68), 7.364 (1.34), 7.383 (1.06), 7.426 (1.51), 7.447 (0.85), 7.470 (0.23), 7.475 (0.35), 7.487 (0.86), 7.492 (0.80), 7.498 (0.96), 7.505 (1.98), 7.511 (0.93), 7.518 (0.88), 7.522 (1.00), 7.535 (0.40), 7.539 (0.25), 7.593 (1.11), 7.614 (1.00), 7.842 (0.90), 7.849 (0.50), 7.860 (0.90), 7.865 (0.76), 8.191 (0.76), 8.196 (0.73), 8.215 (0.71).

Example 30

(−)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

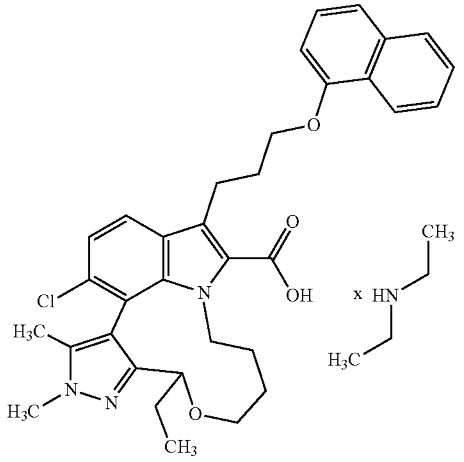

For the preparation of the racemic title compound see Example 25. Separation of enantiomers by preparative chiral HPLC (method see Example 29) gave the title compound (58 mg).

Analytical Chiral HPLC (method see Example 29): $R_t$=7.09 min.

LC-MS (Method 2): $R_t$=0.94 min; MS (ESIpos): m/z=586 $[M+H]^+$

Specific Optical Rotation (Method O1): −47.6° (c=10 mg/mL, DMSO) $^1$H-NMR (400 MHz, DMSO-d6) δ[ppm]: 0.833 (0.99), 0.851 (2.36), 0.869 (1.04), 0.953 (0.45), 0.966 (0.55), 1.107 (16.00), 1.142 (1.90), 1.159 (4.18), 1.178 (2.03), 1.208 (0.20), 1.230 (0.26), 1.816 (5.14), 1.857 (0.33), 1.864 (0.31), 1.876 (0.47), 1.882 (0.43), 1.894 (0.31), 1.900 (0.32), 2.171 (0.35), 2.188 (0.52), 2.205 (0.36), 2.332 (0.17), 2.518 (0.90), 2.522 (0.62), 2.673 (0.20), 2.851 (0.51), 2.869 (1.56), 2.887 (1.53), 2.905 (0.47), 3.019 (0.24), 3.028 (0.20), 3.036 (0.18), 3.046 (0.28), 3.140 (0.24), 3.154 (0.26), 3.173 (0.37), 3.192 (0.25), 3.256 (0.88), 3.272 (0.95), 3.288 (1.15), 3.825 (5.40), 4.084 (0.34), 4.102 (0.67), 4.119 (0.34), 4.149 (0.28), 4.164 (0.56), 4.173 (0.56), 4.180 (0.37), 4.188 (0.32), 4.488 (0.20), 4.521 (0.17), 6.852 (0.58), 6.870 (0.62), 7.080 (0.86), 7.101 (0.88), 7.343 (0.44), 7.363 (0.81), 7.383 (0.64), 7.427 (0.85), 7.448 (0.50), 7.475 (0.20), 7.487 (0.49), 7.492 (0.46), 7.499 (0.53), 7.506 (1.08), 7.511 (0.53), 7.518 (0.48), 7.523 (0.56), 7.535 (0.22), 7.589 (0.62), 7.610 (0.57), 7.843 (0.51), 7.851 (0.29), 7.861 (0.52), 7.867 (0.43), 8.195 (0.44), 8.200 (0.43), 8.219 (0.41).

Example 31

(+)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid (Enantiomer 1)

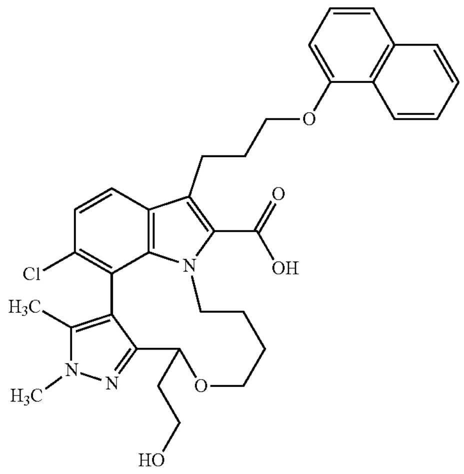 [SMILES: Cc1c2c(nn1C)C(CCO)OCCCCn1c(C(=O)O)c(CCCOc3cccc4ccccc34)c3ccc(Cl)c-2c31]

For the preparation of the racemic title compound see Example 26. Separation of enantiomers by preparative chiral HPLC gave the title compound (34.2 mg).

Preparative Chiral HPLC Method:

Instrument: Sepiatec: Prep SFC100; Column: Chiralpak IG 5 μm 250×30 mm; Eluent A: $CO_2$, Eluent B: Ethanol+0.2 Vol-% aqueous ammonia (32%); Isocratic: 25% B; Flow 100.0 mL/min Temperature: 40° C.; BPR: 150 bar; UV: 220 nm Analytical Chiral HPLC Method:

Instrument: Agilent: 1260, Aurora SFC-Module; Column: Chiralpak IG 5 μm 100×4.6 mm; Eluent A: $CO_2$, Eluent B: Ethanol+0.1 Vol-% aqueous ammonia (32%); Isocratic: 25% B; Flow 4.0 mL/min; Temperature: 37.5° C.; BPR: 100 bar; UV 254 nm Analytical Chiral HPLC: $R_t$=2.01 min.

LC-MS (Method 1): $R_t$=1.39 min; MS (ESIpos): m/z=602 $[M+H]^+$

Specific Optical Rotation (Method O1): +48.1° (c=10 mg/mL, DMSO)

$^1$H-NMR (400 MHz, DMSO-d6) δ[ppm]: 0.707 (0.29), 0.726 (0.70), 0.745 (0.34), 0.815 (0.22), 0.822 (0.22), 0.835 (0.59), 0.841 (0.35), 0.846 (0.84), 0.854 (1.36), 0.862 (2.98), 0.872 (0.72), 0.879 (1.24), 0.903 (0.20), 0.967 (0.86), 0.983 (0.33), 0.995 (0.38), 1.010 (0.41), 1.038 (1.24), 1.062 (0.22), 1.077 (0.16), 1.083 (0.17), 1.107 (16.00), 1.124 (0.27), 1.130 (0.78), 1.135 (1.09), 1.145 (1.03), 1.150 (1.13), 1.159 (0.25), 1.167 (0.19), 1.178 (0.17), 1.206 (0.34), 1.209 (0.37), 1.232 (0.48), 1.257 (0.34), 1.440 (0.42), 1.459 (0.38), 1.804 (5.26), 1.997 (0.29), 2.009 (0.42), 2.016 (0.43), 2.030 (0.34), 2.039 (0.48), 2.054 (0.20), 2.068 (0.27), 2.089 (0.32), 2.103 (0.46), 2.125 (0.17), 2.134 (0.31), 2.177 (0.37), 2.195 (0.61), 2.214 (0.43), 2.222 (0.24), 2.332 (0.42), 2.336 (0.21), 2.518 (1.86), 2.523 (1.36), 2.673 (0.46), 2.678 (0.26), 3.002 (0.19), 3.029 (0.22), 3.210 (0.23), 3.225 (0.29), 3.243 (0.43), 3.268 (0.59), 3.282 (0.81), 3.443 (0.61), 3.829 (5.64), 3.865 (0.20), 3.882 (0.21), 3.899 (0.22), 4.166 (0.42), 4.181 (0.87), 4.357 (0.42), 4.373 (0.34), 4.389 (0.19), 4.408 (0.20), 4.437 (0.36), 4.451 (0.39), 4.458 (0.42), 4.472 (0.32), 6.872 (0.63), 6.890 (0.67), 7.159 (1.01), 7.180 (1.02), 7.361 (0.46), 7.381 (0.88), 7.400 (0.71), 7.441 (0.96), 7.462 (0.53), 7.489 (0.21), 7.501 (0.54), 7.506 (0.51), 7.510 (0.60), 7.518 (1.17), 7.525 (0.61), 7.530 (0.56), 7.534 (0.60), 7.547 (0.22), 7.698 (0.72), 7.719 (0.66), 7.852 (0.56), 7.860 (0.29), 7.870 (0.50), 7.875 (0.46), 8.209 (0.47), 8.215 (0.43), 8.233 (0.42).

Example 32

(−)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid (Enantiomer 2)

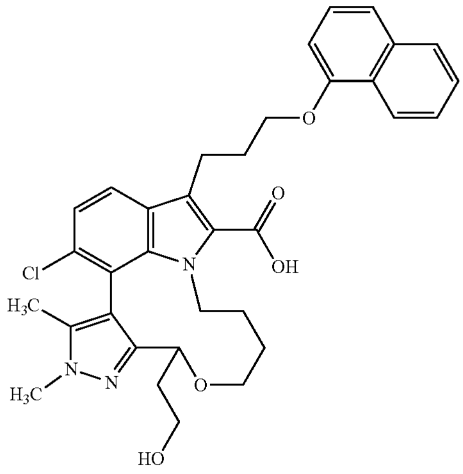 [SMILES: Cc1c2c(nn1C)C(CCO)OCCCCn1c(C(=O)O)c(CCCOc3cccc4ccccc34)c3ccc(Cl)c-2c31]

For the preparation of the racemic title compound see Example 26. Separation of enantiomers by preparative chiral HPLC (method see Example 31) gave the title compound (33.5 mg).

Analytical Chiral HPLC (method see Example 31): $R_t$=3.12 min.

LC-MS (Method 1): $R_t$=1.38 min; MS (ESIpos): m/z=602 $[M+H]^+$

Specific Optical Rotation (Method O1): −43.2° (c=10 mg/mL, DMSO)

$^1$H-NMR (400 MHz, DMSO-d6) δ[ppm]: 0.707 (0.73), 0.726 (1.98), 0.744 (0.89), 0.767 (0.22), 0.772 (0.25), 0.778 (0.25), 0.784 (0.26), 0.795 (0.32), 0.799 (0.33), 0.814 (0.48), 0.835 (1.51), 0.846 (2.29), 0.854 (3.56), 0.862 (7.76), 0.872 (1.83), 0.878 (3.30), 0.894 (0.37), 0.900 (0.43), 0.902 (0.37), 0.913 (0.29), 0.917 (0.40), 0.922 (0.28), 0.935 (0.25), 0.954 (0.32), 0.964 (0.78), 0.967 (1.68), 0.974 (0.57), 0.981 (0.80), 0.995 (0.75), 1.010 (0.78), 1.038 (3.06), 1.062 (0.53), 1.068 (0.36), 1.081 (0.40), 1.092 (0.42), 1.097 (0.32), 1.107 (16.00), 1.124 (0.43), 1.130 (2.04), 1.134 (2.77), 1.145 (2.67), 1.149 (2.87), 1.159 (0.51), 1.165 (0.42), 1.175 (0.32), 1.178 (0.35), 1.197 (0.44), 1.205 (0.60), 1.209 (0.66), 1.214 (0.69), 1.232 (1.00), 1.249 (0.82), 1.259 (0.66), 1.293 (0.22), 1.355 (0.22), 1.388 (0.26), 1.420 (0.42), 1.439 (1.08), 1.458 (1.01), 1.477 (0.32), 1.805 (7.95), 1.831 (0.18), 1.836 (0.18), 1.844 (0.25), 1.907 (0.24), 1.919 (0.17), 1.979 (0.29), 1.993 (0.51), 2.007 (1.04), 2.013 (0.82), 2.028 (0.65), 2.038 (1.21), 2.052 (0.40), 2.067 (0.48), 2.088 (0.58), 2.102 (0.91), 2.122 (0.32), 2.133 (0.86), 2.174 (0.58), 2.196 (0.93), 2.210 (0.89), 2.216 (0.65), 2.269 (0.35), 2.300 (0.29), 2.313 (0.35), 2.318

(0.35), 2.337 (0.33), 2.344 (0.25), 2.380 (0.26), 2.518 (2.73), 2.523 (2.15), 2.546 (0.21), 2.660 (0.47), 2.684 (0.24), 2.699 (0.19), 2.983 (0.18), 3.001 (0.33), 3.027 (0.37), 3.046 (0.21), 3.217 (0.43), 3.234 (0.58), 3.282 (1.25), 3.447 (1.15), 3.829 (9.30), 3.853 (0.32), 3.870 (0.32), 3.888 (0.32), 4.164 (0.62), 4.180 (1.19), 4.353 (0.44), 4.390 (0.33), 4.432 (0.72), 4.445 (0.69), 4.454 (0.71), 4.467 (0.55), 6.870 (0.91), 6.888 (0.97), 7.148 (1.63), 7.169 (1.69), 7.358 (0.68), 7.378 (1.30), 7.397 (1.01), 7.439 (1.54), 7.460 (0.89), 7.483 (0.21), 7.487 (0.28), 7.501 (0.76), 7.505 (0.75), 7.509 (0.97), 7.517 (1.73), 7.525 (0.90), 7.528 (0.91), 7.533 (0.91), 7.546 (0.35), 7.550 (0.22), 7.682 (1.05), 7.703 (0.96), 7.851 (0.94), 7.859 (0.46), 7.868 (0.80), 7.874 (0.79), 8.210 (0.65), 8.215 (0.61), 8.233 (0.64).

Example 33

(+)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

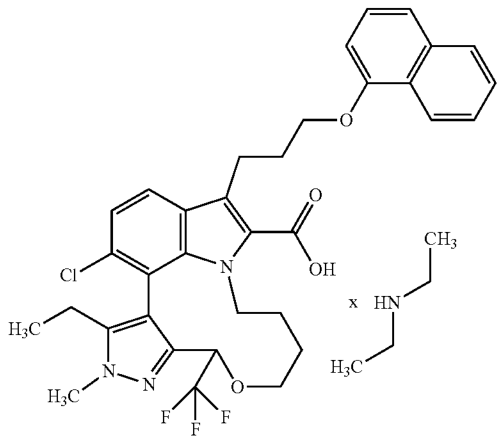

For the preparation of the racemic title compound see Example 27. Separation of enantiomers by preparative chiral HPLC gave the title compound (84.5 mg).

Preparative Chiral HPLC Method:

Instrument: Labomatic HD5000, Labocord-5000; Gilson GX-241, Labcol Vario 4000, Column: Amylose SA 5μ 250×30 mm; Eluent A: hexane+0.1 Vol-% diethylamine (99%); Eluent B: 2-propanol; Gradient: 10-50% B in 9 min, then isocratic 50% B; flow 40.0 mL/min; UV 254 nm Analytical Chiral HPLC Method:

Instrument: Agilent HPLC 1260; Column: Amylose SA 3μ 100×4.6 mm; Eluent A: hexane+0.1 Vol-% diethylamine (99%); Eluent B: 2-propanol; Gradient: 20-50% B in 7 min; flow 1.4 mL/min; temperature: 25° C.; UV: 254 nm Analytical Chiral HPLC: $R_t$=1.49 min.

LC-MS (Method 2): $R_t$=1.03 min; MS (ESIpos): m/z=640 $[M+H]^+$

Specific Optical Rotation (Method O1): +40.9° (c=10 mg/mL, DMSO)

$^1$H-NMR (400 MHz, DMSO-d6) δ[ppm]: 0.776 (0.44), 0.795 (1.05), 0.816 (2.85), 0.835 (6.02), 0.844 (1.31), 0.854 (3.19), 0.862 (1.39), 0.881 (1.03), 0.900 (0.47), 0.932 (0.44), 1.006 (0.83), 1.035 (0.56), 1.084 (1.51), 1.131 (7.41), 1.149 (16.00), 1.167 (7.67), 1.232 (1.05), 1.259 (2.27), 1.487 (0.41), 1.506 (0.44), 2.186 (0.77), 2.204 (1.15), 2.213 (1.23), 2.231 (2.11), 2.250 (1.85), 2.269 (0.57), 2.332 (0.69), 2.518 (3.83), 2.523 (2.68), 2.540 (0.87), 2.673 (0.69), 2.729 (0.98), 2.835 (2.03), 2.853 (6.13), 2.871 (6.07), 2.889 (2.90), 3.173 (0.54), 3.192 (0.83), 3.209 (0.82), 3.227 (0.95), 3.244 (0.75), 3.260 (0.70), 3.482 (0.62), 3.494 (0.51), 3.511 (0.44), 3.646 (0.49), 3.898 (1.44), 3.908 (12.01), 4.154 (0.98), 4.171 (1.98), 4.187 (1.06), 4.563 (0.46), 4.580 (0.59), 4.598 (1.33), 4.616 (0.90), 6.832 (1.39), 6.850 (1.51), 7.106 (1.93), 7.127 (2.03), 7.333 (0.93), 7.354 (1.83), 7.373 (1.42), 7.417 (2.00), 7.438 (1.31), 7.449 (0.49), 7.453 (0.54), 7.466 (1.10), 7.469 (1.11), 7.487 (1.87), 7.492 (1.90), 7.508 (1.28), 7.511 (1.28), 7.525 (0.72), 7.623 (1.49), 7.645 (1.37), 7.836 (1.28), 7.855 (1.33), 7.858 (1.11), 8.145 (1.18), 8.165 (1.10).

Example 34

(−)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

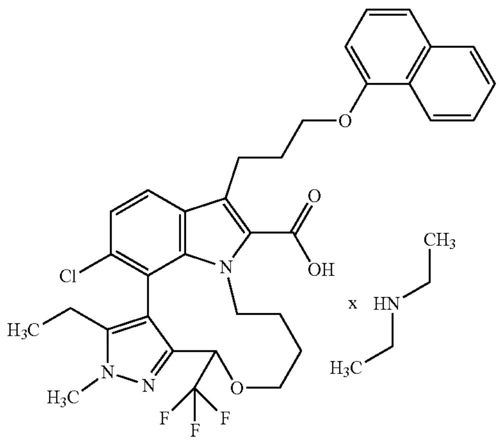

For the preparation of the racemic title compound see Example 27. Separation of enantiomers by preparative chiral HPLC (method see Example 33) gave the title compound (79.7 mg).

Analytical Chiral HPLC (method see Example 33): $R_t$=4.17 min.

LC-MS (Method 1): $R_t$=1.66 min; MS (ESIpos): m/z=640 $[M+H]^+$

Specific Optical Rotation (Method O1): −38.3° (c=10 mg/mL, DMSO)

$^1$H-NMR (400 MHz, DMSO-d6) δ[ppm]: 0.795 (0.73), 0.816 (3.34), 0.835 (7.20), 0.854 (3.73), 0.880 (0.69), 1.006 (0.53), 1.084 (0.85), 1.130 (7.38), 1.147 (16.00), 1.166 (7.82), 1.232 (1.26), 1.259 (1.21), 1.483 (0.48), 2.185 (0.91), 2.204 (1.39), 2.213 (1.53), 2.231 (2.56), 2.250 (2.24), 2.269 (0.69), 2.332 (0.96), 2.518 (6.61), 2.523 (4.39), 2.673 (1.01), 2.836 (2.10), 2.854 (6.31), 2.872 (6.15), 2.891 (1.92), 3.157 (0.46), 3.173 (0.64), 3.190 (1.01), 3.209 (0.94), 3.226 (1.10), 3.243 (0.85), 3.259 (0.78), 3.481 (0.78), 3.495 (0.64), 3.510 (0.55), 3.648 (0.57), 3.908 (14.01), 4.155 (1.21), 4.171 (2.35), 4.187 (1.17), 4.558 (0.55), 4.580 (0.78), 4.599 (1.44), 4.617 (1.05), 6.833 (1.69), 6.852 (1.81), 7.107 (1.97), 7.128 (2.08), 7.335 (1.12), 7.355 (2.22), 7.374 (1.69), 7.418 (2.42), 7.438 (1.42), 7.450 (0.57), 7.454 (0.62), 7.467 (1.33), 7.470 (1.33), 7.487 (2.31), 7.492 (2.22), 7.508 (1.33), 7.511 (1.42), 7.525 (0.69), 7.528 (0.53), 7.625 (1.51), 7.646 (1.37), 7.836 (1.58), 7.855 (1.53), 8.146 (1.46), 8.165 (1.37).

Example 35

(+)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid N-ethylethanamine Salt (Enantiomer 1)

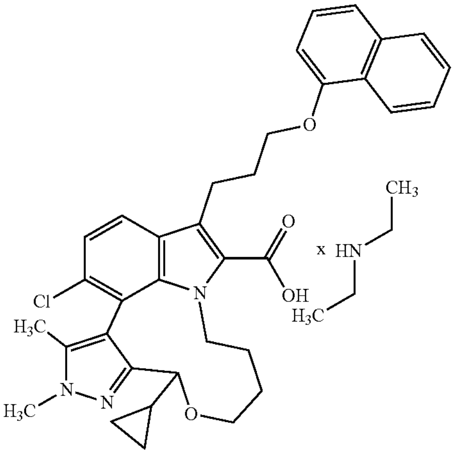

For the preparation of the racemic title compound see Example 28. Separation of stereoisomers by preparative chiral HPLC gave the title compound (91 mg).

Preparative Chiral HPLC Method:

Instrument: Labomatic HD5000, Labocord-5000; Gilson GX-241, Labcol Vario 4000, column: Amylose SA 5μ 250×30 mm; Eluent A: Hexane+0.1 Vol-% Diethylamine (99%); Eluent B: 2-propanol; Gradient: 20-50% B in 7 min, then isocratic 50% B; flow 40.0 mL/min; UV 254 nm Analytical Chiral HPLC Method:

Instrument: Agilent HPLC 1260; Column: Amylose SA 3μ 100×4.6 mm; Eluent A: Hexane+0.1 Vol-% Diethylamine (99%); Eluent B: 2-propanol; Gradient: 20-50% B in 7 min; Flow 1.4 mL/min; Temperature: 25° C.; UV: 254 nm Analytical Chiral HPLC: $R_t$=1.48 min.

LC-MS (Method 2): $R_t$=0.96 min; MS (ESIpos): m/z=598 $[M+H]^+$

Specific Optical Rotation (Method O1): +49.0° (c=10 mg/mL, DMSO)

$^1$H-NMR (400 MHz, DMSO-d6) δ[ppm]: 0.125 (0.41), 0.135 (0.54), 0.147 (0.64), 0.290 (0.63), 0.304 (0.49), 0.313 (0.44), 0.441 (0.48), 0.457 (1.28), 0.477 (1.35), 0.492 (0.45), 0.967 (1.05), 0.980 (1.12), 0.994 (0.99), 1.005 (0.59), 1.009 (0.50), 1.066 (16.00), 1.107 (8.23), 1.140 (5.29), 1.158 (12.03), 1.176 (5.35), 1.208 (0.56), 1.233 (0.75), 1.259 (0.89), 1.278 (0.48), 1.297 (0.44), 1.511 (0.58), 1.522 (0.54), 1.534 (0.56), 1.812 (13.42), 2.160 (0.94), 2.178 (1.43), 2.195 (1.00), 2.518 (2.52), 2.523 (1.73), 2.850 (1.40), 2.868 (4.51), 2.886 (4.31), 2.904 (1.33), 3.108 (0.69), 3.117 (0.69), 3.135 (1.08), 3.152 (0.75), 3.166 (0.87), 3.185 (0.49), 3.226 (0.66), 3.244 (1.20), 3.263 (1.14), 3.278 (1.48), 3.383 (2.18), 3.397 (1.58), 3.411 (1.23), 3.469 (2.27), 3.492 (2.12), 3.789 (0.53), 3.803 (0.54), 3.814 (0.56), 3.821 (0.58), 3.843 (13.91), 4.140 (0.66), 4.156 (1.40), 4.167 (1.42), 4.183 (0.69), 4.451 (0.46), 4.484 (0.44), 6.850 (1.58), 6.868 (1.68), 7.065 (2.07), 7.086 (2.16), 7.341 (1.20), 7.362 (2.19), 7.381 (1.68), 7.428 (2.24), 7.449 (1.33), 7.475 (0.51), 7.489 (1.35), 7.492 (1.20), 7.500 (1.43), 7.506 (2.93), 7.513 (1.47), 7.520 (1.28), 7.523 (1.49), 7.536 (0.56), 7.540 (0.40), 7.574 (1.47), 7.596 (1.34), 7.844 (1.33), 7.851 (0.78), 7.862 (1.38), 7.867 (1.13), 8.200 (1.19), 8.205 (1.14), 8.224 (1.12).

Example 36

(−)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid N-ethylethanamine Salt (Enantiomer 2)

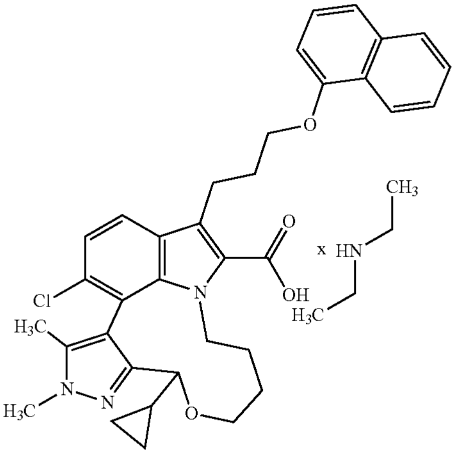

For the preparation of the racemic title compound see Example 28. Separation of enantiomers by preparative chiral HPLC (method see Example 35) gave the title compound (87.7 mg).

Analytical Chiral HPLC (method see Example 35): $R_t$=5.51 min.

LC-MS (Method 2): $R_t$=0.97 min; MS (ESIpos): m/z=598 $[M+H]^+$

Specific Optical Rotation (Method O1): −49.7° (c=10 mg/mL, DMSO)

$^1$H-NMR (400 MHz, DMSO-d6) δ[ppm]: 0.125 (0.50), 0.134 (0.66), 0.147 (0.76), 0.290 (0.74), 0.304 (0.60), 0.312 (0.53), 0.439 (0.60), 0.455 (1.50), 0.475 (1.59), 0.491 (0.51), 0.967 (1.44), 0.979 (1.37), 0.994 (1.31), 1.006 (0.60), 1.009 (0.63), 1.107 (12.64), 1.137 (6.41), 1.156 (14.30), 1.173 (6.56), 1.208 (0.79), 1.231 (0.94), 1.259 (0.68), 1.284 (0.53), 1.300 (0.48), 1.498 (0.43), 1.509 (0.69), 1.520 (0.64), 1.531 (0.68), 1.813 (15.83), 2.159 (1.14), 2.176 (1.74), 2.194 (1.19), 2.331 (0.69), 2.518 (3.37), 2.523 (2.13), 2.846 (1.72), 2.865 (5.40), 2.883 (5.09), 2.901 (1.59), 3.107 (0.88), 3.134 (1.09), 3.143 (0.83), 3.162 (0.98), 3.180 (0.50), 3.223 (0.66), 3.241 (1.26), 3.259 (1.09), 3.274 (1.37), 3.383 (2.05), 3.397 (1.54), 3.410 (1.22), 3.468 (2.63), 3.491 (2.43), 3.782 (0.51), 3.798 (0.61), 3.816 (0.61), 3.844 (16.00), 4.139 (0.79), 4.155 (1.69), 4.167 (1.69), 4.182 (0.79), 4.191 (0.51), 4.457 (0.56), 4.473 (0.46), 4.489 (0.53), 6.850 (1.85), 6.868 (2.02), 7.061 (2.35), 7.082 (2.41), 7.341 (1.37), 7.362 (2.58), 7.381 (2.05), 7.428 (2.68), 7.448 (1.55), 7.472 (0.45), 7.476 (0.63), 7.489 (1.57), 7.493 (1.45), 7.500 (1.67), 7.507 (3.37), 7.512 (1.67), 7.519 (1.57), 7.524 (1.75), 7.536 (0.73), 7.541 (0.50), 7.568 (1.65), 7.589 (1.49), 7.844 (1.60), 7.851 (0.91), 7.863 (1.64), 7.868 (1.36), 8.200 (1.42), 8.205 (1.37), 8.224 (1.31).

Example 37

(rac)-4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic Acid

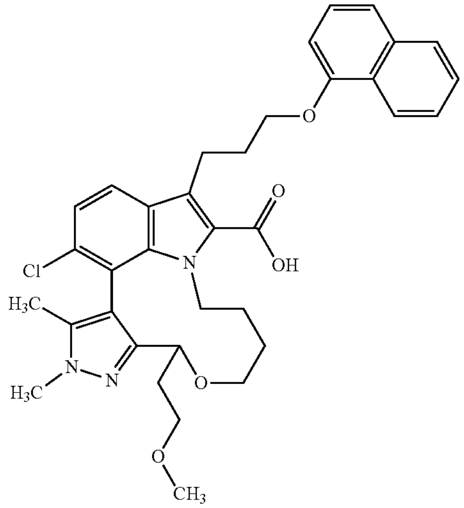 [SMILES: COCCC1OCCCCn2c(C(=O)O)c(CCCOc3cccc4ccccc34)c3ccc(Cl)c(c32)-c2c1nn(C)c2C]

(Rac)-ethyl 4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 75, 22.0 mg) was dissolved in a mixture of 2 mL of tetrahydrofuran and 1 mL of ethanol, aqueous lithium hydroxide solution (68 µL, 1.0 M, 68 µmol) was added and the mixture was stirred over night at 60° C. Aqueous lithium hydroxide solution (50 µL, 1.0 M, 50 µmol) was added and the mixture was stirred for 72 h at 70° C. The reaction mixture was concentrated under reduced pressure, the residue was diluted with water and neutralized using an aqueous solution of citric acid. The mixture was concentrated under reduced pressure to half of its volume and the precipitate was isolated by filtration, washed with water and dried to give 13.3 mg of the title compound.

LC-MS (Method 1): $R_t$=1.55 min; MS (ESIpos): m/z=616 $[M+H]^+$ $^1$H-NMR (400 MHz, DMSO-d6) δ[ppm]: 1.004 (0.57), 1.167 (9.08), 1.196 (0.42), 1.232 (0.89), 1.243 (1.13), 1.251 (1.23), 1.267 (1.78), 1.356 (0.21), 1.806 (10.53), 1.907 (0.15), 2.100 (0.55), 2.117 (1.38), 2.134 (1.34), 2.150 (0.62), 2.182 (0.87), 2.200 (1.23), 2.215 (0.85), 2.331 (0.79), 2.518 (4.39), 2.522 (2.70), 2.673 (0.81), 3.015 (0.25), 3.042 (0.43), 3.058 (0.43), 3.078 (0.36), 3.166 (16.00), 3.220 (0.21), 3.239 (0.43), 3.259 (0.83), 3.273 (1.23), 3.300 (1.12), 3.366 (0.83), 3.383 (1.15), 3.400 (0.62), 3.406 (0.62), 3.424 (0.28), 3.834 (11.37), 3.906 (0.42), 3.924 (0.49), 3.941 (0.51), 3.959 (0.25), 4.176 (1.04), 4.191 (2.08), 4.207 (1.00), 4.344 (0.49), 4.365 (0.43), 4.378 (0.49), 4.393 (0.89), 4.411 (1.40), 4.429 (0.64), 5.400 (0.34), 6.578 (1.27), 6.878 (1.36), 6.896 (1.49), 7.189 (0.23), 7.199 (2.40), 7.210 (0.26), 7.221 (2.46), 7.365 (0.98), 7.386 (1.91), 7.405 (1.55), 7.445 (2.06), 7.466 (1.15), 7.485 (0.30), 7.489 (0.43), 7.502 (1.13), 7.506 (1.10), 7.512 (1.30), 7.519 (2.50), 7.526 (1.36), 7.531 (1.23), 7.535 (1.27), 7.548 (0.49), 7.552 (0.30), 7.750 (1.99), 7.771 (1.80), 7.854 (1.21), 7.862 (0.66), 7.872 (1.12), 7.878 (1.02), 8.204 (0.98), 8.210 (0.98), 8.228 (0.96), 13.279 (0.23).

Example 38

(rac)-4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid

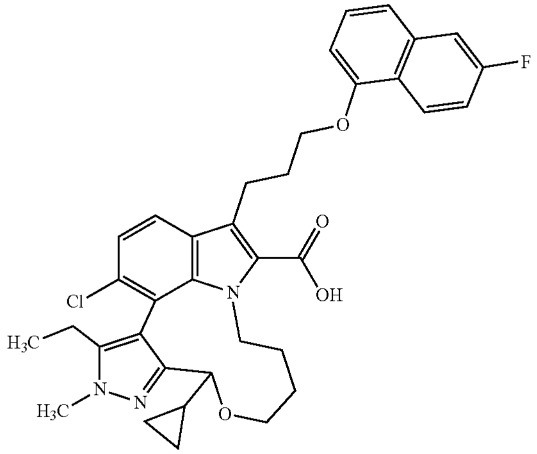 [SMILES: CCc1c2c(nn1C)C(C1CC1)OCCCCn1c(C(=O)O)c(CCCOc3cccc4cc(F)ccc34)c3ccc(Cl)c-2c31]

(Rac)-ethyl 4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 79, 605 mg) was dissolved in a mixture of 7 mL of tetrahydrofuran and 700 µL of ethanol, lithium hydroxide solution (1.8 mL, 1.0 M in water, 1.8 mmol) was added and the mixture was stirred for 72 h at 70° C. Lithium hydroxide solution (0.9 mL, 1.0 M in water, 0.9 mmol) was added and the mixture was stirred for 48 h at 70° C. Water was added and the mixture was adjusted to a pH value of 3-4 with a saturated aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol) to provide 505 mg of the title compound.

LC-MS (Method 2): $R_t$=1.02 min; MS (ESIpos): m/z=630 $[M+H]^+$ $^1$H-NMR (400 MHz, DMSO-d6) δ[ppm]: 0.127 (0.53), 0.138 (0.71), 0.149 (0.72), 0.321 (0.70), 0.332 (0.79), 0.346 (0.56), 0.502 (2.00), 0.523 (1.95), 0.793 (3.20), 0.812 (7.57), 0.830 (3.41), 0.873 (0.22), 0.883 (0.54), 0.901 (1.08), 0.920 (0.53), 0.991 (0.73), 1.008 (1.06), 1.035 (5.75), 1.052 (10.48), 1.070 (5.26), 1.092 (0.57), 1.110 (0.53), 1.153 (0.34), 1.171 (0.35), 1.189 (0.22), 1.229 (0.42), 1.248 (0.34), 1.265 (0.61), 1.283 (0.67), 1.567 (0.30), 1.576 (0.41), 1.588 (0.62), 1.599 (0.63), 1.610 (0.64), 1.619 (0.40), 1.631 (0.28), 1.907 (1.01), 1.986 (0.58), 2.064 (1.32), 2.090 (0.21), 2.131 (0.17), 2.150 (0.80), 2.168 (2.21), 2.190 (2.70), 2.208 (1.56), 2.419 (0.29), 2.437 (0.26), 2.454 (0.24), 2.459 (0.34), 2.465 (0.47), 2.470 (0.67), 2.518 (2.39), 2.522 (1.41), 2.528 (0.27), 2.533 (0.18), 2.538 (0.20), 2.543 (0.20), 2.548 (0.18), 3.124

(0.30), 3.150 (0.61), 3.162 (0.67), 3.188 (0.36), 3.254 (1.09), 3.271 (1.86), 3.291 (1.15), 3.406 (0.98), 3.424 (1.26), 3.431 (1.36), 3.441 (1.16), 3.474 (2.41), 3.499 (2.26), 3.856 (0.48), 3.876 (16.00), 3.891 (0.79), 3.908 (0.72), 3.926 (0.68), 4.016 (0.17), 4.165 (1.13), 4.179 (2.16), 4.194 (1.20), 4.257 (0.37), 4.272 (0.67), 4.288 (0.65), 4.306 (0.60), 4.358 (0.54), 6.837 (1.29), 6.843 (1.32), 6.852 (1.22), 6.858 (1.38), 7.168 (3.59), 7.189 (3.90), 7.341 (0.83), 7.348 (0.96), 7.363 (1.36), 7.370 (1.46), 7.386 (0.89), 7.393 (1.01), 7.398 (0.57), 7.419 (2.36), 7.428 (2.78), 7.434 (5.69), 7.449 (0.49), 7.528 (0.21), 7.535 (0.20), 7.549 (0.46), 7.554 (0.41), 7.564 (0.55), 7.572 (0.48), 7.595 (0.68), 7.612 (0.58), 7.621 (0.69), 7.624 (0.79), 7.634 (1.63), 7.641 (2.00), 7.660 (1.55), 7.667 (1.55), 7.714 (3.29), 7.736 (2.88), 8.188 (1.34), 8.203 (1.40), 8.211 (1.35), 8.226 (1.26), 13.251 (0.23).

The title compound (505 mg) was separated into enantiomers by preparative chiral HPLC to give enantiomer 1 (206 mg, see Example 39) and enantiomer 2 (160 mg, see Example 40).

Preparative Chiral HPLC Method:

Instrument: Labomatic HD5000, Labocord-5000; Gilson GX-241, Labcol Vario 4000, Column: Chiralpak IE 5μ 250×30 mm; Eluent A: Hexane+0.1 Vol-% Diethylamine (99%); Eluent B: Ethanol, Gradient: 20-50% B in 11 min; flow 40 mL/min; UV 254 nm Analytical Chiral HPLC Method:

Instrument: Agilent HPLC 1260; Column: Chiralpak IE 3μ 100×4.6 mm; Eluent A: Hexane+0.1 Vol-% Diethylamine (99%), Eluent B: Ethanol Gradient: 20-50% B, 7 min; Flow 1.4 mL/min; Temperature: 25° C.; UV 254 nm

Example 39

(+)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

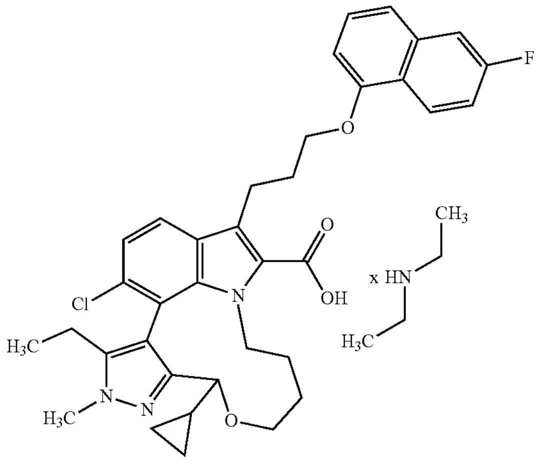

For the preparation of the racemic title compound see Example 38. Separation of enantiomers by preparative chiral HPLC (method see Example 38) gave the title compound (206 mg).

Analytical Chiral HPLC (method see Example 38): $R_t$=3.08 min.

LC-MS (Method 2): $R_t$=1.00 min; MS (ESIpos): m/z=630 $[M+H]^+$

Specific Optical Rotation (Method O1): +40.5° (c=10 mg/mL, DMSO)

$^1$H-NMR (400 MHz, DMSO-d6) δ[ppm]: 0.140 (0.22), 0.147 (0.29), 0.160 (0.45), 0.172 (0.37), 0.277 (0.36), 0.290 (0.40), 0.301 (0.25), 0.309 (0.22), 0.452 (0.30), 0.461 (0.97), 0.473 (0.52), 0.482 (0.97), 0.493 (0.27), 0.796 (0.22), 0.809 (1.57), 0.828 (3.68), 0.838 (0.39), 0.847 (1.66), 0.903 (0.22), 0.921 (0.18), 0.958 (0.61), 0.965 (0.56), 0.972 (0.52), 0.986 (0.28), 0.990 (0.27), 1.082 (0.16), 1.106 (16.00), 1.128 (4.28), 1.147 (9.81), 1.164 (4.41), 1.203 (0.32), 1.218 (0.33), 1.229 (0.42), 1.246 (0.30), 1.258 (0.37), 1.264 (0.34), 1.280 (0.25), 1.296 (0.17), 1.512 (0.19), 1.525 (0.31), 1.536 (0.29), 1.547 (0.30), 1.557 (0.18), 1.959 (0.17), 2.149 (0.20), 2.167 (0.69), 2.186 (1.23), 2.197 (0.78), 2.208 (0.97), 2.226 (0.34), 2.332 (0.38), 2.518 (1.80), 2.523 (1.30), 2.539 (0.26), 2.678 (0.16), 2.835 (1.12), 2.853 (3.53), 2.871 (3.48), 2.890 (1.04), 3.079 (0.22), 3.097 (0.39), 3.106 (0.36), 3.115 (0.41), 3.125 (0.50), 3.147 (0.53), 3.166 (0.67), 3.183 (0.58), 3.198 (0.79), 3.216 (0.66), 3.231 (0.69), 3.450 (2.41), 3.473 (1.91), 3.727 (0.21), 3.744 (0.30), 3.760 (0.34), 3.778 (0.32), 3.795 (0.20), 3.850 (0.21), 3.870 (8.45), 4.130 (0.22), 4.138 (0.36), 4.154 (0.77), 4.166 (0.78), 4.182 (0.38), 4.190 (0.27), 4.206 (0.22), 4.461 (0.27), 4.477 (0.22), 4.494 (0.26), 6.812 (0.60), 6.816 (0.63), 6.828 (0.62), 6.833 (0.65), 7.045 (1.46), 7.066 (1.52), 7.339 (0.39), 7.346 (0.43), 7.362 (0.62), 7.368 (0.68), 7.376 (0.31), 7.384 (0.44), 7.390 (0.53), 7.397 (0.97), 7.413 (2.01), 7.432 (0.30), 7.537 (1.03), 7.558 (0.94), 7.623 (0.74), 7.630 (0.77), 7.649 (0.73), 7.656 (0.75), 8.212 (0.59), 8.227 (0.64), 8.235 (0.63), 8.250 (0.59).

Example 40

(−)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

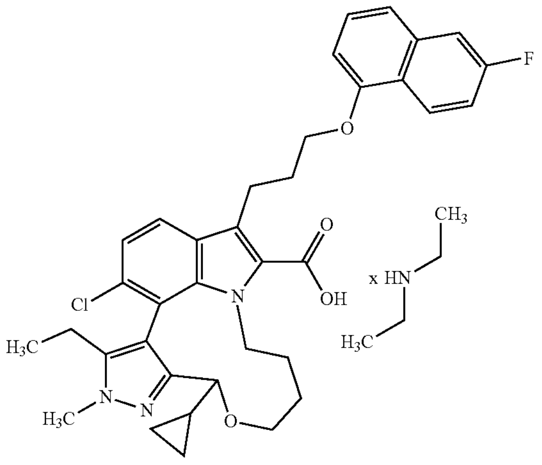

For the preparation of the racemic title compound see Example 38. Separation of enantiomers by preparative chiral HPLC (method see Example 38) gave the title compound (160 mg).

Analytical Chiral HPLC (method see Example 38): $R_t$=4.25 min.

LC-MS (Method 2): $R_t$=0.98 min; MS (ESIpos): m/z=630 $[M+H]^+$

Specific Optical Rotation (Method O1): −41.0° (c=10 mg/mL, DMSO)

$^1$H-NMR (400 MHz, DMSO-d6) δ[ppm]: 0.140 (0.24), 0.149 (0.33), 0.162 (0.50), 0.173 (0.41), 0.280 (0.39), 0.294 (0.45), 0.305 (0.30), 0.463 (1.11), 0.475 (0.61), 0.483 (1.08), 0.797 (0.31), 0.810 (1.75), 0.821 (0.66), 0.829 (4.03), 0.840 (0.49), 0.847 (1.83), 0.886 (0.17), 0.904 (0.30), 0.922 (0.22), 0.962 (0.71), 1.107 (16.00), 1.131 (4.35), 1.150 (9.50), 1.168 (4.56), 1.208 (0.34), 1.229 (0.46), 1.259 (0.45), 1.277 (0.29), 1.508 (0.18), 1.516 (0.22), 1.529 (0.36), 1.539 (0.35), 1.550 (0.35), 1.562 (0.21), 1.570 (0.16), 2.150 (0.24), 2.168 (0.90), 2.186 (1.62), 2.207 (1.25), 2.226 (0.40), 2.518 (1.92), 2.523 (1.32), 2.660 (0.19), 2.836 (1.13), 2.854 (3.47), 2.872 (3.39), 2.890 (1.07), 3.082 (0.22), 3.100 (0.41), 3.110 (0.36), 3.128 (0.50), 3.140 (0.40), 3.154 (0.47), 3.173 (0.67), 3.187 (0.53), 3.204 (0.75), 3.221 (0.59), 3.237 (0.59), 3.454 (1.59), 3.476 (1.43), 3.734 (0.18), 3.751 (0.30), 3.768 (0.34), 3.786 (0.32), 3.802 (0.18), 3.871 (8.71), 4.140 (0.40), 4.155 (0.89), 4.168 (0.90), 4.183 (0.47), 4.191 (0.36), 4.461 (0.30), 4.478 (0.26), 4.494 (0.29), 6.811 (0.69), 6.816 (0.73), 6.828 (0.71), 6.833 (0.73), 7.050 (1.50), 7.071 (1.58), 7.339 (0.44), 7.345 (0.49), 7.361 (0.72), 7.368 (0.78), 7.376 (0.36), 7.384 (0.48), 7.390 (0.58), 7.397 (1.09), 7.414 (2.32), 7.433 (0.33), 7.544 (1.16), 7.565 (1.08), 7.595 (0.18), 7.625 (0.93), 7.632 (0.90), 7.651 (0.82), 7.658 (0.81), 8.212 (0.68), 8.227 (0.71), 8.235 (0.70), 8.250 (0.65).

Example 41

(rac)-4-chloro-3-ethyl-7-{3-[(6-fluoronaphthalen-1-yl)oxy]propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylic Acid

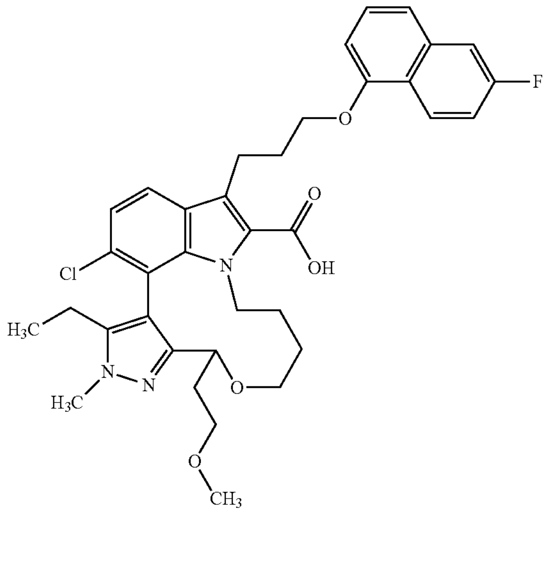 [SMILES: CCc1c2c(nn1C)C(CCOC)OCCCCn1c(C(=O)O)c(CCCOc3cccc4cc(F)ccc34)c3ccc(Cl)c-2c31]

(Rac)-ethyl 4-chloro-3-ethyl-7-{3-[(6-fluoronaphthalen-1-yl)oxy]propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylate (see Intermediate 87, 380 mg) was dissolved in a mixture of 10 mL of tetrahydrofuran and 3 mL of ethanol, aqueous lithium hydroxide solution (1.7 mL, 1.0 M, 1.7 mmol) was added and the mixture was stirred over night at 60° C. Aqueous lithium hydroxide solution (500 μL, 1.0 M, 500 μmol) was added and the mixture was stirred for 16 h at 60° C. The mixture was concentrated, diluted with water, adjusted to pH 7 by addition of an aqueous saturated solution of citric acid and was extracted with ethyl acetate. The combined organic layers were dried over sodium sulfate, filtered and concentrated under reduced pressure. The residue was purified by flash chromatography using silica gel (gradient dichloromethane/ethanol) to provide 237 mg of the title compound.

LC-MS (Method 1): $R_t$=1.60 min; MS (ESIpos): m/z=648 $[M+H]^+$ $^1$H-NMR (400 MHz, DMSO-d6) δ[ppm]: 0.792 (1.98), 0.811 (4.60), 0.830 (2.13), 0.850 (0.27), 0.993 (0.41), 1.172 (0.33), 1.232 (0.86), 1.264 (0.53), 1.282 (0.37), 1.907 (0.17), 2.106 (0.37), 2.123 (0.83), 2.139 (0.98), 2.147 (0.76), 2.157 (0.80), 2.176 (1.27), 2.188 (1.31), 2.195 (1.46), 2.207 (1.30), 2.224 (0.64), 2.243 (0.23), 2.336 (0.26), 2.518 (2.95), 2.523 (2.07), 2.678 (0.26), 3.026 (0.19), 3.051 (0.37), 3.065 (0.37), 3.083 (0.23), 3.090 (0.21), 3.171 (16.00), 3.242 (0.31), 3.257 (0.79), 3.275 (1.30), 3.292 (1.48), 3.375 (0.87), 3.391 (0.97), 3.408 (0.57), 3.414 (0.54), 3.432 (0.26), 3.862 (10.35), 3.888 (0.21), 3.905 (0.37), 3.922 (0.40), 3.939 (0.44), 3.957 (0.20), 4.173 (0.80), 4.188 (1.64), 4.204 (0.80), 4.297 (0.20), 4.311 (0.37), 4.328 (0.33), 4.345 (0.34), 4.361 (0.19), 4.394 (0.60), 4.413 (0.94), 4.430 (0.56), 5.758 (2.65), 6.847 (0.76), 6.854 (0.80), 6.862 (0.70), 6.869 (0.83), 7.204 (2.06), 7.225 (2.17), 7.355 (0.51), 7.362 (0.60), 7.377 (0.81), 7.385 (0.88), 7.400 (0.57), 7.406 (0.80), 7.426 (1.44), 7.435 (1.63), 7.441 (3.53), 7.456 (0.26), 7.565 (0.17), 7.596 (0.19), 7.612 (0.16), 7.622 (0.19), 7.641 (1.04), 7.648 (0.98), 7.667 (0.94), 7.674 (0.93), 7.743 (1.73), 7.765 (1.51), 8.233 (0.81), 8.248 (0.84), 8.256 (0.83), 8.271 (0.77).

The title compound (237 mg) was separated into enantiomers by preparative chiral HPLC to give enantiomer 1 (69.7 mg, see Example 42) and enantiomer 2 (54.8 mg, see Example 43).

Preparative Chiral HPLC Method:

Instrument: Sepiatec: Prep SFC100; column: Chiralpak IG 5μ 250×30 mm; Eluent A: $CO_2$; Eluent B: 2-Propanol+0.4% Diethylamine (99%); Isocratic: 25% B; Flow: 100 mL/min; Temperature: 40° C.; BPR: 150 bar; UV: 254 nm Analytical Chiral HPLC Method:

Instrument: Agilent: 1260, Aurora SFC-Module; column: Chiralpak IG 5μ 100×4.6 mm; Eluent A: $CO_2$; Eluent B: 2-Propanol+0.2% Diethylamine (99%); Isocratic: 25% B; Flow: 4 mL/min; Temperature: 40° C.; BPR: 150 bar; UV: 254 nm Example 42

(+)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

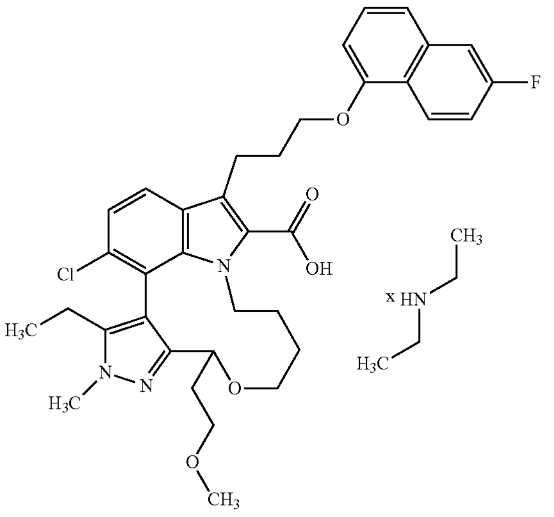

For the preparation of the racemic title compound see Example 41. Separation of enantiomers by preparative chiral HPLC (method see Example 41) gave the title compound (69.7 mg).

Analytical Chiral HPLC (method see Example 41): $R_t$=1.36 min.

LC-MS (Method 1): $R_t$=1.59 min; MS (ESIpos): m/z=646 $[M+H]^+$

Specific Optical Rotation (Method O1): +48.9° (c=10 mg/mL, DMSO)

$^1$H-NMR (400 MHz, DMSO-d6) δ[ppm]: 0.805 (2.00), 0.824 (4.74), 0.843 (2.09), 0.962 (0.72), 0.974 (0.64), 0.992 (0.33), 1.027 (2.24), 1.042 (2.24), 1.135 (4.58), 1.154 (10.00), 1.171 (4.84), 1.189 (0.32), 1.203 (0.33), 1.230 (0.25), 1.247 (0.17), 1.265 (0.22), 1.282 (0.26), 1.293 (0.29), 1.311 (0.32), 2.076 (0.36), 2.084 (0.36), 2.092 (0.70), 2.109 (0.87), 2.116 (0.55), 2.124 (0.70), 2.139 (0.39), 2.159 (0.31), 2.178 (0.88), 2.189 (1.18), 2.197 (1.84), 2.216 (1.56), 2.235 (0.45), 2.518 (1.91), 2.523 (1.40), 2.679 (0.18), 2.845 (1.11), 2.863 (3.37), 2.881 (3.35), 2.899 (1.03), 3.000 (0.20), 3.019 (0.41), 3.029 (0.33), 3.037 (0.32), 3.047 (0.47), 3.065 (0.23), 3.130 (0.19), 3.159 (16.00), 3.171 (0.59), 3.181 (0.61), 3.208 (0.45), 3.227 (0.74), 3.245 (0.65), 3.266 (0.96), 3.280 (1.18), 3.332 (5.02), 3.346 (4.36), 3.363 (2.38), 3.380 (1.64), 3.398 (0.97), 3.404 (0.82), 3.422 (0.45), 3.754 (0.22), 3.770 (0.30), 3.789 (0.35), 3.806 (0.29), 3.824 (0.20), 4.152 (0.48), 4.161 (0.59), 4.168 (0.97), 4.176 (0.97), 4.192 (0.50), 4.351 (0.60), 4.366 (0.70), 4.371 (0.82), 4.386 (0.56), 4.495 (0.31), 4.508 (0.25), 4.528 (0.30), 6.824 (0.79), 6.829 (0.80), 6.840 (0.77), 6.845 (0.82), 7.085 (1.48), 7.106 (1.51), 7.350 (0.51), 7.357 (0.62), 7.373 (0.83), 7.380 (0.91), 7.385 (0.43), 7.395 (0.61), 7.402 (0.89), 7.405 (1.35), 7.423 (2.73), 7.440 (0.34), 7.580 (1.02), 7.601 (0.93), 7.632 (0.94), 7.638 (0.99), 7.658 (0.95), 7.664 (0.95), 8.244 (0.80), 8.259 (0.85), 8.267 (0.82), 8.282 (0.76).

Example 43

(−)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

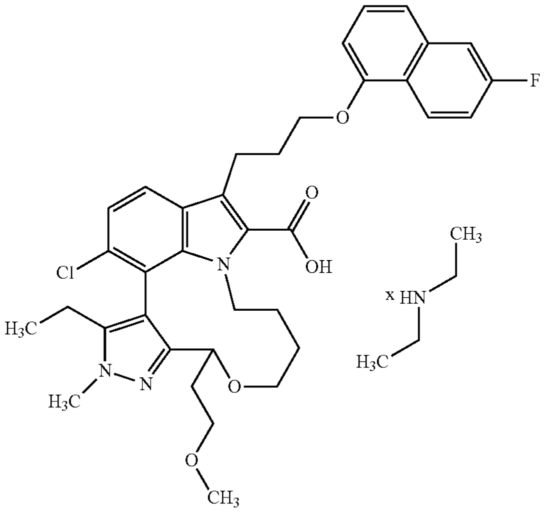

For the preparation of the racemic title compound see Example 41. Separation of enantiomers by preparative chiral HPLC (method see Example 41) gave the title compound (54.8 mg).

Analytical Chiral HPLC (method see Example 41): $R_t$=3.05 min.

LC-MS (Method 1): $R_t$=1.59 min; MS (ESIpos): m/z=646 $[M+H]^+$

Specific Optical Rotation (Method O1): −48.7° (c=10 mg/mL, DMSO)

$^1$H-NMR (400 MHz, DMSO-d6) δ[ppm]: 0.805 (2.07), 0.824 (4.91), 0.843 (2.25), 0.965 (0.81), 1.026 (0.16), 1.132 (4.29), 1.150 (10.14), 1.168 (4.89), 1.202 (0.44), 1.231 (0.31), 1.289 (0.33), 1.308 (0.35), 2.074 (0.38), 2.091 (0.76), 2.109 (0.96), 2.123 (0.81), 2.138 (0.46), 2.178 (0.98), 2.188 (1.32), 2.197 (2.01), 2.216 (1.74), 2.234 (0.59), 2.336 (0.29), 2.518 (7.89), 2.522 (6.31), 2.673 (0.59), 2.678 (0.29), 2.843 (1.18), 2.862 (3.72), 2.880 (3.57), 2.898 (1.19), 3.001 (0.21), 3.018 (0.44), 3.028 (0.37), 3.037 (0.35), 3.046 (0.51), 3.065 (0.26), 3.130 (0.20), 3.159 (16.00), 3.181 (0.78), 3.205 (0.52), 3.225 (0.76), 3.242 (0.60), 3.259 (0.75), 3.266 (0.88), 3.280 (1.03), 3.362 (2.13), 3.380 (1.54), 3.398 (0.92), 3.404 (0.80), 3.421 (0.43), 3.775 (0.29), 3.789 (0.38), 3.808 (0.31), 3.859 (10.49), 4.153 (0.54), 4.168 (1.09), 4.176 (1.10), 4.191 (0.58), 4.351 (0.61), 4.367 (0.72), 4.371 (0.86), 4.386 (0.60), 4.488 (0.33), 4.507 (0.29), 4.521 (0.33), 5.759 (0.98), 6.825 (0.84), 6.830 (0.86), 6.841 (0.84), 6.846 (0.90), 7.086 (1.26), 7.107 (1.35), 7.351 (0.54), 7.358 (0.63), 7.373 (0.88), 7.381 (0.96), 7.386 (0.48), 7.396 (0.65), 7.403 (0.90), 7.407 (1.45), 7.424 (3.06), 7.440 (0.44), 7.547 (0.17), 7.564 (0.25), 7.581 (0.92), 7.595 (0.50), 7.602 (0.88), 7.621 (0.33), 7.632 (1.11), 7.638 (1.13), 7.658 (1.02), 7.664 (1.02), 8.244 (0.85), 8.258 (0.90), 8.266 (0.89), 8.282 (0.82).

Example 44

(rac)-4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylic Acid

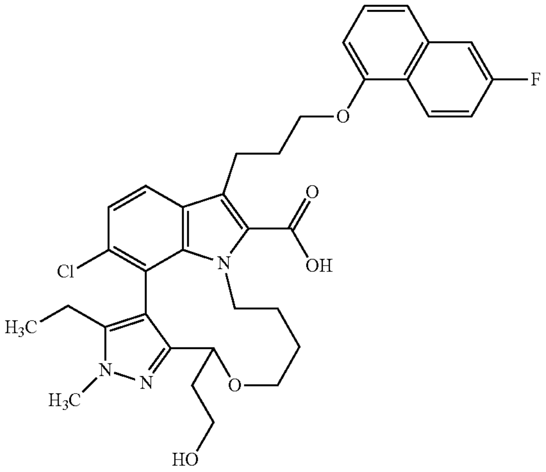 [SMILES: CCc1c2c(nn1C)C(CCO)OCCCCn1c(C(=O)O)c(CCCOc3cccc4cc(F)ccc34)c3ccc(Cl)c-2c31]

(Rac)-ethyl 4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylate (see Intermediate 86, 300 mg, 453 μmol) was dissolved in a mixture of 10 mL of tetrahydrofuran and 3 mL of ethanol, a solution of lithium hydroxide (1.4 mL, 1.0 M, in water 1.4 mmol) was added and the mixture was stirred for 72 h at 60° C. The reaction mixture was concentrated, diluted with water and neutralized with an aqueous saturated solution of citric acid. The precipitate was isolated by filtration to give 256 mg (85% yield) of the title compound.

LC-MS (Method 2): $R_t$=0.90 min; MS (ESIpos): m/z=634 $[M+H]^+$ $^1$H-NMR (400 MHz, DMSO-d6) δ[ppm]: 0.793 (3.20), 0.812 (7.34), 0.831 (3.35), 1.022 (0.90), 1.166 (1.18), 1.243 (0.65), 1.984 (0.42), 1.998 (0.64), 2.018 (0.85), 2.032 (0.68), 2.086 (0.64), 2.107 (0.81), 2.121 (0.67), 2.136 (0.50), 2.142 (0.51), 2.156 (1.00), 2.173 (2.20), 2.182 (2.22), 2.193 (2.66), 2.201 (2.35), 2.211 (1.57), 2.518 (3.36), 2.522 (2.10), 2.673 (0.58), 3.024 (0.63), 3.038 (0.64), 3.228 (0.61), 3.243 (1.04), 3.262 (2.22), 3.280 (3.03), 3.459 (2.06), 3.857 (16.00), 3.884 (0.67), 3.901 (0.65), 3.918 (0.72), 4.164 (1.28), 4.180 (2.56), 4.196 (1.28), 4.322 (0.68), 4.341 (0.74), 4.358 (1.03), 4.447 (1.03), 4.460 (1.13), 4.469 (1.21), 4.483 (0.93), 6.843 (1.29), 6.849 (1.32), 6.858 (1.24), 6.865 (1.35), 7.179 (2.77), 7.200 (2.86), 7.357 (0.83), 7.363 (0.99), 7.379 (1.36), 7.386 (1.50), 7.402 (1.35), 7.408 (1.06), 7.422 (2.35), 7.432 (2.78), 7.438 (5.67), 7.452 (0.50), 7.640 (1.64), 7.646 (1.67), 7.666 (1.57), 7.672 (1.57), 7.712 (2.15), 7.733 (1.95), 8.246 (1.36), 8.261 (1.43), 8.269 (1.38), 8.283 (1.32).

The title compound (256 mg) was separated into enantiomers by preparative chiral HPLC to give enantiomer 1 (71.6 mg, see Example 45) and enantiomer 2 (90.9 mg, see Example 46).

Preparative Chiral HPLC Method:

Instrument: Sepiatec: Prep SFC100; column: Chiralpak IG 5μ 250×30 mm; Eluent A: $CO_2$; Eluent B: Ethanol+0.2 Vol-% aqueous ammonia (32%); Isocratic: 20% B; Flow: 100 mL/min; Temperature: 40° C.; BPR: 150 bar; UV: 220 nm;

Analytical Chiral HPLC Method:

Instrument: Agilent: 1260, Aurora SFC-Module; column: Chiralpak IG 5μ 100×4.6 mm; Eluent A: $CO_2$; Eluent B: Ethanol+0.1 Vol-% aqueous ammonia (32%); Isocratic: 20% B; Flow: 4 mL/min; Temperature: 37.5° C.; BPR: 100 bar; UV: 220 nm

Example 45

(+)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic Acid (Enantiomer 1)

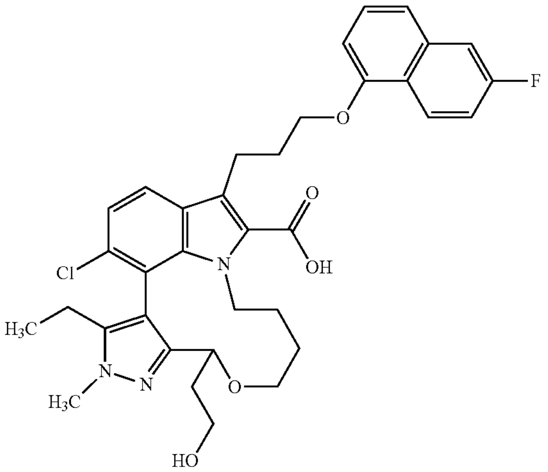 [SMILES: CCc1c2c(nn1C)C(CCO)OCCCCn1c(C(=O)O)c(CCCOc3cccc4cc(F)ccc34)c3ccc(Cl)c-2c31]

For the preparation of the racemic title compound see Example 44. Separation of enantiomers by preparative chiral HPLC (method see Example 44) gave the title compound (71.6 mg).

Analytical Chiral HPLC (method see Example 44): $R_t$=2.75 min.

LC-MS (Method 1): $R_t$=1.44 min; MS (ESIpos): m/z=634 $[M+H]^+$

Specific Optical Rotation (Method O1): +32.2° (c=10 mg/mL, DMSO)

$^1$H-NMR (400 MHz, DMSO-d6) δ[ppm]: 0.707 (0.59), 0.726 (1.54), 0.744 (0.73), 0.778 (1.12), 0.784 (0.75), 0.798 (5.25), 0.803 (2.93), 0.815 (10.57), 0.821 (4.74), 0.834 (4.57), 0.840 (3.27), 0.846 (2.26), 0.853 (2.95), 0.862 (6.40), 0.868 (1.52), 0.872 (1.63), 0.879 (3.46), 0.886 (2.13), 0.896 (1.10), 0.899 (1.36), 0.905 (3.44), 0.917 (1.30), 0.922 (1.97), 0.929 (0.69), 0.934 (0.85), 0.953 (0.49), 0.964 (1.22), 0.972 (0.67), 0.979 (0.96), 0.984 (1.46), 0.993 (1.02), 1.001 (1.12), 1.012 (1.36), 1.030 (1.18), 1.035 (3.50), 1.038 (2.81), 1.048 (0.79), 1.053 (5.25), 1.062 (2.01), 1.070 (2.85), 1.082 (1.08), 1.092 (0.49), 1.100 (0.45), 1.124 (0.67), 1.130 (1.63), 1.135 (2.15), 1.142 (1.40), 1.145 (1.87), 1.150 (2.32), 1.159 (0.75), 1.169 (0.69), 1.178 (0.67), 1.197 (1.28), 1.205 (1.40), 1.222 (0.96), 1.237 (1.06), 1.251 (0.92), 1.256 (0.96), 1.270 (0.63), 1.274 (0.61), 1.293 (0.55), 1.355 (0.49), 1.421 (0.59), 1.440 (1.00), 1.459 (0.89), 1.907 (0.61), 1.979 (0.43), 1.994 (0.73), 2.007 (1.06), 2.014 (1.02), 2.028 (0.77), 2.038 (1.06), 2.047 (0.59), 2.075 (2.77), 2.084 (1.36), 2.090 (0.63), 2.102 (1.16), 2.118 (0.91), 2.133 (0.81), 2.140 (0.69), 2.159 (0.96), 2.178 (2.40), 2.183 (2.07), 2.196 (2.83), 2.202 (2.20), 2.210 (2.20), 2.230 (0.85), 2.318 (0.55), 2.373 (0.45), 2.388 (0.55), 2.394 (0.59), 2.406 (0.59), 2.412 (0.77), 2.518 (5.29), 2.523 (3.58), 2.539 (1.46), 3.022 (0.57), 3.037 (0.61), 3.060 (0.39), 3.227 (0.85), 3.246 (1.52), 3.269 (2.16), 3.290 (2.58), 3.411 (0.89), 3.429 (1.36), 3.446 (1.97), 3.457 (1.93), 3.857 (16.00), 3.877 (0.69), 3.895 (0.65), 4.162 (1.04), 4.178 (2.05), 4.193 (1.08), 4.354 (1.20), 4.386 (0.73), 4.438 (0.96), 4.452 (1.08), 4.461 (1.16), 4.474 (0.91), 6.840 (1.16), 6.846 (1.20), 6.855 (1.16), 6.862 (1.26), 7.159 (2.70), 7.180 (2.79), 7.356 (0.73), 7.362 (0.85), 7.378 (1.24), 7.385 (1.34), 7.400 (1.00), 7.407 (0.91), 7.419 (2.15), 7.430 (2.58), 7.435 (5.22), 7.450 (0.49), 7.638 (1.48), 7.644 (1.55), 7.664 (1.52), 7.670 (1.55), 7.684 (2.01), 7.706 (1.79), 8.247 (1.14), 8.262 (1.22), 8.270 (1.18), 8.285 (1.12).

Example 46

(−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic Acid (Enantiomer 2)

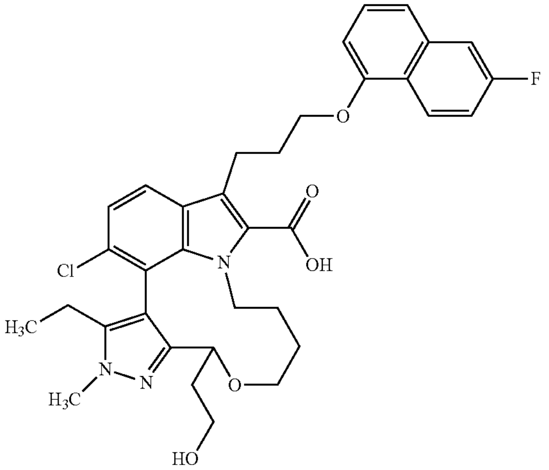 [SMILES: CCc1c2c(nn1C)C(CCO)OCCCCn1c(C(=O)O)c(CCCOc3cccc4cc(F)ccc34)c3ccc(Cl)c-2c31]

For the preparation of the racemic title compound see Example 44. Separation of enantiomers by preparative chiral HPLC (method see Example 44) gave the title compound (90.9 mg).

Analytical Chiral HPLC (method see Example 44): $R_t$=4.06 min.

LC-MS (Method 1): $R_t$=1.43 min; MS (ESIpos): m/z=634 $[M+H]^+$

Specific Optical Rotation (Method O1): −28.1° (c=10 mg/mL, DMSO)

$^1$H-NMR (400 MHz, DMSO-d6) δ[ppm]: 0.705 (0.85), 0.724 (2.14), 0.743 (1.06), 0.756 (0.53), 0.769 (0.42), 0.774 (1.32), 0.777 (1.43), 0.784 (0.90), 0.798 (8.04), 0.803 (4.05), 0.809 (2.94), 0.815 (10.76), 0.821 (6.64), 0.827 (2.33), 0.835 (4.63), 0.840 (4.68), 0.844 (3.73), 0.852 (4.97), 0.857 (5.53), 0.860 (6.56), 0.870 (2.20), 0.877 (4.52), 0.886 (3.07), 0.896 (1.45), 0.898 (1.64), 0.905 (5.63), 0.916 (1.77), 0.922 (3.52), 0.934 (1.19), 0.953 (0.69), 0.962 (1.80), 0.978 (1.82), 0.982 (2.09), 0.993 (1.27), 0.996 (1.45), 1.000 (1.48), 1.012 (1.64), 1.033 (4.10), 1.048 (0.98), 1.053 (2.83), 1.061 (2.33), 1.067 (1.93), 1.070 (1.85), 1.081 (1.38), 1.090 (0.79), 1.100 (0.74), 1.109 (0.61), 1.126 (2.62), 1.130 (3.23), 1.137 (2.35), 1.142 (3.25), 1.145 (3.57), 1.161 (0.98), 1.168 (0.66), 1.191 (1.98), 1.198 (1.96), 1.218 (1.24), 1.222 (1.32), 1.236 (1.45), 1.241 (1.22), 1.255 (1.19), 1.270 (0.69), 1.274 (0.63), 1.289 (0.56), 1.292 (0.77), 1.354 (0.69), 1.361 (0.42), 1.416 (0.90), 1.433 (1.53), 1.452 (1.40), 1.471 (0.53), 1.796 (0.56), 1.836 (0.58), 1.907 (0.93), 1.919 (0.58), 1.976 (0.45), 1.989 (0.98), 2.002 (1.30), 2.009 (1.00), 2.024 (0.90), 2.032 (1.30), 2.042 (0.56), 2.048 (0.58), 2.066 (0.42), 2.074 (0.63), 2.084 (0.90), 2.097 (1.11), 2.104 (1.03), 2.114 (1.14), 2.129 (1.24), 2.162 (0.98), 2.171 (1.69), 2.181 (2.25), 2.190 (2.20), 2.198 (2.35), 2.204 (2.75), 2.210 (2.59), 2.230 (0.95), 2.259 (0.56), 2.290 (0.48), 2.306 (0.50), 2.318 (0.56), 2.359 (0.61), 2.373 (0.69), 2.389 (0.87), 2.394 (0.93), 2.399 (0.53), 2.406 (0.93), 2.412 (1.22), 2.425 (0.50), 2.518 (5.63), 2.523 (4.10), 2.539 (1.53), 2.751 (0.53), 3.019 (0.56), 3.036 (0.63), 3.216 (0.93), 3.234 (1.48), 3.261 (2.17), 3.278 (2.94), 3.457 (1.90), 3.857 (16.00), 3.879 (0.66), 4.162 (0.93), 4.176 (1.77), 4.191 (0.95), 4.358 (1.06), 4.369 (1.03), 4.406 (0.53), 4.433 (0.98), 4.446 (1.00), 4.455 (1.08), 4.468 (0.87), 6.838 (1.14), 6.844 (1.14), 6.854 (1.14), 6.860 (1.22), 7.146 (2.38), 7.167 (2.49), 7.356 (0.74), 7.362 (0.87), 7.378 (1.19), 7.385 (1.32), 7.400 (0.87), 7.407 (0.87), 7.418 (2.04), 7.428 (2.46), 7.433 (5.08), 7.449 (0.48), 7.637 (1.45), 7.643 (1.51), 7.663 (2.22), 7.666 (2.22), 7.669 (2.22), 7.687 (1.56), 8.247 (1.14), 8.262 (1.22), 8.271 (1.19), 8.285 (1.11).

Example 47

(+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic Acid

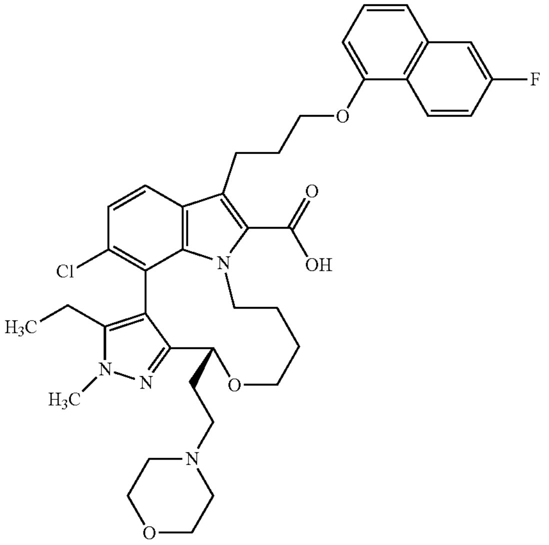 [SMILES: CCc1c2c(nn1C)[C@@H](CCN1CCOCC1)OCCCCn1c(C(=O)O)c(CCCOc3cccc4cc(F)ccc34)c3ccc(Cl)c-2c31]

Ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 129, 2.69 g, 3.68 mmol) was provided in 37 mL of tetrahydrofuran, 18 mL of ethanol and a solution of lithium hydroxide in water (18.4 mL, 1.0 M, 18.4 mmol) were added and the mixture was stirred for 23 h at 70° C. under an argon atmosphere. Citric acid monohydrate (1.31 g, 6.25 mmol) was added and the mixture was stirred for 1 h at rt. The mixture was concentrated under reduced pressure and the residue was purified by flash chromatography using silica gel (gradient dichloromethane/ethanol).

Ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 129, 3.64 g, 4.73 mmol) was provided in 50 mL of tetrahydrofuran, 25 mL of ethanol and a solution of lithium hydroxide in water (25.0 mL, 1.0 M, 25.0 mmol) were added and the mixture was stirred for 23 h at 70° C. under an argon atmosphere. Citric acid monohydrate (1.78 g, 8.46 mmol) was added and the mixture was stirred for 1 h at rt. The mixture was concentrated under reduced pressure and the residue was purified by flash chromatography using silica gel (gradient dichloromethane/ethanol). The resulting material was combined with the material of the first preparation and was further purified by flash chromatography using silica gel (gradient dichloromethane/ethanol) to provide 4.01 g of the title compound.

Specific Optical Rotation (Method O1): +46.3° (c=10 mg/mL, DMSO)

LC-MS (Method 2): $R_t$=0.91 min; MS (ESIpos): m/z=703 $[M+H]^+$ $^1$H-NMR (600 MHz, DMSO-d6) δ[ppm]: 0.82 (t, 3H), 0.97-1.08 (m, 2H), 1.10-1.19 (m, 1H), 1.24-1.31 (m, 1H), 2.09 (q, 2H), 2.14-2.26 (m, 4H), 2.29-2.47 (m, 6H), 3.02-3.07 (m, 1H), 3.24-3.33 (m, 3H), 3.51-3.58 (m, 4H), 3.87 (s, 3H), 3.88-3.94 (m, 1H), 4.16-4.22 (m, 2H), 4.31-4.37 (m, 1H), 4.43 (t, 1H), 6.85 (dd, 1H), 7.21 (d, 1H), 7.38 (td, 1H), 7.41-7.46 (m, 2H), 7.66 (dd, 1H), 7.75 (d, 1H), 8.24 (dd, 1H), 11.40-14.48 (m, 1H).

$^1$H-NMR (400 MHz, DMSO-d6) δ[ppm]: 0.791 (3.23), 0.810 (7.37), 0.829 (3.43), 1.035 (2.68), 1.052 (3.78), 1.070 (2.11), 1.143 (0.54), 1.262 (0.60), 2.073 (1.53), 2.090 (1.64), 2.107 (0.74), 2.159 (0.83), 2.177 (1.91), 2.189 (2.35), 2.196 (2.37), 2.208 (2.48), 2.322 (0.84), 2.326 (1.05), 2.331 (0.98), 2.386 (2.41), 2.518 (3.45), 2.522 (2.22), 2.664 (0.51), 2.669 (0.67), 2.673 (0.52), 3.034 (0.62), 3.049 (0.64), 3.244 (0.56), 3.278 (2.17), 3.291 (2.66), 3.305 (2.39), 3.323 (2.29), 3.410 (0.52), 3.428 (0.77), 3.445 (0.72), 3.861 (16.00), 3.886 (0.73), 3.903 (0.73), 3.920 (0.76), 4.171 (1.36), 4.187 (2.75), 4.201 (1.43), 4.312 (0.68), 4.329 (0.67), 4.346 (0.71), 4.403 (0.95), 4.420 (2.00), 4.438 (0.88), 6.841 (1.28), 6.848 (1.35), 6.857 (1.26), 6.863 (1.47), 7.200 (3.70), 7.221 (3.60), 7.351 (0.82), 7.358 (1.00), 7.374 (1.36), 7.380 (1.53), 7.396 (0.95), 7.402 (1.38), 7.422 (2.33), 7.432 (2.79), 7.438 (5.79), 7.452 (0.54), 7.640 (1.56), 7.646 (1.61), 7.666 (1.58), 7.672 (1.57), 7.742 (3.21), 7.763 (2.82), 8.219 (1.34), 8.234 (1.47), 8.242 (1.41), 8.257 (1.30).

Example 48

(15R)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt

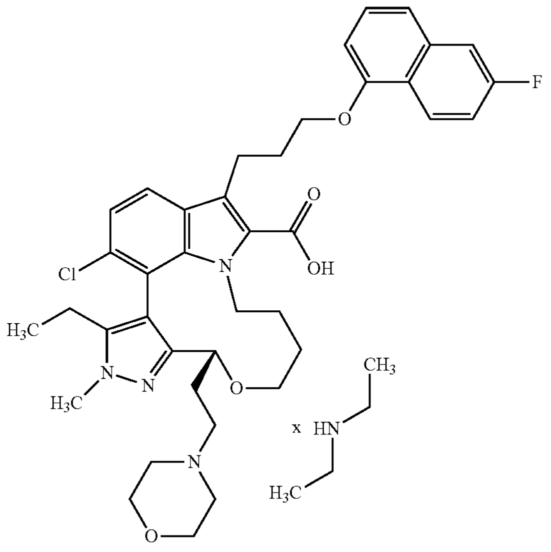

25.5 mg byproduct of Example 47 (90% purity, 1% yield), experimental procedure see Example 47.

Ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylate (2.72 g, 3.82 mmol) was purified by preparative chiral HPLC (method see below) to provide 25.5 mg the single stereoisomer #2 (as byproduct).

Preparative Chiral HPLC Method:

Labomatic HD3000, AS-3000, Labcol Vario 4000 Plus, Knauer DAD 2600; Column: YMC-Triart C18 5μ 150×50 mm; Eluent A: water+0.2 Vol-% ammonia in water (32%), Eluent B: Methanol, Eluent C: Methanol+10 Vol-% ammonia in water (32%); Gradient: 0.00-1.00 min 50% B/4% C (75→150 mL/min), 1.00-5.50 min 50-68% B/4% C (150 mL/min), 5.50-8.30 min 91% B/4% C (150 mL/min); DAD @ 220 nm Analytical Chiral HPLC Method:

Instrument: Waters Acquity UPLCMS SingleQuad; Column: Acquity UPLC BEH C18 1.7 μm, 50×2.1 mm; Eluent A: Water+0.2 Vol-% ammonia in water (32%), Eluent B: Methanol; Gradient: 0-4.5 min 1-99% B, 4.5-5.0 min 99% B; Flow 0.8 ml/min; Temperature: 60° C.; DAD scan: 210-400 nm Analytical Chiral HPLC (method see Example 48): $R_t$=2.98 min.

LC-MS (Method 2): $R_t$=1.09 min; MS (ESIpos): m/z=703 $[M+H]^+$ $^1$H-NMR (400 MHz, DMSO-d6) delta [ppm]: −0.014 (1.04), −0.003 (0.47), 0.787 (3.11), 0.806 (7.06), 0.824 (3.39), 0.866 (0.66), 1.128 (3.20), 1.146 (6.49), 1.164 (3.29), 1.232 (2.73), 1.436 (0.66), 1.649 (0.66), 1.803 (0.66), 1.906 (2.07), 2.040 (0.75), 2.059 (0.85), 2.076 (1.22), 2.095 (1.13), 2.124 (1.13), 2.144 (1.69), 2.163 (2.35), 2.181 (2.92), 2.197

(2.07), 2.256 (4.80), 2.323 (4.24), 2.326 (5.65), 2.331 (4.14), 2.522 (16.00), 2.539 (3.20), 2.665 (4.14), 2.669 (5.55), 2.673 (4.05), 2.860 (0.85), 2.878 (2.26), 2.896 (2.26), 2.915 (0.75), 3.132 (0.94), 3.203 (1.51), 3.222 (1.60), 3.456 (1.22), 3.509 (3.95), 3.520 (5.55), 3.532 (3.76), 3.817 (15.44), 3.832 (1.41), 3.858 (1.60), 4.190 (3.20), 4.248 (1.22), 4.260 (1.22), 4.271 (1.04), 4.283 (0.94), 6.839 (1.32), 6.846 (1.41), 6.861 (1.41), 7.124 (1.04), 7.146 (1.04), 7.359 (0.85), 7.365 (1.04), 7.381 (1.51), 7.388 (1.79), 7.403 (1.04), 7.410 (1.51), 7.417 (2.54), 7.427 (3.86), 7.433 (6.02), 7.637 (2.35), 7.643 (2.35), 7.663 (1.88), 7.669 (1.88), 8.260 (1.41), 8.275 (1.60), 8.283 (1.60), 8.298 (1.41).

Example 49

(rac)-3-Ethyl-4-fluoro-7-{3-[(6-fluoronaphthalen-1-yl)oxy]propyl}-2-methyl-(15-rac)-[2-(morpholin-4-yl)ethyl]-2,10,11,12,13,15-hexahydropyrazolo[4',3':9,10][1,6]oxazacycloundecino[8,7,6-hi]indole-8-carboxylic Acid

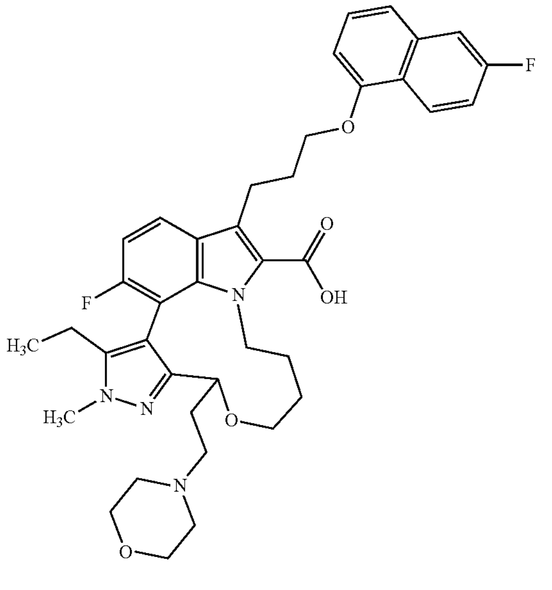 [SMILES: CCc1c2c(nn1C)C(CCN1CCOCC1)OCCCCn1c(C(=O)O)c(CCCOc3cccc4cc(F)ccc34)c3ccc(F)c-2c31]

(Rac)-ethyl-3-ethyl-4-fluoro-7-{3-[(6-fluoronaphthalen-1-yl)oxy]propyl}-2-methyl-(15-rac)-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 96, 790 mg, 1.11 mmol) was provided in a mixture of 8 mL of THF, 800 μL of ethanol and a solution of lithium hydroxide (2.2 mL, 1.0 M in water, 2.20 mmol) were added and the mixture was stirred for 96 h at 70° C. in a sealed tube. Lithium hydroxide (2.2 mL, 1.0 M in water, 2.20 mmol) was added and the mixture was stirred for 48 h at 70° C. Lithium hydroxide (1.1 mL, 1.0 M in water, 1.10 mmol) was added and the mixture was stirred for 24 h at 70° C. The mixture was diluted with water, adjusted to a pH value of 3-4 with a saturated, aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol) to give 345 mg of the title compound.

50 mg of the title compound was purified by preparative HPLC (method P2) to provide 31.7 mg of the title compound.

LC-MS (Method 2): $R_t$=0.91 min; MS (ESIpos): m/z=687 $[M+H]^+$ $^1$H-NMR (400 MHz, DMSO-d6) δ[ppm]: 0.828 (3.40), 0.847 (7.55), 0.866 (3.59), 1.019 (1.05), 1.103 (1.79), 1.231 (1.46), 1.254 (1.31), 2.021 (1.28), 2.037 (1.39), 2.083 (0.55), 2.186 (1.29), 2.203 (1.87), 2.214 (1.41), 2.220 (1.44), 2.232 (1.29), 2.251 (1.72), 2.270 (2.05), 2.277 (2.35), 2.296 (3.20), 2.314 (3.66), 2.322 (3.74), 2.326 (3.77), 2.331 (3.37), 2.518 (5.27), 2.522 (3.27), 2.664 (0.81), 2.669 (1.11), 2.673 (0.81), 2.973 (0.68), 2.982 (0.63), 3.000 (0.72), 3.072 (0.65), 3.284 (4.12), 3.504 (4.48), 3.820 (0.43), 3.863 (16.00), 3.965 (0.59), 3.981 (0.74), 3.998 (0.70), 4.177 (1.52), 4.193 (3.09), 4.208 (1.61), 4.359 (0.83), 4.382 (1.31), 4.400 (2.18), 4.417 (0.94), 6.844 (1.35), 6.851 (1.42), 6.859 (1.28), 6.866 (1.46), 6.962 (1.44), 6.984 (2.46), 7.007 (1.44), 7.354 (0.91), 7.360 (1.02), 7.376 (1.48), 7.383 (1.63), 7.398 (1.02), 7.405 (1.20), 7.423 (2.53), 7.432 (3.02), 7.438 (6.22), 7.452 (0.57), 7.640 (1.66), 7.646 (1.74), 7.666 (1.68), 7.672 (1.68), 7.755 (1.35), 7.769 (1.41), 7.778 (1.39), 7.792 (1.26), 8.229 (1.42), 8.244 (1.50), 8.253 (1.48), 8.267 (1.39).

The title compound (295 mg) was separated into enantiomers by preparative chiral HPLC to give enantiomer 1 (71.6 mg, see Example 50) and enantiomer 2 (99.8 mg, see Example 51).

Preparative Chiral HPLC Method:

Instrument: PrepCon Labomatic HPLC; Column: YMC Amylose SA 5μ 250×30 mm; Eluent A: Hexane+0.1% diethylamine; Eluent B: Ethanol; Gradient: 20-50% B in 15 min; Flow: 40 mL/min; Temperature: 25° C.; UV: 254 nm Analytical Chiral HPLC Method:

Instrument: Waters Alliance 2695; Column: YMC Amylose SA 3μ 100×4.6 mm; Eluent A: Hexane+0.1% diethylamine; Eluent B: Ethanol; Gradient: 20-50% B in 7 min; Flow: 1.4 mL/min; Temperature: 25° C.; UV: 254 nm Example 50

(+)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 1)

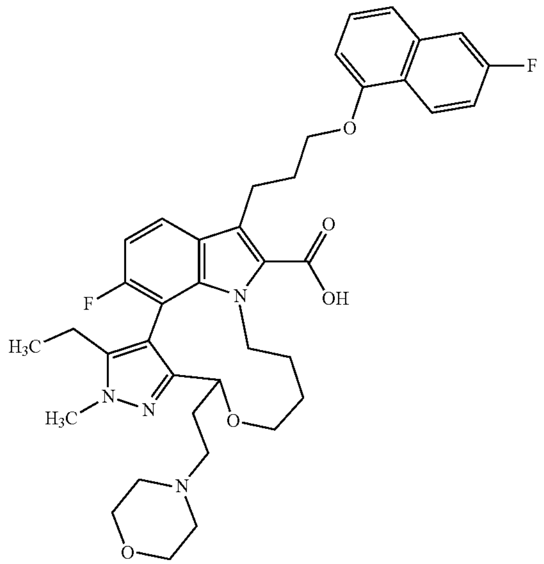 [SMILES: CCc1c2c(nn1C)C(CCN1CCOCC1)OCCCCn1c(C(=O)O)c(CCCOc3cccc4cc(F)ccc34)c3ccc(F)c-2c31]

For the preparation of the racemic title compound see Example 49. Separation of enantiomers by preparative chiral HPLC (method see Example 49) gave the title compound (71.6 mg).

Analytical Chiral HPLC (method see Example 49): $R_t$=2.07 min.

LC-MS (Method 2): $R_t$=0.93 min; MS (ESIpos): m/z=687 $[M+H]^+$

Specific Optical Rotation (Method O1): +61.9° (c=10 mg/mL, DMSO)

$^1$H-NMR (400 MHz, DMSO-d6) δ[ppm]: 0.835 (3.26), 0.854 (7.30), 0.873 (3.37), 0.999 (1.32), 1.013 (1.18), 1.070 (0.46), 1.087 (0.93), 1.105 (0.51), 1.137 (3.68), 1.155 (8.25), 1.173 (4.04), 1.210 (0.60), 1.228 (0.74), 1.303 (0.51), 1.989 (1.25), 2.006 (1.40), 2.026 (0.68), 2.073 (3.44), 2.177 (1.21), 2.194 (1.86), 2.211 (1.58), 2.229 (2.04), 2.248 (3.21), 2.265 (5.16), 2.280 (4.46), 2.299 (1.89), 2.317 (1.12), 2.322 (1.11), 2.327 (1.21), 2.331 (0.95), 2.336 (0.72), 2.518 (4.86), 2.522 (2.93), 2.664 (0.77), 2.669 (1.05), 2.673 (0.77), 2.859 (1.11), 2.877 (3.26), 2.895 (3.23), 2.914 (1.05), 2.957 (0.79), 2.967 (0.63), 2.985 (0.86), 3.004 (0.44), 3.179 (0.68), 3.197 (1.02), 3.211 (1.32), 3.230 (1.88), 3.250 (2.25), 3.483 (4.98), 3.861 (16.00), 3.906 (0.68), 3.922 (0.53), 4.167 (1.35), 4.182 (2.72), 4.198 (1.37), 4.360 (0.93), 4.378 (1.89), 4.394 (0.86), 4.460 (0.60), 4.493 (0.56), 6.830 (1.35), 6.836 (1.42), 6.846 (1.33), 6.851 (1.46), 6.887 (0.95), 6.910 (1.68), 6.932 (0.95), 7.349 (0.84), 7.356 (0.95), 7.371 (1.39), 7.378 (1.54), 7.389 (0.70), 7.394 (0.98), 7.400 (1.09), 7.410 (2.30), 7.426 (5.35), 7.441 (0.56), 7.632 (1.61), 7.639 (1.70), 7.658 (2.04), 7.665 (2.35), 7.688 (0.74), 8.236 (1.37), 8.251 (1.46), 8.259 (1.44), 8.274 (1.32).

Example 51

(−)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 2)

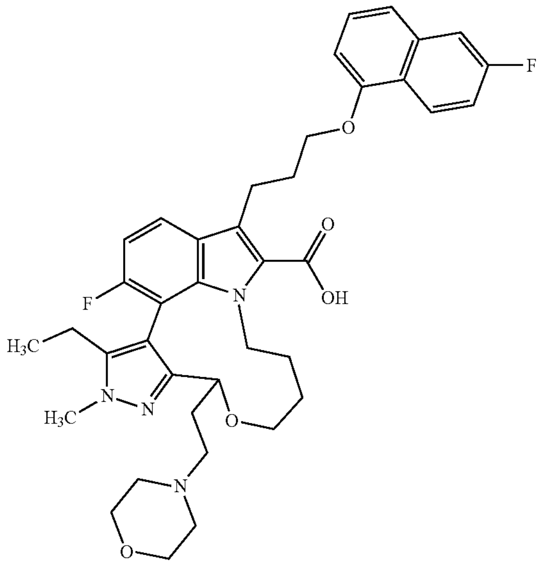 [SMILES: CCc1c2c(nn1C)C(CCN1CCOCC1)OCCCCn1c(C(=O)O)c(CCCOc3cccc4cc(F)ccc34)c3ccc(F)c-2c31]

For the preparation of the racemic title compound see Example 49. Separation of enantiomers by preparative chiral HPLC (method see Example 49) gave the title compound (99.8 mg).

Analytical Chiral HPLC (method see Example 49): $R_t$=3.44 min.

LC-MS (Method 2): $R_t$=0.89 min; MS (ESIpos): m/z=687 $[M+H]^+$

Specific Optical Rotation (Method O1): −57.5° (c=10 mg/mL, DMSO)

$^1$H-NMR (400 MHz, DMSO-d6) δ[ppm]: 0.839 (3.23), 0.858 (7.31), 0.877 (3.40), 0.967 (1.52), 0.994 (1.65), 1.009 (1.48), 1.107 (15.36), 1.144 (2.74), 1.154 (3.25), 1.208 (1.07), 1.325 (0.49), 1.343 (0.51), 1.352 (0.45), 1.960 (0.56), 1.986 (1.09), 1.997 (1.21), 2.158 (0.45), 2.175 (1.19), 2.193 (1.79), 2.210 (1.52), 2.226 (1.89), 2.244 (3.01), 2.264 (4.72), 2.301 (1.59), 2.322 (1.24), 2.327 (1.32), 2.332 (0.95), 2.337 (0.56), 2.518 (4.53), 2.523 (2.94), 2.665 (0.82), 2.669 (1.13), 2.673 (0.80), 2.869 (1.28), 2.883 (1.28), 2.954 (0.74), 2.963 (0.56), 2.981 (0.80), 3.178 (0.62), 3.194 (0.80), 3.212 (1.19), 3.240 (1.07), 3.259 (1.73), 3.276 (2.10), 3.292 (3.05), 3.480 (4.24), 3.812 (0.45), 3.861 (16.00), 3.882 (0.74), 4.164 (1.24), 4.180 (2.51), 4.196 (1.36), 4.355 (0.91), 4.373 (1.81), 4.389 (0.84), 4.499 (0.54), 4.532 (0.52), 6.826 (1.32), 6.831 (1.36), 6.842 (1.34), 6.847 (1.46), 6.862 (0.95), 6.884 (1.57), 6.907 (0.89), 7.349 (0.84), 7.355 (0.95), 7.371 (1.40), 7.378 (1.54), 7.385 (0.68), 7.393 (0.95), 7.400 (1.21), 7.407 (2.24), 7.423 (5.11), 7.440 (0.58), 7.619 (0.74), 7.632 (2.33), 7.638 (2.37), 7.657 (2.00), 7.664 (1.67), 8.239 (1.34), 8.253 (1.44), 8.262 (1.40), 8.276 (1.30).

Example 52

(rac)-4-chloro-3-ethyl-7-{3-[(6-fluoronaphthalen-1-yl)oxy]propyl}-(15-rac)-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic Acid

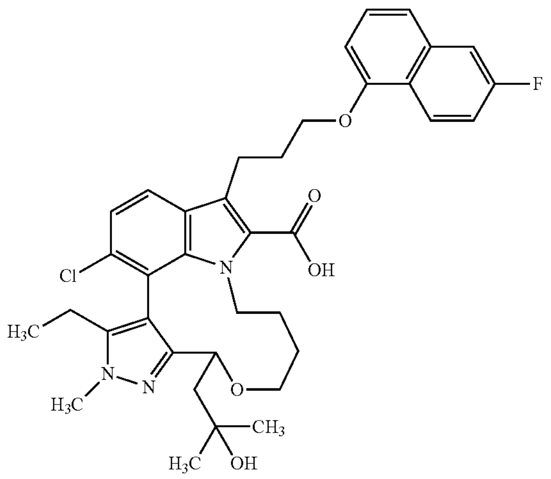 [SMILES: CCc1c2c(nn1C)C(CC(C)(C)O)OCCCCn1c(C(=O)O)c(CCCOc3cccc4cc(F)ccc34)c3ccc(Cl)c-2c31]

(Rac)-ethyl 4-chloro-3-ethyl-7-{3-[(6-fluoronaphthalen-1-yl)oxy]propyl}-(15-rac)-(2-hydroxy-2-methylpropyl)-2-methyl-2,10,11,12,13,15-hexahydropyrazolo[4',3':9,10][1,6]oxazacycloundecino[8,7,6-hi]indole-8-carboxylate (see Intermediate 100, 979 mg) was provided in 6 mL of THF, 600 μL of ethanol and a solution of lithium hydroxide (2.1 mL, 1.0 M in water, 2.10 mmol) was added and the mixture was stirred for 22 h at 70° C. in a sealed tube. A solution of lithium hydroxide (2.1 mL, 1.0 M in water, 2.10 mmol) was added and the mixture was stirred for 48 h at 70° C. The mixture was diluted with water, adjusted to a pH value of 3-4 with a saturated, aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol). The resulting material was dissolved in ethyl acetate and the mixture was washed with water and brine, was filtered through a water resistant filter and concentrated under reduced pressure to give 417 mg of the title compound.

LC-MS (Method 2): $R_t$=0.97 min; MS (ESIpos): m/z=662 $[M+H]^+$ $^1$H-NMR (400 MHz, DMSO-d6) δ[ppm]: 0.792 (3.15), 0.811 (6.98), 0.830 (3.15), 1.009 (0.86), 1.027 (0.97), 1.082 (11.11), 1.096 (11.22), 1.154 (2.62), 1.172 (5.08), 1.189 (2.49), 1.236 (0.42), 1.255 (0.54), 1.273 (0.58), 1.288 (0.50), 1.987 (8.22), 2.041 (0.52), 2.061 (0.52), 2.078 (1.19), 2.097 (1.17), 2.114 (1.22), 2.124 (1.59), 2.142 (0.80), 2.150 (0.81), 2.161 (2.13), 2.179 (2.84), 2.197 (2.76), 2.216 (1.58), 2.235 (0.55), 2.327 (0.96), 2.331 (0.71), 2.518 (3.96), 2.523 (2.50), 2.669 (0.97), 2.673 (0.71), 2.945 (0.45), 2.954 (0.49), 2.969 (0.58), 3.254 (0.83), 3.271 (1.48), 3.287 (1.56), 3.816 (1.23), 3.856 (16.00), 3.885 (0.54), 3.999 (0.62), 4.016 (1.74), 4.034 (1.67), 4.053 (0.55), 4.163 (4.27), 4.174 (1.43), 4.189 (2.62), 4.205 (1.33), 4.293 (0.55), 4.311 (0.58), 4.327 (0.50), 4.696 (0.96), 4.707 (1.23), 4.715 (0.99), 4.726 (0.93), 6.851

(1.23), 6.858 (1.30), 6.867 (1.17), 6.873 (1.33), 7.200 (3.44), 7.221 (3.44), 7.363 (0.86), 7.369 (1.01), 7.386 (1.30), 7.392 (1.48), 7.407 (1.22), 7.414 (1.07), 7.426 (2.34), 7.436 (2.76), 7.442 (5.86), 7.456 (0.52), 7.643 (1.51), 7.650 (1.58), 7.669 (1.51), 7.676 (1.53), 7.731 (2.79), 7.752 (2.42), 8.254 (1.27), 8.268 (1.35), 8.276 (1.41), 8.292 (1.32).

The title compound (417 mg) was separated into enantiomers by preparative chiral HPLC to give enantiomer 1 (177 mg, see Example 53 and enantiomer 2 (178 mg, see Example 54).

Preparative Chiral HPLC Method:

Instrument: Labomatic HD5000, Labocord-5000; Gilson GX-241, Labcol Vario 4000, Column: Amylose SA 5μ 250×30 mm; Eluent A: Hexane+0.1 Vol-% Diethylamine (99%); Eluent B: Ethanol; Isocratic: 80% A+20% B; Flow 50.0 mL/min; UV 254 nm Analytical Chiral HPLC Method:

Instrument: Agilent HPLC 1260; column: Amylose SA 3μ 100×4.6 mm; Eluent A: Hexane+0.1 Vol-% Diethylamine (99%); Eluent B: Ethanol; Isocratic: 80% A+20% B; Flow 1.4 mL/min; Temperature: 25° C.; DAD 254 nm Example 53

(+)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

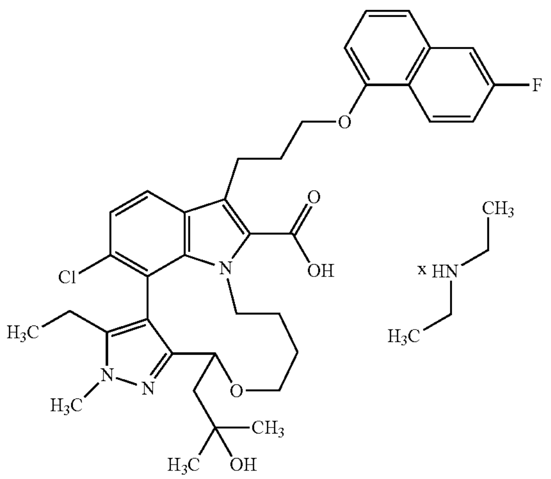

For the preparation of the racemic title compound see Example 52. Separation of enantiomers by preparative chiral HPLC (method see Example 52) gave the title compound (177 mg).

Analytical Chiral HPLC (method see Example 52): $R_t$=1.18 min.

LC-MS (Method 2): $R_t$=0.94 min; MS (ESIpos): m/z=662 $[M+H]^+$

Specific Optical Rotation (Method O1): +40.7° (c=10 mg/mL, DMSO)

$^1$H-NMR (400 MHz, DMSO-d6) δ[ppm]: 0.804 (3.10), 0.823 (7.03), 0.842 (3.08), 0.999 (0.87), 1.021 (0.95), 1.030 (0.67), 1.071 (16.00), 1.153 (6.38), 1.199 (1.20), 1.227 (1.10), 1.903 (2.30), 2.065 (2.20), 2.076 (1.53), 2.085 (1.55), 2.171 (1.75), 2.189 (3.55), 2.208 (2.87), 2.227 (0.85), 2.331 (0.70), 2.518 (3.80), 2.523 (2.37), 2.673 (0.72), 2.863 (2.63), 2.879 (2.60), 2.920 (0.48), 2.938 (0.73), 2.947 (0.55), 2.957 (0.53), 2.965 (0.73), 3.143 (0.57), 3.157 (0.68), 3.176 (0.98), 3.195 (0.60), 3.212 (0.68), 3.231 (1.18), 3.249 (0.98), 3.264 (1.10), 3.339 (4.83), 3.726 (0.55), 3.742 (0.58), 3.759 (0.67), 3.808 (1.22), 3.854 (15.12), 4.123 (2.02), 4.153 (0.83), 4.169 (1.63), 4.177 (1.63), 4.193 (0.83), 4.503 (0.53), 4.519 (0.47), 4.537 (0.48), 4.631 (0.92), 4.644 (0.97), 4.649 (1.30), 4.662 (0.87), 6.823 (1.28), 6.827 (1.27), 6.840 (1.33), 6.844 (1.33), 7.079 (2.53), 7.099 (2.58), 7.358 (0.83), 7.365 (0.97), 7.381 (1.62), 7.388 (1.55), 7.403 (2.72), 7.409 (1.28), 7.421 (4.40), 7.440 (0.65), 7.565 (1.88), 7.586 (1.70), 7.634 (1.50), 7.640 (1.58), 7.660 (1.50), 7.666 (1.52), 8.262 (1.22), 8.276 (1.33), 8.285 (1.30), 8.300 (1.22).

Example 54

(−)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 21

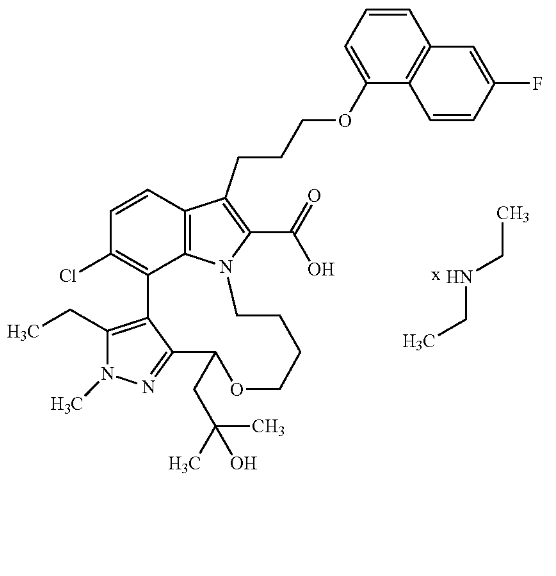

For the preparation of the racemic title compound see Example 52. Separation of enantiomers by preparative chiral HPLC (method see Example 52) gave the title compound (178 mg).

Analytical Chiral HPLC (method see Example 52): $R_t$=2.71 min.

LC-MS (Method 2): $R_t$=0.95 min; MS (ESIpos): m/z=662 [M+H]+

Specific Optical Rotation (Method O1): −31.1° (c=10 mg/mL, DMSO)

$^1$H-NMR (400 MHz, DMSO-d6) δ[ppm]: 0.797 (0.66), 0.805 (2.55), 0.814 (0.97), 0.824 (5.48), 0.842 (2.45), 0.904 (0.45), 0.999 (0.76), 1.020 (0.87), 1.070 (16.00), 1.153 (2.06), 1.202 (1.36), 1.218 (1.15), 2.060 (1.48), 2.066 (1.67), 2.085 (1.22), 2.171 (1.40), 2.190 (2.62), 2.209 (2.12), 2.228 (0.66), 2.331 (0.78), 2.452 (0.99), 2.518 (4.28), 2.522 (2.72), 2.673 (0.82), 2.678 (0.41), 2.875 (0.76), 2.919 (0.68), 2.937 (0.86), 2.964 (0.76), 3.134 (0.49), 3.149 (0.58), 3.166 (0.82), 3.185 (0.49), 3.205 (0.56), 3.224 (0.97), 3.242 (0.78), 3.257 (0.86), 3.714 (0.47), 3.731 (0.51), 3.749 (0.52), 3.807 (0.87), 3.854 (11.39), 4.119 (2.12), 4.151 (0.68), 4.168 (1.32), 4.177 (1.36), 4.193 (0.70), 4.515 (0.43), 4.531 (0.41), 4.548 (0.43), 4.626 (0.80), 4.639 (0.82), 4.645 (1.07), 4.657 (0.76), 6.822 (1.01), 6.827 (1.01), 6.839 (1.07), 6.844 (1.05), 7.069 (2.02), 7.091 (2.08), 7.358 (0.62), 7.365 (0.70), 7.381 (1.42), 7.388 (1.24), 7.403 (2.14), 7.410 (1.05), 7.419 (3.52), 7.439 (0.52), 7.552 (1.59), 7.573 (1.46), 7.633 (1.19), 7.640 (1.26), 7.659 (1.19), 7.666 (1.19), 8.263 (0.93), 8.278 (1.03), 8.286 (1.03), 8.301 (0.93).

Example 55

(rac)-4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—2-hydroxypropane-1,2,3-tricarboxylic Acid Salt

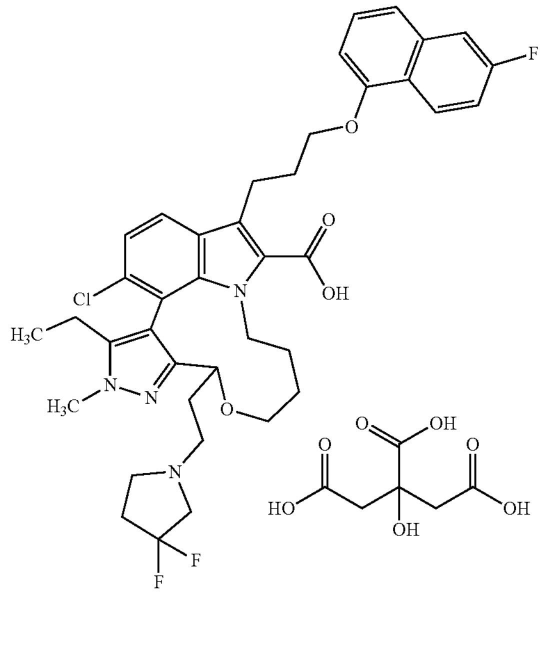

(Rac)-ethyl 4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 105, 264 mg, 60% purity, 0.211 mmol) was dissolved in 2 mL THF and 0.2 mL ethanol and lithium hydroxide (420 μL, 1.0 M in water, 420 μmol) were added and the mixture was stirred for 23 h at 70° C. in a sealed tube. A solution of lithium hydroxide (420 μL, 1.0 M in water, 420 μmol) was added and the mixture was stirred for 96 h at 70° C. The mixture was diluted with water, adjusted to a pH value of 3-4 with a saturated, aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol) to provide 69.7 mg of the title compound.

LC-MS (Method 2): $R_t$=1.03 min; MS (ESIpos): m/z=723 $[M+H]^+$ $^1$H-NMR (400 MHz, DMSO-d6) δ[ppm]: 0.791 (1.75), 0.798 (1.10), 0.810 (4.10), 0.814 (1.55), 0.821 (1.12), 0.829 (1.90), 0.840 (0.47), 0.848 (0.22), 0.865 (0.18), 0.886 (0.47), 0.904 (0.93), 0.922 (0.47), 1.035 (8.11), 1.052 (16.00), 1.070 (8.64), 1.142 (0.30), 1.232 (0.82), 1.255 (0.40), 1.907 (0.47), 2.037 (0.25), 2.055 (0.50), 2.071 (0.65), 2.085 (0.48), 2.105 (0.28), 2.142 (0.28), 2.160 (0.68), 2.165 (0.70), 2.178 (1.40), 2.185 (1.55), 2.204 (1.82), 2.217 (1.15), 2.236 (0.50), 2.318 (0.32), 2.322 (0.70), 2.327 (0.97), 2.332 (0.73), 2.336 (0.33), 2.394 (0.17), 2.412 (0.22), 2.518 (4.24), 2.523 (2.82), 2.616 (1.77), 2.655 (3.54), 2.664 (1.23), 2.669 (1.47), 2.673 (1.20), 2.678 (0.83), 2.718 (3.17), 2.756 (1.58), 2.863 (0.28), 2.884 (0.30), 3.034 (0.28), 3.048 (0.28), 3.072 (0.17), 3.278 (1.05), 3.290 (1.28), 3.406 (0.48), 3.423 (1.17), 3.434 (1.23), 3.441 (1.20), 3.450 (1.13), 3.468 (0.38), 3.783 (0.22), 3.827 (0.18), 3.864 (8.71), 3.880 (0.42), 3.898 (0.35), 3.916 (0.37), 3.933 (0.17), 4.174 (0.67), 4.188 (1.42), 4.204 (0.75), 4.307 (0.35), 4.324 (0.35), 4.343 (0.78), 4.355 (1.00), 4.389 (0.53), 4.409 (0.75), 4.424 (0.47), 6.847 (0.67), 6.853 (0.72), 6.862 (0.62), 6.869 (0.75), 7.206 (2.10), 7.227 (2.22), 7.352 (0.47), 7.358 (0.52), 7.374 (0.70), 7.381 (0.78), 7.396 (0.50), 7.403 (0.73), 7.425 (1.25), 7.434 (1.45), 7.440 (3.20), 7.454 (0.38), 7.641 (0.83), 7.648 (0.92), 7.667 (0.83), 7.674 (0.90), 7.746 (1.84), 7.768 (1.67), 8.219 (0.70), 8.234 (0.75), 8.242 (0.73), 8.257 (0.70).

The title compound (60 mg) was separated into enantiomers by preparative chiral HPLC to give enantiomer 1 (12.3 mg, see Example 56) and enantiomer 2 (10.8 mg, see Example 57).

Preparative Chiral HPLC Method:

Instrument: Labomatic HD5000, Labocord-5000; Gilson GX-241, Labcol Vario 4000, Column: Amylose SA 5μ 250×30 mm; Eluent A: Hexane+0.1 Vol-% Diethylamine (99%); Eluent B: Ethanol; Isocratic: 80% A+20% B; Flow 50.0 mL/min; UV 254 nm Analytical Chiral HPLC Method:

Instrument: Agilent HPLC 1260; column: Amylose SA 3μ 100×4.6 mm; Eluent A: Hexane+0.1 Vol-% Diethylamine (99%); Eluent B: Ethanol; Isocratic: 80% A+20% B; Flow 1.4 mL/min; Temperature: 25° C.; DAD 254 nm Example 56

4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

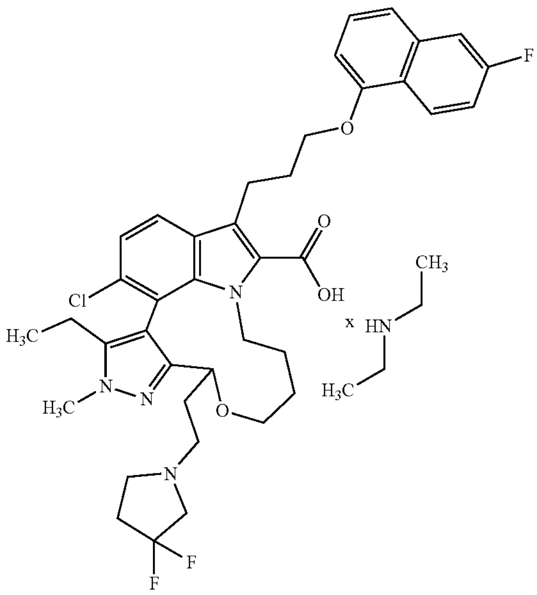

For the preparation of the racemic title compound see Example 55. Separation of enantiomers by preparative chiral HPLC (method see Example 55) gave the title compound (12.3 mg).

Analytical Chiral HPLC (method see Example 55): $R_t$=1.13 min.

LC-MS (Method 2): $R_t$=1.00 min; MS (ESIpos): m/z=723 $[M+H]^+$ $^1$H-NMR (400 MHz, DMSO-d6) δ[ppm]: 0.771 (0.43), 0.802 (3.26), 0.821 (7.64), 0.839 (3.49), 0.852 (0.55), 0.980 (1.36), 0.992 (1.14), 1.135 (6.55), 1.153 (14.82), 1.172 (7.18), 1.187 (0.65), 1.202 (0.71), 1.229 (1.32), 1.259 (0.71), 1.265 (0.69), 1.991 (0.49), 2.011 (0.85), 2.029 (0.95), 2.052 (0.87), 2.072 (0.61), 2.135 (0.67), 2.152 (1.20), 2.173 (2.47), 2.195 (3.69), 2.214 (2.98), 2.336 (0.47), 2.418 (0.71), 2.432 (0.77), 2.439 (0.79), 2.449 (1.03), 2.470 (1.44), 2.518 (5.25), 2.522 (3.29), 2.600 (1.09), 2.606 (1.09), 2.617 (1.85), 2.624 (1.89), 2.634 (1.01), 2.641 (0.97), 2.678 (0.47), 2.756 (0.77), 2.763 (0.61), 2.790 (1.64), 2.822 (1.50), 2.853 (2.37), 2.870 (5.62), 2.889 (5.45), 2.907 (1.70), 3.004 (0.73), 3.013 (0.59), 3.032 (0.83), 3.051 (0.43), 3.157 (0.61), 3.172 (0.79), 3.190 (1.12), 3.211 (1.09), 3.231 (1.46), 3.250 (1.38), 3.266 (1.91), 3.763 (0.55), 3.775 (1.16), 3.795 (0.59), 3.818 (0.41), 3.860 (16.00), 4.158 (1.05), 4.169 (1.85), 4.174 (1.85), 4.186 (1.14), 4.340 (0.89), 4.355 (1.01), 4.360 (1.16), 4.374 (0.85), 4.469 (0.51), 4.485 (0.45), 4.503 (0.47), 6.825 (1.28), 6.830 (1.34), 6.841 (1.30), 6.846 (1.40), 7.097 (2.05), 7.119 (2.17), 7.346 (0.85), 7.353 (0.97), 7.369 (1.36), 7.376 (1.52), 7.384 (0.75), 7.391 (0.99), 7.398 (1.12), 7.405 (2.17), 7.422 (4.66), 7.440 (0.79), 7.597 (1.46), 7.618 (1.34), 7.631 (1.66), 7.637 (1.74), 7.657 (1.60), 7.663 (1.66), 8.230 (1.32), 8.245 (1.38), 8.253 (1.34), 8.268 (1.30).

Example 57

4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid N-ethylethanamine Salt (Enantiomer 2)

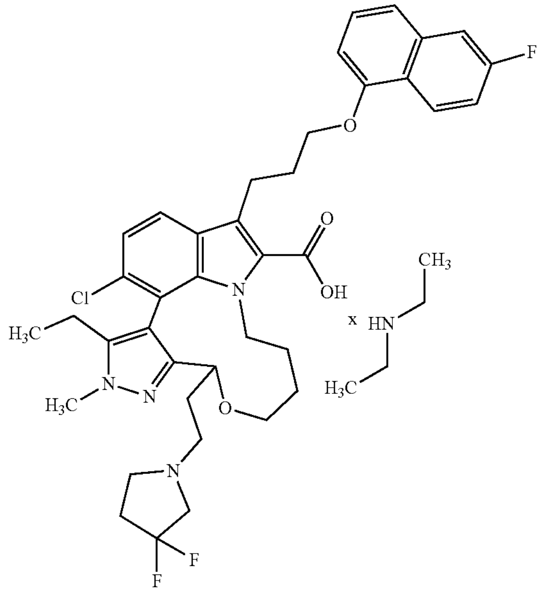

For the preparation of the racemic title compound see Example 55. Separation of enantiomers by preparative chiral HPLC (method see Example 55) gave the title compound (10.8 mg).

Analytical Chiral HPLC (method see Example 55): $R_t$=2.76 min.

LC-MS (Method 2): $R_t$=0.99 min; MS (ESIpos): m/z=723 $[M+H]^+$ $^1$H-NMR (400 MHz, DMSO-d6) δ[ppm]: 0.802 (3.20), 0.821 (7.47), 0.840 (3.34), 0.980 (1.35), 0.993 (1.13), 1.135 (4.75), 1.153 (10.53), 1.171 (5.09), 1.203 (0.72), 1.229 (1.63), 1.258 (0.68), 1.991 (0.50), 2.011 (0.83), 2.031 (0.95), 2.051 (0.83), 2.072 (0.58), 2.134 (0.66), 2.152 (1.15), 2.172 (2.39), 2.195 (3.56), 2.214 (2.94), 2.336 (0.42), 2.418 (0.70), 2.432 (0.76), 2.439 (0.76), 2.452 (0.99), 2.470 (1.55), 2.518 (5.29), 2.522 (3.32), 2.600 (1.05), 2.606 (1.05), 2.617 (1.85), 2.624 (1.85), 2.634 (0.95), 2.641 (0.95), 2.756 (0.74), 2.763 (0.58), 2.791 (1.63), 2.822 (1.47), 2.853 (1.91), 2.871 (3.90), 2.889 (3.80), 2.907 (1.23), 3.004 (0.70), 3.013 (0.54), 3.032 (0.76), 3.157 (0.52), 3.171 (0.68), 3.190 (0.99), 3.211 (0.93), 3.231 (1.23), 3.249 (1.07), 3.265 (1.45), 3.281 (2.01), 3.761 (0.48), 3.778 (0.56), 3.796 (0.54), 3.860 (16.00), 4.160 (1.01), 4.170 (1.77), 4.174 (1.79), 4.185 (1.01), 4.340 (0.89), 4.355 (1.03), 4.360 (1.17), 4.374 (0.83), 4.467 (0.48), 4.486 (0.44), 4.502 (0.46), 6.825 (1.25), 6.830 (1.33), 6.842 (1.25), 6.847 (1.33), 7.098 (1.93), 7.119 (2.01), 7.346 (0.85), 7.353 (0.91), 7.369 (1.33), 7.376 (1.47), 7.385 (0.66), 7.391 (0.93), 7.398 (1.09), 7.406 (2.07), 7.422 (4.55), 7.439 (0.56), 7.597 (1.35), 7.618 (1.27), 7.631 (1.63), 7.637 (1.61), 7.657 (1.55), 7.663 (1.53), 8.230 (1.27), 8.246 (1.35), 8.254 (1.33), 8.268 (1.25).

Example 58

4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid (Enantiomer 1)

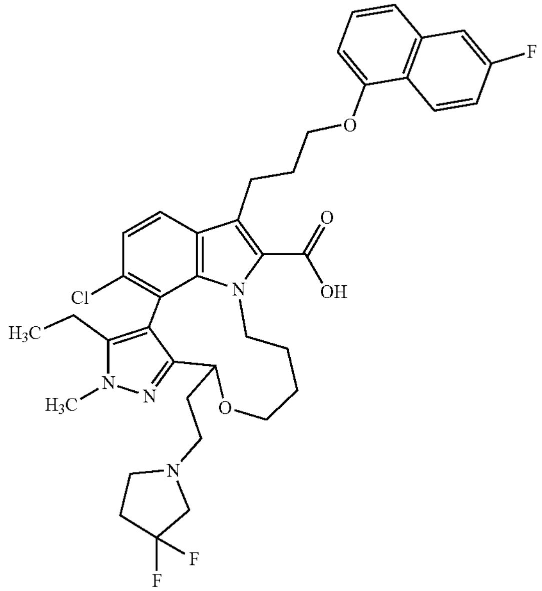 [SMILES: CCc1c2c(nn1C)C(CCN1CCC(F)(F)C1)OCCCCn1c(C(=O)O)c(CCCOc3cccc4cc(F)ccc34)c3ccc(Cl)c-2c31]

The N-ethylethanamine salt from Example 56 was purified by flash chromatography using silica gel (gradient dichloromethane/ethanol) to give 57.3 mg of the title compound.

LC-MS (Method 2): $R_t$=1.06 min; MS (ESIpos): m/z=723 $[M+H]^+$ $^1$H-NMR (400 MHz, DMSO-d6) δ[ppm]: 0.790 (3.71), 0.809 (8.01), 0.828 (3.98), 0.885 (0.32), 0.904 (0.56), 0.922 (0.34), 1.022 (1.32), 1.130 (0.76), 1.231 (1.10), 1.907 (0.78), 2.067 (1.56), 2.185 (4.30), 2.202 (4.69), 2.284 (2.22), 2.326 (1.47), 2.632 (1.49), 2.668 (1.98), 2.808 (0.93), 3.033 (0.88), 3.046 (0.90), 3.826 (0.42), 3.863 (16.00), 3.898 (1.05), 3.915 (1.00), 4.173 (1.83), 4.188 (3.59), 4.203 (1.93), 4.306 (0.90), 4.321 (0.83), 4.339 (0.81), 4.388 (1.20), 4.406 (1.91), 4.423 (1.12), 5.758 (8.48), 6.846 (1.54), 6.853 (1.64), 6.861 (1.61), 6.867 (1.66), 7.096 (0.51), 7.117 (0.56), 7.205 (3.40), 7.226 (3.57), 7.351 (0.88), 7.358 (1.03), 7.374 (1.64), 7.380 (1.78), 7.396 (1.05), 7.403 (1.44), 7.424 (2.83), 7.440 (6.42), 7.455 (1.27), 7.475 (0.64), 7.640 (1.73), 7.646 (1.83), 7.666 (1.78), 7.672 (1.78), 7.745 (3.22), 7.767 (2.91), 8.218 (1.51), 8.233 (1.64), 8.242 (1.59), 8.256 (1.47), 13.276 (0.22).

Example 59

(rac)-4-chloro-3-ethyl-7-{3-[(6-fluoronaphthalen-1-yl)oxy]propyl}-2-methyl-(15-rac)-phenyl-2,10,11,12,13,15-hexahydropyrazolo[4',3':9,10][1,6]oxazacycloundecino[8,7,6-hi]indole-8-carboxylic Acid

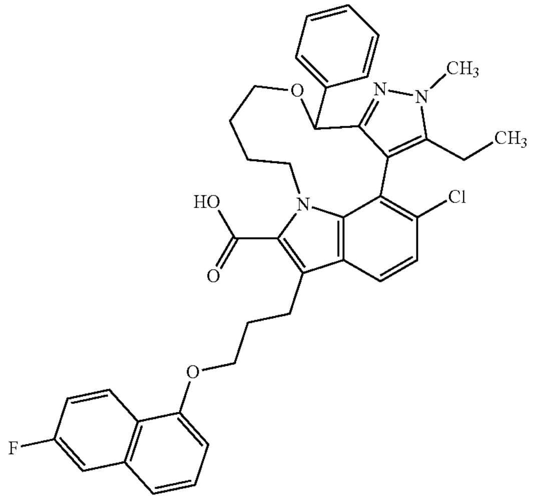 [SMILES: CCc1c2c(nn1C)C(c1ccccc1)OCCCCn1c(C(=O)O)c(CCCOc3cccc4cc(F)ccc34)c3ccc(Cl)c-2c31]

Ethyl-(rac)-4-chloro-3-ethyl-7-{3-[(6-fluoronaphthalen-1-yl)oxy]propyl}-2-methyl-15-phenyl-2,10,11,12,13,15-hexahydropyrazolo[4',3':9,10][1,6]oxazacycloundecino[8,7,6-hi]indole-8-carboxylate (see Intermediate 109, 115 mg, 124 μmol) was dissolved in ethanol (0.5 mL), treated with sodium hydroxide (160 μL, 2.0 M in water, 310 μmol) and the mixture stirred at 70° C. for 16 hours. After cooling to room temperature, hydrogen chloride (1 N solution in water) was added to adjust the pH to 3-4, followed by water, and the mixture was repeatedly extracted with ethyl acetate. The combined organic layers were filtered through a water resistant filter and concentrated under reduced pressure. The residue was purified by HPLC to provide the title compound (42 mg).

LC-MS (Method 5): $R_t$=5.25 min; MS (ESIpos): m/z=668 $[M+H]^+$ $^1$H-NMR (300 MHz, CHLOROFORM-d) delta [ppm]: 0.832 (1.34), 0.858 (3.23), 0.883 (1.51), 0.921 (0.56), 1.587 (0.34), 1.947 (1.36), 2.197 (0.38), 2.222 (0.99), 2.248 (1.01), 2.275 (0.68), 2.300 (0.59), 2.322 (0.41), 3.350 (0.53), 3.368 (0.81), 3.393 (0.94), 3.800 (6.54), 4.113 (0.55), 4.132 (1.08), 4.152 (0.50), 4.441 (0.68), 4.455 (0.50), 5.207 (1.53), 6.617 (0.54), 6.626 (0.48), 6.638 (0.59), 6.646 (0.56), 7.137 (0.39), 7.146 (0.41), 7.168 (0.63), 7.174 (0.85), 7.201 (16.00), 7.210 (1.80), 7.222 (0.74), 7.239 (1.71), 7.250 (0.34), 7.291 (1.60), 7.297 (1.73), 7.307 (0.90), 7.315 (1.00), 7.320 (0.92), 7.340 (0.70), 7.348 (0.63), 7.490 (1.42), 7.513 (1.11), 7.635 (1.41), 7.664 (1.25), 8.252 (0.56), 8.272 (0.58), 8.284 (0.57), 8.302 (0.53).

Example 60

(rac)-4-chloro-3-ethyl-7-{3-[(6-fluoronaphthalen-1-yl)oxy]propyl}-2-methyl-(15-rac)-[2-(oxan-4-yl)ethyl]-2,10,11,12,13,15-hexahydropyrazolo[4',3':9,10][1,6]oxazacycloundecino[8,7,6-hi]indole-8-carboxylic Acid

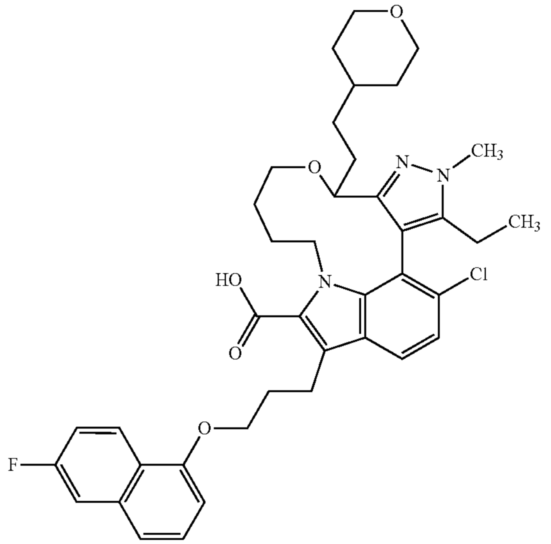 [SMILES: CCc1c2c(nn1C)C(CCC1CCOCC1)OCCCCn1c(C(=O)O)c(CCCOc3cccc4cc(F)ccc34)c3ccc(Cl)c-2c31]

Ethyl-(rac)-4-chloro-3-ethyl-7-{3-[(6-fluoronaphthalen-1-yl)oxy]propyl}-2-methyl-(15-rac)[2-(oxan-4-yl)ethyl]-2,10,11,12,13,15-hexahydropyrazolo[4',3':9,10][1,6]oxazacycloundecino[8,7,6-hi]indole-8-carboxylate (see Intermediate 202, 150 mg, 205 μmol) was dissolved in ethanol (820 μL), treated with sodium hydroxide (260 μL, 2.0 M in water, 510 μmol) and the mixture stirred at 70° C. overnight. After cooling to room temperature, 1.0 M aqueous hydrochloric acid (600 μL) was added. The reaction mixture was concentrated under reduced pressure. The residue was purified by reverse phase column chromatography (10-100% acetonitrile/water gradient buffered with 0.1% formic acid) to give the title compound (122 mg).

LC-MS (Method 7): $R_t$=1.86 min; MS (ESIpos): m/z=705 $[M+H]^+$

1H-NMR (300 MHz, CHLOROFORM-d) delta [ppm]: 0.897 (3.00), 0.922 (7.26), 0.947 (3.01), 1.133 (0.78), 1.246 (1.19), 1.270 (2.06), 1.280 (1.09), 1.294 (1.53), 1.320 (1.30), 1.344 (1.33), 1.372 (1.42), 1.399 (1.28), 1.429 (1.09), 1.471 (0.66), 1.494 (0.57), 1.504 (0.56), 1.528 (0.55), 1.609 (0.87), 1.646 (1.03), 2.014 (2.55), 2.039 (0.79), 2.056 (2.88), 2.063 (1.58), 2.089 (1.27), 2.114 (0.51), 2.239 (0.80), 2.263 (1.94), 2.291 (2.04), 2.316 (1.50), 2.337 (1.30), 2.361 (0.93), 3.224 (0.59), 3.245 (0.55), 3.318 (1.08), 3.324 (1.27), 3.356 (2.21), 3.363 (2.24), 3.395 (2.53), 3.402 (2.11), 3.415 (2.45), 3.443 (1.25), 3.934 (2.00), 3.949 (16.00), 4.078 (0.57), 4.099 (0.72), 4.122 (1.17), 4.146 (0.89), 4.168 (1.38), 4.187 (2.66), 4.207 (1.25), 4.371 (1.34), 4.395 (2.22), 4.419 (1.21), 5.308 (4.72), 6.686 (1.23), 6.693 (1.08), 6.707 (1.34), 6.715 (1.32), 7.196 (3.52), 7.205 (0.97), 7.214 (1.06), 7.225 (3.95), 7.235 (1.30), 7.244 (1.48), 7.323 (0.54), 7.344 (5.43), 7.350 (2.43), 7.364 (2.07), 7.382 (1.62), 7.390 (1.74), 7.415 (1.59), 7.423 (1.44), 7.630 (3.32), 7.658 (2.86), 8.049 (3.97), 8.306 (1.30), 8.326 (1.33), 8.337 (1.36), 8.356 (1.22).

The title compound (67.5 mg) was separated into enantiomers by preparative chiral HPLC to give enantiomer 1 (see Example 61) and enantiomer 2 (27.2 mg, see Example 62).

Preparative Chiral HPLC Method:

Instrument: Labomatic HD5000, Labocord-5000; Gilson GX-241, Labcol Vario 4000, column: Amylose SA 5μ 250×30 mm; Eluent A: Hexane+0.1 Vol-% Diethylamine (99%); Eluent B: 2-Propanol; isocratic: 20% B; Flow 70.0 mL/min; UV 254 nm Analytical Chiral HPLC Method:

Instrument: Agilent HPLC 1260; Column: Amylose SA 3μ 100×4.6 mm; Eluent A: Hexane+0.1 Vol-% Diethylamine (99%); Eluent B: 2-Propanol; Gradient: 20-50% B in 7 min; Flow 1.4 mL/min; Temperature: 25° C.; DAD 254 nm

Example 61

4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic Acid (Enantiomer 1)

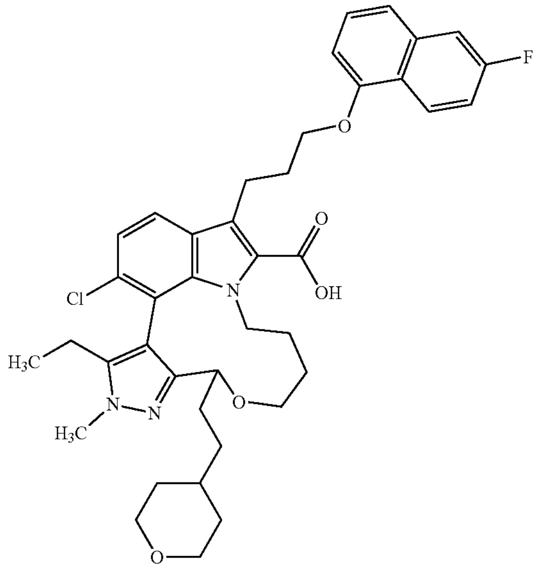 [SMILES: CCc1c2c(nn1C)C(CCC1CCOCC1)OCCCCn1c(C(=O)O)c(CCCOc3cccc4cc(F)ccc34)c3ccc(Cl)c-2c31]

For the preparation of the racemic title compound see Example 60. Separation of enantiomers by preparative chiral HPLC (method see Example 60) and flash chromatography using silica gel (gradient dichloromethane/ethanol) gave the title compound (21.5 mg).

Analytical Chiral HPLC (method see Example 60): $R_t$=1.42 min.

LC-MS (Method 1): $R_t$=1.68 min; MS (ESIpos): m/z=702 $[M+H]^+$ $^1$H-NMR (400 MHz, DMSO-d6) δ[ppm]: 0.789 (1.01), 0.797 (0.29), 0.808 (2.28), 0.827 (1.09), 0.990 (0.30), 1.052 (0.17), 1.080 (0.39), 1.088 (0.33), 1.103 (16.00), 1.132 (0.24), 1.141 (0.28), 1.151 (0.24), 1.182 (0.21), 1.198 (0.21), 1.218 (0.31), 1.234 (0.63), 1.255 (0.55), 1.272 (0.41), 1.289 (0.28), 1.307 (0.17), 1.430 (0.19), 1.527 (0.38), 1.560 (0.32), 1.888 (0.23), 1.907 (0.57), 1.925 (0.50), 1.945 (0.21), 2.152 (0.23), 2.171 (0.57), 2.189 (0.87), 2.206 (0.89), 2.224 (0.51), 2.243 (0.19), 2.331 (0.30), 2.518 (1.55), 2.523 (0.96), 2.673 (0.30), 3.029 (0.19), 3.044 (0.19), 3.073 (5.43), 3.198 (0.39), 3.204 (0.28), 3.227 (0.76), 3.257 (0.81), 3.281 (0.63), 3.296 (0.46), 3.784 (0.48), 3.812 (0.43), 3.856 (4.98), 3.898 (0.19), 3.914 (0.20), 3.932 (0.21), 4.173 (0.38), 4.188 (0.77), 4.205 (0.61), 4.224 (0.64), 4.241 (0.28), 4.306 (0.18), 6.841 (0.40), 6.848 (0.40), 6.855 (0.37), 6.862 (0.42), 7.195 (0.98), 7.215 (0.97), 7.343 (0.27), 7.349 (0.30), 7.365 (0.41), 7.372 (0.45), 7.387 (0.28), 7.394 (0.31), 7.421 (0.75), 7.429 (0.86), 7.436 (1.79), 7.637 (0.48), 7.643 (0.50), 7.663 (0.48), 7.669 (0.48), 7.737 (0.75), 7.758 (0.68), 8.192 (0.43), 8.206 (0.44), 8.215 (0.42), 8.230 (0.40).

Example 62

(−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic Acid (Enantiomer 2)

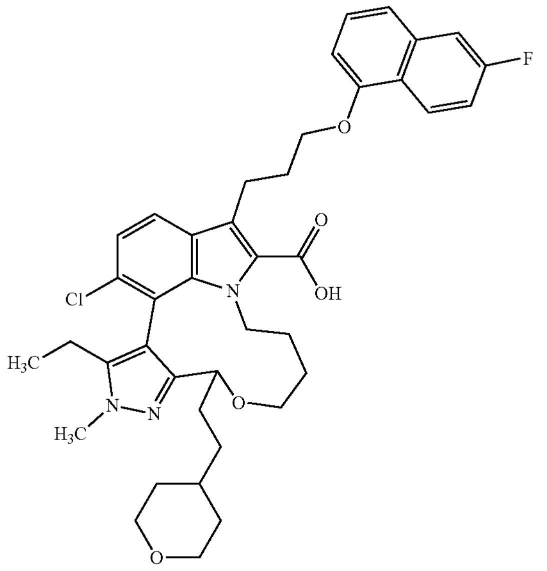 [SMILES: CCc1c2c(nn1C)C(CCC1CCOCC1)OCCCCn1c(C(=O)O)c(CCCOc3cccc4cc(F)ccc34)c3ccc(Cl)c-2c31]

For the preparation of the racemic title compound see Example 60. Separation of enantiomers by preparative chiral HPLC (method see Example 60) gave the title compound (27.2 mg).

Analytical Chiral HPLC (method see Example 60): $R_t$=2.30 min.

LC-MS (Method 2): $R_t$=1.03 min; MS (ESIpos): m/z=702 $[M+H]^+$

Specific Optical Rotation (Method O1): −44.8° (c=10 mg/mL, DMSO)

$^1$H-NMR (400 MHz, DMSO-d6) δ[ppm]: 0.800 (3.02), 0.820 (6.85), 0.839 (3.18), 0.967 (1.42), 1.039 (0.43), 1.068 (1.09), 1.098 (1.23), 1.107 (4.37), 1.120 (0.56), 1.138 (7.66), 1.156 (16.00), 1.174 (8.18), 1.194 (1.18), 1.201 (1.12), 1.208 (1.09), 1.218 (1.18), 1.234 (1.04), 1.258 (1.28), 1.274 (1.07), 1.295 (0.88), 1.314 (0.51), 1.380 (0.45), 1.389 (0.53), 1.408 (0.59), 1.417 (0.48), 1.531 (1.17), 1.864 (0.59), 1.883 (1.26), 1.900 (1.20), 2.176 (1.68), 2.194 (3.44), 2.213 (2.93), 2.231 (0.96), 2.327 (0.91), 2.331 (0.67), 2.518 (3.94), 2.522 (2.40), 2.669 (0.94), 2.673 (0.69), 2.861 (2.06), 2.879 (6.50), 2.898 (6.24), 2.915 (1.92), 3.003 (0.67), 3.013 (0.56), 3.031 (0.74), 3.186 (1.89), 3.215 (3.17), 3.239 (2.03), 3.244 (2.34), 3.269 (1.86), 3.285 (2.03), 3.776 (1.70), 3.789 (1.46), 3.801 (1.70), 3.811 (1.36), 3.830 (0.67), 3.853 (15.01), 4.175 (2.58), 4.193 (2.48), 4.210 (0.93), 4.447 (0.51), 4.465 (0.45), 4.481 (0.48), 6.820 (1.23), 6.825 (1.26), 6.836 (1.23), 6.841 (1.30), 7.103 (2.11), 7.124 (2.18), 7.339 (0.75), 7.346 (0.86), 7.362 (1.26), 7.369 (1.39), 7.384 (1.23), 7.391 (0.94), 7.403 (2.00), 7.421 (4.53), 7.437 (0.54), 7.610 (1.50), 7.629 (2.54), 7.635 (2.02), 7.655 (1.49), 7.661 (1.46), 8.209 (1.22), 8.224 (1.30), 8.232 (1.25), 8.247 (1.18).

Example 63

(+)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

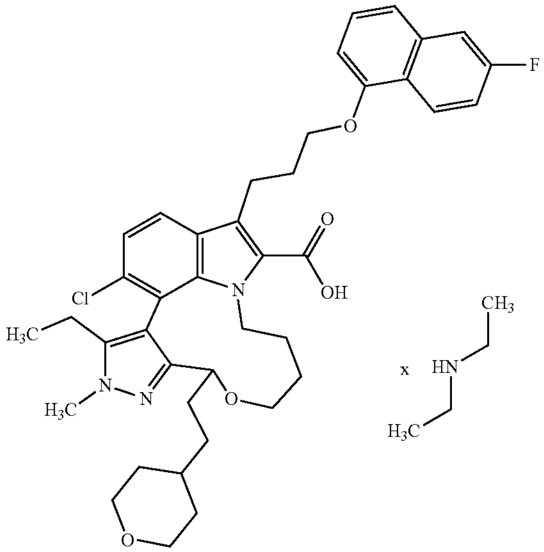

For the preparation of the racemic title compound see Example 62. Separation of enantiomers by preparative chiral HPLC gave the title compound (30.6 mg).

Preparative Chiral HPLC Method:

Instrument: Labomatic HD5000, Labocord-5000; Gilson GX-241, Labcol Vario 4000, column: Amylose SA 5μ 250×30 mm; Eluent A: Hexane+0.1 Vol-% Diethylamine (99%); Eluent B: 2-Propanol; isocratic: 80% A+20% B; Flow 50.0 mL/min; UV 220 nm Analytical Chiral HPLC Method:

Instrument: Agilent HPLC 1260; Column: Amylose SA 3μ 100×4.6 mm; Eluent A: Hexane+0.1 Vol-% Diethylamine (99%); Eluent B: 2-Propanol; Gradient: 20-50% B in 7 min; Flow 1.4 mL/min; Temperature: 25° C.; DAD 220 nm Analytical Chiral HPLC: $R_t$=1.71 min.

LC-MS (Method 1): $R_t$=1.67 min; MS (ESIpos): m/z=702 $[M+H]^+$

Specific Optical Rotation (Method O1): 51.2° (c=10 mg/mL, DMSO)

$^1$H-NMR (400 MHz, DMSO-d6) δ[ppm]: 0.803 (2.97), 0.822 (6.97), 0.841 (3.06), 0.958 (1.21), 0.972 (0.99), 1.066 (0.96), 1.096 (1.07), 1.117 (0.49), 1.133 (6.93), 1.152 (16.00), 1.170 (7.67), 1.192 (1.07), 1.215 (0.77), 1.231 (0.74), 1.259 (0.85), 1.275 (0.94), 1.298 (0.87), 1.309 (0.65), 1.375 (0.42), 1.385 (0.46), 1.394 (0.46), 1.403 (0.53), 1.413 (0.43), 1.499 (0.73), 1.527 (1.04), 1.548 (0.63), 1.877 (1.00), 1.895 (0.97), 1.905 (1.07), 2.177 (1.44), 2.197 (2.80), 2.216 (2.30), 2.235 (0.73), 2.332 (0.66), 2.518 (3.18), 2.523 (1.93), 2.673 (0.66), 2.847 (1.81), 2.865 (5.58), 2.883 (5.57), 2.902 (1.69), 3.000 (0.62), 3.010 (0.49), 3.017 (0.46), 3.028 (0.70), 3.151 (0.53), 3.166 (0.68), 3.183 (2.04), 3.212 (2.66), 3.218 (2.03), 3.242 (2.24), 3.256 (1.65), 3.272 (1.89), 3.774 (1.65), 3.787 (1.50), 3.803 (1.47), 3.822 (0.57), 3.853 (15.49), 4.152 (0.80), 4.169 (2.29), 4.175 (1.81), 4.187 (2.07), 4.204 (0.88), 4.473 (0.46), 4.506 (0.43), 6.818 (1.21), 6.823 (1.25), 6.834 (1.16), 6.839 (1.25), 7.084 (1.93), 7.105 (2.03), 7.340 (0.80), 7.346 (0.88), 7.362 (1.22), 7.369 (1.34), 7.384 (0.94), 7.391 (1.02), 7.402 (1.96), 7.419 (4.27), 7.435 (0.56), 7.582 (1.34), 7.603 (1.22), 7.627 (1.45), 7.634 (1.47), 7.653 (1.42), 7.660 (1.42), 8.213 (1.21), 8.228 (1.25), 8.236 (1.22), 8.251 (1.17).

Example 64

(−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

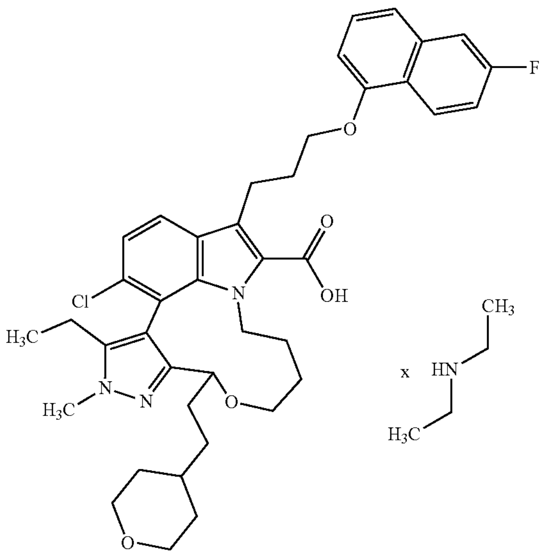

For the preparation of the racemic title compound see Example 62. Separation of enantiomers by preparative chiral HPLC (method see Example 63) gave the title compound (37.2 mg).

Analytical Chiral HPLC (method see Example 63): $R_t$=2.37 min.

LC-MS (Method 1): $R_t$=1.68 min; MS (ESIpos): m/z=702 $[M+H]^+$

Specific Optical Rotation (Method O1): −53.0° (c=10 mg/mL, DMSO)

$^1$H-NMR (400 MHz, DMSO-d6) δ[ppm]: 0.803 (3.11), 0.822 (7.22), 0.841 (3.29), 0.958 (1.28), 0.972 (1.04), 1.066 (0.99), 1.095 (1.11), 1.117 (0.51), 1.133 (7.32), 1.152 (15.58), 1.169 (7.78), 1.191 (1.12), 1.215 (0.79), 1.231 (0.79), 1.259 (0.80), 1.276 (0.96), 1.281 (0.96), 1.298 (0.95), 1.309 (0.66), 1.375 (0.42), 1.385 (0.48), 1.394 (0.48), 1.402 (0.56), 1.411 (0.45), 1.499 (0.77), 1.527 (1.11), 1.552 (0.69), 1.877 (1.08), 1.895 (1.04), 1.905 (1.14), 1.920 (0.42), 2.178

(1.48), 2.197 (2.95), 2.216 (2.44), 2.235 (0.72), 2.518 (3.55), 2.522 (2.18), 2.846 (1.86), 2.864 (5.83), 2.882 (5.73), 2.900 (1.70), 3.000 (0.66), 3.010 (0.51), 3.018 (0.48), 3.028 (0.72), 3.150 (0.50), 3.165 (0.69), 3.183 (2.13), 3.212 (2.76), 3.218 (2.13), 3.241 (2.21), 3.257 (1.54), 3.272 (1.75), 3.774 (1.75), 3.787 (1.65), 3.803 (1.60), 3.853 (16.00), 4.152 (0.83), 4.168 (2.42), 4.175 (1.89), 4.187 (2.18), 4.204 (0.93), 4.477 (0.48), 4.489 (0.40), 4.509 (0.45), 6.817 (1.28), 6.822 (1.32), 6.834 (1.24), 6.839 (1.33), 7.082 (2.12), 7.103 (2.15), 7.340 (0.85), 7.347 (0.91), 7.362 (1.30), 7.369 (1.41), 7.384 (0.95), 7.391 (1.04), 7.401 (2.07), 7.418 (4.46), 7.435 (0.51), 7.580 (1.44), 7.601 (1.32), 7.627 (1.52), 7.634 (1.56), 7.653 (1.52), 7.660 (1.49), 8.214 (1.28), 8.228 (1.35), 8.236 (1.30), 8.252 (1.24).

Example 65

(rac)-4-chloro-3-ethyl-7-{3-[(6-fluoronaphthalen-1-yl)oxy]propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylic Acid

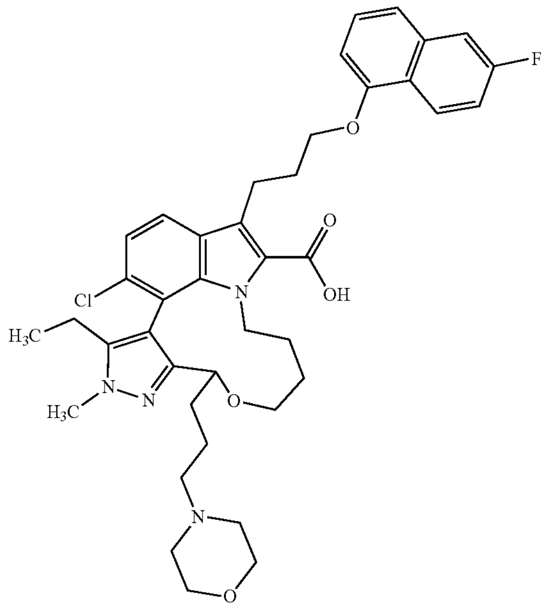 [SMILES: CCc1c2c(nn1C)C(CCCN1CCOCC1)OCCCCn1c(C(=O)O)c(CCCOc3cccc4cc(F)ccc34)c3ccc(Cl)c-2c31]

(Rac)-ethyl-4-chloro-3-ethyl-7-{3-[(6-fluoronaphthalen-1-yl)oxy]propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylate (see Intermediate 114, 440 mg, 590 μmol) was provided in 4 mL of tetrahydrofuran, 400 μL of ethanol and a solution of lithium hydroxide (1.2 mL, 1.0 M in water, 1.20 mmol) were added and the mixture was stirred for 23 h at 70° C. in a sealed tube. A solution of lithium hydroxide (1.2 mL, 1.0 M in water, 1.20 mmol) was added and the mixture was stirred for 7 days at 70° C. The mixture was diluted with water, adjusted to a pH value of 3-4 with a saturated, aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol) to provide 293 mg (64% yield) of the title compound.

LC-MS (Method 2): $R_t$=0.93 min; MS (ESIpos): m/z=717 $[M+H]^+$ $^1$H-NMR (400 MHz, DMSO-d6) δ[ppm]: 0.792 (3.16), 0.796 (2.65), 0.801 (1.32), 0.811 (7.40), 0.820 (2.36), 0.830 (3.28), 0.839 (1.06), 0.885 (1.06), 0.903 (2.18), 0.921 (1.02), 1.016 (0.76), 1.034 (1.97), 1.052 (2.77), 1.069 (1.56), 1.122 (0.44), 1.141 (0.58), 1.159 (0.60), 1.234 (0.48), 1.253 (0.67), 1.268 (0.82), 1.286 (0.57), 1.624 (0.47), 1.907 (0.73), 1.916 (0.84), 1.938 (0.93), 2.162 (0.79), 2.181 (1.92), 2.189 (2.07), 2.200 (2.36), 2.209 (2.31), 2.218 (1.47), 2.228 (1.18), 2.322 (0.67), 2.326 (0.89), 2.331 (0.66), 2.387 (0.42), 2.392 (0.45), 2.405 (0.42), 2.411 (0.57), 2.466 (0.45), 2.470 (0.60), 2.518 (3.77), 2.523 (2.49), 2.532 (0.47), 2.664 (0.86), 2.669 (1.09), 2.673 (0.87), 2.831 (0.41), 3.009 (0.48), 3.034 (0.71), 3.050 (0.71), 3.279 (2.50), 3.293 (3.28), 3.683 (1.06), 3.778 (0.47), 3.827 (0.54), 3.861 (16.00), 3.896 (0.64), 3.910 (0.86), 3.930 (0.70), 4.170 (1.06), 4.185 (2.10), 4.199 (1.16), 4.283 (0.87), 4.302 (1.63), 4.318 (1.30), 4.333 (0.57), 4.352 (0.61), 5.758 (2.31), 6.842 (1.21), 6.849 (1.25), 6.858 (1.14), 6.865 (1.34), 7.202 (3.87), 7.224 (3.87), 7.350 (0.84), 7.357 (0.92), 7.372 (1.28), 7.379 (1.38), 7.395 (0.93), 7.402 (1.25), 7.424 (2.26), 7.433 (2.65), 7.440 (5.65), 7.454 (0.51), 7.642 (1.46), 7.648 (1.59), 7.668 (1.50), 7.674 (1.54), 7.749 (3.06), 7.769 (2.69), 8.211 (1.27), 8.225 (1.34), 8.234 (1.28), 8.249 (1.18).

The title compound was separated into enantiomers by preparative chiral HPLC twice to give enantiomer 1 (42.6 mg, see Example 66) and enantiomer 2 (42.2 mg, see Example 67).

Preparative Chiral HPLC Method 1:

Instrument: Labomatic HD5000, Labocord-5000; Gilson GX-241, Labcol Vario 4000, Column: Chiralpak IF 5μ 250×30 mm; Eluent A: Hexane+0.1 Vol-% Diethylamine (99%); Eluent B: Ethanol; Isocratic: 77% A+23% B; Flow 50.0 mL/min; UV 254 nm Analytical Chiral HPLC Method 1:

Instrument: Agilent HPLC 1260; column: Chiralpak IF 3μ 100×4.6 mm; Eluent A: Hexane+0.1 Vol-% Diethylamine (99%); Eluent B: Ethanol; Isocratic: 77% A+23% B; Flow 1.4 mL/min; Temperature: 25° C.; DAD 254 nm Preparative Chiral HPLC Method 2:

Instrument: Sepiatec: Prep SFC100; Column: Chiralpak IG 5 μm 250×30 mm; Eluent A: $CO_2$, Eluent B: 2-Propanol+0.4 Vol-% Diethylamine (99%); Isocratic: 30% B; Flow 100.0 mL/min Temperature: 40° C.; BPR: 150 bar; MWD @ 254 nm Analytical Chiral HPLC Method 2:

Instrument: Agilent: 1260, Aurora SFC-Module; Column: Chiralpak IG 5 μm 100×4.6 mm; Eluent A: $CO_2$, Eluent B: 2-Propanol+0.2 Vol-% Diethylamine (99%); Isocratic: 30% B; Flow 4.0 mL/min; Temperature: 37.5° C.; BPR: 100 bar; MWD @ 254 nm Example 66

(+)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic Acid (Enantiomer 1)

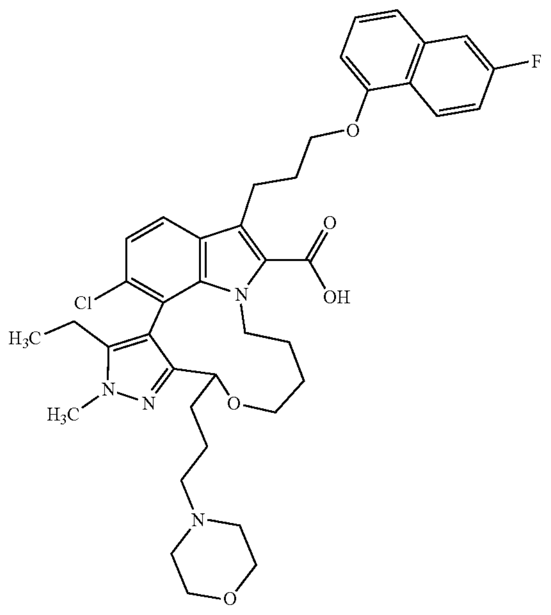 [SMILES: CCc1c2c(nn1C)C(CCCN1CCOCC1)OCCCCn1c(C(=O)O)c(CCCOc3cccc4cc(F)ccc34)c3ccc(Cl)c-2c31]

For the preparation of the racemic title compound see Example 65. Separation of enantiomers by preparative chiral HPLC (method see Example 65) gave the title compound (42.6 mg).

Analytical Chiral HPLC (method see Example 65): $R_t$=1.29 min.

LC-MS (Method 2): $R_t$=0.99 min; MS (ESIpos): m/z=717 $[M+H]^+$

Specific Optical Rotation (Method O1): +37.5° (c=10 mg/mL, DMSO)

$^1$H-NMR (400 MHz, DMSO-d6) δ[ppm]: 0.795 (3.47), 0.814 (7.38), 0.833 (3.41), 0.852 (0.44), 0.859 (0.61), 0.966 (4.06), 1.009 (0.54), 1.107 (7.84), 1.138 (3.95), 1.144 (2.53), 1.156 (8.49), 1.174 (4.31), 1.208 (1.42), 1.230 (1.97), 1.388 (0.71), 1.395 (0.50), 1.411 (0.69), 1.430 (0.82), 1.449 (0.73), 1.471 (0.84), 1.490 (0.71), 1.507 (0.48), 1.875 (0.69), 1.893 (1.61), 1.906 (1.07), 1.912 (1.59), 1.930 (0.61), 2.163 (1.02), 2.181 (2.28), 2.189 (2.53), 2.200 (2.22), 2.207 (2.43), 2.230 (2.18), 2.249 (3.74), 2.266 (3.89), 2.332 (1.00), 2.336 (0.50), 2.518 (4.79), 2.523 (3.20), 2.678 (0.42), 2.867 (1.00), 2.886 (3.01), 2.903 (2.93), 2.922 (0.98), 3.007 (0.69), 3.015 (0.61), 3.034 (0.75), 3.053 (0.44), 3.205 (1.21), 3.224 (2.03), 3.245 (2.66), 3.261 (2.93), 3.497 (3.64), 3.509 (5.33), 3.520 (3.47), 3.817 (0.94), 3.832 (0.71), 3.852 (16.00), 4.160 (1.07), 4.170 (1.80), 4.175 (1.82), 4.184 (1.07), 4.249 (0.88), 4.266 (1.84), 4.283 (0.84), 4.392 (0.52), 4.407 (0.46), 4.425 (0.48), 6.823 (1.23), 6.828 (1.28), 6.839 (1.23), 6.845 (1.34), 7.128 (2.07), 7.150 (2.18), 7.340 (0.84), 7.347 (0.92), 7.362 (1.32), 7.369 (1.44), 7.385 (1.34), 7.391 (1.09), 7.406 (2.11), 7.423 (4.85), 7.439 (0.54), 7.629 (1.67), 7.636 (1.78), 7.646 (1.61), 7.655 (1.86), 7.661 (1.97), 7.667 (1.46), 8.208 (1.25), 8.223 (1.38), 8.231 (1.28), 8.247 (1.25).

Example 67

(−)-4-chloro-3-ethyl-7-{3-[(6-fluoronaphthalen-1-yl)oxy]propyl}-2-methyl-15-[3-(morpholin-4-yl) propyl]-2,10,11,12,13,15-hexahydropyrazolo[4',3':9,10][1,6]oxazacycloundecino[8,7,6-hi]indole-8-carboxylic Acid (Enantiomer 2)

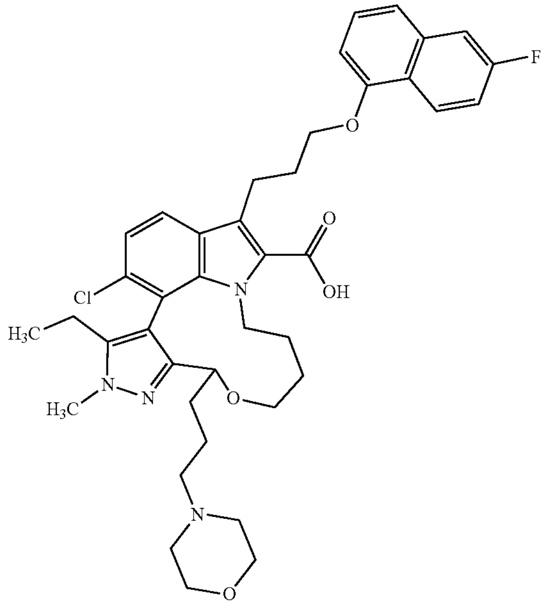 [SMILES: CCc1c2c(nn1C)C(CCCN1CCOCC1)OCCCCn1c(C(=O)O)c(CCCOc3cccc4cc(F)ccc34)c3ccc(Cl)c-2c31]

For the preparation of the racemic title compound see Example 65. Separation of enantiomers by preparative chiral HPLC (method see Example 65) gave the title compound (42.2 mg).

Analytical Chiral HPLC (method see Example 65): $R_t$=2.38 min.

LC-MS (Method 2): $R_t$=0.96 min; MS (ESIpos): m/z=717 $[M+H]^+$

Specific Optical Rotation (Method O1): −31.9° (c=10 mg/mL, DMSO)

$^1$H-NMR (400 MHz, DMSO-d6) δ[ppm]: 0.777 (0.42), 0.797 (3.54), 0.816 (7.45), 0.835 (3.46), 0.859 (0.59), 0.967 (3.67), 1.107 (16.00), 1.138 (5.09), 1.144 (2.21), 1.156 (11.08), 1.175 (5.77), 1.208 (1.19), 1.230 (1.99), 1.350 (0.72), 1.383 (0.76), 1.388 (0.79), 1.411 (0.74), 1.428 (0.79), 1.447 (0.66), 1.472 (0.81), 1.489 (0.70), 1.507 (0.49), 1.872 (0.70), 1.891 (1.61), 1.909 (1.59), 1.928 (0.62), 2.174 (1.57), 2.190 (2.91), 2.209 (2.65), 2.227 (2.61), 2.245 (3.80), 2.264 (3.84), 2.336 (0.51), 2.518 (4.82), 2.523 (3.40), 2.678 (0.42), 2.865 (1.32), 2.884 (3.97), 2.902 (3.95), 2.920 (1.27), 3.005 (0.70), 3.032 (0.76), 3.181 (0.59), 3.196 (0.87), 3.214 (1.40), 3.239 (1.74), 3.260 (1.97), 3.274 (2.25), 3.495 (3.29), 3.507 (5.03), 3.518 (3.20), 3.815 (1.00), 3.852 (15.68), 4.158 (1.08), 4.168 (1.74), 4.173 (1.76), 4.183 (1.08), 4.245 (0.87), 4.263 (1.82), 4.280 (0.83), 4.411 (0.51), 4.427 (0.45), 4.444 (0.49), 6.820 (1.29), 6.826 (1.29), 6.837 (1.25), 6.842 (1.34), 7.117 (2.04), 7.138 (2.10), 7.340 (0.87), 7.347 (0.95), 7.362 (1.38), 7.369 (1.49), 7.384 (1.38), 7.391 (1.12), 7.405 (2.14), 7.421 (4.69), 7.437 (0.55), 7.629 (2.86), 7.635 (2.04), 7.655 (2.16), 7.661 (1.61), 8.211 (1.27), 8.226 (1.38), 8.234 (1.32), 8.249 (1.25).

Example 68

4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Mixture 1 of Stereoisomers)

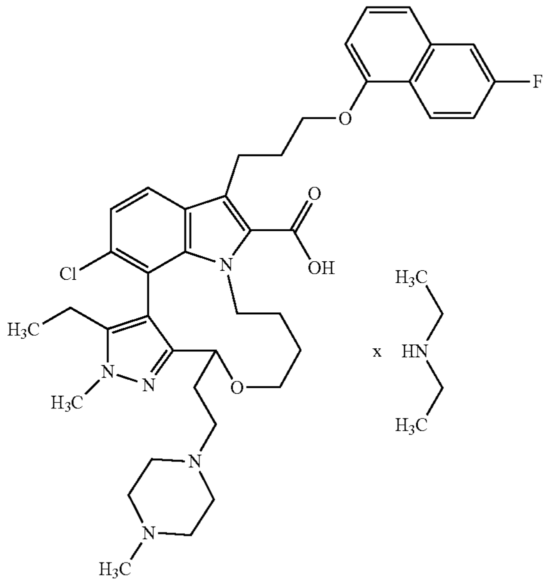

(Rac)-ethyl 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylate (see Intermediate 120, 404 mg, 543 μmol) was provided in 21 mL of tetrahydrofuran, 10.6 mL of ethanol and a solution of aqueous lithium hydroxide (10.9 mL, 1.0 M, 10.9 mmol) were added and the mixture was stirred for 3 days at 70° C. under an argon atmosphere. The reaction mixture concentrated under reduced pressure, the residue diluted with water and extracted with ethyl acetate. The combined organic phases were washed with brine, filtered through a water resistant filter and concentrated under reduced pressure. The residue was purified by preparative HPLC (Method P2) to provide 37 mg of a mixture of the title compound and its diastereomer. The aqueous phase was adjusted to a pH value of 5.5 by addition of citric acid monohydrate (6.28 g) and a 1 M aqueous solution of lithium hydroxide and was extracted with dichloromethane. The combined organic layers were filtered through a water resistant filter and concentrated under reduced pressure to give 251 mg of a mixture of the title compound and its diastereomer. The mixture of the title compound and its diastereomer (37 mg and 251 mg combined) was separated into diastereomers by preparative HPLC to give diastereomer 1 (150 mg, title compound) and diastereomer 2 (115 mg, see Example 71).

Preparative HPLC Method:

Instrument: Labomatic HD5000, Labocord-5000; Gilson GX-241, Labcol Vario 4000, Column: Cellulose SC 5μ 250×30 mm; Eluent A: Hexane+0.1 Vol-% Diethylamine (99%); Eluent B: Ethanol; Gradient: 10-30% B in 15 min; Flow 50.0 mL/min; UV 220 nm LC-MS (Method 2): $R_t$=0.88 min; MS (ESIneg): m/z=714 $[M-H]^-$ $^1$H-NMR (400 MHz, DMSO-d6) δ[ppm]: 0.793 (2.56), 0.812 (5.35), 0.821 (1.15), 0.830 (2.56), 0.904 (0.49), 1.006 (0.55), 1.035 (0.48), 1.052 (0.75), 1.070 (0.41), 1.083 (0.79), 1.127 (5.04), 1.145 (10.93), 1.163 (5.33), 1.204 (0.97), 1.228 (1.50), 1.258 (1.14), 1.316 (0.45), 1.336 (0.50), 1.352 (0.51), 1.391 (0.43), 1.405 (0.50), 1.424 (0.57), 1.440 (0.44), 1.607 (0.48), 1.627 (0.53), 1.763 (0.41), 1.775 (0.53), 1.793 (0.47), 1.901 (16.00), 2.050 (0.40), 2.068 (0.67), 2.084 (7.51), 2.105 (1.30), 2.118 (10.29), 2.137 (1.26), 2.156 (1.35), 2.176 (1.83), 2.194 (1.62), 2.225 (1.99), 2.240 (2.05), 2.253 (2.00), 2.322 (0.93), 2.326 (1.00), 2.331 (0.82), 2.522 (1.50), 2.665 (0.45), 2.669 (0.59), 2.673 (0.45), 2.819 (1.42), 2.837 (4.24), 2.855 (4.14), 2.873 (1.34), 3.095 (0.50), 3.107 (0.80), 3.118 (0.82), 3.127 (0.78), 3.141 (0.96), 3.160 (1.10), 3.178 (0.87), 3.190 (1.12), 3.208 (0.85), 3.223 (0.81), 3.242 (0.72), 3.345 (1.42), 3.416 (1.48), 3.428 (1.41), 3.440 (1.18), 4.167 (0.81), 4.177 (1.38), 4.182 (1.38), 4.193 (0.79), 4.216 (0.80), 4.227 (0.90), 4.239 (0.83), 4.250 (0.89), 4.270 (0.45), 4.287 (0.54), 4.302 (0.41), 6.820 (0.99), 6.825 (1.02), 6.837 (1.01), 6.842 (1.03), 7.055 (2.14), 7.076 (2.18), 7.354 (0.60), 7.361 (0.67), 7.377 (1.10), 7.382 (1.30), 7.401 (1.85), 7.418 (3.31), 7.436 (0.45), 7.522 (1.77), 7.543 (1.58), 7.629 (1.13), 7.635 (1.15), 7.655 (1.15), 7.661 (1.10), 8.264 (0.97), 8.278 (1.02), 8.287 (1.00), 8.302 (0.93).

The title compound was separated into enantiomers by preparative chiral HPLC to give enantiomer 1 (47.0 mg, see Example 69) and enantiomer 2 (51.0 mg, see Example 70).

Preparative Chiral HPLC Method:

Instrument: Labomatic HD5000, Labocord-5000; Gilson GX-241, Labcol Vario 4000, column: Amylose SA 5μ 250×50 mm; Eluent A: 2-Methoxy-2-methylpropane+0.1 Vol-% Diethylamine (99%); Eluent B: Ethanol; Gradient: 10-60% B in 15 min; Flow 100.0 mL/min; UV 325 nm Analytical Chiral HPLC Method:

Instrument: Agilent HPLC 1260; Column: Amylose SA 3μ 100×4.6 mm; Eluent A: 2-Methoxy-2-methylpropane+0.1 Vol-% Diethylamine (99%); Eluent B: Ethanol; Gradient: 2-60% B in 10 min; Flow 1.4 mL/min; Temperature: 25° C.; UV: 325 nm Example 69

(+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Stereoisomer 1)

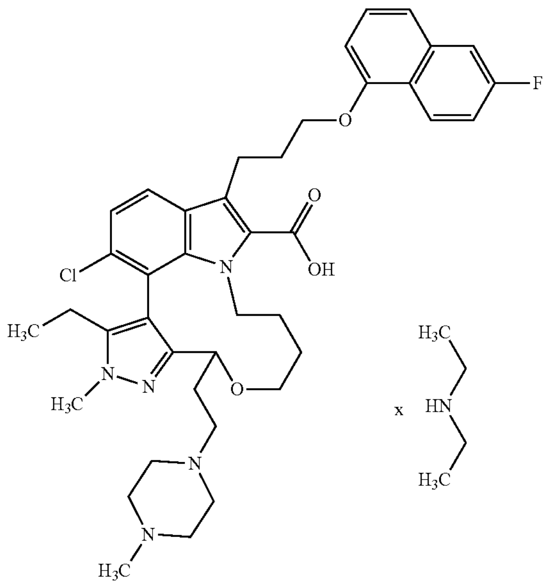

For the preparation of the racemic title compound see Example 68. Separation of enantiomers by preparative chiral HPLC (see Example 68) gave the title compound (47.0 mg).

Analytical Chiral HPLC (method see Example 68): $R_t$=2.27 min.

LC-MS (Method 2): $R_t$=0.92 min; MS (ESIpos): m/z=716 $[M+H]^+$

Specific Optical Rotation (Method O1): +47.7° (c=10 mg/mL, DMSO)

$^1$H-NMR (400 MHz, DMSO-d6) δ[ppm]: 0.782 (3.01), 0.801 (6.74), 0.820 (3.24), 0.851 (0.58), 1.135 (5.58), 1.154 (12.18), 1.172 (5.46), 1.232 (3.21), 1.441 (0.58), 1.614 (0.53), 1.635 (0.58), 1.649 (0.44), 1.780 (0.47), 1.793 (0.58), 1.810 (0.53), 1.906 (0.85), 2.032 (0.55), 2.051 (0.79), 2.069 (1.11), 2.088 (0.91), 2.107 (0.58), 2.115 (0.53), 2.126 (1.08), 2.148 (10.89), 2.163 (1.78), 2.185 (1.96), 2.202 (1.55), 2.220 (1.02), 2.232 (1.26), 2.251 (2.07), 2.265 (1.99), 2.277 (2.01), 2.294 (1.87), 2.318 (2.07), 2.322 (2.60), 2.326 (2.95), 2.331 (2.36), 2.336 (1.61), 2.518 (7.71), 2.522 (4.79), 2.539 (1.23), 2.659 (0.67), 2.664 (1.34), 2.669 (1.78), 2.673 (1.34), 2.678 (0.67), 2.880 (1.43), 2.898 (4.38), 2.916 (4.35), 2.934 (1.34), 3.105 (0.55), 3.128 (0.85), 3.152 (0.53), 3.191 (0.58), 3.206 (0.93), 3.224 (1.72), 3.241 (1.84), 3.258 (1.46), 3.422 (1.37), 3.445 (1.08), 3.816 (16.00), 3.932 (0.58), 3.955 (0.41), 4.175 (1.58), 4.191 (2.74), 4.207 (1.52), 4.239 (0.99), 4.251 (1.08), 4.263 (0.96), 4.274 (0.88), 6.841 (1.23), 6.846 (1.26), 6.856 (1.14), 6.862 (1.28), 7.147 (2.83), 7.168 (2.77), 7.357 (0.82), 7.364 (0.93), 7.380 (1.26), 7.386 (1.37), 7.397 (0.58), 7.402 (0.91), 7.408 (1.08), 7.418 (2.13), 7.428 (2.57), 7.434 (5.20), 7.449 (0.47), 7.638 (1.52), 7.644 (1.72), 7.652 (2.22), 7.664 (1.69), 7.671 (2.36), 8.258 (1.28), 8.273 (1.34), 8.281 (1.31), 8.296 (1.26).

Example 70

(+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Stereoisomer 2)

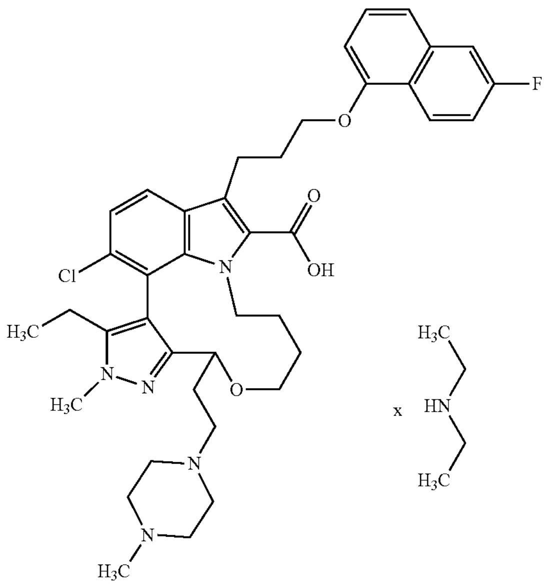

For the preparation of the racemic title compound see Example 68. Separation of enantiomers by preparative chiral HPLC (see Example 68) gave the title compound (51.0 mg).

Analytical Chiral HPLC (method see Example 68): $R_t$=3.10 min.

LC-MS (Method 2): $R_t$=0.90 min; MS (ESIpos): m/z=716 $[M+H]^+$

Specific Optical Rotation (Method O1): +38.9° (c=10 mg/mL, DMSO)

$^1$H-NMR (400 MHz, DMSO-d6) δ[ppm]: 0.785 (3.21), 0.798 (1.88), 0.804 (7.30), 0.814 (1.60), 0.823 (3.65), 0.840 (0.68), 0.851 (0.52), 0.863 (0.52), 0.886 (0.56), 0.904 (1.08), 0.923 (0.56), 0.984 (0.68), 0.999 (0.68), 1.107 (0.40), 1.132 (3.53), 1.137 (1.44), 1.149 (7.18), 1.168 (3.85), 1.232 (2.81), 1.433 (0.64), 1.608 (0.56), 1.630 (0.60), 1.645 (0.52), 1.773 (0.52), 1.786 (0.68), 1.803 (0.56), 1.906 (1.96), 2.038 (0.56), 2.056 (0.84), 2.074 (1.20), 2.093 (1.08), 2.115 (1.20), 2.129 (12.55), 2.142 (1.76), 2.161 (1.80), 2.180 (2.29), 2.199 (1.76), 2.218 (1.64), 2.237 (2.41), 2.252 (2.41), 2.265 (2.41), 2.318 (1.76), 2.322 (2.61), 2.326 (3.09), 2.331 (2.41), 2.336 (1.40), 2.373 (0.44), 2.518 (10.43), 2.522 (6.30), 2.539 (1.80), 2.659 (0.84), 2.664 (1.80), 2.669 (2.45), 2.673 (1.80), 2.678 (0.84), 2.861 (0.80), 2.879 (2.41), 2.897 (2.33), 2.915 (0.76), 3.101 (0.52), 3.124 (0.80), 3.150 (0.56), 3.170 (0.48), 3.185 (0.72), 3.203 (1.52), 3.222 (1.56), 3.240 (0.92), 3.255 (0.84), 3.419 (1.16), 3.443 (0.88), 3.815 (16.00), 3.899 (0.56), 4.172 (1.28), 4.188 (2.53), 4.203 (1.60), 4.232 (1.40), 4.244 (1.32), 4.255 (1.08), 4.267 (0.96), 6.837 (1.28), 6.842 (1.32), 6.853 (1.20), 6.858 (1.36), 7.120 (2.09), 7.141 (2.13), 7.357 (0.84), 7.363 (1.00), 7.379 (1.32), 7.386 (1.48), 7.393 (0.60), 7.402 (0.96), 7.408 (1.20), 7.414 (2.21), 7.425 (2.69), 7.430 (5.37), 7.446 (0.52), 7.614 (1.44), 7.635 (2.81), 7.641 (1.88), 7.661 (1.60), 7.667 (1.56), 8.260 (1.32), 8.275 (1.40), 8.283 (1.36), 8.298 (1.32).

Example 71

(rac)-4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Mixture 2 Od Stereoisomers)

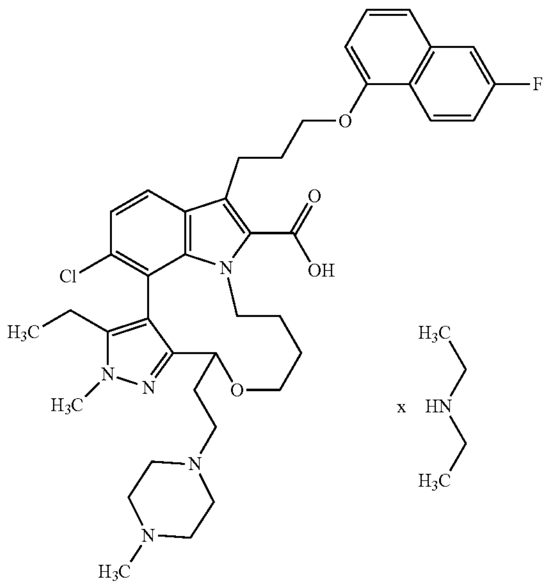

For the preparation of the racemic title compound see Example 68. Separation of the mixture of diastereomers by preparative HPLC (method see Example 68) gave the title compound (115 mg).

LC-MS (Method 2): $R_t$=0.89 min; MS (ESIneg): m/z=714 $[M-H]^-$ $^1$H-NMR (400 MHz, DMSO-d6) δ[ppm]: 0.775 (0.67), 0.794 (2.15), 0.800 (3.79), 0.814 (3.70), 0.820 (8.32), 0.839 (4.08), 0.861 (0.86), 0.880 (0.40), 0.886 (1.09), 0.904 (2.05), 0.922 (1.07), 0.933 (0.56), 0.951 (0.65), 0.982 (1.51), 1.006 (1.82), 1.035 (1.92), 1.052 (3.30), 1.070 (1.67), 1.083 (1.90), 1.133 (5.00), 1.151 (11.17), 1.170 (5.46), 1.204 (1.05), 1.231 (2.45), 1.259 (3.05), 1.421 (0.50), 1.443 (0.42), 1.905 (1.32), 1.986 (0.75), 2.004 (1.74), 2.021 (1.78), 2.038 (0.90), 2.084 (13.57), 2.112 (12.55), 2.173 (2.30), 2.192 (4.29), 2.211 (3.89), 2.230 (2.15), 2.241 (1.59), 2.258 (1.74), 2.273 (2.09), 2.289 (2.45), 2.314 (2.32), 2.322 (2.26), 2.326 (2.53), 2.331 (2.28), 2.344 (1.25), 2.358 (0.94), 2.373 (0.82), 2.388 (0.73), 2.394 (0.69), 2.406 (0.61), 2.412 (0.73), 2.518 (4.98), 2.522 (3.14), 2.539 (8.32), 2.664 (1.02), 2.669 (1.36), 2.673 (1.02), 2.850 (1.38), 2.869 (4.08), 2.886 (3.95), 2.905 (1.30), 2.985 (0.42), 3.003 (0.77), 3.012 (0.65), 3.031 (0.86), 3.049 (0.44), 3.138 (0.50), 3.158 (0.75), 3.172 (0.94), 3.190 (1.34), 3.209 (1.36), 3.229 (1.63), 3.247 (1.55), 3.262 (2.05), 3.428 (1.51), 3.446 (1.32), 3.463 (0.75), 3.772 (0.56), 3.788 (0.67), 3.813 (0.94), 3.853 (16.00), 4.153 (0.92), 4.169 (1.78), 4.177 (1.78), 4.347 (0.96), 4.365 (1.84), 4.381 (0.92), 4.454 (0.59), 4.470 (0.50), 4.487 (0.56), 6.822 (1.34), 6.828 (1.40), 6.839 (1.34), 6.844 (1.42), 7.096 (2.66), 7.117 (2.72), 7.345 (0.88), 7.351 (0.96), 7.367 (1.40), 7.374 (1.53), 7.382 (0.73), 7.389 (1.00), 7.396 (1.23), 7.403 (2.26), 7.420 (4.94), 7.436 (0.59), 7.594 (2.03), 7.615 (1.84), 7.627 (1.72), 7.634 (1.65), 7.653 (1.61), 7.660 (1.55), 8.230 (1.34), 8.246 (1.42), 8.254 (1.38), 8.268 (1.32).

The title compound was separated into enantiomers by preparative chiral HPLC to give enantiomer 1 (60.0 mg, see Example 72) and enantiomer 2 (see Example 73).

Preparative Chiral HPLC Method:

Instrument: Labomatic HD5000, Labocord-5000; Gilson GX-241, Labcol Vario 4000, column: Chiralpak IG 5μ 250×30 mm; Eluent A: Hexane+0.1 Vol-% Diethylamine (99%); Eluent B:

Ethanol; Isocratic: 20% B in 22 min; Flow 40.0 mL/min; UV 254 nm

Analytical Chiral HPLC Method:

Instrument: Agilent HPLC 1260; Column: Chiralpak IG 3μ 100×4.6 mm; Eluent A: Hexane+0.1 Vol-% Diethylamine (99%); Eluent B: Ethanol; Isocratic: 20% B in 10 min; Flow 1.4 mL/min; Temperature: 25° C.; UV: 254 nm Example 72

(−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic Acid—N-ethylethanamine Salt (Stereoisomer 3)

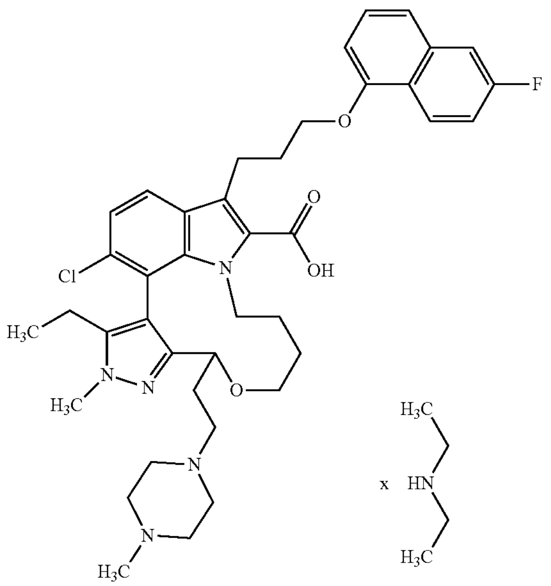

For the preparation of the racemic title compound see Example 71. Separation of enantiomers by preparative chiral HPLC (see Example 71) gave the title compound (60.0 mg).

Analytical Chiral HPLC (method see Example 71): $R_t$=1.82 min.

LC-MS (Method 2): $R_t$=0.91 min; MS (ESIpos): m/z=716 $[M+H]^+$

Specific Optical Rotation (Method O1): −34.4° (c=10 mg/mL, DMSO)

$^1$H-NMR (400 MHz, DMSO-d6) δ[ppm]: 0.697 (1.59), 0.748 (1.25), 0.766 (1.20), 0.783 (0.96), 0.796 (3.47), 0.815

(7.52), 0.834 (3.86), 0.851 (1.01), 0.886 (0.43), 0.904 (0.58), 0.923 (0.43), 0.991 (1.49), 1.107 (1.11), 1.133 (3.61), 1.137 (2.89), 1.151 (7.71), 1.169 (4.24), 1.232 (4.39), 1.293 (1.01), 1.352 (0.48), 1.906 (1.35), 1.997 (0.67), 2.015 (1.59), 2.033 (1.73), 2.050 (0.82), 2.122 (10.89), 2.190 (3.04), 2.208 (2.99), 2.226 (1.69), 2.247 (1.40), 2.265 (1.64), 2.278 (1.88), 2.294 (2.17), 2.306 (1.88), 2.318 (2.36), 2.322 (3.71), 2.326 (4.67), 2.331 (3.37), 2.336 (2.22), 2.356 (1.11), 2.518 (12.29), 2.522 (7.81), 2.539 (4.72), 2.659 (1.06), 2.664 (2.17), 2.669 (2.94), 2.673 (2.17), 2.678 (1.06), 2.869 (0.53), 2.888 (1.45), 2.905 (1.40), 2.924 (0.53), 3.011 (0.67), 3.038 (0.67), 3.203 (0.82), 3.221 (1.30), 3.248 (1.54), 3.816 (1.35), 3.830 (0.63), 3.854 (16.00), 4.182 (1.78), 4.364 (0.87), 4.381 (1.98), 4.398 (1.11), 4.425 (0.48), 6.833 (1.20), 6.839 (1.30), 6.849 (1.20), 6.855 (1.40), 7.136 (2.17), 7.157 (2.27), 7.348 (0.82), 7.355 (0.92), 7.370 (1.25), 7.377 (1.40), 7.392 (1.20), 7.399 (1.01), 7.412 (2.12), 7.422 (2.60), 7.427 (5.20), 7.443 (0.48), 7.633 (1.64), 7.639 (1.78), 7.649 (1.59), 7.659 (1.83), 7.665 (1.98), 7.670 (1.54), 8.227 (1.25), 8.242 (1.30), 8.250 (1.25), 8.264 (1.25).

Example 73

(−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic Acid (Stereoisomer 4)

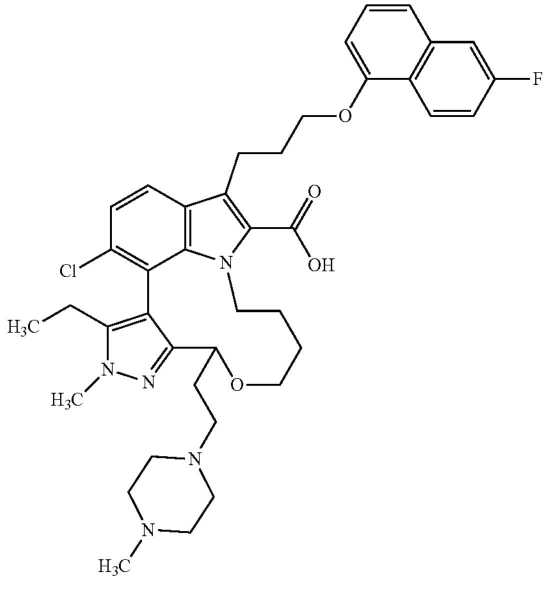 [SMILES: CCc1c2c(nn1C)C(CCN1CCN(C)CC1)OCCCCn1c(C(=O)O)c(CCCOc3cccc4cc(F)ccc34)c3ccc(Cl)c-2c31]

For the preparation of the racemic title compound see Example 71. Separation of enantiomers by preparative chiral HPLC (see Example 71) and further purification by flash chromatography using silica gel (gradient dichloromethane/ethanol/methanol) gave the title compound (26.0 mg).

Analytical Chiral HPLC (method see Example 71): $R_t$=4.65 min.

Specific Optical Rotation (Method O1): −47.1° (c=10 mg/mL, DMSO)

$^{1}$H-NMR (400 MHz, DMSO-d6) δ[ppm]: 0.812 (3.44), 0.831 (7.86), 0.850 (3.88), 0.964 (1.26), 1.137 (0.59), 1.231 (1.41), 1.361 (0.59), 1.976 (1.48), 1.996 (1.53), 2.086 (13.40), 2.163 (2.08), 2.180 (3.56), 2.204 (4.18), 2.223 (3.81), 2.242 (2.35), 2.259 (2.15), 2.273 (2.62), 2.292 (2.67), 2.310 (1.51), 2.322 (2.13), 2.326 (2.23), 2.331 (1.73), 2.518 (7.47), 2.522 (4.65), 2.664 (1.16), 2.669 (1.56), 2.673 (1.19), 2.974 (0.42), 2.992 (0.82), 3.003 (0.67), 3.020 (0.89), 3.038 (0.42), 3.092 (0.59), 3.106 (0.74), 3.124 (1.06), 3.144 (0.57), 3.156 (0.64), 3.174 (1.11), 3.192 (0.79), 3.207 (0.67), 3.278 (1.04), 3.291 (1.19), 3.676 (0.54), 3.690 (0.74), 3.703 (0.52), 3.853 (16.00), 4.141 (0.84), 4.156 (2.00), 4.173 (2.00), 4.189 (0.82), 4.318 (1.01), 4.337 (1.51), 4.352 (0.94), 4.587 (0.74), 4.605 (0.57), 4.619 (0.77), 5.759 (8.21), 6.814 (1.43), 6.818 (1.46), 6.830 (1.48), 6.835 (1.51), 7.008 (3.29), 7.029 (3.36), 7.351 (0.89), 7.357 (1.04), 7.374 (1.83), 7.379 (1.85), 7.396 (3.09), 7.402 (1.63), 7.414 (5.09), 7.431 (0.67), 7.474 (2.82), 7.495 (2.50), 7.624 (1.73), 7.631 (1.76), 7.650 (1.73), 7.657 (1.71), 8.243 (1.36), 8.257 (1.46), 8.265 (1.41), 8.280 (1.31).

Example 74

(rac)-4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic Acid

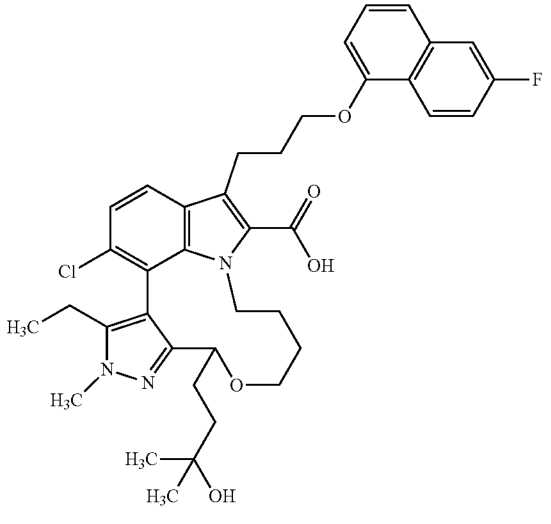 [SMILES: CCc1c2c(nn1C)C(CCC(C)(C)O)OCCCCn1c(C(=O)O)c(CCCOc3cccc4cc(F)ccc34)c3ccc(Cl)c-2c31]

(Rac)-ethyl 4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylate (see Intermediate 136, 245 mg) was dissolved in a mixture of 6 mL of tetrahydrofuran and 3 mL of ethanol, an aqueous lithium hydroxide solution (630 μL, 1.0 M, 630 μmol) was added and the mixture was stirred over night at 50° C. and for 4 h at 60° C. An aqueous lithium hydroxide solution (630 μL, 1.0 M, 630 μmol) was added and the mixture was stirred for 5 h at 60° C. and over night at 70° C. The mixture was diluted with water, adjusted to a pH value of 3-4 with a saturated, aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol) to provide 127 mg of the title compound.

LC-MS (Method 1): $R_t$=1.56 min; MS (ESIpos): m/z=676 $[M+H]^+$ $^1$H-NMR (400 MHz, DMSO-d6) δ[ppm]: 0.790 (2.14), 0.797 (1.12), 0.809 (4.88), 0.820 (1.12), 0.828 (2.29), 0.839 (0.45), 0.849 (0.19), 0.885 (0.34), 0.903 (0.72), 0.913 (0.16), 0.922 (0.40), 0.971 (0.31), 1.026 (0.60), 1.035 (0.66), 1.041 (0.72), 1.049 (0.74), 1.052 (0.77), 1.070 (16.00), 1.125 (0.33), 1.141 (0.41), 1.160 (0.36), 1.230 (0.41), 1.254 (0.46), 1.269 (0.45), 1.281 (0.50), 1.293 (0.45), 1.314 (0.49), 1.325 (0.46), 1.344 (0.41), 1.356 (0.34), 1.408 (0.30), 1.420 (0.40), 1.441 (0.44), 1.450 (0.48), 1.471 (0.27), 1.483 (0.26), 1.878 (0.17), 1.899 (0.27), 1.907 (0.69), 1.926 (0.38), 1.942 (0.46), 1.955 (0.37), 1.975 (0.42), 1.994 (0.26), 2.005 (0.30), 2.133 (0.20), 2.152 (0.51), 2.169 (1.23), 2.180 (1.34), 2.188 (1.55), 2.199 (1.72), 2.216 (1.09), 2.234 (0.42), 2.331 (0.50), 2.411 (0.16), 2.518 (3.14), 2.522 (1.91), 2.673 (0.51), 2.996 (0.21), 3.021 (0.40), 3.036 (0.41), 3.060 (0.23), 3.272 (1.66), 3.285 (1.93), 3.818 (0.16), 3.860 (9.99), 3.892 (0.43), 3.909 (0.44), 3.927 (0.46), 3.944 (0.22), 4.098 (2.30), 4.172 (0.88), 4.187 (1.74), 4.200 (1.34), 4.213 (0.85), 4.220 (0.85), 4.234 (0.57), 4.299 (0.42), 4.317 (0.40), 4.335 (0.38), 5.756 (3.60), 6.843 (0.87), 6.849 (0.92), 6.858 (0.80), 6.865 (0.93), 7.188 (2.21), 7.209 (2.17), 7.350 (0.56), 7.356 (0.66), 7.372 (0.91), 7.379 (1.00), 7.394 (0.63), 7.401 (0.91), 7.422 (1.66), 7.431 (1.87), 7.438 (3.90), 7.452 (0.31), 7.636 (1.03), 7.643 (1.09), 7.662 (1.03), 7.669 (1.07), 7.726 (1.78), 7.748 (1.58), 8.208 (0.87), 8.223 (0.92), 8.231 (0.89), 8.246 (0.87).

The title compound was separated into enantiomers by preparative chiral HPLC to give enantiomer 1 (38.0 mg, see Example 75) and enantiomer 2 (42.0 mg, see Example 76).

Preparative Chiral HPLC Method 2:

Instrument: Sepiatec: Prep SFC100; Column: Chiralpak IC 5 μm 250×30 mm; Eluent A: $CO_2$, Eluent B: 2-Propanol+0.4 Vol-% Diethylamine (99%); Isocratic: 30% B; Flow 100.0 mL/min Temperature: 40° C.; BPR: 150 bar; MWD @ 254 nm Analytical Chiral HPLC Method 2:

Instrument: Agilent: 1260, Aurora SFC-Module; Column: Chiralpak IC 5 μm 100×4.6 mm; Eluent A: $CO_2$, Eluent B: 2-Propanol+0.2 Vol-% Diethylamine (99%); Isocratic: 30% B; Flow 4.0 mL/min; Temperature: 37.5° C.; BPR: 100 bar; MWD @ 254 nm Example 75

(+)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

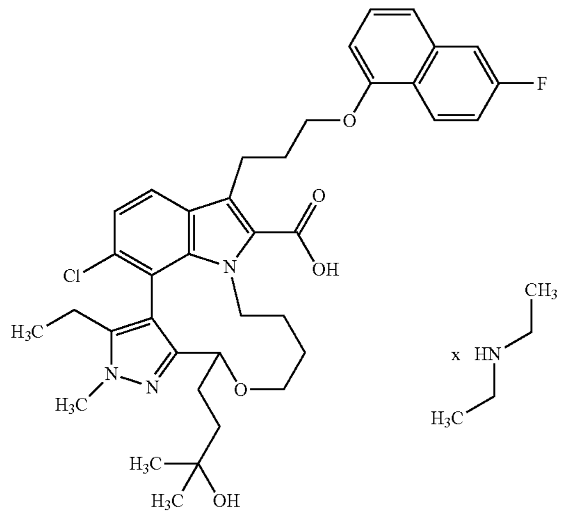

For the preparation of the racemic title compound see Example 74. Separation of enantiomers by preparative chiral HPLC (method see Example 74) gave the title compound (38.0 mg).

Analytical Chiral HPLC (method see Example 74): $R_t$=1.93 min.

LC-MS (Method 2): $R_t$=1.00 min; MS (ESIpos): m/z=676 $[M+H]^+$

Specific Optical Rotation (Method O1): +47.5° (c=10 mg/mL, DMSO)

$^1$H-NMR (400 MHz, DMSO-d6) δ[ppm]: 0.800 (2.03), 0.820 (4.58), 0.838 (2.17), 0.859 (0.34), 0.902 (0.20), 0.967 (2.06), 0.989 (0.86), 1.058 (16.00), 1.107 (6.98), 1.137 (3.12), 1.144 (1.50), 1.156 (6.63), 1.173 (3.52), 1.208 (0.76), 1.230 (1.30), 1.255 (0.63), 1.270 (0.50), 1.291 (0.57), 1.301 (0.53), 1.322 (0.42), 1.333 (0.43), 1.347 (0.29), 1.388 (0.32), 1.423 (0.30), 1.434 (0.39), 1.454 (0.46), 1.464 (0.47), 1.486 (0.27), 1.498 (0.25), 1.855 (0.19), 1.876 (0.27), 1.888 (0.38), 1.906 (0.56), 1.919 (0.39), 1.934 (0.33), 1.956 (0.41), 1.986 (0.30), 2.171 (0.98), 2.188 (2.21), 2.206 (2.04), 2.225 (0.69), 2.331 (0.56), 2.518 (3.39), 2.522 (2.07), 2.673 (0.55), 2.858 (0.77), 2.876 (2.40), 2.894 (2.34), 2.912 (0.72), 2.981 (0.22), 2.999 (0.42), 3.027 (0.46), 3.046 (0.24), 3.150 (0.22), 3.169 (0.34), 3.183 (0.48), 3.200 (0.71), 3.218 (0.70), 3.236 (0.90), 3.255 (0.94), 3.269 (1.33), 3.504 (0.18), 3.794 (0.33), 3.809 (0.37), 3.828 (0.39), 3.857 (9.99), 4.074 (1.19), 4.170 (1.56), 4.177 (1.37), 4.183 (1.30), 4.189 (1.30), 4.203 (0.71), 4.434 (0.30), 4.449 (0.29), 4.469 (0.29), 6.826 (0.83), 6.832 (0.84), 6.842 (0.81), 6.848 (0.86), 7.102 (1.19), 7.123 (1.23), 7.346 (0.52), 7.353 (0.61), 7.369 (0.85), 7.376 (0.93), 7.387 (0.44), 7.391 (0.62), 7.398 (0.66), 7.407 (1.37), 7.424 (3.15), 7.440 (0.34), 7.607 (0.84), 7.629 (1.59), 7.636 (1.16), 7.655 (0.99), 7.662 (0.98), 8.224 (0.81), 8.239 (0.84), 8.247 (0.81), 8.262 (0.77).

Example 76

(−)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

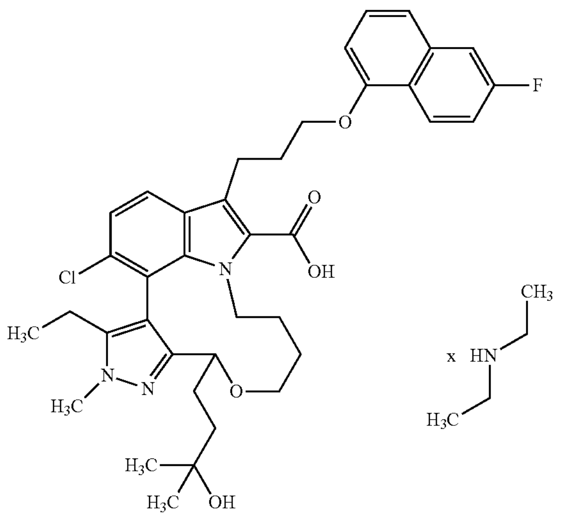

For the preparation of the racemic title compound see Example 74. Separation of enantiomers by preparative chiral HPLC (method see Example 74) gave the title compound (42.0 mg).

Analytical Chiral HPLC (method see Example 74): $R_t$=4.15 min.

LC-MS (Method 2): $R_t$=0.98 min; MS (ESIpos): m/z=676 $[M+H]^+$

Specific Optical Rotation (Method O1): −40.0° (c=10 mg/mL, DMSO)

$^1$H-NMR (400 MHz, DMSO-d6) δ[ppm]: 0.801 (2.04), 0.820 (4.51), 0.839 (2.14), 0.859 (0.40), 0.880 (0.16), 0.902 (0.20), 0.967 (1.94), 0.987 (0.89), 1.058 (16.00), 1.107 (7.19), 1.137 (2.97), 1.144 (1.47), 1.154 (6.49), 1.173 (3.61), 1.230 (1.45), 1.256 (0.76), 1.291 (0.61), 1.301 (0.60), 1.320 (0.45), 1.333 (0.49), 1.348 (0.44), 1.388 (0.31), 1.424 (0.31), 1.434 (0.40), 1.455 (0.45), 1.465 (0.46), 1.486 (0.28), 1.498 (0.25), 1.855 (0.20), 1.874 (0.27), 1.887 (0.40), 1.906 (0.52), 1.918 (0.38), 1.933 (0.32), 1.955 (0.42), 1.985 (0.33), 2.171 (1.05), 2.188 (2.33), 2.207 (2.08), 2.225 (0.68), 2.331 (0.58), 2.518 (3.52), 2.522 (2.16), 2.673 (0.57), 2.855 (0.74), 2.873 (2.31), 2.891 (2.22), 2.909 (0.70), 2.980 (0.20), 2.999 (0.42), 3.027 (0.46), 3.045 (0.23), 3.164 (0.32), 3.179 (0.44), 3.197 (0.64), 3.215 (0.65), 3.233 (0.80), 3.269 (1.05), 3.285 (1.33), 3.504 (0.19), 3.789 (0.32), 3.804 (0.37), 3.822 (0.37), 3.857 (9.58), 4.073 (1.29), 4.168 (1.47), 4.177 (1.39), 4.187 (1.33), 4.201 (0.76), 4.442 (0.32), 4.474 (0.29), 6.826 (0.78), 6.831 (0.82), 6.842 (0.80), 6.848 (0.85), 7.098 (1.17), 7.119 (1.22), 7.347 (0.49), 7.353 (0.57), 7.369 (0.84), 7.376 (0.93), 7.386 (0.42), 7.391 (0.58), 7.398 (0.66), 7.407 (1.34), 7.424 (3.12), 7.440 (0.34), 7.600 (0.78), 7.621 (0.77), 7.629 (1.11), 7.636 (1.05), 7.655 (0.97), 7.662 (0.96), 8.225 (0.78), 8.240 (0.84), 8.248 (0.82), 8.263 (0.77).

Example 77

(rac)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid

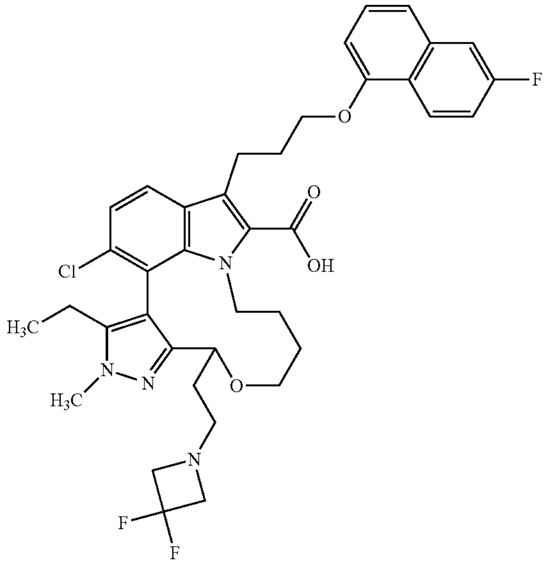 [SMILES: CCc1c2c(nn1C)C(CCN1CC(F)(F)C1)OCCCCn1c(C(=O)O)c(CCCOc3cccc4cc(F)ccc34)c3ccc(Cl)c-2c31]

(Rac)-ethyl 4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 141, 330 mg) was provided in 4 mL of tetrahydrofuran, 400 µL of ethanol and a solution of lithium hydroxide (720 µL, 1.0 M in water, 720 µmol) were added and the mixture was stirred for 19 h at 70° C. in a sealed tube. A solution of lithium hydroxide (720 µL, 1.0 M in water, 720 µmol) was added and the mixture was stirred for 4 days at 70° C. The mixture was diluted with water, adjusted to a pH value of 3-4 with a saturated, aqueous solution of citric acid and was extracted with ethyl acetate. The combined organic layers were filtered through a water resistant filter and concentrated under reduced pressure. The residue was purified by flash chromatography using silica gel (gradient dichloromethane/ethanol) to provide 132 mg of the title compound.

LC-MS (Method 2): $R_t$=1.02 min; MS (ESIpos): m/z=709 $[M+H]^+$ $^1$H-NMR (400 MHz, DMSO-d6) δ[ppm]: 0.788 (3.06), 0.797 (1.49), 0.807 (7.16), 0.814 (1.79), 0.821 (1.59), 0.826 (3.20), 0.839 (0.53), 0.884 (1.09), 0.886 (0.63), 0.902 (2.19), 0.904 (1.08), 0.920 (1.04), 0.922 (0.60), 0.992 (1.03), 1.009 (1.28), 1.026 (1.20), 1.035 (3.06), 1.042 (1.16), 1.052 (6.26), 1.070 (2.99), 1.096 (0.48), 1.115 (0.46), 1.123 (0.44), 1.142 (0.53), 1.160 (0.50), 1.236 (0.74), 1.255 (0.67), 1.895 (0.51), 1.907 (0.74), 1.914 (0.74), 1.931 (0.62), 1.950 (0.56), 1.957 (0.56), 1.971 (0.68), 1.991 (0.53), 2.065 (2.62), 2.091 (0.41), 2.158 (0.79), 2.176 (2.00), 2.182 (2.17), 2.201 (2.77), 2.218 (1.64), 2.237 (0.55), 2.331 (0.77), 2.418 (0.56), 2.437 (0.60), 2.518 (4.31), 2.523 (3.01), 2.557 (0.55), 2.577 (0.84), 2.594 (0.58), 3.022 (0.55), 3.037 (0.56), 3.245 (0.44), 3.278 (2.05), 3.292 (2.34), 3.423 (0.60), 3.434 (0.82), 3.452 (0.74), 3.459

(1.44), 3.475 (1.32), 3.491 (2.36), 3.506 (2.34), 3.523 (1.21), 3.537 (1.21), 3.779 (0.56), 3.858 (16.00), 3.877 (1.06), 3.898 (0.72), 3.917 (0.70), 4.174 (1.30), 4.189 (2.65), 4.204 (1.37), 4.307 (0.62), 4.325 (0.56), 4.343 (0.75), 4.356 (0.63), 4.382 (0.92), 4.397 (1.01), 4.403 (1.15), 4.418 (0.82), 5.758 (0.89), 6.847 (1.23), 6.854 (1.28), 6.862 (1.15), 6.869 (1.32), 7.214 (3.76), 7.234 (3.68), 7.353 (0.85), 7.360 (0.97), 7.376 (1.30), 7.382 (1.42), 7.398 (0.91), 7.405 (1.40), 7.426 (2.34), 7.434 (2.68), 7.441 (5.73), 7.454 (0.62), 7.641 (1.52), 7.648 (1.62), 7.667 (1.54), 7.674 (1.59), 7.749 (3.21), 7.770 (2.82), 8.224 (1.28), 8.238 (1.35), 8.246 (1.30), 8.262 (1.25).

The title compound (125 mg) was separated into enantiomers by preparative chiral HPLC to give enantiomer 1 (50.7 mg, see Example 78) and enantiomer 2 (51.9 mg, see Example 79).

Preparative Chiral HPLC Method:

Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; Isocratic: 20% B in 12 min; Flow 70.0 mL/min; UV 254 nm Analytical Chiral HPLC Method:

Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm

Example 78

(+)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 1)

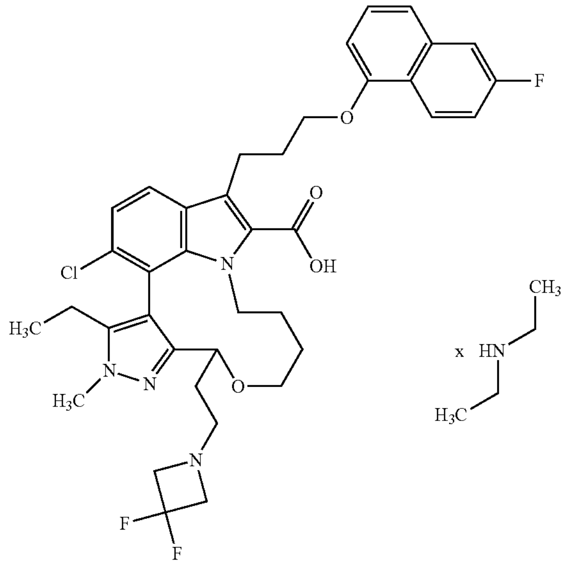

For the preparation of the racemic title compound see Example 77. Separation of enantiomers by preparative chiral HPLC (method see Example 77) gave the title compound (50.7 mg).

Analytical Chiral HPLC (method see Example 77): $R_t$=1.41 min.

LC-MS (Method 2): $R_t$=1.01 min; MS (ESIpos): m/z=709 $[M+H]^+$

Specific Optical Rotation (Method O1): +44.3° (c=10 mg/mL, DMSO)

$^1$H-NMR (400 MHz, DMSO-d6) δ[ppm]: 0.748 (0.57), 0.770 (0.62), 0.799 (3.36), 0.818 (7.49), 0.837 (3.56), 0.859 (0.41), 0.967 (1.84), 0.977 (1.40), 0.994 (1.36), 1.009 (0.80), 1.071 (0.48), 1.083 (0.41), 1.107 (2.28), 1.135 (5.10), 1.144 (2.05), 1.153 (11.45), 1.171 (6.02), 1.208 (1.31), 1.231 (1.56), 1.259 (1.03), 1.862 (0.57), 1.880 (0.76), 1.896 (0.57), 1.905 (0.78), 1.940 (0.55), 1.954 (0.69), 1.974 (0.60), 2.174 (1.79), 2.192 (3.66), 2.211 (2.97), 2.230 (0.94), 2.332 (0.99), 2.336 (0.53), 2.518 (6.87), 2.522 (4.60), 2.540 (0.94), 2.562 (0.92), 2.580 (0.55), 2.673 (0.99), 2.678 (0.48), 2.855 (1.24), 2.873 (3.75), 2.891 (3.70), 2.909 (1.20), 2.994 (0.67), 3.004 (0.55), 3.022 (0.74), 3.146 (0.60), 3.161 (0.53), 3.176 (0.71), 3.195 (1.01), 3.216 (0.97), 3.235 (1.26), 3.274 (1.77), 3.288 (2.34), 3.418 (0.74), 3.443 (1.72), 3.458 (1.68), 3.474 (2.87), 3.490 (2.90), 3.506 (1.47), 3.521 (1.49), 3.766 (0.48), 3.782 (0.55), 3.800 (0.53), 3.855 (16.00), 4.161 (1.03), 4.172 (1.86), 4.176 (1.89), 4.187 (1.06), 4.341 (0.90), 4.355 (1.01), 4.362 (1.10), 4.375 (0.83), 4.462 (0.48), 4.497 (0.44), 6.828 (1.31), 6.833 (1.33), 6.844 (1.26), 6.850 (1.38), 7.112 (1.82), 7.133 (1.89), 7.348 (0.87), 7.355 (0.94), 7.371 (1.36), 7.378 (1.52), 7.387 (0.69), 7.393 (0.97), 7.400 (1.13), 7.408 (2.23), 7.425 (5.03), 7.441 (0.55), 7.608 (1.29), 7.632 (2.37), 7.638 (1.82), 7.658 (1.59), 7.664 (1.56), 8.234 (1.33), 8.249 (1.38), 8.257 (1.33), 8.272 (1.29).

Example 79

(−)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid—N-ethylethanamine Salt (Enantiomer 2)

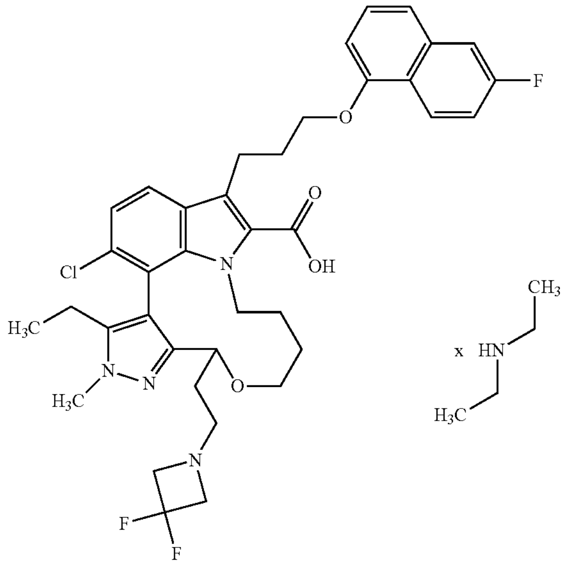

For the preparation of the racemic title compound see Example 77. Separation of enantiomers by preparative chiral HPLC (method see Example 77) gave the title compound (51.9 mg, 97%).

Analytical Chiral HPLC (method see Example 77): $R_t$=2.69 min.

LC-MS (Method 2): $R_t$=1.01 min; MS (ESIpos): m/z=709 $[M+H]^+$

Specific Optical Rotation (Method O1): −39.0° (c=10 mg/mL, DMSO)

$^1$H-NMR (400 MHz, DMSO-d6) δ[ppm]: 0.697 (0.53), 0.748 (1.17), 0.768 (1.22), 0.800 (3.58), 0.819 (7.74), 0.838 (3.67), 0.859 (0.57), 0.967 (1.86), 0.976 (1.65), 1.005 (1.01), 1.034 (0.60), 1.053 (0.53), 1.071 (0.76), 1.084 (0.83), 1.088 (0.99), 1.107 (2.92), 1.137 (3.81), 1.153 (8.10), 1.208 (1.42), 1.231 (2.07), 1.259 (1.45), 1.858 (0.60), 1.877 (0.76), 1.893 (0.60), 1.905 (0.73), 1.939 (0.57), 1.953 (0.73), 1.973 (0.62), 2.174 (1.81), 2.193 (3.47), 2.212 (2.78), 2.231 (0.87), 2.332 (1.03), 2.336 (0.51), 2.518 (7.46), 2.522 (5.05), 2.538 (1.15), 2.560 (0.94), 2.579 (0.53), 2.673 (1.03), 2.678 (0.53), 2.871 (1.91), 2.888 (1.91), 2.993 (0.71), 3.003 (0.57), 3.020 (0.78), 3.155 (0.55), 3.169 (0.73), 3.188 (1.06), 3.212 (0.92), 3.231 (1.33), 3.249 (1.19), 3.264 (1.56), 3.274 (1.93), 3.416 (0.85), 3.442 (1.79), 3.457 (1.72), 3.473 (2.96), 3.488 (2.96), 3.504 (1.56), 3.520 (1.54), 3.757 (0.48), 3.773 (1.10), 3.791 (0.57), 3.844 (1.26), 3.855 (16.00), 4.171 (1.84), 4.176 (1.88), 4.337 (0.90), 4.351 (1.03), 4.358 (1.12), 4.372 (0.85), 4.477 (0.51), 4.511 (0.48), 6.826 (1.31), 6.832 (1.33), 6.843 (1.31), 6.848 (1.38), 7.103 (1.95), 7.124 (2.02), 7.348 (0.87), 7.355 (0.96), 7.371 (1.38), 7.378 (1.54), 7.386 (0.71), 7.393 (0.99), 7.400 (1.19), 7.407 (2.27), 7.424 (4.91), 7.440 (0.60), 7.596 (1.40), 7.617 (1.29), 7.631 (1.63), 7.638 (1.70), 7.658 (1.56), 7.664 (1.58), 8.235 (1.31), 8.250 (1.35), 8.259 (1.35), 8.273 (1.29).

Example 80

(rac)-4-chloro-3-ethyl-7-{3-[(6-fluoronaphthalen-1-yl)oxy]propyl}-(15-rac)-{2-[methoxy(methyl)amino]ethyl}-2-methyl-2,10,11,12,13,15-hexahydropyrazolo[4',3':9,10][1,6]oxazacycloundecino[8,7,6-hi]indole-8-carboxylic Acid

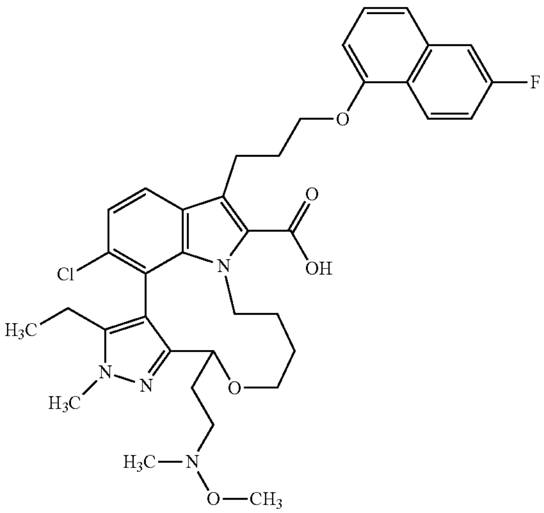 [SMILES: CCc1c2c(nn1C)C(CCN(C)OC)OCCCCn1c(C(=O)O)c(CCCOc3cccc4cc(F)ccc34)c3ccc(Cl)c-2c31]

The title compound (73.8 mg) were isolated as byproduct of Example 77, experimental procedure see Example 77.

LC-MS (Method 2): $R_t$=1.00 min; MS (ESIpos): m/z=677 $[M+H]^+$ $^1$H-NMR (400 MHz, DMSO-d6) δ[ppm]: 0.794 (3.24), 0.813 (7.41), 0.832 (3.38), 1.035 (2.42), 1.052 (3.54), 1.065 (4.54), 1.070 (2.13), 1.082 (2.76), 1.101 (1.36), 1.149 (0.54), 1.230 (0.88), 1.255 (0.74), 1.907 (1.21), 2.064 (0.40), 2.107 (1.03), 2.120 (1.23), 2.159 (1.02), 2.178 (2.21), 2.187 (2.42), 2.197 (2.62), 2.205 (2.51), 2.216 (1.63), 2.445 (13.31), 2.464 (4.87), 2.518 (3.68), 2.522 (2.26), 2.548 (0.48), 2.565 (1.06), 2.581 (1.39), 2.588 (1.85), 2.605 (1.96), 2.623 (1.80), 2.642 (1.21), 3.037 (0.60), 3.050 (0.62), 3.241 (0.56), 3.275 (2.50), 3.290 (2.99), 3.381 (8.51), 3.424 (0.66), 3.756 (6.26), 3.866 (16.00), 3.894 (0.91), 3.913 (0.71), 3.931 (0.77), 4.172 (1.36), 4.187 (2.80), 4.202 (1.44), 4.307 (0.69), 4.325 (0.64), 4.342 (0.66), 4.357 (0.45), 4.475 (0.70), 5.757 (1.50), 6.844 (1.33), 6.851 (1.37), 6.859 (1.29), 6.866 (1.43), 7.196 (3.51), 7.217 (3.47), 7.353 (0.86), 7.359 (0.97), 7.375 (1.40), 7.382 (1.52), 7.397 (0.95), 7.404 (1.39), 7.424 (2.47), 7.433 (2.90), 7.439 (6.08), 7.453 (0.63), 7.640 (1.59), 7.646 (1.70), 7.666 (1.62), 7.672 (1.69), 7.738 (2.96), 7.759 (2.65), 8.226 (1.29), 8.241 (1.41), 8.249 (1.36), 8.264 (1.29).

Example 81

(rac)-4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid

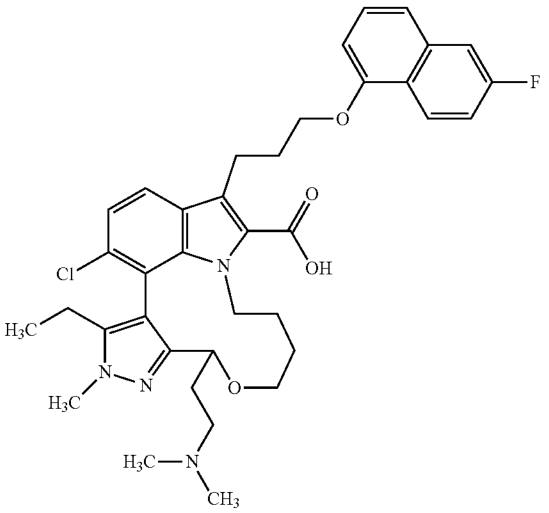 [SMILES: CCc1c2c(nn1C)C(CCN(C)C)OCCCCn1c(C(=O)O)c(CCCOc3cccc4cc(F)ccc34)c3ccc(Cl)c-2c31]

(Rac)-ethyl 4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 147, 270 mg) was provided in 3 mL of tetrahydrofuran, 300 μL of ethanol and a solution of lithium hydroxide (630 μL, 1.0 M in water, 630 μmol) were added and the mixture was stirred for 20 h at 70° C. in a sealed tube. A solution of lithium hydroxide (630 μL, 1.0 M in water, 630 μmol) was added and the mixture was stirred for 3 days at 70° C. The mixture was diluted with water, adjusted to a pH value of 5 with a saturated, aqueous solution of citric acid and was extracted with ethyl acetate. The combined organic layers were filtered through a water resistant filter and concentrated under reduced pressure. The residue was purified by preparative HPLC (Method P2) to provide 25.6 mg of the title compound as a mixture of two diastereomers.

The title compound (25 mg) was separated into stereoisomers by preparative chiral HPLC to give stereoisomer 1 (3.2 mg, see Example 82), stereoisomer 2 (6.3 mg, see Example 83), stereoisomer 3 (9.8 mg, see Example 84) and stereoisomer 4 (12.7 mg, see Example 85).

Preparative Chiral HPLC Method:

Instrument: Labomatic HD5000, Labocord-5000; Gilson GX-241, Labcol Vario 4000, Column: Cellulose SC 5μ 250×30 mm; Eluent A: Hexane+0.1 Vol-% Diethylamine (99%); Eluent B: Ethanol; Gradient: 10-30% B in 20 min; Flow 50.0 mL/min; UV 220 nm Analytical Chiral HPLC Method:

Instrument: Agilent HPLC 1260; Column: Cellulose SC 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 325 nm Example 82

4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid (Stereoisomer 1)

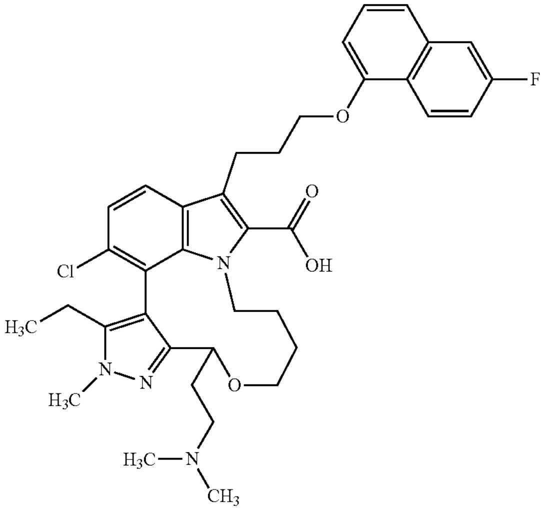 [SMILES: CCc1c2c(nn1C)C(CCN(C)C)OCCCCn1c(C(=O)O)c(CCCOc3cccc4cc(F)ccc34)c3ccc(Cl)c-2c31]

For the preparation of the racemic title compound see Example 81. Separation of stereoisomers by preparative chiral HPLC (method see Example 81) gave the title compound (3.2 mg).

Analytical Chiral HPLC (method see Example 81): $R_t$=2.04 min.

LC-MS (Method 2): $R_t$=0.97 min; MS (ESIpos): m/z=661 $[M+H]^+$ $^1$H-NMR (400 MHz, DMSO-d6) δ[ppm]: 0.786 (2.67), 0.805 (6.14), 0.823 (2.98), 0.851 (0.43), 1.135 (1.05), 1.153 (1.98), 1.171 (1.12), 1.232 (3.22), 1.442 (0.56), 1.698 (0.43), 1.817 (0.50), 1.833 (0.43), 1.907 (1.67), 2.039 (0.50), 2.058 (0.74), 2.076 (1.05), 2.095 (0.93), 2.115 (0.81), 2.132 (1.43), 2.164 (6.14), 2.186 (2.60), 2.203 (1.36), 2.332 (3.16), 2.336 (1.74), 2.518 (16.00), 2.522 (10.29), 2.673 (2.67), 2.678 (1.24), 2.902 (0.56), 2.921 (0.56), 3.136 (0.74), 3.159 (0.81), 3.232 (1.30), 3.249 (1.43), 3.265 (1.18), 3.438 (0.74), 3.463 (0.68), 3.822 (14.76), 3.942 (0.50), 4.176 (1.43), 4.192 (2.54), 4.208 (1.36), 4.251 (0.87), 4.263 (0.99), 4.274 (0.87), 4.285 (0.74), 6.845 (1.18), 6.852 (1.18), 6.860 (1.05), 6.867 (1.18), 7.162 (2.23), 7.184 (2.29), 7.361 (0.81), 7.367 (0.93), 7.383 (1.24), 7.389 (1.30), 7.405 (0.93), 7.412 (0.99), 7.423 (2.11), 7.433 (2.48), 7.438 (4.90), 7.641 (1.43), 7.648 (1.49), 7.667 (1.67), 7.674 (2.79), 7.696 (1.43), 8.259 (1.18), 8.274 (1.18), 8.282 (1.18), 8.297 (1.12).

Example 83

4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid (Stereoisomer 2)

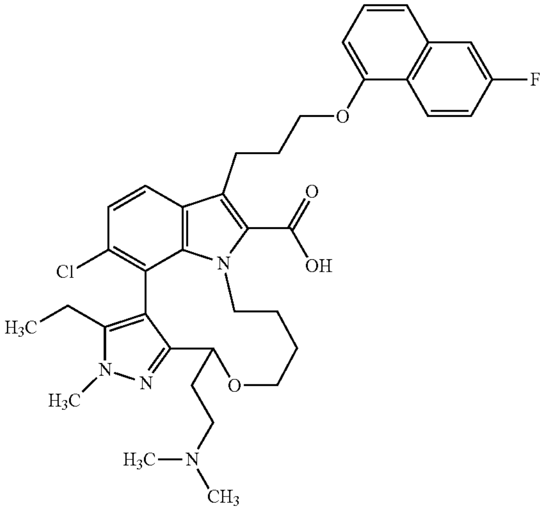 [SMILES: CCc1c2c(nn1C)C(CCN(C)C)OCCCCn1c(C(=O)O)c(CCCOc3cccc4cc(F)ccc34)c3ccc(Cl)c-2c31]

For the preparation of the racemic title compound see Example 81. Separation of stereoisomers by preparative chiral HPLC (method see Example 81) gave the title compound (6.3 mg).

Analytical Chiral HPLC (method see Example 81): $R_t$=2.21 min.

LC-MS (Method 2): $R_t$=0.97 min; MS (ESIpos): m/z=661 $[M+H]^+$ $^1$H-NMR (400 MHz, DMSO-d6) δ[ppm]: 0.000 (0.80), 0.853 (2.67), 0.871 (6.07), 0.890 (2.93), 0.917 (0.40), 1.049 (0.20), 1.072 (0.20), 1.150 (0.33), 1.161 (0.33), 1.200 (1.33), 1.218 (2.80), 1.236 (1.47), 1.299 (2.67), 1.325 (1.73), 1.419 (0.40), 1.509 (0.53), 1.752 (0.47), 1.873 (0.53), 1.972 (2.60), 2.025 (0.27), 2.106 (0.53), 2.125 (0.73), 2.143 (1.07), 2.161 (1.00), 2.181 (1.27), 2.210 (6.47), 2.234 (2.20), 2.253 (2.07), 2.269 (1.20), 2.384 (1.87), 2.388 (3.47), 2.393 (4.53), 2.398 (3.33), 2.402 (1.73), 2.584 (16.00), 2.588 (10.47), 2.726 (1.27), 2.730 (2.93), 2.735 (4.00), 2.740 (2.87), 2.744 (1.33), 2.948 (0.27), 2.966 (0.80), 2.984 (0.80), 3.003 (0.27), 3.178 (0.47), 3.201 (0.73), 3.225 (1.07), 3.237 (0.87), 3.294 (1.27), 3.311 (1.40), 3.329 (1.07), 3.504 (0.80), 3.526 (0.73), 3.888 (14.27), 3.977 (0.67), 4.000 (0.53), 4.242 (1.53), 4.258 (2.60), 4.274 (1.40), 4.314 (0.87), 4.326 (1.00), 4.337 (0.87), 4.349 (0.80), 6.599 (0.27), 6.910 (1.13), 6.916 (1.13), 6.925 (1.07), 6.931 (1.20), 7.024 (0.33), 7.074 (0.40), 7.222 (2.40), 7.244 (2.53), 7.426 (0.80), 7.432 (0.93), 7.448 (1.20), 7.455

(1.27), 7.470 (0.87), 7.477 (1.00), 7.488 (2.00), 7.497 (2.40), 7.503 (4.80), 7.518 (0.47), 7.613 (0.33), 7.631 (0.33), 7.639 (0.33), 7.662 (0.47), 7.678 (0.40), 7.688 (0.47), 7.706 (1.60), 7.712 (1.60), 7.732 (2.80), 7.738 (1.67), 7.753 (1.27), 8.233 (0.20), 8.325 (1.13), 8.339 (1.20), 8.348 (1.13), 8.363 (1.13).

Example 84

4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid (Stereoisomer 3)

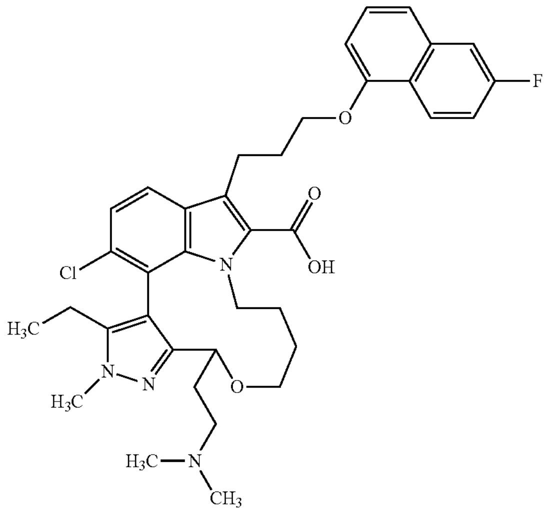 [SMILES: CCc1c2c(nn1C)C(CCN(C)C)OCCCCn1c(C(=O)O)c(CCCOc3cccc4cc(F)ccc34)c3ccc(Cl)c-2c31]

For the preparation of the racemic title compound see Example 81. Separation of stereoisomers by preparative chiral HPLC (method see Example 81) gave the title compound (9.8 mg).

Analytical Chiral HPLC (method see Example 82): $R_t$=2.43 min.

LC-MS (Method 2): $R_t$=1.01 min; MS (ESIpos): m/z=661 $[M+H]^+$ $^1$H-NMR (400 MHz, DMSO-d6) δ[ppm]: −0.065 (0.28), 0.798 (1.59), 0.817 (3.25), 0.836 (1.59), 0.904 (0.23), 0.983 (0.57), 1.084 (0.28), 1.131 (0.74), 1.137 (0.74), 1.150 (1.54), 1.168 (0.80), 1.232 (1.54), 1.259 (0.63), 1.352 (0.23), 1.906 (2.11), 2.070 (0.34), 2.115 (0.46), 2.140 (0.40), 2.174 (1.14), 2.193 (2.45), 2.210 (2.90), 2.332 (2.39), 2.336 (1.14), 2.518 (16.00), 2.522 (10.42), 2.539 (9.68), 2.673 (2.45), 2.678 (1.14), 2.729 (0.23), 2.888 (0.28), 2.897 (0.40), 2.915 (0.40), 3.043 (0.28), 3.159 (0.51), 3.171 (0.51), 3.253 (0.57), 3.818 (0.57), 3.863 (6.55), 4.180 (0.91), 4.337 (0.40), 4.357 (0.51), 4.371 (0.40), 6.838 (0.51), 6.843 (0.63), 6.853 (0.51), 6.859 (0.57), 6.955 (0.17), 7.008 (0.23), 7.148 (0.85), 7.169 (1.02), 7.350 (0.34), 7.357 (0.46), 7.373 (0.63), 7.380 (0.68), 7.395 (0.57), 7.402 (0.46), 7.417 (0.97), 7.426 (1.25), 7.432 (2.45), 7.636 (0.68), 7.642 (0.74), 7.663 (0.91), 7.668 (1.14), 7.690 (0.40), 8.170 (0.17), 8.229 (0.57), 8.243 (0.57), 8.252 (0.57), 8.267 (0.57).

Example 85

4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid (Stereoisomer 4)

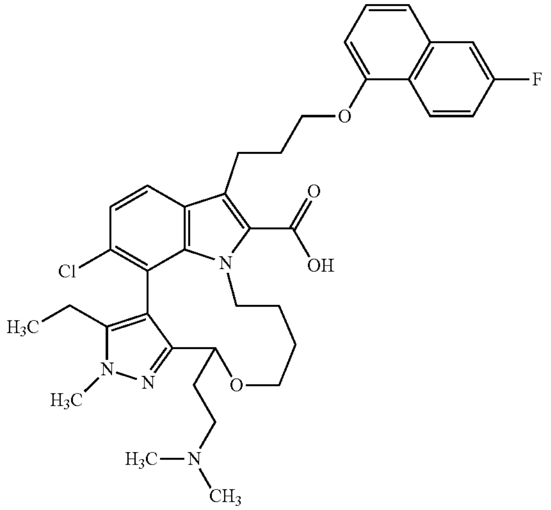 [SMILES: CCc1c2c(nn1C)C(CCN(C)C)OCCCCn1c(C(=O)O)c(CCCOc3cccc4cc(F)ccc34)c3ccc(Cl)c-2c31]

For the preparation of the racemic title compound see Example 81. Separation of stereoisomers by preparative chiral HPLC (method see Example 81) gave the title compound (12.7 mg).

Analytical Chiral HPLC (method see Example 82): $R_t$=2.81 min.

LC-MS (Method 2): $R_t$=0.98 min; MS (ESIpos): m/z=661 $[M+H]^+$ $^1$H-NMR (400 MHz, DMSO-d6) δ[ppm]: 0.800 (1.08), 0.819 (2.42), 0.838 (1.18), 0.991 (0.41), 1.085 (0.36), 1.129 (1.23), 1.137 (0.57), 1.147 (2.73), 1.166 (1.34), 1.233 (1.39), 1.259 (0.77), 1.353 (0.21), 1.907 (1.29), 2.043 (0.26), 2.116 (0.41), 2.175 (2.11), 2.193 (1.49), 2.213 (1.03), 2.337 (1.13), 2.454 (0.77), 2.518 (16.00), 2.523 (10.91), 2.679 (1.08), 2.729 (0.26), 2.872 (0.26), 2.890 (0.87), 2.909 (0.77), 2.928 (0.26), 3.044 (0.21), 3.159 (0.21), 3.172 (0.26), 3.246 (0.36), 3.292 (0.62), 3.862 (4.94), 4.178 (0.67), 4.330 (0.26), 4.350 (0.36), 4.365 (0.26), 6.836 (0.41), 6.843 (0.41), 6.852 (0.41), 6.858 (0.41), 7.135 (0.41), 7.155 (0.41), 7.352 (0.26), 7.358 (0.31), 7.374 (0.41), 7.380 (0.46), 7.396 (0.41), 7.402 (0.36), 7.416 (0.72), 7.426 (0.93), 7.431 (1.75), 7.636 (0.57), 7.642 (0.67), 7.662 (0.67), 7.668 (0.72), 8.231 (0.41), 8.247 (0.46), 8.255 (0.46), 8.269 (0.41), 10.851 (0.15).

Example 86

4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Mixture of Stereoisomers 1)

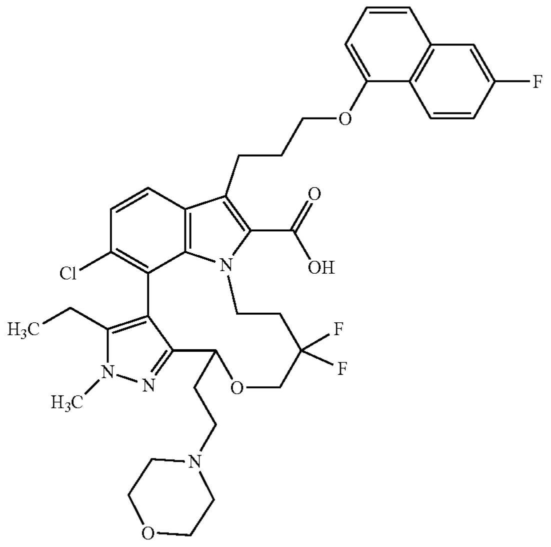 [SMILES: CCc1c2c(nn1C)C(CCN1CCOCC1)OCC(F)(F)CCn1c(C(=O)O)c(CCCOc3cccc4cc(F)ccc34)c3ccc(Cl)c-2c31]

Ethyl 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylate (see Intermediate 156, 328 mg, 427 μmol) was provided in 6.7 mL of tetrahydrofuran, 3.4 mL of ethanol and a solution of lithium hydroxide (3.4 mL, 1.0 M in water, 3.39 mmol) were added and the mixture was stirred for 21 h at 70° C. The mixture was concentrated under reduced pressure. The residue was purified by flash chromatography twice using silica gel (1. gradient dichloromethane/ethanol; 2. Gradient dichloromethane/acetone) to provide 45.0 mg of the title compound as a mixture of stereoisomers and 248 mg of a mixture of stereoisomers.

LC-MS (Method 2): $R_t$=0.96 min; MS (ESIpos): m/z=739 $[M+H]^+$ $^1$H-NMR (400 MHz, DMSO-d6) δ[ppm]: 0.751 (1.17), 0.770 (2.73), 0.789 (1.24), 1.137 (0.37), 1.233 (0.33), 1.684 (0.20), 1.697 (0.21), 1.719 (0.18), 1.907 (0.39), 1.924 (0.20), 1.938 (0.23), 1.957 (0.21), 1.972 (0.18), 2.010 (0.21), 2.028 (0.31), 2.047 (0.46), 2.066 (0.39), 2.076 (0.34), 2.084 (16.00), 2.094 (0.49), 2.114 (0.60), 2.131 (0.44), 2.150 (0.28), 2.168 (0.24), 2.184 (0.39), 2.202 (0.50), 2.221 (0.42), 2.240 (0.23), 2.280 (1.37), 2.299 (0.94), 2.318 (0.72), 2.322 (0.96), 2.326 (1.15), 2.331 (0.80), 2.336 (0.39), 2.518 (3.82), 2.522 (2.55), 2.660 (0.31), 2.664 (0.73), 2.668 (1.01), 2.673 (0.72), 2.678 (0.31), 3.283 (0.52), 3.306 (0.94), 3.517 (1.19), 3.528 (1.74), 3.539 (1.17), 3.684 (0.24), 3.712 (0.29), 3.720 (0.33), 3.748 (0.21), 3.857 (6.80), 3.892 (0.33), 4.188 (0.52), 4.203 (1.06), 4.218 (0.50), 4.442 (0.42), 4.453 (0.60), 4.464 (0.55), 4.476 (0.52), 6.856 (0.49), 6.862 (0.50), 6.871 (0.46), 6.878 (0.52), 7.268 (1.17), 7.289 (1.19), 7.352 (0.33), 7.359 (0.39), 7.375 (0.50), 7.382 (0.55), 7.397 (0.36), 7.404 (0.52), 7.426 (0.88), 7.435 (1.02), 7.441 (2.24), 7.456 (0.18), 7.642 (0.59), 7.648 (0.62), 7.668 (0.60), 7.674 (0.60), 7.786 (0.85), 7.808 (0.75), 8.238 (0.52), 8.252 (0.55), 8.260 (0.54), 8.276 (0.50).

The mixture of stereoisomers (248 mg) was separated by preparative chiral HPLC to give stereoisomer 1 (see Example 87), stereoisomer 2 (see Example 88) and a mixture of two stereoisomers (see Example 89).

Preparative Chiral HPLC Method:

Instrument: Labomatic HD5000, Labocord-5000; Gilson GX-241, Labcol Vario 4000, Column: Chiralpak ID 5μ 250×30 mm; Eluent A: Hexane+0.1 Vol-% trifluoroacetic acids; Eluent B: Isopropanol; Isocratic: 22% B in 15 min; Flow 60.0 mL/min; UV 254 nm Analytical Chiral HPLC Method:

Instrument: Agilent HPLC 1260; Column: Chiralpak ID 3μ 100×4.6 mm; Eluent A: Hexane+0.1 Vol-% trifluoroacetic acid; Eluent B: Isopropanol, Gradient: 20-50% B in 7 min; Flow 1.4 mL/min; Temperature: 25° C.; DAD 254 nm Example 87

(+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 1)

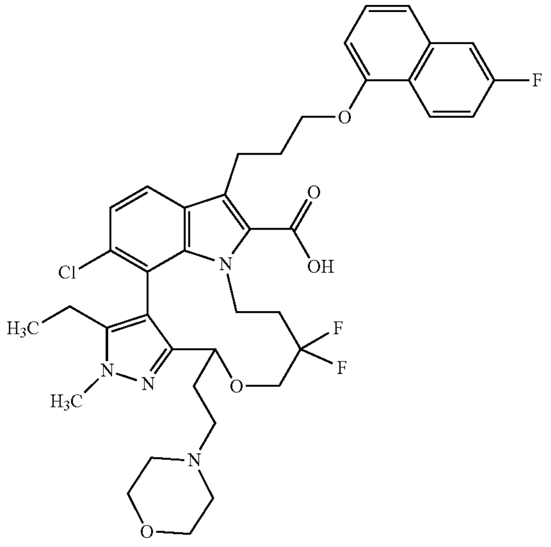 [SMILES: CCc1c2c(nn1C)C(CCN1CCOCC1)OCC(F)(F)CCn1c(C(=O)O)c(CCCOc3cccc4cc(F)ccc34)c3ccc(Cl)c-2c31]

For the preparation of the title compound as a mixture of stereoisomers see Example 86. Separation of stereoisomers by preparative chiral HPLC (see Example 86) gave 35.0 mg of the title compound.

Analytical Chiral HPLC (method see Example 86): $R_t$=2.71 min.

LC-MS (Method 2): $R_t$=0.96 min; MS (ESIpos): m/z=739 $[M+H]^+$

Specific Optical Rotation (Method O1): +41.5° (c=10 mg/mL, DMSO)

$^1$H-NMR (400 MHz, DMSO-d6) δ[ppm]: 0.751 (2.86), 0.770 (6.41), 0.789 (3.02), 0.798 (1.10), 0.802 (0.58), 0.814 (0.91), 0.821 (0.96), 0.840 (0.49), 0.886 (0.44), 0.904 (0.96), 0.922 (0.52), 1.071 (0.44), 1.159 (0.44), 1.231 (1.07), 1.687 (0.47), 1.700 (0.52), 1.722 (0.41), 1.907 (0.63), 1.928 (0.41), 1.941 (0.55), 1.963 (0.49), 2.009 (0.52), 2.028 (0.74), 2.046

(1.07), 2.065 (0.96), 2.084 (1.62), 2.095 (1.04), 2.114 (1.32), 2.132 (1.04), 2.151 (0.71), 2.170 (0.77), 2.185 (0.96), 2.203 (1.21), 2.222 (1.02), 2.288 (3.16), 2.306 (2.14), 2.318 (1.43), 2.322 (2.06), 2.327 (2.42), 2.332 (1.62), 2.518 (6.63), 2.523 (4.43), 2.660 (0.49), 2.665 (1.13), 2.669 (1.65), 2.673 (1.18), 2.678 (0.52), 3.285 (1.35), 3.519 (2.80), 3.530 (4.18), 3.541 (2.83), 3.685 (0.60), 3.713 (0.71), 3.721 (0.80), 3.750 (0.52), 3.858 (16.00), 3.892 (0.80), 4.188 (1.24), 4.203 (2.53), 4.218 (1.21), 4.442 (1.04), 4.454 (1.35), 4.466 (1.29), 4.477 (1.18), 5.759 (7.15), 6.855 (1.13), 6.862 (1.18), 6.871 (1.07), 6.877 (1.24), 7.268 (2.75), 7.290 (2.75), 7.353 (0.80), 7.360 (0.91), 7.376 (1.18), 7.383 (1.32), 7.398 (0.85), 7.404 (1.29), 7.426 (2.09), 7.435 (2.39), 7.442 (5.17), 7.456 (0.41), 7.642 (1.40), 7.649 (1.48), 7.668 (1.43), 7.675 (1.43), 7.787 (2.03), 7.808 (1.81), 8.238 (1.24), 8.252 (1.29), 8.260 (1.26), 8.276 (1.18).

Example 88

(−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 2)

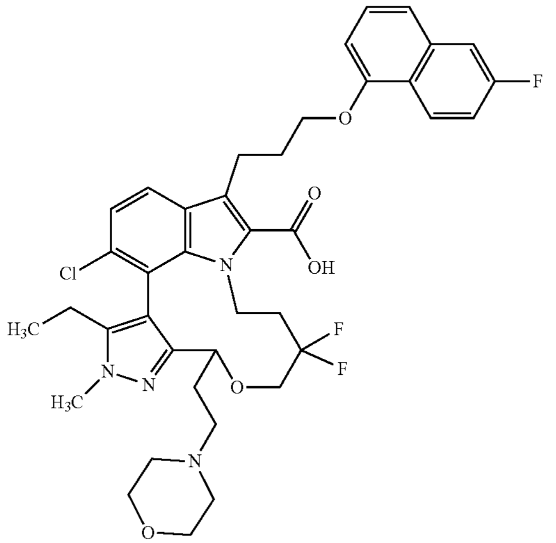 [SMILES: CCc1c2c(nn1C)C(CCN1CCOCC1)OCC(F)(F)CCn1c(C(=O)O)c(CCCOc3cccc4cc(F)ccc34)c3ccc(Cl)c-2c31]

For the preparation of the title compound as a mixture of stereoisomers see Example 86. Separation of stereoisomers by preparative chiral HPLC (see Example 86) gave 35.0 mg of the title compound.

Analytical Chiral HPLC (method see Example 86): $R_t$=4.27 min.

LC-MS (Method 2): $R_t$=0.96 min; MS (ESIpos): m/z=739 $[M+H]^+$

Specific Optical Rotation (Method O1): −34.3° (c=10 mg/mL, DMSO)

$^1$H-NMR (400 MHz, DMSO-d6) δ[ppm]: 0.752 (2.77), 0.771 (6.37), 0.789 (2.93), 0.798 (0.80), 0.814 (0.64), 0.821 (0.64), 0.904 (0.64), 1.162 (0.47), 1.231 (1.16), 1.688 (0.47), 1.701 (0.50), 1.722 (0.42), 1.907 (0.61), 1.930 (0.42), 1.941 (0.53), 1.964 (0.50), 1.976 (0.42), 2.009 (0.55), 2.028 (0.75), 2.045 (1.02), 2.064 (0.94), 2.084 (1.13), 2.096 (1.02), 2.114 (1.27), 2.132 (1.02), 2.151 (0.78), 2.171 (0.97), 2.186 (0.97), 2.204 (1.22), 2.223 (1.00), 2.240 (0.50), 2.289 (2.99), 2.307 (2.02), 2.318 (1.58), 2.322 (2.08), 2.327 (2.55), 2.332 (1.83), 2.336 (0.94), 2.518 (6.89), 2.523 (4.57), 2.539 (1.38), 2.660 (0.53), 2.665 (1.16), 2.669 (1.66), 2.673 (1.19), 2.678 (0.53), 3.287 (1.33), 3.520 (2.74), 3.531 (4.07), 3.542 (2.77), 3.685 (0.58), 3.713 (0.72), 3.721 (0.78), 3.750 (0.53), 3.858 (16.00), 3.891 (0.66), 4.188 (1.22), 4.204 (2.46), 4.218 (1.19), 4.443 (1.05), 4.454 (1.19), 4.466 (1.30), 4.477 (1.19), 5.759 (5.65), 6.855 (1.11), 6.861 (1.13), 6.871 (1.05), 6.877 (1.22), 7.266 (2.24), 7.288 (2.35), 7.354 (0.78), 7.360 (0.89), 7.376 (1.16), 7.383 (1.27), 7.399 (0.80), 7.405 (1.30), 7.426 (1.99), 7.436 (2.33), 7.441 (4.96), 7.456 (0.44), 7.642 (1.38), 7.649 (1.41), 7.668 (1.41), 7.675 (1.38), 7.785 (1.63), 7.806 (1.44), 8.238 (1.22), 8.252 (1.25), 8.260 (1.25), 8.275 (1.16).

Example 89

4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Mixture of Stereoisomers 2)

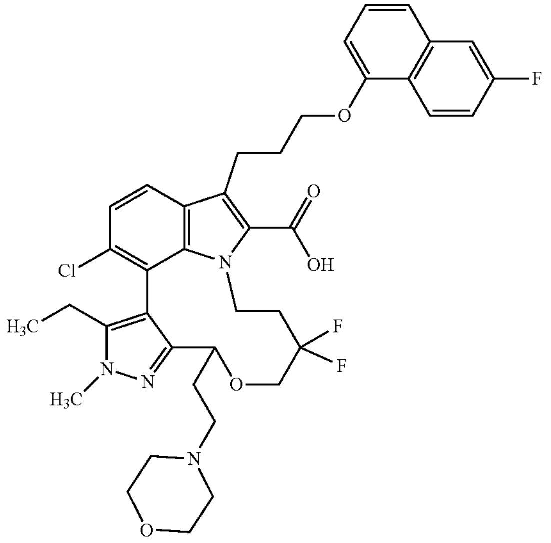 [SMILES: CCc1c2c(nn1C)C(CCN1CCOCC1)OCC(F)(F)CCn1c(C(=O)O)c(CCCOc3cccc4cc(F)ccc34)c3ccc(Cl)c-2c31]

For the preparation of the title compound as a mixture of stereoisomers see Example 86. Separation of stereoisomers by preparative chiral HPLC (see Example 86) gave 85.0 mg of the title compound as a mixture of stereoisomers.

Analytical Chiral HPLC (method see Example 86): $R_t$=2.33 min.

LC-MS (Method 2): $R_t$=0.96 min; MS (ESIpos): m/z=739 $[M+H]^+$

Specific Optical Rotation (Method O1): +6.2° (c=10 mg/mL, DMSO)

$^1$H-NMR (400 MHz, DMSO-d6) δ[ppm]: 0.765 (3.07), 0.784 (7.26), 0.797 (1.22), 0.803 (3.40), 0.814 (0.70), 0.821 (0.67), 0.904 (0.60), 1.230 (0.76), 1.907 (0.47), 1.986 (0.44), 2.084 (1.12), 2.113 (0.45), 2.132 (1.07), 2.150 (2.03), 2.155 (1.95), 2.169 (2.03), 2.174 (2.13), 2.195 (1.66), 2.213 (1.60), 2.231 (1.13), 2.248 (0.42), 2.322 (0.77), 2.327 (1.04), 2.332 (0.85), 2.336 (0.51), 2.411 (1.24), 2.424 (1.26), 2.518 (4.64), 2.523 (3.01), 2.539 (0.57), 2.664 (0.67), 2.669 (0.94), 2.673 (0.70), 3.238 (0.47), 3.253 (0.57), 3.561 (3.48), 3.597 (0.77), 3.680 (0.42), 3.712 (0.71), 3.743 (0.45), 3.893 (16.00), 4.176 (1.21), 4.192 (2.53), 4.207 (1.26), 4.494 (0.41), 4.529 (0.41), 4.799 (0.60), 4.817 (1.09), 4.834 (0.59), 5.758 (4.79), 6.851 (1.19), 6.857 (1.27), 6.867 (1.15), 6.873 (1.33), 7.275 (3.10), 7.295 (3.09), 7.346 (0.79), 7.352 (0.97), 7.368 (1.26), 7.375 (1.42), 7.390 (0.86), 7.397 (0.95), 7.401 (0.56), 7.423 (2.16), 7.432 (2.54), 7.438 (5.58), 7.453 (0.50), 7.638 (1.47), 7.644 (1.57), 7.664 (1.51), 7.670 (1.54), 7.790 (2.37), 7.811 (2.10), 8.198 (1.30), 8.212 (1.38), 8.221 (1.33), 8.236 (1.29).

Preparative chiral HPLC separation of the title compound gave stereoisomer 1 (see Example 90) and stereoisomer 2 (see Example 91).

Preparative Chiral HPLC Method:

Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine; Eluent B: Isopropanol; Gradient: 5-25% B in 15 min; Flow 40.0 mL/min; UV 254 nm Analytical Chiral HPLC Method:

Instrument: Agilent HPLC 1260; Column: Chiralpak IG 3μ 100×4.6 mm; Eluent A: Hexane+0.1 Vol-% Diethylamine; Eluent B: Isopropanol; Gradient: 1-25% B in 7 min; Flow 1.4 mL/min; Temperature: 25° C.; DAD 254 nm

Example 90

(+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 3)

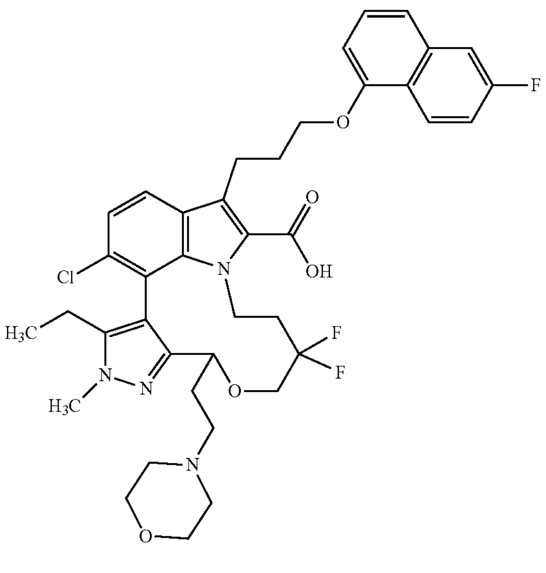 [SMILES: CCc1c2c(nn1C)C(CCN1CCOCC1)OCC(F)(F)CCn1c(C(=O)O)c(CCCOc3cccc4cc(F)ccc34)c3ccc(Cl)c-2c31]

For the preparation of the title compound as a mixture of stereoisomers see Example 89. Separation of stereoisomers by preparative chiral HPLC (see Example 89) gave 39.8 mg of the title compound. Another batch of 102 mg was produced as described in Example 86 and Example 89 starting with 743 mg of ethyl 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylate. The two batches were combined and purified by flash chromatography using silica gel (gradient dichloromethane/ethyl acetate/ethanol) to give 80.8 mg of the title compound.

Analytical Chiral HPLC (method see Example 89): $R_t$=3.87 min.

LC-MS (Method 2): $R_t$=0.97 min; MS (ESIpos): m/z=739 $[M+H]^+$

Specific Optical Rotation (Method O1): +28.2 (c=10 mg/mL, DMSO)

$^1$H-NMR (400 MHz, DMSO-d6) δ[ppm]: 0.697 (0.43), 0.764 (3.80), 0.783 (7.83), 0.802 (4.07), 0.814 (1.22), 0.821 (1.16), 0.840 (0.66), 0.886 (0.53), 0.904 (0.96), 0.922 (0.56), 1.071 (0.43), 1.154 (1.55), 1.231 (1.72), 1.255 (0.66), 1.294 (0.50), 1.327 (0.50), 1.352 (0.43), 1.368 (0.43), 1.907 (1.09), 1.987 (0.73), 2.070 (0.66), 2.089 (0.89), 2.105 (0.76), 2.128 (1.12), 2.147 (2.21), 2.171 (2.38), 2.192 (1.88), 2.211 (2.05), 2.230 (1.45), 2.261 (0.73), 2.275 (0.93), 2.292 (1.29), 2.323 (4.99), 2.326 (5.85), 2.379 (0.69), 2.397 (1.16), 2.412 (0.89), 2.426 (0.76), 2.518 (10.51), 2.522 (6.91), 2.664 (1.45), 2.669 (1.98), 2.673 (1.45), 3.222 (0.60), 3.236 (0.73), 3.526 (4.50), 3.533 (4.46), 3.580 (0.73), 3.653 (0.46), 3.685 (0.79), 3.714 (0.56), 3.856 (0.76), 3.891 (16.00), 4.174 (1.42), 4.189 (2.88), 4.204 (1.49), 4.517 (0.46), 4.804 (0.73), 4.821 (1.32), 4.838 (0.73), 5.758 (4.33), 6.848 (1.42), 6.854 (1.42), 6.864 (1.36), 6.870 (1.45), 7.257 (2.25), 7.279 (2.35), 7.345 (0.86), 7.351 (0.99), 7.367 (1.45), 7.374 (1.62), 7.389 (0.96), 7.396 (1.29), 7.419 (2.45), 7.430 (3.14), 7.435 (5.85), 7.450 (0.56), 7.635 (1.62), 7.642 (1.72), 7.661 (1.62), 7.668 (1.65), 7.764 (1.69), 7.785 (1.52), 8.200 (1.39), 8.215 (1.49), 8.224 (1.45), 8.238 (1.39).

Example 91

(−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic Acid (Enantiomer 4)

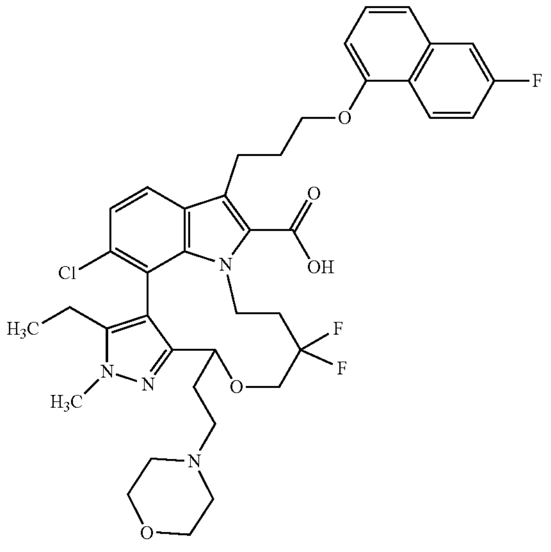 [SMILES: CCc1c2c(nn1C)C(CCN1CCOCC1)OCC(F)(F)CCn1c(C(=O)O)c(CCCOc3cccc4cc(F)ccc34)c3ccc(Cl)c-2c31]

For the preparation of the title compound as a mixture of stereoisomers see Example 89. Separation of stereoisomers by preparative chiral HPLC (see Example 89) gave 23.2 mg of the title compound. Another batch of 84.7 mg was produced as described in Example 86 and Example 89 starting with 743 mg of ethyl 4-chloro-3-ethyl-12,12-difluoro-7-{3-[(6-fluoronaphthalen-1-yl)oxy]propyl}-2- methyl-15-[2-(morpholin-4-yl)ethyl]-2,10,11,12,13,15-hexahydropyrazolo[4',3':9,10][1,6]oxazacycloundecino[8,7,6-hi]indole-8-carboxylate. The two batches were combined and purified by flash chromatography using silica gel (gradient dichloromethane/ethyl acetate/ethanol) to give 65.1 mg of the title compound.

Analytical Chiral HPLC (method see Example 89): $R_t$=4.90 min.

LC-MS (Method 2): $R_t$=0.97 min; MS (ESIpos): m/z=739 $[M+H]^+$

Specific Optical Rotation (Method O1): −23.3 (c=10 mg/mL, DMSO)

$^1$H-NMR (400 MHz, DMSO-d6) δ[ppm]: 0.697 (0.43), 0.764 (3.80), 0.783 (7.83), 0.802 (4.07), 0.814 (1.22), 0.821 (1.16), 0.840 (0.66), 0.886 (0.53), 0.904 (0.96), 0.922 (0.56), 1.071 (0.43), 1.154 (1.55), 1.231 (1.72), 1.255 (0.66), 1.294 (0.50), 1.327 (0.50), 1.352 (0.43), 1.368 (0.43), 1.907 (1.09), 1.987 (0.73), 2.070 (0.66), 2.089 (0.89), 2.105 (0.76), 2.128 (1.12), 2.147 (2.21), 2.171 (2.38), 2.192 (1.88), 2.211 (2.05), 2.230 (1.45), 2.261 (0.73), 2.275 (0.93), 2.292 (1.29), 2.323 (4.99), 2.326 (5.85), 2.379 (0.69), 2.397 (1.16), 2.412 (0.89), 2.426 (0.76), 2.518 (10.51), 2.522 (6.91), 2.664 (1.45), 2.669 (1.98), 2.673 (1.45), 3.222 (0.60), 3.236 (0.73), 3.526 (4.50), 3.533 (4.46), 3.580 (0.73), 3.653 (0.46), 3.685 (0.79), 3.714 (0.56), 3.856 (0.76), 3.891 (16.00), 4.174 (1.42), 4.189 (2.88), 4.204 (1.49), 4.517 (0.46), 4.804 (0.73), 4.821 (1.32), 4.838 (0.73), 5.758 (4.33), 6.848 (1.42), 6.854 (1.42), 6.864 (1.36), 6.870 (1.45), 7.257 (2.25), 7.279 (2.35), 7.345 (0.86), 7.351 (0.99), 7.367 (1.45), 7.374 (1.62), 7.389 (0.96), 7.396 (1.29), 7.419 (2.45), 7.430 (3.14), 7.435 (5.85), 7.450 (0.56), 7.635 (1.62), 7.642 (1.72), 7.661 (1.62), 7.668 (1.65), 7.764 (1.69), 7.785 (1.52), 8.200 (1.39), 8.215 (1.49), 8.224 (1.45), 8.238 (1.39).

Example 92

(rac)-(rac-15)-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylic Acid

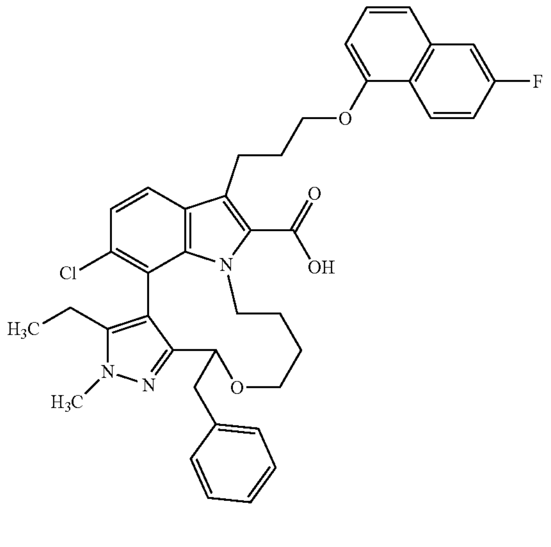 [SMILES: CCc1c2c(nn1C)C(Cc1ccccc1)OCCCCn1c(C(=O)O)c(CCCOc3cccc4cc(F)ccc34)c3ccc(Cl)c-2c31]

A solution of (rac)-ethyl 15-(rac)-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylate (see Intermediate 190, 0.462 g, 652 μmol) in ethanol (3.5 mL) was treated with a solution of sodium hydroxide (2 M in water, 1.14 mL, 2.28 mmol) and stirred at 60° C. for 2 days. After cooling to room temperature, the mixture was concentrated and acidified with 1 N aqueous HCl. The aqueous phase was extracted with ethyl acetate (3×15 mL) and the combined organic phases were washed with brine, dried over sodium sulfate, and concentrated. The crude mixture was purified by flash chromatography on silica gel (0-100% acetone/dichloromethane) to obtain a mixture of desired product and alkene impurity from the previous step. The residue (0.268 g, 395 μmol) was dissolved in ethanol (8 mL) and the solution was purged with nitrogen before adding 10% palladium on carbon (84.0 mg, 79.0 μmol). The resulting suspension was and then placed under a hydrogen atmosphere and stirred for 2 h. After degassing with nitrogen, the mixture was filtered over Celite and concentrated. The crude residue was purified by flash column chromatography on silica gel (10-100% acetone/dichloromethane) to obtain the title compound (0.13 g).

LC-MS (Method 5): $R_t$=5.66 min; MS (ESIpos): m/z=680 $[M+H]^+$ $^1$H NMR (DMSO-d6) δ: 13.18 (s, 10H), 8.26 (dd, 9H), 7.73 (d, 8H), 7.65 (dd, 10H), 7.50-7.33 (m, 27H), 7.31-7.03 (m, 51H), 6.96 (d, 3H), 6.84 (dd, 7H), 4.81 (d, 1H), 4.56-4.42 (m, 10H), 4.36 (dd, 7H), 4.17 (t, 17H), 3.90 (s, 29H), 3.74-3.52 (m, 1H), 3.31 (s, 54H), 3.08 (t, 9H), 2.87 (d, 1H), 2.50 (p, 59H), 2.31-2.14 (m, 18H), 1.23 (s, 9H), 1.20-0.87 (m, 16H), 0.81 (t, 24H), 0.69 (t, 3H).

Example 93

(rac)-4-chloro-3-ethyl-7-{3-[(6-fluoro-1-naphthyl)oxy]propyl}-2,14-dimethyl-(15-rac)-[2-(morpholin-4-yl)ethyl]-10,11,12,13,14,15-hexahydro-2H-pyrazolo[3',4':8,9][1,6]diazacycloundecino[10,11,1-hi]indole-8-carboxylic Acid—Racemate 1

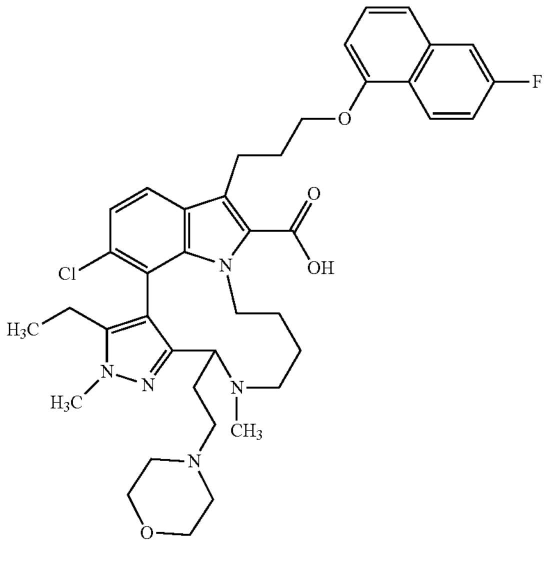 [SMILES: CCc1c2c(nn1C)C(CCN1CCOCC1)N(C)CCCCn1c(C(=O)O)c(CCCOc3cccc4cc(F)ccc34)c3ccc(Cl)c-2c31]

A mixture of ethyl 19-chloro-3-ethyl-15-{3-[(6-fluoronaphthalen-1-yl)oxy]propyl}-4,8-dimethyl-7-[2-(morpholin-4-yl)ethyl]-4,5,8,13-tetraazatetracyclo[11.6.1.$0^{2}$,$^{6}$.$0^{16}$,$^{2}$]icosa-1(20),2,5,14,16,18-hexaene-14-carboxylate (Isomer 2) (375 mg, 0.5 mmol, see Intermediate 162), ethanol (10 mL, 95%) and sodium hydroxide (1N, 5 mL, aqueous) was heated to reflux for 24 hours, cooled to room temperature, volatiles were removed under reduced pressure, the residue was dissolved in HCl (5 mL, 3M, aqueous), and the resulting solution was adsorbed onto celite, purified by reverse phase chromatography on HP C18 eluting with a gradient of 10-100% acetonitrile in water (containing 0.1% formic acid), to afford the title compound as an off white powder (260 mg).

LC-MS (Method 8): $R_t$=2.29 min; MS (ESIneg): m/z=715 $[M-H]^-$ $^{1}$H NMR (400 MHz, DMSO-$d_6$) δ 8.29 (dd, J=9.3, 5.9 Hz, 1H), 8.16 (s, 1H), 7.69 (d, J=8.6 Hz, 1H), 7.65 (dd, J=10.4, 2.7 Hz, 1H), 7.48-7.33 (m, 3H), 7.16 (d, J=8.5 Hz, 1H), 6.84 (dd, J=6.6, 2.1 Hz, 1H), 4.29-4.03 (m, 4H), 3.79 (s, 3H), 3.57 (td, J=4.5, 2.4 Hz, 4H), 3.37 (d, J=10.0 Hz, 1H), 3.25 (hept, J=7.3, 6.8 Hz, 2H), 2.40 (t, J=4.6 Hz, 4H), 2.31 (q, J=7.2 Hz, 3H), 2.16 (dp, J=21.9, 7.1 Hz, 3H), 1.97 (d, J=24.2 Hz, 5H), 1.84 (dd, J=8.6, 5.2 Hz, 1H), 1.65 (h, J=8.1, 6.4 Hz, 1H), 1.45 (d, J=8.7 Hz, 1H), 1.30-1.10 (m, 2H), 1.04 (s, 1H), 0.78 (t, J=7.5 Hz, 3H).

$^{19}$F NMR (376 MHz, DMSO-$d_6$) δ−114.67.

HSQC $^{13}$C NMR (101 MHz, DMSO) δ 124.62, 120.76, 110.28, 119.01, 127.42, 114.99, 120.79, 104.22, 67.31, 40.64, 36.04, 65.70, 63.80, 20.99, 39.52, 53.07, 50.58, 56.62, 30.22, 16.65, 16.74, 38.25, 50.42, 26.10, 26.07, 26.19, 26.35, 20.84, 20.79, 11.92.

$^{1}$H NMR (400 MHz, DMSO) δ 8.29, 7.69, 7.64, 7.43, 7.43, 7.38, 7.16, 6.84, 4.18, 4.12, 3.80, 3.57, 3.38, 3.26, 2.50, 2.40, 2.36, 2.32, 2.19, 2.15, 2.01, 1.94, 1.93, 1.82, 1.64, 1.45, 1.24, 1.16, 1.03, 0.78.

The title compound (246 mg) was separated into enantiomers by preparative chiral HPLC to give enantiomer 1 (87 mg, see Example 94) and enantiomer 2 (101 mg, see Example 95).

Preparative Chiral HPLC Method:

Instrument: Labomatic HD5000, Labocord-5000; Gilson GX-241, Labcol Vario 4000, Column: Amylose SA 5μ 250×30 mm; Eluent A: MtBE+0.1 Vol-% Diethylamine (99%); Eluent B: Ethanol; Isocratic: 80% A+20% B; Flow 50.0 mL/min; UV 254 nm Analytical Chiral HPLC Method:

Instrument: Agilent HPLC 1260; Column: Amylose SA 3μ 100×4.6 mm; Eluent A: MtBE+0.1 Vol-% Diethylamine (99%); Eluent B: Ethanol; Gradient: 2-60% B in 7 min; Flow 1.4 mL/min; Temperature: 25° C.; DAD 254 nm Example 94

4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic Acid—Stereoisomer 1

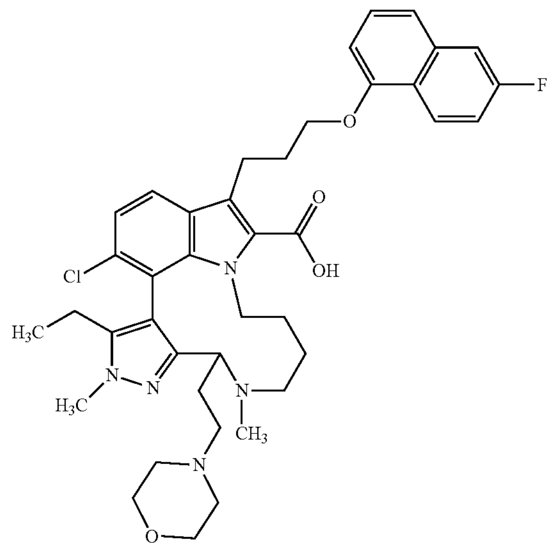 [SMILES: CCc1c2c(nn1C)C(CCN1CCOCC1)N(C)CCCCn1c(C(=O)O)c(CCCOc3cccc4cc(F)ccc34)c3ccc(Cl)c-2c31]

For the preparation of the racemic title compound see Example 93. Separation into enantiomer by preparative chiral HPLC (see Example 93) gave 87 mg of the title compound (100% purity, 35% yield).

Analytical Chiral HPLC (method see Example 93): $R_t$=2.11 min.

LC-MS (Method 2): $R_t$=0.97 min; MS (ESIpos): m/z=716 $[M+H]^+$

Specific Optical Rotation (Method O1): 86.5° (c=10 mg/mL, DMSO)

Example 95

4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic Acid—Stereoisomer 2

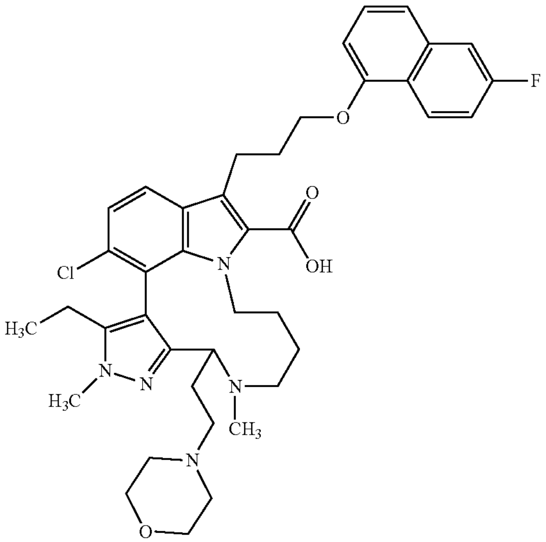 [SMILES: CCc1c2c(nn1C)C(CCN1CCOCC1)N(C)CCCCn1c(C(=O)O)c(CCCOc3cccc4cc(F)ccc34)c3ccc(Cl)c-2c31]

For the preparation of the racemic title compound see Example 93. Separation into enantiomer by preparative chiral HPLC (see Example 93) gave 101 mg of the title compound (100% purity, 35% yield).

Analytical Chiral HPLC (method see Example 93): $R_t$=3.25 min.

LC-MS (Method 2): $R_t$=0.95 min; MS (ESIpos): m/z=716 $[M+H]^+$

Specific Optical Rotation (Method O1): −72.0° (c=10 mg/mL, DMSO)

Example 96

(rac)-4-chloro-3-ethyl-7-{3-[(6-fluoro-1-naphthyl)oxy]propyl}-2,14-dimethyl-15-(rac)-[2-(morpholin-4-yl)ethyl]-10,11,12,13,14,15-hexahydro-2H-pyrazolo[3',4':8,9][1,6]diazacycloundecino[10,11,1-hi]indole-8-carboxylic Acid—Racemate 2

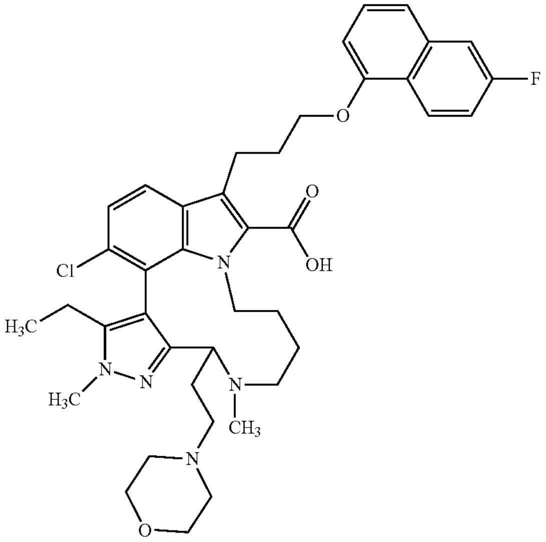 [SMILES: CCc1c2c(nn1C)C(CCN1CCOCC1)N(C)CCCCn1c(C(=O)O)c(CCCOc3cccc4cc(F)ccc34)c3ccc(Cl)c-2c31]

A mixture of (rac)-ethyl 19-chloro-3-ethyl-15-{3-[(6-fluoronaphthalen-1-yl)oxy]propyl}-4,8-dimethyl-(7-rac)-[2-(morpholin-4-yl)ethyl]-4,5,8,13-tetraazatetracyclo[11.6.1.$0^2$,$^6$.$0^{16}$,$^2$]icosa-1(20),2,5,14,16,18-hexaene-14-carboxylate (Isomer 1) (1.05 g, 1.41 mmol, see Intermediate 161), ethanol (25 mL, 95%) and sodium hydroxide (1N, 10 mL, aqueous) was heated to reflux for 24 hours, cooled to room temperature, volatiles were removed under reduced pressure, the residue was dissolved in HCl (5 mL, 3M, aqueous), and the resulting solution was adsorbed onto celite, purified by reverse phase chromatography on HP C18 eluting with a gradient of 10-100% acetonitrile in water (containing 0.1% formic acid), to afford the title compound as an off white powder (740 mg).

LC-MS (Method 8): $R_t$=2.05 min; MS (ESIpos): m/z=717 $[M+H]^+$ $^1H$ NMR (400 MHz, DMSO-$d_6$) δ 8.29 (dd, J=9.3, 5.8 Hz, 1H), 8.23 (s, 1H), 7.70-7.59 (m, 2H), 7.38 (ddd, J=18.0, 9.1, 2.3 Hz, 3H), 7.16 (d, J=8.5 Hz, 1H), 6.82 (dd, J=7.0, 1.7 Hz, 1H), 4.31 (dt, J=12.7, 6.1 Hz, 1H), 4.17 (t, J=6.3 Hz, 2H), 3.84 (s, 3H), 3.77 (dt, J=11.8, 6.0 Hz, 2H), 3.56 (t, J=4.7 Hz, 4H), 3.27 (ddq, J=34.4, 13.6, 7.4 Hz, 2H), 2.63-2.53 (m, 1H), 2.53-2.45 (m, 2H), 2.45-2.36 (m, 3H), 2.30 (q, J=7.6, 6.8 Hz, 1H), 2.25-2.12 (m, 5H), 2.10 (s, 4H), 1.92 (tq, J=10.1, 5.0 Hz, 1H), 1.21 (dd, J=14.4, 6.8 Hz, 1H), 1.11-0.94 (m, 3H), 0.80 (t, J=7.5 Hz, 3H).

$^{19}F$ NMR (376 MHz, DMSO-$d_6$) δ −114.66.

$^{13}C$ NMR (101 MHz, DMSO-$d_6$) δ 163.94, 160.46 (d, J=243.6 Hz), 154.31, 147.93, 142.60, 138.83, 135.10 (d, J=9.5 Hz), 131.61, 130.09, 127.72, 127.15, 124.80 (d, J=9.4 Hz), 123.83, 122.12, 120.78, 120.54, 119.17 (d, J=4.9 Hz), 117.23, 115.02 (d, J=25.0 Hz), 113.53, 110.47 (d, J=20.3 Hz), 104.36, 67.57, 65.83, 58.07, 55.57, 53.03, 46.49, 41.25, 38.12, 36.39, 30.19, 26.71, 21.48, 21.17, 19.07, 17.13, 12.03.

HSQC $^{13}C$ NMR (101 MHz, DMSO) δ 124.63, 120.49, 110.26, 119.02, 127.44, 114.95, 120.66, 104.20, 41.08, 67.42, 36.35, 57.98, 41.20, 65.69, 21.08, 21.03, 55.51, 39.52, 52.92, 52.93, 55.45, 46.42, 30.21, 16.97, 46.48, 21.41, 38.01, 21.27, 26.60, 19.05, 26.62, 11.99.

$^{1}H$ NMR (400 MHz, DMSO) δ 8.28, 7.65, 7.61, 7.40, 7.39, 7.35, 7.14, 6.80, 4.30, 4.16, 3.83, 3.77, 3.76, 3.55, 3.29, 3.23, 2.56, 2.50, 2.48, 2.41, 2.41, 2.30, 2.19, 2.15, 2.15, 2.12, 2.09, 1.90, 1.22, 1.03, 1.02, 0.80.

$^{15}N$ HMBC $^{15}N$ NMR (41 MHz, DMSO) δ 303.15, 194.33, 45.48, 195.26, 34.26

$^{1}H$ NMR (400 MHz, DMSO) δ 3.84, 3.84, 3.56, 2.17, 2.10.

The title compound (730 mg) was separated into enantiomers by preparative chiral HPLC to give enantiomer 1 (264 mg, see Example 97) and enantiomer 2 (260 mg, see Example 98).

Preparative Chiral HPLC Method:

Instrument: Labomatic HD5000, Labocord-5000; Gilson GX-241, Labcol Vario 4000, Column: Amylose SA 5μ 250×30 mm; Eluent A: Methyl-tert.butylether+0.1 Vol-% Diethylamine (99%); Eluent B: Ethanol; Isokratic: 90% A+10% B; Flow 40.0 mL/min; UV 254 nm Analytical Chiral HPLC Method:

Instrument: Agilent HPLC 1260; Column: Amylose SA 3μ 100×4.6 mm; Eluent A: Methyl-tert.butylether+0.1 Vol-% Diethylamine (99%); Eluent B: Ethanol; Gradient: 2-60% B in 7 min; Flow 1.4 mL/min; Temperature: 25° C.; DAD 254 nm.

Example 97

4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic Acid—N-ethylethanamine Salt—Stereoisomer 3

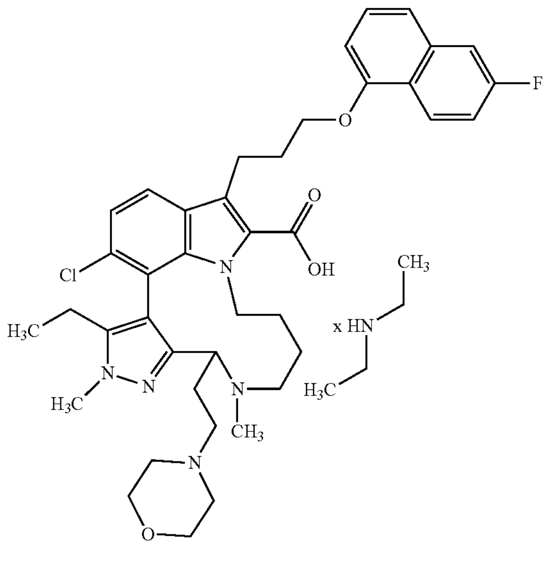

For the preparation of the racemic title compound see Example 96. Separation into enantiomer by preparative chiral HPLC (see Example 96) gave 264 mg of the title compound (100% purity, 33% yield).

Analytical Chiral HPLC (method see Example 96): $R_t$=2.00 min.

LC-MS (Method 2): $R_t$=0.98 min; MS (ESIpos): m/z=716 $[M+H]^+$

Specific Optical Rotation (Method O1): 31.9° (c=10 mg/mL, DMSO)

$^{1}H$-NMR (400 MHz, DMSO-d6) δ[ppm]: 0.778 (3.08), 0.797 (7.07), 0.816 (3.27), 1.004 (1.40), 1.132 (5.46), 1.150 (11.78), 1.168 (5.83), 1.205 (0.61), 1.229 (0.79), 1.811 (0.49), 1.828 (0.54), 1.905 (0.70), 2.006 (8.96), 2.040 (1.00), 2.060 (1.12), 2.105 (0.68), 2.123 (1.38), 2.133 (1.31), 2.143 (1.45), 2.152 (1.56), 2.163 (1.47), 2.169 (1.35), 2.181 (1.70), 2.198 (1.21), 2.216 (0.49), 2.287 (2.05), 2.296 (1.87), 2.318 (1.26), 2.322 (1.63), 2.327 (2.08), 2.331 (1.84), 2.336 (1.42), 2.385 (0.77), 2.398 (0.70), 2.407 (0.63), 2.420 (0.68), 2.437 (0.44), 2.451 (0.42), 2.518 (5.67), 2.522 (3.48), 2.659 (0.49), 2.664 (1.03), 2.669 (1.40), 2.673 (1.03), 2.678 (0.49), 2.847 (1.49), 2.865 (4.59), 2.883 (4.36), 2.902 (1.40), 3.136 (0.47), 3.155 (0.72), 3.169 (0.86), 3.187 (1.21), 3.207 (0.91), 3.233 (1.21), 3.252 (2.03), 3.507 (3.43), 3.519 (5.92), 3.530 (3.38), 3.680 (1.28), 3.689 (1.40), 3.702 (1.42), 3.712 (1.24), 3.822 (16.00), 4.154 (1.19), 4.170 (2.38), 4.187 (1.17), 4.296 (0.44), 4.310 (0.44), 4.326 (0.44), 6.818 (1.35), 6.823 (1.40), 6.836 (1.40), 6.840 (1.45), 7.091 (2.36), 7.112 (2.43), 7.357 (0.86), 7.363 (0.96), 7.379 (1.47), 7.385 (1.68), 7.403 (2.38), 7.408 (1.33), 7.421 (4.52), 7.425 (3.03), 7.442 (0.63), 7.568 (1.80), 7.590 (1.61), 7.634 (1.54), 7.640 (1.54), 7.660 (1.54), 7.667 (1.49), 8.270 (1.31), 8.284 (2.08), 8.293 (1.38), 8.308 (1.21).

Example 98

4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic Acid—N-ethylethanamine Salt—Stereoisomer 4

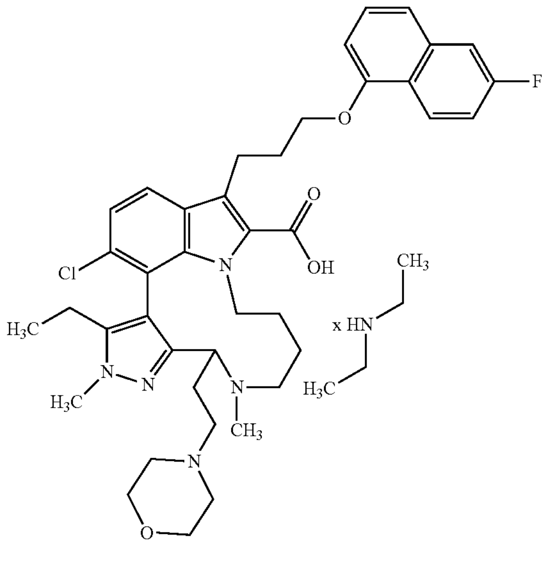

For the preparation of the racemic title compound see Example 96. Separation into enantiomer by preparative chiral HPLC (see Example 96) gave 260 mg of the title compound (100% purity, 32% yield).

Analytical Chiral HPLC (method see Example 96): $R_t$=2.76 min.

LC-MS (Method 2): $R_t$=0.95 min; MS (ESIpos): m/z=716 $[M+H]^+$

Specific Optical Rotation (Method O1): −27.5° (c=10 mg/mL, DMSO)

$^1$H-NMR (400 MHz, DMSO-d6) δ[ppm]: 0.779 (3.41), 0.798 (7.74), 0.817 (3.46), 0.840 (0.47), 0.849 (0.40), 0.864 (0.49), 0.904 (0.59), 1.004 (1.71), 1.134 (6.52), 1.152 (15.00), 1.170 (7.48), 1.229 (1.19), 1.812 (0.52), 1.828 (0.54), 1.904 (0.45), 2.009 (9.34), 2.037 (1.07), 2.048 (1.01), 2.059 (1.10), 2.088 (0.44), 2.106 (0.68), 2.115 (0.65), 2.124 (1.41), 2.134 (1.34), 2.144 (1.57), 2.153 (1.61), 2.163 (1.54), 2.170 (1.41), 2.182 (1.73), 2.199 (1.24), 2.216 (0.52), 2.273 (1.90), 2.283 (2.13), 2.322 (1.55), 2.327 (1.85), 2.331 (1.68), 2.337 (1.41), 2.384 (0.79), 2.397 (0.72), 2.406 (0.68), 2.418 (0.66), 2.436 (0.42), 2.518 (4.52), 2.523 (2.86), 2.659 (0.40), 2.664 (0.80), 2.669 (1.10), 2.673 (0.80), 2.845 (1.73), 2.863 (5.48), 2.881 (5.29), 2.899 (1.62), 3.132 (0.40), 3.151 (0.66), 3.165 (0.79), 3.183 (1.12), 3.203 (0.72), 3.231 (0.94), 3.250 (1.59), 3.268 (1.52), 3.283 (1.83), 3.507 (3.39), 3.518 (5.89), 3.529 (3.35), 3.677 (1.31), 3.687 (1.50), 3.699 (1.45), 3.709 (1.28), 3.821 (16.00), 4.153 (1.19), 4.169 (2.34), 4.185 (1.21), 4.311 (0.47), 4.327 (0.47), 4.344 (0.47), 6.815 (1.38), 6.819 (1.45), 6.832 (1.45), 6.837 (1.47), 7.084 (2.66), 7.105 (2.71), 7.355 (0.86), 7.362 (0.96), 7.378 (1.75), 7.384 (1.57), 7.400 (2.83), 7.407 (1.29), 7.419 (4.33), 7.422 (3.02), 7.440 (0.70), 7.559 (2.08), 7.580 (1.87), 7.633 (1.55), 7.639 (1.59), 7.659 (1.57), 7.665 (1.54), 8.269 (1.34), 8.283 (1.41), 8.292 (1.38), 8.307 (2.25).

Example 99

(rac)-4-chloro-3-ethyl-2,14-dimethyl-(15-rac)-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic

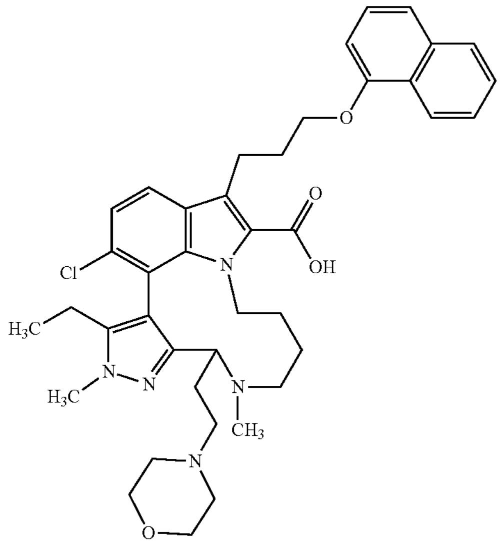 [SMILES: CCc1c2c(nn1C)C(CCN1CCOCC1)N(C)CCCCn1c(C(=O)O)c(CCCOc3cccc4ccccc34)c3ccc(Cl)c-2c31]

A mixture of (rac)-ethyl 19-chloro-3-ethyl-4,8-dimethyl-(7-rac)-[2-(morpholin-4-yl)ethyl]-15-[3-(naphthalen-1-yloxy)propyl]-4,5,8,13-tetraazatetracyclo[11.6.1.0$^{2,6}$.0$^{16,20}$]icosa-1(20),2,5,14,16,18-hexaene-14-carboxylate (258 mg, 0.355 mmol, see Intermediate 165) ethanol (30 mL, 95%) and sodium hydroxide (1N, 5 mL, aqueous) was heated to reflux for 24 hours, cooled to room temperature, volatiles were removed under reduced pressure, the residue was dissolved in HCl (5 mL, 3M, aqueous), and the resulting solution was adsorbed onto celite, purified by reverse phase chromatography on HP C18 eluting with a gradient of 10-100% acetonitrile in water (containing 0.1% formic acid), to afford the title compound as an off white powder (145 mg).

LC-MS (Method 8): $R_t$=2.03 min; MS (ESIpos): m/z=669 $[M+H]^+$ $^1$H NMR (400 MHz, DMSO-$d_6$) δ 8.34-8.22 (m, 1H), 7.92-7.82 (m, 1H), 7.71 (d, J=8.5 Hz, 1H), 7.59-7.47 (m, 2H), 7.46 (d, J=8.2 Hz, 1H), 7.38 (t, J=7.9 Hz, 1H), 7.19 (d, J=8.6 Hz, 1H), 6.88 (d, J=7.5 Hz, 1H), 4.20 (t, J=6.3 Hz, 3H), 3.85 (s, 3H), 3.78 (dd, J=9.1, 4.1 Hz, 1H), 3.56 (t, J=4.7 Hz, 4H), 3.32 (s, 5H), 2.51 (p, J=1.8 Hz, 2H), 2.44-2.27 (m, 4H), 2.27-1.97 (m, 7H), 1.89 (s, 2H), 1.25 (s, 1H), 1.08 (s, 2H), 0.95 (s, 1H), 0.81 (t, J=7.6 Hz, 3H).

Example 100

(rac)-4-chloro-3-ethyl-2,14-dimethyl-(15-rac)-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic

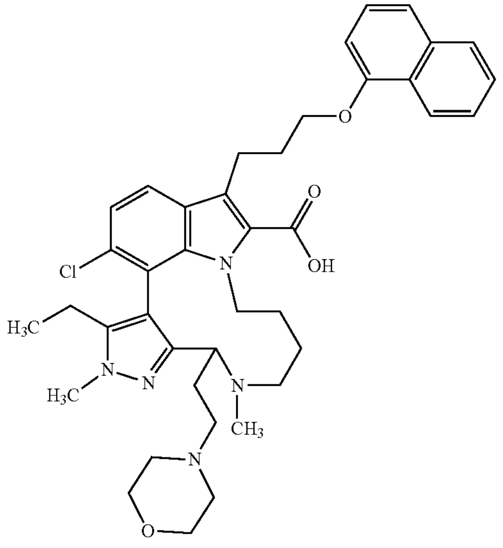 [SMILES: CCc1c2c(nn1C)C(CCN1CCOCC1)N(C)CCCCn1c(C(=O)O)c(CCCOc3cccc4ccccc34)c3ccc(Cl)c-2c31]

A mixture of ethyl 19-chloro-3-ethyl-4,8-dimethyl-7-[2-(morpholin-4-yl)ethyl]-15-[3-(naphthalen-1-yloxy)propyl]-4,5,8,13-tetraazatetracyclo[11.6.1.0$^{2,6}$.0$^{16,20}$]icosa-1(20),2,5,14,16,18-hexaene-14-carboxylate (161 mg, 0.222 mmol, see Intermediate 166) ethanol (30 mL, 95%) and sodium hydroxide (1N, 5 mL, aqueous) was heated to reflux for 24 hours, cooled to room temperature, volatiles were removed under reduced pressure, the residue was dissolved in HCl (5 mL, 3M, aqueous), and the resulting solution was adsorbed onto celite, purified by reverse phase chromatography on HP C18 eluting with a gradient of 10-100% acetonitrile in water (containing 0.1% formic acid), to afford the title compound as an off white powder (46 mg).

LC-MS (Method 8): $R_t$=2.27 min; MS (ESIpos): m/z=669 $[M+H]^+$ $^1$H NMR (400 MHz, DMSO-$d_6$) δ 12.79 (s, 1H), 8.31-8.23 (m, 1H), 7.93-7.85 (m, 1H), 7.71 (d, J=8.6 Hz, 1H), 7.53 (qd, J=7.0, 3.3 Hz, 2H), 7.46 (d, J=8.3 Hz, 1H), 7.39 (t, J=7.9 Hz, 1H), 7.17 (d, J=8.5 Hz, 1H), 6.88 (d, J=7.5 Hz, 1H), 4.20 (t, J=6.3 Hz, 2H), 4.13 (s, 2H), 3.80 (s, 3H), 3.56 (d, J=5.5 Hz, 4H), 3.29 (d, J=21.4 Hz, 5H), 2.34 (d, J=29.1 Hz, 5H), 2.17 (dq, J=21.8, 6.9 Hz, 4H), 1.99 (d, J=23.0 Hz, 4H), 1.80 (s, 1H), 1.66 (s, 1H), 1.46 (d, J=7.9 Hz, 1H), 1.21 (s, 2H), 1.07 (dd, J=10.9, 3.6 Hz, 1H), 0.79 (t, J=7.6 Hz, 3H).

Example 101

4-chloro-3-ethyl-7-{3-[(6-fluoro-1-naphthyl)oxy]propyl}-2,14-dimethyl-15-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylic Acid (Mixture of 4 Stereoisomers)

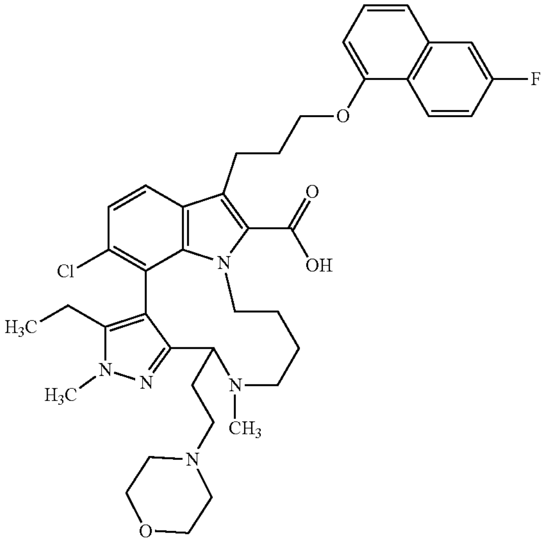 [SMILES: CCc1c2c(nn1C)C(CCN1CCOCC1)N(C)CCCCn1c(C(=O)O)c(CCCOc3cccc4cc(F)ccc34)c3ccc(Cl)c-2c31]

To a room temperature stirred suspension of (rac)- ethyl 4-chloro-3-ethyl-7-{3-[(6-fluoro-1-naphthyl)oxy]propyl}-2,14-dimethyl-15-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylate (see Intermediate 200, 121 mg, 0.16 mmol, 1.00 eq.) in absolute ethanol 3.25 mL, 0.05 M) was added a 2.0 M aqueous solution of sodium hydroxide (406 μL, 0.81 mmol, 5.00 eq.). The resulting mixture was heated at 70° C. for 3 days, cooled to room temperature and then neutralized with 1.0 M aqueous hydrochloric acid (~1.00 mL). The mixture was dry loaded onto Celite and then purified by reverse phase flash column chromatography (30 g HP C18, 20-100% acetonitrile/water gradient buffered with 0.1% formic acid) to give a ~7:3 diastereomeric mixture of title compound as an off white solid (62.5 mg)

LC-MS (Method 8): Major Rt=2.58 min; MS (ESIneg): m/z=713 $[M-H]^-$; Minor Rt=2.62 min; MS (ESIneg): m/z=713 $[M-H]^-$ 1H NMR (400 MHz, DMSO-d6) δ 13.06 (s, 1H), 8.33-8.24 (m, 1H), 7.73-7.49 (m, 3H), 7.49-7.34 (m, 3H), 7.23-7.10 (m, 1H), 6.90-6.81 (m, 1H), 4.28-4.04 (m, 4H), 3.87-3.72 (m, 6H), 3.44-3.04 (m, 11H), 2.31-1.80 (m, 6H), 1.78-1.31 (m, 6H), 1.31-0.93 (m, 2H), 0.85-0.74 (m, 3H).

Example 102

(rac)-18-chloro-1-ethyl-2-methyl-15-[3-(1-naphthyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic Acid (Isomer 1)

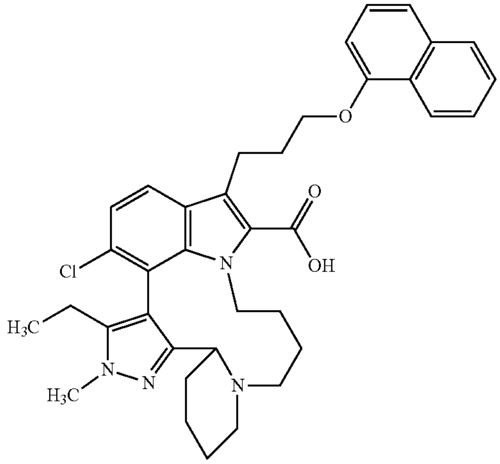 [SMILES: CCc1c2c(nn1C)C1CCCCN1CCCCn1c(C(=O)O)c(CCCOc3cccc4ccccc34)c3ccc(Cl)c-2c31]

(rac)-Ethyl-16-chloro-15-ethyl-14-methyl-1-(3-(naphthalen-1-yloxy)propyl)-4,5,6,7,9,10,11,12,12a,14-decahydropyrazolo[3',4':8,9]pyrido[1',2':6,7][1,6]diazacycloundecino[10,11,1-hi]indole-2-carboxylate (Isomer 1) (see Intermediate 175, 170 mg, 0.26 mmol) was dissolved in ethanol (100 mL, 95%), treated with sodium hydroxide (1 N aqueous, 4 mL), and heated to reflux for 20 hours. The mixture was cooled to room temperature, concentrated under reduced pressure, treated with hydrochloric acid (3N, aqueous), adsorbed onto celite, and purified by flash chromatography using HP C18 (gradient acetonitrile/water with 0.1% formic acid), to afford the title compound as an off white solid (153 mg).

LC-MS (Method 8): $R_t$=2.59 min; MS (ESIneg): m/z=623 $[M-H]^-$ $^1$H NMR (400 MHz, DMSO-$d_6$) δ 9.71 (s, 1H), 8.26 (ddd, J=13.4, 6.3, 3.0 Hz, 1H), 7.88 (dt, J=8.4, 2.8 Hz, 1H), 7.54 (dq, J=6.1, 2.5 Hz, 1H), 7.47 (t, J=7.3 Hz, 1H), 7.40 (dt, J=10.4, 7.9 Hz, 1H), 7.26 (dd, J=29.5, 8.5 Hz, 1H), 6.91 (dd, J=18.9, 7.5 Hz, 1H), 4.63 (d, J=13.5 Hz, 1H), 4.52 (dq, J=13.9, 7.8, 6.4 Hz, 1H), 4.22 (dt, J=20.2, 6.1 Hz, 2H), 4.06-3.85 (m, 3H), 3.85-3.71 (m, 1H), 3.71-2.97 (m, 8H), 2.95-2.66 (m, 1H), 2.51 (p, J=1.8 Hz, 3H), 2.36 (dq, J=15.2, 7.6 Hz, 1H), 2.17 (dp, J=46.1, 6.9 Hz, 3H), 1.96-1.14 (m, 6H), 1.06-0.69 (m, 3H).

HSQC $^{13}$C NMR (101 MHz, DMSO) δ 121.97, 127.86, 122.62, 126.66, 126.05, 120.25, 126.62, 122.19, 121.41, 105.37, 46.37, 60.99, 66.46, 40.98, 67.99, 37.20, 40.92, 57.53, 21.97, 22.01, 57.23, 57.36, 53.58, 47.67, 18.10, 40.29, 30.78, 17.59, 23.10, 22.42, 26.66, 21.84, 12.29, 12.23.

$^1$H NMR (400 MHz, DMSO) δ 8.26, 7.89, 7.89, 7.55, 7.54, 7.48, 7.41, 7.31, 7.23, 6.91, 4.66, 4.63, 4.54, 4.51, 4.24, 3.90, 3.76, 3.57, 3.38, 3.28, 3.23, 3.17, 3.14, 2.82, 2.59, 2.51, 2.22, 2.11, 1.78, 1.63, 1.54, 1.45, 0.99, 0.79.

Example 103

(rac)-18-chloro-1-ethyl-2-methyl-15-[3-(1-naphthyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic Acid (Isomer 2)

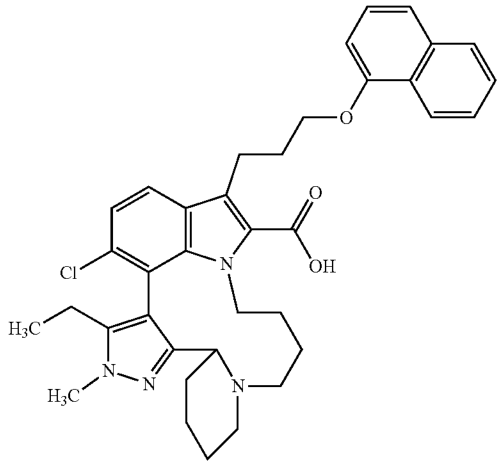 [SMILES: CCc1c2c(nn1C)C1CCCCN1CCCCn1c(C(=O)O)c(CCCOc3cccc4ccccc34)c3ccc(Cl)c-2c31]

(rac)-Ethyl-6-chloro-15-ethyl-14-methyl-1-(3-(naphthalen-1-yloxy)propyl)-4,5,6,7,9,10,11,12,12a,14-decahydropyrazolo[3',4':8,9]pyrido[1',2':6,7][1,6]diazacycloundecino[10,11,1-hi]indole-2-carboxylate (Isomer 2) (see Intermediate 176, 900 mg) was dissolved in ethanol (25 mL, 95%), treated with sodium hydroxide (1N aqueous, 5 mL), and heated to reflux for 6 hours. The mixture was cooled to room temperature, concentrated under reduced pressure, treated with hydrochloric acid (3N, aqueous), adsorbed onto celite, and purified by flash chromatography using HP C18 (gradient acetonitrile/water with 0.1% formic acid), to afford the title compound as a white solid (250 mg).

LC-MS (Method 8): $R_t$=2.55 min; MS (ESIneg): m/z=626 $[M+H]^+$ $^1$H NMR (400 MHz, DMSO-$d_6$) δ 8.28-8.20 (m, 1H), 7.91-7.84 (m, 1H), 7.75 (d, J=8.5 Hz, 1H), 7.56-7.48 (m, 2H), 7.46 (d, J=8.2 Hz, 1H), 7.39 (t, J=7.9 Hz, 1H), 7.21 (d, J=8.5 Hz, 1H), 6.90 (d, J=7.5 Hz, 1H), 4.63 (d, J=13.9 Hz, 1H), 4.21 (t, J=6.2 Hz, 2H), 3.90 (s, 4H), 3.28 (ddt, J=38.2, 13.5, 7.3 Hz, 5H), 2.88 (s, 1H), 2.59 (s, 1H), 2.42-2.14 (m, 5H), 1.92 (d, J=22.3 Hz, 2H), 1.74 (d, J=12.9 Hz, 1H), 1.61 (d, J=18.9 Hz, 2H), 1.42 (s, 1H), 1.28 (s, 1H), 1.10 (s, 2H), 0.84 (t, J=7.6 Hz, 3H).

HSQC $^{13}$C NMR (101 MHz, DMSO) δ 122.02, 127.74, 121.66, 126.69, 125.94, 120.20, 126.67, 120.97, 105.38, 41.84, 68.07, 37.16, 41.98, 56.47, 21.98, 21.84, 52.05, 51.69, 51.51, 17.71, 30.76, 31.43, 24.21, 24.99, 29.30, 15.15, 28.94, 12.50, 15.33.

$^1$H NMR (400 MHz, DMSO) δ 8.24, 7.87, 7.77, 7.53, 7.52, 7.46, 7.40, 7.22, 6.91, 4.62, 4.22, 3.91, 3.88, 3.42, 3.33, 3.25, 2.92, 2.59, 2.38, 2.33, 2.21, 1.96, 1.74, 1.60, 1.43, 1.12, 1.12, 0.85, 0.85.

Example 104

(rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic Acid (Isomer 1, Diasteromer of Example 107)

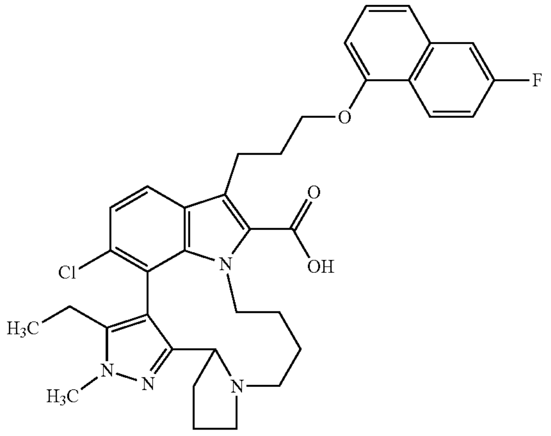 [SMILES: CCc1c2c(nn1C)C1CCCN1CCCCn1c(C(=O)O)c(CCCOc3cccc4cc(F)ccc34)c3ccc(Cl)c-2c31]

Ethyl-15-chloro-14-ethyl-1-(3-((6-fluoronaphthalen-1-yl)oxy)propyl)-13-methyl-4,5,6,7,10,11,11a,13-octahydro-9H-pyrazolo[3',4':8,9]pyrrolo[1',2':6,7][1,6]diazacycloundecino[10,11,1-hi]indole-2-carboxylate (Isomer 2) (see Intermediate 186, 425 mg, 0.86 mmol) was dissolved in ethanol (30 mL, 95%), treated with sodium hydroxide (1N aqueous, 7 mL), and heated to reflux for 24 hours. The mixture was cooled to room temperature, concentrated under reduced pressure, treated with hydrochloric acid (0.9N, aqueous, 9 mL), and stirred at room temperature for 30 minutes. The resulting solid was isolated as a white powder (370 mg, HCl salt of title compound) by filtration, the filtrate was adsorbed onto celite, and purified by flash chromatography using silica gel (gradient methanol/dichloromethane), to afford the title compound as an off white solid (60 mg).

LC-MS (Method 6): $R_t$=1.40 min; MS (ESIneg): m/z=627 $[M-H]^-$

Example 104 Isomer 1 (HCl Salt)

$^1$H NMR (300 MHz, DMSO-$d_6$) δ 13.46 (s, 1H), 10.93 (s, 1H), 8.29 (dd, J=9.2, 5.9 Hz, 1H), 7.84 (d, J=8.6 Hz, 1H), 7.66 (dd, J=10.4, 2.6 Hz, 1H), 7.50-7.34 (m, 3H), 7.25 (d, J=8.6 Hz, 1H), 6.88 (dd, J=5.6, 3.2 Hz, 1H), 4.89 (dt, J=13.2, 6.6 Hz, 1H), 4.68 (d, J=14.2 Hz, 1H), 4.20 (t, J=6.1 Hz, 2H), 3.95 (s, 3H), 3.87 (d, J=15.7 Hz, 1H), 3.65-3.31 (m, 2H), 3.24 (dt, J=13.6, 7.5 Hz, 1H), 3.04 (d, J=9.5 Hz, 1H), 2.89 (s, 1H), 2.40 (p, J=7.7 Hz, 1H), 2.22 (dt, J=15.4, 7.9 Hz, 4H), 1.80 (dd, J=17.7, 8.4 Hz, 2H), 1.67-1.27 (m, 4H), 1.06 (s, 1H), 0.87 (t, J=7.5 Hz, 3H).

Example 104 Isomer 1 (Free Base)

$^1$H NMR (400 MHz, Chloroform-d) δ 7.58 (d, J=8.5 Hz, 1H), 7.45-7.36 (m, 1H), 7.31 (d, J=4.2 Hz, 2H), 7.25-7.17 (m, 1H), 7.15 (d, J=8.5 Hz, 1H), 6.65 (t, J=4.4 Hz, 3H), 4.17 (q, J=6.5, 5.2 Hz, 4H), 3.88 (s, 3H), 3.65 (t, J=8.2 Hz, 1H), 3.38 (dp, J=28.3, 7.0 Hz, 2H), 2.78-2.57 (m, 2H), 2.34 (h, J=7.5 Hz, 2H), 2.17 (tq, J=12.1, 7.2, 5.4 Hz, 3H), 2.09-1.89 (m, 3H), 1.68-1.47 (m, 2H), 1.28 (dtd, J=27.5, 13.6, 12.8, 7.4 Hz, 4H), 0.89 (t, J=7.5 Hz, 3H).

$^{13}$C NMR (101 MHz, Chloroform-d) δ 166.61, 161.30 (d, J=245.7 Hz), 155.08, 150.82, 144.55, 140.07, 135.70, 135.61, 134.53, 127.46, 127.34, 125.00 (d, J=9.0 Hz), 122.81, 121.78, 120.80, 119.42 (d, J=4.8 Hz), 118.84, 115.23 (d, J=24.9 Hz), 112.50, 110.66 (d, J=20.4 Hz), 103.97 (d, J=1.8 Hz), 67.76, 63.44, 52.33, 49.10, 42.28, 36.30, 30.64, 29.49, 27.91, 23.49, 22.64, 21.93, 17.74, 12.57.

$^{19}$F NMR (376 MHz, Chloroform-d) δ −114.89.

The title compound (327 mg) was separated into enantiomers by preparative HPLC to give enantiomer 1 (46.4 mg, see Example 105) and enantiomer 2 (80.1 mg, see Example 106).

Example 105

(+)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic Acid (Enantiomer 1)

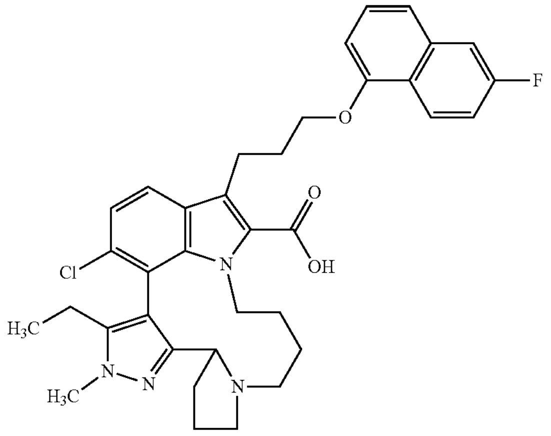 [SMILES: CCc1c2c(nn1C)C1CCCN1CCCCn1c(C(=O)O)c(CCCOc3cccc4cc(F)ccc34)c3ccc(Cl)c-2c31]

For the preparation of the racemic title compound see Example 104. Separation into enantiomer by preparative HPLC (see Example 104) gave 46.4 mg of the title compound.

Preparative Chiral HPLC Method 1:

Instrument: Labomatic HD5000, Labocord-5000; Gilson GX-241, Labcol Vario 4000, Column: Cellulose SC 5μ 250×30 mm; Eluent A: Hexane+0.1 Vol-% Trifluoroacetic acid; Eluent B: 2-Propanol; Isocratic 50% A+50% B; Flow 40.0 mL/min; UV 254 nm Analytical Chiral HPLC Method 1:

Instrument: Agilent HPLC 1260; Column: Cellulose SC 3μ 100×4.6 mm; Eluent A: Hexane+0.1 Vol-% Trifluoroacetic acid; Eluent B: 2-Propanol; Gradient: 20-50% B in 7 min; Flow 1.4 mL/min; Temperature: 25° C.; DAD 254

Preparative Chiral HPLC Method 2:

Instrument: Sepiatec: Prep SFC100; Column: Chiralpak IG 5μ 250×30 mm; Eluent A: $CO_2$; Eluent B: Ethanol+0.2 Vol-% ammonia in water (32%); Isocratic: 25% B; Flow: 100 mL/min; Temperature: 40° C.; BPR: 150 bar; UV: 254 nm Analytical Chiral HPLC Method 2:

Instrument: Agilent: 1260, Aurora SFC-Module; Column: Chiralpak IG 5μ 100×4.6 mm; Eluent A: $CO_2$; Eluent B: Ethanol+0.1 Vol-% ammonia in water (32%); Isocratic: 25% B; Flow: 4 mL/min; Temperature: 37.5° C.; BPR: 100 bar; UV: 254 nm Analytical Chiral HPLC (method 1): $R_t$=5.42 min.

Analytical Chiral HPLC (method 2): $R_t$=1.39 min.

Further purification was done by preparative HPLC (Method P1).

LC-MS (Method 2): $R_t$=1.05 min; MS (ESIpos): m/z=629 $[M+H]^+$

Specific Optical Rotation (Method O1): +7.7° (c=10 mg/mL, DMSO)

$^1$H-NMR (400 MHz, DMSO-d6) δ[ppm]: 0.733 (0.96), 0.752 (0.54), 0.767 (2.38), 0.786 (5.41), 0.805 (2.55), 0.840 (0.83), 0.854 (1.29), 0.859 (1.77), 0.872 (1.90), 0.877 (1.20), 0.888 (2.38), 0.967 (0.70), 1.058 (1.31), 1.107 (16.00), 1.145 (1.73), 1.154 (1.86), 1.161 (1.62), 1.169 (1.75), 1.185 (0.98), 1.209 (0.78), 1.230 (0.96), 1.247 (0.59), 1.259 (1.00), 1.444 (0.54), 1.463 (0.81), 1.482 (0.68), 1.499 (0.46), 1.516 (0.48), 1.856 (1.11), 1.877 (1.22), 1.907 (1.24), 1.923 (0.76), 1.985 (0.48), 2.004 (0.72), 2.021 (1.37), 2.040 (1.07), 2.059 (0.83), 2.068 (0.85), 2.088 (0.83), 2.107 (0.96), 2.125 (0.89), 2.144 (0.92), 2.165 (0.94), 2.183 (1.33), 2.201 (0.92), 2.218 (0.41), 2.518 (5.30), 2.523 (3.45), 2.539 (1.25), 2.632 (0.66), 2.639 (0.65), 3.201 (0.48), 3.216 (0.65), 3.235 (1.01), 3.261 (0.87), 3.281 (1.59), 3.433 (0.92), 3.454 (1.55), 3.474 (0.79), 3.788 (12.42), 4.031 (0.59), 4.043 (0.70), 4.064 (1.07), 4.083 (0.48), 4.157 (1.09), 4.172 (2.25), 4.189 (1.44), 6.823 (1.07), 6.827 (1.11), 6.840 (1.11), 6.844 (1.11), 7.143 (2.66), 7.164 (2.75), 7.368 (0.65), 7.375 (0.72), 7.392 (1.20), 7.397 (1.27), 7.414 (1.97), 7.419 (1.00), 7.432 (3.47), 7.436 (2.36), 7.453 (0.52), 7.644 (1.16), 7.651 (1.20), 7.672 (2.97), 7.676 (1.48), 7.694 (2.10), 8.288 (0.98), 8.302 (1.03), 8.311 (1.01), 8.325 (0.92).

Example 106

(−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic Acid (Enantiomer 2)

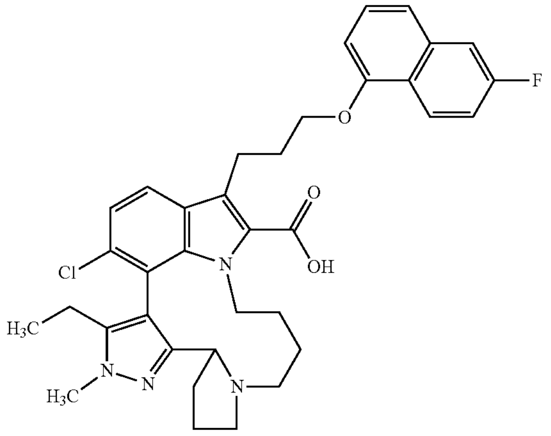 [SMILES: CCc1c2c(nn1C)C1CCCN1CCCCn1c(C(=O)O)c(CCCOc3cccc4cc(F)ccc34)c3ccc(Cl)c-2c31]

For the preparation of the racemic title compound see Example 104. Separation into enantiomer by preparative HPLC (see Example 104) gave 80.1 mg of the title compound.

Preparative Chiral HPLC Method 1:

Instrument: Labomatic HD5000, Labocord-5000; Gilson GX-241, Labcol Vario 4000, Column: Cellulose SC 5μ 250×30 mm; Eluent A: Hexane+0.1 Vol-% Trifluoroacetic acid; Eluent B: 2-Propanol; Isocratic 50% A+50% B; Flow 40.0 mL/min; UV 254 nm Analytical Chiral HPLC Method 1:

Instrument: Agilent HPLC 1260; Column: Cellulose SC 3μ 100×4.6 mm; Eluent A: Hexane+0.1 Vol-% Trifluoroacetic acid; Eluent B: 2-Propanol; Gradient: 20-50% B in 7 min; Flow 1.4 mL/min; Temperature: 25° C.; DAD 254

Preparative Chiral HPLC Method 2:

Instrument: Sepiatec: Prep SFC100; Column: Chiralpak IG 5μ 250×30 mm; Eluent A: $CO_2$; Eluent B: Ethanol+0.2 Vol-% ammonia in water (32%); Isocratic: 25% B; Flow: 100 mL/min; Temperature: 40° C.; BPR: 150 bar; UV: 254 nm Analytical Chiral HPLC Method 2:

Instrument: Agilent: 1260, Aurora SFC-Module; Column: Chiralpak IG 5μ 100×4.6 mm; Eluent A: $CO_2$; Eluent B: Ethanol+0.1 Vol-% ammonia in water (32%); Isocratic: 25% B; Flow: 4 mL/min; Temperature: 37.5° C.; BPR: 100 bar; UV: 254 nm Analytical Chiral HPLC (method 2): $R_t$=2.17 min.

LC-MS (Method 2): $R_t$=1.03 min; MS (ESIpos): m/z=629 $[M+H]^+$

Specific Optical Rotation (Method O1): −9.5° (c=10 mg/mL, DMSO)

$^1$H-NMR (400 MHz, DMSO-d6) δ[ppm]: 0.707 (0.18), 0.725 (0.46), 0.744 (0.22), 0.767 (0.94), 0.786 (2.06), 0.797 (0.45), 0.805 (1.01), 0.814 (0.35), 0.821 (0.30), 0.833 (0.33), 0.839 (0.22), 0.845 (0.54), 0.852 (0.77), 0.862 (1.82), 0.871 (0.46), 0.878 (0.75), 0.885 (0.19), 0.904 (0.32), 0.922 (0.17), 0.967 (0.33), 1.040 (0.74), 1.084 (0.19), 1.101 (0.55), 1.107 (16.00), 1.125 (0.38), 1.131 (0.68), 1.136 (0.95), 1.144 (0.60), 1.146 (0.81), 1.151 (0.99), 1.170 (0.36), 1.178 (0.37), 1.208 (0.27), 1.215 (0.24), 1.222 (0.25), 1.232 (0.25), 1.259 (0.48), 1.424 (0.17), 1.442 (0.39), 1.461 (0.38), 1.481 (0.19), 1.512 (0.19), 1.851 (0.43), 1.873 (0.45), 1.884 (0.38), 1.907 (0.46), 1.922 (0.25), 1.986 (0.19), 2.005 (0.35), 2.009 (0.36), 2.023 (0.55), 2.040 (0.55), 2.060 (0.31), 2.085 (0.30), 2.104 (0.45), 2.122 (0.28), 2.132 (0.29), 2.141 (0.23), 2.164 (0.41), 2.182 (0.52), 2.197 (0.38), 2.331 (0.22), 2.518 (1.32), 2.522 (0.91), 2.539 (0.74), 2.615 (0.16), 2.628 (0.27), 2.635 (0.26), 2.649 (0.16), 2.673 (0.25), 3.191 (0.21), 3.205 (0.27), 3.224 (0.42), 3.243 (0.31), 3.254 (0.35), 3.273 (0.59), 3.292 (0.66), 3.429 (0.45), 3.450 (0.67), 3.470 (0.36), 3.786 (4.95), 4.015 (0.22), 4.040 (0.19), 4.049 (0.18), 4.073 (0.23), 4.094 (0.17), 4.153 (0.43), 4.168 (0.87), 4.184 (0.48), 6.818 (0.40), 6.822 (0.42), 6.836 (0.43), 6.839 (0.42), 7.128 (0.93), 7.149 (0.95), 7.365 (0.23), 7.371 (0.25), 7.388 (0.55), 7.393 (0.45), 7.409 (0.79), 7.416 (0.35), 7.427 (1.16), 7.431 (0.89), 7.449 (0.21), 7.640 (0.47), 7.647 (0.61), 7.651 (0.84), 7.666 (0.54), 7.672 (1.12), 8.285 (0.36), 8.300 (0.38), 8.308 (0.37), 8.323 (0.34).

Example 107

(rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic Acid (Isomer 2, Diastereomer of Example 104)

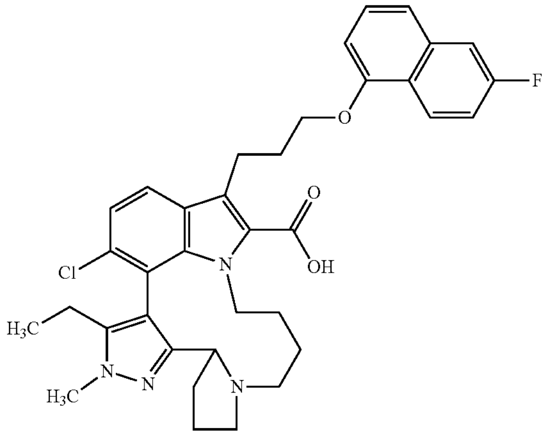 [SMILES: CCc1c2c(nn1C)C1CCCN1CCCCn1c(C(=O)O)c(CCCOc3cccc4cc(F)ccc34)c3ccc(Cl)c-2c31]

ethyl 15-chloro-14-ethyl-1-(3-((6-fluoronaphthalen-1-yl)oxy)propyl)-13-methyl-4,5,6,7,10,11,11a,13-octahydro-9H-pyrazolo[3',4':8,9]pyrrolo[1',2':6,7][1,6]diazacycloundecino[10,11,1-hi]indole-2-carboxylate (Isomer 1) (see Intermediate 185, 290 mg, 0.44 mmol) was dissolved in ethanol (30 mL, 95%), treated with sodium hydroxide (1N aqueous, 7 mL) and heated to reflux for 24 hours. The mixture was cooled to room temperature, concentrated under reduced pressure, treated with hydrochloric acid (0.7N, aqueous, 13 mL), and stirred at room temperature for 30 minutes, the mixture was then adsorbed onto celite and purified by flash chromatography using HP C18 (gradient acetonitrile/water (with 0.1% formic acid), to afford impure title compound which was further purified by flash chromatography using silica gel (gradient methanol/dichloromethane (with 0.5% acetic acid)) to afford the title compound as an off white foam (168 mg).

LC-MS (Method 6): $R_t$=1.40 min; MS (ESIneg): m/z=627 $[M-H]^-$ $^1$H NMR (400 MHz, DMSO-$d_6$) δ 8.24 (d, J=11.8 Hz, 2H), 7.62 (d, J=12.0 Hz, 2H), 7.42 (d, J=17.3 Hz, 2H), 7.10 (dd, J=16.3, 8.6 Hz, 1H), 6.93-6.77 (m, 1H), 4.69 (s, 1H), 4.29-4.06 (m, 2H), 3.95-3.74 (m, 3H), 3.22 (d, J=49.2 Hz, 5H), 2.82 (d, J=51.0 Hz, 2H), 2.44-1.81 (m, 9H), 1.71 (d, J=13.4 Hz, 1H), 1.36 (s, 1H), 1.04 (s, 2H), 0.83 (dt, J=15.7, 7.6 Hz, 3H).

$^{19}$F NMR (376 MHz, DMSO-$d_6$) δ −114.73.

$^1$H NMR (400 MHz, Chloroform-d) δ 8.39 (dd, J=9.3, 5.9 Hz, 1H), 7.66 (d, J=8.6 Hz, 1H), 7.48-7.32 (m, 3H), 7.26 (dd, J=9.0, 2.1 Hz, 1H), 7.22-7.13 (m, 1H), 6.75 (d, J=7.4 Hz, 1H), 4.72 (d, J=14.3 Hz, 1H), 4.64 (d, J=8.0 Hz, 1H), 4.19 (t, J=6.1 Hz, 2H), 3.96 (d, J=1.5 Hz, 3H), 3.85 (t, J=13.1 Hz, 1H), 3.71-3.60 (m, 1H), 3.36 (q, J=10.7, 9.2 Hz, 3H), 3.12 (t, J=11.0 Hz, 1H), 2.68-2.43 (m, 3H), 2.32 (dtd, J=21.7, 14.3, 7.7 Hz, 6H), 2.16 (t, J=12.2 Hz, 1H), 1.85 (s, 1H), 1.46 (s, 1H), 1.06 (h, J=10.9, 10.3 Hz, 2H), 0.93 (t, J=7.5 Hz, 3H).

HSQC $^{13}C$ NMR (101 MHz, $CDCl_3$) δ 124.94, 122.06, 110.52, 127.52, 119.31, 115.31, 121.73, 104.02, 41.90, 56.43, 67.51, 37.32, 41.90, 53.07, 21.98, 53.19, 49.04, 29.53, 21.54, 29.51, 17.87, 30.72, 21.45, 48.88, 20.19, 28.51, 20.10, 28.82, 12.30.

$^{1}H$ NMR (400 MHz, $CDCl_3$) δ 8.39, 7.66, 7.42, 7.39, 7.36, 7.27, 7.19, 6.74, 4.74, 4.64, 4.19, 3.96, 3.84, 3.69, 3.39, 3.34, 3.13, 2.59, 2.48, 2.37, 2.36, 2.31, 2.28, 2.17, 1.89, 1.44, 1.08, 1.05, 0.92.

Example 108

(rac)-4-chloro-3-ethyl-15-[2-(rac)-(3-fluoroazetidin-1-yl)ethyl]-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic Acid

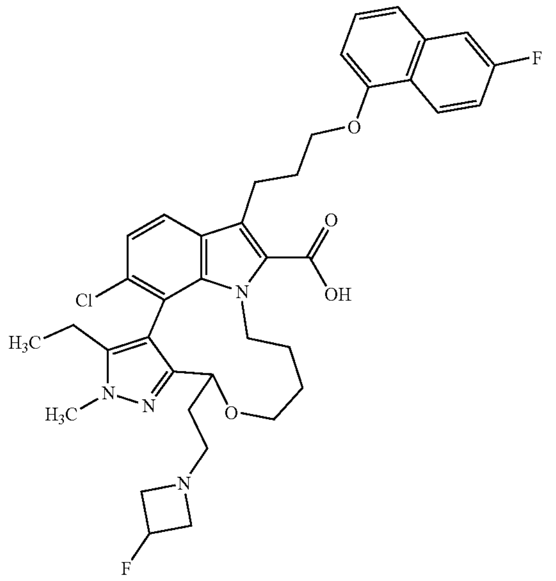 [SMILES: CCc1c2c(nn1C)C(CCN1CC(F)C1)OCCCCn1c(C(=O)O)c(CCCOc3cccc4cc(F)ccc34)c3ccc(Cl)c-2c31]

Ethyl (rac)-4-chloro-3-ethyl-15-[2-(rac)(3-fluoroazetidin-1-yl)ethyl]-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 208, 635 mg, 60% purity, 530 μmol) was dissolved in 6 mL THF. Aqueous lithium hydroxide solution (1.1 mL, 1.0 M, 1.1 mmol) and 1 mL ethanol were added and the reaction mixture was stirred for 22 h at 70° C. Aqueous lithium hydroxide solution (0.55 mL, 1.0 M, 0.55 mmol) was added and the reaction mixture was stirred for 96 h at 70° C. Water was added. With citric acid the pH was adjusted to pH 3-4. The aqueous layer was extracted with ethyl acetate thrice. The collected organic layers were washed with brine, filtered through a water resistant filter and concentrated in vacuum. The crude product was purified by chromatography (Isolera, column: 25 g ultra snap, dichloromethane/ethanol) to provide the target compound in 90% purity: 90 mg, 22% yield.

LC-MS (Method 2): $R_t$=0.94 min; MS (ESIpos): m/z=691 $[M+H]^+$ $^{1}H$-NMR (400 MHz, DMSO-d6) δ[ppm]: 0.696 (0.53), 0.775 (3.04), 0.794 (7.76), 0.797 (7.67), 0.802 (3.44), 0.813 (9.79), 0.821 (5.99), 0.830 (3.35), 0.839 (2.95), 0.850 (1.01), 0.866 (0.71), 0.877 (0.66), 0.885 (3.00), 0.904 (5.86), 0.908 (1.54), 0.922 (2.78), 0.927 (0.84), 0.999 (0.75), 1.035 (1.01), 1.052 (1.28), 1.070 (1.72), 1.089 (2.29), 1.108 (2.12), 1.123 (1.81), 1.142 (2.56), 1.160 (3.35), 1.231 (4.06), 1.255 (2.34), 1.274 (2.16), 1.288 (1.85), 1.328 (4.32), 1.353 (3.66), 1.358 (3.61), 1.379 (3.57), 1.396 (2.73), 1.739 (0.53), 1.798 (0.79), 1.814 (0.75), 1.907 (0.88), 2.026 (0.79), 2.046 (0.93), 2.064 (1.06), 2.083 (1.06), 2.102 (0.53), 2.123 (0.93), 2.141 (1.32), 2.169 (2.29), 2.192 (3.61), 2.210 (3.44), 2.230 (1.63), 2.331 (1.98), 2.336 (0.97), 2.358 (0.71), 2.373 (0.93), 2.388 (1.10), 2.393 (1.15), 2.406 (1.15), 2.411 (1.45), 2.424 (0.48), 2.518 (10.89), 2.523 (6.83), 2.588 (0.71), 2.627 (1.37), 2.673 (2.12), 2.685 (1.15), 2.723 (0.57), 3.008 (0.93), 3.133 (1.01), 3.146 (1.01), 3.260 (3.09), 3.278 (4.41), 3.470 (1.15), 3.658 (0.48), 3.777 (2.07), 3.830 (13.88), 3.873 (11.86), 3.898 (0.97), 3.916 (0.93), 3.951 (1.01), 4.195 (3.70), 4.308 (0.75), 4.320 (0.93), 4.332 (0.97), 4.343 (1.23), 4.376 (0.71), 4.393 (1.01), 4.406 (0.84), 4.415 (0.84), 4.427 (0.66), 5.758 (16.00), 6.849 (1.10), 6.856 (1.94), 6.863 (1.76), 6.870 (2.12), 6.877 (1.32), 7.203 (2.56), 7.215 (2.95), 7.224 (2.73), 7.237 (2.87), 7.358 (0.71), 7.364 (1.06), 7.373 (0.93), 7.380 (1.19), 7.388 (2.03), 7.395 (1.32), 7.402 (0.88), 7.409 (1.50), 7.417 (1.01), 7.433 (2.60), 7.443 (6.44), 7.448 (5.64), 7.650 (1.90), 7.656 (1.76), 7.676 (1.94), 7.733 (2.25), 7.754 (2.20), 7.761 (2.60), 7.782 (2.16), 8.229 (1.01), 8.244 (1.06), 8.253 (1.06), 8.265 (1.32), 8.278 (1.19), 8.287 (1.10), 8.302 (1.10).

Experimental Section—Biological Assays

Examples were tested in selected biological assays one or more times. When tested more than once, data are reported as either average values, median values or as geometric mean values, wherein

- the average value, also referred to as the arithmetic mean value, represents the sum of the values obtained divided by the number of times tested,
- the median value represents the middle number of the group of values when ranked in ascending or descending order. If the number of values in the data set is odd, the median is the middle value. If the number of values in the data set is even, the median is the arithmetic mean of the two middle values, and
- the geometric mean value represents the nth root of the product of n numbers.

Examples were synthesized one or more times. When synthesized more than once, data from biological assays represent average values or median values calculated utilizing data sets obtained from testing of one or more synthetic batch.

An empty field in any of the following tables means that the respective compound has not been tested in that Assay.

The in vitro activity of the compounds of the present invention can be demonstrated in the following assays.

Assay 1

Protein-Protein Interaction Assay: MCL-1/Noxa BH3 Peptide (MCL-1 Assay)

The dose-dependent inhibition by the compounds described in this invention of the interaction between MCL-1 and the BH3 domain of Noxa (both human) was determined using a steady state binding competition assay with time-resolved fluorescence energy transfer (TR-FRET) readout. For that purpose MCL-1 (amino acids 173-321, N-terminal fused to Maltose Binding Protein (MBP) SEQ ID 1)) and a synthetic Noxa BH3-derived peptide of sequence Biotin-PEG2-PEG2-PAELEVE-Nva-ATQLRRFGDKLN-FRQKLL-amide (SEQ ID 2) served as protein receptor and tracer ligand respectively. The MBP-MCL-1 was purchased from Beryllium (Bedford, Mass., USA). The expression and purification of this protein construct has been described elsewhere (DOI:10.1371/journal.pone.0125010). The Noxa BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μL of a 2,5-fold concentrated MBP-MCL-1 solution (usually for a 1 nM end concentration in 5 μL reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between MBP-MCL-1 and the compounds. After that, 3 μL of a 1.67-fold concentrated solution (in assay buffer) consisting of Noxa BH3-derived peptide (1 nM end concentration) and TR-FRET detection reagents [1.67 nM anti-MBP-Eu cryptate and 1.67 nM streptavidin-XL665 (both from Cisbio Bioassays, Codolet, France)], were added.

The mixture was incubated in the dark for one hour at 22° C. and then overnight at 4° C. The formation of MCL-1/Noxa complexes was determined by measuring the resonance energy transfer of the anti-MBP-Eu-cryptate antibody to the streptavidin-XL665 present in the reaction.

For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of MCL-1/NOXA complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except MCL-1 were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

SEQ ID 1:
GKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTGSSELYRQSLEIISRYLREQATGAADTAPMGAS

-continued

GATSRKALETLRRVGDGVQRNHETAFQGMLRKLDIKNEDDVKSLSRVMIH

VFSDGVTNWGRIVTLISFGAFVAKHLKTINQESCIEPLAESITDVLVRTK

RDWLVKQRGWDGFVEFFHV

SEQ ID 2
Biotin-PEG2-PEG2-PAELEVE-Nva-ATQLRRFGDKLNFRQKLL-amide

Assay 2

Protein-Protein Interaction Assay: BCL-XL/Bad BH3 Peptide (BCL-XL Assay)

The dose-dependent inhibition by the compounds described in this invention of the interaction between BCL-XL and the BH3 domain of Bad (both human) was determined using a steady state binding competition assay with time-resolved fluorescence energy transfer (TR-FRET) readout. For that purpose BCL-XL (amino acids 1-212, C-terminal fused to a hexahistidine (6×His) tag (SEQ ID 3) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-XL protein (expressed in *E. coli*) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μL of a 2,5-fold concentrated His-BCL-XL solution (usually for a 1 nM end concentration in 5 μL reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-XL and the compounds. After that, 3 μL of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-XL/Bad complexes was determined by measuring the resonance energy transfer of the anti-His- Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-XL/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-XL were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

SEQ ID 3
MSQSNRELVVDFLSYKLSQKGYSWSQFSDVEENRTEAPEGTESEMETPSA

INGNPSWHLADSPAVNGATGHSSSLDAREVIPMAAVKQALREAGDEFELR

YRRAFSDLTSQLHITPGTAYQSFEQVVNELFRDGVNWGRIVAFFSFGGAL

CVESVDKEMQVLVSRIAAWMATYLNDHLEPWIQENGGWDTFVELYGNNAA

AESRKGQERFNR

SEQ ID 4
Biotin-PEG2-PEG2-NLWAAQRYGRELRR-Nle-SDEFVDSFKKamide

Assay 3

Protein-Protein Interaction Assay: BCL-2/Bad BH3 Peptide (BCL-2 Assay)

The dose-dependent inhibition by the compounds described in this invention of the interaction between BCL-2 and the BH3 domain of Bad (both human) was determined using a steady state binding competition assay with time-resolved fluorescence energy transfer (TR-FRET) readout. For that purpose BCL-2 (amino acids 1-211, C-terminal fused to a hexahistidine (6×His) tag (SEQ ID 5) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-2 protein (expressed in *E. coli*) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μL of a 2,5-fold concentrated His-BCL-2 solution (usually for a 1 nM end concentration in 5 μL reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-2 and the compounds. After that, 3 μL of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-2/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-2/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-2 were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

SEQ ID 5:
MAHAGRTGYDNREIVMKYIHYKLSQRGYEWDAGDVGAAPPGAAPAPGIFS

SQPGHTPHPAASRDPVARTSPLQTPAAPGAAAGPALSPVPPVVHLTLRQA

GDDFSRRYRRDFAEMSSQLHLTPFTARGRFATVVEELFRDGVNWGRIVAF

FEFGGVMCVESVNREMSPLVDNIALWMTEYLNRHLHTWIQDNGGWDAFVE

LYGPSMRPLFD

TABLE 2

$IC_{50}$ values of selected examples in biochemical MCL-1 assay (Assay 1) and biochemical BCL-2 (Assay 3), BCL-XL Assay (Assay 2)

| Example | MCL-1 Assay [M] (median) | BCL-2 Assay [M] (median) | BCL-XL Assay [M] (median) |
|---|---|---|---|
| 1 | 2.2E−9 | >2.00 E−5 | >2.00 E−5 |
| 2 | 1.2E−9 | >2.00 E−5 | >2.00 E−5 |
| 3 | 2.2E−8 | >2.00 E−5 | >2.00 E−5 |
| 4 | 1.1E−9 | | |
| 5 | 1.2E−9 | | |
| 6 | 5.1E−8 | >2.00 E−5 | >2.00 E−5 |
| 7 | 6.6E−10 | >2.00 E−5 | >2.00 E−5 |
| 8 | 5.7E−10 | | |
| 9 | 5.8E−8 | >2.00 E−5 | >2.00 E−5 |
| 10 | 7.2E−10 | >2.00 E−5 | >2.00 E−5 |
| 11 | 5.4E−10 | | |
| 12 | 4.0E−8 | >2.00 E−5 | >2.00 E−5 |
| 13 | 1.6E−9 | >2.00 E−5 | >2.00 E−5 |
| 14 | 5.3E−10 | >2.00 E−5 | >2.00 E−5 |
| 15 | 6.5E−8 | >2.00 E−5 | >2.00 E−5 |
| 16 | 2.0E−9 | >2.00 E−5 | >2.00 E−5 |
| 17 | 1.2E−9 | >2.00 E−5 | >2.00 E−5 |
| 18 | 4.2E−8 | >2.00 E−5 | >2.00 E−5 |
| 19 | 1.6E−9 | >2.00 E−5 | >2.00 E−5 |
| 20 | 7.9E−10 | >2.00 E−5 | >2.00 E−5 |
| 21 | 1.6E−7 | >2.00 E−5 | >2.00 E−5 |
| 22 | 1.5E−9 | >2.00 E−5 | >2.00 E−5 |
| 23 | 6.3E−10 | >2.00 E−5 | >2.00 E−5 |
| 24 | 2.8E−8 | >2.00 E−5 | >2.00 E−5 |
| 25 | 1.9E−9 | >2.00 E−5 | >2.00 E−5 |
| 26 | 1.1E−9 | >2.00 E−5 | >2.00 E−5 |
| 27 | 3.8E−9 | 1.86E−5 | >2.00 E−5 |
| 28 | 1.1E−9 | >2.00 E−5 | 1.98E−5 |
| 29 | 1.0E−9 | >2.00 E−5 | 1.42E−5 |
| 30 | 2.0E−7 | >2.00 E−5 | >2.00 E−5 |
| 31 | 2.6E−10 | >2.00 E−5 | >2.00 E−5 |
| 32 | 7.5E−8 | >2.00 E−5 | >2.00 E−5 |
| 33 | 2.1E−9 | 1.63E−5 | >2.00 E−5 |
| 34 | 3.7E−7 | 1.78E−5 | >2.00 E−5 |

TABLE 2-continued

| IC$_{50}$ values of selected examples in biochemical MCL-1 assay (Assay 1) and biochemical BCL-2 (Assay 3), BCL-XL Assay (Assay 2) | | | |
|---|---|---|---|
| Example | MCL-1 Assay [M] (median) | BCL-2 Assay [M] (median) | BCL-XL Assay [M] (median) |
| 35 | 7.3E−10 | >2.00 E−5 | >2.00 E−5 |
| 36 | 2.8E−7 | 1.46E−5 | 1.38E−5 |
| 37 | 4.8E−10 | >2.00 E−5 | 1.71E−5 |
| 38 | 1.3E−9 | 1.63E−5 | >2.00 E−5 |
| 39 | 7.2E−10 | 1.51E−5 | 1.81E−5 |
| 40 | 4.8E−8 | 1.83E−5 | >2.00 E−5 |
| 41 | 5.2E−10 | 1.81E−5 | 1.50E−5 |
| 42 | 3.3E−10 | >2.00 E−5 | 1.50E−5 |
| 43 | 8.8E−8 | 1.93E−5 | 1.72E−5 |
| 44 | 3.9E−10 | >2.00 E−5 | 1.25E−5 |
| 45 | 5.5E−10 | >2.00 E−5 | >2.00 E−5 |
| 46 | 3.6E−8 | >2.00 E−5 | >2.00 E−5 |
| 47 | 3.7E−10 | >2.00 E−5 | >2.00 E−5 |
| 48 | 3.6E−9 | | |
| 49 | 8.5E−10 | >2.00 E−5 | >2.00 E−5 |
| 50 | 4.8E−10 | >2.00 E−5 | >2.00 E−5 |
| 51 | 6.0E−8 | >2.00 E−5 | >2.00 E−5 |
| 52 | 8.8E−10 | 1.59E−5 | 1.47E−5 |
| 53 | 4.1E−10 | 1.70E−5 | 1.10E−5 |
| 54 | 4.7E−8 | >2.00 E−5 | 1.43E−5 |
| 55 | 7.8E−10 | >2.00 E−5 | >2.00 E−5 |
| 56 | 8.4E−10 | >2.00 E−5 | >2.00 E−5 |
| 57 | 1.6E−7 | >2.00 E−5 | >2.00 E−5 |
| 58 | 7.8E−10 | | |
| 59 | 2.7E−9 | 1.32E−5 | >2.00 E−5 |
| 60 | 6.9E−10 | 1.41E−5 | 1.54E−5 |
| 61 | 4.6E−10 | | |
| 62 | 1.2E−7 | >2.00 E−5 | >2.00 E−5 |
| 63 | 8.8E−10 | | |
| 64 | 4.7E−8 | | |
| 65 | 1.3E−9 | >2.00 E−5 | >2.00 E−5 |
| 66 | 5.4E−10 | | |
| 67 | 7.8E−9 | | |
| 68 | 1.3E−9 | >2.00 E−5 | >2.00 E−5 |
| 69 | 8.0E−10 | | |
| 70 | 6.8E−8 | | |
| 71 | 1.0E−9 | >2.00 E−5 | >2.00 E−5 |
| 72 | 1.1E−9 | | |
| 73 | 1.3E−8 | | |
| 74 | 1.0E−9 | 1.96E−5 | 1.33E−5 |
| 75 | 3.7E−10 | | |
| 76 | 9.0E−8 | | |
| 77 | 1.7E−9 | | |
| 78 | 4.2E−10 | | |
| 79 | 1.4E−8 | | |
| 80 | 3.5E−9 | | |
| 81 | | | |
| 82 | 4.2E−8 | | |
| 83 | 1.1E−9 | | |
| 84 | 1.6E−8 | | |
| 85 | 3.9E−9 | | |
| 86 | 1.6E−9 | | |
| 87 | 5.3E−10 | | |
| 88 | 1.7E−8 | | |
| 89 | 1.0E−9 | | |
| 90 | 4.6E−10 | | |
| 91 | 2.0E−8 | | |
| 92 | 3.2E−9 | 1.22E−5 | 1.32E−5 |
| 93 | 1.1E−9 | | |
| 94 | 6.4E−10 | | |
| 95 | 3.4E−8 | | |
| 96 | 9.5E−10 | | |
| 97 | 6.0E−10 | | |
| 98 | 3.2E−8 | | |
| 99 | 1.1E−9 | | |
| 100 | 2.6E−9 | | |
| 101 | 1.8E−9 | | |
| 102 | 1.4E−9 | | |
| 103 | 9.4E−10 | | |
| 104 | 8.8E−10 | | |
| 105 | 1.1E−9 | | |
| 106 | 1.7E−8 | | |
| 107 | 1.1E−9 | | |
| 108 | 1.2E−9 | | |

One aspect of the invention are compounds of general formula (I) which show an IC$_{50}$ of 1 E-9 or less in the MCL-1 assay.

Cellular Assays

Assay 4

Induction of Caspase-3/7 Activity Upon Treatment of Cells with Selected Compounds The BH3-domain of MCL-1 sequesters pro-apoptotic proteins, thereby inhibiting apoptosis. In contrast, MCL-1 inhibitors are expected to antagonize this effect leading to an increase in apoptosis, which can be determined by measuring the activity of caspase-3/7.

The activity of caspase-3/7 was determined in DLBCL (Diffuse large B-cell lymphoma) cell lines (SUDHL5 and SUDHL10) upon treatment with different compounds, using the Caspase-Glo® 3/7 reagent from Promega (G8092).

The different cell lines were plated in culture medium (RPMI 1640 [GIBCO #22400-089] supplemented with 10% Fetal Bovine Serum) at a density of 3,300 cells in 30 μL/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight.

On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 3 h hours in a humidified incubator at 37° C. After this incubation, 30 μL of Caspase-Glo® 3/7 reagent (Promega G8092) was added to each well using the Multidrop Combi Reagent Dispenser, followed by 1 h incubation at 37° C. Finally, luminescence was read at 0.1 ms, with a gain of 3000 using the PHERAstar FS microplate reader (BMG Labtech).

For the evaluation of the results, the background measured with "medium-only" was subtracted from all other values. Then, the values were normalized to DMSO-only treated cells (every value was divided by the mean of the DMSO control). The *Bella* DRC Master Sheet was used to calculate EC$_{50}$s, with fixed C0=1 and Cl=plateau/max induction for the reference compound.

TABLE 3

| EC$_{50}$ values of selected examples in cellular caspase induction assay (Assay 4) | | |
|---|---|---|
| Example | Caspase SUDHL5 [M] (median) | Caspase SUDHL10 [M] (median) |
| 1 | 2.3E−6 | 5.9E−6 |
| 2 | 1.2E−6 | 2.5E−6 |
| 3 | >3.30E−5 | >3.30E−5 |

TABLE 3-continued

EC$_{50}$ values of selected examples in cellular caspase induction assay (Assay 4)

| Example | Caspase SUDHL5 [M] (median) | Caspase SUDHL10 [M] (median) |
|---|---|---|
| 4 | 5.2E−7 | 9.9E−7 |
| 5 | 3.0E−7 | 5.2E−7 |
| 6 | 2.2E−5 | 3.1E−5 |
| 7 | 2.0E−7 | 3.6E−7 |
| 8 | 6.4E−8 | 1.5E−7 |
| 9 | 6.4E−6 | 1.2E−5 |
| 10 | 1.1E−7 | 2.2E−7 |
| 11 | 9.7E−8 | 1.9E−7 |
| 12 | 2.7E−6 | 7.1E−6 |
| 13 | 7.7E−8 | 1.4E−7 |
| 14 | 9.80E−09 | 3.1E−8 |
| 15 | 2.3E−6 | 1.1E−5 |
| 16 | 6.80E−09 | 1.9E−8 |
| 17 | 5.8E−9 | 9.7E−9 |
| 18 | 5.3E−7 | 2.3E−6 |
| 19 | 7.3E−8 | 7.9E−8 |
| 20 | 2.9E−8 | 3.2E−8 |
| 21 | 1.1E−5 | 1.3E−5 |
| 22 | 1.0E−8 | 2.0E−8 |
| 23 | 3.30E−09 | 7.30E−09 |
| 24 | 1.60E−06 | 6.60E−06 |
| 25 | 2.0E−6 | 1.0E−5 |
| 26 | 1.2E−7 | 9.8E−7 |
| 27 | 3.2E−6 | 6.6E−6 |
| 28 | 2.8E−6 | 7.2E−6 |
| 29 | 8.40E−07 | 3.7E−6 |
| 30 | >3.30E−5 | >3.30E−5 |
| 31 | 2.8E−7 | 2.4E−7 |
| 32 | >3.30E−5 | >3.30E−5 |
| 33 | 1.8E−6 | 4.5E−6 |
| 34 | >3.30E−5 | >3.30E−5 |
| 35 | 2.1E−6 | 5.9E−6 |
| 36 | >3.30E−5 | 2.7E−5 |
| 37 | 2.5E−7 | 2.1E−7 |
| 38 | 3.6E−6 | 5.3E−6 |
| 39 | 7.5E−7 | 1.5E−6 |
| 40 | >3.30E−5 | 2.5E−5 |
| 41 | 9.7E−8 | 1.3E−7 |
| 42 | 1.4E−8 | 5.2E−8 |
| 43 | 2.0E−5 | 2.4E−5 |
| 44 | 1.2E−7 | 1.5E−7 |
| 45 | 1.9E−8 | 9.9E−8 |
| 46 | 4.9E−6 | 4.0E−6 |
| 47 | 6.90E−09 | 6.70E−09 |
| 48 | 1.7E−7 | 1.3E−7 |
| 49 | 3.3E−8 | 2.1E−8 |
| 50 | 1.3E−8 | 2.6E−8 |
| 51 | 5.0E−6 | 9.8E−6 |
| 52 | 4.2E−7 | 1.6E−7 |
| 53 | 7.6E−8 | 1.6E−7 |
| 54 | 6.5E−6 | 1.4E−5 |
| 55 | 3.2E−8 | 4.7E−8 |
| 56 | 1.8E−8 | 2.0E−8 |
| 57 | 7.4E−6 | 7.7E−6 |
| 58 | 2.6E−8 | 2.3E−8 |
| 59 | 4.3E−7 | 5.7E−7 |
| 60 | 5.0E−8 | 7.7E−8 |
| 61 | 3.1E−8 | 2.3E−8 |
| 62 | 4.2E−6 | 6.9E−6 |
| 63 | 3.5E−8 | 5.3E−8 |
| 64 | 7.4E−7 | 1.3E−6 |
| 65 | 4.8E−8 | 4.2E−8 |
| 66 | 8.3E−8 | 3.9E−8 |
| 67 | 1.6E−6 | 4.4E−6 |
| 68 | | 8.2E−8 |
| 69 | 2.5E−7 | 1.5E−7 |
| 70 | 1.3E−5 | 1.4E−5 |
| 71 | | 4.1E−8 |
| 72 | 7.4E−8 | 5.4E−8 |
| 73 | 5.2E−6 | 8.8E−6 |
| 74 | 4.5E−8 | 3.3E−8 |
| 75 | 9.7E−9 | 6.60E−09 |
| 76 | 3.3E−6 | 5.8E−6 |
| 77 | 3.1E−8 | 3.7E−8 |
| 78 | 1.3E−8 | 9.9E−9 |
| 79 | 3.7E−6 | 5.4E−6 |
| 80 | 1.4E−7 | 1.3E−7 |
| 81 | | |
| 82 | 2.7E−6 | 4.5E−6 |
| 83 | 2.3E−7 | 3.4E−7 |
| 84 | 1.8E−6 | 5.4E−6 |
| 85 | 9.5E−7 | 1.6E−6 |
| 86 | 1.0E−7 | 1.4E−7 |
| 87 | 5.8E−8 | 8.4E−8 |
| 88 | 5.6E−7 | 1.1E−6 |
| 89 | 3.0E−8 | 3.0E−8 |
| 90 | 2.7E−8 | 1.3E−8 |
| 91 | 6.6E−7 | 8.9E−7 |
| 92 | 9.6E−7 | 1.1E−6 |
| 93 | 2.0E−8 | 2.3E−8 |
| 94 | 3.6E−8 | 2.3E−8 |
| 95 | 1.5E−6 | 3.5E−6 |
| 96 | 1.9E−8 | 2.8E−8 |
| 97 | 1.1E−8 | 1.1E−8 |
| 98 | 1.0E−6 | 1.5E−6 |
| 99 | 7.6E−8 | 5.9E−8 |
| 100 | 2.1E−7 | 2.3E−7 |
| 101 | 6.9E−8 | 5.1E−8 |
| 102 | 7.7E−7 | 1.0E−6 |
| 103 | 1.4E−6 | 2.2E−6 |
| 104 | 3.3E−7 | 3.6E−7 |
| 105 | 3.3E−7 | 1.3E−7 |
| 106 | 2.7E−6 | 4.80E−06 |
| 107 | 5.4E−7 | 1.20E−06 |
| 108 | 6.6E−8 | 6.7E−8 |

In one embodiment the invention covers compounds of formula (I) which show and EC$_{50}$ in the Caspase SUDHL5 assay of 3×E-7 or <3×E-7.

Assay 5

PIxEL: Protein-Protein Interaction in Permeabilized Cells by ELISA

Most MCL1 protein molecules are localized at the mitochondria outer membrane and sequester pro-apoptotic proteins through binding of their BCL2 homology domain 3 (BH3 domain). MEB buffer (150 mM mannitol, 10 mM HEPES pH 7.5, 50 mM KCl, 20 μM EDTA, 20 μM EGTA, 5 mM potassium succinate, 0.1% protease-free BSA (SIGMA) with low dose digitonin (0.002%) permeabilizes plasma membrane while leaves live mitochondria, where MCL1 maintains its native localization and conformation. Unlike biophysical assays (e.g. TR-FRET) that use truncated recombinant MCL1 protein, this assay uses full length endogenous MCL1 protein at mitochondria outer membrane. It measures the interaction between MCL1 protein and biotinylated BIM BH3 peptide. Compounds can compete with BIM BH3 peptide to bind to MCL1 protein. This serum free assay measures the affinity between MCL1 protein and compound in permeabilized cells, therefore it is not affected by serum binding and cell permeability, and can measure the intrinsic compound affinity.

On day 1, RKO colon cancer cell line cells were plated at 0.8 million cells/ml, 100 μl/well in 96-well flat bottom TC plates (Corning). MCL1 antibody (Santa Cruz sc-12756) were diluted at 200 fold (final concentration 1 μg/ml) in carbonate buffer (Thermo Fisher Scientific, pH 9.6), and 50

μl of diluted antibody was added to each well of high bind ELISA plates (SARSTEDT). Each plate was tapped to make sure liquid covering entire bottom of wells and incubate at 37° C. overnight.

On the second day, MCL1 antibody was washed from ELISA plate. 250 μl Odyssey® Blocking Buffer (PBS) (Li-Cor) was added to each well, incubated at room temperature for at least 1 hour, then washed once with 250 μl 1×PBST. Plates with RKO cells were gently washed once with 100 μl/well PBS, once with 100 μl/well MEB buffer without digitonin, then 100 μl of MEB buffer with 0.002% digitonin was gently added to each well. Compounds were added with HP Tecan compound dispenser in 3-fold dilution series, highest dose 30 μM, 10-dose per compound in quadruplicates. Biotin-BIM peptide (synthesized by 21st Century) was added with HP Tecan compound dispenser at 0.2 μM immediately after the addition of compounds. Plates were rocked for 1 hour at room temperature. Then MEB buffer was aspirated and 50 μl of CHAPS buffer (50 mM Tris-Cl, pH 7.4, 150 mM NaCl, 1% CHAPS, 1 mM EDTA, 1 mM EGTA, cOmplete protease inhibitors (Roche), PhosSTOP (Roche)) was added to each well. Plates were rocked for 1 hour at 4° C., then 45 μl cell lysate from each well were transferred to ELISA plates coated with MCL1 antibody. Plates were incubated overnight in the cold room with rocking.

On the third day, ELISA plates were washed once with 250 μl 1×PBST. Streptavidin-poly-HRP (Thermo Fisher Scientific) was diluted to 20 ng/ml in Odyssey blocking buffer plus 0.05% Triton-100, and 100 μl was added to each well of the ELISA plate. Plates were incubated at room temperature for 1 hour with rocking, then washed with 100 μl 1×PBST for 3 times. Each SuperSignal ELISA Femto Maximum Sensitivity substrate was added to a 50-ml tube and mixed, then 100 μl of mixed substrate was added to each well. Plates were shaken for 1 minute then luminescence was measured by Envision plate reader (HP). Signal of each well were normalized by no-compound control and no-cell control. $IC_{50}$ was calculated using Graphic Pad PRISM software.

Table 4 shows the results of the assay for protein-protein interaction in permeabilized cells by ELISA (assay 5).

TABLE 4

$IC_{50}$ values of selected examples for protein-protein interaction in permeabilized cells by ELISA (Assay 5)

| Example_no | PIxEL [M] (median) |
|---|---|
| 1 | |
| 2 | |
| 3 | |
| 4 | |
| 5 | |
| 6 | |
| 7 | |
| 8 | 6.17E−07 |
| 9 | |
| 10 | 3.25E−07 |
| 11 | >30 uM |
| 12 | 1.94E−05 |
| 13 | |
| 14 | 8.34E−08 |
| 15 | 1.25E−05 |
| 16 | |
| 17 | 3.57E−08 |
| 18 | 2.43E−06 |
| 19 | |
| 20 | 1.00E−07 |
| 21 | |
| 22 | |
| 23 | 2.51E−08 |
| 24 | >30 uM |
| 25 | |
| 26 | 1.25E−06 |
| 27 | 1.96E−06 |
| 28 | 2.33E−06 |
| 29 | 1.06E−06 |
| 30 | |
| 31 | 4.81E−07 |
| 32 | |
| 33 | 1.51E−06 |
| 34 | |
| 35 | 1.64E−06 |
| 36 | |
| 37 | |
| 38 | |
| 39 | 3.17E−07 |
| 40 | |
| 41 | |
| 42 | 4.51E−08 |
| 43 | |
| 44 | |
| 45 | 1.55E−07 |
| 46 | |
| 47 | 8.18E−09 |
| 48 | 2.65E−07 |
| 49 | |
| 50 | 3.68E−08 |
| 51 | 1.20E−05 |
| 52 | |
| 53 | 1.35E−07 |
| 54 | |
| 55 | |
| 56 | 6.67E−09 |
| 57 | |
| 58 | |
| 59 | 1.90E−07 |
| 60 | |
| 61 | |
| 62 | |
| 63 | 1.42E−08 |
| 64 | |
| 65 | |
| 66 | |
| 67 | |
| 68 | 4.54E−08 |
| 69 | 1.32E−07 |
| 70 | 1.46E−05 |
| 71 | 1.78E−07 |
| 72 | 5.92E−08 |
| 73 | 3.42E−06 |
| 74 | |
| 75 | 2.75E−08 |
| 76 | |
| 77 | |
| 78 | 4.34E−08 |
| 79 | |
| 80 | |
| 81 | |
| 82 | |
| 83 | |
| 84 | |
| 85 | |
| 86 | 4.94E−08 |
| 87 | |
| 88 | |
| 89 | |
| 90 | |
| 91 | |
| 92 | |

TABLE 4-continued

IC$_{50}$ values of selected examples for protein-protein interaction in permeabilized cells by ELISA (Assay 5)

| Example_no | PIxEL [M] (median) |
|---|---|
| 93 | |
| 94 | 7.33E−09 |
| 95 | |
| 96 | |
| 97 | |
| 98 | |
| 99 | |
| 100 | |
| 101 | |
| 102 | 5.99E−08 |
| 103 | |
| 104 | |
| 105 | 6.30E−08 |
| 106 | |
| 107 | |
| 108 | |

Assay 6

Induction of Cytotoxicity Upon Treatment of Cells with Selected Compounds

In principle, compounds that induce apoptosis will concomitantly induce cell cytotoxicity. Therefore, cytotoxicity assays were run in parallel in SUDHL5 and SUDHL10 cells.

The different cell lines were plated in culture medium (RPMI 1640 [GIBCO #22400-089] supplemented with 10% Fetal Bovine Serum) at a density of 3,300 cells in 30 μL/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight. On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 5 h hours in a humidified incubator at 37° C. After this incubation, 30 μL of CellTiter-Glo® Luminescent Cell Viability reagent (Promega, G7573) was added to each well using the Multidrop Combi Reagent Dispenser, followed by 15 min incubation on a shaker at room temperature. Finally, luminescence was read at 0.1 ms, with a gain of 3000 using the PHERAstar FS microplate reader (BMG Labtech).

For the evaluation of the results, each value was normalized to DMSO-only treated cells (every value was divided by the mean of the DMSO control). The Bella DRC Master Sheet was used to calculate IC$_{50}$s, with fixed CI=0 and C0=1.

Assay 7

Assessment of the Anti-Proliferative Effect of Compounds in Different Cell Lines The impact of compounds on the proliferation of different cell lines was assessed using the CellTiter-Glo® Luminescent Cell Viability reagent from Promega (G7573). The cell lines used for the proliferation assays are examples of tumor indications and listed in the table below.

TABLE 5 cell lines, sources and indications

| Cell line | Source | Indication |
|---|---|---|
| SUDHL5 | DSMZ | B-cell lymphoma (GC-DLBCL) |
| SUDHL10 | DSMZ | B-cell lymphoma (GC-DLBCL) |
| MV-4-11 | ATCC | Acute monocytic leukemia |
| HMC-1-8 | JCRB | Triple-negative Breast Cancer |
| SK-BR3 | ATCC | Her2-positive Breast Cancer |
| AMO-1 | DSMZ | Multiple Myeloma |
| A2058 | ATCC | Melanoma |
| NCI-H23 | ATCC | Non-Small Cell Lung Cancer |
| REC-1 | ATCC | Mantle cell lymphoma |
| A2780 | ECACC | Ovarian carcinoma |
| SNU-389 | ATCC | Liver Cancer |
| SK-MEL-2 | ATCC | Melanoma |
| SNU-16 | ATCC | Stomach Cancer |
| A-431 | ATCC | Squamous cell carcinoma |
| PA-1 | ECACC | Ovarian Cancer |
| DMS-114 | ATCC | Small Cell Lung Cancer |
| VCAP | ATCC | Prostate Cancer |

The different cell lines were plated in culture medium (RPMI 1640 [Biochrom; #FG 1215] supplemented with 10% Fetal Calf Serum [Biochrom; #S 0415]) at a density of 3,300 cells (for suspension cells) or 800 cells (for adherent cells) in 30 μL/well in a sterile, solid black, flat bottom, polystyrene, TC-treated 384-well microplate (Corning #3571) using Multidrop Combi Reagent Dispenser. In parallel, cells were plated in a reference (day 0) plate for time zero determination. Cells were incubated in a humidified incubator at 37° C. overnight.

On the next day, cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 72 h hours in a humidified incubator at 37° C. The day 0 plate was measured by adding 30 μL/well of CTG solution (CellTiter-Glo® Luminescent Cell Viability reagent, Promega G7573) to time zero wells in the reference plate followed by a 10 minutes incubation and luminescence reading at 0.1 ms. using the PHERAstar FS microplate reader (BMG Labtech).

After 72 h incubation, the treated plates were measured in the same way as the day 0 plate mentioned above. The Bella DRC Master Sheet was used to calculate IC$_{50}$s, with CI=day 0 values and C0=DMSO control values.

Table 6 shows the results of the SUDHL5 and SUDHL10 cytotoxicity and antiproliferation assays.

TABLE 6

IC$_{50}$ values of selected examples in cellular cytotoxicity induction assay 6 and antiproliferation assay 7

| Example PCT | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 1 | 2.8E−6 | 6.6E−6 | 1.5E−6 | 7.0E−6 |
| 2 | 1.3E−6 | 2.5E−6 | 3.5E−6 | 2.9E−6 |
| 3 | >3.30E−5 | 2.6E−5 | 2.0E−5 | 7.0E−6 |
| 4 | 5.5E−7 | 1.1E−6 | 5.0E−7 | |
| 5 | 3.4E−7 | 4.9E−7 | 4.4E−7 | |
| 6 | 2.2E−5 | 2.9E−5 | 8.2E−6 | |
| 7 | 2.4E−7 | 3.8E−7 | 2.0E−7 | 1.6E−7 |
| 8 | 7.6E−8 | 1.4E−7 | 3.0E−8 | |
| 9 | 5.4E−6 | 1.6E−5 | 4.3E−6 | |
| 10 | 1.4E−7 | 3.0E−7 | 1.6E−7 | 1.4E−7 |

TABLE 6-continued

| IC$_{50}$ values of selected examples in cellular cytotoxicity induction assay 6 and antiproliferation assay 7 | | | | |
|---|---|---|---|---|
| Example PCT | Cytotox SUDHL5 [M] (median) | Cytotox SUDHL10 [M] (median) | Antiproli SUDHL5 [M] (median) | Antiproli SUDHL10 [M] (median) |
| 11 | 9.5E−8 | 2.5E−7 | 7.5E−8 | |
| 12 | 3.3E−6 | 8.1E−6 | 2.6E−6 | |
| 13 | 8.9E−8 | 2.1E−7 | 1.1E−7 | |
| 14 | 2.3E−8 | 3.4E−8 | 2.8E−8 | |
| 15 | 2.5E−6 | 9.7E−6 | 2.5E−6 | |
| 16 | 1.9E−8 | 2.2E−8 | 1.9E−8 | |
| 17 | 1.1E−8 | 9.3E−9 | | |
| 18 | 5.3E−7 | 7.7E−7 | | |
| 19 | 8.2E−8 | 1.1E−7 | 7.7E−8 | |
| 20 | 3.3E−8 | 4.1E−8 | 2.0E−8 | |
| 21 | 1.2E−5 | 1.4E−5 | 3.4E−6 | |
| 22 | 1.1E−8 | 2.8E−8 | 1.3E−8 | |
| 23 | 7.80E−09 | 9.70E−09 | 7.0E−9 | 2.6E−9 |
| 24 | 1.7E−6 | 6.60E−06 | 7.2E−7 | |
| 25 | 2.8E−6 | 8.8E−6 | 2.3E−6 | |
| 26 | 4.0E−7 | 8.7E−7 | 4.1E−7 | |
| 27 | 1.9E−6 | 9.6E−6 | 1.7E−7 | |
| 28 | 3.0E−6 | 8.4E−6 | 2.7E−6 | |
| 29 | 1.1E−6 | 3.9E−6 | | |
| 30 | 2.9E−5 | >3.30E−5 | | |
| 31 | 3.7E−7 | 3.5E−7 | 2.4E−7 | |
| 32 | >3.30E−5 | >3.30E−5 | 2.6E−5 | |
| 33 | 1.1E−6 | 3.7E−6 | | |
| 34 | 7.1E−6 | 2.6E−5 | | |
| 35 | 2.0E−6 | 6.7E−6 | 2.7E−6 | |
| 36 | 2.1E−5 | 2.7E−5 | | |
| 37 | 3.9E−7 | 3.6E−7 | 5.1E−7 | |
| 38 | 1.5E−6 | 6.3E−6 | | |
| 39 | 1.0E−6 | 1.4E−6 | 8.8E−7 | |
| 40 | 2.0E−5 | 2.9E−5 | | |
| 41 | 1.7E−7 | 1.6E−7 | 1.6E−7 | |
| 42 | 5.5E−8 | 6.6E−8 | 5.2E−8 | |
| 43 | 1.8E−5 | 1.9E−5 | | |
| 44 | 1.4E−7 | 2.0E−7 | 1.4E−7 | |
| 45 | 7.6E−8 | 7.3E−8 | 9.5E−8 | |
| 46 | 4.3E−6 | 5.5E−6 | | |
| 47 | 8.20E−09 | 7.90E−09 | 5.00E−09 | |
| 48 | 2.1E−7 | 2.0E−7 | 2.3E−7 | |
| 49 | 3.4E−8 | 3.3E−8 | 4.2E−8 | |
| 50 | 1.6E−8 | 2.7E−8 | 1.1E−8 | |
| 51 | 3.4E−6 | 3.7E−6 | 2.3E−6 | |
| 52 | 3.8E−7 | 2.8E−7 | 4.0E−7 | |
| 53 | 9.5E−8 | 1.9E−7 | 9.9E−8 | |
| 54 | 9.4E−6 | 1.7E−5 | 1.3E−5 | |
| 55 | 4.1E−8 | 6.8E−8 | 6.7E−8 | |
| 56 | 2.1E−8 | 3.9E−8 | 8.7E−8 | |
| 57 | 6.8E−6 | 1.0E−5 | 8.7E−6 | |
| 58 | 2.8E−8 | 4.3E−8 | 2.9E−8 | |
| 59 | 6.4E−7 | 1.0E−6 | 5.1E−6 | |
| 60 | 7.7E−8 | 8.7E−8 | 6.5E−8 | |
| 61 | 3.8E−8 | 2.9E−8 | 2.4E−8 | |
| 62 | 6.3E−6 | 7.8E−6 | 5.3E−6 | |

TABLE 6-continued

| IC$_{50}$ values of selected examples in cellular cytotoxicity induction assay 6 and antiproliferation assay 7 | | | | |
|---|---|---|---|---|
| Example PCT | Cytotox SUDHL5 [M] (median) | Cytotox SUDHL10 [M] (median) | Antiproli SUDHL5 [M] (median) | Antiproli SUDHL10 [M] (median) |
| 63 | 4.9E−8 | 6.7E−8 | 4.2E−8 | |
| 64 | 8.1E−7 | 2.6E−6 | 1.6E−6 | |
| 65 | 7.8E−8 | 1.0E−7 | 4.9E−7 | |
| 66 | 1.1E−7 | 5.5E−8 | 9.3E−8 | |
| 67 | 2.6E−6 | 4.9E−6 | 2.1E−6 | |
| 68 | | 1.5E−7 | | |
| 69 | 3.1E−7 | 3.0E−7 | 2.4E−7 | |
| 70 | 1.3E−5 | 2.0E−5 | 5.0E−6 | |
| 71 | | 3.6E−8 | | |
| 72 | 9.6E−8 | 1.1E−7 | 1.1E−7 | |
| 73 | 7.7E−6 | 1.1E−5 | 6.1E−6 | |
| 74 | 5.1E−8 | 5.5E−8 | 6.7E−8 | |
| 75 | 1.2E−8 | 9.7E−9 | 1.1E−8 | |
| 76 | 3.6E−6 | 5.2E−6 | 4.6E−6 | |
| 77 | 4.5E−8 | 1.0E−7 | 7.1E−8 | |
| 78 | 1.4E−8 | 1.2E−8 | 1.6E−8 | |
| 79 | 4.1E−6 | 3.8E−6 | 2.2E−6 | |
| 80 | 1.5E−7 | 2.5E−7 | 1.7E−7 | |
| 81 | | | | |
| 82 | 2.6E−6 | 3.1E−6 | 4.2E−6 | |
| 83 | 2.7E−7 | 3.3E−7 | 4.2E−7 | |
| 84 | 1.7E−6 | 4.4E−6 | 3.1E−6 | |
| 85 | 8.7E−7 | 2.0E−6 | 9.1E−7 | |
| 86 | 1.5E−7 | 1.2E−7 | 2.0E−7 | |
| 87 | 6.1E−8 | 6.5E−8 | 6.8E−8 | |
| 88 | 7.6E−7 | 1.6E−6 | 5.7E−7 | |
| 89 | 4.1E−8 | 4.1E−8 | 3.6E−8 | |
| 90 | 3.0E−8 | 1.7E−8 | 3.0E−8 | |
| 91 | 7.9E−7 | 1.2E−6 | 1.0E−6 | |
| 92 | 1.2E−6 | 1.4E−6 | 1.2E−6 | |
| 93 | 2.7E−8 | 3.6E−8 | 2.0E−8 | |
| 94 | 4.0E−8 | 3.2E−8 | 4.0E−8 | |
| 95 | 2.2E−6 | 5.0E−6 | 2.3E−6 | |
| 96 | 2.5E−8 | 3.4E−8 | 3.0E−8 | |
| 97 | 1.3E−8 | 1.3E−8 | 1.2E−8 | |
| 98 | 1.4E−6 | 1.9E−6 | 1.2E−6 | |
| 99 | 1.0E−7 | 1.1E−7 | 7.1E−8 | |
| 100 | 3.4E−7 | 3.2E−7 | 2.6E−7 | |
| 101 | 1.4E−7 | 7.1E−8 | 1.1E−7 | |
| 102 | 8.0E−7 | 9.5E−7 | 1.4E−6 | |
| 103 | 1.1E−6 | 1.7E−6 | 2.0E−6 | |
| 104 | 3.4E−7 | 4.3E−7 | 5.5E−7 | |
| 105 | 3.7E−7 | 2.9E−7 | 3.4E−7 | |
| 106 | 3.7E−6 | 5.7E−6 | 2.1E−6 | |
| 107 | 6.9E−7 | 8.9E−7 | 1.1E−6 | |
| 108 | 8.4E−8 | 1.3E−7 | 7.0E−8 | |

In one embodiment the invention covers compounds of formula (I) which show an IC$_{50}$ of 5×E-7 or <5×E-7 in the Antiproliferation Assay SUDHL5.

Table 7 shows the results of the MV4-11, AMO-1, HMC-1-8, SK-BR-3 and A2780 antiproliferation assays 7.

TABLE 7

| IC$_{50}$ values of selected examples in the antiproliferation assay | | | | | |
|---|---|---|---|---|---|
| Example | Antiproli MV-4-11 [M] median | Antiproli AMO-1 [M] median | Antiproli HMC-1-8 [M] median | Antiproli SK-BR-3 [M] median | Antiproli A2780 [M] median |
| 01 | | | | | 1.95E−5 |
| 02 | | | | | 2.28E−5 |
| 03 | | | | | 2.99E−5 |
| 04 | 1.75E−6 | 2.56E−6 | | | 1.43E−5 |
| 05 | 1.75E−6 | 9.47E−6 | 6.29E−6 | 7.30E−6 | 1.44E−5 |
| 06 | 2.28E−5 | | | | >3.30E−5 |
| 07 | 1.83E−7 | 4.63E−7 | 1.61E−6 | | 4.08E−6 |
| 08 | 2.44E−7 | 2.21E−7 | 1.43E−6 | | 2.84E−6 |

TABLE 7-continued

IC50 values of selected examples in the antiproliferation assay

| Example | Antiproli MV-4-11 [M] median | Antiproli AMO-1 [M] median | Antiproli HMC-1-8 [M] median | Antiproli SK-BR-3 [M] median | Antiproli A2780 [M] median |
|---|---|---|---|---|---|
| 09 | 1.83E−5 | 1.97E−5 | | | |
| 10 | 1.10E−7 | 4.12E−7 | 1.49E−6 | | 3.43E−6 |
| 11 | 1.44E−7 | 1.59E−7 | 1.03E−6 | | 7.79E−7 |
| 12 | 1.44E−5 | 1.21E−5 | | | |
| 13 | 2.20E−7 | 1.91E−7 | | | |
| 14 | 3.76E−8 | 4.31E−8 | 3.81E−7 | | |
| 15 | 7.84E−6 | 1.05E−5 | | | |
| 16 | 3.46E−8 | 4.83E−8 | 3.22E−7 | 1.08E−7 | |
| 17 | | 2.82E−8 | 2.01E−7 | | |
| 18 | | 2.37E−6 | 1.25E−5 | | |
| 19 | 1.40E−7 | 1.02E−7 | | | |
| 20 | | 9.45E−8 | 4.60E−7 | 1.73E−7 | |
| 21 | | >3.30E−5 | 1.33E−5 | | |
| 22 | | 3.22E−8 | 2.79E−7 | | |
| 23 | | 1.85E−8 | 1.76E−7 | | |
| 24 | | 2.01E−6 | 1.19E−05 | | |
| 25 | | 6.55E−6 | 1.29E−5 | | |
| 26 | | 5.77E−7 | 6.78E−6 | | |
| 27 | | 1.21E−5 | 2.07E−5 | | |
| 28 | | 1.09E−5 | 2.08E−5 | | |
| 29 | | 4.35E−6 | 2.32E−5 | | |
| 30 | | 3.16E−5 | 2.26E−5 | | |
| 31 | | 3.26E−7 | 6.80E−6 | | |
| 32 | | 2.56E−5 | >3.30E−5 | | |
| 33 | | 6.96E−6 | 1.50E−5 | | |
| 34 | | 3.09E−5 | 2.07E−5 | | |
| 35 | | 3.71E−6 | 1.97E−5 | | |
| 36 | | 1.58E−5 | 1.90E−5 | | |
| 37 | | 5.36E−7 | 7.45E−6 | | |
| 38 | | 5.01E−6 | 2.03E−5 | | |
| 39 | | 4.94E−6 | 1.23E−5 | | |
| 40 | | | 2.32E−5 | | |
| 41 | | 1.35E−7 | 1.31E−6 | | |
| 42 | | 9.69E−8 | 1.08E−6 | | |
| 43 | | 2.00E−5 | 2.65E−5 | | |
| 44 | | 1.61E−7 | 2.63E−6 | | |
| 45 | | 1.85E−7 | 2.14E−6 | | |
| 46 | | 8.65E−6 | >3.30E−5 | | |
| 47 | | 1.12E−8 | 7.45E−8 | | |
| 48 | | 1.87E−7 | 2.80E−6 | | |
| 49 | | 7.67E−8 | 1.06E−6 | | |
| 50 | | 6.54E−8 | 3.92E−7 | | |
| 51 | | 1.08E−5 | 2.20E−5 | | |
| 52 | | 1.07E−7 | 3.19E−6 | | |
| 53 | | 1.85E−7 | 9.83E−7 | | |
| 54 | | 2.78E−5 | 2.02E−5 | | |
| 55 | | 7.53E−8 | 1.72E−7 | | |
| 56 | | 2.26E−8 | 1.68E−7 | | |
| 57 | | 4.52E−6 | 1.36E−5 | | |
| 58 | | 1.94E−8 | 3.28E−7 | | |
| 59 | | 7.53E−7 | 3.41E−6 | | |
| 60 | | 9.29E−8 | 9.51E−7 | | |
| 61 | | 2.25E−8 | 1.86E−7 | | |
| 62 | | 1.92E−6 | 2.19E−5 | | |
| 63 | | 2.00E−8 | 3.51E−7 | | |
| 64 | | 1.03E−6 | 7.51E−6 | | |
| 65 | | 8.97E−8 | 4.00E−7 | | |
| 66 | | 2.85E−8 | 1.16E−6 | | |
| 67 | | 6.33E−7 | >3.30E−5 | | |
| 68 | | 7.72E−7 | 2.62E−6 | | |
| 69 | | 2.12E−7 | 4.46E−6 | | |
| 70 | | 1.25E−5 | 1.68E−5 | | |
| 71 | | 2.09E−7 | 1.37E−6 | | |
| 72 | | 1.07E−7 | 2.29E−6 | | |
| 73 | | 3.84E−6 | >3.30E−5 | | |
| 74 | | 3.58E−8 | 3.97E−7 | | |
| 75 | | 1.38E−8 | 1.59E−7 | | |
| 76 | | 3.87E−6 | 1.30E−5 | | |
| 77 | | 3.15E−8 | 5.20E−7 | | |
| 78 | | 1.12E−8 | 5.63E−7 | | |
| 79 | | 3.70E−6 | 2.35E−5 | | |
| 80 | | 4.74E−8 | 1.59E−6 | | |
| 81 | | | | | |

TABLE 7-continued

| $IC_{50}$ values of selected examples in the antiproliferation assay | | | | | |
|---|---|---|---|---|---|
| Example | Antiproli MV-4-11 [M] median | Antiproli AMO-1 [M] median | Antiproli HMC-1-8 [M] median | Antiproli SK-BR-3 [M] median | Antiproli A2780 [M] median |
| 82 | | 7.56E−6 | >3.30E−5 | | |
| 83 | | 6.50E−7 | 8.74E−6 | | |
| 84 | | 9.56E−6 | >3.30E−5 | | |
| 85 | | 5.17E−6 | >3.30E−5 | | |
| 86 | | 1.93E−7 | 1.59E−6 | | |
| 87 | | 6.39E−8 | 1.50E−6 | | |
| 88 | | 1.35E−6 | 3.12E−6 | | |
| 89 | | 2.95E−8 | 7.65E−7 | | |
| 90 | | 2.42E−8 | 4.16E−7 | | |
| 91 | | 7.29E−7 | 6.10E−6 | | |
| 92 | | 1.36E−6 | 7.07E−6 | | |
| 93 | | 5.89E−8 | 5.58E−7 | | |
| 94 | | 4.13E−8 | 7.77E−7 | | |
| 95 | | 4.30E−6 | 8.22E−6 | | |
| 96 | | 3.23E−8 | 7.26E−7 | | |
| 97 | | 1.63E−8 | 4.05E−7 | | |
| 98 | | 8.60E−7 | 1.15E−5 | | |
| 99 | | 8.63E−8 | 1.86E−6 | | |
| 100 | | 2.24E−7 | 3.56E−6 | | |
| 101 | | 9.58E−8 | 1.49E−6 | | |
| 102 | | 5.22E−7 | 7.47E−6 | | |
| 103 | | 1.95E−6 | 1.98E−5 | | |
| 104 | | 5.43E−7 | 2.63E−6 | | |
| 105 | | 2.03E−7 | 2.66E−6 | | |
| 106 | | 4.45E−6 | 2.06E−5 | | |
| 107 | | 1.34E−6 | 6.64E−6 | | |
| 108 | | 5.18E−8 | 1.87E−6 | | |

In one embodiment the invention covers compounds of formula (I) which show an $IC_{50}$ of 1.2×E-6 or <1.2×E-6 in the Antiproli AMO-1 assay.

In another embodiment the invention covers compounds of formula (I) which show an $IC_{50}$ 3.5×E or <3.5×E in the Antiproli HMC-1-8 assay.

Yet another aspect of the invention are compounds of general formula (I) which show an $IC_{50}$ of 1.2×E-6 or <1.2×E-6 in the Antiproli AMO-1 assay and/or an $IC_{50}$ of 3.5×E-6 or <3.5×E-6 in the Antiproli HMC-1-8 assay.

Yet another aspect of the invention are compounds of general formula (I) which show an $IC_{50}$ of 1.2×E-6 or <1.2×E-6 in the Antiproli AMO-1 assay and an $IC_{50}$ of 3.5×E-6 or <3.5×E-6 in the Antiproli HMC-1-8 assay.

Yet another aspect of the invention are compounds of general formula (I) which show an $IC_{50}$ of <0.5×E-6 in the Antiproli AMO-1 assay and an $IC_{50}$ of <2×E-6 in the Antiproli HMC-1-8 assay.

Yet another aspect of the invention are compounds of general formula (I) which show an $IC_{50}$ of 1.2×E-6 or <1.2×E-6 in the Antiproli AMO-1 assay or an $IC_{50}$ of 3.5×E-6 or <3.5×E-6 in the Antiproli HMC-1-8 assay.

In yet another embodiment the invention covers compounds of formula (I) which show an $IC_{50}$ of 5×E-7 or <5×E-7 in the Antiproliferation (=Antiproli) Assay SUDHL5 and/or an $IC_{50}$ of 1.2×E-6 or <1.2×E-6 in the Antiproli AMO-1 assay and/or an $IC_{50}$ 3.5×E or <3.5×E in the Antiproli HMC-1-8 assay In still another embodiment the invention covers compounds of formula (I) which show an $IC_{50}$ of 5×E-7 or <5×E-7 in the Antiproliferation Assay SUDHL5 and an $IC_{50}$ of 1.2×E-6 or <1.2×E-6 in the Antiproli AMO-1 assay and an $IC_{50}$ 3.5×E or <3.5×E in the Antiproli HMC-1-8 assay Yet another aspect of the invention are compounds of general formula (I) which show an $IC_{50}$ of <0.5×E-6 in the Antiproli AMO-1 assay and an $IC_{50}$ of <2×E-6 in the Antiproli HMC-1-8 assay and an IC50 <1×E-9 in the MCL-1/Noxa BH3 Peptide (MCL-1 Assay).

Table 8 shows the results of the NCI-H23, A2058, SNU-389 and REC-1 antiproliferation assays.

TABLE 8

| $IC_{50}$ values of selected examples in antiproliferation assay 7 | | | | |
|---|---|---|---|---|
| Example | Antiproli NCI-H23 [M] | Antiproli A2058 [M] | Antiproli SNU-389 [M] | Antiproli REC-1 [M] |
| 01 | | | | |
| 02 | | | | |
| 03 | | | | |
| 04 | | | 1.07E−5 | 2.1E−5 |
| 05 | 6.98E−6 | 1.28E−5 | | |
| 06 | | | | |
| 07 | | | | |
| 08 | | | | |
| 09 | | | | |
| 10 | | | | |
| 11 | | | | |
| 12 | | | | |
| 13 | | | | |
| 14 | | | 1.83E−7 | |
| 15 | | | | |
| 16 | | | 1.18E−7 | |
| 17 | | | | |
| 18 | | | | |
| 19 | | | | |
| 20 | | | 4.37E−7 | |
| 21 | | | | |
| 22 | | | | |
| 23 | 6.64E−8 | 8.96E−7 | 6.07E−8 | |
| 24 | | | 9.06E−6 | |
| 25 | | | | |
| 26 | | | | |
| 27 | | | | |

TABLE 8-continued

| IC$_{50}$ values of selected examples in antiproliferation assay 7 | | | | |
|---|---|---|---|---|
| Example | Antiproli NCI-H23 [M] | Antiproli A2058 [M] | Antiproli SNU-389 [M] | Antiproli REC-1 [M] |
| 28 | | | | |
| 29 | | | | |
| 30 | | | | |
| 31 | | | | |
| 32 | | | | |
| 33 | | | | |
| 34 | | | | |
| 35 | | | | |
| 36 | | | | |
| 37 | | | | |
| 38 | | | | |
| 39 | | | | |
| 40 | | | | |
| 41 | | | | |
| 42 | | | 2.70E−7 | |
| 43 | | | | |
| 44 | | | | |
| 45 | | | 3.50E−7 | |
| 46 | | | | |
| 47 | | | 8.04E−8 | |
| 48 | | | | |
| 49 | | | | |
| 50 | | | 4.55E−7 | |
| 51 | | | | |
| 52 | | | | |
| 53 | | | | |
| 54 | | | | |
| 55 | | | | |
| 56 | | | | |
| 57 | | | | |
| 58 | | | 2.23E−7 | |
| 59 | | | | |
| 60 | | | | |
| 61 | | | | |
| 62 | | | | |
| 63 | | | 1.83E−7 | |
| 64 | | | | |
| 65 | | | | |
| 66 | | | 3.07E−7 | |
| 67 | | | | |
| 68 | | | | |
| 69 | | | 2.41E−6 | |
| 70 | | | | |
| 71 | | | | |
| 72 | | | | |
| 73 | | | | |
| 74 | | | | |
| 75 | | | 1.33E−7 | |
| 76 | | | | |
| 77 | | | | |
| 78 | | | 1.51E−7 | |
| 79 | | | | |
| 80 | | | | |
| 81 | | | | |
| 82 | | | | |
| 83 | | | | |
| 84 | | | | |
| 85 | | | | |
| 86 | | | | |
| 87 | | | | |
| 88 | | | | |
| 89 | | | | |
| 90 | | | 1.41E−7 | |
| 91 | | | | |
| 92 | | | | |
| 93 | | | | |
| 94 | | | 3.05E−7 | |
| 95 | | | | |
| 96 | | | | |
| 97 | | | | |
| 98 | | | | |
| 99 | | | | |
| 100 | | | | |
| 101 | | | | |
| 102 | | | | |
| 103 | | | | |
| 104 | | | | |
| 105 | | | | |
| 106 | | | | |
| 107 | | | | |
| 108 | | | | |

Table 9 shows the results of the SK-MEL2, SNU-16, A-431, PA-1 and DMS-114 antiproliferation assays.

TABLE 9

| IC$_{50}$ values of selected examples in antiproliferation assay 7 | | | | | |
|---|---|---|---|---|---|
| Example | Antiproli SK-MEL-2 [M] median | Antiproli SNU-16 [M] median | Antiproli A-431 [M] median | Antiproli PA-1 [M] median | Antiproli DM-S114 [M] median |
| 01 | | | | | |
| 02 | | | | | |
| 03 | | | | | |
| 04 | | | | | |
| 05 | 1.16E−5 | | | | |
| 06 | | | | | |
| 07 | | | | | |
| 08 | | | | | |
| 09 | | | | | |
| 10 | | | | | |
| 11 | | | | | |
| 12 | | | | | |
| 13 | | | | | |
| 14 | | | | | 1.50E−7 |
| 15 | | | | | |
| 16 | | | | | |
| 17 | | | | | |
| 18 | | | | | |
| 19 | | | | | |
| 20 | 6.07E−7 | 3.97E−7 | 4.62E−7 | 3.04E−7 | 2.22E−7 |
| 21 | | | | | |
| 22 | | | | | |
| 23 | 5.45E−7 | 3.34E−7 | 3.37E−7 | 2.93E−7 | 1.01E−7 |
| 24 | | | | | 7.29E−6 |
| 25 | | | | | |
| 26 | | | | | |
| 27 | | | | | |
| 28 | | | | | |
| 29 | | | | | |
| 30 | | | | | |
| 31 | | | | | |
| 32 | | | | | |
| 33 | | | | | |
| 34 | | | | | |
| 35 | | | | | |
| 36 | | | | | |
| 37 | | | | | |
| 38 | | | | | |
| 39 | | | | | |
| 40 | | | | | |
| 41 | | | | | |
| 42 | | | | | 1.56E−7 |
| 43 | | | | | |
| 44 | | | | | |
| 45 | | | | | 2.98E−7 |
| 46 | | | | | |
| 47 | 1.12E−7 | 6.63E−8 | 7.56E−8 | 6.46E−8 | 2.80E−3 |
| 48 | | | | | |
| 49 | | | | | |
| 50 | 5.05E−7 | 3.21E−7 | 3.36E−7 | 2.22E−7 | 1.53E−7 |
| 51 | | | | | |
| 52 | | | | | |

TABLE 9-continued

IC50 values of selected examples in antiproliferation assay 7

| Example | Antiproli SK-MEL-2 [M] median | Antiproli SNU-16 [M] median | Antiproli A-431 [M] median | Antiproli PA-1 [M] median | Antiproli DM-S114 [M] median |
|---|---|---|---|---|---|
| 53 | | | | | |
| 54 | | | | | |
| 55 | | | | | |
| 56 | | | | | |
| 57 | | | | | |
| 58 | 7.28E−7 | 1.35E−7 | 4.86E−7 | 1.10E−7 | 8.11E−8 |
| 59 | | | | | |
| 60 | | | | | |
| 61 | | | | | |
| 62 | | | | | |
| 63 | 3.24E−7 | 2.76E−7 | 2.72E−7 | 2.04E−7 | 1.56E−7 |
| 64 | | | | | |
| 65 | | | | | |
| 66 | 5.01E−7 | 1.11E−6 | 4.14E−7 | 8.29E−7 | 7.66E−7 |
| 67 | | | | | |
| 68 | | | | | |
| 69 | 1.81E−6 | 1.49E−6 | 1.66E−6 | 7.95E−7 | 7.62E−7 |
| 70 | | | | | |
| 71 | | | | | |
| 72 | | | | | |
| 73 | | | | | |
| 74 | | | | | |
| 75 | 1.70E−7 | 1.52E−7 | 1.35E−7 | 1.18E−7 | 7.74E−8 |
| 76 | | | | | |
| 77 | | | | | |
| 78 | 1.97E−7 | 1.30E−7 | 1.26E−7 | 1.27E−7 | 8.85E−8 |
| 79 | | | | | |
| 80 | | | | | |
| 81 | | | | | |
| 82 | | | | | |
| 83 | | | | | |
| 84 | | | | | |
| 85 | | | | | |
| 86 | | | | | |
| 87 | | | | | |
| 88 | | | | | |
| 89 | | | | | |
| 90 | 2.52E−7 | 1.11E−6 | 2.09E−7 | 4.22E−7 | 1.63E−7 |
| 91 | | | | | |
| 92 | | | | | |
| 93 | | | | | |
| 94 | 2.99E−7 | 2.21E−7 | 3.61E−7 | 2.18E−7 | 1.33E−7 |
| 95 | | | | | |
| 96 | | | | | |
| 97 | | | | | |
| 98 | | | | | |
| 99 | | | | | |
| 100 | | | | | |
| 101 | | | | | |
| 102 | | | | | |
| 103 | | | | | |
| 104 | | | | | |
| 105 | | | | | |
| 106 | | | | | |
| 107 | | | | | |
| 108 | | | | | |

Additionally Example 47 shows in vitro anti-proliferative activity in prostate cancer cell line VCAP (source ATCC) with an IC50 of 5,29E-8 nM.

Assay 8

The PRISM screen was conducted according to the methods as previously published in Nature Biotechnology, Volume 34, pages 419-423 (2016).

Table 10 shows the results of the Example 23 in anti-proliferative PRISM screen.

TABLE 10

PRISM AUC values of cell lines screened

| CCLE Cell line | Primary Disease | Subtype Disease | PRISM_AUC |
|---|---|---|---|
| 697 | Leukemia | B-cell Acute Lymphoblastic Leukemia ( B-ALL) | 0.46 |
| 143B | Bone Cancer | Osteosarcoma | 1.01 |
| A1207 | Brain Cancer | Glioblastoma | 1.25 |
| A204 | Sarcoma | Rhabdomyosarcoma | 1.13 |
| A253 | Head and Neck Cancer | Head and Neck Cancer | 1.23 |
| A3KAW | Lymphoma | Diffuse Large B-cell Lymphoma (DLBCL) | 0.44 |
| A427 | Lung Cancer | Non-Small Cell Lung Cancer (NSCLC), adenocarcinoma | 0.46 |
| A498 | Kidney Cancer | Kidney Cancer | 1.62 |
| A673STAG2KO16 | Bone Cancer | Ewings Sarcoma | 1.04 |
| A673STAG2KO45 | Bone Cancer | Ewings Sarcoma | 1.04 |
| A673STAG2NT14 | Bone Cancer | Ewings Sarcoma | 1.14 |
| A673STAG2NT23 | Bone Cancer | Ewings Sarcoma | 1.04 |
| AM38 | Brain Cancer | Glioblastoma | 1.16 |
| AMO1 | Myeloma | Multiple Myeloma | 0.60 |
| BHY | Head and Neck Cancer | Head and Neck Cancer | 1.43 |
| BICR18 | Head and Neck Cancer | Head and Neck Cancer | 1.13 |
| BT12 | Rhabdoid | Rhabdoid Tumor | 0.58 |
| BV173 | Leukemia | Chronic Myelogenous Leukemia (CML), blast crisis | 0.70 |
| C32 | Skin Cancer | Medulloblastoma | 1.14 |
| C8166 | Lymphoma | Adult T-cell Lymphoma (ATL) | 1.53 |
| CADOES1 | Bone Cancer | Ewings Sarcoma | 1.09 |

TABLE 10-continued

PRISM AUC values of cell lines screened

| CCLE Cell line | Primary Disease | Subtype Disease | PRISM_AUC |
|---|---|---|---|
| CAS1 | Brain Cancer | Glioblastoma | 1.04 |
| CCK81 | Colon/Colorectal Cancer | Colorectal Cancer | 0.90 |
| CHLA06ATRT | Rhabdoid | Rhabdoid Tumor | 1.03 |
| CHLA10 | Bone Cancer | Ewings Sarcoma | 0.93 |
| CHLA15 | Neuroblastoma | Neuroblastoma | 1.00 |
| CI1 | Lymphoma | B-cell Non-Hodgkins Lymphoma (B-cell NHL) | 0.60 |
| CL11 | Colon/Colorectal Cancer | Colorectal Cancer | 1.99 |
| COGE352 | Bone Cancer | Ewings Sarcoma | 0.39 |
| COLO320 | Colon/Colorectal Cancer | Colorectal Cancer | 0.69 |
| COLO678 | Colon/Colorectal Cancer | Colorectal Cancer | 1.50 |
| COV318 | Ovarian Cancer | Ovarian Cancer, serous | 1.21 |
| CW2 | Colon/Colorectal Cancer | Colorectal Cancer | 1.41 |
| CW9019 | Sarcoma | Rhabdomyosarcoma | 1.09 |
| DAOY | Brain Cancer | Medulloblastoma | 1.03 |
| DEL | Lymphoma | T-cell Anaplastic Large Cell Lymphoma (T-cell ALCL) | 0.59 |
| DL | Rhabdoid | Rhabdoid Tumor | 0.93 |
| DMS79 | Lung Cancer | Small Cell Lung Cancer | 1.34 |
| DND41 | Leukemia | T-cell Acute Lymphoblastic Leukemia (T-cell ALL) | 1.08 |
| DOHH2 | Lymphoma | DLBCL | 0.90 |
| ECC10 | Gastric Cancer | Small Cell Gastric Cancer | 0.77 |
| EFE184 | Endometrial/Uterine Cancer | Endometrial Cancer | 1.14 |
| EKVX | Lung Cancer | Non-Small Cell Lung Cancer, adenocarcinoma | 1.21 |
| EM2 | Leukemia | Chronic Myelogenous Leukemia, blast crisis | 0.63 |
| EOL1 | Leukemia | Acute myelogenous Leukemia (AML), AML-M5 | 0.92 |
| EWS502 | Bone Cancer | Ewings Sarcoma | 0.87 |
| G292CLONEA141B1 | Bone Cancer | Osteosarcoma | 1.45 |
| G402 | Rhabdoid | Rhabdoid Tumor | 0.85 |
| GRANTA519 | Lymphoma | Mantel Cell Lymphoma (MCL) | 1.34 |
| GSS | Gastric Cancer | Gastric Adenocarcinoma | 1.26 |
| GSU | Gastric Cancer | Gastric Adenocarcinoma | 0.99 |
| HCC1954 | Breast Cancer | Breast Ductal Cancer | 0.99 |
| HCC2108 | Lung Cancer | Non-Small Cell Lung Cancer, adenocarcinoma | 1.02 |
| HCC515 | Lung Cancer | Non-Small Cell Lung Cancer, adenocarcinoma | 1.23 |
| HDMYZ | Lymphoma | Hodgkin's Lymphoma | 1.00 |
| HEC50B | Endometrial/Uterine Cancer | Endometrial Cancer | 1.02 |
| HEL | Leukemia | AML-M6 | 0.99 |
| HEPG2 | Liver Cancer | Hepatocellular Carcinoma | 1.25 |
| HH | Lymphoma | cutaneous T-cell NHL | 0.74 |
| HOS | Bone Cancer | Osteosarcoma | 1.00 |
| HPAFII | Pancreatic Cancer | Pancreatic Cancer | 1.38 |
| HS683 | Brain Cancer | Glioma | 1.32 |
| HS729 | Sarcoma | Rhabdomyosarcoma | 0.69 |
| HT | Lymphoma | B-cell NHL | 0.53 |
| HT115 | Colon/Colorectal Cancer | Colorectal Cancer | 0.79 |
| HT1197 | Bladder Cancer | Bladder Cancer | 1.33 |
| HUG1N | Gastric Cancer | Gastric Adenocarcinoma | 0.89 |
| HUH1 | Liver Cancer | Hepatocellular Carcinoma, HBs-antigen carrier | 1.04 |
| HUPT4 | Pancreatic Cancer | Pancreatic Cancer | 0.99 |
| HUT78 | Lymphoma | cutaneous T-cell NHL, Sesary Syndrome | 0.71 |
| IGR39 | Skin Cancer | Melanoma | 1.14 |
| JEKO1 | Lymphoma | MCL | 0.75 |
| JL1 | Lung Cancer | Mesothelioma | 1.24 |
| JM1 | Leukemia | B-cell ALL | 0.78 |
| JR | Sarcoma | Rhabdomyosarcoma | 0.52 |
| JURKAT | Leukemia | T-cell ALL | 0.69 |
| K562 | Leukemia | Chronic Myelogenous Leukemia, blast crisis | 1.06 |

TABLE 10-continued

PRISM AUC values of cell lines screened

| CCLE Cell line | Primary Disease | Subtype Disease | PRISM_AUC |
|---|---|---|---|
| K562GC11 | Leukemia | Chronic Myelogenous Leukemia | 1.07 |
| K562GC12 | Leukemia | Chronic Myelogenous Leukemia | 1.02 |
| K562SMC3F9 | Leukemia | Chronic Myelogenous Leukemia | 1.01 |
| K562SMC3H9 | Leukemia | Chronic Myelogenous Leukemia | 1.05 |
| K562STAG2C2 | Leukemia | Chronic Myelogenous Leukemia | 1.05 |
| K562STAG2D5 | Leukemia | Chronic Myelogenous Leukemia | 1.08 |
| KARPAS299 | Lymphoma | T-cell ALCL | 0.71 |
| KARPAS620 | Leukemia | Plasma Cell Leukemia | 0.53 |
| KASUMI2 | Leukemia | B-cell ALL | 0.72 |
| KCL22 | Leukemia | Chronic Myelogenous Leukemia, blast crisis | 0.89 |
| KE37 | Leukemia | T-cell ALL | 0.77 |
| KE39 | Gastric Cancer | Gastric Cancer | 1.20 |
| KE97 | Gastric Cancer | Gastric Adenocarcinoma | 1.03 |
| KLE | Endometrial/Uterine Cancer | Endometrial Cancer | 1.36 |
| KMH2 | Lymphoma | Hodgkin's Lymphoma | 1.09 |
| KMS11 | Myeloma | Multiple Myeloma | 0.72 |
| KMS18 | Myeloma | Multiple Myeloma | 0.82 |
| KMS21BM | Myeloma | Multiple Myeloma | 0.50 |
| KMS27 | Myeloma | Multiple Myeloma | 0.57 |
| KMS28BM | Myeloma | Multiple Myeloma | 0.68 |
| KOPN8 | Leukemia | B-cell ALL | 0.60 |
| KPNYN | Neuroblastoma | Neuroblastoma | 2.12 |
| KS1 | Brain Cancer | Glioblastoma | 1.28 |
| KU812 | Leukemia | Chronic Myelogenous Leukemia, blast crisis | 0.43 |
| KYO1 | Leukemia | Chronic Myelogenous Leukemia, blast crisis | 1.03 |
| L363 | Leukemia | Plasma Cell Leukemia | 0.50 |
| LN382 | Brain Cancer | Glioblastoma | 1.08 |
| LN464 | Brain Cancer | Glioma | 1.06 |
| LNZ308 | Brain Cancer | Glioblastoma | 1.01 |
| LP1 | Myeloma | Multiple Myeloma | 0.54 |
| M059K | Brain Cancer | Glioblastoma | 1.42 |
| MC116 | Lymphoma | B-cell NHL | 0.37 |
| MDAMB361 | Breast Cancer | Breast Cancer | 1.39 |
| MDST8 | Colon/Colorectal Cancer | Colorectal Cancer | 1.01 |
| MG63 | Bone Cancer | Osteosarcoma | 1.22 |
| MHHES1 | Bone Cancer | Ewings Sarcoma | 1.59 |
| MHHNB11 | Neuroblastoma | Neuroblastoma | 1.47 |
| MM1S | Myeloma | Multiple Myeloma | 0.74 |
| MOLM13 | Leukemia | Acute Myelogenous Leukemia | 0.44 |
| MOLP2 | Myeloma | Multiple Myeloma | 0.57 |
| MOLT16 | Leukemia | T-cell ALL | 0.59 |
| MOLT3 | Leukemia | T-cell ALL | 1.28 |
| MON | Rhabdoid | Rhabdoid Tumor | 0.98 |
| MONOMAC1 | Leukemia | Acute Myelogenous Leukemia | 0.82 |
| MONOMAC6 | Leukemia | AML-M5 | 0.67 |
| NB1 | Neuroblastoma | Neuroblastoma | 0.83 |
| NB4 | Leukemia | AML-M3 | 0.49 |
| NCIH1092 | Lung Cancer | Small Cell Lung Cancer | 0.68 |
| NCIH1105 | Lung Cancer | Small Cell Lung Cancer | 0.86 |
| NCIH1341 | Lung Cancer | Small Cell Lung Cancer | 1.09 |
| NCIH196 | Lung Cancer | Small Cell Lung Cancer | 1.16 |
| NCIH2004RT | Rhabdoid | Rhabdoid Tumor | 1.33 |
| NCIH211 | Lung Cancer | Small Cell Lung Cancer | 0.71 |
| NCIH2171 | Lung Cancer | Small Cell Lung Cancer | 0.91 |
| NCIH2196 | Lung Cancer | Small Cell Lung Cancer | 0.97 |
| NCIH441 | Lung Cancer | Non-Small Cell Lung Cancer, adenocarcinoma | 1.45 |
| NCIH508 | Colon/Colorectal Cancer | Colorectal Cancer | 1.05 |
| NCIH82 | Lung Cancer | Small Cell Lung Cancer | 0.54 |
| NCO2 | Leukemia | Chronic Myelogenous Leukemia | 1.00 |
| NOMO1 | Leukemia | AML-M5 | 0.37 |
| NUDHL1 | Lymphoma | DLBCL | 0.58 |
| OCIAML2 | Leukemia | AML-M4 | 0.44 |

TABLE 10-continued

PRISM AUC values of cell lines screened

| CCLE Cell line | Primary Disease | Subtype Disease | PRISM_AUC |
|---|---|---|---|
| OCIAML3 | Leukemia | AML-M4 | 0.59 |
| OCIAML5 | Leukemia | Acute Myelogenous Leukemia | 0.77 |
| OCILY132 | Lymphoma | T-cell NHL | 0.50 |
| OCILY19 | Lymphoma | DLBCL | 0.63 |
| OCIM1 | Leukemia | AML-M6 | 1.46 |
| ONS76 | Brain Cancer | Medulloblastoma | 1.15 |
| OVKATE | Ovarian Cancer | Ovarian Adenocarcinoma, serous papillary | 1.18 |
| P12ICHIKAWA | Leukemia | T-cell ALL | 0.85 |
| PEDS005TPFAD | Kidney Cancer | Renal Medullary Carcinoma | 1.12 |
| PEDS005TSUSP | Kidney Cancer | Renal Medullary Carcinoma | 0.85 |
| PL21 | Leukemia | AML-M3 | 0.56 |
| RCHACV | Leukemia | B-cell ALL | 0.56 |
| RD | Sarcoma | Rhabdomyosarcoma | 1.30 |
| RERFGC1B | Gastric Cancer | Gastric Adenocarcinoma | 0.94 |
| RH30 | Sarcoma | Rhabdomyosarcoma | 1.10 |
| RH4 | Sarcoma | Rhabdomyosarcoma | 0.90 |
| RHJT | Sarcoma | Rhabdomyosarcoma | 1.16 |
| RPMI8402 | Leukemia | T-cell ALL | 0.74 |
| SCC9 | Head and Neck Cancer | Head and Neck Cancer | 1.17 |
| SEM | Leukemia | B-cell ALL | 0.77 |
| SHP77 | Lung Cancer | Small Cell Lung Cancer | 0.99 |
| SIMA | Neuroblastoma | Neuroblastoma | 1.68 |
| SJSA1 | Bone Cancer | Osteosarcoma | 1.23 |
| SKES1 | Bone Cancer | Ewings Sarcoma | 1.24 |
| SKM1 | Leukemia | Acute Myelogenous Leukemia | 0.53 |
| SKMEL28 | Skin Cancer | Melanoma | 1.13 |
| SKNAS | Neuroblastoma | Neuroblastoma | 0.91 |
| SKNBE2 | Neuroblastoma | Neuroblastoma | 1.00 |
| SKNDZ | Neuroblastoma | Neuroblastoma | 1.18 |
| SKNFI | Neuroblastoma | Neuroblastoma | 1.17 |
| SKNMC | Bone Cancer | Ewings Sarcoma | 0.82 |
| SKNO1 | Leukemia | Acute Myelogenous Leukemia | 0.70 |
| SKPNDW | Bone Cancer | Ewings Sarcoma | 0.84 |
| SNU1 | Gastric Cancer | Gastric Cancer | 0.60 |
| SNU119 | Ovarian Cancer | Ovarian Cancer, Cystadenocarcinoma | 0.75 |
| SNU201 | Brain Cancer | Glioblastoma | 1.44 |
| SNU216 | Gastric Cancer | Gastric Adenocarcinoma | 1.19 |
| SNU899 | Head and Neck Cancer | Head and Neck Cancer | 1.30 |
| SR786 | Lymphoma | T-cell ALCL | 0.78 |
| SUDHL8 | Lymphoma | DLBCL | 0.78 |
| SUPB15 | Leukemia | B-cell ALL | 0.99 |
| SUPT11 | Leukemia | T-cell ALL | 0.41 |
| SW1116 | Colon/Colorectal Cancer | Colorectal Cancer | 1.45 |
| SW1463 | Colon/Colorectal Cancer | Colorectal Cancer | 1.57 |
| SW1783 | Brain Cancer | Astrocytoma | 1.50 |
| T84 | Colon/Colorectal Cancer | Colorectal Cancer | 1.38 |
| TC106 | Bone Cancer | Ewings Sarcoma | 0.91 |
| TC205 | Bone Cancer | Ewings Sarcoma | 0.79 |
| TC71 | Bone Cancer | Ewings Sarcoma | 0.83 |
| TE617T | Sarcoma | Rhabdomyosarcoma | 0.46 |
| TF1GC12 | Leukemia | Acute Myelogenous Leukemia | 0.86 |
| THP1 | Leukemia | AML-M5 | 0.50 |
| TM87 | Rhabdoid | Rhabdoid Tumor | 1.18 |
| TTC1240 | Rhabdoid | Rhabdoid Tumor | 0.48 |
| TTC442 | Sarcoma | Rhabdomyosarcoma | 1.28 |
| TTC549 | Rhabdoid | Rhabdoid Tumor | 0.63 |
| TTC709 | Rhabdoid | Rhabdoid Tumor | 1.19 |
| TYKNU | Ovarian Cancer | Ovarian Adenocarcinoma, high grade serous | 1.48 |
| U178 | Brain Cancer | Glioblastoma | 1.40 |
| U87MG | Brain Cancer | Glioblastoma | 0.99 |
| U937GC11 | Leukemia | Acute Myelogenous Leukemia | 0.77 |
| U937GC13 | Leukemia | Acute Myelogenous Leukemia | 0.91 |
| U937SMC3H10 | Leukemia | Acute Myelogenous Leukemia | 0.75 |
| U937SMC3H8 | Leukemia | Acute Myelogenous Leukemia | 0.76 |
| U937STAG2A2 | Leukemia | Acute Myelogenous Leukemia | 0.83 |

TABLE 10-continued

| PRISM AUC values of cell lines screened | | | |
|---|---|---|---|
| CCLE Cell line | Primary Disease | Subtype Disease | PRISM_AUC |
| U937STAG2E10 | Leukemia | Acute Myelogenous Leukemia | 0.60 |
| UW228 | Brain Cancer | Medulloblastoma | 1.20 |
| WSUDLCL2 | Lymphoma | DLBCL | 0.60 |

Assay 9

Protein-Compound Interaction Assay (SPR Assay)

The ability of the compounds described in this invention to bind to MCL-1 may be determined using surface plasmon resonance (SPR). This allows for the quantification of binding in terms of the equilibrium dissociation constant (KD [M]), as well as association and dissociation rate constants (kon [1/Ms] and koff [1/s], respectively). The measurements may be performed using Biacore® T200 or Biacore® S200 instruments (GE Healthcare).

For SPR measurements, recombinant MCL-1 (amino acids 173-321, N-terminal fused to Maltose Binding Protein (MBP) (SEQ ID1) purchased from Beryllium (Bedford, Mass., USA)) was immobilized using standard amine coupling (Johnsson B et al, Anal Biochem. 1991 Nov. 1; 198(2):268-77). Briefly, carboxymethylated dextran biosensor chips (Series S Sensor Chip CMS, GE Healthcare) were activated with 1-ethyl-3-(3-dimethylaminopropyl)-carbodiimide hydrochloride (EDC) and N-hydroxysuccinimide (NHS) according to the supplier's instructions. MBP-MCL-1 was diluted in 1×PBS-P+ (GE Healthcare) and injected on the activated chip surface. Subsequently, a solution of 1 M ethanolamine-HCl (GE Healthcare) was injected to block unreacted groups, resulting in approximately 400-2500 response units (RU) of immobilized protein. A reference surface was generated by treatment with NHS-EDC and ethanolamine-HCl. Compounds were dissolved in 100% dimethylsulfoxide (DMSO) to a concentration of 10 mM and subsequently diluted in running buffer (1×PBS-P+(GE Healthcare) [generated from PBS-P+Buffer 10× (GE Healthcare): 0.2 M phosphate buffer with 27 mM KCl, 1.37 M NaCl and 0.5% Surfactant P20 (Tween 20).], 1% v/v DMSO). For SPR binding-measurements, serial dilutions of compound (eight dilution steps, typically ranging from 0.2 nM up to 1 μM) were injected over immobilized protein. Binding affinity and kinetics were measured at 25° C. with a flow rate of 100 μl/min in running buffer. Compounds were injected for 60 s followed by a dissociation time of up to 1000 s.

The double-referenced sensorgrams were fit to a simple reversible Langmuir 1:1 reaction mechanism as implemented in the Biacore® T200 and S200 evaluation software (T200 evaluation software version 2.0 and S200 evaluation software version 1.0, GE Healthcare).

TABLE 11

| $K_D$, $k_{on}$ and $k_{off}$ values (geometric mean values) of MCL-1 compound interactions of selected examples as determined in SPR assay 9 | | | |
|---|---|---|---|
| Example | kon [1/M 1/s] | koff [1/s] | KD [M] |
| 01 | | | |
| 02 | 5.9 E6 | 6.7 E−2 | 1.1 E−8 |
| 03 | | | |
| 04 | | | |
| 05 | | | |
| 06 | | | |

TABLE 11-continued

| $K_D$, $k_{on}$ and $k_{off}$ values (geometric mean values) of MCL-1 compound interactions of selected examples as determined in SPR assay 9 | | | |
|---|---|---|---|
| Example | kon [1/M 1/s] | koff [1/s] | KD [M] |
| 07 | | | |
| 08 | 2.9 E7 | 2.5 E−2 | 8.4 E−10 |
| 09 | | | |
| 10 | 9.0 E6 | 1.0 E−2 | 1.1 E−9 |
| 11 | 6.2 E6 | 3.8 E−3 | 6.1 E−10 |
| 12 | 1.5 E5 | 3.4 E−3 | 2.2 E−8 |
| 13 | | | |
| 14 | 2.3 E7 | 3.1 E−2 | 1.3 E−9 |
| 15 | | | |
| 16 | | | |
| 17 | 2.0 E7 | 1.5 E−2 | 7.7 E−10 |
| 18 | | | |
| 19 | | | |
| 20 | 3.2 E7 | 1.8 E−2 | 5.6 E−10 |
| 21 | | | |
| 22 | | | |
| 23 | 2.2 E7 | 9.4 E−3 | 4.3 E−10 |
| 24 | 5.4 E4 | 1.5 E−3 | 2.8 E−8 |
| 25 | | | |
| 26 | | | |
| 27 | | | |
| 28 | | | |
| 29 | 1.7 E6 | 1.4 E−2 | 8.3 E−9 |
| 30 | | | |
| 31 | 4.4 E6 | 8.0 E−3 | 1.8 E−9 |
| 32 | | | |
| 33 | | | |
| 34 | | | |
| 35 | | | |
| 36 | | | |
| 37 | | | |
| 38 | | | |
| 39 | | | |
| 40 | | | |
| 41 | | | |
| 42 | 1.2 E6 | 3.2 E−3 | 2.8 E−9 |
| 43 | | | |
| 44 | | | |
| 45 | 3.0 E6 | 6.8 E−3 | 2.3 E−9 |
| 46 | | | |
| 47 | 8.2 E6 | 2.6 E−3 | 3.2 E−10 |
| 48 | 4.3 E5 | 1.2 E−3 | 2.8 E−9 |
| 49 | | | |
| 50 | 2.5 E7 | 9.0 E−3 | 3.6 E−10 |
| 51 | | | |
| 52 | | | |
| 53 | | | |
| 54 | | | |
| 55 | | | |
| 56 | | | |
| 57 | | | |
| 58 | 7.3 E5 | 1.1 E−3 | 1.5 E−9 |
| 59 | | | |
| 60 | | | |
| 61 | 1.6 E6 | 2.1 E−3 | 1.3 E−9 |
| 62 | | | |
| 63 | 1.1 E6 | 1.6 E−3 | 1.4 E−9 |
| 64 | | | |
| 65 | | | |
| 66 | | | |
| 67 | | | |
| 68 | | | |

TABLE 11-continued $K_D$, $k_{on}$ and $k_{off}$ values (geometric mean values) of MCL-1 compound interactions of selected examples as determined in SPR assay 9

| Example | kon [1/M 1/s] | koff [1/s] | KD [M] |
|---|---|---|---|
| 69 | 3.4 E7 | 1.6 E−2 | 4.6 E−10 |
| 70 | | | |
| 71 | | | |
| 72 | 1.2 E7 | 4.3 E−3 | 3.6 E−10 |
| 73 | | | |
| 74 | | | |
| 75 | 9.0 E6 | 2.2 E−3 | 2.4 E−10 |
| 76 | | | |
| 77 | | | |
| 78 | 3.5 E6 | 1.2 E−3 | 3.3 E−10 |
| 79 | | | |
| 80 | | | |
| 81 | | | |
| 82 | | | |
| 83 | | | |
| 84 | | | |
| 85 | | | |
| 86 | | | |
| 87 | | | |
| 88 | | | |
| 89 | | | |
| 90 | 3.7 E6 | 2.1 E−3 | 5.7 E−10 |
| 91 | | | |
| 92 | | | |
| 93 | | | |
| 94 | 2.1 E7 | 7.4 E−3 | 3.4 E−10 |
| 95 | | | |
| 96 | | | |
| 97 | | | |
| 98 | | | |
| 99 | | | |
| 100 | | | |
| 101 | | | |
| 102 | | | |
| 103 | | | |
| 104 | | | |
| 105 | | | |
| 106 | | | |
| 107 | | | |
| 108 | | | |

Assay 10

Equilibrium Shake Flask Solubility Assay

Thermodynamic solubility was determined by an equilibrium shake flask method [Edward H. Kerns and Li Di (2008) Solubility Methods in: Drug-like Properties: Concepts, Structure Design and Methods, p 276-286. Burlington, Mass.: Academic Press].

A saturated solution of the drug was prepared and the solution was mixed for 24 h to ensure that equilibrium has been reached. The solution was centrifuged to remove the insoluble fraction and the concentration of the compound in solution was determined using a standard calibration curve.

To prepare the sample, 2 mg solid compound was weighed in a 4 mL glass vial. 1 mL phosphate buffer pH 6.5 respectively borate Buffer pH 8 was added. The suspension was put on a stirrer and mixed for 24 hours at room temperature. The solution was centrifuged afterwards. To prepare the sample for the standard calibration, 1-2 mg (accurate weight) solid sample was dissolved in acetonitrile/water 50:50 and diluted to 20 mL. Sample and standards were quantified by HPLC with UV-detection. For each sample two injection volumes (5 and 50 µL) in triplicates were made. Three injection volumes (5 µL, 10 µL and 20 µL) were made for the standard.

Chromatographic conditions were as follows:

HPLC column: Xterra MS C18 2.5 µm 4.6×30 mm

Injection volume: Sample: 3×5 µL and 3×50 µL

Standard: 5 µL, 10 µL, 20 µL

Flow: 1.5 mL/min

Mobile phase: acidic gradient:

A: Water/0.01% trifluoroacidic acid

B: Acetonitrile/0.01% trifluoroacidic acid 0 min→95% A 5% B 0-3 min→35% A 65% B, linear gradient 3-5 min→35% A 65% B, isocratic 5-6 min→95% A 5% B, isocratic UV detector: wavelength near the absorption maximum (between 200 and 400 nm)

The areas of sample- and standard injections as well as the calculation of the solubility value (in mg/L) were determined by using HPLC software (Waters Empower 2 FR).

Assay 11

CYP Inhibition Assay

The inhibitory potency of the test compounds towards cytochrome P450 dependent metabolic pathways was determined in human liver microsomes applying individual CYP isoform-selective standard probes (phenacetin, coumarin, bupropion, amodiaquine, diclofenac, S-mephenytoin, dextromethorphan, chlorzoxazone, midazolam, testosterone). Reference inhibitors were included as positive controls. Incubation conditions (protein and substrate concentration, incubation time) were optimized with regard to linearity of metabolite formation. The assay was processed by using Genesis Workstation (Tecan, Crailsheim, FRG) in 96-well plates at 37° C. After protein precipitation the metabolite formation was quantified by LC-MS/MS analysis followed by inhibition evaluation and $IC_{50}$ calculation.

The potential of an investigational drug to inhibit CYP enzymes, given by determined $IC_{50}$ values of test compounds in vitro, is a basic requirement in order to assess potential drug-drug interactions (DDI) with comedicated drugs which are relevant substrates of studied CYP isoforms. Such investigations are recommended by pertinent guidelines (i.e. EMA and FDA) for the evaluation of DDIs.

Assay 12

CYP Induction Assay

To evaluate the CYP induction potential in vitro, cultured human hepatocytes from three separate livers were treated once daily for three consecutive days with vehicle control, one of eight concentrations of test compound and known human CYP inducers (e.g. omeprazole, phenobarbital, and rifampin). After treatment, the cells were incubated in situ with the appropriate marker substrates for the analysis of CYP3A4, CYP2B6 and CYP1A2 activity by LC-MS/MS. Following the in situ incubation, the same hepatocytes from the same treatment groups were harvested for RNA isolation and analyzed by qRT-PCR to assess the effect of test compound on CYP1A2, CYP2B6 and CYP3A4 mRNA expression levels.

Assay 13

Caco-2 Permeation Assay

Caco-2 cells (purchased from DSMZ Braunschweig, Germany) were seeded at a density of $4.5\times10^4$ cell per well on 24 well insert plates, 0.4 µm pore size, and grown for 15 days in DMEM medium supplemented with 10% fetal bovine serum, 1% GlutaMAX (100×, GIBCO), 100 U/mL penicillin, 100 µg/mL streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by an FCS-free hepes-carbonate transport puffer (pH 7.2). For assessment of monolayer integrity the transepithelial electrical resistance (TEER) was measured. Test compounds were predissolved in DMSO and added either to the apical or basolateral compartment in final concentration of 2 μM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app}=(V_r/P_0)(1/S)(P_2/t)$$

Where $V_r$ is the volume of medium in the receiver chamber, $P_0$ is the measured peak area of the test drug in the donor chamber at t=0, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B-A by the $P_{app}$ A-B. In addition the compound recovery was calculated. As assay control reference compounds were analyzed in parallel.

Assay 14

Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 mL falcon tubes and centrifuged at 50×g for 3 min at room temperature. The cell pellet was resuspended in 30 mL WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0\times10^6$ vital cells/mL. The test compound was added to a final concentration of 1 μM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated using the following formulae: CL'intrinsic [mL/(min*kg)]=kel [1/min]/((cellno/volume of incubation [mL])*fu,inc)*(cellno/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH. The following parameter values were used: Liver blood flow—4.2 L/h/kg rat; specific liver weight—32 g/kg rat body weight; liver cells in vivo—$1.1\times10^8$ cells/g liver, liver cells in vitro—$1.0\times10^6$/mL; fu,inc and fu,blood is taken as 1.

Assay 15

Investigation of In Vitro Metabolic Stability in Rat Hepatocytes in Liver Microsomes(Including Calculation of Hepatic In Vivo Blood Clearance (CL) and of Maximal Oral Bioavailability (Fmax))

The in vitro metabolic stability of test compounds was determined by incubating them at 1 μM in a suspension liver microsomes in 100 mM phosphate buffer, pH7.4 (sodium dihydrogen phosphate monohydrate+disodium hydrogen phosphate dihydrate) and at a protein concentration of 0.5 mg/mL at 37° C. The microsomes were activated by adding a co-factor mix containing 8 mM Glukose-6-Phosphat, 4 mM magnesium chloride; 0.5 mM NADP and 1 IU/mL G-6-P-Dehydrogenase in phosphate buffer, pH 7.4. The metabolic assay was started shortly afterwards by adding the test compound to the incubation at a final volume of 1 mL. Organic solvent in the incubations was limited to ≤0.01% dimethylsulfoxide (DMSO) and ≤1% acetonitrile. During incubation, the microsomal suspensions were continuously shaken at 580 rpm and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The hepatic in vivo blood clearance (CLblood) and the maximal oral bioavailability ($F_{max}$) was calculated using the following formulae: CL'intrinsic [mL/(min*kg)]=kel [1/min]/((mg protein/volume of incubation [mL])*fu,inc)*(mg protein/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH and using the following parameter values: Liver blood flow—1.32 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.; fu,inc and fu,blood is taken as 1.

Assay 16

In Vivo Pharmacokinetics in Rats

For in vivo pharmacokinetic experiments test compounds were administered to male Wistar rats intravenously at doses of 0.3 to 1 mg/kg and intragastral at doses of 0.5 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g., 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g., 48 h, 72 h). Blood was collected into Lithium-Heparintubes (Monovetten®, Sarstedt) and centrifuged for 15 min at 3000 rpm. An aliquot of 100 μL from the supernatant (plasma) was taken and precipitated by addition of 400 μL cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0–tlast)norm: Area under the concentration-time curve from t=0 hours to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

Assay 17

In Vivo Pharmacokinetics in Mouse

For in vivo pharmacokinetic experiments test compounds were administered to female CD1 mouse intravenously at doses of 0.3 to 1 mg/kg formulated as solutions using solubilizers such as PEG400 in well-tolerated amounts.

For pharmacokinetics after intravenous administration test compounds were given as i.v. bolus and blood samples were taken at 2 min, 5 min, 15 min, 30 min, 1 h, 2 h, 4 h, 7 h, and 24 h after dosing. Blood was collected via a vena jugular is catheter into Lithium-Heparin coated tubes (Eppendorf) and centrifuged for 15 min at 3000 rpm. An aliquot from the supernatant (plasma) was taken and precipitated by addition of 1:10 (v/v) ice cold methanol and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t½: terminal half-life (in h); MRT iv (h): mean residence time.

Assay 18

In Vivo Pharmacokinetics in Dog

For in vivo pharmacokinetic experiments test compounds were administered to Beagle dogs intravenously at doses of 0.3 to 1 mg/kg formulated as solutions using solubilizers such as PEG400 in well-tolerated amounts.

For pharmacokinetics after intravenous administration test compounds were given in in dogs as short term infusion (10 min). Blood samples were taken e.g. at 5 min, 10 min (end of short term infusion), 15 min, 30 min, 1 h, 2 h, 4 h, 6 h, 8 h and 24 h after dosing from the vena saphena. Blood was collected into K-EDTA (Monovetten®, Sarstedt) and centrifuged for 15 min at 3000 rpm. An aliquot of 100 μL from the supernatant (plasma) was taken and precipitated by addition of 400 μL cold acetonitrile and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software (e.g. Phoenix WinNonlin®, Certara USA, Inc.).

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0–tlast)norm: Area under the concentration-time curve from t=0 h to the last time point for which plasma concentrations could be measured divided by the administered dose (in kg*h/L); t½: terminal half-life (in h); MRT iv (h): mean residence time.

Assay 19

Assessment of the Anti-Proliferation Effect of Compounds in Tumor Xenografts

The suitability of the compounds of the present invention for the treatment of hyperproliferative disorders can be demonstrated in animal models of the following cancer types: breast cancer; esophageal cancer; liver cancer; lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; melanoma; ovarian cancer; pancreas cancer. For this purpose, human tumor cells of the respective cancer type were injected subcutaneously or intravenously into immunocompromised mice exemplified in the following figures, FIG. 1, FIG. 2 and FIG. 3** and respective tables, with AMO-1 and MOLP-8 as examples for multiple myeloma xenograft models, and SUDHL-10 as an example for a GC-DLBCL xenograft model. Once the primary tumor growth was established the animals were then randomized to receive treatment with either compound at maximum tolerated dose or vehicle control for a certain period of time, The difference between those groups in terms of the tumor growth was used to access the treatment efficacy. The principles of such xenograft studies are summarized in Richmond, A.; Su, Y. (2008). "Mouse xenograft models vs GEM models for human cancer therapeutics". Disease Models and Mechanisms 1 (2-3): 78-82. doi:10.1242/dmm.000976.

FIG. 1 shows a comparison of tumor growth of AMO-1 multiple myeloma cells growing subcutaneously in immunocompromised mice with untreated animals (Vehicle) and groups treated with different concentration of the compound example 47 (n=10 animals/group).

TABLE 12

| calculated tumor/control (T/C) ratio of the final tumor sizes at day 12 (last day of vehicle group) | |
|---|---|
| Groups (Single dose) | T/C |
| 12.5 mg/kg iv | 0.13 |
| 25 mg/kg iv | 0.07 |
| 50 mg/kg iv | 0.07 |

Figure 2:
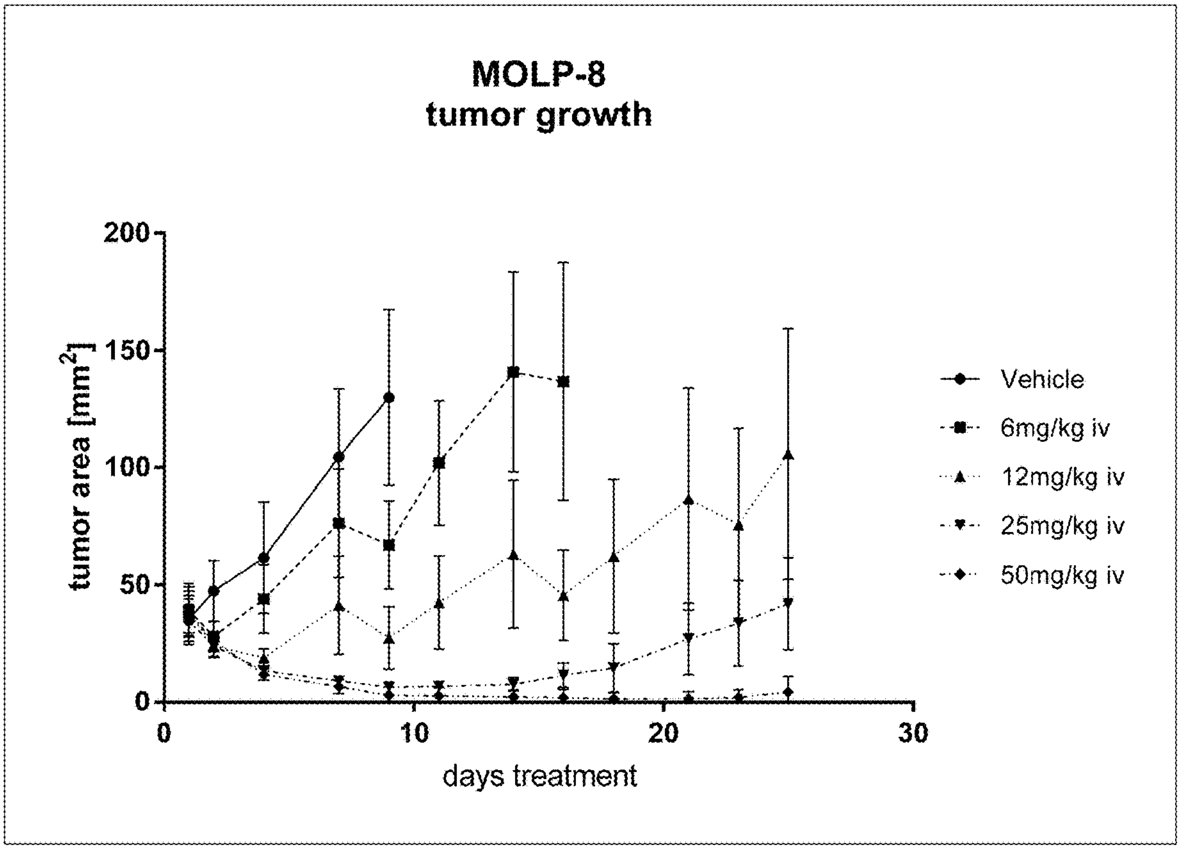
FIG. 2 shows a comparison of tumor growth of MOLP-8 multiple myeloma cells growing subcutaneously in immunocompromised mice with untreated animals (Vehicle) and groups treated with different concentration of the compound example 47 (n=10 animals/group).

FIG. 2 shows a comparison of tumor growth of MOLP-8 multiple myeloma cells growing subcutaneously in immunocompromised mice with untreated animals (Vehicle) and groups treated with different concentration of the compound example 47 (n=10 animals/group).

TABLE 13

| calculated tumor/control (T/C) ratio of the final tumor sizes at day 9 (last day of vehicle group) | |
|---|---|
| Groups | T/C |
| 6 mg/kg | 0.5 |
| 12 mg/kg iv | 0.2 |
| 25 mg/kg iv | 0.1 |
| 50 mg/kg iv | 0.0 |

Figure 3:
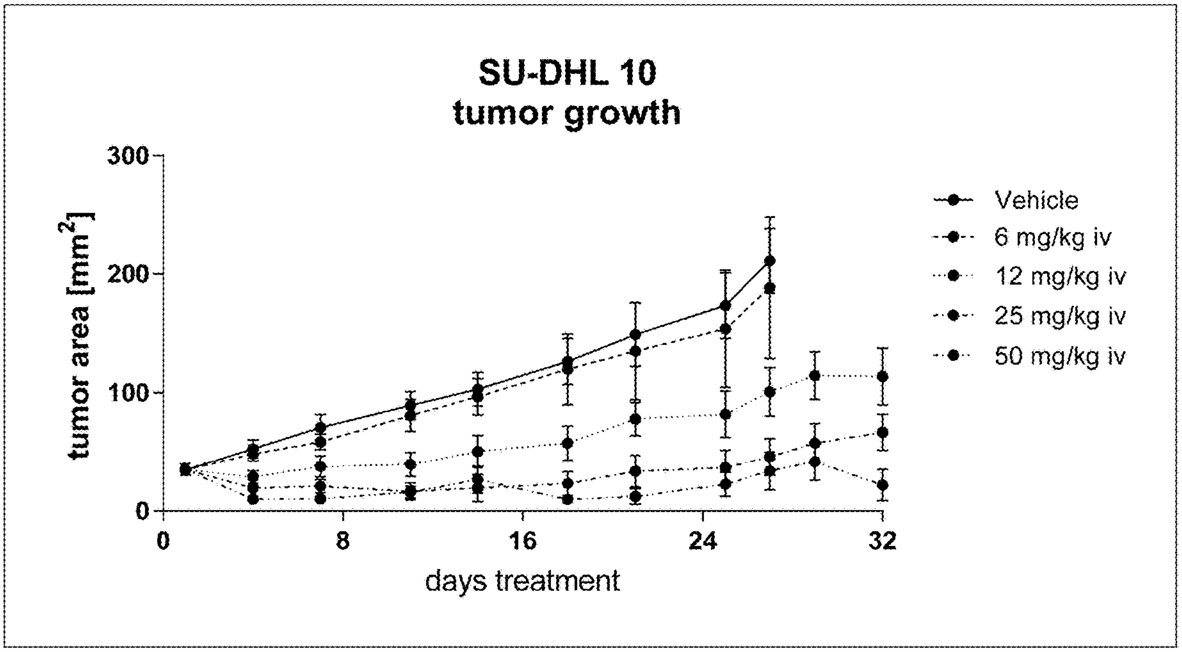
FIG. 3 shows a comparison of tumor growth of SU-DHL 10 GC-DLBCL cells growing subcutaneously in immunocompromised mice with untreated animals (Vehicle) and groups treated with different concentration of the compound example 47 (n=10 animals/group).

FIG. 3 shows a comparison of tumor growth of SU-DHL 10 GC-DLBCL cells growing subcutaneously in immunocompromised mice with untreated animals (Vehicle) and groups treated with different concentration of the compound example 47 (n=10 animals/group).

TABLE 14

| calculated tumor/control (T/C) ratio of the final tumor sizes at day 27 (last day of vehicle group) | |
|---|---|
| Groups | T/C |
| 6 mg/kg | 0.9 |
| 12 mg/kg iv | 0.5 |
| 25 mg/kg iv | 0.2 |
| 50 mg/kg iv | 0.1 |

MCL-1 Structural Analysis—Experiment 20

Crystallization

The crystallization construct (MBP-MCL1) consisted of maltose binding protein (MBP) residues 27-392 (prepended by a single glycine residue), which was connected by a two-residue glycine-serine linker to the N-terminus of the MCL-1 BH3 binding domain (residues 173-321), which also contained surface entropy reduction mutations K194A, K197A and R201A. The final amino acid sequence of MBP-MCL1 is therefore:

SEQ ID 6

```
GKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYNNGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN
```

-continued

```
AASGRQTVDEALKDAQTGSELYRQSLEIISRYLREQATGAADTAPMGASG

ATSRKALETLRRVGDGVQRNHETAFQGMLRKLDIKNEDDVKSLSRVMIHV

FSDGVTNWGRIVTLISFGAFVAKHLKTINQESCIEPLAESITDVLVRTKR

DWLVKQRGWDGFVEFFHV
```

MBP-MCL1 protein was expressed and purified as reported previously (see: A Maltose-Binding Protein Fusion Construct Yields a Robust Crystallography Platform for MCL1. Clifton M C, Dranow D M, Leed A, Fulroth B, Fairman J W, Abendroth J, Atkins K A, Wallace E, Fan D, Xu G, Ni Z J, Daniels D, Van Drie J, Wei G, Burgin A B, Golub T R, Hubbard B K, Serrano-Wu M H. PLoS One. 2015 Apr. 24; 10(4):e0125010. doi: 10.1371/journal-.pone.0125010. eCollection 2015). The final protein solution used in this experiment contained MBP-MCL1 at a concentration of 9.97 mg/ml in protein buffer (20 mM hepes pH7.5, 200 mM NaCl, 1% glycerol, and 2 mM DTT).

Compound solution was prepared containing Example 47 at a concentration of 4 mM in compound buffer (40% DMSO, 40% 2-Methyl-2,4-pentanediol, and 20% PEG400). Seed buffer was prepared containing 16% PEG3350, 50 mM magnesium formate, and 20 mM HEPES pH7.5.

Crystals of MBP-MCL1 in complex with Example 47 were obtained using the hanging-drop vapor diffusion method, using EasyXtal 15-well crystallization tools (Qiagen). Initial $P2_12_12$ crystals of MBP-MCL1 were obtained by mixing 2.25 μL protein solution, 0.75 μL compound buffer, and 3 μL seed buffer, and incubating over a 400 μL reservoir of 2M NaCl. Unliganded MCL1 crystals grew rapidly under these conditions. These initial crystals were then used to produce seed solutions containing diluted $P2_12_12$ MBP-MCL1 crystal microseeds serially diluted in seed buffer using a Seed Bead Kit (Hampton Research), as per manufacturer directions.

Figure 4:
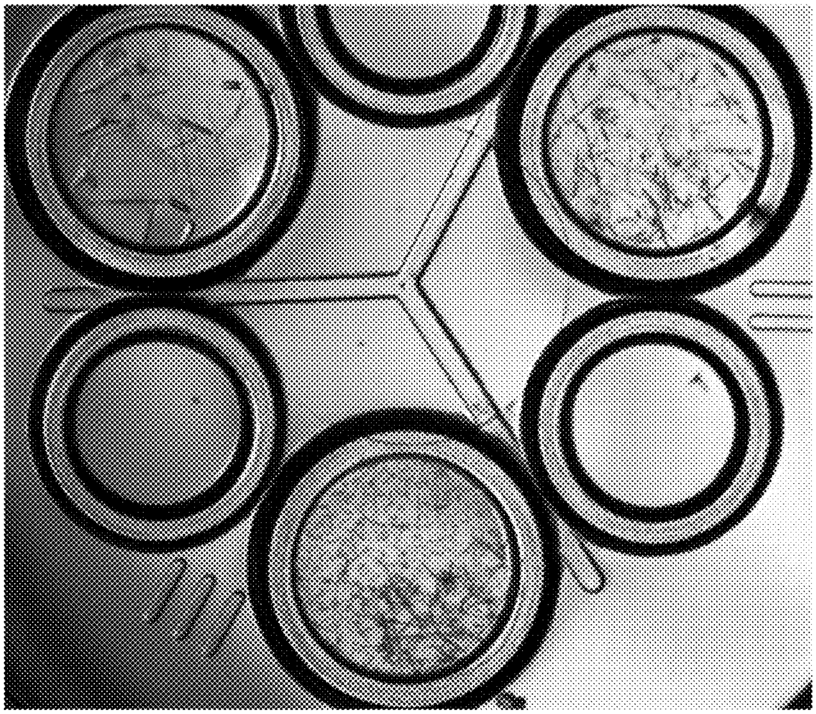
FIG. 4 shows seeded $P2_12_12$ crystals of MBP-MCL1 in complex with Example 47.

To generate a solution of MCL1 in complex with Example 47, 7.5 μL of protein solution was then mixed rapidly into 2.5 μL of compound solution, and the mixture was incubated on ice for 15 minutes. 3 μL of this mixture was then mixed with 3 μL of various seed dilutions and incubated over 400 μL of 1.5M NaCl. Well-formed $P2_12_12$ crystals of MBP-MCL1 in complex with Example 47 formed within 3 days (FIG. 4).

Data Collection, Structure Determination and Refinement

A ~25 μm 75 μm×200 μm $P2_12_12$ crystal of MBP-MCL1 in complex with Example 47 was mounted in a 300 um MicroLoop (Mitegen) and directly flash-frozen in liquid nitrogen. A complete 2.0 Å diffraction data set was collected on Rigaku MicroMax-007-HF generator equipped with Varimax-HF mirrors and a Saturn 944 CCD detector (Table 15). The diffraction data were processed, and the structure solved as described previously. (see citation above, Clifton et al.) The final refined model statistics are given in Table 15.

TABLE 15

| Data collection and refinement statistics | |
|---|---|
| Space group | $P2_12_12$ |
| Unit cell parameters, | |
| axes a, b, c [Å], | 98.7, 136.6, 38.4 |
| angles α, β, γ (°) | 90, 90, 90 |
| Resolution [Å] | 34.6-2.0 (2.05-2.00) |
| Number of unigue reflections | 35825 (2562) |
| Mean I/σ | 19.5 (2.3) |

TABLE 15-continued

| Data collection and refinement statistics | |
|---|---|
| Completeness | 99.3 (99.0) |
| Multiplicity | 6.8 (6.8) |
| Rmeas | 0.069 (0.892) |
| Resolution [Å] | 34.6-2.0 (2.05-2.00) |
| $R_{work}$ | 0.175 (0.405) |
| $R_{free}$ | 0.217 (0.497) |
| r.m.s.d. bonds [Å] | 0.005 |
| r.m.s.d. angles | 0.704 |
| Values in brackets refer to the highest resolution shell | |

Absolute Configuration of Example 47 Bound to MBP-MCL1

The complex of MBP-MCL1 with Example 47 crystallized with a single molecule of MBP-MCL1 in the asymmetric unit, with a single molecule of Example 47 clearly bound to the BH3 binding pocket of MCL-1. For co-crystallization, an enantiomer-pure batch of Example 47 was used for which the exact stereo-configuration was not known.

Figure 5:
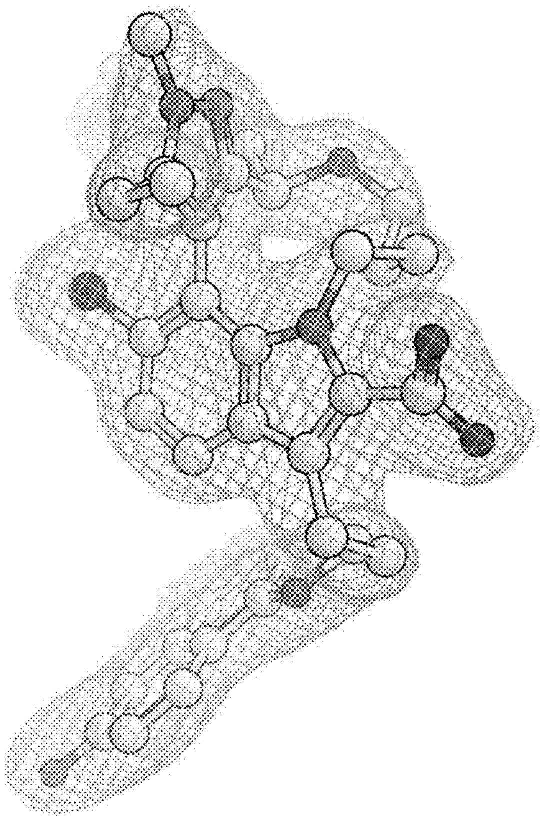
FIG. 5 shows 2Fo-Fc density of Example 47 in complex with MBP-MCL1 contoured to 1 sigma.
Figure 6:
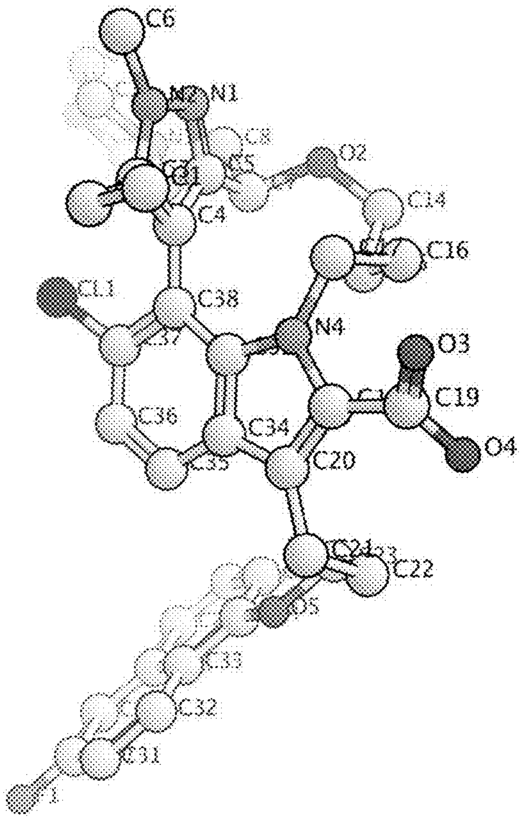
FIG. 6 shows the structure of Example 47 in complex with MBP-MCL1. For clarity only the ligand non-hydrogen atoms are shown. Carbon atom C7 unambiguously features the (R)-configuration and the bound atropisomer as defined by the C4-C38 axis is the ($R_a$)-configuration.

The electron density maps allowed the unambiguous assignment of the stereoisomer bound in the crystal (FIG. 5). The stereo chemistry at carbon atom C7 of Example 47, along with the atropisomer assignment along the C4-C38 bond (FIG. 6) are unambiguously defined by the knowledge of the stereo chemistry of the MBP and MCL-1 proteins. Example 47 unambiguously features the (R)-configuration on carbon atom C7, and has the ($R_a$)-atropisomer configuration along the C4-C38 bond (FIG. 6).

The invention claimed is:

1. A compound of general formula (I):

(I)

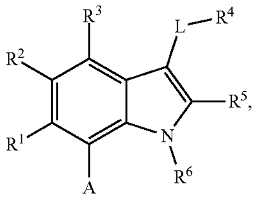

wherein

A is (A1)

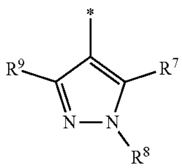

or (A2)

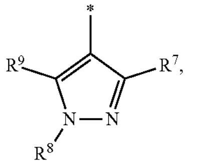

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

or

A is (A3)

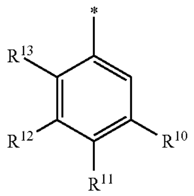

wherein optionally one or two of the groups selected from $CR^{11}$, $CR^{12}$ and $CR^{13}$ are replaced by a nitrogen atom, wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a ($C_1$-$C_3$-alkyl)-S(O)— group, a ($C_1$-$C_3$-alkyl)-$S(O)_2$— group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a C1-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to R$^4$;

m is 2, 3, or 4;

R$^5$ is selected from a COOH group, a

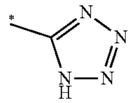 [SMILES: *c1nnn[nH]1]

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

s is 0, 1 or 2;

—R$^6$-R$^7$— is $^\#$—(CH$_2$)$_n$—(B)$_t$—CR$^{22}$R$^{23}$—$^{\#\#}$ or $^\#$—(C$_2$-C$_9$-alkenylene)-(B)$_t$—CR$^{22}$R$^{23}$—$^{\#\#}$, wherein $^\#$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

—R$^6$-R$^{10}$— is $^\#$—(CH$_2$)$_n$—(B)$_t$—CR$^{22}$R$^{23}$—$^{\#\#}$ or $^\#$—(C$_2$-C$_9$-alkenylene)-(B)$_t$—CR$^{22}$R$^{23}$—$^{\#\#}$, where one or more —CH$_2$— groups are substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^\#$ is the point of attachment with the indole nitrogen atom and $^{\#\#}$ is the point of attachment with the carbon atom of the aromatic moiety bearing the R$^{10}$ substituent;

n is 2, 3, 4, 5, 6, 7, 8, or 9, if B is selected from —O—, —S—, —S(O)—, —S(O)$_2$— and —N(R$^{15}$)— and n is 1, 2, 3, 4, 5, 6, 7 or 8 if B is selected from —C(O)NR$^{15}$— group and a —NR$^{15}$C(O)— group and n is 0, 1, 2, 3, 4, 5, 6, or 7 if B is selected from a —N(R$^{15}$)—C(=O)—N(R$^{15}$)— group, a —O—C(=O)—N(R$^{15}$)— group and a —N(R$^{15}$)—C(=O)—O— group;

t is 1;

where the integers selected for variables n and t, together with the methylene group CR$^{22}$R$^{23}$ and the other non-variable atoms of the pyrazole and the indole moiety result in forming a 9-membered to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)— and —S(O)$_2$—;

R$^8$ is selected from a hydrogen atom,
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy group,
a $C_3$-$C_6$-cycloalkyl group, a heterocycloalkyl group and a NR$^{21}$R$^{22}$ group;
a $C_1$-$C_3$-haloalkyl group,
a $C_3$-$C_6$-cycloalkyl group and
a $C_1$-$C_6$-alkyl group in which one or two not directly adjacent carbon atoms are independently replaced by a heteroatom selected from —O— and —NH— and R$^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)-group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a R$^{18}$-(phenylene)-($C_1$-$C_3$-alkylene)-O—($C_1$-$C_3$-alkylene)- group,
a R$^{18}$-(phenylene)-O—($C_1$-$C_3$-alkylene)- group,
a R$^{18}$-(phenylene)-(heteroarylene)-O—($C_1$-$C_3$-alkylene)- group,
a (R$^{18}$)-(heterocycloalkylene)-($C_1$-$C_3$-alkylene)- group,
a (R$^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a (R$^{18}$)-(heteroarylene)-($C_1$-$C_3$-alkylene)-O—($C_1$-$C_3$-alkylene)- group,
a (R$^{18}$)-(heteroarylene)-(phenylene)-O—($C_1$-$C_3$-alkylene)- group,
a (R$^{19}$)—S(O)$_2$-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—N($C_1$-$C_6$-alkyl)-(phenylene)-O—($C_1$-$C_3$-alkylene)- group,
a (R$^{19}$)—S(O)$_2$-(heterocycloalkylene)-(phenylene)-O—($C_1$-$C_3$-alkylene)- group,
a (R$^{18}$)-(heterocycloalkylene)-(heteroarylene)-O—($C_1$-$C_3$-alkylene)- group,
a (R$^{19}$)-(heteroarylene)-O—($C_1$-$C_3$-alkylene)- group,
a (R$^{18}$)-(heteroarylene)-O—($C_1$-$C_3$-alkylene)- group,
a (R$^{19}$)—S(O)$_2$-(heteroarylene)-O—($C_1$-$C_3$-alkylene)- group, a $(R^{19})$—$S(O)_2$-(heterocycloalkylene)-(heteroarylene)-O—($C_1$-$C_3$-alkylene)- group, a $NR^{20}R^{21}$—($C_1$-$C_3$-alkylene)- group, a ($C_1$-$C_3$-alkyl)-NH—($C_1$-$C_3$-alkylene)- group, a ($C_1$-$C_3$-haloalkyl)-($C_1$-$C_3$-alkylene)-NH—($C_1$-$C_3$-alkylene)- group, a ($C_1$-$C_3$-haloalkyl)-NH—($C_1$-$C_3$-alkylene)- group, a ($C_1$-$C_3$-alkyl)-NH—C(O)—($C_1$-$C_3$-alkylene)- group, a ($C_1$-$C_3$-alkyl)-$NR^{15}$—C(O)—($C_1$-$C_3$-alkylene)-group, a ($C_1$-$C_3$-alkyl)-C(O)—NH—($C_1$-$C_3$-alkylene)- group, a ($C_1$-$C_3$-alkyl)-C(O)—$NR^{15}$—($C_1$-$C_3$-alkylene)-group, a

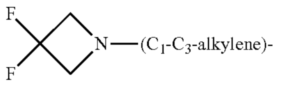

group and a

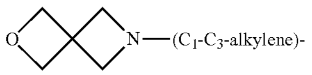

group, where the phenyl ring is unsubstituted or substituted with a halogen atom, a hydroxy group or a $C_1$-$C_3$-alkoxy group and the heterocycloalkyl group is unsubstituted or substituted with an oxo (═O) group or is unsubstituted or substituted with one or more substituents independently selected from a halogen atom, a hydroxy group, a $C_1$-$C_3$-alkyl group and a $C_1$-$C_3$-alkoxy group, or $R^8$ and $R^9$ together form a 5-membered or 6-membered ring optionally comprising one or two heteroatoms independently selected from —O— and —$NR^{14}$—;

$R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group;

$R^{14}$ is a hydrogen atom or a $C_1$-$C_3$-alkyl group;

$R^{15}$ is independently selected from a hydrogen atom, a $C_1$-$C_6$-alkyl group, which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a $(R^{18})$-(heterocycloalkylene)-(arylene)-O— group, a (heterocycloalkyl)-(arylene)-O— group, an aryl-O— group, an aryl-($C_1$-$C_3$-alkylene)-O— group, a $(R^{19})$—$S(O)_2$-arylene-O— group, a $(R^{19})S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group, a $C_1$-$C_3$-alkylene-C(O)— group, a heterocycloalkyl-($C_1$-$C_3$-alkylene)-C(O)— group, a heterocycloalkyl-($C_1$-$C_3$-alkylene)-$S(O)_2$— group, a heterocyclyl-NH—C(O)— group, a heterocycloalkyl-($C_1$-$C_3$-alkylene)-NH—C(O)— group, an aryl-($C_1$-$C_3$-alkylene)-NH—C(O)— group, which is unsubstituted or substituted with 1, 2, or 3 substituents independently selected from a halogen atom, a $C_1$-$C_3$-alkyl group and a $C_1$-$C_3$-alkoxy group, a heterocycloalkyl-heteroarylene-$S(O)_2$— group, a phenyl group, a group

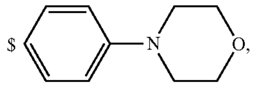

a group

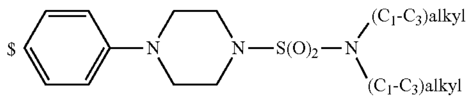

and a group

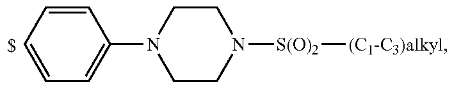

where $ is the point of attachment to the nitrogen atom, to which $R^{15}$ is attached, or $R^{15}$ and $R^{22}$ together, including the atoms to which they are attached, may form a 5- or 6-membered ring optionally comprising one or two additional heteroatoms independently selected from —O— and —$NR^{14}$—;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkyl $S(O)_2$— group and a $C_1$-$C_3$-alkyl-O—C(═O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}OC(O)$—($C_1$-$C_3$-alkylene)- group, a —$C(O)OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_6$-alkyl group; and $R^{22}$ is independently selected from a halogen atom, a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a $(R^{18})$-(heterocycloalkylene)-(arylene)-O— group, a (heterocycloalkyl)-(arylene)-O-group, an aryl-O— group, an aryl-($C_1$-$C_3$-alkylene)-O— group, a $(R^{19})$—$S(O)_2$-arylene-O— group, a $(R^{19})S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group, a $C_1$-$C_3$-alkyl-C(O)— group, a $C_3$-$C_6$-cycloalkyl group, an aryl group, a heterocycloalkyl group and a heteroaryl group;

wherein any heterocycloalkyl group of $R^{22}$ may optionally be itself further substituted with a $C_1$-$C_3$-alkyl group or one or two halogen atoms and $R^{23}$ is independently selected from a hydrogen atom, a halogen atom, a hydroxy group, a $C_1$-$C_6$-alkyl group and a $C_1$-$C_6$-haloalkyl group, or $R^{22}$ and $R^{23}$ together with the carbon atom to which they are attached form a 3-membered to 6-membered carbocyclic ring or a 3-membered to 6-membered heterocyclic ring comprising one or two heteroatoms selected from nitrogen, oxygen or sulfur;

or a tautomer, an N-oxide, or a salt thereof, or a salt of a tautomer, or a salt of an N-oxide, or a mixture of same.

2. The compound of general formula (I) according to claim 1:

wherein

A is (A1)

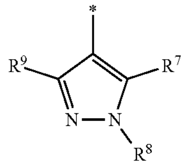

or (A2)

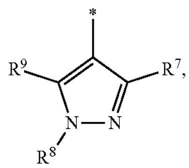

wherein $R^6$ and $R^7$, together with two carbon atoms of the pyrazole ring, two carbon atoms of the indole moiety and the nitrogen atom to which $R^6$ is attached, form a 9-membered to 13-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group;

E is a bond, an oxygen atom, a sulfur atom, or a —$NR^{14}$— group and constitutes the connecting element to $R^4$;

m is 2, 3, or 4;

$R^5$ is selected from a COOH group and a

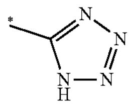 [SMILES: *c1nnn[nH]1]

group;

—$R^6$-$R^7$— is $^{\#}$—$(CH_2)_n$—$(B)_t$—$CR^{22}R^{23}$—$^{\#\#}$ or $^{\#}$—($C_2$-$C_6$-alkenylene)-$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group;

n is 2, 3, 4, 5 or 6 if B is selected from —O—, —S—, —S(O)—, —$S(O)_2$— and —$N(R^{15})$— and n is 1, 2, 3, 4, or 5, if B is selected from —$C(O)NR^{15}$— group and a —$NR^{15}C(O)$— group and n is 0, 1, 2, 3, or 4 if B is selected from a —$N(R^{15})$—C(═O)—$N(R^{15})$— group, a —O—C(═O)—$N(R^{15})$— group and a —$N(R^{15})$—C(═O)—O— group;

t is 1;

where the integers selected for variables n and t, together with the methylene group $CR^{22}R^{23}$ and the other non-variable atoms of the pyrazole and the indole moiety result in forming a 9-membered to 13-membered ring independently from the selection of variable A1 or A2;

B is independently selected from a —$C(O)NR^{15}$— group, a —$NR^{15}C(O)$— group, a —$N(R^{15})$— group, a —$N(R^{15})$—C(═O)—$N(R^{15})$— group, a —O—C(═O)—$N(R^{15})$— group, a —$N(R^{15})$—C(═O)—O— group, —O—, —S—, —S(O)— and —$S(O)_2$—;

$R^8$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group and
a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom,
a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—S$(O)_2$-arylene-O— group, a ($R^{19}$)S$(O)_2$-heterocycloalkylene-arylene-O— group and an aryl-heteroarylene-O— group;
a phenyl group,
a group

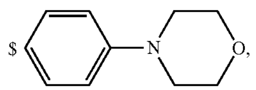

a group

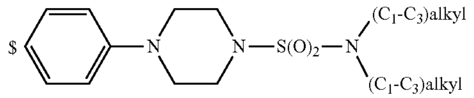

and
a group

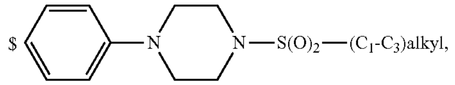

where $ is the point of attachment to the nitrogen atom, to which $R^{15}$ is attached, or $R^{15}$ and $R^{22}$ together, including the atoms to which they are attached, may form a 5-membered or 6-membered ring, both optionally comprising one or two additional heteroatoms independently selected from —O— and —$NR^{14}$—;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkyl S$(O)_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_6$-alkyl group; and $R^{22}$ is independently selected from
a halogen atom,
a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group and a phenyl group,
a $C_3$-$C_6$-cycloalkyl group and
a phenyl group,
whereby any heterocycloalkyl group of $R^{22}$ may optionally be itself further substituted with a $C_1$-$C_3$-alkyl group or one or two halogen atoms and $R^{23}$ is independently selected from a hydrogen atom, a halogen atom, a hydroxy group and a $C_1$-$C_4$-alkyl group or $R^{22}$ and $R^{23}$ together with the carbon atom to which they are attached form a 3-6-membered carbocyclic ring or a 3-membered to 6-membered heterocyclic ring comprising one or two heteroatoms selected from nitrogen, oxygen or sulfur;

or a tautomer, an N-oxide, or a salt thereof, or a salt of a tautomer, or a salt of an N-oxide, or a mixture of same.

3. The compound of general formula (I) according to claim 1 wherein

A is (A1)

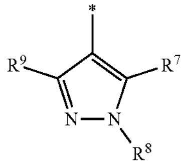

or (A2)

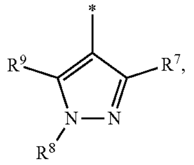

wherein $R^6$ and $R^7$, together with two carbon atoms of the pyrazole ring, two carbon atoms of the indole moiety and the nitrogen atom to which $R^6$ is attached, form a 10-membered to 12-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two or three substituents and each substituent is independently selected from a halogen atom and a $C_1$-$C_3$-alkyl group;

L is a group $-(CH_2)_m$-E-;

E is a bond or an oxygen atom and constitutes the connecting element to $R^4$;

m is 2, 3, or 4;

$R^5$ is a COOH group;

$-R^6$-$R^7-$ is $^{\#}-(CH_2)_n-(B)_t-CR^{22}R^{23}-^{\#\#}$ or $^{\#}-(C_3$-$C_5$-alkenylene)-$(B)_t-CR^{22}R^{23}-$, wherein $^{\#}$ is the point of attachment with the indole nitrogen atom and $^{\#\#}$ is the point of attachment with the pyrazole carbon atom bearing the $R^7$ substituent; and wherein one or more $-CH_2-$ groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group;

n is 3, 4 or 5;

t is 1;

where the integers selected for variables n and t together with the methylene group $CR^{22}R^{23}$ and the other non-variable atoms of the pyrazole and the indole moiety result in forming a 10-membered to 12-membered ring independently from the selection of variable A1 or A2;

B is independently selected from a $-N(R^{15})-$ group and $-O-$;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group, a $C_1$-$C_3$-hydroxyalkyl group, a $C_1$-$C_3$-haloalkyl group, a $C_1$-$C_3$-alkyl-O— group, a $C_1$-$C_3$-haloalkoxy group, a $C_1$-$C_3$-alkyl-O—($C_1$-$C_3$-alkylene)- group, a ($C_3$-$C_6$)-cycloalkyl group, a $R^{19}$-(phenylene)-O—($C_1$-$C_3$-alkylene)- group, a $NR^{20}R^{21}$—($C_1$-$C_3$-alkylene)- group and a ($C_1$-$C_3$-alkyl)-NH—($C_1$-$C_3$-alkylene)- group;

$R^{14}$ is a hydrogen atom or a $C_1$-$C_3$-alkyl group;

$R^{15}$ is independently selected from a hydrogen atom and a $C_1$-$C_6$-alkyl group which is unsubstituted or substituted with a substituent selected from a heterocycloalkyl group and an aryl group; or $R^{15}$ and $R^{22}$ together, including the atoms to which they are attached, may form a 5- or 6-membered ring, both optionally comprising one or two heteroatoms independently selected from —O— and $-NR^{14}-$;

$R^{16}$ and $R^{17}$ are each independently selected from a hydrogen atom, a $C_1$-$C_6$-alkyl group, a $C_1$-$C_6$-haloalkyl group and a $C_1$-$C_6$-alkoxy group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $C(O)OR^{21}$—($C_1$-$C_3$-alkylene)- group, a $-C(O)OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_3$-alkyl group; and $R^{22}$ is independently selected from a halogen atom, a $C_1$-$C_5$-alkyl group which is unsubstituted or substituted with a group selected from a hydroxy group, $NR^{16}R^{17}$ group, a $C_1$-$C_3$-haloalkyl group, a $C_1$-$C_4$-alkoxy group, a $C_3$-$C_6$-cycloalkyl group, a heterocycloalkyl group and a phenyl group, a $C_3$-$C_6$-cycloalkyl group, and a phenyl group, whereby any heterocycloalkyl group of $R^{22}$ may optionally be itself further substituted with a $C_1$-$C_3$-alkyl group or one or two halogen atoms and $R^{23}$ is independently selected from a hydrogen atom, a halogen atom, a hydroxy group and a $C_1$-$C_4$-alkyl group, or $R^{22}$ and $R^{23}$ together form a 3-membered to 6-membered carbocyclic ring;

or a tautomer, an N-oxide, or a salt thereof, or a salt of a tautomer, or a salt of an N-oxide, or a mixture of same.

4. The compound of general formula (I) according to claim 1, wherein

A is (A1)

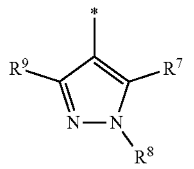

or (A2)

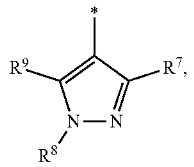

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group $-(CH_2)_m$-E-;

E is an oxygen atom and constitutes the connecting element to $R^4$;

m is 3;

$R^5$ is a COOH group;

$-R^6$-$R^7$- is $^{\#}-(CH_2)_n-(B)_t-CR^{22}R^{23}-^{\#\#}$ or $^{\#}-(C_3$-$C_4$-alkenylene)-$(B)_t-CR^{22}R^{23}-$, wherein $^{\#}$ is the point of attachment with the indole nitrogen atom and $^{\#\#}$ is the point of attachment with the pyrazole carbon atom bearing the $R^7$ substituent;

n is 4;

t is 1;

where the integers selected for variables n and t together with the methylene group $CR^{22}R^{23}$ and the other non-variable atoms of the pyrazole and the indole moiety result in forming a 11-membered ring independently from the selection of variable A1 or A2;

B is independently selected from a —N($R^{15}$)— group and —O—;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group;

$R^{15}$ is independently selected from a hydrogen atom and a $C_1$-$C_6$-alkyl group which is unsubstituted or substituted with a heterocycloalkyl group;

or $R^{15}$ and $R^{22}$ together, including the atoms to which they are attached, may form a 5-membered or 6-membered ring, both optionally comprising one or two heteroatoms independently selected from —O— and —$NR^{14}$—;

$R^{16}$ and $R^{17}$ are each independently selected from a hydrogen atom, a $C_1$-$C_3$-alkyl group, a $C_1$-$C_6$-haloalkyl group and a $C_1$-$C_3$-alkoxy group; and $R^{22}$ is independently selected from a halogen atom, a $C_3$-$C_6$-cycloalkyl group, a phenyl group and a $C_1$-$C_5$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms and $R^{23}$ is independently selected from a hydrogen atom, a halogen atom, a hydroxy group and a $C_1$-$C_3$-alkyl group, or $R^{22}$ and $R^{23}$ together form a 3-6-membered carbocyclic ring;

or a tautomer, an N-oxide, or a salt thereof, or a salt of a tautomer, or a salt of an N-oxide, or a mixture of same.

5. The compound of general formula (I) according to claim 1, wherein

A is (A2)

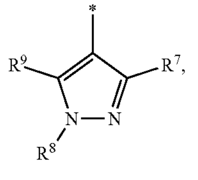

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group which is unsubstituted or substituted with a fluorine atom;

L is a group —$(CH_2)_3$—O—;

$R^5$ is a COOH group;

—$R^6$-$R^7$— is $^{\#}$—$(CH_2)_4$—O—$CR^{22}R^{23}$—$^{\#\#}$, or $^{\#}$—$(CH_2)_4$—$NR^{15}$—$CR^{22}R^{23}$-$^{\#\#}$, wherein $^{\#}$ is the point of attachment with the indole nitrogen atom and $^{\#\#}$ is the point of attachment with the pyrazole carbon atom bearing the $R^7$ substituent;

$R^8$ is a $C_1$-$C_3$-alkyl group;

$R^9$ is a $C_1$-$C_3$-alkyl group;

$R^{15}$ is a $C_1$-$C_3$-alkyl group, or $R^{15}$ and $R^{22}$ together, including the atoms to which they are attached, may form a 5-membered or 6-membered ring;

$R^{16}$ and $R^{17}$ are each independently selected from a hydrogen atom, a $C_1$-$C_3$-alkyl group and a $C_1$-$C_3$-alkoxy group;

$R^{22}$ is independently selected from a $C_3$-$C_6$-cycloalkyl group, a phenyl group and a $C_1$-$C_5$-alkyl group which is unsubstituted or substituted with a substituent selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms; and $R^{23}$ is a hydrogen atom;

or a tautomer, an N-oxide, or a salt thereof, or a salt of a tautomer, or a salt of an N-oxide, or a mixture of same.

6. The compound according to claim 1, which is selected from (rac)-2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 1), 2,3,15-trimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid trifluoroacetic acid salt (stereoisomer 2), (rac)-2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (mixture of stereoisomers), 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (stereoisomer 1), 2,3-dimethyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (stereoisomer 2), (rac)-4-fluoro-2,3-dimethyl-15-[2-(morpholin-4-yl)ethyl]-7-[3-(naphthalen-1-yloxy)propyl]-2,10,11,12, 13,15-hexahydropyrazolo[4',3':9,10][1,6]oxazacycloundecino[8,7,6-hi]indole-8-carboxylic acid, 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-fluoro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-3-ethyl-4-fluoro-2-methyl-15-[2-(morpholin-4-yl)ethyl]-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), 3-ethyl-4-fluoro-2-methyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), 4-chloro-2,3-dimethyl-15-[2-(morpholin-4-yl)ethyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-chloro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), 4-fluoro-7-{3-[(6-fluoronaphthalen-1-yl)oxy]propyl}-2,3-dimethyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 1), (−)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine (enantiomer 2), (rac)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-Chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid, (rac)-4-Chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (+)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-ethyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), (−)-4-chloro-15-(2-hydroxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-2-methyl-7-{3-[(naphthalen-1-yl)oxy]propyl}-15-(trifluoromethyl)-2,10,11,12,13,15-hexahydropyrazolo[4',3':9,10][1,6]oxazacycloundecino[8,7,6-hi]indole-8-carboxylic acid—N-ethylethanamine salt (enantiomer 2), (+)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 1), (−)-4-chloro-15-cyclopropyl-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (enantiomer 2), (rac)-4-chloro-(15-rac)-(2-methoxyethyl)-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-(15-rac)-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-cyclopropyl-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-methoxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(2-methoxyethyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-(2-hydroxyethyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-15-(2-hydroxyethyl)-2-methyl-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10][1,6]oxazacycloundecino[8,7,6-hi]indole-8-carboxylic acid, (15R)-4-chloro-3-ethyl-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt, (rac)-3-Ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-3-ethyl-4-fluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-(15-rac)-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(2-hydroxy-2-methylpropyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—2-hydroxypropane-1,2,3-tricarboxylic acid salt, 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid N-ethylethanamine salt (enantiomer 2), 4-chloro-15-[2-(3,3-difluoropyrrolidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (rac)-4-chloro-3-ethyl-7-{3-[(6-fluoronaphthalen-1-yl)oxy]propyl}-2-methyl-15-phenyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid (enantiomer 2), (+)-4-chloro-3-ethyl-7-{3-[(6-fluoronaphthalen-1-yl)oxy]propyl}-2-methyl-15-[2-(oxan-4-yl)ethyl]-2,10, 11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-2-methyl-15-[2-(oxan-4-yl)ethyl]-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-2-methyl-(15-rac)-[3-(morpholin-4-yl)propyl]-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, (−)-4-chloro-3-ethyl-7-{3-[(6-fluoronaphthalen-1-yl)oxy]propyl}-2-methyl-15-[3-(morpholin-4-yl)propyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 1 of stereoisomers), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 1), (+)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 2), 4-chloro-3-ethyl-7-{3-[(6-fluoronaphthalen-1-yl)oxy]propyl}-2-methyl-(15-rac)-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (mixture 2 of stereoisomers 2), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid—N-ethylethanamine salt (stereoisomer 3), (−)-4-chloro-3-ethyl-7-{3-[(6-fluoronaphthalen-1-yl)oxy]propyl}-2-methyl-15-[2-(4-methylpiperazin-1-yl)ethyl]-2,10,11,12,13,15-hexahydropyrazolo[4',3':9,10][1,6]oxazacycloundecino[8,7,6-hi]indole-8-carboxylic acid (stereoisomer 4), (rac)-4-chloro-3-ethyl-7-{3-[(6-fluoronaphthalen-1-yl)oxy]propyl}-(15-rac)-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-3-ethyl-7-{3-[(6-fluoronaphthalen-1-yl)oxy]propyl}-15-(3-hydroxy-3-methylbutyl)-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-(15-rac)-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 1), (−)-4-chloro-15-[2-(3,3-difluoroazetidin-1-yl)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid—N-ethylethanamine salt (enantiomer 2), (rac)-4-chloro-3-ethyl-7-{3-[(6-fluoronaphthalen-1-yl)oxy]propyl}-(15-rac)-{2-[methoxy(methyl)amino]ethyl}-2-methyl-2,10,11,12,13,15-hexahydropyrazolo[4',3':9,10][1,6]oxazacycloundecino[8,7,6-hi]indole-8-carboxylic acid, (rac)-4-chloro-(15-rac)-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 1), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 2), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 3), 4-chloro-15-[2-(dimethylamino)ethyl]-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (stereoisomer 4), 4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 2), 4-chloro-3-ethyl-12,12-difluoro-7-{3-[(6-fluoronaphthalen-1-yl)oxy]propyl}-2-methyl-15-[2-(morpholin-4-yl)

ethyl]-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 3), (−)-4-chloro-3-ethyl-12,12-difluoro-7-{3-[(6-fluoronaphthalen-1-yl)oxy]propyl}-2-methyl-15-[2-(morpholin-4-yl)ethyl]-2,10,11,12,13,15-hexahydropyrazolo[4',3':9,10][1,6]oxazacycloundecino[8,7,6-hi]indole-8-carboxylic acid (enantiomer 4), (rac)-15-benzyl-4-chloro-3-ethyl-7-{3-[(6-fluoro-1-naphthyl)oxy]propyl}-2-methyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (15R)-4-chloro-3-ethyl-7-{3-[(6-fluoronaphthalen-1-yl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-7-{3-[(6-fluoro-1-naphthyl)oxy]propyl}-2,14-dimethyl-15-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid, (rac)-4-chloro-3-ethyl-2,14-dimethyl-15-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid—N-ethylethanamine salt (Stereoisomer 3), (rac)-4-chloro-3-ethyl-2,14-dimethyl-15-[2-(morpholin-4-yl)ethyl]-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid—N-ethylethanamine salt (Stereoisomer 4), 4-chloro-3-ethyl-7-{3-[(6-fluoro-1-naphthyl)oxy]propyl}-2,14-dimethyl-15-[2-(tetrahydro-2H-pyran-4-yl)ethyl]-10,11,12,13,14,15-hexahydro-2H-pyrazolo[3',4':8,9][1,6]diazacycloundecino[10,11,1-hi]indole-8-carboxylic acid (mixture of 4 Isomers), (rac)-18-chloro-1-ethyl-2-methyl-15-[3-(1-napht (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acidhyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 1), (rac)-18-chloro-1-ethyl-2-methyl-15-[3-(1-naphthyloxy)propyl]-2,3b,4,5,6,7,9,10,11,12-decahydropyrazolo[3',4':8,9]pyrido[1',2':6,7][1,6]diazacycloundecino[10,11,1-hi]indole-14-carboxylic acid (Isomer 2), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (+)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid, (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1), (−)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (enantiomer 2), (rac)-17-chloro-1-ethyl-14-{3-[(6-fluoronaphthalen-1-yl)oxy]propyl}-2-methyl-3b,4,5,6,8,9,10,11-octahydro-2H-pyrazolo[3',4':8,9]pyrrolo[1',2':6,7][1,6]diazacycloundecino[10,11,1-hi]indole-13-carboxylic acid (Isomer 1) and (rac)-4-chloro-3-ethyl-15-[2-(rac)-(3-fluoroazetidin-1-yl)ethyl]-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid;

or a tautomer, or a salt thereof, or a salt of a tautomer, or a mixture of same.

7. A method of preparing a compound of general formula (I) according to claim 1, said method comprising the step of reacting an intermediate compound of general formula (II):

(II)

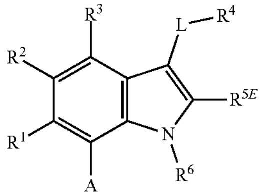

wherein $R^1$, $R^2$, $R^3$, $R^4$, $R^6$, A and L are as defined for the compound of general formula (I) according to claim 1, and $R^{5E}$ represents a carboxylic ester group or a benzyl ester group, with an alkali hydroxide in a mixture of water and THF and/or an aliphatic alcohol of formula $C_1$-$C_3$-alkyl-OH, at a temperature from 0° C. to 100° C., to transform the group $R^{5E}$ into a group $R^5$ as defined for the compounds of general formula (I), and subsequently optionally converting the free acid group $R^5$ into a pharmaceutically acceptable salt thereof to obtain a compound of general formula (I)

(I)

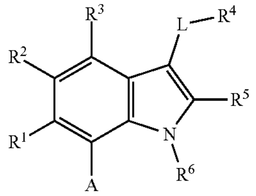

wherein $R^1$, $R^2$, $R^3$, $R^4$, $R^5$, $R^6$, A and L are as defined for the compound of general formula (I) according to claim 1 or a stereoisomer, a tautomer, an N-oxide, a hydrate, a solvate, or a salt thereof, or a salt of a stereoisomer, or a salt of a tautomer, or a salt of an N-oxide, or a mixture of same and optionally separating enantiomers by means of preparative HPLC on a chiral stationary phase.

8. A method of inhibiting proliferation of a cell and/or inducing apoptosis in a cell, comprising contacting the cell with a compound of formula (I) according to claim 1.

9. A method of treating a disease, comprising administering a compound of general formula (I) according to claim 1, wherein the disease is a hyperproliferative disease.

10. The method according to claim 9, wherein the hyperproliferative disease is cancer.

11. The method according to claim 10, wherein the cancer is selected from bladder cancer, bone cancer, brain cancer, breast cancer, colon/colorectal cancer, endometrial/uterine cancer, gastric cancer, head and neck cancer, kidney cancer, leukemia, liver cancer, lymphoma, lung cancer, melanoma, myeloma, neuroblastoma, ovarian cancer, pancreatic cancer, prostate cancer, rhabdoid tumor, sarcoma and skin cancer.

12. The method according to claim 11, wherein the cancer is selected from medulloblastoma, glioma, glioblastoma, ductal breast cancer, colorectal cancer, uterine cancer, stomach cancer, adenocarcinoma, small cell gastric cancer, squamous cell carcinoma, renal medullary carcinoma, acute myelogenous leukemia (AML), acute lymphoblastic leukemia (ALL), chronic myelogenous leukemia, plasma cell leukemia (PCL), hepatocellular carcinoma, non-small cell lung cancer, adenocarcinoma, small cell lung cancer, B-cell lymphoma, diffuse large B-cell lymphoma (DLBCL), mantle cell lymphoma, Hodgkin's lymphoma, B-cell non-Hodgkins lymphoma (NHL), T-cell NHL, cutaneous NHL, mantle cell lymphoma, Sezary syndrome, anaplastic large cell NHL (ALCL), mesothelioma, multiple myeloma, neuroblastoma, ovarian carcinoma, adenocarcinoma high grade serous and serous papillary, serous, cystadenocarcinoma, pancreatic cancer, prostate cancer, rhabdoid tumor, rhabdomyosarcoma, and melanoma.

13. A pharmaceutical composition comprising a compound of general formula (I) according to claim 1 and one or more pharmaceutically acceptable excipients.

14. A pharmaceutical combination comprising:

one or more compounds of general formula (I) according to claim 1, and one or more further anti-cancer agents.

15. An intermediate compound of general formula (II):

(II)

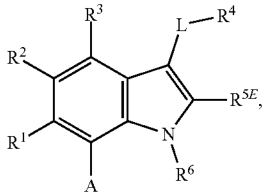

wherein

A is (A1)

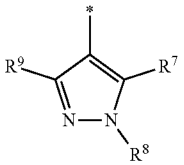

or (A2)

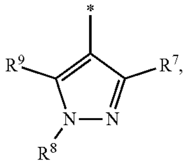

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent:

or

A is (A3)

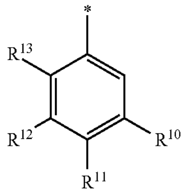

wherein optionally one or two of the groups selected from $CR^{11}$, $CR^{12}$ and $CR^{13}$ are replaced by a nitrogen atom, wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a ($C_1$-$C_3$-alkyl)-S(O)— group, a ($C_1$-$C_3$-alkyl)-

$S(O)_2$— group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)— haloalkyl-S— group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —$S(O)_2$— group and a —$NR^{14}$— group;

E is a bond, an oxygen atom, a sulfur atom, a —S(O)— group, a —$S(O)_2$— group or a —$NR^{14}$— group and constitutes the connecting element to $R^4$;

m is 2, 3, or 4;

$R^{5E}$ represents a carboxylic ester group;

—$R^6$-$R^7$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

—$R^6$-$R^{10}$— is $^{\#}$—$(CH_2)_n$—$(B)_t$—$CR^{22}R^{23}$—$^{\#\#}$ or $^{\#}$—($C_2$-$C_9$-alkenylene)-$(B)_t$—$CR^{22}R^{23}$- $^{\#}$, where one or more —$CH_2$— groups are substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group and a $C_1$-$C_3$-haloalkoxy group, wherein $^{\#}$ is the point of attachment with the indole nitrogen atom and $^{\#\#}$ is the point of attachment with the carbon atom of the aromatic moiety bearing the $R^{10}$ substituent:

n is 2, 3, 4, 5, 6, 7, 8, or 9, if B is selected from —O—, —S—, —S(O)—, —$S(O)_2$— and —$N(R^{15})$— and n is 1, 2, 3, 4, 5, 6, 7 or 8 if B is selected from —$C(O)NR^{15}$— group and a —$NR^{15}C(O)$— group and n is 0, 1, 2, 3, 4, 5, 6, or 7 if B is selected from a —$N(R^{15})$—C(=O)—$N(R^{15})$— group, a —O—C(=O)—$N(R^{15})$— group and a —$N(R^{15})$—C(=O)—O— group;

t is 1;

where the integers selected for variables n and t, together with the methylene group $CR^{22}R^{23}$ and the other non-variable atoms of the pyrazole and the indole moiety result in forming a 9-membered to 16-membered ring independently from the selection of variable A1, A2 or A3:

B is independently selected from a —$C(O)NR^{15}$— group, a —$NR^{15}C(O)$— group, a —$N(R^{15})$— group, a —$N(R^{15})$—C(=O)—$N(R^{15})$— group, a —O—C(=O)—$N(R^{15})$— group, a —$N(R^{15})$—C(=O)—O— group, —O—, —S—, —S(O)— and —$S(O)_2$—;

$R^8$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{21}R^{22}$ group;

a $C_1$-$C_3$-haloalkyl group, a $C_3$-$C_6$-cycloalkyl group and a $C_1$-$C_6$-alkyl group in which one or two not directly adjacent carbon atoms are independently replaced by a heteroatom selected from —O— and —NH— and $R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group, a $C_2$-$C_6$-haloalkenyl group, a $C_1$-$C_6$-alkyl-O— group, a $C_1$-$C_4$-haloalkoxy group, a $C_1$-$C_6$-alkyl-O—($C_1$-$C_3$-alkylene)- group, a ($C_3$-$C_7$)-cycloalkyl group, a ($C_3$-$C_7$)-cycloalkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)-group, a $R^{18}$-(phenylene)-($C_1$-$C_3$-alkylene)-O—($C_1$-$C_3$-alkylene)- group, a $R^{18}$-(phenylene)-O—($C_1$-$C_3$-alkylene)- group, a $R^{18}$-(phenylene)-(heteroarylene)-O—($C_1$-$C_3$-alkylene)- group, a ($R^{18}$)-(heterocycloalkylene)-($C_1$-$C_3$-alkylene)-group, a ($R^{18}$)-(heterocycloalkylene)-(phenylene)-O—($C_1$-$C_3$-alkylene)- group, a (heterocycloalkenyl)-(phenylene)-O—($C_1$-$C_3$-alkylene)- group, a ($R^{18}$)-(heteroarylene)-($C_1$-$C_3$-alkylene)-O—($C_1$-$C_3$-alkylene)- group, a ($R^{18}$)-(heteroarylene)-(phenylene)-O—($C_1$-$C_3$-alkylene)- group, a ($R^{19}$)—$S(O)_2$-(phenylene)-O—($C_1$-$C_3$-alkylene)-group, a ($R^{19}$)—$S(O)_2$—NH-(phenylene)-O—($C_1$-$C_3$-alkylene)- group, a ($R^{19}$)—$S(O)_2$—NH-(phenylene)-O—($C_1$-$C_3$-alkylene)- group, a ($R^{19}$)—$S(O)_2$—N($C_1$-$C_6$-alkyl)-(phenylene)-O—($C_1$-$C_3$-alkylene)- group, a ($R^{19}$)—$S(O)_2$-(heterocycloalkylene)-(phenylene)-O—($C_1$-$C_3$-alkylene)- group, a ($R^{18}$)-(heterocycloalkylene)-(heteroarylene)-O—($C_1$-$C_3$-alkylene)- group, a ($R^{19}$)-(heteroarylene)-O—($C_1$-$C_3$-alkylene)- group, a ($R^{18}$)-(heteroarylene)-O—($C_1$-$C_3$-alkylene)- group, a ($R^{19}$)—$S(O)_2$-(heteroarylene)-O—($C_1$-$C_3$-alkylene)-group, a ($R^{19}$)—$S(O)_2$-(heterocycloalkylene)-(heteroarylene)-O—($C_1$-$C_3$-alkylene)- group, a $NR^{20}R^{21}$—($C_1$-$C_3$-alkylene)- group, a ($C_1$-$C_3$-alkyl)-NH—($C_1$-$C_3$-alkylene)- group, a ($C_1$-$C_3$-haloalkyl)-($C_1$-$C_3$-alkylene)-NH—($C_1$-$C_3$-alkylene)- group, a ($C_1$-$C_3$-haloalkyl)-NH—($C_1$-$C_3$-alkylene)- group, a ($C_1$-$C_3$-alkyl)-NH—C(O)—($C_1$-$C_3$-alkylene)- group, a ($C_1$-$C_3$-alkyl)-$NR^{15}$—C(O)—($C_1$-$C_3$-alkylene)- group, a ($C_1$-$C_3$-alkyl)-C(O)—NH—($C_1$-$C_3$-alkylene)- group, a ($C_1$-$C_3$-alkyl)-C(O)—$NR^{15}$—($C_1$-$C_3$-alkylene)- group, a

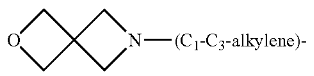

group and a

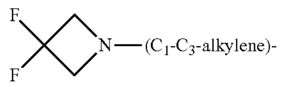

group, where the phenyl ring is unsubstituted or substituted with a halogen atom, a hydroxy group or a $C_1$-$C_3$-alkoxy group and the heterocycloalkyl group is unsubstituted or substituted with an oxo (═O) group or is unsubstituted or substituted with one or more substituents independently selected from a halogen atom, a hydroxy group, a $C_1$-$C_3$-alkyl group and a $C_1$-$C_3$-alkoxy group, or $R^8$ and $R^9$ together form a 5-membered or 6-membered ring optionally comprising one or two heteroatoms independently selected from —O— and —$NR^{14}$—;

$R^{11}$ and $R^{13}$ are each independently selected from a hydrogen atom, a halogen atom, a $C_1$-$C_3$-alkyl group and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group;

$R^{14}$ is a hydrogen atom or a $C_1$-$C_3$-alkyl group;

$R^{15}$ is independently selected from a hydrogen atom, a $C_1$-$C_6$-alkyl group, which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—$S(O)_2$-arylene-O— group, a ($R^{19}$)$S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group, a $C_1$-$C_3$-alkylene-C(O)— group, a heterocycloalkyl-($C_1$-$C_3$-alkylene)-C(O)— group, a heterocycloalkyl-($C_1$-$C_3$-alkylene)-$S(O)_2$— group, a heterocyclyl-NH—C(O)— group, a heterocycloalkyl-($C_1$-$C_3$-alkylene)-NH—C(O)— group, an aryl-($C_1$-$C_3$-alkylene)-NH—C(O)— group, which is unsubstituted or substituted with 1, 2, or 3 substituents independently selected from a halogen atom, a $C_1$-$C_3$-alkyl group and a $C_1$-$C_3$-alkoxy group, a heterocycloalkyl-heteroarylene-$S(O)_2$— group, a phenyl group, a group

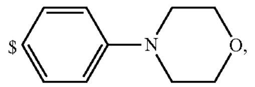

a group

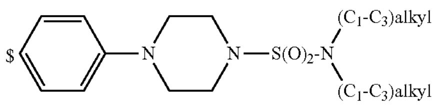

and a group

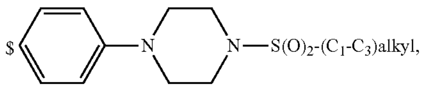

where $ is the point of attachment to the nitrogen atom, to which $R^{15}$ is attached, or $R^{15}$ and $R^{22}$ together, including the atoms to which they are attached, may form a 5- or 6-membered ring optionally comprising one or two additional heteroatoms independently selected from —O— and —$NR^{14}$—;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkyl $S(O)_2$— group and a $C_1$-$C_3$-alkyl-O—C(═O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_6$-alkyl group; and $R^{22}$ is independently selected from a halogen atom, a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a $(R^{18})$-(heterocycloalkylene)-(arylene)-O— group, a (heterocycloalkyl)-(arylene)-O-group, an aryl-O— group, an aryl-($C_1$-$C_3$-alkylene)-O— group, a $(R^{19})$—$S(O)_2$-arylene-O— group, a $(R^{19})S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-$S(O)_2$— group and a heterocycloalkylene-heteroarylene-$S(O)_2$— group, a $C_1$-$C_3$-alkyl-C(O)— group, a $C_3$-$C_6$-cycloalkyl group, an aryl group, a heterocycloalkyl group and a heteroaryl group;

wherein any heterocycloalkyl group of $R^{22}$ may optionally be itself further substituted with a $C_1$-$C_3$-alkyl group or one or two halogen atoms and $R^{23}$ is independently selected from a hydrogen atom, a halogen atom, a hydroxy group, a $C_1$-$C_6$-alkyl group and a $C_1$-$C_6$-haloalkyl group, or $R^{22}$ and $R^{23}$ together with the carbon atom to which they are attached form a 3-membered to 6-membered carbocyclic ring or a 3-membered to 6-membered heterocyclic ring comprising one or two heteroatoms selected from nitrogen, oxygen or sulfur.

* * * * *

UNITED STATES PATENT AND TRADEMARK OFFICE
CERTIFICATE OF CORRECTION

PATENT NO. : 11,440,923 B2
APPLICATION NO. : 16/764668
DATED : September 13, 2022
INVENTOR(S) : Kai Thede et al.

It is certified that error appears in the above-identified patent and that said Letters Patent is hereby corrected as shown below:

In the Claims

At Column 549, Claim number 3, Line number 7, please delete:
“C5-alkenylene)-$(B)_t$-$CR^{22}R^{23}$-,”
And replace with:
--C5-alkenylene)-$(B)_t$-$CR^{22}R^{23}$-$^{\#\#}$,--

At Column 550, Claim number 4, Line number 63, please delete:
“$C_4$-alkenylene)-$(B)_t$-$CR^{22}R^{23}$-,”
And replace with:
--$C_4$-alkenylene)-$(B)_t$-$CR^{22}R^{23}$-$^{\#\#}$,--

At Column 563, Claim number 15, Line 44, please delete:
“$^{\#}$-($C_2$-$C_9$-alkenylene)-$(B)_t$-$CR^{22}R^{23}$-$^{\#}$, where one”
And replace with:
--$^{\#}$-($C_2$-$C_9$-alkenylene)-$(B)_t$-$CR^{22}R^{23}$-$^{\#\#}$, where one--

At Column 565, Claim number 15, Lines 15-25, please delete:
“ 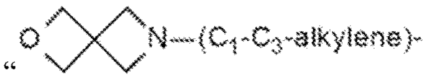
group and a
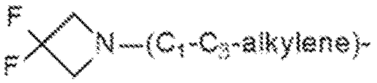 ”
And replace with:
-- 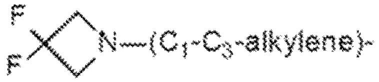

Signed and Sealed this
First Day of August, 2023

Katherine Kelly Vidal
*Director of the United States Patent and Trademark Office* group and a
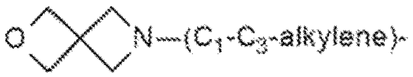
--

SEQUENCE LISTING

<160> NUMBER OF SEQ ID NOS: 6

<210> SEQ ID NO 1
<211> LENGTH: 519
<212> TYPE: PRT
<213> ORGANISM: Artificial Sequence
<220> FEATURE:
<223> OTHER INFORMATION: Modified Sequence

<400> SEQUENCE: 1

Gly Lys Ile Glu Glu Gly Lys Leu Val Ile Trp Ile Asn Gly Asp Lys
1 5 10 15

Gly Tyr Asn Gly Leu Ala Glu Val Gly Lys Lys Phe Glu Lys Asp Thr
20 25 30

Gly Ile Lys Val Thr Val Glu His Pro Asp Lys Leu Glu Glu Lys Phe
35 40 45

Pro Gln Val Ala Ala Thr Gly Asp Gly Pro Asp Ile Ile Phe Trp Ala
50 55 60

His Asp Arg Phe Gly Gly Tyr Ala Gln Ser Gly Leu Leu Ala Glu Ile
65 70 75 80

Thr Pro Asp Lys Ala Phe Gln Asp Lys Leu Tyr Pro Phe Thr Trp Asp
85 90 95

Ala Val Arg Tyr Asn Gly Lys Leu Ile Ala Tyr Pro Ile Ala Val Glu
100 105 110

Ala Leu Ser Leu Ile Tyr Asn Lys Asp Leu Leu Pro Asn Pro Pro Lys
115 120 125

Thr Trp Glu Glu Ile Pro Ala Leu Asp Lys Glu Leu Lys Ala Lys Gly
130 135 140

Lys Ser Ala Leu Met Phe Asn Leu Gln Glu Pro Tyr Phe Thr Trp Pro
145 150 155 160

Leu Ile Ala Ala Asp Gly Gly Tyr Ala Phe Lys Tyr Glu Asn Gly Lys
165 170 175

Tyr Asp Ile Lys Asp Val Gly Val Asp Asn Ala Gly Ala Lys Ala Gly
180 185 190

Leu Thr Phe Leu Val Asp Leu Ile Lys Asn Lys His Met Asn Ala Asp
195 200 205

Thr Asp Tyr Ser Ile Ala Glu Ala Ala Phe Asn Lys Gly Glu Thr Ala
210 215 220

Met Thr Ile Asn Gly Pro Trp Ala Trp Ser Asn Ile Asp Thr Ser Lys
225 230 235 240

Val Asn Tyr Gly Val Thr Val Leu Pro Thr Phe Lys Gly Gln Pro Ser
245 250 255

Lys Pro Phe Val Gly Val Leu Ser Ala Gly Ile Asn Ala Ala Ser Pro
260 265 270

Asn Lys Glu Leu Ala Lys Glu Phe Leu Glu Asn Tyr Leu Leu Thr Asp
275 280 285

Glu Gly Leu Glu Ala Val Asn Lys Asp Lys Pro Leu Gly Ala Val Ala
290 295 300

Leu Lys Ser Tyr Glu Glu Glu Leu Ala Lys Asp Pro Arg Ile Ala Ala
305 310 315 320

Thr Met Glu Asn Ala Gln Lys Gly Glu Ile Met Pro Asn Ile Pro Gln
325 330 335

Met Ser Ala Phe Trp Tyr Ala Val Arg Thr Ala Val Ile Asn Ala Ala
340 345 350

Ser Gly Arg Gln Thr Val Asp Glu Ala Leu Lys Asp Ala Gln Thr Gly
355 360 365

Ser Ser Glu Leu Tyr Arg Gln Ser Leu Glu Ile Ile Ser Arg Tyr Leu
370 375 380

Arg Glu Gln Ala Thr Gly Ala Ala Asp Thr Ala Pro Met Gly Ala Ser
385 390 395 400

Gly Ala Thr Ser Arg Lys Ala Leu Glu Thr Leu Arg Arg Val Gly Asp
405 410 415

Gly Val Gln Arg Asn His Glu Thr Ala Phe Gln Gly Met Leu Arg Lys
420 425 430

Leu Asp Ile Lys Asn Glu Asp Asp Val Lys Ser Leu Ser Arg Val Met
435 440 445

Ile His Val Phe Ser Asp Gly Val Thr Asn Trp Gly Arg Ile Val Thr
450 455 460

Leu Ile Ser Phe Gly Ala Phe Val Ala Lys His Leu Lys Thr Ile Asn
465 470 475 480

Gln Glu Ser Cys Ile Glu Pro Leu Ala Glu Ser Ile Thr Asp Val Leu
485 490 495

Val Arg Thr Lys Arg Asp Trp Leu Val Lys Gln Arg Gly Trp Asp Gly
500 505 510

Phe Val Glu Phe Phe His Val
515

<210> SEQ ID NO 2
<211> LENGTH: 26
<212> TYPE: PRT
<213> ORGANISM: Artificial Sequence
<220> FEATURE:
<221> NAME/KEY: MOD_RES
<222> LOCATION: 1
<223> OTHER INFORMATION: Biotin-PEG-PEG-PEG-PEG
<220> FEATURE:
<223> OTHER INFORMATION: Modified Sequence
<220> FEATURE:
<221> NAME/KEY: MOD_RES
<222> LOCATION: 8
<223> OTHER INFORMATION: Norvalin
<220> FEATURE:
<221> NAME/KEY: MOD_RES
<222> LOCATION: 26
<223> OTHER INFORMATION: AMIDATION

<400> SEQUENCE: 2

Pro Ala Glu Leu Glu Val Glu Val Ala Thr Gln Leu Arg Arg Phe Gly
1 5 10 15

```
Asp Lys Leu Asn Phe Arg Gln Lys Leu Leu
            20                  25


<210> SEQ ID NO 3
<211> LENGTH: 212
<212> TYPE: PRT
<213> ORGANISM: Artificial Sequence
<220> FEATURE:
<223> OTHER INFORMATION: Modified Sequence
<220> FEATURE:
<221> NAME/KEY: MOD_RES
<222> LOCATION: 212
<223> OTHER INFORMATION: HHHHHH

<400> SEQUENCE: 3

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg
    210


<210> SEQ ID NO 4
<211> LENGTH: 25
<212> TYPE: PRT
<213> ORGANISM: Artificial Sequence
<220> FEATURE:
<221> NAME/KEY: MOD_RES
<222> LOCATION: 1
<223> OTHER INFORMATION: Biotin-PEG-PEG-PEG-PEG
<220> FEATURE:
<223> OTHER INFORMATION: Modified Sequence
<220> FEATURE:
<221> NAME/KEY: MOD_RES
<222> LOCATION: 15
<223> OTHER INFORMATION: Norleucin
<220> FEATURE:
<221> NAME/KEY: MOD_RES
<222> LOCATION: 25
<223> OTHER INFORMATION: AMIDATION
```

<400> SEQUENCE: 4

Asn Leu Trp Ala Ala Gln Arg Tyr Gly Arg Glu Leu Arg Arg Leu Ser
1 5 10 15

Asp Glu Phe Val Asp Ser Phe Lys Lys
20 25

<210> SEQ ID NO 5
<211> LENGTH: 211
<212> TYPE: PRT
<213> ORGANISM: Artificial Sequence
<220> FEATURE:
<223> OTHER INFORMATION: Modified Sequence
<220> FEATURE:
<221> NAME/KEY: MOD_RES
<222> LOCATION: 211
<223> OTHER INFORMATION: HHHHHH

<400> SEQUENCE: 5

Met Ala His Ala Gly Arg Thr Gly Tyr Asp Asn Arg Glu Ile Val Met
1 5 10 15

Lys Tyr Ile His Tyr Lys Leu Ser Gln Arg Gly Tyr Glu Trp Asp Ala
20 25 30

Gly Asp Val Gly Ala Ala Pro Pro Gly Ala Ala Pro Ala Pro Gly Ile
35 40 45

Phe Ser Ser Gln Pro Gly His Thr Pro His Pro Ala Ala Ser Arg Asp
50 55 60

Pro Val Ala Arg Thr Ser Pro Leu Gln Thr Pro Ala Ala Pro Gly Ala
65 70 75 80

Ala Ala Gly Pro Ala Leu Ser Pro Val Pro Pro Val Val His Leu Thr
85 90 95

Leu Arg Gln Ala Gly Asp Asp Phe Ser Arg Arg Tyr Arg Arg Asp Phe
100 105 110

Ala Glu Met Ser Ser Gln Leu His Leu Thr Pro Phe Thr Ala Arg Gly
115 120 125

Arg Phe Ala Thr Val Val Glu Glu Leu Phe Arg Asp Gly Val Asn Trp
130 135 140

Gly Arg Ile Val Ala Phe Phe Glu Phe Gly Gly Val Met Cys Val Glu
145 150 155 160

Ser Val Asn Arg Glu Met Ser Pro Leu Val Asp Asn Ile Ala Leu Trp
165 170 175

Met Thr Glu Tyr Leu Asn Arg His Leu His Thr Trp Ile Gln Asp Asn
180 185 190

Gly Gly Trp Asp Ala Phe Val Glu Leu Tyr Gly Pro Ser Met Arg Pro
195 200 205

Leu Phe Asp
210

<210> SEQ ID NO 6
<211> LENGTH: 518
<212> TYPE: PRT
<213> ORGANISM: Artificial Sequence
<220> FEATURE:
<223> OTHER INFORMATION: Modified Sequence
<220> FEATURE:
<221> NAME/KEY: MOD_RES
<222> LOCATION: 194
<223> OTHER INFORMATION: K194A
<220> FEATURE:
<221> NAME/KEY: MOD_RES
<222> LOCATION: 197
<223> OTHER INFORMATION: K197A
<220> FEATURE:
<221> NAME/KEY: MOD_RES
<222> LOCATION: 201
<223> OTHER INFORMATION: R201A

<400> SEQUENCE: 6

```
Gly Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Asn Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Ser Glu Leu Tyr Arg Gln Ser Leu Glu Ile Ile Ser Arg Tyr Leu Arg
    370                 375                 380
```

-continued

```
Glu Gln Ala Thr Gly Ala Ala Asp Thr Ala Pro Met Gly Ala Ser Gly
385                 390                 395                 400

Ala Thr Ser Arg Lys Ala Leu Glu Thr Leu Arg Arg Val Gly Asp Gly
                405                 410                 415

Val Gln Arg Asn His Glu Thr Ala Phe Gln Gly Met Leu Arg Lys Leu
            420                 425                 430

Asp Ile Lys Asn Glu Asp Asp Val Lys Ser Leu Ser Arg Val Met Ile
        435                 440                 445

His Val Phe Ser Asp Gly Val Thr Asn Trp Gly Arg Ile Val Thr Leu
    450                 455                 460

Ile Ser Phe Gly Ala Phe Val Ala Lys His Leu Lys Thr Ile Asn Gln
465                 470                 475                 480

Glu Ser Cys Ile Glu Pro Leu Ala Glu Ser Ile Thr Asp Val Leu Val
                485                 490                 495

Arg Thr Lys Arg Asp Trp Leu Val Lys Gln Arg Gly Trp Asp Gly Phe
            500                 505                 510

Val Glu Phe Phe His Val
        515
```